US012799457B2

(12) United States Patent
Simpson-Abelson et al.

(10) Patent No.: US 12,799,457 B2
(45) Date of Patent: Nov. 17, 2026

(54) SELECTION OF IMPROVED TUMOR REACTIVE T-CELLS

(71) Applicant: Iovance Biotherapeutics, Inc., San Carlos, CA (US)

(72) Inventors: Michelle Simpson-Abelson, Lithia, FL (US); Arvind Natarajan, Tampa, FL (US); Cecile Chartier-Courtaud, Palo Alto, CA (US); Matt Paulson, San Mateo, CA (US)

(73) Assignee: Iovance Biotherapeutics, Inc., San Carlos, CA (US)

( * ) Notice: Subject to any disclaimer, the term of this patent is extended or adjusted under 35 U.S.C. 154(b) by 1194 days.

(21) Appl. No.: 17/290,705

(22) PCT Filed: Nov. 4, 2019

(86) PCT No.: PCT/US2019/059716
§ 371 (c)(1),
(2) Date: Apr. 30, 2021

(87) PCT Pub. No.: WO2020/096986
PCT Pub. Date: May 14, 2020

(65) Prior Publication Data

US 2023/0039976 A1 Feb. 9, 2023

Related U.S. Application Data

(60) Provisional application No. 62/924,602, filed on Oct. 22, 2019, provisional application No. 62/903,629, filed on Sep. 20, 2019, provisional application No. 62/826,831, filed on Mar. 29, 2019, provisional application No. 62/756,006, filed on Nov. 5, 2018.

(51) Int. Cl.

| | |
|---|---|
| ***C12N 5/0783*** | (2010.01) |
| ***A61K 40/11*** | (2025.01) |
| ***A61K 40/32*** | (2025.01) |
| ***A61K 40/42*** | (2025.01) |
| ***A61P 35/00*** | (2006.01) |

(52) U.S. Cl.
CPC ............ *C12N 5/0638* (2013.01); *A61K 40/11* (2025.01); *A61K 40/32* (2025.01); *A61K 40/4201* (2025.01); *A61K 40/428* (2025.01); *A61P 35/00* (2018.01); *C12N 2501/2302* (2013.01); *C12N 2501/515* (2013.01); *C12N 2502/11* (2013.01)

(58) Field of Classification Search
CPC ..... C12N 5/0638; C12N 5/0636; A61K 40/11
See application file for complete search history.

(56) References Cited

U.S. PATENT DOCUMENTS

| | | | |
|---|---|---|---|
| 4,766,106 | A | 8/1988 | Katre et al. |
| 4,897,355 | A | 1/1990 | Eppstein et al. |
| 4,902,502 | A | 2/1990 | Nitecki et al. |
| 5,019,034 | A | 5/1991 | Weaver et al. |
| 5,089,261 | A | 2/1992 | Nitecki et al. |
| 5,128,257 | A | 7/1992 | Baer |
| 5,137,817 | A | 8/1992 | Busta et al. |
| 5,173,158 | A | 12/1992 | Schmukler |
| 5,206,344 | A | 4/1993 | Katre et al. |
| 5,232,856 | A | 8/1993 | Firth |
| 5,273,525 | A | 12/1993 | Hofmann |
| 5,279,833 | A | 1/1994 | Rose |
| 5,304,120 | A | 4/1994 | Crandell et al. |
| 5,318,514 | A | 6/1994 | Hofmann |
| 5,593,875 | A | 1/1997 | Wurm et al. |
| 5,766,902 | A | 6/1998 | Craig et al. |
| 5,811,097 | A | 9/1998 | Allison et al. |
| 5,849,902 | A | 12/1998 | Arrow et al. |
| 5,855,887 | A | 1/1999 | Allison et al. |
| 5,898,031 | A | 4/1999 | Crooke |
| 5,908,635 | A | 6/1999 | Thierry |
| 5,928,893 | A | 7/1999 | Kang et al. |
| 5,977,318 | A | 11/1999 | Linsley et al. |
| 6,010,613 | A | 1/2000 | Walters et al. |
| 6,025,337 | A | 2/2000 | Truong et al. |
| 6,051,227 | A | 4/2000 | Allison et al. |
| 6,056,938 | A | 5/2000 | Unger et al. |
| 6,078,490 | A | 6/2000 | Walters |
| 6,107,094 | A | 8/2000 | Crooke |
| 6,110,490 | A | 8/2000 | Thierry |
| 6,207,156 | B1 | 3/2001 | Kuchroo et al. |
| 6,210,669 | B1 | 4/2001 | Aruffo et al. |
| 6,303,121 | B1 | 10/2001 | Kwon |
| 6,312,700 | B1 | 11/2001 | Weinberg |
| 6,362,325 | B1 | 3/2002 | Kwon |
| 6,410,517 | B1 | 6/2002 | Truong et al. |

(Continued)

FOREIGN PATENT DOCUMENTS

| | | | |
|---|---|---|---|
| CN | 107075479 | A | 8/2017 |
| EP | 0672141 | B1 | 9/1995 |

(Continued)

OTHER PUBLICATIONS

Ye et al. (J. Translational Med. 2011 9:131: 1-13) (Year: 2011).*
Ahmad, Zuhaida Asra et al. "scFv antibody: principles and clinical application." *Clinical & developmental immunology* vol. 2012 (2012): 980250. doi:10.1155/2012/980250.

(Continued)

*Primary Examiner* — Peter J Reddig
(74) *Attorney, Agent, or Firm* — Bryan Richardson

(57) ABSTRACT

The present invention provides methods for preselecting TILs based on PD-1 expression, as well as methods for expanding those preselected PD-1 positive TILs in order to produce therapeutic populations of TILs with enhanced tumor-specific killing capacity (e.g., enhanced cytotoxicity).

9 Claims, 232 Drawing Sheets

Specification includes a Sequence Listing.

(56) References Cited

U.S. PATENT DOCUMENTS 6,475,994 B2 11/2002 Tomalia et al.
6,479,626 B1 11/2002 Kim et al.
6,489,458 B2 12/2002 Hackett et al.
6,506,559 B1 1/2003 Fire et al.
6,534,261 B1 3/2003 Cox et al.
6,534,484 B1 3/2003 Wheeler et al.
6,569,997 B1 5/2003 Kwon
6,607,882 B1 8/2003 Cox et al.
6,627,442 B1 9/2003 Humeau et al.
6,682,736 B1 1/2004 Hanson et al.
6,706,289 B2 3/2004 Lewis et al.
6,746,838 B1 6/2004 Choo et al.
6,794,136 B1 9/2004 Eisenberg et al.
6,824,978 B1 11/2004 Cox et al.
6,866,997 B1 3/2005 Choo et al.
6,887,673 B2 5/2005 Kunkel et al.
6,903,185 B2 6/2005 Kim et al.
6,905,685 B2 6/2005 Kwon
6,933,113 B2 8/2005 Case et al.
6,974,863 B2 12/2005 Kwon
6,979,539 B2 12/2005 Cox et al.
6,984,720 B1 1/2006 Korman et al.
7,013,219 B2 3/2006 Case et al.
7,030,215 B2 4/2006 Liu et al.
7,056,704 B2 6/2006 Tuschl et al.
7,078,196 B2 7/2006 Tuschl et al.
7,109,003 B2 9/2006 Hanson et al.
7,132,281 B2 11/2006 Hanson et al.
7,189,705 B2 3/2007 Lam et al.
7,214,493 B2 5/2007 Kunkel et al.
7,220,719 B2 5/2007 Case et al.
7,241,573 B2 7/2007 Choo et al.
7,241,574 B2 7/2007 Choo et al.
7,282,564 B2 10/2007 Mello et al.
7,288,638 B2 10/2007 Jure-Kunkel et al.
7,432,249 B2 10/2008 Crooke
7,432,250 B2 10/2008 Crooke
7,504,101 B2 3/2009 Weinberg
7,538,095 B2 5/2009 Fire et al.
7,550,140 B2 6/2009 Bakker et al.
7,560,438 B2 7/2009 Fire et al.
7,585,849 B2 9/2009 Liu et al.
7,595,376 B2 9/2009 Kim et al.
7,622,444 B2 11/2009 Weinberg
7,687,070 B2 3/2010 Gebeyehu et al.
7,696,175 B2 4/2010 Epstein et al.
7,943,743 B2 5/2011 Korman et al.
7,960,515 B2 6/2011 Min et al.
8,008,449 B2 8/2011 Korman et al.
8,034,334 B2 10/2011 Dudley et al.
8,133,983 B2 3/2012 Bakker et al.
8,168,757 B2 5/2012 Finnefrock et al.
8,217,149 B2 7/2012 Irving et al.
8,236,930 B2 8/2012 Min et al.
8,287,856 B2 10/2012 Li et al.
8,337,850 B2 12/2012 Ahrens et al.
8,354,509 B2 1/2013 Carven et al.
8,450,460 B2 5/2013 Hill et al.
8,580,247 B2 11/2013 Li et al.
8,586,526 B2 11/2013 Gregory et al.
8,686,119 B2 4/2014 Rotem-Yehudar et al.
8,697,359 B1 4/2014 Zhang
8,735,553 B1 5/2014 Li et al.
8,771,945 B1 7/2014 Zhang
8,779,108 B2 7/2014 Queva et al.
8,795,965 B2 8/2014 Zhang
8,809,050 B2 8/2014 Vera et al.
8,821,867 B2 9/2014 Ahrens et al.
8,865,406 B2 10/2014 Zhang et al.
8,871,445 B2 10/2014 Cong et al.
8,889,356 B2 11/2014 Zhang
8,895,308 B1 11/2014 Zhang et al.
8,906,616 B2 12/2014 Zhang et al.
8,907,053 B2 12/2014 Sasikumar et al.
8,921,519 B2 12/2014 Hill et al.
8,932,814 B2 1/2015 Zhang et al.
8,945,839 B2 2/2015 Zhang
8,956,860 B2 2/2015 Vera et al.
8,962,804 B2 2/2015 Williams et al.
8,993,233 B2 3/2015 Zhang et al.
8,999,641 B2 4/2015 Zhang et al.
9,006,399 B2 4/2015 Liu et al.
9,028,824 B2 5/2015 Min et al.
9,044,442 B2 6/2015 Sasikumar et al.
9,074,185 B2 7/2015 Dudley et al.
9,080,171 B2 7/2015 Khvorova et al.
9,096,642 B2 8/2015 Sasikumar et al.
9,163,085 B2 10/2015 Liu et al.
9,340,599 B2 5/2016 Hill et al.
9,359,420 B2 6/2016 Hill et al.
9,468,678 B2 10/2016 Ahrens et al.
9,790,490 B2 10/2017 Zhang et al.
9,844,569 B2 12/2017 Gros et al.
10,130,659 B2 * 11/2018 Wardell ............. A61K 31/7076
10,166,257 B2 * 1/2019 Wardell ............... C12N 5/0634
10,183,979 B2 1/2019 Alvarez et al.
10,272,113 B2 * 4/2019 Wardell ............... C12N 5/0636
10,363,273 B2 * 7/2019 Wardell ............. A61K 39/4611
10,398,734 B2 * 9/2019 Wardell ............... C12N 5/0634
10,420,799 B2 * 9/2019 Wardell ............... A61K 9/0019
10,463,697 B2 * 11/2019 Wardell ............... C12N 5/0636
10,517,894 B2 * 12/2019 Frank ................. A61K 2239/57
10,633,654 B2 4/2020 Pavco et al.
10,639,330 B2 * 5/2020 Wardell ............... C12N 5/0638
10,646,517 B2 * 5/2020 Wardell .................. A61P 35/00
10,695,372 B2 * 6/2020 Wardell ............. A61K 31/7076
10,894,063 B2 * 1/2021 Wardell ............ A61K 2239/26
10,913,948 B2 2/2021 Khvorova et al.
10,918,666 B2 * 2/2021 Wardell ............. A61K 31/7076
10,925,900 B2 * 2/2021 Wardell ............... A61K 31/675
11,007,225 B1 * 5/2021 Wardell ............... A61K 9/0019
11,007,226 B2 * 5/2021 Wardell ............. A61K 38/2013
11,013,770 B1 * 5/2021 Wardell ............. A61K 38/2013
11,026,974 B2 * 6/2021 Frank ................. A61K 2239/57
11,040,070 B2 * 6/2021 Wardell ............. A61K 31/7076
11,052,115 B2 * 7/2021 Wardell ............... C12N 5/0636
11,052,116 B2 * 7/2021 Wardell ............... C12N 5/0634
11,058,728 B1 * 7/2021 Frank ................... C12N 5/0636
11,083,752 B2 * 8/2021 Wardell ............... C12N 5/0634
11,123,371 B2 * 9/2021 Frank ............... A61K 39/46449
11,141,438 B2 * 10/2021 Frank ................... C12N 5/0636
11,168,303 B2 * 11/2021 Wardell ............... C12N 5/0634
11,168,304 B2 * 11/2021 Wardell ................. A61K 35/17
11,179,419 B2 * 11/2021 Frank ...................... C07K 16/00
11,202,803 B1 * 12/2021 Wardell ............. A61K 31/7076
11,202,804 B2 * 12/2021 Wardell ............... A61K 31/675
11,220,670 B2 * 1/2022 Simpson-Abelson ....................... A61K 39/4611
11,241,456 B2 * 2/2022 Wardell ............... C12N 5/0638
11,254,913 B1 * 2/2022 Wardell ............. A61K 38/2013
11,266,694 B2 * 3/2022 Frank ................. C07K 14/7051
11,273,180 B2 * 3/2022 Wardell ............... A61K 9/0019
11,273,181 B2 * 3/2022 Wardell ............... C12N 5/0636
11,291,687 B2 * 4/2022 Wardell .................. A61P 35/00
11,293,009 B2 * 4/2022 Simpson-Abelson ....................... C12N 5/0638
11,304,979 B2 * 4/2022 Wardell ............... C12N 5/0638
11,304,980 B2 * 4/2022 Frank ...................... A61P 35/00
11,311,578 B2 * 4/2022 Frank ............... A61K 39/46449
11,337,998 B2 * 5/2022 Wardell ............... C12N 5/0638
11,344,579 B2 * 5/2022 Wardell ............... C12N 5/0638
11,344,580 B2 * 5/2022 Frank ................. A61K 39/4611
11,344,581 B2 * 5/2022 Frank ................. G01N 33/5005
11,351,197 B2 * 6/2022 Frank ...................... A61P 35/00
11,351,198 B2 * 6/2022 Frank ................. C07K 14/7051
11,351,199 B2 * 6/2022 Frank ..................... C07K 16/00
11,357,841 B2 * 6/2022 Ritthipichai ... A61K 39/464406
11,364,266 B2 * 6/2022 Frank ..................... C07K 16/00
11,369,637 B2 * 6/2022 Frank ..................... C07K 16/00
11,384,337 B2 * 7/2022 Chartier-Courtaud ....................... C12N 5/0638
11,401,507 B2 * 8/2022 Simpson-Abelson ....................... A61K 35/17
11,433,097 B2 * 9/2022 Fardis .................. G01N 33/574

(56) References Cited

U.S. PATENT DOCUMENTS

| | | | | |
|---|---|---|---|---|
| 11,517,592 | B1 * | 12/2022 | Wardell | A01N 1/0284 |
| 11,529,372 | B1 * | 12/2022 | Wardell | A61K 38/2013 |
| 11,541,077 | B2 * | 1/2023 | Wardell | C12N 5/0638 |
| 11,713,446 | B2 * | 8/2023 | Chartier-Courtaud | A61K 39/464499 424/93.71 |
| 11,857,573 | B2 * | 1/2024 | Frank | C12N 15/85 |
| 11,865,140 | B2 * | 1/2024 | Frank | C12N 15/85 |
| 11,939,596 | B2 * | 3/2024 | Wardell | A61K 2239/57 |
| 11,969,444 | B2 * | 4/2024 | Frank | A61K 2239/57 |
| 11,975,028 | B2 * | 5/2024 | Frank | A61K 2239/57 |
| 11,998,568 | B2 * | 6/2024 | Wardell | A61K 2239/26 |
| 12,024,718 | B2 * | 7/2024 | Chartier-Courtaud | A01N 1/0221 |
| 12,031,157 | B2 * | 7/2024 | Chartier-Courtaud | A61K 35/17 |
| 12,104,172 | B2 * | 10/2024 | Chartier-Courtaud | A61K 39/4611 |
| 12,121,541 | B2 * | 10/2024 | Wardell | A61K 31/7076 |
| 2002/0039581 | A1 | 4/2002 | Carreno et al. | |
| 2002/0086014 | A1 | 7/2002 | Korman et al. | |
| 2003/0051263 | A1 | 3/2003 | Fire et al. | |
| 2003/0055020 | A1 | 3/2003 | Fire et al. | |
| 2003/0056235 | A1 | 3/2003 | Fire et al. | |
| 2004/0265839 | A1 | 12/2004 | Mello et al. | |
| 2005/0095244 | A1 | 5/2005 | Jure-Kunkel et al. | |
| 2005/0100913 | A1 | 5/2005 | Mello et al. | |
| 2005/0106717 | A1 | 5/2005 | Wilson et al. | |
| 2005/0201994 | A1 | 9/2005 | Korman et al. | |
| 2006/0024798 | A1 | 2/2006 | Mello et al. | |
| 2008/0050342 | A1 | 2/2008 | Fire et al. | |
| 2008/0055443 | A1 | 3/2008 | Okamoto et al. | |
| 2008/0081373 | A1 | 4/2008 | Fire et al. | |
| 2008/0248576 | A1 | 10/2008 | Fire et al. | |
| 2009/0028857 | A1 | 1/2009 | Li et al. | |
| 2009/0131360 | A1 | 5/2009 | Woolf et al. | |
| 2010/0136030 | A1 | 6/2010 | Salah-Eddine et al. | |
| 2010/0203056 | A1 | 8/2010 | Irving et al. | |
| 2010/0266617 | A1 | 10/2010 | Carven et al. | |
| 2010/0285013 | A1 | 11/2010 | Li et al. | |
| 2011/0008369 | A1 | 1/2011 | Finnefrock et al. | |
| 2011/0027218 | A1 | 2/2011 | Hill et al. | |
| 2011/0039914 | A1 | 2/2011 | Pavco et al. | |
| 2011/0052530 | A1 | 3/2011 | Dudley et al. | |
| 2011/0111494 | A1 | 5/2011 | Hill et al. | |
| 2011/0136228 | A1 | 6/2011 | Vera et al. | |
| 2011/0201118 | A1 | 8/2011 | Yang et al. | |
| 2012/0244133 | A1 | 9/2012 | Rosenberg et al. | |
| 2013/0022600 | A1 | 1/2013 | Li et al. | |
| 2013/0034559 | A1 | 2/2013 | Queva et al. | |
| 2013/0045200 | A1 | 2/2013 | Irving et al. | |
| 2013/0045201 | A1 | 2/2013 | Irving et al. | |
| 2013/0045202 | A1 | 2/2013 | Irving et al. | |
| 2013/0102075 | A1 | 4/2013 | Vera et al. | |
| 2013/0108651 | A1 | 5/2013 | Carven et al. | |
| 2013/0109843 | A1 | 5/2013 | Carven et al. | |
| 2013/0115617 | A1 | 5/2013 | Wilson | |
| 2013/0117869 | A1 | 5/2013 | Duchateau et al. | |
| 2013/0131141 | A1 | 5/2013 | Khvorova et al. | |
| 2013/0131142 | A1 | 5/2013 | Libertine et al. | |
| 2013/0315884 | A1 | 11/2013 | Galetto et al. | |
| 2014/0065135 | A1 | 3/2014 | Irving et al. | |
| 2014/0227237 | A1 | 8/2014 | June et al. | |
| 2014/0294898 | A1 | 10/2014 | Miller et al. | |
| 2014/0328791 | A1 | 11/2014 | Bossard et al. | |
| 2014/0341917 | A1 | 11/2014 | Nastri et al. | |
| 2014/0377284 | A1 | 12/2014 | Simons et al. | |
| 2014/0377739 | A1 | 12/2014 | Welch et al. | |
| 2015/0073024 | A1 | 3/2015 | Sasikumar et al. | |
| 2015/0073042 | A1 | 3/2015 | Sasikumar et al. | |
| 2015/0087581 | A1 | 3/2015 | Sasikumar et al. | |
| 2015/0110734 | A1 | 4/2015 | Hill et al. | |
| 2015/0125491 | A1 | 5/2015 | Sasikumar et al. | |
| 2015/0126709 | A1 | 5/2015 | Hill et al. | |
| 2015/0126710 | A1 | 5/2015 | Hill et al. | |
| 2015/0132288 | A1 | 5/2015 | Simons et al. | |
| 2015/0175966 | A1 | 6/2015 | Vera et al. | |
| 2015/0190506 | A1 | 7/2015 | Cheung et al. | |
| 2015/0203871 | A1 | 7/2015 | Juillerat et al. | |
| 2016/0010058 | A1 | 1/2016 | Gros et al. | |
| 2016/0120906 | A1 | 5/2016 | Galetto et al. | |
| 2016/0208216 | A1 | 7/2016 | Vera et al. | |
| 2016/0215262 | A1 | 7/2016 | Powell | |
| 2016/0304873 | A1 | 10/2016 | Wolfson et al. | |
| 2017/0044496 | A1 | 2/2017 | Sarnaik et al. | |
| 2017/0081635 | A1 | 3/2017 | Sarnaik et al. | |
| 2017/0107490 | A1 | 4/2017 | Maeurer | |
| 2017/0152478 | A1 | 6/2017 | Rosenberg et al. | |
| 2017/0224800 | A1 * | 8/2017 | Tran | A61P 1/16 |
| 2018/0201889 | A1 | 7/2018 | Sharei et al. | |
| 2018/0280436 | A1 | 10/2018 | Wardell et al. | |
| 2018/0282694 | A1 * | 10/2018 | Wardell | A61K 2239/26 |
| 2018/0325954 | A1 * | 11/2018 | Wardell | A61K 39/4611 |
| 2019/0017072 | A1 | 1/2019 | Ditommaso et al. | |
| 2019/0048096 | A1 | 2/2019 | Hermann et al. | |
| 2019/0048341 | A1 | 2/2019 | Cardia et al. | |
| 2019/0093073 | A1 | 3/2019 | Sharei et al. | |
| 2019/0201334 | A1 | 7/2019 | Hakim et al. | |
| 2019/0211337 | A1 | 7/2019 | Khvorova et al. | |
| 2019/0275133 | A1 | 9/2019 | Charych et al. | |
| 2020/0121719 | A1 | 4/2020 | Lotze et al. | |
| 2020/0181220 | A1 | 6/2020 | Ptacin et al. | |
| 2020/0223907 | A1 | 7/2020 | Balakrishnan et al. | |
| 2020/0270334 | A1 | 8/2020 | Deane et al. | |
| 2020/0299644 | A1 | 9/2020 | Frank et al. | |
| 2020/0330601 | A1 | 10/2020 | Ptacin et al. | |
| 2021/0038684 | A1 | 2/2021 | Losey et al. | |

FOREIGN PATENT DOCUMENTS

| | | | |
|---|---|---|---|
| EP | 0928290 | B9 | 11/2005 |
| EP | 1212422 | B1 | 2/2007 |
| EP | 1309726 | B2 | 12/2009 |
| TW | 201839129 | A | 11/2018 |
| WO | WO 1990014074 | A1 | 11/1990 |
| WO | WO 1991016024 | A1 | 10/1991 |
| WO | WO 1991017424 | A1 | 11/1991 |
| WO | WO 1995012673 | A1 | 5/1995 |
| WO | WO 1995021925 | A1 | 8/1995 |
| WO | WO 1997020574 | A1 | 6/1997 |
| WO | WO 1998030679 | A1 | 1/1998 |
| WO | WO 1998013526 | A1 | 4/1998 |
| WO | WO 1998042752 | A1 | 10/1998 |
| WO | WO 1999032619 | A1 | 7/1999 |
| WO | WO 2000037504 | A9 | 11/2000 |
| WO | WO 2001014424 | A3 | 3/2001 |
| WO | WO 2001029058 | A1 | 4/2001 |
| WO | WO 2003086459 | A1 | 10/2003 |
| WO | WO 2004035607 | A2 | 4/2004 |
| WO | WO 2004081021 | A2 | 9/2004 |
| WO | WO 2005092380 | A2 | 10/2005 |
| WO | WO 2006009649 | A2 | 1/2006 |
| WO | WO 2006029219 | A2 | 3/2006 |
| WO | WO 2006121168 | A1 | 11/2006 |
| WO | WO 2006121810 | A2 | 11/2006 |
| WO | WO 2007067959 | A2 | 6/2007 |
| WO | WO 2008025516 | A2 | 3/2008 |
| WO | WO 2007123737 | A3 | 10/2008 |
| WO | WO 2008156712 | A1 | 12/2008 |
| WO | WO 2009007120 | A2 | 1/2009 |
| WO | WO 2009045457 | A2 | 4/2009 |
| WO | WO 2009100140 | A1 | 8/2009 |
| WO | WO 2009102427 | A2 | 8/2009 |
| WO | WO 2010003766 | A2 | 1/2010 |
| WO | WO 2010010051 | A1 | 1/2010 |
| WO | WO 2010033246 | A1 | 3/2010 |
| WO | WO 2010033247 | A2 | 3/2010 |
| WO | WO 2010042433 | A1 | 4/2010 |
| WO | WO 2010078966 | A1 | 7/2010 |
| WO | WO 2011072088 | A2 | 6/2011 |
| WO | WO 2011119852 | A1 | 9/2011 |
| WO | WO 2011119887 | A1 | 9/2011 |
| WO | WO 2012027328 | A2 | 3/2012 |

(56) References Cited

FOREIGN PATENT DOCUMENTS

| | | | | |
|---|---|---|---|---|
| WO | WO 2012032433 A1 | | 3/2012 | |
| WO | WO 2012065086 A1 | | 5/2012 | |
| WO | WO 2012177788 A1 | | 6/2012 | |
| WO | WO 2012120125 A1 | | 9/2012 | |
| WO | WO 2012129201 A1 | | 9/2012 | |
| WO | WO 2013028231 A1 | | 2/2013 | |
| WO | WO 2013038191 A2 | | 3/2013 | |
| WO | WO 2013057500 A1 | | 4/2013 | |
| WO | WO 2013059343 A1 | | 4/2013 | |
| WO | WO 2013088147 A1 | | 6/2013 | |
| WO | WO 2013173835 A1 | | 11/2013 | |
| WO | WO 2013188427 A1 | | 12/2013 | |
| WO | WO 2014148895 A1 | | 9/2014 | |
| WO | WO 2016053339 A1 | | 10/2014 | |
| WO | WO 2014210036 A1 | | 12/2014 | |
| WO | WO 2015004490 A1 | | 1/2015 | |
| WO | WO 2015119923 A1 | | 2/2015 | |
| WO | WO 2015033301 A1 | | 3/2015 | |
| WO | WO 2015036927 A1 | | 3/2015 | |
| WO | WO 2015189356 A1 | | 12/2015 | |
| WO | WO 2015189357 A1 | | 12/2015 | |
| WO | WO 2016053338 A1 | | 4/2016 | |
| WO | WO 2016096903 A1 | | 6/2016 | |
| WO | WO-2016179006 A1 | * | 11/2016 | ......... A61K 38/1703 |
| WO | WO 2017008063 A1 | | 1/2017 | |
| WO | WO 2017070042 A1 | | 4/2017 | |
| WO | WO 2017070151 A1 | | 4/2017 | |
| WO | WO 2017123663 A1 | | 7/2017 | |
| WO | WO 2018081473 A1 | | 5/2018 | |
| WO | WO 2018129332 A1 | | 7/2018 | |
| WO | WO 2018132496 A1 | | 7/2018 | |
| WO | WO 2018182817 A1 | | 10/2018 | |
| WO | WO 2018204760 A1 | | 11/2018 | |
| WO | WO 2018209115 A1 | | 11/2018 | |
| WO | WO 2018226714 A1 | | 12/2018 | |
| WO | WO 2019136456 A1 | | 7/2019 | |
| WO | WO 2019156568 A8 | | 10/2019 | |
| WO | WO 2019210131 A1 | | 10/2019 | |

OTHER PUBLICATIONS

Ahmadzadeh, Mojgan et al. "Tumor antigen-specific CD8 T cells infiltrating the tumor express high levels of PD-1 and are functionally impaired." *Blood* vol. 114,8 (2009): 1537-44. doi:10.1182/blood-2008-12-195792.

Andersen, Rikke et al. "T-cell Responses in the Microenvironment of Primary Renal Cell Carcinoma-Implications for Adoptive Cell Therapy." *Cancer immunology research* vol. 6,2 (2018): 222-235. doi:10.1158/2326-6066.CIR-17-0467.

Andersen, Rikke et al. "Tumor infiltrating lymphocyte therapy for ovarian cancer and renal cell carcinoma." *Human vaccines & immunotherapeutics* vol. 11,12 (2015): 2790-5. doi:10.1080/21645515.2015.1075106.

Augustyns, K et al. "Incorporation of hexose nucleoside analogues into oligonucleotides: synthesis, base-pairing properties and enzymatic stability." *Nucleic acids research* vol. 20,18 (1992): 4711-6. doi:10.1093/nar/20.18.4711.

Badoual, Cécile et al. "PD-1-expressing tumor-infiltrating T cells are a favorable prognostic biomarker in HPV-associated head and neck cancer." *Cancer research* vol. 73,1 (2013): 128-38. doi:10.1158/0008-5472.CAN-12-2606.

Bally, Alexander P R et al. "Genetic and Epigenetic Regulation of PD-1 Expression." *Journal of immunology* (Baltimore, Md. : 1950) vol. 196,6 (2016): 2431-7. doi:10.4049/jimmunol.1502643.

Barber, Daniel L et al. "Restoring function in exhausted CD8 T cells during chronic viral infection." *Nature* vol. 439,7077 (2006): 682-7. doi:10.1038/nature04444.

Beane, Joal D et al. "Clinical Scale Zinc Finger Nuclease-mediated Gene Editing of PD-1 in Tumor Infiltrating Lymphocytes for the Treatment of Metastatic Melanoma." *Molecular therapy : the journal of the American Society of Gene Therapy* vol. 23,8 (2015): 1380-1390. doi:10.1038/mt.2015.71.

Bergan, R et al. "Electroporation enhances c-myc antisense oligodeoxynucleotide efficacy." *Nucleic acids research* vol. 21,15 (1993): 3567-73. doi:10.1093/nar/21.15.3567.

Besser, Michal J et al. "Adoptive transfer of tumor-infiltrating lymphocytes in patients with metastatic melanoma: intent-to-treat analysis and efficacy after failure to prior immunotherapies." *Clinical cancer research : an official journal of the American Association for Cancer Research* vol. 19,17 (2013): 4792-800. doi:10.1158/1078-0432.CCR-13-0380.

Besser, Michal J et al. "Minimally cultured or selected autologous tumor-infiltrating lymphocytes after a lympho-depleting chemotherapy regimen in metastatic melanoma patients." *Joumal of immunotherapy* (Hagerstown, Md. : 1997) vol. 32,4 (2009): 415-23. doi:10.1097/CJI.0b013e31819c8bda.

Betts, Michael R, and Richard A Koup. "Detection of T-cell degranulation: CD107a and b." *Methods in cell biology* vol. 75 (2004): 497-512. doi:10.1016/s0091-679x(04)75020-7.

Boussiotis, Vassiliki A et al. "Biochemical signaling of PD-1 on T cells and its functional implications." *Cancer journal* (Sudbury, Mass.) vol. 20,4 (2014): 265-71. doi:10.1097/PPO.0000000000000059.

Brahmer, et al., J. Clin. Oncol. 2014, 32, 5s (supplement, abstract 8021).

Byrne, Michael et al. "Novel hydrophobically modified asymmetric RNAi compounds (sd-rxRNA) demonstrate robust efficacy in the eye." *Journal of ocular pharmacology and therapeutics : the official journal of the Association for Ocular Pharmacology and Therapeutics* vol. 29,10 (2013): 855-64. doi:10.1089/jop.2013.0148.

Camacho, L. H. et al, "Phase 1 clinical trial of anti-CTLA4 human monoclonal antibody CP-675,206 in patients (pts) with advanced solid malignancies" Journal of Clinical Oncology (2004) 22:14_suppl, p. 2505-2505.

Campbell, Brittany B et al. "Comprehensive Analysis of Hypermutation in Human Cancer." *Cell* vol. 171,5 (2017): 1042-1056.e10. doi:10.1016/j.cell.2017.09.048.

Canale, Fernando P et al. "CD39 Expression Defines Cell Exhaustion in Tumor-Infiltrating CD8+ T Cells." *Cancer research* vol. 78,1 (2018): 115-128. doi:10.1158/0008-5472.CAN-16-2684.

Cancer Genome Atlas Network. "Comprehensive molecular characterization of human colon and rectal cancer." *Nature* vol. 487,7407 330-7. Jul. 18, 2012, doi:10.1038/nature11252.

Cancer Genome Atlas Research Network et al. "Integrated genomic characterization of endometrial carcinoma." *Nature* vol. 497,7447 (2013): 67-73. doi:10.1038/nature12113.

Cepko, C, and W Pear. "Overview of the retrovirus transduction system." *Current protocols in molecular biology* vol. Chapter 9 (2001): Unit9.9. doi:10.1002/0471142727.mb0909s36.

Chen, C, and H Okayama. "High-efficiency transformation of mammalian cells by plasmid DNA." *Molecular and cellular biology* vol. 7,8 (1987): 2745-52. doi:10.1128/mcb.7.8.2745-2752.1987.

Chikuma, Shunsuke et al. "PD-1-mediated suppression of IL-2 production induces CD8+ T cell anergy in vivo." *Journal of immunology* (Baltimore, Md. : 1950) vol. 182,11 (2009): 6682-9. doi:10.4049/jimmunol.0900080.

Cieri, Nicoletta et al. "IL-7 and IL-15 instruct the generation of human memory stem T cells from naive precursors." *Blood* vol. 121,4 (2013): 573-84. doi:10.1182/blood-2012-05-431718.

Cohen, Cyrille J et al. "Isolation of neoantigen-specific T cells from tumor and peripheral lymphocytes." *The Journal of clinical investigation* vol. 125,10 (2015): 3981-91. doi:10.1172/JCI82416.

Columbus, G. *Avelumab Misses Primary Endpoints in Phase III Ovarian Cancer Trial*. 2018; Available from: https://www.onclive.com/web-exclusives/avelumab-misses-primary-endpoints-in-phase-iii-ovarian-cancer-trial.

Cox, David Benjamin Turitz et al. "Therapeutic genome editing: prospects and challenges." *Nature medicine* vol. 21,2 (2015): 121-31. doi:10.1038/nm.3793.

(56) References Cited

OTHER PUBLICATIONS

Crompton, Joseph G et al. "Uncoupling T-cell expansion from effector differentiation in cell-based immunotherapy." *Immunological reviews* vol. 257,1 (2014): 264-276. doi:10.1111/imr.12135.

Curti, Brendan D et al. "OX40 is a potent immune-stimulating target in late-stage cancer patients." *Cancer research* vol. 73,24 (2013): 7189-7198. doi:10.1158/0008-5472.CAN-12-4174.

Damsky, William E Jr, and Marcus Bosenberg. "Mouse melanoma models and cell lines." *Pigment cell & melanoma research* vol. 23,6 (2010): 853-9. doi:10.1111/j.1755-148X.2010.00777.x.

De Marco, Ario. "Biotechnological applications of recombinant single-domain antibody fragments." *Microbial cell factories* vol. 10 44. Jun. 9, 2011. doi:10.1186/1475-2859-10-44.

Dominguez-Villar, Margarita, and David A Hafler. "Regulatory T cells in autoimmune disease." *Nature immunology* vol. 19,7 (2018): 665-673. doi:10.1038/s41590-018-0120-4.

Donia M, et al. Simplified protocol for clinical-grade tumor-infiltrating lymphocyte manufacturing with use of the Wave bioreactor. Cytotherapy. Aug. 2014;16(8):1117-20. doi:10.1016/j.jcyt.2014.02.004; PubMed PMID: 24831841.

Donia, M et al. "Characterization and comparison of 'standard' and 'young' tumour-infiltrating lymphocytes for adoptive cell therapy at a Danish translational research institution." *Scandinavian journal of immunology* vol. 75,2 (2012): 157-67. doi:10.1111/j.1365-3083.2011.02640.x.

Donia, Marco et al. "PD-1+ Polyfunctional T Cells Dominate the Periphery after Tumor-Infiltrating Lymphocyte Therapy for Cancer." *Clinical cancer research : an official journal of the American Association for Cancer Research* vol. 23,19 (2017): 5779-5788. doi:10.1158/1078-0432.CCR-16-1692.

Dudley, Mark E et al. "Adoptive cell therapy for patients with metastatic melanoma: evaluation of intensive myeloablative chemoradiation preparative regimens." *Journal of clinical oncology : official journal of the American Society of Clinical Oncology* vol. 26,32 (2008): 5233-9. doi:10.1200/JCO.2008.16.5449.

Dudley, Mark E et al. "Adoptive cell transfer therapy following non-myeloablative but lymphodepleting chemotherapy for the treatment of patients with refractory metastatic melanoma." *Journal of clinical oncology : official journal of the American Society of Clinical Oncology* vol. 23,10 (2005): 2346-57. doi:10.1200/JCO.2005.00.240.

Dudley, Mark E et al. "Cancer regression and autoimmunity in patients after clonal repopulation with antitumor lymphocytes." *Science* (New York, N. Y.) vol. 298,5594 (2002): 850-4. doi:10.1126/science.1076514.

Dudley, Mark E et al. "CD8+ enriched "young" tumor infiltrating lymphocytes can mediate regression of metastatic melanoma." *Clinical cancer research : an official journal of the American Association for Cancer Research* vol. 16,24 (2010): 6122-31. doi:10.1158/1078-0432.CCR-10-1297.

Dudley, Mark E et al. "Generation of tumor-infiltrating lymphocyte cultures for use in adoptive transfer therapy for melanoma patients." *Journal of immunotherapy* (Hagerstown, Md. : 1997) vol. 26,4 (2003): 332-42. doi:10.1097/00002371-200307000-00005.

Duhen, Thomas et al. "Co-expression of CD39 and CD103 identifies tumor-reactive CD8 T cells in human solid tumors." *Nature communications* vol. 9,1 2724. Jul. 13, 2018, doi:10.1038/s41467-018-05072-0.

Dull, T et al. "A third-generation lentivirus vector with a conditional packaging system." *Journal of virology* vol. 72,11 (1998): 8463-71. doi:10.1128/JVI.72.11.8463-8471.1998.

Eton, O et al. "A phase II study of "decrescendo" interleukin-2 plus interferon-alpha-2a in patients with progressive metastatic melanoma after chemotherapy." *Cancer* vol. 88,7 (2000): 1703-9.

Fantozzi, Anna, and Gerhard Christofori. "Mouse models of breast cancer metastasis." *Breast cancer research : BCR* vol. 8,4 (2006): 212. doi:10.1186/bcr1530.

Fehniger, T A, and M A Caligiuri. "Interleukin 15: biology and relevance to human disease." *Blood* vol. 97,1 (2001): 14-32. doi:10.1182/blood.v97.1.14.

Felgner, P L et al. "Lipofection: a highly efficient, lipid-mediated DNA-transfection procedure." *Proceedings of the National Academy of Sciences of the United States of America* vol. 84,21 (1987): 7413-7. doi:10.1073/pnas.84.21.7413.

Fernandez-Poma, Sarita M et al. "Expansion of Tumor-Infiltrating CD8+ T cells Expressing PD-1 Improves the Efficacy of Adoptive T-cell Therapy." *Cancer research* vol. 77,13 (2017): 3672-3684. doi:10.1158/0008-5472.CAN-17-0236.

Fisher, Timothy S et al. "Targeting of 4-1BB by monoclonal antibody PF-05082566 enhances T-cell function and promotes anti-tumor activity." *Cancer immunology, immunotherapy : CII* vol. 61,10 (2012): 1721-33. doi:10.1007/s00262-012-1237-1.

Fong, Miranda Y, and Sham S Kakar. "Ovarian cancer mouse models: a summary of current models and their limitations." *Journal of ovarian research* vol. 2.1 12. Sep. 28, 2009, doi:10.1186/1757-2215-2-12.

Ford, C F et al. "Fusion tails for the recovery and purification of recombinant proteins." *Protein expression and purification* vol. 2,2-3 (1991): 95-107. doi:10.1016/1046-5928(91)90057-p.

Fry, Terry J, and Crystal L Mackall. "Interleukin-7: from bench to clinic." *Blood* vol. 99,11 (2002): 3892-904. doi:10.1182/blood.v99.11.3892.

Fuerst, Mark "Metastatic Melanoma Immunotherapy with Pembrolizumab Induces Durable Responses," *Oncology Times* vol. 36, 13 (2014): 35-36. doi: 10.1097/01.COT.0000452086.09862.55.

Gassner, Franz Josef et al. "Fludarabine modulates composition and function of the T cell pool in patients with chronic lymphocytic leukaemia." *Cancer immunology, immunotherapy : CII* vol. 60,1 (2011): 75-85. doi:10.1007/s00262-010-0920-3.

Gattinoni, Luca et al. "A human memory T cell subset with stem cell-like properties." *Nature medicine* vol. 17,10 1290-7. Sep. 18, 2011, doi:10.1038/nm.2446.

Gattinoni, Luca et al. "Adoptive immunotherapy for cancer: building on success." *Nature reviews. Immunology* vol. 6,5 (2006): 383-93. doi:10.1038/nri1842.

Gattinoni, Luca et al. "Paths to stemness: building the ultimate antitumour T cell." *Nature reviews. Cancer* vol. 12,10 (2012): 671-84. doi:10.1038/nrc3322.

Gattinoni, Luca et al. "Wnt signaling arrests effector T cell differentiation and generates CD8+ memory stem cells." *Nature medicine* vol. 15,7 (2009): 808-13. doi:10.1038/nm.1982.

Geukes Foppen, M H et al. "Tumor-infiltrating lymphocytes for the treatment of metastatic cancer." *Molecular oncology* vol. 9,10 (2015): 1918-35. doi:10.1016/j.molonc.2015.10.018.

Gieffers, Christian et al. "APG350 induces superior clustering of TRAIL receptors and shows therapeutic antitumor efficacy independent of cross-linking via Fcγ receptors." *Molecular cancer therapeutics* vol. 12,12 (2013): 2735-47. doi:10.1158/1535-7163.MCT-13-0323.

Goff, Stephanie L et al. "Randomized, Prospective Evaluation Comparing Intensity of Lymphodepletion Before Adoptive Transfer of Tumor-Infiltrating Lymphocytes for Patients With Metastatic Melanoma." *Journal of clinical oncology : official journal of the American Society of Clinical Oncology* vol. 34,20 (2016): 2389-97. doi:10.1200/JCO.2016.66.7220.

Goff, Stephanie L et al. "Tumor infiltrating lymphocyte therapy for metastatic melanoma: analysis of tumors resected for TIL." *Journal of immunotherapy* (Hagerstown, Md. : 1997) vol. 33,8 (2010): 840-7. doi:10.1097/CJI.0b013e3181105b91.

Golubovskaya, Vita, and Lijun Wu. "Different Subsets of T Cells, Memory, Effector Functions, and CAR-T Immunotherapy." *Cancers* vol. 8,3 36. Mar. 15, 2016, doi:10.3390/cancers8030036.

Gontcharova, V., et al., *Persistence of cryopreserved tumor-infiltrating lymphocyte product lifileucel* (*LN-144*) *in C-144-01 study of advanced metastatic melanoma*. Cancer Res, 2019. 79 ((13 Suppl)).

Graham, F L, and A J van der Eb. "A new technique for the assay of infectivity of human adenovirus 5 DNA." *Virology* vol. 52,2 (1973): 456-67. doi:10.1016/0042-6822(73)90341-3.

Griesbeck, Morgane et al. "Sex Differences in Plasmacytoid Dendritic Cell Levels of IRF5 Drive Higher IFN-α Production in Women." *Journal of immunology* (Baltimore, Md. : 1950) vol. 195,11 (2015): 5327-36. doi:10.4049/jimmunol.1501684.

(56) References Cited

OTHER PUBLICATIONS

Gros, Alena et al. "PD-1 identifies the patient-specific CD8+ tumor-reactive repertoire infiltrating human tumors." *The Journal of clinical investigation* vol. 124,5 (2014): 2246-59. doi:10.1172/JCI73639.
Gros, Alena et al. "Prospective identification of neoantigen-specific lymphocytes in the peripheral blood of melanoma patients." *Nature medicine* vol. 22,4 (2016): 433-8. doi:10.1038/nm.4051.
Hackett, Perry B et al. "A transposon and transposase system for human application." *Molecular therapy : the journal of the American Society of Gene Therapy* vol. 18,4 (2010): 674-83. doi:10.1038/mt.2010.2.
Hartemann, Agnès et al. "Low-dose interleukin 2 in patients with type 1 diabetes: a phase 1/2 randomised, double-blind, placebo-controlled trial." *The lancet. Diabetes & endocrinology* vol. 1,4 (2013): 295-305. doi:10.1016/S2213-8587(13)70113-X.
He, Jia et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.
Herreros-Villanueva, Marta et al. "Mouse models of pancreatic cancer." *World journal of gastroenterology* vol. 18,12 (2012): 1286-94. doi:10.3748/wjg.v18.i12.1286.
Huang, Jianping et al. "Survival, persistence, and progressive differentiation of adoptively transferred tumor-reactive T cells associated with tumor regression." *Journal of immunotherapy* (Hagerstown, Md. : 1997) vol. 28,3 (2005): 258-67. doi:10.1097/01.cji.0000158855.92792.7a.
Hurwitz, A A et al. "CTLA-4 blockade synergizes with tumor-derived granulocyte-macrophage colony-stimulating factor for treatment of an experimental mammary carcinoma." *Proceedings of the National Academy of Sciences of the United States of America* vol. 95,17 (1998): 10067-71. doi:10.1073/pnas.95.17.10067.
International Search Report and Written Opinion for International Patent Application No. PCT/US2018/012633 dated May 25, 2018, 14 pages.
International Search Report and Written Opinion for International Patent Application No. PCT/US2019/059716 dated May 12, 2020, 11 pages.
Jaeger, H M, and S R Nagel. "Physics of the granular state." *Science* (New York, N.Y.) vol. 255,5051 (1992): 1523-31. doi:10.1126/science.255.5051.1523.
Jin, Jianjian et al. "Simplified method of the growth of human tumor infiltrating lymphocytes in gas-permeable flasks to numbers needed for patient treatment." *Journal of immunotherapy* (Hagerstown, Md. : 1997) vol. 35,3 (2012): 283-92. doi:10.1097/CJI.0b013e31824e801f.
Jing, Weiqing et al. "Adoptive cell therapy using PD-1+ myeloma-reactive T cells eliminates established myeloma in mice." *Journal for immunotherapy of cancer* vol. 5 51. Jun. 20, 2017, doi:10.1186/s40425-017-0256-z.
Kansy, Benjamin A et al. "PD-1 Status in CD8+ T Cells Associates with Survival and Anti-PD-1 Therapeutic Outcomes in Head and Neck Cancer." *Cancer research* vol. 77,22 (2017): 6353-6364. doi:10.1158/0008-5472.CAN-16-3167.
Keir, Mary E et al. "PD-1 and its ligands in tolerance and immunity." *Annual review of immunology* vol. 26 (2008): 677-704. doi:10.1146/annurev.immunol.26.021607.090331.
Khvorova, Anastasia, and Jonathan K Watts. "The chemical evolution of oligonucleotide therapies of clinical utility." *Nature biotechnology* vol. 35,3 (2017): 238-248. doi:10.1038/nbt.3765.
Kim, Seungwon. "Animal models of cancer in the head and neck region." *Clinical and experimental otorhinolaryngology* vol. 2,2 (2009): 55-60. doi:10.3342/ceo.2009.2.2.55.
Kvistborg, Pia et al. "TIL therapy broadens the tumor-reactive CD8(+) T cell compartment in melanoma patients." *Oncoimmunology* vol. 1,4 (2012): 409-418. doi:10.4161/onci.18851.
Lee, Do Y et al. "4-1BB signaling activates the t cell factor 1 effector/β-catenin pathway with delayed kinetics via ERK signaling and delayed PI3K/AKT activation to promote the proliferation of CD8+ T Cells." *PloS one* vol. 8,7 e69677. Jul. 11, 2013, doi:10.1371/journal.pone.0069677.
Lee, Junghwa et al. "Reinvigorating Exhausted T Cells by Blockade of the PD-1 Pathway." *Forum on immunopathological diseases and therapeutics* vol. 6,1-2 (2015): 7-17. doi:10.1615/ForumImmunDisTher.2015014188.
Levine, Bruce L et al. "Gene transfer in humans using a conditionally replicating lentiviral vector." *Proceedings of the National Academy of Sciences of the United States of America* vol. 103,46 (2006): 17372-7. doi:10.1073/pnas.0608138103.
Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65. doi:10.4049/jimmunol.0901101. Epub Nov. 30, 2009. PubMed PMID: 19949105.
Ligtenberg, Maarten A et al. "Self-Delivering RNAi Targeting PD-1 Improves Tumor-Specific T Cell Functionality for Adoptive Cell Therapy of Malignant Melanoma." *Molecular therapy : the journal of the American Society of Gene Therapy* vol. 26,6 (2018): 1482-1493. doi:10.1016/j.ymthe.2018.04.015.
Malek, Thomas R. "The biology of interleukin-2." *Annual review of immunology* vol. 26 (2008): 453-79. doi:10.1146/annurev.immunol.26.021607.090357.
Massaro, A F et al. "Solid-phase anti-CD3 antibody activation of murine tumor-infiltrating lymphocytes." *Cancer research* vol. 50,9 (1990): 2587-92.
McDermott, David et al. "Durable benefit and the potential for long-term survival with immunotherapy in advanced melanoma." *Cancer treatment reviews* vol. 40,9 (2014): 1056-64. doi:10.1016/j.ctrv.2014.06.012.
McGranahan, Nicholas et al. "Clonal neoantigens elicit T cell immunoreactivity and sensitivity to immune checkpoint blockade." *Science* (New York, N. Y.) vol. 351,6280 (2016): 1463-9. doi:10.1126/science.aaf1490.
Melssen, Marit M et al. "Formation and phenotypic characterization of CD49a, CD49b and CD103 expressing CD8 T cell populations in human metastatic melanoma." *Oncoimmunology* vol. 7,10 e1490855. Aug. 6, 2018, doi:10.1080/2162402X.2018.1490855.
Meuwissen, Ralph, and Anton Berns. "Mouse models for human lung cancer." *Genes & development* vol. 19,6 (2005): 643-64. doi:10.1101/gad.1284505.
Michot, J M et al. "Immune-related adverse events with immune checkpoint blockade: a comprehensive review." *European journal of cancer* (Oxford, England : 1990) vol. 54 (2016): 139-148. doi:10.1016/j.ejca.2015.11.016.
Mokyr, M B et al. "Realization of the therapeutic potential of CTLA-4 blockade in low-dose chemotherapy-treated tumor-bearing mice." *Cancer research* vol. 58,23 (1998): 5301-4.
Monnier, Philippe, et al. "In Vivo Applications of Single Chain Fv (Variable Domain) (ScFv) Fragments." *Antibodies*, vol. 2, No. 4, Apr. 2013, pp. 193-208. https://doi.org/10.3390/antib2020193.
Mullany, Lisa K, and JoAnne S Richards. "Minireview: animal models and mechanisms of ovarian cancer development." *Endocrinology* vol. 153,4 (2012): 1585-92. doi:10.1210/en.2011-2121.
Muranski, Pawel et al. "Increased intensity lymphodepletion and adoptive immunotherapy—how far can we go?." *Nature clinical practice. Oncology* vol. 3,12 (2006): 668-81. doi:10.1038/ncponc0666.
Nelson, Brad H. "IL-2, regulatory T cells, and tolerance." *Journal of immunology* (Baltimore, Md. : 1950) vol. 172,7 (2004): 3983-8. doi:10.4049/jimmunol.172.7.3983.
Nikolova M, Carriere M, Jenabian MA, Limou S, Younas M, et al. (2011) CD39/Adenosine Pathway is Involved in AIDS Progression. PLOS Pathogens 7(7): e1002110. https://doi.org/10.1371/journal.ppat.1002110.
O. R. Musin (2003). "The problem of the twenty-five spheres". Russ. Math. Surv. 58 (4): 794-795.
O'Day, S J et al. "Advantages of concurrent biochemotherapy modified by decrescendo interleukin-2, granulocyte colony-stimulating factor, and tamoxifen for patients with metastatic melanoma." *Journal of clinical oncology : official journal of the American Society of Clinical Oncology* vol. 17,9 (1999): 2752-61. doi:10.1200/JCO.1999.17.9.2752.

(56) References Cited

OTHER PUBLICATIONS

Page, David B et al. "Immune modulation in cancer with antibodies." *Annual review of medicine* vol. 65 (2014): 185-202. doi:10.1146/annurev-med-092012-112807.

Peper, Janet Kerstin et al. "An impedance-based cytotoxicity assay for real-time and label-free assessment of T-cell-mediated killing of adherent cells." *Journal of immunological methods* vol. 405 (2014): 192-8. doi:10.1016/j.jim.2014.01.012.

Petrelli, Alessandra et al. "PD-1+CD8+ T cells are clonally expanding effectors in human chronic inflammation." *The Journal of clinical investigation* vol. 128,10 (2018): 4669-4681. doi:10.1172/JCI96107.

Pfeifer, Gerd P et al. "Mutations induced by ultraviolet light." *Mutation research* vol. 571,1-2 (2005): 19-31. doi:10.1016/j.mrfmmm.2004.06.057.

Philip, Mary et al. "Chromatin states define tumour-specific T cell dysfunction and reprogramming." *Nature* vol. 545,7655 (2017): 452-456. doi:10.1038/nature22367.

Pleasance, Erin D et al. "A small-cell lung cancer genome with complex signatures of tobacco exposure." *Nature* vol. 463,7278 (2010): 184-90. doi:10.1038/nature08629.

Radvanyi, Laszlo G et al. "Specific lymphocyte subsets predict response to adoptive cell therapy using expanded autologous tumor-infiltrating lymphocytes in metastatic melanoma patients." *Clinical cancer research : an official journal of the American Association for Cancer Research* vol. 18,24 (2012): 6758-70. doi:10.1158/1078-0432.CCR-12-1177.

Riddell, S R et al. "Restoration of viral immunity in immunodeficient humans by the adoptive transfer of T cell clones." *Science* (New York, N. Y.) vol. 257,5067 (1992): 238-41. doi:10.1126/science.1352912.

Robbins, Paul F et al. "Cutting edge: persistence of transferred lymphocyte clonotypes correlates with cancer regression in patients receiving cell transfer therapy." *Journal of immunology* (Baltimore, Md. : 1950) vol. 173,12 (2004): 7125-30. doi:10.4049/jimmunol.173.12.7125.

Robert, Caroline et al. "Anti-programmed-death-receptor-1 treatment with pembrolizumab in ipilimumab-refractory advanced melanoma: a randomised dose-comparison cohort of a phase 1 trial." *Lancet* (London, England) vol. 384,9948 (2014): 1109-17. doi:10.1016/S0140-6736(14)60958-2.

Roberts, Steven A et al. "An APOBEC cytidine deaminase mutagenesis pattern is widespread in human cancers." *Nature genetics* vol. 45,9 (2013): 970-6. doi:10.1038/ng.2702.

Rose, J K et al. "A new cationic liposome reagent mediating nearly quantitative transfection of animal cells." *BioTechniques* vol. 10,4 (1991): 520-5.

Rosenberg SA, Dudley ME. Adoptive cell therapy for the treatment of patients with metastatic melanoma. Curr Opin Immunol. Apr. 2009;21(2):233-40.

Rosenberg, "IL-2: The First Effective Immunotherapy for Human Cancer," The Journal of Immunology, col. 192, No. 12, Jun. 6, 2014.

Rosenberg, S A et al. "Use of tumor-infiltrating lymphocytes and interleukin-2 in the immunotherapy of patients with metastatic melanoma. A preliminary report." *The New England journal of medicine* vol. 319,25 (1988): 1676-80. doi:10.1056/NEJM198812223192527.

Rosenberg, Steven A et al. "Durable complete responses in heavily pretreated patients with metastatic melanoma using T-cell transfer immunotherapy." *Clinical cancer research : an official journal of the American Association for Cancer Research* vol. 17,13 (2011): 4550-7. doi:10.1158/1078-0432.CCR-11-0116.

Rosenzwajg, Michelle et al. "Immunological and clinical effects of low-dose interleukin-2 across 11 autoimmune diseases in a single, open clinical trial." *Annals of the rheumatic diseases* vol. 78,2 (2019): 209-217. doi:10.1136/annrheumdis-2018-214229.

Rubio, Valerie et al. "Ex vivo identification, isolation and analysis of tumor-cytolytic T cells." Nature medicine vol. 9,11 (2003): 1377-82. doi: 10.1038/nm942.

Sadeghi, Arian et al. "Rapid expansion of T cells: Effects of culture and cryopreservation and importance of short-term cell recovery." *Acta oncologica* (Stockholm, Sweden) vol. 52,5 (2013): 978-86. doi:10.3109/0284186X.2012.737020.

Sadun, et al., J. Immunother. 2009, 182, 1481-89.

Sage, E. "Distribution and repair of photolesions in DNA: genetic consequences and the role of sequence context." *Photochemistry and photobiology* vol. 57,1 (1993): 163-74. doi:10.1111/j.1751-1097.1993.tb02273.x.

Sano, Daisuke, and Jeffrey N Myers. "Xenograft models of head and neck cancers." *Head & neck oncology* vol. 1 32. Aug. 13, 2009, doi:10.1186/1758-3284-1-32.

Santegoets, Saskia J A M et al. "IL-21 promotes the expansion of CD27+ CD28+ tumor infiltrating lymphocytes with high cytotoxic potential and low collateral expansion of regulatory T cells." *Journal of translational medicine* vol. 11 37. Feb. 12, 2013, doi:10.1186/1479-5876-11-37.

Sarniak, A. *A phase 2, multicenter study to assess the efficacy and safety of autologous tumor-infiltrating lymphocytes (LN-144) for the treatment of patients with metastatic melanoma*. 2018; Available from: https://ascopubs.org/doi/abs/10.1200/JCO.2018.36.15_suppl.TPS9595.

Schumacher, Ton N, and Robert D Schreiber. "Neoantigens in cancer immunotherapy." *Science* (New York, N.Y.) vol. 348,6230 (2015): 69-74. doi:10.1126/science.aaa4971.

Segal, Neil H et al. "Results from an Integrated Safety Analysis of Urelumab, an Agonist Anti-CD137 Monoclonal Antibody." *Clinical cancer research : an official journal of the American Association for Cancer Research* vol. 23,8 (2017): 1929-1936. doi:10.1158/1078-0432.CCR-16-1272.

Shang, Jun et al. "Analysis of PD-1 related immune transcriptional profile in different cancer types." *Cancer cell international* vol. 18 218. Dec. 27, 2018, doi:10.1186/s12935-018-0712-y.

Sharei, Armon et al. "A vector-free microfluidic platform for intracellular delivery." *Proceedings of the National Academy of Sciences of the United States of America* vol. 110,6 (2013): 2082-7. doi:10.1073/pnas.1218705110.

Sharei, Armon et al. "Ex vivo cytosolic delivery of functional macromolecules to immune cells." *PloS one* vol. 10,4 e0118803. Apr. 13, 2015, doi:10.1371/journal.pone.0118803.

Sharma, Padmanee, and James P Allison. "The future of immune checkpoint therapy." Science (New York, N.Y.) vol. 348,6230 (2015): 56-61. doi:10.1126/science.aaa8172.

Shen, Xinglei et al. "Persistence of tumor infiltrating lymphocytes in adoptive immunotherapy correlates with telomere length." *Journal of immunotherapy* (Hagerstown, Md. : 1997) vol. 30,1 (2007): 123-9. doi:10.1097/01.cji.0000211321.07654.b8.

Simon, Sylvain, and Nathalie Labarriere. "PD-1 expression on tumor-specific T cells: Friend or foe for immunotherapy?." *Oncoimmunology* vol. 7,1 e1364828. Sep. 14, 2017, doi:10.1080/2162402X.2017.1364828.

Simoni, Yannick et al. "Bystander CD8+ T cells are abundant and phenotypically distinct in human tumour infiltrates." *Nature* vol. 557,7706 (2018): 575-579. doi:10.1038/s41586-018-0130-2.

Smith, Corey et al. "Ex vivo expansion of human T cells for adoptive immunotherapy using the novel Xeno-free CTS Immune Cell Serum Replacement." *Clinical & translational immunology* vol. 4,1 e31. Jan. 16, 2015, doi:10.1038/cti.2014.31.

Somerville RP, et al.. Clinical scale rapid expansion of lymphocytes for adoptive cell transfer therapy in the WAVE® bioreactor. J Transl Med. Apr. 4, 2012;10:69.

Spolski, Rosanne, and Warren J Leonard. "Interleukin-21: a double-edged sword with therapeutic potential." *Nature reviews. Drug discovery* vol. 13,5 (2014): 379-95. doi:10.1038/nrd4296.

Steinke, J W, and L Borish. "Th2 cytokines and asthma. Interleukin-4: its role in the pathogenesis of asthma, and targeting it for asthma treatment with interleukin-4 receptor antagonists." *Respiratory research* vol. 2,2 (2001): 66-70. doi:10.1186/rr40.

Stevanović, Sanja et al. "A Phase II Study of Tumor-infiltrating Lymphocyte Therapy for Human Papillomavirus-associated Epithelial Cancers." *Clinical cancer research : an official journal of the American Association for Cancer Research* vol. 25,5 (2019): 1486-1493. doi:10.1158/1078-0432.CCR-18-2722.

(56) References Cited

OTHER PUBLICATIONS

Stevanović, Sanja et al. "Complete regression of metastatic cervical cancer after treatment with human papillomavirus-targeted tumor-infiltrating T cells." *Journal of clinical oncology : official journal of the American Society of Clinical Oncology* vol. 33,14 (2015): 1543-50. doi:10.1200/JCO.2014.58.9093.
Swartz, Melody A et al. "Tumor microenvironment complexity: emerging roles in cancer therapy." *Cancer research* vol. 72,10 (2012): 2473-80. doi:10.1158/0008-5472.CAN-12-0122.
Tan, Shuguang et al. "An unexpected N-terminal loop in PD-1 dominates binding by nivolumab." *Nature communications* vol. 8 14369. Feb. 6, 2017, doi:10.1038/ncomms14369.
Thomas, Anish, and Marko Jakopovic. "Immunotherapy for non-small-cell lung cancer." *Expert opinion on biological therapy* vol. 14,8 (2014): 1061-4. doi:10.1517/14712598.2014.925874.
Thommen, Daniela S et al. "A transcriptionally and functionally distinct PD-1+ CD8+ T cell pool with predictive potential in non-small-cell lung cancer treated with PD-1 blockade." *Nature medicine* vol. 24,7 (2018): 994-1004. doi:10.1038/s41591-018-0057-z.
Topalian, Suzanne L et al. "Safety, activity, and immune correlates of anti-PD-1 antibody in cancer." *The New England journal of medicine* vol. 366,26 (2012): 2443-54. doi:10.1056/NEJMoa1200690.
Tran, Eric et al. "Cancer immunotherapy based on mutation-specific CD4+ T cells in a patient with epithelial cancer." *Science* (New York, N.Y.) vol. 344,6184 (2014): 641-5. doi:10.1126/science.1251102.
Tran, Khoi Q et al. "Minimally cultured tumor-infiltrating lymphocytes display optimal characteristics for adoptive cell therapy." *Journal of immunotherapy* (Hagerstown, Md. : 1997) vol. 31,8 (2008): 742-51. doi:10.1097/CJI.0b013e31818403d5.
Tsong. T Y. "Electroporation of cell membranes." *Biophysical journal* vol. 60,2 (1991): 297-306. doi:10.1016/S0006-3495(91)82054-9.
Tsoukas, C D et al. "Activation of resting T lymphocytes by anti-CD3 (T3) antibodies in the absence of monocytes." *Journal of immunology* (Baltimore, Md. : 1950) vol. 135,3 (1985): 1719-23.
Tumeh, Paul C et al. "PD-1 blockade induces responses by inhibiting adaptive immune resistance." *Nature* vol. 515,7528 (2014): 568-71. doi:10.1038/nature13954.
Turcotte, Simon et al. "Phenotype and function of T cells infiltrating visceral metastases from gastrointestinal cancers and melanoma: implications for adoptive cell transfer therapy." *Journal of immunology* (Baltimore, Md. : 1950) vol. 191,5 (2013): 2217-25. doi: 10.4049/jimmunol.1300538.
Wang, Changyu et al. "In vitro characterization of the anti-PD-1 antibody nivolumab, BMS-936558, and in vivo toxicology in non-human primates." *Cancer immunology research* vol. 2,9 (2014): 846-56. doi: 10.1158/2326-6066.CIR-14-0040.
Wardell et al., "A cryopreserved tumor infiltrating lymphocyte (TIL) product for LN-44", Nov. 8, 2017, retrieved from the Internet: URL: http://www.iovance.com/wp-content/uploads/2017/11/SITC2017_Seth_poster_FINAL_SWDE_PRINT_7Nov2017.pdf.
Webb, John R et al. "PD-1 and CD103 Are Widely Coexpressed on Prognostically Favorable Intraepithelial CD8 T Cells in Human Ovarian Cancer." *Cancer immunology research* vol. 3,8 (2015): 926-35. doi: 10.1158/2326-6066.CIR-14-0239.
Weber, Jeffrey S et al. "Safety, efficacy, and biomarkers of nivolumab with vaccine in ipilimumab-refractory or -naive melanoma." *Journal of clinical oncology : official journal of the American Society of Clinical Oncology* vol. 31,34 (2013): 4311-8. doi:10.1200/JCO.2013.51.4802.
Weinberg, Andrew D et al. "Anti-OX40 (CD134) administration to nonhuman primates: immunostimulatory effects and toxicokinetic study." *Journal of immunotherapy* (Hagerstown, Md. : 1997) vol. 29,6 (2006): 575-85. doi:10.1097/01.cji.0000211319.00031.fc.
Westergaard, Marie Christine Wulff et al. "Correction: Tumour-reactive T cell subsets in the microenvironment of ovarian cancer." *British journal of cancer* vol. 120,8 (2019): 870. doi:10.1038/s41416-019-0425-6.
Wigler, M et al. "DNA-mediated transfer of the adenine phosphoribosyltransferase locus into mammalian cells." *Proceedings of the National Academy of Sciences of the United States of America* vol. 76,3 (1979): 1373-6. doi:10.1073/pnas.76.3.1373.
Wolfl, Matthias et al. "Activation-induced expression of CD137 permits detection, isolation, and expansion of the full repertoire of CD8+ T cells responding to antigen without requiring knowledge of epitope specificities." *Blood* vol. 110,1 (2007): 201-10. doi:10.1182/blood-2006-11-056168.
Yossef, Rami et al. "Enhanced detection of neoantigen-reactive T cells targeting unique and shared oncogenes for personalized cancer immunotherapy." *JCI insight* vol. 3,19 e122467. Oct. 4, 2018, doi:10.1172/jci.insight.122467.
Zacharakis, Nikolaos et al. "Immune recognition of somatic mutations leading to complete durable regression in metastatic breast cancer." *Nature medicine* vol. 24,6 (2018): 724-730. doi:10.1038/s41591-018-0040-8.
Zhang, Yan et al. "Programmed death-1 upregulation is correlated with dysfunction of tumor-infiltrating CD8+ T lymphocytes in human non-small cell lung cancer." *Cellular & molecular immunology* vol. 7,5 (2010): 389-95. doi:10.1038/cmi.2010.28.
Zhou, Juhua et al. "Persistence of multiple tumor-specific T-cell clones is associated with complete tumor regression in a melanoma patient receiving adoptive cell transfer therapy." *Journal of immunotherapy* (Hagerstown, Md. : 1997) vol. 28,1 (2005): 53-62. doi:10.1097/00002371-200501000-00007.
Zufferey, R et al. "Multiply attenuated lentiviral vector achieves efficient gene delivery in vivo." *Nature biotechnology* vol. 15,9 (1997): 871-5. doi:10.1038/nbt0997-871.
Abelson, Michelle R. Simpson et al., The T cell Growth Factor Cocktail IL-2/IL-15/IL-21 Enhances Expansion and Effector Function of Tumor, SITC 32nd annual meeting, p. 357, Nov. 8, 2017.
Ellebaek, Eva et al. "Adoptive cell therapy with autologous tumor infiltrating lymphocytes and low-dose Interleukin-2 in metastatic melanoma patients." Journal of translational medicine vol. 10 169. Aug. 21, 2012, doi:10.1186/1479-5876-10-169.
Inozume, Takashi et al. "Selection of CD8+PD-1+ lymphocytes in fresh human melanomas enriches for tumor-reactive T cells." Journal of immunotherapy (Hagerstown, Md. : 1997) vol. 33,9 (2010): 956-64. doi:10.1097/CJI.0b013e3181fad2b0.
International Preliminary Report on Patentability for International Patent Application No. PCT/US2019/059716 dated May 11, 2021, 7 pages.
Ye, Qunrui et al. "Engineered artificial antigen presenting cells facilitate direct and efficient expansion of tumor infiltrating lymphocytes." Journal of translational medicine vol. 9 131. Aug. 9, 2011, doi:10.1186/1479-5876-9-131.
Sakuishi, K et al., "Targeting Tim-3 and PD-1 pathways to reverse T cell exhaustion and restore anti-tumor immunity," J. Exp. Med., vol. 207, No. 10, pp. 2187-2194, Sep. 27, 2010.

* cited by examiner

| Process 2A: about 22 days from Steps A - E | Process GEN 3: about 14-18 days from Steps A - E |
|---|---|
| **STEP A**<br>Obtain Patient Tumor Sample<br>(optionally can be frozen before Step B; optionally tumor sample can be a core/small biopsy) | **STEP A**<br>Obtain Patient Tumor Sample<br>(optionally can be frozen before Step B) |
| **STEP B**<br>First Expansion<br>(physical fragmentation to at least 40 fragments per container grown for about 3 days to 14 days with media comprising IL-2) | **STEP B**<br>Priming First Expansion<br>(physical fragmentation of up to 60 fragments per container grown for about 1 days to 7/8 days with media comprising IL-2, OKT-3, and optionally antigen-presenting feeder cells) |
| **STEP C**<br>First Expansion to Second Expansion Transition<br>(Step B TILs directly move to Step D, optionally on Step B day 11) | **STEP C**<br>Priming First Expansion to Rapid Second Expansion Transition<br>(Step B TILs directly move to Step D on day 7/8) |
| **STEP D**<br>Second Expansion<br>(TILs grown in growth media medium comprising IL-2, OKT-3, and antigen-presenting feeder cells in a closed container) | **STEP D**<br>Rapid Second Expansion<br>(TILs grown in growth media medium comprising IL-2, OKT-3, and 2X antigen-presenting feeder cells; Days 10-11 scale up and add additional IL-2) |
| **STEP E**<br>Harvest TILS from Step D<br>(TILs harvested via closed system) | **STEP E**<br>Harvest TILS from Step D |
| **STEP F**<br>Final Formulation and/or Transfer to Infusion Bag<br>(optionally cryopreserve) | **STEP F**<br>Final Formulation and/or Transfer to Infusion Bag<br>(optionally cryopreserve) |

FIG. 1A

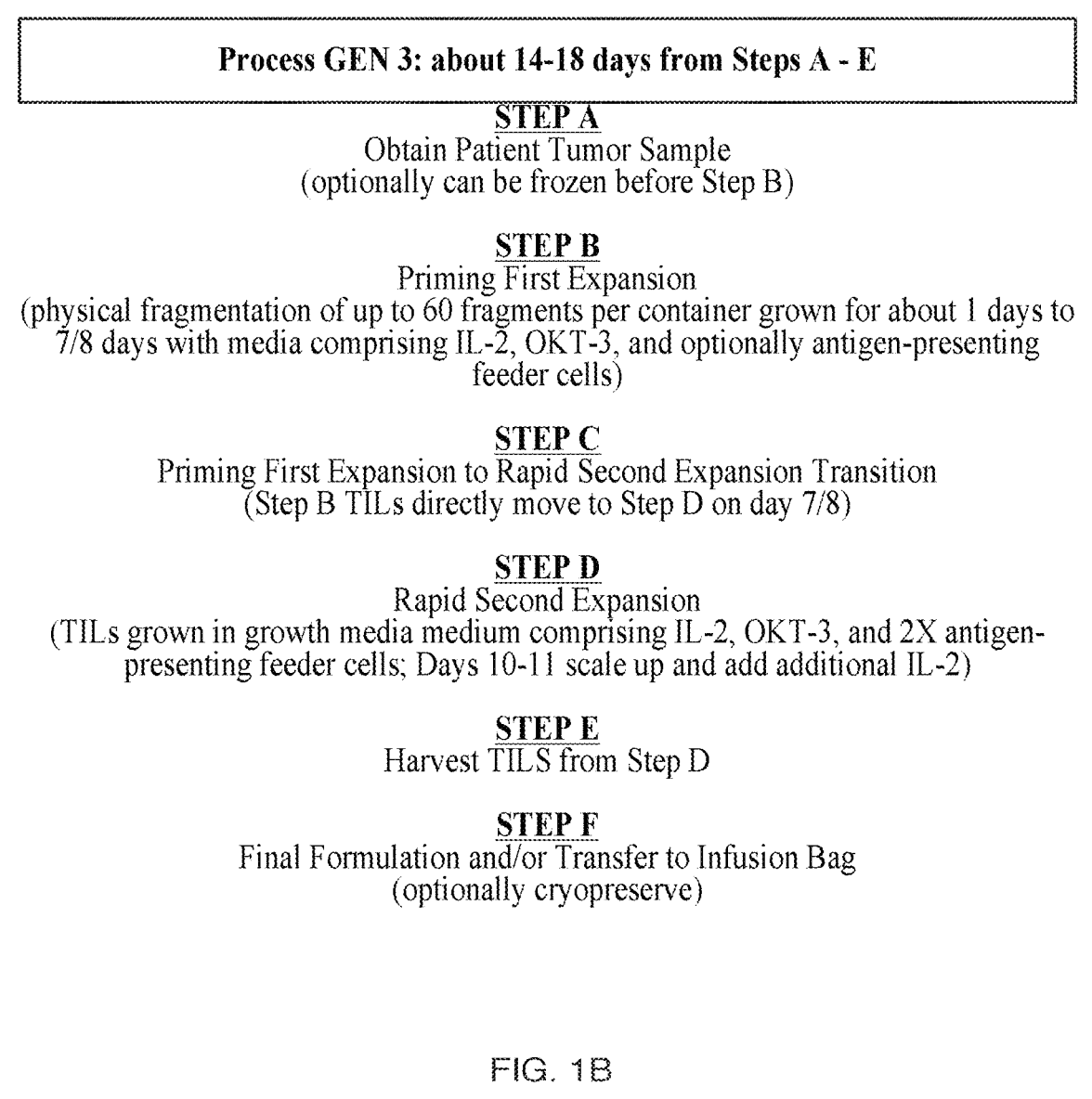

Process GEN 3: about 14-18 days from Steps A - E

STEP A
Obtain Patient Tumor Sample
(optionally can be frozen before Step B)

STEP B
Priming First Expansion
(physical fragmentation of up to 60 fragments per container grown for about 1 days to 7/8 days with media comprising IL-2, OKT-3, and optionally antigen-presenting feeder cells)

STEP C
Priming First Expansion to Rapid Second Expansion Transition
(Step B TILs directly move to Step D on day 7/8)

STEP D
Rapid Second Expansion
(TILs grown in growth media medium comprising IL-2, OKT-3, and 2X antigen-presenting feeder cells; Days 10-11 scale up and add additional IL-2)

STEP E
Harvest TILS from Step D

STEP F
Final Formulation and/or Transfer to Infusion Bag
(optionally cryopreserve)

FIG. 1B

| **Embodiment GEN 3.0: about 14-18 days from Steps A-E** | **Embodiment GEN 3.1 control: about 14-18 days from Steps A - E** | **Embodiment GEN 3.1 Test/F: about 14-18 days from Steps A - E** |
|---|---|---|
| **STEP A** Obtain Patient Tumor Sample (optionally can be frozen before Step B) | **STEP A** Obtain Patient Tumor Sample (optionally can be frozen before Step B) | **STEP A** Obtain Patient Tumor Sample (optionally can be frozen before Step B) |
| **STEP B** Priming First Expansion (physical fragmentation of up to 60 fragments per container grown for about 1 days to 7/8 days with media comprising IL-2) | **STEP B** Priming First Expansion (physical fragmentation of up to 60 fragments per container grown for about 1 days to 7/8 days with media comprising IL-2, and OKT-3) | **STEP B** Priming First Expansion (physical fragmentation of up to 60 fragments per container grown for about 1 days to 7/8 days with media comprising IL-2, OKT-3, and antigen-presenting feeder cells) |
| **STEP C** Priming First Expansion to Rapid Second Expansion Transition (Step B TILs directly move to Step D on day 7/8) | **STEP C** Priming First Expansion to Rapid Second Expansion Transition (Step B TILs directly move to Step D on day 7/8) | **STEP C** Priming First Expansion to Rapid Second Expansion Transition (Step B TILs directly move to Step D on day 7/8) |
| **STEP D** Rapid Second Expansion (TILs grown in growth media medium comprising IL-2, OKT-3, and antigen-presenting feeder cells; Days 10-11 scale up and add additional IL-2) | **STEP D** Rapid Second Expansion (TILs grown in growth media medium comprising IL-2, OKT-3, and 2X antigen-presenting feeder cells; Days 10-11 scale up and add additional IL-2) | **STEP D** Rapid Second Expansion (TILs grown in growth media medium comprising IL-2, OKT-3, and 2X antigen-presenting feeder cells; Days 10-11 scale up and add additional IL-2) |
| **STEP E** Harvest TILS from Step D | **STEP E** Harvest TILS from Step D | **STEP E** Harvest TILS from Step D |
| **STEP F** Final Formulation and/or Transfer to Infusion Bag (optionally cryopreserve) | **STEP F** Final Formulation and/or Transfer to Infusion Bag (optionally cryopreserve) | **STEP F** Final Formulation and/or Transfer to Infusion Bag (optionally cryopreserve) |

FIG. 1C

| Tumor ID | L4054 | | L4055 | | M1085T | |
|---|---|---|---|---|---|---|
| Process | Gen 2 | Gen 3 | Gen 2 | Gen 3 | Gen 2 | Gen 3 |
| # Fragments | 21 | 21 | 24 | 24 | 16 | 16 |

| Tumor ID | L4054 | | L4055 | | M1085T | |
|---|---|---|---|---|---|---|
| Process | Gen 2 | Gen 3 | Gen 2 | Gen 3 | Gen 2 | Gen 3 |
| # Fragments | 21 | 21 | 24 | 24 | 16 | 16 |

A
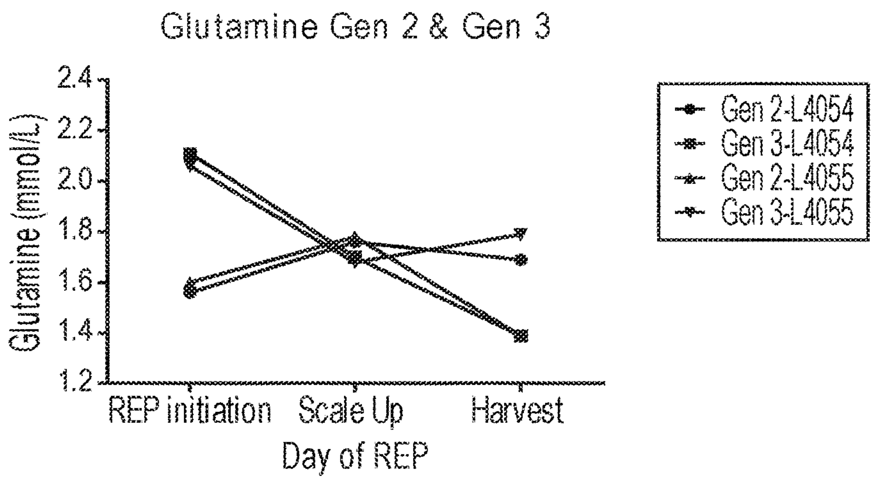
B
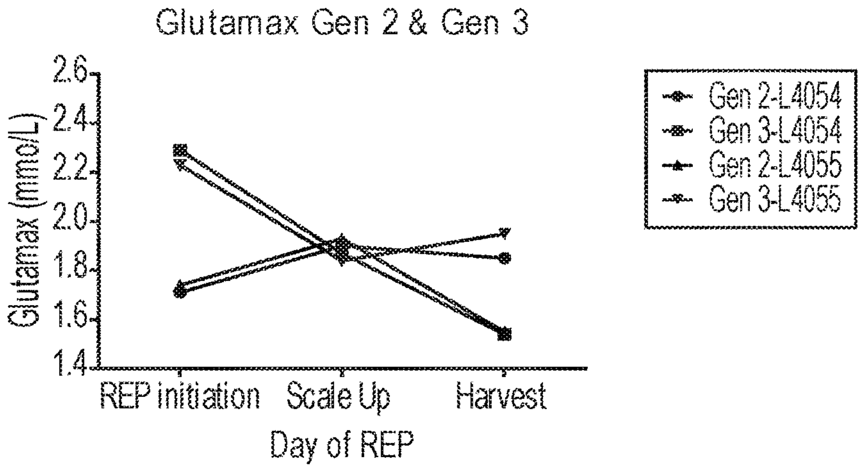
FIG. 10

C

| # uCDR3 (% Overlap) | All uCDR3's | | Top 80% uCDR3's | |
|---|---|---|---|---|
| | Gen 2 | Gen 3 | Gen 2 | Gen 3 |
| Gen 2-L4054 | 8915 | 4355 (48.85%) | 205 | 199 (97.07%) |
| Gen 3-L4054 | - | 18130 | - | 223 |

- 199 sequences are shared between Gen 3 and Gen 2 final product, corresponding to 97.07% of top 80% of unique CDR3 sequences from Gen 2 shared with Gen 3 final product.

| # uCDR3 (% Overlap) | All uCDR3's | | Top 80% uCDR3's | |
|---|---|---|---|---|
| | Gen 2 | Gen 3 | Gen 2 | Gen 3 |
| Gen 2-L4055 | 12996 | 6599 (50.77%) | 1843 | 1833 (99.45%) |
| Gen 3-L4055 | - | 27246 | - | 2616 |

- 1833 sequences are shared between Gen 3 and Gen 2 final product, corresponding to 99.45% of top 80% of unique CDR3 sequences from Gen 2 shared with Gen 3 final product.

Cell counts Day 7-Gen 3 REP initiation

| Volume (mL) | | Count 1 (cells/mL) | Count 2 (cells/mL) | Count 3 (cells/mL) | Average (cells/mL) | Total Cells Average*Volume |
|---|---|---|---|---|---|---|
| 188 | Total | 2.46E+05 | 2.28E+05 | 2.31E+05 | 2.35E+05 | 4.42E+07 |
| | Live | 2.37E+05 | 2.27E+05 | 2.26E+05 | 2.30E+05 | 4.32E+07 |
| | Dead | 9.26E+03 | 7.03E+02 | 4.63E+03 | 4.86E+03 | 9.14E+05 |
| | % Viability | 96.20% | 99.70% | 98.00% | 97.97% | |
| 188 | Total | 8.26E+04 | 8.00E+04 | 7.66E+04 | 7.97E+04 | 1.50E+07 |
| | Live | 7.60E+04 | 7.54E+04 | 6.89E+04 | 7.34E+04 | 1.38E+07 |
| | Dead | 6.61E+03 | 4.63E+03 | 7.73E+03 | 6.32E+03 | 1.19E+06 |
| | % Viability | 92.00% | 94.20% | 89.90% | 92.03% | |
| 200 | Total | 2.44E+04 | 4.20E+04 | 1.05E+04 | 2.56E+04 | 5.13E+06 |
| | Live | 1.74E+04 | 2.80E+04 | 7.03E+03 | 1.75E+04 | 3.50E+06 |
| | Dead | 7.03E+03 | 1.40E+04 | 3.48E+03 | 8.17E+03 | 1.63E+06 |
| | % Viability | 71.20% | 66.70% | 66.90% | 68.27% | |

FIG. 16

*Cell counts Day 11-Gen 2 REP initiation and Gen 3 Scale Up*

| ID | Volume (mL) | | Count 1 (cells/mL) | Count 3 (cells/mL) | Count 2 (cells/mL) | Average (cells/mL) | Total Cells Average*Volume |
|---|---|---|---|---|---|---|---|
| Gen 3 #L4054 First Round | 1000 | Total | 9.11E+05 | 1.01E+06 | 1.08E+06 | 1.00E+06 | 1.00E+09 |
| | | Live | 8.60E+05 | 9.34E+05 | 1.01E+06 | 9.35E+05 | 9.35E+08 |
| | | Dead | 5.09E+04 | 7.49E+04 | 6.74E+04 | 6.44E+04 | 6.44E+07 |
| | | % Viability | 94.40% | 92.60% | 93.70% | 93.57% | |
| Gen 3 #L4055 Second Round | 1000 | Total | 8.56E+05 | 9.04E+05 | 8.81E+05 | 8.80E+05 | 8.80E+08 |
| | | Live | 8.24E+05 | 8.67E+05 | 8.42E+05 | 8.44E+05 | 8.44E+08 |
| | | Dead | 8.17E+04 | 3.70E+04 | 3.87E+04 | 3.58E+04 | 3.58E+07 |
| | | % Viability | 96.30% | 95.90% | 95.60% | 95.93% | |
| Gen 3 #M1085T | 200 | Total | 2.32E+06 | 2.25E+06 | | 2.29E+06 | 4.57E+08 |
| | | Live | 1.68E+06 | 1.57E+06 | | 1.63E+06 | 3.25E+08 |
| | | Dead | 6.41E+05 | 6.79E+05 | | 6.60E+05 | 1.32E+08 |
| | | % Viability | 72.40% | 69.90% | | 71.15% | |
| Gen 2 #L4054 First Round | 142 | Total | 1.08E+06 | 9.84E+05 | 1.00E+06 | 1.02E+06 | 1.45E+08 |
| | | Live | 1.06E+06 | 9.71E+05 | 9.79E+05 | 1.00E+06 | 1.42E+08 |
| | | Dead | 2.05E+04 | 1.26E+04 | 2.12E+04 | 1.81E+04 | 2.57E+06 |
| | | % Viability | 98.10% | 98.70% | 97.90% | 98.23% | |
| Gen 2 #L4055 Second Round | 96 | Total | 2.93E+05 | 3.05E+05 | 2.64E+05 | 2.87E+05 | 2.76E+07 |
| | | Live | 2.88E+05 | 2.96E+05 | 2.55E+05 | 2.80E+05 | 2.68E+07 |
| | | Dead | 4.72E+03 | 9.14E+03 | 8.26E+03 | 7.37E+03 | 7.08E+05 |
| | | % Viability | 98.40% | 97.00% | 96.90% | 97.43% | |
| Gen 2 #M1085T | 200 | Total | 9.10E+04 | 5.60E+04 | | 7.35E+04 | 1.47E+07 |
| | | Live | 8.05E+04 | 4.21E+04 | | 6.13E+04 | 1.23E+07 |
| | | Dead | 1.04E+04 | 1.39E+04 | | 1.22E+04 | 2.43E+06 |
| | | % Viability | 88.50% | 75.20% | | 81.85% | |

FIG. 17

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3 #L4054 First Round -pre LOVO | 1243.1 | Total | 1.40E+07 | 1.46E+07 | | 1.43E+07 | 1.78E+10 |
| | | Live | 1.32E+07 | 1.35E+07 | | 1.34E+07 | 1.66E+10 |
| | | Dead | 8.47E+05 | 1.12E+06 | | 9.84E+05 | 1.22E+09 |
| | | % Viability | 94.00% | 92.40% | | 93.20% | |
| Gen 3 #L4054 First Round -post LOVO | 330 | Total | 6.35E+07 | 6.07E+07 | | 6.21E+07 | 2.05E+10 |
| | | Live | 5.72E+07 | 5.44E+07 | | 5.58E+07 | 1.84E+10 |
| | | Dead | 6.35E+06 | 6.27E+06 | | 6.31E+06 | 2.08E+09 |
| | | % Viability | 90.00% | 89.70% | | 89.85% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3 #L4055 Second Round -pre LOVO | 1032.6 | Total | 9.49E+06 | 1.05E+07 | | 1.00E+07 | 1.03E+10 |
| | | Live | 8.90E+06 | 9.79E+06 | | 9.35E+06 | 9.65E+09 |
| | | Dead | 5.85E+05 | 6.75E+05 | | 6.30E+05 | 6.51E+08 |
| | | % Viability | 93.80% | 93.60% | | 93.70% | |
| Gen 3 #L4055 Second Round -post LOVO | 330 | Total | 3.31E+07 | 2.82E+07 | 3.18E+07 | 3.07E+07 | 1.01E+10 |
| | | Live | 2.85E+07 | 2.46E+07 | 2.77E+07 | 2.66E+07 | 8.67E+09 |
| | | Dead | 4.56+06 | 3.61+06 | 4.12E+06 | 4.09E+06 | 1.35E+09 |
| | | % Viability | 86.20% | 87.20% | 87.10% | 86.70% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3 #M1085T pre-LOVO | 5000 | Total | 2.26E+06 | 2.64E+06 | | 2.45E+06 | 1.23E+10 |
| | | Live | 1.97E+06 | 2.31E+06 | | 2.14E+06 | 1.07E+10 |
| | | Dead | 2.85E+05 | 3.30E+05 | | 3.08E+05 | 1.54E+09 |
| | | % Viability | 87.40% | 87.50% | | 87.45% | |
| Gen 3 #M1085T post LOVO pre CS10 addition | 150 | Total | 6.27E+07 | 5.44E+07 | | 5.86E+07 | 8.78E+09 |
| | | Live | 5.50E+07 | 4.74E+07 | | 5.12E+07 | 7.68E+09 |
| | | Dead | 7.70E+06 | 6.96E+06 | | 7.33E+06 | 1.10E+09 |
| | | % Viability | 87.70% | 87.20% | | 87.45% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #L4054 First Round | 913 | Total | 3.53E+06 | 4.30E+06 | | 3.92E+06 | 3.57E+09 |
| | | Live | 3.35E+06 | 4.00E+06 | | 3.68E+06 | 3.36E+09 |
| | | Dead | 1.75E+05 | 3.03E+05 | | 2.39E+05 | 2.18E+08 |
| | | % Viability | 95.00% | 93.00% | | 94.00% | |
| Gen 2 #L4055 Second Round | 292 | Total | 1.29E+07 | 1.36E+07 | | 1.33E+07 | 3.87E+09 |
| | | Live | 1.16E+07 | 1.23E+07 | | 1.20E+07 | 3.49E+09 |
| | | Dead | 1.27E+06 | 1.23E+06 | | 1.25E+06 | 3.65E+08 |
| | | % Viability | 90.10% | 90.90% | | 90.50% | |
| Gen 2 #M1085T | 369 | Total | 6.75E+06 | 6.98E+06 | | 6.87E+06 | 2.53E+09 |
| | | Live | 5.22E+06 | 5.58E+06 | | 5.40E+06 | 1.99E+09 |
| | | Dead | 1.54E+06 | 1.40E+06 | | 1.47E+06 | 5.42E+08 |
| | | % Viability | 77.20% | 79.90% | | 78.55% | |

FIG. 18

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #L4054 First Round -pre LOVO | 1385.7 | Total | 3.55E+07 | 4.12E+07 | 4.03E+07 | 3.90E+07 | 5.40E+10 |
| | | Live | 3.26E+07 | 3.73E+07 | 3.67E+07 | 3.55E+07 | 4.92E+10 |
| | | Dead | 2.93E+06 | 3.87E+06 | 3.59E+06 | 3.46E+06 | 4.80E+09 |
| | | % Viability | 91.70% | 90.60% | 91.10% | 91.13% | |
| Gen 2 #L4054 First Round -post LOVO | 330 | Total | 1.70E+08 | 1.79E+08 | 1.68E+08 | 1.72E+08 | 5.69E+10 |
| | | Live | 1.49E+08 | 1.58E+08 | 1.48E+08 | 1.52E+08 | 5.01E+10 |
| | | Dead | 2.16E+07 | 2.04E+07 | 2.00E+07 | 2.07E+07 | 6.82E+09 |
| | | % Viability | 87.30% | 88.60% | 88.10% | 87.95% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #L4055 First Round -pre LOVO | 1968.2 | Total | 3.15E+07 | 2.51E+07 | 2.97E+07 | 2.88E+07 | 5.66E+10 |
| | | Live | 2.89E+07 | 2.25E+07 | 2.72E+07 | 2.62E+07 | 5.16E+10 |
| | | Dead | 2.57E+06 | 2.61E+06 | 2.52E+06 | 2.57E+06 | 5.05E+09 |
| | | % Viability | 91.80% | 89.60% | 91.50% | 90.97% | |
| Gen 2 #L4055 First Round -post LOVO | 330 | Total | 2.33E+08 | 1.89E+08 | 1.53E+08 | 1.92E+08 | 6.33E+10 |
| | | Live | 2.03E+08 | 1.66E+08 | 1.33E+08 | 1.67E+08 | 5.52E+10 |
| | | Dead | 3.00E+07 | 2.24E+07 | 1.94E+07 | 2.39E+07 | 7.90E+09 |
| | | % Viability | 87.10% | 88.10% | 87.30% | 87.50% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #M1085T-pre LOVO | N/S | Total | | | | #DIV/0! | #DIV/0! |
| | | Live | | | | #DIV/0! | #DIV/0! |
| | | Dead | | | | #DIV/0! | #DIV/0! |
| | | % Viability | | | | #DIV/0! | |
| Gen 2 #M1085T - post LOVO pre CS10 addition | 150 | Total | 8.51E+07 | 9.05E+07 | | 8.78E+07 | 1.32E+10 |
| | | Live | 7.33E+07 | 7.79E+07 | | 7.56E+07 | 1.13E+10 |
| | | Dead | 1.18E+07 | 1.26E+07 | | 1.22E+07 | 1.83E+09 |
| | | % Viability | 86.10% | 86.10% | | 86.10% | |

For L4054 Gen 2, post LOVO count was extrapolated to 4 flasks, because was the total number of the study. 1 flask was contaminated, and the extrapolation was done for total = 6.67e+10

FIG. 19

| | S1S2A8/Live \| Freq. of Parent (%) | S1S2A8/Live/CD14+ \| Freq. of Parent (%) | S1S2A8/Live/CD14-/CD3-NK \| Freq. of null (%) | S1S2A8/Live/CD14-/CD19 \| Freq. of null (%) | S1S2A8/Live/CD14-/TCRab \| Freq. of null (%) | S1S2A8/Live/CD14-/TCRab/CD4 \| Freq. of null (%) | S1S2A8/Live/CD14-/TCRab/CD4/CD27 \| Freq. of null (%) | S1S2A8/Live/CD14-/TCRab/CD4/CD28 \| Freq. of null (%) | S1S2A8/Live/CD14-/TCRab/CD4/CD56 \| Freq. of null (%) | S1S2A8/Live/CD14-/TCRab/CD4/CD57 \| Freq. of null (%) | S1S2A8/Live/CD14-/TCRab/CD4/Q1: CCR7-PE-A-, CD45RA-AF700-A+ \| Freq. of Parent (%) | S1S2A8/Live/CD14-/TCRab/CD4/Q2: CCR7-PE-A+, CD45RA-AF700-A+ \| Freq. of Parent (%) | S1S2A8/Live/CD14-/TCRab/CD4/Q3: CCR7-PE-A+, CD45RA-AF700-A- \| Freq. of Parent (%) | S1S2A8/Live/CD14-/TCRab/CD4/Q4: CCR7-PE-A-, CD45RA-AF700-A- \| Freq. of Parent (%) | S1S2A8/Live/CD14-/TCRab/CD4/Q5: CD62L-BV421-A-, CD45RA-AF700-A+ \| Freq. of Parent (%) | S1S2A8/Live/CD14-/TCRab/CD4/Q6: CD62L-BV421-A+, CD45RA-AF700-A+ \| Freq. of Parent (%) | S1S2A8/Live/CD14-/TCRab/CD4/Q7: CD62L-BV421-A+, CD45RA-AF700-A- \| Freq. of Parent (%) | S1S2A8/Live/CD14-/TCRab/CD4/Q8: CD62L-BV421-A-, CD45RA-AF700-A- \| Freq. of Parent (%) |
|---|---|---|---|---|---|---|---|---|---|---|---|---|---|---|---|---|---|---|
| | | | | | | | | | | | TEMRA | NAIVE | CM | EM | TEMRA | NAIVE | CM | EM |
| A1 Q812 1St.CS | 87.2 | 1.77E-03 | 0.66 | 0 | 99.9 | 60.6 | 3.36 | 80.1 | 0.06 | 5.34 | 0.25 | 0.073 | 3.37 | 96.3 | 0.056 | 0.032 | 21.1 | 78.8 |
| A2 Q812 2nd.CS | 73.5 | 0 | 0.12 | 0 | 99.7 | 83.1 | 7.94 | 82.6 | 0.14 | 6.18 | 0.16 | 0.047 | 2.39 | 97.4 | 0.036 | 0.014 | 8.3 | 91.6 |
| A3 Q813 1St.CS | 90.4 | 0 | 0.197 | 1.72e-03 | 99.8 | 48.1 | 4.5 | 48.9 | 0.18 | 4.02 | 0.2 | 0.059 | 2.29 | 97.5 | 0.059 | 0.049 | 30.7 | 69.2 |
| A4 Q813 2nd.CS | 72.1 | 2.56E-03 | 0.44 | 0.016 | 99.3 | 64.4 | 6.27 | 94 | 0.26 | 4.3 | 0.25 | 0.18 | 7.12 | 92.5 | 0.12 | 0.072 | 20.1 | 79.7 |
| A5 PBMC.CS | 93.7 | 6.07 | 11.6 | 6.12 | 79.9 | 41.1 | 35.6 | 40.4 | 0.041 | 0.31 | 0.61 | 36.1 | 16.2 | 46.9 | 11.4 | 23.1 | 16.4 | 49.1 |

d area was include to make the graph
TCRab+ are = CD3+

| S1S2A8/Live/CD14-/TCRab/CD8 \| Freq. of null (%) | S1S2A8/Live/CD14-/TCRab/CD8/CD27 \| Freq. of null (%) | S1S2A8/Live/CD14-/TCRab/CD8/CD28 \| Freq. of null (%) | S1S2A8/Live/CD14-/TCRab/CD8/CD56 \| Freq. of null (%) | S1S2A8/Live/CD14-/TCRab/CD8/CD57 \| Freq. of null (%) | S1S2A8/Live/CD14-/TCRab/CD8/Q1: CCR7-PE-A-, CD45RA-AF700-A+ \| Freq. of Parent (%) | S1S2A8/Live/CD14-/TCRab/CD8/Q2: CCR7-PE-A+, CD45RA-AF700-A+ \| Freq. of Parent (%) | S1S2A8/Live/CD14-/TCRab/CD8/Q3: CCR7-PE-A+, CD45RA-AF700-A- \| Freq. of Parent (%) | S1S2A8/Live/CD14-/TCRab/CD8/Q4: CCR7-PE-A-, CD45RA-AF700-A- \| Freq. of Parent (%) | S1S2A8/Live/CD14-/TCRab/CD8/Q5: CD62L-BV421-A-, CD45RA-AF700-A+ \| Freq. of Parent (%) | S1S2A8/Live/CD14-/TCRab/CD8/Q6: CD62L-BV421-A+, CD45RA-AF700-A+ \| Freq. of Parent (%) | S1S2A8/Live/CD14-/TCRab/CD8/Q7: CD62L-BV421-A+, CD45RA-AF700-A- \| Freq. of Parent (%) | S1S2A8/Live/CD14-/TCRab/CD8/Q8: CD62L-BV421-A-, CD45RA-AF700-A- \| Freq. of Parent (%) | S1S2A8/Live/CD14-/TCRgd \| Freq. of Parent (%) |
|---|---|---|---|---|---|---|---|---|---|---|---|---|---|
| | | | | | TEMRA | NAIVE | CM | EM | TEMRA | NAIVE | CM | EM | |
| 37.9 | 3.26 | 37.3 | 0.41 | 2.31 | 0.026 | 0 | 4.24 | 95.7 | 0.033 | 9.37E-03 | 14.1 | 85.9 | 0 |
| 16.1 | 1.68 | 15.6 | 0.67 | 0.17 | 0.042 | 0.014 | 4.76 | 95.2 | 0.071 | 0.014 | 5.24 | 94.7 | 0 |
| 49.2 | 4.83 | 48.5 | 0.71 | 1.53 | 0.056 | 6.97E-03 | 3.11 | 96.8 | 0.077 | 0.017 | 25.5 | 74.4 | 0 |
| 34.6 | 2.46 | 34 | 1.57 | 0.5 | 0.18 | 0.13 | 10.2 | 89.5 | 0.29 | 0.044 | 10.6 | 89.1 | 0 |
| 29.6 | 25.6 | 27.4 | 0.75 | 2.81 | 8.05 | 40.9 | 3.02 | 48 | 22.3 | 27.1 | 6.23 | 44.3 | 0 |

FIG. 20

| | CD3/CD4 | | | | | | |
|---|---|---|---|---|---|---|---|
| | CD38 | HLA-DR | CCR7- CD45RA+ | CCR7+CD45RA+ | CCR7+ CD45RA- | CCR7-CD45RA- | |
| GEN 3-Day 16-Harvest | | 42.4 | 95.2 | 4.96 | 0.7 | 1.22 | 93.1 |
| GEN 2-D22-Harvest | | 50.4 | 98 | 0.61 | 0.13 | 0.3 | 99 |

| CD3 | CD3/CD8 | | | | | | |
|---|---|---|---|---|---|---|---|
| CD8 | CD38 | HLA-DR | CCR7-CD45RA+ | CCR7+CD45RA+ | CCR7+CD45RA- | CCR7-CD45RA- | |
| | 77.6 | 83.2 | 90.3 | 20.5 | 0.013 | 0.06 | 79.5 |
| | 54.3 | 88 | 83.2 | 4.24 | 0.026 | 1.05 | 94.7 |

FIG. 21

| | | | | CD4 | | | | | | | | | | | |
|---|---|---|---|---|---|---|---|---|---|---|---|---|---|---|---|
| | CD3+ | | CD4+ | 2B4+ | BTLA+ | CD103+ | CD25+ | CD69+ | CD95+ | CXCR3+ | KLRG1+ | LAG3+ | PD1+ | TIGIT+ | TIM3+ |
| Gen 2-L4054 | | | | 0.61 | 99.50 | 1.05 | 14.80 | 43.20 | 99.40 | 52.90 | 2.65 | 5.36 | 81.20 | 88.40 | 78.60 |
| Gen 3-L4054 | | | | 1.11 | 99.50 | 2.28 | 21.70 | 45.40 | 99.70 | 56.90 | 8.06 | 5.07 | 76.70 | 74.10 | 79.30 |
| Gen 2-L4055 | | | | 1.61 | 98.60 | 1.58 | 23.10 | 51.10 | 99.80 | 63.30 | 3.86 | 15.30 | 77.60 | 86.00 | 79.50 |
| Gen 3-L4055 | | | | 3.57 | 99.30 | 2.61 | 54.40 | 57.00 | 99.90 | 48.00 | 8.02 | 10.80 | 61.40 | 47.50 | 84.60 |
| | | | | | | | | | | | | | | | |
| | | | | | | | | | | | | | | | |
| | | | | | | | | | | | | | | | |
| | | | | CD8 | | | | | | | | | | | |
| Gen 2-L4054 | | | CD8+ | 2B4+ | BTLA4+ | CD103+ | CD25+ | CD95+ | CD69+ | CXCR3+ | KLRG1+ | LAG3+ | PD1+ | TIGIT+ | TIM3+ |
| Gen 3-L4054 | | | | 35.20 | 99.50 | 74.90 | 11.80 | 99.60 | 58.30 | 99.10 | 8.03 | 33.10 | 80.60 | 99.10 | 88.30 |
| Gen 2-L4055 | | | | 45.50 | 99.60 | 62.40 | 12.10 | 99.90 | 54.00 | 99.30 | 13.40 | 22.10 | 64.90 | 98.50 | 87.50 |
| Gen 3-L4055 | | | | 40.60 | 98.20 | 19.50 | 32.00 | 99.70 | 75.50 | 96.80 | 22.80 | 27.40 | 28.10 | 92.30 | 75.10 |
| | | | | 62.80 | 99.20 | 29.20 | 45.50 | 99.70 | 58.80 | 99.60 | 13.10 | 16.60 | 34.10 | 71.70 | 63.60 |

FIG. 22

| | 1 | 2 | 3 | 4 | 5 | 6 | 7 | 8 | 9 | 10 | 11 | 12 | |
|---|---|---|---|---|---|---|---|---|---|---|---|---|---|
| A | STD1 | STD1 | STD1 | TIL- Gen 2-stimulated | TIL- Gen 2-stimulated | TIL- Gen 2-stimulated | TIL- Gen 2-Un-stimulated | TIL- Gen 2-Un-stimulated | TIL- Gen 2-Un-stimulated | MC-Stimulated xG2 | MC-Stimulated xG2 | MC-Stimulated xG2 | Well ID |
| | 1000 | 1000 | 1000 | 3 | 3 | 3 | 3 | 3 | 3 | 3 | 3 | 3 | Conc/Dil |
| B | STD2 | STD2 | STD2 | TIL- Gen 2-stimulated | TIL- Gen 2-stimulated | TIL- Gen 2-stimulated | TIL- Gen 2-Un-stimulated | TIL- Gen 2-Un-stimulated | TIL- Gen 2-Un-stimulated | MC-Stimulated xG2 | MC-Stimulated xG2 | MC-Stimulated xG2 | Well ID |
| | 500 | 500 | 500 | 9 | 9 | 9 | 9 | 9 | 9 | 9 | 9 | 9 | Conc/Dil |
| C | STD3 | STD3 | STD3 | TIL- Gen 2-stimulated | TIL- Gen 2-stimulated | TIL- Gen 2-stimulated | TIL- Gen 2-Un-stimulated | TIL- Gen 2-Un-stimulated | TIL- Gen 2-Un-stimulated | MC-Unstimulated xG2 | MC-Unstimulated xG2 | MC-Unstimulated xG2 | Well ID |
| | 250 | 250 | 250 | 27 | 27 | 27 | 27 | 27 | 27 | 3 | 3 | 3 | Conc/Dil |
| D | STD4 | STD4 | STD4 | TIL- Gen 2-stimulated | TIL- Gen 2-stimulated | TIL- Gen 2-stimulated | TIL- Gen 2-Un-stimulated | TIL- Gen 2-Un-stimulated | TIL- Gen 2-Un-stimulated | MC-Unstimulated xG2 | MC-Unstimulated xG2 | MC-Unstimulated xG2 | Well ID |
| | 125 | 125 | 125 | 81 | 81 | 81 | 81 | 81 | 81 | 9 | 9 | 9 | Conc/Dil |
| E | STD5 | STD5 | STD5 | TIL- Gen 3-stimulated | TIL- Gen 3-stimulated | TIL- Gen 3-stimulated | TIL- Gen 3-Un-stimulated | TIL- Gen 3-Un-stimulated | TIL- Gen 3-Un-stimulated | MC-Stimulated xG3 | MC-Stimulated xG3 | MC-Stimulated xG3 | Well ID |
| | 62.5 | 62.5 | 62.5 | 3 | 3 | 3 | 3 | 3 | 3 | 3 | 3 | 3 | Conc/Dil |
| F | STD6 | STD6 | STD6 | TIL- Gen 3-stimulated | TIL- Gen 3-stimulated | TIL- Gen 3-stimulated | TIL- Gen 3-Un-stimulated | TIL- Gen 3-Un-stimulated | TIL- Gen 3-Un-stimulated | MC-Stimulated xG3 | MC-Stimulated xG3 | MC-Stimulated xG3 | Well ID |
| | 31.3 | 31.3 | 31.3 | 9 | 9 | 9 | 9 | 9 | 9 | 9 | 9 | 9 | Conc/Dil |
| G | STD7 | STD7 | STD7 | TIL- Gen 3-stimulated | TIL- Gen 3-stimulated | TIL- Gen 3-stimulated | TIL- Gen 3-Un-stimulated | TIL- Gen 3-Un-stimulated | TIL- Gen 3-Un-stimulated | MC-Unstimulated xG3 | MC-Unstimulated xG3 | MC-Unstimulated xG3 | Well ID |
| | 15.6 | 15.6 | 15.6 | 27 | 27 | 27 | 27 | 27 | 27 | 3 | 3 | 3 | Conc/Dil |
| H | STD8 | STD8 | STD8 | TIL- Gen 3-stimulated | TIL- Gen 3-stimulated | TIL- Gen 3-stimulated | TIL- Gen 3-Un-stimulated | TIL- Gen 3-Un-stimulated | TIL- Gen 3-Un-stimulated | MC-Unstimulated xG3 | MC-Unstimulated xG3 | MC-Unstimulated xG3 | Well ID |
| | 0 | 0 | 0 | 81 | 81 | 81 | 81 | 81 | 81 | 9 | 9 | 9 | Conc/Dil |

22.6
22.6

FIG. 23A

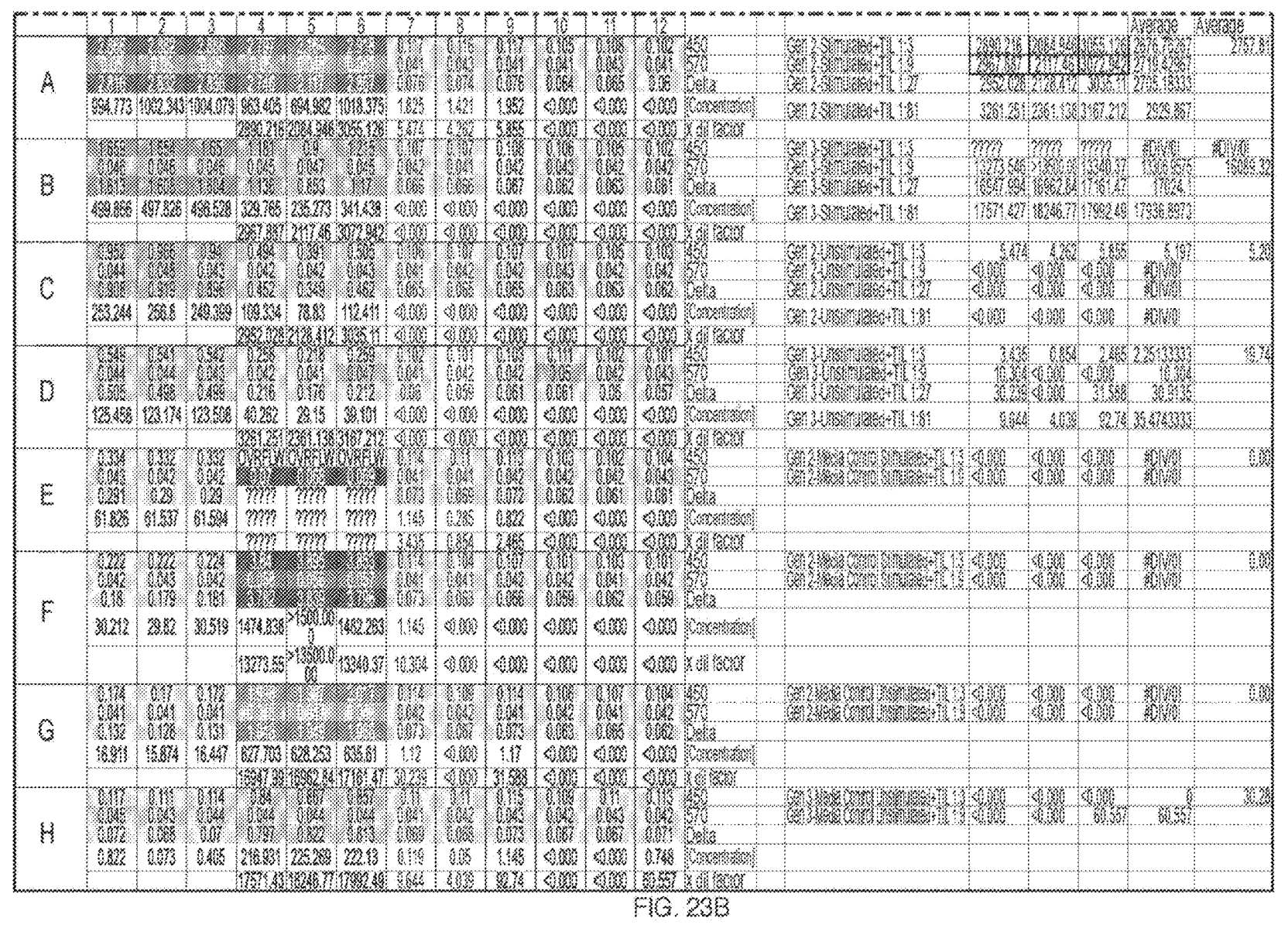

| | 1 | 2 | 3 | 4 | 5 | 6 | 7 | 8 | 9 | 10 | 11 | 12 | | | | | | Average | Average |
|---|---|---|---|---|---|---|---|---|---|---|---|---|---|---|---|---|---|---|---|
| A | [illegible] | [illegible] | [illegible] | [illegible] | [illegible] | [illegible] | 0.117 | 0.116 | 0.117 | 0.105 | 0.108 | 0.102 | 450 | Gen 2-Stimulated+TIL 1:3 | 2890.216 | 2084.946 | 3055.126 | 2676.7627 | 2757.81 |
| | [illegible] | [illegible] | [illegible] | [illegible] | [illegible] | [illegible] | 0.041 | 0.043 | 0.041 | 0.041 | 0.043 | 0.041 | 570 | Gen 2-Stimulated+TIL 1:9 | 2967.887 | 2117.46 | 3072.942 | 2719.4297 | |
| | [illegible] | [illegible] | [illegible] | [illegible] | [illegible] | [illegible] | 0.076 | 0.074 | 0.076 | 0.064 | 0.065 | 0.06 | Delta | Gen 2-Stimulated+TIL 1:27 | 2952.028 | 2128.412 | 3035.11 | 2705.1833 | |
| | 994.773 | 1062.343 | 1004.079 | 963.405 | 694.982 | 1018.375 | 1.825 | 1.421 | 1.952 | <0.000 | <0.000 | <0.000 | [Concentration] | Gen 2-Stimulated+TIL 1:81 | 3261.251 | 2361.138 | 3167.212 | 2929.867 | |
| | | | | 2890.216 | 2084.946 | 3055.126 | 5.474 | 4.262 | 5.855 | <0.000 | <0.000 | <0.000 | X dil factor | | | | | | |
| B | 1.659 | 1.654 | 1.65 | 1.181 | 0.9 | 1.235 | 0.107 | 0.107 | 0.108 | 0.106 | 0.105 | 0.102 | 450 | Gen 3-Stimulated+TIL 1:3 | ????? | ????? | ????? | #DIV/0! | #DIV/0! |
| | 0.046 | 0.046 | 0.046 | 0.045 | 0.047 | 0.045 | 0.042 | 0.041 | 0.042 | 0.045 | 0.042 | 0.042 | 570 | Gen 3-Stimulated+TIL 1:9 | 13273.546 | >13500.00 | 13340.37 | 13306.9575 | 16089.32 |
| | 1.613 | 1.608 | 1.604 | 1.136 | 0.853 | 1.187 | 0.066 | 0.066 | 0.067 | 0.062 | 0.063 | 0.061 | Delta | Gen 3-Stimulated+TIL 1:27 | 16947.994 | 16962.84 | 17161.47 | 17024.1 | |
| | 499.866 | 497.826 | 498.528 | 329.765 | 235.273 | 341.438 | <0.000 | <0.000 | <0.000 | <0.000 | <0.000 | <0.000 | [Concentration] | Gen 3-Stimulated+TIL 1:81 | 17571.427 | 18246.77 | 17992.49 | 17936.8973 | |
| | | | | 2967.887 | 2117.46 | 3072.942 | <0.000 | <0.000 | <0.000 | <0.000 | <0.000 | <0.000 | X dil factor | | | | | | |
| C | 0.952 | 0.955 | 0.94 | 0.494 | 0.391 | 0.505 | 0.106 | 0.107 | 0.107 | 0.107 | 0.105 | 0.103 | 450 | Gen 2-Unstimulated+TIL 1:3 | 5.474 | 4.262 | 5.855 | 5.197 | 5.20 |
| | 0.044 | 0.046 | 0.043 | 0.042 | 0.042 | 0.043 | 0.041 | 0.042 | 0.042 | 0.043 | 0.042 | 0.042 | 570 | Gen 2-Unstimulated+TIL 1:9 | <0.000 | <0.000 | <0.000 | #DIV/0! | |
| | 0.908 | 0.919 | 0.896 | 0.452 | 0.349 | 0.462 | 0.065 | 0.065 | 0.065 | 0.063 | 0.063 | 0.062 | Delta | Gen 2-Unstimulated+TIL 1:27 | <0.000 | <0.000 | <0.000 | #DIV/0! | |
| | 253.244 | 256.8 | 249.369 | 109.334 | 78.83 | 112.411 | <0.000 | <0.000 | <0.000 | <0.000 | <0.000 | <0.000 | [Concentration] | Gen 2-Unstimulated+TIL 1:81 | <0.000 | <0.000 | <0.000 | #DIV/0! | |
| | | | | 2952.028 | 2128.412 | 3035.11 | <0.000 | <0.000 | <0.000 | <0.000 | <0.000 | <0.000 | X dil factor | | | | | | |
| D | 0.548 | 0.541 | 0.542 | 0.258 | 0.218 | 0.259 | 0.102 | 0.101 | 0.103 | 0.111 | 0.102 | 0.101 | 450 | Gen 3-Unstimulated+TIL 1:3 | 3.436 | 0.854 | 2.465 | 2.2513333 | 18.74 |
| | 0.044 | 0.044 | 0.043 | 0.042 | 0.041 | 0.047 | 0.041 | 0.042 | 0.042 | 0.05 | 0.042 | 0.043 | 570 | Gen 3-Unstimulated+TIL 1:9 | 10.304 | <0.000 | <0.000 | 10.304 | |
| | 0.505 | 0.498 | 0.499 | 0.216 | 0.176 | 0.212 | 0.06 | 0.059 | 0.061 | 0.061 | 0.06 | 0.057 | Delta | Gen 3-Unstimulated+TIL 1:27 | 30.239 | <0.000 | 31.588 | 30.9135 | |
| | 125.458 | 123.174 | 123.508 | 40.262 | 29.15 | 39.101 | <0.000 | <0.000 | <0.000 | <0.000 | <0.000 | <0.000 | [Concentration] | Gen 3-Unstimulated+TIL 1:81 | 9.644 | 4.039 | 92.74 | 35.474333 | |
| | | | | 3261.251 | 2361.138 | 3167.212 | <0.000 | <0.000 | <0.000 | <0.000 | <0.000 | <0.000 | X dil factor | | | | | | |
| E | 0.334 | 0.332 | 0.332 | OVRFLW | OVRFLW | OVRFLW | 0.114 | 0.11 | 0.115 | 0.103 | 0.102 | 0.104 | 450 | Gen 2-Media Control Stimulated+TIL 1:3 | <0.000 | <0.000 | <0.000 | #DIV/0! | 0.00 |
| | 0.043 | 0.042 | 0.042 | [illegible] | [illegible] | [illegible] | 0.041 | 0.041 | 0.042 | 0.042 | 0.042 | 0.043 | 570 | Gen 2-Media Control Stimulated+TIL 1:9 | <0.000 | <0.000 | <0.000 | #DIV/0! | |
| | 0.291 | 0.29 | 0.29 | ????? | ????? | ????? | 0.073 | 0.069 | 0.072 | 0.062 | 0.061 | 0.061 | Delta | | | | | | |
| | 61.826 | 61.537 | 61.594 | ????? | ????? | ????? | 1.145 | 0.285 | 0.822 | <0.000 | <0.000 | <0.000 | [Concentration] | | | | | | |
| | | | | ????? | ????? | ????? | 3.435 | 0.854 | 2.465 | <0.000 | <0.000 | <0.000 | X dil factor | | | | | | |
| F | 0.222 | 0.222 | 0.224 | [illegible] | [illegible] | [illegible] | 0.114 | 0.104 | 0.107 | 0.101 | 0.103 | 0.101 | 450 | Gen 2-Media Control Stimulated+TIL 1:3 | <0.000 | <0.000 | <0.000 | #DIV/0! | 0.00 |
| | 0.042 | 0.043 | 0.042 | [illegible] | [illegible] | [illegible] | 0.041 | 0.041 | 0.042 | 0.042 | 0.041 | 0.042 | 570 | Gen 2-Media Control Stimulated+TIL 1:9 | <0.000 | <0.000 | <0.000 | #DIV/0! | |
| | 0.18 | 0.179 | 0.181 | [illegible] | [illegible] | [illegible] | 0.073 | 0.063 | 0.066 | 0.059 | 0.062 | 0.059 | Delta | | | | | | |
| | 30.212 | 29.82 | 30.519 | 1474.838 | >1500.000 | 1482.263 | 1.145 | <0.000 | <0.000 | <0.000 | <0.000 | <0.000 | [Concentration] | | | | | | |
| | | | | 13273.55 | >13500.000 | 13340.37 | 10.304 | <0.000 | <0.000 | <0.000 | <0.000 | <0.000 | X dil factor | | | | | | |
| G | 0.174 | 0.17 | 0.172 | [illegible] | [illegible] | [illegible] | 0.114 | 0.108 | 0.114 | 0.108 | 0.107 | 0.104 | 450 | Gen 2-Media Control Unstimulated+TIL 1:3 | <0.000 | <0.000 | <0.000 | #DIV/0! | 0.00 |
| | 0.041 | 0.041 | 0.041 | [illegible] | [illegible] | [illegible] | 0.042 | 0.042 | 0.041 | 0.042 | 0.041 | 0.042 | 570 | Gen 2-Media Control Unstimulated+TIL 1:9 | <0.000 | <0.000 | <0.000 | #DIV/0! | |
| | 0.132 | 0.128 | 0.131 | [illegible] | [illegible] | [illegible] | 0.073 | 0.067 | 0.073 | 0.063 | 0.066 | 0.062 | Delta | | | | | | |
| | 16.911 | 15.874 | 16.447 | 627.703 | 628.253 | 635.81 | 1.12 | <0.000 | 1.17 | <0.000 | <0.000 | <0.000 | [Concentration] | | | | | | |
| | | | | 16947.99 | 16962.84 | 17161.47 | 30.239 | <0.000 | 31.588 | <0.000 | <0.000 | <0.000 | X dil factor | | | | | | |
| H | 0.117 | 0.111 | 0.114 | 0.84 | 0.867 | 0.857 | 0.11 | 0.11 | 0.115 | 0.109 | 0.11 | 0.113 | 450 | Gen 3-Media Control Unstimulated+TIL 1:3 | <0.000 | <0.000 | <0.000 | 0 | 30.28 |
| | 0.045 | 0.043 | 0.044 | 0.044 | 0.044 | 0.044 | 0.041 | 0.042 | 0.043 | 0.042 | 0.043 | 0.042 | 570 | Gen 3-Media Control Unstimulated+TIL 1:9 | <0.000 | <0.000 | 60.557 | 60.557 | |
| | 0.072 | 0.068 | 0.07 | 0.797 | 0.822 | 0.813 | 0.069 | 0.068 | 0.073 | 0.067 | 0.067 | 0.071 | Delta | | | | | | |
| | 0.822 | 0.873 | 0.405 | 216.931 | 225.269 | 222.13 | 0.119 | 0.05 | 1.146 | <0.000 | <0.000 | 0.748 | [Concentration] | | | | | | |
| | | | | 17571.43 | 18246.77 | 17992.49 | 9.644 | 4.039 | 92.74 | <0.000 | <0.000 | 60.557 | X dil factor | | | | | | |

FIG. 23B

| | 1 | 2 | 3 | 4 | 5 | 6 | 7 | 8 | 9 | 10 | 11 | 12 | |
|---|---|---|---|---|---|---|---|---|---|---|---|---|---|
| A | STD1 | STD1 | STD1 | TIL- Gen 2- stimulated | TIL- Gen 2- stimulated | TIL- Gen 2- stimulated | TIL- Gen 2-Un- stimulated | TIL- Gen 2-Un- stimulated | TIL- Gen 2-Un- stimulated | MC- Stimulate d xG2 | MC- Stimulate d xG2 | MC- Stimulate d xG2 | Well ID |
| | 1000 | 1000 | 1000 | 3 | 3 | 3 | 3 | 3 | 3 | 3 | 3 | 3 | Conc/Dil |
| B | STD2 | STD2 | STD2 | TIL- Gen 2- stimulated | TIL- Gen 2- stimulated | TIL- Gen 2- stimulated | TIL- Gen 2-Un stimulated | TIL- Gen 2-Un stimulated | TIL- Gen 2-Un stimulated | MC- Stimulate d xG2 | MC- Stimulate d xG2 | MC- Stimulate d xG2 | Well ID |
| | 500 | 500 | 500 | 9 | 9 | 9 | 9 | 9 | 9 | 9 | 9 | 9 | Conc/Dil |
| C | STD3 | STD3 | STD3 | TIL- Gen 2- stimulated | TIL- Gen 2- stimulated | TIL- Gen 2- stimulated | TIL- Gen 2-Un- stimulated | TIL- Gen 2-Un- stimulated | TIL- Gen 2-Un- stimulated | MC- Unstimula ted xG2 | MC- Unstimula ted xG2 | MC- Unstimula ted xG2 | Well ID |
| | 250 | 250 | 250 | 27 | 27 | 27 | 27 | 27 | 27 | 3 | 3 | 3 | Conc/Dil |
| D | STD4 | STD4 | STD4 | TIL- Gen 2- stimulated | TIL- Gen 2- stimulated | TIL- Gen 2- stimulated | TIL- Gen 2-Un stimulated | TIL- Gen 2-Un stimulated | TIL- Gen 2-Un stimulated | MC- Unstimula ted xG2 | MC- Unstimula ted xG2 | MC- Unstimula ted xG2 | Well ID |
| | 125 | 125 | 125 | 81 | 81 | 81 | 81 | 81 | 81 | 9 | 9 | 9 | Conc/Dil |
| E | STD5 | STD5 | STD5 | TIL- Gen 3- stimulated | TIL- Gen 3- stimulated | TIL- Gen 3- stimulated | TIL- Gen 3-Un- stimulated | TIL- Gen 3-Un- stimulated | TIL- Gen 3-Un- stimulated | MC- Stimulate d xG3 | MC- Stimulate d xG3 | MC- Stimulate d xG3 | Well ID |
| | 62.5 | 62.5 | 62.5 | 3 | 3 | 3 | 3 | 3 | 3 | 3 | 3 | 3 | Conc/Dil |
| F | STD6 | STD6 | STD6 | TIL- Gen 3- stimulated | TIL- Gen 3- stimulated | TIL- Gen 3- stimulated | TIL- Gen 3-Un stimulated | TIL- Gen 3-Un stimulated | TIL- Gen 3-Un stimulated | MC- Stimulate d xG3 | MC- Stimulate d xG3 | MC- Stimulate d xG3 | Well ID |
| | 31.3 | 31.3 | 31.3 | 9 | 9 | 9 | 9 | 9 | 9 | 9 | 9 | 9 | Conc/Dil |
| G | STD7 | STD7 | STD7 | TIL- Gen 3- stimulated | TIL- Gen 3- stimulated | TIL- Gen 3- stimulated | TIL- Gen 3-Un- stimulated | TIL- Gen 3-Un- stimulated | TIL- Gen 3-Un- stimulated | MC- Unstimula ted xG3 | MC- Unstimula ted xG3 | MC- Unstimula ted xG3 | Well ID |
| | 15.6 | 15.6 | 15.6 | 27 | 27 | 27 | 27 | 27 | 27 | 3 | 3 | 3 | Conc/Dil |
| H | STD8 | STD8 | STD8 | TIL- Gen 3- stimulated | TIL- Gen 3- stimulated | TIL- Gen 3- stimulated | TIL- Gen 3-Un stimulated | TIL- Gen 3-Un stimulated | TIL- Gen 3-Un stimulated | MC- Unstimula ted xG3 | MC- Unstimula ted xG3 | MC- Unstimula ted xG3 | Well ID |
| | 0 | 0 | 0 | 81 | 81 | 81 | 81 | 81 | 81 | 9 | 9 | 9 | Conc/Dil |

22.9
22.9

FIG. 24A

| | 1 | 2 | 3 | 4 | 5 | 6 | 7 | 8 | 9 | 10 | 11 | 12 | | | | | | Average | Average |
|---|---|---|---|---|---|---|---|---|---|---|---|---|---|---|---|---|---|---|---|
| A | [illegible] | [illegible] | [illegible] | [illegible] | [illegible] | [illegible] | 0.128 | 0.126 | 0.132 | 0.11 | 0.111 | 0.107 | 450 | Gen 2-Stimulated+TIL 1.3 | 3435.858 | 2933.14 | 2905.979 | 3091.659 | 3261.65 |
| | [illegible] | [illegible] | [illegible] | [illegible] | [illegible] | [illegible] | 0.041 | 0.041 | 0.042 | 0.042 | 0.041 | 0.042 | 570 | Gen 2-Stimulated+TIL 1.9 | 3676.262 | 3001.429 | 2926.474 | 3201.38833 | |
| | [illegible] | [illegible] | [illegible] | [illegible] | [illegible] | [illegible] | 0.087 | 0.085 | 0.09 | 0.069 | 0.069 | 0.065 | Delta | Gen 2-Stimulated+TIL 1.27 | 3471.282 | 3097.07 | 2994.844 | 3187.732 | |
| | 1001.719 | 986.223 | 1003.483 | 1145.286 | 977.713 | 968.66 | 2.922 | 2.418 | 3.712 | <0.000 | <0.000 | <0.000 | Concentration | Gen 2-Stimulated+TIL 1.81 | 3910.387 | 3552.941 | 3234.126 | 3565.818 | |
| | | | | 3435.858 | 2933.14 | 2905.979 | 8.766 | 7.254 | 11.136 | <0.000 | <0.000 | <0.000 | X dil factor | | | | | | |
| B | 1.668 | 1.635 | 1.669 | 1.411 | 1.199 | 1.177 | 0.119 | 0.118 | 0.126 | 0.112 | 0.112 | 0.114 | 450 | Gen 3-Stimulated+TIL 1.3 | ????? | ????? | ????? | #DIV/0! | #DIV/0! |
| | 0.047 | 0.046 | 0.047 | 0.046 | 0.045 | 0.047 | 0.041 | 0.042 | 0.044 | 0.042 | 0.041 | 0.042 | 570 | Gen 3-Stimulated+TIL 1.9 | 13183.826 | 13421.926 | 12822.143 | 13142.6313 | 15303.54 |
| | 1.622 | 1.589 | 1.622 | 1.365 | 1.154 | 1.13 | 0.078 | 0.076 | 0.082 | 0.07 | 0.07 | 0.072 | Delta | Gen 3-Stimulated+TIL 1.27 | 16231.22 | 16700.175 | 14586.268 | 15839.221 | |
| | 503.563 | 491.203 | 503.336 | 408.474 | 333.492 | 325.164 | 0.931 | 0.531 | 1.786 | <0.000 | <0.000 | <0.000 | Concentration | Gen 3-Stimulated+TIL 1.81 | 17140.679 | 17638.195 | 16007.402 | 16928.7867 | |
| | | | | 3676.262 | 3001.429 | 2926.474 | 8.383 | 4.779 | 16.076 | <0.000 | <0.000 | <0.000 | X dil factor | | | | | | |
| C | 0.974 | 0.957 | 0.939 | 0.576 | 0.528 | 0.518 | 0.115 | 0.116 | 0.125 | 0.111 | 0.114 | 0.115 | 450 | Gen 2-Unstimulated+TIL 1.3 | 8.766 | 7.254 | 11.136 | 9.052 | 27.10 |
| | 0.045 | 0.043 | 0.045 | 0.045 | 0.043 | 0.045 | 0.041 | 0.044 | 0.042 | 0.041 | 0.043 | 0.043 | 570 | Gen 2-Unstimulated+TIL 1.9 | 8.383 | 4.779 | 16.076 | 9.746 | |
| | 0.929 | 0.914 | 0.894 | 0.531 | 0.486 | 0.473 | 0.074 | 0.072 | 0.083 | 0.07 | 0.071 | 0.071 | Delta | Gen 2-Unstimulated+TIL 1.27 | 5.632 | <0.000 | 53.672 | 29.652 | |
| | 256.408 | 251.388 | 244.654 | 128.556 | 114.706 | 110.92 | 0.289 | <0.000 | 1.988 | <0.000 | <0.000 | <0.000 | Concentration | Gen 2-Unstimulated+TIL 1.81 | <0.000 | <0.000 | 59.939 | 59.939 | |
| | | | | 3471.282 | 3097.07 | 2994.844 | 5.632 | <0.000 | 53.672 | <0.000 | <0.000 | <0.000 | X dil factor | | | | | | |
| D | 0.577 | 0.551 | 0.56 | 0.301 | 0.288 | 0.27 | 0.115 | 0.11 | 0.119 | 0.111 | 0.112 | 0.11 | 450 | Gen 3-Unstimulated+TIL 1.3 | 19.738 | 13.255 | 20.614 | 17.869 | 43.28 |
| | 0.044 | 0.042 | 0.044 | 0.042 | 0.045 | 0.041 | 0.042 | 0.043 | 0.042 | 0.042 | 0.041 | 0.042 | 570 | Gen 3-Unstimulated+TIL 1.9 | 13.875 | 31.098 | 19.718 | 21.563 | |
| | 0.533 | 0.509 | 0.516 | 0.259 | 0.243 | 0.229 | 0.073 | 0.067 | 0.077 | 0.069 | 0.07 | 0.068 | Delta | Gen 3-Unstimulated+TIL 1.27 | 0.172 | <0.000 | 33.321 | 16.7465 | |
| | 128.057 | 121.737 | 123.677 | 48.276 | 43.863 | 39.927 | <0.000 | <0.000 | 0.74 | <0.000 | <0.000 | <0.000 | Concentration | Gen 3-Unstimulated+TIL 1.81 | 77.18 | 171.968 | 92.74 | 35.4743333 | |
| | | | | 3910.387 | 3552.941 | 3234.126 | <0.000 | <0.000 | 59.939 | <0.000 | <0.000 | <0.000 | X dil factor | | | | | | |
| E | 0.361 | 0.35 | 0.346 | OVRFLW | OVRFLW | OVRFLW | 0.143 | 0.135 | 0.145 | 0.115 | 0.112 | 0.11 | 450 | Gen 2-Media Control Stimulated+TIL 1.3 | <0.000 | <0.000 | <0.000 | #DIV/0! | 0.00 |
| | 0.042 | 0.042 | 0.042 | [illegible] | [illegible] | [illegible] | 0.041 | 0.042 | 0.042 | 0.041 | 0.043 | 0.041 | 570 | Gen 2-Media Control Stimulated+TIL 1.9 | <0.000 | <0.000 | <0.000 | #DIV/0! | |
| | 0.319 | 0.308 | 0.304 | ????? | ????? | ????? | 0.102 | 0.093 | 0.103 | 0.074 | 0.069 | 0.068 | Delta | | | | | | |
| | 65.323 | 62.385 | 61.049 | ????? | ????? | ????? | 6.579 | 4.418 | 6.871 | 0.076 | <0.000 | <0.000 | Concentration | | | | | | |
| | | | | ????? | ????? | ????? | 19.738 | 13.255 | 20.614 | 0.228 | <0.000 | <0.000 | X dil factor | | | | | | |
| F | 0.237 | 0.233 | 0.239 | [illegible] | [illegible] | [illegible] | 0.122 | 0.144 | 0.125 | 0.114 | 0.112 | 0.111 | 450 | Gen 2-Media Control Stimulated+TIL 1.3 | 0.228 | <0.000 | <0.000 | 0.228 | 0.11 |
| | 0.042 | 0.043 | 0.042 | [illegible] | [illegible] | [illegible] | 0.041 | [illegible] | 0.042 | 0.041 | 0.041 | 0.042 | 570 | Gen 2-Media Control Stimulated+TIL 1.9 | <0.000 | <0.000 | <0.000 | 0 | |
| | 0.195 | 0.19 | 0.197 | [illegible] | [illegible] | [illegible] | 0.081 | 0.089 | 0.084 | 0.073 | 0.071 | 0.069 | Delta | | | | | | |
| | 30.739 | 29.388 | 31.253 | 1464.87 | 1491.325 | 1424.683 | 1.542 | 3.456 | 2.191 | <0.000 | <0.000 | <0.000 | Concentration | | | | | | |
| | | | | 13183.83 | 13421.93 | 12822.14 | 13.875 | 31.098 | 19.718 | <0.000 | <0.000 | <0.000 | X dil factor | | | | | | |
| G | 0.182 | 0.173 | 0.183 | [illegible] | [illegible] | [illegible] | 0.115 | 0.115 | 0.121 | 0.114 | 0.111 | 0.114 | 450 | Gen 2-Media Control Unstimulated+TIL 1.3 | <0.000 | <0.000 | <0.000 | 0 | 0.00 |
| | 0.044 | 0.041 | 0.042 | [illegible] | [illegible] | [illegible] | 0.042 | 0.041 | 0.042 | 0.041 | 0.041 | 0.043 | 570 | Gen 2-Media Control Unstimulated+TIL 1.9 | <0.000 | <0.000 | <0.000 | 0 | |
| | 0.138 | 0.132 | 0.141 | [illegible] | [illegible] | [illegible] | 0.073 | 0.073 | 0.079 | 0.073 | 0.07 | 0.07 | Delta | | | | | | |
| | 15.598 | 14.006 | 16.321 | 601.156 | 618.525 | 540.232 | 0.006 | <0.000 | 1.234 | <0.000 | <0.000 | <0.000 | Concentration | | | | | | |
| | | | | 16231.22 | 16700.18 | 14586.27 | 0.172 | <0.000 | 33.321 | <0.000 | <0.000 | <0.000 | X dil factor | | | | | | |
| H | 0.121 | 0.117 | 0.122 | 0.837 | 0.857 | 0.794 | 0.119 | 0.125 | 0.123 | 0.119 | 0.12 | 0.112 | 450 | Gen 3-Media Control Unstimulated+TIL 1.3 | <0.000 | <0.000 | <0.000 | 0 | 1.53 |
| | 0.045 | 0.042 | 0.047 | 0.043 | 0.045 | 0.043 | 0.041 | 0.041 | 0.043 | 0.045 | 0.044 | 0.042 | 570 | Gen 3-Media Control Unstimulated+TIL 1.9 | 1.357 | 4.779 | <0.000 | 3.068 | |
| | 0.076 | 0.075 | 0.074 | 0.793 | 0.812 | 0.75 | 0.078 | 0.083 | 0.079 | 0.074 | 0.076 | 0.071 | Delta | | | | | | |
| | 0.635 | 0.408 | 0.17 | 211.613 | 217.755 | 197.622 | 0.953 | 2.123 | 1.236 | 0.161 | 0.591 | <0.000 | Concentration | | | | | | |
| | | | | 17140.68 | 17638.2 | 16007.4 | 77.18 | 171.968 | 101.73 | 1.357 | 4.779 | <0.000 | X dil factor | | | | | | |

FIG. 24B

| | 1 | 2 | 3 | 4 | 5 | 6 | 7 | 8 | 9 | 10 | 11 | 12 | |
|---|---|---|---|---|---|---|---|---|---|---|---|---|---|
| A | STD1 | STD1 | STD1 | 2A-BEAD+TIL | 2A-BEAD+TIL | 2A-BEAD+TIL | 2A-MC | 2A-MC | 2A-MC | 2A-Un-stimulated | 2A-Un-stimulated | 2A-Un-stimulated | Well ID |
| | 1000 | 1000 | 1000 | 3 | 3 | 3 | 3 | 3 | 3 | 3 | 3 | 3 | Conc/Dil |
| B | STD2 | STD2 | STD2 | 2A-BEAD+TIL | 2A-BEAD+TIL | 2A-BEAD+TIL | 2A-MC | 2A-MC | 2A-MC | 2A-Un-stimulated | 2A-Un-stimulated | 2A-Un-stimulated | Well ID |
| | 500 | 500 | 500 | 9 | 9 | 9 | 9 | 9 | 9 | 9 | 9 | 9 | Conc/Dil |
| C | STD3 | STD3 | STD3 | 2A-BEAD+TIL | 2A-BEAD+TIL | 2A-BEAD+TIL | 2A-MC | 2A-MC | 2A-MC | 2A-Un-stimulated | 2A-Un-stimulated | 2A-Un-stimulated | Well ID |
| | 250 | 250 | 250 | 27 | 27 | 27 | 27 | 27 | 27 | 27 | 27 | 27 | Conc/Dil |
| D | STD4 | STD4 | STD4 | 2A-BEAD+TIL | 2A-BEAD+TIL | 2A-BEAD+TIL | 2A-MC | 2A-MC | 2A-MC | 2A-Un-stimulated | 2A-Un-stimulated | 2A-Un-stimulated | Well ID |
| | 125 | 125 | 125 | 81 | 81 | 81 | 81 | 81 | 81 | 81 | 81 | 81 | Conc/Dil |
| E | STD5 | STD5 | STD5 | 2A-BEAD+TIL | 2A-BEAD+TIL | 2A-BEAD+TIL | 2B-Un-stimulated | 2B-Un-stimulated | 2B-Un-stimulated | 2B-MC | 2B-MC | 2B-MC | Well ID |
| | 62.5 | 62.5 | 62.5 | 3 | 3 | 3 | 3 | 3 | 3 | 3 | 3 | 3 | Conc/Dil |
| F | STD6 | STD6 | STD6 | 2A-BEAD+TIL | 2A-BEAD+TIL | 2A-BEAD+TIL | 2B-Un-stimulated | 2B-Un-stimulated | 2B-Un-stimulated | 2B-MC | 2B-MC | 2B-MC | Well ID |
| | 31.3 | 31.3 | 31.3 | 9 | 9 | 9 | 9 | 9 | 9 | 9 | 9 | 9 | Conc/Dil |
| G | STD7 | STD7 | STD7 | 2A-BEAD+TIL | 2A-BEAD+TIL | 2A-BEAD+TIL | 2B-Un-stimulated | 2B-Un-stimulated | 2B-Un-stimulated | 2B-MC | 2B-MC | 2B-MC | Well ID |
| | 15.6 | 15.6 | 15.6 | 27 | 27 | 27 | 27 | 27 | 27 | 27 | 27 | 27 | Conc/Dil |
| H | STD8 | STD8 | STD8 | 2A-BEAD+TIL | 2A-BEAD+TIL | 2A-BEAD+TIL | 2B-Un-stimulated | 2B-Un-stimulated | 2B-Un-stimulated | 2B-MC | 2B-MC | 2B-MC | Well ID |
| | 0 | 0 | 0 | 81 | 81 | 81 | 81 | 81 | 81 | 81 | 81 | 81 | Conc/Dil |

FIG. 25A

| | | 1 | 2 | 3 | 4 | 5 | 6 | 7 | 8 | 9 | 10 | 11 | 12 |
|---|---|---|---|---|---|---|---|---|---|---|---|---|---|
| A | 450 | [illegible] | [illegible] | [illegible] | [illegible] | [illegible] | [illegible] | 0.079 | 0.079 | 0.081 | 0.18 | 0.198 | 0.191 |
| | 570 | [illegible] | [illegible] | [illegible] | [illegible] | [illegible] | [illegible] | 0.042 | 0.042 | 0.043 | 0.042 | 0.043 | 0.042 |
| | Delta | [illegible] | [illegible] | [illegible] | [illegible] | [illegible] | [illegible] | 0.037 | 0.037 | 0.037 | 0.1339 | 0.156 | 0.149 |
| | Concentration | 951.965 | 1012.581 | 1035.454 | 1479.442 | >1500.000 | >1500.000 | 0.379 | 0.287 | 0.472 | 37.604 | 44.509 | 41.927 |
| | X dil factor | | | | 4438.326 | >4500.000 | >4500.000 | 1.137 | 0.861 | 1.417 | 112.812 | 133.527 | 125.78 |
| B | 450 | 1.221 | 1.22 | 1.252 | 1.265 | 1.361 | 1.352 | 0.077 | 0.077 | 0.077 | 0.109 | 0.115 | 0.114 |
| | 570 | 0.046 | 0.046 | 0.046 | 0.046 | 0.047 | 0.047 | 0.042 | 0.044 | 0.042 | 0.042 | 0.043 | 0.042 |
| | Delta | 1.175 | 1.174 | 1.206 | 1.219 | 1.314 | 1.304 | 0.035 | 0.033 | 0.035 | 0.067 | 0.072 | 0.072 |
| | Concentration | 496.244 | 485.812 | 511.027 | 517.353 | 563.806 | 558.817 | <0.000 | <0.000 | <0.000 | 10.74 | 12.837 | 12.584 |
| | X dil factor | | | | 4656.178 | 5074.253 | 5029.349 | <0.000 | <0.000 | <0.000 | 96.66 | 113.737 | 113.077 |
| C | 450 | 0.677 | 0.681 | 0.681 | 0.531 | 0.563 | 0.555 | 0.075 | 0.074 | 0.075 | 0.087 | 0.096 | 0.091 |
| | 570 | 0.043 | 0.044 | 0.044 | 0.044 | 0.045 | 0.043 | 0.042 | 0.042 | 0.042 | 0.042 | 0.045 | 0.042 |
| | Delta | 0.634 | 0.637 | 0.637 | 0.488 | 0.518 | 0.511 | 0.033 | 0.032 | 0.033 | 0.045 | 0.05 | 0.049 |
| | Concentration | 245.876 | 247.384 | 247.428 | 182.102 | 195.039 | 192.221 | <0.000 | <0.000 | <0.000 | 2.846 | 4.883 | 4.221 |
| | X dil factor | | | | 4916.763 | 5266.064 | 5189.965 | <0.000 | <0.000 | <0.000 | 76.848 | 131.834 | 113.974 |
| D | 450 | 0.406 | 0.405 | 0.407 | 0.251 | 0.257 | 0.25 | 0.075 | 0.075 | 0.077 | 0.082 | 0.081 | 0.084 |
| | 570 | 0.044 | 0.043 | 0.044 | 0.044 | 0.043 | 0.042 | 0.042 | 0.043 | 0.043 | 0.044 | 0.042 | 0.044 |
| | Delta | 0.363 | 0.362 | 0.363 | 0.207 | 0.214 | 0.208 | 0.033 | 0.032 | 0.035 | 0.039 | 0.039 | 0.04 |
| | Concentration | 128.798 | 128.379 | 128.798 | 84.814 | 67.463 | 65.085 | <0.000 | <0.000 | <0.000 | 0.885 | 1.614 | 1.438 |
| | X dil factor | | | | 5249.956 | 5464.506 | 5272.686 | <0.000 | <0.000 | <0.000 | 71.65 | 82.102 | 116.487 |
| E | 450 | 0.244 | 0.241 | 0.241 | OVRFLW | OVRFLW | OVRFLW | 0.35 | 0.356 | 0.275 | 0.078 | 0.079 | 0.079 |
| | 570 | 0.042 | 0.042 | 0.042 | [illegible] | [illegible] | [illegible] | 0.043 | 0.043 | 0.043 | 0.042 | 0.042 | 0.043 |
| | Delta | 0.201 | 0.199 | 0.199 | ????? | ????? | ????? | 0.307 | 0.314 | 0.232 | 0.036 | 0.038 | 0.036 |
| | Concentration | 65.323 | 61.483 | 61.533 | ????? | ????? | ????? | 105.745 | 108.313 | 74.922 | 0.079 | 0.079 | <0.000 |
| | X dil factor | | | | ????? | ????? | ????? | 317.235 | 324.939 | 224.765 | 0.237 | 0.237 | <0.000 |
| F | 450 | 0.166 | 0.165 | 0.161 | [illegible] | [illegible] | [illegible] | 0.165 | 0.17 | 0.146 | 0.078 | 0.079 | 0.078 |
| | 570 | 0.042 | 0.043 | 0.043 | [illegible] | [illegible] | [illegible] | 0.043 | 0.042 | 0.045 | 0.042 | 0.042 | 0.042 |
| | Delta | 0.124 | 0.122 | 0.119 | [illegible] | [illegible] | [illegible] | 0.123 | 0.128 | 0.101 | 0.036 | 0.037 | 0.036 |
| | Concentration | 31.998 | 31.384 | 30.079 | >1500.000 | 1346.731 | >1500.000 | 31.789 | 33.579 | 23.374 | 0.051 | 0.472 | <0.000 |
| | X dil factor | | | | >1500.000 | 1212.579 | >1500.000 | 285.917 | 302.211 | 210.37 | 0.457 | 4.25 | <0.000 |
| G | 450 | 0.122 | 0.119 | 0.117 | [illegible] | [illegible] | [illegible] | 0.102 | 0.097 | 0.092 | 0.072 | 0.072 | 0.07 |
| | 570 | 0.043 | 0.042 | 0.043 | [illegible] | [illegible] | [illegible] | 0.043 | 0.044 | 0.045 | 0.043 | 0.046 | 0.043 |
| | Delta | 0.079 | 0.076 | 0.074 | [illegible] | [illegible] | [illegible] | 0.059 | 0.054 | 0.046 | 0.029 | 0.026 | 0.027 |
| | Concentration | 14.966 | 14.181 | 13.334 | 566.107 | 482.193 | 603.959 | 7.605 | 5.971 | 3.462 | <0.000 | <0.000 | <0.000 |
| | X dil factor | | | | 15284.891 | 13019.2 | 16306.887 | 205.324 | 161.226 | 93.486 | <0.000 | <0.000 | <0.000 |
| H | 450 | 0.077 | 0.084 | 0.077 | 0.572 | 0.489 | 0.583 | 0.098 | 0.082 | 0.086 | 0.074 | 0.073 | 0.07 |
| | 570 | 0.042 | 0.042 | 0.042 | 0.046 | 0.045 | 0.046 | 0.048 | 0.043 | 0.043 | 0.043 | 0.043 | 0.043 |
| | Delta | 0.036 | 0.042 | 0.036 | 0.526 | 0.443 | 0.537 | 0.05 | 0.038 | 0.043 | 0.031 | 0.03 | 0.027 |
| | Concentration | <0.000 | 2.136 | 0.023 | 198.6 | 163.034 | 203.269 | 4.534 | 0.756 | 2.365 | <0.000 | <0.000 | <0.000 |
| | X dil factor | | | | 16086.64 | 13205.781 | 16467.237 | 367.254 | 61.271 | 186.868 | <0.000 | <0.000 | <0.000 |

| | | | | Average | Average |
|---|---|---|---|---|---|
| 2A-beads+TIL 1:3 | | | | | |
| 2A-beads+TIL 1:9 | 4656.178 | 5074.253 | 5029.349 | 4919.927 | 5124.412 |
| 2A-beads+TIL 1:27 | 4916.763 | 5266.064 | 5189.965 | 5124.264 | |
| 2A-beads+TIL 1:81 | 5249.956 | 5464.506 | 5272.686 | 5329.049 | |
| 2E-beads+TIL 1:3 | ????? | ????? | ????? | #DIV/0! | |
| 2E-beads+TIL 1:9 | | | | #DIV/0! | |
| 2E-beads+TIL 1:27 | 15284.891 | 13019.2 | 16306.887 | 14870.33 | 15061.77 |
| 2E-beads+TIL 1:81 | 16086.64 | 13205.781 | 16467.237 | 15253.21 | |
| 2A-Unstimulated+TIL 1:3 | 112.812 | 133.527 | 125.78 | 124.0397 | 107.374 |
| 2A-Unstimulated+TIL 1:9 | 96.66 | 113.737 | 113.077 | 107.8247 | |
| 2A-Unstimulated+TIL 1:27 | 76.848 | 131.834 | 113.974 | 107.552 | |
| 2A-Unstimulated+TIL 1:81 | 71.65 | 82.102 | 116.487 | 90.07967 | |
| 2E-Unstimulated+TIL 1:3 | 317.235 | 324.939 | 224.765 | 288.9797 | 226.1614 |
| 2E-Unstimulated+TIL 1:9 | 285.917 | 302.211 | 210.37 | 266.166 | |
| 2E-Unstimulated+TIL 1:27 | 205.324 | 161.226 | 93.486 | 153.3387 | |
| 2E-Unstimulated+TIL 1:81 | | | | | |
| 2A-Media Control 1:3 | 1.137 | 0.861 | 1.417 | 1.138333 | 1.138778 |
| 2A-Media Control 1:9 | | | | | |
| 2A-Media Control 1:27 | | | | | |
| 2A-Media Control 1:81 | | | | | |
| 2E-Media Control 1:3 | 0.237 | 0.853 | <0.000 | 0.595 | 1.47425 |
| 2E-Media Control 1:9 | 0.457 | 4.25 | <0.000 | 2.3535 | |
| 2E-Media Control 1:27 | | | | | |
| 2E-Media Control 1:81 | | | | | |

FIG. 25B

| | 1 | 2 | 3 | 4 | 5 | 6 | 7 | 8 | 9 | 10 | 11 | 12 | |
|---|---|---|---|---|---|---|---|---|---|---|---|---|---|
| A | STD1<br>2000 | STD1<br>2000 | STD1<br>2000 | Gen 3-D7<br>1ST RUN | Gen 3-D7<br>1ST RUN | Gen 3-D7<br>1ST RUN | Gen 3-D7<br>2ND RUN | Gen 3-D7<br>2ND RUN | Gen 3-D7<br>2ND RUN | | | | Well ID<br>Conc/Dil |
| B | STD2<br>1000 | STD2<br>1000 | STD2<br>1000 | Gen 3-<br>D11<br>1ST RUN | Gen 3-<br>D11<br>1ST RUN | Gen 3-<br>D11<br>1ST RUN | Gen 3-<br>D11<br>2ND RUN | Gen 3-<br>D11<br>2ND RUN | Gen 3-<br>D11<br>2ND RUN | | | | Well ID<br>Conc/Dil |
| C | STD3<br>500 | STD3<br>500 | STD3<br>500 | Gen 3-<br>D16<br>1ST RUN | Gen 3-<br>D16<br>1ST RUN | Gen 3-<br>D16<br>1ST RUN | Gen 3-<br>D16<br>2ND RUN | Gen 3-<br>D16<br>2ND RUN | Gen 3-<br>D16<br>2ND RUN | | | | Well ID<br>Conc/Dil |
| D | STD4<br>250 | STD4<br>250 | STD4<br>250 | Gen 2-<br>D11<br>1ST RUN | Gen 2-<br>D11<br>1ST RUN | Gen 2-<br>D11<br>1ST RUN | Gen 2-<br>D11<br>2ND RUN | Gen 2-<br>D11<br>2ND RUN | Gen 2-<br>D11<br>2ND RUN | | | | Well ID<br>Conc/Dil |
| E | STD5<br>125 | STD5<br>125 | STD5<br>125 | Gen 2-<br>D16<br>1ST RUN | Gen 2-<br>D16<br>1ST RUN | Gen 2-<br>D16<br>1ST RUN | Gen 2-<br>D16<br>2ND RUN | Gen 2-<br>D16<br>2ND RUN | Gen 2-<br>D16<br>2ND RUN | | | | Well ID<br>Conc/Dil |
| F | STD6<br>62.5 | STD6<br>62.5 | STD6<br>62.5 | Gen 2-<br>D22<br>1ST RUN | Gen 2-<br>D22<br>1ST RUN | Gen 2-<br>D22<br>1ST RUN | Gen 2-<br>D22<br>2ND RUN | Gen 2-<br>D22<br>2ND RUN | Gen 2-<br>D22<br>2ND RUN | | | | Well ID<br>Conc/Dil |
| G | STD7<br>31.3 | STD7<br>31.3 | STD7<br>31.3 | Empty | Empty | Empty | Empty | Empty | Empty | | | | Well ID<br>Conc/Dil |
| H | STD8<br>0 | STD8<br>0 | STD8<br>0 | Empty | Empty | Empty | Empty | Empty | Empty | | | | Well ID<br>Conc/Dil |
| 22 | | | | | | | | | | | | | |
| 22 | | | | | | | | | | | | | |

FIG. 26A

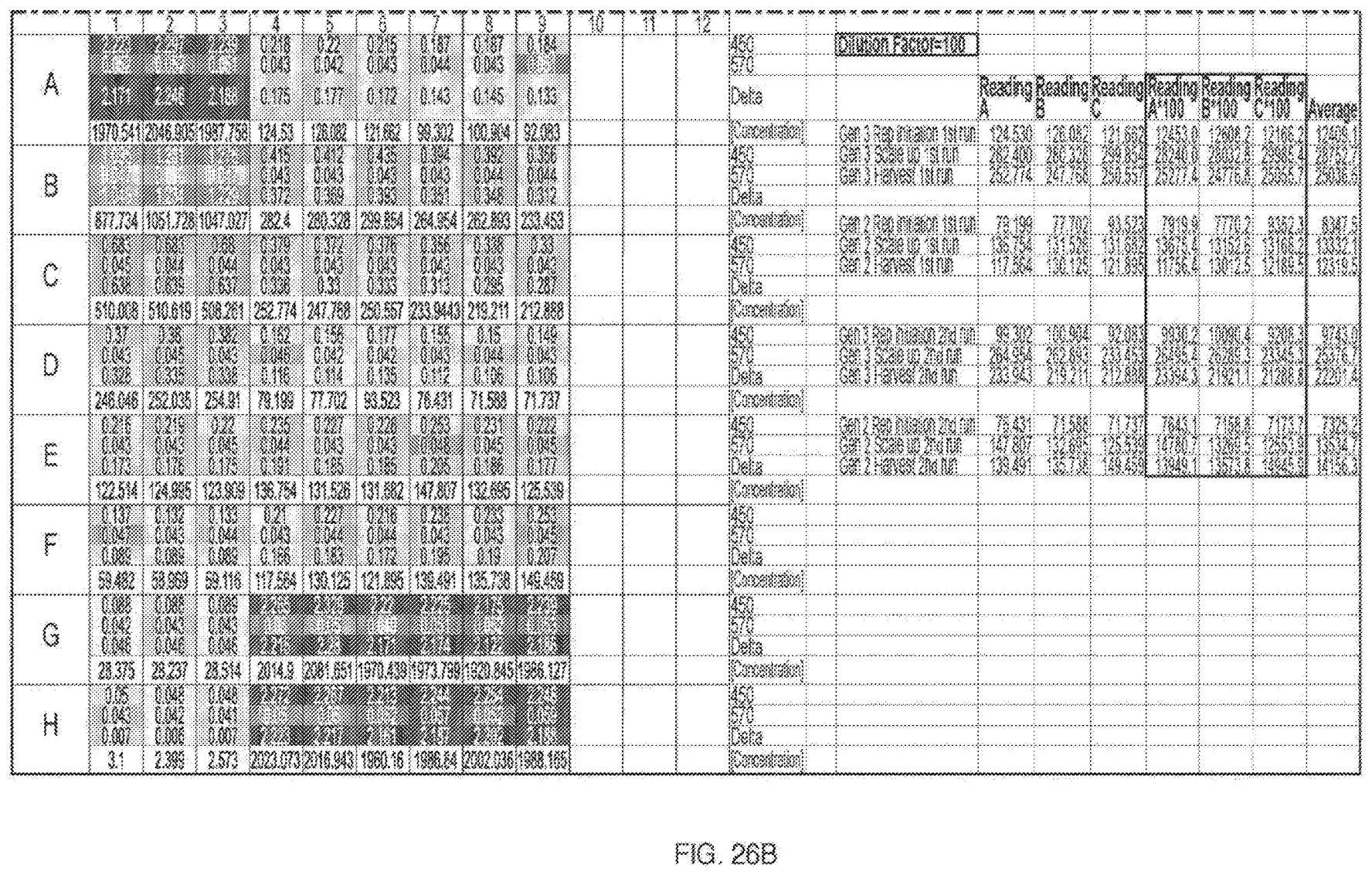

| | 1 | 2 | 3 | 4 | 5 | 6 | 7 | 8 | 9 | 10 | 11 | 12 | |
|---|---|---|---|---|---|---|---|---|---|---|---|---|---|
| A | [illegible] | [illegible] | [illegible] | 0.218 | 0.22 | 0.215 | 0.187 | 0.187 | 0.184 | | | | 450 |
| | [illegible] | [illegible] | [illegible] | 0.043 | 0.042 | 0.043 | 0.044 | 0.043 | [illegible] | | | | 570 |
| | [illegible] | [illegible] | [illegible] | 0.175 | 0.177 | 0.172 | 0.143 | 0.145 | 0.133 | | | | Delta |
| | 1970.541 | 2046.905 | 1987.758 | 124.53 | 128.082 | 121.662 | 99.302 | 100.904 | 92.083 | | | | Concentration |
| B | [illegible] | [illegible] | [illegible] | 0.415 | 0.412 | 0.435 | 0.394 | 0.392 | 0.356 | | | | 450 |
| | [illegible] | [illegible] | [illegible] | 0.043 | 0.043 | 0.043 | 0.043 | 0.044 | 0.044 | | | | 570 |
| | [illegible] | [illegible] | [illegible] | 0.372 | 0.369 | 0.393 | 0.351 | 0.348 | 0.312 | | | | Delta |
| | 877.734 | 1051.728 | 1047.027 | 282.4 | 280.328 | 299.854 | 264.954 | 262.893 | 233.453 | | | | Concentration |
| C | 0.683 | 0.683 | 0.68 | 0.379 | 0.372 | 0.376 | 0.356 | 0.338 | 0.33 | | | | 450 |
| | 0.045 | 0.044 | 0.044 | 0.043 | 0.043 | 0.043 | 0.043 | 0.043 | 0.043 | | | | 570 |
| | 0.638 | 0.639 | 0.637 | 0.336 | 0.33 | 0.333 | 0.313 | 0.295 | 0.287 | | | | Delta |
| | 510.008 | 510.619 | 508.261 | 252.774 | 247.768 | 250.557 | 233.9443 | 219.211 | 212.888 | | | | Concentration |
| D | 0.37 | 0.38 | 0.382 | 0.162 | 0.156 | 0.177 | 0.155 | 0.15 | 0.149 | | | | 450 |
| | 0.043 | 0.045 | 0.043 | 0.046 | 0.042 | 0.042 | 0.043 | 0.044 | 0.043 | | | | 570 |
| | 0.328 | 0.335 | 0.338 | 0.116 | 0.114 | 0.135 | 0.112 | 0.106 | 0.106 | | | | Delta |
| | 246.046 | 252.035 | 254.91 | 79.199 | 77.702 | 93.523 | 76.431 | 71.588 | 71.737 | | | | Concentration |
| E | 0.216 | 0.219 | 0.22 | 0.235 | 0.227 | 0.228 | 0.253 | 0.231 | 0.222 | | | | 450 |
| | 0.043 | 0.043 | 0.045 | 0.044 | 0.043 | 0.043 | 0.048 | 0.045 | 0.045 | | | | 570 |
| | 0.173 | 0.176 | 0.175 | 0.191 | 0.185 | 0.185 | 0.205 | 0.186 | 0.177 | | | | Delta |
| | 122.514 | 124.995 | 123.909 | 136.754 | 131.526 | 131.882 | 147.807 | 132.695 | 125.539 | | | | Concentration |
| F | 0.131 | 0.132 | 0.133 | 0.21 | 0.227 | 0.216 | 0.238 | 0.233 | 0.253 | | | | 450 |
| | 0.047 | 0.043 | 0.044 | 0.043 | 0.044 | 0.044 | 0.043 | 0.043 | 0.045 | | | | 570 |
| | 0.089 | 0.089 | 0.089 | 0.166 | 0.183 | 0.172 | 0.195 | 0.19 | 0.207 | | | | Delta |
| | 59.482 | 58.959 | 59.116 | 117.564 | 130.125 | 121.895 | 139.491 | 135.738 | 149.459 | | | | Concentration |
| G | 0.088 | 0.088 | 0.089 | [illegible] | [illegible] | [illegible] | [illegible] | [illegible] | [illegible] | | | | 450 |
| | 0.042 | 0.043 | 0.043 | [illegible] | [illegible] | [illegible] | [illegible] | [illegible] | [illegible] | | | | 570 |
| | 0.046 | 0.046 | 0.046 | [illegible] | [illegible] | [illegible] | [illegible] | [illegible] | [illegible] | | | | Delta |
| | 28.375 | 28.237 | 28.514 | 2014.9 | 2081.651 | 1970.439 | 1973.799 | 1929.845 | 1986.127 | | | | Concentration |
| H | 0.05 | 0.048 | 0.048 | [illegible] | [illegible] | [illegible] | [illegible] | [illegible] | [illegible] | | | | 450 |
| | 0.043 | 0.042 | 0.041 | [illegible] | [illegible] | [illegible] | [illegible] | [illegible] | [illegible] | | | | 570 |
| | 0.007 | 0.006 | 0.007 | [illegible] | [illegible] | [illegible] | [illegible] | [illegible] | [illegible] | | | | Delta |
| | 3.1 | 2.399 | 2.573 | 2023.073 | 2016.943 | 1960.16 | 1986.64 | 2002.036 | 1998.165 | | | | Concentration |

Dilution Factor=100

| | Reading A | Reading B | Reading C | Reading A*100 | Reading B*100 | Reading C*100 | Average |
|---|---|---|---|---|---|---|---|
| Gen 3 Rep initiation 1st run | 124.530 | 128.082 | 121.662 | 12453.0 | 12808.2 | 12166.2 | 12409.1 |
| Gen 3 Scale up 1st run | 282.400 | 280.328 | 299.854 | 28240.0 | 28032.8 | 29985.4 | 28752.7 |
| Gen 3 Harvest 1st run | 252.774 | 247.768 | 250.557 | 25277.4 | 24776.8 | 25055.7 | 25036.6 |
| Gen 2 Rep initiation 1st run | 79.199 | 77.702 | 93.523 | 7919.9 | 7770.2 | 9352.3 | 8347.5 |
| Gen 2 Scale up 1st run | 136.754 | 131.526 | 131.682 | 13675.4 | 13152.6 | 13168.2 | 13332.1 |
| Gen 2 Harvest 1st run | 117.564 | 130.125 | 121.895 | 11756.4 | 13012.5 | 12189.5 | 12319.5 |
| Gen 3 Rep initiation 2nd run | 99.302 | 100.904 | 92.083 | 9930.2 | 10090.4 | 9208.3 | 9743.0 |
| Gen 3 Scale up 2nd run | 264.954 | 262.893 | 233.453 | 26495.4 | 26289.3 | 23345.3 | 25376.7 |
| Gen 3 Harvest 2nd run | 233.943 | 219.211 | 212.888 | 23394.3 | 21921.1 | 21288.8 | 22201.4 |
| Gen 2 Rep initiation 2nd run | 75.431 | 71.588 | 71.737 | 7543.1 | 7158.8 | 7173.7 | 7325.2 |
| Gen 2 Scale up 2nd run | 147.807 | 132.695 | 125.539 | 14780.7 | 13269.5 | 12553.9 | 13534.7 |
| Gen 2 Harvest 2nd run | 139.491 | 135.738 | 149.459 | 13949.1 | 13573.8 | 14945.9 | 14156.3 |

FIG. 26B

| Sample number # | Description | Glucose (g/L) | Lactate (g/L) | Ammonia (mmol/L) | Glutamine (mmol/L) | Glutamax (mmol/L) | Glutamax-Glutamine (mmol/L) |
|---|---|---|---|---|---|---|---|
| 1 | Gen 2-Rep initiation First Round #L4054 | 1.78 | 0.14 | 2.16 | 1.56 | 1.71 | 0.16 |
| 2 | Gen 2-Scale Up First Round #L4054 | 1.36 | 0.89 | 1.40 | 1.76 | 1.90 | 0.15 |
| 3 | Gen 2-Harvest First Round #L4054 | 0.83 | 1.68 | 2.46 | 1.69 | 1.85 | 0.17 |
| 4 | Gen 3-REP initiation First Round #L4054 | 1.68 | 0.29 | 1.76 | 2.11 | 2.29 | 0.18 |
| 5 | Gen 3-Scale Up First Round #L4054 | 1.28 | 0.94 | 1.64 | 1.70 | 1.87 | 0.16 |
| 6 | Gen 3-Harvest First Round #L4054 | 1.07 | 1.53 | 2.23 | 1.39 | 1.54 | 0.14 |
| | | | | | | | |
| 7 | Gen 2-Rep initiation Second Round #L4055 | 1.91 | 0.08 | 2.29 | 1.60 | 1.74 | 0.14 |
| 8 | Gen 2-Scale up Second Round #L4055 | 1.61 | 0.77 | 1.40 | 1.78 | 1.93 | 0.15 |
| 9 | Gen 2-Harvest Second Round #L4055 | 0.85 | 1.86 | 2.46 | 1.39 | 1.55 | 0.16 |
| 10 | Gen 3-REP initiation Second Round #L4055 | 1.77 | 0.18 | 1.74 | 2.06 | 2.23 | 0.17 |
| 11 | Gen 3-Scale up Second Round #L4055 | 1.60 | 0.72 | 1.54 | 1.68 | 1.84 | 0.15 |
| 12 | Gen 3-Harvest Second Round #L4055 | 1.44 | 1.32 | 2.07 | 1.79 | 1.95 | 0.16 |

FIG. 27

| | $FIL | S/L/1301 \| Geometr | S/L/Pt \| Geometric Mean (FL03-A) |
|---|---|---|---|
| A1 gen2L4054 ne | A1 gen2L4054 neg.fcs | 34.5 | 3.24 |
| A2 gen2L4054 ne | A2 gen2L4054 neg.fcs | 34 | 3.19 |
| A3 gen2L4054 po | A3 gen2L4054 pos.fcs | 1834 | 70.6 |
| A4 gen2L4054 po | A4 gen2L4054 pos.fcs | 1872 | 70.3 |
| A5 gen2L4055 ne | A5 gen2L4055 neg.fcs | 31.9 | 4.23 |
| A6 gen2L4055 ne | A6 gen2L4055 neg.fcs | 32.4 | 4.87 |
| A7 gen2L4055 po | A7 gen2L4055 pos.fcs | 1941 | 88.7 |
| A8 gen2L4055 po | A8 gen2L4055 pos.fcs | 1933 | 91.1 |
| B1 gen3L4054 ne | B1 gen3L4054 neg.fcs | 31.2 | 3.45 |
| B2 gen3L4054 ne | B2 gen3L4054 neg.fcs | 31.9 | 3.39 |
| B3 gen3L4054 po | B3 gen3L4054 pos.fcs | 2016 | 61.3 |
| B4 gen3L4054 po | B4 gen3L4054 pos.fcs | 2014 | 76.2 |
| B5 gen3L4055 ne | B5 gen3L4055 neg.fcs | 33.7 | 6.76 |
| B6 gen3L4055 ne | B6 gen3L4055 neg.fcs | 35.4 | 6.7 |
| B7 gen3L4055 po | B7 gen3L4055 pos.fcs | 2158 | 99.4 |
| B8 gen3L4055 po | B8 gen3L4055 pos.fcs | 1938 | 99.5 |
| Mean | - | 998 | 43.3 |
| SD | - | 999 | 41.3 |

FIG. 28

| Study | Sample | Sample id | Species | Chain | Reads | CDR3 | Unique CDR3 | D50 |
|---|---|---|---|---|---|---|---|---|
| 20180511_Study1_FCA | Gen2-L4054 | 59990 | TRB | h | 1181732 | 1181732 | 8915 | 0 |
| 20180511_Study1_FCA | Gen3-L4054 | 59991 | TRB | h | 1145697 | 1145697 | 18130 | 0 |
| 20180511_Study1_FCA | Gen2-L4055 | 59987 | TRB | h | 1166465 | 1166465 | 12996 | 0.1 |
| 20180511_Study1_FCA | Gen3-L4055 | 59982 | TRB | h | 1059985 | 1059985 | 27246 | 0.9 |

FIG. 29

| STEP | Gen 2 | Gen 2.1 | Gen 3.0 Optimized |
|---|---|---|---|
| **Pre REP- day 0** | ≤ 50 fragments/ 1 G-Rex 100MCS - **11 days** | ≤ 180 fragments/ 3 G-Rex, Pre-formulated CM1 warmed media<br>100MCS - **11 days** | ***Fresh or Frozen Tumor***<br>Whole tumor with ≤ 30 fragments up to 60 fragments per 1 G-Rex.<br>100MCS (up to 4 G-Rex),<br>preformulated warmed media - **7 days. Pre REP, Feeders 2.5 E8 cells + OKT-3 (30ng/mL)** |
| **REP Initiation** | Direct to REP- Day 11-<br>**<200 E6 TIL**<br>1 G-Rex 500MCS | Direct to REP- Day 11-<br>**<200 E6 TIL**<br>Pre-formulated CM2 warmed media in one G-Rex 500MCS | Direct to REP - Day **7-all cells TIL- same G-Rex 100MCS (100MCS up to 4 GREX), Standard media or Defined Media (Serum free). Addition Feeders 5 E8 cells +OKT-3 (30ng/mL)** |
| **TIL propagation or Scale up** | 1 to 5 G-REX 500MCS<br>**Split day 16** | 2 to 5 G-REX 500MCS<br>Pre-formulated CM4 warmed media<br>**Split day 16** | From G-REX 100MCS transfer TIL suspension to G-REX 500MCS, up to 4 GREX 500 MCS- Standard media or Defined Media (Serum Free)<br>**Scale up on day 10 or 11** |
| **Harvest** | **Harvest day 22,**<br>LOVO-automated cell washer | **Harvest day 22,**<br>LOVO-automated cell washer (5 wash cycle) | **Harvest day 14 or 16**<br>LOVO- automated cell washer (5 wash cycle) |
| **Final formulation** | Cryopreserved Product<br>300IU/ml IL2- CS10 in $LN_2$,<br>multiple aliquots | Cryopreserved Product<br>300IU/ml IL2- CS10 in $LN_2$,<br>multiple aliquots | Cryopreserved Product<br>300IU/ml IL-2- CS10 in $LN_2$,<br>multiple aliquots |
| **Process time** | **22 days** | **22 days** | **16 days** |

FIG. 31

| Process Day | Conditions | Gen 3.1 |
|---|---|---|
| Day 0- pre REP initiation | Media CM1 | 500 mL |
| | IL-2 (6000 IU/mL) | + |
| | OKT-3 (30ng/mL) | + |
| | Feeders (250 E+06) | + |

| Process Day | Conditions | Gen 3.1 |
|---|---|---|
| Day 7- REP initiation | Media CM2 | 500 mL |
| | IL-2 (6000 IU/mL) | + |
| | OKT-3 (30ng/mL) added on Day 7 | + |
| | Feeders Added on Day 7 | 500 E06 |
| | Total Feeders at Day | 750 E+06 |

| Process Day | Conditions | Gen 3.1 |
|---|---|---|
| Day 9-11 - Scale Up | From G-REX 100MCS transfer TIL suspension to 1 G-REX 500MCS (up to 3 GREX 500MCS) | Yes |
| Day 16 - Harvest | LOVO- automated cell washer | Yes |

FIG. 32

| Process Comparison | Key Process Changes | Benefit |
|---|---|---|
| **Gen 2 : Gen 2.1** | • Initiate process with two flasks instead of one flask<br>• Divide REP initiation feeder layer between 2 G-Rex500MCS Flasks<br>• Pre-formulate media and warm prior to use | • Potential doubling of final cell count (dose with increased TIL repertoire.<br>• Process redundancy throughout process |
| **Gen 2.1 : Gen 3.1** | • Fresh or Frozen tumor<br>• 14-16 day process (from 22 day)<br>• Reduce total feeder layer on process<br>• Feeder layer and OKT3 present at Day 0<br>• REP initiated with fragments<br>• 100MCS scales to 500MCS<br>• Scales to multiple pre-REP flasks<br>• Standard Media and Defined Media (Serum Free) | • Increased potency<br>• Improved phenotype<br>• Decreased process time<br>• Reduced reagent testing<br>• Decreased process variability<br>• Defined reagents<br>• Increased repertoire<br>• Reduce impurities (feeder)<br>• Comparable or Higher Dose. |

FIG. 33

| Process Comparison | Key Process Changes | Desired Improvement | Criteria for Success | Outcome |
|---|---|---|---|---|
| Gen 2 : Gen 3.0 | • 14-16 days<br>• Initiate REP with fragments up to 4 flask.<br>• 100MCS scales to 500MCS | • Increased potency<br>• Improved phenotype<br>• Decreased process time | • Increase potency as measured by INF-g ✓<br>• Comparable phenotype ✓<br>• Comparable Dose ✓<br>• Comparable purity ✓ (feeder cell)<br>• Maintain clonal diversity ✓ | • Potency increased over Gen2<br>• Improved expression of CD28 on CD8 cells<br>• Maximum capacity of flask reached by day 16 on Gen 3.1<br>• Reduced feeder cell usage<br>• Increased diversity |

FIG. 34

| Process | Gen 2 | Gen 3 |
|---|---|---|
| L4054 | Standard Media | Standard Media |
| L4055 | Standard Media | Standard Media |
| M1085T | Standard Media | Standard Media |

Standard Media:
Pre REP: CM1
REP initiation : CM2
Split or Scale up : CM4

| Process | Gen 3 | Gen 3.1 control | Gen 3.1 |
|---|---|---|---|
| L4063 | Standard Media | Standard Media | Standard Media |
| L4064 | Defined Media | Defined Media | Defined Media |

Defined Media:
CTS Optimizer (Serum Free Media) in each day of the process

FIG. 35

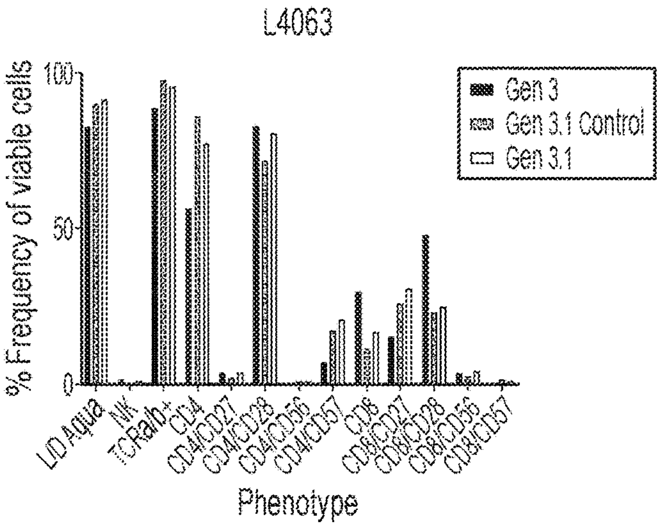
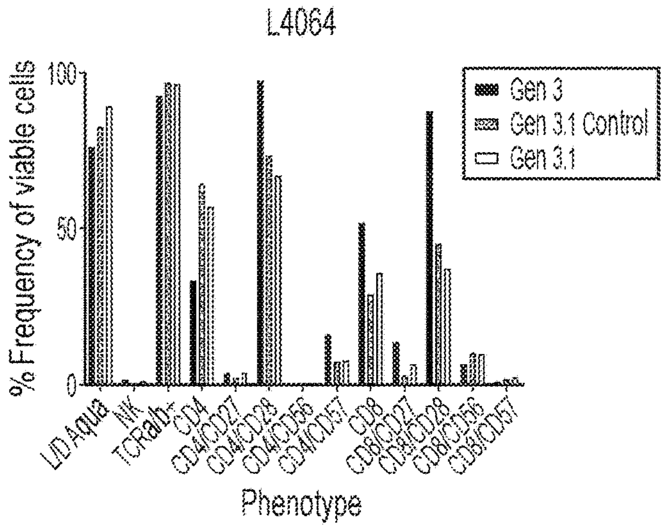
| **Tumor ID** | **L4063 Standard media** | | | **L4064 Defined media** | | |
|---|---|---|---|---|---|---|
| **Process** | **Gen 3.0** | **Gen 3.1 Control** | **Gen 3.1** | **Gen 3.0** | **Gen 3.1 Control** | **Gen 3.1** |
| # Fragments | 53 | 53 | 53 | 21 | 21 | 21 |
| **Tumor ID** | **L4063 in Standard Media** | | | **L4064 in CTS Optimizer Media** | | |
|---|---|---|---|---|---|---|
| Process | **Gen 3.0** | **Gen 3.1 Control** | **Gen 3.1 Test** | **Gen 3.0** | **Gen 3.1 Control** | **Gen 3.1 Test** |
| Number of fragments | **53** | 53 | 53 | **21** | 21 | 21 |
| Average TVC per fragment | 1.37E+08 | 3.19E+08 | 3.53E+08 | 5.90E+08 | 7.57E+08 | 9.29E+08 |
| % viability at Harvest | 79.53% | 89.43% | 94.80% | 88.80% | 81.90% | 84.90% |
| **TVC Harvest** | **7.26E+09** | **1.69E+10** | **1.87E+10 *** | **1.24E+10** | **1.59E+10** | **1.95E+10 *** |
FIG. 36

L4063- Standard Media: L4064- Defined Media

| Process Day | Conditions | Gen 3.0 | Gen 3.1 CT (control) | Gen 3.1 F |
|---|---|---|---|---|
| Day 0- pre REP initiation | Media CM1 | 500 mL | 500 mL | 500 mL |
| | IL-2 (6000 IU/mL) | + | + | + |
| | OKT-3 (30ng/mL) | - | + | + |
| | Feeders (250 E+06) | - | - | + |

| Conditions on Day 0 | Gen 3.0 | Gen 3.1 (control) | Gen 3.1 |
|---|---|---|---|
| Media | 500 mL | 500 mL | 500 mL |
| IL-2 (6E+06) | + | + | + |
| OKT-3 (30ng/mL) | - | + | + |
| Feeders (250 E+06) | - | - | + |

| Number of uCDR3 (% Overlap) | All uCDR3's | | | Top 80% uCDR3's | | |
|---|---|---|---|---|---|---|
| | Gen 3.0 | Gen 3.1 Control | Gen 3.1 | Gen 3.0 | Gen 3.1 control | Gen 3.1 |
| Gen 3.0 | 14005 | 3240 (23) | 2959 (21) | 1105 | 1000 (90) | 975 (88) |
| Gen 3.1 control | - | 18149 | - | - | 2438 | - |
| Gen 3.1 | - | - | 17181 | - | - | 2332 |

| Conditions on Day 0 | Gen 3.0 | Gen 3.1 (control) | Gen 3.1 |
|---|---|---|---|
| Media | 500 mL | 500 mL | 500 mL |
| IL-2 (6E+06) | + | + | + |
| OKT-3 (30ng/mL) | - | + | + |
| Feeders (250 E+06) | - | - | + |

| Number of uCDR3 (% Overlap) | All uCDR3's | | | Top 80% uCDR3's | | |
|---|---|---|---|---|---|---|
| | Gen 3.0 | Gen 3.1 Control | Gen 3.1 | Gen 3.0 | Gen 3.1 control | Gen 3.1 |
| Gen 3.0 | 15107 | 5486 (36) | 5541 (37) | 2479 | 2186 (88) | 2163 (87) |
| Gen 3.1 control | - | 21460 | - | - | 3247 | - |
| Gen 3.1 | - | - | 21503 | - | - | 3264 |

*Shared clones between bulk TIL and PD1⁺ -derived*

D)

| Tumor | Count of shared uCDR3 clones | Bulk TIL Shared % | PD1+-derived Shared % |
|---|---|---|---|
| Breast | 43 | 0.61 | 78.95 |
| Breast | 76 | 79.51 | 88.64 |
| Lung | 40 | 5.26 | 35.16 |
| Lung | 60 | 4.66 | 34.57 |
| Melanoma | 59 | 21.14 | 53.84 |
| Melanoma | 39 | 19.87 | 71.90 |

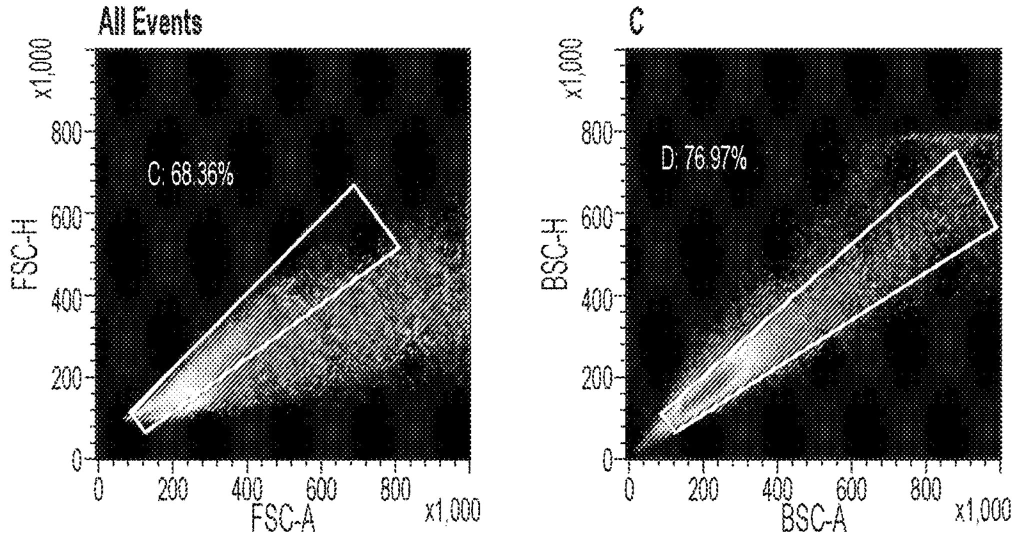
Gates and Statistics
| Name | Events | %Parent | %Total |
|---|---|---|---|
| All Events | 100,000 | 0.00% | 100.00% |
| C | 68,355 | 68.36% | 68.36% |
| D | 52,616 | 76.97% | 52.62% |
| Live | 51,791 | 98.44% | 51.79% |
| CD3 | 3,816 | 7.37% | 3.82% |
| PD1+ | 228 | 5.97% | 0.23% |
| PD1- | 3,148 | 82.49% | 3.15% |
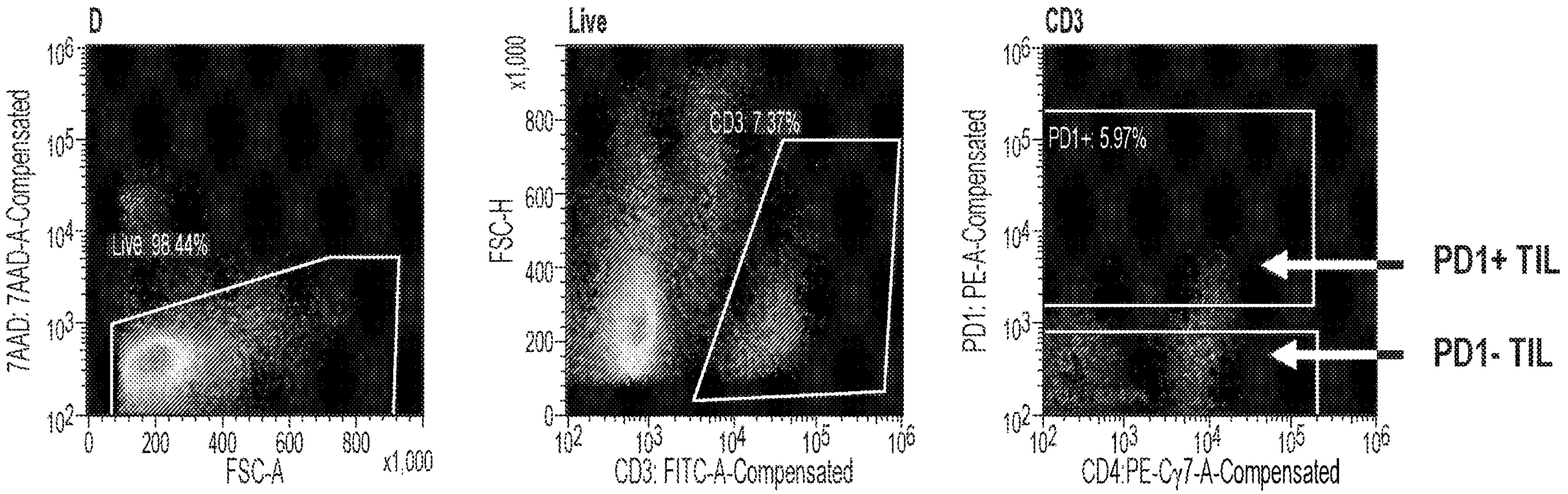
FIG. 53

**Method 1*:** 10ng/ml of Collagenase
1mg/ml of Hyalurodase
500IU/ml of DNaseI

Method 2: 10ng/ml of Collagenase

Method 3: Miltenyi Tumor Dissociation Kit

Method 4:** 170mg/L Collagenase I
56mg/L Collagenase II
170mg/L Collagenase IV
25mg/L Elastase

* NIH Centers for Cancer Research, *Triple Enzyme Mouse Tumor Digestion*, 2006. https://ccr.cancer.gov/sites/default/files/triple enzyme mouse tumor digestion.pdf

**Quatromoni et al. An optimized disaggregation method for human lung tumors that preserves phenotype and function of immune cells. J Leukoc Biol. 2015 Jan; 97 (1): 201-209

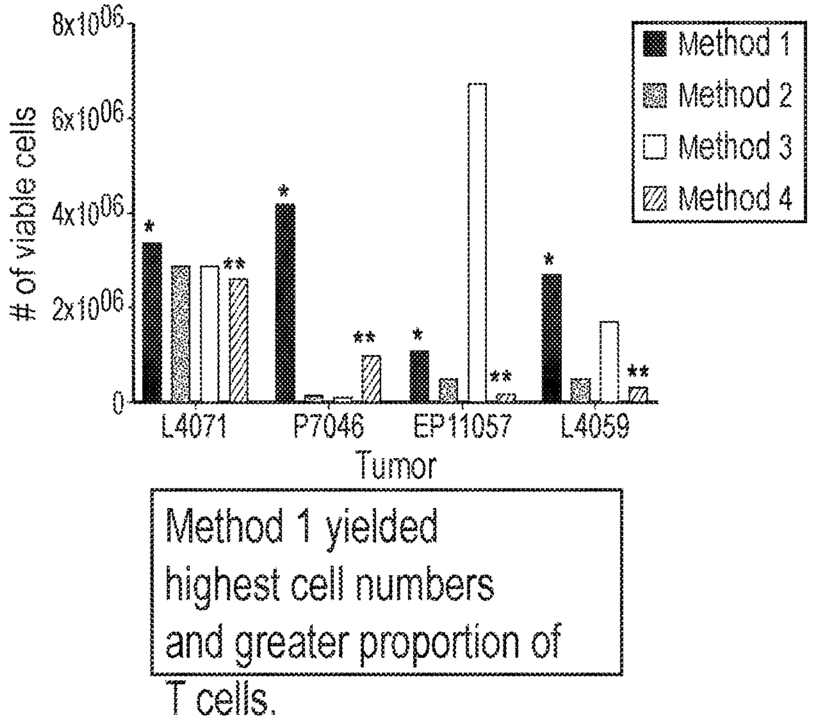

FIG. 54

Method 1: 0.008DMC U/ml Neutral Protease
0.12 PZ U/ml Collagenase
200 IU/ml DNAse I

Method 2: 0.008DMC U/ml Neutral Protease
5.5 PZ U/ml Collagenase
200 IU/ml DNAse I

Method 3: 0.36 DMC U/ml Neutral Protease
0.12 PZ U/ml Collagenase
200 IU/ml DNAse I

Method 4: 0.36 DMC U/ml Neutral Protease
5.5 PZ U/ml Collagenase
200 IU/ml DNAse I

Method 5: 10ng/ml of Collagenase
1mg/ml of Hyalurodase
500IU/ml of DNaseI

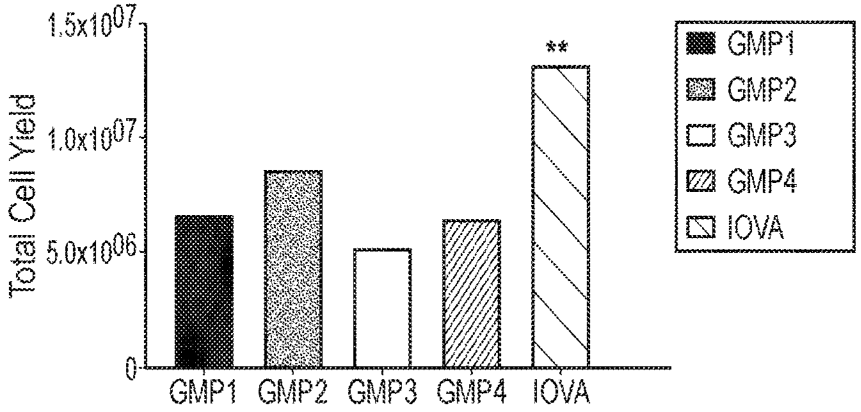

** Likely similar cell numbers to the GMP conditions. More tumor was used for the IOVA condition because this condition was being used for the sort. Future experiments will normalize to tumor weight

FIG. 55

| | M1121 | M1123 | M1125 | M1126 | M1129 | M1130 | EP11032 | EP11040 | EP11043 |
|---|---|---|---|---|---|---|---|---|---|
| %PD1+ | 10.1% | 0.66% | 47.6% | 0.78% | 13.9% | 59.5% | 16.3% | 33.5% | 87% |
| # Sorted | 30,231 | 2,000 | 143,000 | 3,000 | 13,393 | 529,000 | 23,415 | 5,693 | 628,000 |
| Post-sort Purity | NT | 86% | 62% | 35% | 73% | 96% | NT | 96% | 94.6% |
| REP1 seed (#/G-Rex24/10) | 30,231 | 2,000 | 19,000 | 3,000 | 13,393 | 100,000 | 23,415 | 5,693 | 92,000 |
| REP1 yield PD1+ | 1.9e7 | 8.0e5 | 8.21e5 | 1.5e7 | 1.5e7 | 2.3e7 | 2.63e7 | 1.3e6 | 1.33e6 |
| Fold expansion | **628** | **400** | **43** | **5000** | **1045** | **230** | **1,123** | **228** | **15** |
| REP2 seed (#/G-Rex10 /100M) | 100,000 | 80,000 | 100,000 | 100,000 | 100,000 | 100,000 | 100,000 | 100,000 | 100,000 |
| REP2 yield PD1+ | 1.44e8 (~27e9) | 3.0e6 (~3e7) | 3.03e7 (~2/5e8) | 9.48e7 (~14e9) | 1.28e8 (~192e9) | 2.38e8 (~203e9) | 1.68e8 (~44e9) | 1.26e8 (~14e9) | 1.7e8 (~1.5e9) |
| Fold expansion | **1,440** | **37.5** | **303** | **948** | **1280** | **1670** | **1,680** | **1,260** | **1,170** |

Melanoma patients treated with anti-PD1

*Full-scale prep*

© 2018, Iovance Biotherapeutics

FIG. 66

| | *T6042* | *EP11055* | *EP11061* | *L4067* | *L4068* | *L4073* | *L4074* | *L4075* | *L4081* | *L4082* |
|---|---|---|---|---|---|---|---|---|---|---|
| %PD1+ | 33% | 13.3% | 5.2% | 58% | 4.6% | 27% | 6.7% | 13.5% | 78% | 81.8% |
| # Sorted | 23,320 | 33,000 | 5,500 | 115,000 | 32,500 | 88,426 | 8,384 | 11,000 | 390,000 | 135,012 |
| Post-sort Purity | 90% | 72% | 65% | 95% | 59.2% | 78% | 81% | 78% | 61% | 90% |
| REP1 seed (#/G-Rex24/10) | 23,000 | 1K/2K/10K 20K | 5,500 | 100,000 | 32,500 | 10K/25K/ 50K | 8,384 | 1K/2K/ 5K | 50,000 | 30,000 |
| REP1 yield PD1+ | 5.54e6 | 2.6e4/ 5.3e5/ 6.8e5/ 3.28e6 | 6.71e5 | 3.0e7 | 2.32e7 | 8.5e6/ 3.77e7/ 6.09e7 | 2.72e6 | 2.4e4/ 3.4e4/ 2.64e5 | 1.24e8 | 6.36e7 |
| Fold expansion | **240** | **26/61/67 164** | **122** | **300** | **73** | **850/1508/ 1218** | **324** | **25/17 /53** | **2480** | **2120** |
| REP2 seed (#/G-Rex10 /100M) | 5.54e6 | 3.3e6 | 100,000 | 100,000 | 100,000 | 3.77e7 | 2.72e6 | 8.5e5 | 100,000 | 100,000 |
| REP2 yield PD1+ | 1.82e9 (1.82e9) | 1.83e9 (~1.83e9) | 1.6e8 (~1.0e9) | 3.63e8 (~108e9) | 1.17e8 (~27e9) | 3.64e8 (~2.2e9) | 1.97e9 (~2e9) | 1.83e8 (~2e8) | 1.1e8 (~138e9) | 1.99e8 (~396e9) |
| Fold expansion | **328** | **554** | **1570** | **3,600** | **1170** | **20** | **724** | **2,152** | **1110** | **1990** |

FIG. 67

| | S13009 | S13015 | S13016 |
|---|---|---|---|
| %PD1+ | 8% | 94% | 6% |
| # Sorted | 80,000 | 290 | 306 |
| Post-sort Purity | NT | 99.8% | NT |
| REP1 seed (#/G-Rex24/10) | 80,000 | 290 (well$_{96}$) | 306 (well$_{96}$) |
| REP1 yield PD1+ | 2.95e6 | 2.6e4 | 1.96e4 |
| Fold expansion | **37** | **90** | **63** |
| REP2 seed (#/G-Rex10 /100M) | 100,000 | 2.6e4 | 2.0e4 |
| REP2 yield PD1+ | 2.59e8 (~7e9) | 4.13e7 (~4.1e7) | 2.2e5 (2.2e5) |
| Fold expansion | **2,685** | **1,588** | **11** |

Overall, 17/22 (2 in progress) PD1+ TIL preps yielded >1e9 viable cells (Likely an underestimate because the entire tumor was not sorted)

FIG. 68

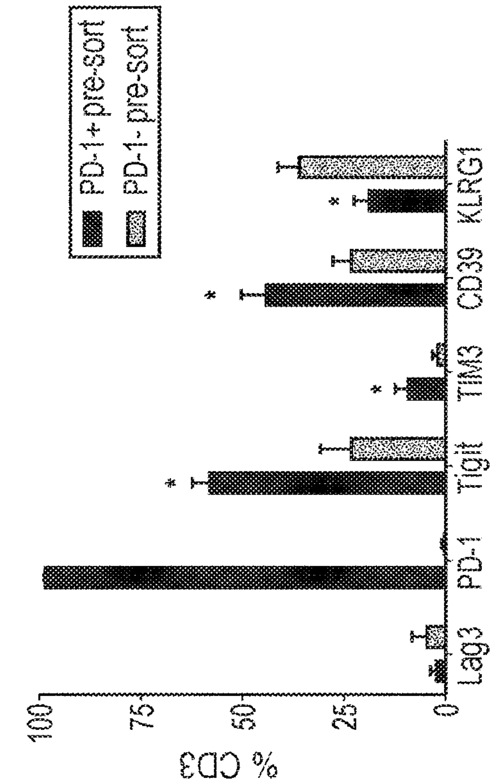
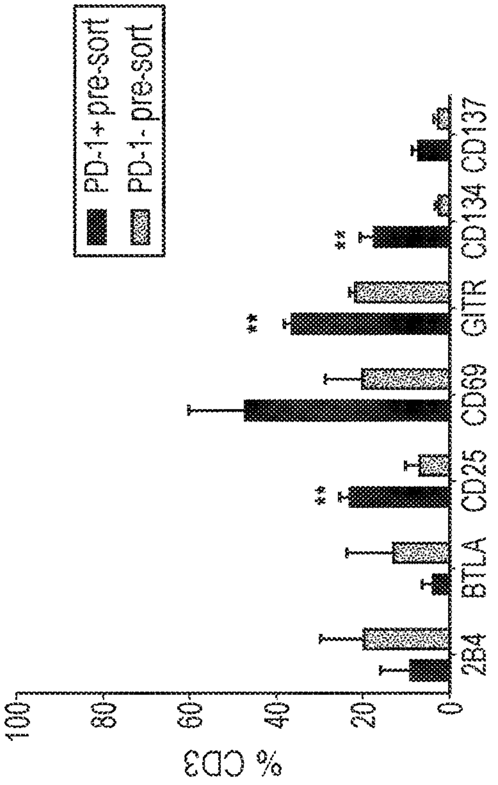
FIG. 71

*Shared clones between bulk TIL and PD1+ -derived*

| Tumor | Count of shared uCDR3 clones | Bulk TIL Shared % | PD1+-derived Shared % |
|---|---|---|---|
| Breast | 43 | 0.61 | 78.95 |
| Breast | 76 | 79.51 | 88.64 |
| Lung | 40 | 5.26 | 35.16 |
| Lung | 60 | 4.66 | 34.57 |
| Melanoma | 59 | 21.14 | 53.84 |
| Melanoma | 39 | 19.87 | 71.90 |

FIG. 79

| | αPD1 clone | % PD1⁺ in digest | # sorted PD1+ cells | Fold expansion [REP1; REP2] | Total yield (extrapolated) | # of uCDR3 | Entropy | Portion Shared (%) [bulk; PD1+] |
|---|---|---|---|---|---|---|---|---|
| M1125 | M1H4 | *47.60%* | 143,000 | 43; 303 | (~2.5e8) | 1281 | 3.6 | 29;36 |
| M1126 | M1H4 | *0.78%* | 3,000 | 5000; 948 | (~14e9) | 786 | 2.3 | 19.9; 71.9 |
| M1129 | M1H4 | *13.90%* | 13,393 | 1045; 1280 | (~192e9) | 18,234 | 7.4 | 38.1; 50.9 |
| EP11040 | M1H4 | *33.50%* | 5,693 | 228; 1260 | (~14e9) | 823 | 2.1 | 0.6; 78.9 |
| EP11043 | M1H4 | *87%* | 628,000 | 15; 1170 | (~1.5e9) | 1518 | 1.4 | 79.5; 88.6 |
| L4067 | M1H4 | *58%* | 115,000 | 300; 3600 | (~108e9) | 566 | 2.4 | 5.3; 35.2 |
| L4068 | M1H4 | *4.60%* | 32,500 | 73; 1170 | (~27e9) | 806 | 3.4 | 4.7; 34.6 |
| L4073 | M1H4 | *27%* | 88,426 | 1218; 20 | (~2.2e9) | 45,947 | 12.5 | 28.7; 39.5 |
| L4074 | M1H4 | *6.70%* | 8,384 | 324; 742 | (~2e9) | 1694 | 4.5 | 5.6; 72.2 |
| L4075 | M1H4 | *13.50%* | 11,000 | 53; 2152 | (~2e8) | 1416 | 4.1 | 17.9; 53.3 |
| M1130 | EH12.2H7 | *59.50%* | 529,000 | 230; 1670 | (~203e9) | 2815 | 6 | 5.7; 52.9 |
| L4081 | EH12.2H7 | *78%* | 390,000 | 2480; 1110 | (~138e9) | 5373 | 8.7 | 41.4; 65.5 |
| L4082 | EH12.2H7 | *81.80%* | 135,012 | 2120; 1990 | (~396e9) | 4467 | 6.4 | 57.8; 56.7 |
| L4089 | EH12.2H7 | *75%* | 826,000 | 46; 2491 | (~950e9) | 10093 | 9.9 | 58.9; 38.7 |
| H3027 | EH12.2H7 | *92%* | 71,929 | 31; 1470 | (~3.17e9) | 808 | 0.8 | 0.06; 0.03 |
| *L4093* | *EH12.2H7* | *79%* | *448,000* | *1336, 483* | *~97e9* | *2886* | *5.7* | *18; 46* |
| *M1135* | *EH12.2H7* | *64%* | *48,000* | *5670, 497* | *~99e9* | *2371* | *5.5* | *4.8; 11.6* |

FIG. 86

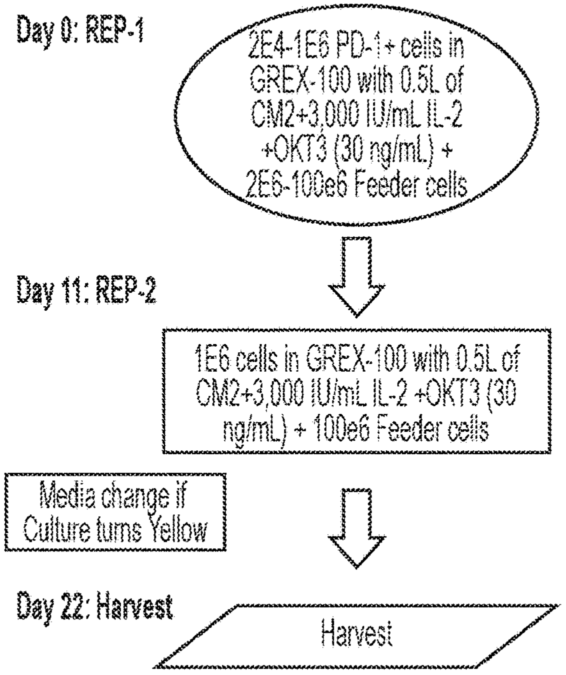
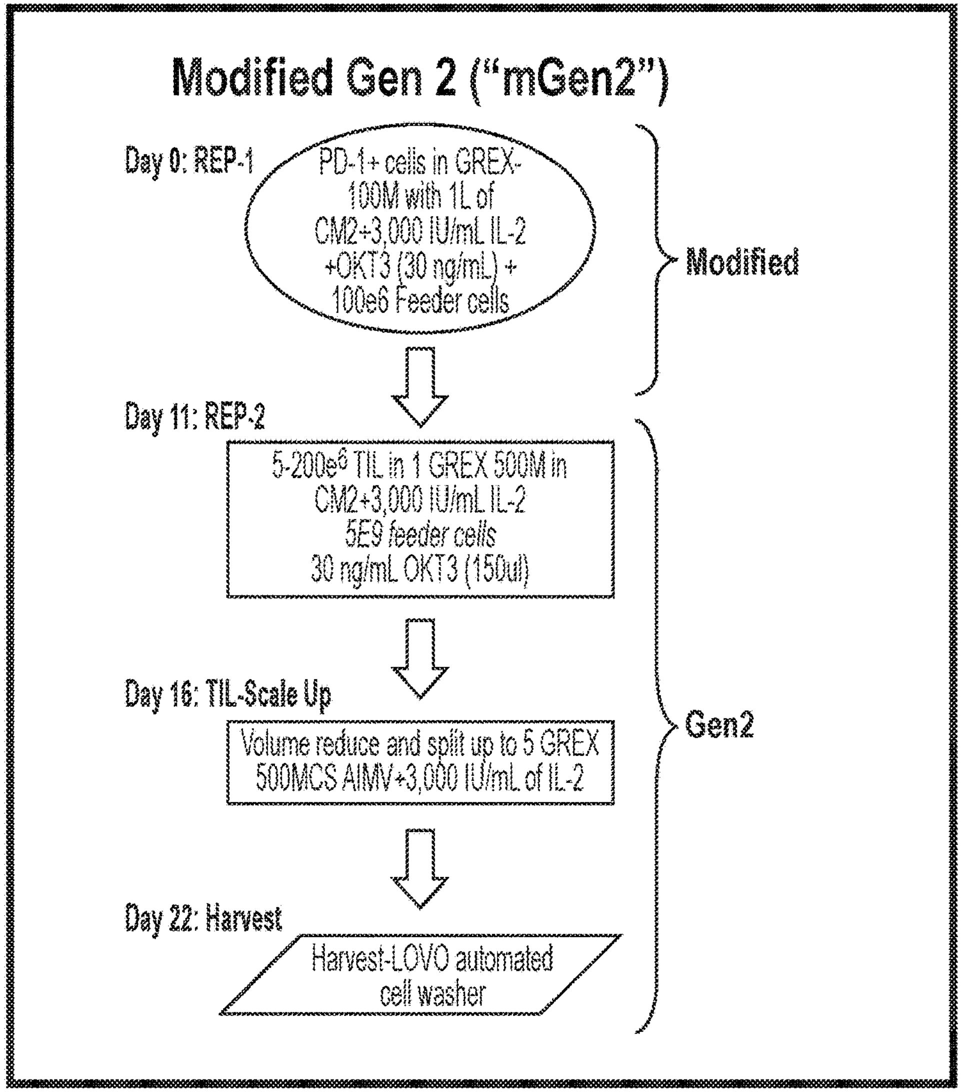
FIG. 96

| | Lung (L4093) | | | | Melanoma (M1135) | | | |
|---|---|---|---|---|---|---|---|---|
| **Flow Sort Summary** | | | | | | | | |
| # Pre-sort (%CD3+PD1+) | 5.6e5 (6.5%) | | | | 4.88 e4 (1.2%) | | | |
| # Sorted (% Yield) | 4.5e5 (80.7%) | | | | 4.8e4 (98.4) | | | |
| *Post-sort Purity (%) | 85% | | | | 75.7% | | | |
| **TIL Expansion Summary** | ***Research PD1+*** | ***Gen 2 PD1+*** | ***Gen 2 DM PD1+*** | ***^ER PD1+*** | ***Research PD1+*** | ***Gen 2 PD1+*** | ***Gen 2 DM PD1+*** | ***^ER PD1+*** |
| # REP1 seed (G-Rex100/100M) | 4.48e5 | 4.48e5 | 4.48e5 | 4.48e5 | 4.8e4 | 4.8e4 | 4.8e4 | 4.8e4 |
| # REP1 Harvest (Extrapolated) | 599e6 | 560e6 | 225e6 | 44e6 | 34e6 | 272e6 | 256e6 | 46e6 |
| REP 1 Fold expansion | 1336 | 1249 | 503 | 99 | 705 | 5670 | 5334 | 958 |
| # REP2 seed (G-Rex100/500M) | 1e6 | 200e6 | 200e6 | 44e6 | 1e6 | 200e6 | 200e6 | 44e6 |
| # REP2 Harvest (Extrapolated) | 24e9 | 97e9 | 64e9 | 55e9 | 4.3e9 | 99e9 | 97e9 | 37e9 |
| REP 2 Fold expansion | 404 | 483 | 318 | 247 | 1282 | 497 | 483 | 270 |

#, Total Viable Cells (TVC)
*, Purity was based on FSC/CD3+/PD1+ but not on Viable cells
^, REP1 on Day 7, REP 2 on Day 17

FIG. 99

| | L4096 | L4097 | L4089 | L4100 | L4101 | L4104 | L4106 | H3035 | H3037 | H3038 |
|---|---|---|---|---|---|---|---|---|---|---|
| %PD1$^{High+}$ | 20% | 78% | 31% | 43% | 32% | 40% | 39% | 28% | 49% | 32% |
| # Sorted | ***10,700*** | ***62,500*** | ***20,303*** | ***46,000*** | ***99,000*** | ***70,000*** | ***20,600*** | ***25,000*** | ***25,000*** | ***3,000*** |
| REP1 seed | 8,000 | 47,000 | 8,184 | 33,000 | 99,000 | 70,000 | 18,200 | 11,000 | 11,300 | 3,000 |
| REP1 yield PD1$^+$ | | 1.08e7 | 1.22e7 | 1.77e7 | 99,000 | 1.2e8 | | 3.85e6 | DISCARDED | |
| Fold expansion | | 229 | 1,493 | 536 | | 1711 | | 350 | | |
| REP2 seed | | 1e5 | 1e5 | 1e5 | | 1e5 | | 1e5 | | |
| REP2 yield PD1$^+$ | | | | | | | | | | |
| Fold expansion | | | | | | | | | | |
| uCDR3 | | | | | | | | | | |
| Entropy | | | | | | | | | | |
| Portion Shared (Bulk) | | | | | | | | | | |

FIG. 128

| | M1132 | M1136 | M1139 | M1141 | OV8030 |
|---|---|---|---|---|---|
| %PD1$^{High+}$ | 12 | 61 | 24 | 11 | 41 |
| # Sorted | ***2,000*** | ***37,000*** | ***42,000*** | ***22,400*** | ***25,000*** |
| REP1 seed | 2,000 | 23,500 | 10,200 | 22,400 | 21,800 |
| REP1 yield PD1$^+$ | 9.94e5 | 2.26e7 | 5.7e6 | | 4.00e7 |
| Fold expansion | 49 | 961 | 556 | | 1836 |
| REP2 seed | 1e5 | 1e5 | 1e5 | | 1e5 |
| REP2 yield PD1$^+$ | | | | | |
| Fold expansion | | | | | |
| uCDR3 | | | | | |
| Entropy | | | | | |
| Portion Shared (Bulk) | | | | | |

FIG. 129

A.
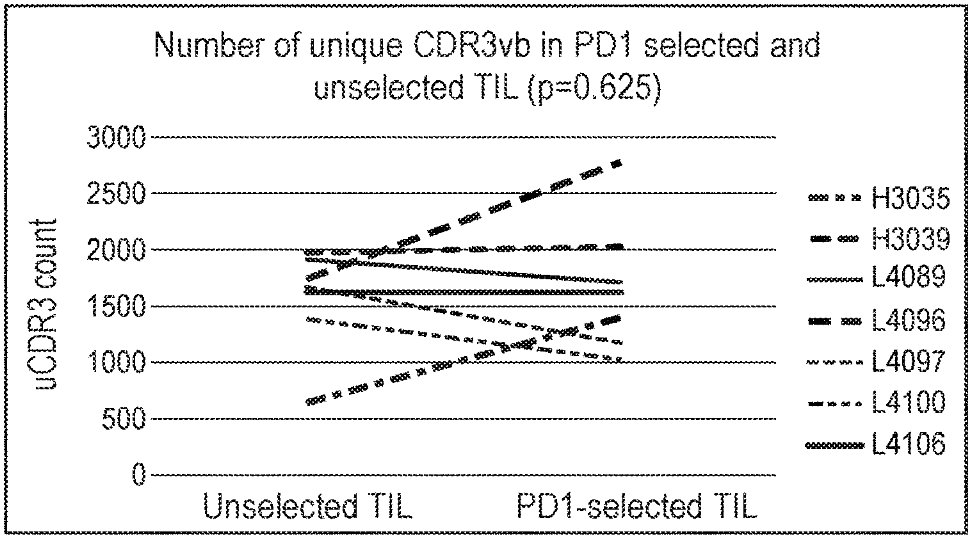
B.
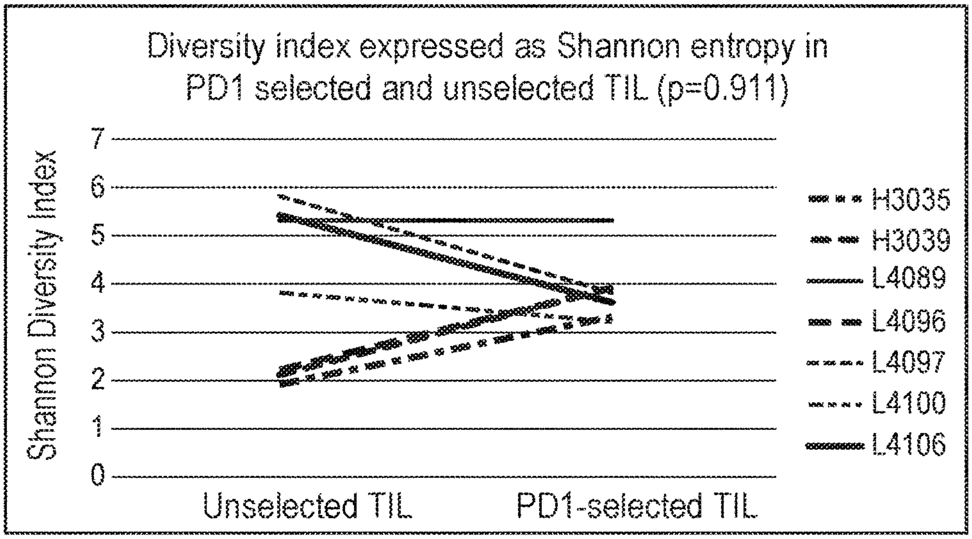
FIG. 134

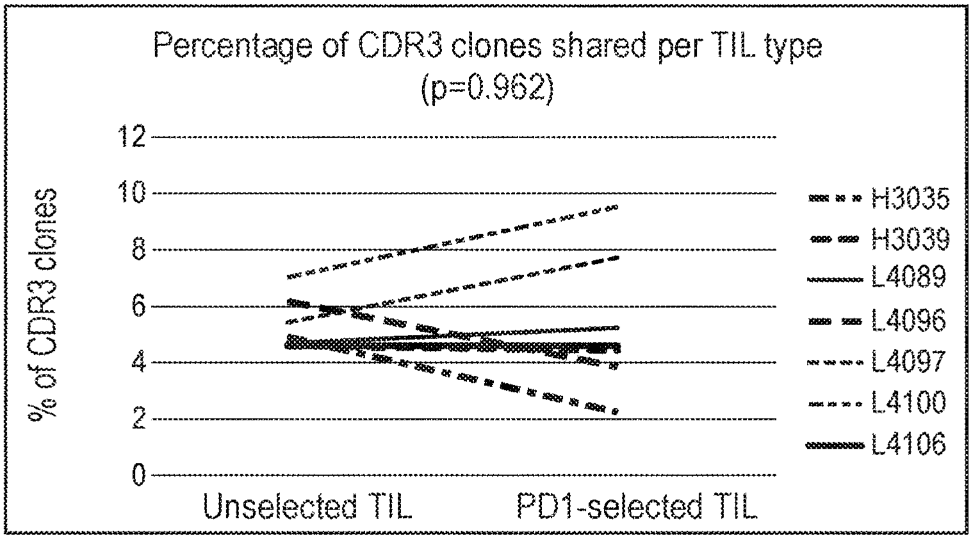
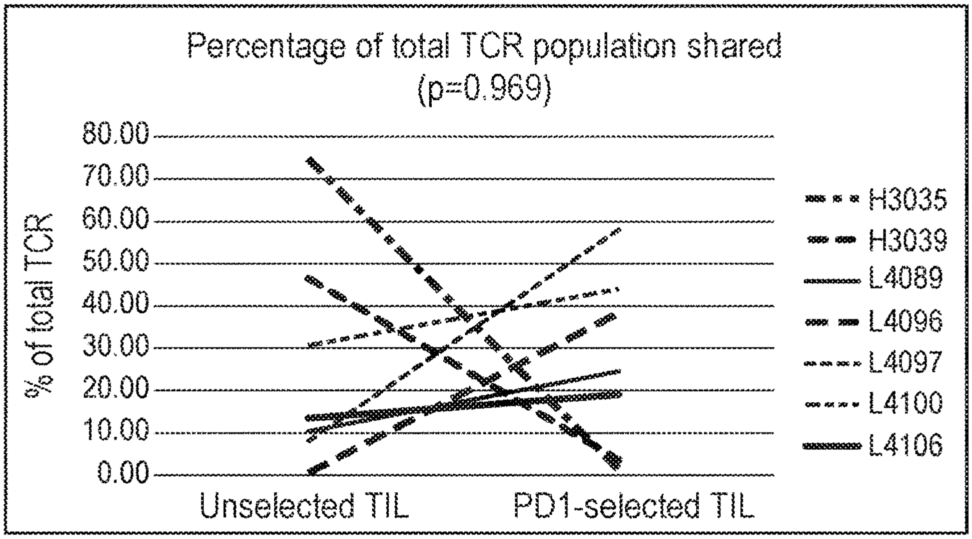
FIG. 135E

| Tumor ID | Histology | PD1-selected TIL generated |
|---|---|---|
| H3035 | HNSCC | Yes |
| H3036 | HNSCC | No<br>Culture Contaminated |
| H3037 | HNSCC | No<br>Culture Contaminated |
| H3038 | HNSCC | Yes |
| H3039 | HNSCC | Yes |
| L4089 | NSCLC | Yes |
| L4096 | NSCLC | Yes |
| L4097 | NSCLC | Yes |
| L4100 | NSCLC | Yes |
| L4101 | NSCLC | Yes |
| L4104 | NSCLC | Yes |
| L4106 | NSCLC | Yes |
| M1132 | Melanoma | Yes |
| M1136 | Melanoma | Yes |
| M1139 | Melanoma | Yes |
| M1141 | Melanoma | Yes |
| OV8030 | Ovarian | Yes |
| OV8042 | Ovarian | Yes |
| OV8042 | Ovarian | Yes |
| T6049 | TNBC | Yes |
| T6056 | TNBC | Yes |
| T6058 | TNBC | Yes |
| T6060 | TNBC | Yes |
| OC20019 | Prostate | Yes |
| OC20030 | Prostate | Yes |
| C10026 | CRC | No<br>Poor digest cell yield |
| CC10027 | CRC | No<br>Poor digest cell yield |
| CC10028 | CRC | Yes |
| CC10029 | CRC | Yes |
| CC10031 | CRC | No<br>Culture Contaminated |
| CC10034 | CRC | Yes |
| CC10037 | CRC | Yes |
| CC10039 | CRC | Yes |

FIG. 137

| Tumor ID | Sample ID | Histology | Date of preparation |
|---|---|---|---|
| H3035 | PD1-selected TIL | HNSCC | 03/15/19 |
| | Unselected TIL | | |
| H3039 | PD1-selected TIL | HNSCC | 04/09/19 |
| | Unselected TIL | | |
| L4089 | PD1-selected TIL | NSCLC | 03/22/19 |
| | Unselected TIL | | |
| L4096 | PD1-selected TIL | NSCLC | 04/04/19 |
| | Unselected TIL | | |
| L4097 | PD1-selected TIL | NSCLC | 03/22/19 |
| | Unselected TIL | | |
| L4100 | PD1-selected TIL | NSCLC | 03/26/19 |
| | Unselected TIL | | |
| L4101 | PD1-selected | NSCLC | 04/04/19 |
| | Unselected TIL | | |
| L4104 | PD1-selected | NSCLC | 03/26/19 |
| | Unselected TIL | | |
| L4106 | PD1-selected | NSCLC | 03/29/19 |
| | Unselected TIL | | |
| M1132 | PD1-selected | Melanoma | 03/26/19 |
| | Unselected TIL | | |
| M1136 | PD1-selected | Melanoma | 03/26/19 |
| | Unselected TIL | | |
| M1139 | PD1-selected | Melanoma | 03/22/19 |
| | Unselected TIL | | |
| M1141 | PD1-selected | Melanoma | 03/29/19 |
| | Unselected TIL | | |

FIG. 139

| Tumor ID | Sample ID | Histology | REP1 Fold Expansion | REP2 Fold Expansion |
|---|---|---|---|---|
| H3035 | PD1-selected TIL | HNSCC | 350 | 2166 |
| | Unselected TIL | | 869 | 1385 |
| H3039 | PD1-selected TIL | HNSCC | 654 | 1082 |
| | Unselected TIL | | 123 | 893 |
| L4089 | PD1-selected TIL | NSCLC | 1502 | 2106 |
| | Unselected TIL | | 2821 | 1416 |
| L4096 | PD1-selected TIL | NSCLC | 582 | 788 |
| | Unselected TIL | | 1749 | 919 |
| L4097 | PD1-selected TIL | NSCLC | 230 | 1982 |
| | Unselected TIL | | 1147 | 2455 |
| L4100 | PD1-selected TIL | NSCLC | 536 | 997 |
| | Unselected TIL | | 1498 | 900 |
| L4101 | PD1-selected | NSCLC | 1346 | 896 |
| | Unselected TIL | | 2196 | 962 |
| L4104 | PD1-selected | NSCLC | 1711 | 1257 |
| | Unselected TIL | | 649 | 1421 |
| L4106 | PD1-selected | NSCLC | 1179 | 1367 |
| | Unselected TIL | | 4500 | 1912 |
| M1132 | PD1-selected | Melanoma | 50 | 234 |
| | Unselected TIL | | 2670 | 1263 |
| M1136 | PD1-selected | Melanoma | 961 | 867 |
| | Unselected TIL | | 693 | 1190 |
| M1139 | PD1-selected | Melanoma | 557 | 1751 |
| | Unselected TIL | | 4908 | 1613 |
| M1141 | PD1-selected | Melanoma | 3429 | 1515 |
| | Unselected TIL | | 4950 | 2107 |

FIG. 141

| Tumor ID | Sample ID | Histology | REP1 Fold Expansion | REP2 Fold Expansion |
|---|---|---|---|---|
| H3035 | PD1-selected TIL | HNSCC | 350 | 2166 |
| | Unselected TIL | | 869 | 1385 |
| H3039 | PD1-selected TIL | HNSCC | 654 | 1082 |
| | Unselected TIL | | 123 | 893 |
| L4089 | PD1-selected TIL | NSCLC | 1502 | 2106 |
| | Unselected TIL | | 2821 | 1416 |
| L4096 | PD1-selected TIL | NSCLC | 582 | 788 |
| | Unselected TIL | | 1749 | 919 |
| L4097 | PD1-selected TIL | NSCLC | 230 | 1982 |
| | Unselected TIL | | 1147 | 2455 |
| L4100 | PD1-selected TIL | NSCLC | 536 | 997 |
| | Unselected TIL | | 1498 | 900 |
| L4101 | PD1-selected | NSCLC | 1346 | 896 |
| | Unselected TIL | | 2196 | 962 |
| L4104 | PD1-selected | NSCLC | 1711 | 1257 |
| | Unselected TIL | | 649 | 1421 |
| L4106 | PD1-selected | NSCLC | 1179 | 1367 |
| | Unselected TIL | | 4500 | 1912 |
| M1132 | PD1-selected | Melanoma | 50 | 234 |
| | Unselected TIL | | 2670 | 1263 |
| M1136 | PD1-selected | Melanoma | 961 | 867 |
| | Unselected TIL | | 693 | 1190 |
| M1139 | PD1-selected | Melanoma | 557 | 1751 |
| | Unselected TIL | | 4908 | 1613 |
| M1141 | PD1-selected | Melanoma | 3429 | 1515 |
| | Unselected TIL | | 4950 | 2107 |

FIG. 142

| Tumor ID | Sample ID | Histology | Date of Preparation | REP1 Fold Expansion | REP2 Fold Expansion |
|---|---|---|---|---|---|
| **H3035** | PD1-selected TIL | HNSCC | 03/15/19 | 350 | 2166 |
| | Unselected TIL | | | 869 | 1385 |
| **H3039** | PD1-selected TIL | HNSCC | 04/09/19 | 654 | 1082 |
| | Unselected TIL | | | 123 | 893 |
| **L4089** | PD1-selected TIL | NSCLC | 03/22/19 | 1502 | 2106 |
| | Unselected TIL | | | 2821 | 1416 |
| **L4096** | PD1-selected TIL | NSCLC | 04/04/19 | 582 | 788 |
| | Unselected TIL | | | 1749 | 919 |
| **L4097** | PD1-selected TIL | NSCLC | 03/22/19 | 230 | 1982 |
| | Unselected TIL | | | 1147 | 2455 |
| **L4100** | PD1-selected TIL | NSCLC | 03/26/19 | 536 | 997 |
| | Unselected TIL | | | 1498 | 900 |
| **L4101** | PD1-selected | NSCLC | 04/04/19 | 1346 | 896 |
| | Unselected TIL | | | 2196 | 962100 |
| **L4104** | PD1-selected | NSCLC | | | |
| | Unselected TIL | | | | |
| **L4106** | PD1-selected | NSCLC | 03/29/19 | 1179 | 1367 |
| | Unselected TIL | | | 4500 | 1912 |
| **M1132** | PD1-selected | Melanoma | 03/26/19 | 50 | 234 |
| | Unselected TIL | | | 2670 | 1263 |
| **M1136** | PD1-selected | Melanoma | 03/26/19 | 961 | 867 |
| | Unselected TIL | | | 693 | 1190 |
| **M1139** | PD1-selected | Melanoma | 03/22/19 | 557 | 1751 |
| | Unselected TIL | | | 4908 | 1613 |
| **M1141** | PD1-selected | Melanoma | 03/29/19 | 3429 | 1515 |
| | Unselected TIL | | | 4950 | 2107 |

FIG. 145

| Tumor ID | Sample ID | Histology | REP1 Fold Expansion | REP2 Fold Expansion |
|---|---|---|---|---|
| **H3035** | PD1-selected TIL | HNSCC | 350 | 2166 |
| | Unselected TIL | | 869 | 1385 |
| **H3039** | PD1-selected TIL | HNSCC | 654 | 1082 |
| | Unselected TIL | | 123 | 893 |
| **L4089** | PD1-selected TIL | NSCLC | 1502 | 2106 |
| | Unselected TIL | | 2821 | 1416 |
| **L4096** | PD1-selected TIL | NSCLC | 582 | 788 |
| | Unselected TIL | | 1749 | 919 |
| **L4097** | PD1-selected TIL | NSCLC | 230 | 1982 |
| | Unselected TIL | | 1147 | 2455 |
| **L4100** | PD1-selected TIL | NSCLC | 536 | 997 |
| | Unselected TIL | | 1498 | 900 |
| **L4101** | PD1-selected | NSCLC | 1346 | 896 |
| | Unselected TIL | | 2196 | 962 |
| **L4104** | PD1-selected | NSCLC | 1711 | 1257 |
| | Unselected TIL | | 649 | 1421 |
| **L4106** | PD1-selected | NSCLC | 1179 | 1367 |
| | Unselected TIL | | 4500 | 1912 |
| **M1132** | PD1-selected | Melanoma | 50 | 234 |
| | Unselected TIL | | 2670 | 1263 |
| **M1136** | PD1-selected | Melanoma | 961 | 867 |
| | Unselected TIL | | 693 | 1190 |
| **M1139** | PD1-selected | Melanoma | 557 | 1751 |
| | Unselected TIL | | 4908 | 1613 |
| **M1141** | PD1-selected | Melanoma | 3429 | 1515 |
| | Unselected TIL | | 4950 | 2107 |

FIG. 147

| Conditions | Full-Scale Process |
|---|---|
| **REP-1**<br>**TIL**<br>**Feeders**<br>**CM1**<br>**IL-2**<br>**OKT3 (30 ng/mL)**<br>**G-Rex** | **Day 0:** REP-1<br>PD1 sort count<br>100e6<br>1 L<br>6000 IU/mL<br>30 ng/mL<br>100MCS |
| **REP-2**<br>**TIL**<br>**Feeders**<br>**CM2**<br>**IL-2**<br>**OKT3 (30 ng/mL)**<br>**G-Rex** | **Day 11:** REP-2<br>5e6-200e6 TVC<br>5e9<br>5 L<br>3000 IU/mL<br>30 ng/mL<br>500MCS |
| **Scale up** | **Day 16:** Volume reduce and split up to 5 G-Rex500MCS in CM4+3000 IU/mL of IL-2 |
| **REP-2 Harvest** | **Day 22:** REP-2 Harvest |

FIG. 154

Legend: PD-1 expression in multiple histologies. Percentage of PD-1+ TIL in the CD3+ TIL population are plotted for individual samples within each histology. Horizontal lines represent the mean percentages of each subset and vertical lines represent the standard errors.

user1/190621 PD-1 sort/Super Sort/CC28 sort ( [2 Way] Data Source - 1 )
Worksheet
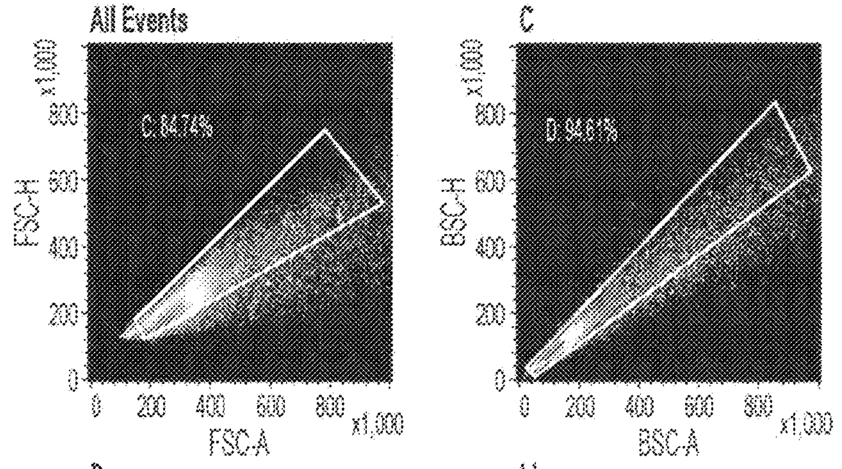
Gates and Statistics
Displaying 100,000 / 707,455 events
| Name | Events | %Parent | %Total |
|---|---|---|---|
| All Events | 100,000 | 0.00% | 100.00% |
| C | 84,736 | 84.74% | 84.74% |
| D | 80,165 | 94.61% | 80.17% |
| Live | 76,009 | 94.82% | 76.01% |
| CD3 | 4,232 | 5.57% | 4.23% |
| PD1 hi | 1,565 | 36.98% | 1.57% |
| PD1- | 767 | 18.12% | 0.77% |
| PD1 mid | 1,720 | 40.64% | 1.72% |
| J | 63,530 | 63.53% | 63.53% |
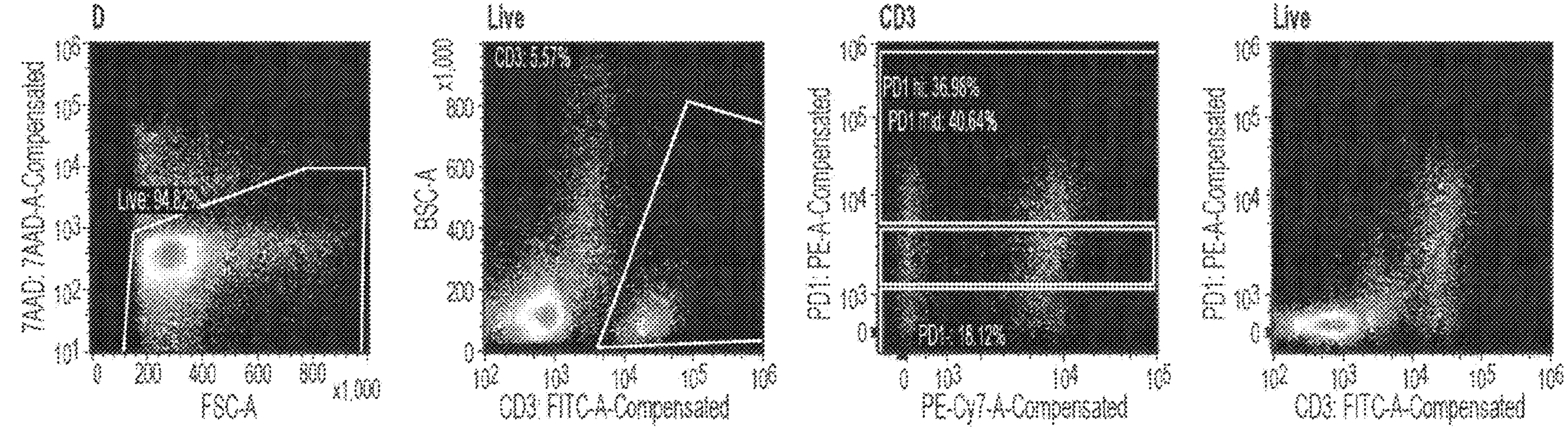
FIG. 158A user1/190621 PD-1 sort/Super Sort/CC29 sort ( [2 Way] Data Source - 1 )
Worksheet
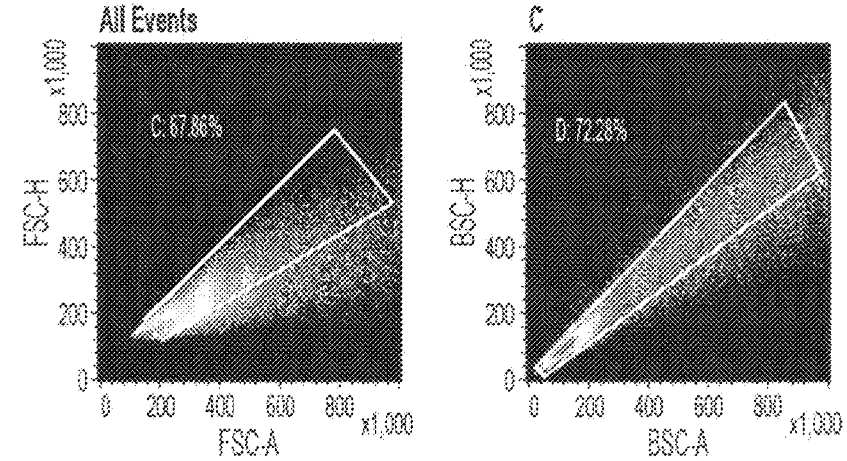
Gates and Statistics
Displaying 100,000 / 1,578,350 events
| Name | Events | %Parent | %Total |
|---|---|---|---|
| □ All Events | 100,000 | 0.00% | 100.00% |
| □ C | 67,857 | 67.86% | 67.86% |
| □ D | 49,049 | 72.28% | 49.05% |
| □ Live | 29,607 | 60.36% | 29.61% |
| □ CD3 | 1,971 | 6.66% | 1.97% |
| □ PD1 hi | 974 | 49.42% | 0.97% |
| □ PD1- | 311 | 15.78% | 0.31% |
| □ PD1 mid | 621 | 31.51% | 0.62% |
| □ J | 25,031 | 25.03% | 25.03% |
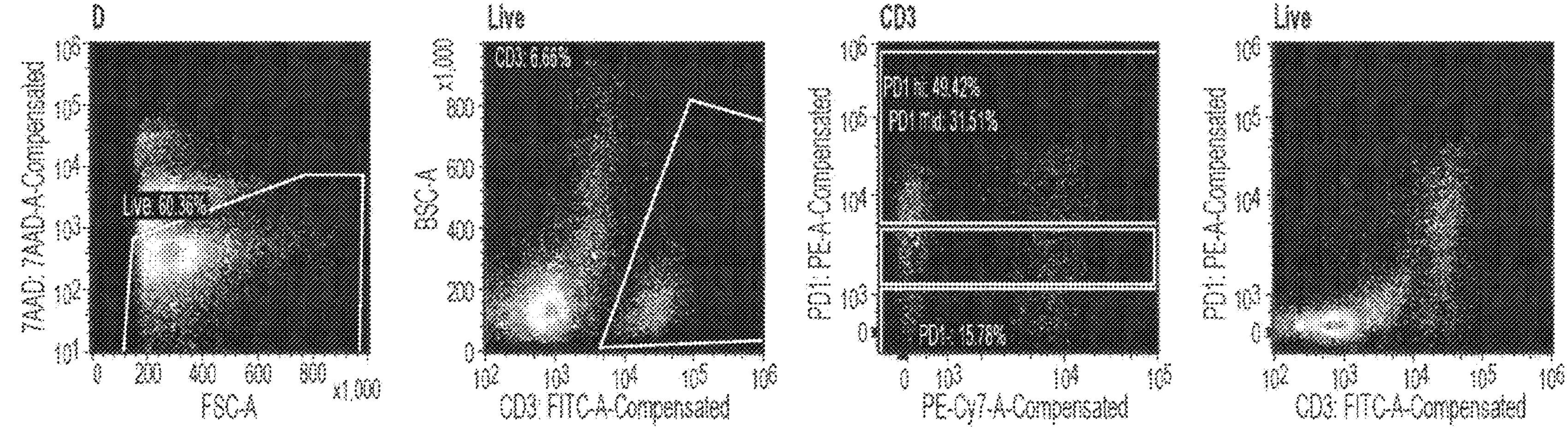
FIG. 158B

| Name | Events | %Parent | %Total |
|---|---|---|---|
| All Events | 100,000 | 0.00% | 100.00% |
| C | 71,513 | 71.51% | 71.51% |
| D | 54,010 | 75.52% | 54.01% |
| Live | 38,419 | 71.13% | 38.42% |
| CD3 | 25,417 | 66.16% | 25.42% |
| PD1 hi | 3,585 | 14.10% | 3.59% |
| PD1- | 11,606 | 45.66% | 11.61% |
| PD1-hi | 3,346 | 13.16% | 3.35% |
| PD1 neg | 11,334 | 44.59% | 11.33% |
| J | 25,739 | 25.74% | 25.74% |

| Name | Events | %Parent | %Total |
|---|---|---|---|
| All Events | 100,000 | 0.00% | 100.00% |
| C | 70,563 | 70.56% | 70.56% |
| D | 55,510 | 78.67% | 55.51% |
| Live | 30,691 | 55.29% | 30.69% |
| CD3 | 16,118 | 52.52% | 16.12% |
| PD1 hi | 2,149 | 13.33% | 2.15% |
| PD1- | 8,044 | 49.91% | 8.04% |
| PD1-hi | 1,995 | 12.38% | 2.00% |
| PD1 neg | 7,854 | 48.73% | 7.85% |
| J | 19,647 | 19.65% | 19.65% |

user1/190301 M1139/Super Sort/H3035 sort - 1 ( [2 Way] Data Source - 1 )
Worksheet
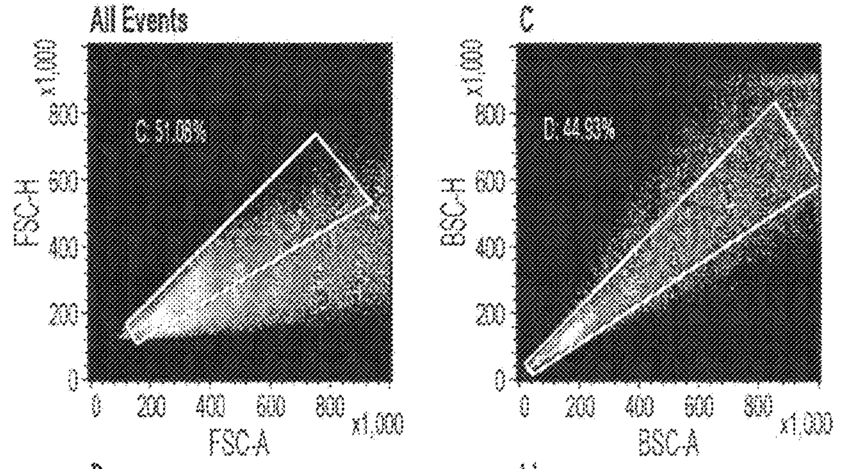
Gates and Statistics
Displaying 100,000 / 360,489 events
| Name | Events | %Parent | %Total |
|---|---|---|---|
| All Events | 100,000 | 0.00% | 100.00% |
| C | 51,082 | 51.08% | 51.08% |
| D | 22,953 | 44.93% | 22.95% |
| Live | 19,910 | 86.74% | 19.91% |
| CD3 | 8,124 | 40.80% | 8.12% |
| PD1 hi | 2,300 | 28.31% | 2.30% |
| PD1- | 2,185 | 26.90% | 2.19% |
| PD1 mid | 3,184 | 39.19% | 3.18% |
| J | 11,577 | 11.58% | 11.58% |
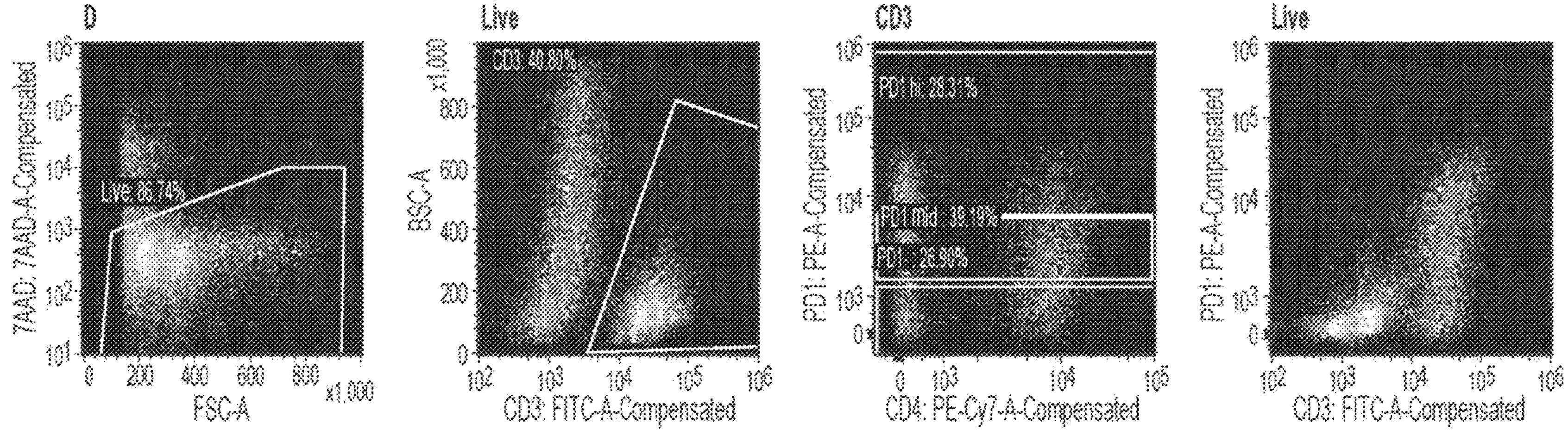
FIG. 158G user1/190318 pd1/Super Sort/H3036 sort ( [2 Way] Data Source - 1 )
Worksheet
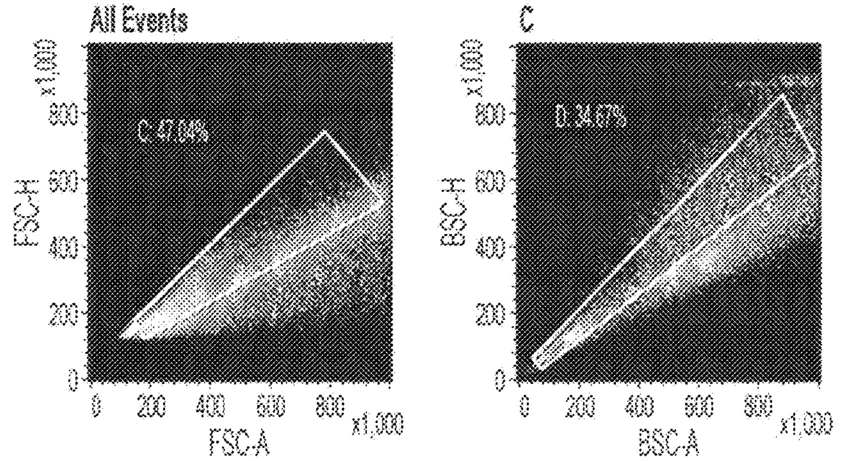
Gates and Statistics
Displaying 100,000 / 1,080,259 events
| Name | Events | %Parent | %Total |
|---|---|---|---|
| All Events | 100,000 | 0.00% | 100.00% |
| C | 47,038 | 47.04% | 47.04% |
| D | 16,307 | 34.67% | 16.31% |
| Live | 14,392 | 88.26% | 14.39% |
| CD3 | 2,789 | 19.38% | 2.79% |
| PD1 hi | 1,440 | 51.63% | 1.44% |
| PD1- | 840 | 30.12% | 0.84% |
| PD1 mid | 461 | 16.53% | 0.46% |
| J | 9,445 | 9.45% | 9.45% |
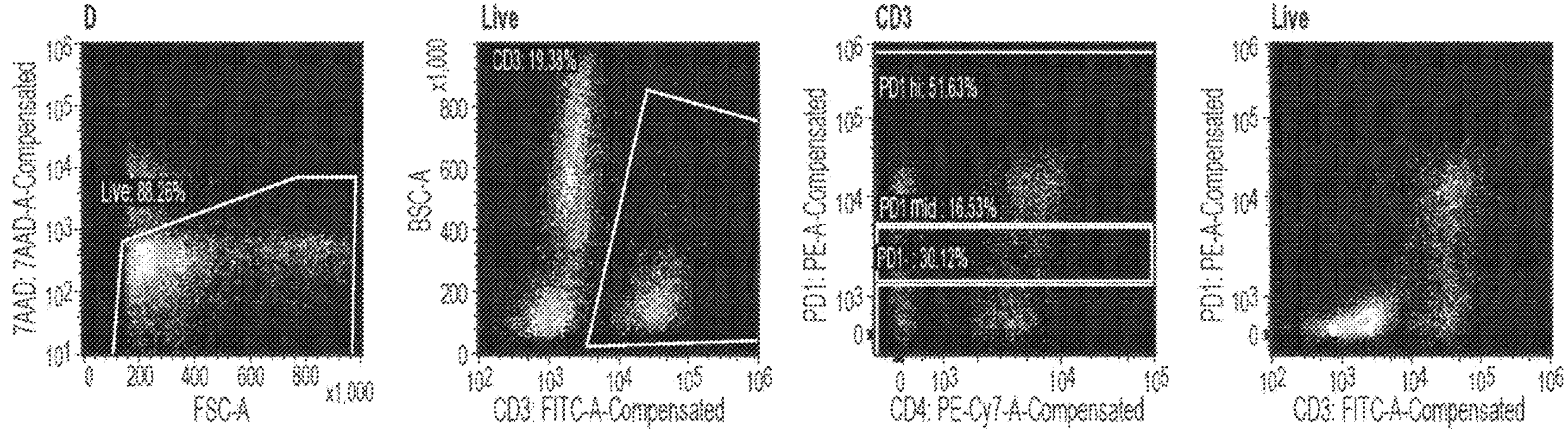
FIG. 158H user1/190318 L4106 pd1/Super Sort/H3037 sort ( [2 Way] Data Source - 1 )
Worksheet
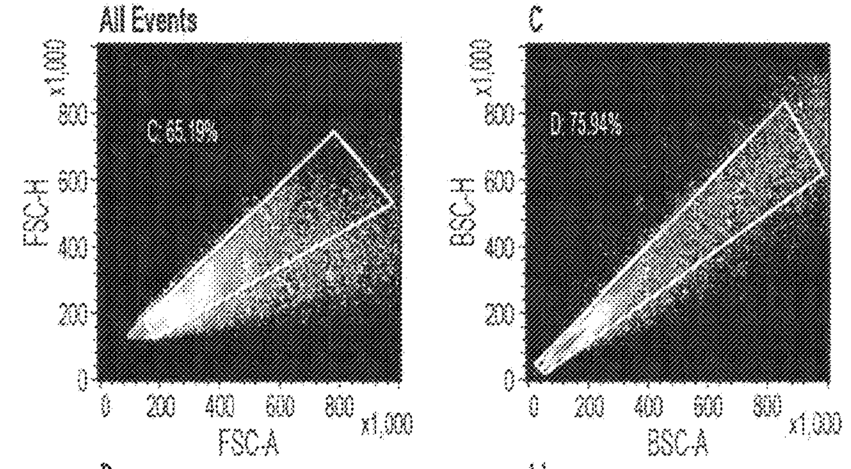
Gates and Statistics
Displaying 100,000 / 2,668,742 events
| Name | Events | %Parent | %Total |
|---|---|---|---|
| All Events | 100,000 | 0.00% | 100.00% |
| C | 65,193 | 65.19% | 65.19% |
| D | 49,505 | 75.94% | 49.51% |
| Live | 40,140 | 81.08% | 40.14% |
| CD3 | 1,175 | 2.93% | 1.18% |
| PD1 hi | 572 | 48.68% | 0.57% |
| PD1- | 278 | 23.66% | 0.28% |
| PD1 mid | 311 | 26.47% | 0.31% |
| J | 25,662 | 25.66% | 25.66% |
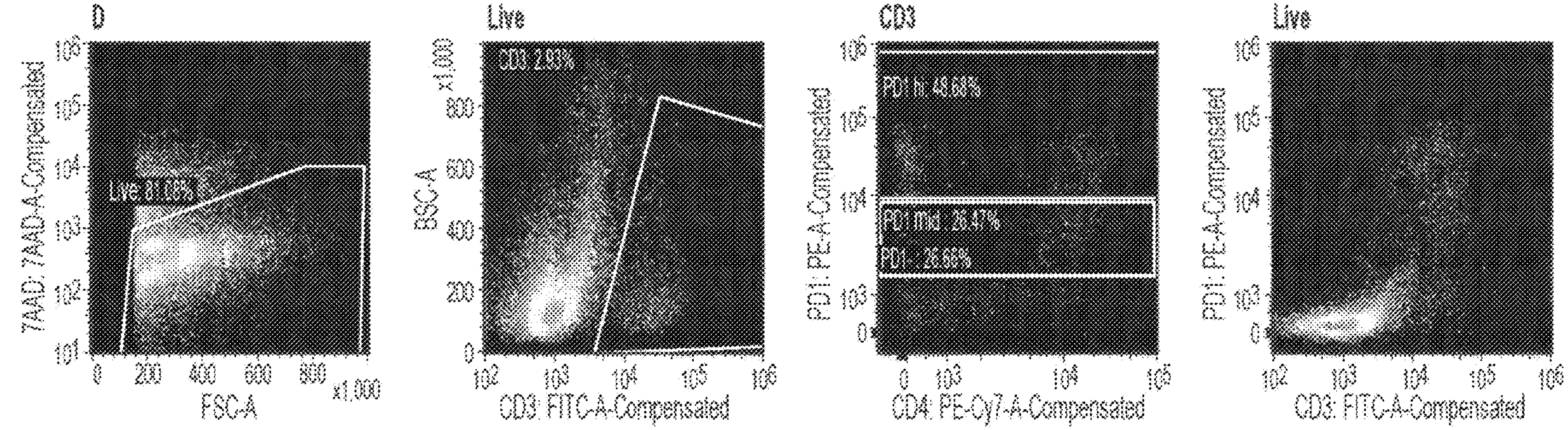
FIG. 158I user1/Experiment 3/13/2019 1:34:52 PM/Super Sort/H3038 sort ( [2 Way] Data Source - 1 )

Worksheet

Gates and Statistics

Displaying 100,000 / 135,889 events

| Name | Events | %Parent | %Total |
|---|---|---|---|
| All Events | 100,000 | 0.00% | 100.00% |
| C | 70,958 | 70.96% | 70.96% |
| D | 45,925 | 64.73% | 45.93% |
| Live | 26,130 | 56.89% | 26.13% |
| CD3 | 8,173 | 31.28% | 8.17% |
| PD1 hi | 2,680 | 32.79% | 2.68% |
| PD1- | 2,286 | 27.97% | 2.29% |
| PD1 mid | 2,977 | 36.42% | 2.98% |
| J | 13,976 | 13.98% | 13.98% |

user1/190318 pd1/Super Sort/H3039 sort ( [2 Way] Data Source - 1 )
Worksheet
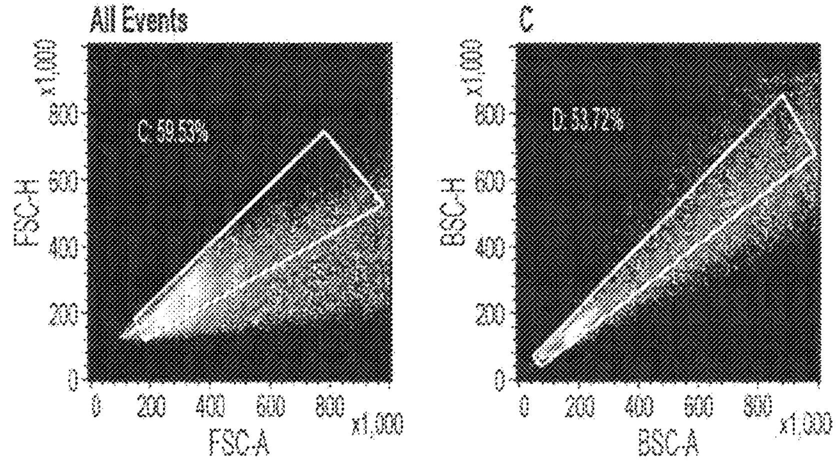
Gates and Statistics
Displaying 100,000 / 177,600 events
| Name | Events | %Parent | %Total |
|---|---|---|---|
| All Events | 100,000 | 0.00% | 100.00% |
| C | 59,528 | 59.53% | 59.53% |
| D | 31,981 | 53.72% | 31.98% |
| Live | 27,816 | 86.98% | 27.82% |
| CD3 | 16,778 | 60.32% | 15.78% |
| PD1 hi | 4,911 | 29.27% | 4.91% |
| PD1- | 6,129 | 36.53% | 6.13% |
| PD1 mid | 5,149 | 30.69% | 5.15% |
| J | 17,783 | 17.78% | 17.78% |
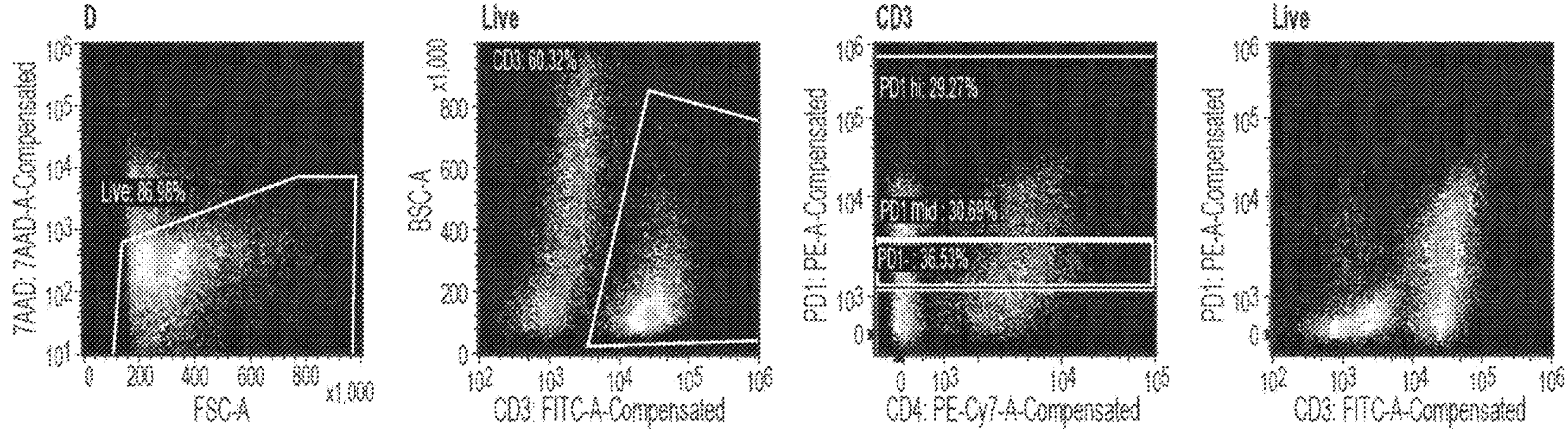
FIG. 158K user1/190228 L4089 L4097/Super Sort/L4089 sort - 2 ( [2 Way] Data Source - 1 )
Worksheet
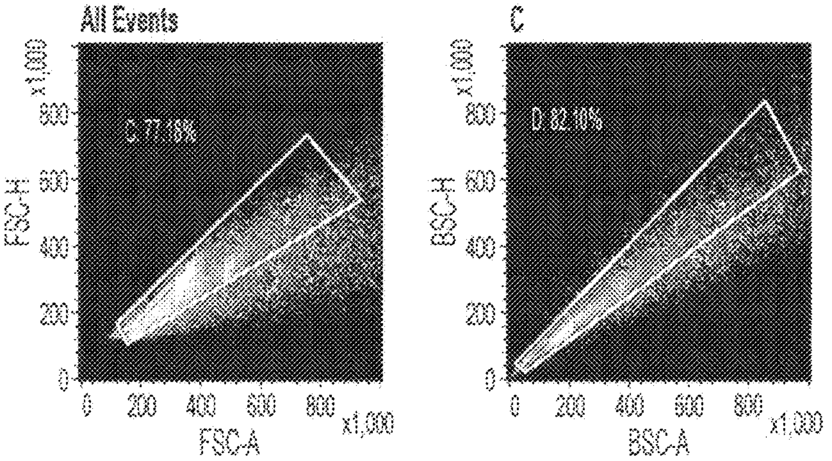
Gates and Statistics
| Name | Events | %Parent | %Total |
|---|---|---|---|
| All Events | 62,076 | 0.00% | 100.00% |
| C | 47,909 | 77.18% | 77.18% |
| D | 39,331 | 82.10% | 63.36% |
| Live | 32,167 | 81.79% | 51.82% |
| CD3 | 13,143 | 40.86% | 21.17% |
| PD1 hi | 4,094 | 31.15% | 6.60% |
| PD1- | 3,813 | 29.01% | 6.14% |
| PD1 mid | 4,582 | 34.86% | 7.38% |
| J | 24,460 | 39.40% | 39.40% |
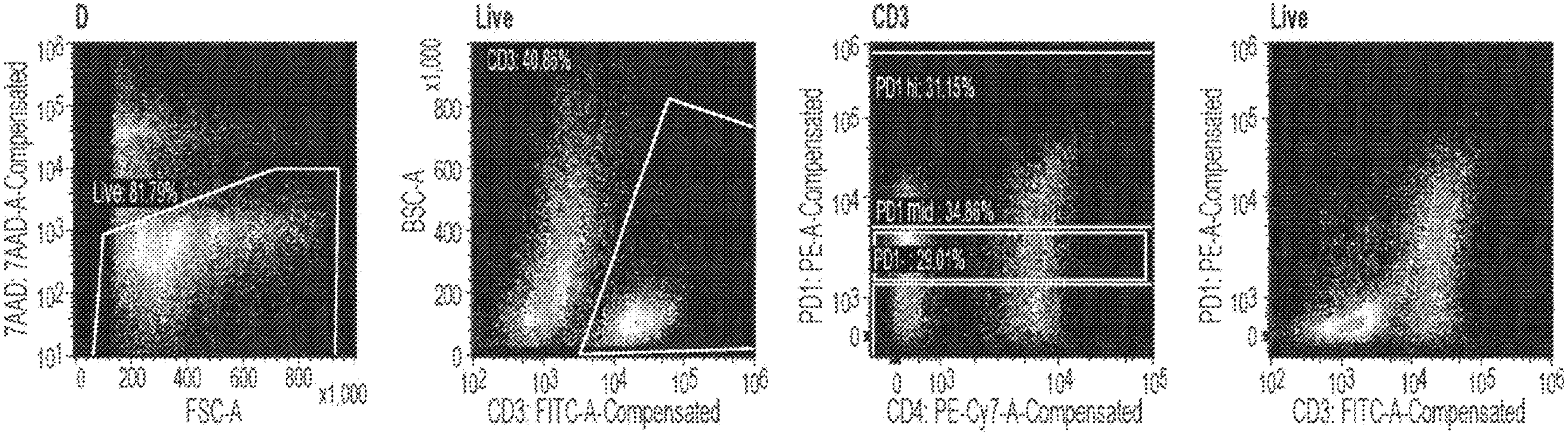
FIG. 158L user1/Experiment 3/13/2019 1:34:52 PM/Super Sort/L4096 sort ( [2 Way] Data Source - 1 )
Worksheet
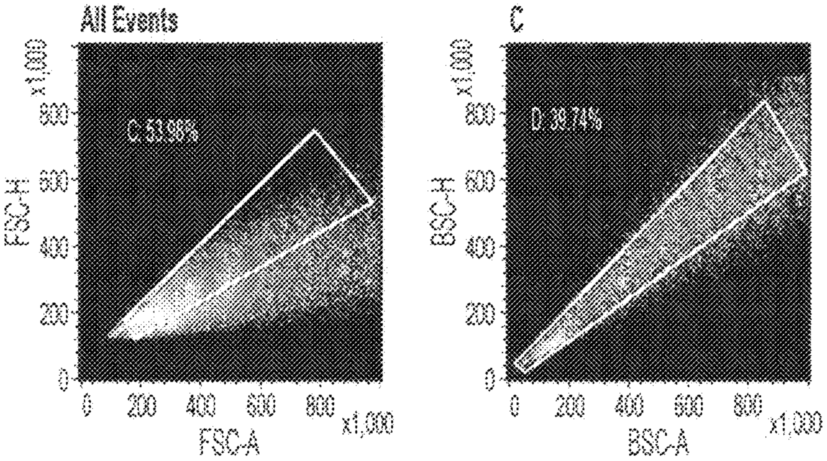
Gates and Statistics
Displaying 100,000 / 946,878 events
| Name | Events | %Parent | %Total |
|---|---|---|---|
| All Events | 100,000 | 0.00% | 100.00% |
| C | 53,980 | 53.98% | 53.98% |
| D | 21,453 | 39.74% | 21.45% |
| Live | 6,296 | 29.35% | 6.30% |
| CD3 | 3,177 | 50.46% | 3.18% |
| PD1 hi | 640 | 20.14% | 0.64% |
| PD1- | 1,251 | 39.38% | 1.25% |
| PD1 mid | 1,206 | 37.96% | 1.21% |
| J | 4,633 | 4.63% | 4.63% |
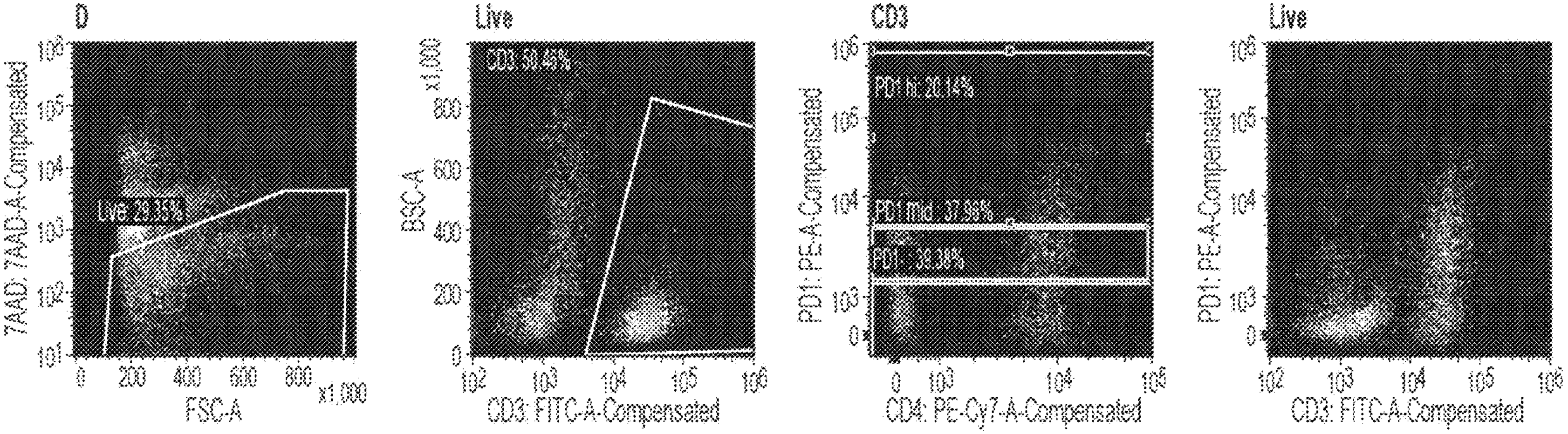
FIG. 158M user1/190228 L4089 L4097/Super Sort/L4097 pd1- and pd1 hi sort ( [2 Way] Data Source - 1 )
Worksheet
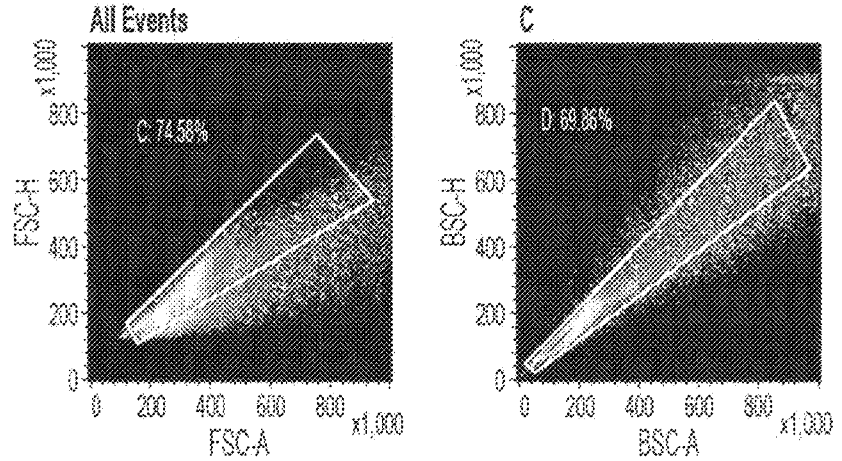
Gates and Statistics Displaying 100,000 / 134,191 events
| Name | Events | %Parent | %Total |
|---|---|---|---|
| All Events | 100,000 | 0.00% | 100.00% |
| C | 74,579 | 74.58% | 74.58% |
| D | 52,101 | 69.86% | 52.10% |
| Live | 38,719 | 74.32% | 38.72% |
| CD3 | 22,209 | 57.36% | 22.21% |
| PD1 hi | 16,533 | 74.44% | 16.53% |
| PD1- | 2,380 | 10.72% | 2.38% |
| PD1 mid | 2,839 | 12.78% | 2.84% |
| J | 25,245 | 25.25% | 25.25% |
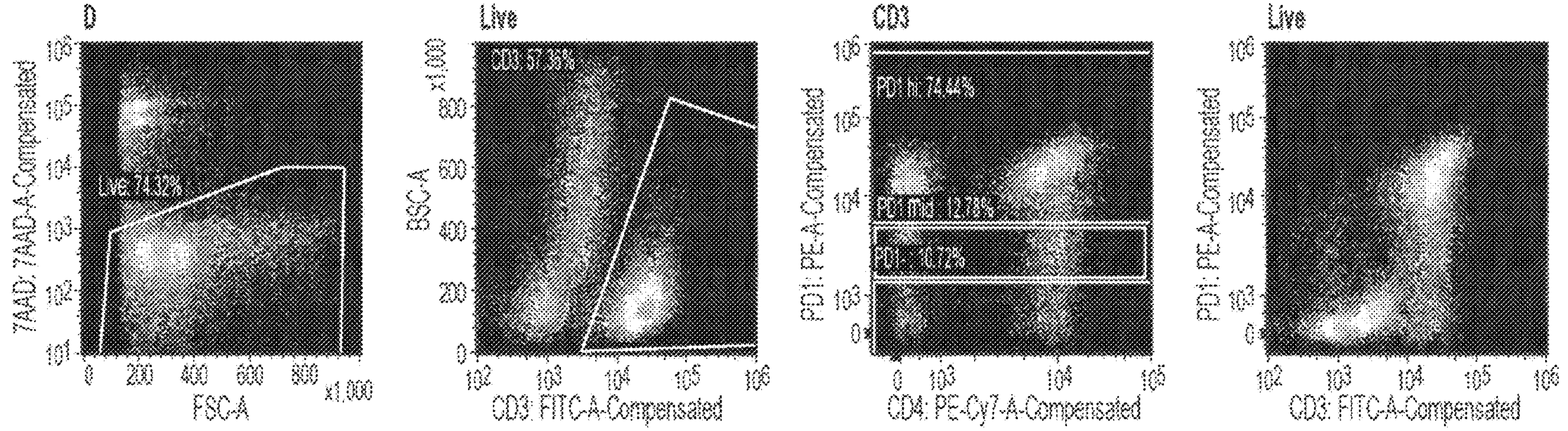
FIG. 158N

| Name | Events | %Parent | %Total |
|---|---|---|---|
| All Events | 100,000 | 0.00% | 100.00% |
| C | 80,171 | 80.17% | 80.17% |
| D | 66,984 | 83.55% | 66.98% |
| Live | 58,623 | 87.52% | 58.62% |
| CD3 | 26,058 | 44.45% | 26.06% |
| PD1 hi | 11,292 | 43.33% | 11.29% |
| PD1- | 3,822 | 14.67% | 3.82% |
| PD1 mid | 10,375 | 39.82% | 10.38% |
| J | 46,314 | 46.31% | 46.31% |

user1/190313 PD1 L4101/Super Sort/L4101 sort ( [2 Way] Data Source - 1 )
Worksheet
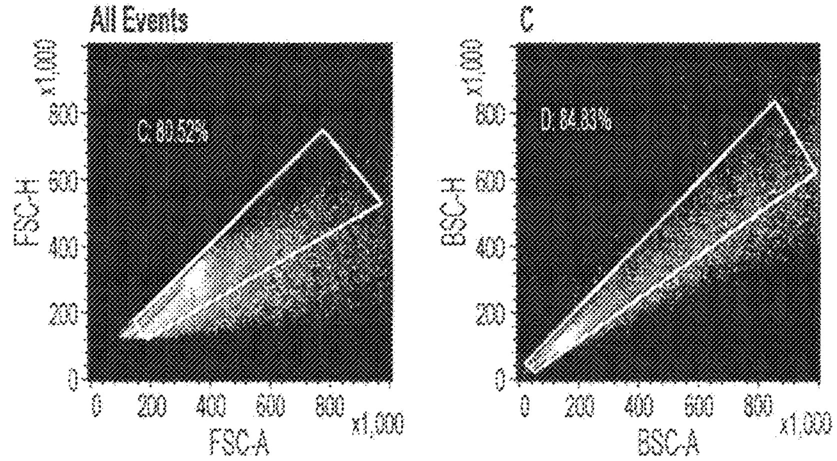
Gates and Statistics
| Name | Events | %Parent | %Total |
|---|---|---|---|
| All Events | 85,559 | 0.00% | 100.00% |
| C | 68,890 | 80.52% | 80.52% |
| D | 58,442 | 84.83% | 68.31% |
| Live | 56,154 | 96.09% | 65.63% |
| CD3 | 30,000 | 53.42% | 35.06% |
| PD1 hi | 9,842 | 32.81% | 11.50% |
| PD1- | 5,882 | 19.61% | 6.87% |
| PD1 mid | 13,382 | 44.61% | 15.64% |
| J | 34,608 | 40.45% | 40.45% |
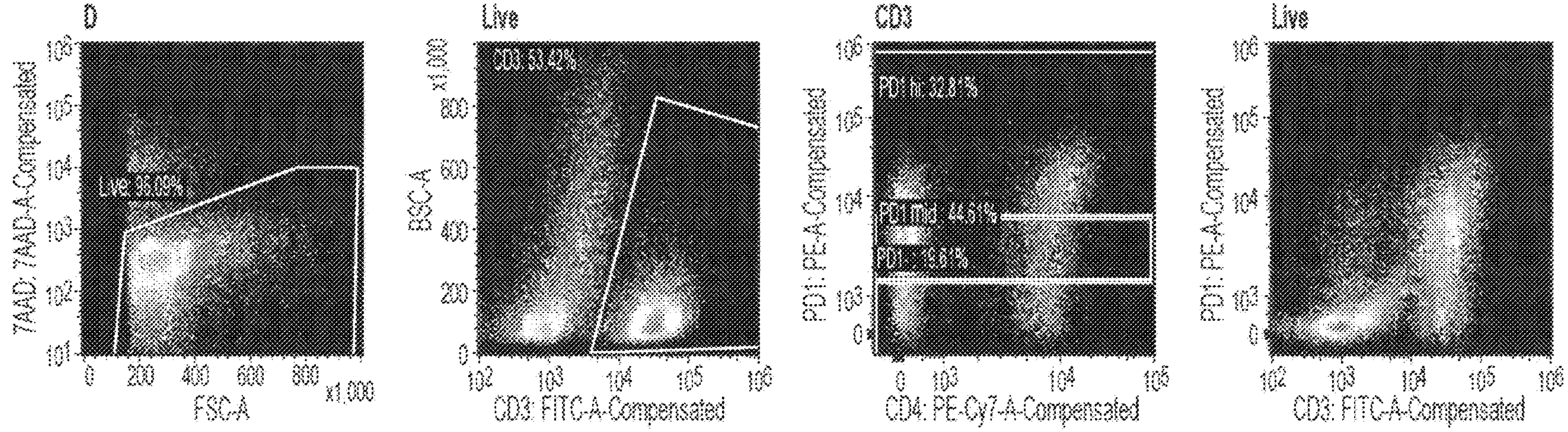
FIG. 158P user1/190308 L4106 pd1/Super Sort/L4106 CD3 pure ( Data Source - 1 )
Worksheet
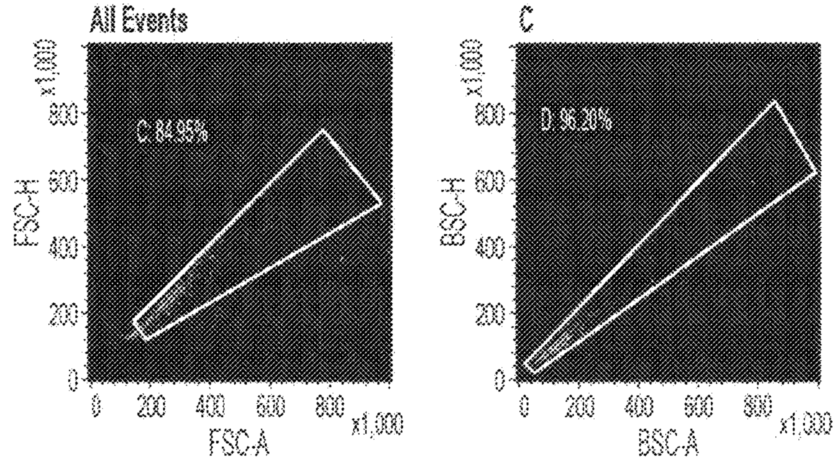
Gates and Statistics
| Name | Events | %Parent | %Total | |
|---|---|---|---|---|
| ☐ All Events | 372 | 0.00% | 100.00% | |
| ☐ C | 316 | 84.95% | 84.95% | |
| ☐ D | 304 | 96.20% | 81.72% | |
| ☐ Live | 300 | 98.68% | 80.65% | |
| ☐ CD3 | 295 | 98.33% | 79.30% | |
| ☐ PD1 hi | 114 | 38.64% | 30.65% | |
| ☐ PD1- | 88 | 29.83% | 23.66% | |
| ☐ PD1 mid | 92 | 31.19% | 24.73% | |
| ☐ J | 223 | 59.95% | 59.95% | |
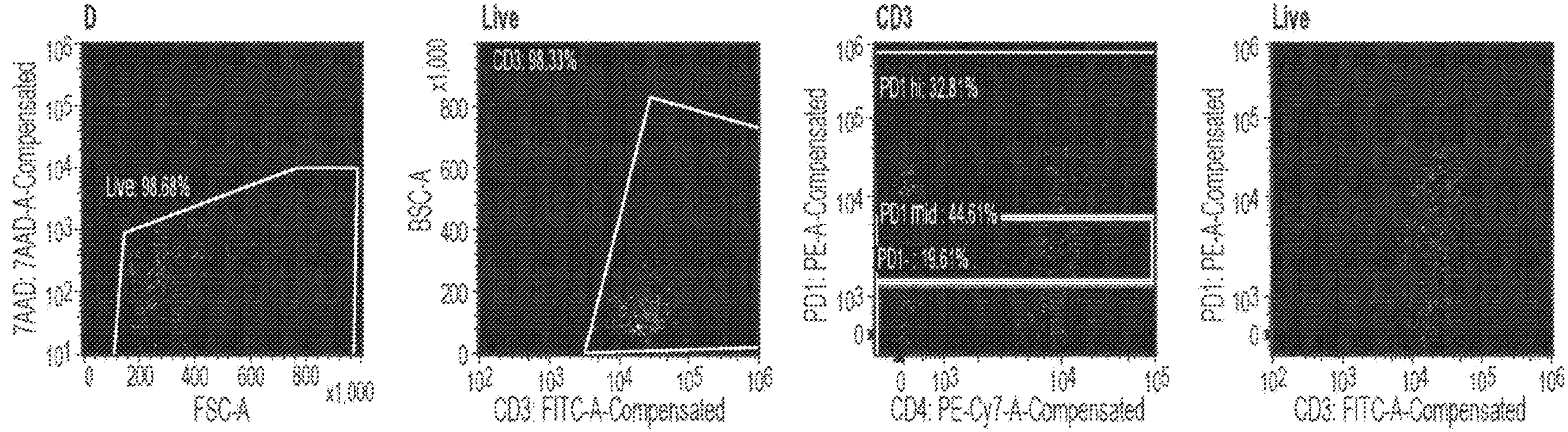
FIG. 158R

| Name | Events | %Parent | %Total |
|---|---|---|---|
| All Events | 100,000 | 0.00% | 100.00% |
| C | 74,151 | 74.15% | 74.15% |
| D | 42,064 | 56.73% | 42.06% |
| Live | 24,634 | 58.56% | 24.63% |
| CD3 | 13,854 | 56.24% | 13.85% |
| PD1 hi | 8,417 | 60.76% | 8.42% |
| PD1- | 2,491 | 17.98% | 2.49% |
| PD1 mid | 2,729 | 19.70% | 2.73% |
| J | 17,974 | 17.97% | 17.97% |

user1/190308 L4106 pd1/Super Sort/M1141 sort - 1 ( [2 Way] Data Source - 1 )
Worksheet
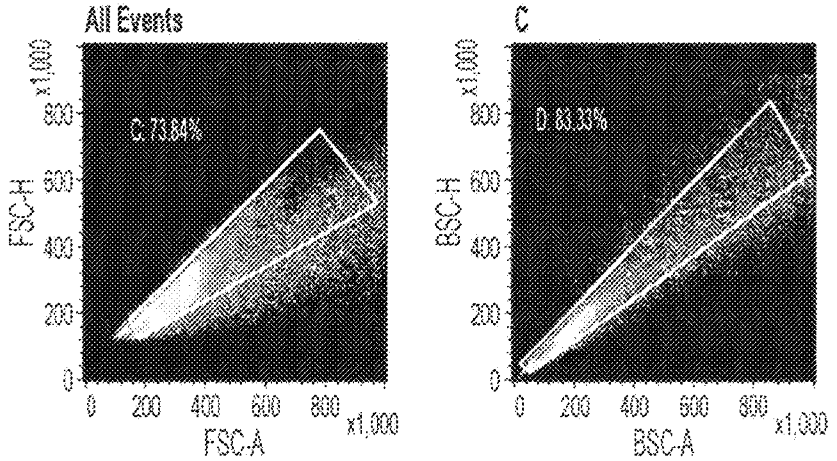
Gates and Statistics
Displaying 100,000 / 435,779 events
| Name | Events | %Parent | %Total |
|---|---|---|---|
| All Events | 100,000 | 0.00% | 100.00% |
| C | 73,837 | 73.84% | 73.84% |
| D | 61,528 | 83.33% | 61.53% |
| Live | 59,662 | 96.97% | 59.66% |
| CD3 | 6,857 | 11.49% | 5.86% |
| PD1 hi | 773 | 11.27% | 0.77% |
| PD1- | 4,394 | 64.08% | 4.39% |
| PD1 mid | 1,321 | 19.26% | 1.32% |
| J | 40,649 | 40.65% | 40.65% |
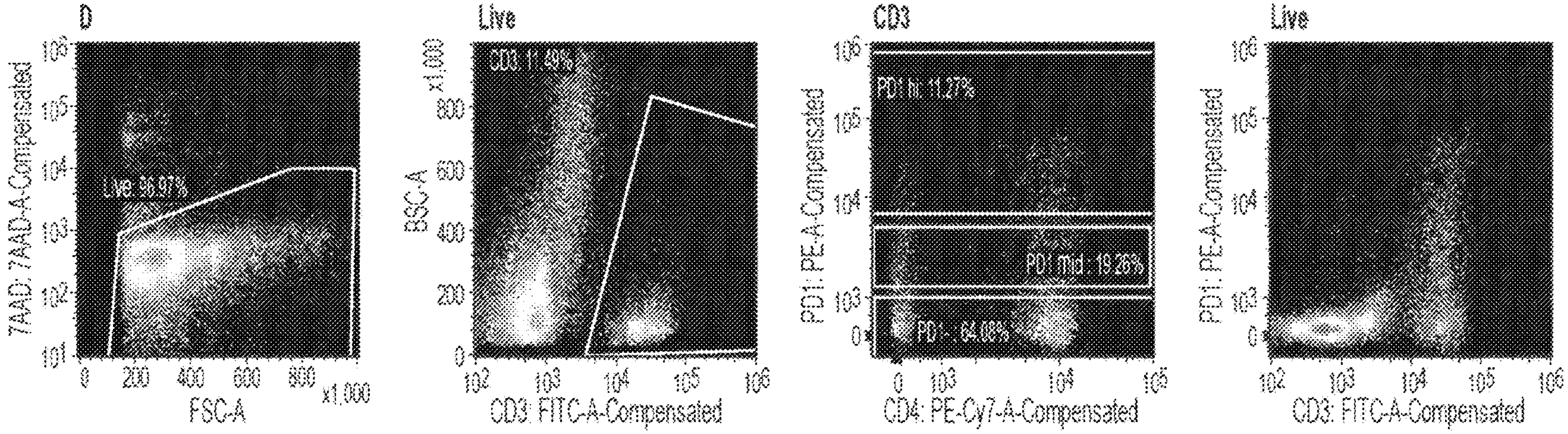
FIG. 158V user1/190403 pd1 research/Super Sort/OC20017 sort ( [2 Way] Data Source - 1 )
Worksheet
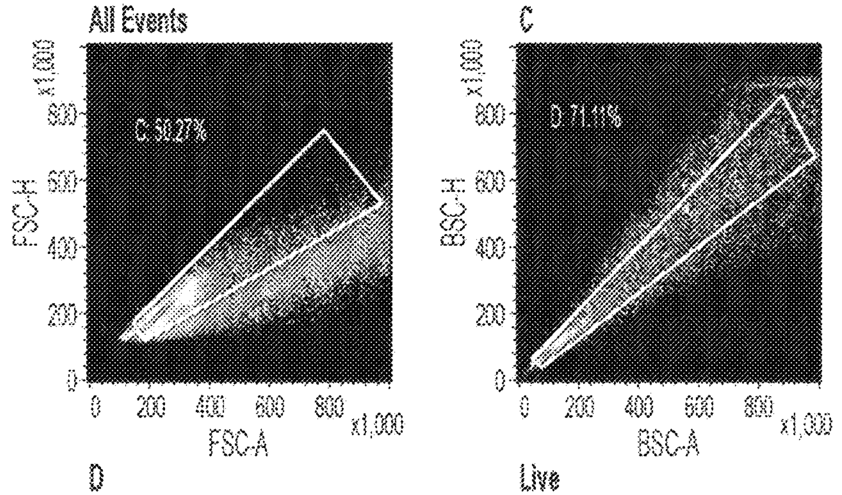
Gates and Statistics Displaying 100,000 / 198,892 events
| Name | Events | %Parent | %Total |
|---|---|---|---|
| All Events | 100,000 | 0.00% | 100.00% |
| C | 50,267 | 50.27% | 50.27% |
| D | 35,745 | 71.11% | 35.75% |
| Live | 33,309 | 93.19% | 33.31% |
| CD3 | 15,030 | 45.12% | 15.03% |
| PD1 hi | 5,920 | 39.39% | 5.92% |
| PD1- | 6,238 | 41.50% | 6.24% |
| PD1 mid | 2,571 | 17.11% | 2.57% |
| J | 22,093 | 22.09% | 22.09% |
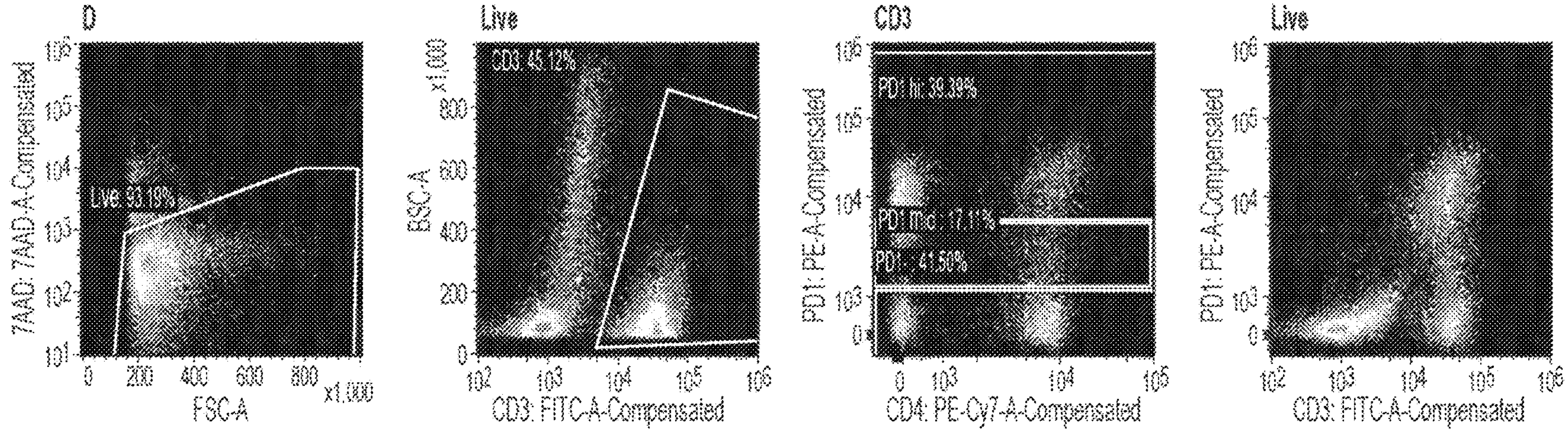
FIG. 158W user1/190425 OC20030/Super Sort/OC20030 cd3 pure ( [2 Way] Data Source - 1 )
Worksheet
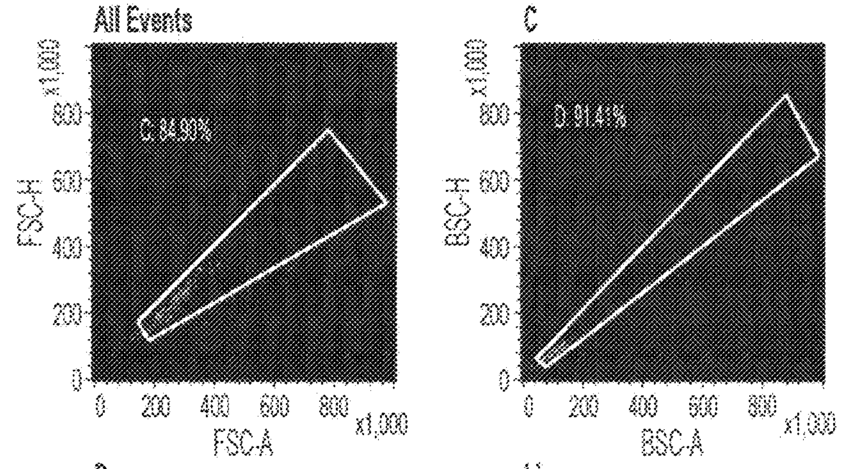
Gates and Statistics
| Name | Events | %Parent | %Total |
|---|---|---|---|
| All Events | 192 | 0.00% | 100.00% |
| C | 163 | 84.90% | 84.90% |
| D | 149 | 91.41% | 77.60% |
| Live | 145 | 97.32% | 75.52% |
| CD3 | 140 | 96.55% | 72.92% |
| PD1 hi | 17 | 12.14% | 8.85% |
| PD1- | 39 | 27.86% | 20.31% |
| PD1 mid | 78 | 55.71% | 40.63% |
| J | 114 | 59.38% | 59.38% |
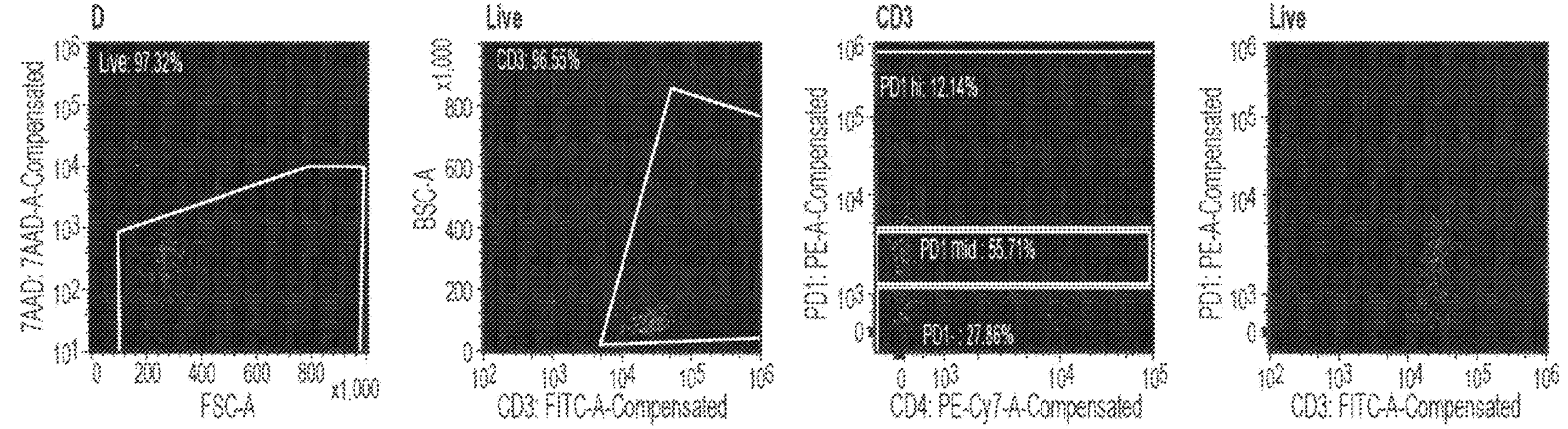
FIG. 158X user1/190304 OV8030 PD1/Super Sort/OV8030 sort - 2 ( [2 Way] Data Source - 1 )

Worksheet

Gates and Statistics Displaying 100,000 / 389,100 events

| Name | Events | %Parent | %Total | |
|---|---|---|---|---|
| All Events | 100,000 | 0.00% | 100.00% | |
| C | 66,706 | 66.71% | 66.71% | |
| D | 49,520 | 74.24% | 49.52% | |
| Live | 8,502 | 17.17% | 8.50% | |
| CD3 | 4,721 | 55.53% | 4.72% | |
| PD1 hi | 2,157 | 45.69% | 2.16% | |
| PD1- | 980 | 20.76% | 0.98% | |
| PD1 mid | 1,486 | 31.48% | 1.49% | |
| J | 8,340 | 8.34% | 8.34% | |

Gates and Statistics — Displaying 100,000 / 893,862 events

| Name | Events | %Parent | %Total |
|---|---|---|---|
| All Events | 100,000 | 0.00% | 100.00% |
| C | 51,109 | 51.11% | 51.11% |
| D | 26,916 | 52.66% | 26.92% |
| Live | 9,209 | 34.21% | 9.21% |
| CD3 | 4,300 | 46.69% | 4.30% |
| PD1 hi | 1,376 | 32.00% | 1.38% |
| PD1- | 783 | 18.21% | 0.78% |
| PD1 mid | 1,957 | 45.51% | 1.96% |
| J | 10,222 | 10.22% | 10.22% |

user1/190401 OV8042/Super Sort/OV8044 sort ( [2 Way] Data Source - 1 )
Worksheet
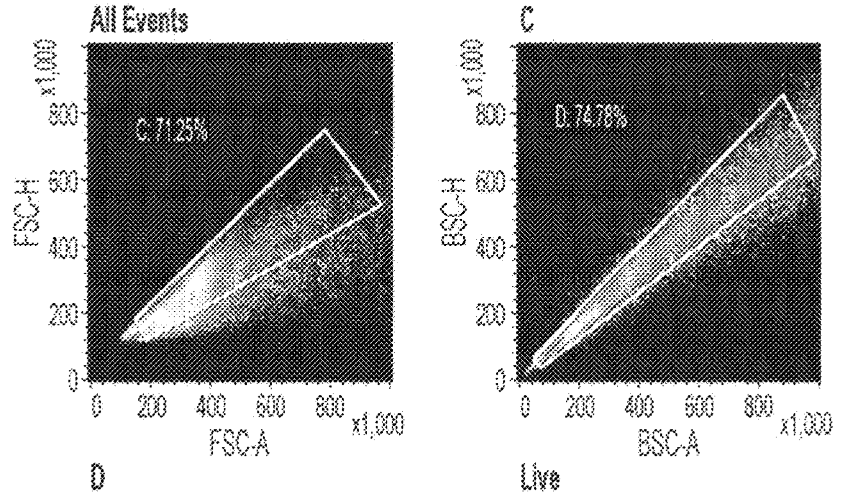
Gates and Statistics
Displaying 100,000 / 191,392 events
| Name | Events | %Parent | %Total |
|---|---|---|---|
| ☐ All Events | 100,000 | 0.00% | 100.00% |
| ☐ C | 71,247 | 71.25% | 71.25% |
| ☐ D | 53,280 | 74.78% | 53.28% |
| ☐ Live | 24,938 | 46.81% | 24.94% |
| ☐ CD3 | 16,122 | 64.65% | 16.12% |
| ☐ PD1 hi | 8,512 | 52.80% | 8.51% |
| ☐ PD1- | 1,543 | 9.57% | 1.54% |
| ☐ PD1 mid | 5,466 | 33.90% | 5.47% |
| ☐ J | 22,012 | 22.01% | 22.01% |
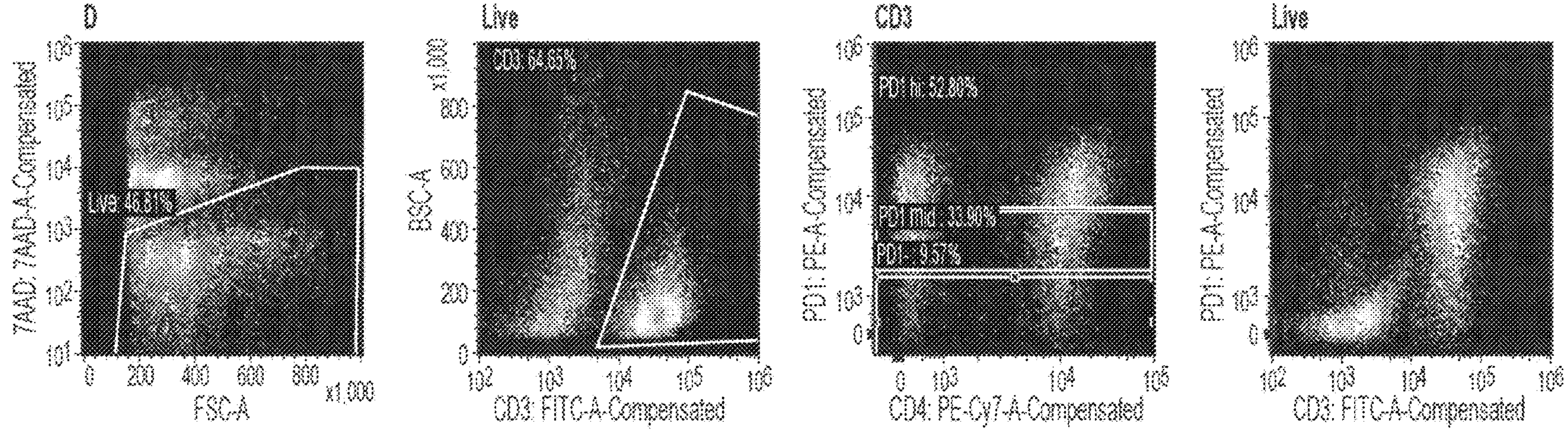
FIG. 158AA

| Name | Events | %Parent | %Total |
|---|---|---|---|
| All Events | 100,000 | 0.00% | 100.00% |
| C | 61,371 | 61.37% | 61.37% |
| D | 30,795 | 50.18% | 30.80% |
| Live | 8,021 | 26.05% | 8.02% |
| CD3 | 2,286 | 28.50% | 2.29% |
| PD1 hi | 618 | 27.03% | 0.62% |
| PD1- | 815 | 35.65% | 0.82% |
| PD1 mid | 783 | 34.25% | 0.78% |
| J | 4,273 | 4.27% | 4.27% |

| Name | Events | %Parent | %Total |
|---|---|---|---|
| All Events | 100,000 | 0.00% | 100.00% |
| C | 48,975 | 48.98% | 48.98% |
| D | 26,705 | 54.53% | 25.71% |
| Live | 13,677 | 51.22% | 13.68% |
| CD3 | 3,830 | 28.00% | 3.83% |
| PD1 hi | 2,222 | 58.02% | 2.22% |
| PD1- | 629 | 16.42% | 0.63% |
| PD1-hi | 2,222 | 58.02% | 2.22% |
| PD1 neg | 542 | 14.15% | 0.54% |
| J | 5,636 | 5.64% | 5.64% |

| | FSC Single Cells/SSC Single Cells/Live/CD3 \| Freq. of Parent | FSC Single Cells/SSC Single Cells/Live/CD3/PD1high \| Freq. of Parent |
|---|---|---|
| B3 CC10026.fcs | 15.4% | 32.5% |
| B4 CC10027.fcs | 16.8% | 31.6% |
| B5 PD-1 FMO.fcs | 34.4% | 0% |
| B6 PBMC.fcs | 16.9% | 4.52% |
| Mean | 20.9% | 17.2% |
| SD | 9.04% | 17.3% |

FIG. 158FF

| Sample Name | Cell Count & Viability | | | | | | | | | | | | | |
|---|---|---|---|---|---|---|---|---|---|---|---|---|---|---|
| | Volume (ml) | Count 1 | | Count 2 | | Counts 1 and 2 within 10% of Mean? | Count 3 | | Count 4 | | Counts 3 and 4 within 10% of Mean? | Average | | Total Viable Cells |
| | | Viable Cells/mL | % Viability | Viable Cells/mL | % Viability | | Viable Cells/mL | % Viability | Viable Cells/mL | % Viability | | Viable Cells/mL | % Viability | |
| Nivo Stability 120h baseline vol 30 C1 | 30 | 4.75E+07 | 90.9 | 5.40E+07 | 89.8 | YES | 5.56E+07 | 91.40 | 5.71E+07 | 91.40 | YES | 5.36E+07 | 90.88 | 1.61E+09 |

FIG. 164

| Tumor Histology | SSorting anti-PD-1 antibody | % PD-1 (of CD3) | PD-1 Post-sort purity | Activation Fold Expansion | REP Fold Expansion | Total viable cell yield (x $10^9$) |
|---|---|---|---|---|---|---|
| Ovarian * | Nivolumab | 79.66 | 98.98 | 2960 | 570 | 114.1 |
| | EH12.2H7 | 69.91 | 97.89 | 4905 | 461 | 92.3 |
| Melanoma * | Nivolumab | 90.10 | 96.28 | 1975 | 434 | 86.8 |
| | EH12.2H7 | 93.57 | 100.00 | 1427 | 559 | 84.1 |
| HNSCC** | Nivolumab | 14.61 | 95.34 | 1291 | 720 | 88.1 |
| | EH12.2H7 | 14.60 | 96.36 | 1486 | 612 | 81.0 |

FIG. 173

SELECTION OF IMPROVED TUMOR REACTIVE T-CELLS

CROSS-REFERENCE TO RELATED APPLICATIONS

This application is a National Phase of International Application No. PCT/US19/59716, filed Nov. 4, 2019, which claims priority to U.S. Provisional Patent Application No. 62/756,006, filed on Nov. 5, 2018, U.S. Provisional Patent Application No. 62/826,831, filed on Mar. 29, 2019, U.S. Provisional Patent Application No. 62/903,629, filed on Sep. 20, 2019, and U.S. Provisional Patent Application No. 62/924,602, filed on Oct. 22, 2019, which are hereby incorporated by reference in their entirety.

SEQUENCE LISTING INCORPORATION PARAGRAPH

The Sequence Listing written in the file named "5020-WO_Sub_SeqList.txt", created on Mar. 30, 2026, having a size in bytes of 138,919 bytes, is hereby incorporated by reference.

BACKGROUND OF THE INVENTION

Treatment of bulky, refractory cancers using adoptive transfer of tumor infiltrating lymphocytes (TILs) represents a powerful approach to therapy for patients with poor prognoses. Gattinoni, et al., Nat. Rev. Immunol. 2006, 6, 383-393. A large number of TILs are required for successful immunotherapy, and a robust and reliable process is needed for commercialization. This has been a challenge to achieve because of technical, logistical, and regulatory issues with cell expansion. IL-2-based TIL expansion followed by a "rapid expansion process" (REP) has become a preferred method for TIL expansion because of its speed and efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. REP can result in a 1,000-fold expansion of TILs over a 14-day period, although it requires a large excess (e.g., 200-fold) of irradiated allogeneic peripheral blood mononuclear cells (PBMCs, also known as mononuclear cells (MNCs)), often from multiple donors, as feeder cells, as well as anti-CD3 antibody (OKT3) and high doses of IL-2. Dudley, et al., *J. Immunother.* 2003, 26, 332-42. TILs that have undergone an REP procedure have produced successful adoptive cell therapy following host immunosuppression in patients with melanoma. Current infusion acceptance parameters rely on readouts of the composition of TILs (e.g., CD28, CD8, or CD4 positivity) and on fold expansion and viability of the REP product.

Current TIL manufacturing processes are limited by length, cost, sterility concerns, and other factors described herein such that the potential to commercialize such processes is severely limited. While there has been characterization of TILs, for example, TILs have been shown to express various receptors, including inhibitory receptors programmed cell death 1 (PD-1; also known as CD279) (see, Gros, A., et al., Clin Invest. 124 (5): 2246-2259 (2014)), the usefulness of this information in developing therapeutic TIL populations has yet to be fully realized. There is an urgent need to provide TIL manufacturing processes and therapies based on such processes that are appropriate for commercial scale manufacturing and regulatory approval for use in human patients at multiple clinical centers. The present invention meets this need by providing methods for preselecting TILs based on PD-1 expression in order to obtain TILs with enhanced tumor-specific killing capacity (e.g., enhanced cytotoxicity).

BRIEF SUMMARY OF THE INVENTION

The present invention provides methods for expanding TILs and producing therapeutic populations of TILs, which includes a PD-1 status preselection step.

In some embodiments, the present invention provides a method for expanding tumor infiltrating lymphocytes (TILs) into a therapeutic population of TILs comprising:

(a) obtaining and/or receiving a first population of TILs from a tumor resected from a subject by processing a tumor sample obtained from the subject into multiple tumor fragments;

(b) selecting PD-1 positive TILs from the first population of TILs in (a) to obtain a PD-1 enriched TIL population;

(c) performing a priming first expansion by culturing the PD-1 enriched TIL population in a cell culture medium comprising IL-2, OKT-3, and antigen presenting cells (APCs) to produce a second population of TILs, wherein the priming first expansion is performed in a container comprising a first gas-permeable surface area, wherein the priming first expansion is performed for first period of about 1 to 7/8 days to obtain the second population of TILs, wherein the second population of TILs is greater in number than the first population of TILs;

(d) performing a rapid second expansion by supplementing the cell culture medium of the second population of TILs with additional IL-2, OKT-3, and APCs, to produce a third population of TILs, wherein the number of APCs added in the rapid second expansion is at least twice the number of APCs added in step (b), wherein the rapid second expansion is performed for a second period of about 1 to 11 days to obtain the third population of TILs, wherein the third population of TILs is a therapeutic population of TILs, wherein the rapid second expansion is performed in a container comprising a second gas-permeable surface area;

(e) harvesting the therapeutic population of TILs obtained from step (d); and (f) transferring the harvested TIL population from step (e) to an infusion bag.

In some embodiments, the present invention provides a method for expanding tumor infiltrating lymphocytes (TILs) into a therapeutic population of TILs comprising:

a) obtaining and/or receiving a first population of TILs from a tumor resected from a subject by processing a tumor sample obtained from the subject into multiple tumor fragments;

b) selecting PD-1 positive TILs from the first population of TILs in (a) to obtain a PD-1 enriched TIL population;

c) performing a priming first expansion by culturing the PD-1 enriched TIL population in a cell culture medium comprising IL-2, OKT-3, and optionally comprising antigen presenting cells (APCs), to produce a second population of TILs, wherein the priming first expansion is performed for a first period of about 1 to 7/8 days to obtain the second population of TILs, wherein the second population of TILs is greater in number than the first population of TILs;

d) performing a rapid second expansion by contacting the second population of TILs with a cell culture medium comprising IL-2, OKT-3, and APCs, to produce a third population of TILs, wherein the rapid second expansion is performed for a second period of about 1 to 11 days to obtain the third population of TILs, wherein the third population of TILs is a therapeutic population of TILs; and e) harvesting the therapeutic population of TILs obtained from step (d).

In some embodiments, "obtaining" indicates the TILs employed in the method and/or process can be derived directly from the sample (including from a surgical resection, needle biopsy, core biopsy, small biopsy, or other sample) as part of the method and/or process steps. In some embodiments, "receiving" indicates the TILs employed in the method and/or process can be derived indirectly from the sample (including from a surgical resection, needle biopsy, core biopsy, small biopsy, or other sample) and then employed in the method and/or process, (for example, where step (a) begins will TILs that have already been derived from the sample by a separate process not included in part (a), such TILs could be referred to as "received").

In some embodiments, in step (b) the cell culture medium further comprises antigen-presenting cells (APCs), and wherein the number of APCs in the culture medium in step (c) is greater than the number of APCs in the culture medium in step (b).

In some embodiments in step (b) the cell culture medium further comprises antigen-presenting cells (APCs), and wherein the number of APCs in the culture medium in step (c) is equal to the number of APCs in the culture medium in step (b).

In some embodiments, the PD-1 positive TILs are PD-1 high TILS.

In some embodiments, the present invention provides a method for expanding tumor infiltrating lymphocytes (TILs) into a therapeutic population of TILs comprising:

(a) performing a priming first expansion by culturing a first population of TILs which have been selected to be PD-1 positive, said first population of TILs obtainable by processing a tumor sample from a subject by tumor digestion and selecting for the PD-1 positive TILs, in a cell culture medium comprising IL-2, OKT-3, and antigen presenting cells (APCs) to produce a second population of TILs, wherein the priming first expansion is performed in a container comprising a first gas-permeable surface area, wherein the priming first expansion is performed for first period of about 1 to 7/8 days to obtain the second population of TILs, wherein the second population of TILs is greater in number than the first population of TILs;

(b) performing a rapid second expansion by contacting the second population of TILs to a cell culture medium of the second population of TILs with additional IL-2, OKT-3, and APCs, to produce a third population of TILs, wherein the number of APCs in the rapid second expansion is at least twice the number of APCs in step (a), wherein the rapid second expansion is performed for a second period of about 1 to 11 days to obtain the third population of TILs, wherein the third population of TILs is a therapeutic population of TILs, wherein the rapid second expansion is performed in a container comprising a second gas-permeable surface area; and (c) harvesting the therapeutic population of TILs obtained from step (b).

In some embodiments, the present invention provides a method for expanding tumor infiltrating lymphocytes (TILs) into a therapeutic population of TILs comprising:

(a) performing a priming first expansion of TILs which have been selected to be PD-1 positive by culturing a first population of TILs in a cell culture medium comprising IL-2, OKT-3, and optionally comprising antigen presenting cells (APCs), to produce a second population of TILs, wherein the priming first expansion is performed for a first period of about 1 to 7/8 days to obtain the second population of TILs, wherein the second population of TILs is greater in number than the first population of TILs;

(b) performing a rapid second expansion by contacting the second population of TILs with a cell culture medium comprising IL-2, OKT-3, and APCs, to produce a third population of TILs, wherein the rapid second expansion is performed for a second period of about 1 to 11 days to obtain the third population of TILs, wherein the third population of TILs is a therapeutic population of TILs; and c) harvesting the therapeutic population of TILs obtained from step (c).

In some embodiments, in step (b) the cell culture medium further comprises antigen-presenting cells (APCs), and wherein the number of APCs in the culture medium in step (c) is greater than the number of APCs in the culture medium in step (b).

In some embodiments, in step (b) the cell culture medium further comprises antigen-presenting cells (APCs), and wherein the number of APCs in the culture medium in step (c) is the equal to the number of APCs in the culture medium in step (b).

In some embodiments, the PD-1 positive TILs are PD-1 high TILS.

In some embodiments, the selection of step (b) comprises the steps of (i) exposing the first population of TILs to an excess of a monoclonal anti-PD-1 IgG4 antibody that binds to PD-1 through an N-terminal loop outside the IgV domain of PD-1, (ii) adding an excess of an anti-IgG4 antibody conjugated to a fluorophore, and (iii) performing a flow-based cell sort based on the fluorophore to obtain a PD-1 enriched TIL population.

In some embodiments, the monoclonal anti-PD-1 IgG4 antibody is nivolumab or variants, fragments, or conjugates thereof. In some embodiments, the the anti-IgG4 antibody is clone anti-human IgG4, Clone HP6023.

In some embodiments, the ratio of the number of APCs in the rapid second expansion to the number of APCs in the priming first expansion is selected from a range of from about 1.5:1 to about 20:1.

In some embodiments, the ratio is selected from a range of from about 1.5:1 to about 10:1.

In some embodiments, the ratio is selected from a range of from about 2:1 to about 5:1.

In some embodiments, the ratio is selected from a range of from about 2:1 to about 3:1.

In some embodiments, the ratio is about 2:1.

In some embodiments, the number of APCs in the priming first expansion is selected from the range of about $1\times10^8$ APCs to about $3.5\times10^8$ APCs, and wherein the number of APCs in the rapid second expansion is selected from the range of about $3.5\times10^8$ APCs to about $1\times10^9$ APCs.

In some embodiments, the number of APCs in the priming first expansion is selected from the range of about $1.5\times10^8$ APCs to about $3\times10^8$ APCs, and wherein the number of APCs in the rapid second expansion is selected from the range of about $4\times10^8$ APCs to about $7.5\times10^8$ APCs.

In some embodiments, the number of APCs in the priming first expansion is selected from the range of about $2\times10^8$ APCs to about $2.5\times10^8$ APCs, and wherein the number of APCs in the rapid second expansion is selected from the range of about $4.5\times10^8$ APCs to about $5.5\times10^8$ APCs.

In some embodiments, about $2.5\times10^8$ APCs are added to the priming first expansion and $5\times10^8$ APCs are added to the rapid second expansion.

In some embodiments, the ratio of the number of TILs in the second population of TILs to the number of TILs in the first population of TILs is about 1.5:1 to about 100:1.

In some embodiments, the ratio of the number of TILs in the second population of TILs to the number of TILs in the first population of TILs is about 50:1.

In some embodiments, the ratio of the number of TILs in the second population of TILs to the number of TILs in the first population of TILs is about 25:1.

In some embodiments, the ratio of the number of TILs in the second population of TILs to the number of TILs in the first population of TILs is about 20:1.

In some embodiments, the ratio of the number of TILs in the second population of TILs to the number of TILs in the first population of TILs is about 10:1.

In some embodiments, the second population of TILs is at least 50-fold greater in number than the first population of TILs.

In some embodiments, the method comprises performing, after the step of harvesting the therapeutic population of TILs, the additional step of: transferring the harvested therapeutic population of TILs to an infusion bag.

In some embodiments, the multiple tumor fragments are distributed into a plurality of separate containers, in each of which separate containers the second population of TILs is obtained from the first population of TILs in the step of the priming first expansion, and the third population of TILs is obtained from the second population of TILs in the step of the rapid second expansion, and wherein the therapeutic population of TILs obtained from the third population of TILs is collected from each of the plurality of containers and combined to yield the harvested TIL population.

In some embodiments, the plurality of separate containers comprises at least two separate containers.

In some embodiments, the plurality of separate containers comprises from two to twenty separate containers.

In some embodiments, the plurality of separate containers comprises from two to ten separate containers.

In some embodiments, the plurality of separate containers comprises from two to five separate containers.

In some embodiments, each of the separate containers comprises a first gas-permeable surface area.

In some embodiments, the multiple tumor fragments are distributed in a single container.

In some embodiments, the single container comprises a first gas-permeable surface area.

In some embodiments, in the step of the priming first expansion the cell culture medium comprises antigen-presenting cells (APCs) and the APCs are layered onto the first gas-permeable surface area at an average thickness of about one cell layer to about three cell layers.

In some embodiments, in the step of the priming first expansion the APCs are layered onto the first gas-permeable surface area at an average thickness of about 1.5 cell layers to about 2.5 cell layers.

In some embodiments, in the step of the priming first expansion the APCs are layered onto the first gas-permeable surface area at an average thickness of about 2 cell layers.

In some embodiments, in the step of the rapid second expansion the APCs are layered onto the first gas-permeable surface area at a thickness of about 3 cell layers to about 5 cell layers.

In some embodiments, in the step of the rapid second expansion the APCs are layered onto the first gas-permeable surface area at a thickness of about 3.5 cell layers to about 4.5 cell layers.

In some embodiments, in the step of the rapid second expansion the APCs are layered onto the first gas-permeable surface area at a thickness of about 4 cell layers.

In some embodiments, in the step of the priming first expansion the priming first expansion is performed in a first container comprising a first gas-permeable surface area and in the step of the rapid second expansion the rapid second expansion is performed in a second container comprising a second gas-permeable surface area.

In some embodiments, the second container is larger than the first container.

In some embodiments, in the step of the priming first expansion the cell culture medium comprises antigen-presenting cells (APCs) and the APCs are layered onto the first gas-permeable surface area at an average thickness of about one cell layer to about three cell layers.

In some embodiments, in the step of the priming first expansion the APCs are layered onto the first gas-permeable surface area at an average thickness of about 1.5 cell layers to about 2.5 cell layers.

In some embodiments, in the step of the priming first expansion the APCs are layered onto the first gas-permeable surface area at an average thickness of about 2 cell layers.

In some embodiments, in the step of the rapid second expansion the APCs are layered onto the second gas-permeable surface area at an average thickness of about 3 cell layers to about 5 cell layers.

In some embodiments, in the step of the rapid second expansion the APCs are layered onto the second gas-permeable surface area at an average thickness of about 3.5 cell layers to about 4.5 cell layers.

In some embodiments, in the step of the rapid second expansion the APCs are layered onto the second gas-permeable surface area at an average thickness of about 4 cell layers.

In some embodiments, for each container in which the priming first expansion is performed on a first population of TILs the rapid second expansion is performed in the same container on the second population of TILs produced from such first population of TILs.

In some embodiments, each container comprises a first gas-permeable surface area.

In some embodiments, in the step of the priming first expansion the cell culture medium comprises antigen-presenting cells (APCs) and the APCs are layered onto the first gas-permeable surface area at an average thickness of from about one cell layer to about three cell layers.

In some embodiments, in the step of the priming first expansion the APCs are layered onto the first gas-permeable surface area at an average thickness of from about 1.5 cell layers to about 2.5 cell layers.

In some embodiments, in the step of the priming first expansion the APCs are layered onto the first gas-permeable surface area at an average thickness of about 2 cell layers.

In some embodiments, in the step of the rapid second expansion the APCs are layered onto the first gas-permeable surface area at an average thickness of about 3 cell layers to about 5 cell layers.

In some embodiments, in the step of the rapid second expansion the APCs are layered onto the first gas-permeable surface area at an average thickness of about 3.5 cell layers to about 4.5 cell layers.

In some embodiments, in the step of the rapid second expansion the APCs are layered onto the first gas-permeable surface area at an average thickness of about 4 cell layers.

In some embodiments, for each container in which the priming first expansion is performed on a first population of TILs in the step of the priming first expansion the first container comprises a first surface area, the cell culture medium comprises antigen-presenting cells (APCs), and the APCs are layered onto the first gas-permeable surface area, and wherein the ratio of the average number of layers of APCs layered in the step of the priming first expansion to the average number of layers of APCs layered in the step of the rapid second expansion is selected from the range of about 1:1.1 to about 1:10.

In some embodiments, the ratio of the average number of layers of APCs layered in the step of the priming first expansion to the average number of layers of APCs layered in the step of the rapid second expansion is selected from the range of about 1:1.2 to about 1:8.

In some embodiments, the ratio of the average number of layers of APCs layered in the step of the priming first expansion to the average number of layers of APCs layered in the step of the raid second expansion is selected from the range of about 1:1.3 to about 1:7.

In some embodiments, the ratio of the average number of layers of APCs layered in the step of the priming first expansion to the average number of layers of APCs layered in the step of the rapid second expansion is selected from the range of about 1:1.4 to about 1:6.

In some embodiments, the ratio of the average number of layers of APCs layered in the step of the priming first expansion to the average number of layers of APCs layered in the step of the rapid second expansion is selected from the range of about 1:1.5 to about 1:5.

In some embodiments, the ratio of the average number of layers of APCs layered in the step of the priming first expansion to the average number of layers of APCs layered in the step of the rapid second expansion is selected from the range of about 1:1.6 to about 1:4.

In some embodiments, the ratio of the average number of layers of APCs layered in the step of the priming first expansion to the average number of layers of APCs layered in the step of the rapid second expansion is selected from the range of about 1:1.7 to about 1:3.5.

In some embodiments, the ratio of the average number of layers of APCs layered in the step of the priming first expansion to the average number of layers of APCs layered in the step of the rapid second expansion is selected from the range of about 1:1.8 to about 1:3.

In some embodiments, the ratio of the average number of layers of APCs layered in the step of the priming first expansion to the average number of layers of APCs layered in the step of the rapid second expansion is selected from the range of about 1:1.9 to about 1:2.5.

In some embodiments, the ratio of the average number of layers of APCs layered in the step of the priming first expansion to the average number of layers of APCs layered in the step of the rapid second expansion is about 1:2.

In some embodiments, after 2 to 3 days in the step of the rapid second expansion, the cell culture medium is supplemented with additional IL-2.

In some embodiments, the method further comprises cryopreserving the harvested TIL population in the step of harvesting the therapeutic population of TILs using a cryopreservation process.

In some embodiments, the method further comprises the step of cryopreserving the infusion bag.

In some embodiments, the cryopreservation process is performed using a 1:1 ratio of harvested TIL population to cryopreservation media.

In some embodiments, the antigen-presenting cells are peripheral blood mononuclear cells (PBMCs).

In some embodiments, the PBMCs are irradiated and allogeneic.

In some embodiments, in the step of the priming first expansion the cell culture medium comprises peripheral blood mononuclear cells (PBMCs), and wherein the total number of PBMCs in the cell culture medium in the step of the priming first expansion is $2.5\times10^{8}$.

In some embodiments, in the step of the rapid second expansion the antigen-presenting cells (APCs) in the cell culture medium are peripheral blood mononuclear cells (PBMCs), and wherein the total number of PBMCs added to the cell culture medium in the step of the rapid second expansion is $5\times10^{8}$.

In some embodiments, the antigen-presenting cells are artificial antigen-presenting cells.

In some embodiments, the harvesting in the step of harvesting the therapeutic population of TILs is performed using a membrane-based cell processing system.

In some embodiments, the harvesting in step (d) is performed using a LOVO cell processing system.

In some embodiments, the multiple fragments comprise about 60 fragments per container in the step of the priming first expansion, wherein each fragment has a volume of about 27 $mm^3$.

In some embodiments, the multiple fragments comprise about 30 to about 60 fragments with a total volume of about 1300 $mm^3$ to about 1500 $mm^3$.

In some embodiments, the multiple fragments comprise about 50 fragments with a total volume of about 1350 $mm^3$.

In some embodiments, the multiple fragments comprise about 50 fragments with a total mass of about 1 gram to about 1.5 grams.

In some embodiments, the cell culture medium is provided in a container selected from the group consisting of a G-container and a Xuri cellbag.

In some embodiments, after 2 to 3 days in step (d), the cell culture medium is supplemented with additional IL-2.

In some embodiments, the IL-2 concentration is about 10,000 IU/mL to about 5,000 IU/mL.

In some embodiments, the IL-2 concentration is about 6,000 IU/mL.

In some embodiments, the infusion bag in the step of transferring the harvested therapeutic population of TILs to an infusion bag is a HypoThermosol-containing infusion bag.

In some embodiments, the cryopreservation media comprises dimethlysulfoxide (DMSO).

In some embodiments, the cryopreservation media comprises 7% to 10% DMSO.

In some embodiments, the first period in the step of the priming first expansion and the second period in the step of the rapid second expansion are each individually performed within a period of 5 days, 6 days, 7 days, 8 days, 9 days, 10 days, or 11 days.

In some embodiments, the first period in the step of the priming first expansion is performed within a period of 5 days, 6 days, or 7 days.

In some embodiments, the second period in the step of the rapid second expansion is performed within a period of 7 days, 8 days, or 9 days.

In some embodiments, the first period in the step of the priming first expansion and the second period in the step of the rapid second expansion are each individually performed within a period of 7 days.

In some embodiments, the steps of the priming first expansion through the harvesting of the therapeutic population of TILs are performed within a period of about 14 days to about 16 days.

In some embodiments, the steps of the priming first expansion through the harvesting of the therapeutic population of TILs are performed within a period of about 15 days to about 16 days.

In some embodiments, the steps of the priming first expansion through the harvesting of the therapeutic population of TILs are performed within a period of about 14 days.

In some embodiments, the steps of the priming first expansion through the harvesting of the therapeutic population of TILs are performed within a period of about 15 days.

In some embodiments, the steps the priming first expansion through the harvesting of the therapeutic population of TILs are performed within a period of about 16 days.

In some embodiments, the method further comprises the step of cryopreserving the harvested therapeutic population of TILs using a cryopreservation process, wherein steps of the priming first expansion through the harvesting of the therapeutic population of TILs and cryopreservation are performed in 16 days or less.

In some embodiments, the therapeutic population of TILs harvested in the step of harvesting of the therapeutic population of TILs comprises sufficient TILs for a therapeutically effective dosage of the TILs.

In some embodiments, the number of TILs sufficient for a therapeutically effective dosage is from about $2.3\times10^{10}$ to about $13.7\times10^{10}$.

In some embodiments, the third population of TILs in the step of the rapid second expansion provides for increased efficacy, increased interferon-gamma production, and/or increased polyclonality.

In some embodiments, the third population of TILs in the step of the rapid second expansion provides for at least a one-fold to five-fold or more interferon-gamma production as compared to TILs prepared by a process longer than 16 days.

In some embodiments, the effector T cells and/or central memory T cells obtained from the third population of TILs in the step of the rapid second expansion exhibit increased CD8 and CD28 expression relative to effector T cells and/or central memory T cells obtained from the second population of TILs in the step of the priming first expansion.

In some embodiments, the therapeutic population of TILs from the step of the harvesting of the therapeutic population of TILs are infused into a patient.

In some embodiments, the method further comprises the step of cryopreserving the infusion bag comprising the harvested TIL population in step (f) using a cryopreservation process.

In some embodiments, the cryopreservation process is performed using a 1:1 ratio of harvested TIL population to cryopreservation media.

In some embodiments, the antigen-presenting cells are peripheral blood mononuclear cells (PBMCs).

In some embodiments, the PBMCs are irradiated and allogeneic.

In some embodiments, the antigen-presenting cells are artificial antigen-presenting cells.

In some embodiments, the harvesting in step (e) is performed using a membrane-based cell processing system.

In some embodiments, the harvesting in step (e) is performed using a LOVO cell processing system.

In some embodiments, the multiple fragments comprise about 60 fragments per first gas-permeable surface area in step (c), wherein each fragment has a volume of about 27 $mm^3$.

In some embodiments, the multiple fragments comprise about 30 to about 60 fragments with a total volume of about 1300 $mm^3$ to about 1500 $mm^3$.

In some embodiments, the multiple fragments comprise about 50 fragments with a total volume of about 1350 $mm^3$.

In some embodiments, the multiple fragments comprise about 50 fragments with a total mass of about 1 gram to about 1.5 grams.

In some embodiments, the cell culture medium is provided in a container selected from the group consisting of a G-container and a Xuri cellbag.

In some embodiments, the IL-2 concentration is about 10,000 IU/mL to about 5,000 IU/mL. In some embodiments, the IL-2 concentration is about 6,000 IU/mL.

In some embodiments, the infusion bag in step (d) is a HypoThermosol-containing infusion bag.

In some embodiments, the cryopreservation media comprises dimethlysulfoxide (DMSO).

In some embodiments, the cryopreservation media comprises 7% to 10% DMSO.

In some embodiments, the first period in step (c) and the second period in step (c) are each individually performed within a period of 5 days, 6 days, or 7 days.

In some embodiments, the first period in step (c) is performed within a period of 5 days, 6 days, or 7 days.

In some embodiments, the second period in step (d) is performed within a period of 7 days, 8 days, or 9 days.

In some embodiments, the first period in step (c) and the second period in step (c) are each individually performed within a period of 7 days.

In some embodiments, steps (a) through (f) are performed within a period of about 14 days to about 16 days.

In some embodiments, steps (a) through (f) are performed within a period of about 15 days to about 16 days.

In some embodiments, steps (a) through (f) are performed within a period of about 14 days.

In some embodiments, steps (a) through (f) are performed within a period of about 15 days.

In some embodiments, steps (a) through (f) are performed within a period of about 16 days.

In some embodiments, steps (a) through (f) and cryopreservation are performed in 16 days or less.

In some embodiments, the therapeutic population of TILs harvested in step (f) comprises sufficient TILs for a therapeutically effective dosage of the TILs.

In some embodiments, the number of TILs sufficient for a therapeutically effective dosage is from about $2.3\times10^{10}$ to about $13.7\times10^{10}$.

In some embodiments, the container in step (c) is larger than the container in step (b).

In some embodiments, the third population of TILs in step (d) provides for increased efficacy, increased interferon-gamma production, and/or increased polyclonality.

In some embodiments, the third population of TILs in step (d) provides for at least a one-fold to five-fold or more interferon-gamma production as compared to TILs prepared by a process longer than 16 days.

In some embodiments, the effector T cells and/or central memory T cells obtained from the third population of TILs step (d) exhibit increased CD8 and CD28 expression relative to effector T cells and/or central memory T cells obtained from the second population of cells step (c).

In some embodiments, the TILs from step (f) are infused into a patient.

In some embodiments, the present invention provides a method for treating a subject with cancer, the method comprising administering expanded tumor infiltrating lymphocytes (TILs) comprising:

(a) obtaining and/or receiving a first population of TILs from a tumor resected from a subject by processing a tumor sample obtained from the subject into multiple tumor fragments;
(b) selecting PD-1 positive TILs from the first population of TILs in (a) to obtain a PD-1 enriched TIL population;
(c) performing a priming first expansion by culturing the PD-1 enriched TIL population in a cell culture medium comprising IL-2, OKT-3, and antigen presenting cells (APCs) to produce a second population of TILs, wherein the priming first expansion is performed in a container comprising a first gas-permeable surface area, wherein the priming first expansion is performed for about 1 to 7 days to obtain the second population of TILs, wherein the second population of TILs is at least 50-fold greater in number than the first population of TILs;
(d) performing a rapid second expansion by supplementing the cell culture medium of the second population of TILs with additional IL-2, OKT-3, and APCs, to produce a third population of TILs, wherein the number of APCs added to the rapid second expansion is at least twice the number of APCs added in step (b), wherein the rapid second expansion is performed for about 1 to 11 days to obtain the third population of TILs, wherein the third population of TILs is a therapeutic population of TILs, wherein the rapid second expansion is performed in a container comprising a second gas-permeable surface area;
(e) harvesting the therapeutic population of TILs obtained from step (c);
(f) transferring the harvested TIL population from step (d) to an infusion bag; and
(g) administering a therapeutically effective dosage of the TILs from step (e) to the subject.

In some embodiments, the number of TILs sufficient for administering a therapeutically effective dosage in step (g) is from about $2.3\times10^{10}$ to about $13.7\times10^{10}$.

In some embodiments, the PD-1 positive TILs are PD-1 high TILS.

In some embodiments, the selection of step (b) comprises the steps of (i) exposing the first population of TILs to an excess of a monoclonal anti-PD-1 IgG4 antibody that binds to PD-1 through an N-terminal loop outside the IgV domain of PD-1, (ii) adding an excess of an anti-IgG4 antibody conjugated to a fluorophore, and (iii) performing a flow-based cell sort based on the fluorophore to obtain a PD-1 enriched TIL population.

In some embodiments, the monoclonal anti-PD-1 IgG4 antibody is nivolumab or variants, fragments, or conjugates thereof.

In some embodiments, the the anti-IgG4 antibody is clone anti-human IgG4, Clone HP6023.

In some embodiments, the antigen presenting cells (APCs) are PBMCs.

In some embodiments, prior to administering a therapeutically effective dosage of TIL cells in step (g), a non-myeloablative lymphodepletion regimen has been administered to the patient.

In some embodiments, the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In some embodiments, the method further comprises the step of treating the patient with a high-dose IL-2 regimen starting on the day after administration of the TIL cells to the patient in step (g).

In some embodiments, the high-dose IL-2 regimen comprises 600,000 or 720,000 IU/kg administered as a 15-minute bolus intravenous infusion every eight hours until tolerance.

In some embodiments, the third population of TILs in step (c) provides for increased efficacy, increased interferon-gamma production, and/or increased polyclonality.

In some embodiments, the third population of TILs in step (d) provides for at least a one-fold to five-fold or more interferon-gamma production as compared to TILs prepared by a process longer than 16 days.

In some embodiments, the effector T cells and/or central memory T cells obtained from the third population of TILs in step (d) exhibit increased CD8 and CD28 expression relative to effector T cells and/or central memory T cells obtained from the second population of cells in step (c).

In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma.

In some embodiments, the cancer is selected from the group consisting of melanoma, HNSCC, cervical cancers, NSCLC, glioblastoma (including GBM), and gastrointestinal cancer.

In some embodiments, the cancer is melanoma.

In some embodiments, the cancer is HNSCC.

In some embodiments, the cancer is a cervical cancer.

In some embodiments, the cancer is NSCLC.

In some embodiments, the cancer is glioblastoma (including GBM).

In some embodiments, the cancer is gastrointestinal cancer.

In some embodiments, the cancer is a hypermutated cancer.

In some embodiments, the cancer is a pediatric hypermutated cancer.

In some embodiments, the container is a GREX-10.

In some embodiments, the closed container comprises a GREX-100.

In some embodiments, the closed container comprises a GREX-500.

In some embodiments, the subject has been previously treated with an anti-PD-1 antibody.

In some embodiments, the subject has not been previously treated with an anti-PD-1 antibody.

In some embodiments, in step (b) the PD-1 positive TILs are selected from the first population of TILs by performing the step of contacting the first population of TILs with an anti-PD-1 antibody to form a first complex of the anti-PD-1 antibody and TIL cells in the first population of TILs, and then performing the step of isolating the first complex to obtain the PD-1 enriched TIL population.

In some embodiments, the anti-PD-1 antibody comprises an Fc region, wherein after the step of forming the first complexes and before the step of isolating the first complex the method further comprises the step of contacting the first complex with an anti-Fc antibody that binds to the Fc region of the anti-PD-1 antibody to form a second complex of the anti-Fc antibody and the first complex, and wherein the step of isolating the first complex is performed by isolating the second complex.

In some embodiments, the anti-PD-1 antibody for use in the selection in step (b) is selected from the group consisting of EH12.2H7, PD1.3.1, M1H4, nivolumab (BMS-936558, Bristol-Myers Squibb; Opdivo®), pembrolizumab (lambrolizumab, MK03475 or MK-3475, Merck; Keytruda®), H12.1, PD1.3.1, NAT 105, humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), humanized anti-PD-1 IgG4 antibody PDR001 (Novartis), and RMP1-14 (rat IgG)-BioXcell cat #BP0146.

In some embodiments, the anti-PD-1 antibody for use in the selection is EH12.2H7.

In some embodiments, the anti-PD-1 antibody for use in the selection in step (b) binds to a different epitope than nivolumab or pembrolizumab.

In some embodiments, the anti-PD-1 antibody for use in the selection in step (b) binds to the same epitope as EH12.2H7 or nivolumab.

In some embodiments, the anti-PD-1 antibody for use in the selection in step (b) is nivolumab.

In some embodiments, the subject has been previously treated with a first anti-PD-1 antibody, wherein in step (b) the PD-1 positive TILs are selected by contacting the first population of TILs with a second anti-PD-1 antibody, and wherein the second anti-PD-1 antibody is not blocked from binding to the first population of TILs by the first anti-PD-1 antibody insolubilized on the first population of TILs.

In some embodiments, the subject has been previously treated with a first anti-PD1 antibody, wherein in step (b) the PD-1 positive TILs are selected by contacting the first population of TILs with a second anti-PD-1 antibody, and wherein the second anti-PD-1 antibody is blocked from binding to the first population of TILs by the first anti-PD-1 antibody insolubilized on the first population of TILs.

In some embodiments, the subject has been previously treated with a first anti-PD1 antibody, wherein in step (b) the PD-1 positive TILs are selected by performing the step of contacting the first population of TILs with a second anti-PD-1 antibody to form a first complex of the second anti-PD-1 antibody and the first population of TILs, wherein the second anti-PD-1 antibody is not blocked from binding to the first population of TILs by the first anti-PD-1 antibody insolubilized on the first population of TILs, and then performing the step of isolating the first complex to obtain the PD-1 enriched TIL population.

In some embodiments, the first anti-PD-1 antibody and the second anti-PD-1 antibody comprise an Fc region, wherein after the step of forming the first complex and before the step of isolating the first complex the method further comprises the step of contacting the first complex with an anti-Fc antibody that binds to the Fc region of the first anti-PD-1 antibody and the Fc region of the second anti-PD-1 antibody to form a second complex of the anti-Fc antibody and the first complex, and wherein the step of isolating the first complex is performed by isolating the second complex.

In some embodiments, the second anti-PD-1 antibody comprises an Fc region, the subject has been previously treated with a first anti-PD1 antibody, wherein in step (b) the PD-1 positive TILs are selected by performing the step of contacting the first population of TILs with a second anti-PD-1 antibody to form a first complex of the second anti-PD-1 antibody and the first population of TILs, wherein the second anti-PD-1 antibody is not blocked from binding to the first population of TILs by the first anti-PD-1 antibody insolubilized on the first population of TILs, and wherein after the step of forming the first complex the method further comprises the step of contacting the first complex with an anti-Fc antibody that binds to the Fc region of the second anti-PD-1 antibody to form a second complex of the anti-Fc antibody and the first complex, and then performing the step of isolating the second complex to obtain the PD-1 enriched TIL population.

In some embodiments, the subject has been previously treated with a first anti-PD1 antibody, wherein in step (b) the PD-1 positive TILs are selected by performing the step of contacting the first population of TILs with a second anti-PD-1 antibody to form a first complex of the second anti-PD-1 antibody and the first population of TILs, wherein the second anti-PD-1 antibody is blocked from binding to the PD-1 positive TILs by the first anti-PD-1 antibody insolubilized on the first population of TILs, wherein the first anti-PD-1 antibody and the second anti-PD-1 antibody comprise an Fc region, wherein after the step of forming the first complex and before the step of obtaining the PD-1 enriched TIL population the method further comprises the step of contacting the first complex with an anti-Fc antibody that binds to the Fc region of the second anti-PD-1 antibody to form a second complex of the anti-Fc antibody and the first complex and contacting the first anti-PD-1 antibody insolubilized on the first population of TILs with the anti-Fc antibody to form a third complex of the anti-Fc antibody and the first anti-PD-1 antibody insolubilized on the first population of TILs, and performing the step of isolating the second and third complexes to obtain the PD-1 enriched TIL population.

In some embodiments, the PD-1 positive TILs are PD-1 high TILS.

In some embodiments, the present invention provides a therapeutic population of tumor infiltrating lymphocytes (TILs) prepared from PD-1 positive cells selected from the tumor tissue of a patient, wherein the therapeutic population of TILs provides for increased efficacy and/or increased interferon-gamma production.

In some embodiments, the present invention provides a therapeutic population of tumor infiltrating lymphocytes (TILs) prepared from PD-1 positive cells selected from the tumor tissue of a patient, wherein the therapeutic population of TILs provides for increased efficacy and/or increased interferon-gamma production.

In some embodiments, the present invention provides a therapeutic population of tumor infiltrating lymphocytes (TILs) prepared from PD-1 positive cells selected from the tumor tissue of a patient, wherein the therapeutic population of TILs provides for increased increased interferon-gamma production.

In some embodiments, the present invention provides a therapeutic population of tumor infiltrating lymphocytes (TILs) prepared from PD-1 positive cells selected from the tumor tissue of a patient, wherein the therapeutic population of TILs provides for increased efficacy.

In some embodiments, the present invention provides a therapeutic population of tumor infiltrating lymphocytes (TILs) prepared from PD-1 positive cells selected from the tumor tissue of a patient, wherein the therapeutic population of TILs is capable of at least one-fold more interferon-gamma production as compared to TILs prepared by a process longer than 16 days.

In some embodiments, the present invention provides a therapeutic population of tumor infiltrating lymphocytes (TILs) prepared from PD-1 positive cells selected from the tumor tissue of a patient, wherein the therapeutic population of TILs is capable of at least one-fold more interferon-gamma production as compared to TILs prepared by a process longer than 16-22 days.

In some embodiments, selecting PD-1 positive TILs from the first population of TILs to obtain a PD-1 enriched TIL population comprises the selecting a population of TILs from a first population of TILs that are at least 11.27% to 74.4% PD-1 positive TILs.

In some embodiments, the selection of step comprises the steps of:

(i) exposing the first population of TILs and a population of PBMC to an excess of a monoclonal anti-PD-1 IgG4 antibody that binds to PD-1 through an N-terminal loop outside the IgV domain of PD-1, (ii) adding an excess of an anti-IgG4 antibody conjugated to a fluorophore, (iii) obtaining the PD-1 enriched TIL population based on the intensity of the fluorophore of the PD-1 positive TILs in the first population of TILs compared to the intensity in the population of PBMCs as performed by fluorescence-activated cell sorting (FACS).

In some embodiments, the intensity of the fluorophore in both the first population and the population of PBMCs is used to set up FACS gates for establishing low, medium, and high levels of intensity that correspond to PD-1 negative TILs, PD-1 intermediate TILs, and PD-1 positive TILs, respectively.

In some embodiments, the FACS gates are set-up after step (a).

In some embodiments, the PD-1 positive TILs are PD-1 high TILs.

In some embodiments, at least 80% of the PD-1 enriched TIL population are PD-1 positive TILs.

The present invention also provides a method for expanding tumor infiltrating lymphocytes (TILs) into a therapeutic population of TILs comprising:

(a) obtaining and/or receiving a first population of TILs from a tumor resected from a subject by processing a tumor sample obtained from the subject into multiple tumor fragments;

(b) selecting PD-1 positive TILs from the first population of TILs in (a) to obtain a PD-1 enriched TIL population, wherein at least a range of 10% to 80% of the first population of TILs are PD-1 positive TILs;

(c) performing a priming first expansion by culturing the PD-1 enriched TIL population in a cell culture medium comprising IL-2, OKT-3, and antigen presenting cells (APCs) to produce a second population of TILs, wherein the priming first expansion is performed in a container comprising a first gas-permeable surface area, wherein the priming first expansion is performed for first period of about 1 to 7/8 days to obtain the second population of TILs, wherein the second population of TILs is greater in number than the first population of TILs;

(d) performing a rapid second expansion by supplementing the cell culture medium of the second population of TILs with additional IL-2, OKT-3, and APCs, to produce a third population of TILs, wherein the number of APCs added in the rapid second expansion is at least twice the number of APCs added in step (b), wherein the rapid second expansion is performed for a second period of about 1 to 11 days to obtain the third population of TILs, wherein the third population of TILs is a therapeutic population of TILs, wherein the rapid second expansion is performed in a container comprising a second gas-permeable surface area;

(e) harvesting the therapeutic population of TILs obtained from step (d); and (f) transferring the harvested TIL population from step (e) to an infusion bag.

In some embodiments, the selection of step (b) comprises the steps of:

(i) exposing the first population of TILs and a population of PBMC to an excess of a monoclonal anti-PD-1 IgG4 antibody that binds to PD-1 through an N-terminal loop outside the IgV domain of PD-1, (ii) adding an excess of an anti-IgG4 antibody conjugated to a fluorophore, (iii) obtaining the PD-1 enriched TIL population based on the intensity of the fluorophore of the PD-1 positive TILs in the first population of TILs compared to the intensity in the population of PBMCs as performed by fluorescence-activated cell sorting (FACS).

In some embodiments, the intensity of the fluorophore in both the first population and the population of PBMCs is used to set up FACS gates for establishing low, medium, and high levels of intensity that correspond to PD-1 negative TILs, PD-1 intermediate TILs, and PD-1 positive TILs, respectively.

In some embodiments, the FACS gates are set-up after step (a).

In some embodiments, the PD-1 positive TILs are PD-1 high TILs.

In some embodiments, at least 80% of the PD-1 enriched TIL population are PD-1 positive TILs.

In some embodiments, the third population of TILs comprises at least about $1\times10^8$ TILs in the container.

In some embodiments, the third population of TILs comprises at least about $1\times10^9$ TILs in the container.

In some embodiments, the number of PD-1 enriched TILs in the priming first expansion is from about $1\times10^4$ to about $1\times10^6$.

In some embodiments, the number of PD-1 enriched TILs in the priming first expansion is from about $5\times10^4$ to about $1\times10^6$.

In some embodiments, the number of PD-1 enriched TILs in the priming first expansion is from about $2\times10^5$ to about $1\times10^6$.

In some embodiments, the method further comprises the step of cyropreserving the first population of TILs from the tumor resected from the subject before performing step (a).

BRIEF DESCRIPTION OF THE DRAWINGS

FIG. 1A-1C: A) Shows a comparison between the 2A process (approximately 22-day process) and an embodiment of the Gen 3 process for TIL manufacturing (approximately 14-days to 16-days process). B) Exemplary Process PD-1 Gen3 chart providing an overview of Steps A through F (approximately 14-days to 16-days process). C) Chart providing three exemplary Gen 3 processes with an overview of Steps A through F (approximately 14-days to 16-days process) for each of the three process variations.

FIG. 10A-10C: A) Quantification of L-glutamine in spent media for L4054 and L4055. B) Quantification of Glutamax in spent media for L4054 and L4055. C) Quantification of ammonia in spent media for L4054 and L4055.

FIG. 16: Raw data for cell counts Day 7-Gen 3 REP initiation presented in Table 22 (see Example 5 below).

FIG. 17: Raw data for cell counts Day 11-Gen 2 REP initiation and Gen 3 Scale Up presented in Table 22 (see Example 5 below).

FIG. 18: Raw data for cell counts Day 16-Gen 2 Scale Up and Gen 3 Harvest (e.g., day 16) presented in Table 23 (see Example 5 below).

FIG. 19: Raw data for cell counts Day 22-Gen 2 Harvest (e.g., day 22) presented in Table 23 (see Example 5 below). For L4054 Gen 2, post LOVO count was extrapolated to 4 flasks, because was the total number of the study. 1 flask was contaminated, and the extrapolation was done for total=6.67E+10.

FIG. 20: Raw data for flow cytometry results depicted in FIGS. 3A, 4A, and 4B.

FIG. 21: Raw data for flow cytometry results depicted in FIGS. 3C and 4C.

FIG. 22: Raw data for flow cytometry results depicted in FIGS. 5 and 6.

FIG. 23A-23B: Raw data for IFNγ production assay results for L4054 samples depicted in FIG. 7.

FIG. 24A-24B: Raw data for IFNγ production assay results for L4055 samples depicted in FIG. 7.

FIG. 25A-25B: Raw data for IFNγ production assay results for M1085T samples depicted in FIG. 7.

FIG. 26A-26B: Raw data for IL-2 ELISA assay results depicted in FIG. 8.

FIG. 27: Raw data for the metabolic substrate and metabolic analysis results presented in FIGS. 9 and 10.

FIG. 28: Raw data for the relative telomere length anaylsis results presented in FIG. 11.

FIG. 29: Raw data for the unique CD3 sequence and clonal diversity analyses results presented in FIGS. 12 and 15.

FIG. 31: Table describing various features of embodiments of the Gen 2, Gen 2.1 and Gen 3.0 process.

FIG. 32: Overview of the media conditions for an embodiment of the Gen 3 process, referred to as Gen 3.1.

FIG. 33: Table describing various features of embodiments of the Gen 2, Gen 2.1 and Gen 3.0 process.

FIG. 34: Table comparing various features of embodiments of the Gen 2 and Gen 3.0 processes.

FIG. 35: Table providing media uses in the various embodiments of the described expansion processes.

FIG. 36: Phenotype comparison: Gen 3.0 and Gen 3.1 embodiments of the process showed comparable CD28, CD27 and CD57 expression.

FIG. 53: Selecting PD1+ cells from tumor digests, using fluorescence-activated cell sorting.

FIG. 54: Identification of a tumor tissue digestion method.

FIG. 55: Identification of a tumor tissue digestion method using GMP available reagents.

FIG. 66: Sort and Expansion Results for PD1 selection.

FIG. 67: Sort and Expansion Results for PD1 selection.

FIG. 68: Sort and Expansion Results for PD1 selection.

FIG. 71: PD1+ TIL demonstrate a different phenotypic profile, compared to PD1-TIL.

FIG. 79: PD1+ selected TIL are oligoclonal and compromised of a fraction of clones present in bulk TIL.

FIG. 86: PD-1 selected TIL data and information, including uCDR numbers as well as expansion data.

FIG. 96: Schematic of an exemplary embodiment of a modified Gen 2 process developed for PD1 selected TIL.

FIG. 99: Data showing Early REP harvest on Day 17 for PD1+ condition yielded 55e9 and 37e9 TILs.

FIG. 108A-108B: Shows TIL profile characteristics for two tumor samples for multiple expansion process conditions as described in FIGS. 96 and 98. Activation and Exhaustion status on CD4+ were similar.

FIG. 109A-109B: Shows TIL profile characteristics for two tumor samples for multiple expansion process conditions as described in FIGS. 96 and 98. Activation and Exhaustion status on CD8+ were similar.

Figure 122:
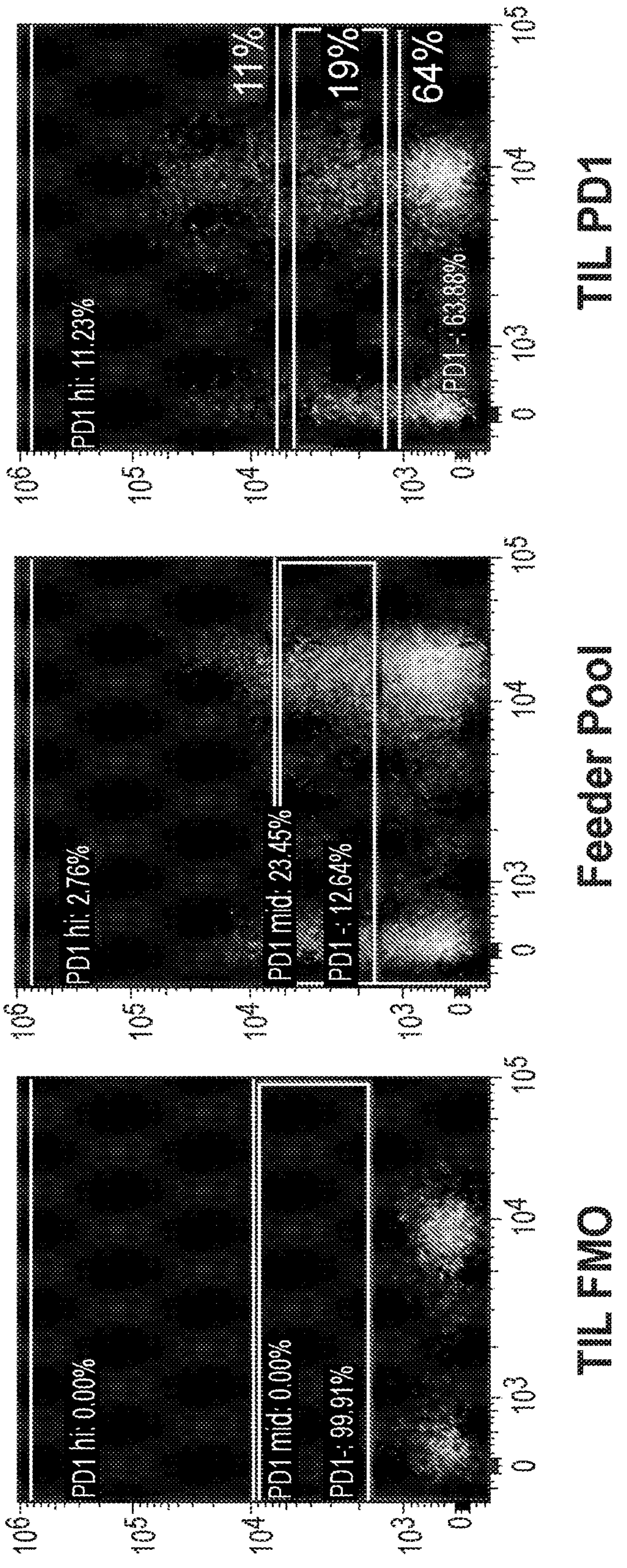

FIG. 122: Exemplary data showing PD1$^+$ Selection: Gating on PD1+ high (PD-1high) for L1141 tumor sample.

Figure 123:
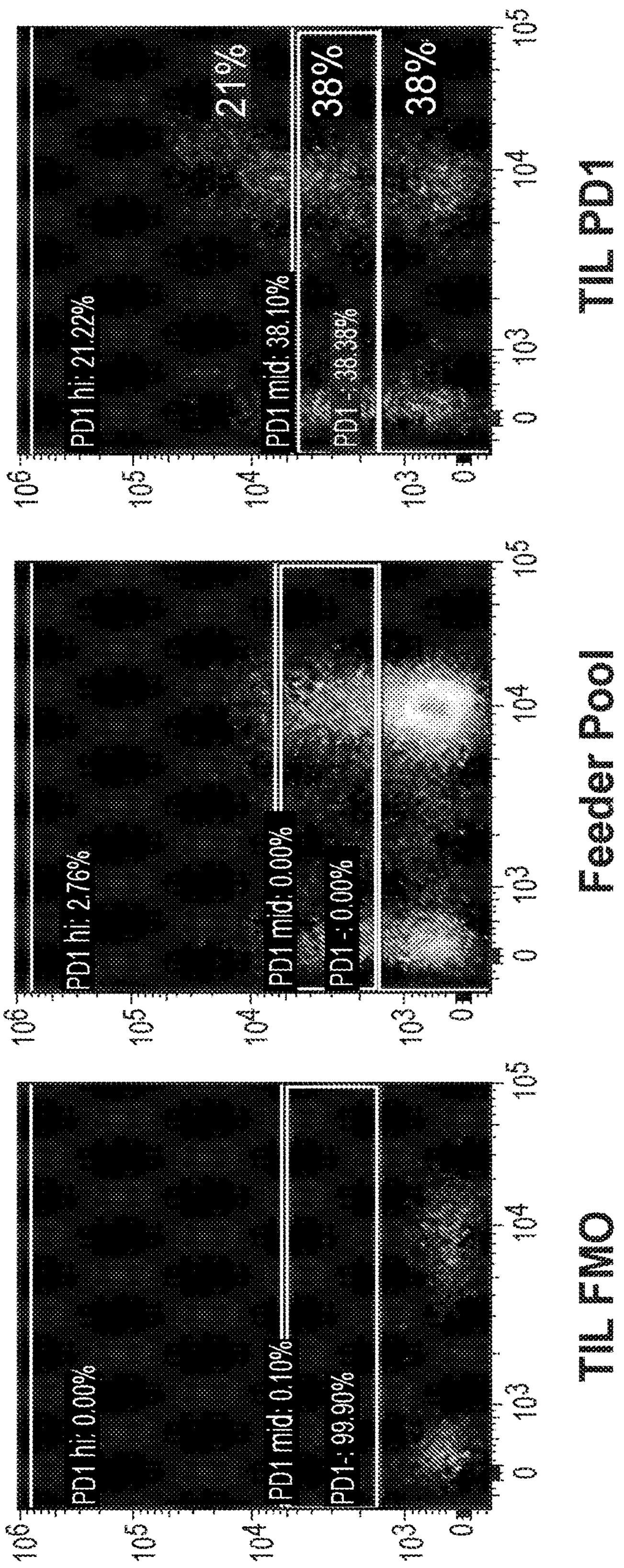

FIG. 123: Exemplary data showing PD1$^+$ Selection: Gating on PD1+ high (PD-1high) for L4096 tumor sample.

Figure 124:
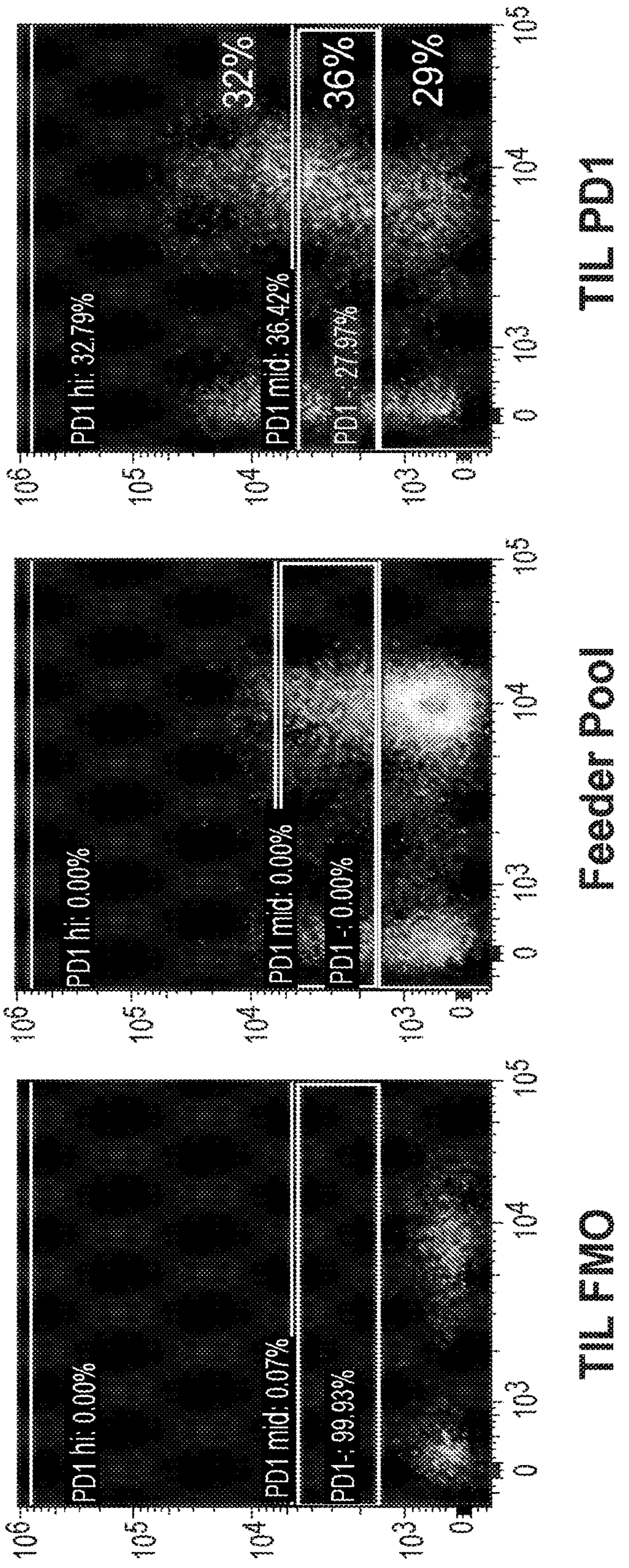

FIG. 124: Exemplary data showing PD1$^+$ Selection: Gating on PD1+ high (PD-1high) for H3038 tumor sample.

Figure 125:
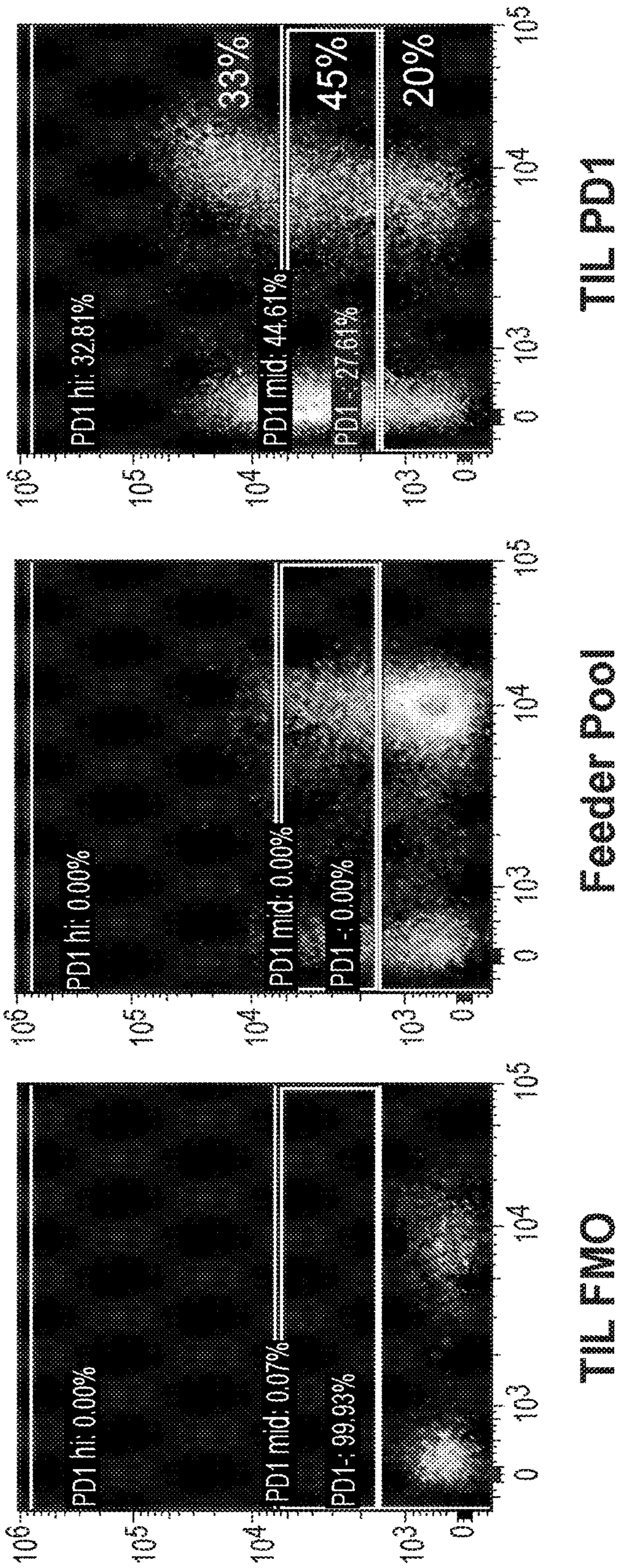

FIG. 125: Exemplary data showing PD1$^+$ Selection: Gating on PD1+ high (PD-1high) for L4101 tumor sample. (Note: potential gating issue with CD8 in third panel.)

Figure 126:
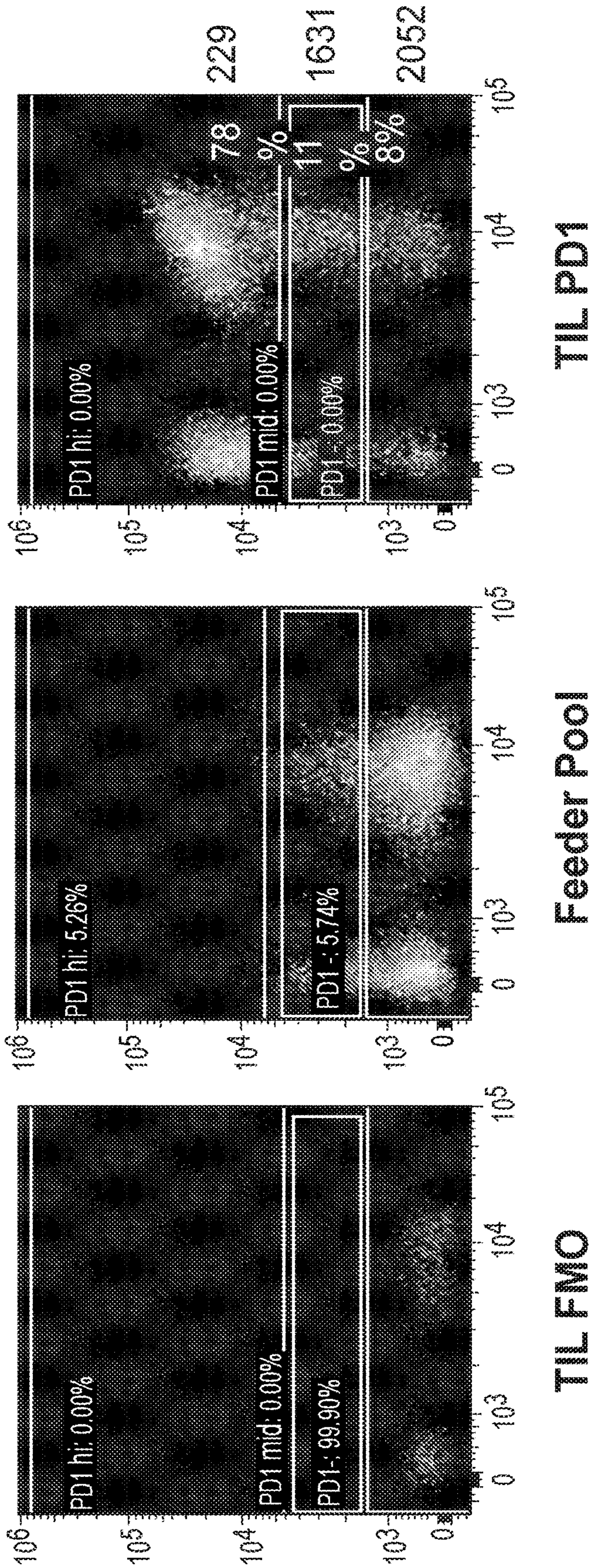

FIG. 126: Exemplary data showing PD1$^+$ Selection: Gating on PD1+ high (PD-1high) for L4097 tumor sample.

Figure 127:
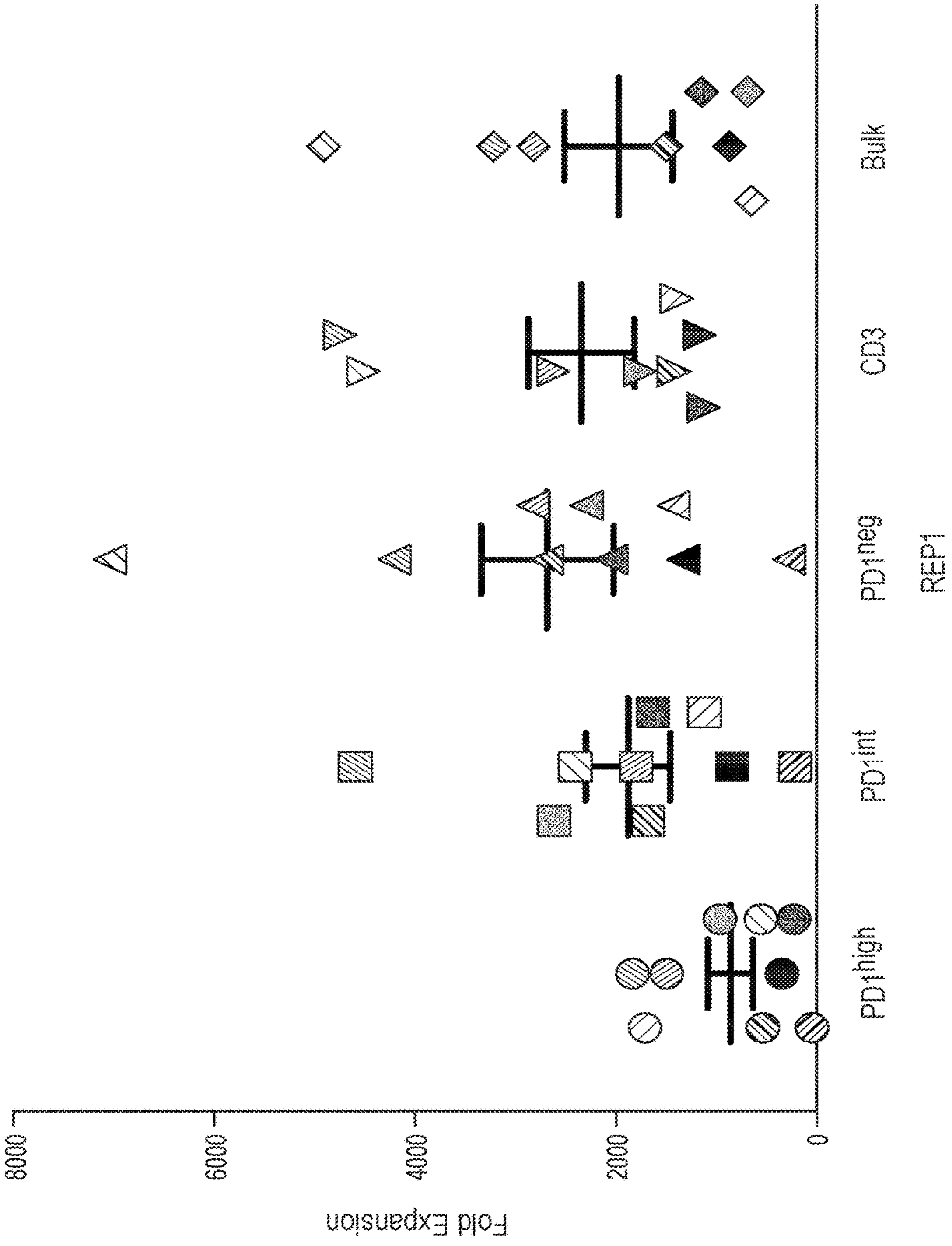

FIG. 127: Data showing expansion in the various PD-1 selected populations. PD-1high expanded cells may have reduced expansion in REP1.

FIG. 128: Summary of sort and expansion results for PD-1 selection. Sorting PD $1^{high}$ cells using the EH12.2H7 anti-PD-1 antibody.

FIG. 129: Summary of sort and expansion results for PD-1 selection. Sorting PD $1^{high}$ cells using the EH12.2H7 anti-PD-1 antibody.

Figure 130:
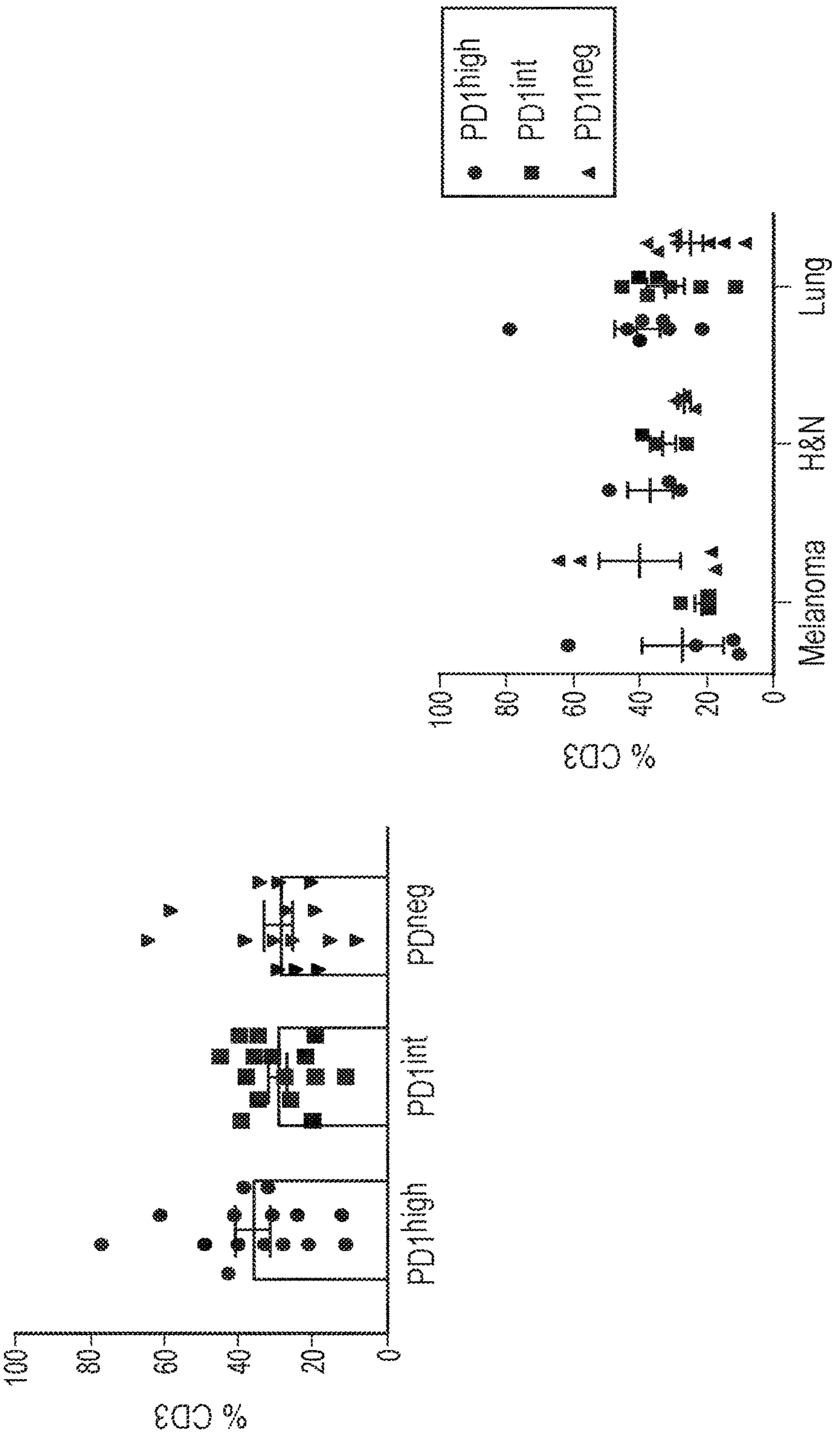

FIG. 130: Graphical representation of the summary data for the sort and expansion results for PD-1 selection from FIGS. 128 and 129. Sorting PD$1^{high}$ cells using the EH12.2H7 anti-PD-1 antibody.

Figure 131:
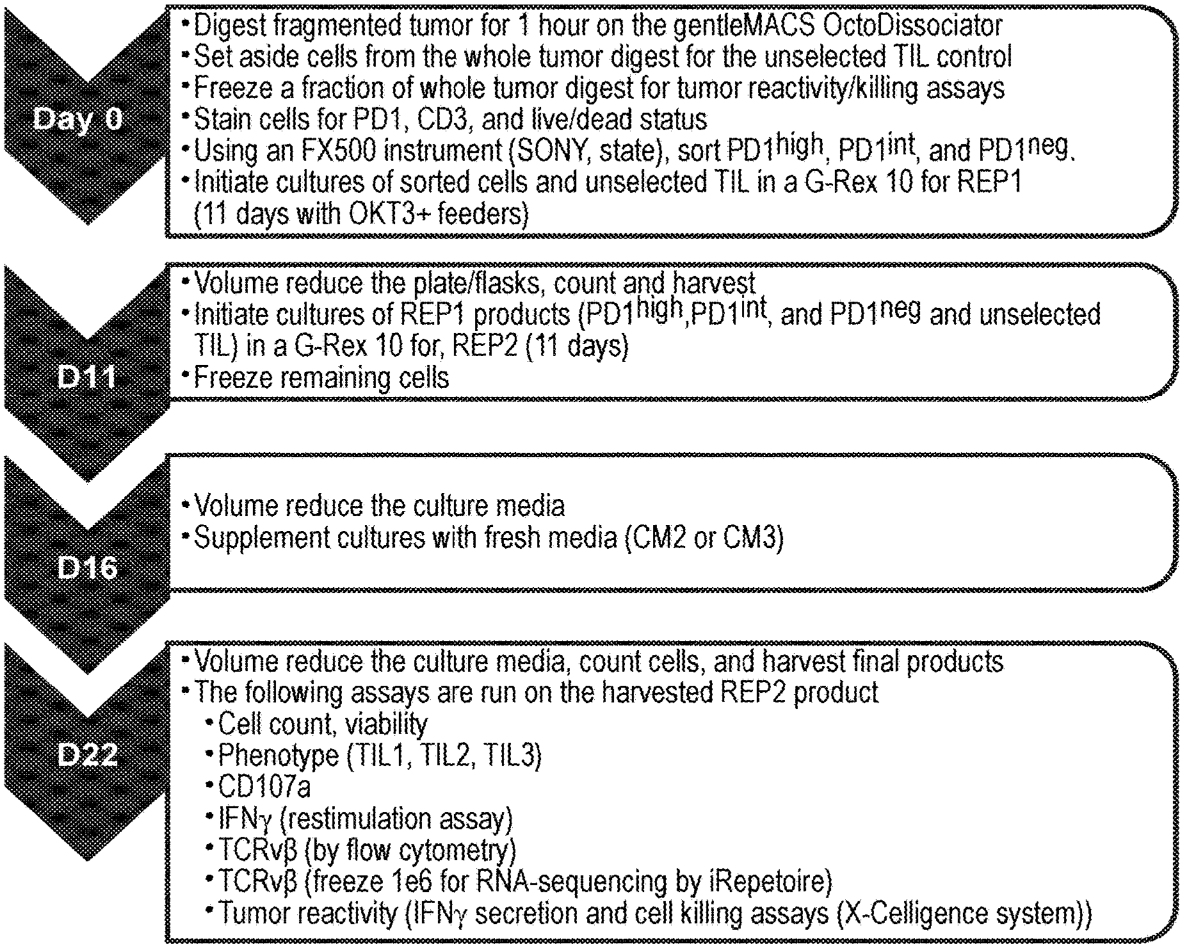

FIG. 131: Provides the structures I-A and I-B, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including CH3 and CH2 domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a VH and a VL chain connected by a linker that may comprise hydrophilic residues and Gly and Ser sequences for flexibility, as well as Glu and Lys for solubility.

Figure 132:
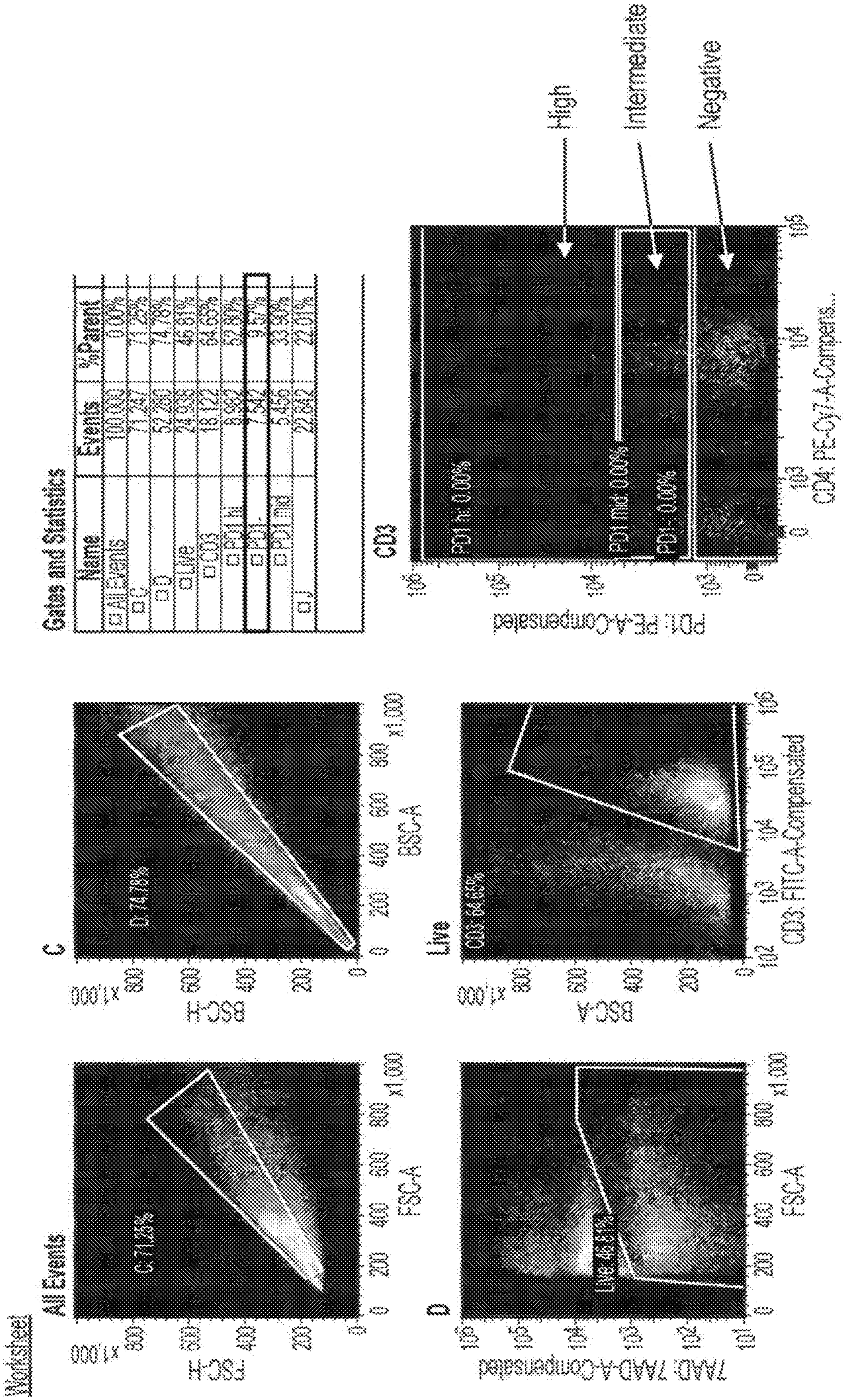

FIG. 132: Data showing selected 100,000 cell collections for both drop-down menus seen above. Verified that the cell populations were gated correctly. The gates were set at high, medium, and low by using the PBMC, the FMO control, and the sample itself to distinguish the three populations.

Figure 133:
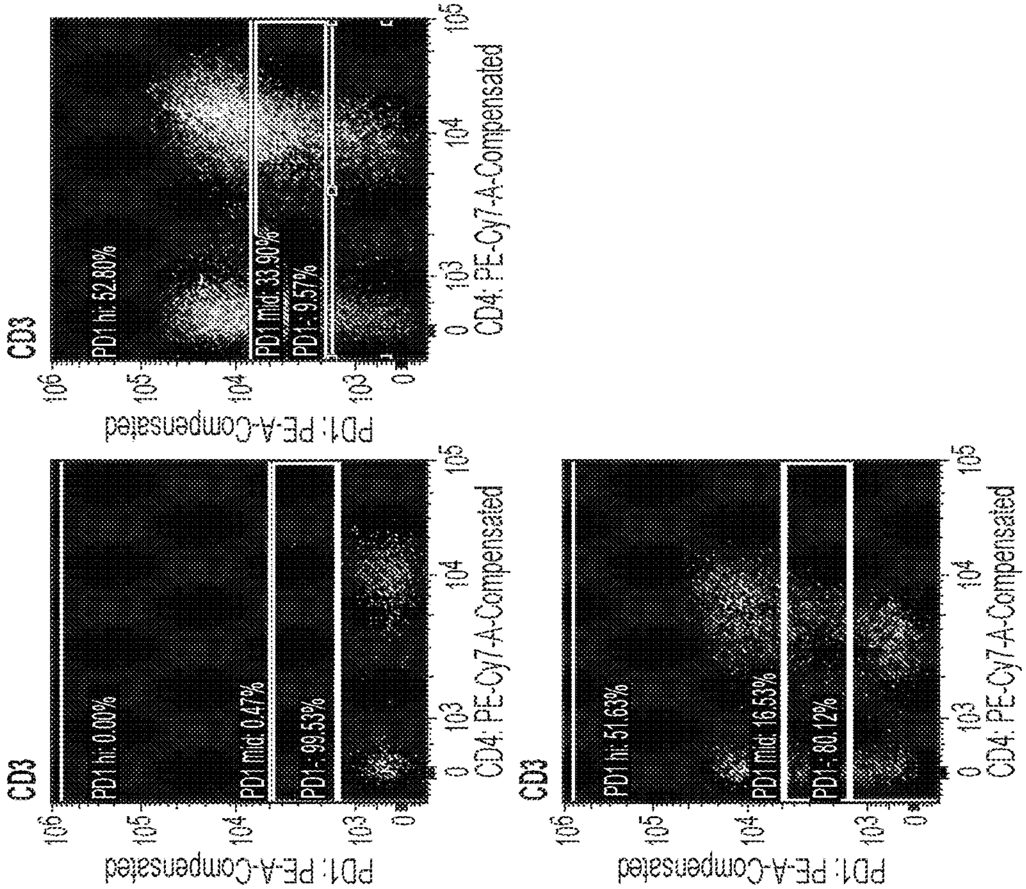
Figure 135A:
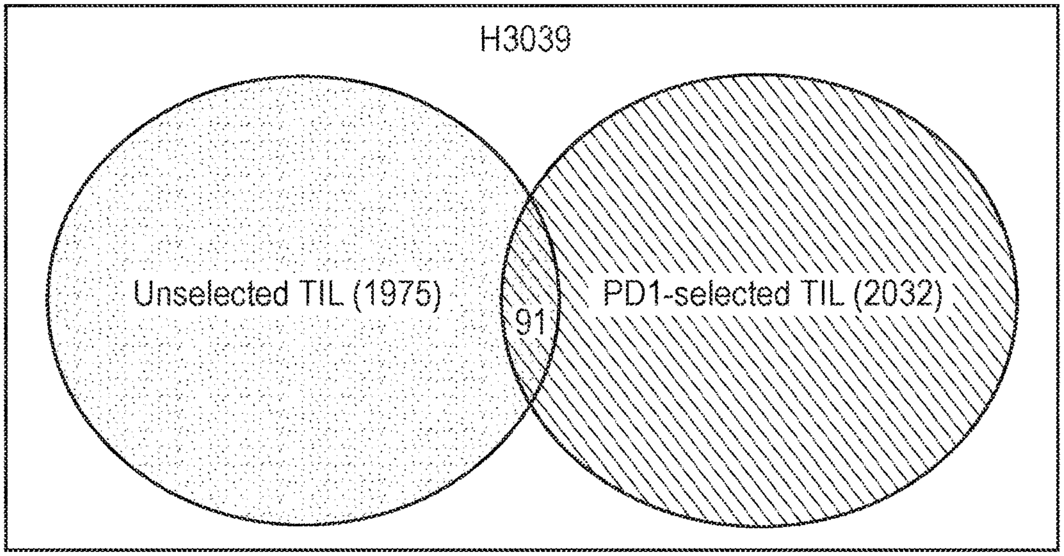
Figure 135B:
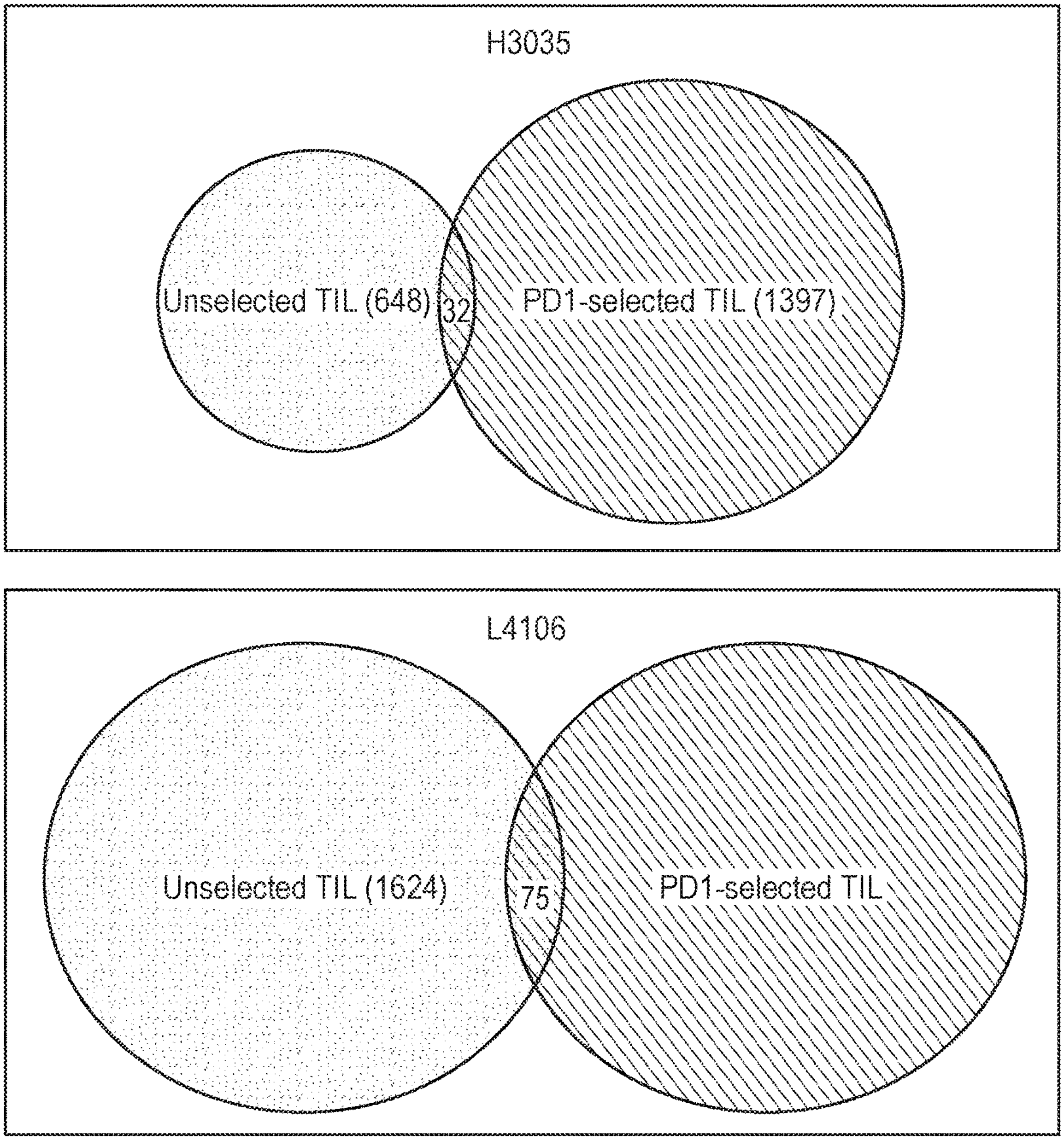
Figure 135C:
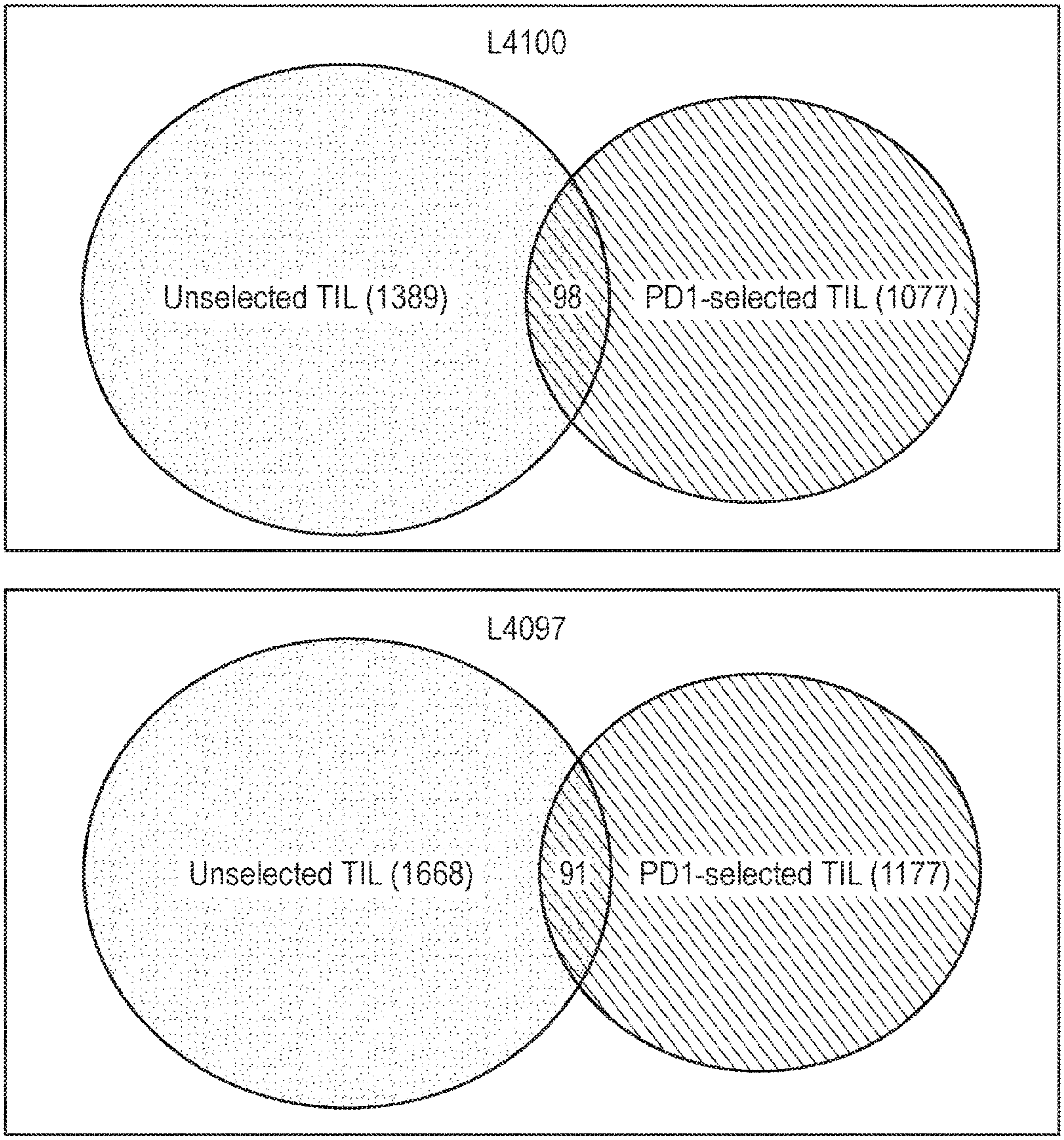
Figure 135D:
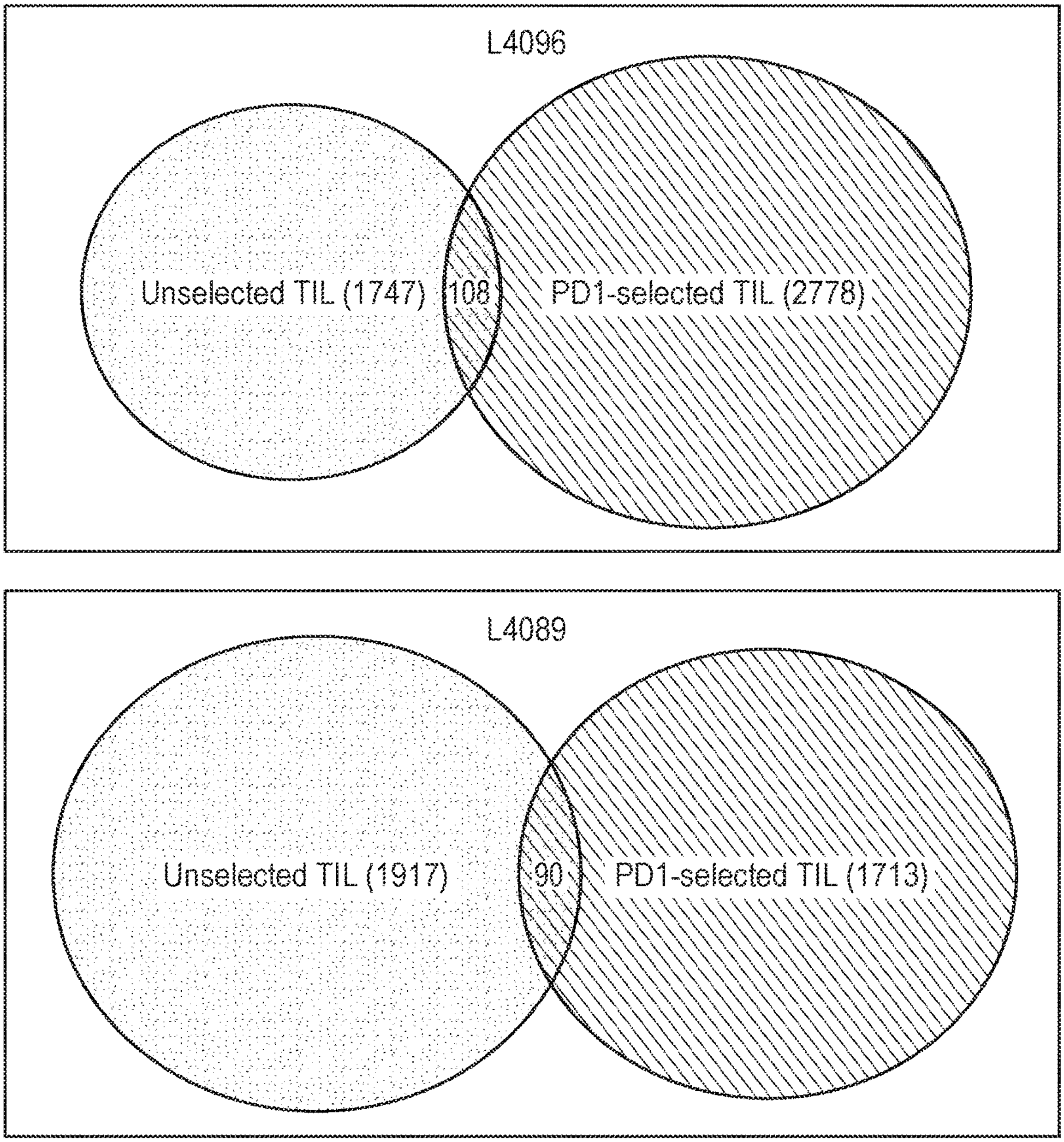

FIG. 133: Top Left: This is the FMO control. Make sure the int and high gates are less than 0.5%. Top Right: A representative plot in which the separation of high and mid is not clear. The background was higher on this day causing the negative gate to be higher. Bottom: A clear representation of high and mid. Data provides it could be necessary to adjust the BSC or FSC settings. Did not adjust the voltages for any other channels. Adjusted the PD1 gate as necessary.

FIG. 134: Unique CDR3vβ composition of PD1-selected and unselected TIL. Expanded unselected and PD1-selected TIL from 2 HNSCC and 5 NSCLC were analyzed for their repertoire of CDR3vβ. Number of unique CDR3B, noted uCDR3 count, (A.) and Diversity index expressed as Shannon entropy (B.) are plotted for each individual sample. P-values calculated by paired t-test are noted on their respective graphs.

FIG. 135A-135E: Graphs showing clonal overlap between PD1-selected and unselected TIL. Expanded TIL from 2 HNSCC and 5 NSCLC were analyzed for their repertoire of CDR3vβ. A. Number of unique CDR3vβ shared between PD1-selected (blue) and unselected (red) TIL samples are shown in the intersect of a Venn diagram for each individual tumor sample (B.-D). Percent and portion shared TIL in unselected and PD1-selected TIL are plotted for each individual sample (E.). P-values calculated by paired t-test are noted on their respective graphs.

Figure 136A:
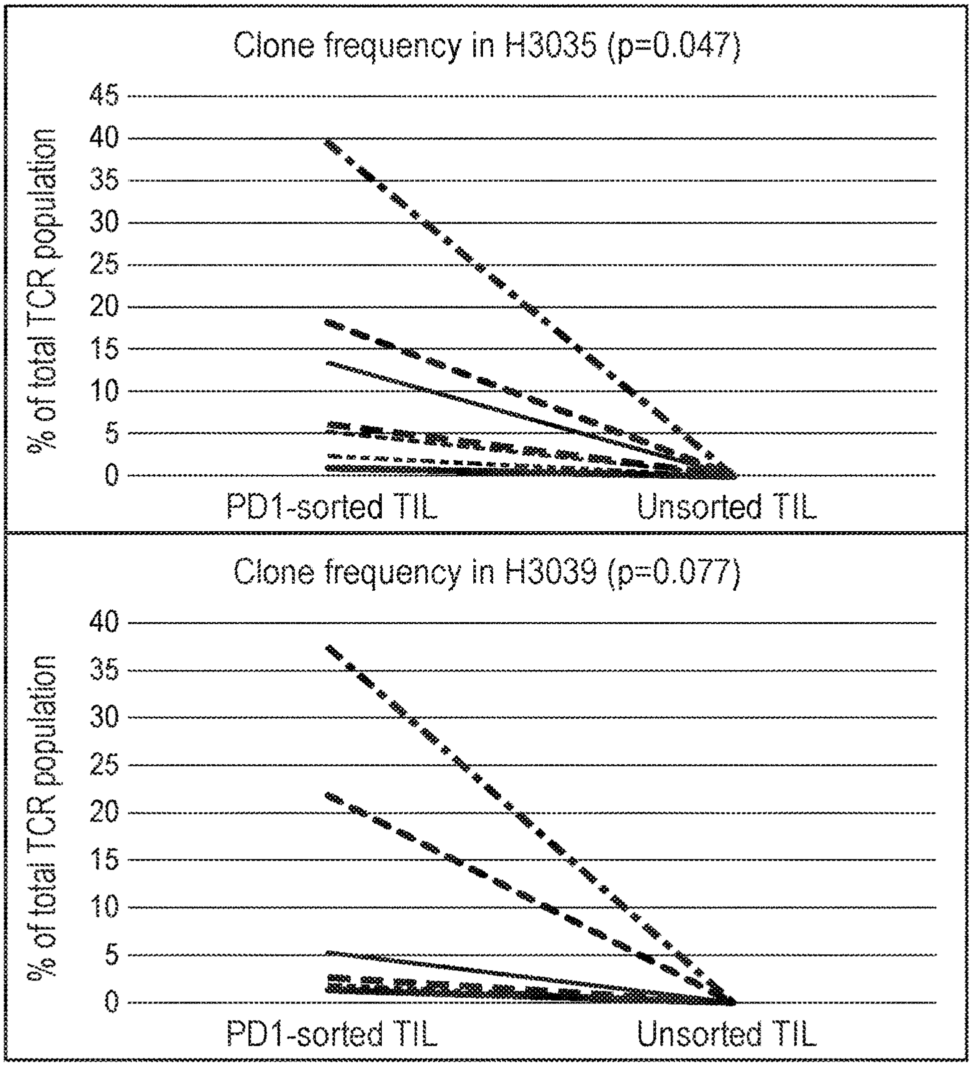
Figure 136B:
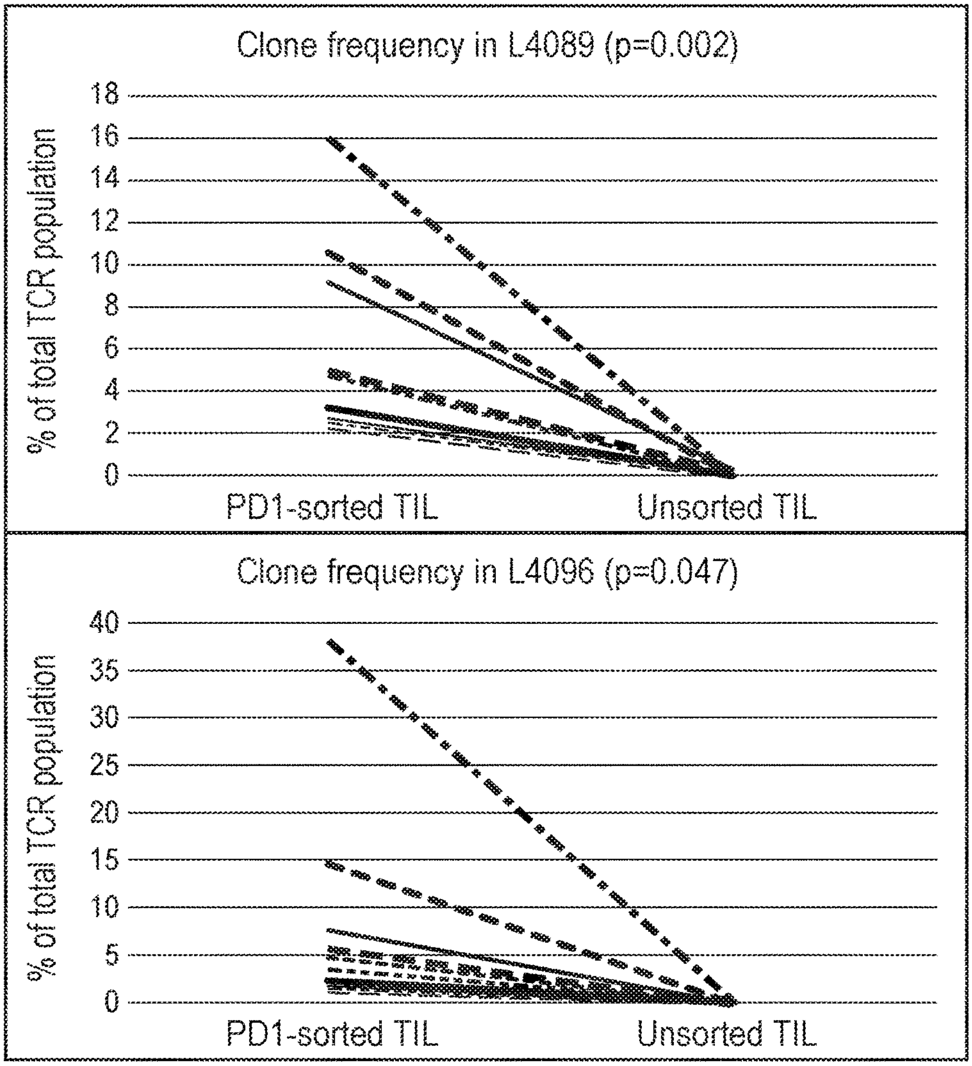
Figure 136C:
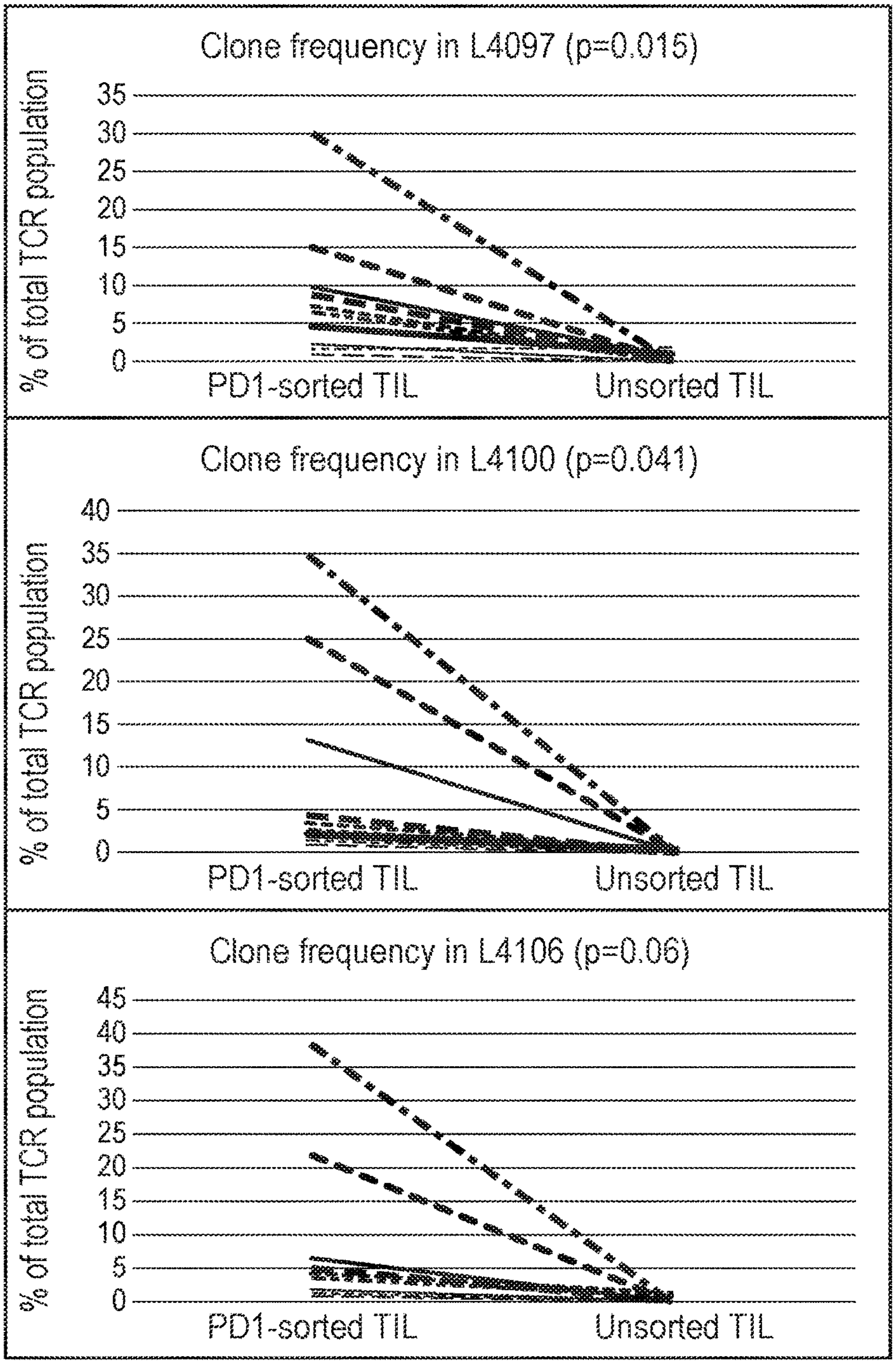

FIG. 136A-136C: Frequency of the top 10 PD1-selected TIL clones in the unselected TIL product. (A.-C.) Expanded PD1-selected and unselected TIL from 2 HNSCC and 5 NSCLC were analyzed for their repertoire of CDR3vβ. Unique CDR3vβ sequences identified in the PD1-selected TIL product were ranked from most to least frequent. The frequencies of each individual top 10 PD1-selected TIL clones in each one of the paired products is plotted. Paired samples are linked by plain lines. P-values calculated by paired t-test are noted on their respective graphs.

FIG. 137: Description of Tumor Digests used for these studies.

Figure 138:
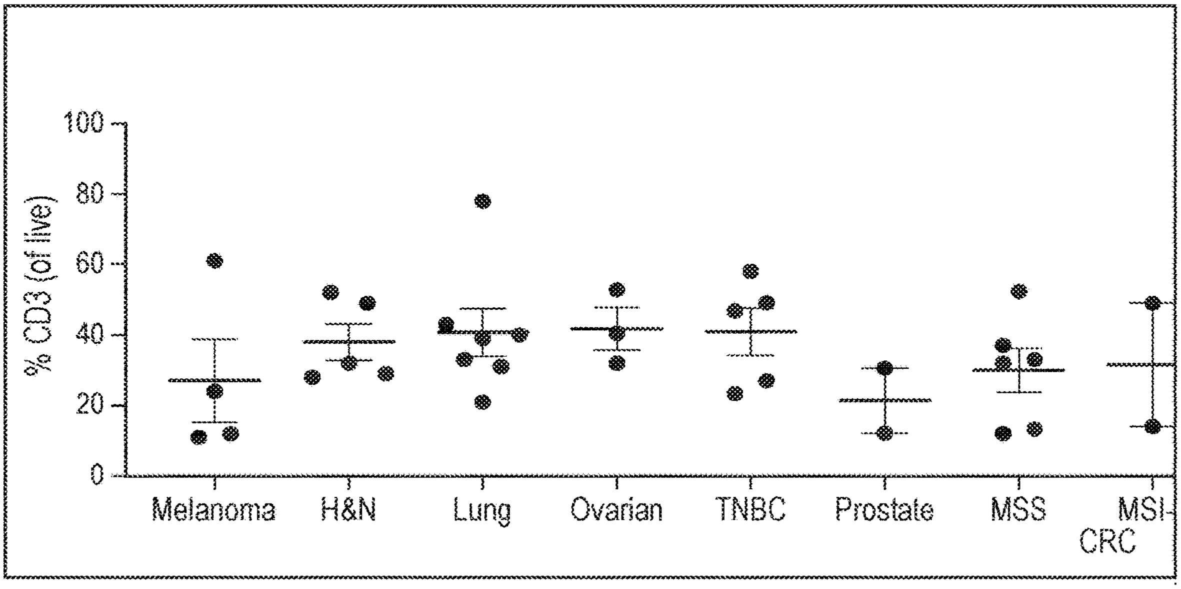

FIG. 138: Detection of PD1+ cells in tumor digests from various histologies. Legend: PD1 expression in multiple histologies. Percentage of PD1+ TIL in the CD3+ TIL population are plotted for individual samples within each histology. Horizontal lines represent the mean percentages of each subset and vertical lines represent the standard errors.

FIG. 139: Description of PD1-selected and unselected TIL used for this study.

Figure 140:
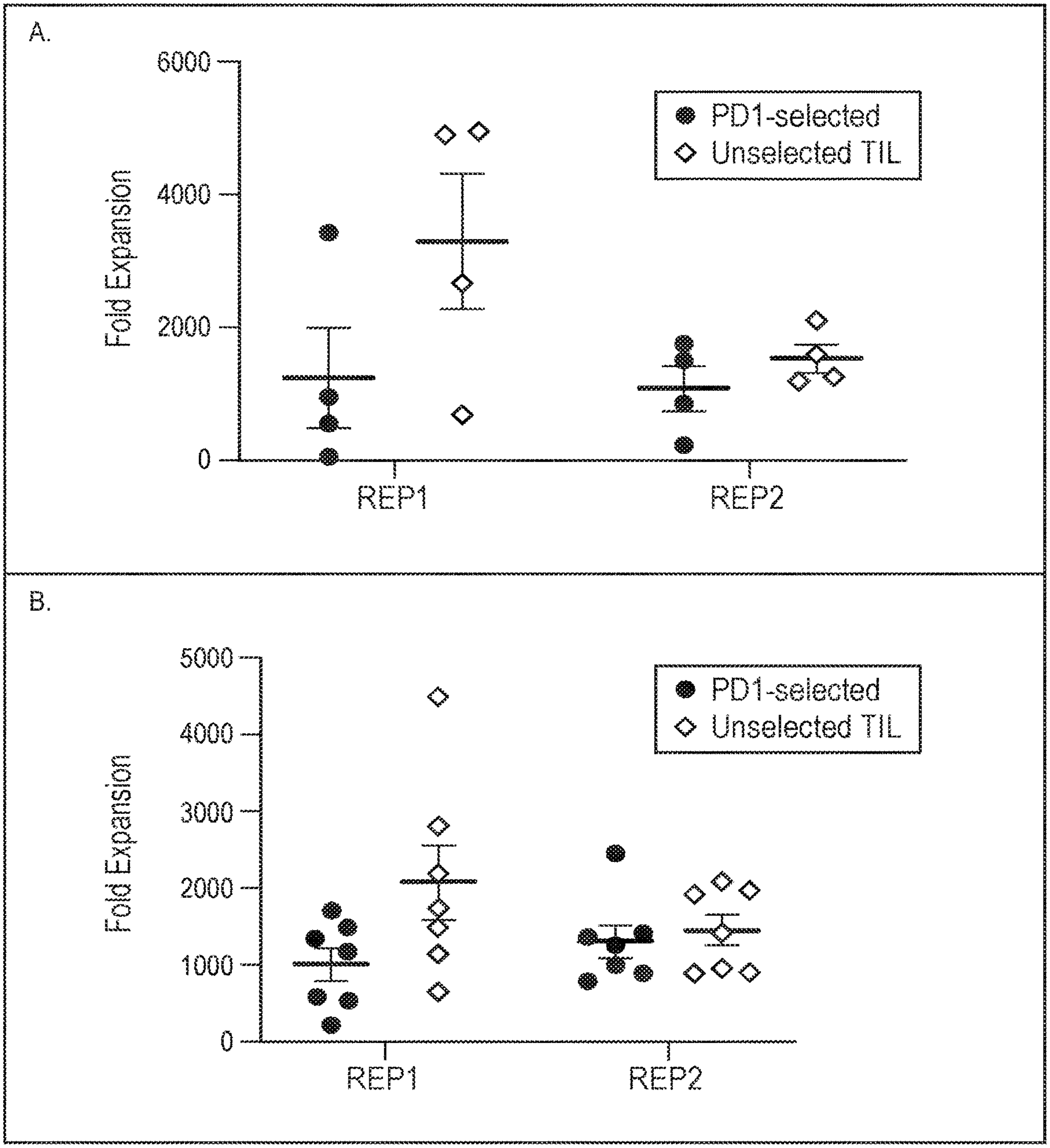
Figure 140:
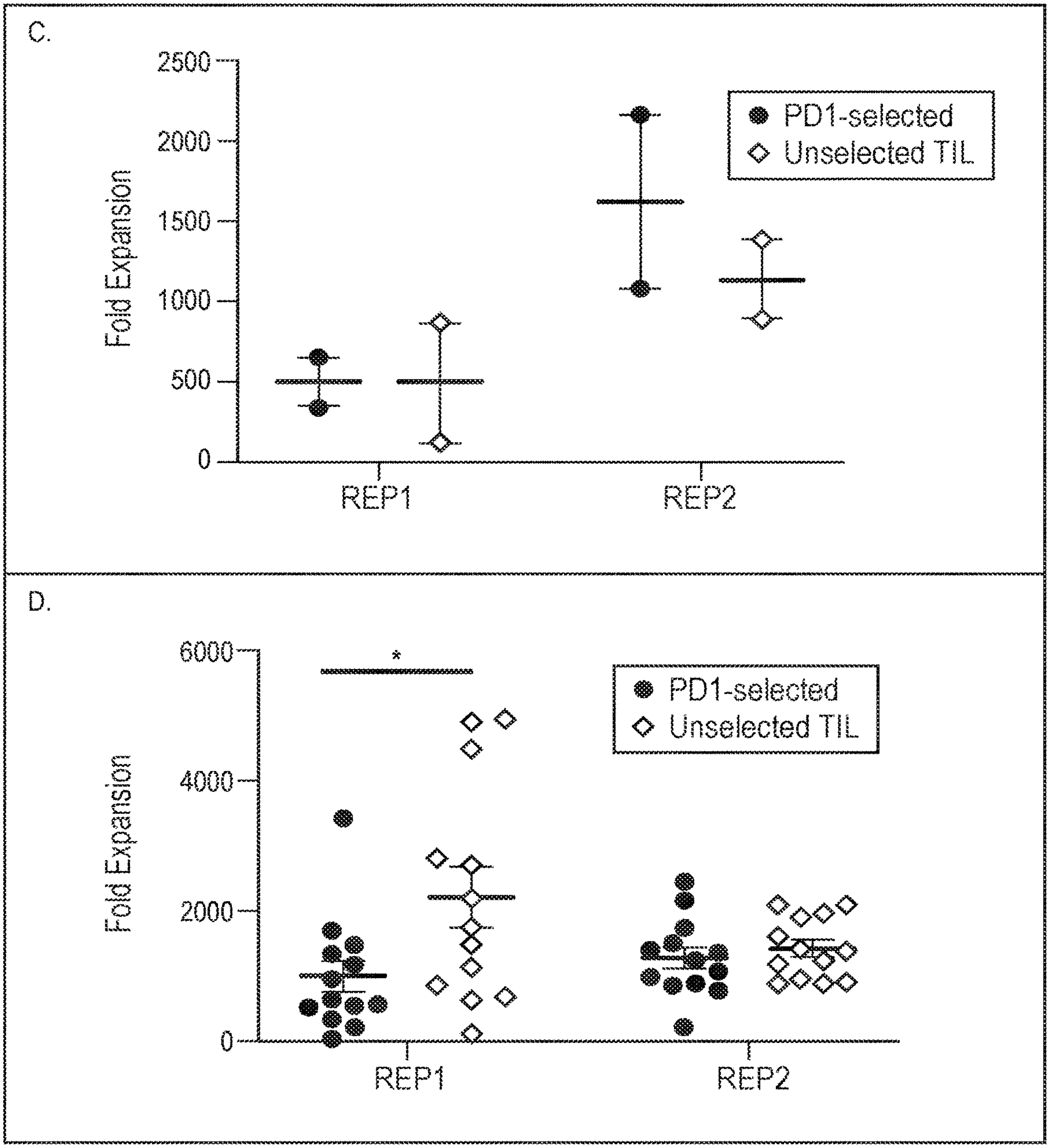

FIG. 140: Reduced Fold Expansion in PD1-selected TIL during REP1, but not REP2. Legend: PD1-sorted and unselected from (A) melanoma, (B) NSCLC and (C) HNSCC were expanded through two 11-day REPs. Fold expansion for all assayed tumors is shown in (D). Total cell counts at the completion of REP1 and REP2 were used to calculate fold expansions in the TIL populations. Results are plotted for individual samples, with the black dots representing the PD1-selected TIL and the gray triangles representing the unselected TIL. Horizontal lines represent the mean percentages of each subset and vertical lines represent the standard errors. Statistical significance was assessed by a paired student t-test; * designates a p value <0.05.

FIG. 141: Expansion results from various tumor samples.

FIG. 142: Description of PD1-selected and unselected TIL used for this study. PD1-selected and unselected TIL products were obtained from 4 melanoma, 7 NSCLC and 2 HNSCC according to procedure TMP-18-015. Briefly, whole tumor biopsies were digested using a cocktail of DNAse, Hyaluronidase, and Collagenase IV. A portion of the resulting single cell suspension was stained for PD1 and sorted on an FX500 instrument (Sony, HQ, New York). PD1-sorted cells and unselected whole tumor digest were subjected to two 11-day rapid expansion phases (REP) to obtain PD1-selected TIL and unselected TIL, respectively.

Figure 143:
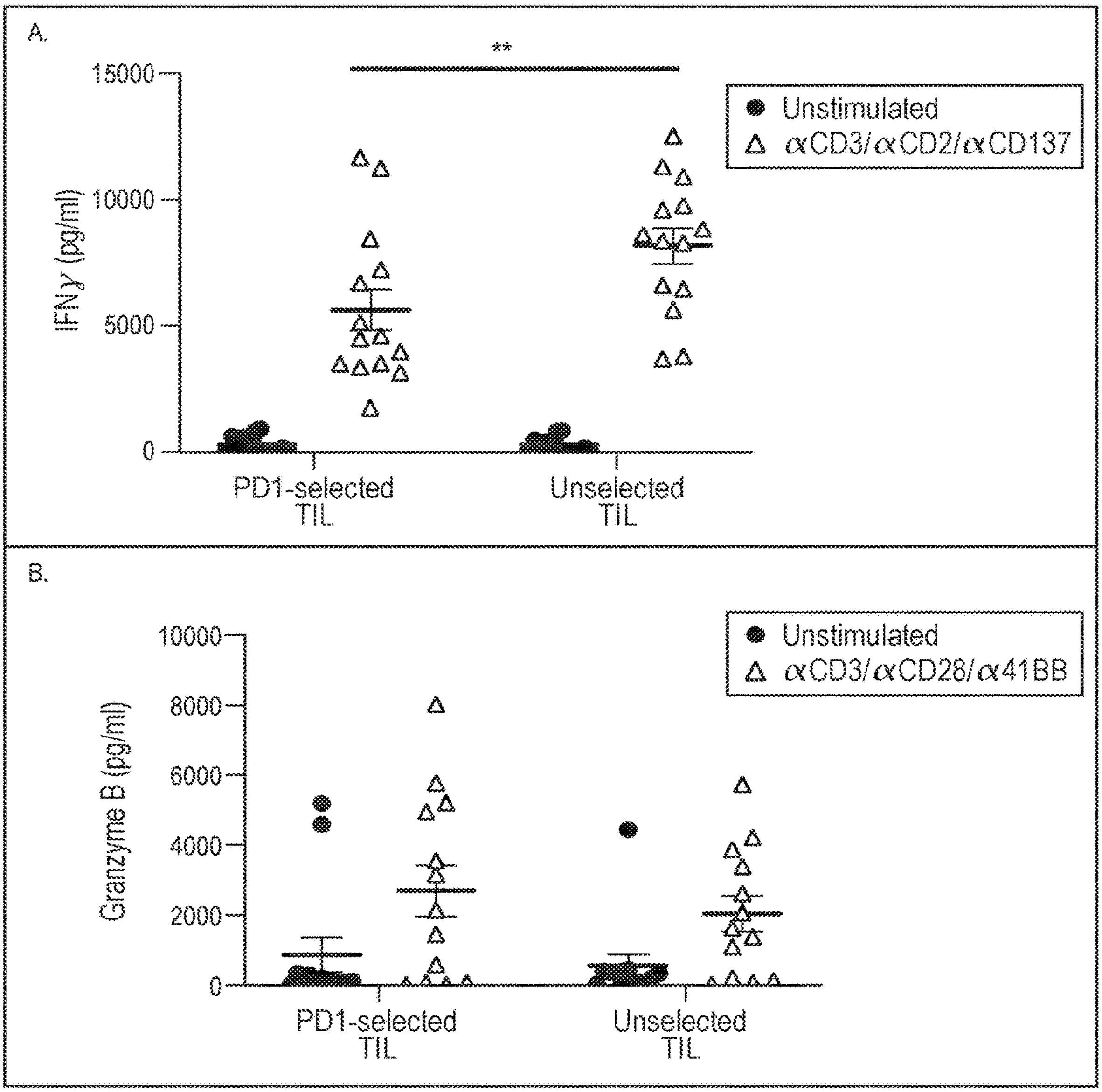

FIG. 143: PD1-selected TIL and unselected TIL produce IFNγ and Granzyme B in response to stimulation with activation beads. Legend: PD1-selected TIL and unselected TIL from 4 melanoma, 7 NSCLC and 2 HNSCC were assessed for the secretion of (A) IFNγ and (B) Granzyme. Results are plotted for individual samples, with the black dots representing the unstimulated condition and the gray triangles representing the αCD3/αCD28/α41BB stimulated condition. Horizontal lines represent the mean percentages of each subset and vertical lines represent the standard errors. Statistical significance was assessed by a paired student t-test; ** designates a p value <0.01.

Figure 144:
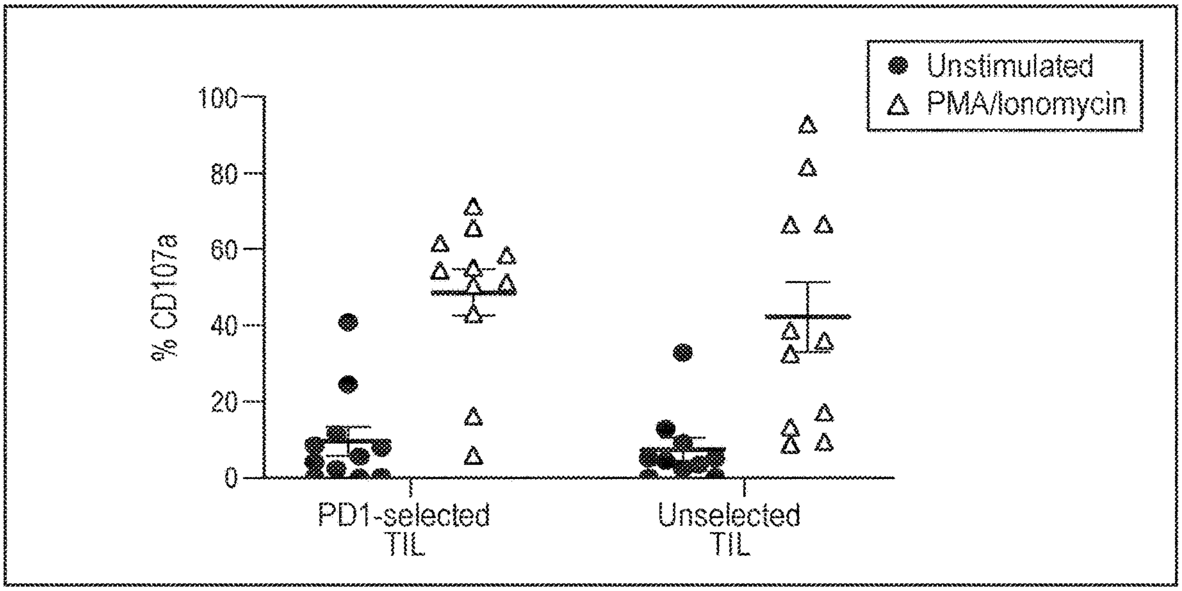

FIG. 144: PD1-selected and unselected TIL mobilize CD107a in response to PMA/Ionomycin stimulation. Legend: PD1-selected and unselected TIL from 4 melanoma 5 NSCLC and 1 HNSCC were assessed by flow cytometry for cell surface expression of CD107a, in response to PMA and Ionomycin (BioLegend, CA) stimulation. Results are plotted for individual samples, with the black dots representing the unstimulated condition and the gray triangles representing the PMA/Ionomycin stimulated condition. Horizontal lines represent the mean percentages of each subset and vertical lines represent the standard errors.

FIG. 145: Description of PD1-selected and unselected TIL used for this study.

Figure 146:
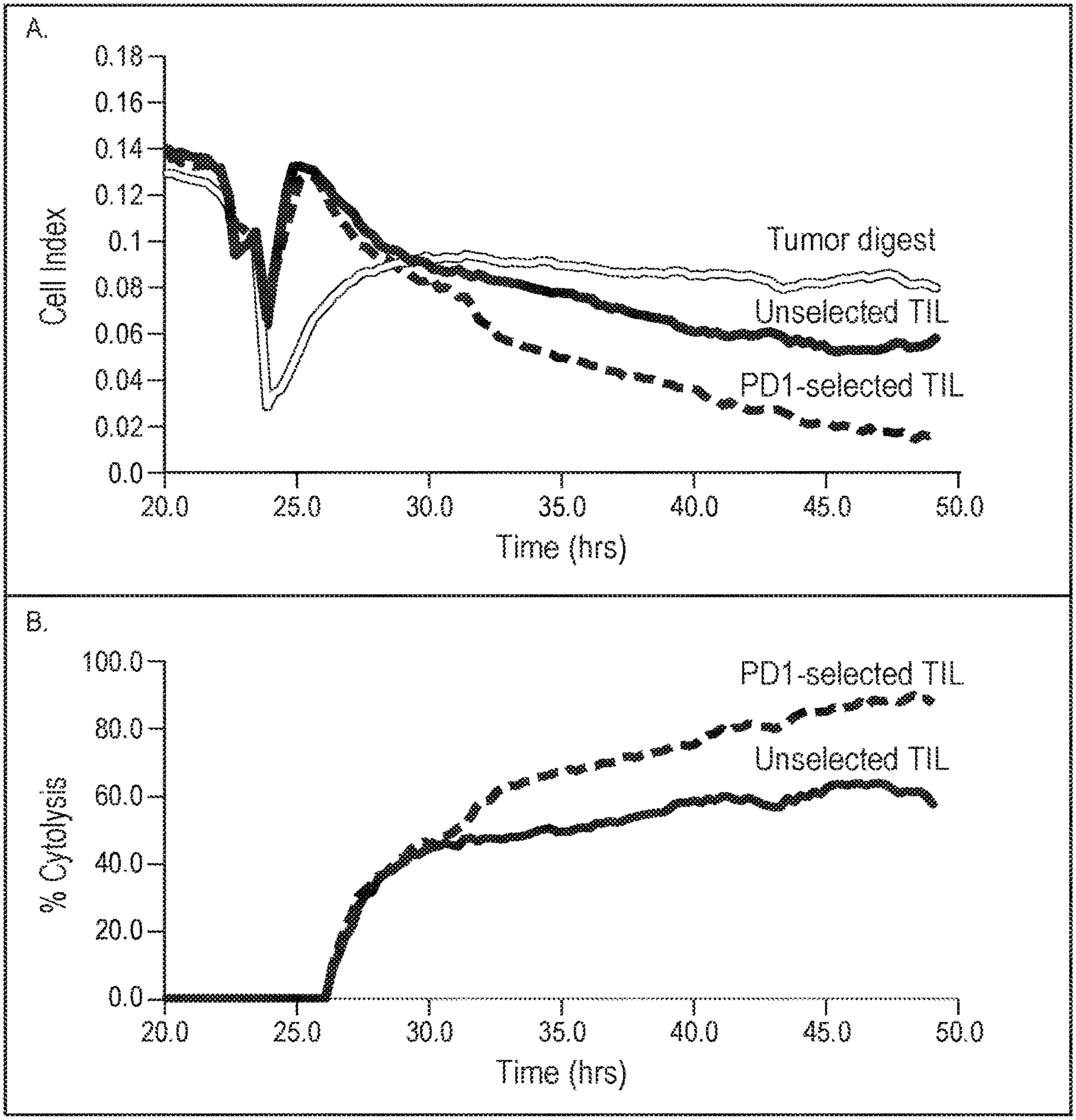

FIG. 146: PD1-selected and unselected TIL demonstrate autologous tumor-reactivity in vitro. Tumor killing, and reactivity were assessed in PD1-selected TIL and unselected TIL. (A) Cell indices and (B) tumor cell killing (% cytolysis) are shown for a melanoma sample. Supernatants from 2 NSCLC and 3 melanoma were assessed for (C) IFNγ release by ELISA. Mean values are plotted as bars and standard errors shown as vertical lines. Statistical significance was assessed by a paired student t-test; ** designates a p value <0.01.

FIG. 147: Description of PD1-selected and unselected TIL used for Example 16. PD1-selected and unselected TIL products were obtained from 4 melanoma, 7 NSCLC and 2 HNSCC according to procedure TMP-18-015. Briefly, whole tumor biopsies were digested using a cocktail of DNAse, Hyaluronidase, and Collagenase IV. A portion of the resulting single cell suspension was stained for PD1 and sorted on an FX500 instrument (Sony, HQ, New York). PD1-selected and unselected TIL were subjected to two 11-day REP's.

Figure 148:
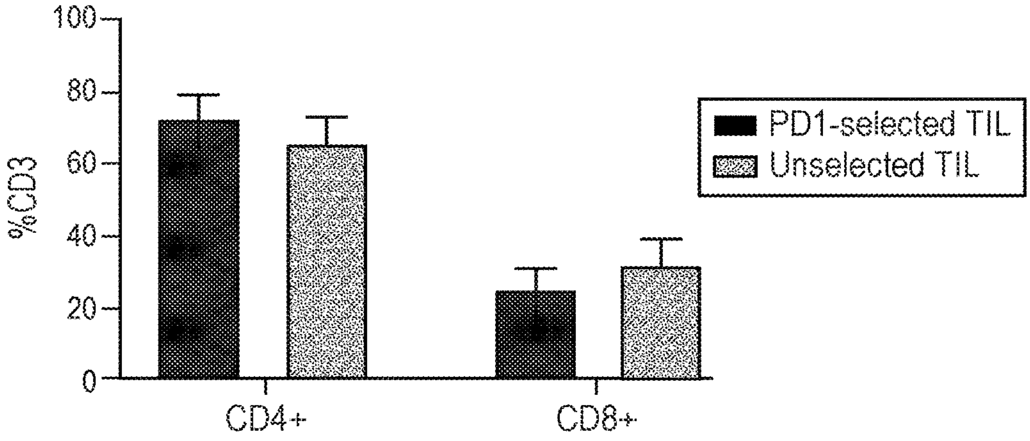

FIG. 148: FIG. 1: Compared levels of CD4+ and CD8+ T cells in PD1-selected and unselected TIL. Legend: PD1-selected and unselected TIL from 4 melanoma, 7 NSCLC, and 2 HNSCC were assessed for T cell lineage (CD4 and CD8) using flow cytometry. Results are expressed as percentages of CD3+ cells. Mean values are plotted as bars and standard errors shown as vertical lines.

Figure 149:
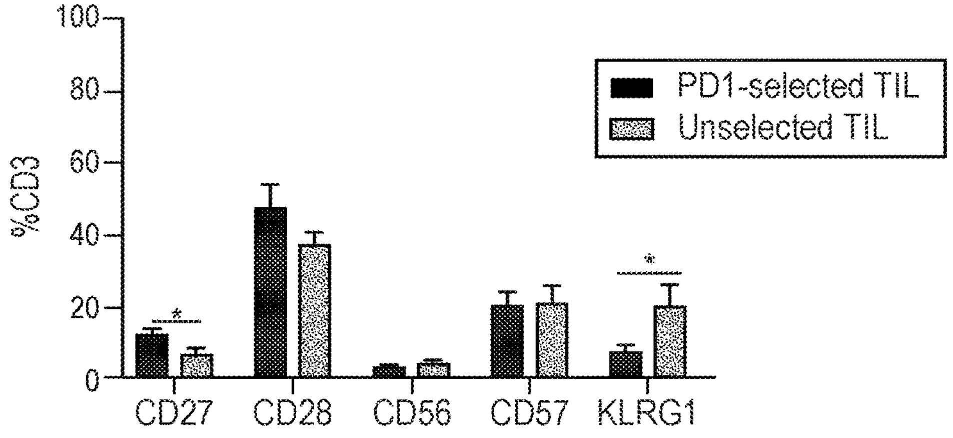

FIG. 149: Compared differentiation status of PD1$^-$ selected TIL with that of unselected TIL. Legend: PD1-selected TIL and unselected TIL from 4 melanoma, 7 NSCLC and 2 HNSCC were assessed for expression of CD27, CD28, CD56, CD57, and KLRGI using flow cytometry. Results are expressed as percentages of CD3+ cells. Mean values are plotted as bars and standard errors shown as vertical lines. Statistical significance was assessed by a paired student t-test; * designates a p value <0.05.

Figure 150:
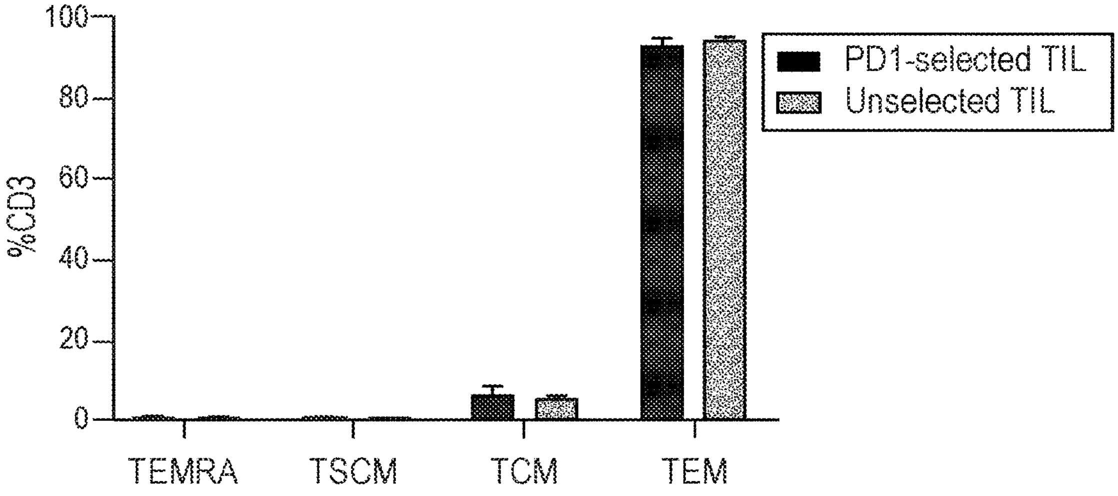

FIG. 150: Compared distribution of memory T cell subsets in PD1-selected TIL and unselected TIL. Legend: PD1-selected TIL and unselected TIL from 4 melanoma, 7 NSCLC and 2 HNSCC were assessed for the expression of the memory markers CD45RA and CCR7 by flow cytometry. T cell memory subsets were determined as indicated and average percentages of each subset plotted as black bars for PD1-selected TIL and gray bars for unselected TIL. Standard errors are shown as vertical lines.

Figure 151:
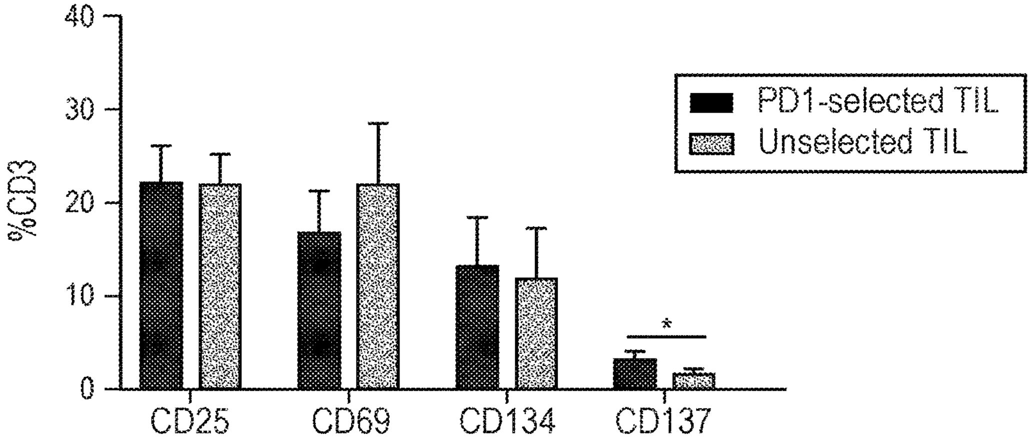

FIG. 151: Compared activation status of PD1-selected TIL and unselected TIL. Legend: PD1-selected TIL and unselected TIL from 4 melanoma, 7 NSCLC and 2 HNSCC were assessed for the expression of CD25, CD69, CD134, and CD137. Average percentages of CD3+ T cells were plotted as black bars for PD1-selected TIL and gray bars for unselected TIL. Standard errors are shown as vertical lines. Statistical significance was assessed by a paired student t-test; * designates a p value <0.05.

Figure 152:
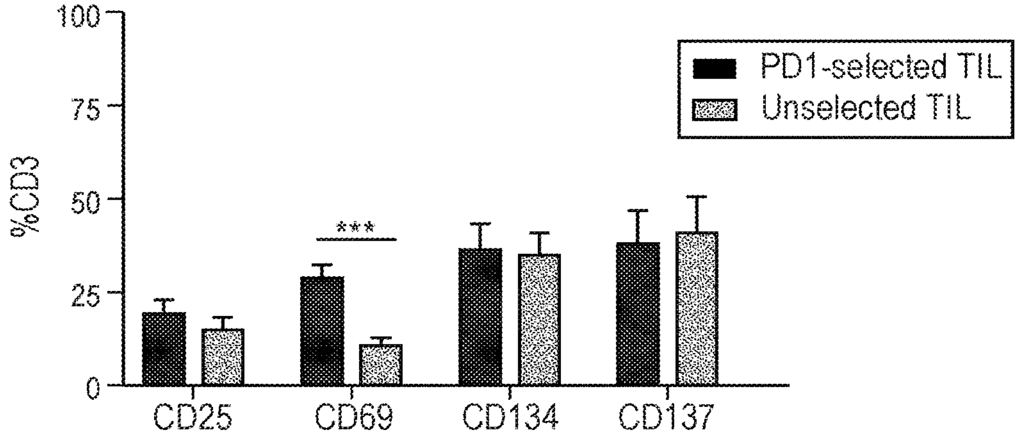

FIG. 152: Compared expression of exhaustion/inhibition markers in PD1-selected TIL and unselected TIL. Legend: PD1-selected TIL and unselected TIL from 4 melanoma, 7 NSCLC, and 2 HNSCC were assessed for the expression of LAG3, PD1, TIM3, and CD101 by flow cytometry. Mean values are plotted as bars and standard errors shown as vertical lines. Statistical significance was assessed by a paired student t-test; *** indicates a p value <0.001.

Figure 153:
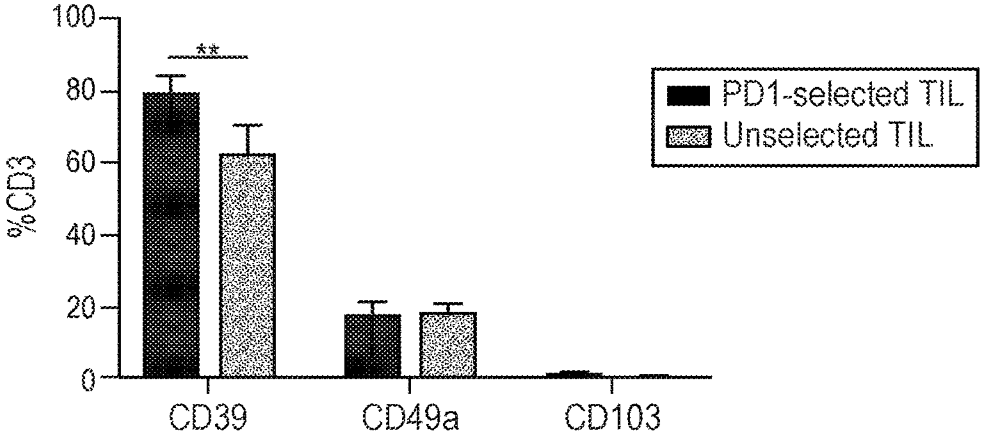

FIG. 153: Compared expression of resident memory T cell markers in PD1-selected and unselected TIL. PD1-selected TIL and unselected TIL from 4 melanoma, 7 NSCLC and 2 HNSCC were assessed for the expression of CD39, CD49a and CD103 by flow cytometry. Mean values are plotted as bars and standard errors shown as vertical lines. Statistical significance was assessed by a paired student t-test; ** indicates a p value <0.01.

FIG. 154: Full-Scale Processes embodiments for PD1 TIL culture.

Figure 155:
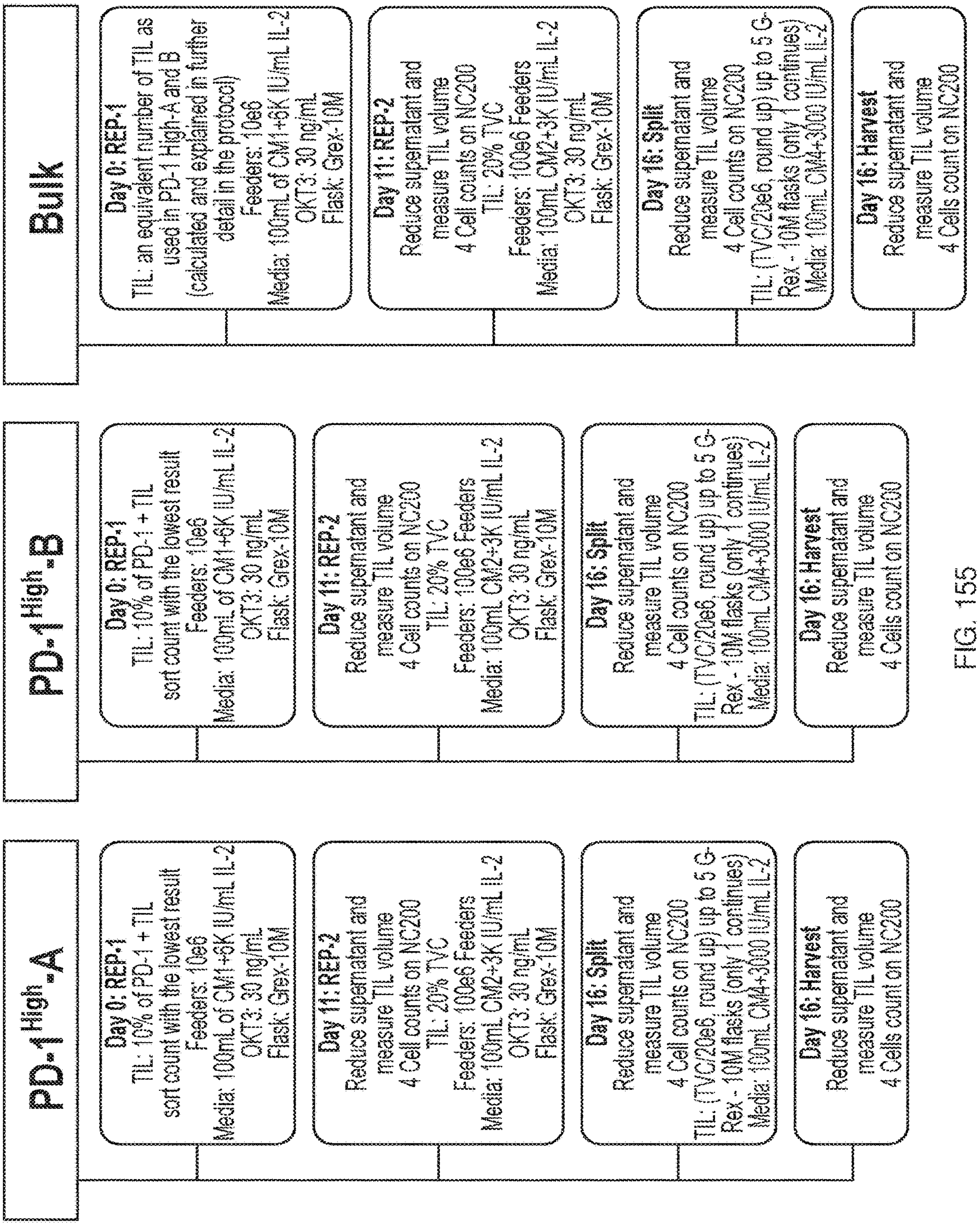

FIG. 155: Small-Scale Process Overview: PD1-A is the condition that uses the Nivolumab staining procedure outlined in this protocol. PD1-B is the condition that uses the anti-PD1-PE (Clone #EH12.2H7) staining method. Bulk condition serves as a control.

Figure 156A:
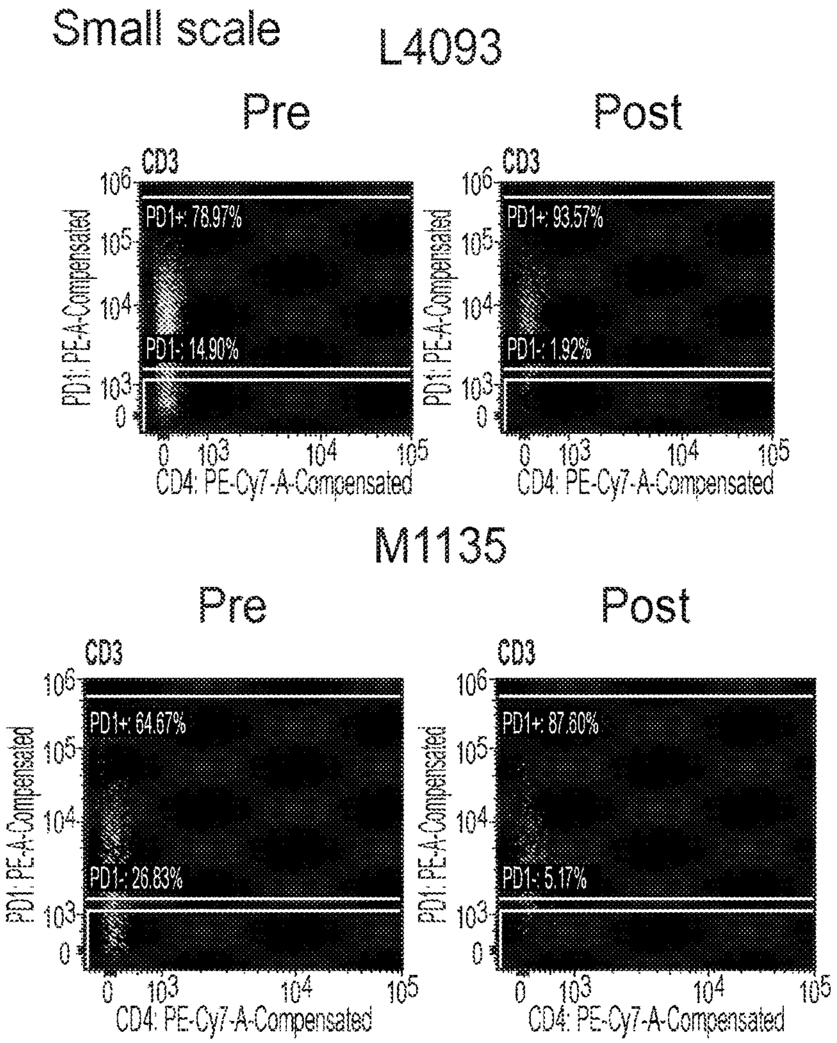
Figure 156B:
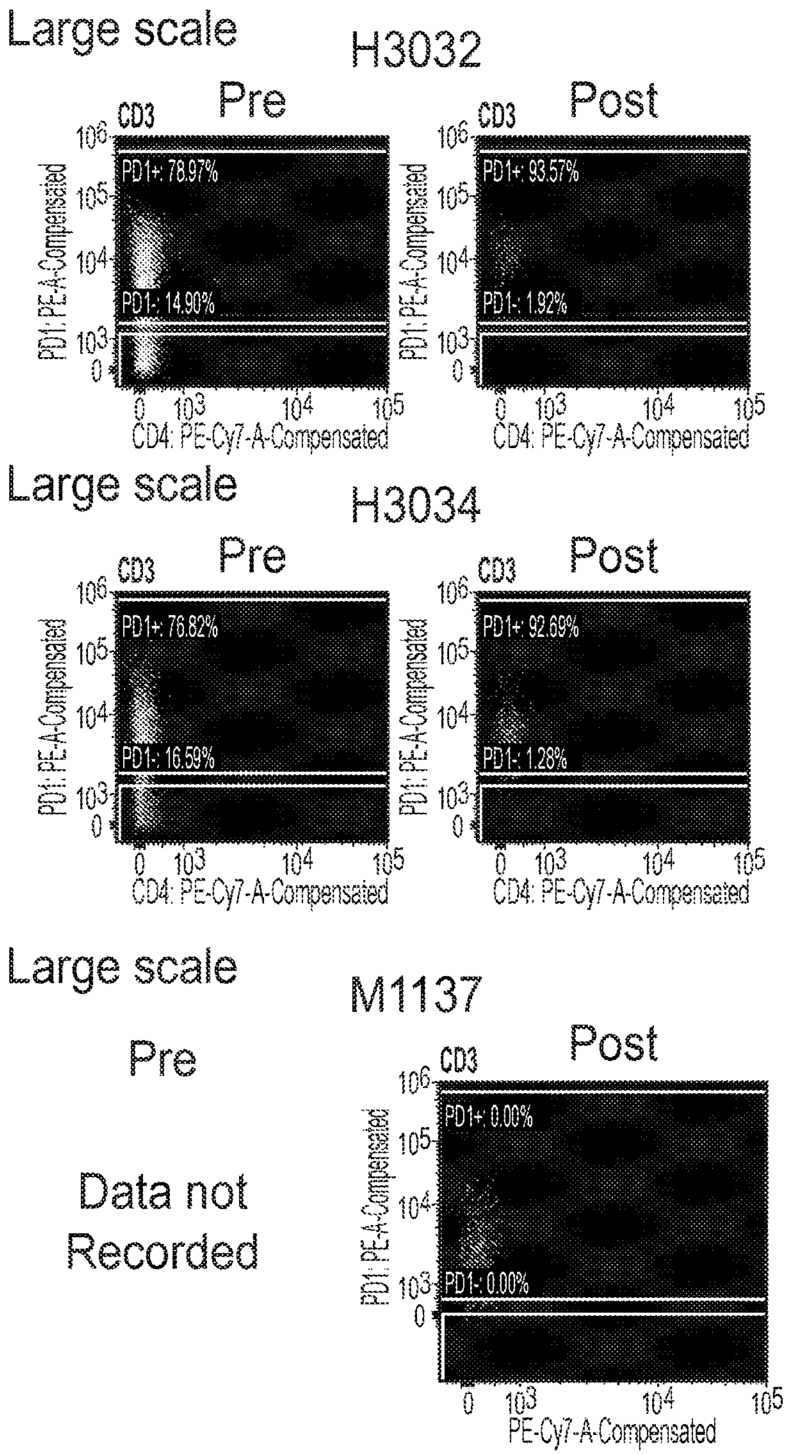

FIG. 156A-156B: Post sorted purity (% PD-1+) for all three tumors met the criterion of >80% (A. & B.). The slightly lower purity observed for the melanoma tumor relative to the Hea and Neck tumors is most likely due to the lower expression of PD-1+ cells while sorting.

Figure 157:
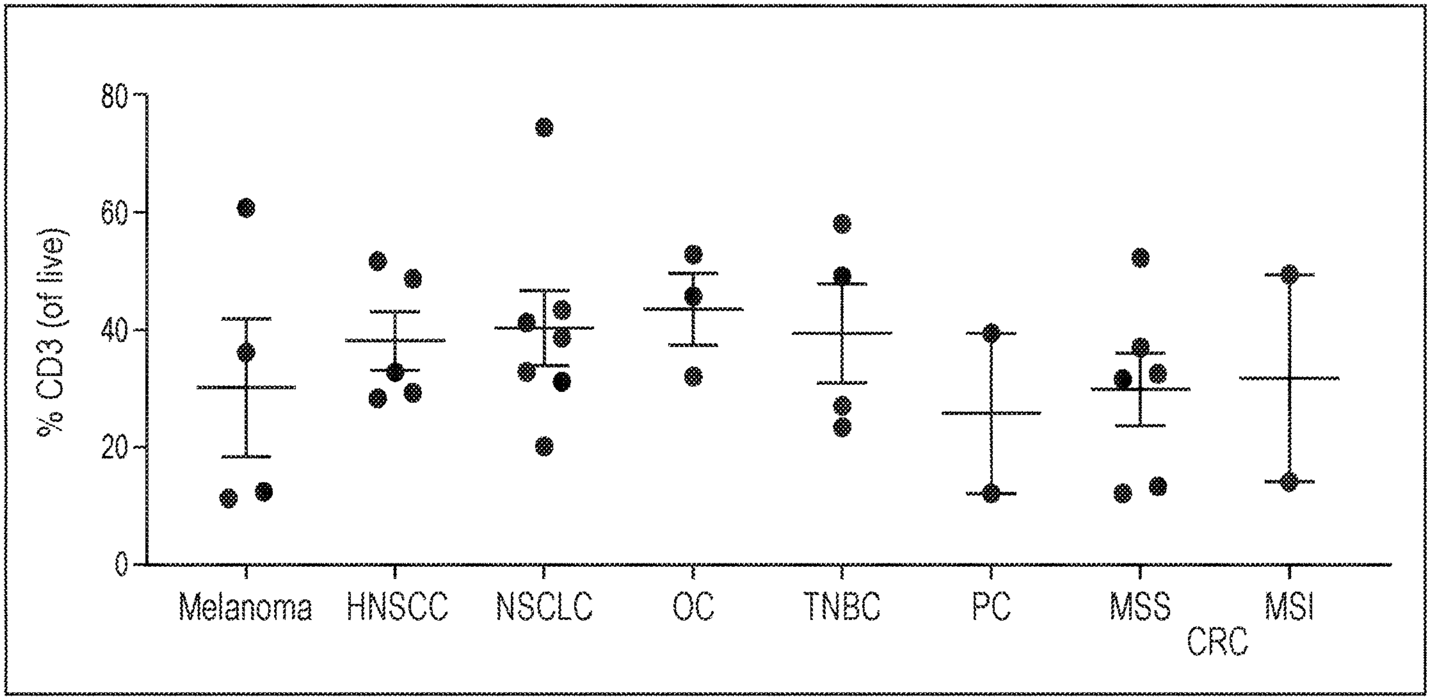
Figure 158C:
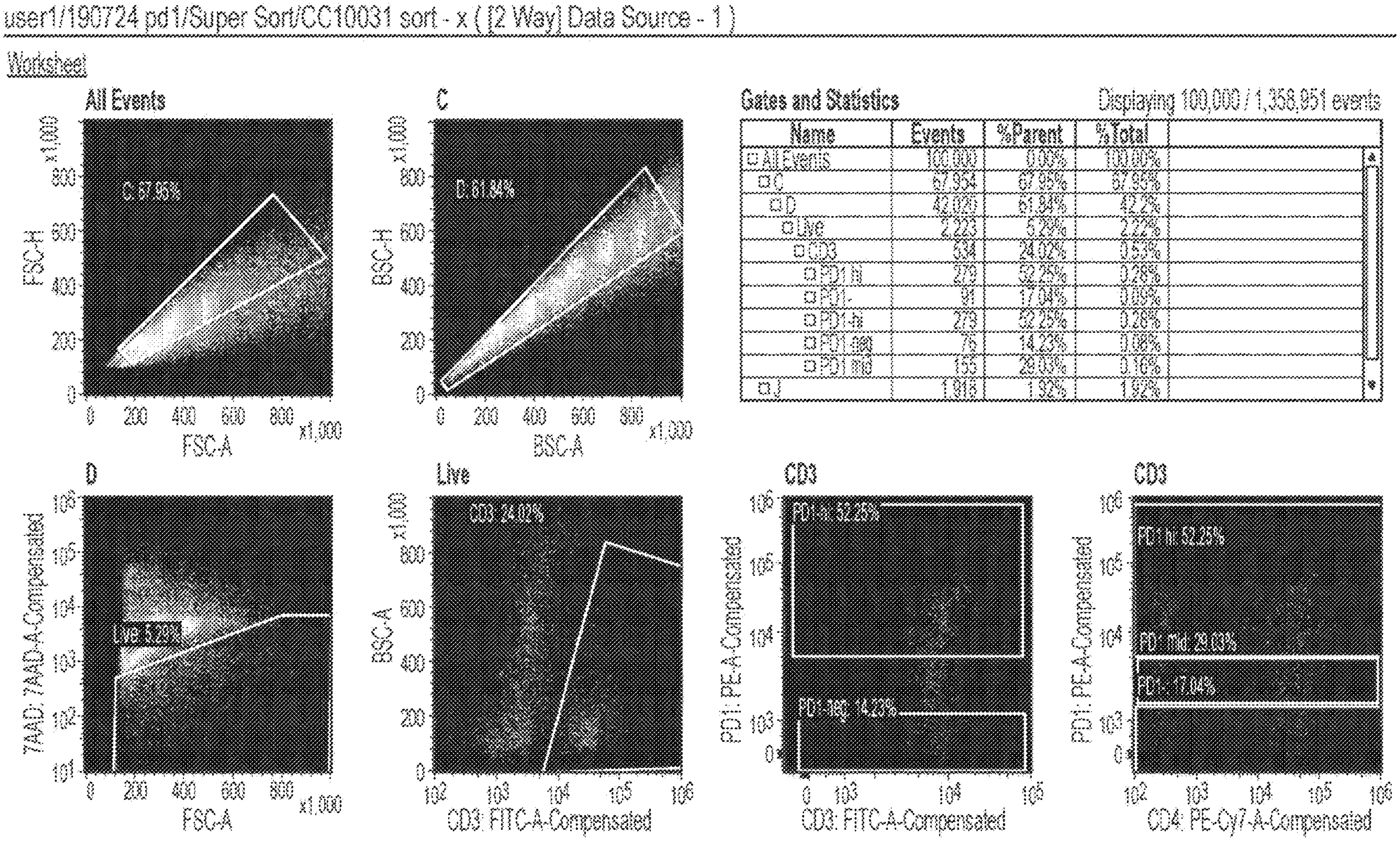
Figure 158D:
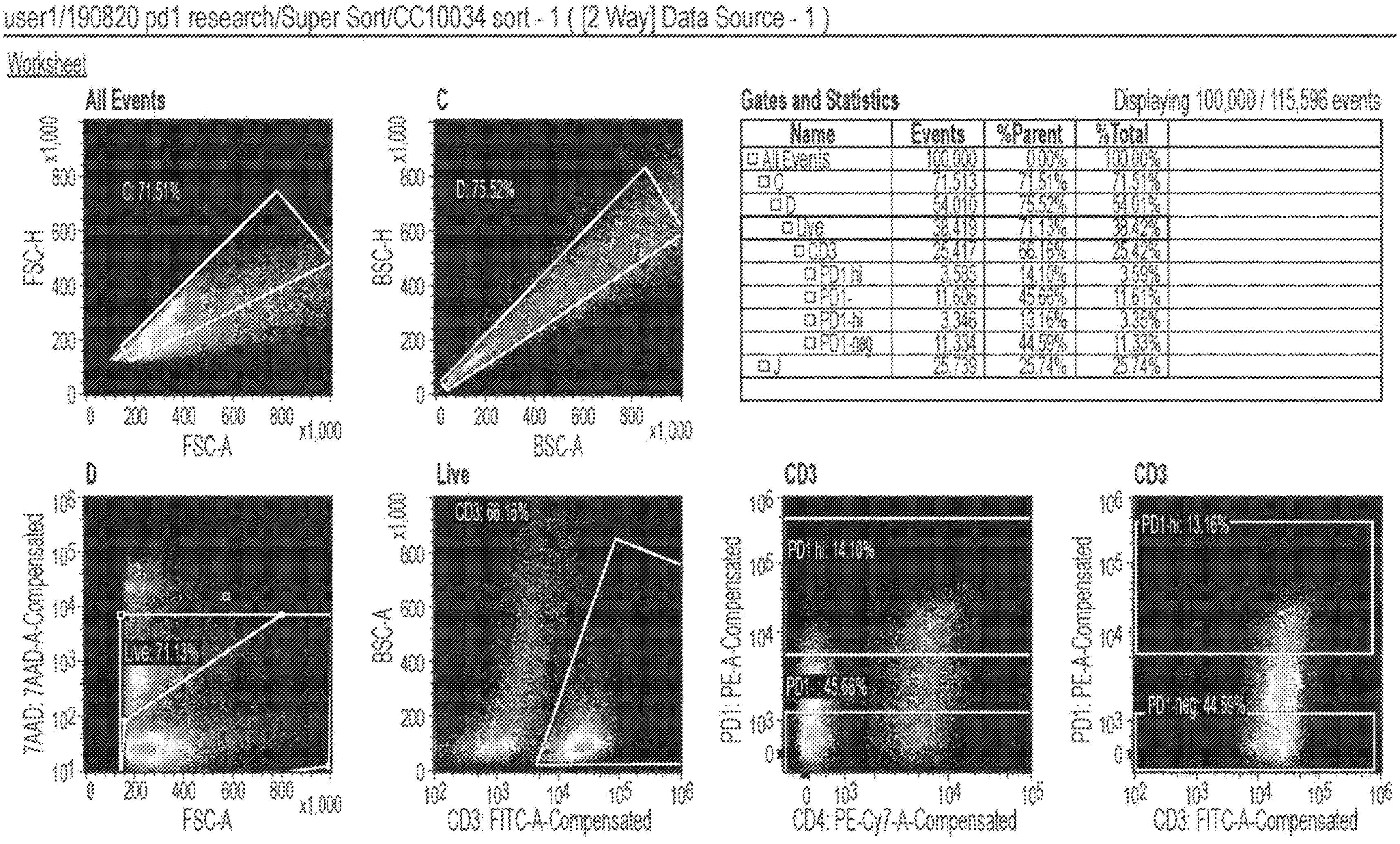
Figure 158E:
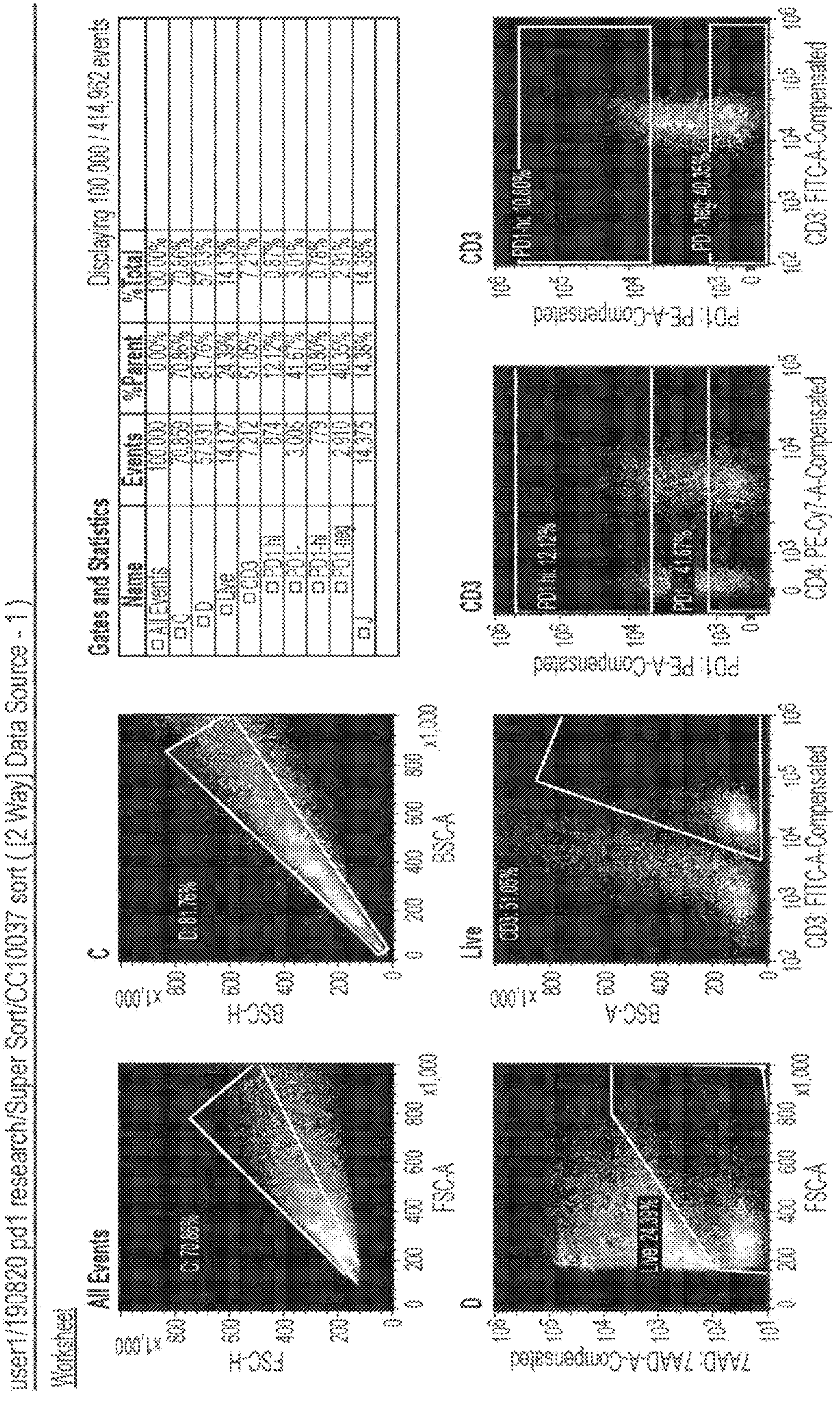
Figure 158F:
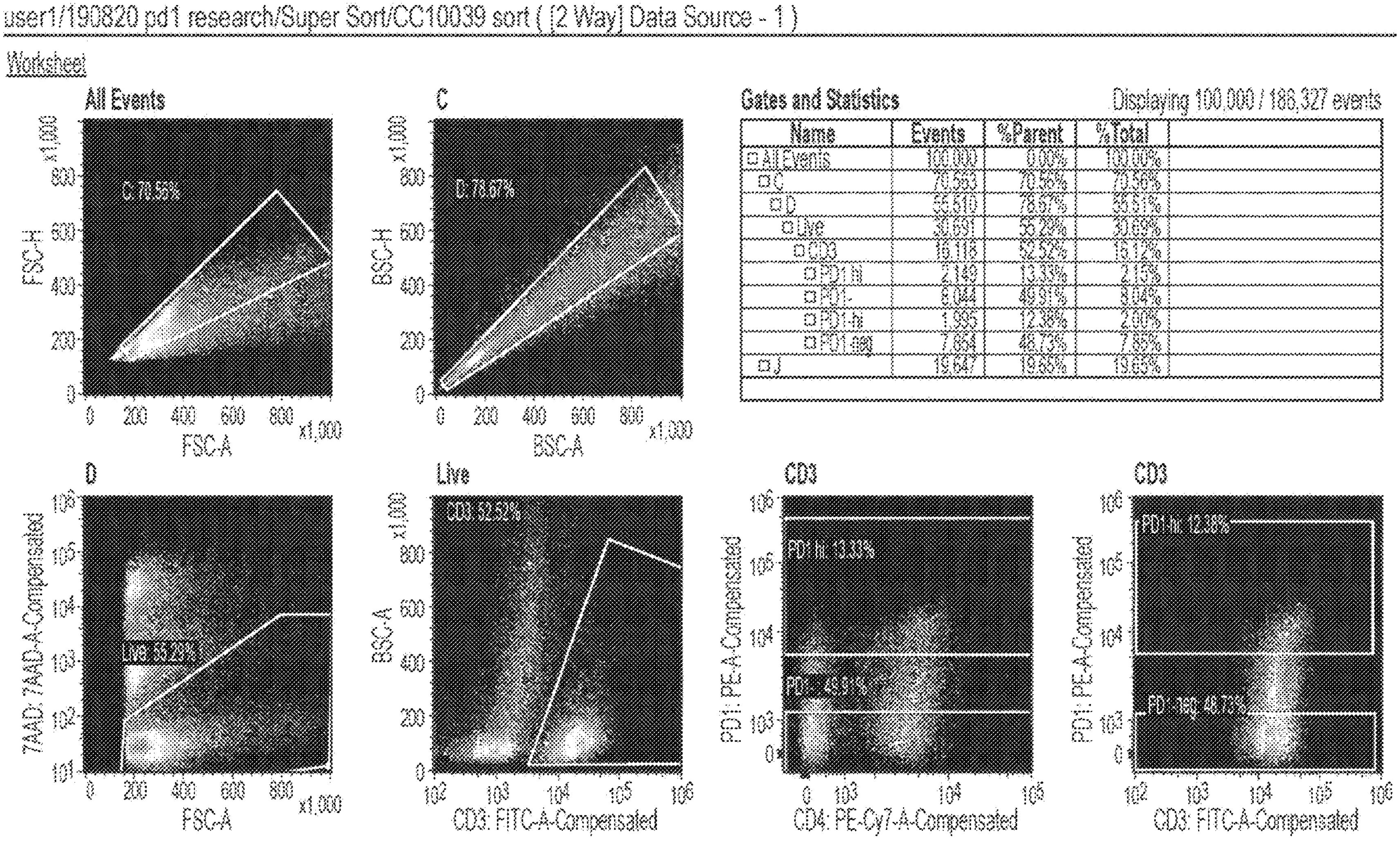
Figure 158J:
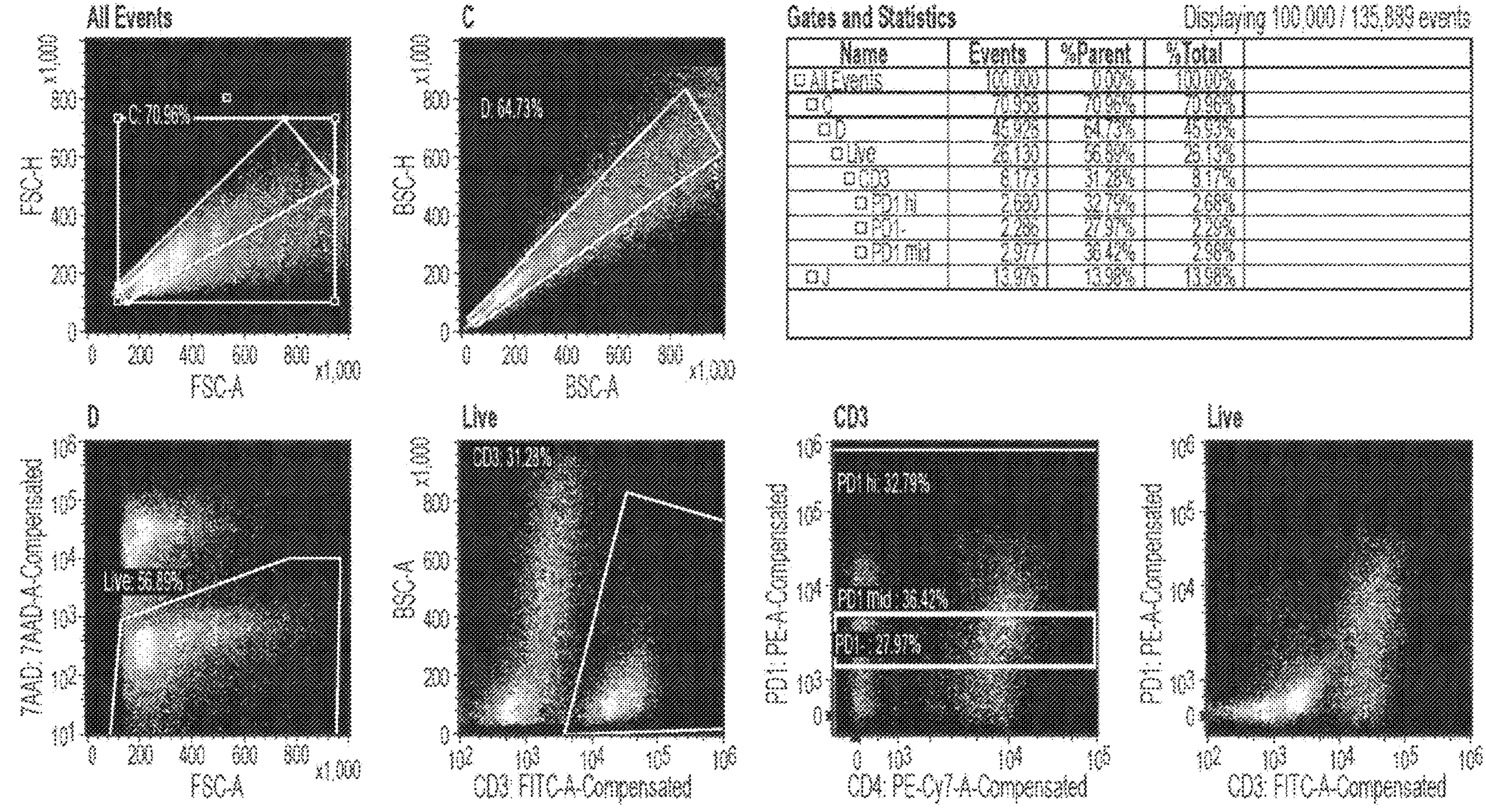
Figure 158O:
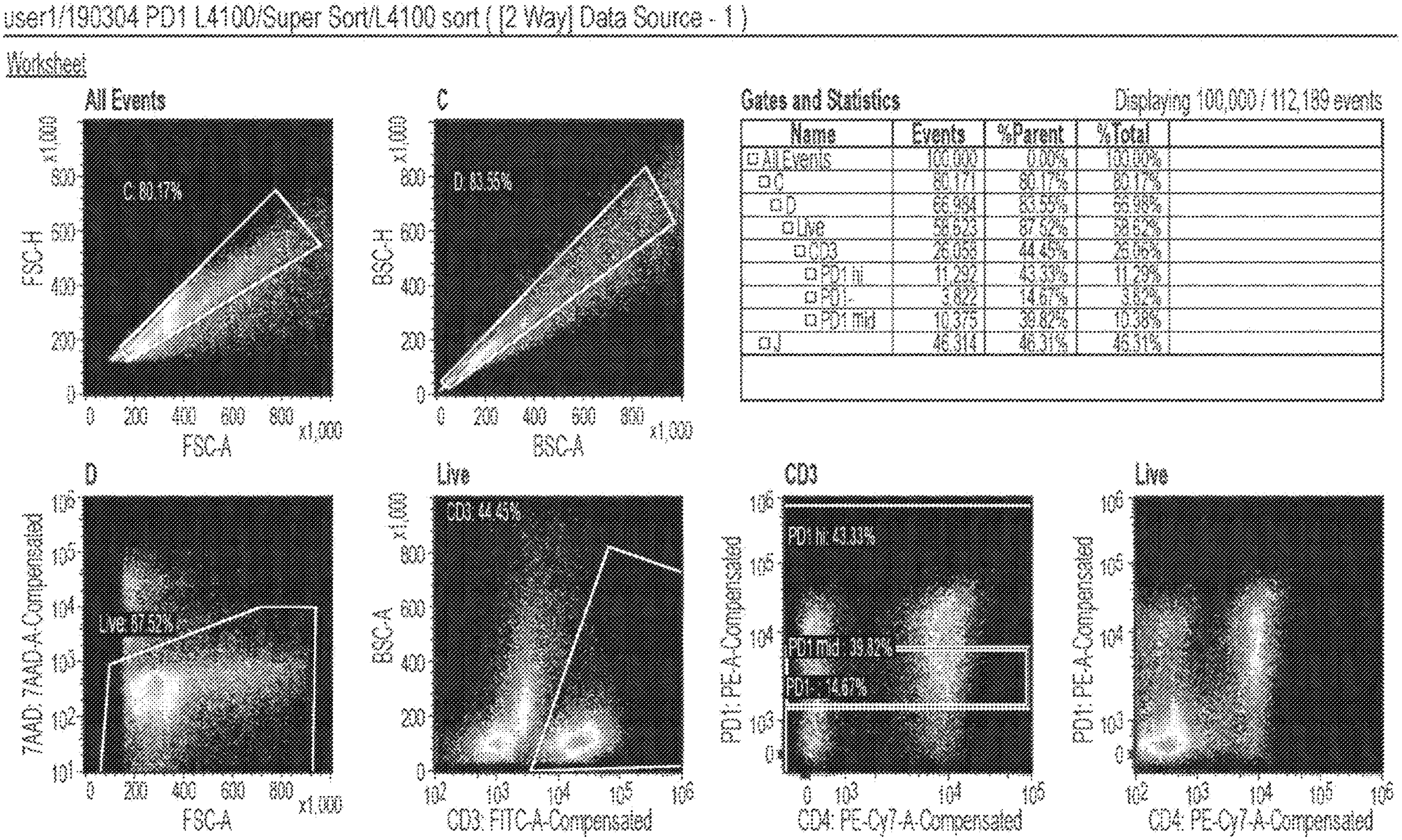
Figure 158Q:
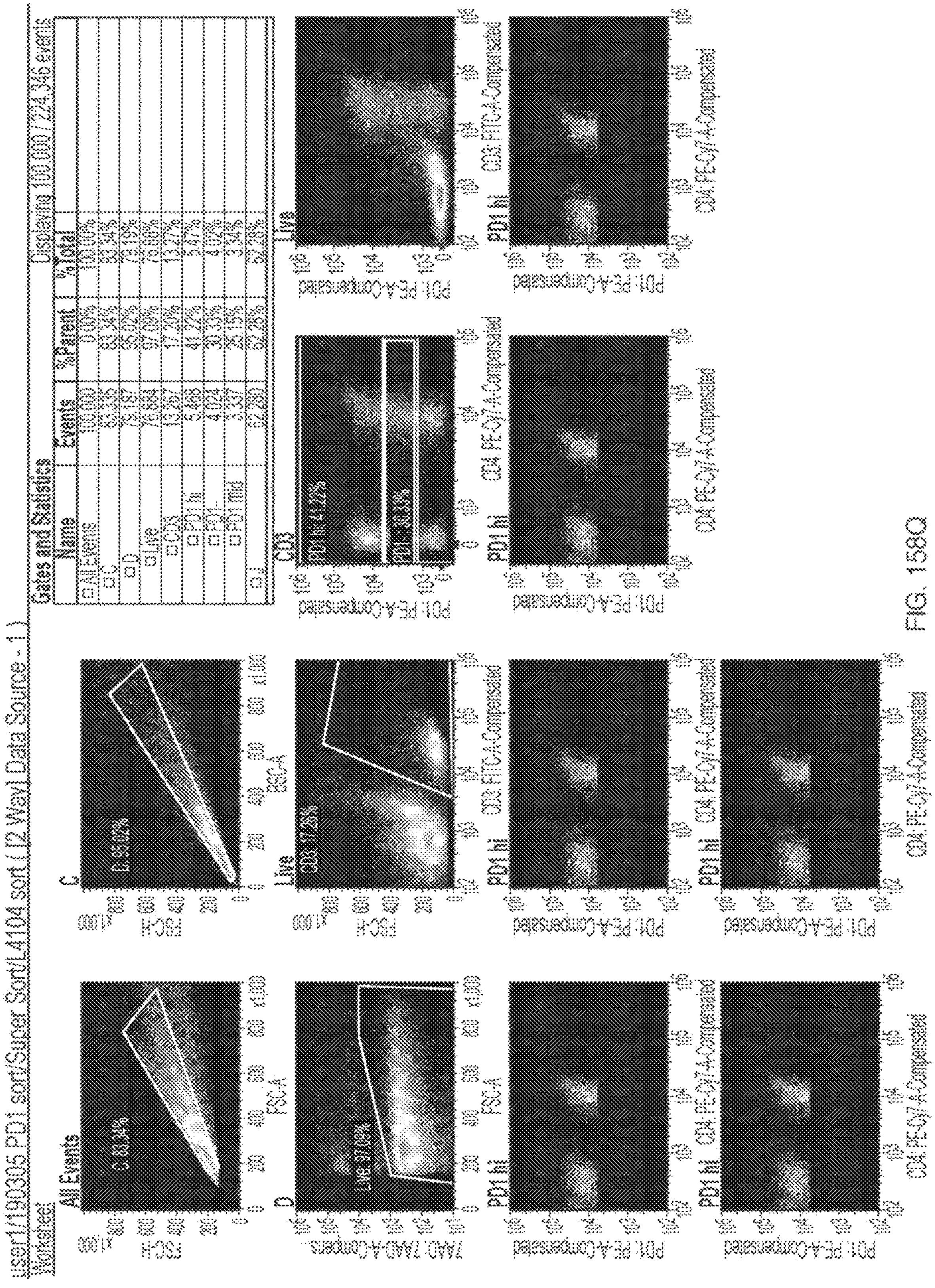
Figure 158S:
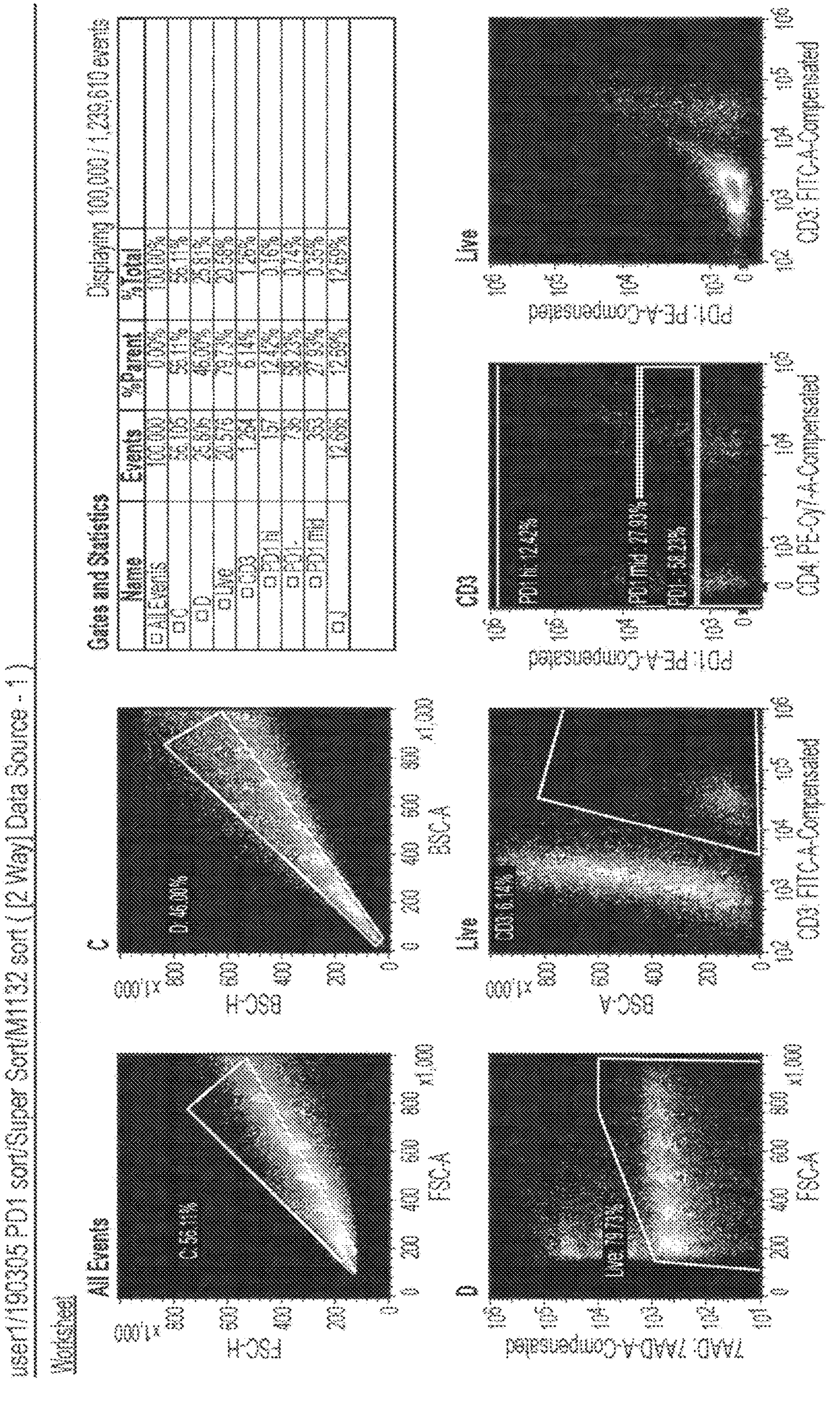
Figure 158T:
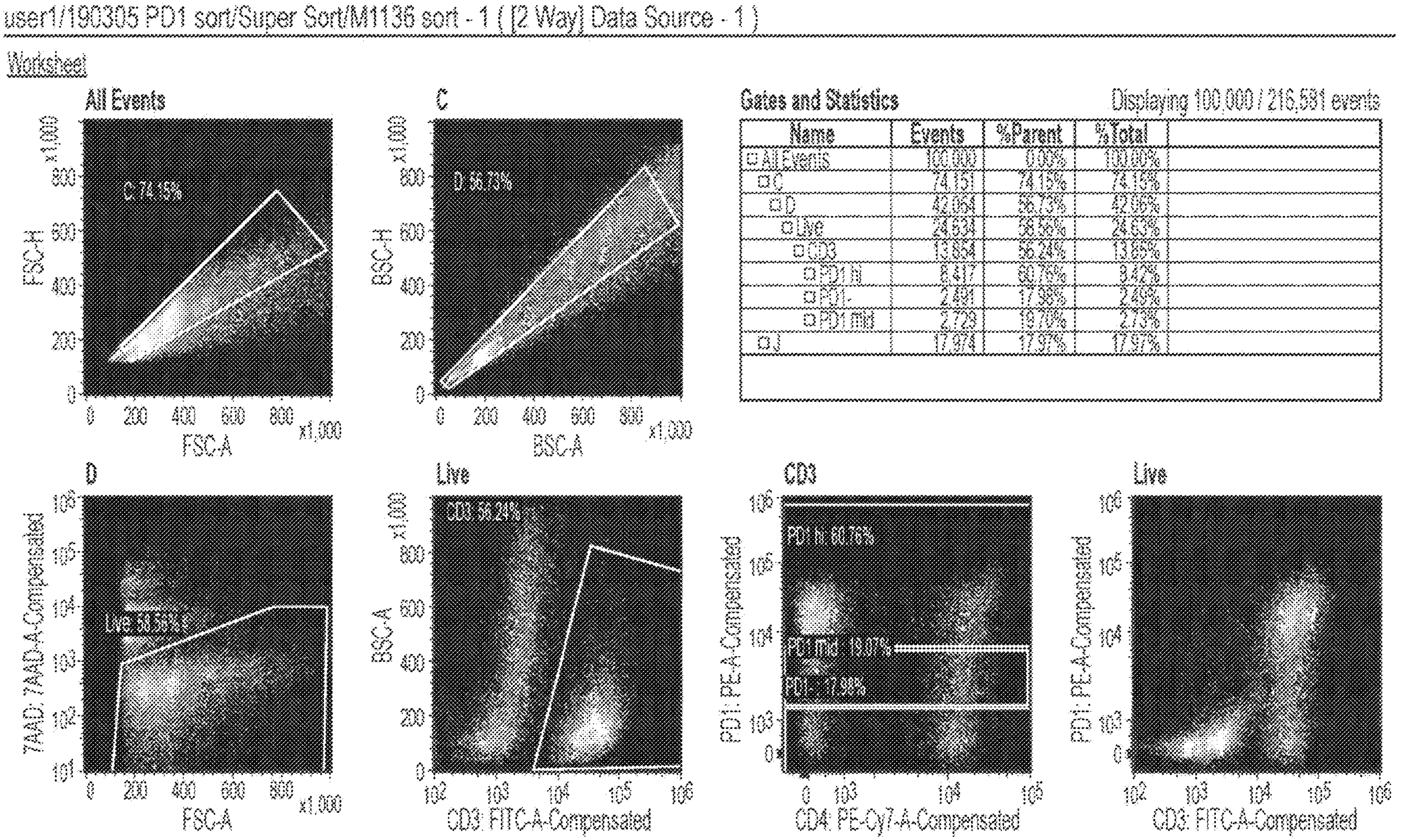
Figure 158U:
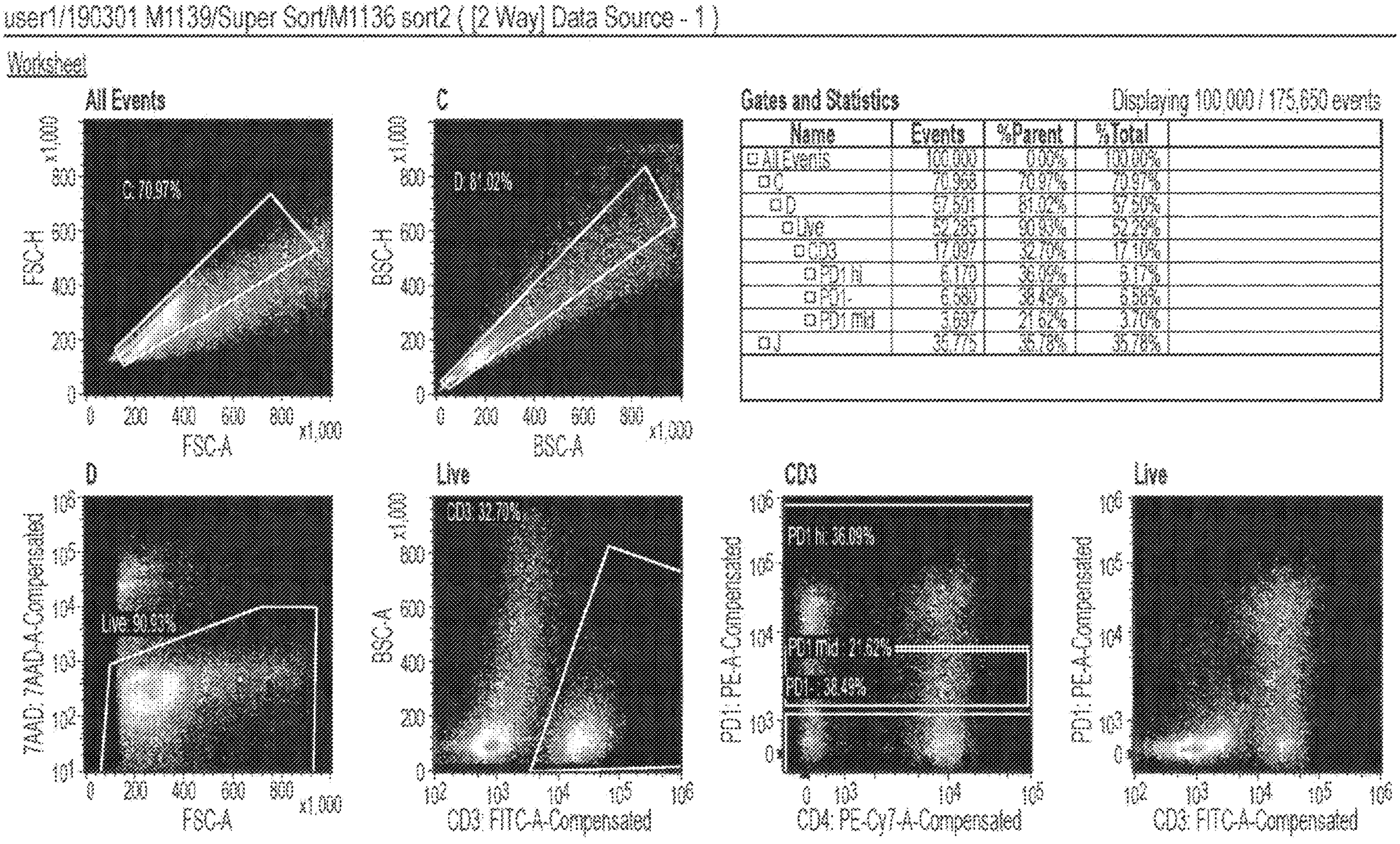
Figure 158Y:
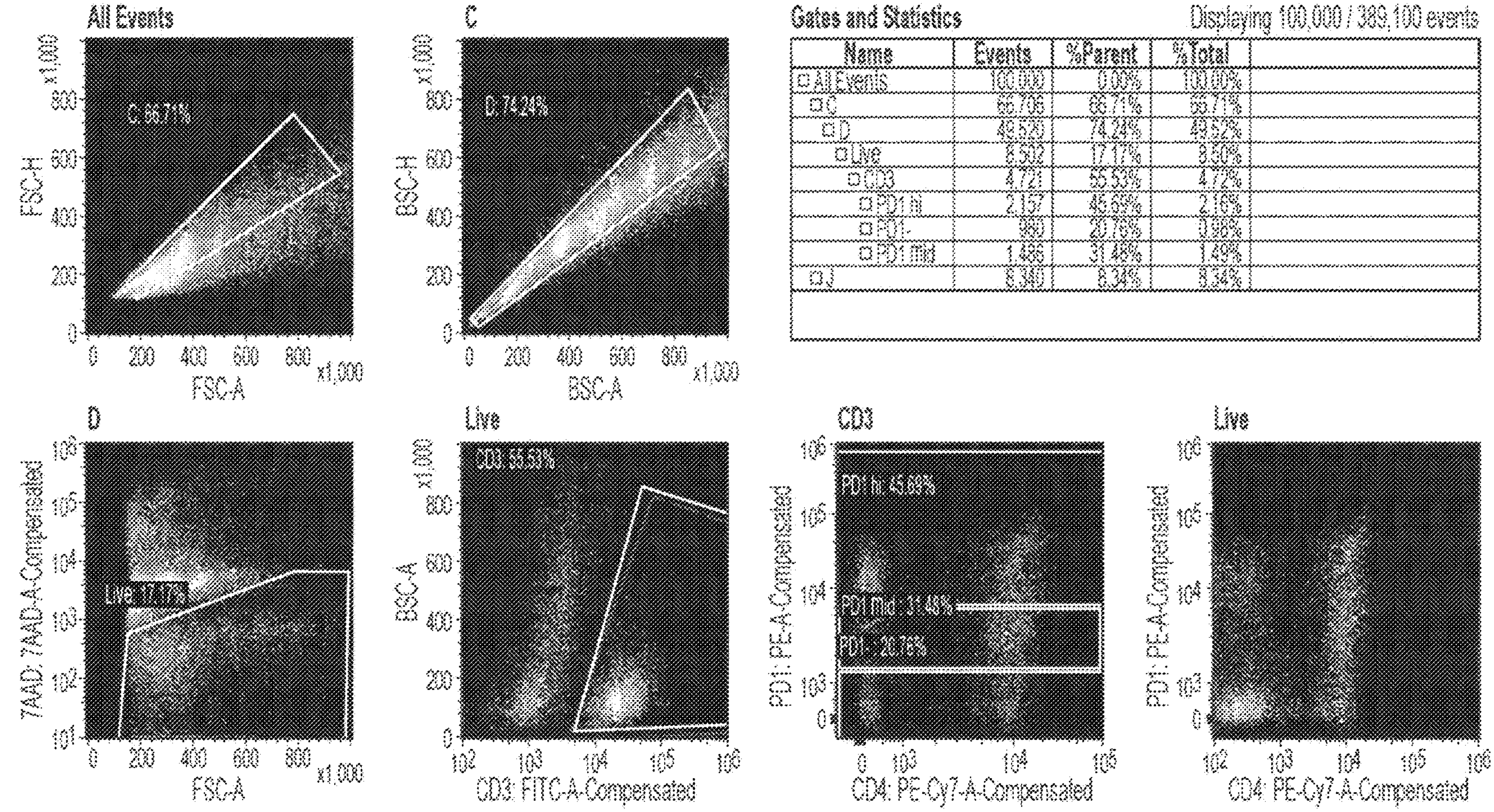
Figure 158Z:
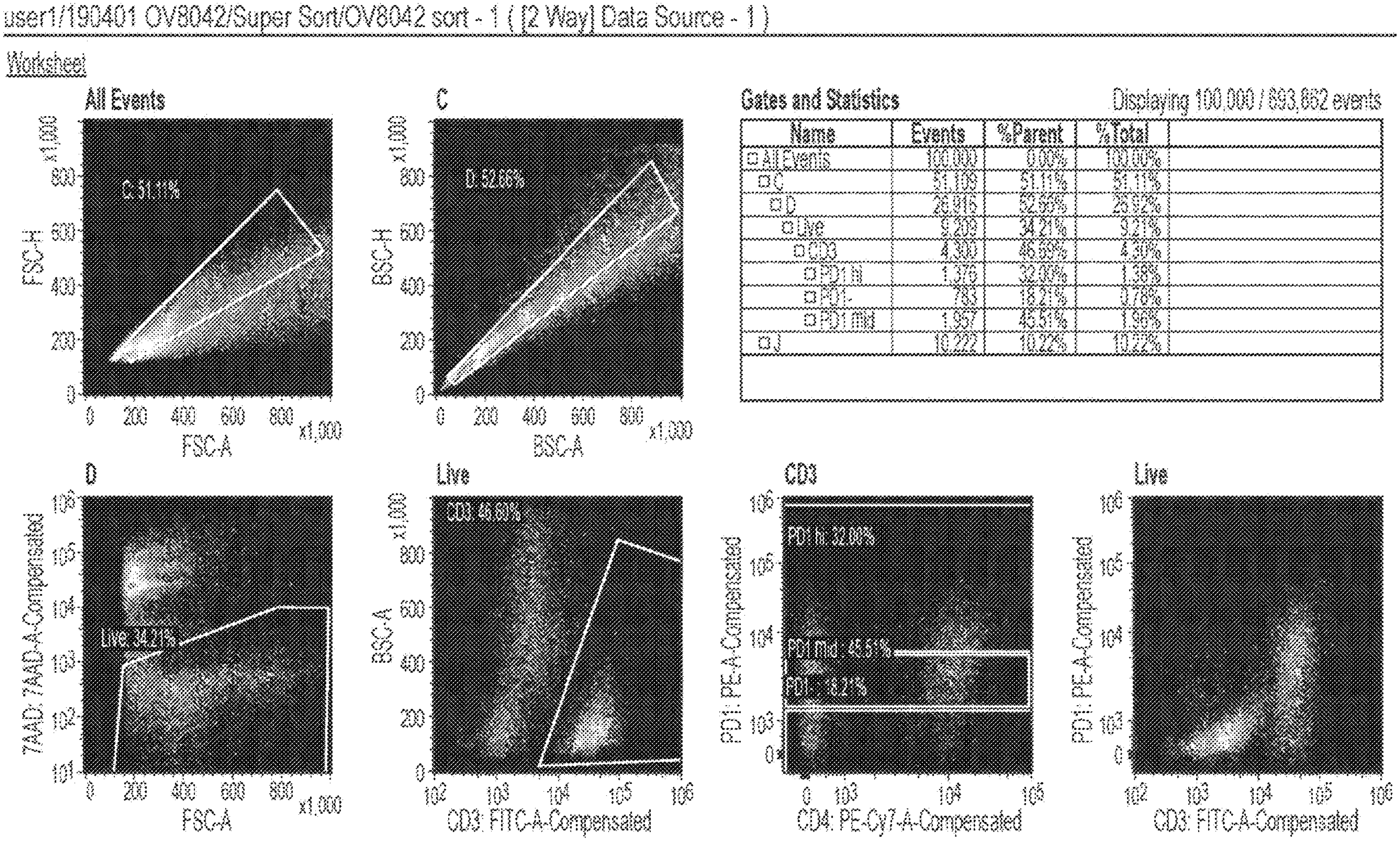
Figure 158B:
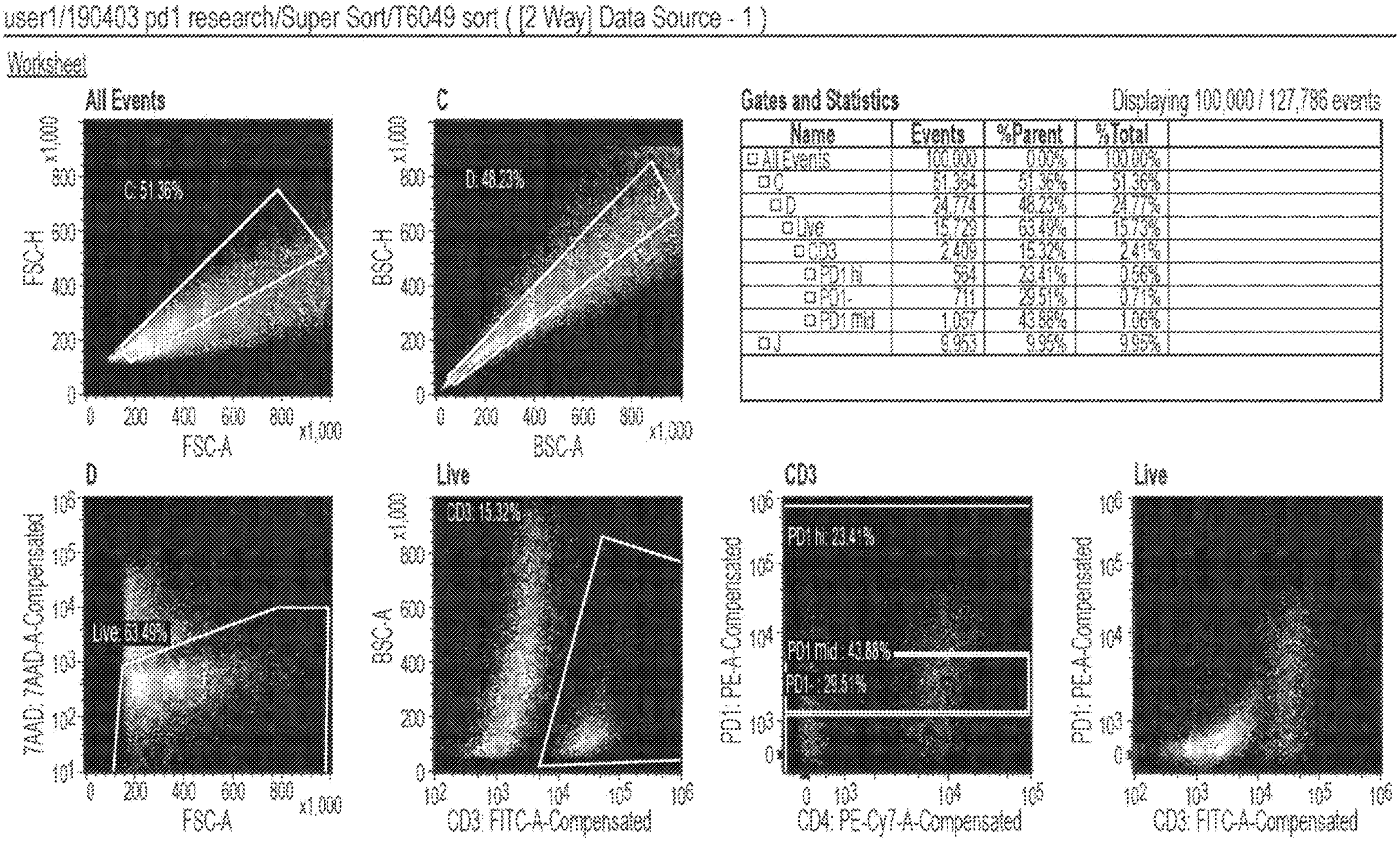
Figure 158C:
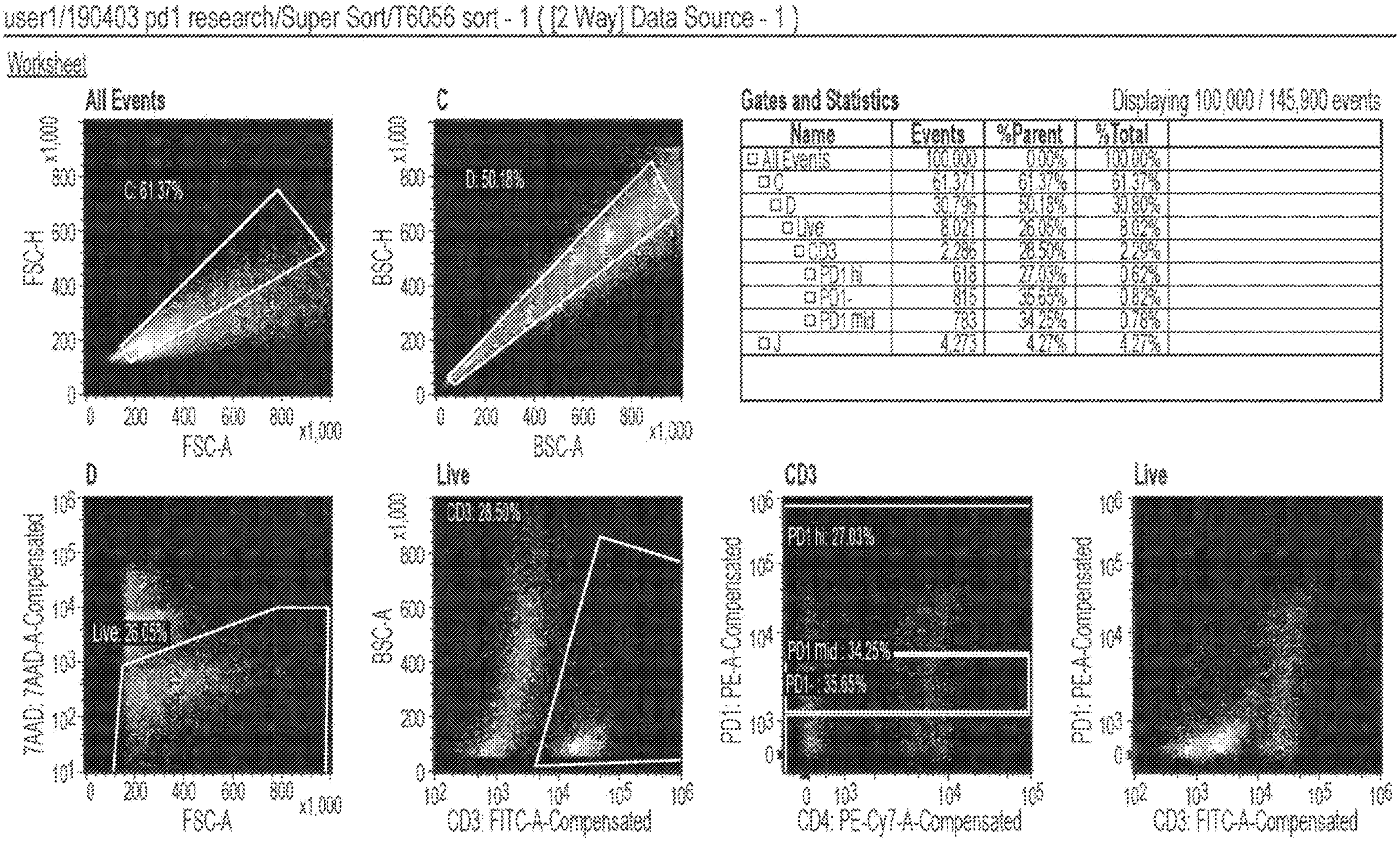
Figure 158D:
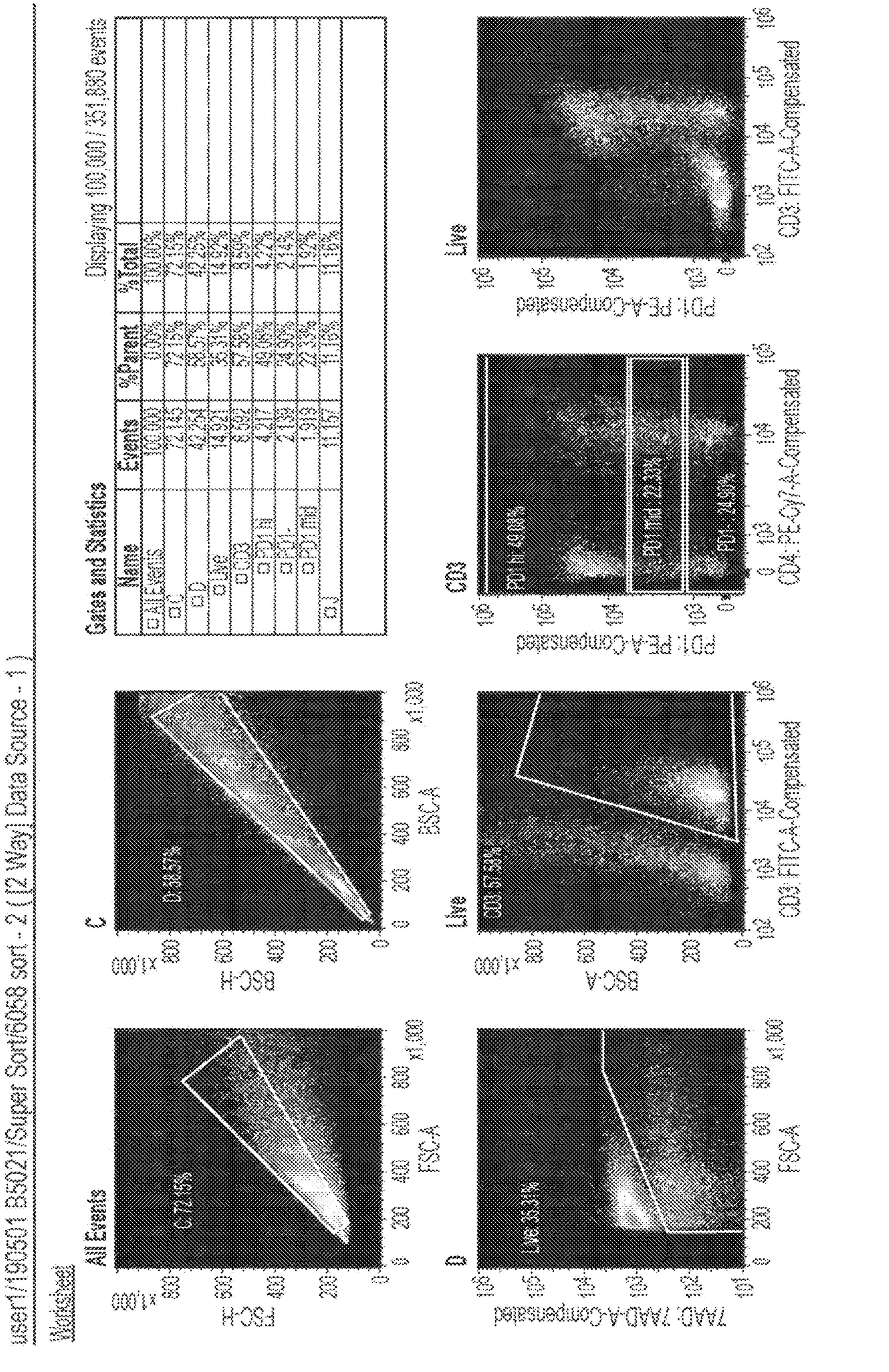
Figure 158E:
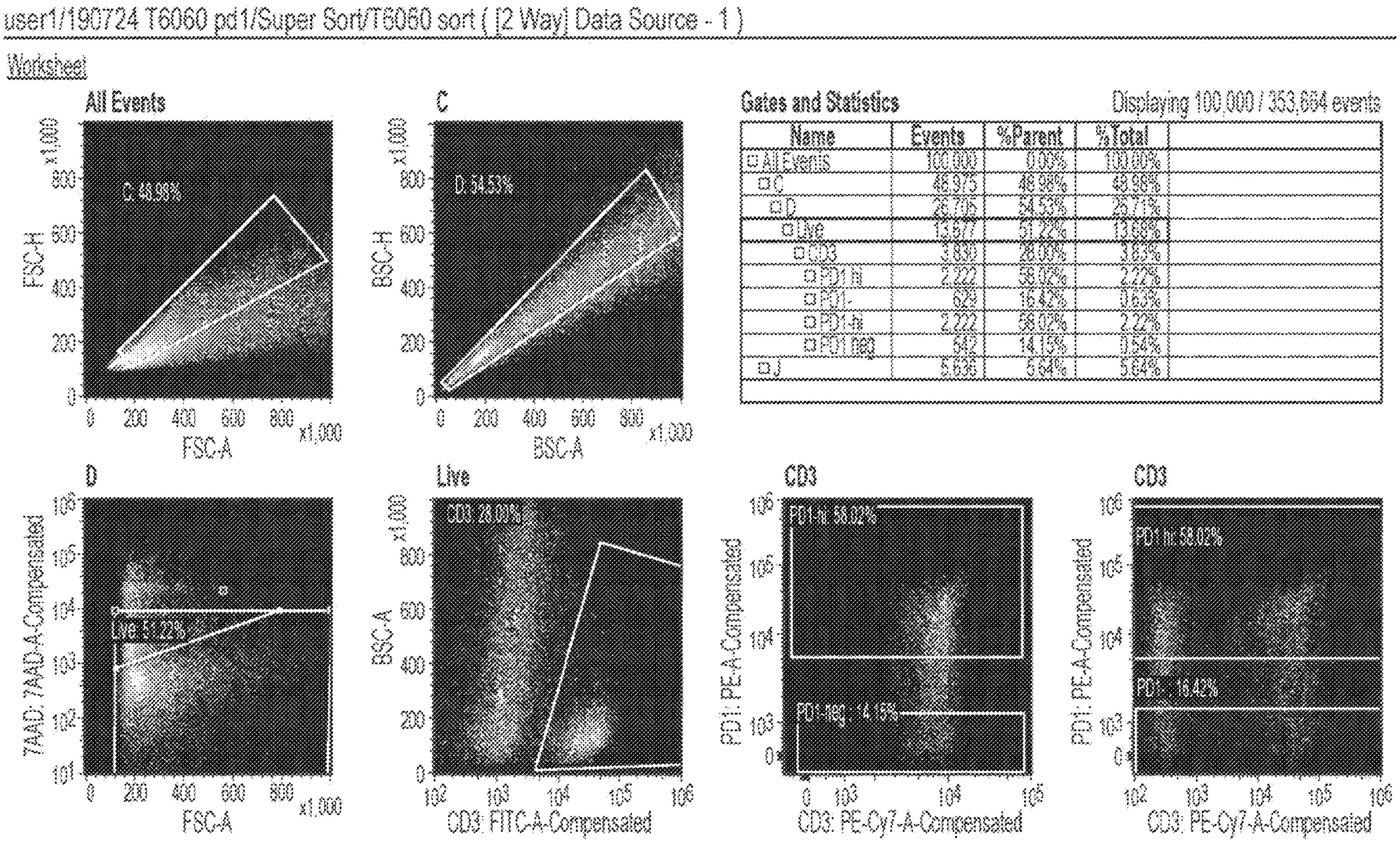

FIG. 157: Detection of PD-1+ cells in tumor digests from various histologies. PD-1 expression in multiple histologies. Percentage of PD-1+ TIL in the CD3+ TIL population are plotted for individual samples within each histology. Horizontal lines represent the mean percentages of each subset and vertical lines represent the standard errors.

FIGS. 158A-158FF: FACS data plots.

Figure 159:
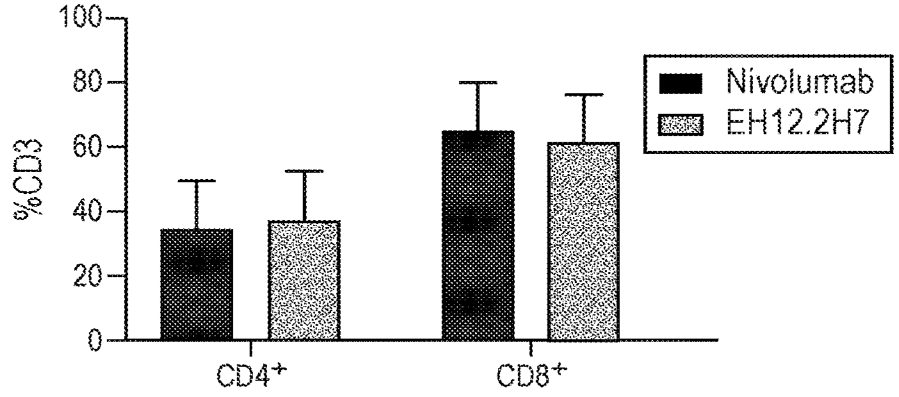

FIG. 159: PD-1-selected TIL sorted using either nivolumab or EH12.2H7 to identify the PD-1+ TIL from 1 ovarian, 1 melanoma, and 1 HNSCC were assessed for T cell lineage (CD4 and CD8) using flow cytometry. Results are expressed as percentages of CD3+ cells. Mean values are plotted as bars and standard errors shown as vertical lines.

Figure 160:
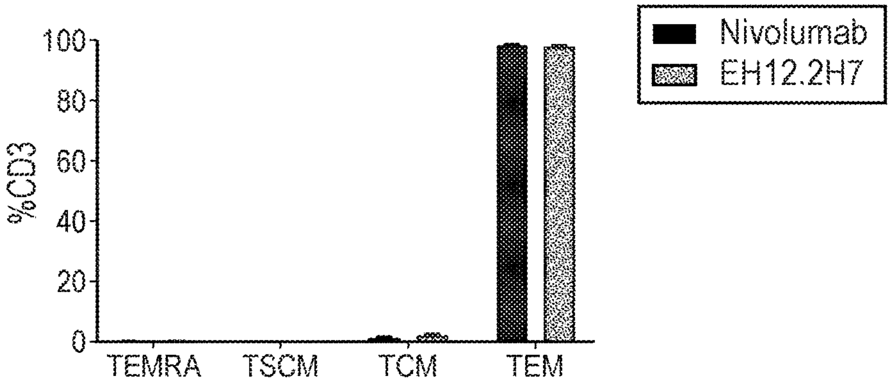

FIG. 160: PD-1-selected TIL from 1 ovarian, 1 melanoma and 1 HNSCC tumor samples, sorted using either nivolumab or EH12.2H7 to identify the PD-1+ TIL, were assessed for the expression of the memory markers CD45RA and CCR7 by flow cytometry. T cell memory subsets (TN/TSCM) were determined as indicated and average percentages of each subset plotted as black bars for nivolumab PD-1-selected TIL and gray bars for EH12.2H7 PD-1-selected TIL. Standard errors are shown as vertical lines.

Figure 161A:
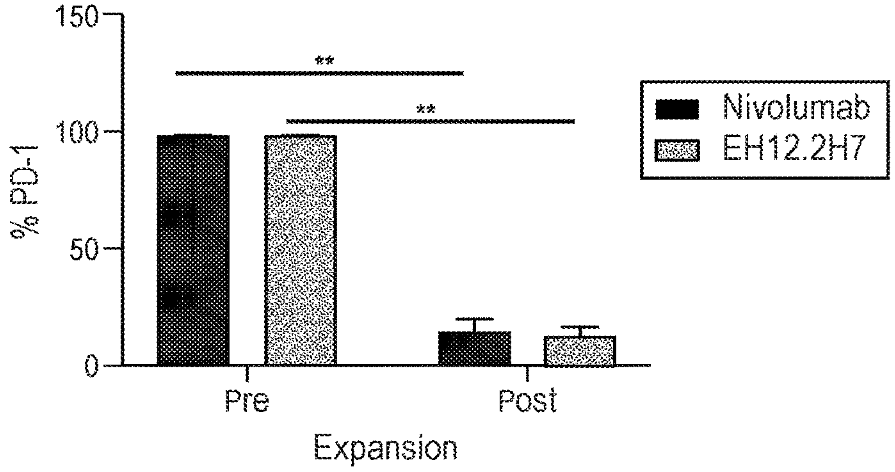

FIG. 161A: PD-1-sorted TIL from 1 ovarian, 1 melanoma and 1 HNSCC, sorted using either nivolumab or EH12.2H7 to identify the $PD-1^+$ TIL, were assessed for expression of PD-1 expression pre- and post-expansion. Post-sort purity of the PD-1-sorted product was used to determine the percentage of $PD-1^+$ prior to expansion. Mean values are plotted as bars and standard errors shown as vertical lines. Statistical significance was assessed by a paired student t-test; indicates a p value <0.01.

Figure 161B:
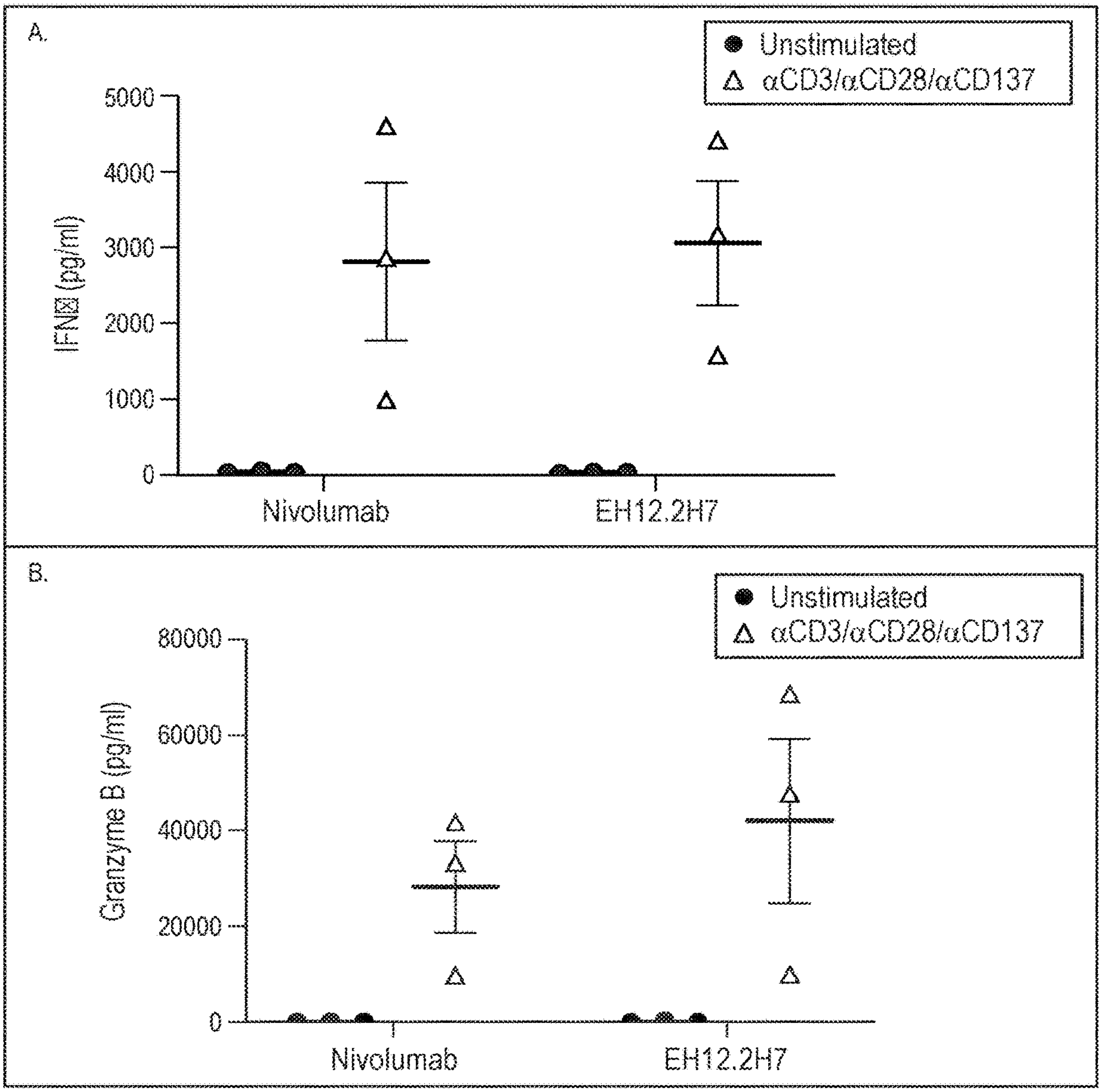

FIG. 161B: PD-1-selected TIL from 1 ovarian, 1 melanoma and 1 HNSCC, sorted using either nivolumab or EH12.2H7 to identify the PD-1+ TIL, were assessed for secretion of (A) IFNγ and (B) Granzyme B. Results are plotted for individual samples, with the black dots representing the unstimulated condition and the gray triangles representing the αCD3/αCD28/α41BB stimulated condition. Horizontal lines represent the mean percentages of each subset and vertical lines represent the standard error.

Figure 162:
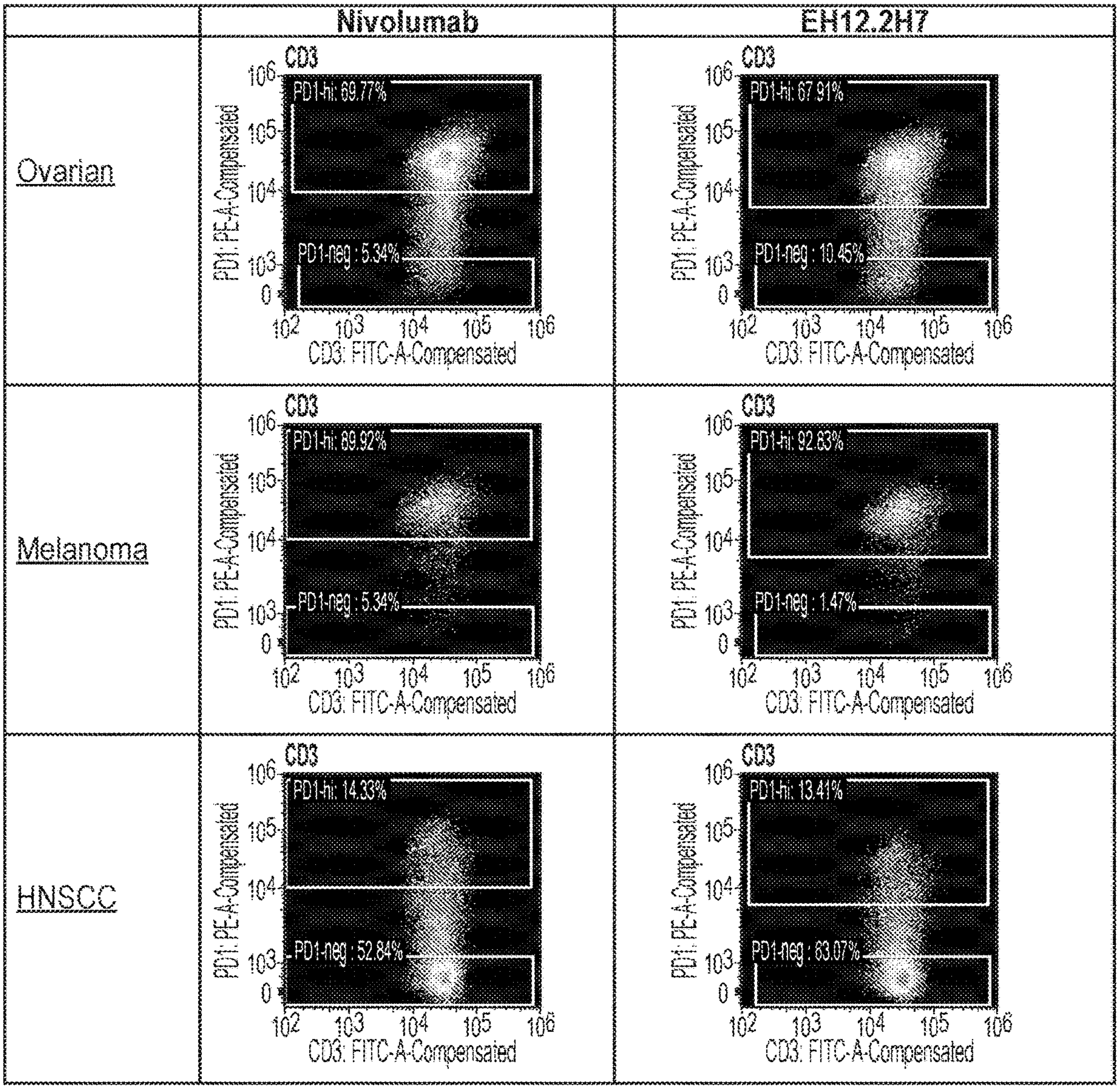

FIG. 162: Pre sort PD-1 Levels in Nivolumab and EH12.2H7-stained TIL. Whole tumor digests were split and stained with either nivolumab or EH12.2H7 and assessed by flow cytometry. The $PD-1^+$ cells, identified using each antibody, from 1 ovarian, 1 melanoma and 1 HNSCC were then sorted using the FX500 cell sorter (SONY, NY).

Figure 163:
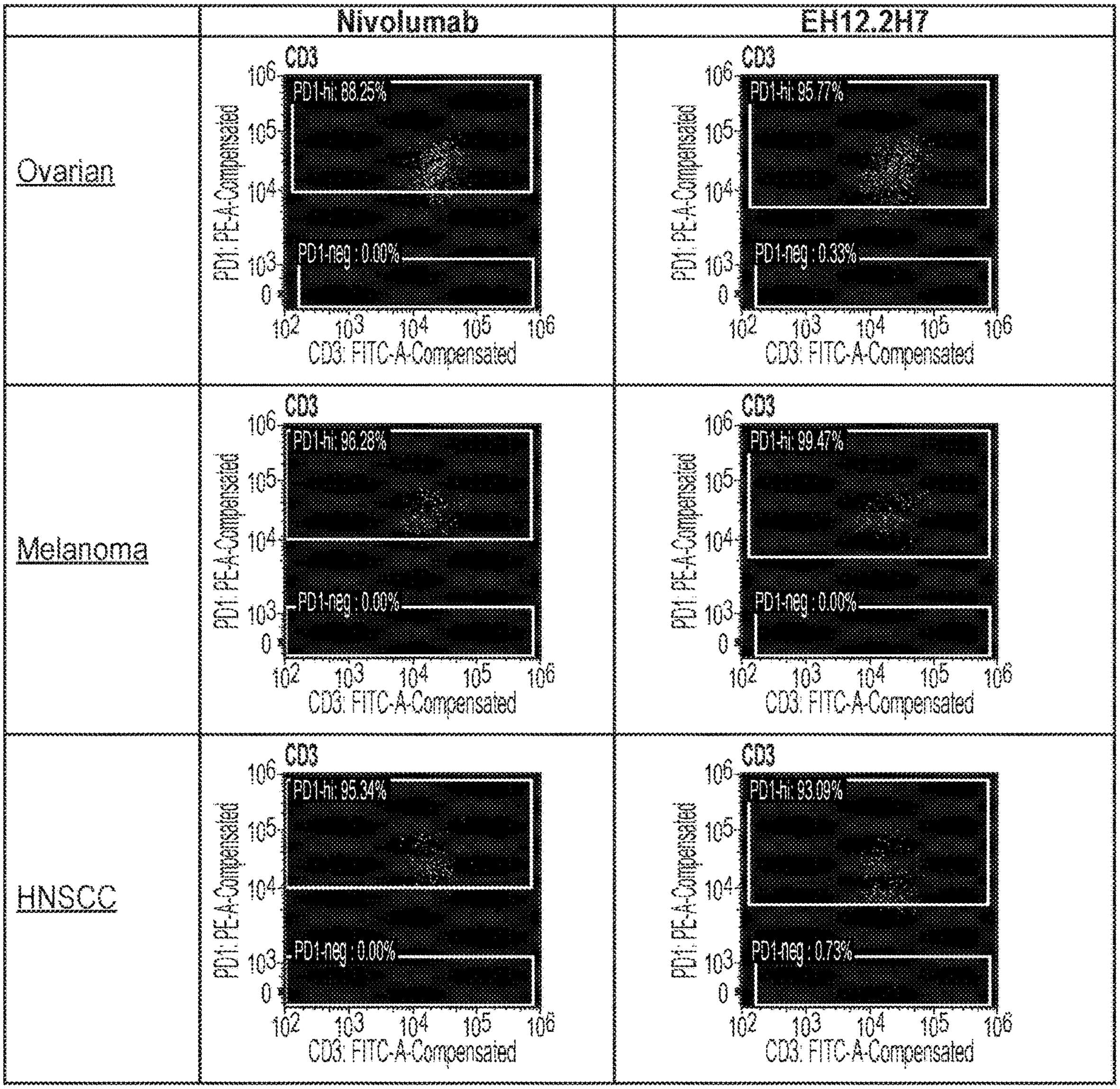

FIG. 163: Post sort PD-1 Levels in Nivolumab and EH12.2H7-stained TIL.

FIG. 164: Whole tumor digests were split and stained with either nivolumab or EH12.2H7 and assessed by flow cytometry. The PD-1+ cells, identified using each antibody, from 1 ovarian, 1 melanoma and 1 HNSCC were then sorted using the FX500 cell sorter (SONY, NY).

Figure 165:
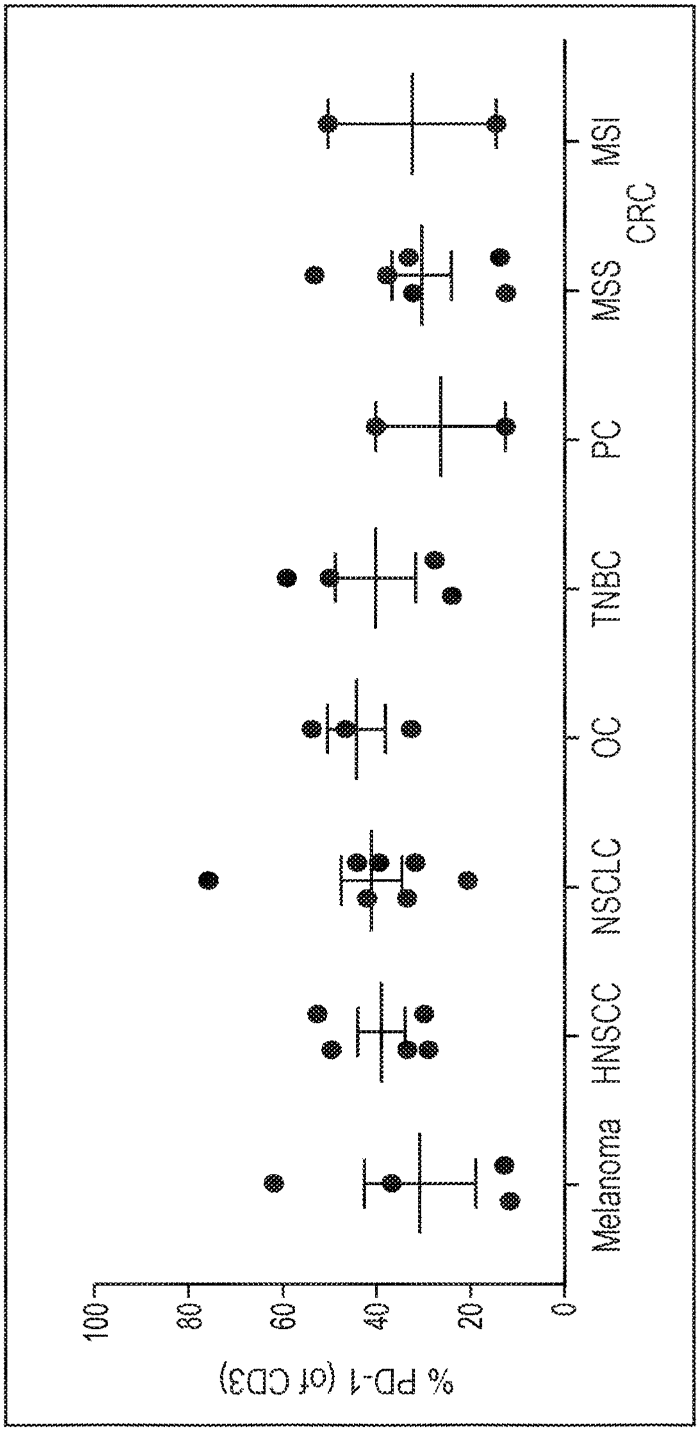

FIG. 165: Detection of $PD-1^+$ Cells in Tumor Digests from Various Histologies. PD-1 expression in multiple histologies. Percentage of PD-1+ TIL in the CD3+ TIL population are plotted for individual samples within each histology. Horizontal lines represent the mean percentages of each subset and vertical lines represent the standard errors.

Figure 166:
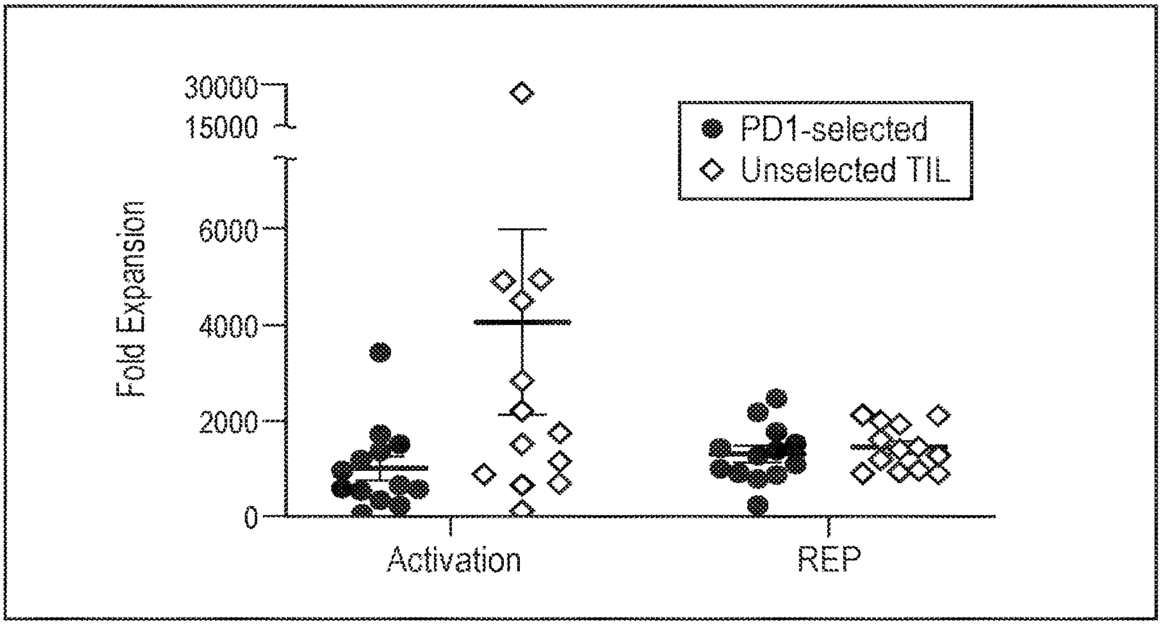

FIG. 166: Reduced Fold Expansion in PD-1 selected TIL during the Activation phase, but not the REP. PD-1-sorted TIL and whole tumor digests from 4 melanoma, 7 NSCLC and 2 HNSCC tumor samples were expanded using a two-step process consisting of an 11-day Activation step followed by an 11-day REP. Fold expansion for all assayed tumors are shown. Total cell counts at the completion of the Activation and REP steps were used to calculate fold expansions in the TIL populations. Results are plotted for individual samples, with the black dots representing the PD-1-selected TIL and the gray triangles representing the unselected TIL. Horizontal lines represent the mean percentages of each subset and vertical lines represent the standard errors.

Figure 167:
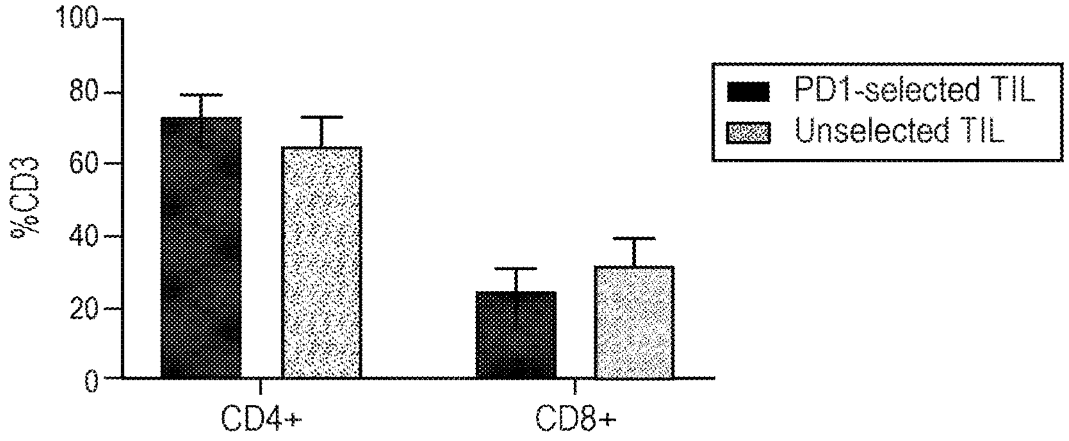

FIG. 167: Levels of $CD4^+$ and $CD8^+$ T cells in PD-1 selected and Unselected TIL. PD-1-selected and unselected TIL from 4 melanoma, 7 NSCLC, and 2 HNSCC tumor samples were assessed for T cell lineage (CD4 and CD8) using flow cytometry. Results are expressed as percentages of CD3+ cells. Mean values are plotted as bars and standard errors shown as vertical lines.

Figure 168:
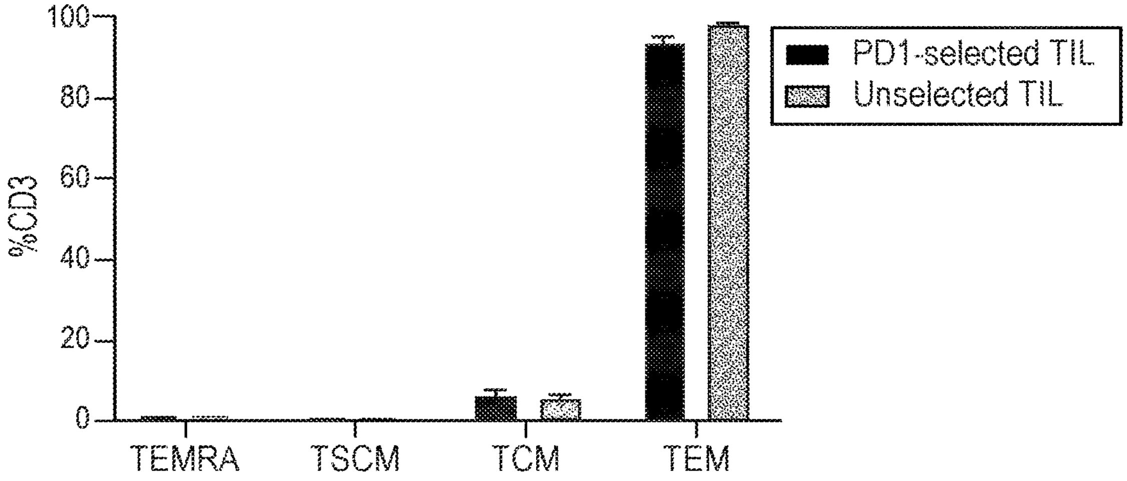

FIG. 168: Compared distribution of memory T cell subsets in PD-1-selected TIL and Unselected TIL. PD-1-selected TIL and unselected TIL from 4 melanoma, 6 NSCLC and 2 HNSCC tumor samples were assessed for the expression of the memory markers CD45RA and CCR7 by flow cytometry. T cell memory subsets were determined as indicated and average percentages of each subset plotted as black bars for PD-1-selected TIL and gray bars for unselected TIL. Standard errors are shown as vertical lines.

Figure 169:
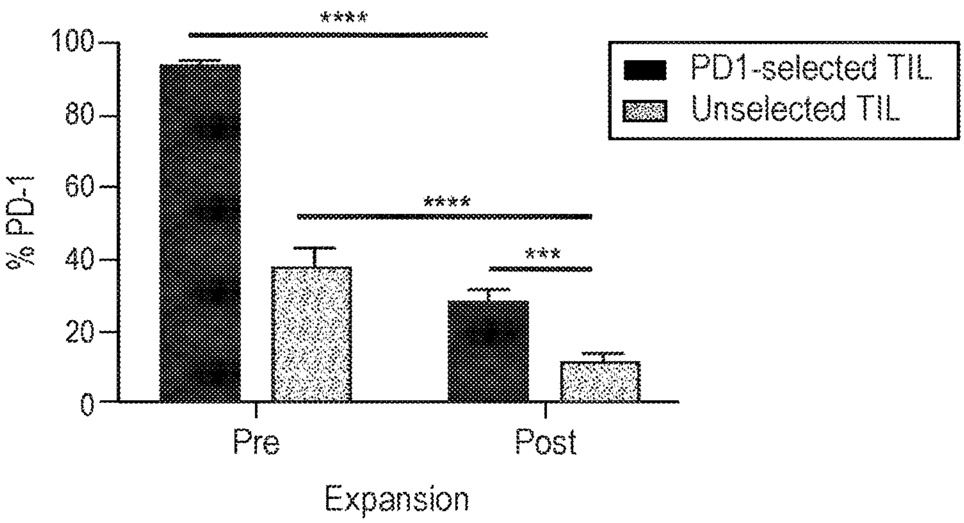

FIG. 169: PD-1 Expression in $PD-1^+$ Sorted TIL and Unselected TIL Prior to and Post-expansion. PD-1-sorted TIL and whole tumor digests from 3 melanoma, 7 NSCLC, and 2 HNSCC tumor samples were assessed for the expression of PD-1 pre- and post-expansion. Post-sort purity of the $PD1^+$ sorted product was used to determine the percentage of PD-1+ TIL prior to expansion. Mean values are plotted as bars and standard errors shown as vertical lines. Statistical significance was assessed by a paired student t-test; * and ** indicates a p value <0.001, and <0.0001 respectively.

Figure 170:
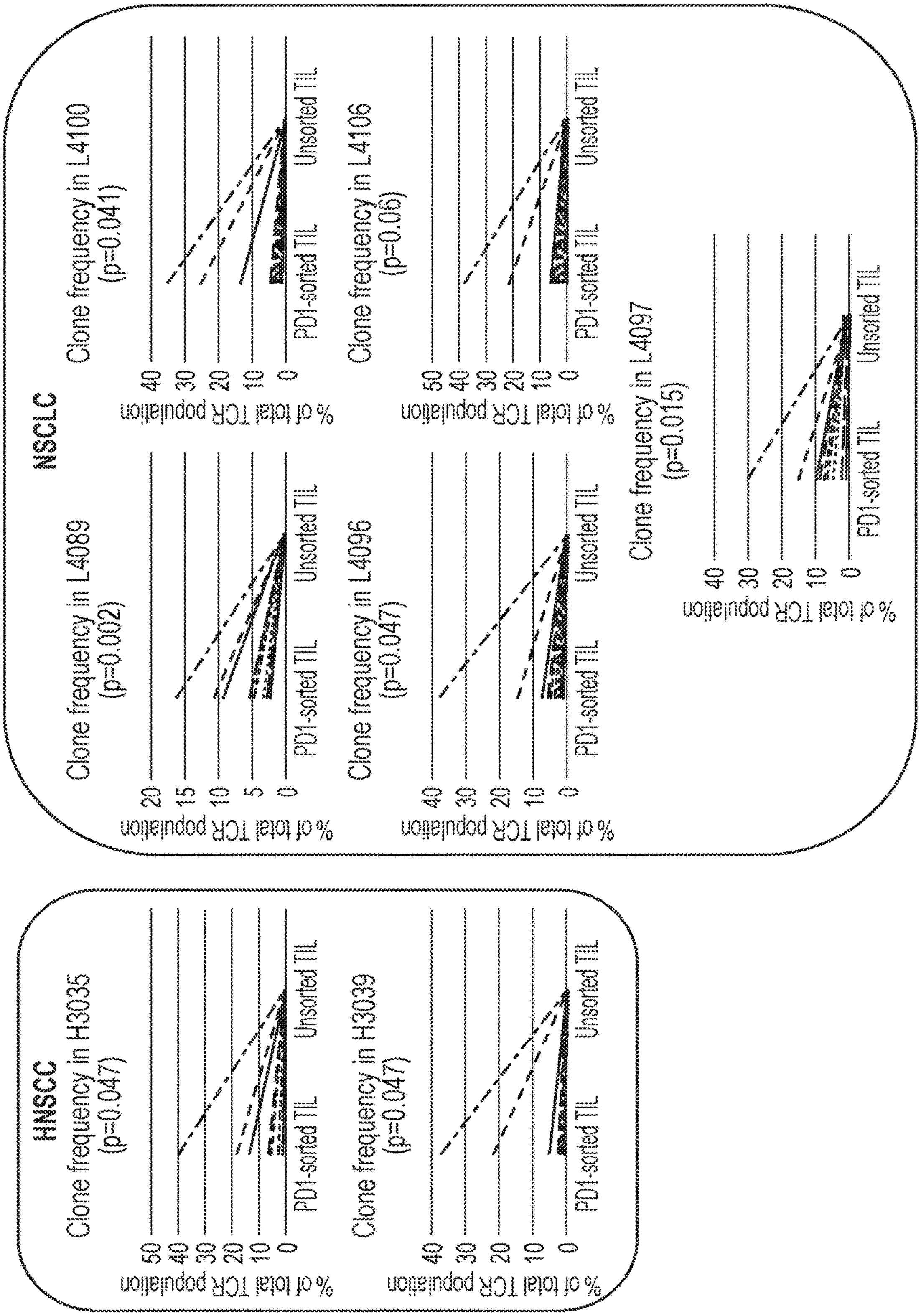

FIG. 170: Frequency of the Top 10 PD-1-Selected TCRvβ clones in Unselected TIL. Legend: Expanded PD-1-selected and unselected TIL from 2 HNSCC and 5 NSCLC tumor samples were analyzed for their repertoire of CDR3vβ. Unique CDR3vβ sequences identified in the PD-1-selected TIL product were ranked from most to least frequent. The frequencies of the "top 10" (i.e., the 10 most frequent clones) PD-1-selected TIL clones in each one of the paired products is plotted. Paired samples are linked by plain lines. P-values calculated by paired t-test are noted on their respective graphs.

Figure 171:
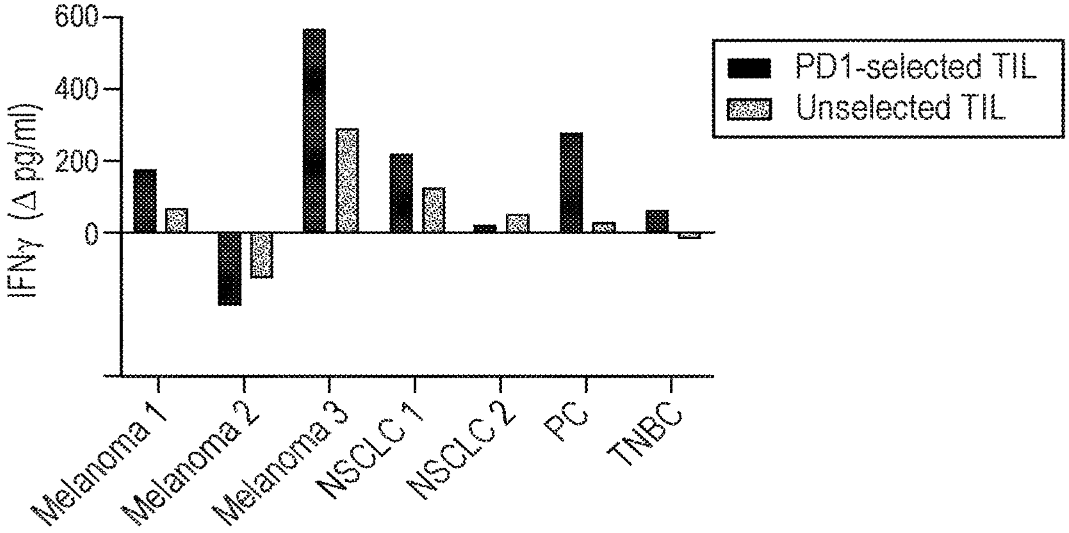

FIG. 171: PD-1-Selected TIL Demonstrate Superior Autologous Tumor Reactivity, Compared with Matched Unselected TIL. PD-1-selected and matched unselected TIL obtained from 3 melanoma, 2 NSCLC, 1 PC, and 1 TNBC samples were tested for IFNO secretion by ELISA, in response to an 18-24-hour incubation with autologous tumor digests. Difference in IFN concentration measured with and without an HLA class I blocking antibody is shown for each individual sample. Positive values reflect HLA-specific anti-tumor responses, while null or negative values reflect non-specific responses.

FIG. 172A-172B: PD-1-Selected and Unselected TIL Demonstrate Autologous Tumor Killing. Tumor killing, and reactivity were assessed in PD-1-selected TIL and unselected TIL using the xCELLigence real-time cell analysis system. (A) Cell indices and (B) tumor cell killing (% cytolysis) are shown for a melanoma sample.

Figure 172:
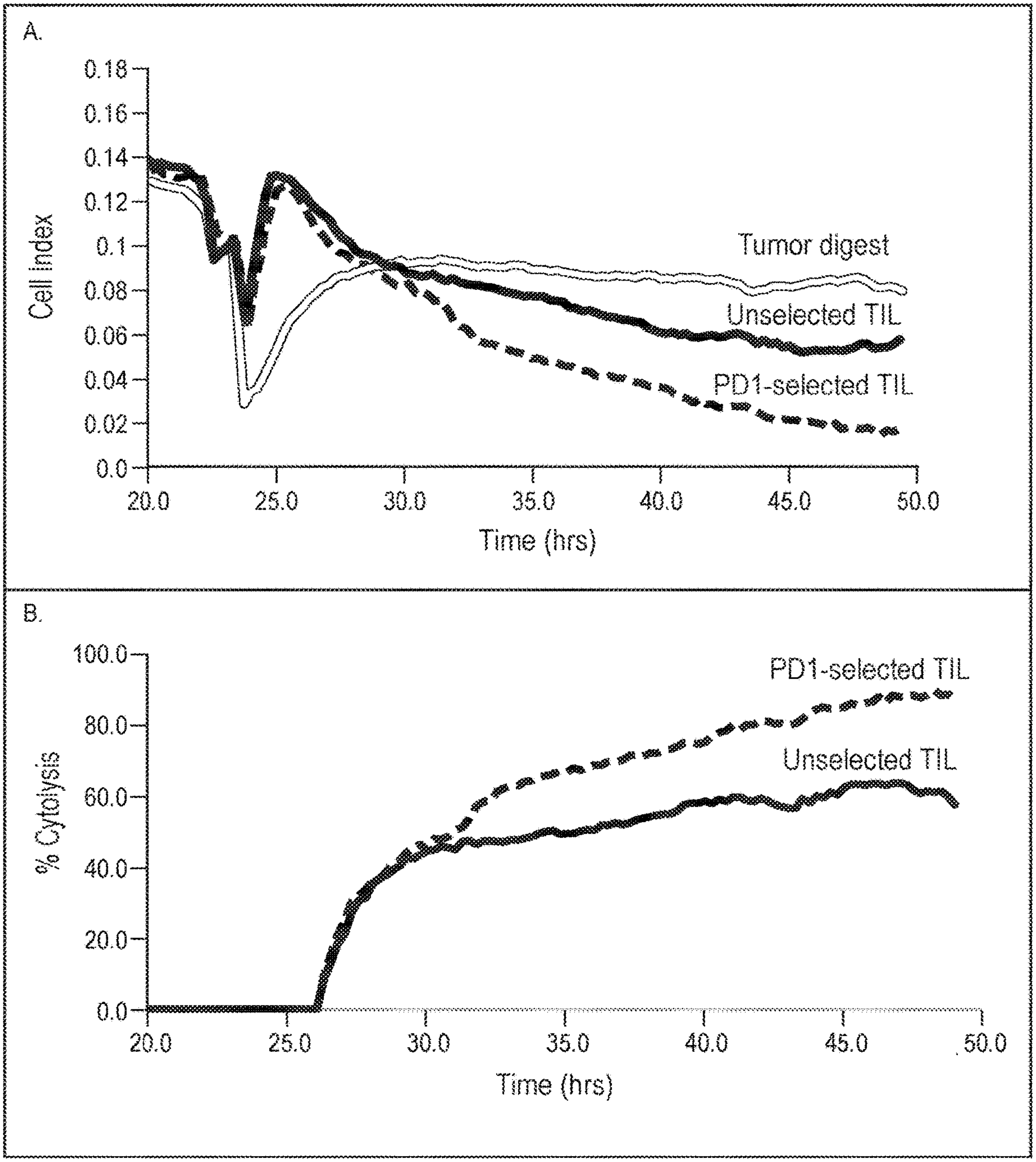
Figure 172C:
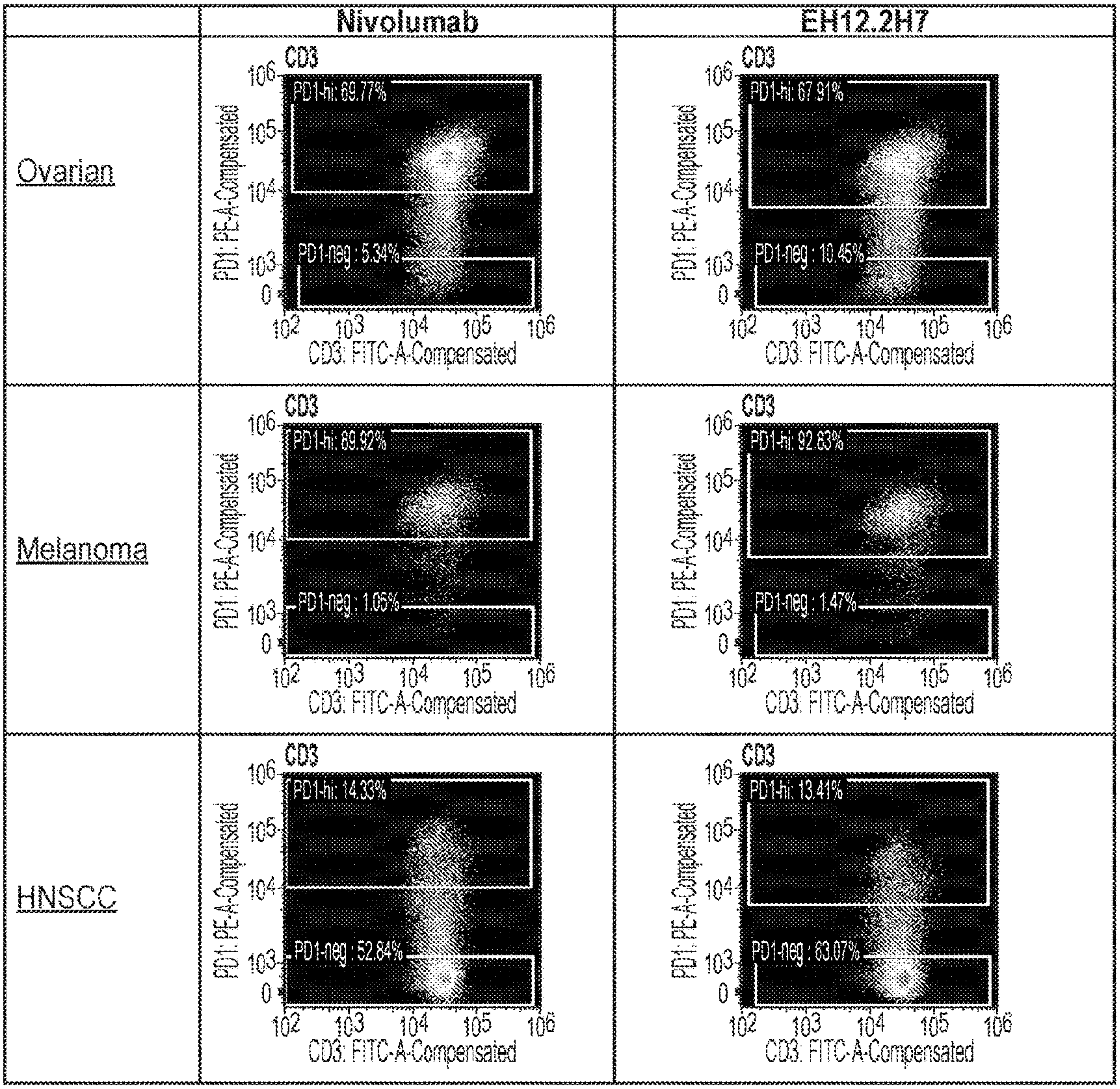

FIG. 172C: PD-1 Levels in Nivolumab and EH12.2H7-stained TIL. Whole tumor digests were split and stained with either nivolumab or EH12.2H7 and assessed by flow cytometry. The PD-1$^+$ cells, identified using each antibody, from 1 ovarian, 1 melanoma and 1 HNSCC were then sorted using the FX500 cell sorter (SONY, NY).

FIG. 173: Final Product Yield of Nivolumab and EH12.2H7 stained PD-1-sorted TIL. PD-1-sorted TIL derived from staining TIL with nivolumab and EH12.2H7 from 1 ovarian, 1 melanoma and 1 HNSCC, were expanded using an 11-day activation step, followed by an 11-day REP. Number of CD3+ cells seeded, fold expansion and extrapolated/actual cell counts are shown. The ovarian and melanoma tumors designated by * were small-scale experiments, and the HNSCC designated by ** was performed full-scale.

Figure 174:
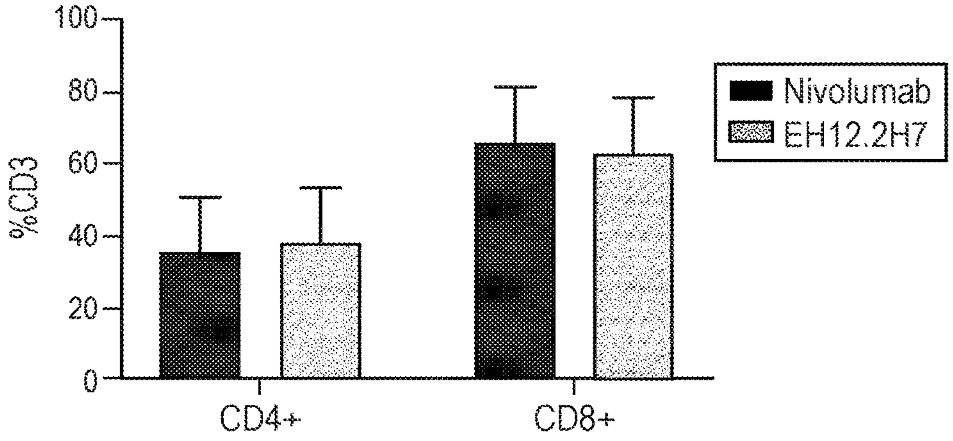

FIG. 174: Expression of CD4+ and CD8+ TIL in PD-1-Selected TIL using EH12.2H7 and Nivolumab. PD-1-selected TIL sorted using either nivolumab or EH12.2H7 to identify the PD-1$^+$ TIL from 1 ovarian, 1 melanoma, and 1 HNSCC were assessed for T cell lineage (CD4 and CD8) using flow cytometry. Results are expressed as percentages of CD3$^+$ cells. Mean values are plotted as bars and standard errors shown as vertical lines.

Figure 175:
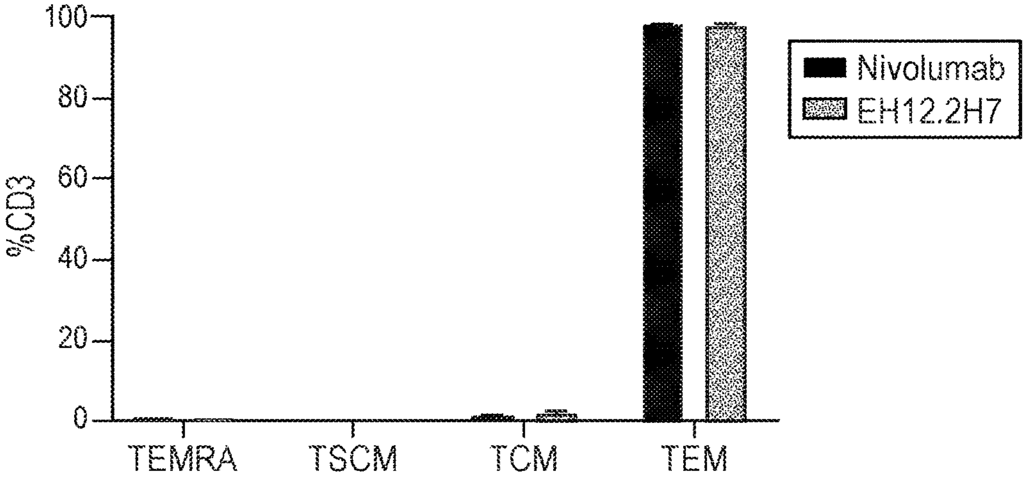

FIG. 175: Memory Populations in EH12.2H7 and Nivolumab-sorted PD-1+ TIL. PD-1-selected TIL from 1 ovarian, 1 melanoma and 1 HNSCC tumor samples, sorted using either nivolumab or EH12.2H7 to identify the PD-1+ TIL, were assessed for the expression of the memory markers CD45RA and CCR7 by flow cytometry. T cell memory subsets were determined as indicated and average percentages of each subset plotted as black bars for nivolumab PD-1-selected TIL and gray bars for EH12.2H7 PD-1-selected TIL. Standard errors are shown as vertical lines.

Figure 176:
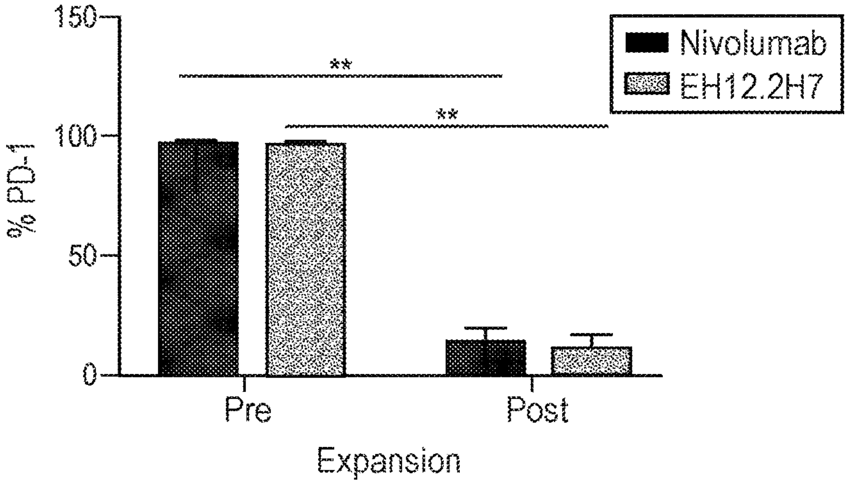

FIG. 176: TIL Expression of PD-1 expression in PD-1-Sorted TIL Generated using EH12.2H7 and Nivolumab, Prior to and Post-Expansion. PD-1-sorted TIL from 1 ovarian, 1 melanoma and 1 HNSCC, sorted using either nivolumab or EH12.2H7 to identify the PD-1$^+$ TIL, were assessed for expression of PD-1 expression pre- and post-expansion. Post-sort purity of the PD-1-sorted product was used to determine the percentage of PD-1$^+$ prior to expansion. Mean values are plotted as bars and standard errors shown as vertical lines. Statistical significance was assessed by a paired student t-test; ** indicates a p value <0.01.

Figure 177:
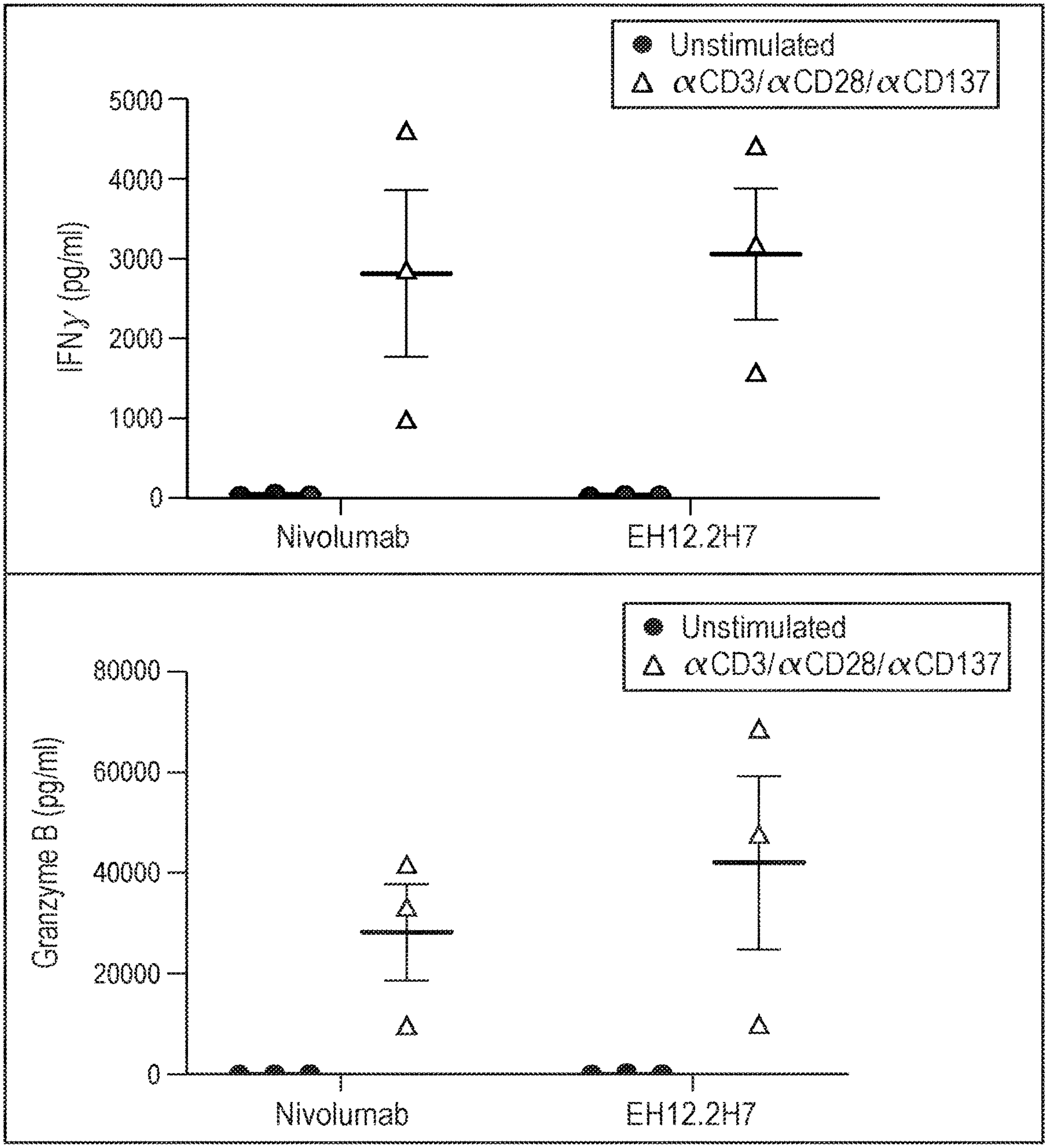

FIG. 177: PD-1-Selected TIL generated using EH12.2H7 and Nivolumab sorted PD-1$^+$ TILProduced IFNγ and Granzyme B is response to Non-Specific Stimulation. PD-1-selected TIL from 1 ovarian, 1 melanoma and 1 HNSCC, sorted using either nivolumab or EH12.2H7 to identify the PD-1$^+$ TIL, were assessed for secretion of (A) IFNγ and (B) Granzyme B. Results are plotted for individual samples, with the black dots representing the unstimulated condition and the gray triangles representing the αCD3/αCD28/α41BB stimulated condition. Horizontal lines represent the mean percentages of each subset and vertical lines represent the standard error.

Figure 178:
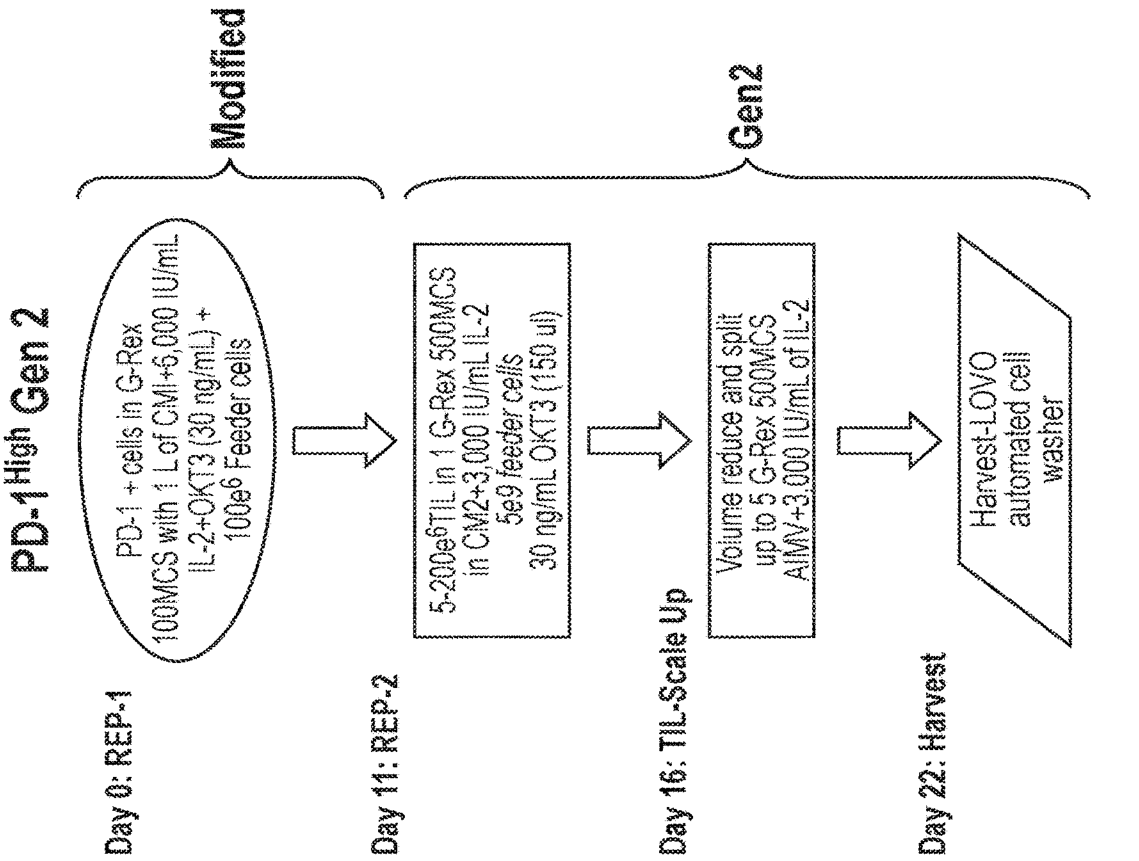

FIG. 178: Overview of an embodiment of the PD-1+ High Gen-2 Process.

Figure 179:
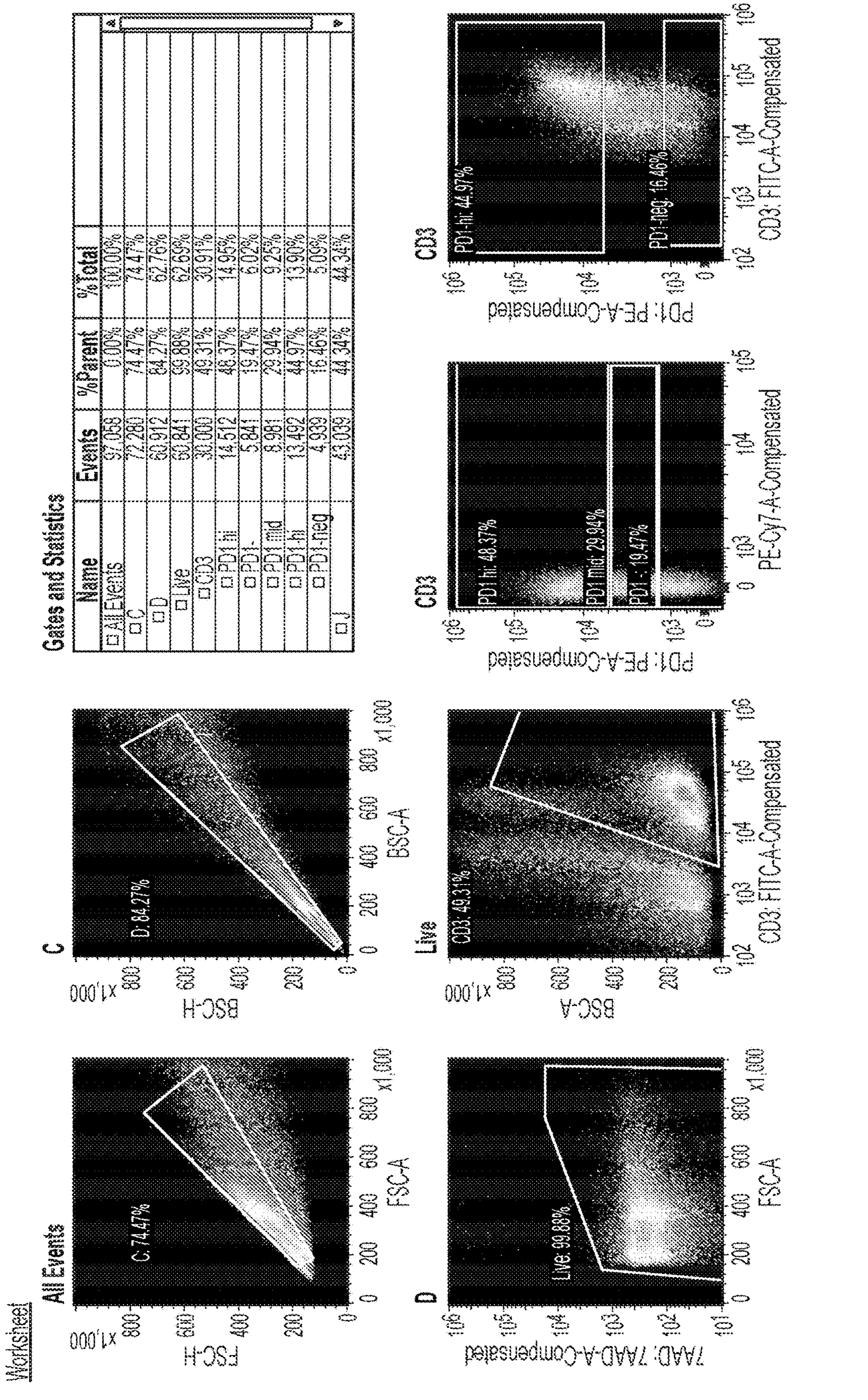

FIG. 179: FACS plot data.

BRIEF DESCRIPTION OF THE SEQUENCE LISTING

SEQ ID NO: 1 is the amino acid sequence of the heavy chain of muromonab.

SEQ ID NO:2 is the amino acid sequence of the light chain of muromonab.

SEQ ID NO:3 is the amino acid sequence of a recombinant human IL-2 protein.

SEQ ID NO:4 is the amino acid sequence of aldesleukin.

SEQ ID NO:5 is the amino acid sequence of a recombinant human IL-4 protein.

SEQ ID NO:6 is the amino acid sequence of a recombinant human IL-7 protein.

SEQ ID NO:7 is the amino acid sequence of a recombinant human IL-15 protein.

SEQ ID NO:8 is the amino acid sequence of a recombinant human IL-21 protein.

SEQ ID NO:9 is the amino acid sequence of human 4-1BB.

SEQ ID NO: 10 is the amino acid sequence of murine 4-1BB.

SEQ ID NO: 11 is the heavy chain for the 4-1BB agonist monoclonal antibody utomilumab (PF-05082566).

SEQ ID NO: 12 is the light chain for the 4-1BB agonist monoclonal antibody utomilumab (PF-05082566).

SEQ ID NO:13 is the heavy chain variable region (VH) for the 4-1BB agonist monoclonal antibody utomilumab (PF-05082566).

SEQ ID NO: 14 is the light chain variable region (VL) for the 4-1BB agonist monoclonal antibody utomilumab (PF-05082566).

SEQ ID NO: 15 is the heavy chain CDR1 for the 4-1BB agonist monoclonal antibody utomilumab (PF-05082566).

SEQ ID NO:16 is the heavy chain CDR2 for the 4-1BB agonist monoclonal antibody utomilumab (PF-05082566).

SEQ ID NO: 17 is the heavy chain CDR3 for the 4-1BB agonist monoclonal antibody utomilumab (PF-05082566).

SEQ ID NO:18 is the light chain CDR1 for the 4-1BB agonist monoclonal antibody utomilumab (PF-05082566).

SEQ ID NO:19 is the light chain CDR2 for the 4-1BB agonist monoclonal antibody utomilumab (PF-05082566).

SEQ ID NO:20 is the light chain CDR3 for the 4-1BB agonist monoclonal antibody utomilumab (PF-05082566).

SEQ ID NO:21 is the heavy chain for the 4-1BB agonist monoclonal antibody urelumab (BMS-663513).

SEQ ID NO:22 is the light chain for the 4-1BB agonist monoclonal antibody urelumab (BMS-663513).

SEQ ID NO:23 is the heavy chain variable region (VH) for the 4-1BB agonist monoclonal antibody urelumab (BMS-663513).

SEQ ID NO:24 is the light chain variable region (VL) for the 4-1BB agonist monoclonal antibody urelumab (BMS-663513).

SEQ ID NO:25 is the heavy chain CDR1 for the 4-1BB agonist monoclonal antibody urelumab (BMS-663513).

SEQ ID NO:26 is the heavy chain CDR2 for the 4-1BB agonist monoclonal antibody urelumab (BMS-663513).

SEQ ID NO:27 is the heavy chain CDR3 for the 4-1BB agonist monoclonal antibody urelumab (BMS-663513).

SEQ ID NO:28 is the light chain CDR1 for the 4-1BB agonist monoclonal antibody urelumab (BMS-663513).

SEQ ID NO:29 is the light chain CDR2 for the 4-1BB agonist monoclonal antibody urelumab (BMS-663513).

SEQ ID NO:30 is the light chain CDR3 for the 4-1BB agonist monoclonal antibody urelumab (BMS-663513).

SEQ ID NO:31 is an Fc domain for a TNFRSF agonist fusion protein.

SEQ ID NO:32 is a linker for a TNFRSF agonist fusion protein.

SEQ ID NO:33 is a linker for a TNFRSF agonist fusion protein.

SEQ ID NO:34 is a linker for a TNFRSF agonist fusion protein.

SEQ ID NO:35 is a linker for a TNFRSF agonist fusion protein.

SEQ ID NO:36 is a linker for a TNFRSF agonist fusion protein.

SEQ ID NO:37 is a linker for a TNFRSF agonist fusion protein.

SEQ ID NO:38 is a linker for a TNFRSF agonist fusion protein.

SEQ ID NO:39 is a linker for a TNFRSF agonist fusion protein.

SEQ ID NO:40 is a linker for a TNFRSF agonist fusion protein.

SEQ ID NO:41 is a linker for a TNFRSF agonist fusion protein.

SEQ ID NO:42 is an Fc domain for a TNFRSF agonist fusion protein.

SEQ ID NO:43 is a linker for a TNFRSF agonist fusion protein.

SEQ ID NO:44 is a linker for a TNFRSF agonist fusion protein.

SEQ ID NO:45 is a linker for a TNFRSF agonist fusion protein.

SEQ ID NO:46 is a 4-1BB ligand (4-1BBL) amino acid sequence.

SEQ ID NO:47 is a soluble portion of 4-1BBL polypeptide.

SEQ ID NO:48 is a heavy chain variable region (VH) for the 4-1BB agonist antibody 4B4-1-1 version 1.

SEQ ID NO:49 is a light chain variable region (VL) for the 4-1BB agonist antibody 4B4-1-1 version 1.

SEQ ID NO:50 is a heavy chain variable region (VH) for the 4-1BB agonist antibody 4B4-1-1 version 2.

SEQ ID NO:51 is a light chain variable region (VL) for the 4-1BB agonist antibody 4B4-1-1 version 2.

SEQ ID NO:52 is a heavy chain variable region (VH) for the 4-1BB agonist antibody H39E3-2.

SEQ ID NO:53 is a light chain variable region (VL) for the 4-1BB agonist antibody H39E3-2.

SEQ ID NO:54 is the amino acid sequence of human OX40.

SEQ ID NO:55 is the amino acid sequence of murine OX40.

SEQ ID NO:56 is the heavy chain for the OX40 agonist monoclonal antibody tavolixizumab (MEDI-0562).

SEQ ID NO:57 is the light chain for the OX40 agonist monoclonal antibody tavolixizumab (MEDI-0562).

SEQ ID NO:58 is the heavy chain variable region (VH) for the OX40 agonist monoclonal antibody tavolixizumab (MEDI-0562).

SEQ ID NO:59 is the light chain variable region (VL) for the OX40 agonist monoclonal antibody tavolixizumab (MEDI-0562).

SEQ ID NO:60 is the heavy chain CDR1 for the OX40 agonist monoclonal antibody tavolixizumab (MEDI-0562).

SEQ ID NO:61 is the heavy chain CDR2 for the OX40 agonist monoclonal antibody tavolixizumab (MEDI-0562).

SEQ ID NO:62 is the heavy chain CDR3 for the OX40 agonist monoclonal antibody tavolixizumab (MEDI-0562).

SEQ ID NO:63 is the light chain CDR1 for the OX40 agonist monoclonal antibody tavolixizumab (MEDI-0562).

SEQ ID NO:64 is the light chain CDR2 for the OX40 agonist monoclonal antibody tavolixizumab (MEDI-0562).

SEQ ID NO:65 is the light chain CDR3 for the OX40 agonist monoclonal antibody tavolixizumab (MEDI-0562).

SEQ ID NO: 66 is the heavy chain for the OX40 agonist monoclonal antibody 11D4.

SEQ ID NO: 67 is the light chain for the OX40 agonist monoclonal antibody 11D4.

SEQ ID NO:68 is the heavy chain variable region (VH) for the OX40 agonist monoclonal antibody 11D4.

SEQ ID NO:69 is the light chain variable region (VL) for the OX40 agonist monoclonal antibody 11D4.

SEQ ID NO:70 is the heavy chain CDR1 for the OX40 agonist monoclonal antibody 11D4.

SEQ ID NO:71 is the heavy chain CDR2 for the OX40 agonist monoclonal antibody 11D4.

SEQ ID NO:72 is the heavy chain CDR3 for the OX40 agonist monoclonal antibody 11D4.

SEQ ID NO:73 is the light chain CDR1 for the OX40 agonist monoclonal antibody 11D4.

SEQ ID NO:74 is the light chain CDR2 for the OX40 agonist monoclonal antibody 11D4.

SEQ ID NO:75 is the light chain CDR3 for the OX40 agonist monoclonal antibody 11D4.

SEQ ID NO: 76 is the heavy chain for the OX40 agonist monoclonal antibody 18D8.

SEQ ID NO:77 is the light chain for the OX40 agonist monoclonal antibody 18D8.

SEQ ID NO:78 is the heavy chain variable region (VH) for the OX40 agonist monoclonal antibody 18D8.

SEQ ID NO:79 is the light chain variable region (VL) for the OX40 agonist monoclonal antibody 18D8.

SEQ ID NO:80 is the heavy chain CDR1 for the OX40 agonist monoclonal antibody 18D8.

SEQ ID NO:81 is the heavy chain CDR2 for the OX40 agonist monoclonal antibody 18D8.

SEQ ID NO:82 is the heavy chain CDR3 for the OX40 agonist monoclonal antibody 18D8.

SEQ ID NO:83 is the light chain CDR1 for the OX40 agonist monoclonal antibody 18D8.

SEQ ID NO:84 is the light chain CDR2 for the OX40 agonist monoclonal antibody 18D8.

SEQ ID NO:85 is the light chain CDR3 for the OX40 agonist monoclonal antibody 18D8.

SEQ ID NO:86 is the heavy chain variable region (VH) for the OX40 agonist monoclonal antibody Hu119-122.

SEQ ID NO:87 is the light chain variable region (VL) for the OX40 agonist monoclonal antibody Hu119-122.

SEQ ID NO:88 is the heavy chain CDR1 for the OX40 agonist monoclonal antibody Hu119-122.

SEQ ID NO:89 is the heavy chain CDR2 for the OX40 agonist monoclonal antibody Hu119-122.

SEQ ID NO:90 is the heavy chain CDR3 for the OX40 agonist monoclonal antibody Hu119-122.

SEQ ID NO:91 is the light chain CDR1 for the OX40 agonist monoclonal antibody Hu119-122.

SEQ ID NO:92 is the light chain CDR2 for the OX40 agonist monoclonal antibody Hu119-122.

SEQ ID NO:93 is the light chain CDR3 for the OX40 agonist monoclonal antibody Hu119-122.

SEQ ID NO:94 is the heavy chain variable region (VH) for the OX40 agonist monoclonal antibody Hu106-222.

SEQ ID NO:95 is the light chain variable region (VL) for the OX40 agonist monoclonal antibody Hu106-222.

SEQ ID NO:96 is the heavy chain CDR1 for the OX40 agonist monoclonal antibody Hu106-222.

SEQ ID NO:97 is the heavy chain CDR2 for the OX40 agonist monoclonal antibody Hu106-222.

SEQ ID NO:98 is the heavy chain CDR3 for the OX40 agonist monoclonal antibody Hu106-222.

SEQ ID NO:99 is the light chain CDR1 for the OX40 agonist monoclonal antibody Hu106-222.

SEQ ID NO:100 is the light chain CDR2 for the OX40 agonist monoclonal antibody Hu106-222.

SEQ ID NO:101 is the light chain CDR3 for the OX40 agonist monoclonal antibody Hu106-222.

SEQ ID NO:102 is an OX40 ligand (OX40L) amino acid sequence.

SEQ ID NO: 103 is a soluble portion of OX40L polypeptide.

SEQ ID NO: 104 is an alternative soluble portion of OX40L polypeptide.

SEQ ID NO: 105 is the heavy chain variable region (VH) for the OX40 agonist monoclonal antibody 008.

SEQ ID NO:106 is the light chain variable region (VL) for the OX40 agonist monoclonal antibody 008.

SEQ ID NO: 107 is the heavy chain variable region (VH) for the OX40 agonist monoclonal antibody 011.

SEQ ID NO: 108 is the light chain variable region (VL) for the OX40 agonist monoclonal antibody 011.

SEQ ID NO: 109 is the heavy chain variable region (VH) for the OX40 agonist monoclonal antibody 021.

SEQ ID NO:110 is the light chain variable region (VL) for the OX40 agonist monoclonal antibody 021.

SEQ ID NO:111 is the heavy chain variable region (VH) for the OX40 agonist monoclonal antibody 023.

SEQ ID NO: 112 is the light chain variable region (VL) for the OX40 agonist monoclonal antibody 023.

SEQ ID NO: 113 is the heavy chain variable region (VH) for an OX40 agonist monoclonal antibody.

SEQ ID NO:114 is the light chain variable region (VL) for an OX40 agonist monoclonal antibody.

SEQ ID NO:115 is the heavy chain variable region (VH) for an OX40 agonist monoclonal antibody.

SEQ ID NO:116 is the light chain variable region (VL) for an OX40 agonist monoclonal antibody.

SEQ ID NO:117 is the heavy chain variable region (VH) for a humanized OX40 agonist monoclonal antibody.

SEQ ID NO:118 is the heavy chain variable region (VH) for a humanized OX40 agonist monoclonal antibody.

SEQ ID NO: 119 is the light chain variable region (VL) for a humanized OX40 agonist monoclonal antibody.

SEQ ID NO: 120 is the light chain variable region (VL) for a humanized OX40 agonist monoclonal antibody.

SEQ ID NO: 121 is the heavy chain variable region (VH) for a humanized OX40 agonist monoclonal antibody.

SEQ ID NO: 122 is the heavy chain variable region (VH) for a humanized OX40 agonist monoclonal antibody.

SEQ ID NO: 123 is the light chain variable region (VL) for a humanized OX40 agonist monoclonal antibody.

SEQ ID NO:124 is the light chain variable region (VL) for a humanized OX40 agonist monoclonal antibody.

SEQ ID NO:125 is the heavy chain variable region (VH) for an OX40 agonist monoclonal antibody.

SEQ ID NO:126 is the light chain variable region (VL) for an OX40 agonist monoclonal antibody.

SEQ ID NO: 127 is a TCR CDR3 beta chain amino acid sequence.

SEQ ID NO: 128 is a TCR CDR3 beta chain amino acid sequence.

SEQ ID NO:129 is a TCR CDR3 beta chain amino acid sequence.

SEQ ID NO:130 is a TCR CDR3 beta chain amino acid sequence.

SEQ ID NO:131 is a TCR CDR3 beta chain amino acid sequence.

SEQ ID NO: 132 is a TCR CDR3 beta chain amino acid sequence.

SEQ ID NO:133 is a TCR CDR3 beta chain amino acid sequence.

SEQ ID NO:134 is a TCR CDR3 beta chain amino acid sequence.

SEQ ID NO:135 is a TCR CDR3 beta chain amino acid sequence.

SEQ ID NO:136 is a TCR CDR3 beta chain amino acid sequence.

SEQ ID NO:137 is a TCR CDR3 beta chain amino acid sequence.

SEQ ID NO:138 is a TCR CDR3 beta chain amino acid sequence.

SEQ ID NO: 139 is a TCR CDR3 beta chain amino acid sequence.

SEQ ID NO:140 is a TCR CDR3 beta chain amino acid sequence.

SEQ ID NO:141 is a TCR CDR3 beta chain amino acid sequence.

SEQ ID NO: 142 is a TCR CDR3 beta chain amino acid sequence.

SEQ ID NO: 143 is a TCR CDR3 beta chain amino acid sequence.

SEQ ID NO:144 is a TCR CDR3 beta chain amino acid sequence.

SEQ ID NO:145 is a TCR CDR3 beta chain amino acid sequence.

SEQ ID NO: 146 is a TCR CDR3 beta chain amino acid sequence.

SEQ ID NO:147 is a TCR CDR3 beta chain amino acid sequence.

SEQ ID NO: 148 is a TCR CDR3 beta chain amino acid sequence.

SEQ ID NO: 149 is a TCR CDR3 beta chain amino acid sequence.

SEQ ID NO: 150 is a TCR CDR3 beta chain amino acid sequence.

SEQ ID NO:151 is a TCR CDR3 beta chain amino acid sequence.

SEQ ID NO: 152 is a TCR CDR3 beta chain amino acid sequence.

SEQ ID NO:153 is a TCR CDR3 beta chain amino acid sequence.

SEQ ID NO:154 is a TCR CDR3 beta chain amino acid sequence.

SEQ ID NO:155 is a TCR CDR3 beta chain amino acid sequence.

SEQ ID NO:156 is a TCR CDR3 beta chain amino acid sequence.

SEQ ID NO: 157 is a TCR CDR3 beta chain amino acid sequence.

SEQ ID NO:158 is a TCR CDR3 beta chain amino acid sequence.

SEQ ID NO:159 is a TCR CDR3 beta chain amino acid sequence.

SEQ ID NO: 160 is a TCR CDR3 beta chain amino acid sequence.

SEQ ID NO: 161 is a TCR CDR3 beta chain amino acid sequence.

SEQ ID NO:162 is a TCR CDR3 beta chain amino acid sequence.

SEQ ID NO:163 is a TCR CDR3 beta chain amino acid sequence.

SEQ ID NO: 164 is a TCR CDR3 beta chain amino acid sequence.

SEQ ID NO:165 is a TCR CDR3 beta chain amino acid sequence.

SEQ ID NO: 166 is a TCR CDR3 beta chain amino acid sequence.

SEQ ID NO:167 is a TCR CDR3 beta chain amino acid sequence.

SEQ ID NO: 168 is a TCR CDR3 beta chain amino acid sequence.

SEQ ID NO: 169 is a TCR CDR3 beta chain amino acid sequence.

SEQ ID NO:170 is a TCR CDR3 beta chain amino acid sequence.

SEQ ID NO:171 is a TCR CDR3 beta chain amino acid sequence.

SEQ ID NO: 172 is a TCR CDR3 beta chain amino acid sequence.

SEQ ID NO:173 is a TCR CDR3 beta chain amino acid sequence.

SEQ ID NO:174 is a TCR CDR3 beta chain amino acid sequence.

SEQ ID NO:175 is a TCR CDR3 beta chain amino acid sequence.

SEQ ID NO:176 is a TCR CDR3 beta chain amino acid sequence.

SEQ ID NO:177 is a TCR CDR3 beta chain amino acid sequence.

SEQ ID NO:178 is a TCR CDR3 beta chain amino acid sequence.

SEQ ID NO: 179 is a TCR CDR3 beta chain amino acid sequence.

SEQ ID NO: 180 is a TCR CDR3 beta chain amino acid sequence.

SEQ ID NO:181 is a TCR CDR3 beta chain amino acid sequence.

SEQ ID NO: 182 is a TCR CDR3 beta chain amino acid sequence.

SEQ ID NO: 183 is a TCR CDR3 beta chain amino acid sequence.

SEQ ID NO:184 is a TCR CDR3 beta chain amino acid sequence.

SEQ ID NO: 185 is a TCR CDR3 beta chain amino acid sequence.

SEQ ID NO:186 is a TCR CDR3 beta chain amino acid sequence.

SEQ ID NO:187 is a TCR CDR3 beta chain amino acid sequence.

SEQ ID NO: 188 is a TCR CDR3 beta chain amino acid sequence.

SEQ ID NO:189 is a TCR CDR3 beta chain amino acid sequence.

SEQ ID NO: 190 is a TCR CDR3 beta chain amino acid sequence.

SEQ ID NO: 191 is a TCR CDR3 beta chain amino acid sequence.

SEQ ID NO: 192 is a TCR CDR3 beta chain amino acid sequence.

SEQ ID NO:193 is a TCR CDR3 beta chain amino acid sequence.

SEQ ID NO: 194 is a TCR CDR3 beta chain amino acid sequence.

SEQ ID NO:195 is a TCR CDR3 beta chain amino acid sequence.

SEQ ID NO: 196 is a TCR CDR3 beta chain amino acid sequence.

I. Definitions

Unless defined otherwise, all technical and scientific terms used herein have the same meaning as is commonly understood by one of skill in the art to which this invention belongs. All patents and publications referred to herein are incorporated by reference in their entireties.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are outlined below.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to as "freshly obtained" or "freshly isolated"), and "secondary TILs" are any TIL cell populations that have been expanded or proliferated as discussed herein, including, but not limited to bulk TILs and expanded TILs ("REP TILs" or "post-REP TILs"). TIL cell populations can include genetically modified TILs.

By "population of cells" (including TILs) herein is meant a number of cells that share common traits. In general, populations generally range from $1\times10^6$ to $1\times10^{10}$ in number, with different TIL populations comprising different numbers. For example, initial growth of primary TILs in the presence of IL-2 results in a population of bulk TILs of roughly $1\times10^8$ cells. REP expansion is generally done to provide populations of $1.5\times10^9$ to $1.5\times10^{10}$ cells for infusion.

By "cryopreserved TILs" herein is meant that TILs, either primary, bulk, or expanded (REP TILs), are treated and stored in the range of about −150° C. to −60° C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally and alternatively, TILs can be functionally defined by their ability to infiltrate solid tumors upon reintroduction into a patient.

The term "cryopreservation media" or "cryopreservation medium" refers to any medium that can be used for cryopreservation of cells. Such media can include media comprising 7% to 10% DMSO. Exemplary media include CryoStor CS10, Hyperthermasol, as well as combinations thereof. The term "CS10" refers to a cryopreservation medium which is obtained from Stemcell Technologies or from Biolife Solutions. The CS10 medium may be referred to by the trade name "CryoStor® CS10". The CS10 medium is a serum-free, animal component-free medium which comprises DMSO.

The term "central memory T cell" refers to a subset of T cells that in the human are CD45R0+ and constitutively express CCR7 ($CCR7^{hi}$) and CD62L ($CD62^{hi}$). The surface phenotype of central memory T cells also includes TCR, CD3, CD127 (IL-7R), and IL-15R. Transcription factors for central memory T cells include BCL-6, BCL-6B, MBD2, and BMI1. Central memory T cells primarily secret IL-2 and CD40L as effector molecules after TCR triggering. Central memory T cells are predominant in the CD4 compartment in blood, and in the human are proportionally enriched in lymph nodes and tonsils.

The term "effector memory T cell" refers to a subset of human or mammalian T cells that, like central memory T cells, are CD45R0+, but have lost the constitutive expression of CCR7 ($CCR71^{lo}$) and are heterogeneous or low for CD62L expression ($CD62L1^{lo}$). The surface phenotype of central memory T cells also includes TCR, CD3, CD127 (IL-7R), and IL-15R. Transcription factors for central memory T cells include BLIMP1. Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. CD8+ effector memory T cells carry large amounts of perforin.

The term "closed system" refers to a system that is closed to the outside environment. Any closed system appropriate for cell culture methods can be employed with the methods of the present invention. Closed systems include, for example, but are not limited to closed G-containers. Once a tumor segment is added to the closed system, the system is no opened to the outside environment until the TILs are ready to be administered to the patient.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

The terms "peripheral blood mononuclear cells" and "PBMCs" refers to a peripheral blood cell having a round nucleus, including lymphocytes (T cells, B cells, NK cells) and monocytes. When used as antigen-presenting cells (PBMCs are a type of antigen-presenting cell), the peripheral blood mononuclear cells are preferably irradiated allogeneic peripheral blood mononuclear cells.

The terms "peripheral blood lymphocytes" and "PBLs" refer to T cells expanded from peripheral blood. In some embodiments, PBLs are separated from whole blood or apheresis product from a donor. In some embodiments, PBLs are separated from whole blood or apheresis product from a donor by positive or negative selection of a T cell phenotype, such as the T cell phenotype of CD3+CD45+.

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Anti-CD3 antibodies also include the UHCT1 clone, also known as T3 and CD3E. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, CA, USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

TABLE 1

Amino acid sequences of muromonab.

| Identifier | Sequence (One-Letter Amino Acid Symbols) |
|---|---|
| SEQ ID NO: 1 | QVQLQQSGAE LARPGASVKM SCKASGYTFT RYTMHWVKQR PGQGLEWIGY INPSRGYTNY 60 |
| Muromonab | NQKFKDKATL TTDKSSSTAY MQLSSLTSED SAVYYCARYY DDHYCLDYWG QGTTLTVSSA 120 |
| heavy | KTTAPSVYPL APVCGGTTGS SVTLGCLVKG YFPEPVTLTW NSGSLSSGVH TFPAVLQSDL 180 |
| chain | YTLSSSVTVT SSTWPSQSIT CNVAHPASST KVDKKIEPRP KSCDKTHTCP PCPAPELLGG 240 |
| | PSVFLFPPKP KDTLMISRTP EVTCVVVDVS HEDPEVKFNW YVDGVEVHNA KTKPREEQYN 300 |
| | STYRVVSVLT VLHQDWLNGK EYKCKVSNKA LPAPIEKTIS KAKGQPREPQ VYTLPPSRDE 360 |
| | LTKNQVSLTC LVKGFYPSDI AVEWESNGQP ENNYKTTPPV LDSDGSFFLY SKLTVDKSRW 420 |
| | QQGNVFSCSV MHEALHNHYT QKSLSLSPGK 450 |

TABLE 1-continued

| Amino acid sequences of muromonab. | | |
|---|---|---|
| Identifier | Sequence (One-Letter Amino Acid Symbols) | |
| SEQ ID NO: 2 | QIVLTQSPAI MSASPGEKVT MTCSASSSVS YMNWYQQKSG TSPKRWIYDT SKLASGVPAH | 60 |
| Muromonab | FRGSGSGTSY SLTISGMEAE DAATYYCQQW SSNPFTFGSG TKLEINRADT APTVSIFPPS | 120 |
| light | SEQLTSGGAS VVCFLNNFYP KDINVKWKID GSERQNGVLN SWTDQDSKDS TYSMSSTLTL | 180 |
| chain | TKDEYERHNS YTCEATHKTS TSPIVKSFNR NEC | 213 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, *J. Immunol.* 2004, 172, 3983-88 and Malek, *Annu. Rev. Immunol.* 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, NH, USA (CELLGRO GMP) or ProSpec-Tany TechnoGene Ltd., East Brunswick, NJ, USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, CA, USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4902,502, the disclosures of which are incorporated by reference herein. Formulations of IL-2 suitable for use in the invention are described in U.S. Pat. No. 6,706,289, the disclosure of which is incorporated by reference herein.

TABLE 2

| Amino acid sequences of interleukins. | | |
|---|---|---|
| Identifier | Sequence (One-Letter Amino Acid Symbols) | |
| SEQ ID NO: 3 | MAPTSSSTKK TQLQLEHLLL DLQMILNGIN NYKNPKLTRM LTFKFYMPKK ATELKHLQCL | 60 |
| recombinant | EEELKPLEEV LNLAQSKNFH LRPRDLISNI NVIVLELKGS ETTFMCEYAD ETATIVEFLN | 120 |
| human IL-2 | RWITFCQSII STLT | 134 |
| (rhIL-2) | | |
| SEQ ID NO: 4 | PTSSSTKKTQ LQLEHLLLDL QMILNGINNY KNPKLTRMLT FKFYMPKKAT ELKHLQCLEE | 60 |
| Aldesleukin | ELKPLEEVLN LAQSKNFHLR PRDLISNINV IVLELKGSET TFMCEYADET ATIVEFLNRW | 120 |
| | ITFSQSIIST LT | 132 |
| SEQ ID NO: 5 | MHKCDITLQE IIKTLNSLTE QKTLCTELTV TDIFAASKNT TEKETFCRAA TVLRQFYSHH | 60 |
| recombinant | EKDTRCLGAT AQQFHRHKQL IRFLKRLDRN LWGLAGLNSC PVKEANQSTL ENFLERLKTI | 120 |
| human IL-4 | MREKYSKCSS | 130 |
| (rhIL-4) | | |
| SEQ ID NO: 6 | MDCDIEGKDG KQYESVLMVS IDQLLDSMKE IGSNCLNNEF NFFKRHICDA NKEGMFLFRA | 60 |
| recombinant | ARKLRQFLKM NSTGDFDLHL LKVSEGTTIL LNCTGQVKGR KPAALGEAQP TKSLEENKSL | 120 |
| human IL-7 | KEQKKLNDLC FLKRLLQEIK TCWNKILMGT KEH | 153 |
| (rhIL-7) | | |
| SEQ ID NO: 7 | MNWVNVISDL KKIEDLIQSM HIDATLYTES DVHPSCKVTA MKCFLLELQV ISLESGDASI | 60 |
| recombinant | HDTVENLIIL ANNSLSSNGN VTESGCKECE ELEEKNIKEF LQSFVHIVQM FINTS | 115 |
| human IL-15 | | |
| (rhIL-15) | | |
| SEQ ID NO: 8 | MQDRHMIRMR QLIDIVDQLK NYVNDLVPEF LPAPEDVETN CEWSAFSCFQ KAQLKSANTG | 60 |
| recombinant | NNERIINVSI KKLKRKPPST NAGRRQKHRL TCPSCDSYEK KPPKEFLERF KSLLQKMIHQ | 120 |
| human IL-21 | HLSSRTHGSE DS | 132 |
| (rhIL-21) | | |

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, *Respir. Res.* 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and $IgG_1$ expression from B cells. Recombinant human IL-4 suitable for use in the invention is commercially available from multiple suppliers, including ProSpec-Tany TechnoGene Ltd., East Brunswick, NJ, USA (Cat. No. CYT-211) and ThermoFisher Scientific, Inc., Waltham, MA, USA (human IL-15 recombinant protein, Cat. No. Gibco CTP0043). The amino acid sequence of recombinant human IL-4 suitable for use in the invention is given in Table 2 (SEQ ID NO:5).

The term "IL-7" (also referred to herein as "IL7") refers to a glycosylated tissue-derived cytokine known as interleukin 7, which may be obtained from stromal and epithelial cells, as well as from dendritic cells. Fry and Mackall, Blood 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the invention is commercially available from multiple suppliers, including ProSpec-Tany TechnoGene Ltd., East Brunswick, NJ, USA (Cat. No. CYT-254) and ThermoFisher Scientific, Inc., Waltham, MA, USA (human IL-15 recombinant protein, Cat. No. Gibco PHC0071). The amino acid sequence of recombinant human IL-7 suitable for use in the invention is given in Table 2 (SEQ ID NO: 6).

The term "IL-15" (also referred to herein as "IL15") refers to the T cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri, *Blood* 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, NJ, USA (Cat. No. CYT-230-b) and ThermoFisher Scientific, Inc., Waltham, MA, USA (human IL-15 recombinant protein, Cat. No. 34-8159-82). The amino acid sequence of recombinant human IL-15 suitable for use in the invention is given in Table 2 (SEQ ID NO:7).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, *Nat. Rev. Drug. Disc.* 2014, 13, 379-95, the disclosure of which is incorporated by reference herein. IL-21 is primarily produced by natural killer T cells and activated human CD4+ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, NJ, USA (Cat. No. CYT-408-b) and ThermoFisher Scientific, Inc., Waltham, MA, USA (human IL-21 recombinant protein, Cat. No. 14-8219-80). The amino acid sequence of recombinant human IL-21 suitable for use in the invention is given in Table 2 (SEQ ID NO:8).

When "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the tumor infiltrating lymphocytes (e.g. secondary TILs or genetically modified cytotoxic lymphocytes) described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{10}$, $10^6$ to $10^{11}$, $10^7$ to $10^{11}$, $10^7$ to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Tumor infiltrating lymphocytes (including in some cases, genetically modified cytotoxic lymphocytes) compositions may also be administered multiple times at these dosages. The tumor infiltrating lymphocytes (including in some cases, genetically) can be administered by using infusion techniques that are commonly known in immunotherapy (see, e.g., Rosenberg et al., *New Eng. J. of Med.* 319:1676, 1988). The optimal dosage and treatment regime for a particular patient can readily be determined by one skilled in the art of medicine by monitoring the patient for signs of disease and adjusting the treatment accordingly.

The term "hematological malignancy," "hematologic malignancy" or terms of correlative meaning refer to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMOL), Hodgkin's lymphoma, and non-Hodgkin's lymphomas. The term "B cell hematological malignancy" refers to hematological malignancies that affect B cells.

The term "solid tumor" refers to an abnormal mass of tissue that usually does not contain cysts or liquid areas. Solid tumors may be benign or malignant. The term "solid tumor cancer refers to malignant, neoplastic, or cancerous solid tumors. Solid tumor cancers include, but are not limited to, sarcomas, carcinomas, and lymphomas, such as cancers of the lung, breast, prostate, colon, rectum, and bladder. The tissue structure of solid tumors includes interdependent tissue compartments including the parenchyma (cancer cells) and the supporting stromal cells in which the cancer cells are dispersed and which may provide a supporting microenvironment.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs). TILs obtained from liquid tumors, including liquid tumors circulating in peripheral blood, may also be referred to herein as PBLs. The terms MIL, TIL, and PBL are used interchangeably herein and differ only based on the tissue type from which the cells are derived.

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., *Cancer Res.,* 2012, 72, 2473. Although tumors express antigens that should be recognized by T cells, tumor clearance by the immune system is rare because of immune suppression by the microenvironment.

In an embodiment, the invention includes a method of treating a cancer with a population of TILs, wherein a patient is pre-treated with non-myeloablative chemotherapy prior to an infusion of TILs according to the invention. In some embodiments, the population of TILs may be provided wherein a patient is pre-treated with nonmyeloablative chemotherapy prior to an infusion of TILs according to the present invention. In an embodiment, the non-myeloablative chemotherapy is cyclophosphamide 60 mg/kg/d for 2 days (days 27 and 26 prior to TIL infusion) and fludarabine 25 $mg/m^2/d$ for 5 days (days 27 to 23 prior to TIL infusion). In an embodiment, after non-myeloablative chemotherapy and TIL infusion (at day 0) according to the invention, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the rTILs of the invention.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, at least one potassium channel agonist in combination with a plurality of TILs) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The terms "sequence identity," "percent identity," and "sequence percent identity" (or synonyms thereof, e.g., "99% identical") in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

As used herein, the term "variant" encompasses but is not limited to antibodies or fusion proteins which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody. The term variant also includes pegylated antibodies or proteins.

By "tumor infiltrating lymphocytes" or "TILs" herein is meant a population of cells originally obtained as white blood cells that have left the bloodstream of a subject and migrated into a tumor. TILs include, but are not limited to, CD8+ cytotoxic T cells (lymphocytes), Th1 and Th17 CD4+ T cells, natural killer cells, dendritic cells and M1 macrophages. TILs include both primary and secondary TILs. "Primary TILs" are those that are obtained from patient tissue samples as outlined herein (sometimes referred to as "freshly obtained" or "freshly isolated"), and "secondary TILs" are any TIL cell populations that have been expanded or proliferated as discussed herein, including, but not limited to bulk TILs, expanded TILs ("REP TILs") as well as "reREP TILs" as discussed herein. reREP TILs can include for example second expansion TILs or second additional expansion TILs (such as, for example, those described in Step D of FIG. 27, including TILs referred to as reREP TILs).

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally, and alternatively, TILs can be functionally defined by their ability to infiltrate solid tumors upon reintroduction into a patient. TILS may further be characterized by potency—for example, TILS may be considered potent if, for example, interferon (IFN) release is greater than about 50 μg/mL, greater than about 100 μg/mL, greater than about 150 μg/mL, or greater than about 200 μg/mL.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

The term "PD-1 high" or "PD-1 high" or "PD-1high" refers to a high level of PD-1 protein expression by a cell such as, but not limited to, a tumor infiltrating lymphocyte or a T cell relative to a control cell from a healthy subject. In some embodiments, the level of PD-1 expression is determined using a standard method known to those skilled in the art for measuring protein levels present on a cell such as flow cytometry, fluorescence activated cell sorting (FACS), immunocytochemistry, and the like. In some cases, a PD-1 high TIL expresses a greater level of PD-1 compared to an immune cell from a healthy subject. In some cases, a population of PD-1 high TILs expresses a greater level of PD-1 compared to a population of immune cells (e.g., peripheral blood mononuclear cells) from a healthy subject or a group of healthy subjects. PD-1 high cells can be referred to as PD-1 bright cells.

The term "PD-1 intermediate" or "PD-lint" or "PD-1int" refers to an intermediate or moderate level of PD-1 protein expression by a cell such as, but not limited to, a tumor infiltrating lymphocyte or a T cell relative to a control cell from a healthy subject. For instance, a PD-lint T cell expresses PD-1 protein at a level or range that is similar to or substantially equivalent to the highest range of PD-1 protein expressed by a control cell (e.g., peripheral blood mononuclear cell) from a healthy subject. In other words, a PD-lint TIL has a PD-1 expression level that is similar to or substantially equivalent to a background level of PD-1 expression by a control immune cell from a healthy subject. PD-lint cells can be referred to as PD-1 dim cells. One skilled in the art recognizes that a PD-1 positive TIL can be a PD-1 high TIL or a PD-lint TIL.

The term "PD-1 negative" or "PD-1neg" or "PD-1neg" refers to negative or low level of PD-1 protein expression by a cell such as, but not limited to, a tumor infiltrating lymphocyte or a T cell relative to a control cell from a healthy subject. For instance, a PD-1neg T cell does not expresses PD-1 protein. In some instances, a PD-1neg T cell expresses PD-1 protein at a level that is similar to or substantially equivalent to the lowest level of PD-1 protein expressed by a control cell (e.g., peripheral blood mononuclear cell) from a healthy subject. PD-1neg lymphocytes can express PD-1 at the same level or range as a majority of lymphocytes in a control population.

PD-1 high, PD-lint, and PD-1neg TILs are distinct and different subsets of TILs expanded ex vivo according to the methods described herein. In some embodiments, a population of ex vivo expanded TILs comprises PD-1 high TILs, PD-lint TILs, and PD-1neg TILs.

II. TIL Manufacturing Processes (Embodiments of GEN3 Processes, Optionally Including Defined Media)

Without being limited to any particular theory, it is believed that the priming first expansion that primes an activation of T cells followed by the rapid second expansion that boosts the activation of T cells as described in the methods of the invention allows the preparation of expanded T cells that retain a "younger" phenotype, and as such the expanded T cells of the invention are expected to exhibit greater cytotoxicity against cancer cells than T cells expanded by other methods. In particular, it is believed that an activation of T cells that is primed by exposure to an anti-CD3 antibody (e.g. OKT-3), IL-2 and optionally antigen-presenting cells (APCs) and then boosted by subsequent exposure to additional anti-CD-3 antibody (e.g. OKT-3), IL-2 and APCs as taught by the methods of the invention limits or avoids the maturation of T cells in culture, yielding a population of T cells with a less mature phenotype, which T cells are less exhausted by expansion in culture and exhibit greater cytotoxicity against cancer cells. In some embodiments, the step of rapid second expansion is split into a plurality of steps to achieve a scaling up of the culture by: (a) performing the rapid second expansion by culturing T cells in a small scale culture in a first container, e.g., a G-REX 100 MCS container, for a period of about 3 to 4 days, and then (b) effecting the transfer of the T cells in the small scale culture to a second container larger than the first container, e.g., a G-REX 500 MCS container, and culturing the T cells from the small scale culture in a larger scale culture in the second container for a period of about 4 to 7 days. In some embodiments, the step of rapid expansion is split into a plurality of steps to achieve a scaling out of the culture by: (a) performing the rapid second expansion by culturing T cells in a first small scale culture in a first container, e.g., a G-REX 100 MCS container, for a period of about 3 to 4 days, and then (b) effecting the transfer and apportioning of the T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the T cells from first small scale culture transferred to such second container is cultured in a second small scale culture for a period of about 4 to 7 days. In some embodiments, the step of rapid expansion is split into a plurality of steps to achieve a scaling out and scaling up of the culture by: (a) performing the rapid second expansion by culturing T cells in a small scale culture in a first container, e.g., a G-REX 100 MCS container, for a period of about 3 to 4 days, and then (b) effecting the transfer and apportioning of the T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500 MCS containers, wherein in each second container the portion of the T cells from the small scale culture transferred to such second container is cultured in a larger scale culture for a period of about 4 to 7 days. In some embodiments, the step of rapid expansion is split into a plurality of steps to achieve a scaling out and scaling up of the culture by: (a) performing the rapid second expansion by culturing T cells in a small scale culture in a first container, e.g., a G-REX 100 MCS container, for a period of about 4 days, and then (b) effecting the transfer and apportioning of the T cells from the small scale culture into and amongst 2, 3 or 4 second containers that are larger in size than the first container, e.g., G-REX 500 MCS containers, wherein in each second container the portion of the T cells from the small scale culture transferred to such second container is cultured in a larger scale culture for a period of about 5 days.

In some embodiments, the rapid second expansion is performed after the activation of T cells effected by the priming first expansion begins to decrease, abate, decay or subside.

In some embodiments, the rapid second expansion is performed after the activation of T cells effected by the priming first expansion has decreased by at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In some embodiments, the rapid second expansion is performed after the activation of T cells effected by the priming first expansion has decreased by a percentage in the range of at or about 1% to 100%.

In some embodiments, the rapid second expansion is performed after the activation of T cells effected by the priming first expansion has decreased by a percentage in the range of at or about 1% to 10%, 10% to 20%, 20% to 30%, 30% to 40%, 40% to 50%, 50% to 60%, 60% to 70%, 70% to 80%, 80% to 90%, or 90% to 100%.

In some embodiments, the rapid second expansion is performed after the activation of T cells effected by the priming first expansion has decreased by at least at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In some embodiments, the rapid second expansion is performed after the activation of T cells effected by the priming first expansion has decreased by up to at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In some embodiments, the decrease in the activation of T cells effected by the priming first expansion is determined by a reduction in the amount of interferon gamma released by the T cells in response to stimulation with antigen.

In some embodiments, the priming first expansion of T cells is performed during a period of up to at or about 7 days or about 8 days.

In some embodiments, the priming first expansion of T cells is performed during a period of up to at or about 1 day, 2 days, 3 days, 4 days, 5 days, 6 days, 7 days, or 8 days.

In some embodiments, the priming first expansion of T cells is performed during a period of 1 day, 2 days, 3 days, 4 days, 5 days, 6 days, 7 days, or 8 days.

In some embodiments, the rapid second expansion of T cells is performed during a period of up to at or about 11 days.

In some embodiments, the rapid second expansion of T cells is performed during a period of up to at or about 1 day, 2 days, 3 days, 4 days, 5 days, 6 days, 7 days, 8 days, 9 days, 10 days or 11 days.

In some embodiments, the rapid second expansion of T cells is performed during a period of 1 day, 2 days, 3 days, 4 days, 5 days, 6 days, 7 days, 8 days, 9 days, 10 days or 11 days.

In some embodiments, the priming first expansion of T cells is performed during a period of from at or about 1 day to at or about 7 days and the rapid second expansion of T cells is performed during a period of from at or about 1 day to at or about 11 days.

In some embodiments, the priming first expansion of T cells is performed during a period of up to at or about 1 day, 2 days, 3 days, 4 days, 5 days, 6 days, 7 days, or 8 days and the rapid second expansion of T cells is performed during a period of up to at or about 1 day, 2 days, 3 days, 4 days, 5 days, 6 days, 7 days, 8 days, 9 days, 10 days or 11 days.

In some embodiments, the priming first expansion of T cells is performed during a period of from at or about 1 day to at or about 8 days and the rapid second expansion of T cells is performed during a period of from at or about 1 day to at or about 9 days.

In some embodiments, the priming first expansion of T cells is performed during a period of 8 days and the rapid second expansion of T cells is performed during a period of 9 days.

In some embodiments, the priming first expansion of T cells is performed during a period of from at or about 1 day to at or about 7 days and the rapid second expansion of T cells is performed during a period of from at or about 1 day to at or about 9 days.

In some embodiments, the priming first expansion of T cells is performed during a period of 7 days and the rapid second expansion of T cells is performed during a period of 9 days.

In some embodiments, the T cells are tumor infiltrating lymphocytes (TILs).

In some embodiments, the T cells are marrow infiltrating lymphocytes (MILs).

In some embodiments, the T cells are peripheral blood lymphocytes (PBLs).

In some embodiments, the T cells are obtained from a donor suffering from a cancer.

In some embodiments, the T cells are TILs obtained from a tumor excised from a patient suffering from a cancer.

In some embodiments, the T cells are MILs obtained from bone marrow of a patient suffering from a hematologic malignancy.

In some embodiments, the T cells are PBLs obtained from peripheral blood mononuclear cells (PBMCs) from a donor. In some embodiments, the donor is suffering from a cancer. In some embodiments, the donor is suffering from a hematologic malignancy.

In certain aspects of the present disclosure, immune effector cells, e.g., T cells, can be obtained from a unit of blood collected from a subject using any number of techniques known to the skilled artisan, such as FICOLL separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations. In one aspect, T cells are isolated from peripheral blood lymphocytes by lysing the red blood cells and depleting the monocytes, for example, by centrifugation through a PERCOLL gradient or by counterflow centrifugal elutriation.

In some embodiments, the T cells are PBLs separated from whole blood or apheresis product enriched for lymphocytes from a donor. In some embodiments, the donor is suffering from a cancer. In some embodiments, the donor is suffering from a cancer. In some embodiments, the cancer is the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the donor is suffering from a tumor. In some embodiments, the tumor is a liquid tumor. In some embodiments, the tumor is a solid tumor. In some embodiments, the donor is suffering from a hematologic malignancy.

In certain aspects of the present disclosure, immune effector cells, e.g., T cells, can be obtained from a unit of blood collected from a subject using any number of techniques known to the skilled artisan, such as FICOLL separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations. In one aspect, T cells are isolated from peripheral blood lymphocytes by lysing the red blood cells and depleting the monocytes, for example, by centrifugation through a PERCOLL gradient or by counterflow centrifugal elutriation.

In some embodiments, the T cells are PBLs separated from whole blood or apheresis product enriched for lymphocytes from a donor. In some embodiments, the donor is suffering from a cancer. In some embodiments, the cancer is the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the donor is suffering from a tumor. In some embodiments, the tumor is a liquid tumor. In some embodiments, the tumor is a solid tumor. In some embodiments, the donor is suffering from a hematologic malignancy. In some embodiments, the PBLs are isolated from whole blood or apheresis product enriched for lymphocytes by using positive or negative selection methods, i.e., removing the PBLs using a marker(s), e.g., CD3+ CD45+, for T cell phenotype, or removing non-T cell phenotype cells, leaving PBLs. In other embodiments, the PBLs are isolated by gradient centrifugation. Upon isolation of PBLs from donor tissue, the priming first expansion of PBLs can be initiated by seeding a suitable number of isolated PBLs (in some embodiments, approximately $1\times10^7$ PBLs) in the priming first expansion culture according to the priming first expansion step of any of the methods described herein.

Figure 30:
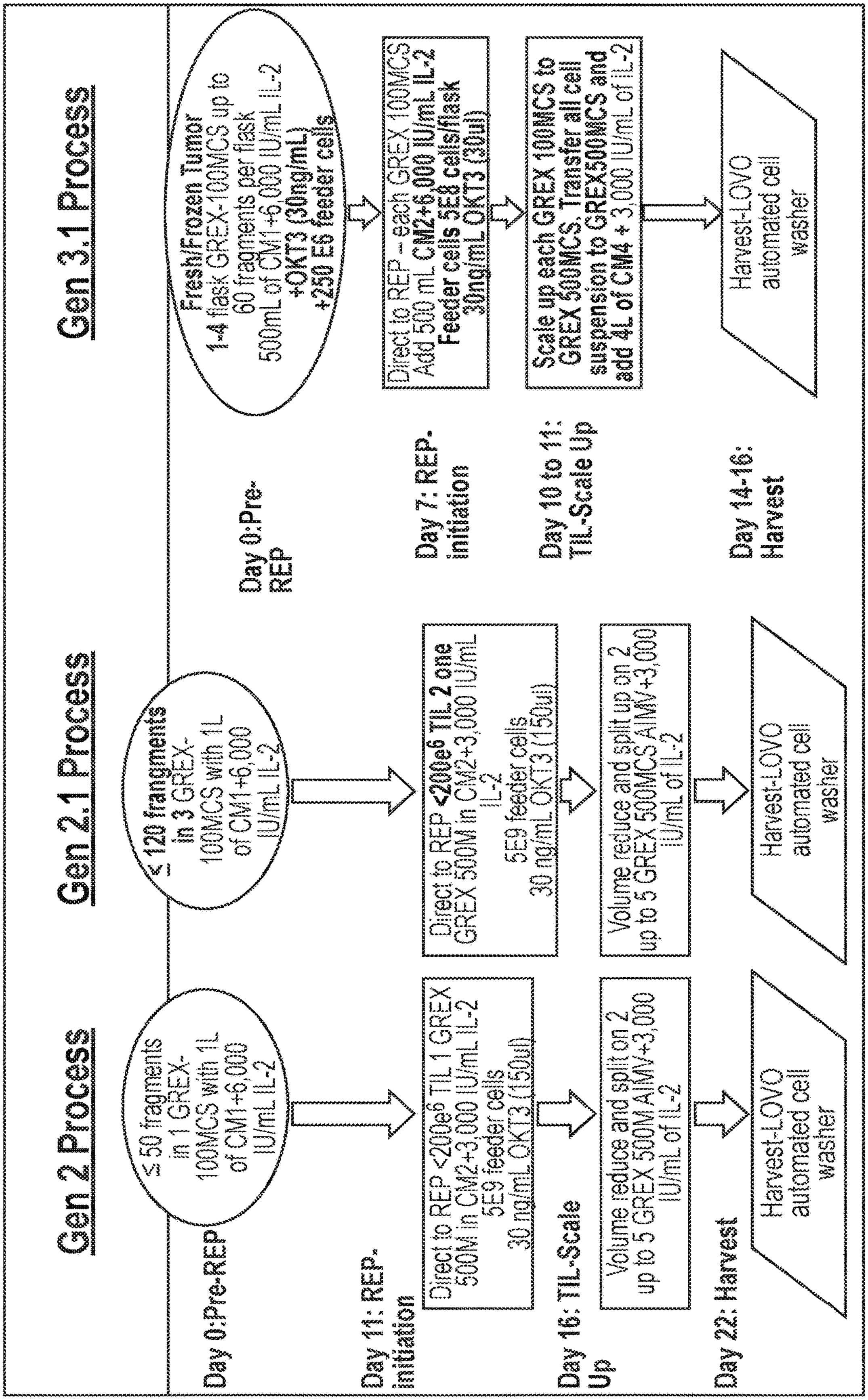
FIG. 30: Shows a comparison between various Gen 2 (2A process) and the Gen 3.1 process embodiment.
Figure 37:
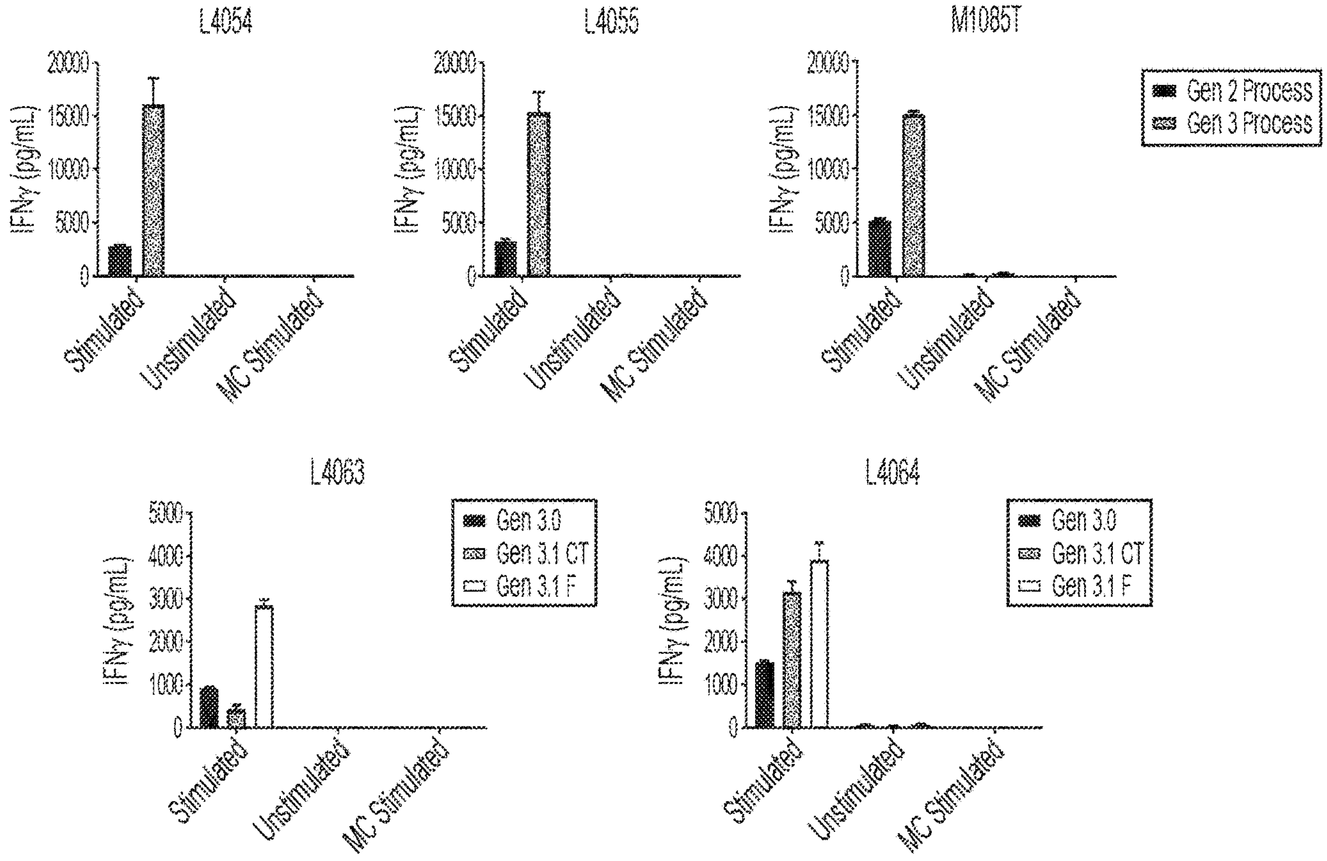
FIG. 37: Higher production of IFNγ on Gen 3 final product. IFNγ analysis (by ELISA) was assessed in the culture frozen supernatant to compared both processes. For each tumor overnight stimulation with coated anti-CD3 plate, using fresh TIL product on each Gen 2 (e.g., day 22) and Gen 3 process (e.g., day 16). Each bar represents here are IFNγ levels of stimulated, unstimulated and media control.
Figure 38:
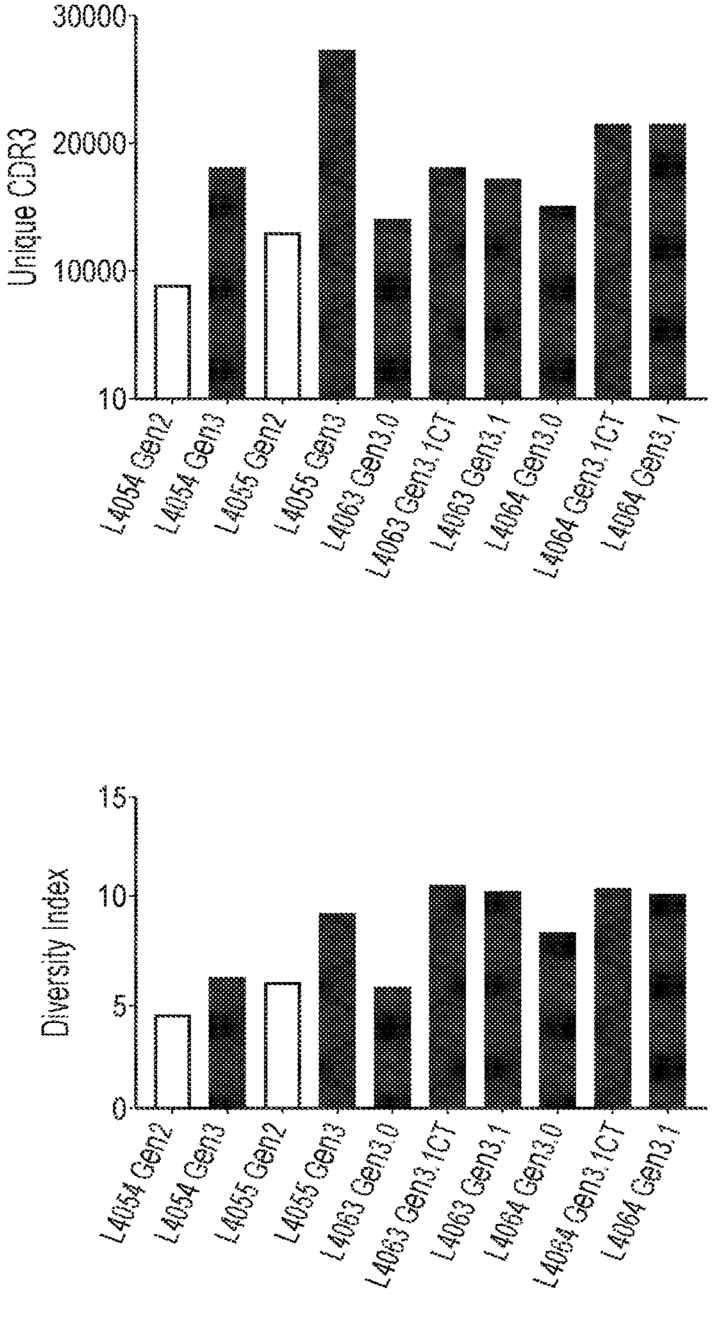
FIG. 38: Top: Unique CDR3 sequence analysis for TIL final product: Columns show the number of unique TCR B clonotypes identified from $1\times10^6$ cells collected on Gen 2 (e.g., day 22) and Gen 3 process (e.g., day 14-16). Gen 3 shows higher clonal diversity compared to Gen 2 based on the number of unique peptide CDRs within the sample. Bottom: Diversity Index for TIL final product: Shanon entropy diversity index is a more reliable a common metric for comparison. Gen 3 showed a slightly higher diversity than Gen 2.
Figure 39:
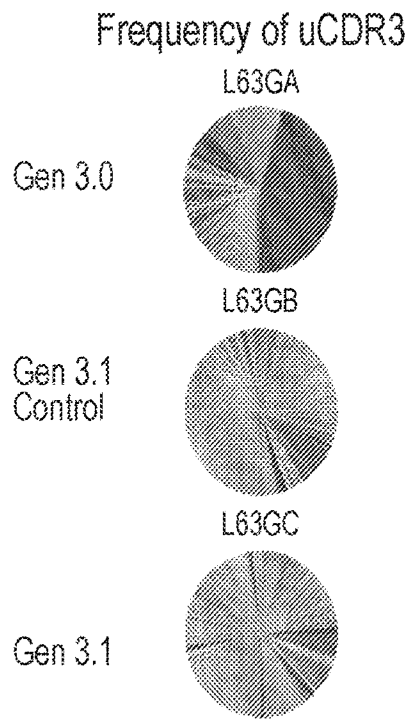
FIG. 39: 199 sequences are shared between Gen 3 and Gen 2 final product, corresponding to 97.07% of top 80% of unique CDR3 sequences from Gen 2 shared with Gen 3 final product.
Figure 40:
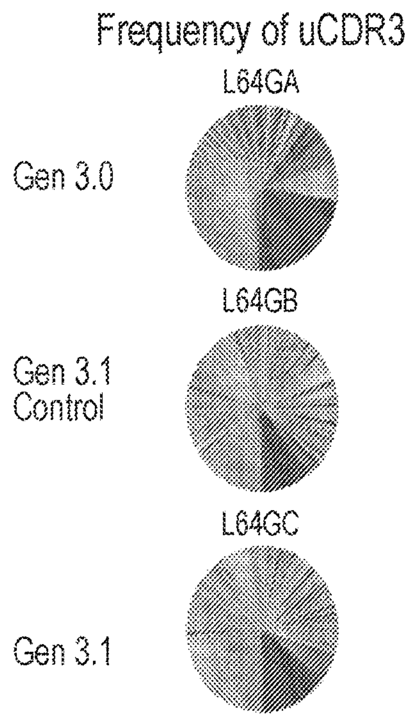
FIG. 40: 1833 sequences are shared between Gen 3 and Gen 2 final product, corresponding to 99.45% of top 80% of unique CDR3 sequences from Gen 2 shared with Gen 3 final product.
Figure 41:
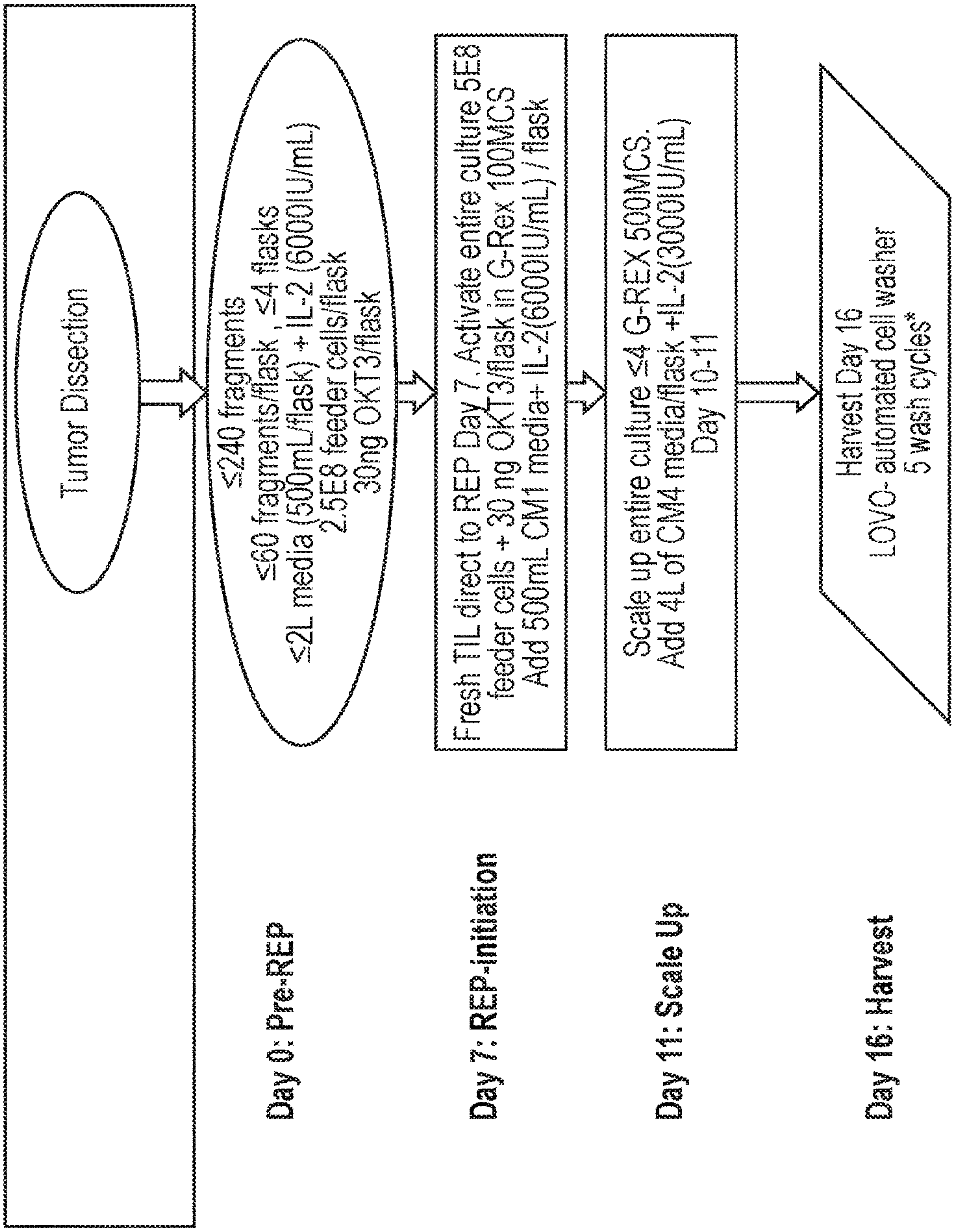
FIG. 41: Schematic of an exemplary embodiment of the Gen 3 process (a 16-day process).
Figure 42:
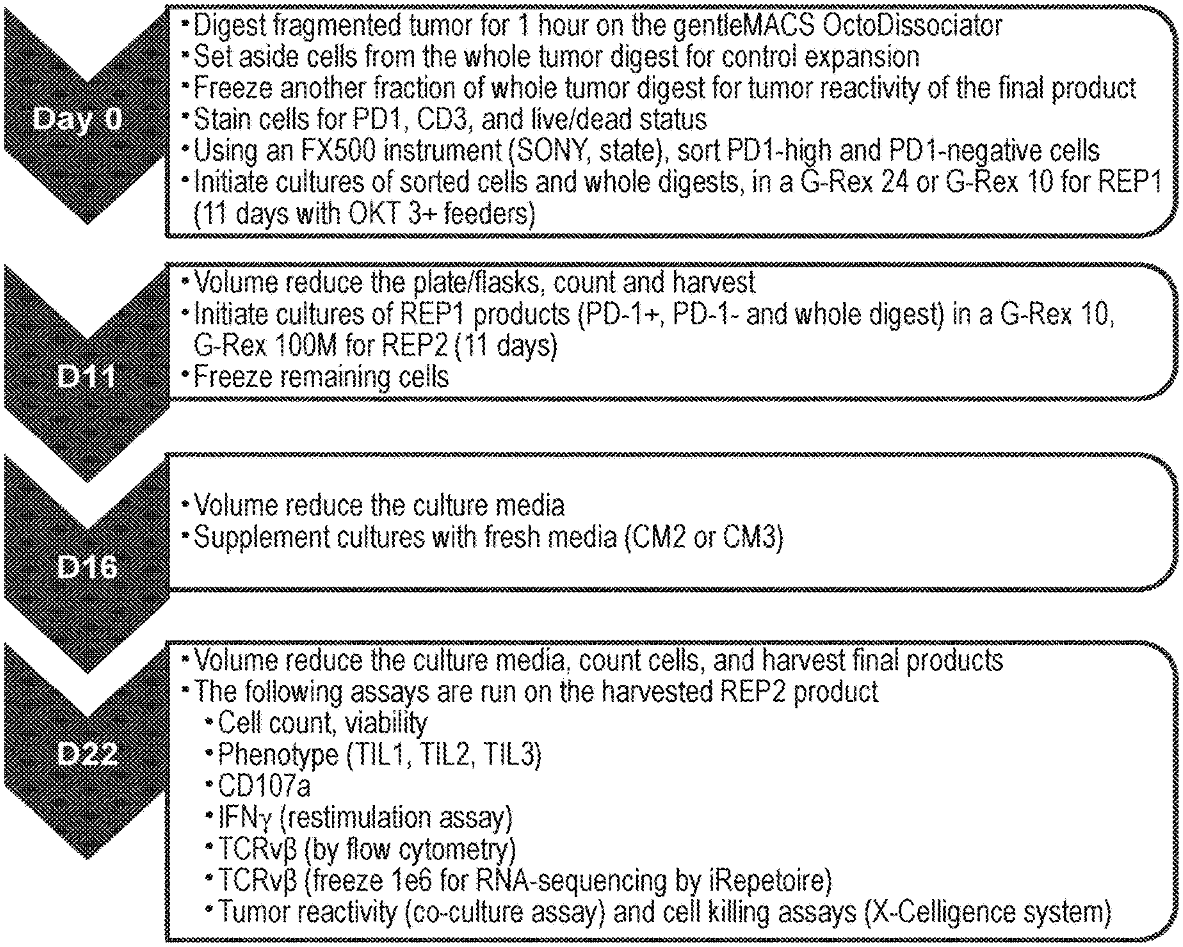
FIG. 42: Schematic diagram of PD-1 selection prior to expansion.
Figure 43:
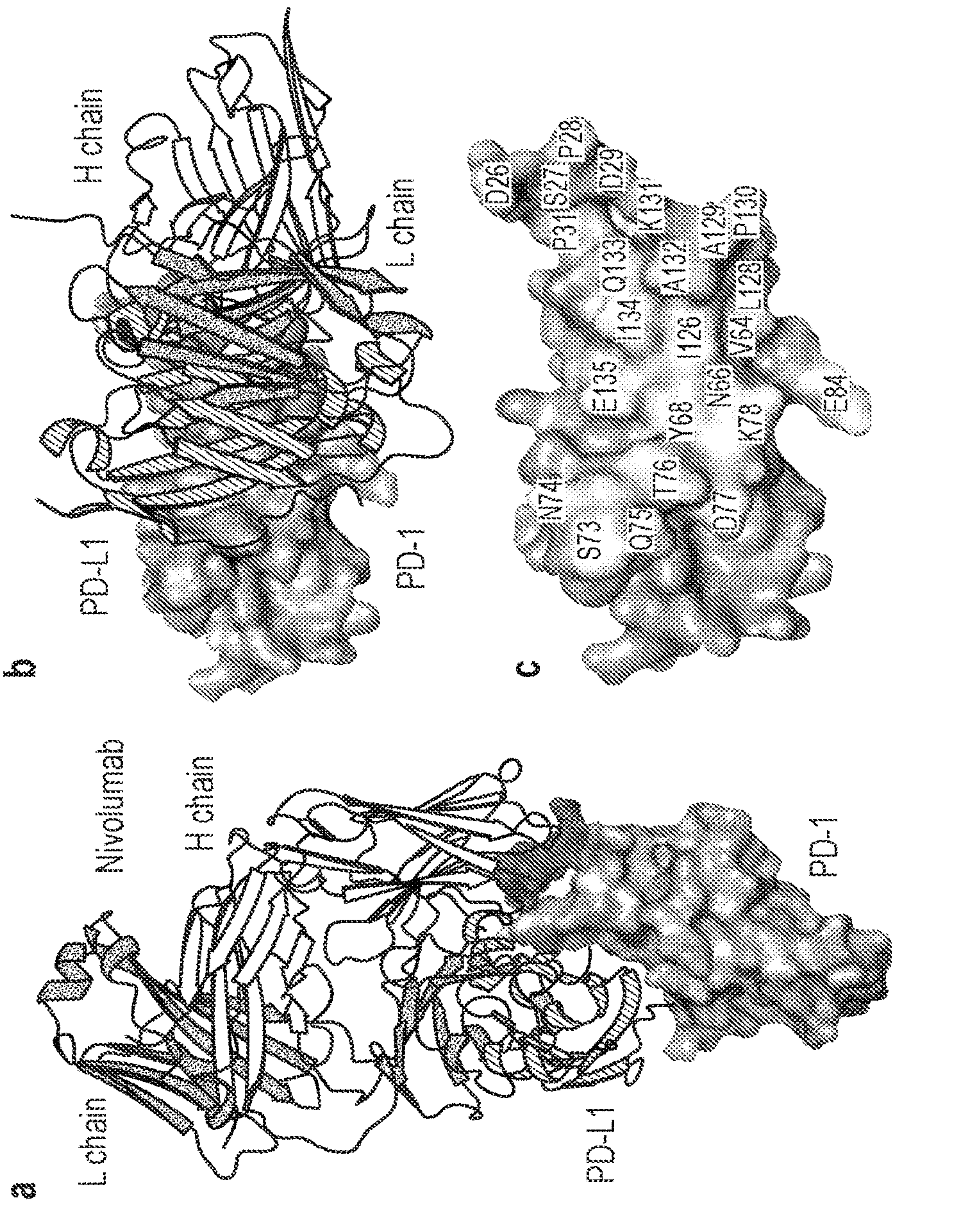
FIG. 43A-43C: Binding structure of nivolumab with PD-1. See, FIG. 5 from Tan, S. et al. (Tan, S. et al., *Nature Communications,* 8:14369| DOI: 10.1038/ncomms14369 (2017)).
Figure 44:
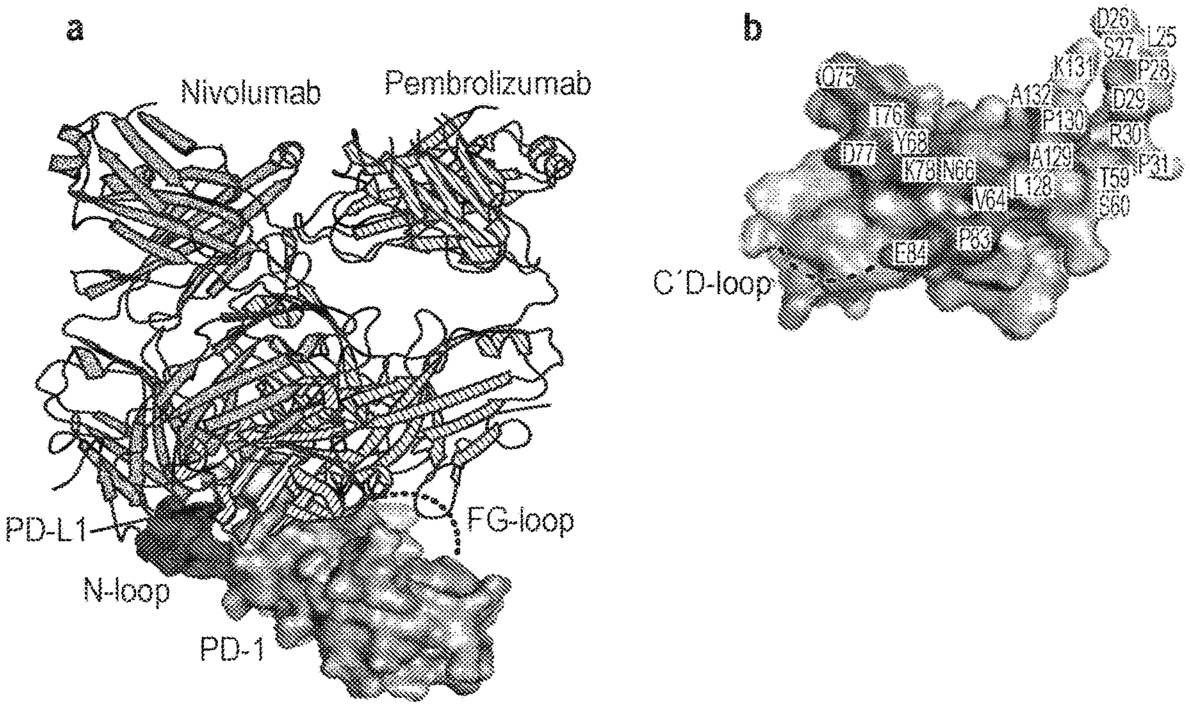
FIG. 44A-44B: Binding structure of pembrolizumab with PD-1. See, FIG. 5 from Tan, S. et al. (Tan, S. et al., *Nature Communications,* 8:14369| DOI: 10.1038/ncomms14369 (2017)).
Figure 45:
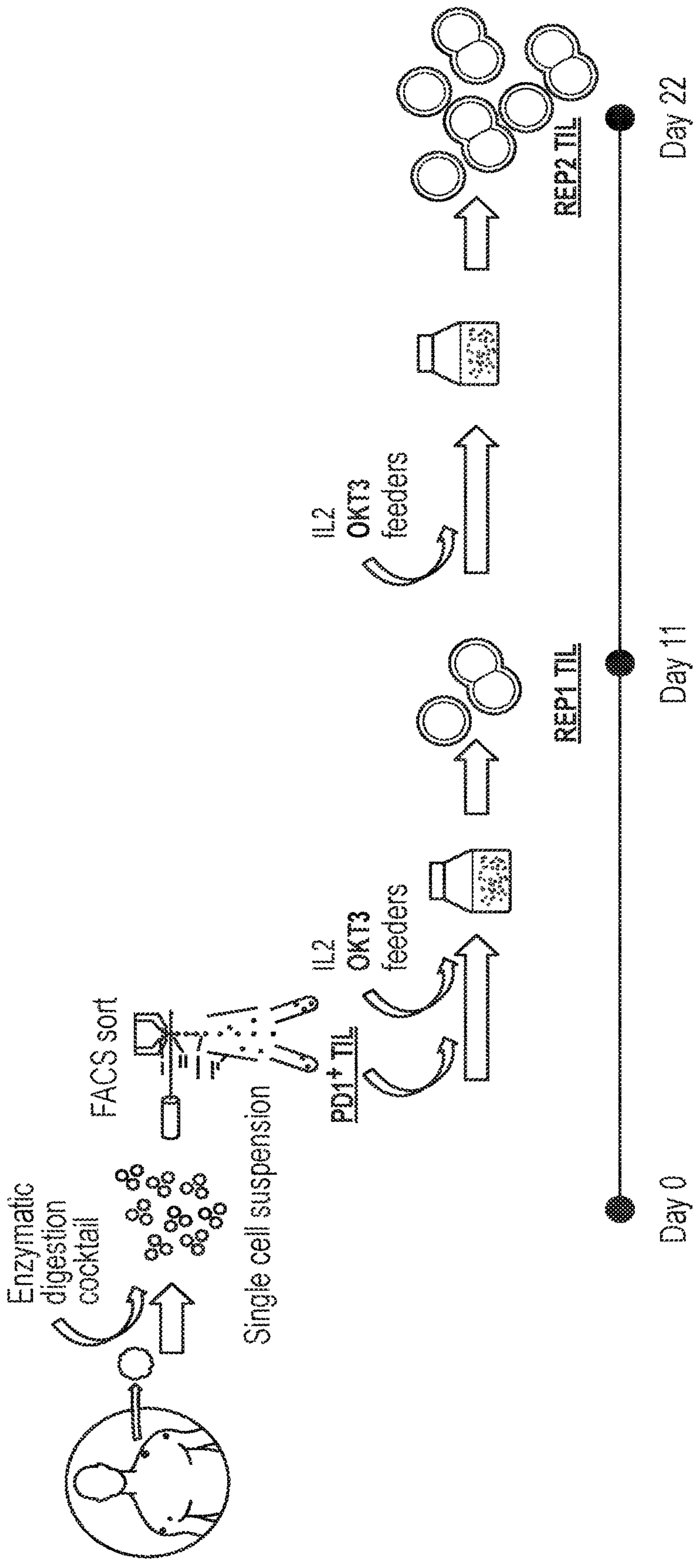
FIG. 45: A streamlined protocol was developed to expand PD1+ TIL to clinically relevant levels. The tumor is excised from the patient and transported to research laboratories. Upon arrival, the tumor is digested, and the single-cell suspension stained for CD3 and PD1. PD1+ TIL are sorted by FACS using an FX500 instrument (Sony). The PD1+ cell fraction is placed into a flask with an anti-human CD3 antibody (OKT3; 30 ng/ml) and irradiated allogeneic PBMCs (feeders) at 1:100 (TIL: feeder) ratio) and rapidly expanded for 22 days (REP).
Figure 46:
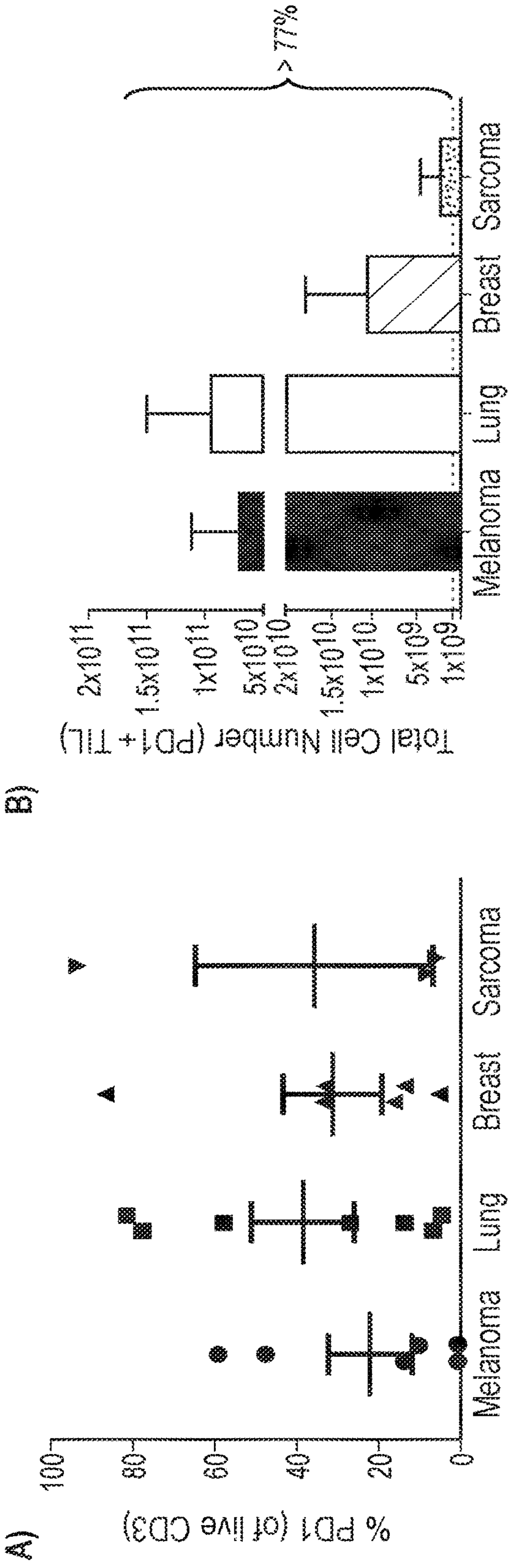
FIG. 46A-46B: Frequency of PD1+ TIL varies across tumor samples but in vitro expansion process reliably yields more than 1 billion TIL. Selected and bulk TIL were expanded from melanoma (n=6), lung cancer (n=7), breast cancer (n=6), and sarcoma (n=3) (A) Frequencies of PD1+ cells in fresh tumor digests are shown for each individual sample. Horizontal and vertical lines represent the mean values and standard errors, respectively. (B) PD1+ and PD1-sorted cells, and bulk digests were expanded as described in FIG. 1. Cells were counted at the completion of the REP and fold expansions (final cell count/seeding cell count) calculated that were used to extrapolate total cell counts. For Bulk TIL, seeding cell count was estimated using the percentage of T cells in the tumor digests. Mean values are plotted as bars and standard errors shown as vertical lines.
Figure 47:
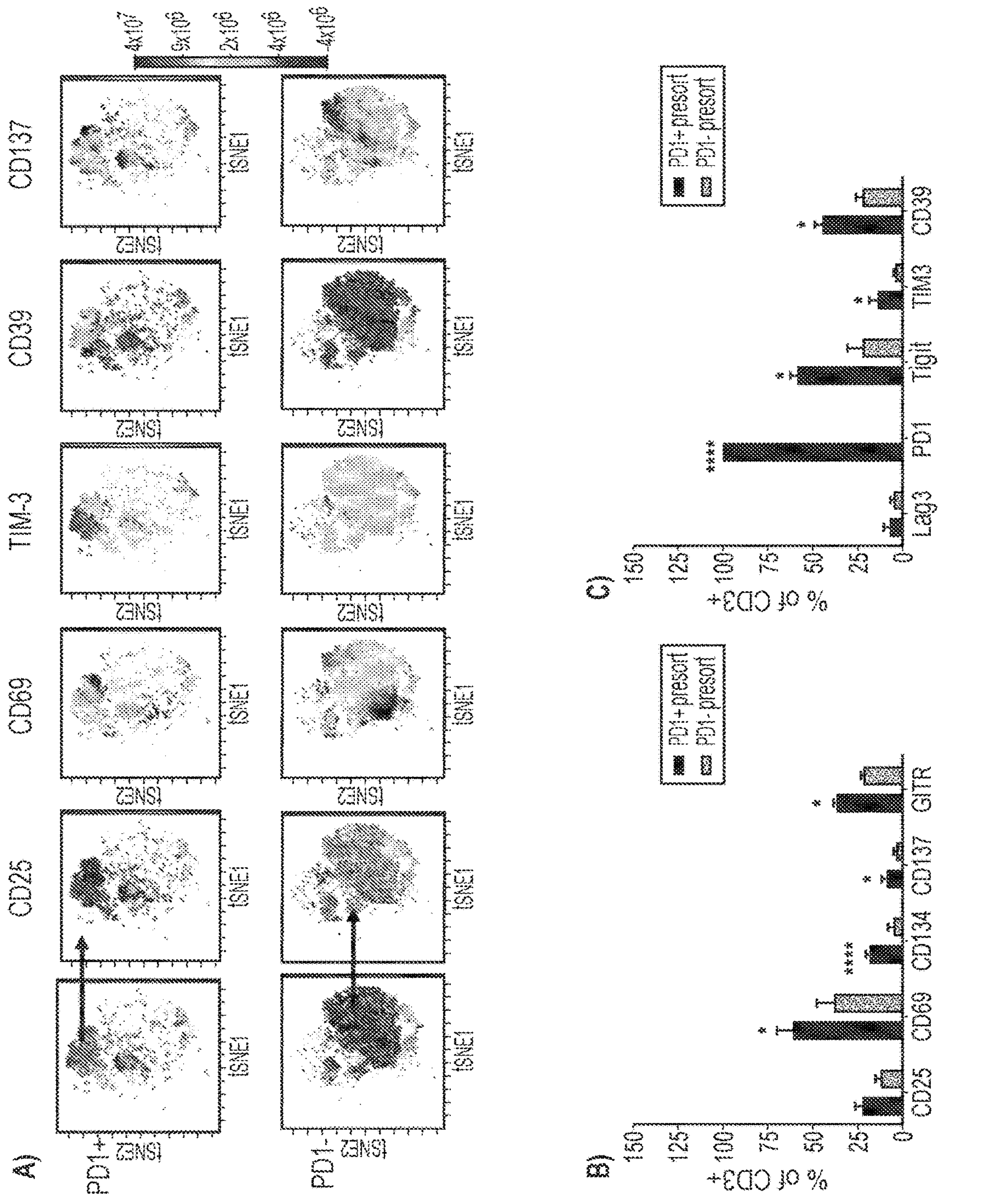
FIG. 47A-47C: PD1+ TIL demonstrate a different phenotypic profile, compared to PD1-TIL. Digested tumors from melanoma (n=2), lung (n=2), and breast (n=2) were assessed phenotypically by flow cytometry, prior to sorting. (A) Representative plots of surface marker expression on TIL from a digested melanoma tumor. The specimen was first gated on CD3 and a biaxial plot for positive and negative PD1 events. Then the two fractions were subjected to unsupervised viSNE clustering. The top row contains the PD1 positive events, and the bottom row PD1 negative events. (B-C) Live lymphocytes were gated on CD3+ cells and assessed for PD1+ and PD1−. The PD1+ and PD1-populations were assessed for cell surface expression of (B) activation and (C) exhaustion markers. Mean values are plotted as bars and standard errors shown as vertical lines. Statistical significance was assessed by a paired student t-test ****P<0.0001, *p<0.05.
Figure 48:
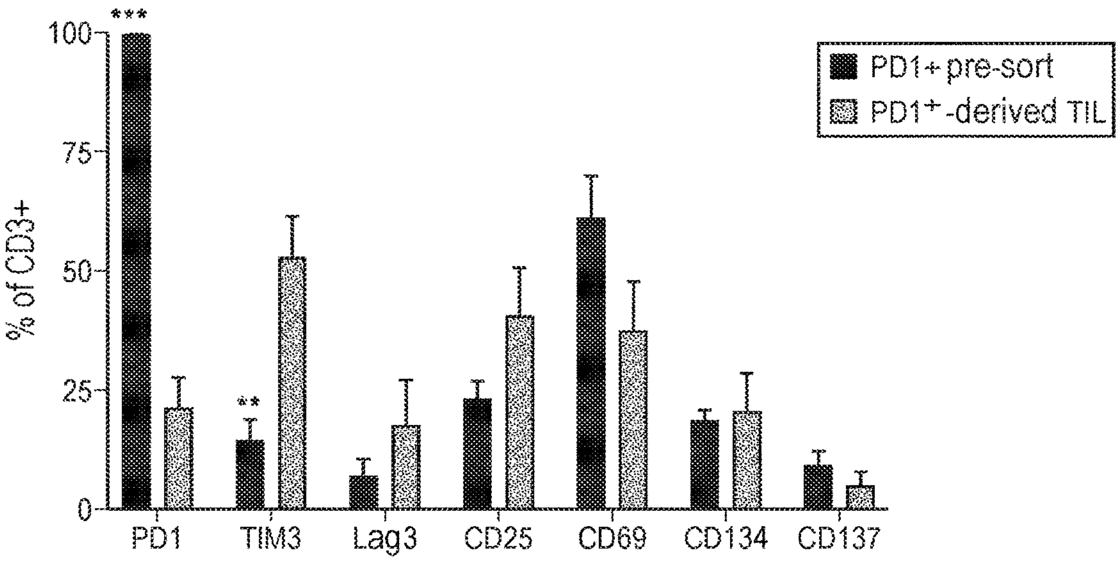
FIG. 48: PD1 expression decreases upon in vitro expansion of PD1+ TIL. PD1+ pre-sort TIL and in vitro expanded PD1+ TIL (PD1+-derived TIL) from melanoma (n=1), lung (n=4), and breast (n=2) were assessed by flow cytometry for cell surface expression of T cell markers. Bars represent the mean percentages of each subset in the 2 TIL preparations and vertical lines represent the standard errors. Statistical significance was assessed by paired student t test *P<0.001, p<0.01.
Figure 49:
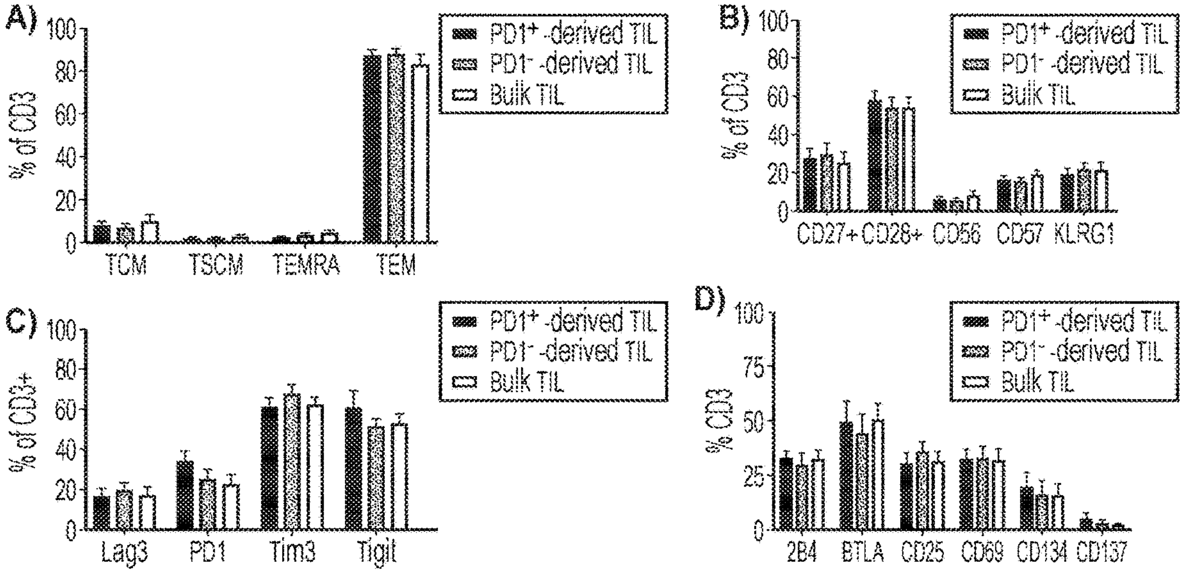
FIG. 49A-49D: In vitro expanded PD1+ TIL are phenotypically similar to bulk TIL. PD1+-derived TIL, PD1−-derived TIL, and bulk TIL from melanoma (n=5), lung (n=7) breast (n=6) and sarcoma (n=3) were assessed phenotypically by flow cytometry for the cell surface expression of T cell markers. (A) Four effector/memory subsets were identified based on the levels of (CD45RA and CCR7) on the CD3+ cells. TEM=effector memory (CD45RA−, CCR7−), TCM=central memory (CD45RA−, CCR7+), TSCM=stem cell memory (CD45RA+, CCR7+), TEMRA=effector T cells (CD45RA+, CCR7−). (B) Markers for differentiation, (C) exhaustion and (D) activation were also assessed. Bars represent the mean percentages of each subset in all 3 TIL preparations and vertical lines represent the standard errors.
Figure 50:
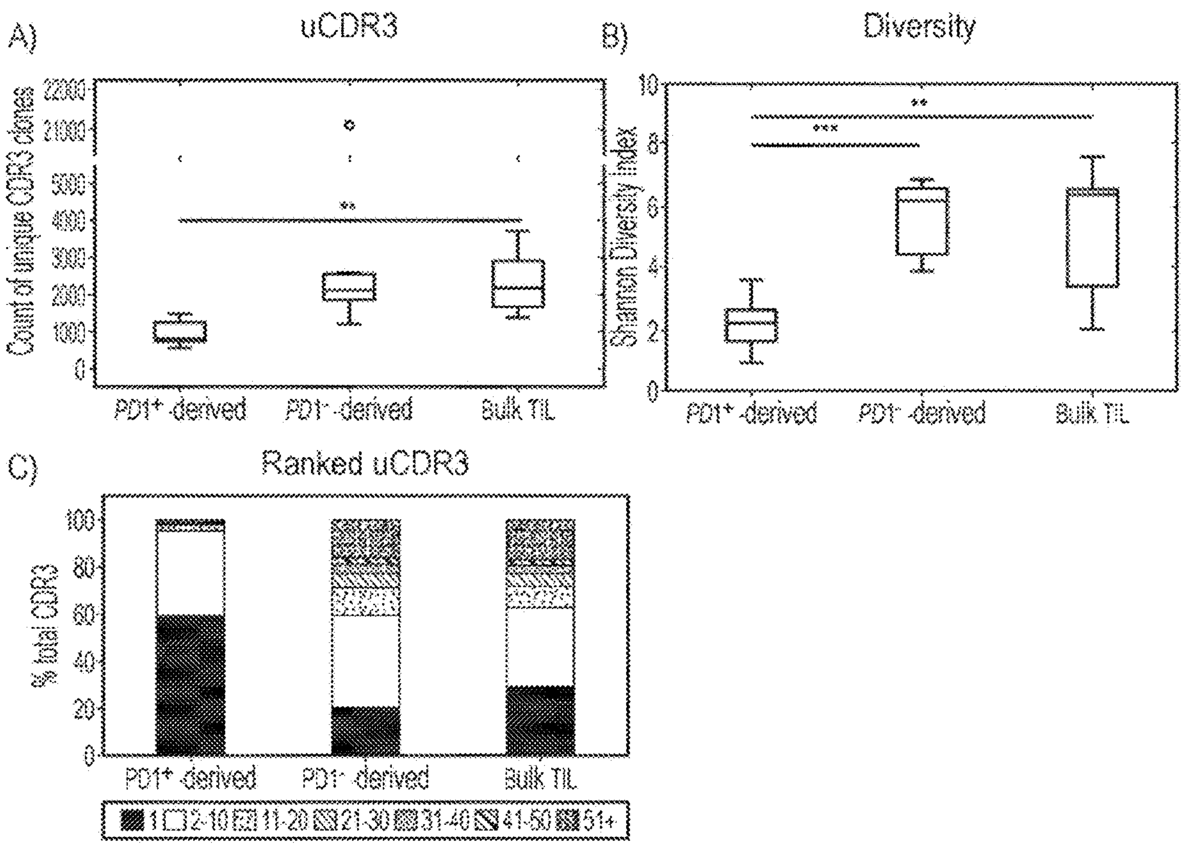
FIG. 50A-50D: Expanded PD1+ TIL are oligoclonal and comprise a fraction of the clones present in bulk TIL. PD1 selected and bulk TIL from melanoma (n=2), breast (n=2) and lung (n=2) were analyzed by RNA-sequencing. (A) Unique CDR3 (uCDR3) peptide sequences were numbered and boxplots were generated using the pandas and matplotlib libraries of Python 3.6.3, Anaconda, Inc. (B) Shannon Diversity indices were calculated for each sample by iRepertoire and boxplots were generated using the pandas and matplotlib libraries of Python 3.6.3, Anaconda, Inc). Bars represent the mean percentages of each subset and vertical lines represent the standard errors. Statistical significance was assessed by a paired student t-test *P<0.001, p<0.01. (C) The uCDR3 frequencies were ranked in descending order and reported or summed in intervals indicated (top ranking uCDR3, CDR3s ranked 2-10, 11-20, etc.) for each of the samples sequenced. The frequencies were then averaged by group and plotted using Excel v. 1803. (D) Shared uCDR3 clones were identified in the complementary Bulk TIL and PD1+-derived samples. The sum of the frequencies of each of the shared unique CDR3 clones is reported in the "shared %" columns.
Figure 51:
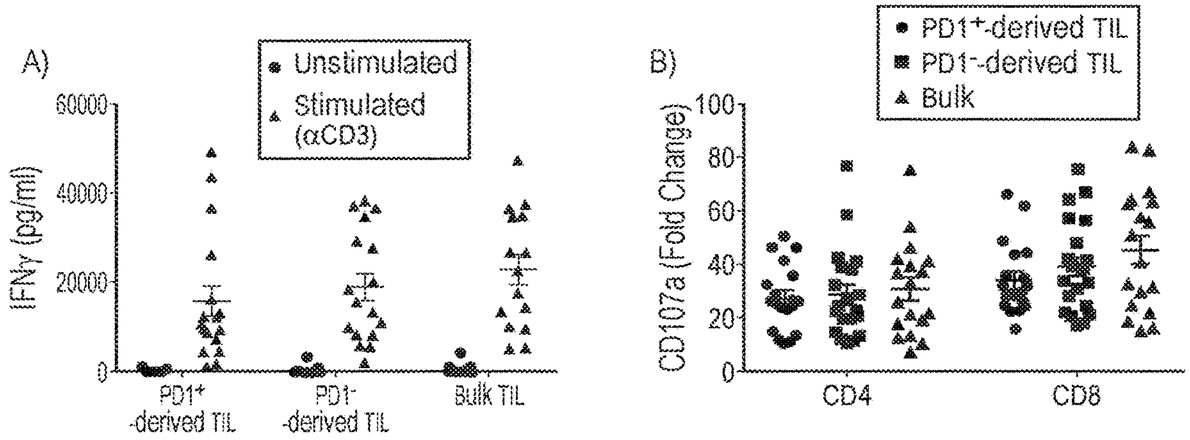
FIG. 51A-51B: Expanded PD1+ TIL are functional as determined by IFNγ secretion and CD107a mobilization in response to non-specific stimulation. A) PD1+-derived TIL, PD1−-derived TIL, and bulk TIL from melanoma (n=5), lung (n=6), and breast (n=6) were stimulated for 18 hours with plate-bound anti-CD3. Supernatants were assessed for IFNγ secretion by ELISA. Results are plotted for individual samples. (B) PD1+-derived TIL, PD1−-derived TIL, and bulk TIL from melanoma (n=5), lung (n=7), breast (n=6), and sarcoma (n=1) were assessed for CD107a cell surface expression in response to PMA stimulation for 4 hours on the CD4+ and CD8+ cells, by flow cytometry. Results are plotted for individual samples. Horizontal lines represent the mean percentages of each subset and vertical lines represent the standard errors.
Figure 52:
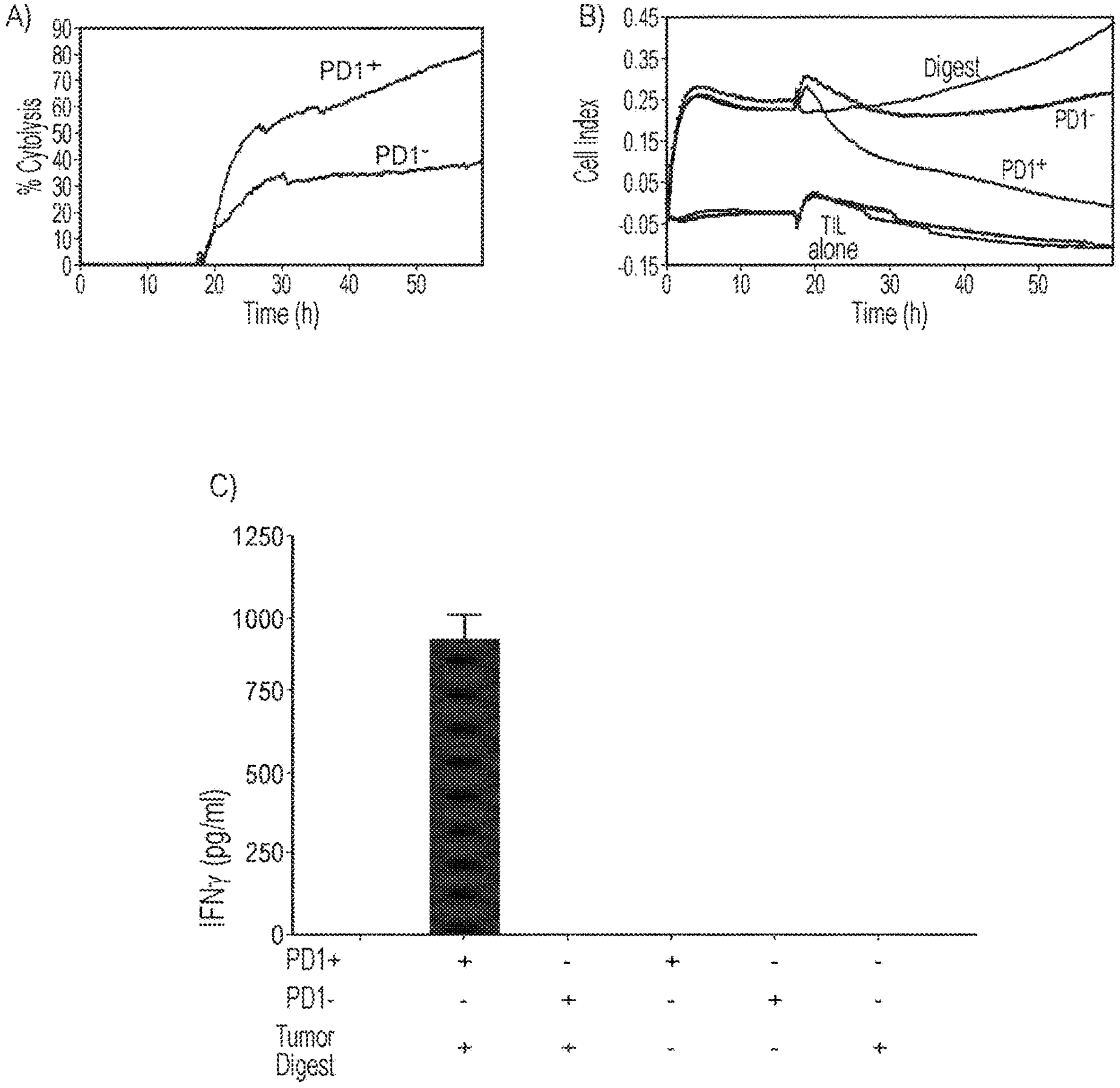
FIG. 52A-52C: Expanded PD1+ TIL demonstrate an enhancement in autologous melanoma cell killing and tumor reactivity relative to PD1-TIL. Tumor reactivity was assessed on PD1 selected TIL product from one melanoma sample. (A) Whole tumor digest was cleaned up using a dead cell removal kit (Miltenyi). 1e5 live cells were plated per well of a 96 well plate and permitted to adhere for 18 hours at 370 C in the xCELLigence instrument (ACEA Biosciences, Inc.). 1e5 PD1+- and PD1−-derived autologous TIL were added to their respective wells, resulting in a 1:1 (TIL: target) cell ratio, and incubated for 48 hours. Killing of the autologous target cells was recorded as increased impedance resulting from cell detachment. Cell killing (% cytolysis) (left most graph) was calculated using the formula % Cytolysis=[1−(NCIst)/(AvgNCIRt)]×100, where NCIst is the Normalized cell index for the sample and NCIRt is the average of the Normalized Cell Index for the matching reference wells (digest alone). Right graph shows the normalized cell indices of the samples. (B) 1e5 cells from the whole tumor digest were cocultured with 1e5 TIL (or digest and TIL alone) for 18 hours. Supernatants were assessed for IFNγ release by ELISA (R&D systems). Bars represent the mean values of duplicate wells and vertical lines represent the standard errors.
Figure 56:
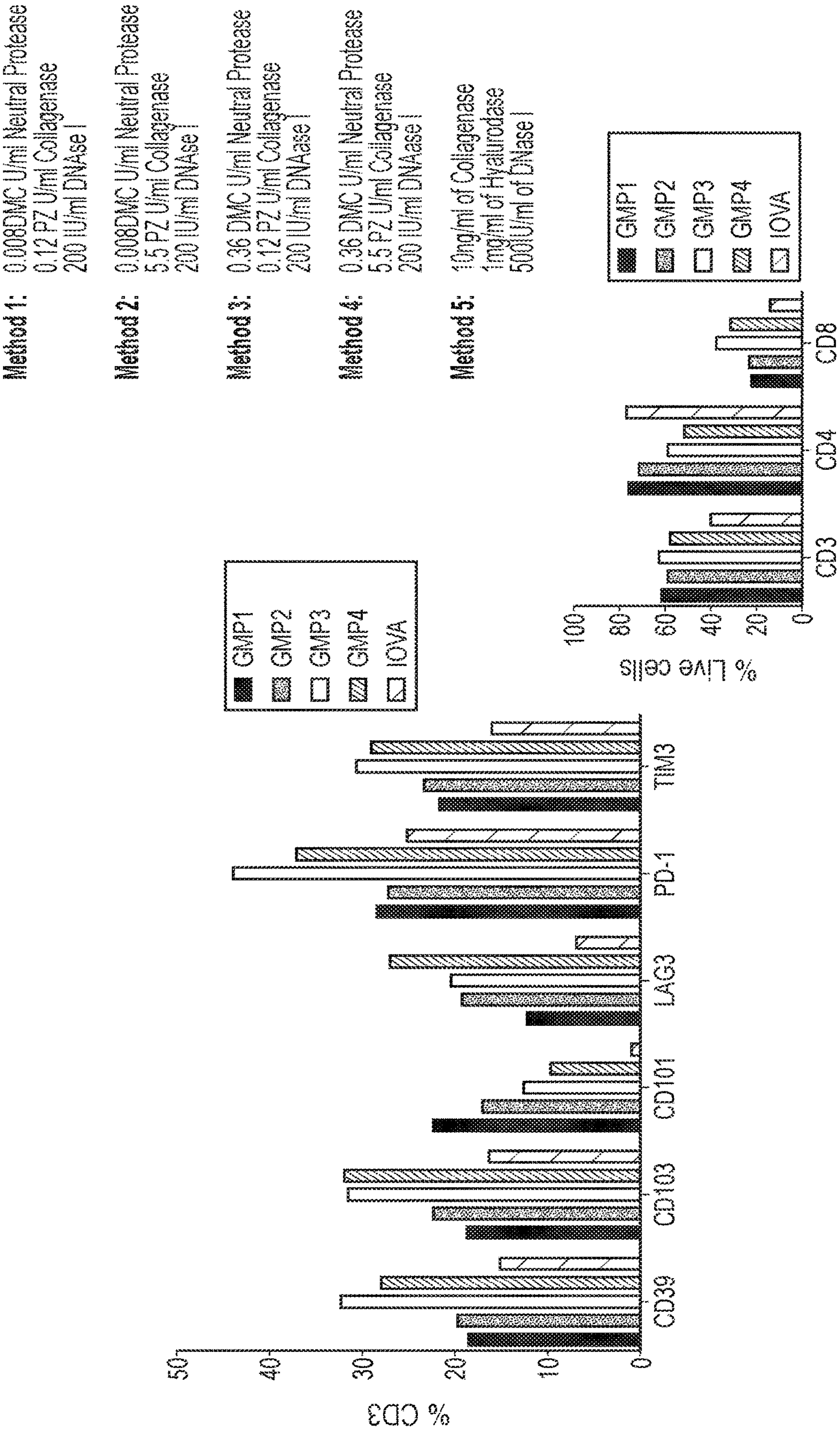
FIG. 56: Identification of a tumor tissue digestion method using GMP available reagents.
Figure 57:
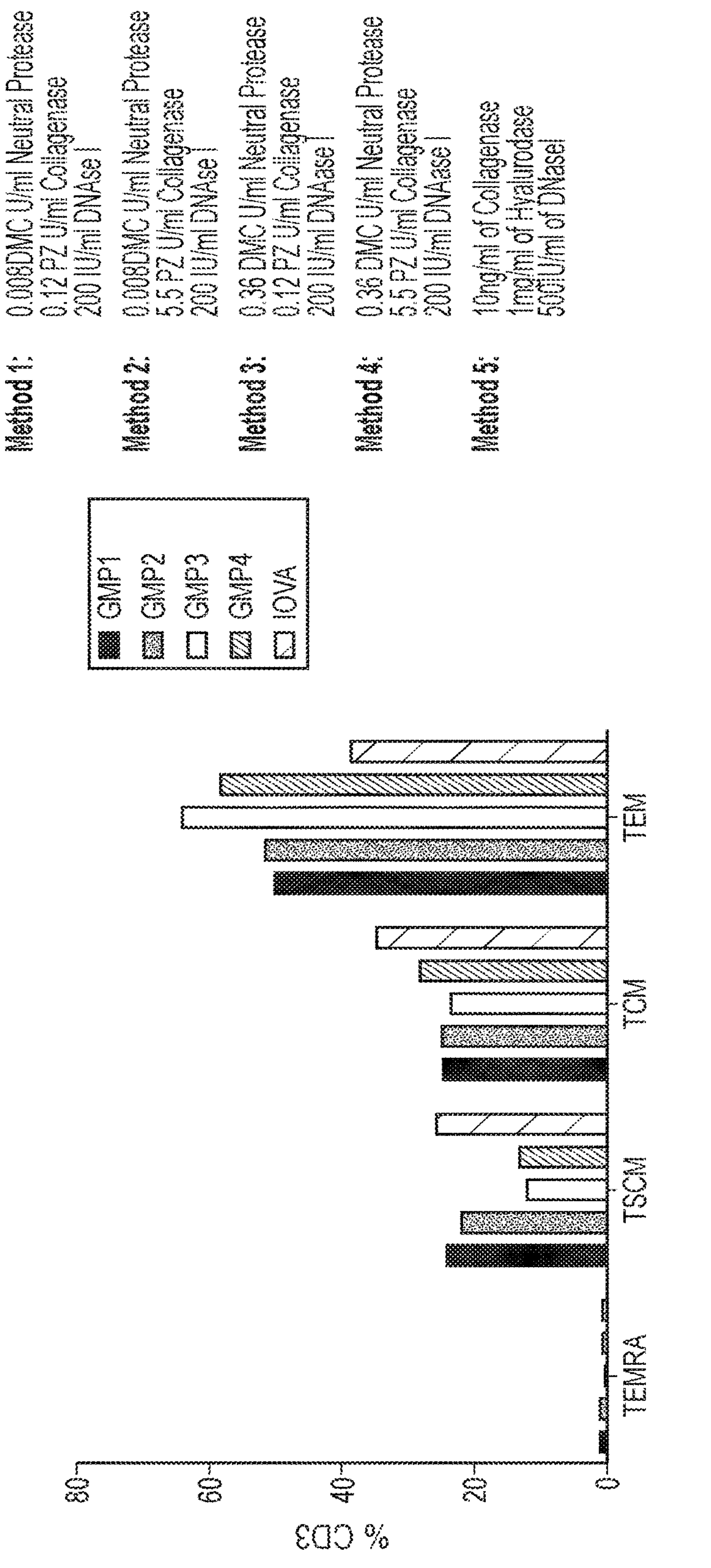
FIG. 57: Identification of a tumor tissue digestion method using GMP available reagents.
Figure 58:
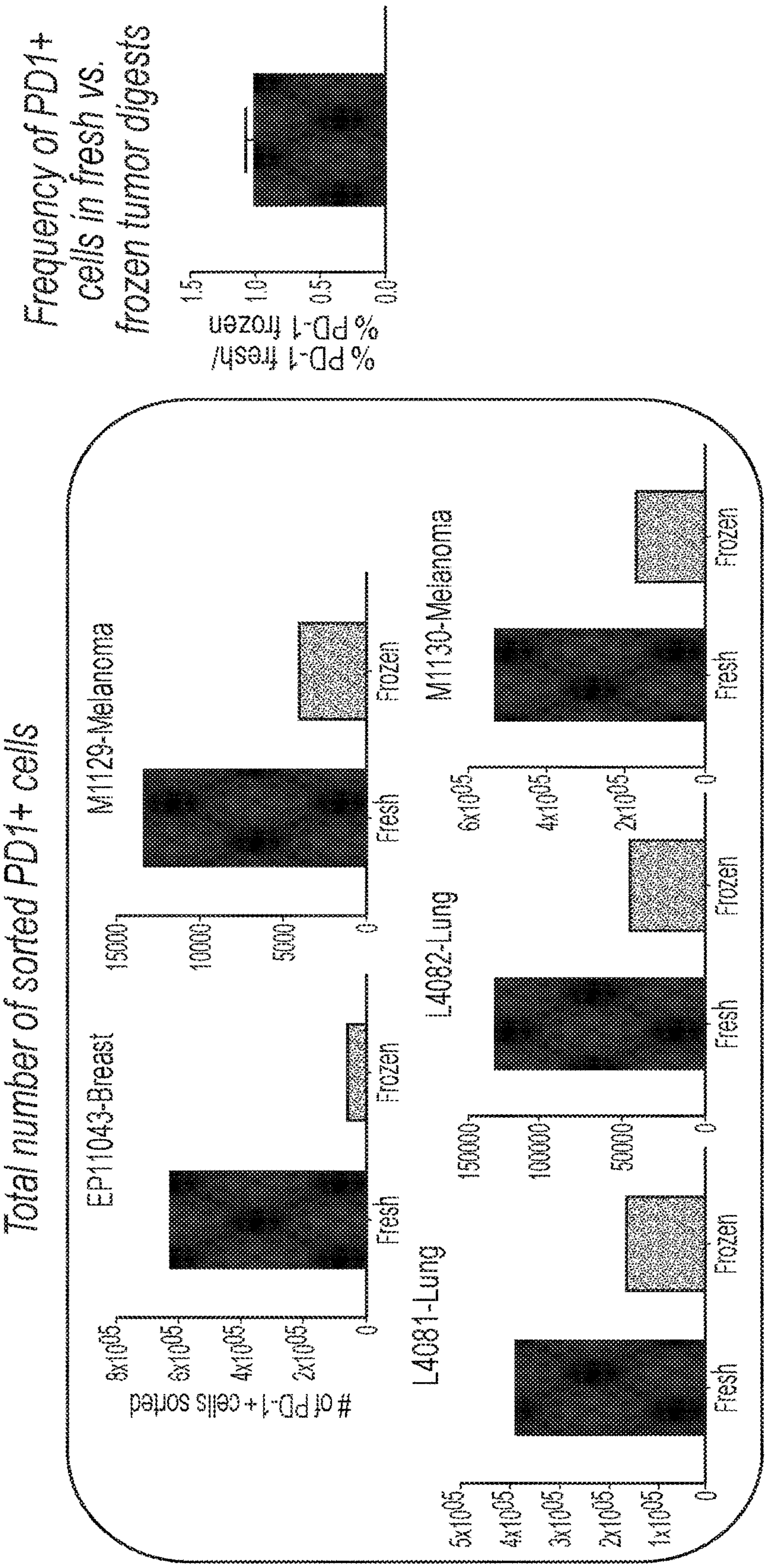
FIG. 58: Sort yield was higher from fresh than frozen tumor digests.
Figure 59:
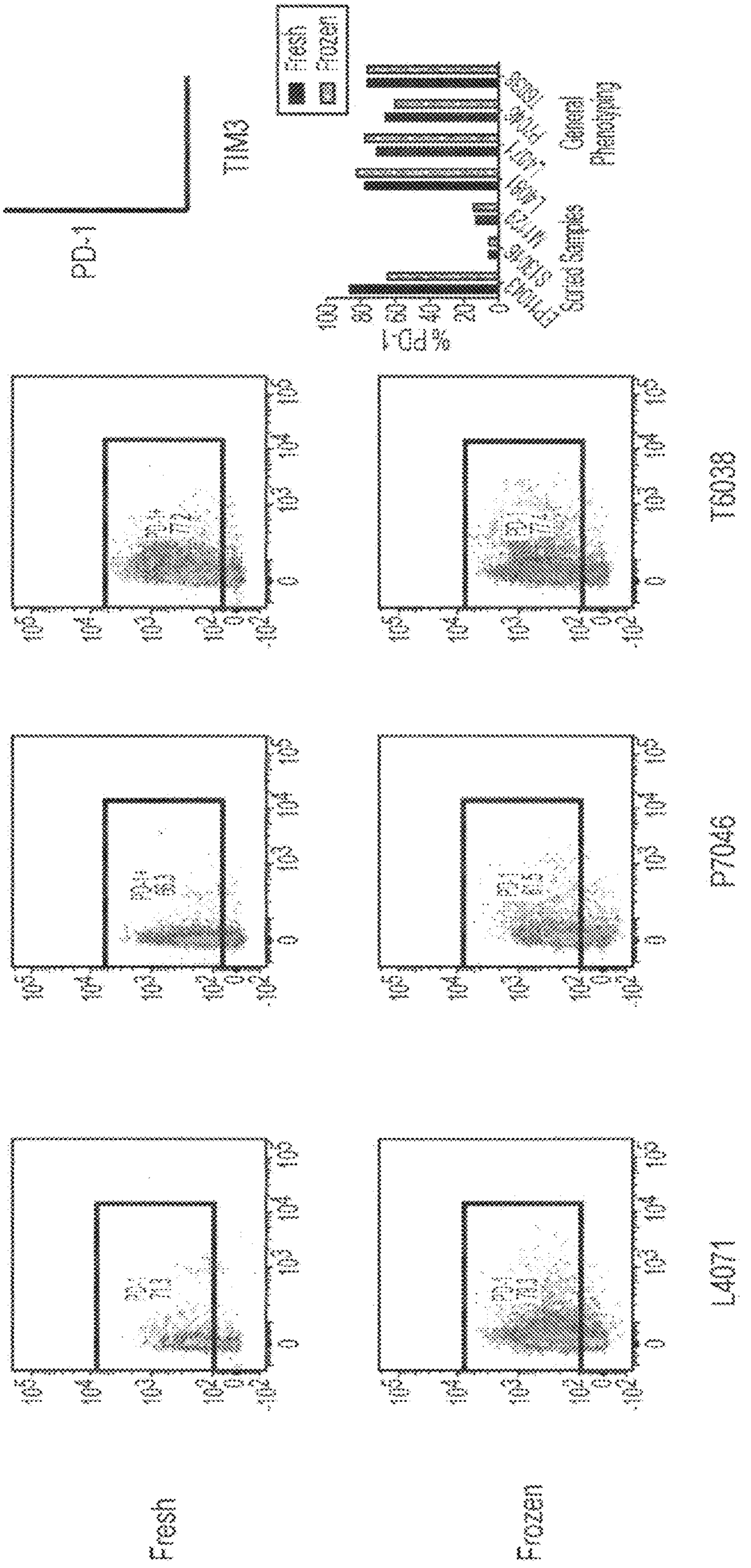
FIG. 59: Similar Expression of PD1 in Fresh and Frozen TIL.
Figure 60:
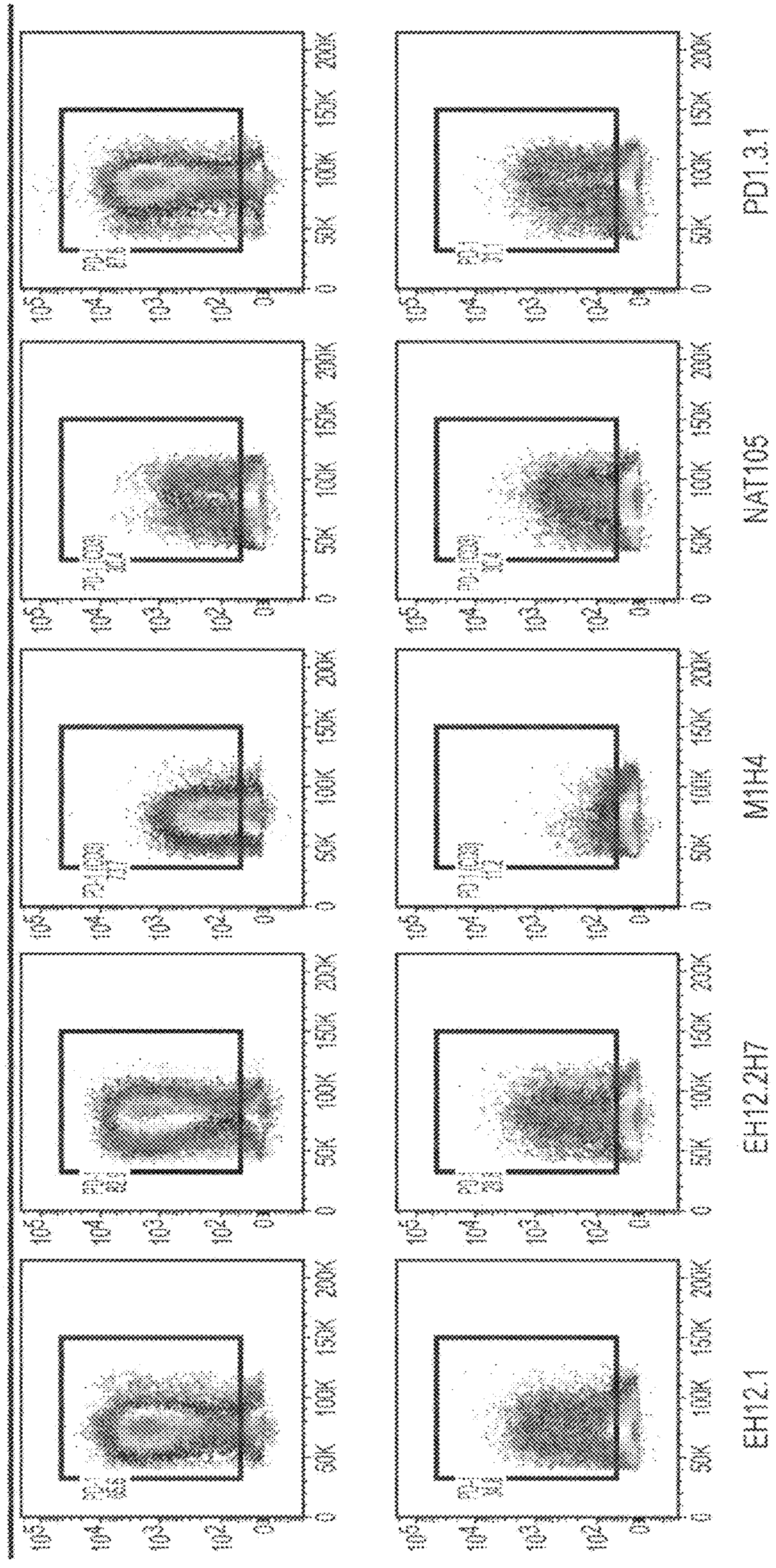
FIG. 60: PD1 antibody titration: Variable expression of PD1 using commercially available clones.
Figure 61:
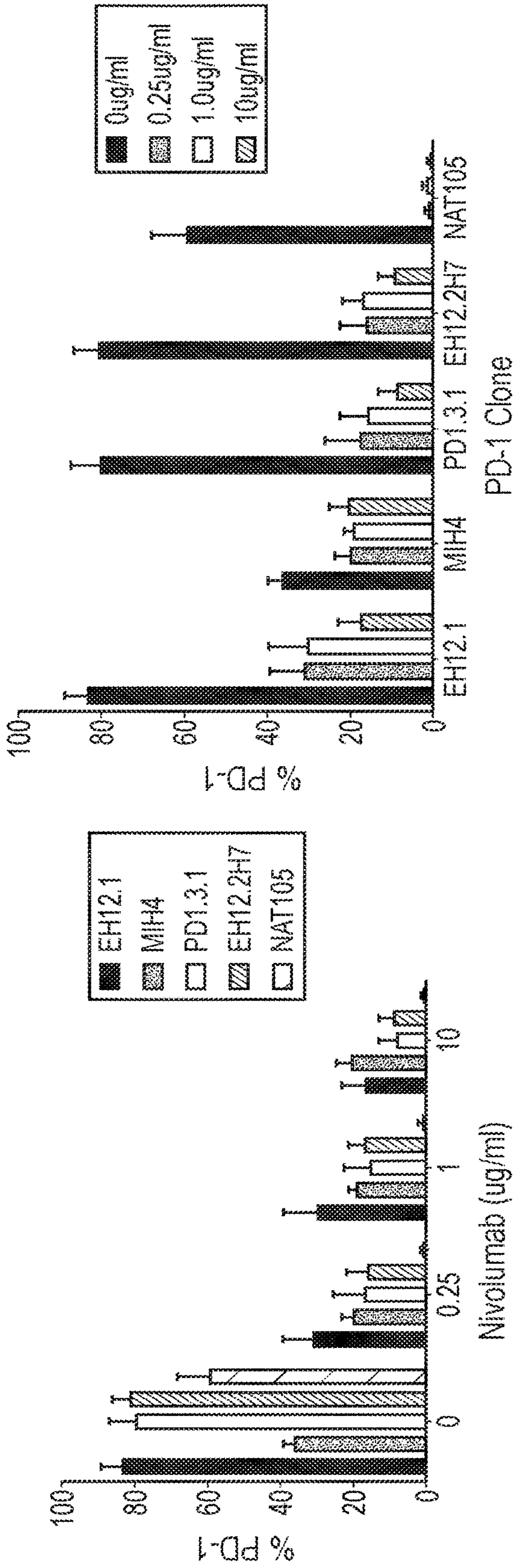
FIG. 61: Nivolumab inhibits the binding of the 5 commercially available PD1 staining antibodies.
Figure 62:
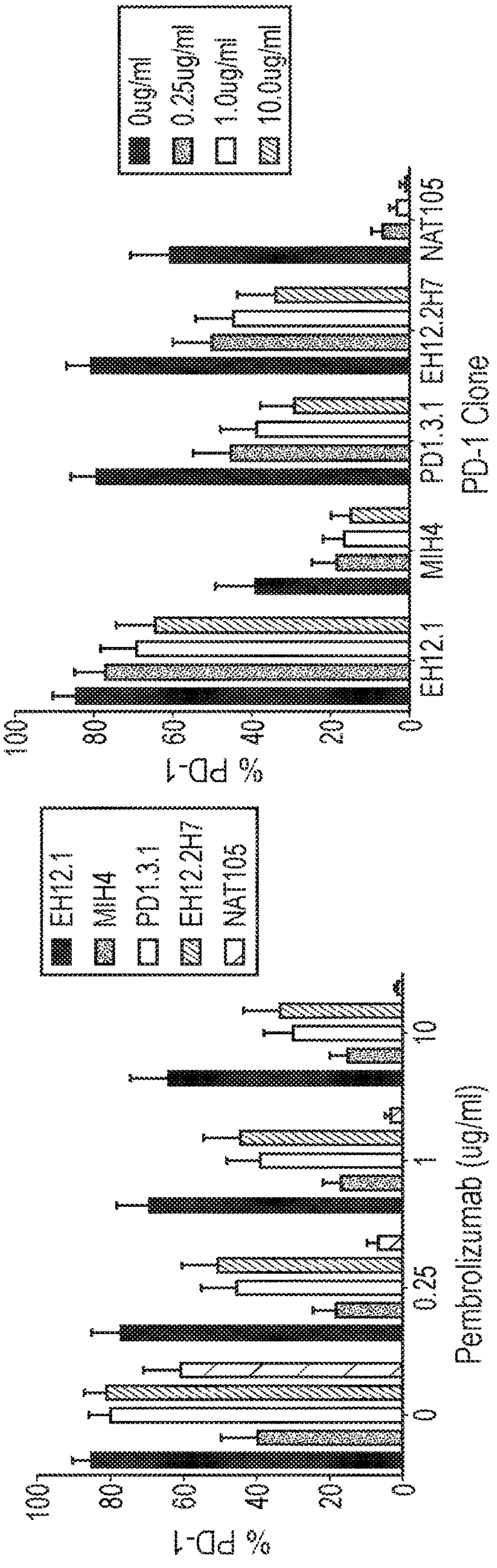
FIG. 62: Pembrolizumab differentially inhibits the binding of the 5 commercially available PD1 staining antibodies.
Figure 63:
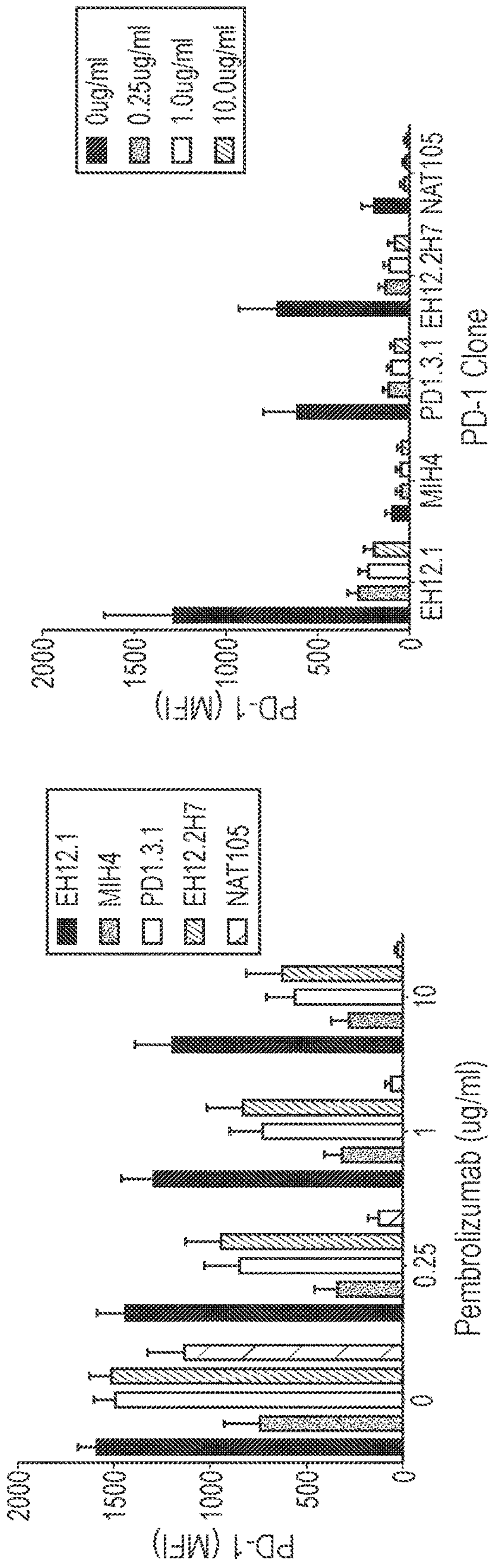
FIG. 63: PD-1 MFI was significantly reduced when cells were preincubated with Pembrolizumab.
Figure 64:
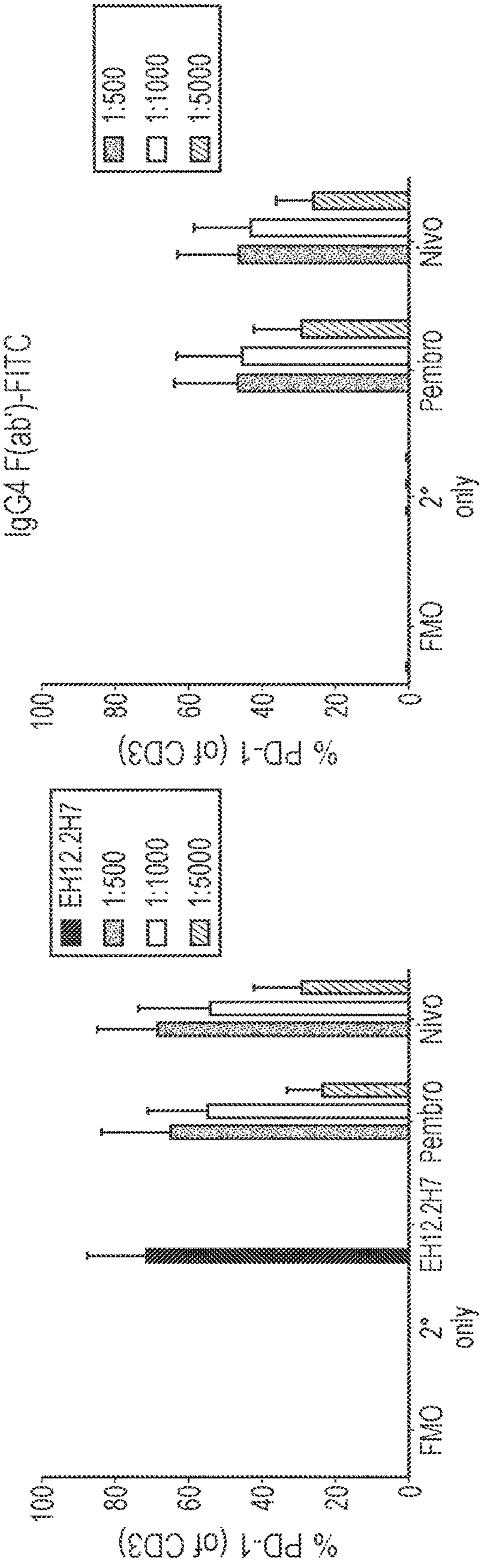
FIG. 64: TIL co-incubated with Pembro and Nivo and stained with an IgG4 secondary demonstrate similar expression of PD-1 when compared to the EH12.2H7 clone.
Figure 65:
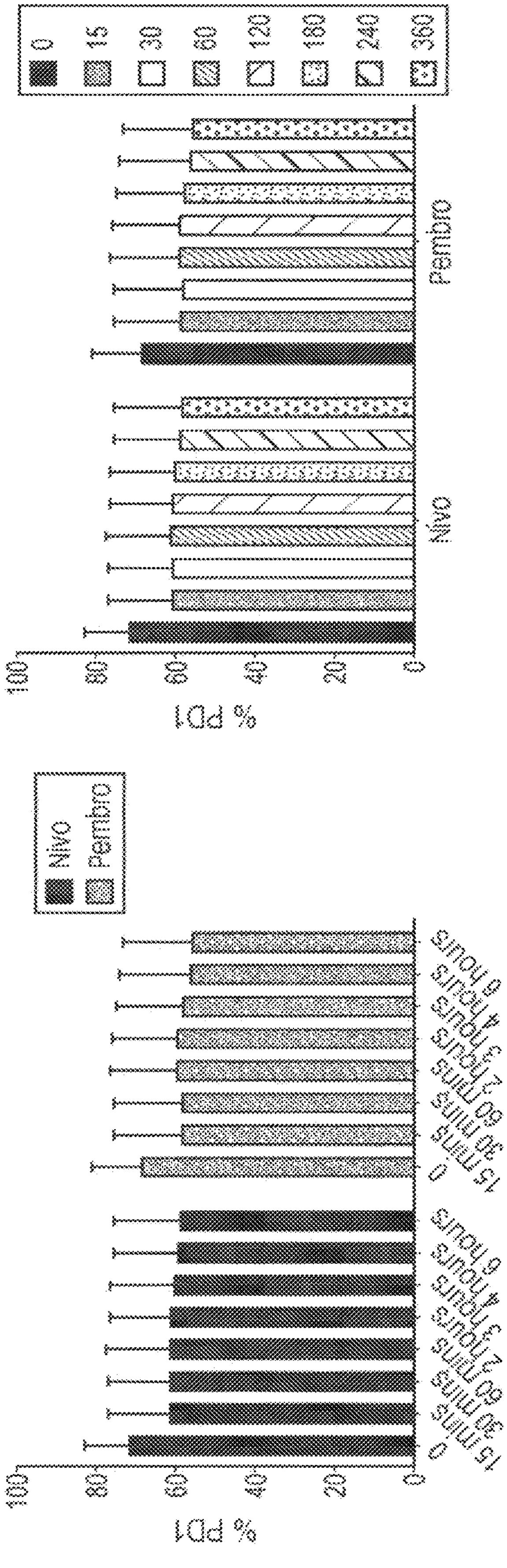
FIG. 65: Incubating TIL with Pembro and Nivo did not alter the ability to detect surface PD1 expression.
Figure 69:
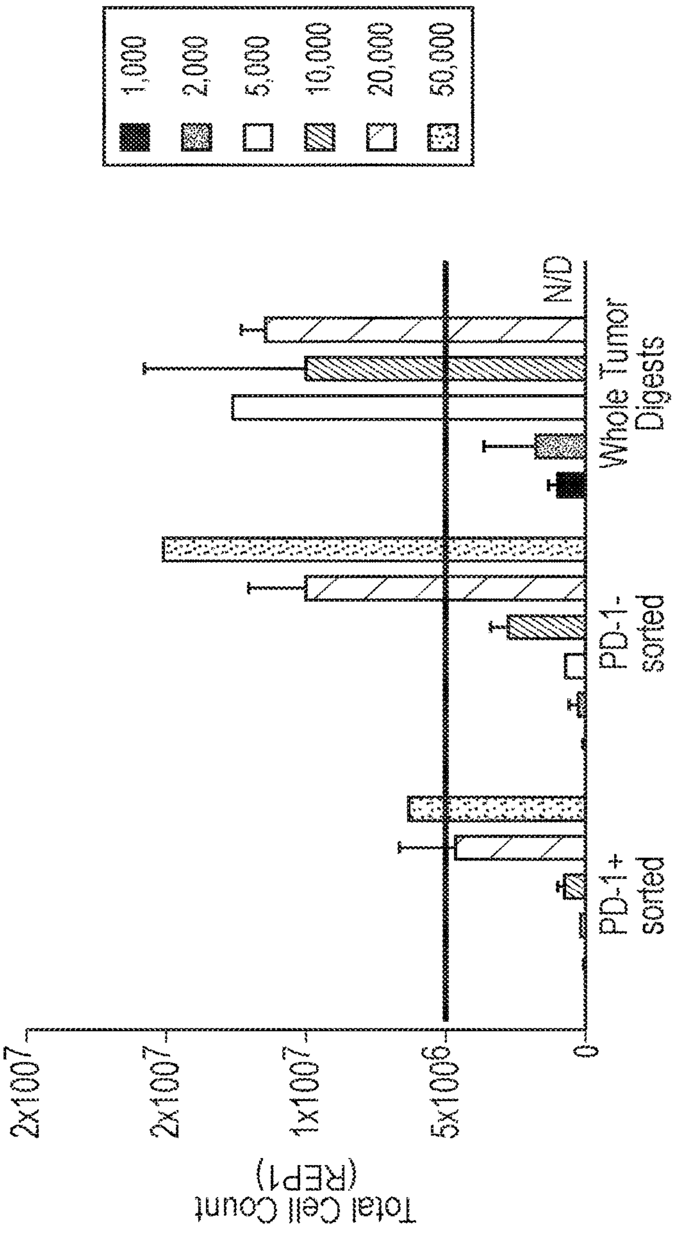
FIG. 69: Optimal seeding density for PD1+-derived TIL is greater than 10,000 cells.
Figure 70:
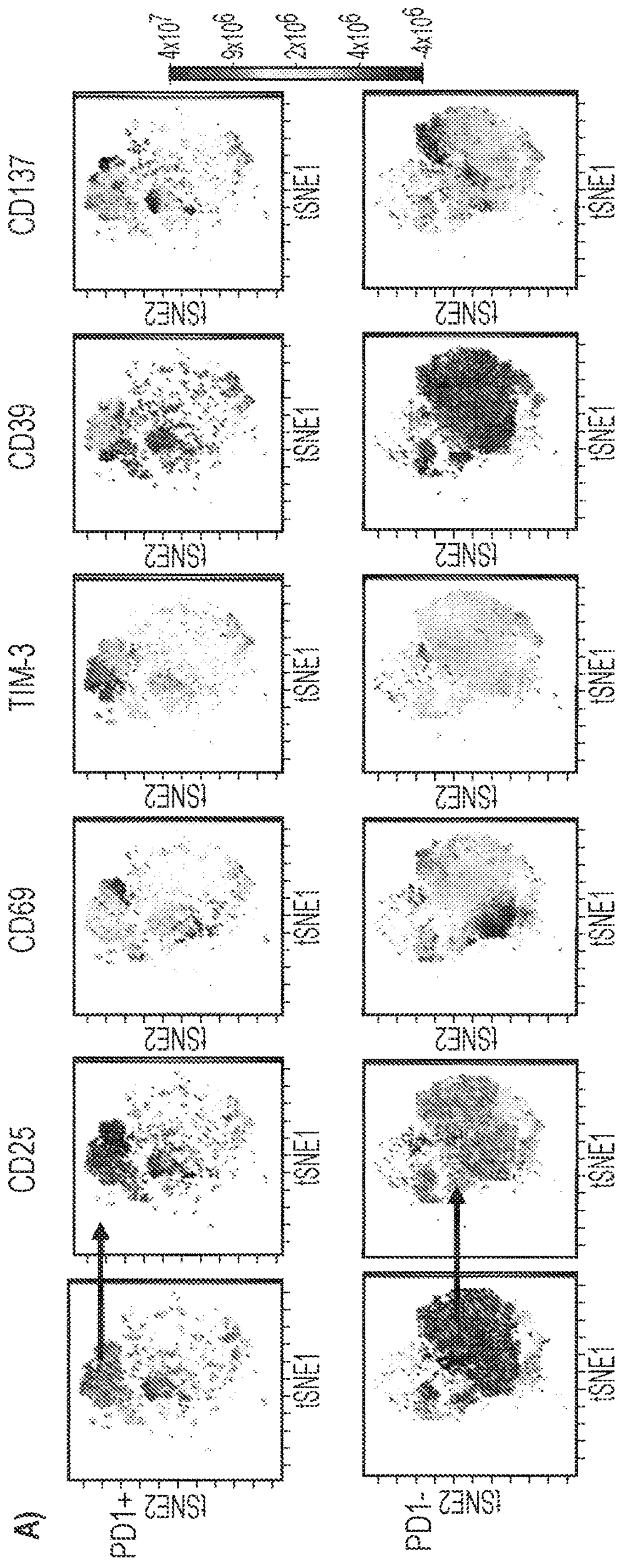
FIG. 70: PD1+ TIL demonstrate a different phenotypic profile, compared to PD1-TIL.
Figure 72:
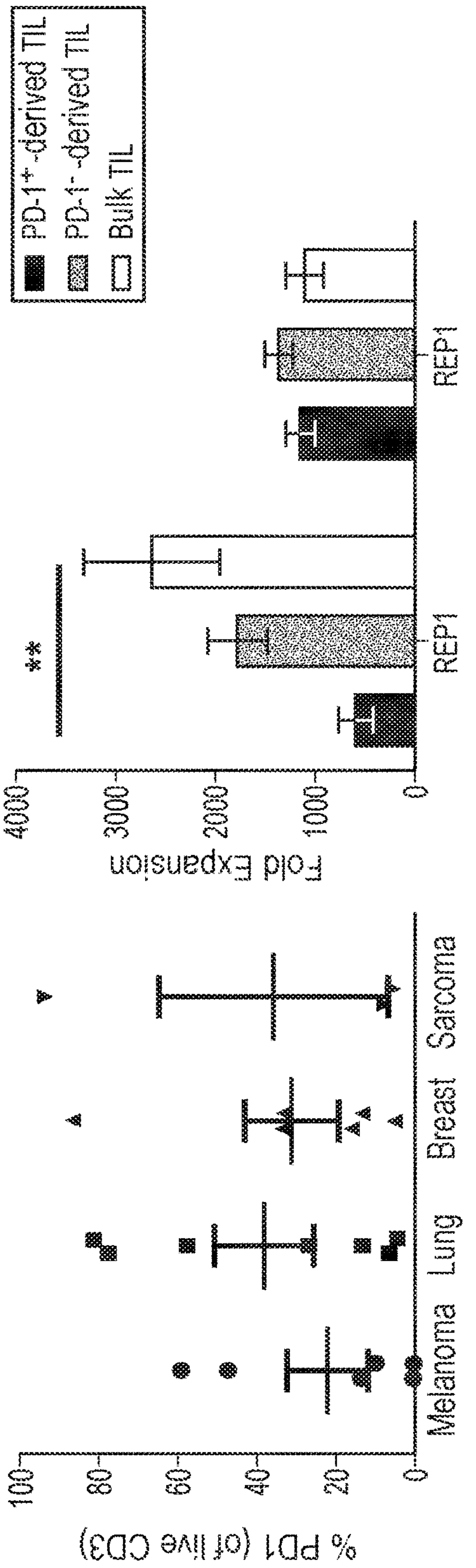
FIG. 72: Frequency of PD1+ TIL varied across tumor samples and required 2 REP cycles to overcome a low initial proliferation rate.
Figure 73:
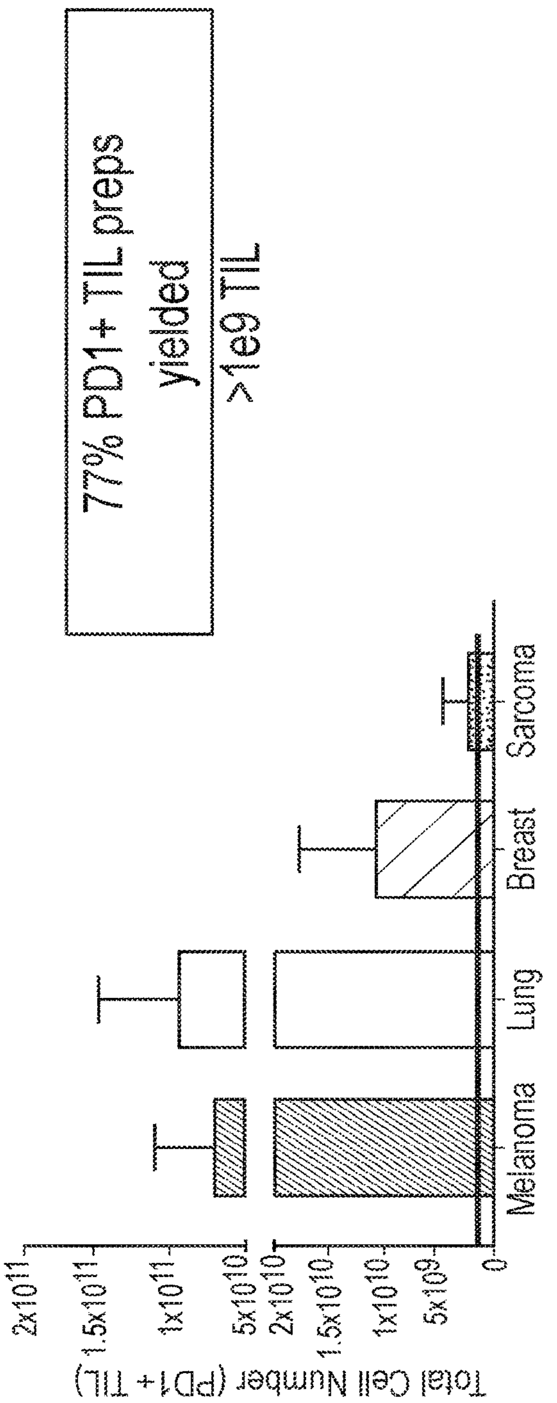
FIG. 73: Frequency of PD1+ TIL varied across tumor samples and required 2 REP cycles to overcome an initial proliferative defect.
Figure 74:
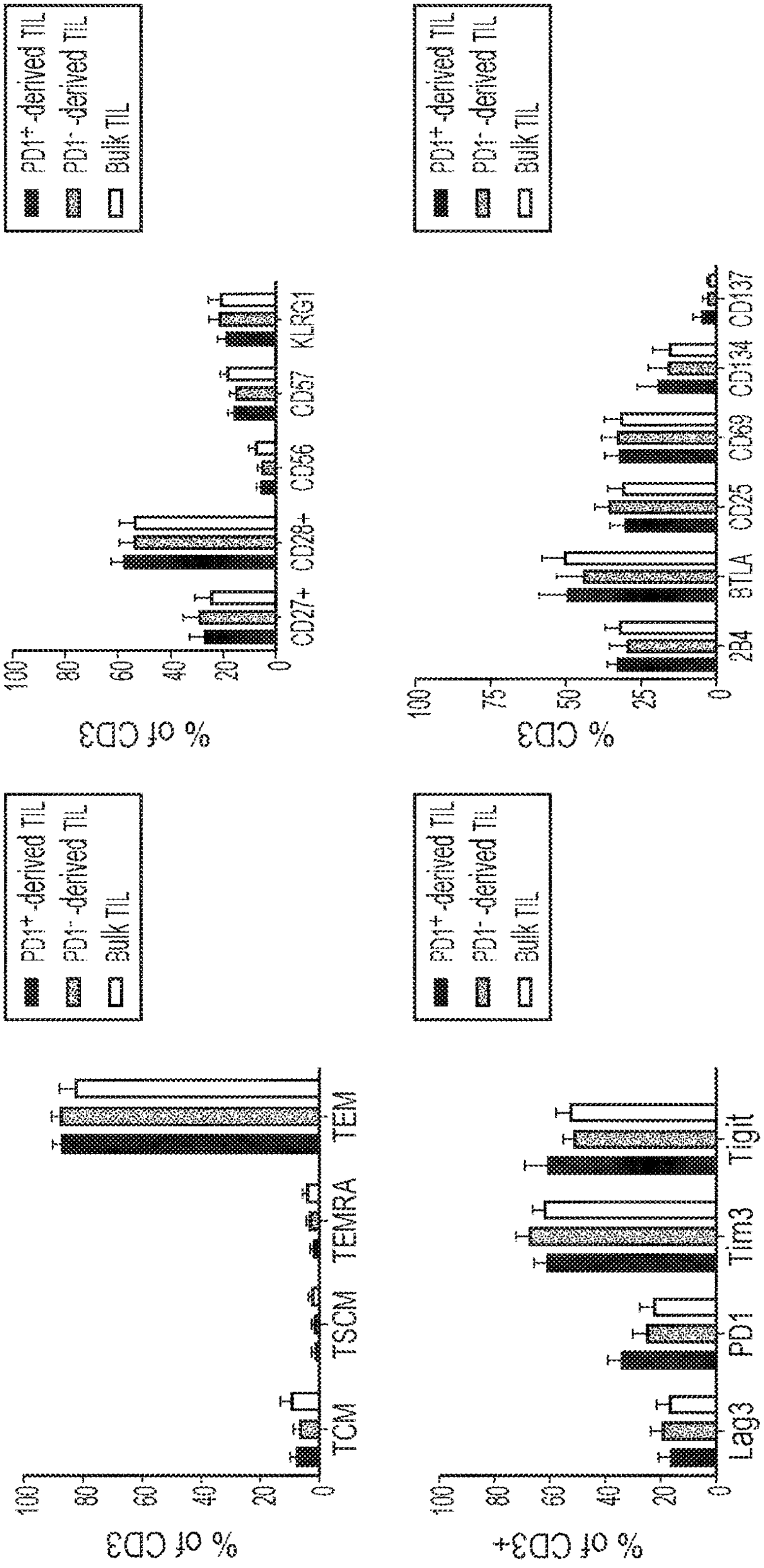
FIG. 74: In vitro expanded PD1+ TIL were phenotypically similar to bulk TIL.
Figure 75:
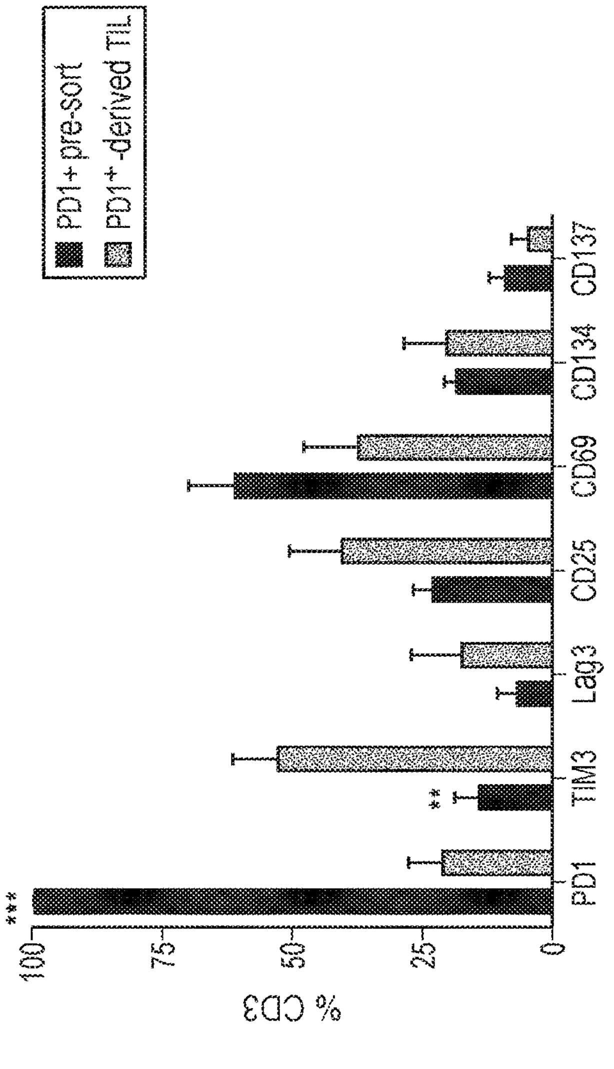
FIG. 75: PD1 expression decreased upon in vitro expansion of PD1+ TIL.
Figure 76:
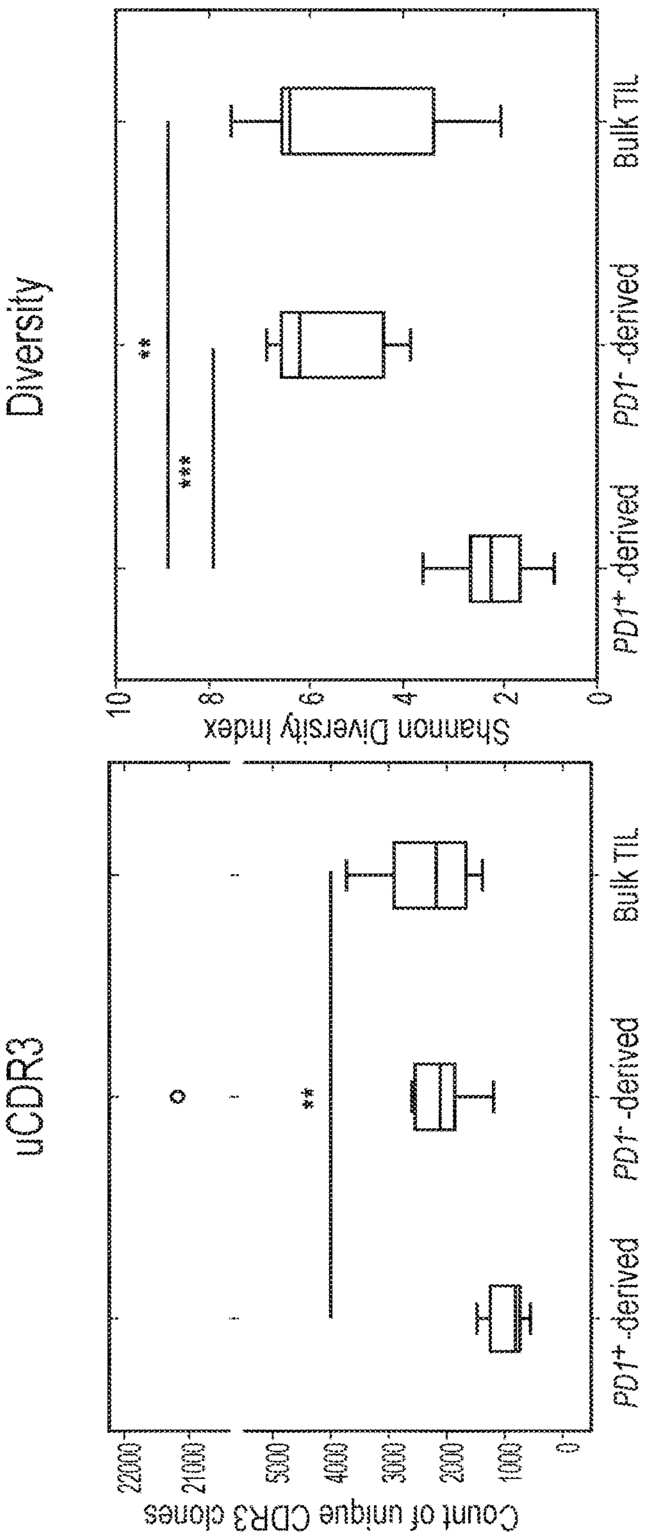
FIG. 76: PD1+ selected TIL are oligoclonal and compromised of a fraction of clones present in bulk TIL.
Figure 77:
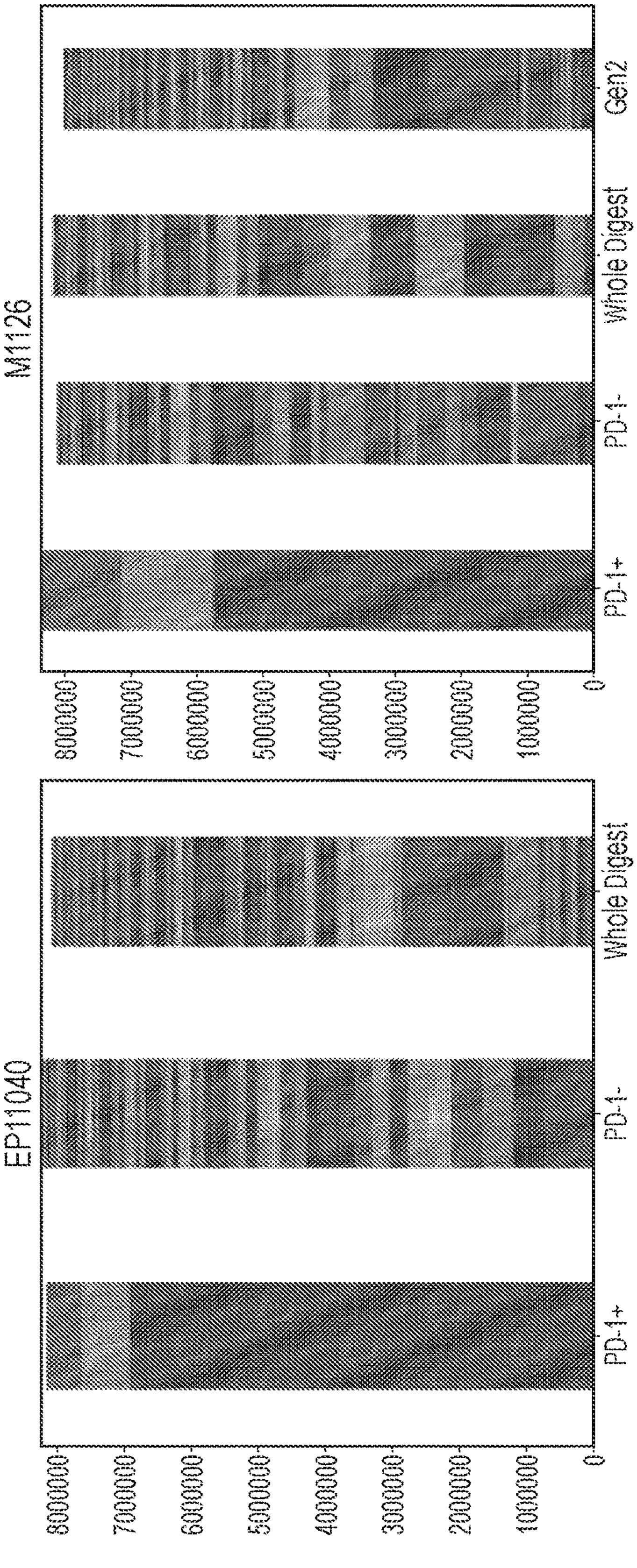
FIG. 77: PD1+ selected TIL are oligoclonal and compromised of a fraction of clones present in bulk TIL.
Figure 78:
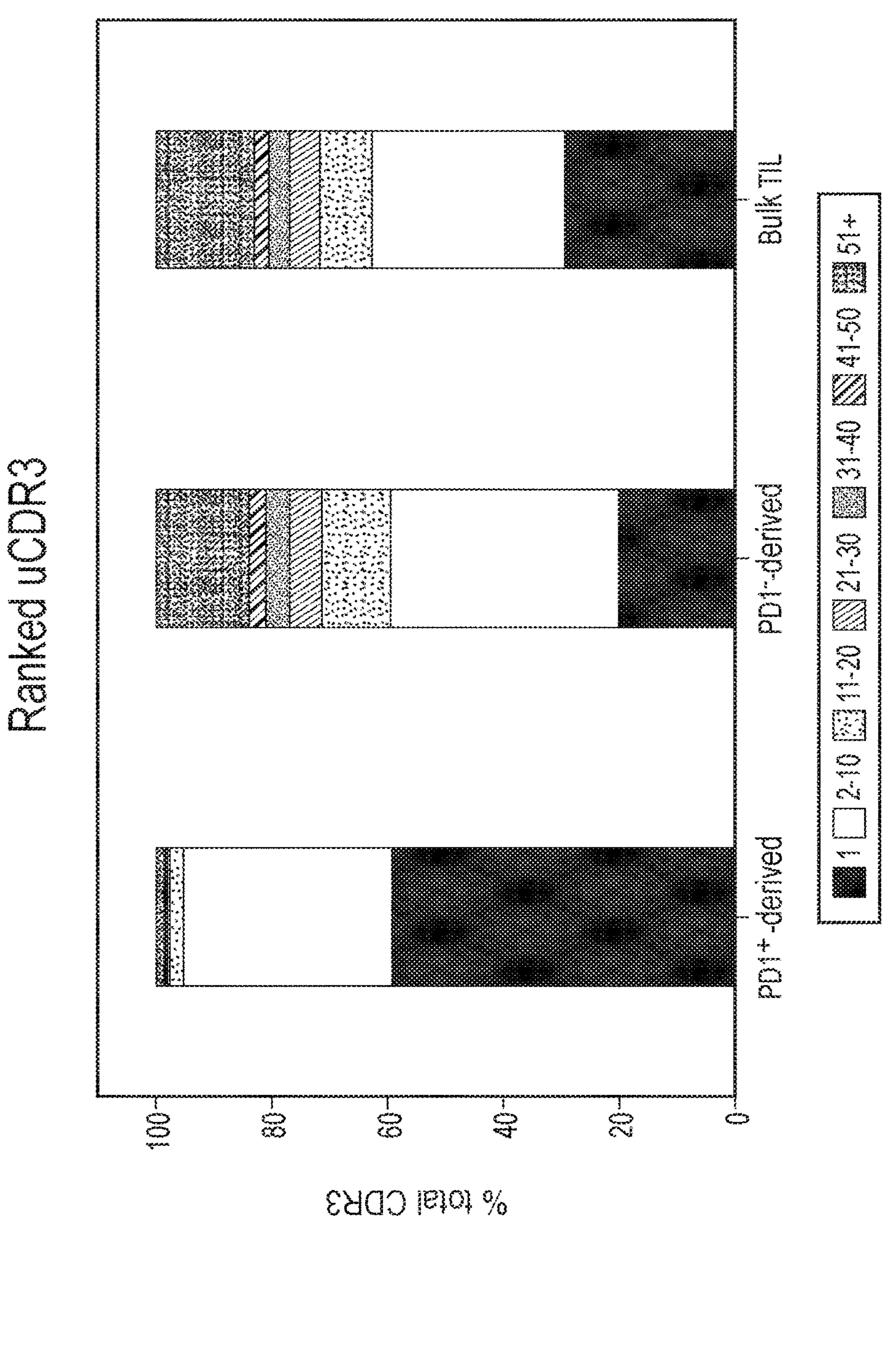
FIG. 78: PD1+ selected TIL are oligoclonal and compromised of a fraction of clones present in bulk TIL.
Figure 80:
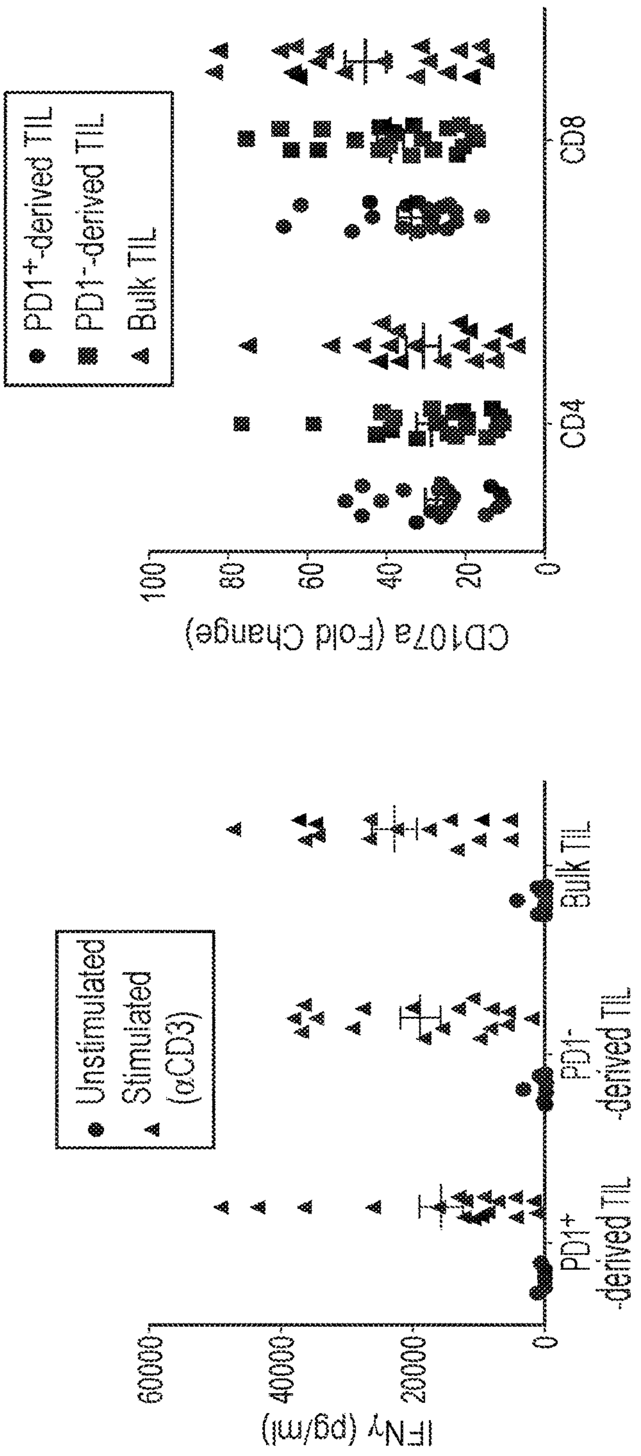
FIG. 80: PD1+-derived TIL are functional as determined by IFNγ secretion and CD107a mobilization in response to non-specific stimulation.
Figure 81:
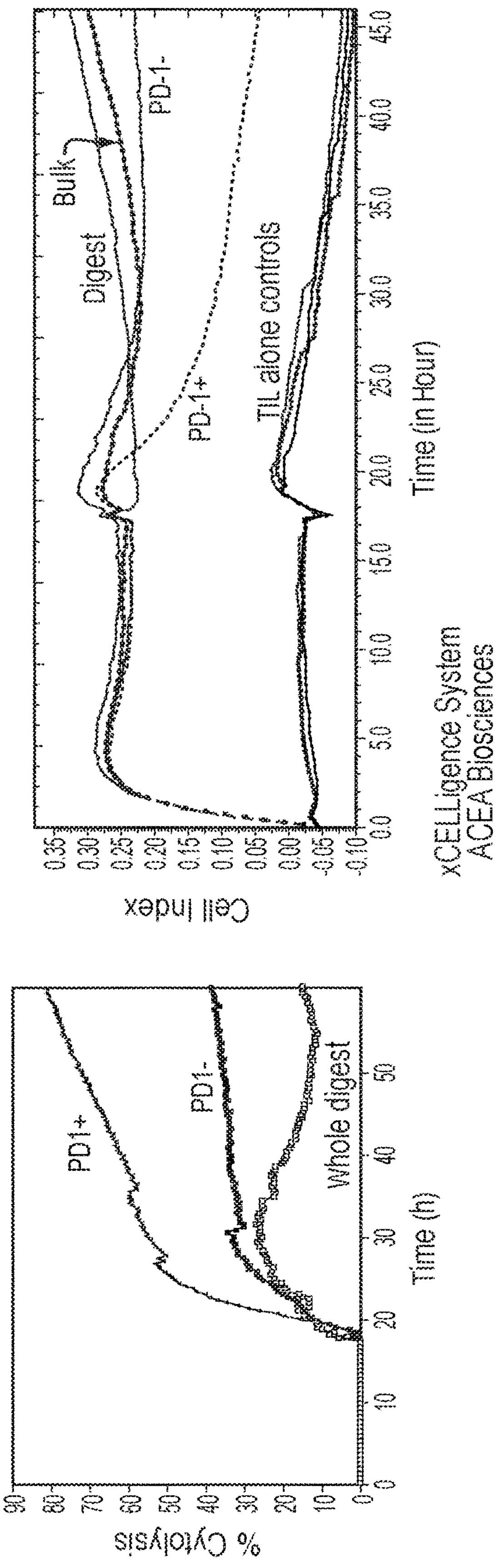
FIG. 81: PD1+-derived TIL demonstrate enhanced killing in comparison to the PD1−-derived TIL and bulk TIL in melanoma.
Figure 82:
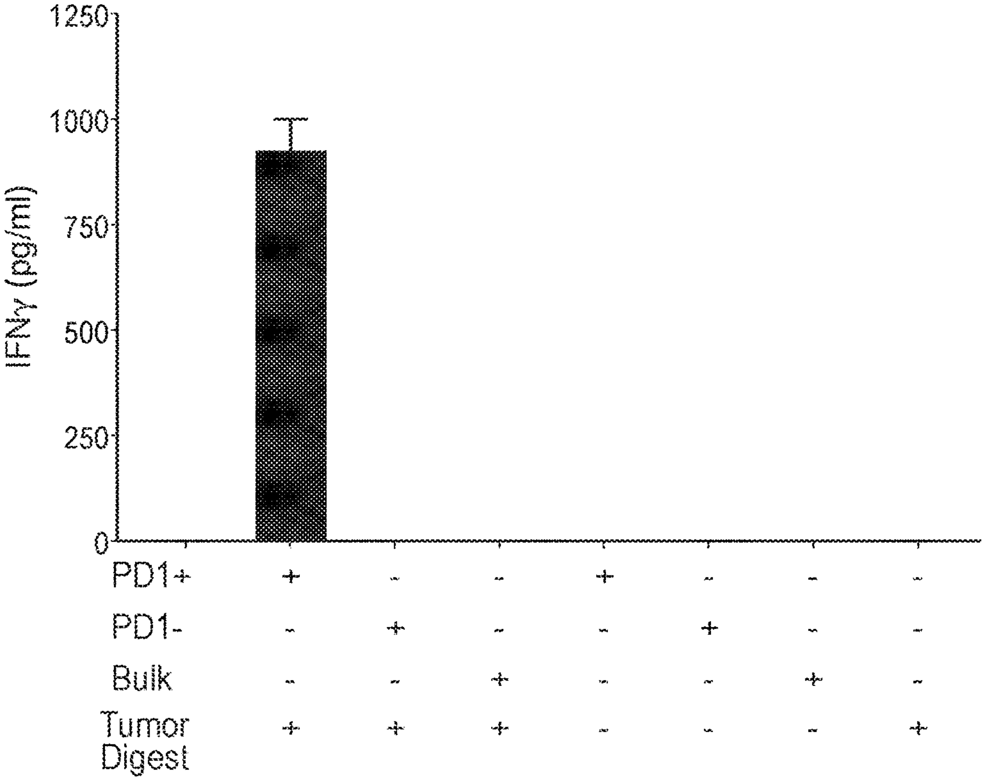
FIG. 82: PD1+-derived TIL demonstrated enhanced tumor cell killing in comparison to the PD and bulk-derived TIL in melanoma.
Figure 83:
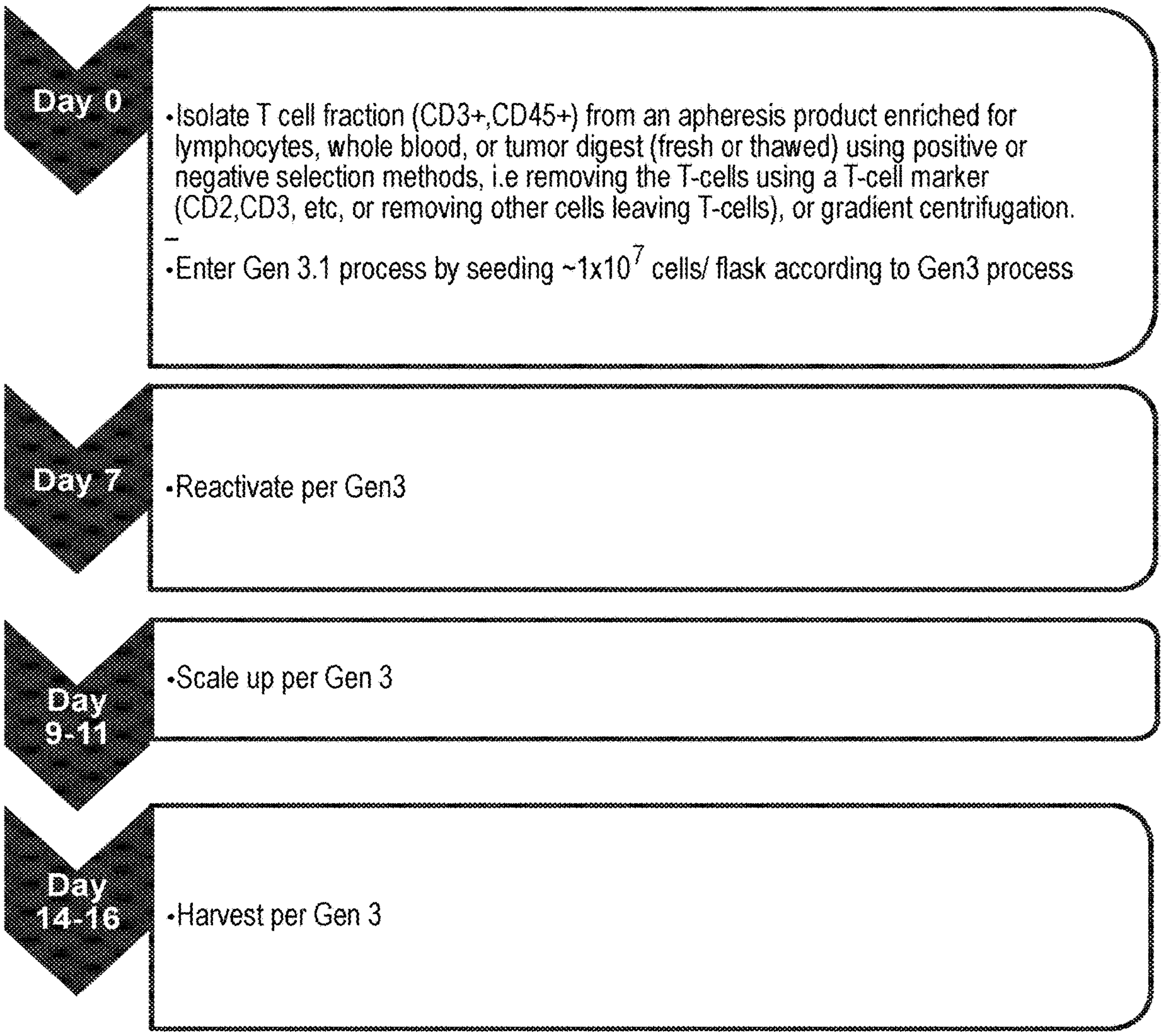
FIG. 83: Illustrative embodiments of a method for expanding TILs from hematopoietic malignancies using Gen 3 expansion platform.
Figure 84:
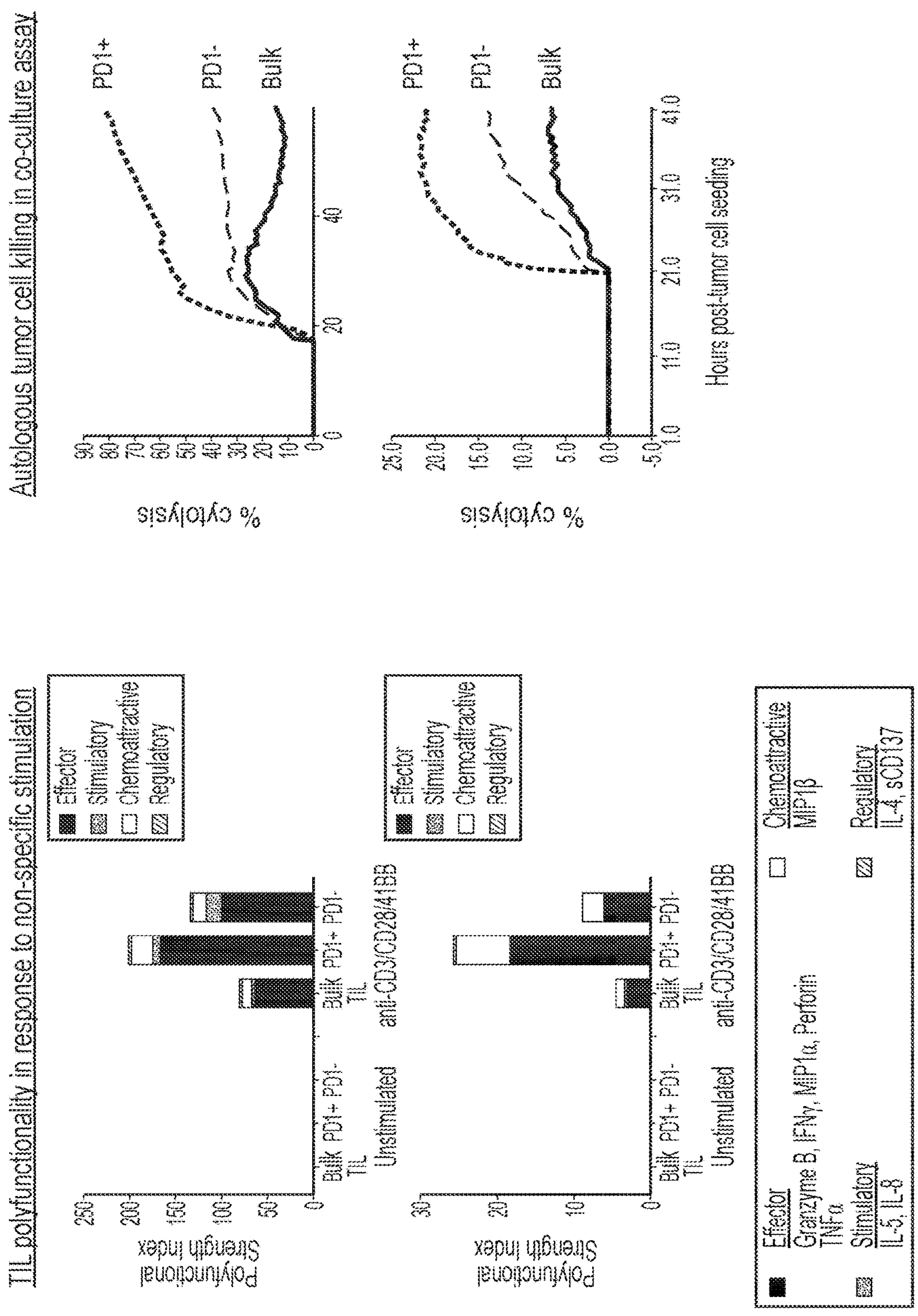
FIG. 84: Ex vivo expanded PD1+ TIL demonstrated effector activity in several in vitro assays. Data indicates that PD1+-selected TIL are antigen-specific and have greater effector function.
Figure 85:
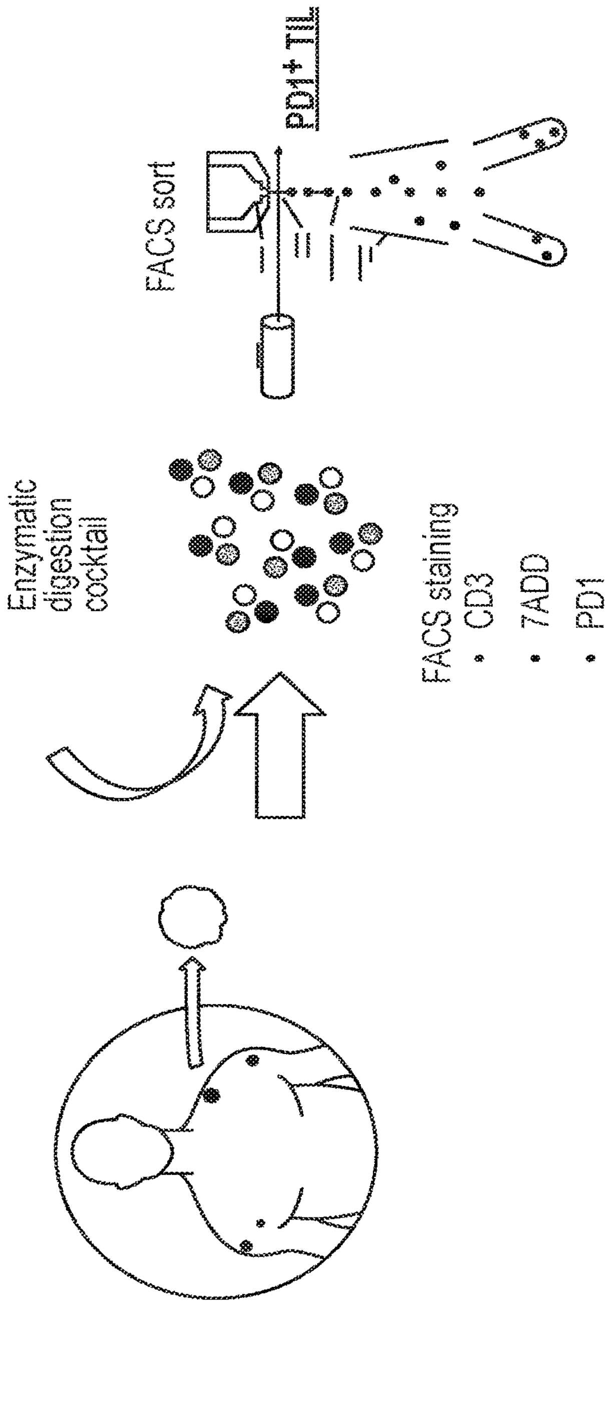
FIG. 85: Schematic representation of exemplary embodiment for the tumor digestion and PD-1+ selection step, including PD-1 high selection.
Figure 87:
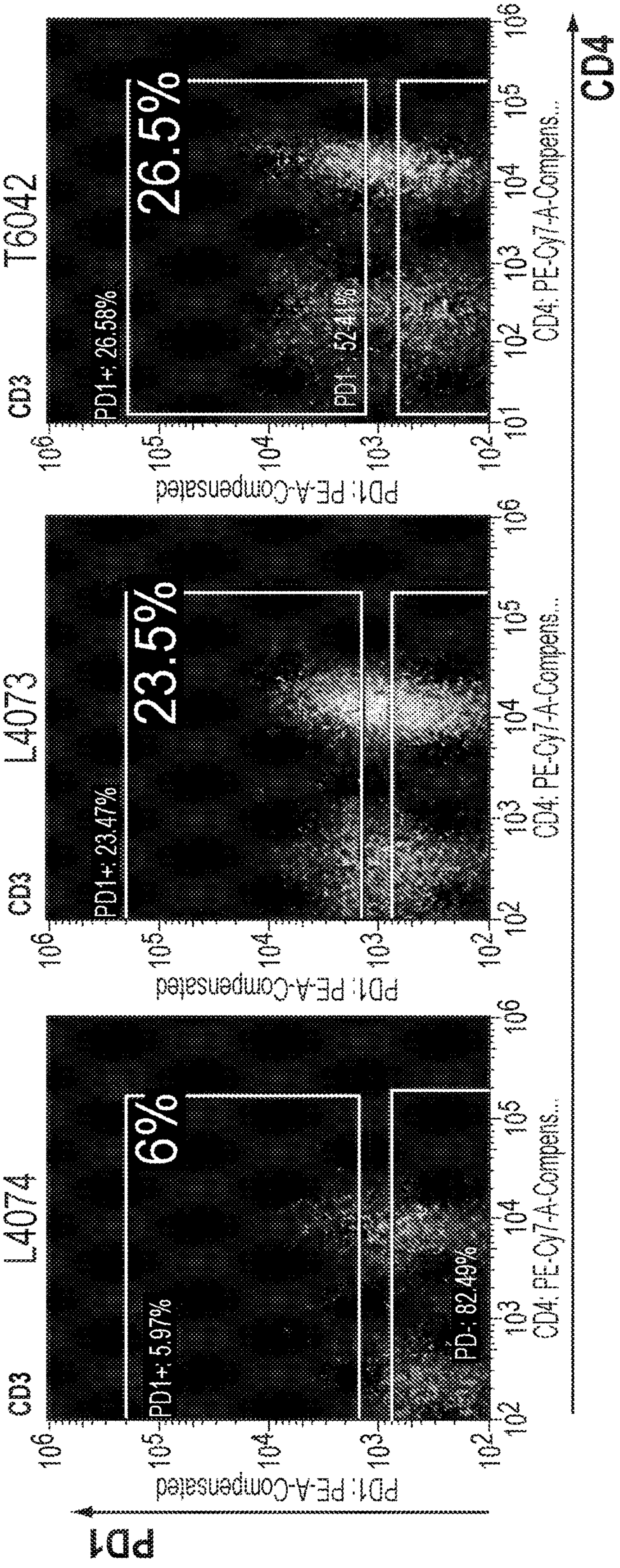
FIG. 87: PD-1 selected TIL sorting strategy and data using EH12.2H7 anti-PD-1 antibody rather than M1H4 anti-PD-1 antibody.
Figure 88:
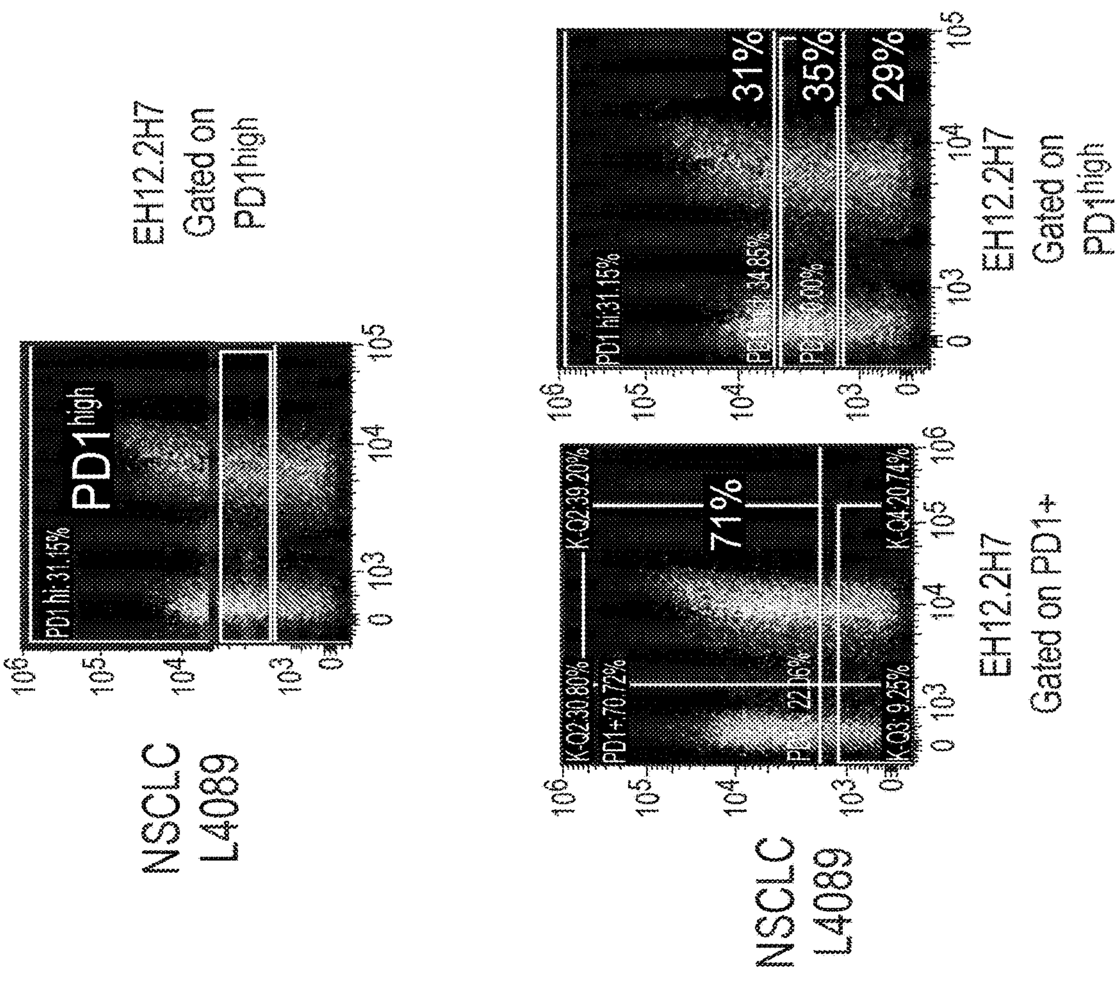
FIG. 88: PD-1 selected TIL sorting data showing populations in the PD-1 high gating strategy using EH12.2H7 anti-PD-1 antibody.
Figure 89:
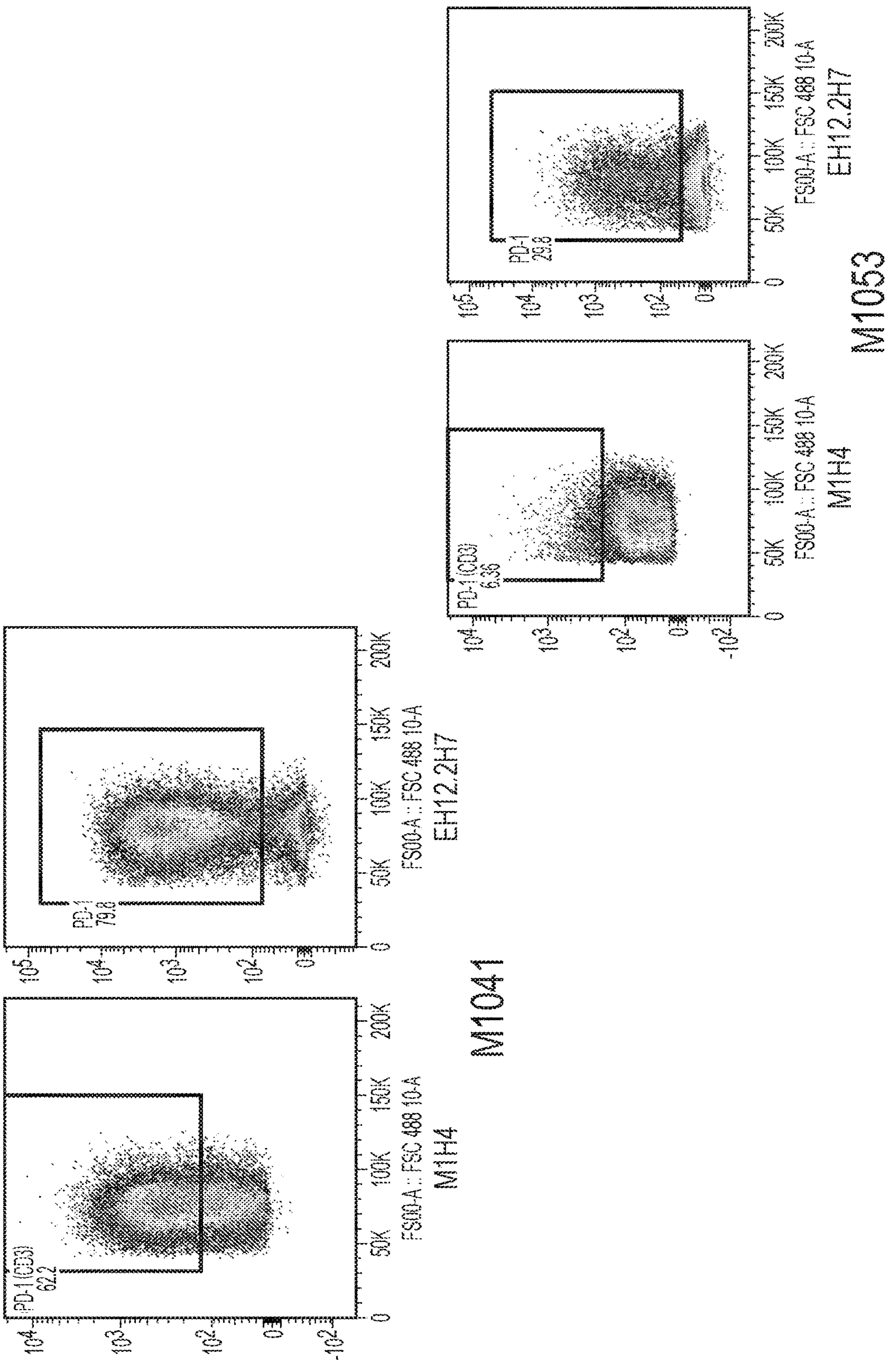
FIG. 89: PD1+ sorting strategy data showing assessment of anti-PD1 antibodies for sorting M1H4 anti-PD-1 antibody and EH12.2H7 anti-PD-1 antibody.
Figure 90:
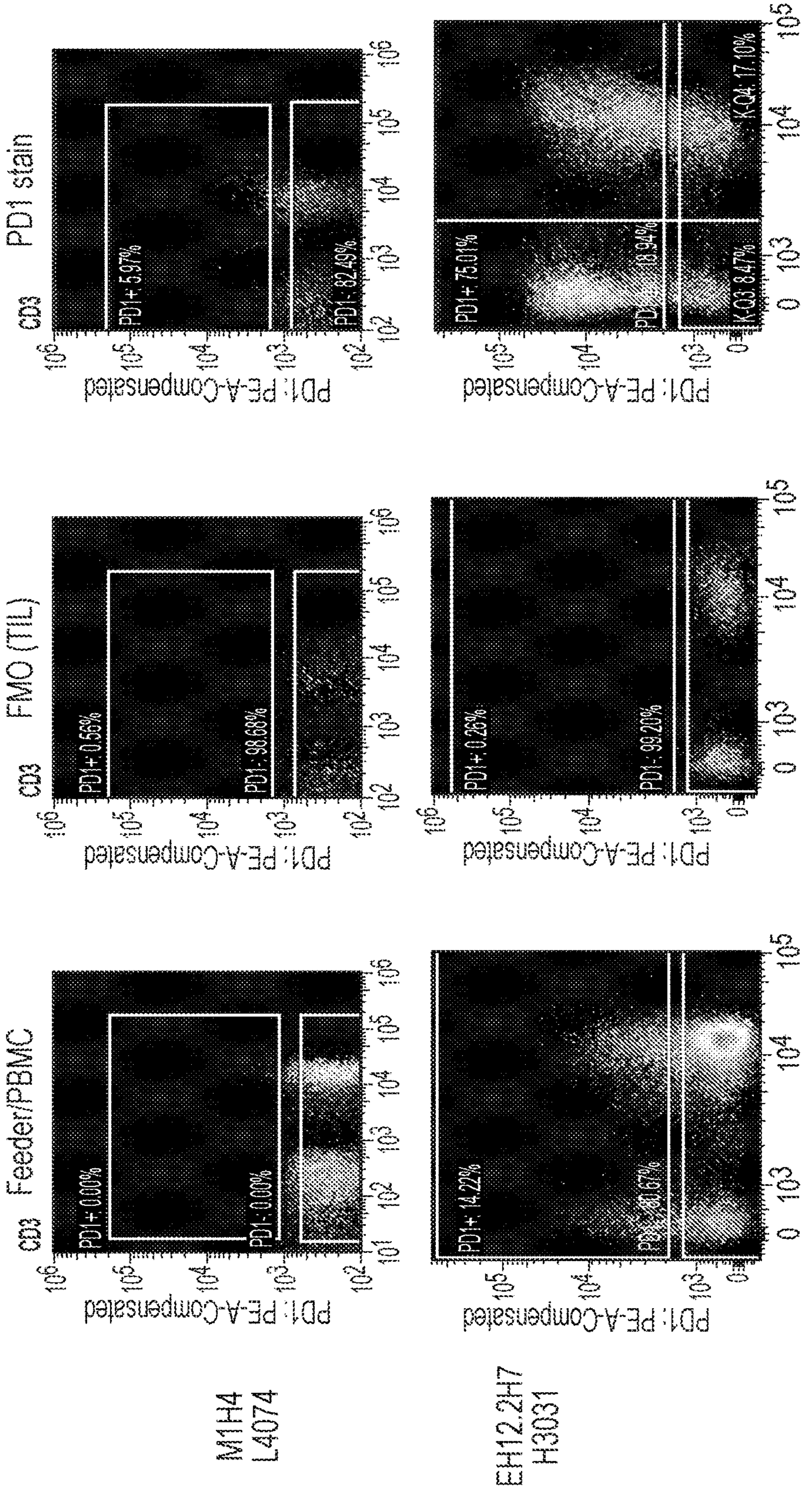
FIG. 90: PD-1 staining for TIL selection. Data shows EH12.2H7 and M1H4 demonstrate different PD1 profiles in PBMC's and TIL.
Figure 91:
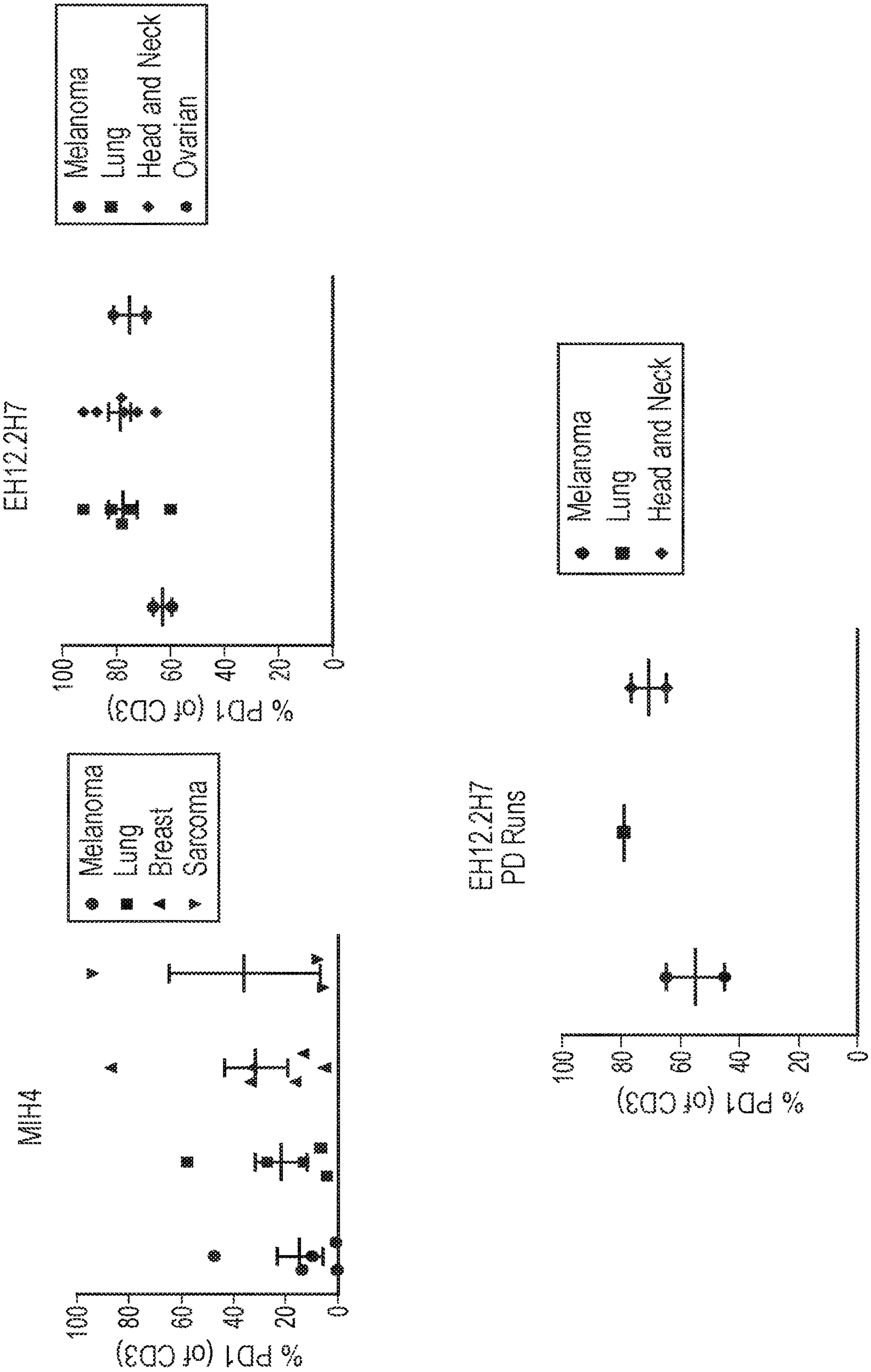
FIG. 91: Comparative analysis of M1H4-derived TIL vs. EH12.2H7-derived TIL. Increased Frequency of PD1+ in EH12.2H7 sorted TIL.
Figure 92:
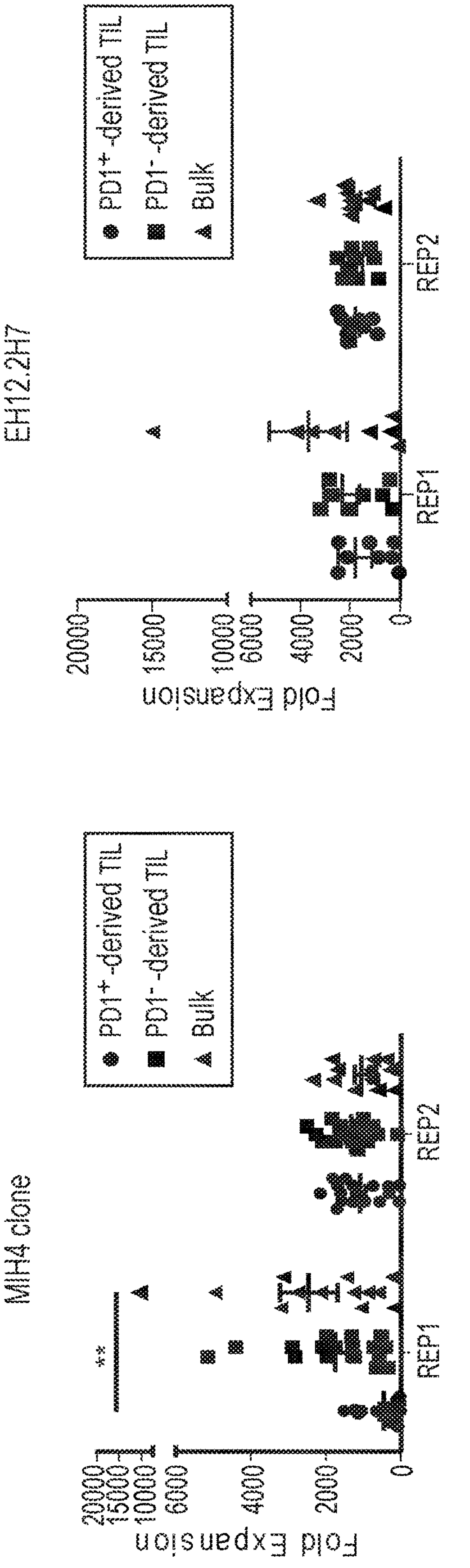
FIG. 92: Reduced fold expansion in PD1+-derived TIL, during REP1 using the M1H4 clone.
Figure 93:
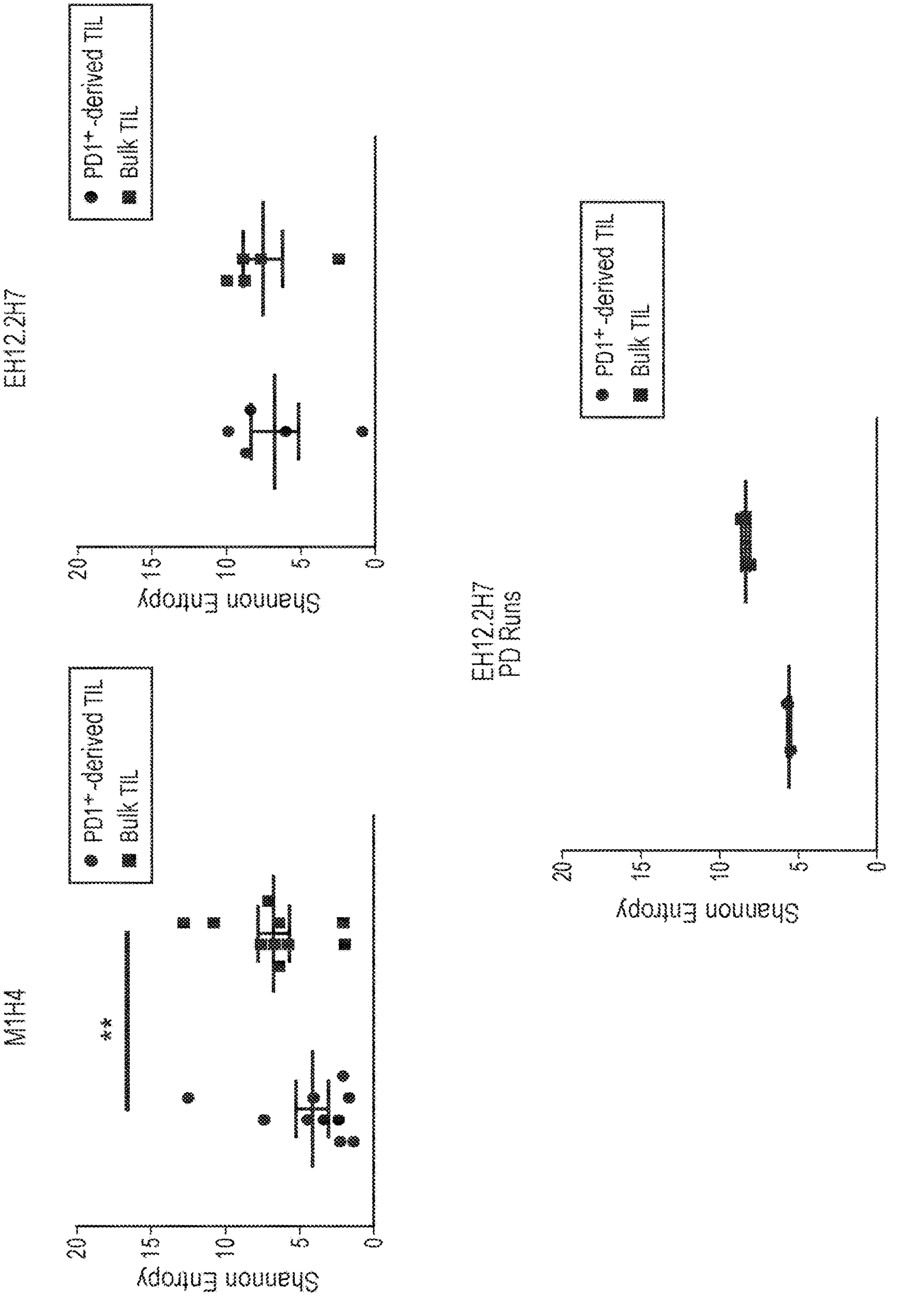
FIG. 93: Comparative analysis of M1H4-derived TIL and EH12.2H7-derived TIL. Greater oligoclonality (decreased diversity) was observed in M1H4 sorted TIL. (Shannon Entropy is a standard measure that reflects how many different types of a species are present.)
Figure 94:
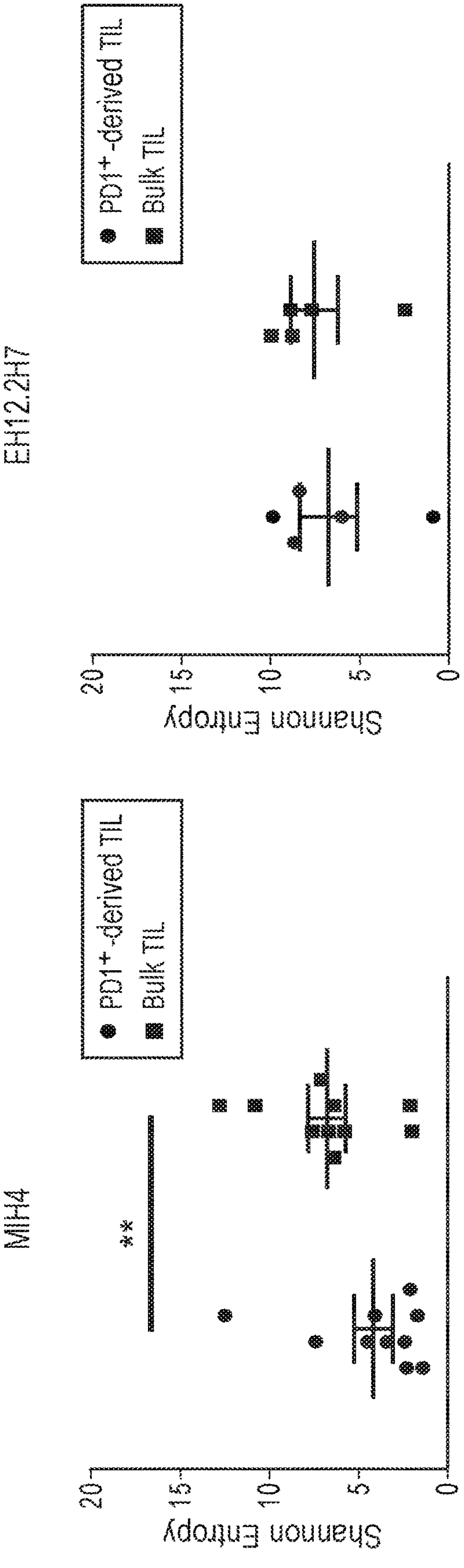
FIG. 94: Greater oligoclonality (decreased diversity) was observed in the PD1+-derived TIL, compared to bulk TIL with the M1H4 clone, compared to the EH12.2H7 clone. (Shannon Entropy is a standard measure that reflects how many different types of a species are present.)
Figure 95:
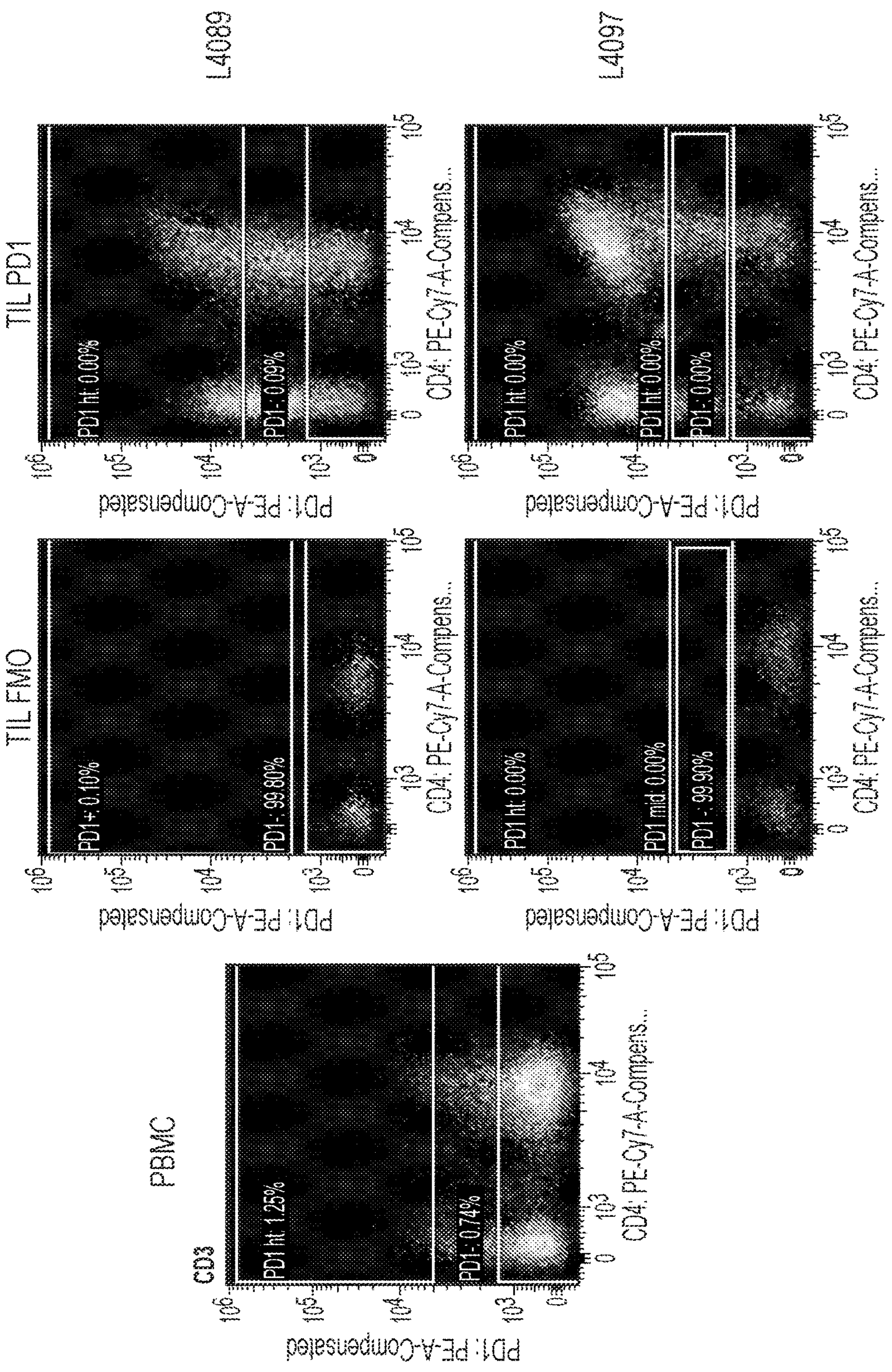
FIG. 95: Exemplary data showing $PD1^{+}$ Selection: Gating on PD1+ high (PD-1 high).
Figure 97:
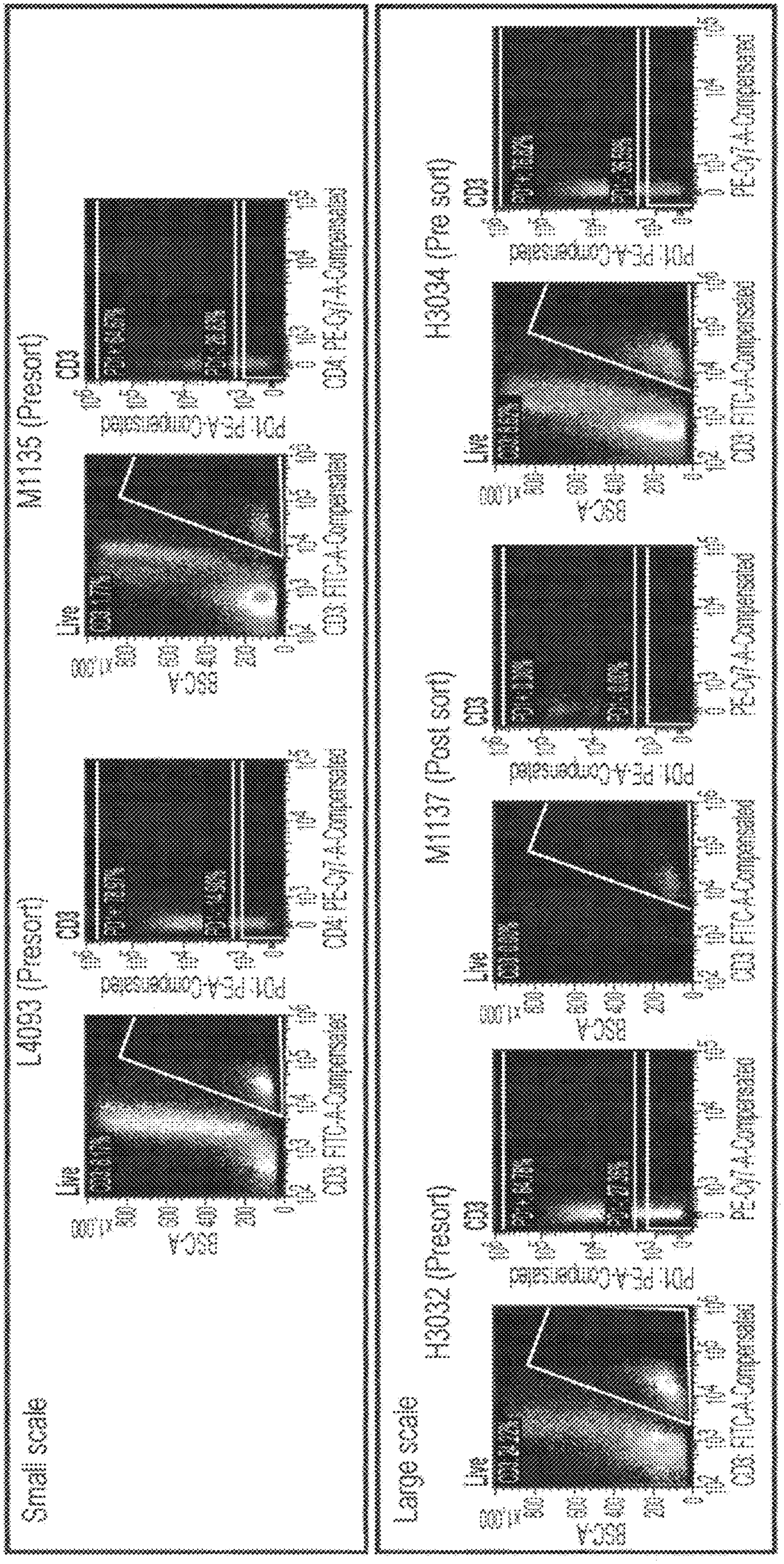
FIG. 97: Exemplary data showing $PD1^{+}$ Selection: Gating on PD1+ high (PD-1 high) for different tumor samples on small (top) and large (bottom) scales.
Figure 98:
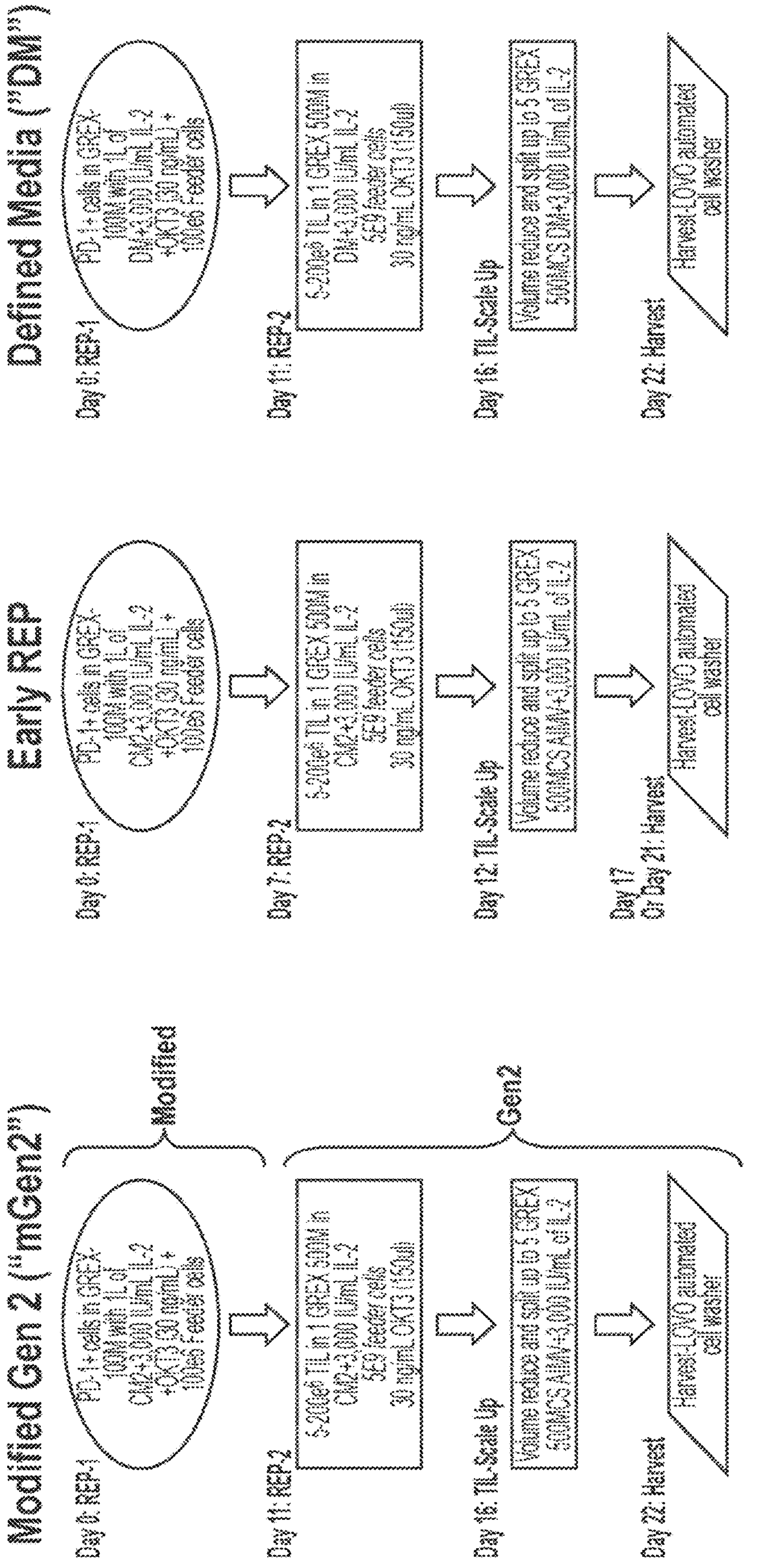
FIG. 98: Schematic of an exemplary embodiments of a modified expansion processes developed for PD1 selected TIL.
Figure 100:
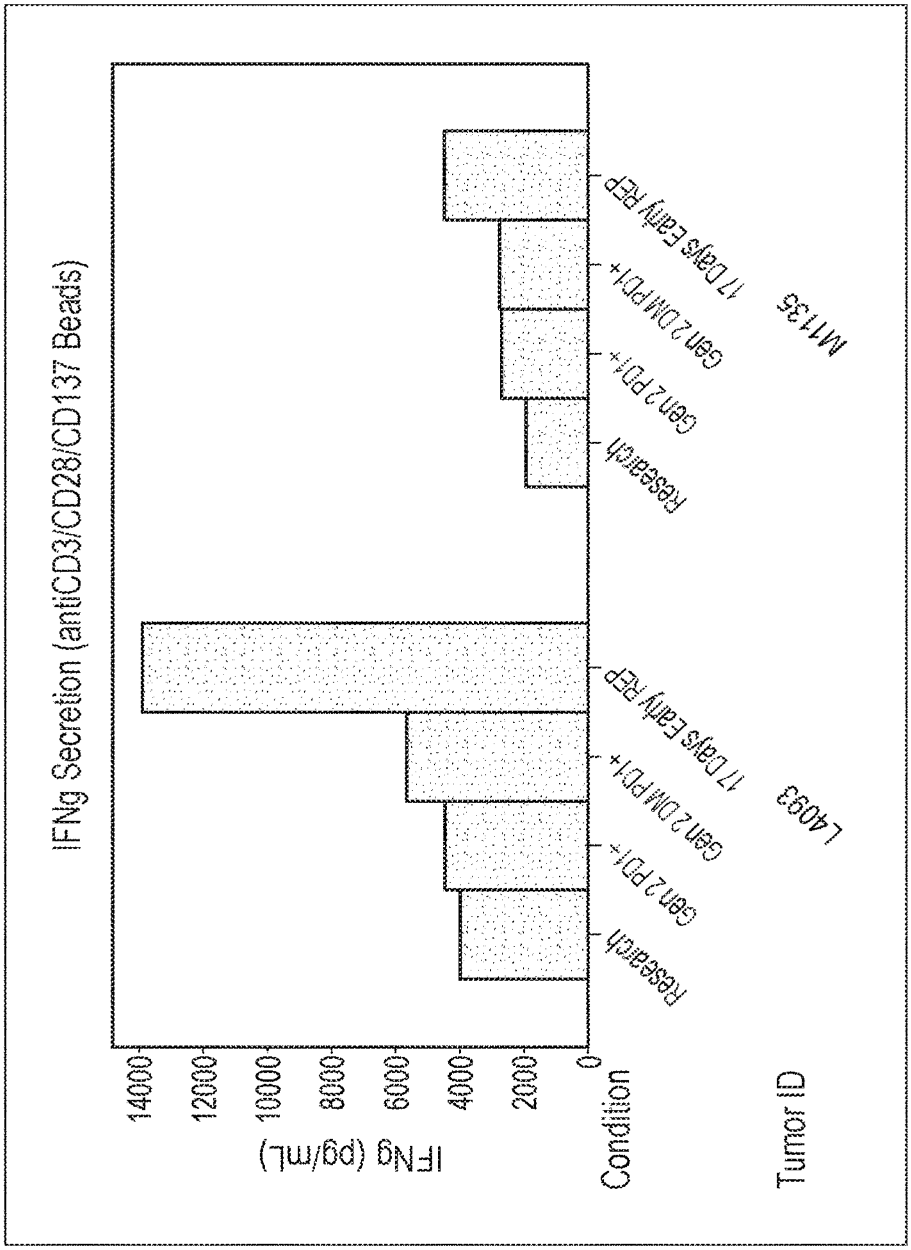
FIG. 100: Shows IFNγ secretion in two tumor samples for multiple expansion process conditions as described in FIGS. 96 and 98.
Figure 101:
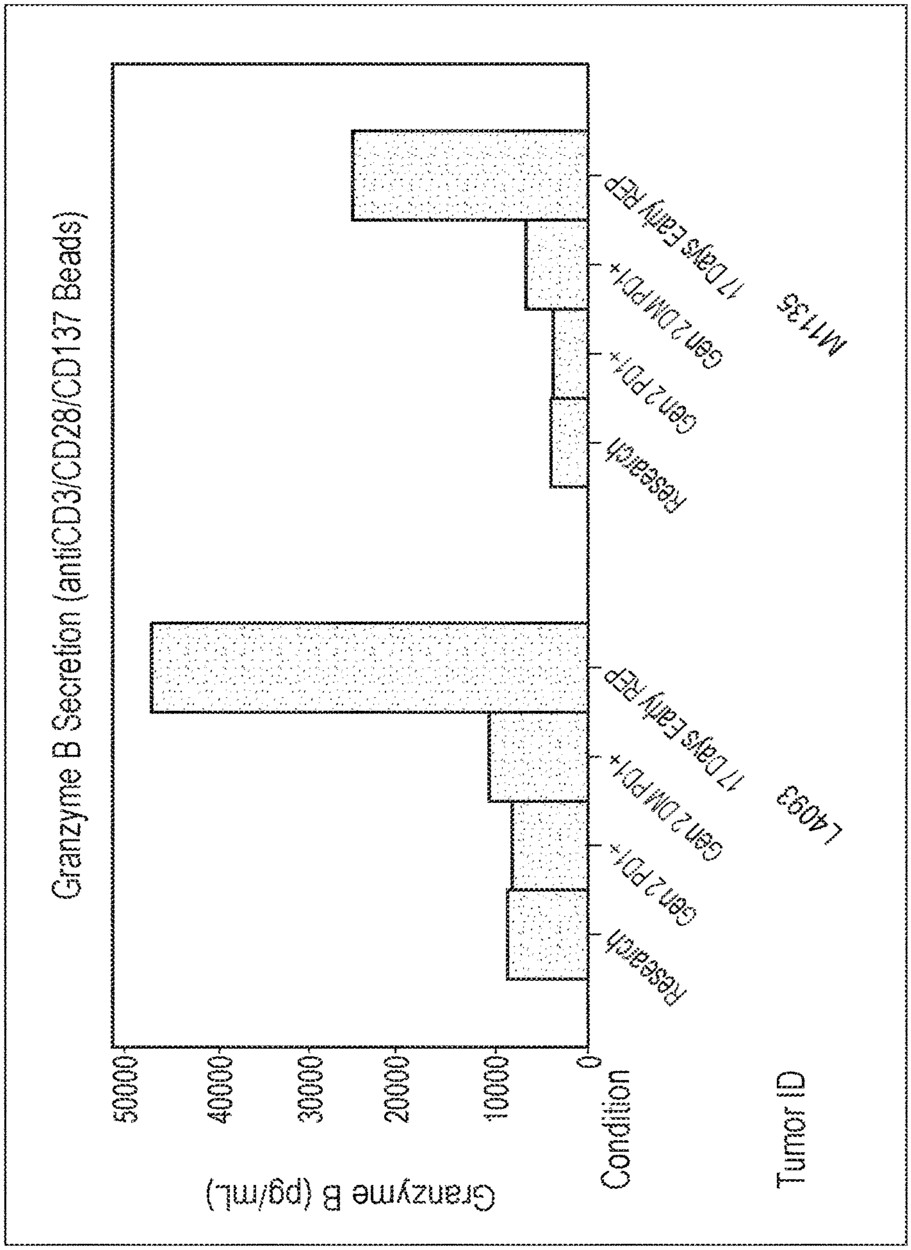
FIG. 101: Shows Granzyme B secretion in two tumor samples for multiple expansion process conditions as described in FIGS. 96 and 98.
Figure 102:
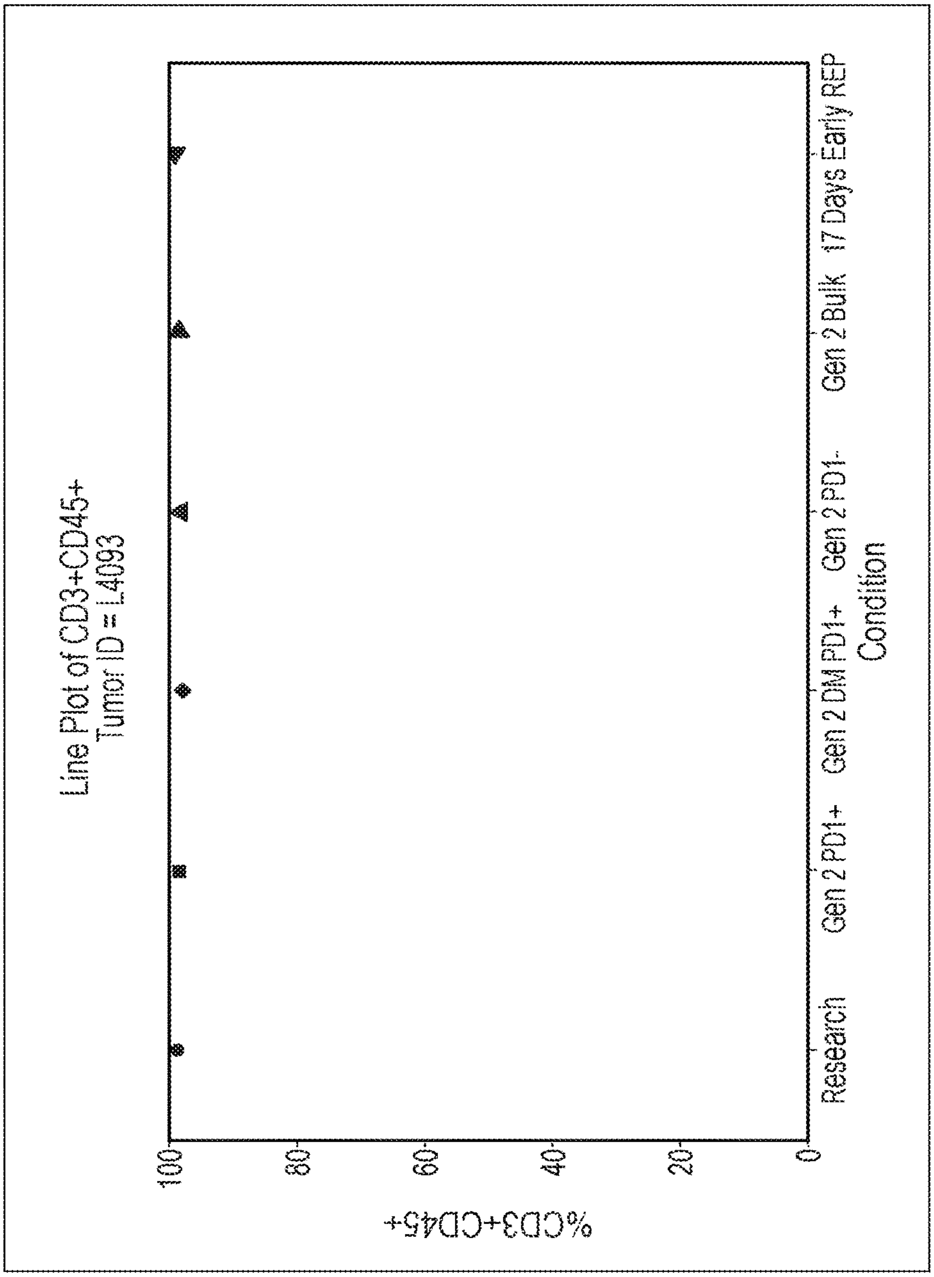
FIG. 102: Shows CD3+CD45+ populations in one tumor sample for multiple expansion process conditions as described in FIGS. 96 and 98. PD1+ Gen 2 condition were >90% CD3+CD45+.
Figure 103:
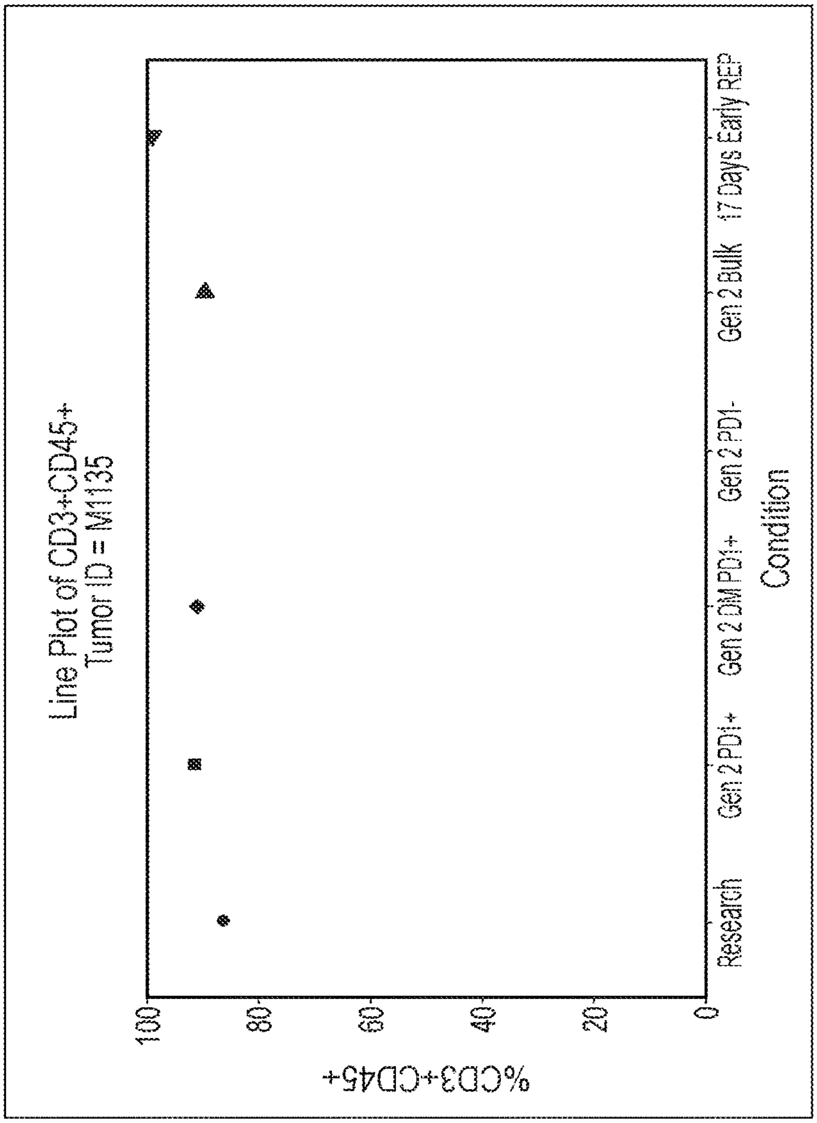
FIG. 103: Shows CD3+CD45+ populations in one tumor sample for multiple expansion process conditions as described in FIGS. 96 and 98. PD1+ Gen 2 condition were >90% CD3+CD45+.
Figure 104:
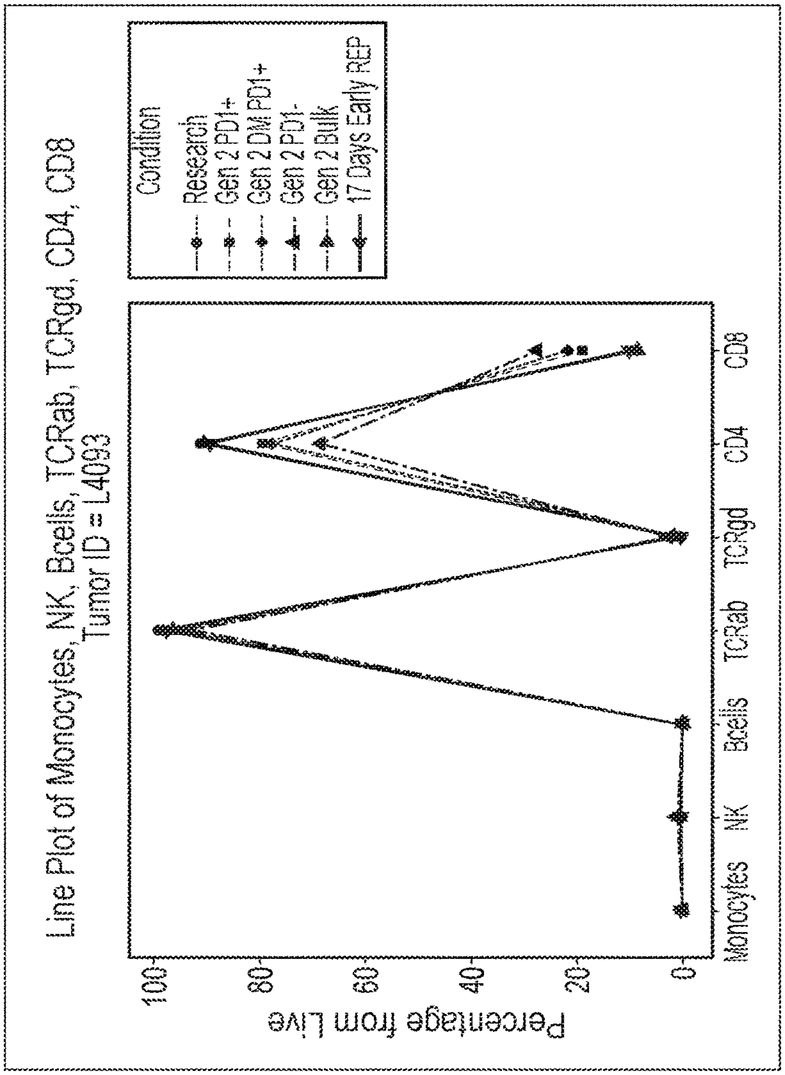
FIG. 104: Shows TIL profile characteristics for one tumor sample for multiple expansion process conditions as described in FIGS. 96 and 98. Purity: >90% TCR a/b+ and No Detectable NK or Monocytes or B cells.
Figure 105:
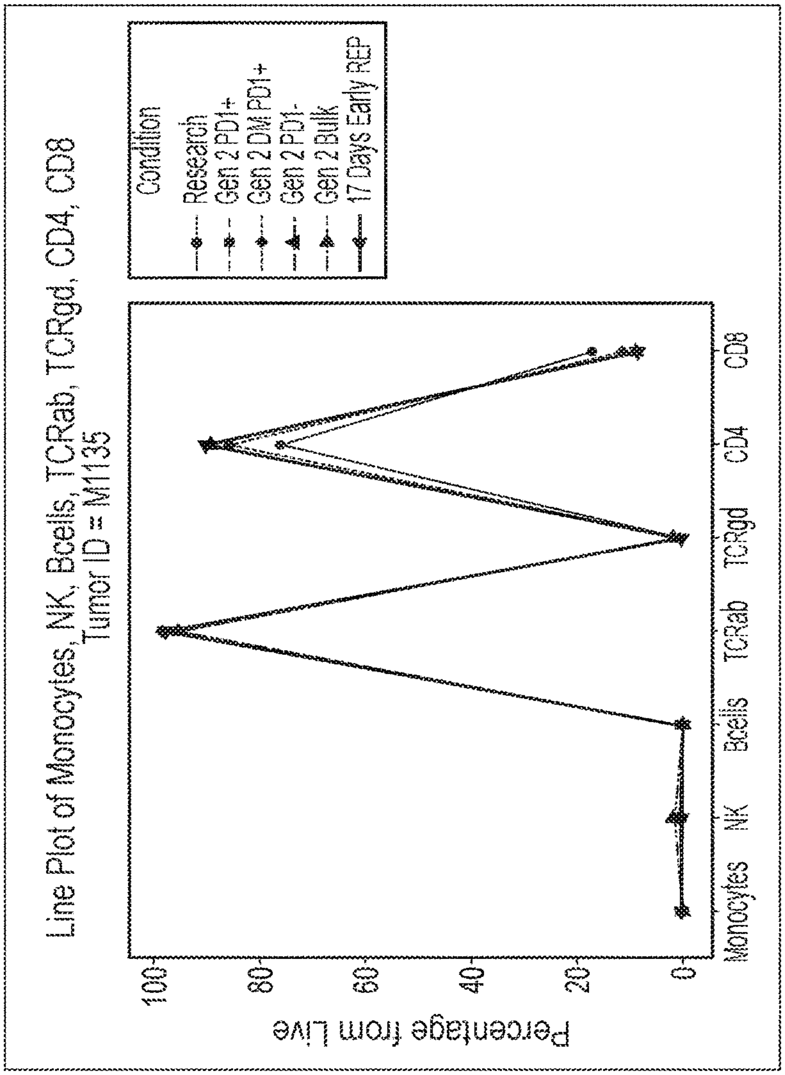
FIG. 105: Shows TIL profile characteristics for one tumor sample for multiple expansion process conditions as described in FIGS. 96 and 98. Purity: >90% TCR a/b+ and No Detectable NK or Monocytes or B cells.
Figure 106A:
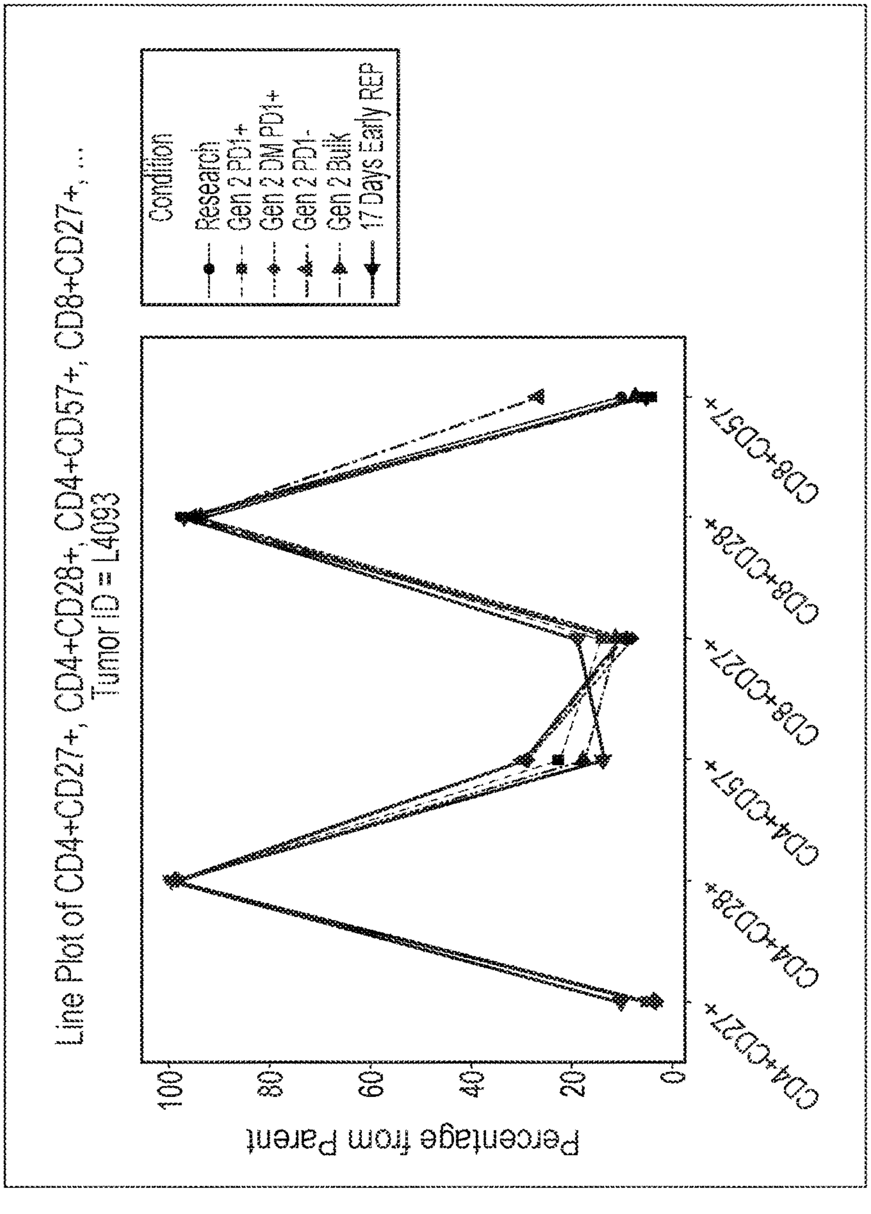
FIG. 106A-106B: Shows TIL profile characteristics for two tumor samples for multiple expansion process conditions as described in FIGS. 96 and 98. Differentiation: PD1+ Gen 2 Differentiation status were comparable
Figure 106B:
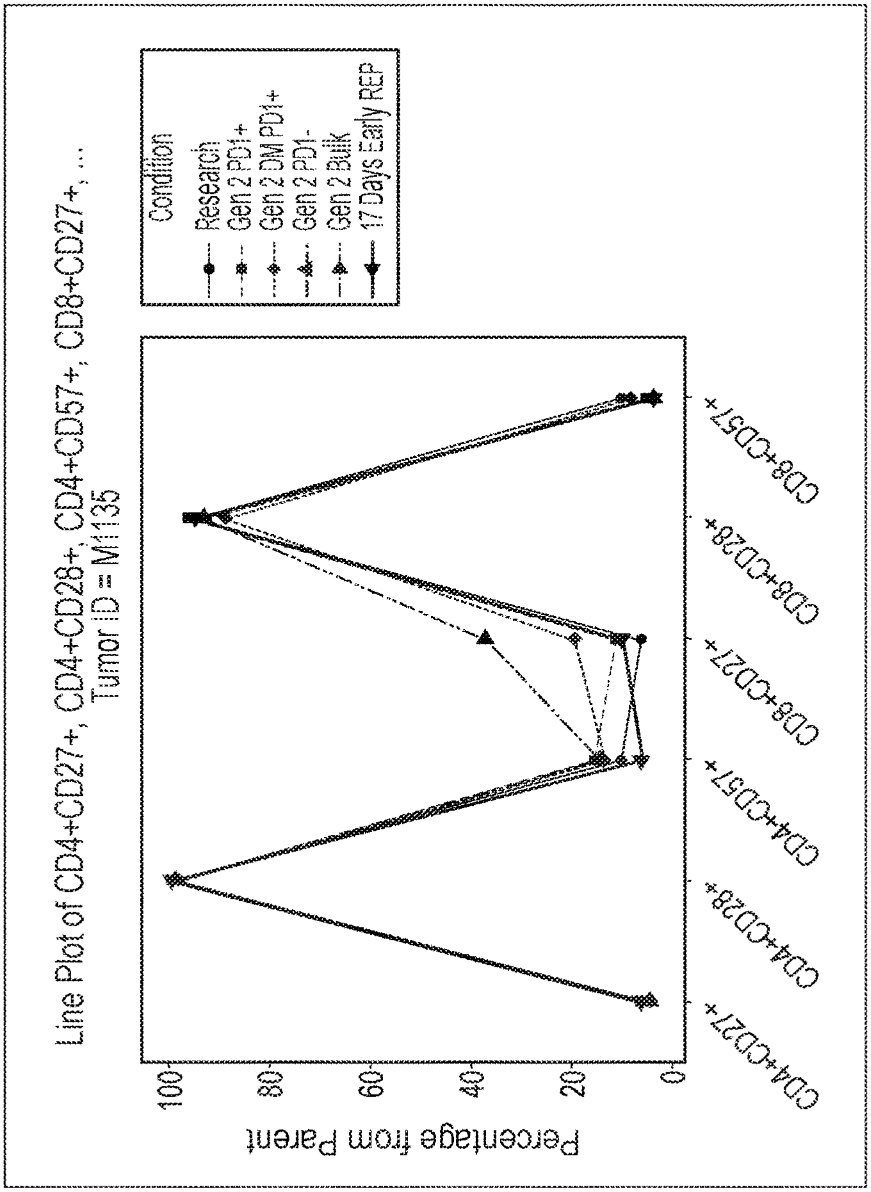
Figure 107A:
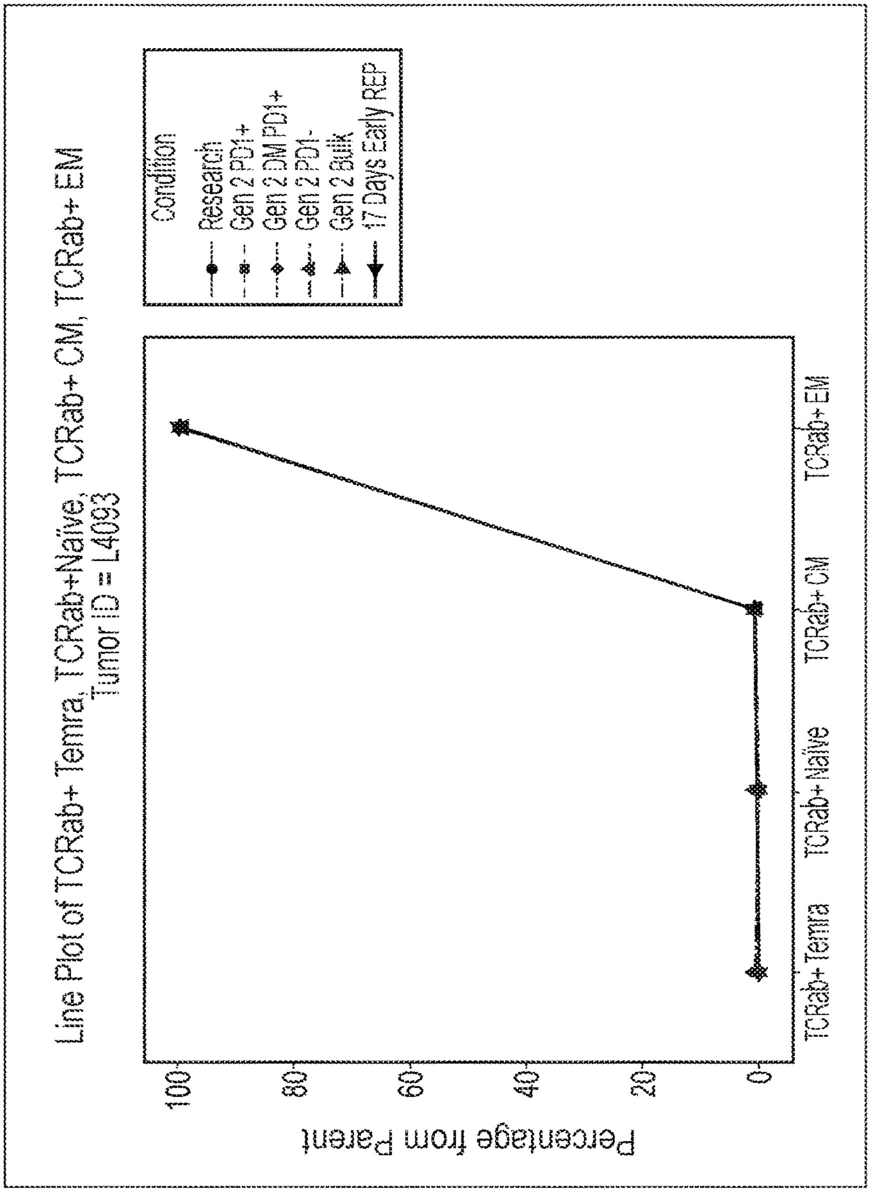
FIG. 107A-107B: Shows TIL profile characteristics for two tumor samples for multiple expansion process conditions as described in FIGS. 96 and 98. Memory: PD1+ Gen 2 were mostly Effector Memory TIL
Figure 107B:
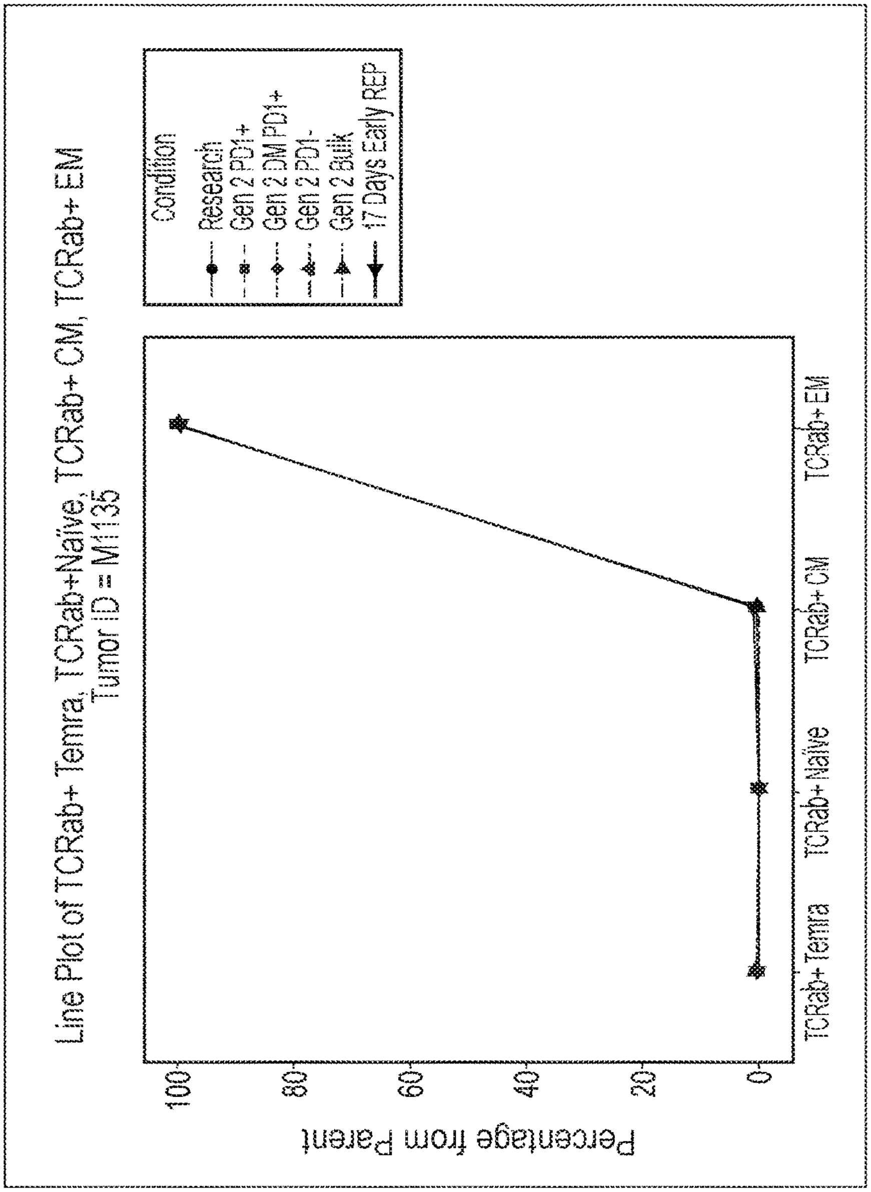
Figure 108A:
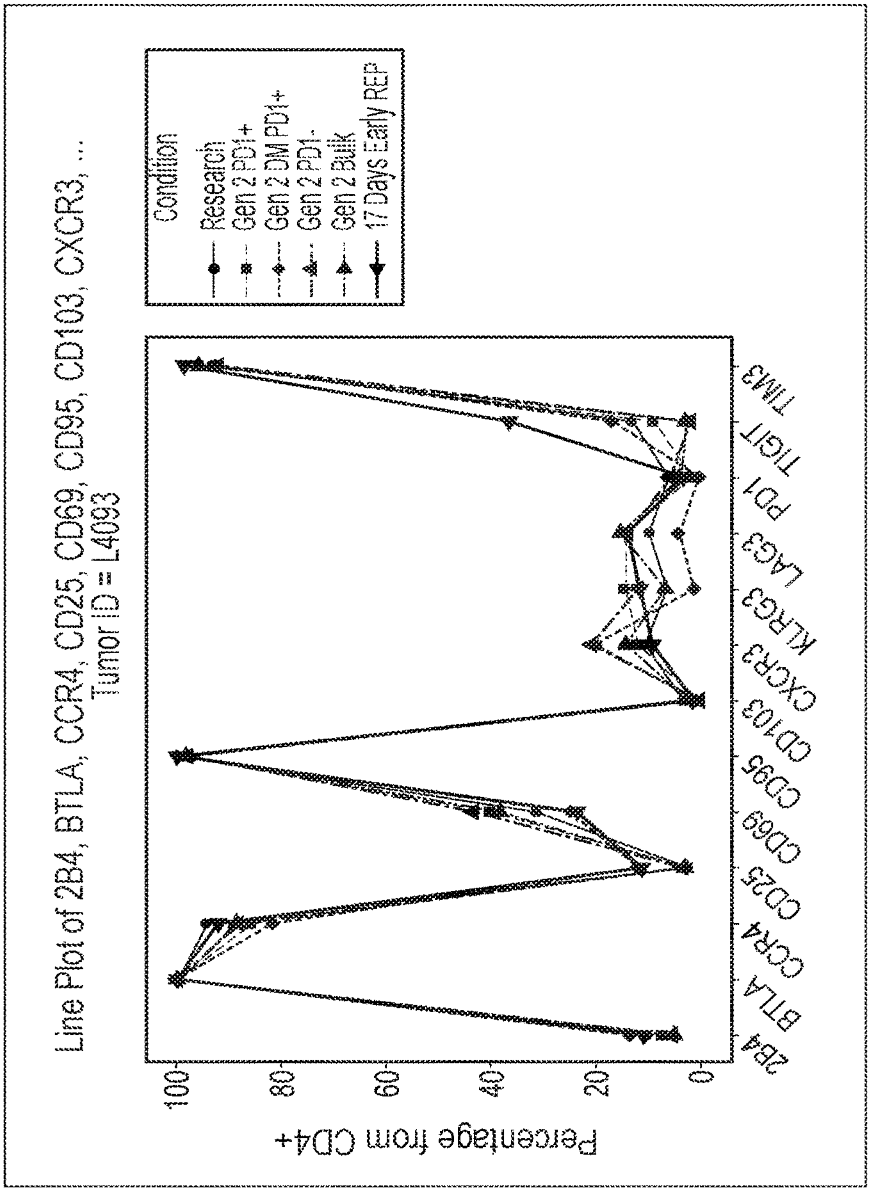
Figure 108B:
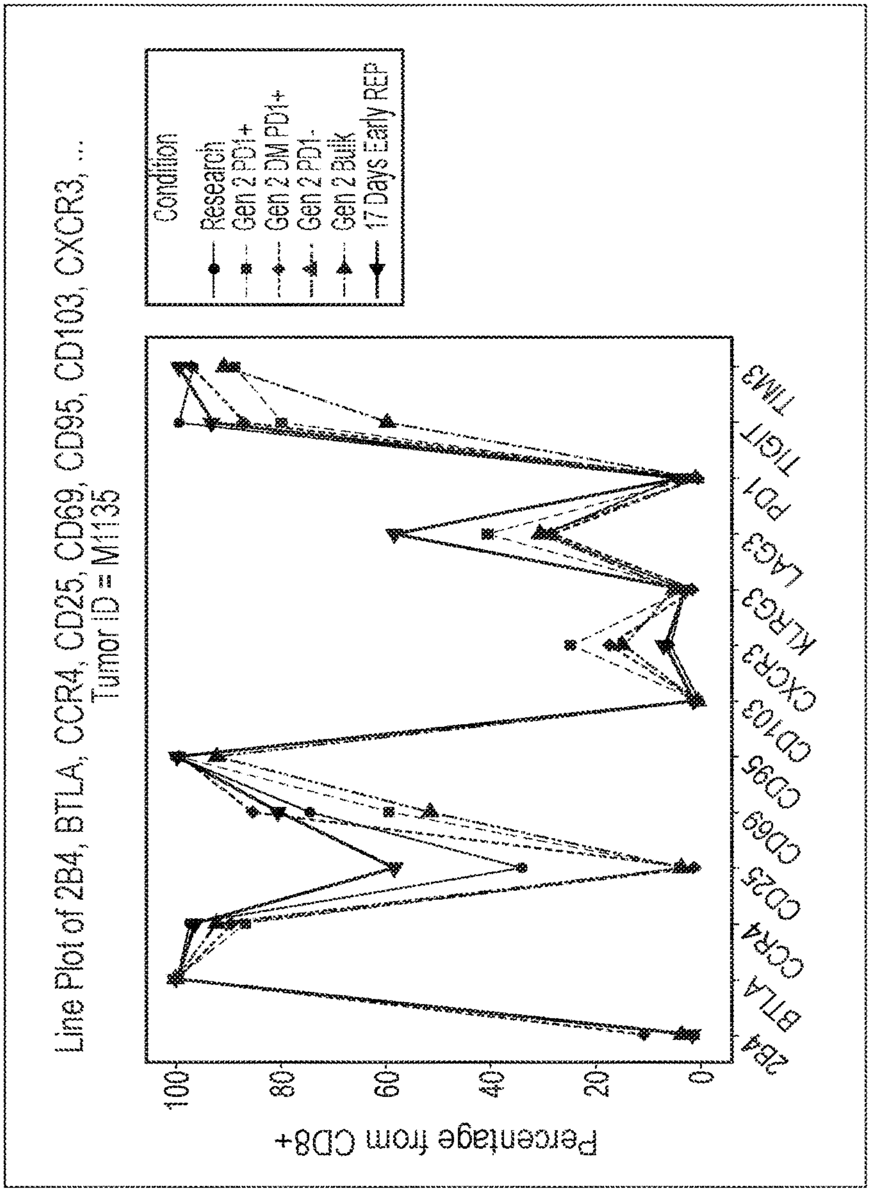
Figure 109A:
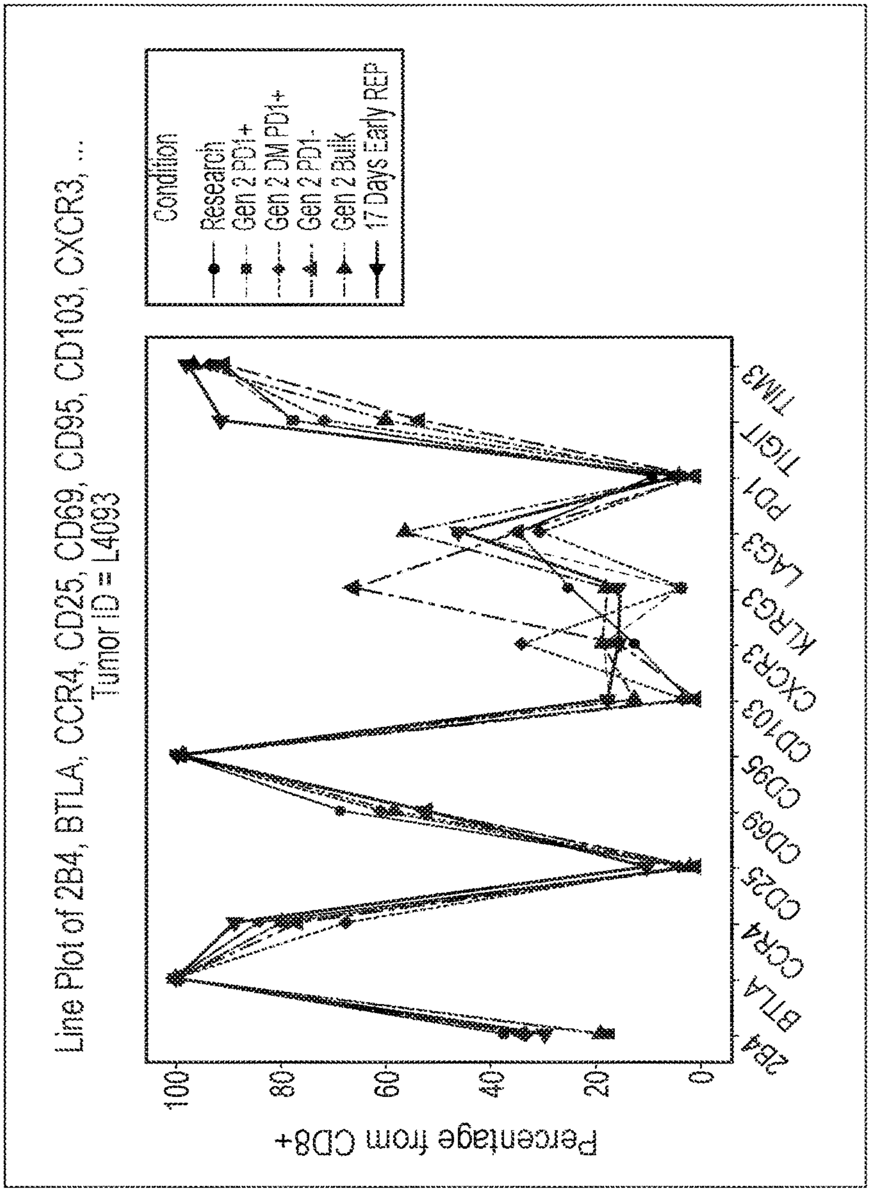
Figure 109B:
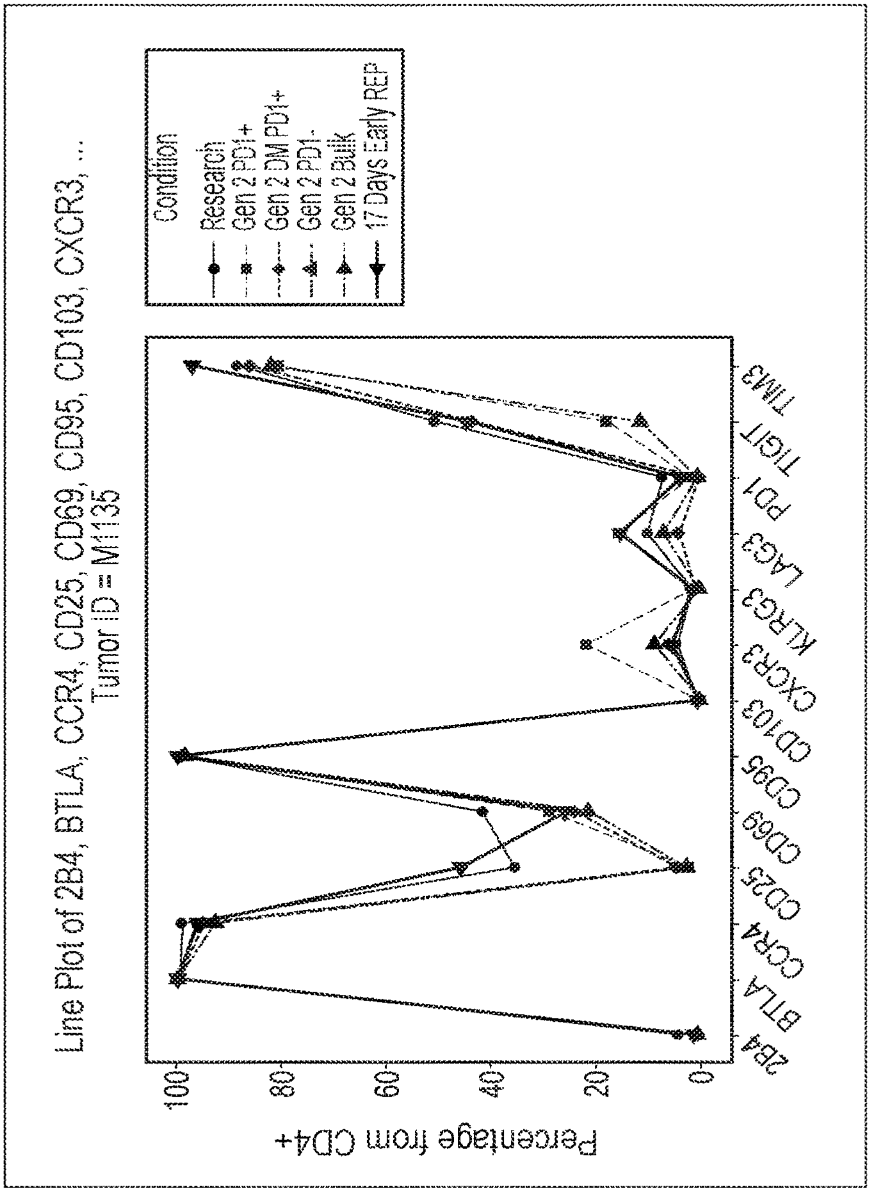
Figure 110:
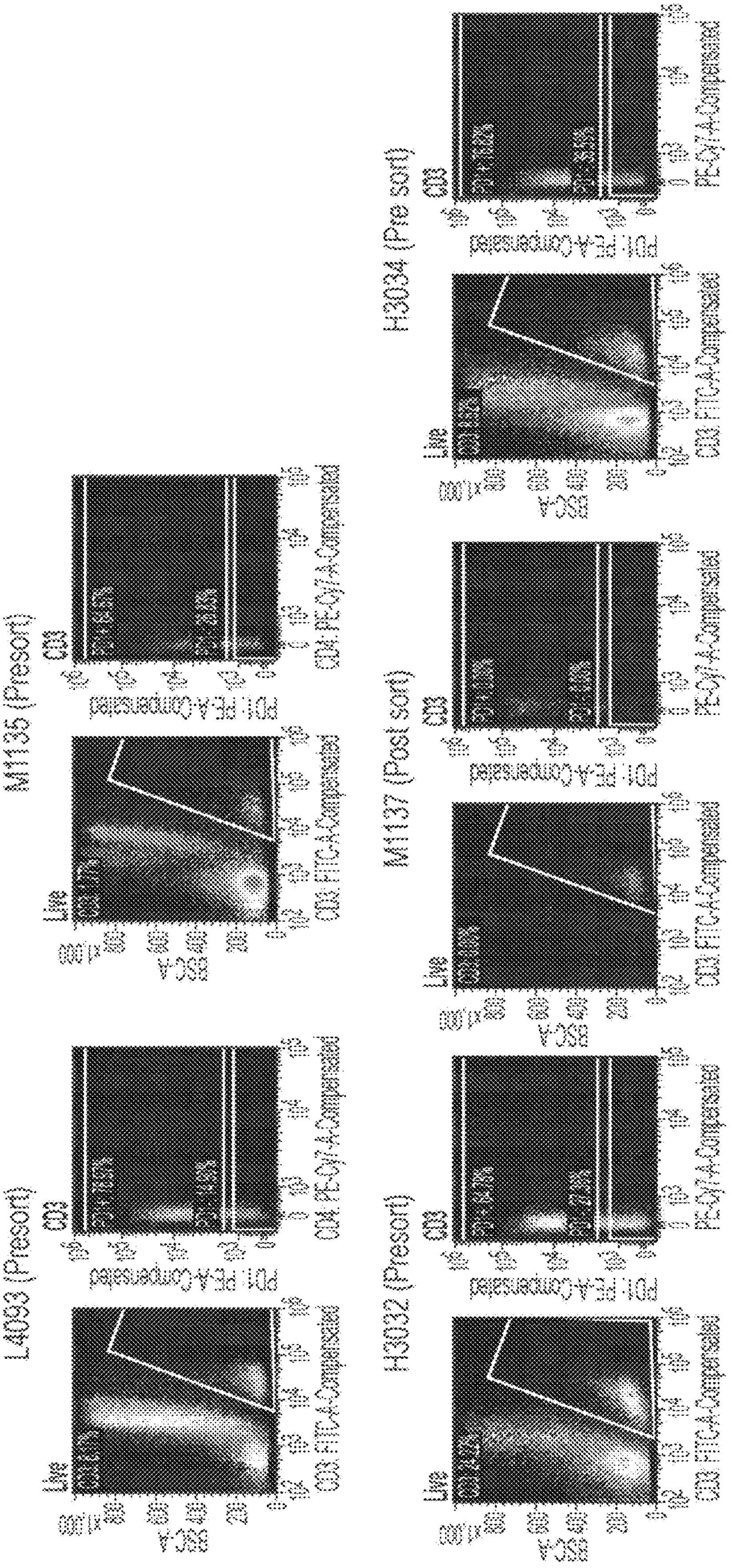
FIG. 110: Exemplary data showing PD1$^+$ Selection: Gating on PD1+ high (PD-1high) for different tumor samples, comparing presort and postsort.
Figure 111:
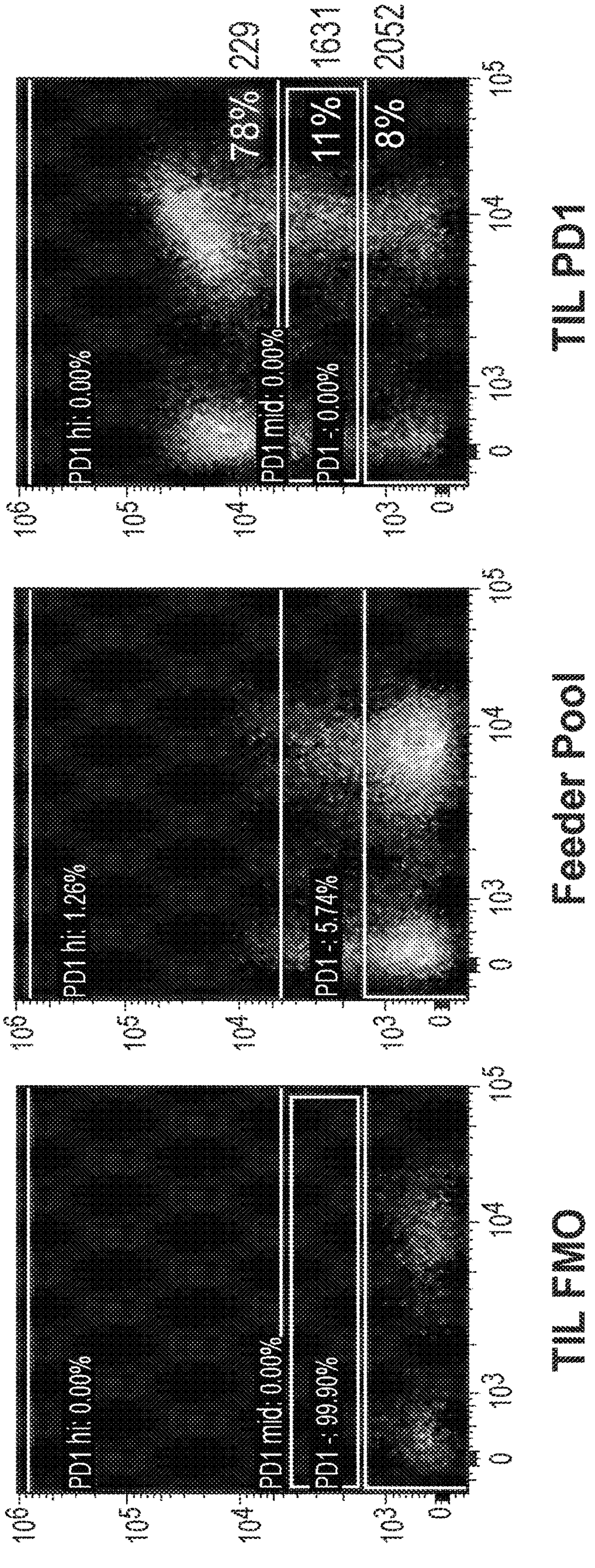
FIG. 111: Exemplary data showing PD1$^+$ Selection: Gating on PD1+ high (PD-1high) for L4097 tumor sample.
Figure 112:
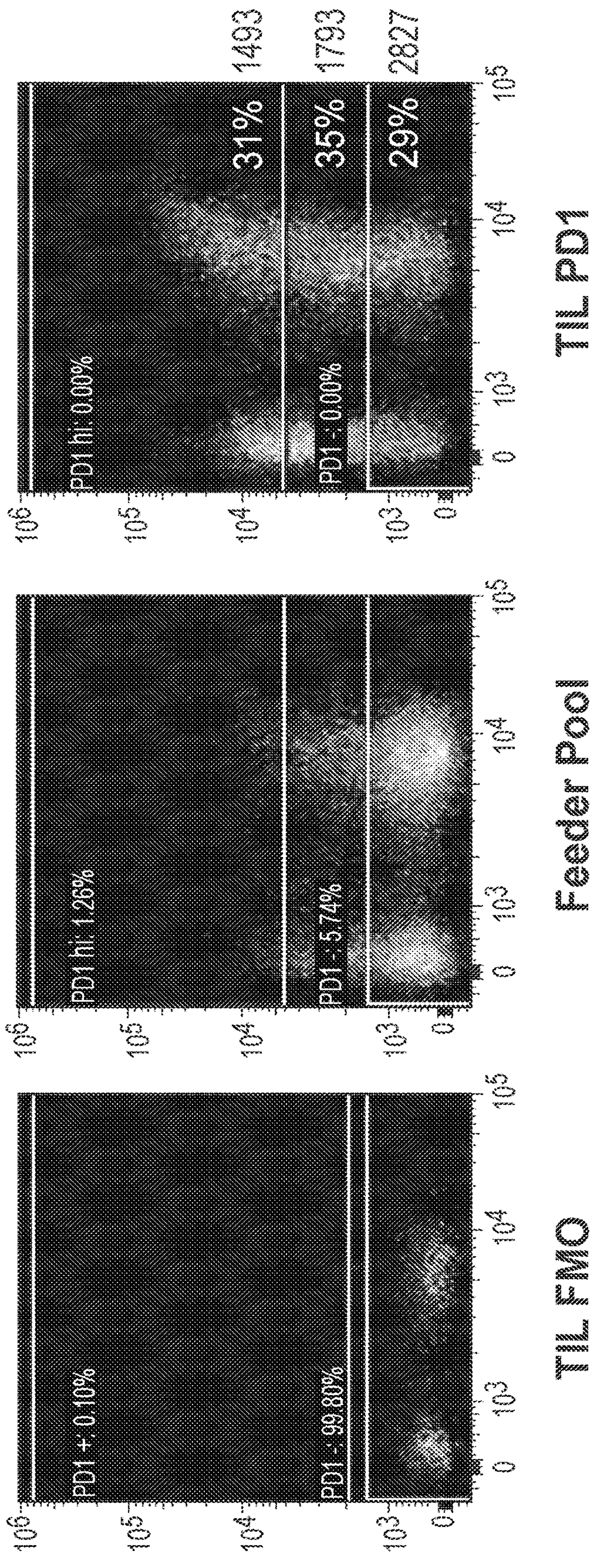
FIG. 112: Exemplary data showing PD1$^+$ Selection: Gating on PD1+ high (PD-1high) for L4089 tumor sample.
Figure 113:
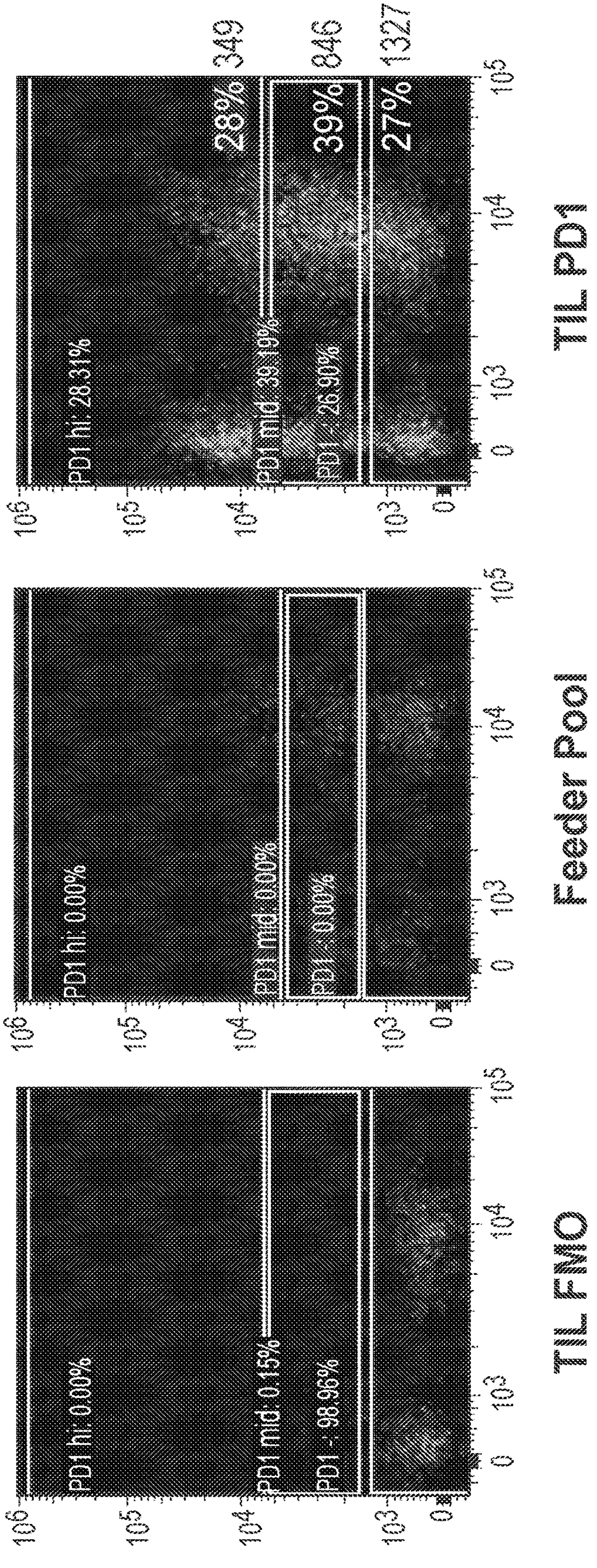
FIG. 113: Exemplary data showing PD1$^+$ Selection: Gating on PD1+ high (PD-1high) for H3035 tumor sample.
Figure 114:
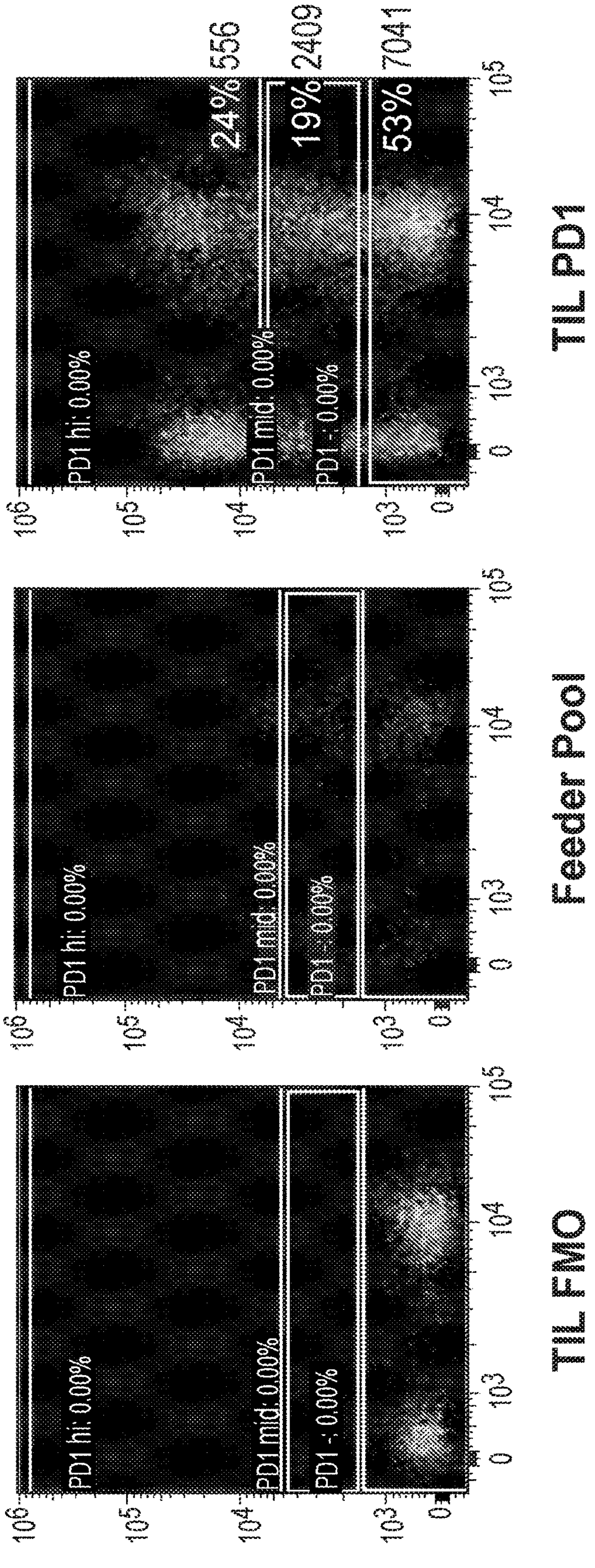
FIG. 114: Exemplary data showing PD1$^+$ Selection: Gating on PD1+ high (PD-1high) for M1139 tumor sample.
Figure 115:
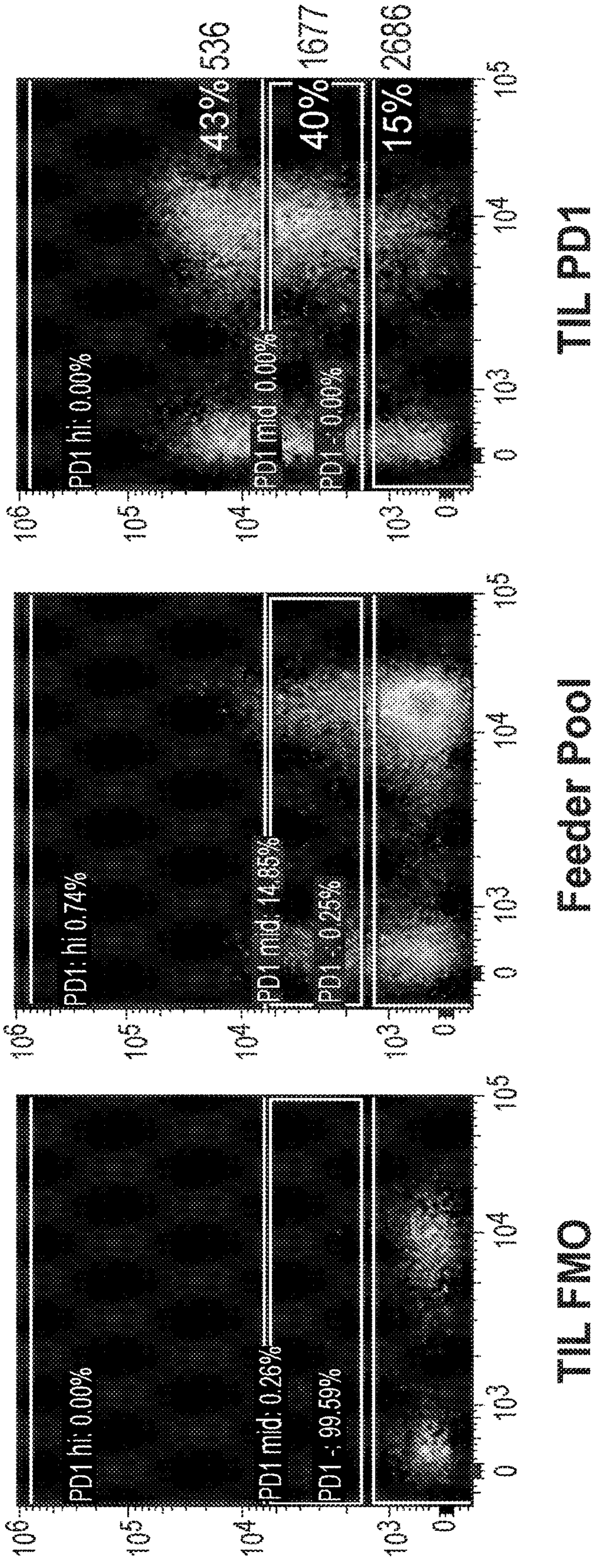
FIG. 115: Exemplary data showing PD1$^+$ Selection: Gating on PD1+ high (PD-1high) for L4100 tumor sample.
Figure 116:
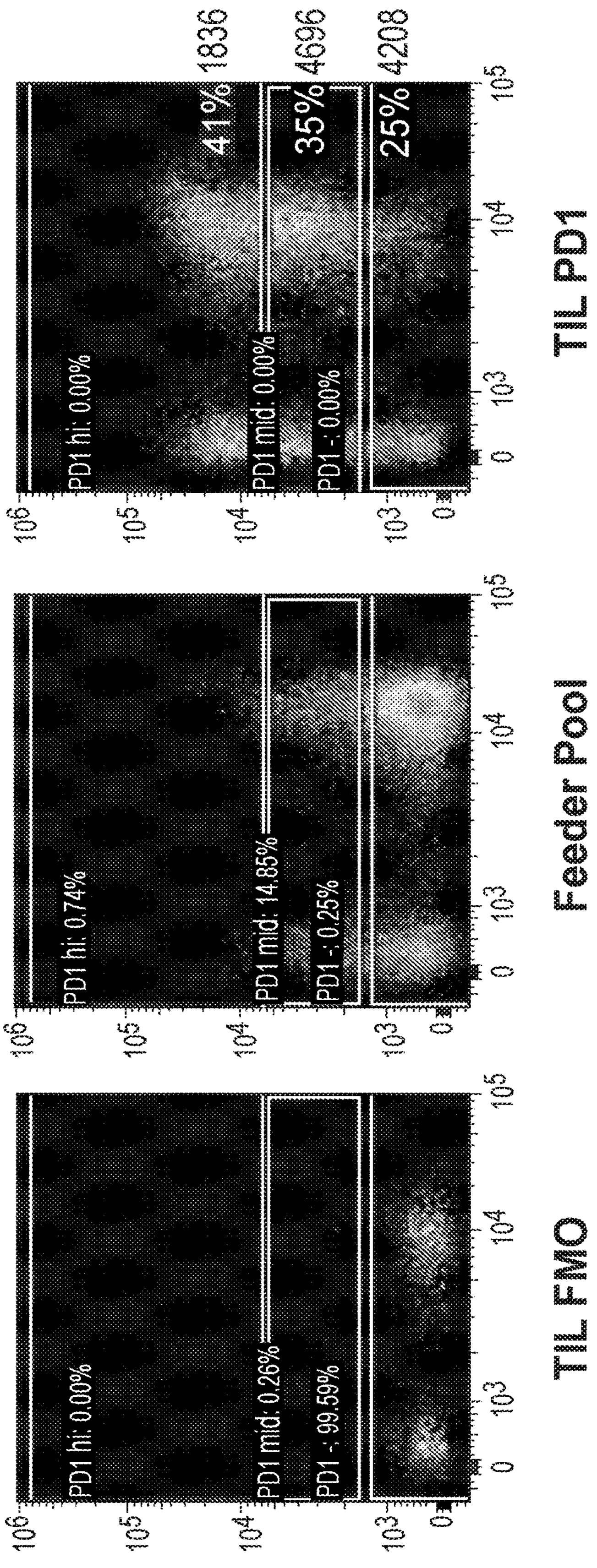
FIG. 116: Exemplary data showing PD1$^+$ Selection: Gating on PD1+ high (PD-1high) for OV8030 tumor sample.
Figure 117:
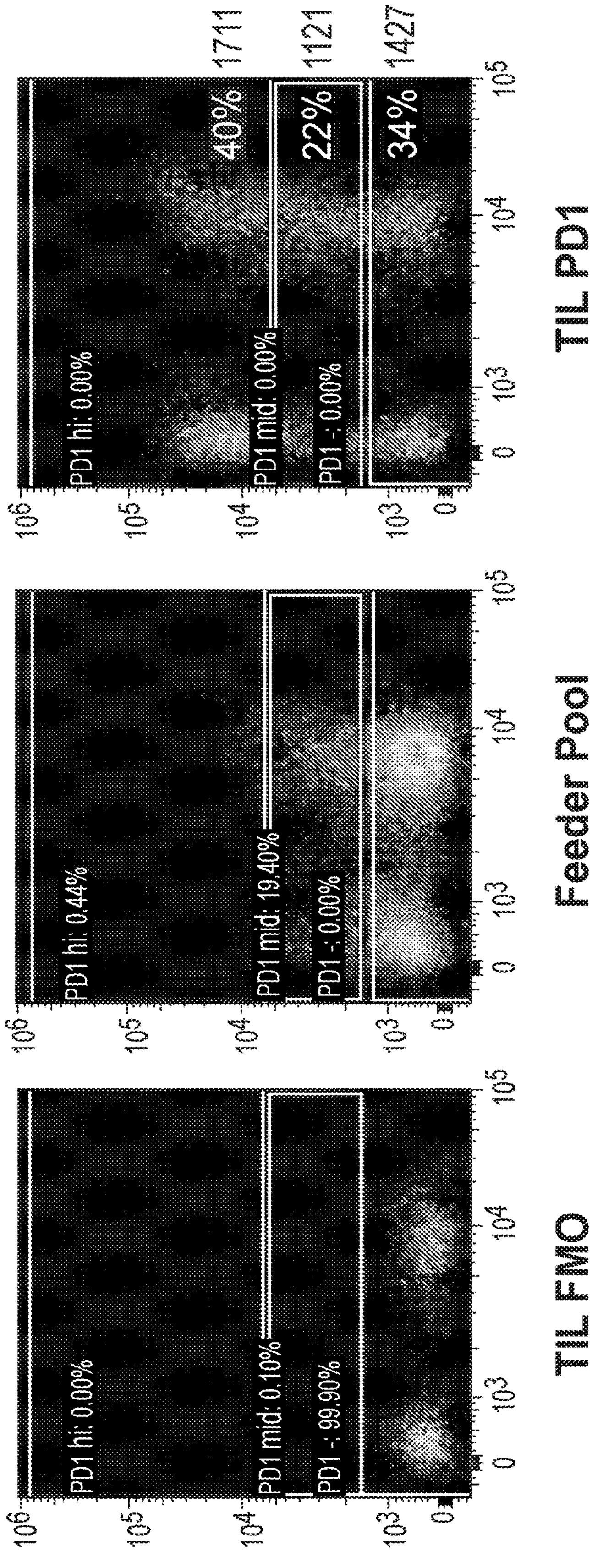
FIG. 117: Exemplary data showing PD1$^+$ Selection: Gating on PD1+ high (PD-1high) for L4104 tumor sample.
Figure 118:
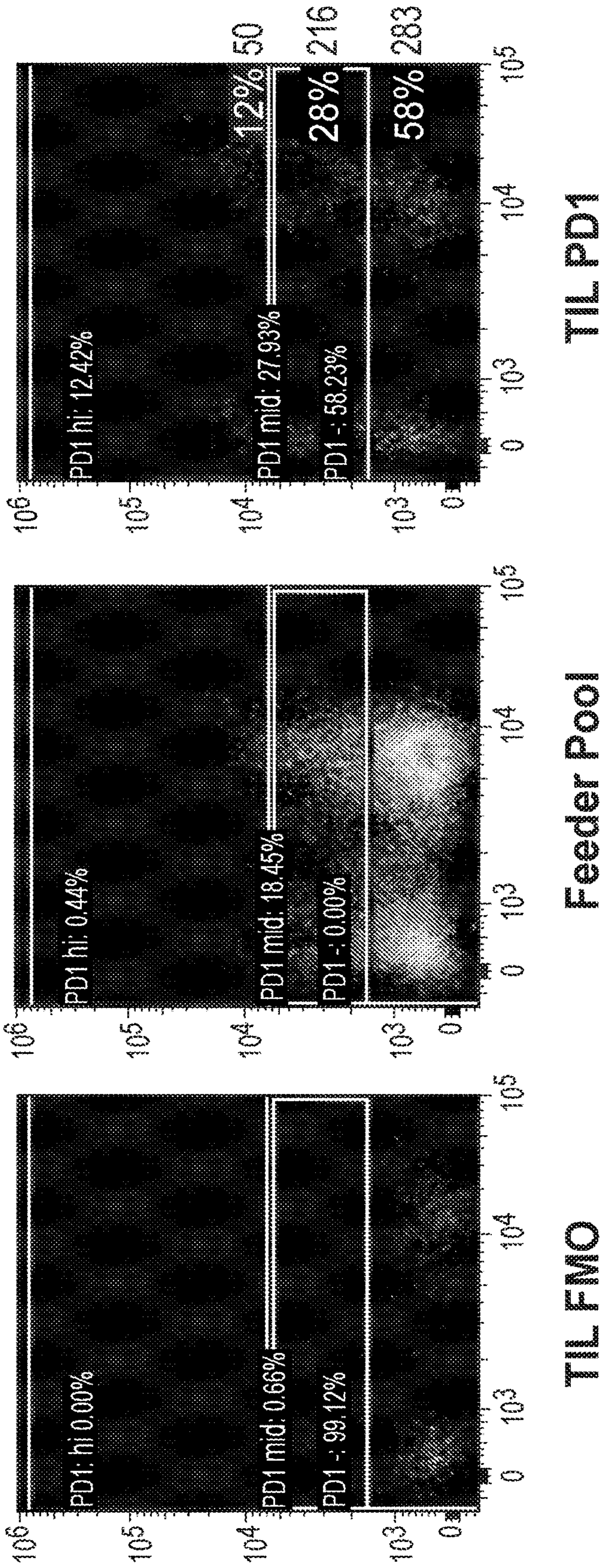
FIG. 118: Exemplary data showing PD1$^+$ Selection: Gating on PD1+ high (PD-1high) for M1132 tumor sample.
Figure 119:
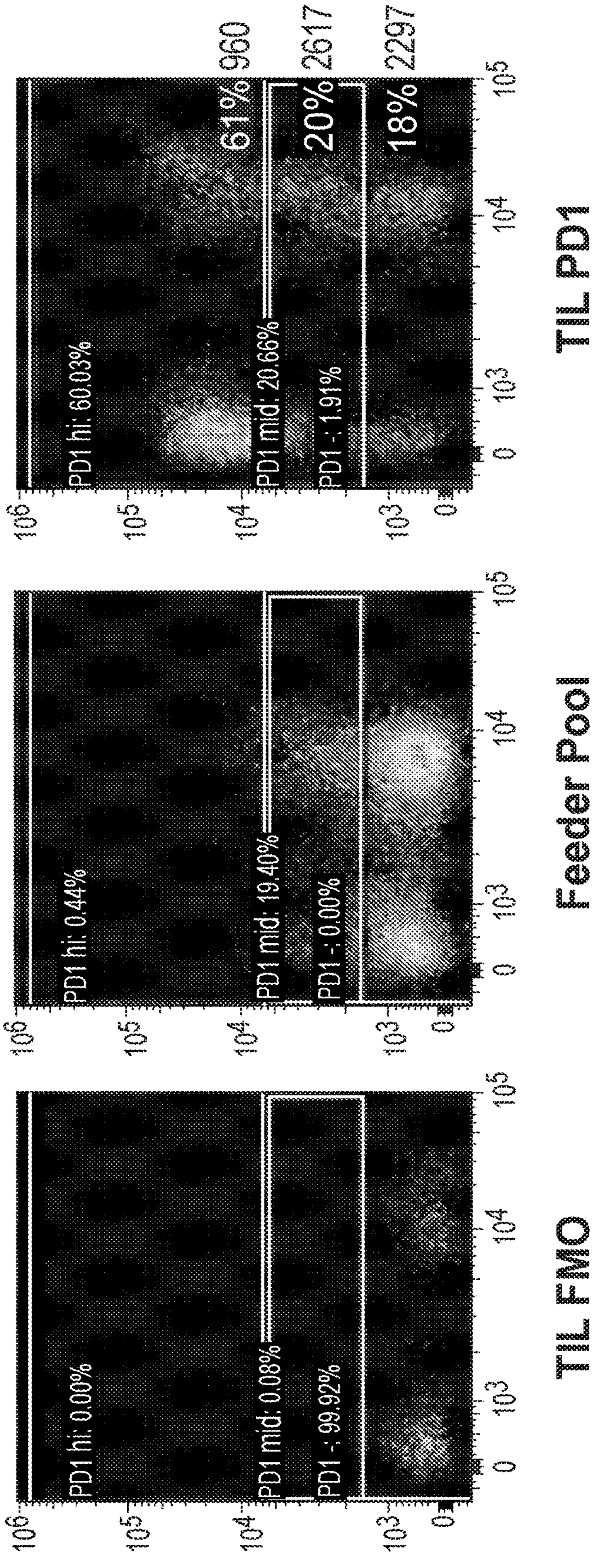
FIG. 119: Exemplary data showing PD1$^+$ Selection: Gating on PD1+ high (PD-1 high) for M1136 tumor sample.
Figure 120:
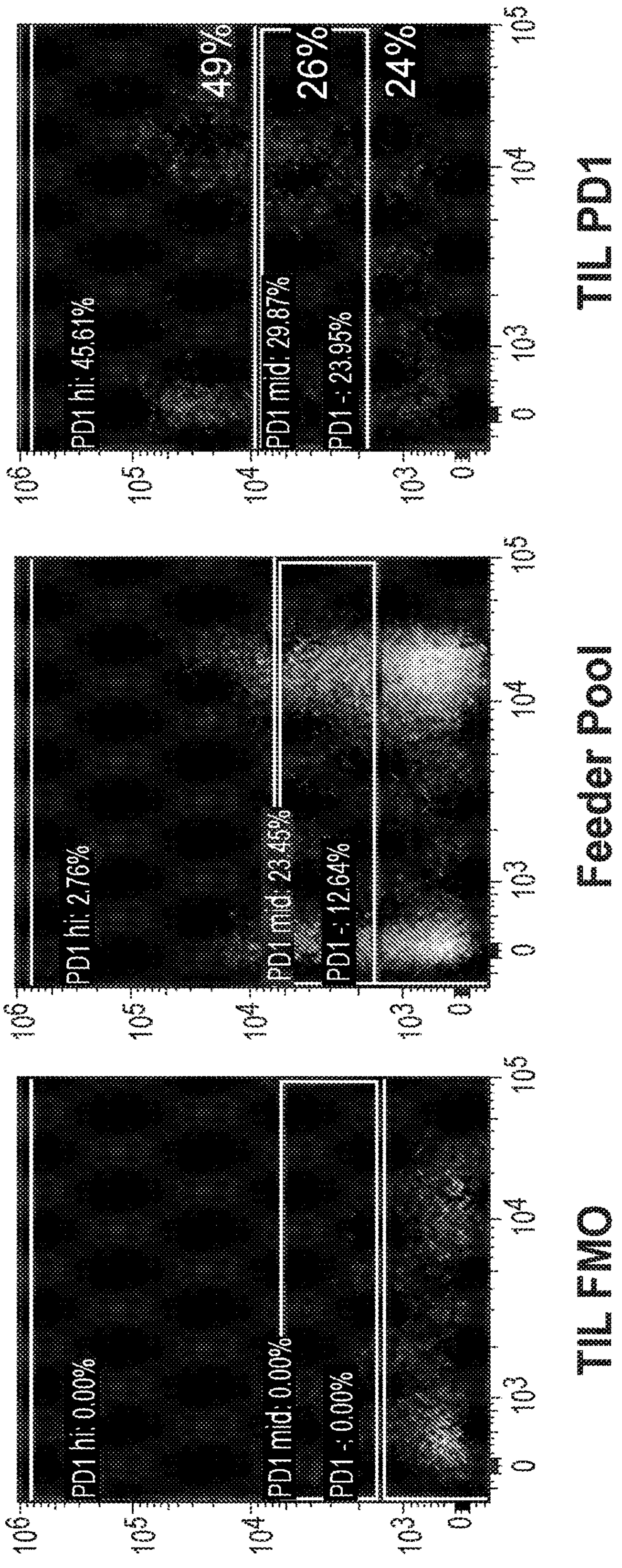
FIG. 120: Exemplary data showing PD1$^+$ Selection: Gating on PD1+ high (PD-1high) for H3037 tumor sample.
Figure 121:
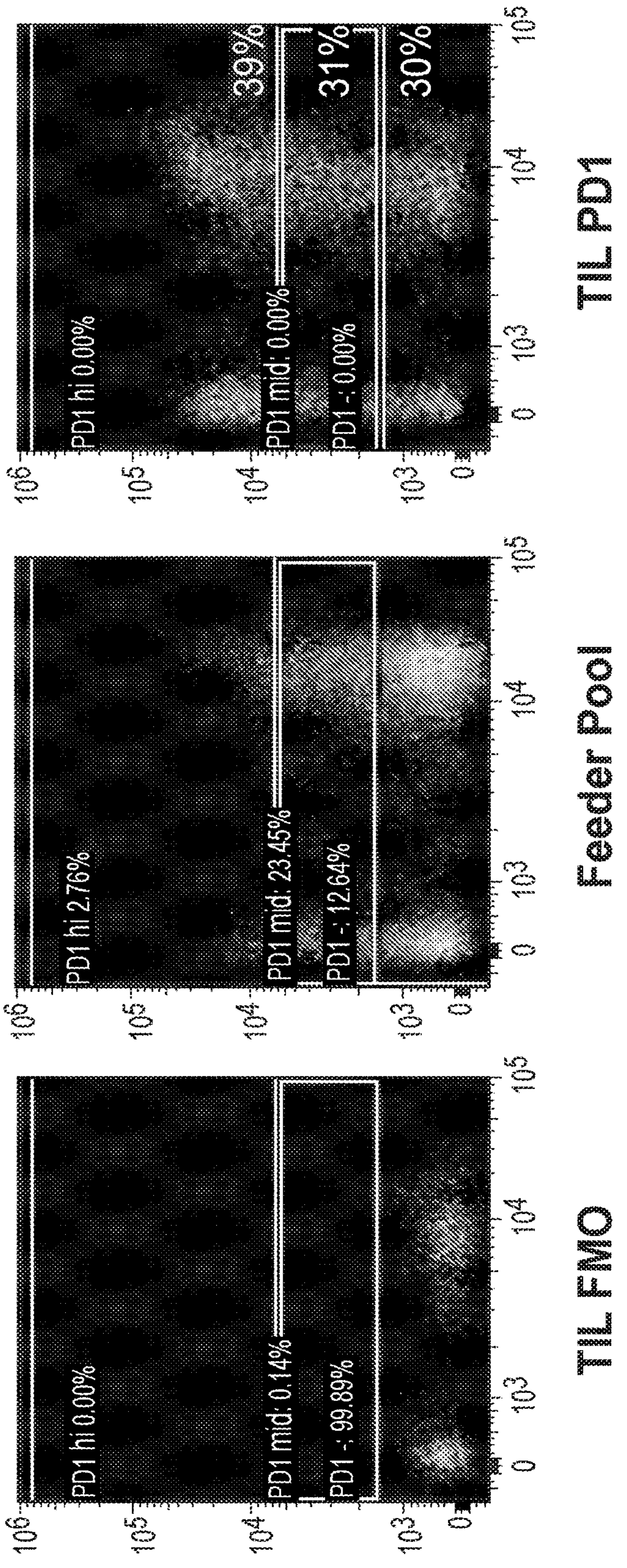
FIG. 121: Exemplary data showing PD1$^+$ Selection: Gating on PD1+ high (PD-1high) for L4106 tumor sample.

An exemplary TIL process known as process 3 (also referred to herein as GEN3) containing some of these features is depicted in FIG. 1 (in particular, e.g., FIG. 1B), and some of the advantages of this embodiment of the present invention over process 2A are described in FIGS. 1, 2, 30, and 31 (in particular, e.g., FIG. 1B). Two embodiments of process 3 are shown in FIGS. 1 and 30 (in particular, e.g., FIG. 1B). Process 2A or Gen 2 is also described in U.S. Patent Publication No. 2018/0280436, incorporated by reference herein in its entirety. The Gen 3 process is also described in U.S. Ser. No. 62/755,954 filed on Nov. 5, 2018 (116983-5045-PR).

As discussed and generally outlined herein, TILs are taken from a patient sample and manipulated to expand their number prior to transplant into a patient using the TIL expansion process described herein and referred to as Gen 3. In some embodiments, the TILs may be optionally genetically manipulated as discussed below. In some embodiments, the TILs may be cryopreserved prior to or after expansion. Once thawed, they may also be restimulated to increase their metabolism prior to infusion into a patient.

In some embodiments, the priming first expansion (including processes referred herein as the pre-Rapid Expansion (Pre-REP), as well as processes shown in FIG. 1 (in particular, e.g., FIG. 1B and/or FIG. 1C) as Step B) is shortened to 1 to 8 days and the rapid second expansion (including processes referred to herein as Rapid Expansion Protocol (REP) as well as processes shown in FIG. 1 (in particular, e.g., FIG. 1B and/or FIG. 1C) as Step D) is shortened to 1 to 9 days, as discussed in detail below as well as in the examples and figures. In some embodiments, the priming first expansion (including processes referred herein as the pre-Rapid Expansion (Pre-REP), as well as processes shown in FIG. 1 (in particular, e.g., FIG. 1B and/or FIG. 1C) as Step B) is shortened to 1 to 8 days and the rapid second expansion (including processes referred to herein as Rapid Expansion Protocol (REP) as well as processes shown in FIG. 1 (in particular, e.g., FIG. 1B and/or FIG. 1C) as Step D) is shortened to 1 to 8 days, as discussed in detail below as well as in the examples and figures. In some embodiments, the priming first expansion (including processes referred herein as the pre-Rapid Expansion (Pre-REP), as well as processes shown in FIG. 1 (in particular, e.g., FIG. 1B and/or FIG. 1C) as Step B) is shortened to 1 to 7 days and the rapid second expansion (including processes referred to herein as Rapid Expansion Protocol (REP) as well as processes shown in FIG. 1 (in particular, e.g., FIG. 1B and/or FIG. 1C) as Step D) is shortened to 1 to 9 days, as discussed in detail below as well as in the examples and figures. In some embodiments, the priming first expansion (including processes referred herein as the pre-Rapid Expansion (Pre-REP), as well as processes shown in FIG. 1 (in particular, e.g., FIG. 1B and/or FIG. 1C) as Step B) is 1 to 7 days and the rapid second expansion (including processes referred to herein as Rapid Expansion Protocol (REP) as well as processes shown in FIG. 1 (in particular, e.g., FIG. 1B and/or FIG. 1C) as Step D) is 1 to 10 days, as discussed in detail below as well as in the examples and figures. In some embodiments, the priming first expansion (for example, an expansion described as Step B in FIG. 1 (in particular, e.g., FIG. 1B and/or FIG. 1C)) is shortened to 8 days and the rapid second expansion (for example, an expansion as described in Step D in FIG. 1 (in particular, e.g., FIG. 1B and/or FIG. 1C)) is 7 to 9 days. In some embodiments, the priming first expansion (for example, an expansion described as Step B in FIG. 1 (in particular, e.g., FIG. 1B and/or FIG. 1C)) is 8 days and the rapid second expansion (for example, an expansion as described in Step D in FIG. 1 (in particular, e.g., FIG. 1B and/or FIG. 1C)) is 8 to 9 days. In some embodiments, the priming first expansion (for example, an expansion described as Step B in FIG. 1 (in particular, e.g., FIG. 1B and/or FIG. 1C)) is shortened to 7 days and the rapid second expansion (for example, an expansion as described in Step D in FIG. 1 (in particular, e.g., FIG. 1B and/or FIG. 1C)) is 7 to 8 days. In some embodiments, the priming first expansion (for example, an expansion described as Step B in FIG. 1 (in particular, e.g., FIG. 1B and/or FIG. 1C)) is shortened to 8 days and the rapid second expansion (for example, an expansion as described in Step D in FIG. 1 (in particular, e.g., FIG. 1B and/or FIG. 1C)) is 8 days. In some embodiments, the priming first expansion (for example, an expansion described as Step B in FIG. 1 (in particular, e.g., FIG. 1B and/or FIG. 1C)) is 8 days and the rapid second expansion (for example, an expansion as described in Step D in FIG. 1 (in particular, e.g., FIG. 1B and/or FIG. 1C)) is 9 days. In some embodiments, the priming first expansion (for example, an expansion described as Step B in FIG. 1 (in particular, e.g., FIG. 1B and/or FIG. 1C)) is 8 days and the rapid second expansion (for example, an expansion as described in Step D in FIG. 1 (in particular, e.g., FIG. 1B and/or FIG. 1C)) is 10 days. In some embodiments, the priming first expansion (for example, an expansion described as Step B in FIG. 1 (in particular, e.g., FIG. 1B and/or FIG. 1C)) is 7 days and the rapid second expansion (for example, an expansion as described in Step D in FIG. 1 (in particular, e.g., FIG. 1B and/or FIG. 1C)) is 7 to 10 days. In some embodiments, the priming first expansion (for example, an expansion described as Step B in FIG. 1 (in particular, e.g., FIG. 1B and/or FIG. 1C)) is 7 days and the rapid second expansion (for example, an expansion as described in Step D in FIG. 1 (in particular, e.g., FIG. 1B and/or FIG. 1C)) is 8 to 10 days. In some embodiments, the priming first expansion (for example, an expansion described as Step B in FIG. 1 (in particular, e.g., FIG. 1B and/or FIG. 1C)) is 7 days and the rapid second expansion (for example, an expansion as described in Step D in FIG. 1 (in particular, e.g., FIG. 1B and/or FIG. 1C)) is 9 to 10 days. In some embodiments, the priming first expansion (for example, an expansion described as Step B in FIG. 1 (in particular, e.g., FIG. 1B and/or FIG. 1C)) is shortened to 7 days and the rapid second expansion (for example, an expansion as described in Step D in FIG. 1 (in particular, e.g., FIG. 1B and/or FIG. 1C)) is 7 to 9 days. In some embodiments, the combination of the priming first expansion and rapid second expansion (for example, expansions described as Step B and Step D in FIG. 1 (in particular, e.g., FIG. 1B and/or FIG. 1C)) is 14-16 days, as discussed in detail below and in the examples and figures. Particularly, it is considered that certain embodiments of the present invention comprise a priming first expansion step in which TILs are activated by exposure to an anti-CD3 antibody, e.g., OKT-3 in the presence of IL-2 or exposure to an antigen in the presence of at least IL-2 and an anti-CD3 antibody e.g. OKT-3. In certain embodiments, the TILs which are activated in the priming first expansion step as described above are a first population of TILs i.e., which are a primary cell population.

The "Step" Designations A, B, C, etc., below are in reference to the non-limiting example in FIG. 1 (in particular, e.g., FIG. 1B and/or FIG. 1C) and in reference to certain non-limiting embodiments described herein. The ordering of the Steps below and in FIG. 1 (in particular, e.g., FIG. 1B and/or FIG. 1C) is exemplary and any combination or order of steps, as well as additional steps, repetition of steps, and/or omission of steps is contemplated by the present application and the methods disclosed herein.

A. STEP A: Obtain Patient Tumor Sample

In general, TILs are initially obtained from a patient tumor sample ("primary TILs") or from circulating lymphocytes, such as peripherial blood lymphocytes, including perpherial blood lymphocytes having TIL-like characteristics, and are then expanded into a larger population for further manipulation as described herein, optionally cryopreserved, and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, the cancer is selected from cervical cancer, head and neck cancer (including, for example, head and neck squamous cell carcinoma (HNSCC)), glioblastoma (GBM), gastrointestinal cancer, ovarian cancer, sarcoma, pancreatic cancer, bladder cancer, breast cancer, triple negative breast cancer, and non-small cell lung carcinoma. In some embodiments, useful TILs are obtained from malignant melanoma tumors, as these have been reported to have particularly high levels of TILs.

Once obtained, the tumor sample is generally fragmented using sharp dissection into small pieces of between 1 to about 8 $mm^3$, with from about 2-3 $mm^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

As indicated above, in some embodiments, the TILs are derived from solid tumors. In some embodiments, the solid tumors are not fragmented. In some embodiments, the solid tumors are not fragmented and are subjected to enzymatic digestion as whole tumors. In some embodiments, the tumors are digested in in an enzyme mixture comprising collagenase, DNase, and hyaluronidase. In some embodiments, the tumors are digested in in an enzyme mixture comprising collagenase, DNase, and hyaluronidase for 1-2 hours. In some embodiments, the tumors are digested in in an enzyme mixture comprising collagenase, DNase, and hyaluronidase for 1-2 hours at 37° C., 5% $CO_2$. In some embodiments, the tumors are digested in in an enzyme mixture comprising collagenase, DNase, and hyaluronidase for 1-2 hours at 37° C., 5% $CO_2$ with rotation. In some embodiments, the tumors are digested overnight with constant rotation. In some embodiments, the tumors are digested overnight at 37° C., 5% $CO_2$ with constant rotation. In some embodiments, the whole tumor is combined with with the enzymes to form a tumor digest reaction mixture.

In some embodiments, the tumor is reconstituted with the lyophilized enzymes in a sterile buffer. In some embodiments, the buffer is sterile HBSS.

In some embodiments, the enzyme mixture comprises collagenase. In some embodiments, the collagenase is collagenase IV. In some embodiments, the working stock for the collagenase is a 100 mg/ml 10× working stock.

In some embodiments, the enzyme mixture comprises DNAse. In some embodiments, the working stock for the DNAse is a 10,000 IU/ml 10× working stock.

In some embodiments, the enzyme mixture comprises hyaluronidase. In some embodiments, the working stock for the hyaluronidase is a 10-mg/ml 10× working stock.

In some embodiments, the enzyme mixture comprises 10 mg/ml collagenase, 1000 IU/ml DNAse, and 1 mg/ml hyaluronidase.

In some embodiments, the enzyme mixture comprises 10 mg/ml collagenase, 500 IU/ml DNAse, and 1 mg/ml hyaluronidase.

In some embodiments, the enzyme mixture comprises about 10 mg/ml collagenase, about 1000 IU/ml DNAse, and about 1 mg/ml hyaluronidase.

In general, the cell suspension obtained from the tumor is called a "primary cell population" or a "freshly obtained" or a "freshly isolated" cell population. In certain embodiments, the freshly obtained cell population of TILs is exposed to a cell culture medium comprising antigen presenting cells, IL-12 and OKT-3.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 1 (in particular, e.g., FIG. 1B and/or FIG. 1C)). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the step of fragmentation is an in vitro or ex-vivo process. In some embodiments, the tumor is fragmented and 10, 20, 30, 40 or more fragments or pieces are placed in each container for the priming first expansion. In some embodiments, the tumor is fragmented and 30 or 40 fragments or pieces are placed in each container for the priming first expansion. In some embodiments, the tumor is fragmented and 40 fragments or pieces are placed in each container for the priming first expansion. In some embodiments, the multiple fragments comprise about 4 to about 50 fragments, wherein each fragment has a volume of about 27 $mm^3$. In some embodiments, the multiple fragments comprise about 30 to about 60 fragments with a total volume of about 1300 $mm^3$ to about 1500 $mm^3$. In some embodiments, the multiple fragments comprise about 50 fragments with a total volume of about 1350 $mm^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 $mm^3$ and 10 $mm^3$. In some embodiments, the tumor fragment is between about 1 $mm^3$ and 8 $mm^3$. In some embodiments, the tumor fragment is about 1 $mm^3$. In some embodiments, the tumor fragment is about 2 $mm^3$. In some embodiments, the tumor fragment is about 3 $mm^3$. In some embodiments, the tumor fragment is about 4 $mm^3$. In some embodiments, the tumor fragment is about 5 $mm^3$. In some embodiments, the tumor fragment is about 6 $mm^3$. In some embodiments, the tumor fragment is about 7 $mm^3$. In some embodiments, the tumor fragment is about 8 $mm^3$. In some embodiments, the tumor fragment is about 9 $mm^3$. In some embodiments, the tumor fragment is about 10 $mm^3$. In some embodiments, the tumor fragments are 1-4 mm×1-4 mm×1-4 mm. In some embodiments, the tumor fragments are 1 mm×1 mm×1 mm. In some embodiments, the tumor fragments are 2 mm×2 mm×2 mm. In some embodiments, the tumor fragments are 3 mm×3 mm×3 mm. In some embodiments, the tumor fragments are 4 mm×4 mm×4 mm.

In some embodiments, the tumors are fragmented in order to minimize the amount of hemorrhagic, necrotic, and/or fatty tissues on each piece. In some embodiments, the tumors are fragmented in order to minimize the amount of hemorrhagic tissue on each piece. In some embodiments, the tumors are fragmented in order to minimize the amount of necrotic tissue on each piece. In some embodiments, the tumors are fragmented in order to minimize the amount of fatty tissue on each piece. In certain embodiments, the step of fragmentation of the tumor is an in vitro or ex-vivo method.

In some embodiments, the tumor fragmentation is performed in order to maintain the tumor internal structure. In some embodiments, the tumor fragmentation is performed without preforming a sawing motion with a scalpel. In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the cell suspension prior to the priming first expansion step is called a "primary cell population" or a "freshly obtained" or "freshly isolated" cell population.

In some embodiments, cells can be optionally frozen after sample isolation (e.g., after obtaining the tumor sample and/or after obtaining the cell suspension from the tumor sample) and stored frozen prior to entry into the expansion described in Step B, which is described in further detail below, as well as exemplified in FIG. 1 (in particular, e.g., FIG. 1B and/or FIG. 1C).

1. Core/Small Biopsy Derived TILS

In some embodiments, TILs are initially obtained from a patient tumor sample ("primary TILs") obtained by a core biopsy or similar procedure and then expanded into a larger population for further manipulation as described herein, optionally cryopreserved, and optionally evaluated for phenotype and metabolic parameters.

In some embodiments, a patient tumor sample may be obtained using methods known in the art, generally via small biopsy, core biopsy, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. In some embodiments, the sample can be from multiple small tumor samples or biopsies. In some embodiments, the sample can comprise multiple tumor samples from a single tumor from the same patient. In some embodiments, the sample can comprise multiple tumor samples from one, two, three, or four tumors from the same patient. In some embodiments, the sample can comprise multiple tumor samples from multiple tumors from the same patient. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, the cancer is selected from cervical cancer, head and neck cancer (including, for example, head and neck squamous cell carcinoma (HNSCC)), glioblastoma (GBM), gastrointestinal cancer, ovarian cancer, sarcoma, pancreatic cancer, bladder cancer, breast cancer, triple negative breast cancer, and non-small cell lung carcinoma (NSCLC). In some embodiments, useful TILs are obtained from malignant melanoma tumors, as these have been reported to have particularly high levels of TILs.

In general, the cell suspension obtained from the tumor core or fragment is called a "primary cell population" or a "freshly obtained" or a "freshly isolated" cell population. In certain embodiments, the freshly obtained cell population of TILs is exposed to a cell culture medium comprising antigen presenting cells, IL-2 and OKT-3.

In some embodiments, if the tumor is metastatic and the primary lesion has been efficiently treated/removed in the past, removal of one of the metastatic lesions may be needed. In some embodiments, the least invasive approach is to remove a skin lesion, or a lymph node on the neck or axillary area when available. In some embodiments, a skin lesion is removed or small biopsy thereof is removed. In some embodiments, a lymph node or small biopsy thereof is removed. In some embodiments, a lung or liver metastatic lesion, or an intra-abdominal or thoracic lymph node or small biopsy can thereof can be employed.

In some embodiments, the tumor is a melanoma. In some embodiments, the small biopsy for a melanoma comprises a mole or portion thereof.

In some embodiments, the small biopsy is a punch biopsy. In some embodiments, the punch biopsy is obtained with a circular blade pressed into the skin. In some embodiments, the punch biopsy is obtained with a circular blade pressed into the skin. around a suspicious mole. In some embodiments, the punch biopsy is obtained with a circular blade pressed into the skin, and a round piece of skin is removed. In some embodiments, the small biopsy is a punch biopsy and round portion of the tumor is removed.

In some embodiments, the small biopsy is an excisional biopsy. In some embodiments, the small biopsy is an excisional biopsy and the entire mole or growth is removed. In some embodiments, the small biopsy is an excisional biopsy and the entire mole or growth is removed along with a small border of normal-appearing skin.

In some embodiments, the small biopsy is an incisional biopsy. In some embodiments, the small biopsy is an incisional biopsy and only the most irregular part of a mole or growth is taken. In some embodiments, the small biopsy is an incisional biopsy and the incisional biopsy is used when other techniques can't be completed, such as if a suspicious mole is very large.

In some embodiments, the small biopsy is a lung biopsy. In some embodiments, the small biopsy is obtained by bronchoscopy. Generally, bronchoscopy, the patient is put under anesthesia, and a small tool goes through the nose or mouth, down the throat, and into the bronchial passages, where small tools are used to remove some tissue. In some embodiments, where the tumor or growth cannot be reached via bronchoscopy, a transthoracic needle biopsy can be employed. Generally, for a transthoracic needle biopsy, the patient is also under anesthesia and a needle is inserted through the skin directly into the suspicious spot to remove a small sample of tissue. In some embodiments, a transthoracic needle biopsy may require interventional radiology (for example, the use of x-rays or CT scan to guide the needle). In some embodiments, the small biopsy is obtained by needle biopsy. In some embodiments, the small biopsy is obtained endoscopic ultrasound (for example, an endoscope with a light and is placed through the mouth into the esophagus). In some embodiments, the small biopsy is obtained surgically.

In some embodiments, the small biopsy is a head and neck biopsy. In some embodiments, the small biopsy is an incisional biopsy. In some embodiments, the small biopsy is an incisional biopsy, wherein a small piece of tissue is cut from an abnormal-looking area. In some embodiments, if the abnormal region is easily accessed, the sample may be taken without hospitalization. In some embodiments, if the tumor is deeper inside the mouth or throat, the biopsy may need to be done in an operating room, with general anesthesia. In some embodiments, the small biopsy is an excisional biopsy. In some embodiments, the small biopsy is an excisional biopsy, wherein the whole area is removed. In some embodiments, the small biopsy is a fine needle aspiration (FNA). In some embodiments, the small biopsy is a fine needle aspiration (FNA), wherein a very thin needle attached to a syringe is used to extract (aspirate) cells from a tumor or lump. In some embodiments, the small biopsy is a punch biopsy. In some embodiments, the small biopsy is a punch biopsy, wherein punch forceps are used to remove a piece of the suspicious area.

In some embodiments, the small biopsy is a cervical biopsy. In some embodiments, the small biopsy is obtained via colposcopy. Generally, colposcopy methods employ the use of a lighted magnifying instrument attached to magnifying binoculars (a colposcope) which is then used to biopsy a small section of the surface of the cervix. In some embodiments, the small biopsy is a conization/cone biopsy. In some embodiments, the small biopsy is a conization/cone biopsy, wherein an outpatient surgery may be needed to remove a larger piece of tissue from the cervix. In some embodiments, the cone biopsy, in addition to helping to confirm a diagnosis, a cone biopsy can serve as an initial treatment.

The term "solid tumor" refers to an abnormal mass of tissue that usually does not contain cysts or liquid areas. Solid tumors may be benign or malignant. The term "solid tumor cancer refers to malignant, neoplastic, or cancerous solid tumors. Solid tumor cancers include, but are not limited to, sarcomas, carcinomas, and lymphomas, such as cancers of the lung, breast, triple negative breast cancer, prostate, colon, rectum, and bladder. In some embodiments, the cancer is selected from cervical cancer, head and neck cancer, glioblastoma, ovarian cancer, sarcoma, pancreatic cancer, bladder cancer, breast cancer, triple negative breast cancer, and non-small cell lung carcinoma. The tissue structure of solid tumors includes interdependent tissue compartments including the parenchyma (cancer cells) and the supporting stromal cells in which the cancer cells are dispersed and which may provide a supporting microenvironment.

In some embodiments, the sample from the tumor is obtained as a fine needle aspirate (FNA), a core biopsy, a small biopsy (including, for example, a punch biopsy). In some embodiments, sample is placed first into a G-Rex 10. In some embodiments, sample is placed first into a G-Rex 10 when there are 1 or 2 core biopsy and/or small biopsy samples. In some embodiments, sample is placed first into a G-Rex 100 when there are 3, 4, 5, 6, 8, 9, or 10 or more core biopsy and/or small biopsy samples. In some embodiments, sample is placed first into a G-Rex 500 when there are 3, 4, 5, 6, 8, 9, or 10 or more core biopsy and/or small biopsy samples.

The FNA can be obtained from a tumor selected from the group consisting of lung, melanoma, head and neck, cervical, ovarian, pancreatic, glioblastoma, colorectal, and sarcoma. In some embodiments, the FNA is obtained from a lung tumor, such as a lung tumor from a patient with non-small cell lung cancer (NSCLC). In some cases, the patient with NSCLC has previously undergone a surgical treatment.

TILs described herein can be obtained from an FNA sample. In some cases, the FNA sample is obtained or isolated from the patient using a fine gauge needle ranging from an 18 gauge needle to a 25 gauge needle. The fine gauge needle can be 18 gauge, 19 gauge, 20 gauge, 21 gauge, 22 gauge, 23 gauge, 24 gauge, or 25 gauge. In some embodiments, the FNA sample from the patient can contain at least 400,000 TILs, e.g., 400,000 TILs, 450,000 TILs, 500,000 TILs, 550,000 TILs, 600,000 TILs, 650,000 TILs, 700,000 TILs, 750,000 TILs, 800,000 TILs, 850,000 TILs, 900,000 TILs, 950,000 TILs, or more.

In some cases, the TILs described herein are obtained from a core biopsy sample. In some cases, the core biopsy sample is obtained or isolated from the patient using a surgical or medical needle ranging from an 11 gauge needle to a 16 gauge needle. The needle can be 11 gauge, 12 gauge, 13 gauge, 14 gauge, 15 gauge, or 16 gauge. In some embodiments, the core biopsy sample from the patient can contain at least 400,000 TILs, e.g., 400,000 TILs, 450,000 TILs, 500,000 TILs, 550,000 TILs, 600,000 TILs, 650,000 TILs, 700,000 TILs, 750,000 TILs, 800,000 TILs, 850,000 TILs, 900,000 TILs, 950,000 TILs, or more.

In general, the harvested cell suspension is called a "primary cell population" or a "freshly harvested" cell population.

In some embodiments, the TILs are not obtained from tumor digests. In some embodiments, the solid tumor cores are not fragmented.

In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

2. Methods of Expanding Peripheral Blood Lymphocytes (PBLs) from Peripheral Blood PBL Method 1. In an embodiment of the invention, PBLs are expanded using the processes described herein. In an embodiment of the invention, the method comprises obtaining a PBMC sample from whole blood. In an embodiment, the method comprises enriching T-cells by isolating pure T-cells from PBMCs using negative selection of a non-CD19+ fraction. In an embodiment, the method comprises enriching T-cells by isolating pure T-cells from PBMCs using magnetic bead-based negative selection of a non-CD19+ fraction.

In an embodiment of the invention, PBL Method 1 is performed as follows: On Day 0, a cryopreserved PBMC sample is thawed and PBMCs are counted. T-cells are isolated using a Human Pan T-Cell Isolation Kit and LS columns (Miltenyi Biotec).

PBL Method 2. In an embodiment of the invention, PBLs are expanded using PBL Method 2, which comprises obtaining a PBMC sample from whole blood. The T-cells from the PBMCs are enriched by incubating the PBMCs for at least three hours at 37° C. and then isolating the non-adherent cells.

In an embodiment of the invention, PBL Method 2 is performed as follows: On Day 0, the cryopreserved PMBC sample is thawed and the PBMC cells are seeded at 6 million cells per well in a 6 well plate in CM-2 media and incubated for 3 hours at 37 degrees Celsius. After 3 hours, the non-adherent cells, which are the PBLs, are removed and counted.

PBL Method 3. In an embodiment of the invention, PBLs are expanded using PBL Method 3, which comprises obtaining a PBMC sample from peripheral blood. B-cells are isolated using a CD19+ selection and T-cells are selected using negative selection of the non-CD19+ fraction of the PBMC sample.

In an embodiment of the invention, PBL Method 3 is performed as follows: On Day 0, cryopreserved PBMCs derived from peripheral blood are thawed and counted. CD19+B-cells are sorted using a CD19 Multisort Kit, Human (Miltenyi Biotec). Of the non-CD19+ cell fraction, T-cells are purified using the Human Pan T-cell Isolation Kit and LS Columns (Miltenyi Biotec).

In an embodiment, PBMCs are isolated from a whole blood sample. In an embodiment, the PBMC sample is used as the starting material to expand the PBLs. In an embodiment, the sample is cryopreserved prior to the expansion process. In another embodiment, a fresh sample is used as the starting material to expand the PBLs. In an embodiment of the invention, T-cells are isolated from PBMCs using methods known in the art. In an embodiment, the T-cells are isolated using a Human Pan T-cell isolation kit and LS columns. In an embodiment of the invention, T-cells are isolated from PBMCs using antibody selection methods known in the art, for example, CD19 negative selection.

In an embodiment of the invention, the PBMC sample is incubated for a period of time at a desired temperature effective to identify the non-adherent cells. In an embodiment of the invention, the incubation time is about 3 hours. In an embodiment of the invention, the temperature is about 37° Celsius. The non-adherent cells are then expanded using the process described above.

In some embodiments, the PBMC sample is from a subject or patient who has been optionally pre-treated with a regimen comprising a kinase inhibitor or an ITK inhibitor. In some embodiments, the tumor sample is from a subject or patient who has been pre-treated with a regimen comprising a kinase inhibitor or an ITK inhibitor. In some embodiments, the PBMC sample is from a subject or patient who has been pre-treated with a regimen comprising a kinase inhibitor or an ITK inhibitor, has undergone treatment for at least 1 month, at least 2 months, at least 3 months, at least 4 months, at least 5 months, at least 6 months, or 1 year or more. In another embodiment, the PBMCs are derived from a patient who is currently on an ITK inhibitor regimen, such as ibrutinib.

In some embodiments, the PBMC sample is from a subject or patient who has been pre-treated with a regimen comprising a kinase inhibitor or an ITK inhibitor and is refractory to treatment with a kinase inhibitor or an ITK inhibitor, such as ibrutinib.

In some embodiments, the PBMC sample is from a subject or patient who has been pre-treated with a regimen comprising a kinase inhibitor or an ITK inhibitor but is no longer undergoing treatment with a kinase inhibitor or an ITK inhibitor. In some embodiments, the PBMC sample is from a subject or patient who has been pre-treated with a regimen comprising a kinase inhibitor or an ITK inhibitor but is no longer undergoing treatment with a kinase inhibitor or an ITK inhibitor and has not undergone treatment for at least 1 month, at least 2 months, at least 3 months, at least 4 months, at least 5 months, at least 6 months, or at least 1 year or more. In another embodiment, the PBMCs are derived from a patient who has prior exposure to an ITK inhibitor, but has not been treated in at least 3 months, at least 6 months, at least 9 months, or at least 1 year.

In an embodiment of the invention, at Day 0, cells are selected for CD19+ and sorted accordingly. In an embodiment of the invention, the selection is made using antibody binding beads. In an embodiment of the invention, pure T-cells are isolated on Day 0 from the PBMCs.

In an embodiment of the invention, for patients that are not pre-treated with ibrutinib or other ITK inhibitor, 10-15 ml of Buffy Coat will yield about $5\times10^9$ PBMC, which, in turn, will yield about $5.5\times10^7$ PBLs.

In an embodiment of the invention, for patients that are pre-treated with ibrutinib or other ITK inhibitor, the expansion process will yield about $20\times10^9$ PBLs. In an embodiment of the invention, $40.3\times10^6$ PBMCs will yield about $4.7\times10^5$ PBLs.

In any of the foregoing embodiments, PBMCs may be derived from a whole blood sample, by apheresis, from the buffy coat, or from any other method known in the art for obtaining PBMCs.

3. Methods of Expanding Marrow Infiltrating Lymphocytes (MILs) from PBMCs Derived from Bone Marrow MIL Method 3. In an embodiment of the invention, the method comprises obtaining PBMCs from the bone marrow. On Day 0, the PBMCs are selected for CD3+/CD33+/CD20+/CD14+ and sorted, and the non-CD3+/CD33+/CD20+/CD14+ cell fraction is sonicated and a portion of the sonicated cell fraction is added back to the selected cell fraction.

In an embodiment of the invention, MIL Method 3 is performed as follows: On Day 0, a cryopreserved sample of PBMCs is thawed and PBMCs are counted. The cells are stained with CD3, CD33, CD20, and CD14 antibodies and sorted using a S3e cell sorted (Bio-Rad). The cells are sorted into two fractions—an immune cell fraction (or the MIL fraction) (CD3+CD33+CD20+CD14+) and an AML blast cell fraction (non-CD3+CD33+CD20+CD14+).

In an embodiment of the invention, PBMCs are obtained from bone marrow. In an embodiment, the PBMCs are obtained from the bone marrow through apheresis, aspiration, needle biopsy, or other similar means known in the art. In an embodiment, the PBMCs are fresh. In another embodiment, the PBMCs are cryopreserved.

In an embodiment of the invention, MILs are expanded from 10-50 ml of bone marrow aspirate. In an embodiment of the invention, 10 ml of bone marrow aspirate is obtained from the patient. In another embodiment, 20 ml of bone marrow aspirate is obtained from the patient. In another embodiment, 30 ml of bone marrow aspirate is obtained from the patient. In another embodiment, 40 ml of bone marrow aspirate is obtained from the patient. In another embodiment, 50 ml of bone marrow aspirate is obtained from the patient.

In an embodiment of the invention, the number of PBMCs yielded from about 10-50 ml of bone marrow aspirate is about $5\times10^7$ to about $10\times10^7$ PBMCs. In another embodiment, the number of PMBCs yielded is about $7\times10^7$ PBMCs.

In an embodiment of the invention, about $5\times10^7$ to about $10\times10^7$ PBMCs, yields about $0.5\times10^6$ to about $1.5\times10^6$ MILs. In an embodiment of the invention, about $1\times10^6$ MILs is yielded.

In an embodiment of the invention, $12\times10^6$ PBMC derived from bone marrow aspirate yields approximately $1.4\times10^5$ MILs.

In any of the foregoing embodiments, PBMCs may be derived from a whole blood sample, from bone marrow, by apheresis, from the buffy coat, or from any other method known in the art for obtaining PBMCs.

4. Preselection Selection for PD-1 (as Exemplified in Step A2 of FIG. 1)

According to the methods of the present invention, the TILs are preselected for being PD-1 positive (PD-1+) prior to the priming first expansion.

In some embodiments, a minimum of 3,000 TILs are needed for seeding into the first expansion. In some embodiments, the preselection step yields a minimum of 3,000 TILs. In some embodiments, a minimum of 4,000 TILs are needed for seeding into the first expansion. In some embodiments, the preselection step yields a minimum of 4,000 TILs. In some embodiments, a minimum of 5,000 TILs are needed for seeding into the first expansion. In some embodiments, the preselection step yields a minimum of 5,000 TILs. In some embodiments, a minimum of 6,000 TILs are needed for seeding into the first expansion. In some embodiments, the preselection step yields a minimum of 6,000 TILs. In some embodiments, a minimum of 7,000 TILs are needed for seeding into the first expansion. In some embodiments, the preselection step yields a minimum of 7,000 TILs. In some embodiments, a minimum of 8,000 TILs are needed for seeding into the first expansion. In some embodiments, the preselection step yields a minimum of 8,000 TILs. In some embodiments, a minimum of 9,000 TILs are needed for seeding into the first expansion. In some embodiments, the preselection step yields a minimum of 9,000 TILs. In some embodiments, a minimum of 10,000 TILs are needed for seeding into the first expansion. In some embodiments, the preselection step yields a minimum of 10,000 TILs. In some embodiments, cells are grown or expanded to a density of 200,000. In some embodiments, cells are grown or expanded to a density of 200,000 to provide about 2e8 TILs for initiating rapid second expansion. In some embodiments, cells are grown or expanded to a density of 150,000. In some embodiments, cells are grown or expanded to a density of 150,000 to provide about 2e8 TILs for initiating rapid second expansion. In some embodiments, cells are grown or expanded to a density of 250,000. In some embodiments, cells are grown or expanded to a density of 250,000 to provide about 2e8 TILs for initiating rapid second expansion. In some embodiments, the minimum cell density is 10,000 cells to give 10e6 for initiating rapid second expansion. In some embodiments, a 10e6 seeding density for initiating the rapid second expansion could yield greater than 1e9 TILs.

In some embodiments the TILs for use in the priming first expansion are PD-1 positive (PD-1+) (for example, after preselection and before the priming first expansion). In some embodiments, TILs for use in the priming first expansion are at least 75% PD-1 positive, at least 80% PD-1 positive, at least 85% PD-1 positive, at least 90% PD-1 positive, at least 95% PD-1 positive, at least 98% PD-1 positive or at least 99% PD-1 positive (for example, after preselection and before the priming first expansion). In some embodiments, the PD-1 population is PD-1 high. In some embodiments, TILs for use in the priming first expansion are at least 25% PD-1high, at least 30% PD-1 high, at least 35% PD-1 high, at least 40% PD-1 high, at least 45% PD-1 high, at least 50% PD-1 high, at least 55% PD-1 high, at least 60% PD-1 high, at least 65% PD-1 high, at least 70% PD-1high, at least 75% PD-1 high, at least 80% PD-1 high, at least 85% PD-1 high, at least 90% PD-1high, at least 95% PD-1 high, at least 98% PD-1 high or at least 99% PD-1high (for example, after preselection and before the priming first expansion).

In some embodiments, the preselection of PD-1 positive TILs is performed by staining primary cell population, whole tumor digests, and/or whole tumor cell suspensions TILs with an anti-PD-1 antibody. In some embodiments, the anti-PD-1 antibody is a polycloncal antibody e.g., a mouse anti-human PD-1 polyclonal antibody, a goat anti-human PD-1 polyclonal antibody, etc. In some embodiments, the anti-PD-1 antibody is a monoclonal antibody. In some embodiments the anti-PD-1 antibody includes, e.g., but is not limited to EH12.2H7, PD1.3.1, MIH4, nivolumab (BMS-936558, Bristol-Myers Squibb; Opdivo®), pembrolizumab (lambrolizumab, MK03475 or MK-3475, Merck; Keytruda®), H12.1, PD1.3.1, NAT 105, humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)-BioXcell cat #BP0146. Other suitable antibodies for use in the preselection of PD-1 positive TILs for use in the expansion of TILs according to the methods of the invention, as exemplified by Steps A through F, as described herein are anti-PD-1 antibodies disclosed in U.S. Pat. No. 8,008,449, herein incorporated by reference. In some embodiments, the anti-PD-1 antibody for use in the preselection binds to a different epitope than nivolumab (BMS-936558, Bristol-Myers Squibb; Opdivo®). In some embodiments, the anti-PD-1 antibody for use in the preselection binds to a different epitope than pembrolizumab (lambrolizumab, MK03475 or MK-3475, Merck; Keytruda®). In some embodiments, the anti-PD-1 antibody for use in the preselection binds to a different epitope than humanized anti-PD-1 antibody JS001 (ShangHai JunShi). In some embodiments, the anti-PD-1 antibody for use in the preselection binds to a different epitope than monoclonal anti-PD-1 antibody TSR-042 (Tesaro, Inc.). In some embodiments, the anti-PD-1 antibody for use in the preselection binds to a different epitope than Pidilizumab (anti-PD-1 mAb CT-011, Medivation). In some embodiments, the anti-PD-1 antibody for use in the preselection binds to a different epitope than anti-PD-1 monoclonal Antibody BGB-A317 (BeiGene). In some embodiments, the anti-PD-1 antibody for use in the preselection binds to a different epitope than anti-PD-1 antibody SHR-1210 (ShangHai HengRui). In some embodiments, the anti-PD-1 antibody for use in the preselection binds to a different epitope than human monoclonal antibody REGN2810 (Regeneron). In some embodiments, the anti-PD-1 antibody for use in the preselection binds to a different epitope than human monoclonal antibody MDX-1106 (Bristol-Myers Squibb). In some embodiments, the anti-PD-1 antibody for use in the preselection binds to a different epitope than humanized anti-PD-1 IgG4 antibody PDR001 (Novartis). In some embodiments, the anti-PD-1 antibody for use in the preselection binds to a different epitope than RMP1-14 (rat IgG)-BioXcell cat #BP0146. The structures for binding of nivolumab and pembrolizumab binding to PD-1 are known and have been described in, for example, Tan, S. et al. (Tan, S. et al., *Nature Communications,* 8:14369| DOI: 10.1038/ncomms14369 (2017); incorporated by reference herein in its entirety for all purposes). In some embodiments, the anti-PD-1 antibody is EH12.2H7. In some embodiments, the anti-PD-1 antibody is PD1.3.1. In some embodiments, the anti-PD-1 antibody is not PD1.3.1. In some embodiments, the anti-PD-1 antibody is M1H4. In some embodiments, the anti-PD-1 antibody is not M1H4.

In some embodiments, the anti-PD-1 antibody for use in the preselection binds at least 75%, at least 80%, at least 85%, at least 90%, at least 95%, at least 98%, at least 99% or at least 100% of the cells expressing PD-1.

In some embodiments, the patient has been treated with an anti-PD-1 antibody. In some embodiments, the subject is anti-PD-1 antibody treatment naïve. In some embodiments, the subject has not been treated with an anti-PD-1 antibody. In some embodiments, the subject has been previously treated with a chemotherapeutic agent. In some embodiments, the subject has been previously treated with a chemotherapeutic agent but is no longer being treated with the chemotherapeutic agent. In some embodiments, the subject is post-chemotherapeutic treatment or post anti-PD-1 antibody treatment. In some embodiments, the subject is post-chemotherapeutic treatment and post anti-PD-1 antibody treatment. In some embodiments, the patient is anti-PD-1 antibody treatment naïve. In some embodiments, the subject has treatment naïve cancer or is post-chemotherapeutic treatment but anti-PD-1 antibody treatment naïve. In some embodiments, the subject is treatment naïve and post-chemotherapeutic treatment but anti-PD-1 antibody treatment naive.

In some embodiments in which the patient has been previously treated with a first anti-PD-1 antibody, the preseletion is performed by staining the primary cell population, whole tumor digests, and/or whole tumor cell suspensions TILs with a second anti-PD-1 antibody that is not blocked by the first anti-PD-1 antibody from binding to PD-1 on the surface of the primary cell population TILs.

In some embodiments in which the patient has been previously treated with an anti-PD-1 antibody, the preselection is performed by staining the primary cell population TILs with an antibody (an "anti-Fc antibody") that binds to the Fc region of the anti-PD-1 antibody insolubilized on the surface of the primary cell population TILs. In some embodiments, the anti-Fc antibody is a polyclonal antibody e.g. mouse anti-human Fc polycloncal antibody, goat anti-human Fc polyclonal antibody, etc. In some embodiments, the anti-Fc antibody is a monoclonal antibody. In some embodiments in which the patient has been previously treated with an anti-PD-1 human or humanized IgG antibody, and the primary cell population TILs are stained with an anti-human IgG antibody. In some embodiments in which the patient has been previously treated with an anti-PD-1 human or humanized IgG1 antibody, the primary cell population TILs are stained with an anti-human IgG1 antibody. In some embodiments in which the patient has been previously treated with an anti-PD-1 human or humanized IgG2 antibody, the primary cell population TILs are stained with an anti-human IgG2 antibody. In some embodiments in which the patient has been previously treated with an anti-PD-1 human or humanized IgG3 antibody, the primary cell population TILs are stained with an anti-human IgG3 antibody. In some embodiments in which the patient has been previously treated with an anti-PD-1 human or humanized IgG4 antibody, the primary cell population TILs are stained with an anti-human IgG4 antibody.

In some embodiments in which the patient has been previously treated with an anti-PD-1 antibody, the preselection is performed by contacting the primary cell population TILs with the same anti-PD-1 antibody and then staining the primary cell population TILs with an anti-Fc antibody that binds to the Fc region of the anti-PD-1 antibody insolubilized on the surface of the primary cell population TILs.

In some embodiments, preselection is performed using a cell sorting method. In some embodiments, the cell sorting method is a flow cytometry method, e.g., flow activated cell sorting (FACS). In some embodiments, the intensity of the fluorophore in both the first population and the population of PBMCs is used to set up FACS gates for establishing low, medium, and high levels of intensity that correspond to PD-1 negative TILs, PD-1 intermediate TILs, and PD-1 positive TILs, respectively. In some embodiments, the cell sorting method is performed such that the gates are set at high, medium (also referred to as intermediate), and low (also referred to as negative) using the PBMC, the FMO control, and the sample itself to distinguish the three populations. In some embodiments, the PBMC is used as the gating control. In some embodiments, the PD-1high population is defined as the population of cells that is positive for PD-1 above what is observed in PBMCs. In some embodiments, the intermediate PD-1+ population in the TIL is encompasses the PD-1+ cells in the PBMC. In some embodiments, the negatives are gated based upon the FMO. In some embodiments, the FACS gates are set-up after the step of obtaining and/or receiving a first population of TILs from a tumor resected from a subject by processing a tumor sample obtained from the subject into multiple tumor fragments. In some embodiments, the gating is set up each sort. In some embodiments, the gating is set-up for each sample of PBMCs. In some embodiments, the gating is set-up for each sample of PBMCs. In some embodiments, the gating template is set-up from PBMC's every 10 days, 20 days, 30 days, 40 days, 50 days, or 60 days. In some embodiments, the gating template is set-up from PBMC's every 60 days. In some embodiments, the gating template is set-up for each sample of PBMC's every 10 days, 20 days, 30 days, 40 days, 50 days, or 60 days. In some embodiments, the gating template is set-up for each sample of PBMC's every 60 days.

In some embodiments, preselection involves selecting PD-1 positive TILs from the first population of TILs to obtain a PD-1 enriched TIL population comprises the selecting a population of TILs from a first population of TILs that are at least 11.27% to 74.4% PD-1 positive TILs. In some embodiments, the first population of TILs are at least 20% to 80% PD-1 positive TILs, at least 20% to 80% PD-1 positive TILs, at least 30% to 80% PD-1 positive TILs, at least 40% to 80% PD-1 positive TILs, at least 50% to 80% PD-1 positive TILs, at least 10% to 70% PD-1 positive TILs, at least 20% to 70% PD-1 positive TILs, at least 30% to 70% PD-1 positive TILs, or at least 40% to 70% PD-1 positive TILs.

In some embodiments, the selection step (e.g., preselection and/or selecting PD-1 positive cells) comprises the steps of:

(i) exposing the first population of TILs and a population of PBMC to an excess of a monoclonal anti-PD-1 IgG4 antibody that binds to PD-1 through an N-terminal loop outside the IgV domain of PD-1, (ii) adding an excess of an anti-IgG4 antibody conjugated to a fluorophore, (iii) obtaining the PD-1 enriched TIL population based on the intensity of the fluorophore of the PD-1 positive TILs in the first population of TILs compared to the intensity in the population of PBMCs as performed by fluorescence-activated cell sorting (FACS).

In some embodiments, the the PD-1 positive TILs are PD-1 high TILs.

In some embodiments, at least 70% of the PD-1 enriched TIL population are PD-1 positive TILs. In some embodiments, at least 80% of the PD-1 enriched TIL population are PD-1 positive TILs. In some embodiments, at least 90% of the PD-1 enriched TIL population are PD-1 positive TILs. In some embodiments, at least 95% of the PD-1 enriched TIL population are PD-1 positive TILs. In some embodiments, at least 99% of the PD-1 enriched TIL population are PD-1 positive TILs. In some embodiments, 100% of the PD-1 enriched TIL population are PD-1 positive TILs.

Different anti-PD-1 antibodies exhibit different binding characteristics to different epitopes within PD-1. In some embodiments, the anti-PD-1 antibody binds to a different epitope than pembrolizumab. In some embodiments, the anti-PD1 antibody binds to an epitope in the N-terminal loop outside the IgV domain of PD-1. In some embodiments, the anti-PD1 antibody binds through an N-terminal loop outside the IgV domain of PD-1. In some embodiments, the anti-PD-1 antibody is an anti-PD-1 antibody that binds to PD-1 binds through an N-terminal loop outside the IgV domain of PD-1. In some embodiments, the anti-PD-1 antibody is a monoclonal anti-PD-1 antibody that binds to PD-1 binds through an N-terminal loop outside the IgV domain of PD-1. In some embodiments, the monoclonal anti-PD-1 antibody is an anti-PD-1 IgG4 antibody that binds to PD-1 binds through an N-terminal loop outside the IgV domain of PD-1. See, for example, Tan, S. Nature Comm. Vol 8, Argicle 14369:1-10 (2017).

In some embodiments, the selection step, exemplified as Step A2 of FIG. 1, comprises the steps of (i) exposing the first population of TILs to an excess of a monoclonal anti-PD-1 IgG4 antibody that binds to PD-1 through an N-terminal loop outside the IgV domain of PD-1, (ii) adding an excess of an anti-IgG4 antibody conjugated to a fluorophore, and (iii) performing a flow-based cell sort based on the fluorophore to obtain a PD-1 enriched TIL population. In some embodiments, the monoclonal anti-PD-1 IgG4 antibody is nivolumab or variants, fragments, or conjugates thereof. In some embodiments, the anti-IgG4 antibody is clone anti-human IgG4, Clone HP6023. In some embodiments, the anti-PD-1 antibody for use in the selection in step (b) binds to the same epitope as EH12.2H7 or nivolumab.

In some embodiments, the PD-1 gating method of WO2019156568 is employed. To determine if TILs derived from a tumor sample are PD-1 high, one skilled in the art can utilize a reference value corresponding to the level of expression of PD-1 in peripheral T cells obtained from a blood sample from one or more healthy human subjects. PD-1 positive cells in the reference sample can be defined using fluorescence minus one controls and matching isotype controls. In some embodiments, the expression level of PD-1 is measured in CD3+/PD-1+ peripheral T cells from a healthy subject (e.g., the reference cells) is used to establish a threshold value or cut-off value of immunostaining intensity of PD-1 in TILs obtained from a tumor. The threshold value can be defined as the minimal intensity of PD-1 immunostaining of PD-1 high T cells. As such, TILs with a PD-1 expression that is the same or above the threshold value can be considered to be PD-1high cells. In some instances, the PD-1high TILs represent those with the highest intensity of PD-1 immunostaining corresponding to a maximum 1% or less of the total CD3+ cells. In other instances, the PD-1 high TILs represent those with the highest intensity of PD-1 immunostaining corresponding to the maximum 0.75% or less of the total CD3+ cells. In some instances, the PD-1high TILs represent those with the highest intensity of PD-1 immunostaining corresponding to the maximum 0.50% or less of the total CD3+ cells. In one instance, the PD-1 high TILs represent those with the highest intensity of PD-1 immunostaining corresponding to the maximum 0.25% or less of the total CD3+ cells.

a. Flurophores

In some embodiments, the primary cell population TILs are stained with a cocktail that includes an anti-PD-1 antibody linked to a fluorophore and an anti-CD3 antibody linked to a fluorophore. In some embodiments, the primary cell population TILs are stained with a cocktail that includes an anti-PD-1 antibody linked to a fluorophore (for example, PE, live/dead violet) and anti-CD3-FITC. In some embodiments, the primary cell population TILs are stained with a cocktail that includes anti-PD-1-PE, anti-CD3-FITC and live/dead blue stain (ThermoFisher, MA, Cat #L23105). In some embodiments, the after incubation with the anti-PD1 antibody, PD-1 positive cells are selected for expansion according to the priming first expansion a described herein, for example, in Step B.

In some embodiments, the flurophore includes, but is not limited to PE (Phycoerythrin), APC (allophycocyanin), PerCP (peridinin chlorophyll protein), DyLight 405, Alexa Fluor 405, Pacific Blue, Alexa Fluor 488, FITC (fluorescein isothiocyanate), DyLight 550, Alexa Fluor 647, DyLight 650, and Alexa Fluor 700. In some embodiments, the flurophore includes, but is not limited to PE-Alexa Fluor® 647, PE-Cy5, PerCP-Cy5.5, PE-Cy5.5, PE-Alexa Fluor® 750, PE-Cy7, and APC-Cy7. In some embodiments, the flurophore includes, but is not limited to a fluorescein dye. Examples of fluorescein dyes include, but are not limited to, 5-carboxyfluorescein, fluorescein-5-isothiocyanate and 6-carboxyfluorescein, 5,6-dicarboxyfluorescein, 5-(and 6)-sulfofluorescein, sulfonefluorescein, succinyl fluorescein, 5-(and 6)-carboxy SNARF-1, carboxyfluorescein sulfonate, carboxyfluorescein zwitterion, carbxoyfluorescein quaternary ammonium, carboxyfluorescein phosphonate, carboxyfluorescein GABA, 5' (6')-carboxyfluorescein, carboxyfluorescein-cys-Cy5, and fluorescein glutathione. In some embodiments, the fluorescent moiety is a rhodamine dye. Examples of rhodamine dyes include, but are not limited to, tetramethylrhodamine-6-isothiocyanate, 5-carboxytetramethylrhodamine, 5-carboxy rhodol derivatives, carboxy rhodamine 110, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®). In some embodiments, the fluorescent moiety is a cyanine dye. Examples of cyanine dyes include, but are not limited to, Cy3, Cy3B, Cy3.5, Cy5, Cy5.5, and Cy 7.

B. STEP B: Priming First Expansion

In some embodiments, the present methods provide for younger TILs, which may provide additional therapeutic benefits over older TILs (i.e., TILs which have further undergone more rounds of replication prior to administration to a subject/patient). Features of young TILs have been described in the literature, for example Donia, at al., *Scandinavian Journal of Immunology,* 75:157-167 (2012); Dudley et al., *Clin Cancer Res,* 16:6122-6131 (2010); Huang et al., *J Immunother,* 28 (3): 258-267 (2005); Besser et al., *Clin Cancer Res,* 19 (17): OF1-OF9 (2013); Besser et al., *J Immunother* 32:415-423 (2009); Robbins, et al., *J Immunol* 2004; 173:7125-7130; Shen et al., J Immunother, 30:123-129 (2007); Zhou, et al., *J Immunother,* 28:53-62 (2005); and Tran, et al., J Immunother, 31:742-751 (2008), all of which are incorporated herein by reference in their entireties.

After dissection or digestion (for example to obtain whole tumor digests and/or whole tumor cell suspensions) of tumor fragments and/or tumor fragments, for example such as described in Step A of FIG. 1 (in particular, e.g., FIG. 1B and/or FIG. 1C), the resulting cells are cultured in serum containing IL-2, OKT-3, and feeder cells (e.g., antigen-presenting feeder cells or allogenic irradiated PBMCs), under conditions that favor the growth of TILs over tumor and other cells. In some embodiments, the IL-2, OKT-3, and feeder cells are added at culture initiation along with the tumor digest and/or tumor fragments (e.g., at Day 0). In some embodiments, the tumor digests and/or tumor fragments are incubated in a container with up to 60 fragments (in embodiments where fragments are employed) per container and with 6000 IU/mL of IL-2. In some embodiments, this primary cell population is cultured for a period of days, generally from 1 to 8 days, resulting in a bulk TIL population, generally about $1\times10^8$ bulk TIL cells. In some embodiments, this primary cell population is cultured for a period of days, generally from 1 to 7 days, resulting in a bulk TIL population, generally about $1\times10^8$ bulk TIL cells. In some embodiments, priming first expansion occurs for a period of 1 to 8 days, resulting in a bulk TIL population, generally about $1\times10^8$ bulk TIL cells. In some embodiments, priming first expansion occurs for a period of 1 to 7 days, resulting in a bulk TIL population, generally about $1\times10^8$ bulk TIL cells. In some embodiments, this priming first expansion occurs for a period of 5 to 8 days, resulting in a bulk TIL population, generally about $1\times10^8$ bulk TIL cells. In some embodiments, this priming first expansion occurs for a period of 5 to 7 days, resulting in a bulk TIL population, generally about $1\times10^8$ bulk TIL cells. In some embodiments, this priming first expansion occurs for a period of about 6 to 8 days, resulting in a bulk TIL population, generally about $1\times10^8$ bulk TIL cells. In some embodiments, this priming first expansion occurs for a period of about 6 to 7 days, resulting in a bulk TIL population, generally about $1\times10^8$ bulk TIL cells. In some embodiments, this priming first expansion occurs for a period of about 7 to 8 days, resulting in a bulk TIL population, generally about $1\times10^8$ bulk TIL cells. In some embodiments, this priming first expansion occurs for a period of about 7 days, resulting in a bulk TIL population, generally about $1\times10^8$ bulk TIL cells. In some embodiments, this priming first expansion occurs for a period of about 8 days, resulting in a bulk TIL population, generally about $1\times10^8$ bulk TIL cells.

In some embodiments,

Any suitable dose of TILs can be administered. In some embodiments, from about $2.3\times10^{10}$ to about $13.7\times10^{10}$ TILs are administered, with an average of around $7.8\times10^{10}$ TILs, particularly if the cancer is melanoma. In an embodiment, about $1.2\times10^{10}$ to about $4.3\times10^{10}$ of TILs are administered. In some embodiments, about $3\times10^{10}$ to about $12\times10^{10}$ TILs are administered. In some embodiments, about $4\times10^{10}$ to about $10\times10^{10}$ TILs are administered. In some embodiments, about $5\times10^{10}$ to about $8\times10^{10}$ TILs are administered. In some embodiments, about $6\times10^{10}$ to about $8\times10^{10}$ TILs are administered. In some embodiments, about $7\times10^{10}$ to about $8\times10^{10}$ TILs are administered. In some embodiments, the therapeutically effective dosage is about $2.3\times10^{10}$ to about $13.7\times10^{10}$. In some embodiments, the therapeutically effective dosage is about $7.8\times10^{10}$ TILs, particularly of the cancer is melanoma. In some embodiments, the therapeutically effective dosage is about $1.2\times10^{10}$ to about $4.3\times10^{10}$ of TILs. In some embodiments, the therapeutically effective dosage is about $3\times10^{10}$ to about $12\times10^{10}$ TILs. In some embodiments, the therapeutically effective dosage is about $4\times10^{10}$ to about $10\times10^{10}$ TILs. In some embodiments, the therapeutically effective dosage is about $5\times10^{10}$ to about $8\times10^{10}$ TILs. In some embodiments, the therapeutically effective dosage is about $6\times10^{10}$ to about $8\times10^{10}$ TILs. In some embodiments, the therapeutically effective dosage is about $7\times10^{10}$ to about $8\times10^{10}$ TILs.

In some embodiments, the number of the TILs provided in the pharmaceutical compositions of the invention is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$ In an embodiment, the number of the TILs provided in the pharmaceutical compositions of the invention is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In a preferred embodiment, expansion of TILs may be performed using a priming first expansion step (for example such as those described in Step B of FIG. 1 (in particular, e.g., FIG. 1B and/or FIG. 1C), which can include processes referred to as pre-REP or priming REP and which contains feeder cells from Day 0 and/or from culture initiation) as described below and herein, followed by a rapid second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein. In some embodiments, the tumor fragment is between about 1 $mm^3$ and 10 $mm^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin.

In some embodiments, there are less than or equal to 240 tumor fragments. In some embodiments, there are less than or equal to 240 tumor fragments placed in less than or equal to 4 containers. In some embodiments, the containers are GREX100 MCS flasks. In some embodiments, less than or equal to 60 tumor fragments are placed in 1 container. In some embodiments, each container comprises less than or equal to 500 mL of media per container. In some embodiments, the media comprises IL-2. In some embodiments, the media comprises 6000 IU/mL of IL-2. In some embodiments, the media comprises antigen-presenting feeder cells (also referred to herein as "antigen-presenting cells"). In some embodiments, the media comprises $2.5\times10^8$ antigen-presenting feeder cells per container. In some embodiments, the media comprises OKT-3. In some embodiments, the media comprises 30 ng/mL of OKT-3 per container. In some embodiments, the container is a GREX100 MCS flask. In some embodiments, the media comprises 6000 IU/mL of IL-2, 30 ng of OKT-3, and $2.5\times10^8$ antigen-presenting feeder cells. In some embodiments, the media comprises 6000 IU/mL of IL-2, 30 ng/ml of OKT-3, and $2.5\times10^8$ antigen-presenting feeder cells per container.

After preparation of the tumor fragments, whole tumor digests, and/or whole tumor cell suspensions, the resulting cells (i.e., fragments and/or digests which is a primary cell population) are cultured in media containing IL-2, antigen-presenting feeder cells and OKT-3 under conditions that favor the growth of TILs over tumor and other cells and which allow for TIL priming and accelerated growth from initiation of the culture on Day 0. In some embodiments, the tumor digests and/or tumor fragments are incubated in with 6000 IU/mL of IL-2, as well as antigen-presenting feeder cells and OKT-3. This primary cell population is cultured for a period of days, generally from 1 to 8 days, resulting in a bulk TIL population, generally about $1\times10^8$ bulk TIL cells. In some embodiments, the growth media during the priming first expansion comprises IL-2 or a variant thereof, as well as antigen-presenting feeder cells and OKT-3. In some embodiments, this primary cell population is cultured for a period of days, generally from 1 to 7 days, resulting in a bulk TIL population, generally about $1\times10^8$ bulk TIL cells. In some embodiments, the growth media during the priming first expansion comprises IL-2 or a variant thereof, as well as antigen-presenting feeder cells and OKT-3. In some embodiments, the IL-2 is recombinant human IL-2 (rhIL-2). In some embodiments the IL-2 stock solution has a specific activity of $20\text{-}30\times10^6$ IU/mg for a 1 mg vial. In some embodiments the IL-2 stock solution has a specific activity of $20\times10^6$ IU/mg for a 1 mg vial. In some embodiments the IL-2 stock solution has a specific activity of $25\times10^6$ IU/mg for a 1 mg vial. In some embodiments the IL-2 stock solution has a specific activity of $30\times10^6$ IU/mg for a 1 mg vial. In some embodiments, the IL-2 stock solution has a final concentration of $4\text{-}8\times10^6$ IU/mg of IL-2. In some embodiments, the IL-2 stock solution has a final concentration of $5\text{-}7\times10^6$ IU/mg of IL-2. In some embodiments, the IL-2 stock solution has a final concentration of $6\times10^6$ IU/mg of IL-2. In some embodiments, the IL-2 stock solution is prepare as described in Example C. In some embodiments, the priming first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the priming first expansion culture media comprises about 9,000 IU/mL of IL-2 to about 5,000 IU/mL of IL-2. In some embodiments, the priming first expansion culture media comprises about 8,000 IU/mL of IL-2 to about 6,000 IU/mL of IL-2. In some embodiments, the priming first expansion culture media comprises about 7,000 IU/mL of IL-2 to about 6,000 IU/mL of IL-2. In some embodiments, the priming first expansion culture media comprises about 6,000 IU/mL of IL-2. In an embodiment, the cell culture medium further comprises IL-2. In some embodiments, the priming first expansion cell culture medium comprises about 3000 IU/mL of IL-2. In an embodiment, the priming first expansion cell culture medium further comprises IL-2. In a preferred embodiment, the priming first expansion cell culture medium comprises about 3000 IU/mL of IL-2. In an embodiment, the priming first expansion cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the priming first expansion cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, priming first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the priming first expansion culture media comprises about 500 IU/mL of IL-15 to about 100 IU/mL of IL-15. In some embodiments, the priming first expansion culture media comprises about 400 IU/mL of IL-15 to about 100 IU/mL of IL-15. In some embodiments, the priming first expansion culture media comprises about 300 IU/mL of IL-15 to about 100 IU/mL of IL-15. In some embodiments, the priming first expansion culture media comprises about 200 IU/mL of IL-15. In some embodiments, the priming first expansion cell culture medium comprises about 180 IU/mL of IL-15. In an embodiment, the priming first expansion cell culture medium further comprises IL-15. In a preferred embodiment, the priming first expansion cell culture medium comprises about 180 IU/mL of IL-15.

IU/mL of IL-21 to about 0.5 IU/mL of IL-21. In some embodiments, the priming first expansion culture media comprises about 5 IU/mL of IL-21 to about 1 IU/mL of IL-21. In some embodiments, the priming first expansion culture media comprises about 2 IU/mL of IL-21. In some embodiments, the priming first expansion cell culture medium comprises about 1 IU/mL of IL-21. In some embodiments, the priming first expansion cell culture medium comprises about 0.5 IU/mL of IL-21. In an embodiment, the cell culture medium further comprises IL-21. In a preferred embodiment, the priming first expansion cell culture medium comprises about 1 IU/mL of IL-21.

In an embodiment, the priming first expansion cell culture medium comprises OKT-3 antibody. In some embodiments, the priming first expansion cell culture medium comprises about 30 ng/ml of OKT-3 antibody. In an embodiment, the priming first expansion cell culture medium comprises about 0.1 ng/mL, about 0.5 ng/mL, about 1 ng/ml, about 2.5 ng/ml, about 5 ng/ml, about 7.5 ng/mL, about 10 ng/ml, about 15 ng/ml, about 20 ng/mL, about 25 ng/ml, about 30 ng/mL, about 35 ng/mL, about 40 ng/ml, about 50 ng/ml, about 60 ng/ml, about 70 ng/ml, about 80 ng/ml, about 90 ng/mL, about 100 ng/ml, about 200 ng/ml, about 500 ng/ml, and about 1 μg/mL of OKT-3 antibody. In an embodiment, the cell culture medium comprises between 0.1 ng/ml and 1 ng/mL, between 1 ng/mL and 5 ng/mL, between 5 ng/ml and 10 ng/mL, between 10 ng/ml and 20 ng/mL, between 20 ng/mL and 30 ng/mL, between 30 ng/ml and 40 ng/mL, between 40 ng/ml and 50 ng/mL, and between 50 ng/ml and 100 ng/ml of OKT-3 antibody. In an embodiment, the cell culture medium comprises between 15 ng/ml and 30 ng/ml of OKT-3 antibody. In an embodiment, the cell culture medium comprises 30 ng/ml of OKT-3 antibody. In some embodiments, the OKT-3 antibody is muromonab.

TABLE 3

Amino acid sequences of muromonab (exemplary OKT-3 antibody)

| Identifier | Sequence (One-Letter Amino Acid Symbols) |
|---|---|
| SEQ ID NO: 1 Muromonab heavy chain | QVQLQQSGAE LARPGASVKM SCKASGYTFT RYTMHWVKQR PGQGLEWIGY INPSRGYTNY 60<br>NQKFKDKATL TTDKSSSTAY MQLSSLTSED SAVYYCARYY DDHYCLDYWG QGTTLTVSSA 120<br>KTTAPSVYPL APVCGGTTGS SVTLGCLVKG YFPEPVTLTW NSGSLSSGVH TFPAVLQSDL 180<br>YTLSSSVTVT SSTWPSQSIT CNVAHPASST KVDKKIEPRP KSCDKTHTCP PCPAPELLGG 240<br>PSVFLFPPKP KDTLMISRTP EVTCVVVDVS HEDPEVKFNW YVDGVEVHNA KTKPREEQYN 300<br>STYRVVSVLT VLHQDWLNGK EYKCKVSNKA LPAPIEKTIS KAKGQPREPQ VYTLPPSRDE 360<br>LTKNQVSLTC LVKGFYPSDI AVEWESNGQP ENNYKTTPPV LDSDGSFFLY SKLTVDKSRW 420<br>QQGNVFSCSV MHEALHNHYT QKSLSLSPGK 450 |
| SEQ ID NO: 2 Muromonab light chain | QIVLTQSPAI MSASPGEKVT MTCSASSSVS YMNWYQQKSG TSPKRWIYDT SKLASGVPAH 60<br>FRGSGSGTSY SLTISGMEAE DAATYYCQQW SSNPFTFGSG TKLEINRADT APTVSIFPPS 120<br>SEQLTSGGAS VVCFLNNFYP KDINVKWKID GSERQNGVLN SWTDQDSKDS TYSMSSTLTL 180<br>TKDEYERHNS YTCEATHKTS TSPIVKSFNR NEC 213 |

In some embodiments, priming first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the priming first expansion culture media comprises about 20 IU/mL of IL-21 to about 0.5 IU/mL of IL-21. In some embodiments, the priming first expansion culture media comprises about 15 IU/mL of IL-21 to about 0.5 IU/mL of IL-21. In some embodiments, the priming first expansion culture media comprises about 12 IU/mL of IL-21 to about 0.5 IU/mL of IL-21. In some embodiments, the priming first expansion culture media comprises about 10

In some embodiments, the priming first expansion cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the priming first expansion cell culture medium further comprises IL-2 at an initial concentration of about 3000 IU/mL and OKT-3 antibody at an initial concentration of about 30 ng/ml, and wherein the one or more TNFRSF agonists comprises a 4-1BB agonist. In some embodiments, in addition to one or more TNFRSF agonists, the priming first expansion cell culture medium further comprises IL-2 at an initial concentration of about 6000 IU/mL and OKT-3 antibody at an initial concentration of about 30 ng/ml, and wherein the one or more TNFRSF agonists comprises a 4-1BB agonist.

In some embodiments, the priming first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In some embodiments, the CM is the CM1 described in the Examples, see, Example A. In some embodiments, the priming first expansion occurs in an initial cell culture medium or a first cell culture medium. In some embodiments, the priming first expansion culture medium or the initial cell culture medium or the first cell culture medium comprises IL-2, OKT-3 and antigen-presenting feeder cells (also referred to herein as feeder cells).

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T-cell Expansion Basal Medium, CTS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the defined medium further comprises L-glutamine, sodium bicarbonate and/or 2-mercaptoethanol.

In some embodiments, the CTSTMOpTmizer™ T-cell Immune Cell Serum Replacement is used with conventional growth media, including but not limited to CTS™ OpTmizer™ T-cell Expansion Basal Medium, CTS™ OpTmizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific). In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTSTMOpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTSTMOpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM. In some embodiments, the final concentration of 2-mercaptoethanol in the media is 55 μM.

In some embodiments, the defined media described in International PCT Publication No. WO/1998/030679, which is herein incorporated by reference, are useful in the present invention.

In that publication, serum-free eukaryotic cell culture media are described. The serum-free, eukaryotic cell culture medium includes a basal cell culture medium supplemented with a serum-free supplement capable of supporting the growth of cells in serum-free culture. The serum-free eukaryotic cell culture medium supplement comprises or is obtained by combining one or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table A below. In other embodiments, the non-trace element moiety ingredients in the defined medium are present in the final concentrations listed in the column under the heading "A Preferred Embodiment of the 1× Medium" in Table A below. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table A below.

TABLE A

Concentrations of Non-Trace Element Moiety Ingredients

| Ingredient | A preferred embodiment in supplement (mg/L) (About) | Concentration range in 1X medium (mg/L) (About) | A preferred embodiment in 1X medium (mg/L) (About) |
|---|---|---|---|
| Glycine | 150 | 5-200 | 53 |
| L-Histidine | 940 | 5-250 | 183 |
| L-Isoleucine | 3400 | 5-300 | 615 |
| L-Methionine | 90 | 5-200 | 44 |
| L-Phenylalanine | 1800 | 5-400 | 336 |
| L-Proline | 4000 | 1-1000 | 600 |
| L-Hydroxyproline | 100 | 1-45 | 15 |
| L-Serine | 800 | 1-250 | 162 |
| L-Threonine | 2200 | 10-500 | 425 |
| L-Tryptophan | 440 | 2-110 | 82 |
| L-Tyrosine | 77 | 3-175 | 84 |
| L-Valine | 2400 | 5-500 | 454 |
| Thiamine | 33 | 1-20 | 9 |
| Reduced Glutathione | 10 | 1-20 | 1.5 |
| Ascorbic Acid-2-$PO_4$ (Mg Salt) | 330 | 1-200 | 50 |
| Transferrin (iron saturated) | 55 | 1-50 | 8 |
| Insulin | 100 | 1-100 | 10 |
| Sodium Selenite | 0.07 | 0.000001-0.0001 | 0.00001 |
| AlbuMAX ®I | 83,000 | 5000-50,000 | 12,500 |

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., "Ex vivo expansion of human T cells for adoptive immunotherapy using the novel Xeno-free CTS Immune Cell Serum Replacement," Clin Transl Immunology, 4 (1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME or BME; also known as 2-mercaptoethanol, CAS 60-24-2).

In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 1 to 8 days, as discussed in the examples and figures. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 2 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 3 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 4 to 8 days, as discussed in the examples and figures. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 1 to 7 days, as discussed in the examples and figures. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 2 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 2 to 7 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 3 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 3 to 7 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 4 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 4 to 7 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 5 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 5 to 7 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 6 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 6 to 7 days. In some embodiments, the priming first expansion (including processes such as for example those provided in Step B of FIG. 1 (in particular, e.g., FIG. 1B and/or FIG. 1C), which can include those sometimes referred to as the pre-REP or priming REP) process is 7 to 8 days. In some embodiments, the priming first expansion (including processes such as for example those provided in Step B of FIG. 1 (in particular, e.g., FIG. 1B and/or FIG. 1C), which can include those sometimes referred to as the pre-REP or priming REP) process is 8 days. In some embodiments, the priming first expansion (including processes such as for example those provided in Step B of FIG. 1 (in particular, e.g., FIG. 1B and/or FIG. 1C), which can include those sometimes referred to as the pre-REP or priming REP) process is 7 days.

In some embodiments, the priming first TIL expansion can proceed for 1 days to 8 days from when fragmentation occurs and/or when the first priming expansion step is initiated. In some embodiments, the priming first TIL expansion can proceed for 1 days to 7 days from when fragmentation occurs and/or when the first priming expansion step is initiated. In some embodiments, the priming first TIL expansion can proceed for 2 days to 8 days from when fragmentation occurs and/or when the first priming expansion step is initiated. In some embodiments, the priming first TIL expansion can proceed for 2 days to 7 days from when fragmentation occurs and/or when the first priming expansion step is initiated. In some embodiments, the priming first TIL expansion can proceed for 3 days to 8 days from when fragmentation occurs and/or when the first priming expansion step is initiated. In some embodiments, the priming first TIL expansion can proceed for 3 days to 7 days from when fragmentation occurs and/or when the first priming expansion step is initiated. In some embodiments, the priming first TIL expansion can proceed for 4 days to 8 days from when fragmentation occurs and/or when the first priming expansion step is initiated. In some embodiments, the priming first TIL expansion can proceed for 4 days to 7 days from when fragmentation occurs and/or when the first priming expansion step is initiated. In some embodiments, the priming first TIL expansion can proceed for 5 days to 8 days from when fragmentation occurs and/or when the first priming expansion step is initiated. In some embodiments, the priming first TIL expansion can proceed for 5 days to 7 days from when fragmentation occurs and/or when the first priming expansion step is initiated. In some embodiments, the priming first TIL expansion can proceed for 6 days to 8 days from when fragmentation occurs and/or when the first priming expansion step is initiated. In some embodiments, the priming first TIL expansion can proceed for 6 days to 7 days from when fragmentation occurs and/or when the first priming expansion step is initiated. In some embodiments, the priming first TIL expansion can proceed for 7 to 8 days from when fragmentation occurs and/or when the first priming expansion step is initiated. In some embodiments, the priming first TIL expansion can proceed for 8 days from when fragmentation occurs and/or when the first priming expansion step is initiated. In some embodiments, the priming first TIL expansion can proceed for 7 days from when fragmentation occurs and/or when the first priming expansion step is initiated.

In some embodiments, the priming first expansion of the TILs can proceed for 1 day, 2 days, 3 days, 4 days, 5 days, 6 days, 7 days, 8 days, 9 days, 10 days, or 11 days. In some embodiments, the first TIL expansion can proceed for 1 day to 8 days. In some embodiments, the first TIL expansion can proceed for 1 day to 7 days. In some embodiments, the first TIL expansion can proceed for 2 days to 7 days. In some embodiments, the first TIL expansion can proceed for 3 days to 7 days. In some embodiments, the first TIL expansion can proceed for 4 days to 7 days. In some embodiments, the first TIL expansion can proceed for 5 days to 7 days. In some embodiments, the first TIL expansion can proceed for 6 days to 7 days. In some embodiments, the first TIL expansion can proceed for 2 days to 8 days. In some embodiments, the first TIL expansion can proceed for 3 days to 8 days. In some embodiments, the first TIL expansion can proceed for 4 days to 8 days. In some embodiments, the first TIL expansion can proceed for 5 days to 8 days. In some embodiments, the first TIL expansion can proceed for 6 days to 8 days. In some embodiments, the first TIL expansion can proceed for 2 days to 9 days. In some embodiments, the first TIL expansion can proceed for 3 days to 9 days. In some embodiments, the first TIL expansion can proceed for 4 days to 9 days. In some embodiments, the first TIL expansion can proceed for 5 days to 9 days. In some embodiments, the first TIL expansion can proceed for 6 days to 9 days. In some embodiments, the first TIL expansion can proceed for 2 days to 10 days. In some embodiments, the first TIL expansion can proceed for 3 days to 10 days. In some embodiments, the first TIL expansion can proceed for 4 days to 10 days. In some embodiments, the first TIL expansion can proceed for 5 days to 10 days. In some embodiments, the first TIL expansion can proceed for 6 days to 10 days. In some embodiments, the first TIL expansion can proceed for 2 days to 11 days. In some embodiments, the first TIL expansion can proceed for 3 days to 11 days. In some embodiments, the first TIL expansion can proceed for 4 days to 11 days. In some embodiments, the first TIL expansion can proceed for 5 days to 11 days. In some embodiments, the first TIL expansion can proceed for 6 days to 11 days. In some embodiments, the first TIL expansion can proceed for 7 days. In some embodiments, the first TIL expansion can proceed for 8 days. In some embodiments, the first TIL expansion can proceed for 9 days. In some embodiments, the first TIL expansion can proceed for 10 days. In some embodiments, the first TIL expansion can proceed for 11 days.

In some embodiments, a combination of IL-2, IL-7, IL-15, and/or IL-21 are employed as a combination during the priming first expansion. In some embodiments, IL-2, IL-7, IL-15, and/or IL-21 as well as any combinations thereof can be included during the priming first expansion, including for example during a Step B processes according to FIG. 1 (in particular, e.g., FIG. 1B), as well as described herein. In some embodiments, a combination of IL-2, IL-15, and IL-21 are employed as a combination during the priming first expansion. In some embodiments, IL-2, IL-15, and IL-21 as well as any combinations thereof can be included during Step B processes according to FIG. 1 (in particular, e.g., FIG. 1B and/or FIG. 1C) and as described herein.

In some embodiments, the priming first expansion, for example, Step B according to FIG. 1 (in particular, e.g., FIG. 1B and/or FIG. 1C), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-10 or a G-REX-100. In some embodiments, the bioreactor employed is a G-REX-100. In some embodiments, the bioreactor employed is a G-REX-10.

1. Feeder Cells and Antigen Presenting Cells

In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion (priming REP). In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during days 4-8. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during days 4-7. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during days 5-8. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during days 5-7. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during days 6-8. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during days 6-7. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during day 7 or 8. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during day 7. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during day 8.

In an embodiment, the priming first expansion procedures described herein (for example including expansion such as those described in Step B from FIG. 1 (in particular, e.g., FIG. 1B and/or FIG. 1C), as well as those referred to as pre-REP or priming REP) require feeder cells (also referred to herein as "antigen-presenting cells") at the initiation of the TIL expansion and during the priming first expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In some embodiments, $2.5\times10^8$ feeder cells are used during the priming first expansion. In some embodiments, $2.5\times10^8$ feeder cells per container are used during the priming first expansion. In some embodiments, $2.5\times10^8$ feeder cells per GREX-10 are used during the priming first expansion. In some embodiments, $2.5\times10^8$ feeder cells per GREX-100 are used during the priming first expansion.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and acceptable for use in the TIL expansion procedures described herein if the total number of viable cells on day 14 is less than the initial viable cell number put into culture on day 0 of the priming first expansion.

In some embodiments, PBMCs are considered replication incompetent and acceptable for use in the TIL expansion procedures described herein if the total number of viable cells, cultured in the presence of OKT3 and IL-2, on day 7 have not increased from the initial viable cell number put into culture on day 0 of the priming first expansion. In some embodiments, the PBMCs are cultured in the presence of 30 ng/mL OKT3 antibody and 3000 IU/mL IL-2. In some embodiments, the PBMCs are cultured in the presence of 30 ng/ml OKT3 antibody and 6000 IU/ml IL-2.

In some embodiments, PBMCs are considered replication incompetent and acceptable for use in the TIL expansion procedures described herein if the total number of viable cells, cultured in the presence of OKT3 and IL-2, on day 7 have not increased from the initial viable cell number put into culture on day 0 of the priming first expansion. In some embodiments, the PBMCs are cultured in the presence of 5-60 ng/mL OKT3 antibody and 1000-6000 IU/mL IL-2. In some embodiments, the PBMCs are cultured in the presence of 10-50 ng/ml OKT3 antibody and 2000-5000 IU/mL IL-2. In some embodiments, the PBMCs are cultured in the presence of 20-40 ng/ml OKT3 antibody and 2000-4000 IU/mL IL-2. In some embodiments, the PBMCs are cultured in the presence of 25-35 ng/ml OKT3 antibody and 2500-3500 IU/mL IL-2. In some embodiments, the PBMCs are cultured in the presence of 30 ng/ml OKT3 antibody and 6000 IU/mL IL-2. In some embodiments, the PBMCs are cultured in the presence of 15 ng/ml OKT3 antibody and 3000 IU/mL IL-2. In some embodiments, the PBMCs are cultured in the presence of 15 ng/mL OKT3 antibody and 6000 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the priming first expansion procedures described herein require a ratio of about $2.5\times10^8$ feeder cells to about $100\times10^6$ TILs. In another embodiment, the priming first expansion procedures described herein require a ratio of about $2.5\times10^8$ feeder cells to about $50\times10^6$ TILs. In yet another embodiment, the priming first expansion described herein require about $2.5\times 10^8$ feeder cells to about $25\times10^6$ TILs. In yet another embodiment, the priming first expansion described herein require about $2.5\times10^8$ feeder cells. In yet another embodiment, the priming first expansion requires one-fourth, one-third, five-twelfths, or one-half of the number of feeder cells used in the rapid second expansion.

In some embodiments, the media in the priming first expansion comprises IL-2. In some embodiments, the media in the priming first expansion comprises 6000 IU/mL of IL-2. In some embodiments, the media in the priming first expansion comprises antigen-presenting feeder cells. In some embodiments, the media in the priming first expansion comprises $2.5\times10^8$ antigen-presenting feeder cells per container. In some embodiments, the media in the priming first expansion comprises OKT-3. In some embodiments, the media comprises 30 ng of OKT-3 per container. In some embodiments, the container is a GREX100 MCS flask. In some embodiments, the media comprises 6000 IU/mL of IL-2, 30 ng/mL of OKT-3, and $2.5\times10^8$ antigen-presenting feeder cells. In some embodiments, the media comprises 6000 IU/mL of IL-2, 30 ng/ml of OKT-3, and $2.5\times10^8$ antigen-presenting feeder cells per container. In some embodiments, the media comprises 500 mL of culture medium and 15 μg of OKT-3 per $2.5\times10^8$ antigen-presenting feeder cells per container. In some embodiments, the media comprises 500 mL of culture medium and 15 μg of OKT-3 per container. In some embodiments, the container is a GREX100 MCS flask. In some embodiments, the media comprises 500 mL of culture medium and 6000 IU/mL of IL-2, 30 ng/ml of OKT-3, and $2.5\times10^8$ antigen-presenting feeder cells. In some embodiments, the media comprises 500 mL of culture medium and 6000 IU/mL of IL-2, 15 μg of OKT-3, and $2.5\times10^8$ antigen-presenting feeder cells per container. In some embodiments, the media comprises 500 mL of culture medium and 15 μg of OKT-3 per $2.5\times10^8$ antigen-presenting feeder cells per container.

In an embodiment, the priming first expansion procedures described herein require an excess of feeder cells over TILs during the second expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In an embodiment, artificial antigen-presenting (aAPC) cells are used in place of PBMCs.

In general, the allogenic PBMCs are inactivated, either via irradiation or heat treatment, and used in the TIL expansion procedures described herein, including the exemplary procedures described in the figures and examples.

In an embodiment, artificial antigen presenting cells are used in the priming first expansion as a replacement for, or in combination with, PBMCs.

2. Cytokines

The expansion methods described herein generally use culture media with high doses of a cytokine, in particular IL-2, as is known in the art.

Alternatively, using combinations of cytokines for the priming first expansion of TILs is additionally possible, with combinations of two or more of IL-2, IL-15 and IL-21 as is generally outlined in International Publication No. WO 2015/189356 and WO 2015/189357, hereby expressly incorporated by reference in their entirety. Thus, possible combinations include IL-2 and IL-15, IL-2 and IL-21, IL-15 and IL-21, and IL-2, IL-15 and IL-21, with the latter finding particular use in many embodiments. The use of combinations of cytokines specifically favors the generation of lymphocytes, and in particular T-cells as described therein.

TABLE 4

| Amino acid sequences of interleukins. | | |
|---|---|---|
| **Identifier** | **Sequence (One-Letter Amino Acid Symbols)** | |
| SEQ ID NO: 3 recombinant human IL-2 (rhIL-2) | MAPTSSSTKK TQLQLEHLLL DLQMILNGIN NYKNPKLTRM LTFKFYMPKK ATELKHLQCL | 60 |
| | EEELKPLEEV LNLAQSKNFH LRPRDLISNI NVIVLELKGS ETTFMCEYAD ETATIVEFLN | 120 |
| | RWITFCQSII STLT | 134 |
| SEQ ID NO: 4 Aldesleukin | PTSSSTKKTQ LQLEHLLLDL QMILNGINNY KNPKLTRMLT FKFYMPKKAT ELKHLQCLEE | 60 |
| | ELKPLEEVLN LAQSKNFHLR PRDLISNINV IVLELKGSET TFMCEYADET ATIVEFLNRW | 120 |
| | ITFSQSIIST LT | 132 |
| SEQ ID NO: 5 recombinant human IL-4 (rhIL-4) | MHKCDITLQE IIKTLNSLTE QKTLCTELTV TDIFAASKNT TEKETFCRAA TVLRQFYSHH | 60 |
| | EKDTRCLGAT AQQFHRHKQL IRFLKRLDRN LWGLAGLNSC PVKEANQSTL ENFLERLKTI | 120 |
| | MREKYSKCSS | 130 |
| SEQ ID NO: 6 recombinant human IL-7 (rhIL-7) | MDCDIEGKDG KQYESVLMVS IDQLLDSMKE IGSNCLNNEF NFFKRHICDA NKEGMFLFRA | 60 |
| | ARKLRQFLKM NSTGDFDLHL LKVSEGTTIL LNCTGQVKGR KPAALGEAQP TKSLEENKSL | 120 |
| | KEQKKLNDLC FLKRLLQEIK TCWNKILMGT KEH | 153 |
| SEQ ID NO: 7 recombinant human IL-15 (rhIL-15) | MNWVNVISDL KKIEDLIQSM HIDATLYTES DVHPSCKVTA MKCFLLELQV ISLESGDASI | 60 |
| | HDTVENLIIL ANNSLSSNGN VTESGCKECE ELEEKNIKEF LQSFVHIVQM FINTS | 115 |
| SEQ ID NO: 8 recombinant human IL-21 (rhIL-21) | MQDRHMIRMR QLIDIVDQLK NYVNDLVPEF LPAPEDVETN CEWSAFSCFQ KAQLKSANTG | 60 |
| | NNERIINVSI KKLKRKPPST NAGRRQKHRL TCPSCDSYEK KPPKEFLERF KSLLQKMIHQ | 120 |
| | HLSSRTHGSE DS | 132 |

C. STEP C: Priming First Expansion to Rapid Second Expansion Transition

In some cases, the bulk TIL population obtained from the priming first expansion (which can include expansions sometimes referred to as pre-REP), including, for example, the TIL population obtained from for example, Step B as indicated in FIG. 1 (in particular, e.g., FIG. 1B and/or FIG. 1C), can be subjected to a rapid second expansion (which can include expansions sometimes referred to as Rapid Expansion Protocol (REP)) and then cryopreserved as discussed below. Similarly, in the case where genetically modified TILs will be used in therapy, the expanded TIL population from the priming first expansion or the expanded TIL population from the rapid second expansion can be subjected to genetic modifications for suitable treatments prior to the expansion step or after the priming first expansion and prior to the rapid second expansion.

In some embodiments, the TILs obtained from the priming first expansion (for example, from Step B as indicated in FIG. 1 (in particular, e.g., FIG. 1B and/or FIG. 1C)) are stored until phenotyped for selection. In some embodiments, the TILs obtained from the priming first expansion (for example, from Step B as indicated in FIG. 1 (in particular, e.g., FIG. 1B and/or FIG. 1C)) are not stored and proceed directly to the rapid second expansion. In some embodiments, the TILs obtained from the priming first expansion are not cryopreserved after the priming first expansion and prior to the rapid second expansion. In some embodiments, the transition from the priming first expansion to the second expansion occurs at about 2 days, 3 days, 4, days, 5 days, 6 days, 7 days, or 8 days from when tumor fragmentation occurs and/or when the first priming expansion step is initiated. In some embodiments, the transition from the priming first expansion to the rapid second expansion occurs at about 3 days to 7 days from when fragmentation occurs and/or when the first priming expansion step is initiated. In some embodiments, the transition from the priming first expansion to the rapid second expansion occurs at about 3 days to 8 days from when fragmentation occurs and/or when the first priming expansion step is initiated. In some embodiments, the transition from the priming first expansion to the second expansion occurs at about 4 days to 7 days from when fragmentation occurs and/or when the first priming expansion step is initiated. In some embodiments, the transition from the priming first expansion to the second expansion occurs at about 4 days to 8 days from when fragmentation occurs and/or when the first priming expansion step is initiated. In some embodiments, the transition from the priming first expansion to the second expansion occurs at about 5 days to 7 days from when fragmentation occurs and/or when the first priming expansion step is initiated. In some embodiments, the transition from the priming first expansion to the second expansion occurs at about 5 days to 8 days from when fragmentation occurs and/or when the first priming expansion step is initiated. In some embodiments, the transition from the priming first expansion to the second expansion occurs at about 6 days to 7 days from when fragmentation occurs and/or when the first priming expansion step is initiated. In some embodiments, the transition from the priming first expansion to the second expansion occurs at about 6 days to 8 days from when fragmentation occurs and/or when the first priming expansion step is initiated. In some embodiments, the transition from the priming first expansion to the second expansion occurs at about 7 days to 8 days from when fragmentation occurs and/or when the first priming expansion step is initiated. In some embodiments, the transition from the priming first expansion to the second expansion occurs at about 7 days from when fragmentation occurs and/or when the first priming expansion step is initiated. In some embodiments, the transition from the priming first expansion to the second expansion occurs at about 8 days from when fragmentation occurs and/or when the first priming expansion step is initiated.

In some embodiments, the transition from the priming first expansion to the rapid second expansion occurs at 1 day, 2 days, 3 days, 4 days, 5 days, 6 days, 7 days, or 8 days from when fragmentation occurs and/or when the first priming expansion step is initiated. In some embodiments, the transition from the priming first expansion to the rapid second expansion occurs 1 day to 7 days from when fragmentation occurs and/or when the first priming expansion step is initiated. In some embodiments, the transition from the priming first expansion to the rapid second expansion occurs 1 day to 8 days from when fragmentation occurs and/or when the first priming expansion step is initiated. In some embodiments, the transition from the priming first expansion to the second expansion occurs 2 days to 7 days from when fragmentation occurs and/or when the first priming expansion step is initiated. In some embodiments, the transition from the priming first expansion to the second expansion occurs 2 days to 8 days from when fragmentation occurs and/or when the first priming expansion step is initiated. In some embodiments, the transition from the priming first expansion to the second expansion occurs 3 days to 7 days from when fragmentation occurs and/or when the first priming expansion step is initiated. In some embodiments, the transition from the priming first expansion to the second expansion occurs 3 days to 8 days from when fragmentation occurs and/or when the first priming expansion step is initiated. In some embodiments, the transition from the priming first expansion to the rapid second expansion occurs 4 days to 7 days from when fragmentation occurs and/or when the first priming expansion step is initiated. In some embodiments, the transition from the priming first expansion to the rapid second expansion occurs 4 days to 8 days from when fragmentation occurs and/or when the first priming expansion step is initiated. In some embodiments, the transition from the priming first expansion to the rapid second expansion occurs 5 days to 7 days from when fragmentation occurs and/or when the first priming expansion step is initiated. In some embodiments, the transition from the priming first expansion to the rapid second expansion occurs 5 days to 8 days from when fragmentation occurs and/or when the first priming expansion step is initiated. In some embodiments, the transition from the priming first expansion to the rapid second expansion occurs 6 days to 7 days from when fragmentation occurs and/or when the first priming expansion step is initiated. In some embodiments, the transition from the priming first expansion to the rapid second expansion occurs 6 days to 8 days from when fragmentation occurs and/or when the first priming expansion step is initiated. In some embodiments, the transition from the priming first expansion to the rapid second expansion occurs 7 days to 8 days from when fragmentation occurs and/or when the first priming expansion step is initiated. In some embodiments, the transition from the priming first expansion to the rapid second expansion occurs 7 days from when fragmentation occurs and/or when the first priming expansion step is initiated. In some embodiments, the transition from the priming first expansion to the rapid second expansion occurs 8 days from when fragmentation occurs and/or when the first priming expansion step is initiated.

In some embodiments, the TILs are not stored after the primary first expansion and prior to the rapid second expansion, and the TILs proceed directly to the rapid second expansion (for example, in some embodiments, there is no storage during the transition from Step B to Step D as shown in FIG. 1 (in particular, e.g., FIG. 1B and/or FIG. 1C). In some embodiments, the transition occurs in closed system, as described herein. In some embodiments, the TILs from the priming first expansion, the second population of TILs, proceeds directly into the rapid second expansion with no transition period.

In some embodiments, the transition from the priming first expansion to the rapid second expansion, for example, Step C according to FIG. 1 (in particular, e.g., FIG. 1B), is performed in a closed system bioreactor. In some embodiments, a closed system is employed for the TIL expansion, as described herein. In some embodiments, a single bioreactor is employed. In some embodiments, the single bioreactor employed is for example a GREX-10 or a GREX-100. In some embodiments, the closed system bioreactor is a single bioreactor. In some embodiments, the transition from the priming first expansion to the rapid second expansion involves a scale-up in container size. In some embodiments, the priming first expansion is performed in a smaller container than the rapid second expansion. In some embodiments, the priming first expansion is performed in a GREX-100 and the rapid second expansion is performed in a GREX-500.

In some embodiments, a maximum of $1\times10^6$ cells TILs are obtained at the end of the priming first expansion. In some embodiments, $0.1\times10^6$, $0.2\times10^6$, $0.3\times10^6$, $0.4\times10^6$, $0.5\times10^6$, $0.6\times10^6$, $0.7\times10^6$, $0.8\times10^6$, $0.9\times10^6$, $1.0\times10^6$, $1.1\times10^6$, $1.2\times10^6$, $1.3\times10^6$, $1.4\times10^6$, or $0.5\times10^6$ TILs are obtained at the end of the priming first expansion. In some embodiments, the TILs at the end of the priming first expansion are about 9% to about 40% PD-1+. In some embodiments, the TILs at the end of the priming first expansion are about 10% to about 40% PD-1+. In some embodiments, the TILs at the end of the priming first expansion are about 15% to about 30% PD-1+. In some embodiments, the TILs at the end of the priming first expansion are about 20% to about 40% PD-1+. In some embodiments, the TILs at the end of the priming first expansion are about 20% to about 30% PD-1+. In some embodiments, the TILs at the end of the priming first expansion are about 10% to about 20% PD-1+. In some embodiments, the TILs at the end of the priming first expansion are about 9%, about 10%, about 15%, about 20%, about 25%, about 30%, about 35%, or about 40% PD-1+. In some embodiments, the TILs at the end of the priming first expansion are about 9% to about 40% PD-1 high. In some embodiments, the TILs at the end of the priming first expansion are about 15% to about 30% PD-1 high. In some embodiments, the TILs at the end of the priming first expansion are about 20% to about 40% PD-1 high. In some embodiments, the TILs at the end of the priming first expansion are about 20% to about 30% PD-1 high. In some embodiments, the TILs at the end of the priming first expansion are about 10% to about 20% PD-1 high. In some embodiments, the TILs at the end of the priming first expansion are about 9%, about 10%, about 15%, about 20%, about 25%, about 30%, about 35%, or about 40% PD-1high.

D. STEP D: Rapid Second Expansion

In some embodiments, the TIL cell population is further expanded in number after harvest and the priming first expansion, after Step A and Step B, and the transition referred to as Step C, as indicated in FIG. 1 (in particular, e.g., FIG. 1B and/or FIG. 1C). This further expansion is referred to herein as the rapid second expansion, which can include expansion processes generally referred to in the art as a rapid expansion process (Rapid Expansion Protocol or REP; as well as processes as indicated in Step D of FIG. 1 (in particular, e.g., FIG. 1B and/or FIG. 1C). The rapid second expansion is generally accomplished using a culture media comprising a number of components, including feeder cells, a cytokine source, and an anti-CD3 antibody, in a gas-permeable container. In some embodiments, 1 day, 2 days, 3 days, or 4 days after initiation of the rapid second expansion (i.e., at days 8, 9, 10, or 11 of the overall Gen 3 process), the TILs are transferred to a larger volume container.

In some embodiments, a maximum of $1\times10^6$ cells TILs are added at the beginning of the rapid second expansion. In some embodiments, $0.1\times10^6$, $0.2\times10^6$, $0.3\times10^6$, $0.4\times10^6$, $0.5\times10^6$, $0.6\times10^6$, $0.7\times10^6$, $0.8\times10^6$, $0.9\times10^6$, $1.0\times10^6$, $1.1\times10^6$, $1.2\times10^6$, $1.3\times10^6$, $1.4\times10^6$, or $0.5\times10^6$ TILs are added at the beginning of the rapid second expansion. In some embodiments, the maximum cell density from the priming first expansion is 1e6 cells to provide 1e9 for initiating the rapid second expansion.

In some embodiments, the rapid second expansion (which can include expansions sometimes referred to as REP; as well as processes as indicated in Step D of FIG. 1 (in particular, e.g., FIG. 1B and/or FIG. 1C) of TIL can be performed using any TIL flasks or containers known by those of skill in the art. In some embodiments, the second TIL expansion can proceed for 1 day, 2 days, 3 days, 4, days, 5 days, 6 days, 7 days, 8 days, 9 days or 10 days after initiation of the rapid second expansion. In some embodiments, the second TIL expansion can proceed for about 1 days to about 9 days after initiation of the rapid second expansion. In some embodiments, the second TIL expansion can proceed for about 1 days to about 10 days after initiation of the rapid second expansion. In some embodiments, the second TIL expansion can proceed for about 2 days to about 9 days after initiation of the rapid second expansion. In some embodiments, the second TIL expansion can proceed for about 2 days to about 10 days after initiation of the rapid second expansion. In some embodiments, the second TIL expansion can proceed for about 3 days to about 9 days after initiation of the rapid second expansion. In some embodiments, the second TIL expansion can proceed for about 3 days to about 10 days after initiation of the rapid second expansion. In some embodiments, the second TIL expansion can proceed for about 4 days to about 9 days after initiation of the rapid second expansion. In some embodiments, the second TIL expansion can proceed for about 4 days to about 10 days after initiation of the rapid second expansion. In some embodiments, the second TIL expansion can proceed for about 5 days to about 9 days after initiation of the rapid second expansion. In some embodiments, the second TIL expansion can proceed for about 5 days to about 10 days after initiation of the rapid second expansion. In some embodiments, the second TIL expansion can proceed for about 6 days to about 9 days after initiation of the rapid second expansion. In some embodiments, the second TIL expansion can proceed for about 6 days to about 10 days after initiation of the rapid second expansion. In some embodiments, the second TIL expansion can proceed for about 7 days to about 9 days after initiation of the rapid second expansion. In some embodiments, the second TIL expansion can proceed for about 7 days to about 10 days after initiation of the rapid second expansion. In some embodiments, the second TIL expansion can proceed for about 8 days to about 9 days after initiation of the rapid second expansion. In some embodiments, the second TIL expansion can proceed for about 8 days to about 10 days after initiation of the rapid second expansion. In some embodiments, the second TIL expansion can proceed for about 9 days to about 10 days after initiation of the rapid second expansion. In some embodiments, the second TIL expansion can proceed for about 1 day after initiation of the rapid second expansion. In some embodiments, the second TIL expansion can proceed for about 2 days after initiation of the rapid second expansion. In some embodiments, the second TIL expansion can proceed for about 3 days after initiation of the rapid second expansion. In some embodiments, the second TIL expansion can proceed for about 4 days after initiation of the rapid second expansion. In some embodiments, the second TIL expansion can proceed for about 5 days after initiation of the rapid second expansion. In some embodiments, the second TIL expansion can proceed for about 6 days after initiation of the rapid second expansion. In some embodiments, the second TIL expansion can proceed for about 7 days after initiation of the rapid second expansion. In some embodiments, the second TIL expansion can proceed for about 8 days after initiation of the rapid second expansion. In some embodiments, the second TIL expansion can proceed for about 9 days after initiation of the rapid second expansion. In some embodiments, the second TIL expansion can proceed for about 10 days after initiation of the rapid second expansion.

In an embodiment, the rapid second expansion can be performed in a gas permeable container using the methods of the present disclosure (including for example, expansions referred to as REP; as well as processes as indicated in Step D of FIG. 1 (in particular, e.g., FIG. 1B and/or FIG. 1C). In some embodiments, the TILs are expanded in the rapid second expansion in the presence of IL-2, OKT-3, and feeder cells (also referred herein as "antigen-presenting cells"). In some embodiments, the TILs are expanded in the rapid second expansion in the presence of IL-2, OKT-3, and feeder cells, wherein the feeder cells are added to a final concentration that is twice, 2.4 times, 2.5 times, 3 times, 3.5 times or 4 times the concentration of feeder cells present in the priming first expansion. For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gpl 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In some embodiments, the cell culture medium comprises about 30 ng/ml of OKT-3 antibody. In an embodiment, the cell culture medium comprises about 0.1 ng/mL, about 0.5 ng/ml, about 1 ng/mL, about 2.5 ng/ml, about 5 ng/ml, about 7.5 ng/mL, about 10 ng/ml, about 15 ng/ml, about 20 ng/mL, about 25 ng/mL, about 30 ng/mL, about 35 ng/ml, about 40 ng/ml, about 50 ng/mL, about 60 ng/mL, about 70 ng/mL, about 80 ng/mL, about 90 ng/mL, about 100 ng/ml, about 200 ng/ml, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/ml and 100 ng/ml of OKT-3 antibody. In an embodiment, the cell culture medium comprises between 30 ng/ml and 60 ng/ml of OKT-3 antibody. In an embodiment, the cell culture medium comprises about 60 ng/ml OKT-3. In some embodiments, the OKT-3 antibody is muromonab.

In some embodiments, the media in the rapid second expansion comprises IL-2. In some embodiments, the media comprises 6000 IU/mL of IL-2. In some embodiments, the media in the rapid second expansion comprises antigen-presenting feeder cells. In some embodiments, the media in the rapid second expansion comprises $7.5\times10^8$ antigen-presenting feeder cells per container. In some embodiments, the media in the rapid second expansion comprises OKT-3. In some embodiments, the in the rapid second expansion media comprises 500 mL of culture medium and 30 μg of OKT-3 per container. In some embodiments, the container is a GREX100 MCS flask. In some embodiments, the in the rapid second expansion media comprises 6000 IU/mL of IL-2, 60 ng/ml of OKT-3, and $7.5\times10^8$ antigen-presenting feeder cells. In some embodiments, the media comprises 500 mL of culture medium and 6000 IU/mL of IL-2, 30 μg of OKT-3, and $7.5\times10^8$ antigen-presenting feeder cells per container.

In some embodiments, the media in the rapid second expansion comprises IL-2. In some embodiments, the media comprises 6000 IU/mL of IL-2. In some embodiments, the media in the rapid second expansion comprises antigen-presenting feeder cells. In some embodiments, the media comprises between $5\times10^8$ and $7.5\times10^8$ antigen-presenting feeder cells per container. In some embodiments, the media in the rapid second expansion comprises OKT-3. In some embodiments, the media in the rapid second expansion comprises 500 mL of culture medium and 30 μg of OKT-3 per container. In some embodiments, the container is a GREX100 MCS flask. In some embodiments, the media in the rapid second expansion comprises 6000 IU/mL of IL-2, 60 ng/ml of OKT-3, and between $5\times10^8$ and $7.5\times10^8$ antigen-presenting feeder cells. In some embodiments, the media in the rapid second expansion comprises 500 mL of culture medium and 6000 IU/mL of IL-2, 30 μg of OKT-3, and between $5\times10^8$ and $7.5\times10^8$ antigen-presenting feeder cells per container.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the cell culture medium further comprises IL-2 at an initial concentration of about 3000 IU/mL and OKT-3 antibody at an initial concentration of about 30 ng/ml, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including for example during a Step D processes according to FIG. 1 (in particular, e.g., FIG. 1B and/or FIG. 1C), as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 1 (in particular, e.g., FIG. 1B and/or FIG. 1C) and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments, the antigen-presenting feeder cells (APCs) are PBMCs. In an embodiment, the ratio of TILs to PBMCs and/or antigen-presenting cells in the rapid expansion and/or the second expansion is about 1 to 10, about 1 to 15, about 1 to 20, about 1 to 25, about 1 to 30, about 1 to 35, about 1 to 40, about 1 to 45, about 1 to 50, about 1 to 75, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the rapid second expansion is performed in flasks with the bulk TILs being mixed with a 100- or 200-fold excess of inactivated feeder cells, wherein the feeder cell concentration is at least 1.1 times (1.1×), 1.2×, 1.3×, 1.4×, 1.5×, 1.6×, 1.7×, 1.8×, 1.8×, 2×, 2.1×2.2×, 2.3×, 2.4×, 2.5×, 2.6×, 2.7×, 2.8×, 2.9×, 3.0×, 3.1×, 3.2×, 3.3×, 3.4×, 3.5×, 3.6×, 3.7×, 3.8×, 3.9× or 4.0× the feeder cell concentration in the priming first expansion, 30 ng/ml OKT3 anti-CD3 antibody and 6000 IU/mL IL-2 in 150 ml media. Media replacement is done (generally ⅔ media replacement via aspiration of ⅔ of spent media and replacement with an equal volume of fresh media) until the cells are transferred to an alternative growth chamber. Alternative growth chambers include G-REX flasks and gas permeable containers as more fully discussed below.

In some embodiments, the rapid second expansion (which can include processes referred to as the REP process) is 7 to 9 days, as discussed in the examples and figures. In some embodiments, the second expansion is 7 days. In some embodiments, the second expansion is 8 days. In some embodiments, the second expansion is 9 days.

In an embodiment, the second expansion (which can include expansions referred to as REP, as well as those referred to in Step D of FIG. 1 (in particular, e.g., FIG. 1B and/or FIG. 1C) may be performed in 500 mL capacity gas permeable flasks with 100 cm gas-permeable silicon bottoms (G-Rex 100, commercially available from Wilson Wolf Manufacturing Corporation, New Brighton, MN, USA), $5\times10^6$ or $10\times10^6$ TIL may be cultured with PBMCs in 400 mL of 50/50 medium, supplemented with 5% human AB serum, 3000 IU per mL of IL-2 and 60 ng per ml of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 6000 IU per mL of IL-2, and added back to the original GREX-100 flasks. When TIL are expanded serially in GREX-100 flasks, on day 10 or 11 the TILs can be moved to a larger flask, such as a GREX-500. The cells may be harvested on day 14 of culture. The cells may be harvested on day 15 of culture. The cells may be harvested on day 16 of culture. In some embodiments, media replacement is done until the cells are transferred to an alternative growth chamber. In some embodiments, ⅔ of the media is replaced by aspiration of ⅔ of spent media and replacement with an equal volume of fresh media. In some embodiments, alternative growth chambers include GREX flasks and gas permeable containers as more fully discussed below.

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T-cell Expansion Basal Medium, CTS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^+$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^+$, $Sn^{2+}$ and $Zr^{4+}$. In some embodiments, the defined medium further comprises L-glutamine, sodium bicarbonate and/or 2-mercaptoethanol.

In some embodiments, the CTSTMOpTmizer™ T-cell Immune Cell Serum Replacement is used with conventional growth media, including but not limited to CTS™ OpTmizer™ T-cell Expansion Basal Medium, CTS™ OpTmizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTSTMOpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTSTMOpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTSTMOpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM. In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM.

In some embodiments, the defined media described in International PCT Publication No. WO/1998/030679, which is herein incorporated by reference, are useful in the present invention. In that publication, serum-free eukaryotic cell culture media are described. The serum-free, eukaryotic cell culture medium includes a basal cell culture medium supplemented with a serum-free supplement capable of supporting the growth of cells in serum-free culture. The serum-free eukaryotic cell culture medium supplement comprises or is obtained by combining one or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3+}$, $Ge^{4}$, $Se^{4}$, Br, T, $Mn^{2}$, P, $Si^{4+}$, $V^{5+}$, Most, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table A below. In other embodiments, the non-trace element moiety ingredients in the defined medium are present in the final concentrations listed in the column under the heading "A Preferred Embodiment of the 1× Medium" in Table A below. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table A below.

TABLE A

Concentrations of Non-Trace Element Moiety Ingredients

| Ingredient | A preferred embodiment in supplement (mg/L) (About) | Concentration range in 1X medium (mg/L) (About) | A preferred embodiment in 1X medium (mg/L) (About) |
|---|---|---|---|
| Glycine | 150 | 5-200 | 53 |
| L-Histidine | 940 | 5-250 | 183 |
| L-Isoleucine | 3400 | 5-300 | 615 |
| L-Methionine | 90 | 5-200 | 44 |
| L-Phenylalanine | 1800 | 5-400 | 336 |
| L-Proline | 4000 | 1-1000 | 600 |
| L-Hydroxyproline | 100 | 1-45 | 15 |
| L-Serine | 800 | 1-250 | 162 |
| L-Threonine | 2200 | 10-500 | 425 |
| L-Tryptophan | 440 | 2-110 | 82 |
| L-Tyrosine | 77 | 3-175 | 84 |
| L-Valine | 2400 | 5-500 | 454 |
| Thiamine | 33 | 1-20 | 9 |
| Reduced Glutathione | 10 | 1-20 | 1.5 |
| Ascorbic Acid-2-$PO_4$ (Mg Salt) | 330 | 1-200 | 50 |
| Transferrin (iron saturated) | 55 | 1-50 | 8 |
| Insulin | 100 | 1-100 | 10 |
| Sodium Selenite | 0.07 | 0.000001-0.0001 | 0.00001 |
| AlbuMAX ®I | 83,000 | 5000-50,000 | 12,500 |

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., "Ex vivo expansion of human T cells for adoptive immunotherapy using the novel Xeno-free CTS Immune Cell Serum Replacement," *Clin Transl Immunol-*

*ogy,* 4 (1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME or BME; also known as 2-mercaptoethanol, CAS 60-24-2)

In an embodiment, the rapid second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the rapid second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the standard Cellometer K2 Image Cytometer Automatic Cell Counter protocol.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

In some embodiments, the rapid second expansion culture medium (e.g., sometimes referred to as CM2 or the second cell culture medium), comprises IL-2, OKT-3, as well as the antigen-presenting feeder cells (APCs), as discussed in more detail below. In some embodiments, the rapid second expansion culture medium (e.g., sometimes referred to as CM2 or the second cell culture medium), comprises 6000 IU/mL IL-2, 30 μg/flask OKT-3, as well as $7.5\times10^8$ antigen-presenting feeder cells (APCs), as discussed in more detail below. In some embodiments, the rapid second expansion culture medium (e.g., sometimes referred to as CM2 or the second cell culture medium), comprises IL-2, OKT-3, as well as the antigen-presenting feeder cells (APCs), as discussed in more detail below. In some embodiments, the rapid second expansion culture medium (e.g., sometimes referred to as CM2 or the second cell culture medium), comprises 6000 IU/mL IL-2, 30 μg/flask OKT-3, as well as $5\times10^8$ antigen-presenting feeder cells (APCs), as discussed in more detail below.

In some embodiments, the rapid second expansion, for example, Step D according to FIG. 1 (in particular, e.g., FIG. 1B and/or FIG. 1C), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-100 or a G-REX-500. In some embodiments, the bioreactor employed is a G-REX-100. In some embodiments, the bioreactor employed is a G-REX-500.

1. Feeder Cells and Antigen Presenting Cells

In an embodiment, the rapid second expansion procedures described herein (for example including expansion such as those described in Step D from FIG. 1 (in particular, e.g., FIG. 1B and/or FIG. 1C), as well as those referred to as REP) require an excess of feeder cells during REP TIL expansion and/or during the rapid second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and acceptable for use in the TIL expansion procedures described herein if the total number of viable cells on day 7 or 14 is less than the initial viable cell number put into culture on day 0 of the REP and/or day 0 of the second expansion (i.e., the start day of the second expansion).

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/ml OKT3 antibody and 3000 IU/ml IL-2. In some embodiments, the PBMCs are cultured in the presence of 60 ng/ml OKT3 antibody and 6000 IU/ml IL-2. In some embodiments, the PBMCs are cultured in the presence of 60 ng/ml OKT3 antibody and 3000 IU/ml IL-2. In some embodiments, the PBMCs are cultured in the presence of 30 ng/ml OKT3 antibody and 6000 IU/ml IL-2.

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30-60 ng/ml OKT3 antibody and 1000-6000 IU/ml IL-2. In some embodiments, the PBMCs are cultured in the presence of 30-60 ng/ml OKT3 antibody and 2000-5000 IU/ml IL-2. In some embodiments, the PBMCs are cultured in the presence of 30-60 ng/ml OKT3 antibody and 2000-4000 IU/ml IL-2. In some embodiments, the PBMCs are cultured in the presence of 30-60 ng/ml OKT3 antibody and 2500-3500 IU/ml IL-2. In some embodiments, the PBMCs are cultured in the presence of 30-60 ng/ml OKT3 antibody and 6000 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 10, about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $5\times10^8$ feeder cells to about $100\times10^6$ TILs. In an embodiment, the second expansion procedures described herein require a ratio of about $7.5\times10^8$ feeder cells to about $100\times10^6$ TILs. In another embodiment, the second expansion procedures described herein require a ratio of about $5\times10^8$ feeder cells to about $50\times10^6$ TILs. In another embodiment, the second expansion procedures described herein require a ratio of about $7.5\times10^8$ feeder cells to about $50\times10^6$ TILs. In yet another embodiment, the second expansion procedures described herein require about $5\times10^8$ feeder cells to about $25\times10^6$ TILs. In yet another embodiment, the second expansion procedures described herein require about $7.5\times10^8$ feeder cells to about $25\times10^6$ TILs. In yet another embodiment, the rapid second expansion requires twice the number of feeder cells as the rapid second expansion. In yet another embodiment, when the priming first expansion described herein requires about $2.5\times10^8$ feeder cells, the rapid second expansion requires about $5\times10^8$ feeder cells. In yet another embodiment, when the priming first expansion described herein requires about $2.5\times10^8$ feeder cells, the rapid second expansion requires about $7.5\times10^8$ feeder cells. In yet another embodiment, the rapid second expansion requires two times (2.0×), 2.5×, 3.0×, 3.5× or 4.0× the number of feeder cells as the priming first expansion.

In some embodiments, the second expansion procedures described herein require a ratio of about $5\times10^8$ feeder cells to about $100\times10^6$ TILs. In an embodiment, the second expansion procedures described herein require a ratio of about $7.5\times10^8$ feeder cells to about $100\times10^6$ TILs. In another embodiment, the second expansion procedures described herein require a ratio of about $5\times10^8$ feeder cells to about $50\times10^6$ TILs. In another embodiment, the second expansion procedures described herein require a ratio of about $7.5\times10^8$ feeder cells to about $50\times10^6$ TILs. In yet another embodiment, the second expansion procedures described herein require about $5\times10^8$ feeder cells to about $25\times10^6$ TILs. In yet another embodiment, the second expansion procedures described herein require about $7.5\times10^8$ feeder cells to about $25\times10^6$ TILs. In yet another embodiment, the rapid second expansion requires the same number of feeder cells as the rapid second expansion. In yet another embodiment, when the priming first expansion described herein requires about $2.5\times10^8$ feeder cells, the rapid second expansion requires about $2.5\times10^8$ feeder cells. In yet another embodiment, when the priming first expansion described herein requires about $5\times10^8$ feeder cells, the rapid second expansion requires about $5\times10^8$ feeder cells. In yet another embodiment, when the priming first expansion described herein requires about $7.5\times10^8$ feeder cells, the rapid second expansion requires about $7.5\times10^8$ feeder cells. In yet another embodiment, the rapid second expansion requires two times (2.0×), 2.5×, 3.0×, 3.5× or 4.0× the number of feeder cells as the priming first expansion.

In some embodiments, the second expansion procedures described herein require a ratio of about $5\times10^8$ feeder cells to about $100\times10^6$ TILs. In an embodiment, the second expansion procedures described herein require a ratio of about $7.5\times10^8$ feeder cells to about $100\times10^6$ TILs. In another embodiment, the second expansion procedures described herein require a ratio of about $5\times10^8$ feeder cells to about $50\times10^6$ TILs. In another embodiment, the second expansion procedures described herein require a ratio of about $7.5\times10^8$ feeder cells to about $50\times10^6$ TILs. In yet another embodiment, the second expansion procedures described herein require about $5\times10^8$ feeder cells to about $25\times10^6$ TILs. In yet another embodiment, the second expansion procedures described herein require about $7.5\times10^8$ feeder cells to about $25\times10^6$ TILs. In yet another embodiment, the rapid second expansion requires the same number of feeder cells as the rapid second expansion. In yet another embodiment, when the priming first expansion described herein requires about $2.5\times10^8$ feeder cells, the rapid second expansion requires about $2.5\times10^8$ feeder cells. In yet another embodiment, when the priming first expansion described herein requires about $5\times10^8$ feeder cells, the rapid second expansion requires about $5\times10^8$ feeder cells. In yet another embodiment, when the priming first expansion described herein requires about $7.5\times10^8$ feeder cells, the rapid second expansion requires about $7.5\times10^8$ feeder cells.

In an embodiment, the rapid second expansion procedures described herein require an excess of feeder cells during the rapid second expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In an embodiment, artificial antigen-presenting (aAPC) cells are used in place of PBMCs. In some embodiments, the PBMCs are added to the rapid second expansion at twice the concentration of PBMCs that were added to the priming first expansion.

In general, the allogenic PBMCs are inactivated, either via irradiation or heat treatment, and used in the TIL expansion procedures described herein, including the exemplary procedures described in the figures and examples.

In an embodiment, artificial antigen presenting cells are used in the rapid second expansion as a replacement for, or in combination with, PBMCs.

Any suitable dose of TILs can be administered. In some embodiments, from about $2.3\times10^{10}$ to about $13.7\times10^{10}$ TILs are administered, with an average of around $7.8\times10^{10}$ TILs, particularly if the cancer is melanoma. In an embodiment, about $1.2\times10^{10}$ to about $4.3\times10^{10}$ of TILs are administered. In some embodiments, about $3\times10^{10}$ to about $12\times10^{10}$ TILs are administered. In some embodiments, about $4\times10^{10}$ to about $10\times10^{10}$ TILs are administered. In some embodiments, about $5\times10^{10}$ to about $8\times10^{10}$ TILs are administered. In some embodiments, about $6\times10^{10}$ to about $8\times10^{10}$ TILs are administered. In some embodiments, about $7\times10^{10}$ to about $8\times10^{10}$ TILs are administered. In some embodiments, the therapeutically effective dosage is about $2.3\times10^{10}$ to about $13.7\times10^{10}$. In some embodiments, the therapeutically effective dosage is about $7.8\times10^{10}$ TILs, particularly of the cancer is melanoma. In some embodiments, the therapeutically effective dosage is about $1.2\times10^{10}$ to about $4.3\times10^{10}$ of TILs. In some embodiments, the therapeutically effective dosage is about $3\times10^{10}$ to about $12\times10^{10}$ TILs. In some embodiments, the therapeutically effective dosage is about $4\times10^{10}$ to about $10\times10^{10}$ TILs. In some embodiments, the therapeutically effective dosage is about $5\times10^{10}$ to about $8\times10^{10}$ TILs. In some embodiments, the therapeutically effective dosage is about $6\times10^{10}$ to about $8\times10^{10}$ TILs. In some embodiments, the therapeutically effective dosage is about $7\times10^{10}$ to about $8\times10^{10}$ TILs.

In some embodiments, the number of the TILs provided in the pharmaceutical compositions of the invention is about $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In an embodiment, the number of the TILs provided in the pharmaceutical compositions of the invention is in the range of $1\times10^{6}$ to $5\times10^{6}$, $5\times10^{6}$ to $1\times10^{7}$, $1\times10^{7}$ to $5\times10^{7}$, $5\times10^{7}$ to $1\times10^{8}$, $1\times10^{8}$ to $5\times10^{8}$, $5\times10^{8}$ to $1\times10^{9}$, $1\times10^{9}$ to $5\times10^{9}$, $5\times10^{9}$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

2. Cytokines

The rapid second expansion methods described herein generally use culture media with high doses of a cytokine, in particular IL-2, as is known in the art.

Alternatively, using combinations of cytokines for the rapid second expansion of TILs is additionally possible, with combinations of two or more of IL-2, IL-15 and IL-21 as is generally outlined in International Publication No. WO 2015/189356 and WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

E. STEP E: Harvest TILS

After the rapid second expansion step, cells can be harvested. In some embodiments the TILs are harvested after one, two, three, four or more expansion steps, for example as provided in FIG. 1 (in particular, e.g., FIG. 1B and/or FIG. 1C). In some embodiments the TILs are harvested after two expansion steps, for example as provided in FIG. 1 (in particular, e.g., FIG. 1B and/or FIG. 1C). In some embodiments the TILs are harvested after two expansion steps, one priming first expansion and one rapid second expansion, for example as provided in FIG. 1 (in particular, e.g., FIG. 1B).

TILs can be harvested in any appropriate and sterile manner, including for example by centrifugation. Methods for TIL harvesting are well known in the art and any such known methods can be employed with the present process. In some embodiments, TILS are harvested using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing system is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the rapid second expansion, for example, Step D according to FIG. 1 (in particular, e.g., FIG. 1B and/or FIG. 1C), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-100 or a G-REX-500. In some embodiments, the bioreactor employed is a G-REX-100. In some embodiments, the bioreactor employed is a G-REX-500.

In some embodiments, Step E according to FIG. 1 (in particular, e.g., FIG. 1B and/or FIG. 1C), is performed according to the processes described herein. In some embodiments, the closed system is accessed via syringes under sterile conditions in order to maintain the sterility and closed nature of the system. In some embodiments, a closed system as described herein is employed.

In some embodiments, TILs are harvested according to the methods described herein. In some embodiments, TILs between days 14 and 16 are harvested using the methods as described herein. In some embodiments, TILs are harvested at 14 days using the methods as described herein. In some embodiments, TILs are harvested at 15 days using the methods as described herein. In some embodiments, TILs are harvested at 16 days using the methods as described herein.

F. STEP F: Final Formulation/Transfer to Infusion Bag

After Steps A through E as provided in an exemplary order in FIG. 1 (in particular, e.g., FIG. 1B and/or FIG. 1C) and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using the methods of the present disclosure are administered to a patient as a pharmaceutical composition. In an embodiment, the pharmaceutical composition is a suspension of TILs in a sterile buffer. TILs expanded as disclosed herein may be administered by any suitable route as known in the art. In some embodiments, the TILs are administered as a single intra-arterial or intravenous infusion, which preferably lasts approximately 30 to 60 minutes. Other suitable routes of administration include intraperitoneal, intrathecal, and intralymphatic.

G. PBMC Feeder Cell Ratios

In some embodiments, the culture media used in expansion methods described herein (see for example, FIG. 1 (in particular, e.g., FIG. 1B and/or FIG. 1C) include an anti-CD3 antibody e.g. OKT-3. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

In an embodiment, the number of PBMC feeder layers is calculated as follows:

A. Volume of a T-cell (10 μm diameter): $V=(4/3)\pi r^3=523.6\ \mu m^3$

B. Columne of G-Rex 100 (M) with a 40 μm (4 cells) height: $V=(4/3)\pi r^3=4\times10^{12}\ \mu m^3$ C. Number cell required to fill column B: $4\times10^{12}\ \mu m^3/523.6\ \mu m^3=7.6\times10^8\ \mu m^3*0.64=4.86\times10^8$ D. Number cells that can be optimally activated in 4D space: $4.86\times10^8/24=20.25\times10^6$ E. Number of feeders and TIL extrapolated to G-Rex 500: TIL: $100\times10^6$ and Feeder: $2.5\times10^9$ In this calculation, an approximation of the number of mononuclear cells required to provide an icosahedral geometry for activation of TIL in a cylinder with a 100 $cm^2$ base is used. The calculation derives the experimental result of ~$5\times10^8$ for threshold activation of T-cells which closely mirrors NCI experimental data.[(1)] (C) The multiplier (0.64) is the random packing density for equivalent spheres as calculated by Jaeger and Nagel in 1992[(2)]. (D) The divisor 24 is the number of equivalent spheres that could contact a similar object in 4 dimensional space "the Newton number."[(3)].

[(1)] Jin, Jianjian, et. al., Simplified Method of the Growth of Human Tumor Infiltrating Lymphocytes (TIL) in Gas-Permeable Flasks to Numbers Needed for Patient Treatment. J Immunother. 2012 April; 35 (3): 283-292.

[(2)] Jaeger H M, Nagel S R. Physics of the granular state. Science. 1992 Mar. 20; 255 (5051): 1523-31.

[(3)] O. R. Musin (2003). "The problem of the twenty-five spheres". Russ. Math. Surv. 58 (4): 794-795.

In an embodiment, the number of antigen-presenting feeder cells exogenously supplied during the priming first expansion is approximately one-half the number of antigen-presenting feeder cells exogenously supplied during the rapid second expansion. In certain embodiments, the method comprises performing the priming first expansion in a cell culture medium which comprises approximately 50% fewer antigen presenting cells as compared to the cell culture medium of the rapid second expansion.

In another embodiment, the number of antigen-presenting feeder cells (APCs) exogenously supplied during the rapid second expansion is greater than the number of APCs exogenously supplied during the priming first expansion.

In another embodiment, the ratio of the number of APCs exogenously supplied during the rapid second expansion to the number of APCs exogenously supplied during the priming first expansion is selected from a range of from at or about 1.1:1 to at or about 20:1.

In another embodiment, the ratio of the number of APCs exogenously supplied during the rapid second expansion to the number of APCs exogenously supplied during the priming first expansion is selected from a range of from at or about 1.1:1 to at or about 10:1.

In another embodiment, the ratio of the number of APCs exogenously supplied during the rapid second expansion to the number of APCs exogenously supplied during the priming first expansion is selected from a range of from at or about 1.1:1 to at or about 9:1.

In another embodiment, the ratio of the number of APCs exogenously supplied during the rapid second expansion to the number of APCs exogenously supplied during the priming first expansion is selected from a range of from at or about 1.1:1 to at or about 8:1.

In another embodiment, the ratio of the number of APCs exogenously supplied during the rapid second expansion to the number of APCs exogenously supplied during the priming first expansion is selected from a range of from at or about 1.1:1 to at or about 7:1.

In another embodiment, the ratio of the number of APCs exogenously supplied during the rapid second expansion to the number of APCs exogenously supplied during the priming first expansion is selected from a range of from at or about 1.1:1 to at or about 6:1.

In another embodiment, the ratio of the number of APCs exogenously supplied during the rapid second expansion to the number of APCs exogenously supplied during the priming first expansion is selected from a range of from at or about 1.1:1 to at or about 5:1.

In another embodiment, the ratio of the number of APCs exogenously supplied during the rapid second expansion to the number of APCs exogenously supplied during the priming first expansion is selected from a range of from at or about 1.1:1 to at or about 4:1.

In another embodiment, the ratio of the number of APCs exogenously supplied during the rapid second expansion to the number of APCs exogenously supplied during the priming first expansion) is selected from a range of from at or about 1.1:1 to at or about 3:1.

In another embodiment, the ratio of the number of APCs exogenously supplied during the rapid second expansion to the number of APCs exogenously supplied during the priming first expansion is selected from a range of from at or about 1.1:1 to at or about 2.9:1.

In another embodiment, the ratio of the number of APCs exogenously supplied during the rapid second expansion to the number of APCs exogenously supplied during the priming first expansion is selected from a range of from at or about 1.1:1 to at or about 2.8:1.

In another embodiment, the ratio of the number of APCs exogenously supplied during the rapid second expansion to the number of APCs exogenously supplied during the priming first expansion is selected from a range of from at or about 1.1:1 to at or about 2.7:1.

In another embodiment, the ratio of the number of APCs exogenously supplied during the rapid second expansion to the number of APCs exogenously supplied during the priming first expansion is selected from a range of from at or about 1.1:1 to at or about 2.6:1.

In another embodiment, the ratio of the number of APCs exogenously supplied during the rapid second expansion to the number of APCs exogenously supplied during the priming first expansion is selected from a range of from at or about 1.1:1 to at or about 2.5:1.

In another embodiment, the ratio of the number of APCs exogenously supplied during the rapid second expansion to the number of APCs exogenously supplied during the priming first expansion is selected from a range of from at or about 1.1:1 to at or about 2.4:1.

In another embodiment, the ratio of the number of APCs exogenously supplied during the rapid second expansion to the number of APCs exogenously supplied during the priming first expansion is selected from a range of from at or about 1.1:1 to at or about 2.3:1.

In another embodiment, the ratio of the number of APCs exogenously supplied during the rapid second expansion to the number of APCs exogenously supplied during the priming first expansion is selected from a range of from at or about 1.1:1 to at or about 2.2:1.

In another embodiment, the ratio of the number of APCs exogenously supplied during the rapid second expansion to the number of APCs exogenously supplied during the priming first expansion is selected from a range of from at or about 1.1:1 to at or about 2.1:1.

In another embodiment, the ratio of the number of APCs exogenously supplied during the rapid second expansion to the number of APCs exogenously supplied during the priming first expansion is selected from a range of from at or about 1.1:1 to at or about 2:1.

In another embodiment, the ratio of the number of APCs exogenously supplied during the rapid second expansion to the number of APCs exogenously supplied during the priming first expansion is selected from a range of from at or about 2:1 to at or about 10:1.

In another embodiment, the ratio of the number of APCs exogenously supplied during the rapid second expansion to the number of APCs exogenously supplied during the priming first expansion is selected from a range of from at or about 2:1 to at or about 5:1.

In another embodiment, the ratio of the number of APCs exogenously supplied during the rapid second expansion to the number of APCs exogenously supplied during the priming first expansion is selected from a range of from at or about 2:1 to at or about 4:1.

In another embodiment, the ratio of the number of APCs exogenously supplied during the rapid second expansion to the number of APCs exogenously supplied during the priming first expansion is selected from a range of from at or about 2:1 to at or about 3:1.

In another embodiment, the ratio of the number of APCs exogenously supplied during the rapid second expansion to the number of APCs exogenously supplied during the priming first expansion is selected from a range of from at or about 2:1 to at or about 2.9:1.

In another embodiment, the ratio of the number of APCs exogenously supplied during the rapid second expansion to the number of APCs exogenously supplied during the priming first expansion is selected from a range of from at or about 2:1 to at or about 2.8:1.

In another embodiment, the ratio of the number of APCs exogenously supplied during the rapid second expansion to the number of APCs exogenously supplied during the priming first expansion is selected from a range of from at or about 2:1 to at or about 2.7:1.

In another embodiment, the ratio of the number of APCs exogenously supplied during the rapid second expansion to the number of APCs exogenously supplied during the priming first expansion is selected from a range of from at or about 2:1 to at or about 2.6:1.

In another embodiment, the ratio of the number of APCs exogenously supplied during the rapid second expansion to the number of APCs exogenously supplied during the priming first expansion is selected from a range of from at or about 2:1 to at or about 2.5:1.

In another embodiment, the ratio of the number of APCs exogenously supplied during the rapid second expansion to the number of APCs exogenously supplied during the priming first expansion is selected from a range of from at or about 2:1 to at or about 2.4:1.

In another embodiment, the ratio of the number of APCs exogenously supplied during the rapid second expansion to the number of APCs exogenously supplied during the priming first expansion is selected from a range of from at or about 2:1 to at or about 2.3:1.

In another embodiment, the ratio of the number of APCs exogenously supplied during the rapid second expansion to the number of APCs exogenously supplied during the priming first expansion is selected from a range of from at or about about 2:1 to at or about 2.2:1.

In another embodiment, the ratio of the number of APCs exogenously supplied during the rapid second expansion to the number of APCs exogenously supplied during the priming first expansion is selected from a range of from at or about 2:1 to at or about 2.1:1.

In another embodiment, the ratio of the number of APCs exogenously supplied during the rapid second expansion to the number of APCs exogenously supplied during the priming first expansion is at or about 2:1.

In another embodiment, the ratio of the number of APCs exogenously supplied during the rapid second expansion to the number of APCs exogenously supplied during the priming first expansion is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the number of APCs exogenously supplied during the priming first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs, and the number of APCs exogenously supplied during the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$ APCs.

In another embodiment, the number of APCs exogenously supplied during the priming first expansion is selected from the range of at or about $1.5\times10^8$ APCs to at or about $3\times10^8$ APCs, and the number of APCs exogenously supplied during the rapid second expansion is selected from the range of at or about $4\times10^8$ APCs to at or about $7.5\times10^8$ APCs.

In another embodiment, the number of APCs exogenously supplied during the priming first expansion is selected from the range of at or about $2\times10^8$ APCs to at or about $2.5\times10^8$ APCs, and the number of APCs exogenously supplied during the rapid second expansion is selected from the range of at or about $4.5\times10^8$ APCs to at or about $5.5\times10^8$ APCs.

In another embodiment, the number of APCs exogenously supplied during the priming first expansion is at or about $2.5\times10^8$ APCs, and the number of APCs exogenously supplied during the rapid second expansion is at or about $5\times10^8$ APCs.

In an embodiment, the number of APCs (including, for example, PBMCs) added at day 0 of the priming first expansion is approximately one-half of the number of PBMCs added at day 7 of the priming first expansion (e.g., day 7 of the method). In certain embodiments, the method comprises adding antigen presenting cells at day 0 of the priming first expansion to the first population of TILs and adding antigen presenting cells at day 7 to the second population of TILs, wherein the number of antigen presenting cells added at day 0 is approximately 50% of the number of antigen presenting cells added at day 7 of the priming first expansion (e.g., day 7 of the method).

In another embodiment, the number of APCs (including, for example, PBMCs) exogenously supplied at day 7 of the rapid second expansion is greater than the number of PBMCs exogenously supplied at day 0 of the priming first expansion.

In another embodiment, the APCs exogenously supplied in the priming first expansion are seeded in the culture flask at a density selected from a range of at or about $1.0\times10^6$ APCs/cm$^2$ to at or about $4.5\times10^6$ APCs/cm$^2$.

In another embodiment, the APCs exogenously supplied in the priming first expansion are seeded in the culture flask at a density selected from a range of at or about $1.5\times10^6$ APCs/cm$^2$ to at or about $3.5\times10^6$ APCs/cm$^2$ In another embodiment, the APCs exogenously supplied in the priming first expansion are seeded in the culture flask at a density selected from a range of at or about $2\times10^6$ APCs/cm$^2$ to at or about $3\times10^6$ APCs/cm$^2$.

In another embodiment, the APCs exogenously supplied in the priming first expansion are seeded in the culture flask at a density of at or about $2\times10^6$ APCs/cm$^2$.

In another embodiment, the APCs exogenously supplied in the priming first expansion are seeded in the culture flask at a density of at or about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$ or $4.5\times10^6$ APCs/cm$^2$.

In another embodiment, the APCs exogenously supplied in the rapid second expansion are seeded in the culture flask at a density selected from a range of at or about $2.5\times10^6$ APCs/cm$^2$ to at or about $7.5\times10^6$ APCs/cm$^2$.

In another embodiment, the APCs exogenously supplied in the rapid second expansion are seeded in the culture flask at a density selected from a range of at or about $3.5\times10^6$ APCs/cm$^2$ to about $6.0\times10^6$ APCs/cm$^2$.

In another embodiment, the APCs exogenously supplied in the rapid second expansion are seeded in the culture flask at a density selected from a range of at or about $4.0\times10^6$ APCs/cm$^2$ to about $5.5\times10^6$ APCs/cm$^2$.

In another embodiment, the APCs exogenously supplied in the rapid second expansion are seeded in the culture flask at a density selected from a range of at or about $4.0\times10^6$ APCs/cm$^2$.

In another embodiment, the APCs exogenously supplied in the rapid second expansion are seeded in the culture flask at a density of at or about $2.5\times10^6$ APCs/cm$^2$, $2.6\times10^6$ APCs/cm$^2$, $2.7\times10^6$ APCs/cm$^2$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.1\times10^6$, $6.2\times10^6$, $6.3\times10^6$, $6.4\times10^6$, $6.5\times10^6$, $6.6\times10^6$, $6.7\times10^6$, $6.8\times10^6$, $6.9\times10^6$, $7\times10^6$, $7.1\times10^6$, $7.2\times10^6$, $7.3\times10^6$, $7.4\times10^6$ or $7.5\times10^6$ APCs/cm$^2$.

In another embodiment, the APCs exogenously supplied in the priming first expansion are seeded in the culture flask at a density of at or about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$ or $4.5\times10^6$ APCs/cm$^2$ and the the APCs exogenously supplied in the rapid second expansion are seeded in the culture flask at a density of at or about $2.5\times10^6$ APCs/cm$^2$, $2.6\times10^6$ APCs/cm$^2$, $2.7\times10^6$ APCs/cm$^2$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.1\times10^6$, $6.2\times10^6$, $6.3\times10^6$, $6.4\times10^6$, $6.5\times10^6$, $6.6\times10^6$, $6.7\times10^6$, $6.8\times10^6$, $6.9\times10^6$, $7\times10^6$, $7.1\times10^6$, $7.2\times10^6$, $7.3\times10^6$, $7.4\times10^6$ or $7.5\times10^6$ APCs/cm$^2$.

In another embodiment, the APCs exogenously supplied in the priming first expansion are seeded in the culture flask at a density selected from a range of at or about $1.0\times10^6$ APCs/cm$^2$ to at or about $4.5\times10^6$ APCs/cm$^2$, and the APCs exogenously supplied in the rapid second expansion are seeded in the culture flask at a density selected from a range of at or about $2.5\times10^6$ APCs/cm$^2$ to at or about $7.5\times10^6$ APCs/cm$^2$.

In another embodiment, the APCs exogenously supplied in the priming first expansion are seeded in the culture flask at a density selected from a range of at or about $1.5\times10^6$ APCs/cm$^2$ to at or about $3.5\times10^6$ APCs/cm$^2$, and the APCs exogenously supplied in the rapid second expansion are seeded in the culture flask at a density selected from a range of at or about $3.5\times10^6$ APCs/cm$^2$ to at or about $6\times10^6$ APCs/cm$^2$.

In another embodiment, the APCs exogenously supplied in the priming first expansion are seeded in the culture flask at a density selected from a range of at or about $2\times10^6$ APCs/cm$^2$ to at or about $3\times10^6$ APCs/cm$^2$, and the APCs exogenously supplied in the rapid second expansion are seeded in the culture flask at a density selected from a range of at or about $4\times10^6$ APCs/cm$^2$ to at or about $5.5\times10^6$ APCs/cm$^2$.

In another embodiment, the APCs exogenously supplied in the priming first expansion are seeded in the culture flask at a density at or about $2\times10^6$ APCs/cm$^2$ and the APCs exogenously supplied in the rapid second expansion are seeded in the culture flask at a density of at or about $4\times10^6$ APCs/cm$^2$.

In another embodiment, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 20:1.

In another embodiment, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 10:1.

In another embodiment, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 3:1.

In another embodiment, the ratio of the number of APCs (including, for example, PBMCs) exogenously supplied at day 7 of the rapid second expansion to the number of APCs selected from a range of from at or about 1.1:1 to at or about 2.9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.2:1.

In another embodiment, the ratio of the number of APCs (including, for example, PBMCs) exogenously supplied at day 7 of the rapid second expansion to the number of APCs selected from a range of from at or about 1.1:1 to at or about 2.1:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 10:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.8:1.

In another embodiment, the ratio of the number of APCs (including, for example, PBMCs) exogenously supplied at day 7 of the rapid second expansion to the number of APCs selected from a range of from at or about 2:1 to at or about 2.7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about about 2:1 to at or about 2.2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.1:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is at or about 2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the number of APCs (including, for example, PBMCs) exogenously supplied at day 0 of the priming first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs (including, for example, PBMCs), and the number of APCs (including, for example, PBMCs) exogenously supplied at day 7 of the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$ APCs (including, for example, PBMCs).

In another embodiment, the number of APCs (including, for example, PBMCs) exogenously supplied at day 0 of the priming first expansion is selected from the range of at or about $1\times10^8$ APCs (including, for example, PBMCs) to at or about $3.5\times10^8$ APCs (including, for example, PBMCs), and the number of APCs (including, for example, PBMCs) exogenously supplied at day 7 of the rapid second expansion is selected from the range of at or about $3.5\times10^8$ APCs (including, for example, PBMCs) to at or about $1\times10^9$ APCs (including, for example, PBMCs).

In another embodiment, the number of APCs (including, for example, PBMCs) exogenously supplied at day 0 of the priming first expansion is selected from the range of at or about $1.5\times10^8$ APCs to at or about $3\times10^8$ APCs (including, for example, PBMCs), and the number of APCs (including, for example, PBMCs) exogenously supplied at day 7 of the rapid second expansion is selected from the range of at or about $4\times10^8$ APCs (including, for example, PBMCs) to at or about $7.5\times10^8$ APCs (including, for example, PBMCs).

In another embodiment, the number of APCs (including, for example, PBMCs) exogenously supplied at day 0 of the priming first expansion is selected from the range of at or about $1\times10^8$ APCs (including, for example, PBMCs) to at or about $3.5\times10^8$ APCs (including, for example, PBMCs), and the number of APCs (including, for example, PBMCs) exogenously supplied at day 7 of the rapid second expansion is selected from the range of at or about $3.5\times10^8$ APCs (including, for example, PBMCs) to at or about $1\times10^9$ APCs (including, for example, PBMCs).

In another embodiment, the number of APCs (including, for example, PBMCs) exogenously supplied at day 0 of the priming first expansion is selected from the range of at or about $1.5\times10^8$ APCs to at or about $3\times10^8$ APCs (including, for example, PBMCs), and the number of APCs (including, for example, PBMCs) exogenously supplied at day 7 of the rapid second expansion is selected from the range of at or about $4\times10^8$ APCs (including, for example, PBMCs) to at or about $7.5\times10^8$ APCs (including, for example, PBMCs).

In another embodiment, the number of APCs (including, for example, PBMCs) exogenously supplied at day 0 of the priming first expansion is selected from the range of at or about $2\times10^8$ APCs (including, for example, PBMCs) to at or about $2.5\times10^8$ APCs (including, for example, PBMCs), and the number of APCs (including, for example, PBMCs) exogenously supplied at day 7 of the rapid second expansion is selected from the range of at or about $4.5\times10^8$ APCs (including, for example, PBMCs) to at or about $5.5\times10^8$ APCs (including, for example, PBMCs).

In another embodiment, the number of APCs (including, for example, PBMCs) exogenously supplied at day 0 of the priming first expansion is at or about $2.5\times10^8$ APCs (including, for example, PBMCs) and the number of APCs (including, for example, PBMCs) exogenously supplied at day 7 of the rapid second expansion is at or about $5\times10^8$ APCs (including, for example, PBMCs).

In an embodiment, the number of layers of APCs (including, for example, PBMCs) added at day 0 of the priming first expansion is approximately one-half of the number of layers of APCs (including, for example, PBMCs) added at day 7 of the rapid second expansion. In certain embodiments, the method comprises adding antigen presenting cell layers at day 0 of the priming first expansion to the first population of TILs and adding antigen presenting cell layers at day 7 to the second population of TILs, wherein the number of antigen presenting cell layer added at day 0 is approximately 50% of the number of antigen presenting cell layers added at day 7.

In another embodiment, the number of layers of APCs (including, for example, PBMCs) exogenously supplied at day 7 of the rapid second expansion is greater than the number of layers of APCs (including, for example, PBMCs) exogenously supplied at day 0 of the priming first expansion.

In another embodiment, day 0 of the priming first expansion occurs in the presence of layered APCs (including, for example, PBMCs) with an average thickness of at or about 2 cell layers and day 7 of the rapid second expansion occurs in the presence of layered APCs (including, for example, PBMCs) with an average thickness of at or about 4 cell layers.

In another embodiment, day 0 of the priming first expansion occurs in the presence of layered APCs (including, for example, PBMCs) with an average thickness of at or about one cell layer and day 7 of the rapid second expansion occurs in the presence of layered APCs (including, for example, PBMCs) with an average thickness of at or about 3 cell layers.

In another embodiment, day 0 of the priming first expansion occurs in the presence of layered APCs (including, for example, PBMCs) with an average thickness of at or about 1.5 cell layers to at or about 2.5 cell layers and day 7 of the rapid second expansion occurs in the presence of layered APCs (including, for example, PBMCs) with an average thickness of at or about 3 cell layers.

In another embodiment, day 0 of the priming first expansion occurs in the presence of layered APCs (including, for example, PBMCs) with an average thickness of at or about one cell layer and day 7 of the rapid second expansion occurs in the presence of layered APCs (including, for example, PBMCs) with an average thickness of at or about 2 cell layers.

In another embodiment, day 0 of the priming first expansion occurs in the presence of layered APCs (including, for example, PBMCs) with an average thickness of of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers and day 7 of the rapid second expansion occurs in the presence of layered APCs (including, for example, PBMCs) with an average thickness of at or about 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, day 0 of the priming first expansion occurs in the presence of layered APCs (including, for example, PBMCs) with an average thickness of at or about 1 cell layer to at or about 2 cell layers and day 7 of the rapid second expansion occurs in the presence of layered APCs (including, for example, PBMCs) with an average thickness of at or about 3 cell layers to at or about 10 cell layers.

In another embodiment, day 0 of the priming first expansion occurs in the presence of layered APCs (including, for example, PBMCs) with an average thickness of at or about 2 cell layers to at or about 3 cell layers and day 7 of the rapid second expansion occurs in the presence of layered APCs (including, for example, PBMCs) with an average thickness of at or about 4 cell layers to at or about 8 cell layers.

In another embodiment, day 0 of the priming first expansion occurs in the presence of layered APCs (including, for example, PBMCs) with an average thickness of at or about 2 cell layers and day 7 of the rapid second expansion occurs in the presence of layered APCs (including, for example, PBMCs) with an average thickness of at or about 4 cell layers to at or about 8 cell layers.

In another embodiment, day 0 of the priming first expansion occurs in the presence of layered APCs (including, for example, PBMCs) with an average thickness of at or about 1, 2 or 3 cell layers and day 7 of the rapid second expansion occurs in the presence of layered APCs (including, for example, PBMCs) with an average thickness of at or about 3, 4, 5, 6, 7, 8, 9 or 10 cell layers.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:10.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:8.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:7.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:6.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:4.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:3.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:2.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.2 to at or about 1:8.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.3 to at or about 1:7.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.4 to at or about 1:6.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.5 to at or about 1:5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.6 to at or about 1:4.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.7 to at or about 1:3.5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.8 to at or about 1:3.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.9 to at or about 1:2.5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is at or about 1:2.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from at or about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, APCs in the rapid second expansion is selected from the range of about $2.5\times10^6$ APCs/cm$^2$ to about $7.5\times10^6$ APCs/cm$^2$.

In some embodiments, the number of APCs in the priming first expansion is selected from the range of about $1.5\times10^6$ APCs/cm$^2$ to about $3.5\times10^6$ APCs/cm$^2$, and the number of APCs in the rapid second expansion is selected from the range of about $3.5\times10^6$ APCs/cm$^2$ to about $6.0\times10^6$ APCs/cm$^2$.

In some embodiments, the number of APCs in the priming first expansion is selected from the range of about $2.0\times10^6$ APCs/cm$^2$ to about $3.0\times10^6$ APCs/cm$^2$, and the number of APCs in the rapid second expansion is selected from the range of about $4.0\times10^6$ APCs/cm$^2$ to about $5.5\times10^6$ APCs/cm$^2$.

H. Optional Cell Medium Components

1. Anti-CD3 Antibodies

In some embodiments, the culture media used in expansion methods described herein (see for example, FIG. 1 (in particular, e.g., FIG. 1B and/or FIG. 1C) include an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-McNeil, Raritan, NJ or Miltenyi Biotech, Auburn, CA).

TABLE 5

Amino acid sequences of muromonab (exemplary OKT-3 antibody)

| Identifier | Sequence (One-Letter Amino Acid Symbols) | |
|---|---|---|
| SEQ ID NO: 1 | QVQLQQSGAE LARPGASVKM SCKASGYTFT RYTMHWVKQR PGQGLEWIGY INPSRGYTNY | 60 |
| Muromonab | NQKFKDKATL TTDKSSSTAY MQLSSLTSED SAVYYCARYY DDHYCLDYWG QGTTLTVSSA | 120 |
| heavy | KTTAPSVYPL APVCGGTTGS SVTLGCLVKG YFPEPVTLTW NSGSLSSGVH TFPAVLQSDL | 180 |
| chain | YTLSSSVTVT SSTWPSQSIT CNVAHPASST KVDKKIEPRP KSCDKTHTCP PCPAPELLGG | 240 |
| | PSVFLFPPKP KDTLMISRTP EVTCVVVDVS HEDPEVKFNW YVDGVEVHNA KTKPREEQYN | 300 |
| | STYRVVSVLT VLHQDWLNGK EYKCKVSNKA LPAPIEKTIS KAKGQPREPQ VYTLPPSRDE | 360 |
| | LTKNQVSLTC LVKGFYPSDI AVEWESNGQP ENNYKTTPPV LDSDGSFFLY SKLTVDKSRW | 420 |
| | QQGNVFSCSV MHEALHNHYT QKSLSLSPGK | 450 |
| SEQ ID NO: 2 | QIVLTQSPAI MSASPGEKVT MTCSASSSVS YMNWYQQKSG TSPKRWIYDT SKLASGVPAH | 60 |
| Muromonab | FRGSGSGTSY SLTISGMEAE DAATYYCQQW SSNPFTFGSG TKLEINRADT APTVSIFPPS | 120 |
| light | SEQLTSGGAS VVCFLNNFYP KDINVKWKID GSERQNGVLN SWTDQDSKDS TYSMSSTLTL | 180 |
| chain | TKDEYERHNS YTCEATHKTS TSPIVKSFNR NEC | 213 |

1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

In some embodiments, the number of APCs in the priming first expansion is selected from the range of about $1.0\times10^6$ APCs/cm$^2$ to about $4.5\times10^6$ APCs/cm$^2$, and the number of

2. 4-1BB (CD137) Agonists

In an embodiment, the cell culture medium of the priming first expansion and/or the rapid second expansion comprises a TNFRSF agonist. In an embodiment, the TNFRSF agonist is a 4-1BB (CD137) agonist. The 4-1BB agonist may be any 4-1BB binding molecule known in the art. The 4-1BB binding molecule may be a monoclonal antibody or fusion protein capable of binding to human or mammalian 4-1BB. The 4-1BB agonists or 4-1BB binding molecules may comprise an immunoglobulin heavy chain of any isotype (e.g., IgG, IgE, IgM, IgD, IgA, and IgY), class (e.g., IgG1, IgG2, IgG3, IgG4, IgAQ1 and IgA2) or subclass of immunoglobulin molecule. The 4-1BB agonist or 4-1BB binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to 4-1BB. In an embodiment, the 4-1BB agonist is an antigen binding protein that is a fully human antibody. In an embodiment, the 4-1BB agonist is an antigen binding protein that is a humanized antibody. In some embodiments, 4-1BB agonists for use in the presently disclosed methods and compositions include anti-4-1BB antibodies, human anti-4-1BB antibodies, mouse anti-4-1BB antibodies, mammalian anti-4-1BB antibodies, monoclonal anti-4-1BB antibodies, polyclonal anti-4-1BB antibodies, chimeric anti-4-1BB antibodies, anti-4-1BB adnectins, anti-4-1BB domain antibodies, single chain anti-4-1BB fragments, heavy chain anti-4-1BB fragments, light chain anti-4-1BB fragments, anti-4-1BB fusion proteins, and fragments, derivatives, conjugates, variants, or biosimilars thereof. Agonistic anti-4-1BB antibodies are known to induce strong immune responses. Lee, et al., *PLOS One* 2013, 8, e69677. In a preferred embodiment, the 4-1BB proteins are described, e.g., in Gieffers, et al., *Mol. Cancer Therapeutics* 2013, 12, 2735-47.

Agonistic 4-1BB antibodies and fusion proteins are known to induce strong immune responses. In a preferred embodiment, the 4-1BB agonist is a monoclonal antibody or fusion protein that binds specifically to 4-1BB antigen in a manner sufficient to reduce toxicity. In some embodiments, the 4-1BB agonist is an agonistic 4-1BB monoclonal antibody or fusion protein that abrogates antibody-dependent cellular toxicity (ADCC), for example NK cell cytotoxicity. In some embodiments, the 4-1BB agonist is an agonistic 4-1BB monoclonal antibody or fusion protein that abrogates antibody-dependent cell phagocytosis (ADCP). In some embodiments, the 4-1BB agonist is an agonistic 4-1BB monoclonal antibody or fusion protein that abrogates complement-dependent cytotoxicity (CDC). In some embodiments, the 4-1BB agonist is an agonistic 4-1BB monoclonal antibody or fusion protein which abrogates Fc region functionality.

In some embodiments, the 4-1BB agonists are characterized by binding to human 4-1BB (SEQ ID NO:9) with high affinity and agonistic activity. In an embodiment, the 4-1BB agonist is a binding molecule that binds to human 4-1BB (SEQ ID NO:9). In an embodiment, the 4-1BB agonist is a binding molecule that binds to murine 4-1BB (SEQ ID NO:10). The amino acid sequences of 4-1BB antigen to which a 4-1BB agonist or binding molecule binds are summarized in Table 6.

TABLE 6

Amino acid sequences of 4-1BB antigens.

| Identifier | Sequence (One-Letter Amino Acid Symbols) |
|---|---|
| SEQ ID NO: 9 human 4-1BB, Tumor necrosis factor receptor superfamily, member 9 (Homo sapiens) | MGNSCYNIVA TLLLVLNFER TRSLQDPCSN CPAGTFCDNN RNQICSPCPP NSFSSAGGQR 60<br>TCDICRQCKG VFRTRKECSS TSNAECDCTP GFHCLGAGCS MCEQDCKQGQ ELTKKGCKDC 120<br>CFGTFNDQKR GICRPWTNCS LDGKSVLVNG TKERDVVCGP SPADLSPGAS SVTPPAPARE 180<br>PGHSPQIISF FLALTSTALL FLLFFLTLRF SVVKRGRKKL LYIFKQPFMR PVQTTQEEDG 240<br>CSCRFPEEEE GGCEL 255 |
| SEQ ID NO: 10 murine 4-1BB, Tumor necrosis factor receptor superfamily, member 9 (Mus musculus) | MGNNCYNVVV IVLLLVGCEK VGAVQNSCDN CQPGTFCRKY NPVCKSCPPS TFSSIGGQPN 60<br>CNICRVCAGY FRFKKFCSST HNAECECIEG FHCLGPQCTR CEKDCRPGQE LTKQGCKTCS 120<br>LGTFNDQNGT GVCRPWTNCS LDGRSVLKTG TTEKDVVCGP PVVSFSPSTT ISVTPEGGPG 180<br>GHSLQVLTLF LALTSALLLA LIFITLLFSV LKWIRKKFPH IFKQPFKKTT GAAQEEDACS 240<br>CRCPQEEEGG GGGYEL 256 |

agonist is an agonistic, anti-4-1BB humanized or fully human monoclonal antibody (i.e., an antibody derived from a single cell line). In an embodiment, the 4-1BB agonist is EU-101 (Eutilex Co. Ltd.), utomilumab, or urelumab, or a fragment, derivative, conjugate, variant, or biosimilar thereof. In a preferred embodiment, the 4-1BB agonist is utomilumab or urelumab, or a fragment, derivative, conjugate, variant, or biosimilar thereof.

In a preferred embodiment, the 4-1BB agonist or 4-1BB binding molecule may also be a fusion protein. In a preferred embodiment, a multimeric 4-1BB agonist, such as a trimeric or hexameric 4-1BB agonist (with three or six ligand binding domains), may induce superior receptor (4-1BBL) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion In some embodiments, the compositions, processes and methods described include a 4-1BB agonist that binds human or murine 4-1BB with a $K_D$ of about 100 μM or lower, binds human or murine 4-1BB with a $K_D$ of about 90 μM or lower, binds human or murine 4-1BB with a $K_D$ of about 80 μM or lower, binds human or murine 4-1BB with a $K_D$ of about 70 μM or lower, binds human or murine 4-1BB with a $K_D$ of about 60 μM or lower, binds human or murine 4-1BB with a $K_D$ of about 50 μM or lower, binds human or murine 4-1BB with a $K_D$ of about 40 μM or lower, or binds human or murine 4-1BB with a $K_D$ of about 30 μM or lower.

In some embodiments, the compositions, processes and methods described include a 4-1BB agonist that binds to human or murine 4-1BB with a $k_{assoc}$ of about $7.5\times10^5$ 1/M·s or faster, binds to human or murine 4-1BB with a $k_{assoc}$ of about $7.5\times10^5$ 1/M·s or faster, binds to human or murine 4-1BB with a $k_{assoc}$ of about $8\times10^5$ 1/M·s or faster, binds to human or murine 4-1BB with a $k_{assoc}$ of about $8.5\times10^5$ 1/M·s or faster, binds to human or murine 4-1BB with a $k_{assoc}$ of about $9\times10^5$ 1/M·s or faster, binds to human or murine 4-1BB with a $k_{assoc}$ of about $9.5\times10^5$ 1/M·s or faster, or binds to human or murine 4-1BB with a $k_{assoc}$ of about $1\times10^6$ 1/M·s or faster.

In some embodiments, the compositions, processes and methods described include a 4-1BB agonist that binds to human or murine 4-1BB with a $k_{dissoc}$ of about $2\times10^{-5}$ 1/s or slower, binds to human or murine 4-1BB with a $k_{dissoc}$ of about $2.1\times10^{-5}$ 1/s or slower, binds to human or murine 4-1BB with a $k_{dissoc}$ of about $2.2\times10^{-5}$ 1/s or slower, binds to human or murine 4-1BB with a $k_{dissoc}$ of about $2.3\times10^{-5}$ 1/s or slower, binds to human or murine 4-1BB with a $k_{dissoc}$ of about $2.4\times10^{-5}$ 1/s or slower, binds to human or murine 4-1BB with a $k_{dissoc}$ of about $2.5\times10^{-5}$ 1/s or slower, binds to human or murine 4-1BB with a $k_{dissoc}$ of about $2.6\times10^{-5}$ 1/s or slower or binds to human or murine 4-1BB with a $k_{dissoc}$ of about $2.7\times10^{-5}$ 1/s or slower, binds to human or murine 4-1BB with a $k_{dissoc}$ of about $2.8\times10^{-5}$ 1/s or slower, binds to human or murine 4-1BB with a $k_{dissoc}$ of about $2.9\times10^{-5}$ 1/s or slower, or binds to human or murine 4-1BB with a $k_{dissoc}$ of about $3\times10^{-5}$ 1/s or slower.

In some embodiments, the compositions, processes and methods described include a 4-1BB agonist that binds to human or murine 4-1BB with an $IC_{50}$ of about 10 nM or lower, binds to human or murine 4-1BB with an $IC_{50}$ of about 9 nM or lower, binds to human or murine 4-1BB with an $IC_{50}$ of about 8 nM or lower, binds to human or murine 4-1BB with an $IC_{50}$ of about 7 nM or lower, binds to human or murine 4-1BB with an $IC_{50}$ of about 6 nM or lower, binds to human or murine 4-1BB with an $IC_{50}$ of about 5 nM or lower, binds to human or murine 4-1BB with an $IC_{50}$ of about 4 nM or lower, binds to human or murine 4-1BB with an $IC_{50}$ of about 3 nM or lower, binds to human or murine 4-1BB with an $IC_{50}$ of about 2 nM or lower, or binds to human or murine 4-1BB with an $IC_{50}$ of about 1 nM or lower.

In a preferred embodiment, the 4-1BB agonist is utomilumab, also known as PF-05082566 or MOR-7480, or a fragment, derivative, variant, or biosimilar thereof. Utomilumab is available from Pfizer, Inc. Utomilumab is an immunoglobulin G2-lambda, anti-[*Homo sapiens* TNFRSF9 (tumor necrosis factor receptor (TNFR) superfamily member 9, 4-1BB, T cell antigen ILA, CD137)], *Homo sapiens* (fully human) monoclonal antibody. The amino acid sequences of utomilumab are set forth in Table 7. Utomilumab comprises glycosylation sites at Asn59 and Asn292; heavy chain intrachain disulfide bridges at positions 22-96 ($V_H$-$V_L$), 143-199 ($C_H1$-$C_L$), 256-316 ($C_H2$) and 362-420 ($C_H3$); light chain intrachain disulfide bridges at positions 22'-87' ($V_H$-$V_L$) and 136'-195' ($C_H1$-$C_L$); interchain heavy chain-heavy chain disulfide bridges at IgG2A isoform positions 218-218, 219-219, 222-222, and 225-225, at IgG2A/B isoform positions 218-130, 219-219, 222-222, and 225-225, and at IgG2B isoform positions 219-130 (2), 222-222, and 225-225; and interchain heavy chain-light chain disulfide bridges at IgG2A isoform positions 130-213' (2), IgG2A/B isoform positions 218-213' and 130-213', and at IgG2B isoform positions 218-213' (2). The preparation and properties of utomilumab and its variants and fragments are described in U.S. Pat. Nos. 8,821,867; 8,337,850; and 9,468,678, and International Patent Application Publication No. WO 2012/032433 A1, the disclosures of each of which are incorporated by reference herein. Preclinical characteristics of utomilumab are described in Fisher, et al., *Cancer Immunolog. & Immunother.* 2012, 61, 1721-33. Current clinical trials of utomilumab in a variety of hematological and solid tumor indications include U.S. National Institutes of Health clinicaltrials.gov identifiers NCT02444793, NCT01307267, NCT02315066, and NCT02554812.

In an embodiment, a 4-1BB agonist comprises a heavy chain given by SEQ ID NO:11 and a light chain given by SEQ ID NO:12. In an embodiment, a 4-1BB agonist comprises heavy and light chains having the sequences shown in SEQ ID NO:11 and SEQ ID NO:12, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:11 and SEQ ID NO:12, respectively. In an embodiment, a 4-1BB agonist comprises heavy and light chains that are each at least 98% identical to the sequences shown in SEQ ID NO:11 and SEQ ID NO: 12, respectively. In an embodiment, a 4-1BB agonist comprises heavy and light chains that are each at least 97% identical to the sequences shown in SEQ ID NO:11 and SEQ ID NO:12, respectively. In an embodiment, a 4-1BB agonist comprises heavy and light chains that are each at least 96% identical to the sequences shown in SEQ ID NO: 11 and SEQ ID NO:12, respectively. In an embodiment, a 4-1BB agonist comprises heavy and light chains that are each at least 95% identical to the sequences shown in SEQ ID NO:11 and SEQ ID NO:12, respectively.

In an embodiment, the 4-1BB agonist comprises the heavy and light chain CDRs or variable regions (VRs) of utomilumab. In an embodiment, the 4-1BB agonist heavy chain variable region ($V_H$) comprises the sequence shown in SEQ ID NO:13, and the 4-1BB agonist light chain variable region ($V_L$) comprises the sequence shown in SEQ ID NO:14, and conservative amino acid substitutions thereof. In an embodiment, a 4-1BB agonist comprises $V_H$ and $V_L$ regions that are each at least 99% identical to the sequences shown in SEQ ID NO:13 and SEQ ID NO:14, respectively. In an embodiment, a 4-1BB agonist comprises $V_H$ and $V_L$ regions that are each at least 98% identical to the sequences shown in SEQ ID NO: 13 and SEQ ID NO:14, respectively. In an embodiment, a 4-1BB agonist comprises $V_H$ and $V_L$ regions that are each at least 97% identical to the sequences shown in SEQ ID NO:13 and SEQ ID NO:14, respectively. In an embodiment, a 4-1BB agonist comprises $V_H$ and $V_L$ regions that are each at least 96% identical to the sequences shown in SEQ ID NO: 13 and SEQ ID NO:14, respectively. In an embodiment, a 4-1BB agonist comprises $V_H$ and $V_L$ regions that are each at least 95% identical to the sequences shown in SEQ ID NO:13 and SEQ ID NO: 14, respectively. In an embodiment, a 4-1BB agonist comprises an scFv antibody comprising $V_H$ and $V_L$ regions that are each at least 99% identical to the sequences shown in SEQ ID NO:13 and SEQ ID NO:14.

In an embodiment, a 4-1BB agonist comprises heavy chain CDR1, CDR2 and CDR3 domains having the sequences set forth in SEQ ID NO:15, SEQ ID NO:16, and SEQ ID NO:17, respectively, and conservative amino acid substitutions thereof, and light chain CDR1, CDR2 and CDR3 domains having the sequences set forth in SEQ ID NO:18, SEQ ID NO:19, and SEQ ID NO: 20, respectively, and conservative amino acid substitutions thereof.

In an embodiment, the 4-1BB agonist is a 4-1BB agonist biosimilar monoclonal antibody approved by drug regulatory authorities with reference to utomilumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is utomilumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is utomilumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab.

TABLE 7

Amino acid sequences for 4-1BB agonist antibodies related to utomilumab.

| Identifier | Sequence (One-Letter Amino Acid Symbols) |
| --- | --- |
| SEQ ID NO: 11 heavy chain for utomilumab | EVQLVQSGAE VKKPGESLRI SCKGSGYSFS TYWISWVRQM PGKGLEWMGK IYPGDSYTNY 60<br>SPSFQGQVTI SADKSISTAY LQWSSLKASD TAMYYCARGY GIFDYWGQGT LVTVSSASTK 120<br>GPSVFPLAPC SRSTSESTAA LGCLVKDYFP EPVTVSWNSG ALTSGVHTFP AVLQSSGLYS 180<br>LSSVVTVPSS NFGTQTYTCN VDHKPSNTKV DKTVERKCCV ECPPCPAPPV AGPSVFLFPP 240<br>KPKDTLMISR TPEVTCVVVD VSHEDPEVQF NWYVDGVEVH NAKTKPREEQ FNSTFRVVSV 300<br>LTVVHQDWLN GKEYKCKVSN KGLPAPIEKT ISKTKGQPRE PQVYTLPPSR EEMTKNQVSL 360<br>TCLVKGFYPS DIAVEWESNG QPENNYKTTP PMLDSDGSFF LYSKLTVDKS RWQQGNVFSC 420<br>SVMHEALHNH YTQKSLSLSP G 441 |
| SEQ ID NO: 12 light chain for utomilumab | SYELTQPPSV SVSPGQTASI TCSGDNIGDQ YAHWYQQKPG QSPVLVIYQD KNRPSGIPER 60<br>FSGSNSGNTA TLTISGTQAM DEADYYCATY TGFGSLAVFG GGTKLTVLGQ PKAAPSVTLF 120<br>PPSSEELQAN KATLVCLISD FYPGAVTVAW KADSSPVKAG VETTTPSKQS NNKYAASSYL 180<br>SLTPEQWKSH RSYSCQVTHE GSTVEKTVAP TECS 214 |
| SEQ ID NO: 13 heavy chain variable region for utomilumab | EVQLVQSGAE VKKPGESLRI SCKGSGYSFS TYWISWVRQM PGKGLEWMG KIYPGDSYTN 60<br>YSPSFQGQVT ISADKSISTA YLQWSSLKAS DTAMYYCARG YGIFDYWGQ GTLVTVSS 118 |
| SEQ ID NO: 14 light chain variable region for utomilumab | SYELTQPPSV SVSPGQTASI TCSGDNIGDQ YAHWYQQKPG QSPVLVIYQD KNRPSGIPER 60<br>FSGSNSGNTA TLTISGTQAM DEADYYCATY TGFGSLAVFG GGTKLTVL 108 |
| SEQ ID NO: 15 heavy chain CDR1 for utomilumab | STYWIS 6 |
| SEQ ID NO: 16 heavy chain CDR2 for utomilumab | KIYPGDSYTN YSPSFQG 17 |
| SEQ ID NO: 17 heavy chain CDR3 for utomilumab | RGYGIFDY 8 |
| SEQ ID NO: 18 light chain CDR1 for utomilumab | SGDNIGDQYA H 11 |
| SEQ ID NO: 19 light chain CDR2 for utomilumab | QDKNRPS 7 |
| SEQ ID NO: 20 light chain CDR3 for utomilumab | ATYTGFGSLA V 11 |

In a preferred embodiment, the 4-1BB agonist is the monoclonal antibody urelumab, also known as BMS-663513 and 20H4.9.h4a, or a fragment, derivative, variant, or biosimilar thereof. Urelumab is available from Bristol-Myers Squibb, Inc., and Creative Biolabs, Inc. Urelumab is an immunoglobulin G4-kappa, anti-[*Homo sapiens* TNFRSF9 (tumor necrosis factor receptor superfamily member 9, 4-1BB, T cell antigen ILA, CD137)], *Homo sapiens* (fully human) monoclonal antibody. The amino acid sequences of urelumab are set forth in Table EE. Urelumab comprises N-glycosylation sites at positions 298 (and 298"); heavy chain intrachain disulfide bridges at positions 22-95 ($V_H$-$V_L$), 148-204 ($C_H1$-$C_L$), 262-322 ($C_H2$) and 368-426 ($C_H3$) (and at positions 22"-95", 148"-204", 262"-322", and 368"-426"); light chain intrachain disulfide bridges at positions 23'-88' ($V_H$-$V_L$) and 136'-196' ($C_H1$-$C_L$) (and at positions 23'"-88'" and 136'"-196'"); interchain heavy chain-heavy chain disulfide bridges at positions 227-227" and 230-230"; and interchain heavy chain-light chain disulfide bridges at 135-216' and 135"-216'". The preparation and properties of urelumab and its variants and fragments are described in U.S. Pat. Nos. 7,288,638 and 8,962,804, the disclosures of which are incorporated by reference herein. The preclinical and clinical characteristics of urelumab are described in Segal, et al., *Clin. Cancer Res.* 2016, available at http:/dx.doi.org/10.1158/1078-0432.CCR-16-1272. Current clinical trials of urelumab in a variety of hematological and solid tumor indications include U.S. National Institutes of Health clinicaltrials. gov identifiers NCT01775631, NCT02110082, NCT02253992, and NCT01471210.

In an embodiment, a 4-1BB agonist comprises a heavy chain given by SEQ ID NO:21 and a light chain given by SEQ ID NO:22. In an embodiment, a 4-1BB agonist comprises heavy and light chains having the sequences shown in SEQ ID NO:21 and SEQ ID NO:22, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:21 and SEQ ID NO:22, respectively. In an embodiment, a 4-1BB agonist comprises heavy and light chains that are each at least 98% identical to the sequences shown in SEQ ID NO:21 and SEQ ID NO:22, respectively. In an embodiment, a 4-1BB agonist comprises heavy and light chains that are each at least 97% identical to the sequences shown in SEQ ID NO:21 and SEQ ID NO:22, respectively. In an embodiment, a 4-1BB agonist comprises heavy and light chains that are each at least 96% identical to the sequences shown in SEQ ID NO: 21 and SEQ ID NO:22, respectively. In an embodiment, a 4-1BB agonist comprises heavy and light chains that are each at least 95% identical to the sequences shown in SEQ ID NO:21 and SEQ ID NO:22, respectively.

In an embodiment, the 4-1BB agonist comprises the heavy and light chain CDRs or variable regions (VRs) of urelumab. In an embodiment, the 4-1BB agonist heavy chain variable region ($V_H$) comprises the sequence shown in SEQ ID NO:23, and the 4-1BB agonist light chain variable region ($V_L$) comprises the sequence shown in SEQ ID NO:24, and conservative amino acid substitutions thereof. In an embodiment, a 4-1BB agonist comprises $V_H$ and $V_L$ regions that are each at least 99% identical to the sequences shown in SEQ ID NO:23 and SEQ ID NO:24, respectively. In an embodiment, a 4-1BB agonist comprises $V_H$ and $V_L$ regions that are each at least 98% identical to the sequences shown in SEQ ID NO:23 and SEQ ID NO:24, respectively. In an embodiment, a 4-1BB agonist comprises $V_H$ and $V_L$ regions that are each at least 97% identical to the sequences shown in SEQ ID NO:23 and SEQ ID NO:24, respectively. In an embodiment, a 4-1BB agonist comprises $V_H$ and $V_L$ regions that are each at least 96% identical to the sequences shown in SEQ ID NO: 23 and SEQ ID NO:24, respectively. In an embodiment, a 4-1BB agonist comprises $V_H$ and $V_L$ regions that are each at least 95% identical to the sequences shown in SEQ ID NO:23 and SEQ ID NO: 24, respectively. In an embodiment, a 4-1BB agonist comprises an scFv antibody comprising $V_H$ and $V_L$ regions that are each at least 99% identical to the sequences shown in SEQ ID NO:23 and SEQ ID NO:24.

In an embodiment, a 4-1BB agonist comprises heavy chain CDR1, CDR2 and CDR3 domains having the sequences set forth in SEQ ID NO:25, SEQ ID NO:26, and SEQ ID NO:27, respectively, and conservative amino acid substitutions thereof, and light chain CDR1, CDR2 and CDR3 domains having the sequences set forth in SEQ ID NO:28, SEQ ID NO:29, and SEQ ID NO: 30, respectively, and conservative amino acid substitutions thereof.

In an embodiment, the 4-1BB agonist is a 4-1BB agonist biosimilar monoclonal antibody approved by drug regulatory authorities with reference to urelumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is urelumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is urelumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab.

TABLE 8

Amino acid sequences for 4-1BB agonist antibodies related to urelumab.

| Identifier | Sequence (One-Letter Amino Acid Symbols) |
|---|---|
| SEQ ID NO: 21 heavy chain for urelumab | QVQLQQWGAG LLKPSETLSL TCAVYGGSFS GYYWSWIRQS PEKGLEWIGE INHGGYVTYN 60<br>PSLESRVTIS VDTSKNQFSL KLSSVTAADT AVYYCARDYG PGNYDWYFDL WGRGTLVTVS 120<br>SASTKGPSVF PLAPCSRSTS ESTAALGCLV KDYFPEPVTV SWNSGALTSG VHTFPAVLQS 180<br>SGLYSLSSVV TVPSSSLGTK TYTCNVDHKP SNTKVDKRVE SKYGPPCPPC PAPEFLGGPS 240<br>VFLFPPKPKD TLMISRTPEV TCVVVDVSQE DPEVQFNWYV DGVEVHNAKT KPREEQFNST 300<br>YRVVSVLTVL HQDWLNGKEY KCKVSNKGLP SSIEKTISKA KGQPREPQVY TLPPSQEEMT 360<br>KNQVSLTCLV KGFYPSDIAV EWESNGQPEN NYKTTPPVLD SDGSFFLYSR LTVDKSRWQE 420<br>GNVFSCSVMH EALHNHYTQK SLSLSLGK 448 |
| SEQ ID NO: 22 light chain for urelumab | EIVLTQSPAT LSLSPGERAT LSCRASQSVS SYLAWYQQKP GQAPRLLIYD ASNRATGIPA 60<br>RFSGSGSGTD FTLTISSLEP EDFAVYYCQQ RSNWPPALTF CGGTKVEIKR TVAAPSVFIF 120<br>PPSDEQLKSG TASVVCLLNN FYPREAKVQW KVDNALQSGN SQESVTEQDS KDSTYSLSST 180<br>LTLSKADYEK HKVYACEVTH QGLSSPVTKS FNRGEC 216 |
| SEQ ID NO: 23 variable heavy chain for urelumab | MKHLWFFLLL VAAPRWVLSQ VQLQQWGAGL LKPSETLSLT CAVYGGSFSG YYWSWIRQSP 60<br>EKGLEWIGEI NHGGYVTYNP SLESRVTISV DTSKNQFSLK LSSVTAADTA VYYCARDYGP 120 |
| SEQ ID NO: 24 variable light chain for urelumab | MEAPAQLLFL LLLWLPDTTG EIVLTQSPAT LSLSPGERAT LSCRASQSVS SYLAWYQQKP 60<br>GQAPRLLIYD ASNRATGIPA RFSGSGSGTD FTLTISSLEP EDFAVYYCQQ 110 |
| SEQ ID NO: 25 heavy chain CDR1 for urelumab | GYYWS 5 |
| SEQ ID NO: 26 heavy chain CDR2 for urelumab | EINHGGYVTY NPSLES 16 |
| SEQ ID NO: 27 heavy chain CDR3 for urelumab | DYGPGNYDWY FDL 13 |
| SEQ ID NO: 28 light chain CDR1 for urelumab | RASQSVSSYL A 11 |
| SEQ ID NO: 29 light chain CDR2 for urelumab | DASNRAT 7 |
| SEQ ID NO: 30 light chain CDR3 for urelumab | QQRSDWPPAL T 11 |

In an embodiment, the 4-1BB agonist is selected from the group consisting of 1D8, 3Elor, 4B4 (BioLegend 309809), H4-1BB-M127 (BD Pharmingen 552532), BBK2 (Thermo Fisher MS621PABX), 145501 (Leinco Technologies B591), the antibody produced by cell line deposited as ATCC No. HB-11248 and disclosed in U.S. Pat. No. 6,974,863, 5F4 (BioLegend 31 1503), C65-485 (BD Pharmingen 559446), antibodies disclosed in U.S. Patent Application Publication No. US 2005/0095244, antibodies disclosed in U.S. Pat. No. 7,288,638 (such as 20H4.9-IgG1 (BMS-663031), antibodies disclosed in U.S. Pat. No. 6,887,673 (such as 4E9 or BMS-554271), antibodies disclosed in U.S. Pat. No. 7,214,493, antibodies disclosed in U.S. Pat. No. 6,303,121, antibodies disclosed in U.S. Pat. No. 6,569,997, antibodies disclosed in U.S. Pat. No. 6,905,685 (such as 4E9 or BMS-554271), antibodies disclosed in U.S. Pat. No. 6,362,325 (such as 1D8 or BMS-469492; 3H3 or BMS-469497; or 3E1), antibodies disclosed in U.S. Pat. No. 6,974,863 (such as 53A2); antibodies disclosed in U.S. Pat. No. 6,210,669 (such as 1D8, 3B8, or 3E1), antibodies described in U.S. Pat. No. 5,928,893, antibodies disclosed in U.S. Pat. No. 6,303,121, antibodies disclosed in U.S. Pat. No. 6,569,997, antibodies disclosed in International Patent Application Publication Nos. WO 2012/177788, WO 2015/119923, and WO 2010/042433, and fragments, derivatives, conjugates, variants, or biosimilars thereof, wherein the disclosure of each of the foregoing patents or patent application publications is incorporated by reference here.

In an embodiment, the 4-1BB agonist is a 4-1BB agonistic fusion protein described in International Patent Application Publication Nos. WO 2008/025516 A1, WO 2009/007120 A1, WO 2010/003766 A1, WO 2010/010051 A1, and WO 2010/078966 A1; U.S. Patent Application Publication Nos. US 2011/0027218 A1, US 2015/0126709 A1, US 2011/

0111494 A1, US 2015/0110734 A1, and US 2015/0126710 A1; and U.S. Pat. Nos. 9,359,420, 9,340,599, 8,921,519, and 8,450,460, the disclosures of which are incorporated by reference herein.

In an embodiment, the 4-1BB agonist is a 4-1BB agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof as provided in FIG. 131.

In structures I-A and I-B, the cylinders refer to individual polypeptide binding domains. Structures I-A and I-B comprise three linearly-linked TNFRSF binding domains derived from e.g., 4-1BBL (4-1BB ligand, CD137 ligand (CD137L), or tumor necrosis factor superfamily member 9 (TNFSF9) or an antibody that binds 4-1BB, which fold to form a trivalent protein, which is then linked to a second triavelent protein through IgG1-Fc (including CH3 and CH2 domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility. Any scFv domain design may be used, such as those described in de Marco, *Microbial Cell Factories,* 2011, 10, 44; Ahmad, et al., *Clin. & Dev. Immunol.* 2012, 980250; Monnier, et al., *Antibodies,* 2013, 2, 193-208; or in references incorporated elsewhere herein. Fusion protein structures of this form are described in U.S. Pat. Nos. 9,359,420, 9,340,599, 8,921,519, and 8,450,460, the disclosures of which are incorporated by reference herein.

Amino acid sequences for the other polypeptide domains of structure I-A are given in Table 9. The Fc domain preferably comprises a complete constant domain (amino acids 17-230 of SEQ ID NO: 31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides.

TABLE 9

Amino acid sequences for TNFRSF agonist fusion proteins, including 4-1BB agonist fusion proteins, with C-terminal Fc-antibody fragment fusion protein design (structure I-A).

| Identifier | Sequence (One-Letter Amino Acid Symbols) | |
|---|---|---|
| SEQ ID NO: 31<br>Fc domain | KSCDKTHTCP PCPAPELLGG PSVFLFPPKP KDTLMISRTP EVTCVVVDVS HEDPEVKFNW<br>YVDGVEVHNA KTKPREEQYN STYRVVSVLT VLHQDWLNGK EYKCKVSNKA LPAPIEKTIS<br>KAKGQPREPQ VYTLPPSREE MTKNQVSLTC LVKGFYPSDI AVEWESNGQP ENNYKTTPPV<br>LDSDGSFFLY SKLTVDKSRW QQGNVFSCSV MHEALHNHYT QKSLSLSPGK | 60<br>120<br>180<br>230 |
| SEQ ID NO: 32<br>linker | GGPGSSKSCD KTHTCPPCPA PE | 22 |
| SEQ ID NO: 33<br>linker | GGSGSSKSCD KTHTCPPCPA PE | 22 |
| SEQ ID NO: 34<br>linker | GGPGSSSSSS SKSCDKTHTC PPCPAPE | 27 |
| SEQ ID NO: 35<br>linker | GGSGSSSSSS SKSCDKTHTC PPCPAPE | 27 |
| SEQ ID NO: 36<br>linker | GGPGSSSSSS SSSKSCDKTH TCPPCPAPE | 29 |
| SEQ ID NO: 37<br>linker | GGSGSSSSSS SSSKSCDKTH TCPPCPAPE | 29 |
| SEQ ID NO: 38<br>linker | GGPGSSGSGS SDKTHTCPPC PAPE | 24 |
| SEQ ID NO: 39<br>linker | GGPGSSGSGS DKTHTCPPCP APE | 23 |
| SEQ ID NO: 40<br>linker | GGPSSSGSDK THTCPPCPAP E | 21 |
| SEQ ID NO: 41<br>linker | GGSSSSSSSS GSDKTHTCPP CPAPE | 25 |

Amino acid sequences for the other polypeptide domains of structure I-B are given in Table 10. If an Fc antibody fragment is fused to the N-terminus of an TNRFSF agonist fusion protein as in structure I-B, the sequence of the Fc module is preferably that shown in SEQ ID NO:42, and the linker sequences are preferably selected from those embodiments set forth in SED ID NO: 43 to SEQ ID NO: 45.

TABLE 10

Amino acid sequences for TNFRSF agonist fusion proteins, including 4-1BB agonist fusion proteins, with N-terminal Fc-antibody fragment fusion protein design (structure I-B).

| Identifier | Sequence (One-Letter Amino Acid Symbols) | |
|---|---|---|
| SEQ ID NO: 42 Fc domain | METDTLLLWV LLLWVPAGNG DKTHTCPPCP APELLGGPSV FLFPPKPKDT LMISRTPEVT | 60 |
| | CVVVDVSHED PEVKFNWYVD GVEVHNAKTK PREEQYNSTY RVVSVLTVLH QDWLNGKEYK | 120 |
| | CKVSNKALPA PIEKTISKAK GQPREPQVYT LPPSREEMTK NQVSLTCLVK GFYPSDIAVE | 180 |
| | WESNGQPENN YKTTPPVLDS DGSFFLYSKL TVDKSRWQQG NVFSCSVMHE ALHNHYTQKS | 240 |
| | LSLSPG | 246 |
| SEQ ID NO: 43 linker | SGSGSGSGSG S | 11 |
| SEQ ID NO: 44 linker | SSSSSSGSGS GS | 12 |
| SEQ ID NO: 45 linker | SSSSSSGSGS GSGSGS | 16 |

In an embodiment, a 4-1BB agonist fusion protein according to structures I-A or I-B comprises one or more 4-1BB binding domains selected from the group consisting of a variable heavy chain and variable light chain of utomilumab, a variable heavy chain and variable light chain of urelumab, a variable heavy chain and variable light chain of utomilumab, a variable heavy chain and variable light chain selected from the variable heavy chains and variable light chains described in Table 10, any combination of a variable heavy chain and variable light chain of the foregoing, and fragments, derivatives, conjugates, variants, and biosimilars thereof.

In an embodiment, a 4-1BB agonist fusion protein according to structures I-A or I-B comprises one or more 4-1BB binding domains comprising a 4-1BBL sequence. In an embodiment, a 4-1BB agonist fusion protein according to structures I-A or I-B comprises one or more 4-1BB binding domains comprising a sequence according to SEQ ID NO:46. In an embodiment, a 4-1BB agonist fusion protein according to structures I-A or I-B comprises one or more 4-1BB binding domains comprising a soluble 4-1BBL sequence. In an embodiment, a 4-1BB agonist fusion protein according to structures I-A or I-B comprises one or more 4-1BB binding domains comprising a sequence according to SEQ ID NO:47.

In an embodiment, a 4-1BB agonist fusion protein according to structures I-A or I—B comprises one or more 4-1BB binding domains that is a scFv domain comprising $V_H$ and $V_L$ regions that are each at least 95% identical to the sequences shown in SEQ ID NO:13 and SEQ ID NO:14, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:23 and SEQ ID NO:24, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the $V_H$ and $V_L$ sequences given in Table 11, wherein the $V_H$ and $V_L$ domains are connected by a linker.

TABLE 11

Additional polypeptide domains useful as 4-1BB binding domains in fusion proteins or as scFv 4-1BB agonist antibodies.

| Identifier | Sequence (One-Letter Amino Acid Symbols) | |
|---|---|---|
| SEQ ID NO: 46 4-1BBL | MEYASDASLD PEAPWPPAPR ARACRVLPWA LVAGLLLLLL LAAACAVFLA CPWAVSGARA | 60 |
| | SPGSAASPRL REGPELSPDD PAGLLDLRQG MFAQLVAQNV LLIDGPLSWY SDPGLAGVSL | 120 |
| | TGGLSYKEDT KELVVAKAGV YYVFFQLELR RVVAGEGSGS VSLALHLQPL RSAAGAAALA | 180 |
| | LTVDLPPASS EARNSAFGFQ GRLLHLSAGQ RLGVHLHTEA RARHAWQLTQ GATVLGLFRV | 240 |
| | TPEIPAGLPS PRSE | 254 |
| SEQ ID NO: 47 4-1BBL soluble domain | LRQGMFAQLV AQNVLLIDGP LSWYSDPGLA GVSLTGGLSY KEDTKELVVA KAGVYYVFFQ | 60 |
| | LELRRVVAGE GSGSVSLALH LQPLRSAAGA AALALTVDLP PASSEARNSA FGFQGRLLHL | 120 |
| | SAGQRLGVHL HTEARARHAW QLTQGATVLG LFRVTPEIPA GLPSPRSE | 168 |
| SEQ ID NO: 48 variable heavy chain for 4B4-1-1 version 1 | QVQLQQPGAE LVKPGASVKL SCKASGYTFS SYWMHWVKQR PGQVLEWIGE INPGNGHTNY | 60 |
| | NEKFKSKATL TVDKSSSTAY MQLSSLTSED SAVYYCARSF TTARGFAYWG QGTLVTVS | 118 |
| SEQ ID NO: 49 variable light chain for 4B4-1-1 version 1 | DIVMTQSPAT QSVTPGDRVS LSCRASQTIS DYLHWYQQKS HESPRLLIKY ASQSISGIPS | 60 |
| | RFSGSGSGSD FTLSINSVEP EDVGVYYCQD GHSFPPTFGG GTKLEIK | 107 |

TABLE 11-continued

Additional polypeptide domains useful as 4-1BB binding domains in fusion proteins or as scFv 4-1BB agonist antibodies.

| Identifier | Sequence (One-Letter Amino Acid Symbols) |
|---|---|
| SEQ ID NO: 50 variable heavy chain for 4B4-1-1 version 2 | QVQLQQPGAE LVKPGASVKL SCKASGYTFS SYWMHWVKQR PGQVLEWIGE INPGNGHTNY 60<br>NEKFKSKATL TVDKSSSTAY MQLSSLTSED SAVYYCARSF TTARGFAYWG QGTLVTVSA 119 |
| SEQ ID NO: 51 variable light chain for 4B4-1-1 version 2 | DIVMTQSPAT QSVTPGDRVS LSCRASQTIS DYLHWYQQKS HESPRLLIKY ASQSISGIPS 60<br>RFSGSGSGSD FTLSINSVEP EDVGVYYCQD GHSFPPTFGG GTKLEIKR 108 |
| SEQ ID NO: 52 variable heavy chain for H39E3-2 | MDWTWRILFL VAAATGAHSE VQLVESGGGL VQPGGSLRLS CAASGFTFSD YWMSWVRQAP 60<br>GKGLEWVADI KNDGSYTNYA PSLTNRFTIS RDNAKNSLYL QMNSLRAEDT AVYYCARELT 120 |
| SEQ ID NO: 53 variable light chain for H39E3-2 | MEAPAQLLFL LLLWLPDTTG DIVMTQSPDS LAVSLGERAT INCKSSQSLL SSGNQKNYL 60<br>WYQQKPGQPP KLLIYYASTR QSGVPDRFSG SGSGTDFTLT ISSLQAEDVA 110 |

In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, and wherein the additional domain is a Fab or Fc fragment domain. In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, wherein the additional domain is a Fab or Fc fragment domain, wherein each of the soluble 4-1BB domains lacks a stalk region (which contributes to trimerisation and provides a certain distance to the cell membrane, but is not part of the 4-1BB binding domain) and the first and the second peptide linkers independently have a length of 3-8 amino acids.

In an embodiment, the 4-1BB agonist is a 4-1BB agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein each TNF superfamily cytokine domain is a 4-1BB binding domain.

In an embodiment, the 4-1BB agonist is a 4-1BB agonistic scFv antibody comprising any of the foregoing $V_H$ domains linked to any of the foregoing $V_L$ domains.

In an embodiment, the 4-1BB agonist is BPS Bioscience 4-1BB agonist antibody catalog no. 79097-2, commercially available from BPS Bioscience, San Diego, CA, USA. In an embodiment, the 4-1BB agonist is Creative Biolabs 4-1BB agonist antibody catalog no. MOM-18179, commercially available from Creative Biolabs, Shirley, NY, USA.

3. Ox40 (Cd134) Agonists

In an embodiment, the TNFRSF agonist is an OX40 (CD134) agonist. The OX40 agonist may be any OX40 binding molecule known in the art. The OX40 binding molecule may be a monoclonal antibody or fusion protein capable of binding to human or mammalian OX40. The OX40 agonists or OX40 binding molecules may comprise an immunoglobulin heavy chain of any isotype (e.g., IgG, IgE, IgM, IgD, IgA, and IgY), class (e.g., IgG1, IgG2, IgG3, IgG4, IgAQ1 and IgA2) or subclass of immunoglobulin molecule. The OX40 agonist or OX40 binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to OX40. In an embodiment, the OX40 agonist is an antigen binding protein that is a fully human antibody. In an embodiment, the OX40 agonist is an antigen binding protein that is a humanized antibody. In some embodiments, OX40 agonists for use in the presently disclosed methods and compositions include anti-OX40 antibodies, human anti-OX40 antibodies, mouse anti-OX40 antibodies, mammalian anti-OX40 antibodies, monoclonal anti-OX40 antibodies, polyclonal anti-OX40 antibodies, chimeric anti-OX40 antibodies, anti-OX40 adnectins, anti-OX40 domain antibodies, single chain anti-OX40 fragments, heavy chain anti-OX40 fragments, light chain anti-OX40 fragments, anti-OX40 fusion proteins, and fragments, derivatives, conjugates, variants, or biosimilars thereof. In a preferred embodiment, the OX40 agonist is an agonistic, anti-OX40 humanized or fully human monoclonal antibody (i.e., an antibody derived from a single cell line).

In a preferred embodiment, the OX40 agonist or OX40 binding molecule may also be a fusion protein. OX40 fusion proteins comprising an Fc domain fused to OX40L are described, for example, in Sadun, et al., *J. Immunother.* 2009, 182, 1481-89. In a preferred embodiment, a multimeric OX40 agonist, such as a trimeric or hexameric OX40 agonist (with three or six ligand binding domains), may induce superior receptor (OX40L) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic OX40 antibodies and fusion proteins are known to induce strong immune responses. Curti, et al., *Cancer Res.* 2013, 73, 7189-98. In a preferred embodiment, the OX40 agonist is a monoclonal antibody or fusion protein that binds specifically to OX40 antigen in a manner sufficient to reduce toxicity. In some embodiments, the OX40 agonist is an agonistic OX40 monoclonal antibody or fusion protein that abrogates antibody-dependent cellular toxicity (ADCC), for example NK cell cytotoxicity. In some embodiments, the OX40 agonist is an agonistic OX40 monoclonal antibody or fusion protein that abrogates antibody-dependent cell phagocytosis (ADCP). In some embodiments, the OX40 agonist is an agonistic OX40 monoclonal antibody or fusion protein that abrogates complement-dependent cytotoxicity (CDC). In some embodiments, the OX40 agonist is an agonistic OX40 monoclonal antibody or fusion protein which abrogates Fc region functionality.

In some embodiments, the OX40 agonists are characterized by binding to human OX40 (SEQ ID NO:54) with high affinity and agonistic activity. In an embodiment, the OX40 agonist is a binding molecule that binds to human OX40 (SEQ ID NO:54). In an embodiment, the OX40 agonist is a binding molecule that binds to murine OX40 (SEQ ID NO:55). The amino acid sequences of OX40 antigen to which an OX40 agonist or binding molecule binds are summarized in Table 12.

human or murine OX40 with a $k_{assoc}$ of about $7.5\times10^5$ 1/M·s or faster, binds to human or murine OX40 with a $k_{assoc}$ of about $7.5\times10^5$ 1/M's or faster, binds to human or murine OX40 with a $k_{assoc}$ of about $8\times10^5$ 1/M·s or faster, binds to human or murine OX40 with a $k_{assoc}$ of about $8.5\times10^5$ 1/M·s or faster, binds to human or murine OX40 with a $k_{assoc}$ of about $9\times10^5$ 1/M·s or faster, binds to human or murine OX40 with a $k_{assoc}$ of about $9.5\times10^5$ 1/M·s or faster, or binds to human or murine OX40 with a $k_{assoc}$ of about $1\times10^6$ 1/M·s or faster.

In some embodiments, the compositions, processes and methods described include a OX40 agonist that binds to human or murine OX40 with a $k_{dissoc}$ of about $2\times10^{-5}$ 1/s or slower, binds to human or murine OX40 with a $k_{dissoc}$ of about $2.1\times10^{-5}$ 1/s or slower, binds to human or murine OX40 with a $k_{dissoc}$ of about $2.2\times10^{-5}$ 1/s or slower, binds to human or murine OX40 with a $k_{dissoc}$ of about $2.3\times10^{-5}$ 1/s or slower, binds to human or murine OX40 with a $k_{dissoc}$ of about $2.4\times10^{-5}$ 1/s or slower, binds to human or murine OX40 with a $k_{dissoc}$ of about $2.5\times10^{-5}$ 1/s or slower, binds to human or murine OX40 with a $k_{dissoc}$ of about $2.6\times10^{-5}$ 1/s or slower or binds to human or murine OX40 with a $k_{dissoc}$ of about $2.7\times10^{-5}$ 1/s or slower, binds to human or murine OX40 with a $k_{dissoc}$ of about $2.8\times10^{-5}$ 1/s or slower, binds to human or murine OX40 with a $k_{dissoc}$ of about $2.9\times10^{-5}$ 1/s or slower, or binds to human or murine OX40 with a $k_{dissoc}$ of about $3\times10^{-5}$ 1/s or slower.

In some embodiments, the compositions, processes and methods described include OX40 agonist that binds to human or murine OX40 with an $IC_{50}$ of about 10 nM or lower, binds to human or murine OX40 with an $IC_{50}$ of about 9 nM or lower, binds to human or murine OX40 with an $IC_{50}$ of about 8 nM or lower, binds to human or murine OX40 with an $IC_{50}$ of about 7 nM or lower, binds to human or murine OX40 with an $IC_{50}$ of about 6 nM or lower, binds to human or murine OX40 with an $IC_{50}$ of about 5 nM or lower, binds to human or murine OX40 with an $IC_{50}$ of about 4 nM or lower, binds to human or murine OX40 with an $IC_{50}$ of about 3 nM or lower, binds to human or murine OX40 with an $IC_{50}$ of about 2 nM or lower, or binds to human or murine OX40 with an $IC_{50}$ of about 1 nM or lower.

TABLE 12

Amino acid sequences of OX40 antigens.

| Identifier | Sequence (One-Letter Amino Acid Symbols) |
|---|---|
| SEQ ID NO: 54<br>human OX40<br>(Homo sapiens) | MCVGARRLGR GPCAALLLLG LGLSTVTGLH CVGDTYPSND RCCHECRPGN GMVSRCSRSQ 60<br>NTVCRPCGPG FYNDVVSSKP CKPCTWCNLR SGSERKQLCT ATQDTVCRCR AGTQPLDSYK 120<br>PGVDCAPCPP GHFSPGDNQA CKPWTNCTLA GKHTLQPASN SSDAICEDRD PPATQPQETQ 180<br>GPPARPITVQ PTEAWPRTSQ GPSTRPVEVP GGRAVAAILG LGLVLGLLGP LAILLALYLL 240<br>RRDQRLPPDA HKPPGGGSFR TPIQEEQADA HSTLAKI 277 |
| SEQ ID NO: 55<br>murine OX40<br>(Mus musculus) | MYVWVQQPTA LLLLGLTLGV TARRLNCVKH TYPSGHKCCR ECQPGHGMVS RCDHTRDTLC 60<br>HPCETGFYNE AVNYDTCKQC TQCNHRSGSE LKQNCTPTQD TVCRCRPGTQ PRQDSGYKLG 120<br>VDCVPCPPGH FSPGNNQACK PWTNCTLSGK QTRHPASDSL DAVCEDRSLL ATLLWETQRP 180<br>TFRPTTVQST TVWPRTSELP SPPTLVTPEG PAFAVLLGLG LGLLAPLTVL LALYLLRKAW 240<br>RLPNTPKPCW GNSFRTPIQE EHTDAHFTLA KI 272 |

In some embodiments, the compositions, processes and methods described include a OX40 agonist that binds human or murine OX40 with a $K_D$ of about 100 μM or lower, binds human or murine OX40 with a $K_D$ of about 90 μM or lower, binds human or murine OX40 with a $K_D$ of about 80 μM or lower, binds human or murine OX40 with a $K_D$ of about 70 μM or lower, binds human or murine OX40 with a $K_D$ of about 60 μM or lower, binds human or murine OX40 with a $K_D$ of about 50 μM or lower, binds human or murine OX40 with a $K_D$ of about 40 μM or lower, or binds human or murine OX40 with a $K_D$ of about 30 μM or lower.

In some embodiments, the compositions, processes and methods described include a OX40 agonist that binds to In some embodiments, the OX40 agonist is tavolixizumab, also known as MEDI0562 or MEDI-0562. Tavolixizumab is available from the MedImmune subsidiary of AstraZeneca, Inc. Tavolixizumab is immunoglobulin G1-kappa, anti-[*Homo sapiens* TNFRSF4 (tumor necrosis factor receptor (TNFR) superfamily member 4, OX40, CD134)], humanized and chimeric monoclonal antibody. The amino acid sequences of tavolixizumab are set forth in Table 13. Tavolixizumab comprises N-glycosylation sites at positions 301 and 301", with fucosylated complex bi-antennary CHO-type glycans; heavy chain intrachain disulfide bridges at positions 22-95 ($V_H$-$V_L$), 148-204 ($C_H1$-$C_L$), 265-325 ($C_H2$) and 371-429 ($C_H3$) (and at positions 22"-95", 148"-204", 265"-325", and 371"-429"); light chain intrachain disulfide bridges at positions 23'-88' ($V_H$-$V_L$) and 134'-194' (CH 1-CL) (and at positions 23'"-88'" and 134'"-194'""); interchain heavy chain-heavy chain disulfide bridges at positions 230-230" and 233-233"; and interchain heavy chain-light chain disulfide bridges at 224-214' and 224"-214'". Current clinical trials of tavolixizumab in a variety of solid tumor indications include U.S. National Institutes of Health clinicaltrials. gov identifiers NCT02318394 and NCT02705482.

In an embodiment, a OX40 agonist comprises a heavy chain given by SEQ ID NO:56 and a light chain given by SEQ ID NO:57. In an embodiment, a OX40 agonist comprises heavy and light chains having the sequences shown in SEQ ID NO:56 and SEQ ID NO:57, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:56 and SEQ ID NO:57, respectively. In an embodiment, a OX40 agonist comprises heavy and light chains that are each at least 98% identical to the sequences shown in SEQ ID NO:56 and SEQ ID NO:57, respectively. In an embodiment, a OX40 agonist comprises heavy and light chains that are each at least 97% identical to the sequences shown in SEQ ID NO:56 and SEQ ID NO:57, respectively. In an embodiment, a OX40 agonist comprises heavy and light chains that are each at least 96% identical to the sequences shown in SEQ ID NO: 56 and SEQ ID NO:57, respectively. In an embodiment, a OX40 agonist comprises heavy and light chains that are each at least 95% identical to the sequences shown in SEQ ID NO:56 and SEQ ID NO:57, respectively.

In an embodiment, the OX40 agonist comprises the heavy and light chain CDRs or variable regions (VRs) of tavolixizumab. In an embodiment, the OX40 agonist heavy chain variable region ($V_H$) comprises the sequence shown in SEQ ID NO:58, and the OX40 agonist light chain variable region ($V_L$) comprises the sequence shown in SEQ ID NO:59, and conservative amino acid substitutions thereof. In an embodiment, a OX40 agonist comprises $V_H$ and $V_L$ regions that are each at least 99% identical to the sequences shown in SEQ ID NO:58 and SEQ ID NO:59, respectively. In an embodiment, a OX40 agonist comprises $V_H$ and $V_L$ regions that are each at least 98% identical to the sequences shown in SEQ ID NO:58 and SEQ ID NO:59, respectively. In an embodiment, a OX40 agonist comprises $V_H$ and $V_L$ regions that are each at least 97% identical to the sequences shown in SEQ ID NO:58 and SEQ ID NO:59, respectively. In an embodiment, a OX40 agonist comprises $V_H$ and $V_L$ regions that are each at least 96% identical to the sequences shown in SEQ ID NO: 58 and SEQ ID NO:59, respectively. In an embodiment, a OX40 agonist comprises $V_H$ and $V_L$ regions that are each at least 95% identical to the sequences shown in SEQ ID NO:58 and SEQ ID NO: 59, respectively. In an embodiment, an OX40 agonist comprises an scFv antibody comprising $V_H$ and $V_L$ regions that are each at least 99% identical to the sequences shown in SEQ ID NO:58 and SEQ ID NO:59.

In an embodiment, a OX40 agonist comprises heavy chain CDR1, CDR2 and CDR3 domains having the sequences set forth in SEQ ID NO:60, SEQ ID NO:61, and SEQ ID NO:62, respectively, and conservative amino acid substitutions thereof, and light chain CDR1, CDR2 and CDR3 domains having the sequences set forth in SEQ ID NO:63, SEQ ID NO:64, and SEQ ID NO: 65, respectively, and conservative amino acid substitutions thereof.

In an embodiment, the OX40 agonist is a OX40 agonist biosimilar monoclonal antibody approved by drug regulatory authorities with reference to tavolixizumab. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tavolixizumab. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is tavolixizumab. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab.

TABLE 13

Amino acid sequences for OX40 agonist antibodies related to tavolixizumab.

| Identifier | Sequence (One-Letter Amino Acid Symbols) |
|---|---|
| SEQ ID NO: 56 heavy chain for tavolixizumab | QVQLQESGPG LVKPSQTLSL TCAVYGGSFS SGYWNWIRKH PGKGLEYIGY ISYNGITYHN 60<br>PSLKSRITIN RDTSKNQYSL QLNSVTPEDT AVYYCARYKY DYDGGHAMDY WGQGTLVTVS 120<br>SASTKGPSVF PLAPSSKSTS GGTAALGCLV KDYFPEPVTV SWNSGALTSG VHTFPAVLQS 180<br>SGLYSLSSVV TVPSSSLGTQ TYICNVNHKP SNTKVDKRVE PKSCDKTHTC PPCPAPELLG 240<br>GPSVFLFPPK PKDTLMISRT PEVTCVVVDV SHEDPEVKFN WYVDGVEVHN AKTKPREEQY 300<br>NSTYRVVSVL TVLHQDWLNG KEYKCKVSNK ALPAPIEKTI SKAKGQPREP QVYTLPPSRE 360<br>EMTKNQVSLT CLVKGFYPSD IAVEWESNGQ PENNYKTTPP VLDSDGSFFL YSKLTVDKSR 420<br>WQQGNVFSCS VMHEALHNHY TQKSLSLSPG K 451 |

TABLE 13-continued

| Amino acid sequences for OX40 agonist antibodies related to tavolixizumab. | | |
|---|---|---|
| Identifier | Sequence (One-Letter Amino Acid Symbols) | |
| SEQ ID NO:57 light chain for tavolixizumab | DIQMTQSPSS LSASVGDRVT ITCRASQDIS NYLNWYQQKP GKAPKLLIYY TSKLHSGVPS<br>RFSGSGSGTD YTLTISSLQP EDFATYYCQQ GSALPWTFGQ GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 58 heavy chain variable region for tavolixizumab | QVQLQESGPG LVKPSQTLSL TCAVYGGSFS SGYWNWIRKH PGKGLEYIGY ISYNGITYHN<br>PSLKSRITIN RDTSKNQYSL QLNSVTPEDT AVYYCARYKY DYDGGHAMDY WGQGTLVT | 60<br>118 |
| SEQ ID NO: 59 light chain variable region for tavolixizumab | DIQMTQSPSS LSASVGDRVT ITCRASQDIS NYLNWYQQKP GKAPKLLIYY TSKLHSGVPS<br>RFSGSGSGTD YTLTISSLQP EDFATYYCQQ GSALPWTFGQ GTKVEIKR | 60<br>108 |
| SEQ ID NO: 60 heavy chain CDR1 for tavolixizumab | GSFSSGYWN | 9 |
| SEQ ID NO: 61 heavy chain CDR2 for tavolixizumab | YIGYISYNGI TYH | 13 |
| SEQ ID NO: 62 heavy chain CDR3 for tavolixizumab | RYKYDYDGGH AMDY | 14 |
| SEQ ID NO: 63 light chain CDR1 for tavolixizumab | QDISNYLN | 8 |
| SEQ ID NO: 64 light chain CDR2 for tavolixizumab | LLIYYTSKLH S | 11 |
| SEQ ID NO: 65 light chain CDR3 for tavolixizumab | QQGSALPW | 8 |

In some embodiments, the OX40 agonist is 11D4, which is a fully human antibody available from Pfizer, Inc. The preparation and properties of 11D4 are described in U.S. Pat. Nos. 7,960,515; 8,236,930; and 9,028,824, the disclosures of which are incorporated by reference herein. The amino acid sequences of 11D4 are set forth in Table 14.

In an embodiment, a OX40 agonist comprises a heavy chain given by SEQ ID NO:66 and a light chain given by SEQ ID NO:67. In an embodiment, a OX40 agonist comprises heavy and light chains having the sequences shown in SEQ ID NO:66 and SEQ ID NO:67, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:66 and SEQ ID NO:67, respectively. In an embodiment, a OX40 agonist comprises heavy and light chains that are each at least 98% identical to the sequences shown in SEQ ID NO:66 and SEQ ID NO:67, respectively. In an embodiment, a OX40 agonist comprises heavy and light chains that are each at least 97% identical to the sequences shown in SEQ ID NO:66 and SEQ ID NO:67, respectively. In an embodiment, a OX40 agonist comprises heavy and light chains that are each at least 96% identical to the sequences shown in SEQ ID NO: 66 and SEQ ID NO:67, respectively. In an embodiment, a OX40 agonist comprises heavy and light chains that are each at least 95% identical to the sequences shown in SEQ ID NO:66 and SEQ ID NO:67, respectively.

In an embodiment, the OX40 agonist comprises the heavy and light chain CDRs or variable regions (VRs) of 11D4. In an embodiment, the OX40 agonist heavy chain variable region ($V_H$) comprises the sequence shown in SEQ ID NO:68, and the OX40 agonist light chain variable region ($V_L$) comprises the sequence shown in SEQ ID NO:69, and conservative amino acid substitutions thereof. In an embodiment, a OX40 agonist comprises $V_H$ and $V_L$ regions that are each at least 99% identical to the sequences shown in SEQ ID NO:68 and SEQ ID NO:69, respectively. In an embodiment, a OX40 agonist comprises $V_H$ and $V_L$ regions that are each at least 98% identical to the sequences shown in SEQ ID NO:68 and SEQ ID NO:69, respectively. In an embodiment, a OX40 agonist comprises $V_H$ and $V_L$ regions that are each at least 97% identical to the sequences shown in SEQ ID NO:68 and SEQ ID NO:69, respectively. In an embodiment, a OX40 agonist comprises $V_H$ and $V_L$ regions that are each at least 96% identical to the sequences shown in SEQ ID NO:68 and SEQ ID NO:69, respectively. In an embodiment, a OX40 agonist comprises $V_H$ and $V_L$ regions that are each at least 95% identical to the sequences shown in SEQ ID NO:68 and SEQ ID NO:69, respectively.

In an embodiment, a OX40 agonist comprises heavy chain CDR1, CDR2 and CDR3 domains having the sequences set forth in SEQ ID NO:70, SEQ ID NO:71, and SEQ ID NO:72, respectively, and conservative amino acid substitutions thereof, and light chain CDR1, CDR2 and CDR3 domains having the sequences set forth in SEQ ID NO:73, SEQ ID NO:74, and SEQ ID NO: 75, respectively, and conservative amino acid substitutions thereof.

In an embodiment, the OX40 agonist is a OX40 agonist biosimilar monoclonal antibody approved by drug regulatory authorities with reference to 11D4. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 11D4. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 11D4. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4.

TABLE 14

Amino acid sequences for OX40 agonist antibodies related to 11D4.

| Identifier | Sequence (One-Letter Amino Acid Symbols) | |
|---|---|---|
| SEQ ID NO: 66 heavy chain for 11D4 | EVQLVESGGG LVQPGGSLRL SCAASGFTFS SYSMNWVRQA PGKGLEWVSY ISSSSSTIDY | 60 |
| | ADSVKGRFTI SRDNAKNSLY LQMNSLRDED TAVYYCARES GWYLFDYWGQ GTLVTVSSAS | 120 |
| | TKGPSVFPLA PCSRSTSEST AALGCLVKDY FPEPVTVSWN SGALTSGVHT FPAVLQSSGL | 180 |
| | YSLSSVVTVP SSNFGTQTYT CNVDHKPSNT KVDKTVERKC CVECPPCPAP PVAGPSVFLF | 240 |
| | PPKPKDTLMI SRTPEVTCVV VDVSHEDPEV QFNWYVDGVE VHNAKTKPRE EQFNSTFRVV | 300 |
| | SVLTVVHQDW LNGKEYKCKV SNKGLPAPIE KTISKTKGQP REPQVYTLPP SREEMTKNQV | 360 |
| | SLTCLVKGFY PSDIAVEWES NGQPENNYKT TPPMLDSDGS FFLYSKLTVD KSRWQQGNVF | 420 |
| | SCSVMHEALH NHYTQKSLSL SPGK | 444 |
| SEQ ID NO: 67 light chain for 11D4 | DIQMTQSPSS LSASVGDRVT ITCRASQGIS SWLAWYQQKP EKAPKSLIYA ASSLQSGVPS | 60 |
| | RFSGSGSGTD FTLTISSLQP EDFATYYCQQ YNSYPPTFGG GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 68 heavy chain variable region for 11D4 | EVQLVESGGG LVQPGGSLRL SCAASGFTFS SYSMNWVRQA PGKGLEWVSY ISSSSSTIDY | 60 |
| | ADSVKGRFTI SRDNAKNSLY LQMNSLRDED TAVYYCARES GWYLFDYWGQ GTLVTVSS | 118 |
| SEQ ID NO: 69 light chain variable region for 11D4 | DIQMTQSPSS LSASVGDRVT ITCRASQGIS SWLAWYQQKP EKAPKSLIYA ASSLQSGVPS | 60 |
| | RFSGSGSGTD FTLTISSLQP EDFATYYCQQ YNSYPPTFGG GTKVEIK | 107 |
| SEQ ID NO: 70 heavy chain CDR1 for 11D4 | SYSMN | 5 |
| SEQ ID NO: 71 heavy chain CDR2 for 11D4 | YISSSSSTID YADSVKG | 17 |
| SEQ ID NO: 72 heavy chain CDR3 for 11D4 | ESGWYLFDY | 9 |
| SEQ ID NO: 73 light chain CDR1 for 11D4 | RASQGISSWL A | 11 |

TABLE 14-continued

| Amino acid sequences for OX40 agonist antibodies related to 11D4. | | |
|---|---|---|
| Identifier | Sequence (One-Letter Amino Acid Symbols) | |
| SEQ ID NO: 74 light chain CDR2 for 11D4 | AASSLQS | 7 |
| SEQ ID NO: 75 light chain CDR3 for 11D4 | QQYNSYPPT | 9 |

In some embodiments, the OX40 agonist is 18D8, which is a fully human antibody available from Pfizer, Inc. The preparation and properties of 18D8 are described in U.S. Pat. Nos. 7,960,515; 8,236,930; and 9,028,824, the disclosures of which are incorporated by reference herein. The amino acid sequences of 18D8 are set forth in Table 15.

In an embodiment, a OX40 agonist comprises a heavy chain given by SEQ ID NO:76 and a light chain given by SEQ ID NO:77. In an embodiment, a OX40 agonist comprises heavy and light chains having the sequences shown in SEQ ID NO:76 and SEQ ID NO:77, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:76 and SEQ ID NO:77, respectively. In an embodiment, a OX40 agonist comprises heavy and light chains that are each at least 98% identical to the sequences shown in SEQ ID NO:76 and SEQ ID NO:77, respectively. In an embodiment, a OX40 agonist comprises heavy and light chains that are each at least 97% identical to the sequences shown in SEQ ID NO:76 and SEQ ID NO:77, respectively. In an embodiment, a OX40 agonist comprises heavy and light chains that are each at least 96% identical to the sequences shown in SEQ ID NO: 76 and SEQ ID NO:77, respectively. In an embodiment, a OX40 agonist comprises heavy and light chains that are each at least 95% identical to the sequences shown in SEQ ID NO:76 and SEQ ID NO:77, respectively.

In an embodiment, the OX40 agonist comprises the heavy and light chain CDRs or variable regions (VRs) of 18D8. In an embodiment, the OX40 agonist heavy chain variable region ($V_H$) comprises the sequence shown in SEQ ID NO:78, and the OX40 agonist light chain variable region ($V_L$) comprises the sequence shown in SEQ ID NO:79, and conservative amino acid substitutions thereof. In an embodiment, a OX40 agonist comprises $V_H$ and $V_L$ regions that are each at least 99% identical to the sequences shown in SEQ ID NO:78 and SEQ ID NO:79, respectively. In an embodiment, a OX40 agonist comprises $V_H$ and $V_L$ regions that are each at least 98% identical to the sequences shown in SEQ ID NO:78 and SEQ ID NO:79, respectively. In an embodiment, a OX40 agonist comprises $V_H$ and $V_L$ regions that are each at least 97% identical to the sequences shown in SEQ ID NO:78 and SEQ ID NO:79, respectively. In an embodiment, a OX40 agonist comprises $V_H$ and $V_L$ regions that are each at least 96% identical to the sequences shown in SEQ ID NO:78 and SEQ ID NO:79, respectively. In an embodiment, a OX40 agonist comprises $V_H$ and $V_L$ regions that are each at least 95% identical to the sequences shown in SEQ ID NO:78 and SEQ ID NO:79, respectively.

In an embodiment, a OX40 agonist comprises heavy chain CDR1, CDR2 and CDR3 domains having the sequences set forth in SEQ ID NO:80, SEQ ID NO:81, and SEQ ID NO:82, respectively, and conservative amino acid substitutions thereof, and light chain CDR1, CDR2 and CDR3 domains having the sequences set forth in SEQ ID NO:83, SEQ ID NO:84, and SEQ ID NO: 85, respectively, and conservative amino acid substitutions thereof.

In an embodiment, the OX40 agonist is a OX40 agonist biosimilar monoclonal antibody approved by drug regulatory authorities with reference to 18D8. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 18D8. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 18D8. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8.

TABLE 15

Amino acid sequences for OX40 agonist antibodies related to 18D8.

| Identifier | Sequence (One-Letter Amino Acid Symbols) |
|---|---|
| SEQ ID NO: 76 heavy chain for 18D8 | EVQLVESGGG LVQPGRSLRL SCAASGFTFD DYAMHWVRQA PGKGLEWVSG ISWNSGSIGY 60<br>ADSVKGRFTI SRDNAKNSLY LQMNSLRAED TALYYCAKDQ STADYYFYYG MDVWGQGTTV 120<br>TVSSASTKGP SVFPLAPCSR STSESTAALG CLVKDYFPEP VTVSWNSGAL TSGVHTFPAV 180<br>LQSSGLYSLS SVVTVPSSNF GTQTYTCNVD HKPSNTKVDK TVERKCCVEC PPCPAPPVAG 240<br>PSVFLFPPKP KDTLMISRTP EVTCVVVDVS HEDPEVQFNW YVDGVEVHNA KTKPREEQFN 300<br>STFRVVSVLT VVHQDWLNGK EYKCKVSNKG LPAPIEKTIS KTKGQPREPQ VYTLPPSREE 360<br>MTKNQVSLTC LVKGFYPSDI AVEWESNGQP ENNYKTTPPM LDSDGSFFLY SKLTVDKSRW 420<br>QQGNVFSCSV MHEALHNHYT QKSLSLSPGK 450 |
| SEQ ID NO: 77 light chain for 18D8 | EIVVTQSPAT LSLSPGERAT LSCRASQSVS SYLAWYQQKP GQAPRLLIYD ASNRATGIPA 60<br>RFSGSGSGTD FTLTISSLEP EDFAVYYCQQ RSNWPTFGQG TKVEIKRTVA APSVFIFPPS 120<br>DEQLKSGTAS VVCLLNNFYP REAKVQWKVD NALQSGNSQE SVTEQDSKDS TYSLSSTLTL 180<br>SKADYEKHKV YACEVTHQGL SSPVTKSFNR GEC 213 |
| SEQ ID NO: 78 heavy chain variable region for 18D8 | EVQLVESGGG LVQPGRSLRL SCAASGFTFD DYAMHWVRQA PGKGLEWVSG ISWNSGSIGY 60<br>ADSVKGRFTI SRDNAKNSLY LQMNSLRAED TALYYCAKDQ STADYYFYYG MDVWGQGTTV 120<br>TVSS 124 |
| SEQ ID NO:79 light chain variable region for 18D8 | EIVVTQSPAT LSLSPGERAT LSCRASQSVS SYLAWYQQKP GQAPRLLIYD ASNRATGIPA 60<br>RFSGSGSGTD FTLTISSLEP EDFAVYYCQQ RSNWPTFGQG TKVEIK 106 |
| SEQ ID NO: 80 heavy chain CDR1 for 18D8 | DYAMH 5 |
| SEQ ID NO: 81 heavy chain CDR2 for 18D8 | GISWNSGSIG YADSVKG 17 |
| SEQ ID NO: 82 heavy chain CDR3 for 18D8 | DQSTADYYFY YGMDV 15 |
| SEQ ID NO: 83 light chain CDR1 for 18D8 | RASQSVSSYL A 11 |
| SEQ ID NO: 84 light chain CDR2 for 18D8 | DASNRAT 7 |
| SEQ ID NO: 85 light chain CDR3 for 18D8 | QQRSNWPT 8 |

In some embodiments, the OX40 agonist is Hu119-122, which is a humanized antibody available from GlaxoSmithKline plc. The preparation and properties of Hu119-122 are described in U.S. Pat. Nos. 9,006,399 and 9,163,085, and in International Patent Publication No. WO 2012/027328, the disclosures of which are incorporated by reference herein. The amino acid sequences of Hu119-122 are set forth in Table 16.

In an embodiment, the OX40 agonist comprises the heavy and light chain CDRs or variable regions (VRs) of Hu119-122. In an embodiment, the OX40 agonist heavy chain variable region ($V_H$) comprises the sequence shown in SEQ ID NO:86, and the OX40 agonist light chain variable region ($V_L$) comprises the sequence shown in SEQ ID NO:87, and conservative amino acid substitutions thereof. In an embodiment, a OX40 agonist comprises $V_H$ and $V_L$ regions that are each at least 99% identical to the sequences shown in SEQ ID NO:86 and SEQ ID NO:87, respectively. In an embodiment, a OX40 agonist comprises $V_H$ and $V_L$ regions that are each at least 98% identical to the sequences shown in SEQ ID NO:86 and SEQ ID NO:87, respectively. In an embodiment, a OX40 agonist comprises $V_H$ and $V_L$ regions that are each at least 97% identical to the sequences shown in SEQ ID NO:86 and SEQ ID NO:87, respectively. In an embodiment, a OX40 agonist comprises $V_H$ and $V_L$ regions that are each at least 96% identical to the sequences shown in SEQ ID NO:86 and SEQ ID NO:87, respectively. In an embodiment, a OX40 agonist comprises $V_H$ and $V_L$ regions that are each at least 95% identical to the sequences shown in SEQ ID NO:86 and SEQ ID NO:87, respectively.

In an embodiment, a OX40 agonist comprises heavy chain CDR1, CDR2 and CDR3 domains having the sequences set forth in SEQ ID NO:88, SEQ ID NO:89, and SEQ ID NO:90, respectively, and conservative amino acid substitutions thereof, and light chain CDR1, CDR2 and CDR3 domains having the sequences set forth in SEQ ID NO:91, SEQ ID NO:92, and SEQ ID NO: 93, respectively, and conservative amino acid substitutions thereof.

In an embodiment, the OX40 agonist is a OX40 agonist biosimilar monoclonal antibody approved by drug regulatory authorities with reference to Hu119-122. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu119-122. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu119-122. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122.

TABLE 16

Amino acid sequences for OX40 agonist antibodies related to Hu119-122.

| Identifier | Sequence (One-Letter Amino Acid Symbols) | |
|---|---|---|
| SEQ ID NO: 86 heavy chain variable region for Hu119-122 | EVQLVESGGG LVQPGGSLRL SCAASEYEFP SHDMSWVRQA PGKGLELVAA INSDGGSTYY<br>PDTMERRFTI SRDNAKNSLY LQMNSLRAED TAVYYCARHY DDYYAWFAYW GQGTMVTVSS | 60<br>120 |
| SEQ ID NO: 87 light chain variable region for Hu119-122 | EIVLTQSPAT LSLSPGERAT LSCRASKSVS TSGYSYMHWY QQKPGQAPRL LIYLASNLES<br>GVPARFSGSG SGTDFTLTIS SLEPEDFAVY YCQHSRELPL TFGGGTKVEI K | 60<br>111 |
| SEQ ID NO: 88 heavy chain CDR1 for Hu119-122 | SHDMS | 5 |
| SEQ ID NO: 89 heavy chain CDR2 for Hu119-122 | AINSDGGSTY YPDTMER | 17 |
| SEQ ID NO: 90 heavy chain CDR3 for Hu119-122 | HYDDYYAWFA Y | 11 |
| SEQ ID NO: 91 light chain CDR1 for Hu119-122 | RASKSVSTSG YSYMH | 15 |
| SEQ ID NO: 92 light chain CDR2 for Hu119-122 | LASNLES | 7 |
| SEQ ID NO: 93 light chain CDR3 for Hu119-122 | QHSRELPLT | 9 |

In some embodiments, the OX40 agonist is Hu106-222, which is a humanized antibody available from GlaxoSmithKline plc. The preparation and properties of Hu106-222 are described in U.S. Pat. Nos. 9,006,399 and 9,163,085, and in International Patent Publication No. WO 2012/027328, the disclosures of which are incorporated by reference herein. The amino acid sequences of Hu106-222 are set forth in Table 17.

In an embodiment, the OX40 agonist comprises the heavy and light chain CDRs or variable regions (VRs) of Hu106-222. In an embodiment, the OX40 agonist heavy chain variable region ($V_H$) comprises the sequence shown in SEQ ID NO:94, and the OX40 agonist light chain variable region ($V_L$) comprises the sequence shown in SEQ ID NO:95, and conservative amino acid substitutions thereof. In an embodiment, a OX40 agonist comprises $V_H$ and $V_L$ regions that are each at least 99% identical to the sequences shown in SEQ ID NO:94 and SEQ ID NO:95, respectively. In an embodiment, a OX40 agonist comprises $V_H$ and $V_L$ regions that are each at least 98% identical to the sequences shown in SEQ ID NO:94 and SEQ ID NO:95, respectively. In an embodiment, a OX40 agonist comprises $V_H$ and $V_L$ regions that are each at least 97% identical to the sequences shown in SEQ ID NO:94 and SEQ ID NO:95, respectively. In an embodiment, a OX40 agonist comprises $V_H$ and $V_L$ regions that are each at least 96% identical to the sequences shown in SEQ ID NO:94 and SEQ ID NO:95, respectively. In an embodiment, a OX40 agonist comprises $V_H$ and $V_L$ regions that are each at least 95% identical to the sequences shown in SEQ ID NO:94 and SEQ ID NO:95, respectively.

In an embodiment, a OX40 agonist comprises heavy chain CDR1, CDR2 and CDR3 domains having the sequences set forth in SEQ ID NO:96, SEQ ID NO:97, and SEQ ID NO:98, respectively, and conservative amino acid substitutions thereof, and light chain CDR1, CDR2 and CDR3 domains having the sequences set forth in SEQ ID NO:99, SEQ ID NO: 100, and SEQ ID NO: 101, respectively, and conservative amino acid substitutions thereof.

In an embodiment, the OX40 agonist is a OX40 agonist biosimilar monoclonal antibody approved by drug regulatory authorities with reference to Hu106-222. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu106-222. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu106-222. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222.

TABLE 17

Amino acid sequences for OX40 agonist antibodies related to Hu106-222.

| Identifier | Sequence (One-Letter Amino Acid Symbols) | |
|---|---|---|
| SEQ ID NO: 94 heavy chain variable region for Hu106-222 | QVQLVQSGSE LKKPGASVKV SCKASGYTFT DYSMHWVRQA PGQGLKWMGW INTETGEPTY<br>ADDFKGRFVF SLDTSVSTAY LQISSLKAED TAVYYCANPY YDYVSYYAMD YWGQGTTVTV<br>SS | 60<br>120<br>122 |
| SEQ ID NO: 95 light chain variable region for Hu106-222 | DIQMTQSPSS LSASVGDRVT ITCKASQDVS TAVAWYQQKP GKAPKLLIYS ASYLYTGVPS<br>RFSGSGSGTD FTFTISSLQP EDIATYYCQQ HYSTPRTFGQ GTKLEIK | 60<br>107 |
| SEQ ID NO: 96 heavy chain CDR1 for Hu106-222 | DYSMH | 5 |
| SEQ ID NO: 97 heavy chain CDR2 for Hu106-222 | WINTETGEPT YADDFKG | 17 |
| SEQ ID NO: 98 heavy chain CDR3 for Hu106-222 | PYYDYVSYYA MDY | 13 |
| SEQ ID NO: 99 light chain CDR1 for Hu106-222 | KASQDVSTAV A | 11 |
| SEQ ID NO: 100 light chain CDR2 for Hu106-222 | SASYLYT | 7 |
| SEQ ID NO: 101 light chain CDR3 for Hu106-222 | QQHYSTPRT | 9 |

In some embodiments, the OX40 agonist antibody is MEDI6469 (also referred to as 9B12). MEDI6469 is a murine monoclonal antibody. Weinberg, et al., *J. Immunother.* 2006, 29, 575-585. In some embodiments the OX40 agonist is an antibody produced by the 9B12 hybridoma, deposited with Biovest Inc. (Malvern, MA, USA), as described in Weinberg, et al., *J. Immunother.* 2006, 29, 575-585, the disclosure of which is hereby incorporated by reference in its entirety. In some embodiments, the antibody comprises the CDR sequences of MEDI6469. In some embodiments, the antibody comprises a heavy chain variable region sequence and/or a light chain variable region sequence of MEDI6469.

In an embodiment, the OX40 agonist is L106 BD (Pharmingen Product #340420). In some embodiments, the OX40 agonist comprises the CDRs of antibody L106 (BD Pharmingen Product #340420). In some embodiments, the OX40 agonist comprises a heavy chain variable region sequence and/or a light chain variable region sequence of antibody L106 (BD Pharmingen Product #340420). In an embodiment, the OX40 agonist is ACT35 (Santa Cruz Biotechnology, Catalog #20073). In some embodiments, the OX40 agonist comprises the CDRs of antibody ACT35 (Santa Cruz Biotechnology, Catalog #20073). In some embodiments, the OX40 agonist comprises a heavy chain variable region sequence and/or a light chain variable region sequence of antibody ACT35 (Santa Cruz Biotechnology, Catalog #20073). In an embodiment, the OX40 agonist is the murine monoclonal antibody anti-mCD134/mOX40 (clone OX86), commercially available from In VivoMAb, BioXcell Inc, West Lebanon, NH.

In an embodiment, the OX40 agonist is selected from the OX40 agonists described in International Patent Application Publication Nos. WO 95/12673, WO 95/21925, WO 2006/121810, WO 2012/027328, WO 2013/028231, WO 2013/038191, and WO 2014/148895; European Patent Application EP 0672141; U.S. Patent Application Publication Nos. US 2010/136030, US 2014/377284, US 2015/190506, and US 2015/132288 (including clones 20E5 and 12H3); and U.S. Pat. Nos. 7,504,101, 7,550,140, 7,622,444, 7,696,175, 7,960,515, 7,961,515, 8,133,983, 9,006,399, and 9,163,085, the disclosure of each of which is incorporated herein by reference in its entirety.

In an embodiment, the OX40 agonist is an OX40 agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof. The properties of structures I-A and I-B are described above and in U.S. Pat. Nos. 9,359,420, 9,340,599, 8,921,519, and 8,450,460, the disclosures of which are incorporated by reference herein. Amino acid sequences for the polypeptide domains of structure I-A are given in Table 9. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides. Likewise, amino acid sequences for the polypeptide domains of structure I-B are given in Table 10. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO: 43 to SEQ ID NO:45.

In an embodiment, an OX40 agonist fusion protein according to structures I-A or I—B comprises one or more OX40 binding domains selected from the group consisting of a variable heavy chain and variable light chain of tavolixizumab, a variable heavy chain and variable light chain of 11D4, a variable heavy chain and variable light chain of 18D8, a variable heavy chain and variable light chain of Hu119-122, a variable heavy chain and variable light chain of Hu106-222, a variable heavy chain and variable light chain selected from the variable heavy chains and variable light chains described in Table 17, any combination of a variable heavy chain and variable light chain of the foregoing, and fragments, derivatives, conjugates, variants, and biosimilars thereof.

In an embodiment, an OX40 agonist fusion protein according to structures I-A or I—B comprises one or more OX40 binding domains comprising an OX40L sequence. In an embodiment, an OX40 agonist fusion protein according to structures I-A or I-B comprises one or more OX40 binding domains comprising a sequence according to SEQ ID NO: 102. In an embodiment, an OX40 agonist fusion protein according to structures I-A or I-B comprises one or more OX40 binding domains comprising a soluble OX40L sequence. In an embodiment, a OX40 agonist fusion protein according to structures I-A or I-B comprises one or more OX40 binding domains comprising a sequence according to SEQ ID NO:103. In an embodiment, a OX40 agonist fusion protein according to structures I-A or I-B comprises one or more OX40 binding domains comprising a sequence according to SEQ ID NO:104.

In an embodiment, an OX40 agonist fusion protein according to structures I-A or I—B comprises one or more OX40 binding domains that is a scFv domain comprising $V_H$ and $V_L$ regions that are each at least 95% identical to the sequences shown in SEQ ID NO:58 and SEQ ID NO:59, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:68 and SEQ ID NO:69, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO: 78 and SEQ ID NO:79, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:86 and SEQ ID NO:87, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:94 and SEQ ID NO:95, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the $V_H$ and $V_L$ sequences given in Table 14, wherein the $V_H$ and $V_L$ domains are connected by a linker.

TABLE 18

Additional polypeptide domains useful as OX40 binding domains in fusion proteins (e.g., structures I-A and I-B) or as scFv OX40 agonist antibodies.

| Identifier | Sequence (One-Letter Amino Acid Symbols) |
|---|---|
| SEQ ID NO: 102<br>OX40L | MERVQPLEEN VGNAARPRFE RNKLLLVASV IQGLGLLLCF TYICLHFSAL QVSHRYPRIQ 60<br>SIKVQFTEYK KEKGFILTSQ KEDEIMKVQN NSVIINCDGF YLISLKGYFS QEVNISLHYQ 120<br>KDEEPLFQLK KVRSVNSLMV ASLTYKDKVY LNVTTDNTSL DDFHVNGGEL ILIHQNPGEF 180<br>CVL 183 |

TABLE 18-continued

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 103 OX40L soluble domain | SHRYPRIQSI KVQFTEYKKE KGFILTSQKE DEIMKVQNNS VIINCDGFYL ISLKGYFSQE<br>VNISLHYQKD EEPLFQLKKV RSVNSLMVAS LTYKDKVYLN VTTDNTSLDD FHVNGGELIL<br>IHQNPGEFCV L | 60<br>120<br>131 |
| SEQ ID NO: 104 OX40L soluble domain (alternative) | YPRIQSIKVQ FTEYKKEKGF ILTSQKEDEI MKVQNNSVII NCDGFYLISL KGYFSQEVNI<br>SLHYQKDEEP LFQLKKVRSV NSLMVASLTY KDKVYLNVTT DNTSLDDFHV NGGELILIHQ<br>NPGEFCVL | 60<br>120<br>128 |
| SEQ ID NO: 105 variable heavy chain for 008 | EVQLVESGGG LVQPGGSLRL SCAASGFTFS NYTMNWVRQA PGKGLEWVSA ISGSGGSTYY<br>ADSVKGRFTI SRDNSKNTLY LQMNSLRAED TAVYYCAKDR YSQVHYALDY WGQGTLVTVS | 60<br>120 |
| SEQ ID NO: 106 variable light chain for 008 | DIVMTQSPDS LPVTPGEPAS ISCRSSQSLL HSNGYNYLDW YLQKAGQSPQ LLIYLGSNRA<br>SGVPDRFSGS GSGTDFTLKI SRVEAEDVGV YYCQQYYNHP TTFGQGTK | 60<br>108 |
| SEQ ID NO: 107 variable heavy chain for 011 | EVQLVESGGG VVQPGRSLRL SCAASGFTFS DYTMNWVRQA PGKGLEWVSS ISGGSTYYAD<br>SRKGRFTISR DNSKNTLYLQ MNNLRAEDTA VYYCARDRYF RQQNAFDYWG QGTLVTVSSA | 60<br>120 |
| SEQ ID NO: 108 variable light chain for 011 | DIVMTQSPDS LPVTPGEPAS ISCRSSQSLL HSNGYNYLDW YLQKAGQSPQ LLIYLGSNRA<br>SGVPDRFSGS GSGTDFTLKI SRVEAEDVGV YYCQQYYNHP TTFGQGTK | 60<br>108 |
| SEQ ID NO: 109 variable heavy chain for 021 | EVQLVESGGG LVQPRGSLRL SCAASGFTFS SYAMNWVRQA PGKGLEWVAV ISYDGSNKYY<br>ADSVKGRFTI SRDNSKNTLY LQMNSLRAED TAVYYCAKDR YITLPNALDY WGQGTLVTVS | 60<br>120 |
| SEQ ID NO: 110 variable light chain for 021 | DIQMTQSPVS LPVTPGEPAS ISCRSSQSLL HSNGYNYLDW YLQKPGQSPQ LLIYLGSNRA<br>SGVPDRFSGS GSGTDFTLKI SRVEAEDVGV YYCQQYKSNP PTFGQGTK | 60<br>108 |
| SEQ ID NO: 111 variable heavy chain for 023 | EVQLVESGGG LVHPGGSLRL SCAGSGFTFS SYAMHWVRQA PGKGLEWVSA IGTGGGTYYA<br>DSVMGRFTIS RDNSKNTLYL QMNSLRAEDT AVYYCARYDN VMGLYWFDYW GQGTLVTVSS | 60<br>120 |
| SEQ ID NO: 112 variable light chain for 023 | EIVLTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPPAFGG GTKVEIKR | 60<br>108 |
| SEQ ID NO: 113 heavy chain variable region | EVQLQQSGPE LVKPGASVKM SCKASGYTFT SYVMHWVKQK PGQGLEWIGY INPYNDGTKY<br>NEKFKGKATL TSDKSSSTAY MELSSLTSED SAVYYCANYY GSSLSMDYWG QGTSVTVSS | 60<br>119 |
| SEQ ID NO: 114 light chain variable region | DIQMTQTTSS LSASLGDRVT ISCRASQDIS NYLNWYQQKP DGTVKLLIYY TSRLHSGVPS<br>RFSGSGSGTD YSLTISNLEQ EDIATYFCQQ GNTLPWTFGG GTKLEIKR | 60<br>108 |
| SEQ ID NO: 115 heavy chain variable region | EVQLQQSGPE LVKPGASVKI SCKTSGYTFK DYTMHWVKQS HGKSLEWIGG IYPNNGGSTY<br>NQNFKDKATL TVDKSSSTAY MEFRSLTSED SAVYYCARMG YHGPHLDFDV WGAGTTVTVS<br>P | 60<br>120<br>121 |
| SEQ ID NO: 116 light chain variable region | DIVMTQSHKF MSTSLGDRVS ITCKASQDVG AAVAWYQQKP GQSPKLLIYW ASTRHTGVPD<br>RFTGGGSGTD FTLTISNVQS EDLTDYFCQQ YINYPLTFGG GTKLEIKR | 60<br>108 |
| SEQ ID NO: 117 heavy chain variable region of humanized antibody | QIQLVQSGPE LKKPGETVKI SCKASGYTFT DYSMHWVKQA PGKGLKWMGW INTETGEPTY<br>ADDFKGRFAF SLETSASTAY LQINNLKNED TATYFCANPY YDYVSYYAMD YWGHGTSVTV<br>SS | 60<br>120<br>122 |
| SEQ ID NO: 118 heavy chain variable region of humanized antibody | QVQLVQSGSE LKKPGASVKV SCKASGYTFT DYSMHWVRQA PGQGLKWMGW INTETGEPTY<br>ADDFKGRFVF SLDTSVSTAY LQISSLKAED TAVYYCANPY YDYVSYYAMD YWGQGTTVTV<br>SS | 60<br>120<br>122 |
| SEQ ID NO: 119 light chain variable region of humanized antibody | DIVMTQSHKF MSTSVRDRVS ITCKASQDVS TAVAWYQQKP GQSPKLLIYS ASYLYTGVPD<br>RFTGSGSGTD FTFTISSVQA EDLAVYYCQQ HYSTPRTFGG GTKLEIK | 60<br>107 |

TABLE 18-continued

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 120 light chain variable region of humanized antibody | DIVMTQSHKF MSTSVRDRVS ITCKASQDVS TAVAWYQQKP GQSPKLLIYS ASYLYTGVPD | 60 |
| | RFTGSGSGTD FTFTISSVQA EDLAVYYCQQ HYSTPRTFGG GTKLEIK | 107 |
| SEQ ID NO: 121 heavy chain variable region of humanized antibody | EVQLVESGGG LVQPGESLKL SCESNEYEFP SHDMSWVRKT PEKRLELVAA INSDGGSTYY | 60 |
| | PDTMERRFII SRDNTKKTLY LQMSSLRSED TALYYCARHY DDYYAWFAYW GQGTLVTVSA | 120 |
| SEQ ID NO: 122 heavy chain variable region of humanized antibody | EVQLVESGGG LVQPGGSLRL SCAASEYEFP SHDMSWVRQA PGKGLELVAA INSDGGSTYY | 60 |
| | PDTMERRFTI SRDNAKNSLY LQMNSLRAED TAVYYCARHY DDYYAWFAYW GQGTMVTVSS | 120 |
| SEQ ID NO: 123 light chain variable region of humanized antibody | DIVLTQSPAS LAVSLGQRAT ISCRASKSVS TSGYSYMHWY QQKPGQPPKL LIYLASNLES | 60 |
| | GVPARFSGSG SGTDFTLNIH PVEEEDAATY YCQHSRELPL TFGAGTKLEL K | 111 |
| SEQ ID NO: 124 light chain variable region of humanized antibody | EIVLTQSPAT LSLSPGERAT LSCRASKSVS TSGYSYMHWY QQKPGQAPRL LIYLASNLES | 60 |
| | GVPARFSGSG SGTDFTLTIS SLEPEDFAVY YCQHSRELPL TFGGGTKVEI K | 111 |
| SEQ ID NO: 125 heavy chain variable region | MYLGLNYVFI VFLLNGVQSE VKLEESGGGL VQPGGSMKLS CAASGFTFSD AWMDWVRQSP | 60 |
| | EKGLEWVAEI RSKANNHATY YAESVNGRFT ISRDDSKSSV YLQMNSLRAE DTGIYYCTWG | 120 |
| | EVFYFDYWGQ GTTLTVSS | 138 |
| SEQ ID NO: 126 light chain variable region | MRPSIQFLGL LLFWLHGAQC DIQMTQSPSS LSASLGGKVT ITCKSSQDIN KYIAWYQHKP | 60 |
| | GKGPRLLIHY TSTLQPGIPS RFSGSGSGRD YSFSISNLEP EDIATYYCLQ YDNLLTFGAG | 120 |
| | TKLELK | 126 |

In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, and wherein the additional domain is a Fab or Fc fragment domain. In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, wherein the additional domain is a Fab or Fc fragment domain wherein each of the soluble OX40 binding domains lacks a stalk region (which contributes to trimerisation and provides a certain distance to the cell membrane, but is not part of the OX40 binding domain) and the first and the second peptide linkers independently have a length of 3-8 amino acids.

In an embodiment, the OX40 agonist is an OX40 agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein the TNF superfamily cytokine domain is an OX40 binding domain.

In some embodiments, the OX40 agonist is MEDI6383. MEDI6383 is an OX40 agonistic fusion protein and can be prepared as described in U.S. Pat. No. 6,312,700, the disclosure of which is incorporated by reference herein.

In an embodiment, the OX40 agonist is an OX40 agonistic scFv antibody comprising any of the foregoing $V_H$ domains linked to any of the foregoing $V_L$ domains.

In an embodiment, the OX40 agonist is Creative Biolabs OX40 agonist monoclonal antibody MOM-18455, commercially available from Creative Biolabs, Inc., Shirley, NY, USA.

In an embodiment, the OX40 agonist is OX40 agonistic antibody clone Ber-ACT35 commercially available from BioLegend, Inc., San Diego, CA, USA.

I. Optional Cell Viability Analyses

Optionally, a cell viability assay can be performed after the priming first expansion (sometimes referred to as the initial bulk expansion), using standard assays known in the art. Thus, in certain embodiments, the method comprises performing a cell viability assay subsequent to the priming first expansion. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCanto™ flow cytometer (BD Biosciences). The cells can be counted manually using a disposable c-chip hemocytometer (VWR, Batavia, IL) and viability can be assessed using any method known in the art, including but not limited to trypan blue staining. The cell viability can also be assayed based on U.S. Ser. No. 15/863,634, incorporated by reference herein in its entirety. Cell viability can also be assayed based on U.S. Patent Publication No. 2018/0280436 or International Patent Publication No. WO/2018/081473, both of which are incorporate herein in their entireties for all purposes.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

2. Cell Cultures

In an embodiment, a method for expanding TILs, including those discussed above as well as exemplified in FIG. 1, in particular, e.g., FIG. 1B and/or FIG. 1C, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium. In some embodiments, the media in the priming first expansion is serum free. In some embodiments, the media in the second expansion is serum free. In some embodiments, the media in the priming first expansion and the second expansion (also referred to as rapid second expansion)_are both serum free. In an embodiment, expanding the number of TILs uses no more than one type of cell culture medium. Any suitable cell culture medium may be used, e.g., AIM-V cell medium (L-glutamine, 50 μM streptomycin sulfate, and 10 μM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell culture medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 8 days, e.g., about 8 days as a priming first expansion; transferring the TILs to a second gas permeable container and expanding the number of TILs in the second gas permeable container containing cell medium including IL-2, 2× antigen-presenting feeder cells, and OKT-3 for a duration of about 7 to 9 days, e.g., about 7 days, about 8 days, or about 9 days.

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 7 days, e.g., about 7 days as a priming first expansion; transferring the TILs to a second gas permeable container and expanding the number of TILs in the second gas permeable container containing cell medium including IL-2, 2× antigen-presenting feeder cells, and OKT-3 for a duration of about 7 to 9 days, e.g., about 7 days, about 8 days, or about 9 days.

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 7 days, e.g., about 7 days as a priming first expansion; transferring the TILs to a second gas permeable container and expanding the number of TILs in the second gas permeable container containing cell medium including IL-2, 2× antigen-presenting feeder cells, and OKT-3 for a duration of about 7 to 10 days, e.g., about 7 days, about 8 days, about 9 days or about 10 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5\times10^5$ cells/cm$^2$ to between $10\times10^6$ and $30\times10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No.

US 2011/0136228 A1, U.S. Patent No. U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Patent No. U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy,* 2012, 35:283-292.

J. Optional Genetic Engineering of TILs

In some embodiments, the expanded TILs of the present invention are further manipulated before, during, or after an expansion step, including during closed, sterile manufacturing processes, each as provided herein, in order to alter protein expression in a transient manner. In some embodiments, the transiently altered protein expression is due to transient gene editing. In some embodiments, the expanded TILs of the present invention are treated with transcription factors (TFs) and/or other molecules capable of transiently altering protein expression in the TILs. In some embodiments, the TFs and/or other molecules that are capable of transiently altering protein expression provide for altered expression of tumor antigens and/or an alteration in the number of tumor antigen-specific T cells in a population of TILs.

In certain embodiments, the method comprises genetically editing a population of TILs. In certain embodiments, the method comprises genetically editing the first population of TILs, the second population of TILs and/or the third population of TILs.

In some embodiments, the present invention includes genetic editing through nucleotide insertion, such as through ribonucleic acid (RNA) insertion, including insertion of messenger RNA (mRNA) or small (or short) interfering RNA (siRNA), into a population of TILs for promotion of the expression of one or more proteins or inhibition of the expression of one or more proteins, as well as simultaneous combinations of both promotion of one set of proteins with inhibition of another set of proteins.

In some embodiments, the expanded TILs of the present invention undergo transient alteration of protein expression. In some embodiments, the transient alteration of protein expression occurs in the bulk TIL population prior to first expansion, including, for example in the TIL population obtained from for example, Step A as indicated in FIG. 1 (particularly FIG. 1B and FIG. 1C). In some embodiments, the transient alteration of protein expression occurs during the first expansion, including, for example in the TIL population expanded in for example, Step B as indicated in FIG. 1 (for example FIG. 1B). In some embodiments, the transient alteration of protein expression occurs after the first expansion, including, for example in the TIL population in transition between the first and second expansion (e.g. the second population of TILs as described herein), the TIL population obtained from for example, Step B and included in Step C as indicated in FIG. 1. In some embodiments, the transient alteration of protein expression occurs in the bulk TIL population prior to second expansion, including, for example in the TIL population obtained from for example, Step C and prior to its expansion in Step D as indicated in FIG. 1. In some embodiments, the transient alteration of protein expression occurs during the second expansion, including, for example in the TIL population expanded in for example, Step D as indicated in FIG. 1 (e.g. the third population of TILs). In some embodiments, the transient alteration of protein expression occurs after the second expansion, including, for example in the TIL population obtained from the expansion in for example, Step D as indicated in FIG. 1.

In an embodiment, a method of transiently altering protein expression in a population of TILs includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. In an embodiment, a method of transiently altering protein expression in population of TILs includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of transiently altering protein expression in a population of TILs includes the step of liposomal transfection. Liposomal transfection methods, such as methods that employ a 1:1 (w/w) liposome formulation of the cationic lipid N-[1-(2,3-dioleyloxy) propyl]-n,n,n-trimethylammonium chloride (DOTMA) and dioleoyl phophotidylethanolamine (DOPE) in filtered water, are known in the art and are described in Rose, et al., Biotechniques 1991, 10, 520-525 and Felgner, et al., *Proc. Natl. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of transiently altering protein expression in a population of TILs includes the step of transfection using methods described in U.S. Pat. Nos. 5,766,902; 6,025,337; 6,410,517; 6,475,994; and 7,189,705; the disclosures of each of which are incorporated by reference herein.

In some embodiments, transient alteration of protein expression results in an increase in Stem Memory T cells (TSCMs). TSCMs are early progenitors of antigen-experienced central memory T cells. TSCMs generally display the long-term survival, self-renewal, and multipotency abilities that define stem cells, and are generally desirable for the generation of effective TIL products. TSCM have shown enhanced anti-tumor activity compared with other T cell subsets in mouse models of adoptive cell transfer (Gattinoni et al. Nat Med 2009, 2011; Gattinoni, Nature Rev. Cancer, 2012; Cieri et al. Blood 2013). In some embodiments, transient alteration of protein expression results in a TIL population with a composition comprising a high proportion of TSCM. In some embodiments, transient alteration of protein expression results in an at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% increase in TSCM percentage. In some embodiments, transient alteration of protein expression results in an at least a 1-fold, 2-fold, 3-fold, 4-fold, 5-fold, or 10-fold increase in TSCMs in the TIL population. In some embodiments, transient alteration of protein expression results in a TIL population with at least at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs. In some embodiments, transient alteration of protein expression results in a therapeutic TIL population with at least at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs.

In some embodiments, transient alteration of protein expression results in rejuvenation of antigen-experienced T-cells. In some embodiments, rejuvenation includes, for example, increased proliferation, increased T-cell activation, and/or increased antigen recognition.

In some embodiments, transient alteration of protein expression alters the expression in a large fraction of the T-cells in order to preserve the tumor-derived TCR repertoire. In some embodiments, transient alteration of protein expression does not alter the tumor-derived TCR repertoire. In some embodiments, transient alteration of protein expression maintains the tumor-derived TCR repertoire.

In some embodiments, transient alteration of protein results in altered expression of a particular gene. In some embodiments, the transient alteration of protein expression targets a gene including but not limited to PD-1 (also referred to as PDCD1 or CC279), TGFBR2, CCR4/5, CBLB (CBL-B), CISH, CCRs (chimeric co-stimulatory receptors), IL-2, IL-12, IL-15, IL-21, NOTCH ½ ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, and/or cAMP protein kinase A (PKA). In some embodiments, the transient alteration of protein expression targets a gene selected from the group consisting of PD-1, TGFBR2, CCR4/5, CBLB (CBL-B), CISH, CCRs (chimeric co-stimulatory receptors), IL-2, IL-12, IL-15, IL-21, NOTCH ½ ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, and/or cAMP protein kinase A (PKA). In some embodiments, the transient alteration of protein expression targets PD-1. In some embodiments, the transient alteration of protein expression targets TGFBR2. In some embodiments, the transient alteration of protein expression targets CCR4/5. In some embodiments, the transient alteration of protein expression targets CBLB. In some embodiments, the transient alteration of protein expression targets CISH. In some embodiments, the transient alteration of protein expression targets CCRs (chimeric co-stimulatory receptors). In some embodiments, the transient alteration of protein expression targets IL-2. In some embodiments, the transient alteration of protein expression targets IL-12. In some embodiments, the transient alteration of protein expression targets IL-15. In some embodiments, the transient alteration of protein expression targets IL-21. In some embodiments, the transient alteration of protein expression targets NOTCH ½ ICD. In some embodiments, the transient alteration of protein expression targets TIM3. In some embodiments, the transient alteration of protein expression targets LAG3. In some embodiments, the transient alteration of protein expression targets TIGIT. In some embodiments, the transient alteration of protein expression targets TGFB. In some embodiments, the transient alteration of protein expression targets CCR1. In some embodiments, the transient alteration of protein expression targets CCR2. In some embodiments, the transient alteration of protein expression targets CCR4. In some embodiments, the transient alteration of protein expression targets CCR5. In some embodiments, the transient alteration of protein expression targets CXCR1. In some embodiments, the transient alteration of protein expression targets CXCR2. In some embodiments, the transient alteration of protein expression targets CSCR3. In some embodiments, the transient alteration of protein expression targets CCL2 (MCP-1). In some embodiments, the transient alteration of protein expression targets CCL3 (MIP-1α). In some embodiments, the transient alteration of protein expression targets CCL4 (MIP1-β). In some embodiments, the transient alteration of protein expression targets CCL5 (RANTES). In some embodiments, the transient alteration of protein expression targets CXCL1. In some embodiments, the transient alteration of protein expression targets CXCL8. In some embodiments, the transient alteration of protein expression targets CCL22. In some embodiments, the transient alteration of protein expression targets CCL17. In some embodiments, the transient alteration of protein expression targets VHL. In some embodiments, the transient alteration of protein expression targets CD44. In some embodiments, the transient alteration of protein expression targets PIK3CD. In some embodiments, the transient alteration of protein expression targets SOCS1. In some embodiments, the transient alteration of protein expression targets cAMP protein kinase A (PKA).

In some embodiments, the transient alteration of protein expression results in increased and/or overexpression of a chemokine receptor. In some embodiments, the chemokine receptor that is overexpressed by transient protein expression includes a receptor with a ligand that includes but is not limited to CCL2 (MCP-1), CCL3 (MIP-1α), CCL4 (MIP1-β), CCL5 (RANTES), CXCL1, CXCL8, CCL22, and/or CCL17.

In some embodiments, the transient alteration of protein expression results in a decrease and/or reduced expression of PD-1, CTLA-4, TIM-3, LAG-3, TIGIT, TGFBR2, and/or TGFβ (including resulting in, for example, TGFβ pathway blockade). In some embodiments, the transient alteration of protein expression results in a decrease and/or reduced expression of CBLB (CBL-B). In some embodiments, the transient alteration of protein expression results in a decrease and/or reduced expression of CISH.

In some embodiments, the transient alteration of protein expression results in increased and/or overexpression of chemokine receptors in order to, for example, improve TIL trafficking or movement to the tumor site. In some embodiments, the transient alteration of protein expression results in increased and/or overexpression of a CCR (chimeric co-stimulatory receptor). In some embodiments, the transient alteration of protein expression results in increased and/or overexpression of a chemokine receptor selected from the group consisting of CCR1, CCR2, CCR4, CCR5, CXCR1, CXCR2, and/or CSCR3.

In some embodiments, the transient alteration of protein expression results in increased and/or overexpression of an interleukin. In some embodiments, the transient alteration of protein expression results in increased and/or overexpression of an interleukin selected from the group consisting of IL-2, IL-12, IL-15, and/or IL-21.

In some embodiments, the transient alteration of protein expression results in increased and/or overexpression of NOTCH ½ ICD. In some embodiments, the transient alteration of protein expression results in increased and/or overexpression of VHL. In some embodiments, the transient alteration of protein expression results in increased and/or overexpression of CD44. In some embodiments, the transient alteration of protein expression results in increased and/or overexpression of PIK3CD. In some embodiments, the transient alteration of protein expression results in increased and/or overexpression of SOCS1, In some embodiments, the transient alteration of protein expression results in decreased and/or reduced expression of cAMP protein kinase A (PKA).

In some embodiments, the transient alteration of protein expression results in decreased and/or reduced expression of a molecule selected from the group consisting of PD-1, LAG3, TIM3, CTLA-4, TIGIT, CISH, TGFBR2, PKA, CBLB, BAFF (BR3), and combinations thereof. In some embodiments, the transient alteration of protein expression results in decreased and/or reduced expression of two molecules selected from the group consisting of PD-1, LAG3, TIM3, CTLA-4, TIGIT, CISH, TGFBR2, PKA, CBLB, BAFF (BR3), and combinations thereof. In some embodiments, the transient alteration of protein expression results in decreased and/or reduced expression of PD-1 and one molecule selected from the group consisting of LAG3, TIM3, CTLA-4, TIGIT, CISH, TGFBR2, PKA, CBLB, BAFF (BR3), and combinations thereof. In some embodiments, the transient alteration of protein expression results in decreased and/or reduced expression of PD-1, LAG-3, CISH, CBLB, TIM3, and combinations thereof. In some embodiments, the transient alteration of protein expression results in decreased and/or reduced expression of PD-1 and one of LAG3, CISH, CBLB, TIM3, and combinations thereof. In some embodiments, the transient alteration of protein expression results in decreased and/or reduced expression of PD-1 and LAG3. In some embodiments, the transient alteration of protein expression results in decreased and/or reduced expression of PD-1 and CISH. In some embodiments, the transient alteration of protein expression results in decreased and/or reduced expression of PD-1 and CBLB. In some embodiments, the transient alteration of protein expression results in decreased and/or reduced expression of LAG3 and CISH. In some embodiments, the transient alteration of protein expression results in decreased and/or reduced expression of LAG3 and CBLB. In some embodiments, the transient alteration of protein expression results in decreased and/or reduced expression of CISH and CBLB. In some embodiments, the transient alteration of protein expression results in decreased and/or reduced expression of TIM3 and PD-1. In some embodiments, the transient alteration of protein expression results in decreased and/or reduced expression of TIM3 and LAG3. In some embodiments, the transient alteration of protein expression results in decreased and/or reduced expression of TIM3 and CISH. In some embodiments, the transient alteration of protein expression results in decreased and/or reduced expression of TIM3 and CBLB.

In some embodiments, an adhesion molecule selected from the group consisting of CCR2, CCR4, CCR5, CXCR2, CXCR3, CX3CR1, and combinations thereof, is inserted by a gammaretroviral or lentiviral method into the first population of TILs, second population of TILs, or harvested population of TILs (e.g., the expression of the adhesion molecule is increased).

In some embodiments, the transient alteration of protein expression results in decreased and/or reduced expression of a molecule selected from the group consisting of PD-1, LAG3, TIM3, CTLA-4, TIGIT, CISH, TGFBR2, PKA, CBLB, BAFF (BR3), and combinations thereof, and increased and/or enhanced expression of CCR2, CCR4, CCR5, CXCR2, CXCR3, CX3CR1, and combinations thereof. In some embodiments, the transient alteration of protein expression results in decreased and/or reduced expression of a molecule selected from the group consisting of PD-1, LAG3, TIM3, CISH, CBLB, and combinations thereof, and increased and/or enhanced expression of CCR2, CCR4, CCR5, CXCR2, CXCR3, CX3CR1, and combinations thereof.

In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%, In some embodiments, there is a reduction in expression of at least about 90%. In some embodiments, there is a reduction in expression of at least about 95%. In some embodiments, there is a reduction in expression of at least about 99%.

In some embodiments, there is an increase in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is an increase in expression of at least about 65%, about 70%, about 75%, about 80%, about 85%, about 90%, or about 95%. In some embodiments, there is an increase in expression of at least about 75%, about 80%, about 85%, about 90%, or about 95%. In some embodiments, there is an increase in expression of at least about 80%, about 85%, about 90%, or about 95%. In some embodiments, there is an increase in expression of at least about 85%, about 90%, or about 95%. In some embodiments, there is an increase in expression of at least about 80%.

In some embodiments, there is an increase in expression of at least about 85%, In some embodiments, there is an increase in expression of at least about 90%. In some embodiments, there is an increase in expression of at least about 95%. In some embodiments, there is an increase in expression of at least about 99%.

In some embodiments, transient alteration of protein expression is induced by treatment of the TILs with transcription factors (TFs) and/or other molecules capable of transiently altering protein expression in the TILs. In some embodiments, the SQZ vector-free microfluidic platform is employed for intracellular delivery of the transcription factors (TFs) and/or other molecules capable of transiently altering protein expression. Such methods demonstrating the ability to deliver proteins, including transcription factors, to a variety of primary human cells, including T cells (Sharei et al. PNAS 2013, as well as Sharei et al. PLOS ONE 2015 and Greisbeck et al. J. Immunology vol. 195, 2015) have been described; see, for example, International Patent Publications WO 2013/059343A1, WO 2017/008063A1, and WO 2017/123663A1, all of which are incorporated by reference herein in their entireties. Such methods as described in International Patent Publications WO 2013/

059343A1, WO 2017/008063A1, and WO 2017/123663A1 can be employed with the present invention in order to expose a population of TILs to transcription factors (TFs) and/or other molecules capable of inducing transient protein expression, wherein said TFs and/or other molecules capable of inducing transient protein expression provide for increased expression of tumor antigens and/or an increase in the number of tumor antigen-specific T cells in the population of TILs, thus resulting in reprogramming of the TIL population and an increase in therapeutic efficacy of the reprogrammed TIL population as compared to a non-reprogrammed TIL population. In some embodiments, the reprogramming results in an increased subpopulation of effector T cells and/or central memory T cells relative to the starting or prior population (i.e., prior to reprogramming) population of TILs, as described herein.

In some embodiments, the transcription factor (TF) includes but is not limited to TCF-1, NOTCH ½ ICD, and/or MYB. In some embodiments, the transcription factor (TF) is TCF-1. In some embodiments, the transcription factor (TF) is NOTCH ½ ICD. In some embodiments, the transcription factor (TF) is MYB. In some embodiments, the transcription factor (TF) is administered with induced pluripotent stem cell culture (iPSC), such as the commercially available KNOCKOUT Serum Replacement (Gibco/ThermoFisher), to induce additional TIL reprogramming. In some embodiments, the transcription factor (TF) is administered with an iPSC cocktail to induce additional TIL reprogramming. In some embodiments, the transcription factor (TF) is administered without an iPSC cocktail. In some embodiments, reprogramming results in an increase in the percentage of TSCMs. In some embodiments, reprogramming results in an increase in the percentage of TSCMs by about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95% TSCMs.

In some embodiments, a method of transient altering protein expression, as described above, may be combined with a method of genetically modifying a population of TILs includes the step of stable incorporation of genes for production of one or more proteins. In certain embodiments, the method comprises a step of genetically modifying a population of TILs. In certain embodiments, the method comprises genetically modifying the first population of TILs, the second population of TILs and/or the third population of TILs. In an embodiment, a method of genetically modifying a population of TILs includes the step of retroviral transduction. In an embodiment, a method of genetically modifying a population of TILs includes the step of lentiviral transduction. Lentiviral transduction systems are known in the art and are described, e.g., in Levine, et al., Proc. Nat'l *Acad. Sci.* 2006, 103, 17372-77; Zufferey, et al., *Nat. Biotechnol.* 1997, 15, 871-75; Dull, et al., *J. Virology* 1998, 72, 8463-71, and U.S. Pat. No. 6,627,442, the disclosures of each of which are incorporated by reference herein. In an embodiment, a method of genetically modifying a population of TILs includes the step of gamma-retroviral transduction. Gamma-retroviral transduction systems are known in the art and are described, e.g., Cepko and Pear, Cur. Prot. *Mol. Biol.* 1996, 9.9.1-9.9.16, the disclosure of which is incorporated by reference herein. In an embodiment, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tel-like transposase (SB or Sleeping Beauty transposase), such as SB10, SB11, and SB100x, and engineered enzymes with increased enzymatic activity, are described in, e.g., Hackett, et al., Mol. Therapy 2010, 18, 674-83 and U.S. Pat. No. 6,489,458, the disclosures of each of which are incorporated by reference herein.

In some embodiments, transient alteration of protein expression is a reduction in expression induced by self-delivering RNA interference (sdRNA), which is a chemically-synthesized asymmetric siRNA duplex with a high percentage of 2'-OH substitutions (typically fluorine or —$OCH_3$) which comprises a 20-nucleotide antisense (guide) strand and a 13 to 15 base sense (passenger) strand conjugated to cholesterol at its 3' end using a tetraethylenglycol (TEG) linker. In some embodiments, the method comprises transient alteration of protein expression in a population of TILs, comprising the use of self-delivering RNA interference (sdRNA), which is a chemically-synthesized asymmetric siRNA duplex with a high percentage of 2'-OH substitutions (typically fluorine or —$OCH_3$) which comprises a 20-nucleotide antisense (guide) strand and a 13 to 15 base sense (passenger) strand conjugated to cholesterol at its 3' end using a tetraethylenglycol (TEG) linker. Methods of using sdRNA have been described in Khvorova and Watts, *Nat. Biotechnol.* 2017, 35, 238-248; Byrne, et al., *J. Ocul. Pharmacol. Ther.* 2013, 29, 855-864; and Ligtenberg, et al., *Mol. Therapy,* 2018, in press, the disclosures of which are incorporated by reference herein. In an embodiment, delivery of sdRNA to a TIL population is accomplished without use of electroporation, SQZ, or other methods, instead using a 1 to 3 day period in which a TIL population is exposed to sdRNA at a concentration of 1 μM/10,000 TILs in medium. In certain embodiments, the method comprises delivery sdRNA to a TILs population comprising exposing the TILs population to sdRNA at a concentration of 1 μM/10,000 TILs in medium for a period of between 1 to 3 days. In an embodiment, delivery of sdRNA to a TIL population is accomplished using a 1 to 3 day period in which a TIL population is exposed to sdRNA at a concentration of 10 μM/10,000 TILs in medium. In an embodiment, delivery of sdRNA to a TIL population is accomplished using a 1 to 3 day period in which a TIL population is exposed to sdRNA at a concentration of 50 μM/10,000 TILs in medium. In an embodiment, delivery of sdRNA to a TIL population is accomplished using a 1 to 3 day period in which a TIL population is exposed to sdRNA at a concentration of between 0.1 μM/10,000 TILs and 50 μM/10,000 TILs in medium. In an embodiment, delivery of sdRNA to a TIL population is accomplished using a 1 to 3 day period in which a TIL population is exposed to sdRNA at a concentration of between 0.1 μM/10,000 TILs and 50 μM/10,000 TILs in medium, wherein the exposure to sdRNA is performed two, three, four, or five times by addition of fresh sdRNA to the media. Other suitable processes are described, for example, in U.S. Patent Application Publication No. US 2011/0039914 A1, US 2013/0131141 A1, and US 2013/0131142 A1, and U.S. Pat. No. 9,080,171, the disclosures of which are incorporated by reference herein.

In some embodiments, sdRNA is inserted into a population of TILs during manufacturing. In some embodiments, the sdRNA encodes RNA that interferes with NOTCH ½

ICD, PD-1, CTLA-4 TIM-3, LAG-3, TIGIT, TGFβ, TGFBR2, CAMP protein kinase A (PKA), BAFF BR3, CISH, and/or CBLB. In some embodiments, the reduction in expression is determined based on a percentage of gene silencing, for example, as assessed by flow cytometry and/or qPCR. In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%, In some embodiments, there is a reduction in expression of at least about 90%. In some embodiments, there is a reduction in expression of at least about 95%. In some embodiments, there is a reduction in expression of at least about 99%.

The self-deliverable RNAi technology based on the chemical modification of siRNAs can be employed with the methods of the present invention to successfully deliver the sdRNAs to the TILs as described herein. The combination of backbone modifications with asymmetric siRNA structure and a hydrophobic ligand (see, for example, Ligtenberg, et al., *Mol. Therapy,* 2018 and US20160304873) allow sdRNAs to penetrate cultured mammalian cells without additional formulations and methods by simple addition to the culture media, capitalizing on the nuclease stability of sdRNAs. This stability allows the support of constant levels of RNAi-mediated reduction of target gene activity simply by maintaining the active concentration of sdRNA in the media. While not being bound by theory, the backbone stabilization of sdRNA provides for extended reduction in gene expression effects which can last for months in non-dividing cells.

In some embodiments, over 95% transfection efficiency of TILs and a reduction in expression of the target by various specific sdRNA occurs. In some embodiments, sdRNAs containing several unmodified ribose residues were replaced with fully modified sequences to increase potency and/or the longevity of RNAi effect. In some embodiments, a reduction in expression effect is maintained for 12 hours, 24 hours, 36 hours, 48 hours, 5 days, 6 days, 7 days, or 8 days or more. In some embodiments, the reduction in expression effect decreases at 10 days or more post sdRNA treatment of the TILs. In some embodiments, more than 70% reduction in expression of the target expression is maintained. In some embodiments, more than 70% reduction in expression of the target expression is maintained TILs. In some embodiments, a reduction in expression in the PD-1/PD-L1 pathway allows for the TILs to exhibit a more potent in vivo effect, which is in some embodiments, due to the avoidance of the suppressive effects of the PD-1/PD-L1 pathway. In some embodiments, a reduction in expression of PD-1 by sdRNA results in an increase TIL proliferation.

Small interfering RNA (siRNA), sometimes known as short interfering RNA or silencing RNA, is a double stranded RNA molecule, generally 19-25 base pairs in length. siRNA is used in RNA interference (RNAi), where it interferes with expression of specific genes with complementary nucleotide sequences.

Double stranded DNA (dsRNA) can be generally used to define any molecule comprising a pair of complementary strands of RNA, generally a sense (passenger) and antisense (guide) strands, and may include single-stranded overhang regions. The term dsRNA, contrasted with siRNA, generally refers to a precursor molecule that includes the sequence of an siRNA molecule which is released from the larger dsRNA molecule by the action of cleavage enzyme systems, including Dicer.

sdRNA (self-deliverable RNA) are a new class of covalently modified RNAi compounds that do not require a delivery vehicle to enter cells and have improved pharmacology compared to traditional siRNAs. "Self-deliverable RNA" or "sdRNA" is a hydrophobically modified RNA interfering-antisense hybrid, demonstrated to be highly efficacious in vitro in primary cells and in vivo upon local administration. Robust uptake and/or silencing without toxicity has been demonstrated. sdRNAs are generally asymmetric chemically modified nucleic acid molecules with minimal double stranded regions. sdRNA molecules typically contain single stranded regions and double stranded regions, and can contain a variety of chemical modifications within both the single stranded and double stranded regions of the molecule. Additionally, the sdRNA molecules can be attached to a hydrophobic conjugate such as a conventional and advanced sterol-type molecule, as described herein. sdRNAs and associated methods for making such sdRNAs have also been described extensively in, for example, US20160304873, WO2010033246, WO2017070151, WO2009102427, WO2011119887, WO2010033247A2, WO2009045457, WO2011119852, all of which are incorporated by reference herein in their entireties for all purposes. To optimize sdRNA structure, chemistry, targeting position, sequence preferences, and the like, a proprietary algorithm has been developed and utilized for sdRNA potency prediction (see, for example, US20160304873). Based on these analyses, functional sdRNA sequences have been generally defined as having over 70% reduction in expression at 1 μM concentration, with a probability over 40%.

In some embodiments, the sdRNA sequences used in the invention exhibit a 70% reduction in expression of the target gene. In some embodiments, the sdRNA sequences used in the invention exhibit a 75% reduction in expression of the target gene. In some embodiments, the sdRNA sequences used in the invention exhibit an 80% reduction in expression of the target gene. In some embodiments, the sdRNA sequences used in the invention exhibit an 85% reduction in expression of the target gene. In some embodiments, the sdRNA sequences used in the invention exhibit a 90% reduction in expression of the target gene. In some embodiments, the sdRNA sequences used in the invention exhibit a 95% reduction in expression of the target gene. In some embodiments, the sdRNA sequences used in the invention exhibit a 99% reduction in expression of the target gene. In some embodiments, the sdRNA sequences used in the invention exhibit a reduction in expression of the target gene when delivered at a concentration of about 0.25 μM to about 4 μM. In some embodiments, the sdRNA sequences used in the invention exhibit a reduction in expression of the target gene when delivered at a concentration of about 0.25 μM. In some embodiments, the sdRNA sequences used in the invention exhibit a reduction in expression of the target gene when delivered at a concentration of about 0.5 μM. In some embodiments, the sdRNA sequences used in the invention exhibit a reduction in expression of the target gene when delivered at a concentration of about 0.75 μM. In some embodiments, the sdRNA sequences used in the invention exhibit a reduction in expression of the target gene when delivered at a concentration of about 1.0 μM. In some embodiments, the sdRNA sequences used in the invention exhibit a reduction in expression of the target gene when delivered at a concentration of about 1.25 μM. In some embodiments, the sdRNA sequences used in the invention exhibit a reduction in expression of the target gene when delivered at a concentration of about 1.5 μM. In some embodiments, the sdRNA sequences used in the invention exhibit a reduction in expression of the target gene when delivered at a concentration of about 1.75 μM. In some embodiments, the sdRNA sequences used in the invention exhibit a reduction in expression of the target gene when delivered at a concentration of about 2.0 μM. In some embodiments, the sdRNA sequences used in the invention exhibit a reduction in expression of the target gene when delivered at a concentration of about 2.25 μM. In some embodiments, the sdRNA sequences used in the invention exhibit a reduction in expression of the target gene when delivered at a concentration of about 2.5 μM. In some embodiments, the sdRNA sequences used in the invention exhibit a reduction in expression of the target gene when delivered at a concentration of about 2.75 μM. In some embodiments, the sdRNA sequences used in the invention exhibit a reduction in expression of the target gene when delivered at a concentration of about 3.0 μM. In some embodiments, the sdRNA sequences used in the invention exhibit a reduction in expression of the target gene when delivered at a concentration of about 3.25 μM. In some embodiments, the sdRNA sequences used in the invention exhibit a reduction in expression of the target gene when delivered at a concentration of about 3.5 μM. In some embodiments, the sdRNA sequences used in the invention exhibit a reduction in expression of the target gene when delivered at a concentration of about 3.75 μM. In some embodiments, the sdRNA sequences used in the invention exhibit a reduction in expression of the target gene when delivered at a concentration of about 4.0 μM.

In some embodiments, the oligonucleotide agents comprise one or more modification to increase stability and/or effectiveness of the therapeutic agent, and to effect efficient delivery of the oligonucleotide to the cells or tissue to be treated. Such modifications can include a 2'-O-methyl modification, a 2'-O-Fluro modification, a diphosphorothioate modification, 2' F modified nucleotide, a 2'-O-methyl modified and/or a 2'deoxy nucleotide. In some embodiments, the oligonucleotide is modified to include one or more hydrophobic modifications including, for example, sterol, cholesterol, vitamin D, naphtyl, isobutyl, benzyl, indol, tryptophane, and/or phenyl. In an additional particular embodiment, chemically modified nucleotides are combination of phosphorothioates, 2'-O-methyl, 2'deoxy, hydrophobic modifications and phosphorothioates. In some embodiments, the sugars can be modified and modified sugars can include but are not limited to D-ribose, 2'-O-alkyl (including 2'-O-methyl and 2'-0-ethyl), i.e., 2'-alkoxy, 2'-amino, 2'-S-alkyl, 2'-halo (including 2'-fluoro), T-methoxyethoxy, 2'-allyloxy (—$OCH_2CH{=}CH_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., Nucl. Acids. Res. 18:4711 (1992)).

In some embodiments, the double-stranded oligonucleotide of the invention is double-stranded over its entire length, i.e., with no overhanging single-stranded sequence at either end of the molecule, i.e., is blunt-ended. In some embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). In some embodiments, when a single nucleic acid molecule is used a portion of the molecule at either end can remain single-stranded.

In some embodiments, a double-stranded oligonucleotide of the invention contains mismatches and/or loops or bulges, but is double-stranded over at least about 70% of the length of the oligonucleotide. In some embodiments, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In some embodiments, a double-stranded oligonucleotide of the invention is double-stranded over at least about 96%-98% of the length of the oligonucleotide. In some embodiments, the double-stranded oligonucleotide of the invention contains at least or up to 1, 2, 3, 4, 5, 6, 7, 8, 9, 10, 11, 12, 13, 14, or 15 mismatches.

In some embodiments, the oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" can also include "end blocking groups" or "exonuclease blocking groups" which protect the 5' and 3' termini of the oligonucleotide, including modified nucleotides and non-nucleotide exonuclease resistant structures.

In some embodiments, at least a portion of the contiguous polynucleotides within the sdRNA are linked by a substitute linkage, e.g., a phosphorothioate linkage.

In some embodiments, chemical modification can lead to at least a 1.5, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500 enhancements in cellular uptake. In some embodiments, at least one of the C or U residues includes a hydrophobic modification. In some embodiments, a plurality of Cs and Us contain a hydrophobic modification. In some embodiments, at least 10%, 15%, 20%, 30%, 40%, 50%, 55%, 60% 65%, 70%, 75%, 80%, 85%, 90% or at least 95% of the Cs and Us can contain a hydrophobic modification. In some embodiments, all of the Cs and Us contain a hydrophobic modification.

In some embodiments, the sdRNA or sd-rxRNAs exhibit enhanced endosomal release of sd-rxRNA molecules through the incorporation of protonatable amines. In some embodiments, protonatable amines are incorporated in the sense strand (in the part of the molecule which is discarded after RISC loading). In some embodiments, the sdRNA compounds of the invention comprise an asymmetric compound comprising a duplex region (required for efficient RISC entry of 10-15 bases long) and single stranded region of 4-12 nucleotides long; with a 13 nucleotide duplex. In some embodiments, a 6 nucleotide single stranded region is employed. In some embodiments, the single stranded region of the sdRNA comprises 2-12 phosphorothioate internucleotide linkages (referred to as phosphorothioate modifications). In some embodiments, 6-8 phosphorothioate internucleotide linkages are employed. In some embodiments, the sdRNA compounds of the invention also include a unique chemical modification pattern, which provides stability and is compatible with RISC entry.

The guide strand, for example, may also be modified by any chemical modification which confirms stability without interfering with RISC entry. In some embodiments, the chemical modification pattern in the guide strand includes the majority of C and U nucleotides being 2' F modified and the 5'end being phosphorylated.

In some embodiments, at least 30% of the nucleotides in the sdRNA or sd-rxRNA are modified. In some embodiments, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the sdRNA or sd-rxRNA are modified. In some embodiments, 100% of the nucleotides in the sdRNA or sd-rxRNA are modified.

In some embodiments, the sdRNA molecules have minimal double stranded regions. In some embodiments the region of the molecule that is double stranded ranges from 8-15 nucleotides long. In some embodiments, the region of the molecule that is double stranded is 8, 9, 10, 11, 12, 13, 14 or 15 nucleotides long. In some embodiments the double stranded region is 13 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. In some embodiments, the single stranded region can be 4, 5, 6, 7, 8, 9, 10, 11 or 12 nucleotides long. In some embodiments, the single stranded region can also be less than 4 or greater than 12 nucleotides long. In certain embodiments, the single stranded region is 6 or 7 nucleotides long.

In some embodiments, the sdRNA molecules have increased stability. In some instances, a chemically modified sdRNA or sd-rxRNA molecule has a half-life in media that is longer than 1, 2, 3, 4, 5, 6, 7, 8, 9, 10, 11, 12, 13, 14, 15, 16, 17, 18, 19, 20, 21, 22, 23, 24 or more than 24 hours, including any intermediate values. In some embodiments, the sd-rxRNA has a half-life in media that is longer than 12 hours.

In some embodiments, the sdRNA is optimized for increased potency and/or reduced toxicity. In some embodiments, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-O-methyl(2'OMe) modifications can in some aspects influence toxicity of the molecule. In some embodiments, reduction in 2'F content of a molecule is predicted to reduce toxicity of the molecule. In some embodiments, the number of phosphorothioate modifications in an RNA molecule can influence the uptake of the molecule into a cell, for example the efficiency of passive uptake of the molecule into a cell. In some embodiments, the sdRNA has no 2'F modification and yet are characterized by equal efficacy in cellular uptake and tissue penetration.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contain 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2'OMe modified. For example, C and U nucleotides in positions 11-18 of a 19 nt guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

The self-deliverable RNAi technology provides a method of directly transfecting cells with the RNAi agent, without the need for additional formulations or techniques. The ability to transfect hard-to-transfect cell lines, high in vivo activity, and simplicity of use, are characteristics of the compositions and methods that present significant functional advantages over traditional siRNA-based techniques, and as such, the sdRNA methods are employed in several embodiments related to the methods of reduction in expression of the target gene in the TILs of the present invention. The sdRNAi methods allows direct delivery of chemically synthesized compounds to a wide range of primary cells and tissues, both ex-vivo and in vivo. The sdRNAs described in some embodiments of the invention herein are commercially available from Advirna LLC, Worcester, MA, USA.

The sdRNA are formed as hydrophobically-modified siRNA-antisense oligonucleotide hybrid structures, and are disclosed, for example in Byrne et al., December 2013, J. Ocular Pharmacology and Therapeutics, 29 (10): 855-864, incorporated by reference herein in its entirety.

In some embodiments, the sdRNA oligonucleotides can be delivered to the TILs described herein using sterile electroporation. In certain embodiments, the method comprises sterile electroporation of a population of TILs to deliver sdRNA oligonucleotides.

In some embodiments, the oligonucleotides can be delivered to the cells in combination with a transmembrane delivery system. In some embodiments, this transmembrane delivery system comprises lipids, viral vectors, and the like. In some embodiments, the oligonucleotide agent is a self-delivery RNAi agent, that does not require any delivery agents. In certain embodiments, the method comprises use of a transmembrane delivery system to deliver sdRNA oligonucleotides to a population of TILs.

Oligonucleotides and oligonucleotide compositions are contacted with (e.g., brought into contact with, also referred to herein as administered or delivered to) and taken up by TILs described herein, including through passive uptake by TILs. The sdRNA can be added to the TILs as described herein during the first expansion, for example Step B, after the first expansion, for example, during Step C, before or during the second expansion, for example before or during Step D, after Step D and before harvest in Step E, during or after harvest in Step F, before or during final formulation and/or transfer to infusion Bag in Step F, as well as before any optional cryopreservation step in Step F. Moreover, sdRNA can be added after thawing from any cryopreservation step in Step F. In an embodiment, one or more sdRNAs targeting genes as described herein, including PD-1, LAG-3, TIM-3, CISH, and CBLB, may be added to cell culture media comprising TILs and other agents at concentrations selected from the group consisting of 100 nM to 20 mM, 200 nM to 10 mM, 500 nm to 1 mM, 1 μM to 100 μM, and 1 μM to 100 μM. In an embodiment, one or more sdRNAs targeting genes as described herein, including PD-1, LAG-3, TIM-3, CISH, and CBLB, may be added to cell culture media comprising TILs and other agents at amounts selected from the group consisting of 0.1 μM sdRNA/10,000 TILs/100 μL media, 0.5 μM sdRNA/10,000 TILs/100 μL media, 0.75 μM sdRNA/10,000 TILs/100 μL media, 1 μM sdRNA/10,000 TILs/100 μL media, 1.25 μM sdRNA/10,000 TILs/100 μL media, 1.5 μM sdRNA/10,000 TILs/100 μL media, 2 μM sdRNA/10,000 TILs/100 μL media, 5 μM sdRNA/10,000 TILs/100 μL media, or 10 μM sdRNA/10,000 TILs/100 μL media. In an embodiment, one or more sdRNAs targeting genes as described herein, including PD-1, LAG-3, TIM-3, CISH, and CBLB, may be added to TIL cultures during the pre-REP or REP stages twice a day, once a day, every two days, every three days, every four days, every five days, every six days, or every seven days.

Oligonucleotide compositions of the invention, including sdRNA, can be contacted with TILs as described herein during the expansion process, for example by dissolving sdRNA at high concentrations in cell culture media and allowing sufficient time for passive uptake to occur. In certain embodiments, the method of the present invention comprises contacting a population of TILs with an oligonucleotide composition as described herein. In certain embodiments, the method comprises dissolving an oligonucleotide e.g. sdRNA in a cell culture media and contacting the cell culture media with a population of TILs. The TILs may be a first population, a second population and/or a third population as described herein.

In some embodiments, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see, e.g., WO 90/14074; WO 91/16024; WO 91/17424; U.S. Pat. No. 4,897,355; Bergan et a 1993. Nucleic Acids Research. 21:3567).

In some embodiments, more than one sdRNA is used to reduce expression of a target gene. In some embodiments, one or more of PD-1, TIM-3, CBLB, LAG3 and/or CISH targeting sdRNAs are used together. In some embodiments, a PD-1 sdRNA is used with one or more of TIM-3, CBLB, LAG3 and/or CISH in order to reduce expression of more than one gene target. In some embodiments, a LAG3 sdRNA is used in combination with a CISH targeting sdRNA to reduce gene expression of both targets. In some embodiments, the sdRNAs targeting one or more of PD-1, TIM-3, CBLB, LAG3 and/or CISH herein are commercially available from Advirna LLC, Worcester, MA, USA.

In some embodiments, the sdRNA targets a gene selected from the group consisting of PD-1, LAG3, TIM3, CTLA-4, TIGIT, CISH, TGFBR2, PKA, CBLB, BAFF (BR3), and combinations thereof. In some embodiments, the sdRNA targets a gene selected from the group consisting of PD-1, LAG3, TIM3, CTLA-4, TIGIT, CISH, TGFBR2, PKA, CBLB, BAFF (BR3), and combinations thereof. In some embodiments, one sdRNA targets PD-1 and another sdRNA targets a gene selected from the group consisting of LAG3, TIM3, CTLA-4, TIGIT, CISH, TGFBR2, PKA, CBLB, BAFF (BR3), and combinations thereof. In some embodiments, the sdRNA targets a gene selected from PD-1, LAG-3, CISH, CBLB, TIM3, and combinations thereof. In some embodiments, the sdRNA targets a gene selected from PD-1 and one of LAG3, CISH, CBLB, TIM3, and combinations thereof. In some embodiments, one sdRNA targets PD-1 and one sdRNA targets LAG3. In some embodiments, one sdRNA targets PD-1 and one sdRNA targets CISH. In some embodiments, one sdRNA targets PD-1 and one sdRNA targets CBLB. In some embodiments, one sdRNA targets LAG3 and one sdRNA targets CISH. In some embodiments, one sdRNA targets LAG3 and one sdRNA targets CBLB. In some embodiments, one sdRNA targets CISH and one sdRNA targets CBLB. In some embodiments, one sdRNA targets TIM3 and one sdRNA targets PD-1. In some embodiments, one sdRNA targets TIM3 and one sdRNA targets LAG3. In some embodiments, one sdRNA targets TIM3 and one sdRNA targets CISH. In some embodiments, one sdRNA targets TIM3 and one sdRNA targets CBLB.

As discussed above, embodiments of the present invention provide tumor infiltrating lymphocytes (TILs) that have been genetically modified via gene-editing to enhance their therapeutic effect. Embodiments of the present invention embrace genetic editing through nucleotide insertion (RNA or DNA) into a population of TILs for both promotion of the expression of one or more proteins and inhibition of the expression of one or more proteins, as well as combinations thereof. Embodiments of the present invention also provide methods for expanding TILs into a therapeutic population, wherein the methods comprise gene-editing the TILs. There are several gene-editing technologies that may be used to genetically modify a population of TILs, which are suitable for use in accordance with the present invention.

In some embodiments, the method comprises a method of genetically modifying a population of TILs which include the step of stable incorporation of genes for production of one or more proteins. In an embodiment, a method of genetically modifying a population of TILs includes the step of retroviral transduction. In an embodiment, a method of genetically modifying a population of TILs includes the step of lentiviral transduction. Lentiviral transduction systems are known in the art and are described, e.g., in Levine, et al., *Proc. Nat'l Acad. Sci.* 2006, 103, 17372-77; Zufferey, et al., *Nat. Biotechnol.* 1997, 15, 871-75; Dull, et al., *J. Virology* 1998, 72, 8463-71, and U.S. Pat. No. 6,627,442, the disclosures of each of which are incorporated by reference herein. In an embodiment, a method of genetically modifying a population of TILs includes the step of gamma-retroviral transduction. Gamma-retroviral transduction systems are known in the art and are described, e.g., Cepko and Pear, *Cur. Prot. Mol. Biol.* 1996, 9.9.1-9.9.16, the disclosure of which is incorporated by reference herein. In an embodiment, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tel-like transposase (SB or Sleeping Beauty transposase), such as SB10, SB11, and SB100x, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In an embodiment, the method comprises a method of genetically modifying a population of TILs e.g. a first population, a second population and/or a third population as described herein. In an embodiment, a method of genetically modifying a population of TILs includes the step of stable incorporation of genes for production or inhibition (e.g., silencing) of one ore more proteins. In an embodiment, a method of genetically modifying a population of TILs includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. Other electroporation methods known in the art, such as those described in U.S. Pat. Nos. 5,019,034; 5,128,257; 5,137,817; 5,173,158; 5,232,856; 5,273,525; 5,304,120; 5,318,514; 6,010,613 and 6,078,490, the disclosures of which are incorporated by reference herein, may be used. In an embodiment, the electroporation method is a sterile electroporation method. In an embodiment, the electroporation method is a pulsed electroporation method. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse amplitude. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse width. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein a first pulse interval for a first set of two of the at least three pulses is different from a second pulse interval for a second set of two of the at least three pulses. In an embodiment, the electroporation method is a pulsed electroporation method comprising the steps of treating TILs with pulsed electrical fields to induce pore formation in the TILs, comprising the step of applying a sequence of at least three DC electrical pulses, having field strengths equal to or greater than 100 V/cm, to TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses, such that induced pores are sustained for a relatively long period of time, and such that viability of the TILs is maintained. In an embodiment, a method of genetically modifying a population of TILs includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of genetically modifying a population of TILs includes the step of liposomal transfection. Liposomal transfection methods, such as methods that employ a 1:1 (w/w) liposome formulation of the cationic lipid N-[1-(2,3-dioleyloxy) propyl]-n,n,n-trimethylammonium chloride (DOTMA) and dioleoyl phophotidylethanolamine (DOPE) in filtered water, are known in the art and are described in Rose, et al., Biotechniques 1991, 10, 520-525 and Felgner, et al., *Proc. Natl. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of genetically modifying a population of TILs includes the step of transfection using methods described in U.S. Pat. Nos. 5,766,902; 6,025,337; 6,410,517; 6,475,994; and 7,189,705; the disclosures of each of which are incorporated by reference herein. The TILs may be a first population, a second population and/or a third population of TILs as described herein.

According to an embodiment, the gene-editing process may comprise the use of a programmable nuclease that mediates the generation of a double-strand or single-strand break at one or more immune checkpoint genes. Such programmable nucleases enable precise genome editing by introducing breaks at specific genomic loci, i.e., they rely on the recognition of a specific DNA sequence within the genome to target a nuclease domain to this location and mediate the generation of a double-strand break at the target sequence. A double-strand break in the DNA subsequently recruits endogenous repair machinery to the break site to mediate genome editing by either non-homologous end-joining (NHEJ) or homology-directed repair (HDR). Thus, the repair of the break can result in the introduction of insertion/deletion mutations that disrupt (e.g., silence, repress, or enhance) the target gene product.

Major classes of nucleases that have been developed to enable site-specific genomic editing include zinc finger nucleases (ZFNs), transcription activator-like nucleases (TALENs), and CRISPR-associated nucleases (e.g., CRISPR/Cas9). These nuclease systems can be broadly classified into two categories based on their mode of DNA recognition: ZFNs and TALENs achieve specific DNA binding via protein-DNA interactions, whereas CRISPR systems, such as Cas9, are targeted to specific DNA sequences by a short RNA guide molecule that base-pairs directly with the target DNA and by protein-DNA interactions. See, e.g., Cox et al., *Nature Medicine,* 2015, Vol. 21, No. 2.

Non-limiting examples of gene-editing methods that may be used in accordance with TIL expansion methods of the present invention include CRISPR methods, TALE methods, and ZFN methods, which are described in more detail below. According to an embodiment, a method for expanding TILs into a therapeutic population may be carried out in accordance with any embodiment of the methods described herein (e.g., GEN 3 process) or as described in PCT/US2017/058610, PCT/US2018/012605, or PCT/US2018/012633, wherein the method further comprises gene-editing at least a portion of the TILs by one or more of a CRISPR method, a TALE method or a ZFN method, in order to generate TILs that can provide an enhanced therapeutic effect. According to an embodiment, gene-edited TILs can be evaluated for an improved therapeutic effect by comparing them to non-modified TILs in vitro, e.g., by evaluating in vitro effector function, cytokine profiles, etc. compared to unmodified TILs. In certain embodiments, the method comprises gene editing a population of TILs using CRISPR, TALE and/or ZFN methods.

In some embodiments of the present invention, electroporation is used for delivery of a gene editing system, such as CRISPR, TALEN, and ZFN systems. In some embodiments of the present invention, the electroporation system is a flow electroporation system. An example of a suitable flow electroporation system suitable for use with some embodiments of the present invention is the commercially-available MaxCyte STX system. There are several alternative commercially-available electroporation instruments which may be suitable for use with the present invention, such as the AgilePulse system or ECM 830 available from BTX-Harvard Apparatus, Cellaxess Elektra (Cellectricon), Nucleofector (Lonza/Amaxa), GenePulser MXcell (BIORAD), iPorator-96 (Primax) or siPORTer96 (Ambion). In some embodiments of the present invention, the electroporation system forms a closed, sterile system with the remainder of the TIL expansion method. In some embodiments of the present invention, the electroporation system is a pulsed electroporation system as described herein, and forms a closed, sterile system with the remainder of the TIL expansion method.

A method for expanding TILs into a therapeutic population may be carried out in accordance with any embodiment of the methods described herein (e.g., process GEN 3) or as described in PCT/US2017/058610, PCT/US2018/012605, or PCT/US2018/012633, wherein the method further comprises gene-editing at least a portion of the TILs by a CRISPR method (e.g., CRISPR/Cas9 or CRISPR/Cpf1). According to particular embodiments, the use of a CRISPR method during the TIL expansion process causes expression of one or more immune checkpoint genes to be silenced or reduced in at least a portion of the therapeutic population of TILs. Alternatively, the use of a CRISPR method during the TIL expansion process causes expression of one or more immune checkpoint genes to be enhanced in at least a portion of the therapeutic population of TILs.

CRISPR stands for "Clustered Regularly Interspaced Short Palindromic Repeats." A method of using a CRISPR system for gene editing is also referred to herein as a CRISPR method. There are three types of CRISPR systems which incorporate RNAs and Cas proteins, and which may be used in accordance with the present invention: Types I, II, and III. The Type II CRISPR (exemplified by Cas9) is one of the most well-characterized systems.

CRISPR technology was adapted from the natural defense mechanisms of bacteria and archaea (the domain of single-celled microorganisms). These organisms use CRISPR-derived RNA and various Cas proteins, including Cas9, to foil attacks by viruses and other foreign bodies by chopping up and destroying the DNA of a foreign invader. A CRISPR is a specialized region of DNA with two distinct characteristics: the presence of nucleotide repeats and spacers. Repeated sequences of nucleotides are distributed throughout a CRISPR region with short segments of foreign DNA (spacers) interspersed among the repeated sequences. In the type II CRISPR/Cas system, spacers are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Target recognition by the Cas9 protein requires a "seed" sequence within the crRNA and a conserved dinucleotide-containing protospacer adjacent motif (PAM) sequence upstream of the crRNA-binding region. The CRISPR/Cas system can thereby be retargeted to cleave virtually any DNA sequence by redesigning the crRNA. The crRNA and tracrRNA in the native system can be simplified into a single guide RNA (sgRNA) of approximately 100 nucleotides for use in genetic engineering. The CRISPR/Cas system is directly portable to human cells by co-delivery of plasmids expressing the Cas9 endonuclease and the necessary crRNA components. Different variants of Cas proteins may be used to reduce targeting limitations (e.g., orthologs of Cas9, such as Cpf1).

Non-limiting examples of genes that may be silenced or inhibited by permanently gene-editing TILs via a CRISPR method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a CRISPR method include CCR2, CCR4, CCR5, CXCR2, CXCR3, CX3CR1, IL-2, IL12, IL-15, and IL-21.

Examples of systems, methods, and compositions for altering the expression of a target gene sequence by a CRISPR method, and which may be used in accordance with embodiments of the present invention, are described in U.S. Pat. Nos. 8,697,359; 8,993,233; 8,795,965; 8,771,945; 8,889,356; 8,865,406; 8,999,641; 8,945,839; 8,932,814; 8,871,445; 8,906,616; and 8,895,308, which are incorporated by reference herein. Resources for carrying out CRISPR methods, such as plasmids for expressing CRISPR/Cas9 and CRISPR/Cpf1, are commercially available from companies such as GenScript.

In an embodiment, genetic modifications of populations of TILs, as described herein, may be performed using the CRISPR/Cpf1 system as described in U.S. Patent No. U.S. Pat. No. 9,790,490, the disclosure of which is incorporated by reference herein.

A method for expanding TILs into a therapeutic population may be carried out in accordance with any embodiment of the methods described herein (e.g., process 2A) or as described in PCT/US2017/058610, PCT/US2018/012605, or PCT/US2018/012633, wherein the method further comprises gene-editing at least a portion of the TILs by a TALE method. According to particular embodiments, the use of a TALE method during the TIL expansion process causes expression of one or more immune checkpoint genes to be silenced or reduced in at least a portion of the therapeutic population of TILs. Alternatively, the use of a TALE method during the TIL expansion process causes expression of one or more immune checkpoint genes to be enhanced in at least a portion of the therapeutic population of TILs.

TALE stands for "Transcription Activator-Like Effector" proteins, which include TALENs ("Transcription Activator-Like Effector Nucleases"). A method of using a TALE system for gene editing may also be referred to herein as a TALE method. TALEs are naturally occurring proteins from the plant pathogenic bacteria genus *Xanthomonas*, and contain DNA-binding domains composed of a series of 33-35-amino-acid repeat domains that each recognizes a single base pair. TALE specificity is determined by two hypervariable amino acids that are known as the repeat-variable di-residues (RVDs). Modular TALE repeats are linked together to recognize contiguous DNA sequences. A specific RVD in the DNA-binding domain recognizes a base in the target locus, providing a structural feature to assemble predictable DNA-binding domains. The DNA binding domains of a TALE are fused to the catalytic domain of a type IIS FokI endonuclease to make a targetable TALE nuclease. To induce site-specific mutation, two individual TALEN arms, separated by a 14-20 base pair spacer region, bring FokI monomers in close proximity to dimerize and produce a targeted double-strand break.

Several large, systematic studies utilizing various assembly methods have indicated that TALE repeats can be combined to recognize virtually any user-defined sequence. Custom-designed TALE arrays are also commercially available through Cellectis Bioresearch (Paris, France), Transposagen Biopharmaceuticals (Lexington, KY, USA), and Life Technologies (Grand Island, NY, USA). TALE and TALEN methods suitable for use in the present invention are described in U.S. Patent Application Publication Nos. US 2011/0201118 A1; US 2013/0117869 A1; US 2013/0315884 A1; US 2015/0203871 A1 and US 2016/0120906 A1, the disclosures of which are incorporated by reference herein.

Non-limiting examples of genes that may be silenced or inhibited by permanently gene-editing TILs via a TALE method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a TALE method include CCR2, CCR4, CCR5, CXCR2, CXCR3, CX3CR1, IL-2, IL12, IL-15, and IL-21.

Examples of systems, methods, and compositions for altering the expression of a target gene sequence by a TALE method, and which may be used in accordance with embodiments of the present invention, are described in U.S. Pat. No. 8,586,526, which is incorporated by reference herein.

A method for expanding TILs into a therapeutic population may be carried out in accordance with any embodiment of the methods described herein (e.g., process GEN 3) or as described in PCT/US2017/058610, PCT/US2018/012605, or PCT/US2018/012633, wherein the method further comprises gene-editing at least a portion of the TILs by a zinc finger or zinc finger nuclease method. According to particular embodiments, the use of a zinc finger method during the TIL expansion process causes expression of one or more immune checkpoint genes to be silenced or reduced in at least a portion of the therapeutic population of TILs. Alternatively, the use of a zinc finger method during the TIL expansion process causes expression of one or more immune checkpoint genes to be enhanced in at least a portion of the therapeutic population of TILs.

An individual zinc finger contains approximately 30 amino acids in a conserved ββα configuration. Several amino acids on the surface of the α-helix typically contact 3 bp in the major groove of DNA, with varying levels of selectivity. Zinc fingers have two protein domains. The first domain is the DNA binding domain, which includes eukaryotic transcription factors and contain the zinc finger. The second domain is the nuclease domain, which includes the FokI restriction enzyme and is responsible for the catalytic cleavage of DNA.

The DNA-binding domains of individual ZFNs typically contain between three and six individual zinc finger repeats and can each recognize between 9 and 18 base pairs. If the zinc finger domains are specific for their intended target site then even a pair of 3-finger ZFNs that recognize a total of 18 base pairs can, in theory, target a single locus in a mammalian genome. One method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Alternatively, selection-based approaches, such as oligomerized pool engineering (OPEN) can be used to select for new zinc-finger arrays from randomized libraries that take into consideration context-dependent interactions between neighboring fingers. Engineered zinc fingers are available commercially; Sangamo Biosciences (Richmond, CA, USA) has developed a propriety platform (CompoZr®) for zinc-finger construction in partnership with Sigma-Aldrich (St. Louis, MO, USA).

Non-limiting examples of genes that may be silenced or inhibited by permanently gene-editing TILs via a zinc finger method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a zinc finger method include CCR2, CCR4, CCR5, CXCR2, CXCR3, CX3CR1, IL-2, IL12, IL-15, and IL-21.

Examples of systems, methods, and compositions for altering the expression of a target gene sequence by a zinc finger method, which may be used in accordance with embodiments of the present invention, are described in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, which are incorporated by reference herein.

Other examples of systems, methods, and compositions for altering the expression of a target gene sequence by a zinc finger method, which may be used in accordance with embodiments of the present invention, are described in Beane, et al., *Mol. Therapy,* 2015, 23 1380-1390, the disclosure of which is incorporated by reference herein.

In some embodiments, the TILs are optionally genetically engineered to include additional functionalities, including, but not limited to, a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19). In certain embodiments, the method comprises genetically engineering a population of TILs to include a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19). Aptly, the population of TILs may be a first population, a second population and/or a third population as described herein.

K. Closed Systems for TIL Manufacturing

The present invention provides for the use of closed systems during the TIL culturing process. Such closed systems allow for preventing and/or reducing microbial contamination, allow for the use of fewer flasks, and allow for cost reductions. In some embodiments, the closed system uses two containers.

Such closed systems are well-known in the art and can be found, for example, at http://www.fda.gov/cber/guidelines.htm and https://www.fda.gov/BiologicsBloodVaccines/GuidanceComplianceRegulatoryInformation/Guidances/Blood/ucm076779.htm.

Sterile connecting devices (STCDs) produce sterile welds between two pieces of compatible tubing. This procedure permits sterile connection of a variety of containers and tube diameters. In some embodiments, the closed systems include luer lock and heat sealed systems as described in for example, Example G. In some embodiments, the closed system is accessed via syringes under sterile conditions in order to maintain the sterility and closed nature of the system. In some embodiments, a closed system as described in Example G is employed. In some embodiments, the TILs are formulated into a final product formulation container according to the method described in Example G, section "Final Formulation and Fill".

In some embodiments, the closed system uses one container from the time the tumor fragments are obtained until the TILs are ready for administration to the patient or cryopreserving. In some embodiments when two containers are used, the first container is a closed G-container and the population of TILs is centrifuged and transferred to an infusion bag without opening the first closed G-container. In some embodiments, when two containers are used, the infusion bag is a HypoThermosol-containing infusion bag. A closed system or closed TIL cell culture system is characterized in that once the tumor sample and/or tumor fragments have been added, the system is tightly sealed from the outside to form a closed environment free from the invasion of bacteria, fungi, and/or any other microbial contamination.

In some embodiments, the reduction in microbial contamination is between about 5% and about 100%. In some embodiments, the reduction in microbial contamination is between about 5% and about 95%. In some embodiments, the reduction in microbial contamination is between about 5% and about 90%. In some embodiments, the reduction in microbial contamination is between about 10% and about 90%. In some embodiments, the reduction in microbial contamination is between about 15% and about 85%. In some embodiments, the reduction in microbial contamination is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or about 100%.

The closed system allows for TIL growth in the absence and/or with a significant reduction in microbial contamination.

Moreover, pH, carbon dioxide partial pressure and oxygen partial pressure of the TIL cell culture environment each vary as the cells are cultured. Consequently, even though a medium appropriate for cell culture is circulated, the closed environment still needs to be constantly maintained as an optimal environment for TIL proliferation. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. In some embodiments, the present invention provides a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

In some embodiments, the pressure within the closed environment is continuously or intermittently controlled. That is, the pressure in the closed environment can be varied by means of a pressure maintenance device for example, thus ensuring that the space is suitable for growth of TILs in a positive pressure state, or promoting exudation of fluid in a negative pressure state and thus promoting cell proliferation. By applying negative pressure intermittently, moreover, it is possible to uniformly and efficiently replace the circulating liquid in the closed environment by means of a temporary shrinkage in the volume of the closed environment.

In some embodiments, optimal culture components for proliferation of the TILs can be substituted or added, and including factors such as IL-2 and/or OKT3, as well as combination, can be added.

L. Optional Cryopreservation of TILs

Either the bulk TIL population (for example the second population of TILs) or the expanded population of TILs (for example the third population of TILs) can be optionally cryopreserved. In some embodiments, cryopreservation occurs on the therapeutic TIL population. In some embodiments, cryopreservation occurs on the TILs harvested after the second expansion. In some embodiments, cryopreservation occurs on the TILs in exemplary Step F of FIG. 1 (in particular, e.g., FIG. 1B and/or FIG. 1C). In some embodiments, the TILs are cryopreserved in the infusion bag. In some embodiments, the TILs are cryopreserved prior to placement in an infusion bag. In some embodiments, the TILs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

In a preferred embodiment, a population of TILs is cryopreserved using CS10 cryopreservation media (CryoStor 10, BioLife Solutions). In a preferred embodiment, a population of TILs is cryopreserved using a cryopreservation media containing dimethylsulfoxide (DMSO). In a preferred embodiment, a population of TILs is cryopreserved using a 1:1 (vol:vol) ratio of CS10 and cell culture media. In a preferred embodiment, a population of TILs is cryopreserved using about a 1:1 (vol:vol) ratio of CS10 and cell culture media, further comprising additional IL-2.

As discussed above, and exemplified in Steps A through E as provided in FIG. 1 (in particular, e.g., FIG. 1B and/or FIG. 1C), cryopreservation can occur at numerous points throughout the TIL expansion process. In some embodiments, the expanded population of TILs after the second expansion (as provided for example, according to Step D of FIG. 1 (in particular, e.g., FIG. 1B and/or FIG. 1C) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Example D.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

In some cases, the Step B TIL population can be cryopreserved immediately, using the protocols discussed below. Alternatively, the bulk TIL population can be subjected to Step C and Step D and then cryopreserved after Step D. Similarly, in the case where genetically modified TILs will be used in therapy, the Step B or Step D TIL populations can be subjected to genetic modifications for suitable treatments.

M. Phenotypic Characteristics of Expanded TILs

In some embodiment, the TILs are analyzed for expression of numerous phenotype markers after expansion, including those described herein and in the Examples. In an embodiment, expression of one or more phenotypic markers is examined. In some embodiments, the phenotypic characteristics of the TILs are analyzed after the first expansion in Step B. In some embodiments, the phenotypic characteristics of the TILs are analyzed during the transition in Step C. In some embodiments, the phenotypic characteristics of the TILs are analyzed during the transition according to Step C and after cryopreservation. In some embodiments, the phenotypic characteristics of the TILs are analyzed after the second expansion according to Step D. In some embodiments, the phenotypic characteristics of the TILs are analyzed after two or more expansions according to Step D.

In some embodiments, the marker is selected from the group consisting of CD8 and CD28. In some embodiments, expression of CD8 is examined. In some embodiments, expression of CD28 is examined. In some embodiments, the expression of CD8 and/or CD28 is higher on TILs produced according the current invention process, as compared to other processes (e.g., the Gen 3 process as provided for example in FIG. 1 (in particular, e.g., FIG. 1B), as compared to the 2A process as provided for example in FIG. 1 (in particular, e.g., FIG. 1B). In some embodiments, the expression of CD8 is higher on TILs produced according the current invention process, as compared to other processes (e.g., the Gen 3 process as provided for example in FIG. 1 (in particular, e.g., FIG. 1B and/or FIG. 1C), as compared to the 2A process as provided for example in FIG. 1 (in particular, e.g., FIG. 1B and/or FIG. 1C). In some embodiments, the expression of CD28 is higher on TILs produced according the current invention process, as compared to other processes (e.g., the Gen 3 process as provided for example in FIG. 1 (in particular, e.g., FIG. 1B and/or FIG. 1C), as compared to the 2A process as provided for example in FIG. 1 (in particular, e.g., FIG. 1A). In some embodiments, high CD28 expression is indicative of a younger, more presisitent TIL phenotype. In an embodiment, expression of one or more regulatory markers is measured.

In an embodiment, no selection of the first population of TILs, second population of TILs, third population of TILs, or harvested TIL population based on CD8 and/or CD28 expression is performed during any of the steps for the method for expanding tumor infiltrating lymphocytes (TILs) described herein.

In some embodiments, the percentage of central memory cells is higher on TILs produced according the current invention process, as compared to other processes (e.g., the Gen 3 process as provided for example in FIG. 1 (in particular, e.g., FIG. 1B), as compared to the 2A process as provided for example in FIG. 1 (in particular, e.g., FIG. 1A). In some embodiments the memory marker for central memory cells is selected from the group consisting of CCR7 and CD62L.

In some embodiments, the CD4+ and/or CD8+ TIL Memory subsets can be divided into different memory subsets. In some embodiments, the CD4+ and/or CD8+ TILs comprise the naïve (CD45RA+CD62L+) TILS. In some embodiments, the CD4+ and/or CD8+ TILs comprise the central memory (CM; CD45RA-CD62L+) TILs. In some embodiments, the CD4+ and/or CD8+ TILs comprise the effector memory (EM; CD45RA-CD62L−) TILs. In some embodiments, the CD4+ and/or CD8+ TILs comprise the, RA+ effector memory/effector (TEMRA/TEFF; CD45RA+ CD62L+) TILs.

In some embodiments, the TILs express one more markers selected from the group consisting of granzyme B, perforin, and granulysin. In some embodiments, the TILs express granzyme B. In some embodiments, the TILs express perforin. In some embodiments, the TILs express granulysin.

In an embodiment, restimulated TILs can also be evaluated for cytokine release, using cytokine release assays. In some embodiments, TILs can be evaluated for interferon-γ (IFN-γ) secretion. In some embodiments, the IFN-γ secretion is measured by an ELISA assay. In some embodiments, the IFN-γ secretion is measured by an ELISA assay after the rapid second expansion step, after Step D as provided in for example, FIG. 1 (in particular, e.g., FIG. 1B and/or FIG. 1C). In some embodiments, TIL health is measured by IFN-gamma (IFN-γ) secretion. In some embodiments, IFN-γ secretion is indicative of active TILs. In some embodiments, a potency assay for IFN-γ production is employed. IFN-γ production is another measure of cytotoxic potential. IFN-γ production can be measured by determining the levels of the cytokine IFN-γ in the media of TIL stimulated with antibodies to CD3, CD28, and CD137/4-1BB. IFN-γ levels in media from these stimulated TIL can be determined using by measuring IFN-γ release. In some embodiments, an increase in IFN-γ production in for example Step D in the Gen 3 process as provided in FIG. 1 (in particular, e.g., FIG. 1B and/or FIG. 1C) TILs as compared to for example Step D in the 2A process as provided in FIG. 1 (in particular, e.g., FIG. 1A) is indicative of an increase in cytotoxic potential of the Step D TILs. In some embodiments, IFN-γ secretion is increased one-fold, two-fold, three-fold, four-fold, or five-fold or more. In some embodiments, IFN-γ secretion is increased one-fold. In some embodiments, IFN-γ secretion is increased two-fold. In some embodiments, IFN-γ secretion is increased three-fold. In some embodiments, IFN-γ secretion is increased four-fold. In some embodiments, IFN-γ secretion is increased five-fold. In some embodiments, IFN-γ is measured using a Quantikine ELISA kit. In some embodiments, IFN-γ is measured in TILs ex vivo. In some embodiments, IFN-γ is measured in TILs ex vivo, including TILs produced by the methods of the present invention, including, for example, FIG. 1B and/or FIG. 1C methods.

In some embodiments, TILs capable of at least one-fold, two-fold, three-fold, four-fold, or five-fold or more IFN-γ secretion are TILs produced by the expansion methods of the present invention, including, for example FIG. 1B and/or FIG. 1C methods. In some embodiments, TILs capable of at least one-fold more IFN-γ secretion are TILs produced by the expansion methods of the present invention, including, for example FIG. 1B and/or FIG. 1C methods. In some embodiments, TILs capable of at least two-fold more IFN-γ secretion are TILs produced by the expansion methods of the present invention, including, for example FIG. 1B and/or FIG. 1C methods. In some embodiments, TILs capable of at least three-fold more IFN-γ secretion are TILs produced by the expansion methods of the present invention, including, for example FIG. 1B and/or FIG. 1C methods. In some embodiments, TILs capable of at least four-fold more IFN-γ secretion are TILs produced by the expansion methods of the present invention, including, for example FIG. 1B and/or FIG. 1C methods. In some embodiments, TILs capable of at least five-fold more IFN-γ secretion are TILs produced by the expansion methods of the present invention, including, for example FIG. 1B and/or FIG. 1C methods.

Figure 12:
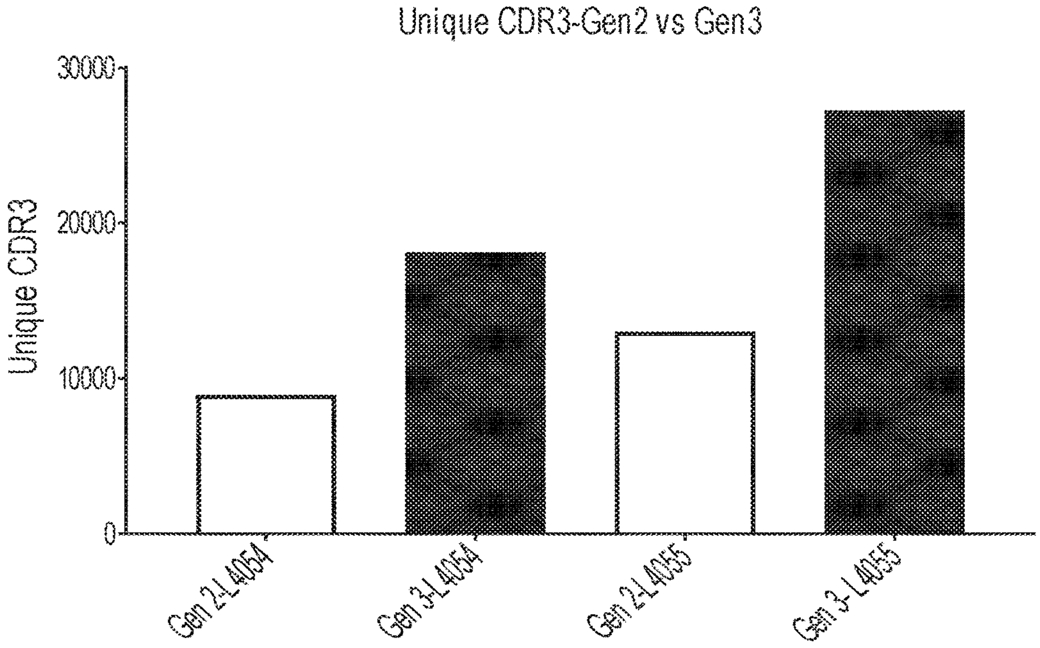
FIG. 12: Unique CDR3 sequence analysis for TIL final product on L4054 and L4055 under Gen 2 and Gen 3 process. Columns show the number of unique TCR B clonotypes identified from $1\times10^6$ cells collected on Harvest Day Gen 2 (e.g., day 22) and Gen 3 process (e.g., day 14-16). Gen 3 shows higher clonal diversity compared to Gen 2 based on the number of unique peptide CDRs within the sample.
Figure 13:
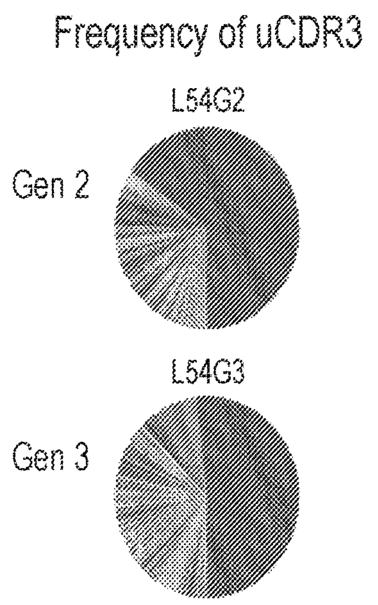
FIG. 13: Frequency of unique CDR3 sequences on L4054 IL harvested final cell product (Gen 2 (e.g., day 22) and Gen 3 process (e.g., day 14-16)).

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including, for example, methods other than those embodied in FIG. 1 (in particular, e.g., FIG. 1B and/or FIG. 1C). In some embodiments, the TILs obtained by the present method exhibit an increase in the T-cell repertoire diversity as compared to freshly harvested TILs and/or TILs prepared using methods referred to as process 2A, as exemplified in FIG. 1 (in particular, e.g., FIG. 1A). In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β). In some embodiments, the process as described herein (e.g., the Gen 3 process) shows higher clonal diversity as compared to other processes, for example the process referred to as the Gen 2 based on the number of unique peptide CDRs within the sample (see, for example FIGS. 12-14).

In some embodiments, the TILs prepared by the methods of the present invention, including those as described for example in FIG. 1, exhibit increased polyclonality as compared to TILs produced by other methods, including those not exemplified in FIG. 1, such as for example, methods referred to as process 1C methods. In some embodiments, significantly improved polyclonality and/or increased polyclonality is indicative of treatment efficacy and/or increased clinical efficacy for cancer treatment. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 1. In some embodiments, polyclonality is increased one-fold as compared to an untreated patient and/or as compared to a patient treated with TILs prepared using other methods than those provide herein including for example, methods other than those embodied in FIG. 1. In some embodiments, polyclonality is increased two-fold as compared to an untreated patient and/or as compared to a patient treated with TILs prepared using other methods than those provide herein including for example, methods other than those embodied in FIG. 1. In some embodiments, polyclonality is increased ten-fold as compared to an untreated patient and/or as compared to a patient treated with TILs prepared using other methods than those provide herein including for example, methods other than those embodied in FIG. 1. In some embodiments, polyclonality is increased 100-fold as compared to an untreated patient and/or as compared to a patient treated with TILs prepared using other methods than those provide herein including for example, methods other than those embodied in FIG. 1. In some embodiments, polyclonality is increased 500-fold as compared to an untreated patient and/or as compared to a patient treated with TILs prepared using other methods than those provide herein including for example, methods other than those embodied in FIG. 1. In some embodiments, polyclonality is increased 1000-fold as compared to an untreated patient and/or as compared to a patient treated with TILs prepared using other methods than those provide herein including for example, methods other than those embodied in FIG. 1.

In some embodiments, the activation and exhaustion of TILs can be determined by examining one or more markers. In some embodiments, the activation and exhaustion can be determined using multicolor flow cytometry. In some embodiments, the activation and exhaustion of markers include but not limited to one or more markers selected from the group consisting of CD3, PD-1, 2B4/CD244, CD8, CD25, BTLA, KLRG, TIM-3, CD194/CCR4, CD4, TIGIT, CD183, CD69, CD95, CD127, CD103, and/or LAG-3). In some embodiments, the activation and exhaustion of markers include but not limited to one or more markers selected from the group consisting of BTLA, CTLA-4, ICOS, Ki67, LAG-3, PD-1, TIGIT, and/or TIM-3. In some embodiments, the activation and exhaustion of markers include but not limited to one or more markers selected from the group consisting of BTLA, CTLA-4, ICOS, Ki67, LAG-3, CD103+/CD69+, CD103+/CD69−, PD-1, TIGIT, and/or TIM-3. In some embodiments, the T-cell markers (including activation and exhaustion markers) can be determined and/or analyzed to examine T-cell activation, inhibition, or function. In some embodiments, the T-cell markers can include but are not limited to one or more markers selected from the group consisting of TIGIT, CD3, FoxP3, Tim-3, PD-1, CD103, CTLA-4, LAG-3, BTLA-4, ICOS, Ki67, CD8, CD25, CD45, CD4, and/or CD59.

In some embodiments, the phenotypic characterization is examined after cryopreservation.

N. Additional Process Embodiments

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 8 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 10 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX 100 MCS container, for a period of about 2 to 4 days, and then (2) effecting the transfer of the second population of TILs from the small scale culture to a second container larger than the first container, e.g., a G-REX 500 MCS container, wherein in the second container the second population of TILs from the small scale culture is cultured in a larger scale culture for a period of about 4 to 8 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX 100 MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 8 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100 MCS container, for a period of about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500 MCS containers, wherein in each second container the portion of the second population of TILs transferred from the small scale culture to such second container is cultured in a larger scale culture for a period of about 4 to 8 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100 MCS container, for a period of about 3 to 4 days, and then (2) effecting the transfer and apportioning of the second population of TILs from the first small scale culture into and amongst 2, 3 or 4 second containers that are larger in size than the first container, e.g., G-REX 500 MCS containers, wherein in each second container the portion of the second population of TILs transferred from the small scale culture to such second container is cultured in a larger scale culture for a period of about 5 to 7 days.

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 8 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 8 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX 100 MCS container, for a period of about 2 to 4 days, and then (2) effecting the transfer of the second population of TILs from the small scale culture to a second container larger than the first container, e.g., a G-REX 500 MCS container, wherein in the second container the second population of TILs from the small scale culture is cultured in a larger scale culture for a period of about 4 to 8 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX 100 MCS container, for a period of about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 6 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100 MCS container, for a period of about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500 MCS containers, wherein in each second container the portion of the second population of TILs transferred from the small scale culture to such second container is cultured in a larger scale culture for a period of about 4 to 6 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100 MCS container, for a period of about 3 to 4 days, and then (2) effecting the transfer and apportioning of the second population of TILs from the first small scale culture into and amongst 2, 3 or 4 second containers that are larger in size than the first container, e.g., G-REX 500 MCS containers, wherein in each second container the portion of the second population of TILs transferred from the small scale culture to such second container is cultured in a larger scale culture for a period of about 4 to 5 days.

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 7 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 11 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX 100 MCS container, for a period of about 3 to 4 days, and then (2) effecting the transfer of the second population of TILs from the small scale culture to a second container larger than the first container, e.g., a G-REX 500 MCS container, wherein in the second container the second population of TILs from the small scale culture is cultured in a larger scale culture for a period of about 4 to 7 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX 100 MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 7 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100 MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500 MCS containers, wherein in each second container the portion of the second population of TILs transferred from the small scale culture to such second container is cultured in a larger scale culture for a period of about 4 to 7 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100 MCS container, for a period of about 4 days, and then (2) effecting the transfer and apportioning of the second population of TILs from the first small scale culture into and amongst 2, 3 or 4 second containers that are larger in size than the first container, e.g., G-REX 500 MCS containers, wherein in each second container the portion of the second population of TILs transferred from the small scale culture to such second container is cultured in a larger scale culture for a period of about 5 days.

In another embodiment, the invention provides the method described in any of the preceding paragraphs as applicable above modified such that in step (b) the primary first expansion is performed by contacting the first population of TILs with a culture medium which further comprises exogenous antigen-presenting cells (APCs), wherein the number of APCs in the culture medium in step (c) is greater than the number of APCs in the culture medium in step (b).

In another embodiment, the invention provides the method described in any of the preceding paragraphs as applicable above modified such that in step (c) the culture medium is supplemented with additional exogenous APCs.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 20:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 10:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 9:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 8:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 7:1.

In another embodiment, the invention provides the method described in any of the preceding paragraphs as applicable above modified such that the ratio of number of APCs added in at or about 1.1:1 to at or about 6:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 5:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 4:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 3:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.9:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.8:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.7:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.6:1.

In another embodiment, the invention provides the method described in any of the preceding paragraphs as applicable above modified such that the ratio of number of APCs added in at or about 1.1:1 to at or about 2.5:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.4:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.3:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.2:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.1:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 10:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 5:1.

In another embodiment, the invention provides the method described in any of the preceding paragraphs as applicable above modified such that the ratio of number of APCs added in at or about 2:1 to at or about 4:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 3:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.9:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.8:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.7:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.6:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.5:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.4:1.

In another embodiment, the invention provides the method described in any of the preceding paragraphs as applicable above modified such that the ratio of number of APCs added in at or about 2:1 to at or about 2.3:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.2:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.1:1.

In another embodiment, the invention provides the method described in any of the preceding paragraphs as applicable above modified such that the ratio of number of APCs added in the rapid second expansion to the number of APCs added in step (b) is at or about 2:1.

In another embodiment, the invention provides the method described in any of the preceding paragraphs as applicable above modified such that the ratio of number of APCs added in the rapid second expansion to the number of APCs added in step (b) is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the invention provides the method described in any of the preceding paragraphs as applicable above modified such that the number of APCs added in the primary first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs, and such that the number of APCs added in the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$ APCs.

In another embodiment, the invention provides the method described in any of the preceding paragraphs as applicable above modified such that the number of APCs added in the primary first expansion is selected from the range of at or about $1\times10^8$ APCs to at or about $3.5\times10^8$ APCs, and wherein the number of APCs added in the rapid second expansion is selected from the range of at or about $3.5\times10^8$ APCs to at or about $1\times10^9$ APCs.

In another embodiment, the invention provides the method described in any of the preceding paragraphs as applicable above modified such that the number of APCs added in the primary first expansion is selected from the range of at or about $1.5\times10^8$ APCs to at or about $3\times10^8$ APCs, and wherein the number of APCs added in the rapid second expansion is selected from the range of at or about $4\times10^8$ APCs to at or about $7.5\times10^8$ APCs.

In another embodiment, the invention provides the method described in any of the preceding paragraphs as applicable above modified such that the number of APCs added in the primary first expansion is selected from the range of at or about $2\times10^8$ APCs to at or about $2.5\times10^8$ APCs, and wherein the number of APCs added in the rapid second expansion is selected from the range of at or about $4.5\times10^8$ APCs to at or about $5.5\times10^8$ APCs.

In another embodiment, the invention provides the method described in any of the preceding paragraphs as applicable above modified such that at or about $2.5\times10^8$ APCs are added to the primary first expansion and at or about $5\times10^8$ APCs are added to the rapid second expansion.

In another embodiment, the invention provides the method described in any of the preceding paragraphs as applicable above modified such that the antigen-presenting cells are peripheral blood mononuclear cells (PBMCs).

In another embodiment, the invention provides the method described in any of the preceding paragraphs as applicable above modified such that the multiple tumor fragments are distributed into a plurality of separate containers, in each of which separate containers the first population of TILs is obtained in step (a), the second population of TILs is obtained in step (b), and the third population of TILs is obtained in step (c), and the therapeutic populations of TILs from the plurality of containers in step (c) are combined to yield the harvested TIL population from step (d).

In another embodiment, the invention provides the method described in any of the preceding paragraphs as applicable above modified such that the multiple tumors are evenly distributed into the plurality of separate containers.

In another embodiment, the invention provides the method described in any of the preceding paragraphs as applicable above modified such that the plurality of separate containers comprises at least two separate containers.

In another embodiment, the invention provides the method described in any of the preceding paragraphs as applicable above modified such that the plurality of separate containers comprises from two to twenty separate containers.

In another embodiment, the invention provides the method described in any of the preceding paragraphs as applicable above modified such that the plurality of separate containers comprises from two to fifteen separate containers.

In another embodiment, the invention provides the method described in any of the preceding paragraphs as applicable above modified such that the plurality of separate containers comprises from two to ten separate containers.

In another embodiment, the invention provides the method described in any of the preceding paragraphs as applicable above modified such that the plurality of separate containers comprises from two to five separate containers.

In another embodiment, the invention provides the method described in any of the preceding paragraphs as applicable above modified such that the plurality of separate containers comprises 2, 3, 4, 5, 6, 7, 8, 9, 10, 11, 12, 13, 14, 15, 16, 17, 18, 19, or 20 separate containers.

In another embodiment, the invention provides the method described in any of the preceding paragraphs as applicable above modified such that for each container in which the priming first expansion is performed on a first population of TILs in step (b) the rapid second expansion in step (c) is performed in the same container on the second population of TILs produced from such first population of TILs.

In another embodiment, the invention provides the method described in any of the preceding paragraphs as applicable above modified such that each of the separate containers comprises a first gas-permeable surface area.

In another embodiment, the invention provides the method described in any of the preceding paragraphs as applicable above modified such that the multiple tumor fragments are distributed in a single container.

In another embodiment, the invention provides the method described in any of the preceding paragraphs as applicable above modified such that the single container comprises a first gas-permeable surface area.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable above modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the first gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the first gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the first gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the first gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the priming first expansion is performed in a first container comprising a first gas-permeable surface area and in step (c) the rapid second expansion is performed in a second container comprising a second gas-permeable surface area.

In another embodiment, the invention provides the method described in any of the preceding paragraphs as applicable above modified such that the second container is larger than the first container.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the second gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the second gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the second gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the second gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the priming first expansion is performed in a first container comprising a first gas-permeable surface area and in step (c) the rapid second expansion is performed in the first container.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable above modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the first gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the first gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the first gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the first gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:10.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:9.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:8.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:7.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:6.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:4.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:3.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:2.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.2 to at or about 1:8.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.3 to at or about 1:7.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.4 to at or about 1:6.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.5 to at or about 1:5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.6 to at or about 1:4.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.7 to at or about 1:3.5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.8 to at or about 1:3.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.9 to at or about 1:2.5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:2.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from at or about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

In another embodiment, the invention provides the method described in any of preceding paragraphs as applicable above modified such that the ratio of the number of TILs in the second population of TILs to the number of TILs in the first population of TILs is at or about 1.5:1 to at or about 100:1.

In another embodiment, the invention provides the method described in any of the preceding paragraphs as applicable above modified such that the ratio of the number of TILs in the second population of TILs to the number of TILs in the first population of TILs is at or about 50:1.

In another embodiment, the invention provides the method described in any of the preceding paragraphs as applicable above modified such that the ratio of the number of TILs in the second population of TILs to the number of TILs in the first population of TILs is at or about 25:1.

In another embodiment, the invention provides the method described in any of the preceding paragraphs as applicable above modified such that the ratio of the number of TILs in the second population of TILs to the number of TILs in the first population of TILs is at or about 20:1.

In another embodiment, the invention provides the method described in any of the preceding paragraphs as applicable above modified such that the ratio of the number of TILs in the second population of TILs to the number of TILs in the first population of TILs is at or about 10:1.

In another embodiment, the invention provides the method described in any of the preceding paragraphs as applicable above modified such that the second population of TILs is at least at or about 50-fold greater in number than the first population of TILs.

In another embodiment, the invention provides the method described in any of the preceding paragraphs as applicable above modified such that the second population of TILs is at least at or about 1-, 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49- or 50-fold greater in number than the first population of TILs.

In another embodiment, the invention provides the method described in any of the preceding paragraphs as applicable above modified such that at or about 2 days or at or about 3 days after the commencement of the second period in step (c), the cell culture medium is supplemented with additional IL-2.

In another embodiment, the invention provides the method described in any of the preceding paragraphs as applicable above modified to further comprise the step of cryopreserving the harvested TIL population in step (d) using a cryopreservation process.

In another embodiment, the invention provides the method described in any of of the preceding paragraphs as applicable above modified to comprise performing after step (d) the additional step of (e) transferring the harvested TIL population from step (d) to an infusion bag that optionally contains HypoThermosol.

In another embodiment, the invention provides the method described in any of the preceding paragraphs as applicable above modified to comprise the step of cryopreserving the infusion bag comprising the harvested TIL population in step (e) using a cryopreservation process.

In another embodiment, the invention provides the method described in any of the preceding paragraphs as applicable above modified such that the cryopreservation process is performed using a 1:1 ratio of harvested TIL population to cryopreservation media.

In another embodiment, the invention provides the method described in any of the preceding paragraphs as applicable above modified such that the antigen-presenting cells are peripheral blood mononuclear cells (PBMCs).

In another embodiment, the invention provides the method described in any of the preceding paragraphs as applicable above modified such that the PBMCs are irradiated and allogeneic.

In another embodiment, the invention provides the method described in any of the preceding paragraphs as applicable above modified such that the total number of APCs added to the cell culture in step (b) is $2.5\times10^8$.

In another embodiment, the invention provides the method described in any of the preceding paragraphs as applicable above modified such that the total number of APCs added to the cell culture in step (c) is $5\times10^8$.

In another embodiment, the invention provides the method described in any of the preceding paragraphs as applicable above modified such that the APCs are PBMCs.

In another embodiment, the invention provides the method described in any of the preceding paragraphs as applicable above modified such that the PBMCs are irradiated and allogeneic.

In another embodiment, the invention provides the method described in any of the preceding paragraphs as applicable above modified such that the antigen-presenting cells are artificial antigen-presenting cells.

In another embodiment, the invention provides the method described in any of the preceding paragraphs as applicable above modified such that the harvesting in step (d) is performed using a membrane-based cell processing system.

In another embodiment, the invention provides the method described in any of the preceding paragraphs as applicable above modified such that the harvesting in step (d) is performed using a LOVO cell processing system.

In another embodiment, the invention provides the method described in any of the preceding paragraphs as applicable above modified such that the multiple fragments comprise at or about 5 to at or about 60 fragments per container in step (b).

In another embodiment, the invention provides the method described in any of the preceding paragraphs as applicable above modified such that the multiple fragments comprise at or about 10 to at or about 60 fragments per container in step (b).

In another embodiment, the invention provides the method described in any of the preceding paragraphs as applicable above modified such that the multiple fragments comprise at or about 15 to at or about 60 fragments per container in step (b).

In another embodiment, the invention provides the method described in any of the preceding paragraphs as applicable above modified such that the multiple fragments comprise at or about 20 to at or about 60 fragments per container in step (b).

In another embodiment, the invention provides the method described in any of the preceding paragraphs as applicable above modified such that the multiple fragments comprise at or about 25 to at or about 60 fragments per container in step (b).

In another embodiment, the invention provides the method described in any of the preceding paragraphs as applicable above modified such that the multiple fragments comprise at or about 30 to at or about 60 fragments per container in step (b).

In another embodiment, the invention provides the method described in any of the preceding paragraphs as applicable above modified such that the multiple fragments comprise at or about 35 to at or about 60 fragments per container in step (b).

In another embodiment, the invention provides the method described in any of the preceding paragraphs as applicable above modified such that the multiple fragments comprise at or about 40 to at or about 60 fragments per container in step (b).

In another embodiment, the invention provides the method described in any of the preceding paragraphs as applicable above modified such that the multiple fragments comprise at or about 45 to at or about 60 fragments per container in step (b).

In another embodiment, the invention provides the method described in any of the preceding paragraphs as applicable above modified such that the multiple fragments comprise at or about 50 to at or about 60 fragments per container in step (b).

In another embodiment, the invention provides the method described in any of the preceding paragraphs as applicable above modified such that the multiple fragments comprise at or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 fragment(s) per container in step (b).

In another embodiment, the invention provides the method described in any of the preceding paragraphs as applicable above modified such that each fragment has a volume of at or about 27 $mm^3$.

In another embodiment, the invention provides the method described in any of the preceding paragraphs as applicable above modified such that each fragment has a volume of at or about 20 $mm^3$ to at or about 50 $mm^3$.

In another embodiment, the invention provides the method described in any of the preceding paragraphs as applicable above modified such that each fragment has a volume of at or about 21 $mm^3$ to at or about 30 $mm^3$.

In another embodiment, the invention provides the method described in any of the preceding paragraphs as applicable above modified such that each fragment has a volume of at or about 22 $mm^3$ to at or about 29.5 $mm^3$.

In another embodiment, the invention provides the method described in any of the preceding paragraphs as applicable above modified such that each fragment has a volume of at or about 23 $mm^3$ to at or about 29 $mm^3$.

In another embodiment, the invention provides the method described in any of the preceding paragraphs as applicable above modified such that each fragment has a volume of at or about 24 $mm^3$ to at or about 28.5 $mm^3$.

In another embodiment, the invention provides the method described in any of the preceding paragraphs as applicable above modified such that each fragment has a volume of at or about 25 $mm^3$ to at or about 28 $mm^3$.

In another embodiment, the invention provides the method described in any of the preceding paragraphs as applicable above modified such that each fragment has a volume of at or about 26.5 $mm^3$ to at or about 27.5 $mm^3$.

In another embodiment, the invention provides the method described in any of the preceding paragraphs as applicable above modified such that each fragment has a volume of at or about 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 $mm^3$.

In another embodiment, the invention provides the method described in any of the preceding paragraphs as applicable above modified such that the multiple fragments comprise at or about 30 to at or about 60 fragments with a total volume of at or about 1300 $mm^3$ to at or about 1500 $mm^3$.

In another embodiment, the invention provides the method described in any of the preceding paragraphs as applicable above modified such that the multiple fragments comprise at or about 50 fragments with a total volume of at or about 1350 $mm^3$.

In another embodiment, the invention provides the method described in any of the preceding paragraphs as applicable above modified such that the multiple fragments comprise at or about 50 fragments with a total mass of at or about 1 gram to at or about 1.5 grams.

In another embodiment, the invention provides the method described in any of the preceding paragraphs as applicable above modified such that the cell culture medium is provided in a container that is a G-container or a Xuri cellbag.

In another embodiment, the invention provides the method described in any of the preceding paragraphs as applicable above modified such that the IL-2 concentration in the cell culture medium is about 10,000 IU/mL to about 5,000 IU/mL.

In another embodiment, the invention provides the method described in any of the preceding paragraphs as applicable above modified such that the IL-2 concentration in the cell culture medium is about 6,000 IU/mL.

In another embodiment, the invention provides the method described in any of the preceding paragraphs as applicable above modified such that the cryopreservation media comprises dimethlysulfoxide (DMSO).

In another embodiment, the invention provides the method described in any of the preceding paragraphs as applicable above modified such that the cryopreservation media comprises 7% to 10% DMSO.

In another embodiment, the invention provides the method described in any of the preceding paragraphs as applicable above modified such that the first period in step (b) is performed within a period of at or about 1 day, 2 days, 3 days, 4 days, 5 days, 6 days, or 7 days.

In another embodiment, the invention provides the method described in any of the preceding paragraphs as applicable above modified such that the second period in step (c) is performed within a period of at or about 1 day, 2 days, 3 days, 4 days, 5 days, 6 days, 7 days, 8 days, 9 days, 10 days or 11 days.

In another embodiment, the invention provides the method described in any of the preceding paragraphs as applicable above modified such that the first period in step (b) and the second period in step (c) are each individually performed within a period of at or about 1 day, 2 days, 3 days, 4 days, 5 days, 6 days, or 7 days.

In another embodiment, the invention provides the method described in any of the preceding paragraphs as applicable above modified such that the first period in step (b) and the second period in step (c) are each individually performed within a period of at or about 5 days, 6 days, or 7 days.

In another embodiment, the invention provides the method described in any of the preceding paragraphs as applicable above modified such that the first period in step (b) and the second period in step (c) are each individually performed within a period of at or about 7 days.

In another embodiment, the invention provides the method described in any of the preceding paragraphs as applicable above modified such that steps (a) through (d) are performed in a total of at or about 14 days to at or about 18 days.

In another embodiment, the invention provides the method described in any of the preceding paragraphs as applicable above modified such that steps (a) through (d) are performed in a total of at or about 15 days to at or about 18 days.

In another embodiment, the invention provides the method described in any of the preceding paragraphs as applicable above modified such that steps (a) through (d) are performed in a total of at or about 16 days to at or about 18 days.

In another embodiment, the invention provides the method described in any of the preceding paragraphs as applicable above modified such that steps (a) through (d) are performed in a total of at or about 14 days to at or about 17 days.

In another embodiment, the invention provides the method described in any of the preceding paragraphs as applicable above modified such that steps (a) through (d) are performed in a total of at or about 15 days to at or about 17 days.

In another embodiment, the invention provides the method described in any of the preceding paragraphs as applicable above modified such that steps (a) through (d) are performed in a total of at or about 14 days to at or about 16 days.

In another embodiment, the invention provides the method described in any of the preceding paragraphs as applicable above modified such that steps (a) through (d) are performed in a total of at or about 15 days to at or about 16 days.

In another embodiment, the invention provides the method described in any of the preceding paragraphs as applicable above modified such that steps (a) through (d) are performed in a total of at or about 14 days.

In another embodiment, the invention provides the method described in any of the preceding paragraphs as applicable above modified such that steps (a) through (d) are performed in a total of at or about 15 days.

In another embodiment, the invention provides the method described in any of the preceding paragraphs as applicable above modified such that steps (a) through (d) are performed in a total of at or about 16 days.

In another embodiment, the invention provides the method described in any of the preceding paragraphs as applicable above modified such that steps (a) through (d) are performed in a total of at or about 17 days.

In another embodiment, the invention provides the method described in any of the preceding paragraphs as applicable above modified such that steps (a) through (d) are performed in a total of at or about 18 days.

In another embodiment, the invention provides the method described in any of the preceding paragraphs as applicable above modified such that steps (a) through (d) are performed in a total of at or about 14 days or less.

In another embodiment, the invention provides the method described in any of the preceding paragraphs as applicable above modified such that steps (a) through (d) are performed in a total of at or about 15 days or less.

In another embodiment, the invention provides the method described in any of the preceding paragraphs as applicable above modified such that steps (a) through (d) are performed in a total of at or about 16 days or less.

In another embodiment, the invention provides the method described in any of the preceding paragraphs as applicable above modified such that steps (a) through (d) are performed in a total of at or about 17 days or less.

In another embodiment, the invention provides the method described in any of the preceding paragraphs as applicable above modified such that steps (a) through (d) are performed in a total of at or about 18 days or less.

In another embodiment, the invention provides the method described in any of the preceding paragraphs as applicable above modified such that the therapeutic population of TILs harvested in step (d) comprises sufficient TILs for a therapeutically effective dosage of the TILs.

In another embodiment, the invention provides the method described in any of the preceding paragraphs as applicable above modified such that the number of TILs sufficient for a therapeutically effective dosage is from at or about $2.3\times10^{10}$ to at or about $13.7\times10^{10}$.

In another embodiment, the invention provides the method described in any of the preceding paragraphs as applicable above modified such that the third population of TILs in step (c) provides for increased efficacy, increased interferon-gamma production, and/or increased polyclonality.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 16 days.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 17 days.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 18 days.

In another embodiment, the invention provides the method described in any of the preceding paragraphs as applicable above modified such that the effector T cells and/or central memory T cells obtained from the third population of TILs step (c) exhibit increased CD8 and CD28 expression relative to effector T cells and/or central memory T cells obtained from the second population of cells step (b).

In another embodiment, the invention provides the method described in any of the preceding paragraphs as applicable above modified such that each container recited in the method is a closed container.

In another embodiment, the invention provides the method described in any of the preceding paragraphs as applicable above modified such that each container recited in the method is a G-container.

In another embodiment, the invention provides the method described in any of the preceding paragraphs as applicable above modified such that each container recited in the method is a GREX-10.

In another embodiment, the invention provides the method described in any of the preceding paragraphs as applicable above modified such that each container recited in the method is a GREX-100.

In another embodiment, the invention provides the method described in any of the preceding paragraphs as applicable above modified such that each container recited in the method is a GREX-500.

In another embodiment, the invention provides the therapeutic population of tumor infiltrating lymphocytes (TILs) made by the method described in any of the preceding paragraphs as applicable above.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added antigen-presenting cells (APCs) or OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added antigen-presenting cells (APCs).

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed with no added antigen-presenting cells (APCs) and no added OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 16 days.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 17 days.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 18 days.

In another embodiment, the invention provides for the therapeutic population of TILs described in any of the preceding paragraphs as applicable above that provides for increased interferon-gamma production.

In another embodiment, the invention provides for the therapeutic population of TILs described in any of the preceding paragraphs as applicable above that provides for increased polyclonality.

In another embodiment, the invention provides for the therapeutic population of TILs described in any of the preceding paragraphs as applicable above that provides for increased efficacy.

In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 16 days. In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 17 days. In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 18 days. In some embodiments, the TILs are rendered capable of the at least one-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 16 days. In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 17 days. In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 18 days. In some embodiments, the TILs are rendered capable of the at least two-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 16 days. In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 17 days. In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 18 days. In some embodiments, the TILs are rendered capable of the at least three-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for a therapeutic population of tumor infiltrating lymphocytes (TILs) that is capable of at least one-fold more interferon-gamma production as compared to TILs prepared by a process in which the first expansion of TILs is performed without any added antigen-presenting cells (APCs). In some embodiments, the TILs are rendered capable of the at least one-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for a therapeutic population of tumor infiltrating lymphocytes (TILs) that is capable of at least one-fold more interferon-gamma production as compared to TILs prepared by a process in which the first expansion of TILs is performed without any added OKT3. In some embodiments, the TILs are rendered capable of the at least one-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for a therapeutic population of TILs that is capable of at least two-fold more interferon-gamma production as compared to TILs prepared by a process in which the first expansion of TILs is performed without any added APCs.

In another embodiment, the invention provides for a therapeutic population of TILs that is capable of at least two-fold more interferon-gamma production as compared to TILs prepared by a process in which the first expansion of TILs is performed without any added APCs. In some embodiments, the TILs are rendered capable of the at least two-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for a therapeutic population of TILs that is capable of at least two-fold more interferon-gamma production as compared to TILs prepared by a process in which the first expansion of TILs is performed without any added OKT3. In some embodiments, the TILs are rendered capable of the at least two-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for a therapeutic population of TILs that is capable of at least three-fold more interferon-gamma production as compared to TILs prepared by a process in which the first expansion of TILs is performed without any added APCs. In some embodiments, the TILs are rendered capable of the at least one-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for a therapeutic population of TILs that is capable of at least three-fold more interferon-gamma production as compared to TILs prepared by a process in which the first expansion of TILs is performed without any added OKT3. In some embodiments, the TILs are rendered capable of the at least three-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides a method of expanding T cells comprising: (a) performing a priming first expansion of a first population of T cells obtained from a donor by culturing the first population of T cells to effect growth and to prime an activation of the first population of T cells; (b) after the activation of the first population of T cells primed in step (a) begins to decay, performing a rapid second expansion of the first population of T cells by culturing the first population of T cells to effect growth and to boost the activation of the first population of T cells to obtain a second population of T cells; and (c) harvesting the second population of T cells. In another embodiment, the step of rapid second expansion is split into a plurality of steps to achieve a scaling up of the culture by: (a) performing the rapid second expansion by culturing the first population of T cells in a small scale culture in a first container, e.g., a G-REX 100 MCS container, for a period of about 3 to 4 days, and then (b) effecting the transfer of the first population of T cells from the small scale culture to a second container larger than the first container, e.g., a G-REX 500 MCS container, and culturing the first population of T cells from the small scale culture in a larger scale culture in the second container for a period of about 4 to 7 days. In another embodiment, the step of rapid expansion is split into a plurality of steps to achieve a scaling out of the culture by: (a) performing the rapid second expansion by culturing the first population of T cells in a first small scale culture in a first container, e.g., a G-REX 100 MCS container, for a period of about 3 to 4 days, and then (b) effecting the transfer and apportioning of the first population of T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the first population of T cells from first small scale culture transferred to such second container is cultured in a second small scale culture for a period of about 4 to 7 days. In another embodiment, the step of rapid expansion is split into a plurality of steps to achieve a scaling out and scaling up of the culture by: (a) performing the rapid second expansion by culturing the first population of T cells in a small scale culture in a first container, e.g., a G-REX 100 MCS container, for a period of about 3 to 4 days, and then (b) effecting the transfer and apportioning of the first population of T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500 MCS containers, wherein in each second container the portion of the first population of T cells from the small scale culture transferred to such second container is cultured in a larger scale culture for a period of about 4 to 7 days. In another embodiment, the step of rapid expansion is split into a plurality of steps to achieve a scaling out and scaling up of the culture by: (a) performing the rapid second expansion by culturing the first population of T cells in a small scale culture in a first container, e.g., a G-REX 100 MCS container, for a period of about 4 days, and then (b) effecting the transfer and apportioning of the first population of T cells from the small scale culture into and amongst 2, 3 or 4 second containers that are larger in size than the first container, e.g., G-REX 500 MCS containers, wherein in each second container the portion of the first population of T cells from the small scale culture transferred to such second container is cultured in a larger scale culture for a period of about 5 days.

In another embodiment, the invention provides the method described in any of the preceding paragraphs as applicable above modified such that the step of rapid second expansion is split into a plurality of steps to achieve a scaling up of the culture by: (a) performing the rapid second expansion by culturing the first population of T cells in a small scale culture in a first container, e.g., a G-REX 100 MCS container, for a period of about 2 to 4 days, and then (b) effecting the transfer of the first population of T cells from the small scale culture to a second container larger than the first container, e.g., a G-REX 500 MCS container, and culturing the first population of T cells from the small scale culture in a larger scale culture in the second container for a period of about 5 to 7 days.

In another embodiment, the invention provides the method described in any of the preceding paragraphs as applicable above modified such that the step of rapid expansion is split into a plurality of steps to achieve a scaling out of the culture by: (a) performing the rapid second expansion by culturing the first population of T cells in a first small scale culture in a first container, e.g., a G-REX 100 MCS container, for a period of about 2 to 4 days, and then (b) effecting the transfer and apportioning of the first population of T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the first population of T cells from first small scale culture transferred to such second container is cultured in a second small scale culture for a period of about 5 to 7 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100 MCS container, for a period of about 2 to 4 days, and then (b) effecting the transfer and apportioning of the first population of T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500 MCS containers, wherein in each second container the portion of the first population of T cells from the small scale culture transferred to such second container is cultured in a larger scale culture for a period of about 5 to 7 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100 MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500 MCS containers, wherein in each second container the portion of the first population of T cells from the small scale culture transferred to such second container is cultured in a larger scale culture for a period of about 5 to 6 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100 MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500 MCS containers, wherein in each second container the portion of the first population of T cells from the small scale culture transferred to such second container is cultured in a larger scale culture for a period of about 5 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100 MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500 MCS containers, wherein in each second container the portion of the first population of T cells from the small scale culture transferred to such second container is cultured in a larger scale culture for a period of about 6 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100 MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500 MCS containers, wherein in each second container the portion of the first population of T cells from the small scale culture transferred to such second container is cultured in a larger scale culture for a period of about 7 days.

In another embodiment, the invention provides the method described in any of the preceding paragraphs as applicable above modified such that the priming first expansion of step (a) is performed during a period of up to 7 days.

In another embodiment, the invention provides the method described in any of the preceding paragraphs as applicable above modified such that the rapid second expansion of step (b) is performed during a period of up to 8 days.

In another embodiment, the invention provides the method described in any of the preceding paragraphs as applicable above modified such that the rapid second expansion of step (b) is performed during a period of up to 9 days.

In another embodiment, the invention provides the method described in any of the preceding paragraphs as applicable above modified such that the rapid second expansion of step (b) is performed during a period of up to 10 days.

In another embodiment, the invention provides the method described in any of the preceding paragraphs as applicable above modified such that the rapid second expansion of step (b) is performed during a period of up to 11 days.

In another embodiment, the invention provides the method described in any of the preceding paragraphs as applicable above modified such that the priming first expansion in step (a) is performed during a period of 7 days and the rapid second expansion of step (b) is performed during a period of up to 9 days.

In another embodiment, the invention provides the method described in any of the preceding paragraphs as applicable above modified such that the priming first expansion in step (a) is performed during a period of 7 days and the rapid second expansion of step (b) is performed during a period of up to 10 days.

In another embodiment, the invention provides the method described in any of the preceding paragraphs as applicable above modified such that the priming first expansion in step (a) is performed during a period of 7 days or 8 days and the rapid second expansion of step (b) is performed during a period of up to 9 days.

In another embodiment, the invention provides the method described in any of the preceding paragraphs as applicable above modified such that the priming first expansion in step (a) is performed during a period of 7 days or 8 days and the rapid second expansion of step (b) is performed during a period of up to 10 days.

In another embodiment, the invention provides the method described in any of the preceding paragraphs as applicable above modified such that the priming first expansion in step (a) is performed during a period of 8 days and the rapid second expansion of step (b) is performed during a period of up to 9 days.

In another embodiment, the invention provides the method described in any of the preceding paragraphs as applicable above modified such that the priming first expansion in step (a) is performed during a period of 8 days and the rapid second expansion of step (b) is performed during a period of up to 8 days.

In another embodiment, the invention provides the method described in any of the preceding paragraphs as applicable above modified such that in step (a) the first population of T cells is cultured in a first culture medium comprising OKT-3 and IL-2.

In another embodiment, the invention provides the method described in any of the preceding paragraphs as applicable above modified such that the first culture medium comprises 4-1BB agonist, OKT-3 and IL-2.

In another embodiment, the invention provides the method described in any of the preceding paragraphs as applicable above modified such that the first culture medium comprises OKT-3, IL-2 and antigen-presenting cells (APCs).

In another embodiment, the invention provides the method described in any of the preceding paragraphs as applicable above modified such that the first culture medium comprises 4-1BB agonist, OKT-3, IL-2 and antigen-presenting cells (APCs).

In another embodiment, the invention provides the method described in any of the preceding paragraphs as applicable above modified such that in step (a) the first population of T cells is cultured in a first culture medium in a container comprising a first gas-permeable surface, wherein the first culture medium comprises OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that in step (a) the first population of T cells is cultured in a first culture medium in a container comprising a first gas-permeable surface, wherein the first culture medium comprises 4-1BB agonist, OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that in step (a) the first population of T cells is cultured in a first culture medium in a container comprising a first gas-permeable surface, wherein the first culture medium comprises OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises 4-1BB agonist, OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that in step (a) the first population of T cells is cultured in a first culture medium in a container comprising a first gas-permeable surface, wherein the first culture medium comprises 4-1BB agonist, OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises 4-1BB agonist, OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that the ratio of the number of APCs in the second population of APCs to the number of APCs in the first population of APCs is about 2:1.

In another embodiment, the invention provides the method described in any of the preceding paragraphs as applicable above modified such that the number of APCs in the first population of APCs is about $2.5\times10^8$ and the number of APCs in the second population of APCs is about $5\times10^8$.

In another embodiment, the invention provides the method described in any of the preceding paragraphs as applicable above modified such that in step (a) the first population of APCs is layered onto the first gas-permeable surface at an average thickness of 2 layers of APCs.

In another embodiment, the invention provides the method described in any of the preceding paragraphs as applicable above modified such that in step (b) the second population of APCs is layered onto the first gas-permeable surface at an average thickness selected from the range of 4 to 8 layers of APCs.

In another embodiment, the invention provides the method described in any of the preceding paragraphs as applicable above modified such that the ratio of the average number of layers of APCs layered onto the first gas-permeable surface in step (b) to the average number of layers of APCs layered onto the first gas-permeable surface in step (a) is 2:1.

In another embodiment, the invention provides the method described in any of the preceding paragraphs as applicable above modified such that in step (a) the first population of APCs is seeded on the first gas permeable surface at a density selected from the range of at or about $1.0\times10^6$ APCs/cm$^2$ to at or about $4.5\times10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $1.5\times10^6$ APCs/cm$^2$ to at or about $3.5\times10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $2.0\times10^6$ APCs/cm$^2$ to at or about $3.0\times10^6$ APCs/cm$^2$ In another embodiment, the invention provides the method described in any of the preceding paragraphs as applicable above modified such that in step (a) the first population of APCs is seeded on the first gas permeable surface at a density of at or about $2.0\times10^6$ APCs/cm$^2$.

In another embodiment, the invention provides the method described in any of the preceding paragraphs as applicable above modified such that in step (b) the second population of APCs is seeded on the first gas permeable surface at a density selected from the range of at or about $2.5\times10^6$ APCs/cm$^2$ to at or about $7.5\times10^6$ APCs/cm$^2$.

In another embodiment, the invention provides the method described in any of the preceding paragraphs as applicable above modified such that in step (b) the second population of APCs is seeded on the first gas permeable surface at a density selected from the range of at or about $3.5\times10^6$ APCs/cm$^2$ to at or about $6.0\times10^6$ APCs/cm$^2$.

In another embodiment, the invention provides the method described in any of the preceding paragraphs as applicable above modified such that in step (b) the second population of APCs is seeded on the first gas permeable surface at a density selected from the range of at or about $4.0\times10^6$ APCs/cm$^2$ to at or about $5.5\times10^6$ APCs/cm$^2$.

In another embodiment, the invention provides the method described in any of the preceding paragraphs as applicable above modified such that in step (b) the second population of APCs is seeded on the first gas permeable surface at a density of at or about $4.0\times10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $1.0\times10^6$ APCs/cm$^2$ to at or about $4.5\times10^6$ APCs/cm$^2$ and in step (b) the second population of APCs is seeded on the first gas permeable surface at a density selected from the range of at or about $2.5\times10^6$ APCs/cm$^2$ to at or about $7.5\times10^6$ APCs/cm$^2$.

In another embodiment, the invention provides the method described in any of the preceding paragraphs as applicable modified such that in step (a) the first population of APCs is seeded on the first gas permeable surface at a density selected from the range of at or about $1.5\times10^6$ APCs/cm$^2$ to at or about $3.5\times10^6$ APCs/cm$^2$ and in step (b) the second population of APCs is seeded on the first gas permeable surface at a density selected from the range of at or about $3.5\times10^6$ APCs/cm$^2$ to at or about $6.0\times10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $2.0\times10^6$ APCs/cm$^2$ to at or about $3.0\times10^6$ APCs/cm$^2$ and in step (b) the second population of APCs is seeded on the first gas permeable surface at a density selected from the range of at or about $4.0\times10^6$ APCs/cm$^2$ to at or about $5.5\times10^6$ APCs/cm$^2$.

In another embodiment, the invention provides the method described in any of the preceding paragraphs as applicable above modified such that in step (a) the first population of APCs is seeded on the first gas permeable surface at a density of at or about $2.0\times10^6$ APCs/cm$^2$ and in step (b) the second population of APCs is seeded on the first gas permeable surface at a density of at or about $4.0\times10^6$ APCs/cm$^2$.

In another embodiment, the invention provides the method described in any of the preceding paragraphs as applicable above modified such that the APCs are peripheral blood mononuclear cells (PBMCs).

In another embodiment, the invention provides the method described in any of the preceding paragraphs as applicable above modified such that the PBMCs are irradiated and exogenous to the donor of the first population of T cells.

In another embodiment, the invention provides the method described in any of the preceding paragraphs as applicable above modified such that the T cells are tumor infiltrating lymphocytes (TILs).

In another embodiment, the invention provides the method described in any of the preceding paragraphs as applicable above modified such that the T cells are marrow infiltrating lymphocytes (MILs).

In another embodiment, the invention provides the method described in any of the preceding paragraphs as applicable above modified such that the T cells are peripheral blood lymphocytes (PBLs).

In another embodiment, the invention provides the method described in any of the preceding paragraphs as applicable above modified such that the first population of T cells is obtained by separation from the whole blood of the donor.

In another embodiment, the invention provides the method described in any of the preceding paragraphs as applicable above modified such that the first population of T cells is obtained by separation from the apheresis product of the donor.

In another embodiment, the invention provides the method described in any of the preceding paragraphs as applicable above modified such that the first population of T cells is separated from the whole blood or apheresis product of the donor by positive or negative selection of a T cell phenotype.

In another embodiment, the invention provides the method described in any of the preceding paragraphs as applicable above modified such that the T cell phenotype is CD3+ and CD45+.

In another embodiment, the invention provides the method described in any of the preceding paragraphs as applicable above modified such that before performing the priming first expansion of the first population of T cells the T cells are separated from NK cells. In another embodiment, the T cells are separated from NK cells in the first population of T cells by removal of CD3-CD56+ cells from the first population of T cells. In another embodiment, the CD3-CD56+ cells are removed from the first population of T cells by subjecting the first population of T cells to cell sorting using a gating strategy that removes the CD3-CD56+ cell fraction and recovers the negative fraction. In another embodiment, the foregoing method is utilized for the expansion of T cells in a first population of T cells characterized by a high percentage of NK cells. In another embodiment, the foregoing method is utilized for the expansion of T cells in a first population of T cells characterized by a high percentage of CD3-CD56+ cells. In another embodiment, the foregoing method is utilized for the expansion of T cells in tumor tissue characterized by the present of a high number of NK cells. In another embodiment, the foregoing method is utilized for the expansion of T cells in tumor tissue characterized by a high number of CD3-CD56+ cells. In another embodiment, the foregoing method is utilized for the expansion of T cells in tumor tissue obtained from a patient suffering from a tumor characterized by the presence of a high number of NK cells. In another embodiment, the foregoing method is utilized for the expansion of T cells in tumor tissue obtained from a patient suffering from a tumor characterized by the presence of a high number of CD3-CD56+ cells. In another embodiment, the foregoing method is utilized for the expansion of T cells in tumor tissue obtained from a patient suffering from ovarian cancer.

In another embodiment, the invention provides the method described in any of the preceding paragraphs as applicable above modified such that at or about $1\times10^7$ T cells from the first population of T cells are seeded in a container to initiate the primary first expansion culture in such container.

In another embodiment, the invention provides the method described in any of the preceding paragraphs as applicable above modified such that the first population of T cells is distributed into a plurality of containers, and in each container at or about $1\times10^7$ T cells from the first population of T cells are seeded to initiate the primary first expansion culture in such container.

In another embodiment, the invention provides the method described in any of the preceding paragraphs as applicable above modified such that the second population of T cells harvested in step (c) is a therapeutic population of TILs.

III. Pharmaceutical Compositions, Dosages, and Dosing Regimens

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3\times10^{10}$ to about $13.7\times10^{10}$ TILs are administered, with an average of around $7.8\times10^{10}$ TILs, particularly if the cancer is melanoma. In an embodiment, about $1.2\times10^{10}$ to about $4.3\times10^{10}$ of TILs are administered. In some embodiments, about $3\times10^{10}$ to about $12\times10^{10}$ TILs are administered. In some embodiments, about $4\times10^{10}$ to about $10\times10^{10}$ TILs are administered. In some embodiments, about $5\times10^{10}$ to about $8\times10^{10}$ TILs are administered. In some embodiments, about $6\times10^{10}$ to about $8\times10^{10}$ TILs are administered. In some embodiments, about $7\times10^{10}$ to about $8\times10^{10}$ TILs are administered. In some embodiments, the therapeutically effective dosage is about $2.3\times10^{10}$ to about $13.7\times10^{10}$. In some embodiments, the therapeutically effective dosage is about $7.8\times10^{10}$ TILs, particularly of the cancer is melanoma. In some embodiments, the therapeutically effective dosage is about $1.2\times10^{10}$ to about $4.3\times10^{10}$ of TILs. In some embodiments, the therapeutically effective dosage is about $3\times10^{10}$ to about $12\times10^{10}$ TILs. In some embodiments, the therapeutically effective dosage is about $4\times10^{10}$ to about $10\times10^{10}$ TILs. In some embodiments, the therapeutically effective dosage is about $5\times10^{10}$ to about $8\times10^{10}$ TILs. In some embodiments, the therapeutically effective dosage is about $6\times10^{10}$ to about $8\times10^{10}$ TILs. In some embodiments, the therapeutically effective dosage is about $7\times10^{10}$ to about $8\times10^{10}$ TILs.

In some embodiments, the number of the TILs provided in the pharmaceutical compositions of the invention is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In an embodiment, the number of the TILs provided in the pharmaceutical compositions of the invention is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to 1x1011, $5\times10^{11}$ to $1\times10^{12}$, $1\times10^{12}$ to $5\times10^{12}$, and $5\times10^{12}$ to $1\times10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25%, 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $\mathbf{1\times10^{12}}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

In another embodiment, the invention provides an infusion bag comprising the therapeutic population of TILs described in any of the preceding paragraphs as applicable above.

In another embodiment, the invention provides a tumor infiltrating lymphocyte (TIL) composition comprising the therapeutic population of TILs described in any of the preceding paragraphs as applicable above and a pharmaceutically acceptable carrier.

In another embodiment, the invention provides an infusion bag comprising the TIL composition described in any of the preceding paragraphs as applicable above.

In another embodiment, the invention provides a cryopreserved preparation of the therapeutic population of TILs described in any of the preceding paragraphs as applicable above.

In another embodiment, the invention provides a tumor infiltrating lymphocyte (TIL) composition comprising the therapeutic population of TILs described in any of the preceding paragraphs as applicable above and a cryopreservation media.

In another embodiment, the invention provides the TIL composition described in any of the preceding paragraphs as applicable above modified such that the cryopreservation media contains DMSO.

In another embodiment, the invention provides the TIL composition described in any of the preceding paragraphs as applicable above modified such that the cryopreservation media contains 7-10% DMSO.

In another embodiment, the invention provides a cryopreserved preparation of the TIL composition described in any of the preceding paragraphs as applicable.

IV. Methods of Treating Patients

Methods of treatment begin with the initial TIL collection and culture of TILs. Such methods have been both described in the art by, for example, Jin et al., *J. Immunotherapy,* 2012, 35 (3): 283-292, incorporated by reference herein in its entirety. Embodiments of methods of treatment are described throughout the sections below, including the Examples.

The expanded TILs produced according the methods described herein, including for example as described in Steps A through F above or according to Steps A through F above (also as shown, for example, in FIG. 1 (in particular, e.g., FIG. 1B) find particular use in the treatment of patients with cancer (for example, as described in Goff, et al., *J. Clinical Oncology,* 2016, 34 (20): 2389-239, as well as the supplemental content; incorporated by reference herein in its entirety. In some embodiments, TIL were grown from resected deposits of metastatic melanoma as previously described (see, Dudley, et al., *J Immunother.,* 2003, 26:332-342; incorporated by reference herein in its entirety). Fresh tumor can be dissected under sterile conditions. A representative sample can be collected for formal pathologic analysis. Single fragments of 2 $mm^3$ to 3 $mm^3$ may be used. In some embodiments, 5, 10, 15, 20, 25 or 30 samples per patient are obtained. In some embodiments, 20, 25, or 30 samples per patient are obtained. In some embodiments, 20, 22, 24, 26, or 28 samples per patient are obtained. In some embodiments, 24 samples per patient are obtained. Samples can be placed in individual wells of a 24-well plate, maintained in growth media with high-dose IL-2 (6,000 IU/mL), and monitored for destruction of tumor and/or proliferation of TIL. Any tumor with viable cells remaining after processing can be enzymatically digested into a single cell suspension and cryopreserved, as described herein.

In some embodiments, successfully grown TIL can be sampled for phenotype analysis (CD3, CD4, CD8, and CD56) and tested against autologous tumor when available. TIL can be considered reactive if overnight coculture yielded interferon-gamma (IFN-γ) levels >200 μg/mL and twice background. (Goff, et al., *J Immunother.,* 2010, 33:840-847; incorporated by reference herein in its entirety). In some embodiments, cultures with evidence of autologous reactivity or sufficient growth patterns can be selected for a second expansion (for example, a second expansion as provided in according to Step D of FIG. 1 (in particular, e.g., FIG. 1B), including second expansions that are sometimes referred to as rapid expansion (REP). In some embodiments, expanded TILs with high autologous reactivity (for example, high proliferation during a second expansion), are selected for an additional second expansion. In some embodiments, TILs with high autologous reactivity (for example, high proliferation during second expansion as provided in Step D of FIG. 1 (in particular, e.g., FIG. 1B), are selected for an additional second expansion according to Step D of FIG. 1 (in particular, e.g., FIG. 1B).

In some embodiments, the patient is not moved directly to ACT (adoptive cell transfer), for example, in some embodiments, after tumor harvesting and/or a first expansion, the cells are not utilized immediately. In some embodiments, TILs can be cryopreserved and thawed 2 days before administration to a patient. In some embodiments, TILs can be cryopreserved and thawed 1 day before administration to a patient. In some embodiments, the TILs can be cryopreserved and thawed immediately before the administration to a patient.

Cell phenotypes of cryopreserved samples of infusion bag TIL can be analyzed by flow cytometry (e.g., FlowJo) for surface markers CD3, CD4, CD8, CCR7, and CD45RA (BD BioSciences), as well as by any of the methods described herein. Serum cytokines were measured by using standard enzyme-linked immunosorbent assay techniques. A rise in serum IFN-g was defined as >100 μg/mL and greater than 4 3 baseline levels.

In some embodiments, the TILs produced by the methods provided herein, for example those exemplified in FIG. 1 (in particular, e.g., FIG. 1B), provide for a surprising improvement in clinical efficacy of the TILs. In some embodiments, the TILs produced by the methods provided herein, for example those exemplified in FIG. 1 (in particular, e.g., FIG. 1B), exhibit increased clinical efficacy as compared to TILs produced by methods other than those described herein, including for example, methods other than those exemplified in FIG. 1 (in particular, e.g., FIG. 1B). In some embodiments, the methods other than those described herein include methods referred to as process 1C and/or Generation 1 (Gen 1). In some embodiments, the increased efficacy is measured by DCR, ORR, and/or other clinical responses. In some embodiments, the TILS produced by the methods provided herein, for example those exemplified in FIG. 1 (in particular, e.g., FIG. 1B), exhibit a similar time to response and safety profile compared to TILs produced by methods other than those described herein, including for example, methods other than those exemplified in FIG. 1 (in particular, e.g., FIG. 1B), for example the Gen 1 process.

In some embodiments, IFN-gamma (IFN-γ) is indicative of treatment efficacy and/or increased clinical efficacy. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood, serum, or TILs ex vivo of a subject treated with TILs prepared by the methods of the present invention, including those as described for example in FIG. 1 (in particular, e.g., FIG. 1B). In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including for example, methods other than those embodied in FIG. 1 (in particular, e.g., FIG. 1B). In some embodiments, IFN-γ secretion is increased one-fold as compared to an untreated patient and/or as compared to a patient treated with TILs prepared using other methods than those provide herein including for example, methods other than those embodied in FIG. 1 (in particular, e.g., FIG. 1B). In some embodiments, IFN-γ secretion is increased two-fold as compared to an untreated patient and/or as compared to a patient treated with TILs prepared using other methods than those provide herein including for example, methods other than those embodied in FIG. 1 (in particular, e.g., FIG. 1B). In some embodiments, IFN-γ secretion is increased three-fold as compared to an untreated patient and/or as compared to a patient treated with TILs prepared using other methods than those provide herein including for example, methods other than those embodied in FIG. 1 (in particular, e.g., FIG. 1B). In some embodiments, IFN-γ secretion is increased four-fold as compared to an untreated patient and/or as compared to a patient treated with TILs prepared using other methods than those provide herein including for example, methods other than those embodied in FIG. 1 (in particular, e.g., FIG. 1B). In some embodiments, IFN-γ secretion is increased five-fold as compared to an untreated patient and/or as compared to a patient treated with TILs prepared using other methods than those provide herein including for example, methods other than those embodied in FIG. 1 (in particular, e.g., FIG. 1B). In some embodiments, IFN-γ is measured using a Quantikine ELISA kit. In some embodiments, IFN-γ is measured in TILs ex vivo of a subject treated with TILs prepared by the methods of the present invention, including those as described for example in FIG. 1 (in particular, e.g., FIG. 1B). In some embodiments, IFN-γ is measured in blood of a subject treated with TILs prepared by the methods of the present invention, including those as described for example in FIG. 1 (in particular, e.g., FIG. 1B). In some embodiments, IFN-γ is measured in TILs serum of a subject treated with TILs prepared by the methods of the present invention, including those as described for example in FIG. 1 (in particular, e.g., FIG. 1B).

In some embodiments, the TILs prepared by the methods of the present invention, including those as described for example in FIG. 1 (in particular, e.g., FIG. 1B), exhibit increased polyclonality as compared to TILs produced by other methods, including those not exemplified in FIG. 1 (in particular, e.g., FIG. 1B), such as for example, methods referred to as process 1C methods. In some embodiments, significantly improved polyclonality and/or increased polyclonality is indicative of treatment efficacy and/or increased clinical efficacy. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 1 (in particular, e.g., FIG. 1B). In some embodiments, polyclonality is increased one-fold as compared to an untreated patient and/or as compared to a patient treated with TILs prepared using other methods than those provide herein including for example, methods other than those embodied in FIG. 1 (in particular, e.g., FIG. 1B). In some embodiments, polyclonality is increased two-fold as compared to an untreated patient and/or as compared to a patient treated with TILs prepared using other methods than those provide herein including for example, methods other than those embodied in FIG. 1 (in particular, e.g., FIG. 1B). In some embodiments, polyclonality is increased ten-fold as compared to an untreated patient and/or as compared to a patient treated with TILs prepared using other methods than those provide herein including for example, methods other than those embodied in FIG. 1 (in particular, e.g., FIG. 1B). In some embodiments, polyclonality is increased 100-fold as compared to an untreated patient and/or as compared to a patient treated with TILs prepared using other methods than those provide herein including for example, methods other than those embodied in FIG. 1 (in particular, e.g., FIG. 1B). In some embodiments, polyclonality is increased 500-fold as compared to an untreated patient and/or as compared to a patient treated with TILs prepared using other methods than those provide herein including for example, methods other than those embodied in FIG. 1 (in particular, e.g., FIG. 1B). In some embodiments, polyclonality is increased 1000-fold as compared to an untreated patient and/or as compared to a patient treated with TILs prepared using other methods than those provide herein including for example, methods other than those embodied in FIG. 1 (in particular, e.g., FIG. 1B).

Measures of efficacy can include the disease control rate (DCR) as well as overall response rate (ORR), as known in the art as well as described herein.

1. Methods of Treating Cancers and Other Diseases

The compositions and methods described herein can be used in a method for treating diseases. In an embodiment, they are for use in treating hyperproliferative disorders. They may also be used in treating other disorders as described herein and in the following paragraphs.

In some embodiments, the hyperproliferative disorder is cancer. In some embodiments, the hyperproliferative disorder is a solid tumor cancer. In some embodiments, the solid tumor cancer is selected from the group consisting of glioblastoma (GBM), gastrointestinal cancer, melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma. In some embodiments, the hyperproliferative disorder is a hematological malignancy. In some embodiments, the solid tumor cancer is selected from the group consisting of chronic lymphocytic leukemia, acute lymphoblastic leukemia, diffuse large B cell lymphoma, non-Hodgkin's lymphoma, Hodgkin's lymphoma, follicular lymphoma, and mantle cell lymphoma.

In some embodiments, the cancer is a hypermutated cancer phenotype. Hypermutated cancers are extensively described in Campbell, et al. (Cell, 171:1042-1056 (2017); incorporated by reference herein in its entirety for all purposes). In some embodiments, a hypermutated tumors comprise between 9 and 10 mutations per megabase (Mb). In some embodiments, pediatric hypermutated tumors comprise 9.91 mutations per megabase (Mb). In some embodiments, adult hypermutated tumors comprise 9 mutations per megabase (Mb). In some embodiments, enhanced hypermutated tumors comprise between 10 and 100 mutations per megabase (Mb). In some embodiments, enhanced pediatric hypermutated tumors comprise between 10 and 100 mutations per megabase (Mb). In some embodiments, enhanced adult hypermutated tumors comprise between 10 and 100 mutations per megabase (Mb). In some embodiments, an ultra-hypermutated tumors comprise greater than 100 mutations per megabase (Mb). In some embodiments, pediatric ultra-hypermutated tumors comprise greater than 100 mutations per megabase (Mb). In some embodiments, adult ultra-hypermutated tumors comprise greater than 100 mutations per megabase (Mb).

In some embodiments, the hypermutated tumors have mutations in replication repair pathways. In some embodiments, the hypermutated tumors have mutations in replication repair associated DNA polymerases. In some embodiments, the hypermutated tumors have microsatellite instability. In some embodiments, the ultra-hypermutated tumors have mutations in replication repair associated DNA polymerases and have microsatellite instability. In some embodiments, hypermutation in the tumor is correlated with response to immune checkpoint inhibitors. In some embodiments, hypermutated tumors are resistant to treatment with immune checkpoint inhibitors. In some embodiments, hypermutated tumors can be treated using the TILs of the present invention. In some embodiments, hypermutation in the tumor is caused by environmental factors (extrinsic exposures). For example, UV light can be the primary cause of the high numbers of mutations in malignant melanoma (see, for example, Pfeifer, G. P., You, Y. H., and Besaratinia, A. (2005). Mutat. Res. 571, 19-31; Sage, E. (1993). Photochem. Photobiol. 57, 163-174). In some embodiments, hypermutation in the tumor can be caused by the greater than 60 carcinogens in tobacco smoke for tumors of the lung and larynx, as well as other tumors, due to direct mutagen exposure (see, for example, Pleasance, E. D., Stephens, P. J., O'Meara, S., McBride, D. J., Meynert, A., Jones, D., Lin, M. L., Beare, D., Lau, K. W., Greenman, C., et al. (2010). Nature 463, 184-190). In some embodiments, hypermutation in the tumor is caused by dysregulation of apolipoprotein B mRNA editing enzyme, catalytic polypeptide-like (APOBEC) family members, which has been shown to result in increased levels of C to T transitions in a wide range of cancers (see, for example, Roberts, S. A., Lawrence, M. S., Klimczak, L. J., Grimm, S. A., Fargo, D., Stojanov, P., Kiezun, A., Kryukov, G. V., Carter, S. L., Saksena, G., et al. (2013). Nat. Genet. 45, 970-976). In some embodiments, hypermutation in the tumor is caused by defective DNA replication repair by mutations that compromise proofreading, which is performed by the major replicative enzymes Pol3 and Pold1. In some embodiments, hypermutation in the tumor is caused by defects in DNA mismatch repair, which are associated with hypermutation in colorectal, endometrial, and other cancers (see, for example, Kandoth, C., Schultz, N., Cherniack, A. D., Akbani, R., Liu, Y., Shen, H., Robertson, A. G., Pashtan, I., Shen, R., Benz, C. C., et al.; (2013). Nature 497, 67-73; Muzny, D. M., Bainbridge, M. N., Chang, K., Dinh, H. H., Drummond, J. A., Fowler, G., Kovar, C. L., Lewis, L. R., Morgan, M. B., Newsham, I. F., et al.; (2012). Nature 487, 330-337). In some embodiments, DNA replication repair mutations are also found in cancer predisposition syndromes, such as constitutional or biallelic mismatch repair deficiency (CMMRD), Lynch syndrome, and polymerase proofreading-associated polyposis (PPAP).

In an embodiment, the invention includes a method of treating a cancer with a population of TILs, wherein the cancer is a hypermutated cancer. In an embodiment, the invention includes a method of treating a cancer with a population of TILs, wherein the cancer is an enhanced hypermutated cancer. In an embodiment, the invention includes a method of treating a cancer with a population of TILs, wherein the cancer is an ultra-hypermutated cancer.

In an embodiment, the invention includes a method of treating a cancer with a population of TILs, wherein a patient is pre-treated with non-myeloablative chemotherapy prior to an infusion of TILs according to the present disclosure. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 intravenously at 720,000 IU/kg every 8 hours to physiologic tolerance.

Efficacy of the compounds and combinations of compounds described herein in treating, preventing and/or managing the indicated diseases or disorders can be tested using various models known in the art, which provide guidance for treatment of human disease. For example, models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for pancreatic cancer are described in Herreros-Villanueva, et al., *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development,* 2005, 19, 643-664. Models for determining efficacy of treatments for lung cancer are described, e.g., in Kim, *Clin. Exp.* Otorhinolaryngol. 2009, 2, 55-60; and Sano, Head Neck Oncol. 2009, 1, 32.

In some embodiments, IFN-gamma (IFN-γ) is indicative of treatment efficacy for hyperproliferative disorder treatment. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood of a subject treated with TILs prepared by the methods of the present invention, including those as described for example in FIG. 1 (in particular, e.g., FIG. 1B). In some embodiments, the TILs obtained by the present method provide for increased IFN-γ in the blood of subjects treated with the TILs of the present method as compared subjects treated with TILs prepared using methods referred to as the Gen 3 process, as exemplified FIG. 1 (in particular, e.g., FIG. 1B) and throughout this application. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including for example, methods other than those embodied in FIG. 1 (in particular, e.g., FIG. 1B). In some embodiments, IFN-γ secretion is increased one-fold as compared to an untreated patient and/or as compared to a patient treated with TILs prepared using other methods than those provide herein including for example, methods other than those embodied in FIG. 1 (in particular, e.g., FIG. 1B). In some embodiments, IFN-γ secretion is increased two-fold as compared to an untreated patient and/or as compared to a patient treated with TILs prepared using other methods than those provide herein including for example, methods other than those embodied in FIG. 1 (in particular, e.g., FIG. 1B). In some embodiments, IFN-γ secretion is increased three-fold as compared to an untreated patient and/or as compared to a patient treated with TILs prepared using other methods than those provide herein including for example, methods other than those embodied in FIG. 1 (in particular, e.g., FIG. 1B). In some embodiments, IFN-γ secretion is increased four-fold as compared to an untreated patient and/or as compared to a patient treated with TILs prepared using other methods than those provide herein including for example, methods other than those embodied in FIG. 1 (in particular, e.g., FIG. 1B). In some embodiments, IFN-γ secretion is increased five-fold as compared to an untreated patient and/or as compared to a patient treated with TILs prepared using other methods than those provide herein including for example, methods other than those embodied in FIG. 1 (in particular, e.g., FIG. 1B). In some embodiments, IFN-γ is measured using a Quantikine ELISA kit. In some embodiments, IFN-γ is measured using a Quantikine ELISA kit. In some embodiments, IFN-γ is measured in TILs ex vivo from a patient treated with the TILs produced by the methods of the present invention. In some embodiments, IFN-γ is measured in blood in a patient treated with the TILs produced by the methods of the present invention. In some embodiments, IFN-γ is measured in serum in a patient treated with the TILs produced by the methods of the present invention.

In some embodiments, the TILs prepared by the methods of the present invention, including those as described for example in FIG. 1 (in particular, e.g., FIG. 1B), exhibit increased polyclonality as compared to TILs produced by other methods, including those not exemplified in FIG. 1 (in particular, e.g., FIG. 1B), such as for example, methods referred to as process 1C methods. In some embodiments, significantly improved polyclonality and/or increased polyclonality is indicative of treatment efficacy and/or increased clinical efficacy for cancer treatment. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 1 (in particular, e.g., FIG. 1B). In some embodiments, polyclonality is increased one-fold as compared to an untreated patient and/or as compared to a patient treated with TILs prepared using other methods than those provide herein including for example, methods other than those embodied in FIG. 1 (in particular, e.g., FIG. 1B). In some embodiments, polyclonality is increased two-fold as compared to an untreated patient and/or as compared to a patient treated with TILs prepared using other methods than those provide herein including for example, methods other than those embodied in FIG. 1 (in particular, e.g., FIG. 1B). In some embodiments, polyclonality is increased ten-fold as compared to an untreated patient and/or as compared to a patient treated with TILs prepared using other methods than those provide herein including for example, methods other than those embodied in FIG. 1 (in particular, e.g., FIG. 1B). In some embodiments, polyclonality is increased 100-fold as compared to an untreated patient and/or as compared to a patient treated with TILs prepared using other methods than those provide herein including for example, methods other than those embodied in FIG. 1 (in particular, e.g., FIG. 1B). In some embodiments, polyclonality is increased 500-fold as compared to an untreated patient and/or as compared to a patient treated with TILs prepared using other methods than those provide herein including for example, methods other than those embodied in FIG. 1 (in particular, e.g., FIG. 1B). In some embodiments, polyclonality is increased 1000-fold as compared to an untreated patient and/or as compared to a patient treated with TILs prepared using other methods than those provide herein including for example, methods other than those embodied in FIG. 1 (in particular, e.g., FIG. 1B).

2. Methods of Co-Administration

In some embodiments, the TILs produced as described herein, including for example TILs derived from a method described in Steps A through F of FIG. 1 (in particular, e.g., FIG. 1B), can be administered in combination with one or more immune checkpoint regulators, such as the antibodies described below. For example, antibodies that target PD-1 and which can be co-administered with the TILs of the present invention include, e.g., but are not limited to nivolumab (BMS-936558, Bristol-Myers Squibb; Opdivo®), pembrolizumab (lambrolizumab, MK03475 or MK-3475, Merck; Keytruda®), H12.1, PD1.3.1, NAT 105, humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)-BioXcell cat #BP0146. Other suitable antibodies suitable for use in co-administration methods with TILs produced according to Steps A through F as described herein are anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in co-administration methods with TILs produced according to Steps A through F as described herein. For example, antibodies that target PD-L1 and are in clinical trials, include BMS-936559 (Bristol-Myers Squibb) and MPDL3280A (Genentech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are suitable for use in co-administration methods with TILs produced according to Steps A through F as described herein. In some embodiments, the subject administered the combination of TILs produced according to Steps A through F is co administered with a and anti-PD-1 antibody when the patient has a cancer type that is refractory to administration of the anti-PD-1 antibody alone. In some embodiments, the patient is administered TILs in combination with and anti-PD-1 when the patient has refractory melanoma. In some embodiments, the patient is administered TILs in combination with and anti-PD-1 when the patient has non-small-cell lung carcinoma (NSCLC).

3. Optional Lymphodepletion Preconditioning of Patients

In an embodiment, the invention includes a method of treating a cancer with a population of TILs, wherein a patient is pre-treated with non-myeloablative chemotherapy prior to an infusion of TILs according to the present disclosure. In an embodiment, the invention includes a population of TILs for use in the treatment of cancer in a patient which has been pre-treated with non-myeloablative chemotherapy. In an embodiment, the population of TILs is for administration by infusion. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 (aldesleukin, commercially available as PROLEUKIN) intravenously at 720,000 IU/kg every 8 hours to physiologic tolerance. In certain embodiments, the population of TILs is for use in treating cancer in combination with IL-2, wherein the IL-2 is administered after the population of TILs.

Experimental findings indicate that lymphodepletion prior to adoptive transfer of tumor-specific T lymphocytes plays a key role in enhancing treatment efficacy by eliminating regulatory T cells and competing elements of the immune system ('cytokine sinks'). Accordingly, some embodiments of the invention utilize a lymphodepletion step (sometimes also referred to as "immunosuppressive conditioning") on the patient prior to the introduction of the TILs of the invention.

In general, lymphodepletion is achieved using administration of fludarabine or cyclophosphamide (the active form being referred to as mafosfamide) and combinations thereof. Such methods are described in Gassner, et al., *Cancer Immunol. Immunother.* 2011, 60, 75-85, Muranski, et al., *Nat. Clin. Pract. Oncol.,* 2006, 3, 668-681, Dudley, et al., *J. Clin. Oncol.* 2008, 26, 5233-5239, and Dudley, et al., *J. Clin. Oncol.* 2005, 23, 2346-2357, all of which are incorporated by reference herein in their entireties.

In some embodiments, the fludarabine is administered at a concentration of 0.5 g/mL-10 μg/mL fludarabine. In some embodiments, the fludarabine is administered at a concentration of 1 μg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 μg/mL-10 μg/mL by administration of cyclophosphamide. In some embodiments, mafosfamide, the active form of cyclophosphamide, is obtained at a concentration of 1 μg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m$^2$/day, 150 mg/m$^2$/day, 175 mg/m$^2$/day, 200 mg/m$^2$/day, 225 mg/m$^2$/day, 250 mg/m$^2$/day, 275 mg/m$^2$/day, or 300 mg/m$^2$/day. In some embodiments, the cyclophosphamide is administered intravenously (i.e., i.v.) In some embodiments, the cyclophosphamide treatment is administered for 2-7 days at 35 mg/kg/day. In some embodiments, the cyclophosphamide treatment is administered for 4-5 days at 250 mg/m$^2$/day i.v. In some embodiments, the cyclophosphamide treatment is administered for 4 days at 250 mg/m$^2$/day i.v.

In some embodiments, lymphodepletion is performed by administering the fludarabine and the cyclophosphamide together to a patient. In some embodiments, fludarabine is administered at 25 mg/m$^2$/day i.v. and cyclophosphamide is administered at 250 mg/m$^2$/day i.v. over 4 days.

In an embodiment, the lymphodepletion is performed by administration of cyclophosphamide at a dose of 60 mg/m$^2$/day for two days followed by administration of fludarabine at a dose of 25 mg/m$^2$/day for five days.

4. IL-2 Regimens

In an embodiment, the IL-2 regimen comprises a high-dose IL-2 regimen, wherein the high-dose IL-2 regimen comprises aldesleukin, or a biosimilar or variant thereof, administered intravenously starting on the day after administering a therapeutically effective portion of the therapeutic population of TILs, wherein the aldesleukin or a biosimilar or variant thereof is administered at a dose of 0.037 mg/kg or 0.044 mg/kg IU/kg (patient body mass) using 15-minute bolus intravenous infusions every eight hours until tolerance, for a maximum of 14 doses. Following 9 days of rest, this schedule may be repeated for another 14 doses, for a maximum of 28 doses in total.

In an embodiment, the IL-2 regimen comprises a decrescendo IL-2 regimen. Decrescendo IL-2 regimens have been described in O'Day, et al., *J. Clin. Oncol.* 1999, 17, 2752-61 and Eton, et al., *Cancer* 2000, 88, 1703-9, the disclosures of which are incorporated herein by reference. In an embodiment, a decrescendo IL-2 regimen comprises 18×10$^6$ IU/m$^2$ administered intravenously over 6 hours, followed by 18×10$^6$ IU/m$^2$ administered intravenously over 12 hours, followed by 18× 106 IU/m$^2$ administered intravenously over 24 hrs, followed by 4.5×10$^6$ IU/m$^2$ administered intravenously over 72 hours. This treatment cycle may be repeated every 28 days for a maximum of four cycles. In an embodiment, a decrescendo IL-2 regimen comprises 18,000,000 IU/m$^2$ on day 1, 9,000,000 IU/m$^2$ on day 2, and 4,500,000 IU/m$^2$ on days 3 and 4.

In an embodiment, the IL-2 regimen comprises administration of pegylated IL-2 every 1, 2, 4, 6, 7, 14 or 21 days at a dose of 0.10 mg/day to 50 mg/day.

5. Adoptive Cell Transfer

Adoptive cell transfer (ACT) is a very effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). TILs for ACT can be prepared as described herein. In some embodiments, the TILs are prepared, for example, according to a method as described in FIG. 1 (in particular, e.g., FIG. 1B). They can also be derived or from blood if they are genetically engineered to express antitumor T-cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. U.S. Publication No. 2011/0052530 relates to a method for performing adoptive cell therapy to promote cancer regression, primarily for treatment of patients suffering from metastatic melanoma, which is incorporated by reference in its entirety for these methods. In some embodiments, TILs can be administered as described herein. In some embodiments, TILs can be administered in a single dose. Such administration may be by injection, e.g., intravenous injection. In some embodiments, TILs and/or cytotoxic lymphocytes may be administered in multiple doses. Dosing may be once, twice, three times, four times, five times, six times, or more than six times per year. Dosing may be once a month, once every two weeks, once a week, or once every other day. Administration of TILs and/or cytotoxic lymphocytes may continue as long as necessary.

6. Additional Methods of Treatment

In another embodiment, the invention provides a method for treating a subject with cancer comprising administering to the subject a therapeutically effective dosage of the therapeutic TIL population described in any of the preceding paragraphs as applicable above.

In another embodiment, the invention provides a method for treating a subject with cancer comprising administering to the subject a therapeutically effective dosage of the TIL composition described in any of the preceding paragraphs as applicable above.

In another embodiment, the invention provides the method for treating a subject with cancer described in any of the preceding paragraphs as applicable above modified such that prior to administering the therapeutically effective dosage of the therapeutic TIL population and the TIL composition described in any of the preceding paragraphs as applicable above, respectively, a non-myeloablative lymphodepletion regimen has been administered to the subject.

In another embodiment, the invention provides the method for treating a subject with cancer described in any of the preceding paragraphs as applicable above modified such that the non-myeloablative lymphodepletion regimen comprises the steps of administration of cyclophosphamide at a dose of 60 $mg/m^2$/day for two days followed by administration of fludarabine at a dose of 25 $mg/m^2$/day for five days.

In another embodiment, the invention provides the method for treating a subject with cancer described in any of the preceding paragraphs as applicable above modified to further comprise the step of treating the subject with a high-dose IL-2 regimen starting on the day after administration of the TIL cells to the subject.

In another embodiment, the invention provides the method for treating a subject with cancer described in any of the preceding paragraphs as applicable above modified such that the the high-dose IL-2 regimen comprises 600,000 or 720,000 IU/kg administered as a 15-minute bolus intravenous infusion every eight hours until tolerance.

In another embodiment, the invention provides the method for treating a subject with cancer described in any of the preceding paragraphs as applicable above modified such that the cancer is a solid tumor.

In another embodiment, the invention provides the method for treating a subject with cancer described in any of the preceding paragraphs as applicable above modified such that the cancer is melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In another embodiment, the invention provides the method for treating a subject with cancer described in any of the preceding paragraphs as applicable above modified such that the cancer is melanoma, HNSCC, cervical cancers, NSCLC, glioblastoma (including GBM), and gastrointestinal cancer.

In another embodiment, the invention provides the method for treating a subject with cancer described in any of the preceding paragraphs as applicable above modified such that the cancer is melanoma.

In another embodiment, the invention provides the method for treating a subject with cancer described in any of the preceding paragraphs as applicable above modified such that the cancer is HNSCC.

In another embodiment, the invention provides the method for treating a subject with cancer described in any of the preceding paragraphs as applicable above modified such that the cancer is a cervical cancer.

In another embodiment, the invention provides the method for treating a subject with cancer described in any of the preceding paragraphs as applicable above modified such that the cancer is NSCLC.

In another embodiment, the invention provides the method for treating a subject with cancer described in any of the preceding paragraphs as applicable above modified such that the cancer is glioblastoma (including GBM).

In another embodiment, the invention provides the method for treating a subject with cancer described in any of the preceding paragraphs as applicable above modified such that the cancer is gastrointestinal cancer.

In another embodiment, the invention provides the method for treating a subject with cancer described in any of the preceding paragraphs as applicable above modified such that the cancer is a hypermutated cancer.

In another embodiment, the invention provides the method for treating a subject with cancer described in any of the preceding paragraphs as applicable above modified such that the cancer is a pediatric hypermutated cancer.

In another embodiment, the invention provides the therapeutic TIL population described in any of the preceding paragraphs as applicable above for use in a method for treating a subject with cancer comprising administering to the subject a therapeutically effective dosage of the therapeutic TIL population.

In another embodiment, the invention provides the TIL composition described in any of the preceding paragraphs as applicable above for use in a method for treating a subject with cancer comprising administering to the subject a therapeutically effective dosage of the TIL composition.

In another embodiment, the invention provides the therapeutic TIL population described in any of the preceding paragraphs as applicable above or the TIL composition described in any of the preceding paragraphs as applicable above modified such that prior to administering to the subject the therapeutically effective dosage of the therapeutic TIL population described in any of the preceding paragraphs as applicable above or the TIL composition described in any of the preceding paragraphs as applicable above, a non-myeloablative lymphodepletion regimen has been administered to the subject.

In another embodiment, the invention provides the therapeutic TIL population or the TIL composition described in any of the preceding paragraphs as applicable above modified such that the non-myeloablative lymphodepletion regimen comprises the steps of administration of cyclophosphamide at a dose of 60 $mg/m^2$/day for two days followed by administration of fludarabine at a dose of 25 $mg/m^2$/day for five days.

In another embodiment, the invention provides the therapeutic TIL population or the TIL composition described in any of the preceding paragraphs as applicable above modified to further comprise the step of treating patient with a high-dose IL-2 regimen starting on the day after administration of the TIL cells to the patient.

In another embodiment, the invention provides the therapeutic TIL population or the TIL composition described in any of the preceding paragraphs as applicable above modified such that the high-dose IL-2 regimen comprises 600,000 or 720,000 IU/kg administered as a 15-minute bolus intravenous infusion every eight hours until tolerance.

In another embodiment, the invention provides the therapeutic TIL population or the TIL composition described in any of the preceding paragraphs as applicable above modified such that the cancer is a solid tumor.

In another embodiment, the invention provides the therapeutic TIL population or the TIL composition described in any of the preceding paragraphs as applicable above modified such that the cancer is melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In another embodiment, the invention provides the therapeutic TIL population or the TIL composition described in any of the preceding paragraphs as applicable above modified such that the cancer is melanoma, HNSCC, cervical cancers, NSCLC, glioblastoma (including GBM), and gastrointestinal cancer.

In another embodiment, the invention provides the therapeutic TIL population or the TIL composition described in any of the preceding paragraphs as applicable above modified such that the cancer is melanoma.

In another embodiment, the invention provides the therapeutic TIL population or the TIL composition described in any of the preceding paragraphs as applicable above modified such that the cancer is HNSCC.

In another embodiment, the invention provides the therapeutic TIL population or the TIL composition described in any of the preceding paragraphs as applicable above modified such that the cancer is a cervical cancer.

In another embodiment, the invention provides the therapeutic TIL population or the TIL composition described in any of the preceding paragraphs as applicable above modified such that the cancer is NSCLC.

In another embodiment, the invention provides the therapeutic TIL population or the TIL composition described in any of the preceding paragraphs as applicable above modified such that the cancer is glioblastoma (including GBM).

In another embodiment, the invention provides the therapeutic TIL population or the TIL composition described in any of the preceding paragraphs as applicable above modified such that the cancer is gastrointestinal cancer.

In another embodiment, the invention provides the therapeutic TIL population or the TIL composition described in any of the preceding paragraphs as applicable above modified such that the cancer is a hypermutated cancer.

In another embodiment, the invention provides the therapeutic TIL population or the TIL composition described in any of the preceding paragraphs as applicable above modified such that the cancer is a pediatric hypermutated cancer.

In another embodiment, the invention provides the use of the therapeutic TIL population described in any of the preceding paragraphs as applicable above in a method of treating cancer in a subject comprising administering to the subject a therapeutically effective dosage of the therapeutic TIL population.

In another embodiment, the invention provides the use of the TIL composition described in any of the preceding paragraphs as applicable above in a method of treating cancer in a subject comprising administering to the subject a therapeutically effective dosage of the TIL composition.

In another embodiment, the invention provides the use of the therapeutic TIL population described any of the preceding paragraphs as applicable above or the TIL composition described in any of the preceding paragraphs as applicable above in a method of treating cancer in a subject comprising administering to the subject a non-myeloablative lymphodepletion regimen and then administering to the subject the therapeutically effective dosage of the therapeutic TIL population described in any of the preceding paragraphs as applicable above or the therapeutically effective dosage of the TIL composition described in any of the preceding paragraphs as applicable above.

In another embodiment, the invention provides the use of the therapeutic TIL population or the TIL composition described in any of the preceding paragraphs as applicable above modified such that the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In another embodiment, the invention provides the use of the therapeutic TIL population or the TIL composition described in any of the preceding paragraphs as applicable above modified to further comprise the step of treating patient with a high-dose IL-2 regimen starting on the day after administration of the TIL cells to the patient.

In another embodiment, the invention provides the use of the therapeutic TIL population or the TIL composition described in any of the preceding paragraphs as applicable above modified such that the high-dose IL-2 regimen comprises 600,000 or 720,000 IU/kg administered as a 15-minute bolus intravenous infusion every eight hours until tolerance.

In another embodiment, the invention provides the use of the therapeutic TIL population or the TIL composition described in any of the preceding paragraphs as applicable above modified such that the cancer is a solid tumor.

In another embodiment, the invention provides the use of the therapeutic TIL population or the TIL composition described in any of the preceding paragraphs as applicable above modified such that the cancer is melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In another embodiment, the invention provides the use of the therapeutic TIL population or the TIL composition described in any of the preceding paragraphs as applicable above modified such that the cancer is melanoma, HNSCC, cervical cancers, NSCLC, glioblastoma (including GBM), and gastrointestinal cancer.

In another embodiment, the invention provides the use of the therapeutic TIL population or the TIL composition described in any of the preceding paragraphs as applicable above modified such that the cancer is melanoma.

In another embodiment, the invention provides the use of the therapeutic TIL population or the TIL composition described in any of the preceding paragraphs as applicable above modified such that the cancer is HNSCC.

In another embodiment, the invention provides the use of the therapeutic TIL population or the TIL composition described in any of the preceding paragraphs as applicable above modified such that the cancer is a cervical cancer.

In another embodiment, the invention provides the use of the therapeutic TIL population or the TIL composition described in any of the preceding paragraphs as applicable above modified such that the cancer is NSCLC.

In another embodiment, the invention provides the use of the therapeutic TIL population or the TIL composition described in any of the preceding paragraphs as applicable above modified such that the cancer is glioblastoma (including GBM).

In another embodiment, the invention provides the use of the therapeutic TIL population or the TIL composition described in any of the preceding paragraphs as applicable above modified such that the cancer is gastrointestinal cancer.

In another embodiment, the invention provides the use of the therapeutic TIL population or the TIL composition described in any of the preceding paragraphs as applicable above modified such that the cancer is a hypermutated cancer.

In another embodiment, the invention provides the use of the therapeutic TIL population or the TIL composition described in any of the preceding paragraphs as applicable above modified such that the cancer is a pediatric hypermutated cancer.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Preparation of Media for Pre-Rep and Rep Processes

This Example describes the procedure for the preparation of tissue culture media for use in protocols involving the culture of tumor infiltrating lymphocytes (TIL) derived from various tumor types including, but not limited to, metastatic melanoma, head and neck squamous cell carcinoma (HNSCC), ovarian carcinoma, triple-negative breast carcinoma, and lung adenocarcinoma. This media can be used for preparation of any of the TILs described in the present application and Examples.

Preparation of CM1

Removed the following reagents from cold storage and warmed them in a 37° C. water bath: (RPMI1640, Human AB serum, 200 mM L-glutamine). Prepared CM1 medium according to Table 19 below by adding each of the ingredients into the top section of a 0.2 μm filter unit appropriate to the volume to be filtered. Stored at 4° C.

TABLE 19

Preparation of CM1

| Ingredient | Final concentration | Final Volume 500 ml | Final Volume IL |
|---|---|---|---|
| RPMI1640 | NA | 450 ml | 900 ml |
| Human AB serum, heat-inactivated 10% | 50 ml | 100 ml | |
| 200 mM L-glutamine | 2 mM | 5 ml | 10 ml |
| 55 mM BME | 55 μM | 0.5 ml | 1 ml |
| 50 mg/ml gentamicin sulfate | 50 μg/ml | 0.5 ml | 1 ml |

On the day of use, prewarmed required amount of CM1 in 37° C. water bath and add 6000 IU/ml IL-2.

Additional supplementation—as needed according to Table 20.

TABLE 20

Additional supplementation of CM1, as needed.

| Supplement | Stock concentration | Dilution | Final concentration |
|---|---|---|---|
| GlutaMAX ™ | 200 mM | 1:100 | 2 mM |
| Penicillin/ streptomycin | 10,000 U/ml penicillin 10,000 μg/ml streptomycin | 1:100 | 100 U/ml penicillin 100 μg/ml streptomycin |
| Amphotericin B | 250 μg/ml | 1:100 | 2.5 μg/ml |

Preparation of CM2

Removed prepared CM1 from refrigerator or prepare fresh CM1 as per Table 19 above. Removed AIM-V® from refrigerator and prepared the amount of CM2 needed by mixing prepared CM1 with an equal volume of AIM-V® in a sterile media bottle. Added 3000 IU/ml IL-2 to CM2 medium on the day of usage. Made sufficient amount of CM2 with 3000 IU/ml IL-2 on the day of usage. Labeled the CM2 media bottle with its name, the initials of the preparer, the date it was filtered/prepared, the two-week expiration date and stored at 4° C. until needed for tissue culture.

Preparation of CM3

Prepared CM3 on the day it was required for use. CM3 was the same as AIM-V® medium, supplemented with 3000 IU/ml IL-2 on the day of use. Prepared an amount of CM3 sufficient to experimental needs by adding IL-2 stock solution directly to the bottle or bag of AIM-V. Mixed well by gentle shaking. Labeled bottle with “3000 IU/ml IL-2” immediately after adding to the AIM-V. If there was excess CM3, stored it in bottles at 4° C. labeled with the media name, the initials of the preparer, the date the media was prepared, and its expiration date (7 days after preparation). Discarded media supplemented with IL-2 after 7 days storage at 4° C.

Preparation of CM4

CM4 was the same as CM3, with the additional supplement of 2 mM GlutaMAX™ (final concentration). For every 1 L of CM3, added 10 ml of 200 mM GlutaMAX™. Prepared an amount of CM4 sufficient to experimental needs by adding IL-2 stock solution and GlutaMAX™ stock solution directly to the bottle or bag of AIM-V. Mixed well by gentle shaking. Labeled bottle with “3000 IL/nil IL-2 and GlutaMAX” immediately after adding to the AIM-V. If there was excess CM4, stored it in bottles at 4° C. labeled with the media name, “GlutaMAX”, and its expiration date (7 days after preparation). Discarded media supplemented with IL-2 after 7-days storage at 4° C.

Example 2: Use of IL-2, IL-15, and IL-21 Cytokine Cocktail

This example describes the use of IL-2, IL-15, and IL-21 cytokines, which serve as additional T cell growth factors, in combination with the TIL process of Examples A to G.

Using the processes described herein, TILs were grown from colorectal, melanoma, cervical, triple negative breast, lung and renal tumors in presence of IL-2 in one arm of the experiment and, in place of IL-2, a combination of IL-2, IL-15, and IL-21 in another arm at the initiation of culture. At the completion of the pre-REP, cultures were assessed for expansion, phenotype, function (CD107a+ and IFN-γ) and TCR VB repertoire. IL-15 and IL-21 are described elsewhere herein and in Gruijl, et al., IL-21 promotes the expansion of CD27+CD28+ tumor infiltrating lymphocytes with high cytotoxic potential and low collateral expansion of regulatory T cells, *Santegoets*, S. J., J Transl Med., 2013, 11:37 (https://www.ncbi.nlm.nih.gov/pmc/articles/PMC3626797/).

The results showed that enhanced TIL expansion (>20%), in both CD4+ and CD8+ cells in the IL-2, IL-15, and IL-21 treated conditions were observed in multiple histologies relative to the IL-2 only conditions. There was a skewing towards a predominantly CD8+ population with a skewed TCR VB repertoire in the TILs obtained from the IL-2, IL-15, and IL-21 treated cultures relative to the IL-2 only cultures. IFN-γ and CD107a were elevated in the IL-2, IL-15, and IL-21 treated TILs, in comparison to TILs treated only IL-2.

Example 3: Preparation of IL-2 Stock Solution (Cellgenix)

This Example describes the process of dissolving purified, lyophilized recombinant human interleukin-2 into stock samples suitable for use in further tissue culture protocols, including all of those described in the present application and Examples, including those that involve using rhIL-2.

Procedure

Prepared 0.2% Acetic Acid solution (HAc). Transferred 29 mL sterile water to a 50 mL conical tube. Added ImL IN acetic acid to the 50 ml conical tube. Mixed well by inverting tube 2-3 times. Sterilized the HAc solution by filtration using a Steriflip filter Prepared 1% HSA in PBS. Added 4 mL of 25% HSA stock solution to 96 mL PBS in a 150 mL sterile filter unit. Filtered solution. Stored at 4° C. For each vial of rhIL-2 prepared, fill out forms.

Prepared rhIL-2 stock solution ($6\times10^6$ IU/mL final concentration). Each lot of rhIL-2 was different and required information found in the manufacturer's Certificate of Analysis (COA), such as: 1) Mass of rhIL-2 per vial (mg), 2) Specific activity of rhIL-2 (IU/mg) and 3) Recommended 0.2% HAc reconstitution volume (mL).

Calculated the volume of 1% HSA required for rhIL-2 lot by using the equation below:

$$\left(\frac{\text{Vial Mass (mg)}\times\text{Biological Activity}\left(\frac{IU}{\text{mg}}\right)}{6\times10^6\frac{IU}{\text{mL}}}\right)-HAc\ vol\ (\text{mL})=1\%\ HSA\ vol\,(\text{mL})$$

For example, according to CellGenix's rhIL-2 lot 10200121 COA, the specific activity for the 1 mg vial is $25\times10^6$ IU/mg. It recommends reconstituting the rhIL-2 in 2 mL 0.2% HAc.

$$\left(\frac{1\ \text{mg}\times25\times10^6\frac{IU}{\text{mg}}}{6\times10^6\frac{IU}{\text{mL}}}\right)-2\ \text{mL}=2.167\ \text{mL}\ HSA$$

Wiped rubber stopper of IL-2 vial with alcohol wipe. Using a 16G needle attached to a 3 mL syringe, injected recommended volume of 0.2% HAc into vial. Took care to not dislodge the stopper as the needle is withdrawn. Inverted vial 3 times and swirled until all powder was dissolved. Carefully removed the stopper and set aside on an alcohol wipe. Added the calculated volume of 1% HSA to the vial.

Storage of rhIL-2 solution. For short-term storage (<72 hrs), stored vial at 4° C. For long-term storage (>72 hrs), aliquoted vial into smaller volumes and stored in cryovials at −20° C. until ready to use. Avoided freeze/thaw cycles. Recorded expiration date of 6 months after date of preparation. Rh-IL-2 labels included vendor and catalog number, lot number, expiration date, operator initials, concentration and volume of aliquot.

Example 4: Cryopreservation Process

This example describes the cryopreservation process method for TILs prepared with the abbreviated, closed procedure described in Example G using the CryoMed Controlled Rate Freezer, Model 7454 (Thermo Scientific).

The equipment used was as follows: aluminum cassette holder rack (compatible with CS750 freezer bags), cryostorage cassettes for 750 mL bags, low pressure (22 psi) liquid nitrogen tank, refrigerator, thermocouple sensor (ribbon type for bags), and CryoStore CS750 Freezing bags (OriGen Scientific).

The freezing process provided for a 0.5° C. rate from nucleation to −20° C. and 1° C. per minute cooling rate to −80° C. end temperature. The program parameters are as follows: Step 1-wait at 4° C.; Step 2:1.0° C./min (sample temperature) to −4° C.; Step 3:20.0° C./min (chamber temperature) to −45° C.; Step 4:10.0° C./min (chamber temperature) to −10.0° C.; Step 5:0.5° C./min (chamber temperature) to −20° C.; and Step 6:1.0° C./min (sample temperature) to −80° C.

Example 5: Gen 3 Exemplary Process

The example provides a comparison between the Gen 2 and Gen 3 processes. This example describes the development of a robust TIL expansion platform. The modifications to the Gen 2 process reduce risk and streamline the manufacturing process by reducing the number of operator interventions, reduce the overall time of manufacturing, optimize the use of reagents, and facilitate a flexible semi-closed and semi-automated cell production process amenable to high-throughput manufacturing on a commercial scale.

Process Gen 2 and Gen 3 TILs are composed of autologous TIL derived from an individual patient through surgical resection of a tumor and then expanded ex vivo. The Priming First Expansion step of the Gen 3 process was a cell culture in the presence of interleukin-2 (IL-2) and the monoclonal antibody OKT3, which targets the T-cell co-receptor CD3 on a scaffold of irradiated peripheral blood mononuclear cells (PBMCs).

The manufacture of Gen 2 TIL products consisted of two phases: 1) pre-Rapid Expansion (Pre-REP) and 2) Rapid Expansion Protocol (REP). During the Pre-REP resected tumors were cut up into ≤50 fragments 2-3 mm in each dimension which were cultured with serum-containing culture medium (RPMI 1640 media containing 10% HuSAB supplemented) and 6,000 IU/mL of Interleukin-2 (IL-2) for a period of 11 days. On day 11 TIL were harvested and introduced into the large-scale secondary REP expansion. The REP consists of activation of $\leq200\times10^6$ of the viable cells from pre-REP in a co-culture of $5\times10^9$ irradiated allogeneic PBMCs feeder cells loaded with 150 μg of monoclonal anti-CD3 antibody (OKT3) in a 5 L volume of CM2 supplemented with 3000 IU/mL of rhIL-2 for 5 days. On day 16 the culture is volume reduced 90% and the cell fraction is split into multiple G-REX-500 flasks at $\geq1\times10^9$ viable lymphocytes/flask and QS to 5 L with CM4. TIL are incubated an additional 6 days. The REP is harvested on day 22, washed, formulated, and cryo-preserved prior to shipping at −150° C. to the clinical site for infusion.

The manufacture of Gen 3 TIL products consisted of three phases: 1) Priming First Expansion Protocol 2) Rapid Second Expansion Protocol (also referred to as rapid expansion phase or REP) and 3) Subculture Split. To effect the Priming First Expansion TIL propagation, resected tumor was cut up into ≤120 fragments 2-3 mm in each dimension. On day 0 of the Priming First Expansion, a feeder layer of approximately $2.5\times10^8$ allogeneic irradiated PBMCs feeder cells was established on a surface area of approximately 100 $cm^2$ in each of 3 100 MCS vessels. The tumor fragments were distributed among and cultured in the 3 100 MCS vessels each with 500 mL serum-containing CM1 culture medium and 6,000 IU/mL of Interleukin-2 (IL-2) and 15 μg OKT-3 for a period of 7 days. On day 7, REP was initiated by incorporating an additional feeder cell layer of approximately $5\times10^8$ allogeneic irradiated PBMCs feeder cells into the tumor fragmented culture phase in each of the 3 100 MCS vessels and culturing with 500 mL CM2 culture medium and 6,000 IU/mL IL-2 and 30 μg OKT-3. The REP initiation was enhanced by activating the entire Priming First Expansion culture in the same vessel using closed system fluid transfer of OKT3 loaded feeder cells into the 100 MCS vessel. For Gen 3, the TIL scale up or split involved process steps where the whole cell culture was scaled to a larger vessel through closed system fluid transfer and was transferred (from 100 M flask to a 500 M flask) and additional 4 L of CM4 media was added. The REP cells were harvested on day 16, washed, formulated, and cryo-preserved prior to shipping at −150° C. to the clinical site for infusion.

Overall, the Gen 3 process is a shorter, more scalable, and easily modifiable expansion platform that will accommodate to fit robust manufacturing and process comparability.

On day 0, for both processes, the tumor was washed 3 times and the fragments were randomized and divided into two pools; one pool per process. For the Gen 2 Process, the fragments were transferred to one GREX 100 MCS flask with 1 L of CM1 media containing 6,000 IU/mL rhIL-2. For the Gen 3 Process, fragments were transferred to one GREX100 MCS flask with 500 mL of CM1 containing 6,000 IU/mL rhIL-2, 15 μg OKT-3 and $2.5\times10^8$ feeder cells.

Seeding of TIL for Rep initiation day occurred on different days according to each process. For the Gen 2 Process, in which the G-REX 100 MCS flask was 90% volume reduced, collected cell suspension was transferred to a new G-REX 500 MCS to start REP initiation on day 11 in CM2 media containing IL-2 (3000 IU/mL), plus 5e9 feeder cells and OKT-3 (30 ng/mL). Cells were expanded and split on day 16 into multiple GREX 500 MCS flasks with CM4 media with IL-2 (3000 IU/mL) per protocol. The culture was then harvested and cryopreserved on day 22 per protocol. For the Gen 3 process, the REP initiation occurred on day 7, in which the same G-REX 100 MCS used for REP initiation. Briefly, 500 mL of CM2 media containing IL-2 (6000 IU/mL) and $5\times10^8$ feeder cells with 30 μg OKT-3 was added to each flask. On day 9-11 the culture was scaled up. The entire volume of the G-Rex100M (1 L) was transferred to a G-REX 500 MCS and 4 L of CM4 containing IL-2 (3000 IU/mL) was added. Flasks were incubated 5 days. Cultures were harvested and cryopreserved on Day 16.

Three different tumors were included in the comparison, two lung tumors (L4054 and L4055) and one melanoma tumor (M1085T).

CM1 (culture media 1), CM2 (culture media 2), and CM4 (culture media 4) media were prepared in advance and held at 4° C. for L4054 and L4055. CM1 and CM2 media were prepared without filtration to compare cell growth with and without filtration of media.

TABLE 21

Comparison of Exemplary Gen 2 and Exemplary Gen 3 manufacturing process.

| Step | Process (Gen 2) | Process (Gen 3) |
|---|---|---|
| Pre REP-day 0 | Up to 50 fragments/1-G-Rex 100MCS - 11 days<br>In 1 L of CM1 media + IL-2 (6000 IU/mL) | Whole tumor up to 120 fragments divided evenly among up to 3 flasks. 1 flask: 1-60 fragments<br>2 flasks: 61-89 fragments<br>3 flasks 90-120 fragments<br>7 days in 500 mL/flask of CM1 media + IL-2 (6000 IU/mL)<br>$2.5\times10^8$ feeder cells/flask<br>15 ug OKT-3/flask |
| REP Initiation | Direct to REP-Day 11-<200e$^6$ TIL<br>(1)G-Rex 500MCS in 5 L CM2 media<br>IL-2 (3000 IU/mL)<br>$5\times10^9$ feeder cells<br>150 ug OKT-3 | Direct to REP- Day 7-all cells TIL- same G-Rex 100MCS<br>Add 500 mL/flask CM2 media<br>IL-2 (6000 IU/mL)<br>$5\times10^8$ feeder cells/flask<br>30 ug OKT-3/flask |
| TIL propagation or Scale up | Volume reduce and split cell fraction in up to 5 G-REX 500MCS<br>4.5 L CM4 media + IL-2 (3000 IU/mL) ≥ $1\times10^9$ TVC/flask<br>Split day 16 | Each G-REX 100MCS(1 L) transfers to 1 G-REX 500MCS<br>Add 4 L CM4 media + IL-2 (3000 IU/mL)<br>Scale up on day 9 to 11 |
| Harvest | Harvest day 22,<br>LOVO-automated cell washer | Harvest day 16<br>LOVO- automated cell washer |
| Final formulation | Cryopreserved Product<br>300 IU/ml IL2- CS10 in $LN_2$, multiple aliquots | Cryopreserved product<br>300 IU/ml IL-2-CS10 in $LN_2$, multiple aliquots |
| Process time | 22 days | 16 days |

Media was warmed at 37° C. up to 24 hours in advance for L4055 tumor on REP initiation and scale-up.

Results Summary

Gen 3 will fell within 30% of Gen 2 for total viable cells achieved. Gen 3 final product exhibited higher production of INF-γ after restimulation. Gen 3 final product exhibited an increased clonal diversity as measured by total unique CDR3 sequences present. Gen 3 final product exhibited longer mean telomere length.

Results Achieved

Cell Count and % Viability:

Pre REP and REP expansion on Gen 2 and Gen 3 processes followed details described above.

Table 22: Pre-REP cell counts. For each tumor, the two pools contained equal number of fragments. Due to the small size of tumors, the maximum number of fragments per flask was not achieved. Total pre-REP cells (TVC) were harvested and counted at day 11 for the Gen 2 process and at day 7 for the Gen 3 process. To compare the two pre-REP arms, the cell count was divided over the number of fragments provided in the culture in order to calculate an average of viable cells per fragment. As indicated in the table below, the Gen 2 process consistently grew more cells per fragment compared to the Gen 3 Process. An extrapolated calculation of the number of TVC expected for Gen 3 process at day 11, which was calculated dividing the pre-REP TVC by 7 and then multiply by 11.

TABLE 22 pre-REP cell counts

| | Tumor ID | | | | | |
|---|---|---|---|---|---|---|
| | L4054 | | L4055* | | M1085T | |
| Process | Gen 2 | Gen 3 | Gen 2 | Gen 3 | Gen 2 | Gen 3 |
| pre-REP TVC | 1.42E+08 | 4.32E+07 | 2.68E+07 | 1.38E+07 | 1.23E+07 | 3.50E+06 |
| Number of fragments | 21 | 21 | 24 | 24 | 16 | 16 |
| Average TVC per fragment at pre-REP | 6.65E+06 | 2.06E+06 | 1.12E+06 | 5.75E+05 | 7.66E+05 | 2.18E+05 |
| Gen 3 extrapolated value at pre REP day 11 | N/A | 6.79E+07 | N/A | 2.17E+07 | N/A | 5.49E+06 |

*L4055, unfiltered media.

Table 23: Total viable cell count and fold expansion on TIL final product: For the Gen 2 and Gen 3 processes, TVC was counted per process condition and percent viable cells was generated for each day of the process. On harvest, day 22 (Gen 2) and day 16 (Gen 3) cells were collected and the TVC count was established. The TVC was then divided by the number of fragments provided on day 0, to calculate an average of viable cells per fragment. Fold expansion was calculated by dividing harvest TVC by over the REP initiation TVC. As exhibited in the table, comparing Gen 2 and the Gen 3, fold expansions were similar for L4054; in the case of L4055, the fold expansion was higher for the Gen 2 process. Specifically, in this case, the media was warmed up 24 in advance of REP initiation day. A higher fold expansion was also observed in Gen 3 for M1085T. An extrapolated calculation of the number of TVC expected for Gen 3 process at day 22, which was calculated dividing the REP TVC by 16 and then multiply by 22.

TABLE 23

Total viable cell count and fold expansion on TIL final product

| | Tumor ID | | | | | |
|---|---|---|---|---|---|---|
| | L4054 | | L4055 | | M1085T | |
| Process | Gen 2 | Gen 3 | Gen 2 | Gen 3 | Gen 2 | Gen 3 |
| # Fragments | 21 | 21 | 24 | 24 | 16 | 16 |
| TVC/fragment (at Harvest) | 3.18E+09 | 8.77E+08 | 2.30E+09 | 3.65E+08 | 7.09E+08 | 4.80E+08 |
| REP initiation | 1.42E+08 | 4.32E+07 | 2.68E+07 | 1.38E+07 | 1.23E+07 | 3.50E+06 |
| Scale up | 3.36E+09 | 9.35E+08 | 3.49E+09 | 8.44E+08 | 1.99E+09 | 3.25E+08 |
| Harvest | 6.67E+10 | 1.84E+10 | 5.52E+10 | 8.76E+09 | 1.13E+10 | 7.68E+09 |
| Fold Expansion Harvest/ REP initiation | 468.4 | 425.9 | 2056.8 | 634.6 | 925.0 | 2197.2 |
| Gen 3 extrapolated value at REP harvest day 22 | N/A | 2.53E+10 | N/A | 1.20E+10 | N/A | 1.06E+10 |

*L4055, unfiltered media.

Table 24: % Viability of TIL final product: Upon harvest, the final TIL REP products were compared against release criteria for % viability. All of the conditions for the Gen 2 and Gen 3 processes surpassed the 70% viability criterion and were comparable across processes and tumors.

TABLE 24

| % Viability of REP | | | | | | |
|---|---|---|---|---|---|---|
| | Tumor ID | | | | | |
| | L4054 | | L4055 | | M1085T | |
| Process | Gen 2 | Gen 3 | Gen 2 | Gen 3 | Gen 2 | Gen 3 |
| REP initiation | 98.23% | 97.97% | 97.43% | 92.03% | 81.85% | 68.27% |
| Scale up | 94.00% | 93.57% | 90.50% | 95.93% | 78.55% | 71.15% |
| Harvest | 87.95% | 89.85% | 87.50% | 86.70% | 86.10% | 87.45% |

Table 25: Estimate cell count per additional flask for Gen 3 process. Due to the number of fragments per flask below the maximum required number, an estimated cell count at harvest day was calculated for each tumor. The estimation was based on the expectation that clinical tumors were large enough to seed 2 or 3 flasks on day 0.

TABLE 25

| Extrapolated estimate cell count calculation to full scale 2 and 3 flask on Gen 3 Process | | | | | | |
|---|---|---|---|---|---|---|
| | Tumor ID | | | | | |
| | L4054 | | L4055 | | M1085T | |
| Gen 3 Process | 2 flasks | 3 Flasks | 2 flasks | 3 Flasks | 2 flasks | 3 Flasks |
| Estimate Harvest | 3.68E+10 | 5.52E+10 | 1.75E+10 | 2.63E+10 | 1.54E+10 | 2.30E+10 |

Immunophenotyping:

Phenotypic Markers Comparison on TIL Final Product:

Three tumors L4054, L4055, and M1085T underwent TIL expansion in both the Gen 2 and Gen 3 processes. Upon harvest, the REP TIL final products were subjected to flow cytometry analysis to test purity, differentiation, and memory markers. For all the conditions the percentage of TCR a/b+ cells was over 90%.

Figure 3:
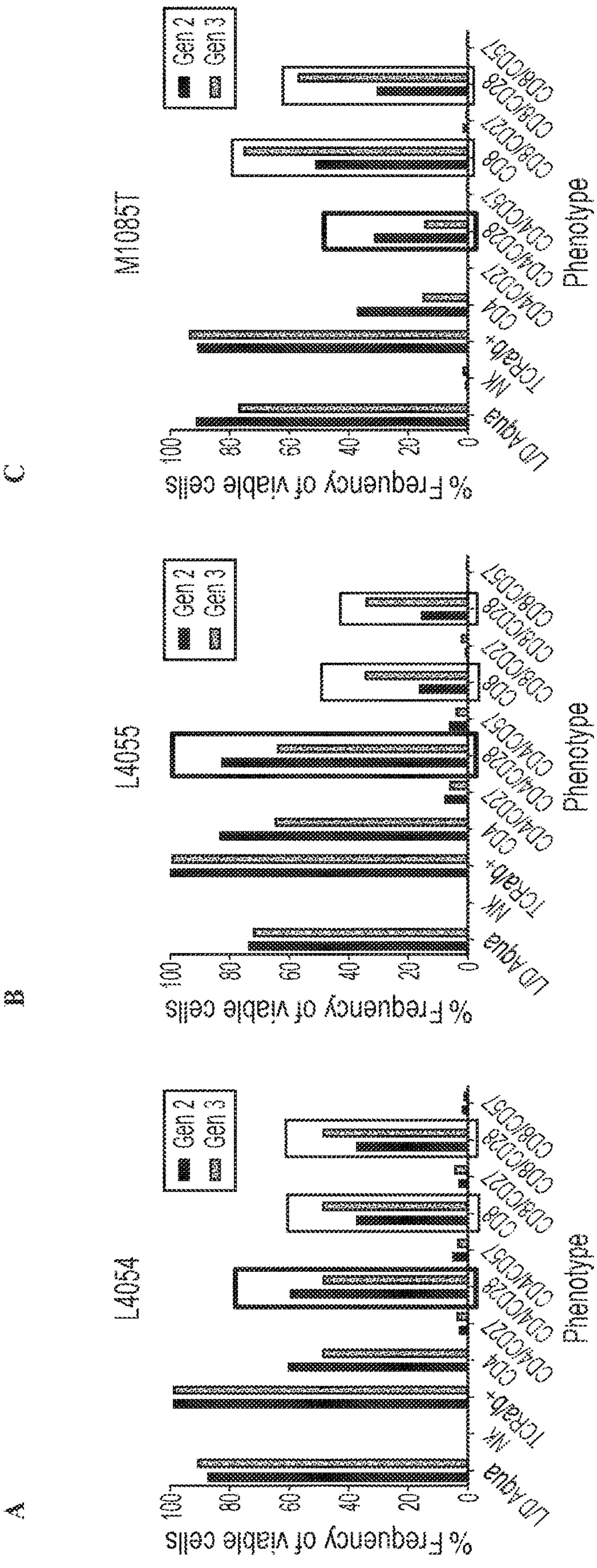
FIG. 3A-3C: A) L4054-Phenotypic characterization on TIL product on Gen 2 and Gen 3 process. B) L4055-Phenotypic characterization on TIL product on Gen 2 and Gen 3 process. C) M1085T-Phenotypic characterization on TIL product on Gen 2 and Gen 3 process.

TIL harvested from the Gen 3 process showed a higher expression of CD8 and CD28 compared to TIL harvested from the Gen 2 process. The Gen 2 process showed a higher percentage of CD4+. See, FIG. 3 (A, B, C).

Figure 4:
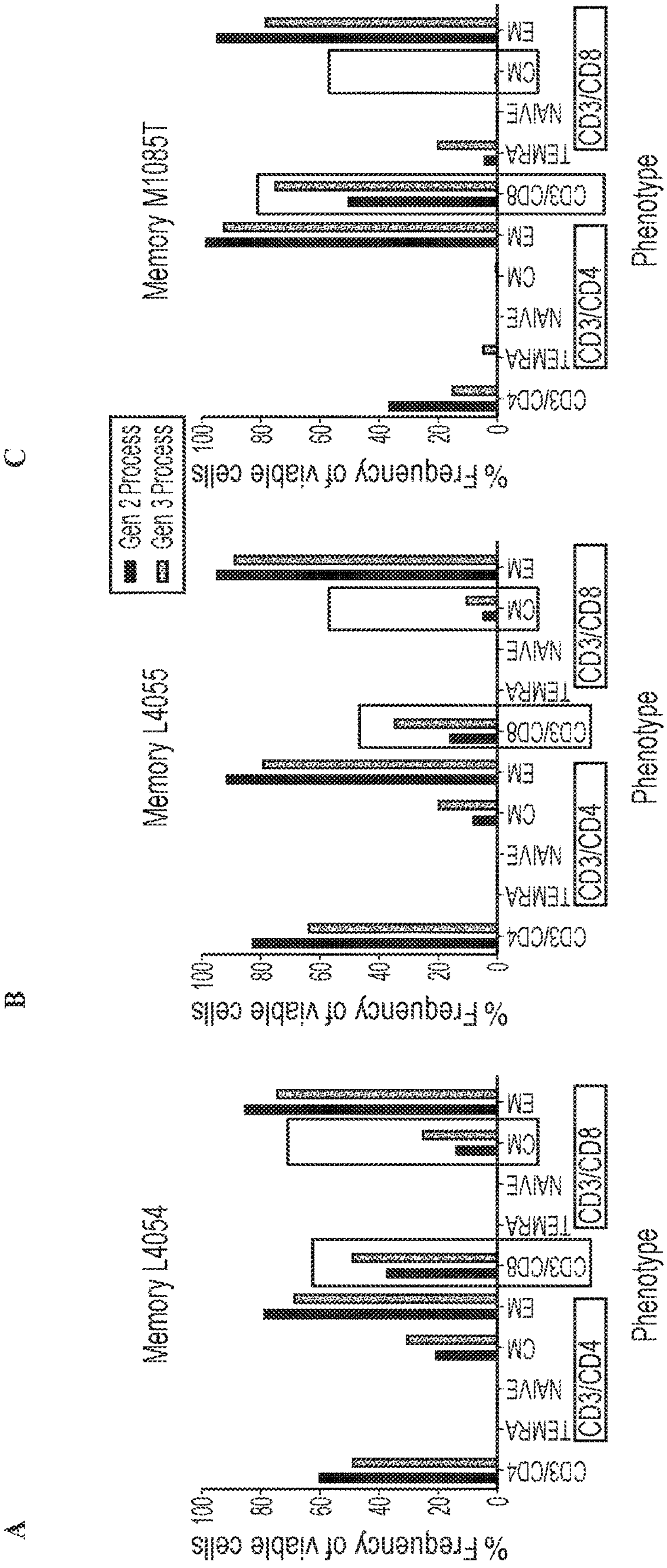
FIG. 4A-4C: A) L4054-Memory markers analysis on TIL product from the Gen 2 and Gen 3 processes. B) L4055-Memory markers analysis on TIL product from the Gen 2 and Gen 3 processes. C) M1085T-Memory markers analysis on TIL product from the Gen 2 and Gen 3 processes.

Memory Markers Comparison on TIL Final Product:

TIL harvested from the Gen 3 process showed a higher expression on central memory compartments compared to TIL from the Gen 2 process. See, FIG. 4 (A, B, C).

Figure 5:
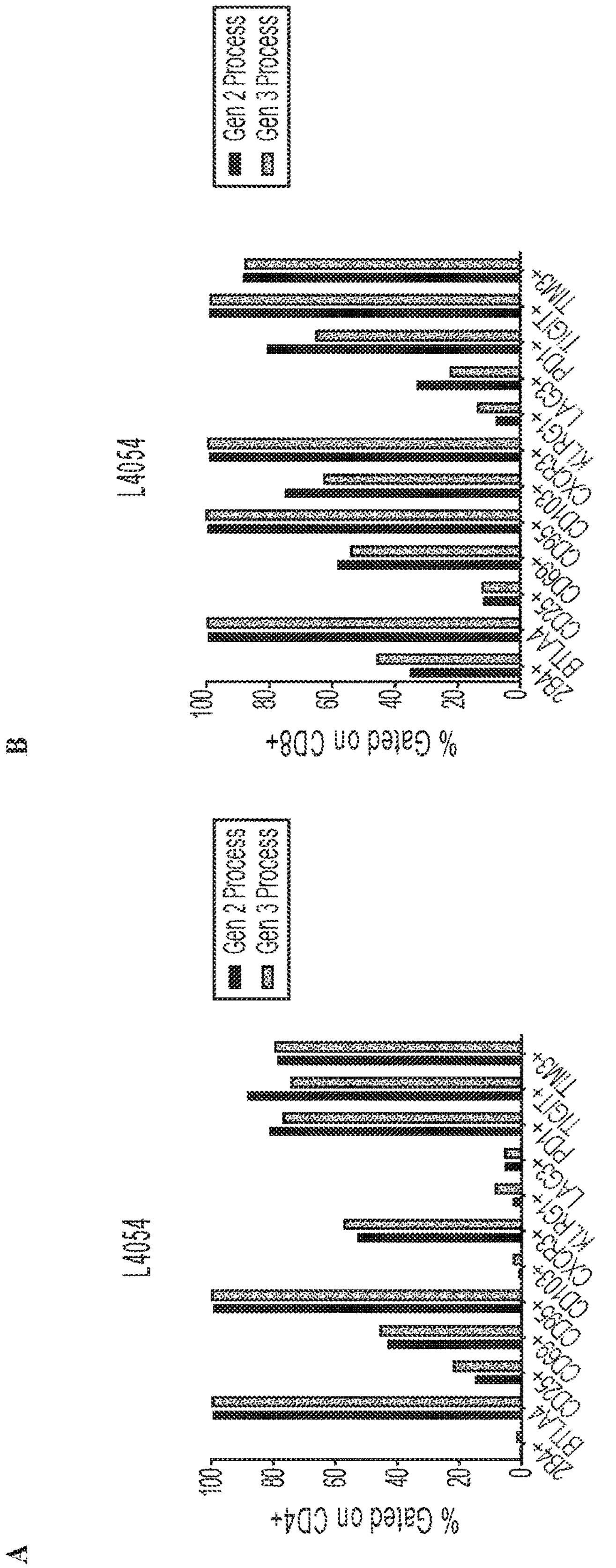
FIG. 5A-5B: L4054 Activation and exhaustion markers (A) Gated on CD4+, (B) Gated on CD8+.
Figure 6:
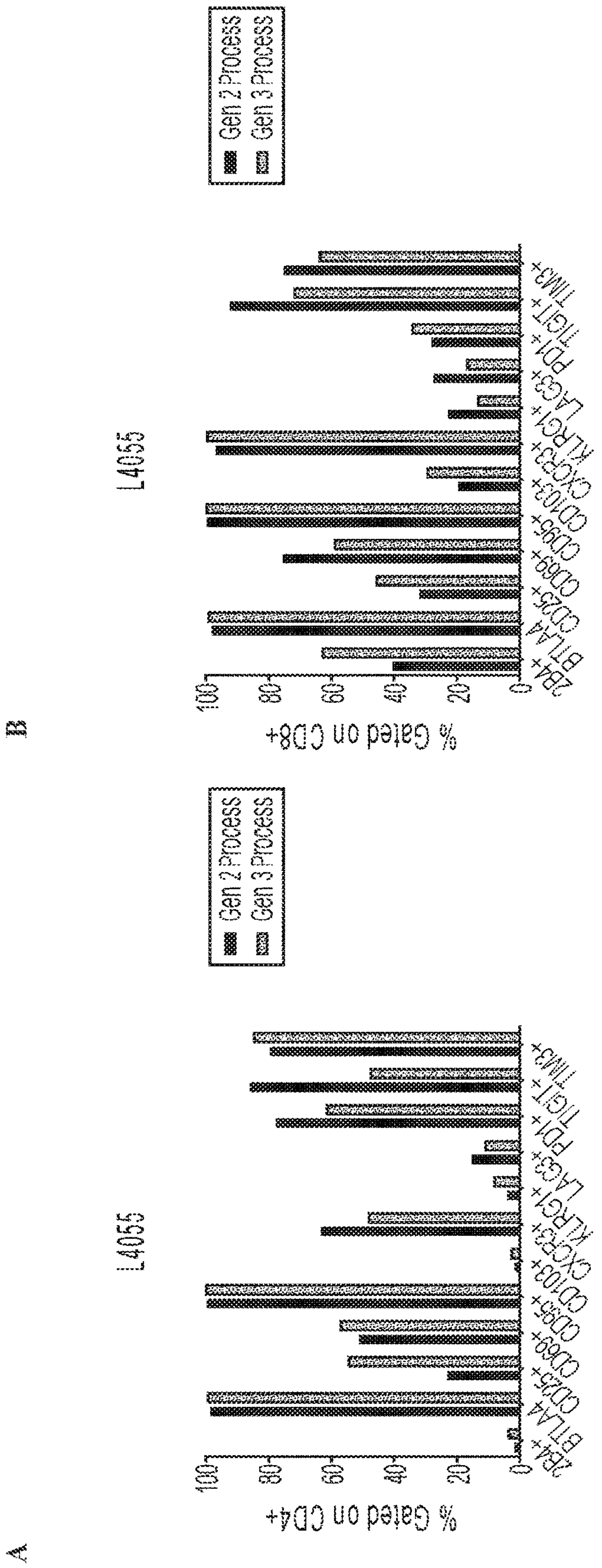
FIG. 6A-6B: L4055 Activation and exhaustion markers (A) Gated on CD4+, (B) Gated on CD8+.

Activation and Exhaustion Markers Comparison on TIL Final Product:

Activation and exhaustion marker were analyzed in TIL from two, tumors L4054 and L4055 to compare the final TIL product by from the Gen 2 and Gen 3 TIL expansion processes. Activation and exhaustion markers were comparable between the Gen 2 and Gen 3 processes. See, FIG. 5 (A, B); FIG. 6 (A, B).

Figure 7:
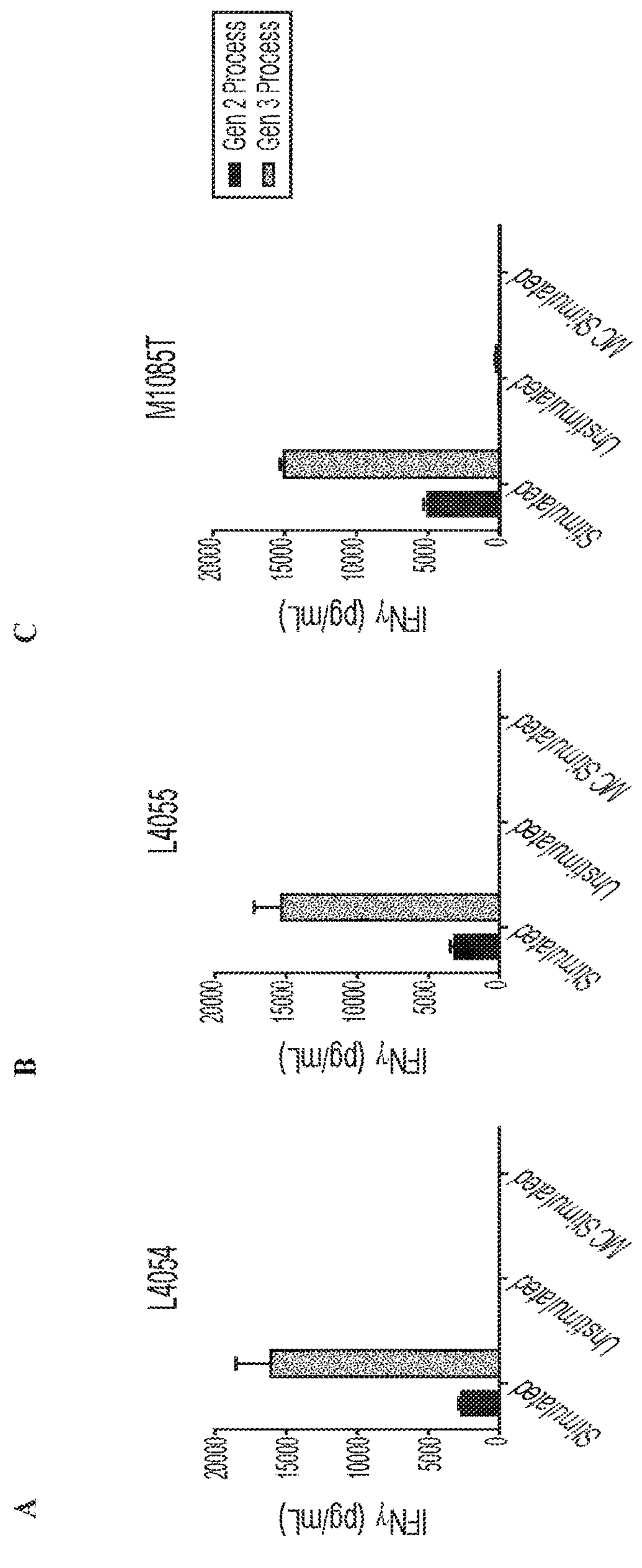
FIG. 7A-7C: IFNγ production (pg/mL): (A) L4054, (B) L4055, and (C) M1085T for the Gen 2 and Gen 3 processes: Each bar represented here is mean±SEM for IFNγ. levels of stimulated, unstimulated, and media control. Optical density measured at 450 nm.

Interferon Gamma Secretion Upon Restimulation:

On harvest day 22 for Gen 2 and day 16 for Gen 3, TIL underwent an overnight restimulation with coated anti-CD3 plates for L4054 and L4055. The restimulation on M1085T was performed using anti-CD3, CD28, and CD137 beads. Supernatant was collected after 24 hours of the restimulation in all conditions and the supernatant was frozen. IFNγ analysis by ELISA was assessed on the supernatant from both processes at the same time using the same ELISA plate. Higher production of IFNγ from the Gen 3 process was observed in the three tumors analyzed. See, FIG. 7 (A, B, C).

Figure 8:
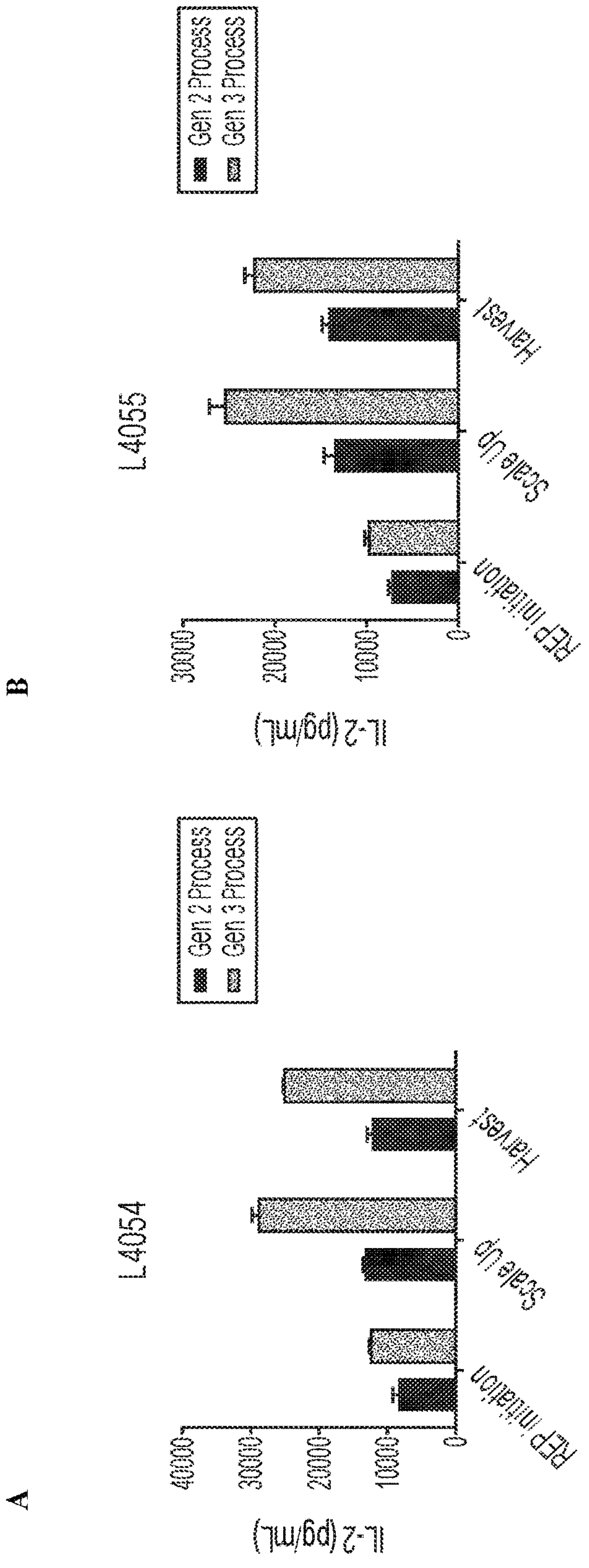
FIG. 8A-8B: ELISA analysis of IL-2 concentration in cell culture supernatant: (A) L4054 and (B) L4055. Each bar represented here is mean±SEM for IL-2 levels on spent media. Optical density measured at 450 nm.

Measurement of IL-2 Levels in Culture Media:

To compare the IL-2 consumption between Gen 2 and Gen 3 process, cell supernatant was collected on REP initiation, scale up, and harvest day, on tumor L4054 and L4055. The quantity of IL-2 in cell culture supernatant was measured by Quantitate ELISA Kit from R&D. The general trend indicates that the IL-2 concentration remains higher in the Gen 3 process when compared to the Gen 2 process. This is likely due to the higher concentration of IL-2 on REP initiation (6000 IU/mL) for Gen 3 coupled with the carry-over of the media throughout the process. See, FIG. 8 (A, B).

Metabolic Substrate and Metabolite Analysis

Figure 9:
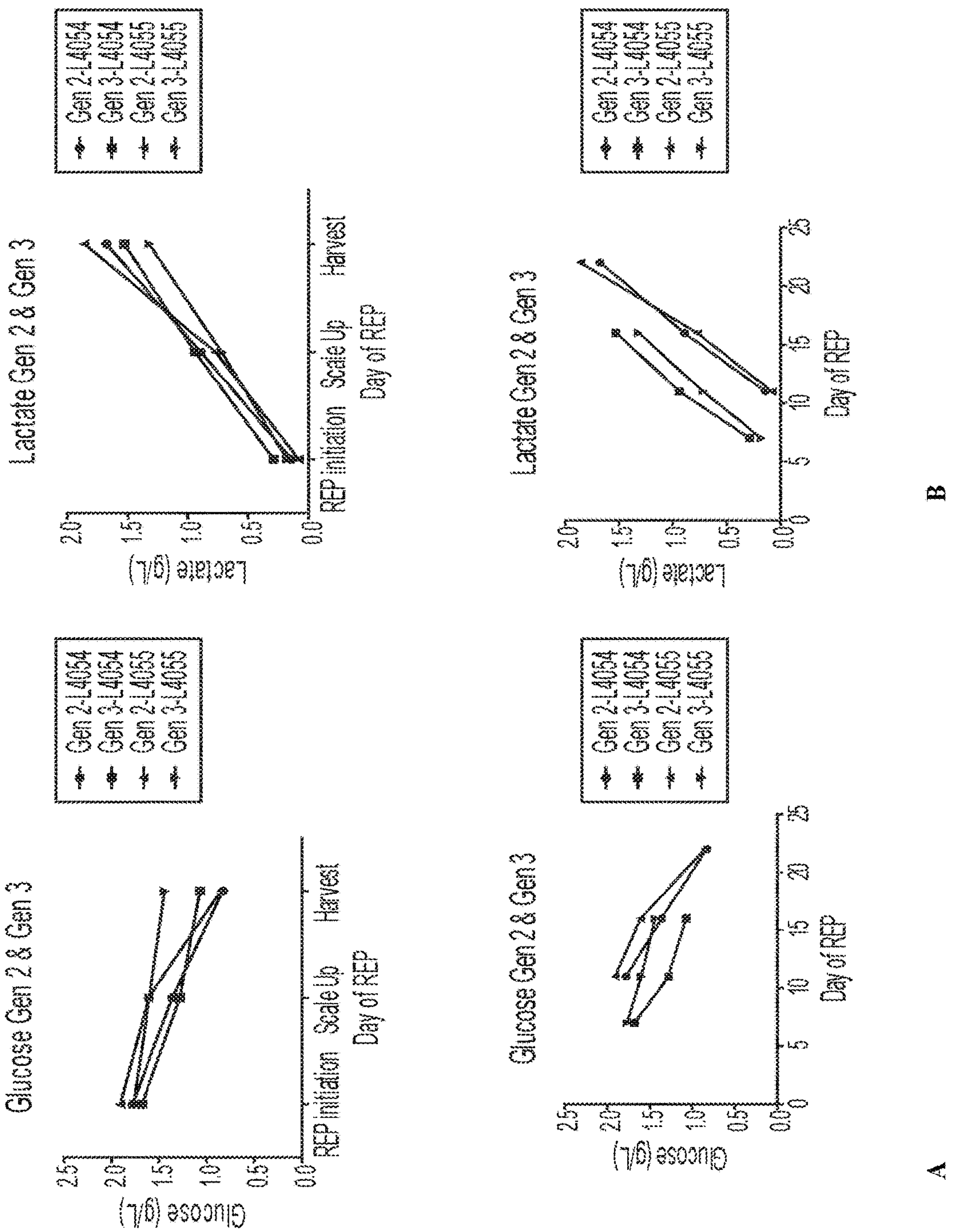
FIG. 9A-9B: Quantification of glucose and lactate (g/L) in spent media: (A) Glucose and (B) Lactate: In the two tumor lines, and in both processes, a decrease in glucose was observed. throughout the REP expansion. Conversely, as expected, an increase in lactate was observed. Both the decrease in glucose and the increase in lactate were comparable between the Gen 2 and Gen 3 processes.

The levels of metabolic substrates such as D-glucose and L-glutamine were measured as surrogates of overall media consumption. Their reciprocal metabolites, such lactic acid and ammonia, were measured. Glucose is a simple sugar in media that is utilized by mitochondria to produce energy in the form of ATP. When glucose is oxidized, lactic acid is produced (lactate is an ester of lactic acid). Lactate is strongly produced during the cells exponential growth phase. High levels of lactate have a negative impact on cell culture processes. See, FIG. 9 (A, B).

Spent media for L4054 and L4055 was collected at REP initiation, scale up, and harvest days for both process Gen 2 and Gen 3. The spent media collection was for Gen 2 on Day 11, day 16 and day 22; for Gen 3 was on day 7, day 11 and day 16. Supernatant was analyzed on a CEDEX Bio-analyzer for concentrations of glucose, lactic acid, glutamine, glutamax, and ammonia.

Figure 10C:
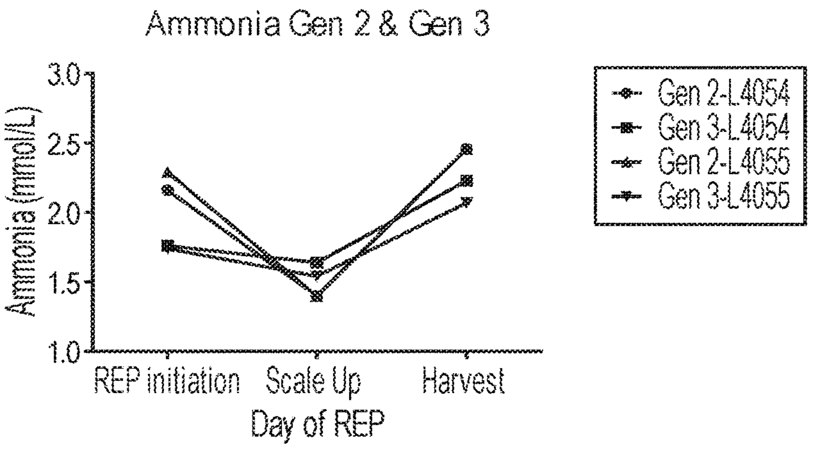
Figure 11:
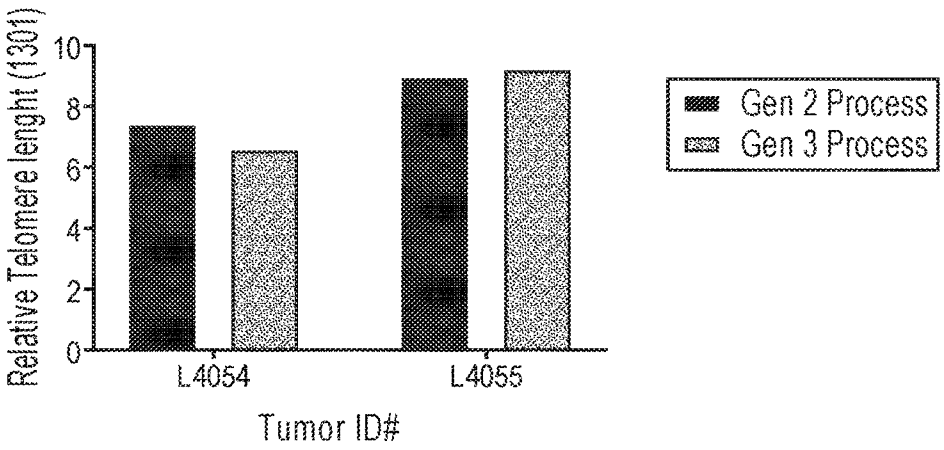
FIG. 11: Telomere length analysis: The above RTL value indicates that the average telomere fluorescence per chromosome/genome in Gen 2 and Gen 3 process of the telomere fluorescence per chromosome/genome in the control cells line (1301 Leukemia cell line) using DAKO kit.

L-glutamine is an unstable essential amino acid required in cell culture media formulations. Glutamine contains an amine, and this amide structural group can transport and deliver nitrogen to cells. When L-glutamine oxidizes, a toxic ammonia by-product is produced by the cell. To counteract the degradation of L-glutamine the media for the Gen 2 and Gen 3 processes was supplemented with Glutamax, which is more stable in aqueous solutions and does not spontaneously degrade. In the two tumor lines, the Gen 3 arm showed a decrease in L-glutamine and Glutamax during the process and an increase in ammonia throughout the REP. In the Gen 2 arm a constant concentration of L-glutamine and Glutamax, and a slight increase in the ammonia production was observed. The Gen 2 and Gen 3 processes were comparable at harvest day for ammonia and showed a slight difference in L-glutamine degradation. See, FIG. 10 (A, B, C).

Telomere Repeats by Flow-Fish:

Flow-FISH technology was used to measure the average length of the telomere repeat on L4054 and L4055 under Gen 2 and Gen 3 process. The determination of a relative telomere length (RTL) was calculated using Telomere PNA kit/FITC for flow cytometry analysis from DAKO. Gen 3 showed comparable telomere length to Gen 2.

CD3 Analysis

To determine the clonal diversity of the cell products generated in each process, TIL final product harvested for L4054 and L4055, were sampled and assayed for clonal diversity analysis through sequencing of the CDR3 portion of the T-cell receptors.

Table 26: Comparison of Gen 2 and Gen3 of percentage shared unique CDR3 sequences on L4054 on TIL harvested cell product. 199 sequences are shared between Gen 3 and Gen 2 final product, corresponding to 97.07% of top 80% of unique CDR3 sequences from Gen 2 shared with Gen 3 final product.

TABLE 26

Comparison of shared uCDR3 sequences between Gen 2 and Gen 3 processes on L4054.

| # uCDR3 | All uCDR3's | | Top 80% uCDR3's | |
|---|---|---|---|---|
| (% Overlap) | Gen 2 | Gen 3 | Gen 2 | Gen 3 |
| Gen 2-L4054 | 8915 | 4355 (48.85%) | 205 | 199 (97.07%) |
| Gen 3-L4054 | — | 18130 | — | 223 |

Table 27: Comparison of Gen 2 and Gen3 of percentage shared unique CDR3 sequences on L4055 on TIL harvested cell product. 1833 sequences are shared between Gen 3 and Gen 2 final product, corresponding to 99.45% of top 80% of unique CDR3 sequences from Gen 2 shared with Gen 3 final product.

TABLE 27

Comparison of shared uCDR3 sequences between Gen 2 and Gen 3 processes on L4055.

| # uCDR3 | All uCDR3's | | Top 80% uCDR3's | |
|---|---|---|---|---|
| (% Overlap) | Gen 2 | Gen 3 | Gen 2 | Gen 3 |
| Gen 2-L4055 | 12996 | 6599 (50.77%) | 1843 | 1833 (99.45%) |
| Gen 3-L4055 | — | 27246 | — | 2616 |

CM1 and CM2 media was prepared in advanced without filtration and held at 4 degree C. until use for tumor L4055 to use on Gen 2 and Gen 3 process.

Media was warmed up at 37 degree C. for 24 hours in advance for tumor L4055 on REP initiation day for Gen 2 and Gen 3 process.

LDH was not measured in the supernatants collected on the processes.

M1085T TIL cell count was executed with K2 cellometer cell counter.

On tumor M1085T, samples were not available such as supernatant for metabolic analysis, TIL product for activation and exhaustion markers analysis, telomere length and CD3-TCR vb Analysis.

Conclusions

This example compares 3 independent donor tumors tissue in terms of functional quality attributes, plus extended phenotypic characterization and media consumption among Gen 2 and Gen 3 processes.

Gen 2 and Gen 3 pre-REP and REP expansion comparison were evaluated in terms of total viable cells generated and viability of the total nucleated cell population. TVC cell doses at harvest day was not comparable between Gen 2 (22 days) and Gen 3 (16 days). Gen 3 cell doses were lower than Gen 2 at around 40% of total viable cells collected at harvest.

An extrapolated cell number was calculated for Gen 3 process assuming the pre-REP harvest occurred at day 11 instead day 7 and REP Harvest at Day 22 instead day 16. In both cases shows closer number on TVC compared to Gen 2 process, indicating that the early activation could allow an overall better performance on TIL growth. Table 4 and 5 bottom row.

In the case of extrapolated value for extra flasks (2 or 3) on Gen 3 process assuming a bigger size of tumor processed, and reaching the maximum number of fragments required per process as described. It was observed that a similar dose can be reachable on TVC at Day 16 Harvest for Gen 3 process compared to Gen 2 process at Day 22. This observation is important and indicates an early activation of the culture can allow better performance of TIL in less processing time Gen 2 and Gen 3 pre-REP and REP expansion comparison were evaluated in terms of total viable cells generated and viability of the total nucleated cell population. TVC cell doses at harvest day was not comparable between Gen 2 (22 days) and Gen 3 (16 days). Gen 3 cell doses were lower than Gen 2 at around 40% of total viable cells collected at harvest.

In terms of phenotypic characterization a higher CD8+ and CD28+ expression was observed on three tumors on Gen 3 process compared to Gen 2 process. This data indicates the Gen 3 process has improved attributes of final TIL product compared to Gen 2.

Gen 3 process showed slightly higher central memory compartments compared to Gen 2 process.

Gen 2 and Gen 3 process showed comparable activation and exhaustion markers, despite the shorter duration of the Gen 3 process.

IFN gamma (IFNγ) production was 3 times higher on Gen 3 final product compared to Gen 2 in the three tumors analyzed. This data indicates the Gen 3 process generated a highly functional and more potent TIL product as compared to the Gen 2 process, possibly due to the higher expression of CD8 and CD28 expression on Gen 3. Phenotypic characterization suggested positive trends in Gen 3 toward CD8+CD28+ expression on three tumors compared to Gen 2 process.

Telomere length on TIL final product between Gen 2 and Gen 3 were comparable.

Glucose and Lactate levels were comparable between Gen 2 and Gen 3 final product, suggesting the levels of nutrients on the media of Gen 3 process were not affected due to the non-execution of volume reduction removal in each day of the process and less volume media overall in the process, compared to Gen 2.

Overall Gen 3 process showed a reduction almost two times of the processing time compared to Gen 2 process, which would yield a substantial reduction on the cost of goods (COGs) for TIL product expanded by the Gen 3 process IL-2 consumption indicates a general trend of IL-2 consumption on Gen 2 process, and in Gen 3 process IL-2 was higher due to the non-removal of the old media.

The Gen 3 process showed a higher clonal diversity measured by CDR3 TCRab sequence analysis.

The addition of feeders and OKT3 on day 0 of the pre-REP, allowed an early activation of TIL and overall a better growth TIL performance using the Gen 3 process.

Table 28 describes various embodiments and outcomes for the Gen 3 process as compared to the current Gen 2 process:

TABLE 28

Exemplary Gen 3 process.

| Step | Process Gen 2 | Process Gen 3-Optimized |
|---|---|---|
| Pre REP-day 0 | ≤50 fragments<br>1X G-Rex 100MCS<br>IL media<br>IL-2 (6000 IU/mL)<br>11 days | ≤240 fragments<br>≤60 fragments/flask<br>≤4 flasks<br>≤2 L media (500 mL/flask)<br>IL-2 (6000 IU/mL)<br>2.5 × $10^8$ feeder cells/flask<br>15 ug OKT3/flask |
| REP Initiation | Fresh TIL direct to REP<br>Day 11<br>≤200e$^6$ viable cells<br>5 × $10^9$ feeder cells<br>G-Rex 500MCS<br>5 L CM2 media + IL-2 (3000 IU/mL)<br>150 ug OKT3 | Fresh TIL direct to REP<br>Day 7<br>Activate entire culture<br>5 × $10^8$ feeder cells<br>30 ug OKT3/flask<br>G-Rex 100MCS<br>500 mL media + IL-2(6000 IU/mL) |
| TIL Sub-culture or Scale up | ≤5 G-REX 500MCS<br>≤1 × 10 viable cells/flask<br>5 L/flask<br>Day 16 | ≤4 G-REX 500MCS<br>Scale up entire culture<br>4 L/flask<br>Day 10-11 |
| Harvest | Harvest Day 22, LOVO-automated cell washer 2 wash cycles | Harvest Day 16 LOVO- automated cell washer 5 wash cycles |
| Final formulation | Cryopreserved Product 300 IU/ml IL2- CS10 in $LN_2$, multiple aliquots | Cryopreserved product 300 IU/ml IL-2-CS10 in $LN_2$, multiple aliquots |
| Process time | 22 days | 16 days |

Example 6: Selecting and Expanding PD-1+ Cells Directly Ex Vivo: a Process for Enhancing Tumor-Reactive TIL for Act Therapy Introduction Adoptive T cell therapy with autologous tumor infiltrating lymphocytes (TIL) has demonstrated durable response rates in a cohort of patients with metastatic melanoma [1]. TIL products used for treatment are comprised of heterogeneous T cells, which recognize tumor-specific antigens, mutation-derived patient-specific neoantigens, and non-tumor related antigens [2,3]. Studies have demonstrated that neoantigen-specific T cells contribute significantly to the anti-tumor activity of TIL [4]. Strategies enriching TIL for tumor-reactivity are expected to yield more potent therapeutic products, especially in epithelial cancers known to contain a high proportion of bystander T cells [5]. Several studies have demonstrated that expression of PD1, a marker often associated with T cell exhaustion, on TIL identifies the autologous tumor-reactive T cells [6, 7, 8]. Presented here is the development of a new protocol designed to select PD1+ cells and enrich the TIL product for autologous tumor-reactive T cells. The present example provides a protocol to sort and expand PD1+ TIL and characterize the resulting product.

This protocol involves expanding ex vivo sorted PD1+ TIL from melanoma, lung cancer, breast cancer (triple negative and ER/PR tumors), and sarcoma, using a 2-REP protocol. The expanded TIL are assessed for growth, viability, phenotype, function (IFNγ secretion, CD107a mobilization), tumor killing (X-CELLigence), and TCR VB repertoire (by flow cytometry and RNA-sequencing). The exemplary methods are described in the chart provided in FIG. 7.

This example covers the PD1 selection project which is aimed at enriching the TIL product for TAA-specific TIL. It is based on the idead that tumor/neoantigen-specific T cells are responsible for the therapeutic activity of the TIL products and that the PD1+ subset of TIL comprises the tumor-reactive T cells.

Methods-Procedure

Tumor Preparation

Freshly resected tumor samples are received from research alliances (UPMC, Moffitt) and tissue procurement vendors (Biotheme and MTG group). The tumors are shipped overnight in HypoThermosol (Biolife Solutions, Washington, Cat #101104) (with antibiotic) or RPMI 1640 (Fisher Scientific, Pennsylvania, Cat #11875-085)+ male human AB serum (Access Biologicals, California, A13012).

Remove the tumor from its primary and secondary packaging, weigh the vial with the tumor and shipping media and record the mass. Remove the tumor from the vial and reweight the vial and shipping media. Calculate the mass of the tumor (Mass of vial+shipping media+tumor)−(vial+shipping media).

Fragment the entire tumor into approximately 4-6-mm$^3$ fragments for tumor digest. If the tumor is large enough, four 3 mm$^3$ fragments are set up processing.

Enzyme Preparation for Tumor Digestion

Reconstitute the lyophilized enzymes in the amount of sterile HBSS indicated for each of the digestion enzymes below. These enzymes are being prepared as 10×. Be sure to capture any residual powder from the sides of the bottles and from the protective foil on the bottles opening. Pipette up and down several times and swirl to ensure complete reconstitution.

Reconstitute 1-g of Collagenase IV (Sigma, MO, C5138) in 10-ml HBSS (to make a 100-mg/ml stock). Mix by pipetting up and down to dissolve. If not dissolved after reconstitution, place in a 37° C. $H_2O$ bath for 5 minutes. Aliquot into 1-ml vials. This is the 100-mg/ml 10× working stock for collagenase.

Prepare the DNAse (Sigma, MO, D5025) stock solution (10,000-IU/ml). The units of DNAse for each lot is provided in the accompanying data sheet. Calculate the appropriate volume of HBSS to reconstitute the 100-mg lyophilized DNAse stock. For example, if the DNAse stock is 2000-U/mg, the total DNAse in the stock is 200,000-IU (2000-IU/mg×100-mg). To dilute to a working stock of 10,000 IU, add 20-ml of HBSS to the 100 mg of DNAse (200,000 IU/20 ml=10,000U/ml). Aliquot into 1-ml vials. This is the 10,000 IU/ml 10× working stock for DNAse.

Prepare the hyaluronidase 10-mg/ml (Sigma, MO, H2126) stock solution. Reconstitute the 500-mg vial with 50-ml of HBSS to make a 10-mg/ml stock solution. Aliquot into 1-ml vials. This is the 10-mg/ml 10× working stock for hyaluronidase.

Tumor Processing and Digestion

Dilute the stock digest enzymes to 1×. To make a 1× working solution, add 500-μl each of the collagenase, DNase and hyaluronidase to 3.5-ml of HBSS.

If using GentleMACS OctoDissociator transfer the tumor fragments to a GentleMACS C-Tube (C-tube) or 50-ml conical tube in the 5-ml of digest cocktail (in HBSS) indicated above. Transfer 2-3 fragments (4-6 mm) to each C-tube.

Transfer each C-tube (Miltenyi Biotec, Germany, 130-096-334) to the GentleMACS OctoDissociator (Miltenyi Biotec, Germany, 130-095-937). Use according to the manufacturer's directions. Note, each tumor histology has a recommended program for tumor dissociation. Select the appropriate program for the respective tumor histology. The dissociation will be approximately one hour.

If the GentleMACS OctoDissociator is not available, use a standard rotator. Place 2-3 tumor fragments in a 50-ml conical tube (sealed with parafilm to avoid leakage) and secure to the rotator. Place the rotator, at 37° C., 5% $CO_2$ humidified incubator on constant rotation for 1-2 hours. Alternatively, the tumor fragments can be digested at RT overnight, also with constant rotation.

Post-digest, remove the C-tube from the Octodissociator or rotator. Attach a 0.22-μm strainer to sterile Falcon conical tube. Using a pipette, pass all contents from the C-tube/or 50-ml conical (5 ml) through the 0.22-μm strainer into a 50-ml conical. Wash the C-tube/50-ml conical with 10-ml of HBSS and apply to the strainer. Use the flat end of a sterile syringe plunger to dissociate any remaining non-digested tumor through the filter. Add CM1 or HBSS up to 50-ml and cap the tube.

Pellet the samples by centrifugation, 1500 rpm, 5 min at RT. Carefully remove the liquid, resuspend pellet in 5-ml of CM1 for cell counting and viability assessment.

Put aside whole tumor digest for the following: 1. Cell culture (control for PD1+ and PD1−) 2. FMO flow cytometry controls 3. Pre-sort whole tumor digest phenotyping assays 4. Frozen for tumor reactivity/cell killing assays. The number of cells put aside will depend on the total digest yield and tumor histology.

Cell Counting and Viability

The procedures for obtaining cell and viability counts, using the Nexcelom Cellometer K2 (Nexcelom, MA) have been described.

Staining Digested Tumor for Flow Cytometry Analysis and Cell Sorting

The tumor digest will be stained with a cocktail that includes an incubation with Nivolumab and staining with live/dead violet, anti-IgG4 Fc-PE (secondary antibody for Nivolumab) and CD3-FITC according to the following methods.

Post-count, resuspend the cells in 10-ml HBSS. Pellet the cells by centrifugation, 1500 rpm, 5 min at RT (acceleration and deacceleration of 9). Resuspend pellet in 5-ml of HBSS. Add 5-μl of live/dead blue dye (ThermoFisher, MA, Cat #L23105) for a final concentration of 1/1000. Incubate on ice for 20-30 min. Pellet the cells by centrifugation, 1500 rpm, 5 min at RT.

Resuspend pellet in FACS buffer (1×HBSS, 1 mM EDTA, 2% fetal bovine serum). The amount of FACS buffer added to the pellet is based upon the size of the pellet. The staining volume should be about 3 times the size of the pellet. Therefore, if there is 300-μl of cells, the volume of buffer should be at least 900-μl. Add 1 μg/ml of Nivolumab (Creative Biolabs, NY, Cat #TAB-770). The dilution will be dependent on the antibody stock. Incubate at 4° C. for 30 minutes. Resuspend pellet in 5-ml of cold HBSS.

Pellet the cells by centrifugation, 1500 rpm, 5 min at RT (acceleration and deacceleration of 9). Repeat the wash 2×. Resuspend pellet in 5 ml cold HBSS. Add 5-μl of live/dead blue dye (ThermoFisher, MA, Cat #L23105) for a final concentration of 1/1000. Incubate on 4° C. for 20-30 min.

Pellet the cells by centrifugation, 1500 rpm, 5 min at RT (acceleration and deacceleration of 9). As indicated above, resuspend pellet in FACS buffer (1×HBSS, 1 mM EDTA, 2% fetal bovine serum). The amount of FACS buffer added to the pellet is based upon the size of the pellet. The staining volume should be about 3 times the size of the pellet. Therefore, if there is 300-μl of cells, the volume of buffer should be at least 900-μl.

For antibody addition, each 100-μl of volume is equivalent to one test (titered amount of antibody). i.e. If there is 1-ml of volume, 10× the amount of titered antibody is required. Add 3-μl of anti-CD3-FITC (BD Biosciences, NJ, Cat #561807) per 100-μl of sample. Add anti-IgG4 Fc-PE at 1:500 (Southern Biotech, AL, Cat #9200-09). Therefore, add 1 μl of anti-IgG4 Fc-PE for every 500 μl of FACS buffer. Incubate cells on ice for 30 minutes. Protect from light during incubation. Agitate a couple times during incubation. Resuspend cells in 20-ml of FACS buffer. Pass solution through a 70-μm cell strainer into a new 50-ml conical. Centrifuge, 1500 rpm, 5 min at RT (acceleration and deacceleration of 9). Aspirate. Resuspend cells in up to 10e6 TOTAL (live+dead) in FACS buffer. Minimum volume is 300-μl.

Transfer to sterile polypropylene FACS tubes. 3-ml/tube for FACS sorting.

FACS Sorting (FX500 Startup)

While setting up the system and waiting for the calibration to complete prepare the following:

- Prepare five sterile 15-ml conical tubes with 10-ml of sterile D.I. water.
- Prepare five sterile 5-ml FACS tubes with 4-ml of sterile D.I. water.
- Prepare five sterile 15-ml conical tubes with 12-ml of 70% EtOH.
- Prepare five sterile 15-ml conical tubes with 12-ml of 10% Sodium Hypochlorite.

Sample Collection

Verify that the sample and collection chambers are at 5° C. and that the vortex as Agitate sample is selected. Adjust the PD1 gate as necessary.

When the gates are satisfactory, record as many events as possible (or 20,000 CD3 events maximum). You may set the sample pressure to 10 to speed up this collection. Stop the collection and remove the tube.

Open the Sample Chamber door and load the 15-ml collection chamber block to the chamber. Load the collection tubes containing the collection buffer into the chamber block. Adjust the sample pressure to maintain a sorting efficiency of at least 85%. Record 50,000 CD3 events. If there are over $4.5\times10^6$ cells collected in either fraction, the collection tube(s) will need to be changed. Continue sorting until all the sample is gone from the sample tube.

REP1 Initiation (Initiation of Priming First Expansion Step)

The condition that has the fewest number of cells (PD1+ or PD1−) is used to determine the number of CD3+ cells for REP1 initiation. The % of CD3 cells, (determined during the sort) will be used to calculate the total number of cells in the whole digest that are required to initiate REP1 with the same number of CD3 cells as the PD1+ and PD1− samples. Total number of whole digest cells for REP 1 initiation=Number of sorted cells inoculated in REP1/% of CD3 cells.

Approximately 1000-100,000 cells CD3+ cells are placed into either a G-Rex 24 or G-Rex10, with 7-ml or 40-ml of CM2 respectively (50% RPMI 1640+10% human serum, glutamax, gentamycin and 50% AimV) with 3000-IU/ml of IL-2 for 11 days. At least one G-Rex flask is initiated for the PD1+ and PD1− sorted populations and the whole tumor digest. Anti-CD3 (clone: OKT3) (30-ng/ml) and Feeders (1:100 ratio (TIL: feeders)) are added to each flask at the initiation of culture.

Incubate the cells in the plates/flasks for 11 days, no media changes are performed (REP1).

At the completion of REP1, remove approximately 5-ml of media for a G-Rex 24 and 30-ml of media for a G-Rex 10.

Resuspend the cells in the remaining media by pipetting up and down. Place cells in a 50-ml conical and centrifuge at 1500 rpm for 5 min.

Aspirate the media and resuspend cells in 10-20-ml of CM2 for counting and viability assessment.

REP2 Initiation (Initiation of Second Rapid Expansion)

For mini-REP2 initiation, 1e5 cells are placed into a G-Rex 10 with 40-ml of CM2 media and 3000-IU/ml of IL-2. Anti-CD3 (clone: OKT3) (30-ng/ml) and Feeders (1:100 ratio, TIL: feeders) are added at culture initiation.

For "full-scale runs", 2e6-30e6 cells are expanded in a G-Rex 100M in 1-L of CM2 media and 3000-IU/m of IL-2. Anti-CD3 (clone: OKT3) (30-ng/ml) and Feeders (1:100 ratio, TIL: feeders) are added at culture initiation.

A media change (For mini-scale) or media change+split (for "full scale runs) is performed at Day 5 of REP2 (Day 16 of process). The flasks are volume reduced to approximately 10-ml (G-Rex 10) or 100-ml (G-Rex 100M) and supplemented to 40-ml (G-Rex 10) or 1-L (G-Rex 100M) with either CM2 or AimV+3000-IU/ml IL-2. For "full scale runs", the flasks are split 1:2.

At Day 11 of REP2 (or Day 22 of the process), flasks are volume reduced, centrifuged at 1500 rpm for 5 min at RT.

The final product is assessed for cell count, viability, phenotype (TIL1, TIL2 (TIL2 panel for Surface Antigen Staining of TIL), TIL3 and function (CD107a (Assessing TIL function by CD107a mobilization, and IFNγ assay). The VB repertoire is assessed by FACS (Beckman Coulter, California, Cat #IM3497), which assesses 24 specificities (70% of the total VB family), according to the manufacturer's directions. Additional cells (1e6-5e6 cells) are pelleted and frozen for RNA-sequencing and analysis. Final Product is also assessed for tumor reactivity in a co-culture assay and assessed for IFNγ. When possible, thawed whole tumor digests will be co-cultured with TIL and assessed for tumor reactivity by co-culture and/or killing (% cytolysis) using the xCELLigence system (ACEA Biosciences, CA).

Materials and Methods

PD1-positive (PD1+) cells were sorted via flow cytometry directly from fresh tumor digests and expanded in vitro.

Samples from six melanomas, three sarcomas, six breast cancers, and eight lung cancer were evaluated.

3 populations were studied:

PD1+ sorted TIL.

PD-sorted TIL

Bulk TIL (whole tumor unsorted digest)

TIL were evaluated for yield (cell count), phenotype (flow cytometry), TCR VB repertoire (RNA-sequencing), non-specific functionality (anti-CD3 and PMA), and tumor reactivity and killing (co-culture assays).

A protocol has been developed for the expansion of PD1-selected TIL to clinically relevant numbers from melanoma, lung cancer, breast cancer, and sarcoma.

In vitro expansion of PD1-selected TIL resulted in products phenotypically comparable with bulk TIL.

T cell markers are upregulated relative to presort TIL, suggesting a high activation level. T cell markers regulated at the surface of expanded PD1+ TIL relative to pre-sort TIL included PD1 and CD25 and suggest a high activation level. Importantly, in vitro expansion of PD1+ TIL resulted in products phenotypically comparable with bulk TIL, indicating a strong therapeutic potential. Functionality of the expanded PD1+ TIL was confirmed by robust IFNγ and CD107a expression in response to non-specific stimulation. Expanded PD1+ TIL demonstrate oligoclonality, compared to PD1−-derived TIL and bulk TIL, a sign of antigen-driven clonal expansion at the tumor site. Preliminary data demonstrate autologous tumor cell killing by PD1+ but not PD1−-derived TIL.

PD1+-derived TIL demonstrate oligoclonality, compared to PD1−-derived TIL and bulk TIL.

All TIL products are functional as assessed by non-specific stimulation.

Autologous melanoma cell killing were observed in PD1+-derived TIL, but not in PD1-derived TIL and bulk TIL.

Results and Acceptance Criteria

The PD1+ sorted cells will show a defect in proliferative capacity. The final product yield will be > or =1e9. The PD1+ cells are will be oligoclonal, in comparison to PD1−. Based upon the premise that PD1+ cells are more likely to be antigen specific, PD1+ cells will likely exhibit enhanced tumor-specific killing capacity in comparison to their PD1-counterparts.

REFERENCED DOCUMENTS

1. Rosenberg, S. A., et al., Durable complete responses in heavily pretreated patients with metastatic melanoma using T-cell transfer immunotherapy. Clin Cancer Res, 2011. 17(13): p. 4550-7.
2. Kvistborg, P., et al., TIL therapy broadens the tumor-reactive CD8(+) T cell compartment in melanoma patients. Oncoimmunology, 2012. 1(4): p. 409-418.
3. Simoni, Y., et al., Bystander CD8(+) T cells are abundant and phenotypically distinct in human tumour infiltrates. Nature, 2018. 557(7706): p. 575-579.
4. Schumacher, T. N. and R. D. Schreiber, Neoantigens in cancer immunotherapy. Science, 2015. 348(6230): p. 69-74.
5. Turcotte, S., et al., Phenotype and function of T cells infiltrating visceral metastases from gastrointestinal cancers and melanoma: implications for adoptive cell transfer therapy. J Immunol, 2013. 191(5): p. 2217-25.
6. Inozume, T., et al., Selection of CD8+PD-1+ lymphocytes in fresh human melanomas enriches for tumor-reactive T cells. J Immunother, 2010. 33(9): p. 956-64.
7. Gros, A., et al., PD-1 identifies the patient-specific CD8 (+) tumor-reactive repertoire infiltrating human tumors. J Clin Invest, 2014. 124(5): p. 2246-59.
8 Thommen, D. S., et al., A transcriptionally and functionally distinct PD-1(+) CD8(+) T cell pool with predictive potential in non-small-cell lung cancer treated with PD-1 blockade. Nat Med, 2018.
9 Cohen et al., Isolation of neoantigen-specific T cells from tumor and peripheral lymphocytes J Clin Invest. 2015; 125(10): 3981-3991.

Example 7: Further Embodiment for Selecting and Expanding PD-1+ Cells Directly Ex Vivo: A Process for Enhancing Tumor-Reactive TIL for Act Therapy Research: Detecting PD1 with the M1H4 and EH12.2H7 Clones Anti-PD1 MIH4 mAb was used for early Research work, based on previous data. Feasibility of PD1 selected TIL expansion and functionality of the product were demonstrated, using the M1H4-sorted cells:

Staining protocol was prepared to:

Insure the staining of all PD1+ TIL.

Incorporate a conjugated anti-IgG4 for the detection of pre-bound receptors.

Protocol using the anti-PD1 EH12.2H7 mAb was used.

Further characterization of PD1 sorting protocol in order to verify that the appropriate PD1+ population is being selected, a new sorting strategy has been initiated to select the PD1high TIL, using the Stragegy:

a) 16 tumors in H&N (n=4), melanoma (n=4) and lung (n=7)

5 experiments are direct comparisons (i.e. PD1+vs PD 1high)

b) Analysis (includes functional and TCRvβ repertoire)

TABLE 29

| Protocol comparison | | |
|---|---|---|
| Step | Other protocols | Examplary protocol used in the present Eaxmple |
| Digest Procedure | GentleMACS dissociator | GentleMACS dissociation followed by Ficoll (if necessary) |
| Digest Cocktail | UNKNOWN | GMP Digest Cocktail developed at lovance No Ficoll Step |
| Cell Sorter | MACSQuantTyto | SONY FX500 |
| PD1 clone used for Sorting | PD1.3.1 (Miltenyi) | EH12.2H7 (BioLegend) + IgG4 |
| PD1+ sorting strategy | PD1+ | PD1+ or $PD1^{high}$ |
| Culturing Method | REP (14-days) | 2-REP process (11 days each) |

Preliminary Results and Summary:

The difference in phenotype and functionality of the expanded TIL (after REP1 and REP2) vs. the sorted PD1high population provide for a novel selection/sorting strategy.

Studies at have demonstrated that $PD1^{+}$-selected TIL, from lung and melanoma are antigen-specific and have greater effector function.

Cold tumors" with no PD1 activity (PD1/PD-L1 axis) are not appropriate for PD1 selection.

PD $1^{high}$ TIL tumors are ideal for selection due to the association of PD $1^{high}$ cells with neo-antigen/tumor specificity.

Further analyses will include phenotyping, funcationality, physiology, clonality, and analysis for impurities.

Phenotyping:

T-cell subsets (memory/alpha-beta vs gamma-delta)

Functionality

IFNg and Granzyme (Bead stimulation)

CD107a (PMA/IO stimulation)

Tumor reactivity by IFNg or CD107a/TNF or Granzyme B (Tumor Digest or HLA matched or HLA mismatched or other cancer antigens)

Tumor Killing assay (Xcelligence)

Polyfunctionality (IsoLight)?

Physiology

Telomere length

Fold expansion of cells

Cell cycle analysis, mitotic index

Exhaustion/senescence/activation markers

Clonality

Diversity (#unique clones)

Overlap in identity of unique clones iREP

Shannon entropy index

Impurities

Contaminating tumor cells, NK cells, other cells, process residuals

Example 8: Tumor Expansion Processes with Defined Medium

The processes disclosed in Examples 1 through 7 are performed with substituting the CM1 and CM2 media with a defined medium according to the present invention (e.g., CTS™ OpTmizer™ T-Cell Expansion SFM, ThermoFisher, including for example DM1 and DM2).

Example 9: Selection and Expansion of PD-1+ TIL for Full Scale Manufacturing

Purpose

This example describes the results from the selection and expansion of PD-1+ TIL in small- and full-scale manufacturing experiments as described in this example.

Information

Several studies had demonstrated that surface expression of PD-1, a marker often associated with T cell exhaustion, identifies the autologous tumor-reactive T cells in the tumor micro-environment. A protocol was designed to select PD-1 positive (PD-1+) cells from tumor digests to enrich the TIL product for autologous tumor-reactive T cells. The protocol was adapted and modified for use for both small and full-scale manufacturing.

Scope

Small-scale PD-1+ selected Gen 2 process (PD-1+ Gen2) was used to expand PD-1+ selected TIL from one Lung tumor digest and one Melanoma tumor digest. TIL final products were characterized per protocol TP-19-004.

Full-scale PD-1+ selected Gen 2 process (PD-1+ Gen2) was used to expand the PD-1+ selected TIL from two Head and Neck tumor digests and one Melanoma tumor digest. TIL final products were characterized per protocol TP-19-004.

Experiment Design

The description of the small scale and full scale manufacturing processes are shown in Tables 30, 31 below.

Small scale studies (Phase 1) were feasibility study to scale up and optimize the TIL expansion process to clinical scale. Additional conditions were tested to explore the use of Defined media and Early REP (Shorted REP 1) in the PD-1+ TIL expansion.

TABLE 30

| Overview of Small-Scale Processes for PD-1+ TIL Culture (Research/PD-1+ Gen 2/Defined Media/Early REP) | | | | |
|---|---|---|---|---|
| Conditions | PD-1+ Research | PD-1+ Gen 2* | PD-1+ Defined Media Gen 2^λ^ | PD-1+ Early REP |
| REP-1 | Day 0: REP-1 | Day 0: REP-1 | Day 0: REP-1 | Day 0: REP-1 |
| TIL | 10% of PD-1+ sort count | 10% of PD-1+ sort count | 10% of PD-1+ sort count | 10% of PD-1+ sort count |
| Feeders | Varies TIL to Feed at 1:100 | 10e6 | 10e6 | 10e6 |
| CM2 | 50 mL | 100 mL | 100 mL | 100 mL |
| IL-2 | 3000 IU/mL | 3000 IU/mL | 3000 IU/mL | 3000 IU/mL |
| OK13 (30 ng/mL) | 30 ng/mL | 30 ng/mL | 30 ng/mL | 30 ng/mL |
| G-Rex | 10 | 10M | 10M | 10M |
| REP-2 | Day 11: REP-2 | Day 11: REP-2 | Day 11: REP-2 | Day 7: REP-2 |
| TIL | 100,000 TVC | 20% TVC | 20% TVC | 20% TVC |
| Feeders | 10e6 | 100e6 | 100e6 | 100e6 |
| CM2 | 50 mL | 100 mL | 100 mL | 100 mL |
| IL-2 | 3000 IU/mL | 3000 IU/mL | 3000 IU/mL | 3000 IU/mL |
| OKT3 (30 ng/mL) | 30 ng/mL | 30 ng/mL | 30 ng/mL | 30 ng/mL |
| G-Rex | 10 | 10M | 10M | 10M |
| Scale up | No Scale up | Day 16: Volume reduce and split (TVC/20e6, round up) up to 5 10M flasks | Day 16: Volume reduce and split (TVC/20e6, round up) up to 5 10M flasks | Day 12: Volume reduce and split (TVC/20e6, round up) up to 5 10M flasks |
| REP-2 Harvest | Day 22: REP-2Harvest | Day 22: REP-2 Harvest | Day 22: REP-2 Harvest | Day 17: REP-2 Harvest |
| Extrapolation Calculation: | | | | |
| REP-1 | Multiply by Harvest TVC by 10 | Multiply REP-1 Harvest TVC by 10 | Multiply REP-1 Harvest TVC by 10 | Multiply REP-1 Harvest TVC by 10 |
| REP-2 | Multiply by Harvest TVC by REP-2 TVC/1e5 | Multiply by REP-2 Harvest by 50 x # of split flasks | Multiply by REP-2 Harvest by 50 x # of split flasks | Multiply by REP-2 Harvest by 50 x # of split flasks |

*PD-1$^{neg}$ Gen 2 and PD-1 Bulk TIL Gen 2 use the same conditions for small scale culture as the PD-1+ Gen 2

$^{\lambda}$Defined media condition use CTS OpTmizer with 3% CTS Immune Cell Serum replacement

TABLE 31

| Overview of Full-Scale Processes for PD-1+ TIL culture (PD-1 + Gen 2) | |
|---|---|
| Conditions | PD-1+ Gen 2 |
| REP-1 | Day 0: REP-1 |
| TIL | PD-1+ sort count |
| Feeders | 100e6 |
| CM2 | 1000 mL |
| IL-2 | 3000 IU/mL |
| OKT3 (30 ng/mL) | 30 ng/mL |
| G-Rex | 100MCS |
| REP-2 | Day 11: REP-2 |
| TIL | 5e6-200e6 TVC |
| Feeders | 5e9 |
| CM2 | 5 L |
| IL-2 | 3000 IU/mL |
| OKT3 (30 ng/mL) | 30 ng/mL |
| G-Rex | 500MCS |
| Scale up | Day 16: Volume reduce and split up to 5 G-Rex500 MCS in CM4 + 3000 IU/mL of IL-2 |
| REP-2 Harvest | Day 22: REP-2 Harvest |

Table 31 below lists the tumors used in this study and the associated histologies.

TABLE 31

| Tumors Used in the Study | | | |
|---|---|---|---|
| Experiments | Histology | ID | Additional Tumor information |
| Phase 1 Small-Scale (1/10$^{th}$/1/50$^{th}$ scale of intended clinical manufacturing process) | | | |
| Small scale 1 | Lung | L4093 | Vendor ID: 535-C055, 0.5 gms |
| Small scale 2 | Melanoma | M1135 | Vendor ID: 061-Y025, Lymph node |
| Phase 2 Full-Scale (intended clinical manufacturing process) | | | |
| Full scale 1 | Head and Neck | H3032 | Vendor ID: M4190034 A4, Oral cavity, 0.35 gms |
| Full scale 2 | Melanoma | M1137 | Vendor ID: 093-Y032 |
| Full scale 3 | Head and Neck | H3034 | Vendor ID: 747048A1, 0.3 gms |

Acceptance Criteria

Characterization testing of these lots for the parameters listed in Tables 3 and 4 below were performed for information only.

Table 33 below specifies the acceptance criteria used to evaluate the performance of the Phase 2/full-scale lots.

TABLE 33

| Harvest Product Testing and Acceptance Criteria | | |
|---|---|---|
| Test Type | Method | Acceptance Criterion |
| In-Process Testing | | |
| Post-sort Purity (% PD1+) | Flow Cytometry | ≥80% |
| Release Testing | | |
| Appearance | Visual Inspection | Bag intact, no sign of clumps |
| Cell viability | Fluorescence | ≥70% |
| Total Viable Cell Count | Fluorescence | $1 \times 10^9$ to $150 \times 10^9$ |
| Identity (% CD45+ CD3+) | Flow Cytometry | ≥90% CD45+ CD3+ cells |
| IFNg(Stimulated − Unstimulated) | Bead stimulation and ELISA | ≥500 pg/mL |

Table 34 below specifies the additional final product characterization testing performed for information only for the Phase 2 full scale lots.

TABLE 34

| Final Product Characterization (for information only) | | |
|---|---|---|
| Test Type | Method | Report Results |
| Purity and Memory T cell subset Phenotype | Flow Cytometry (LAB-055) | Report results |
| Activation and Exhaustion marker Phenotype | Flow Cytometry (LAB-061) | Report results |
| Telomere length | Flow FISH (Attachment -1) | Report results |
| Granzyme B | Bead stimulation and ELISA (LAB-064) | Report results |
| CD107A | Mitogen stimulation and flow cytometry (LAB-061) | Report results |
| TCR Vbeta Sequencing | Deep sequencing (Irepertoire, Inc) | Report results (if available) |
| Metabolite analysis | Cedex Biochemical analyzer | Report results |

Results

Phase 1 Small-Scale Feasibility Results

Lung (L4093) and Melanoma (M1135) tumors were used in the Phase 1 study. Briefly, each tumor was enzymatically digested, sorted by FACS for PD-1+ cells, and the following cultures were initiated on Day 0 as test conditions:

(1) PD-1+ Research (2) PD-1+ Gen 2

(3) PD-1+ Defined media (4) PD-1+ Early REP.

Two additional cultures were also initiated from each tumor as controls. These two conditions were compared with PD-1+ condition for Expansion kinetics and TCR-Vbeta clonotypes.

(5) PD-1neg Gen 2

(6) Bulk TIL Gen 2

The PD-1+ Early REP cuture was harvested on Day 17 whereas all other cultures were harvested on Day 22 (See Table-la).

Cell Sorting Output

Outputs from the FACS of the two tumors used in the Phase 1 study are summarized in Table 35 below.

TABLE 35

| Pre- and Post-Sort Purity of PD-1+ TIL by Flow Cytometry. | | |
|---|---|---|
| Attribute | Lung (L4093) | Melanoma (M1135) |
| % CD3+ | 8.17% | 1.77% |
| % PD-1+ (of CD3+) | 79% | 65% |
| Estimated TVC Pre-Sort (% CD3+ PD-1+) | 5.6e5 (6.5%) | 4.88e4 (1.2%) |
| TVC Sorted (% Yield) | 4.5e5 (80.7%) | 4.8e4 (98.4) |
| Post-sort Purity (% PD-1+)** | 94% | 88% |

*Purity was based on FSC/CD3+/PD-1+ but not on Viable cells because viability dye is not added during flow sorting of cells for subsequent culture The % yield and post-sort purity of PD-1+ cells was high for both tumors. These results indicate that the experimental parameters used for the small scale feasibility study were satisfactory.

REP1 and REP2 Outputs

Total viable cells (TVC) were measured after REP-1 and REP-2 using an NC 200, and are shown in Table 36 below. The numbers represented in the table for TVC are extrapolated to the full-scale process using the factors.

TABLE 36

Summary of Small-Scale Manufacturing and Product Attributes

| | | Tumor ID | | | | | | | |
|---|---|---|---|---|---|---|---|---|---|
| | | L4093 | | | | M1135 | | | |
| REP | Attribute Measured | PD1+ Research | PD-1+ Gen 2 | PD-1+ Defined Media | PD-1+ Early REP | PD1+ Research | PD-1+ Gen 2 | PD-1+ Defined Media | PD-1+ Early REP |
| REP-1 | TVC seeded (Extrapolated) | 4.48e5 | 4.48e5 | 4.48e5 | 4.48e5 | 4.8e4 | 4.8e4 | 4.8e4 | 4.8e4 |
| | TVC harvested (Extrapolated) | 599e6 | 560e6 | 225e6 | 44e6 | 34e6 | 272e6 | 256e6 | 46e6 |
| | REP-1 Fold expansion | 1336 | 1249 | 503 | 99 | 705 | 5670 | 5334 | 958 |
| REP-2 | TVC seeded (Extrapolated) | 599e6 | 200e6 | 200e6 | 44e6 | 34e6 | 200e6 | 200e6 | 44e6 |
| | TVC harvested (Extrapolated) | 24e9 | 97e9 | 64e9 | 55e9 | 4.3e9 | 99e9 | 97e9 | 37e9 |

TABLE 36-continued

Summary of Small-Scale Manufacturing and Product Attributes

| REP | Attribute Measured | L4093 PD1+ Research | L4093 PD-1+ Gen 2 | L4093 PD-1+ Defined Media | L4093 PD-1+ Early REP | M1135 PD1+ Research | M1135 PD-1+ Gen 2 | M1135 PD-1+ Defined Media | M1135 PD-1+ Early REP |
|---|---|---|---|---|---|---|---|---|---|
| | REP-2 Fold expansion | 40 | 483 | 318 | 1235 | 128 | 497 | 483 | 811 |
| | % Viability | 96 | 98 | 95 | 92 | 95 | 98 | 94 | 93 |
| | % CD45+ CD3+ | 98.5 | 96.8 | 98.2 | 99.1 | 88.2 | 94.3 | 90.4 | 98.7 |
| | IFNγ (pg/mL) | 4005 | 4446 | 5646 | 14009 | 1784 | 3147 | 2757 | 4458 |
| | Granzyme-B (pg/mL) | 8397 | 7903 | 10387 | 46654 | 3642 | 3428 | 6336 | 25194 |
| | % CD4+ CD107A (Stimulated) | NT | 40 | 44 | 42 | NT | 40 | 38 | 55 |
| | % CD8+ CD107A (Stimulated) | NT | 68 | 43 | 66 | NT | 42 | 47 | 82 |

Fold expansion = TVC harvested/TVC seeded

% CD107A was calculated from CD3+ CD4+ or CD3+ CD8+ gated population

Process Yield: The PD-1+ Gen 2 arm of the experiment yielded more than 200e6 at REP-1 harvest, and more than 90e9 TIL with >98% viability and 94% CD45+CD3+ cells at REP-2 harvest, suggesting that PD1+ Gen 2 is a feasible process to produce enough cells for full scale manufacturing. REP-1 harvested TIL from the PD-1+ Gen 2 condition showed lower fold expansion when compared to PD-1neg or Bulk TIL conditions. This finding was consistent with previous Research findings.

Function: TIL expanded from the PD-1+ Gen 2 process released IFNγ and Granzyme B at similar levels to TIL generated using the Research process in response to anti-CD3/CD28/CD137 bead stimulation (Table 34). The REP-1 and REP-2 product from the PD-1+ Defined Media condition was similar to the corresponding products for PD-1+ Gen 2 condition across all parameters tested. Interestingly, PD-1+ Early REP condition with a total culture duration of 17 days (vs 22 days for PD-1+ Gen 2 process) yielded 57% (Rep-1) and 37% (REP-2) of the corresponding PD-1+ Gen 2 condition. Further, PD-1+ Early REP TIL produced 2 times more IFNγ and Granzyme B levels when compared to other conditions, indicating that the PD-1+ Early REP TIL are likely actively growing and metabolically more active than TIL generated using other conditions. Given that the doubling time of TIL in culture is typically <1 day, together this suggests that a comparable cell output (with respect to cell numbers) and higher functionality (with respect to IFN and Granzyme B release) may be achieved by slightly increasing the PD-1+ Early REP culture duration to 18 or 19 days vs. 22 days for PD-1+ Gen 2, CD107A expression on activated T cell surface is a measure of T lymphocyte function. All the PD1+ TIL expressed high levels CD107A when stimulated with PMA/IO (both CD4+ and CD8+ TIL)

TIL Longevity: Table 37 describes the TIL Telomere Length, as determined by Fluorescence In-Situ Hybridization flow cytometry (FISH Flow), for the REP-2 Harvest.

TABLE 37

Summary of Relative Telomere Length (RTL) Compared to the Control (1301) Cell Line

| TIL Characterization | L4093 PD-1+ Gen 2 | L4093 Bulk TIL Gen 2 | M1135 PD-1+ Gen 2 | M1135 Bulk TIL Gen 2 |
|---|---|---|---|---|
| Relative Telomere length | 8.1 | 5.2 | 6.5 | 7.5 |

Telomere length in samples of L4093 and M1135 was compared to a control cell line (1301 leukemia). The control is a tetraploid cell line having long stable telomeres that allows calculation of a relative telomere length. Telomeres of PD1+ TIL were longer in one case and slightly shorter in the other case when compared to Bulk TIL, suggesting that PD-1+ TIL maintained their longevity relative to Bulk TIL.

TIL Clonality: Table 38 describes the clonality of TIL from REP 2 Harvest as measured by the TCR VB repertoire.

TABLE 38

TCR Vβ Repertoire Summary for L4093 and M1135

| TIL Characterization | L4093 PD-1+ Gen 2 | L4093 Bulk TIL Gen 2 | M1135 PD-1+ Gen 2 | M1135 Bulk TIL Gen 2 |
|---|---|---|---|---|
| uCDR3 | 2886 | 6537 | 2371 | 7128 |
| Shannon Entropy Index | 5.7 | 8.1 | 5.5 | 8.6 |
| Portion shared with Bulk condition | 46 | n/a | 12 | n/a |

The number of unique CDR3 sequences for the PD-1+ Gen2 condition for both lung and melanoma TIL were comparable. Additionally, the TCR VB repertoire for PD-1+ Gen 2 condition showed more than 10% overlap with the corresponding repertoire for bulk TIL. Diversity index (Shanon Entropy) for PD-1+ Gen2 condition was less than the diversity index for bulk TIL, suggesting that TCR VB repertoire for PD1+ Gen 2 condition is less polyclonal and more oligoclonal than the corresponding repertoire for bulk TIL.

Extended Phenotyping: Tables 39-41 describe results from Extended Phenotype analysis of TIL. Multicolor flow cytometry was used to characterize TIL Purity, identity, memory subset, activation and exhaustion status of REP-2 TIL.

TABLE 39

TIL Purity, Identity and Memory phenotypic characterization

| | L4093 | | | | M1135 | | | |
|---|---|---|---|---|---|---|---|---|
| Characteristic (%) | PD1+ Research | PD-1+ Gen 2 | PD-1+ Defined Media | PD-1+ Early REP | PD1+ Research | PD-1+ Gen 2 | PD-1+ Defined Media | PD-1+ Early REP |
| NK cells | 0 | 0 | 0.1 | 0 | 0 | 0 | 0.3 | 0.1 |
| B cells (CD3− CD19+) | 0 | 0 | 0 | 0 | 0 | 0 | 0 | 0 |
| Monocytes (CD14+) | 0.1 | 0.1 | 0 | 0 | 0.1 | 0 | 0 | 0 |
| TCRαβ | 98.8 | 97.9 | 99.2 | 99.3 | 98.7 | 95.6 | 98.8 | 98.8 |
| TCRγδ | 0.1 | 0.1 | 0.1 | 0 | 0.1 | 0 | 0 | 0 |
| TCRαβ$^+$ CD4$^+$ | 91.1 | 79.6 | 77.8 | 89.1 | 75.8 | 90.6 | 86.1 | 90.4 |
| TCRαβ$^+$ CD8$^+$ | 8.5 | 20.2 | 21.8 | 10.5 | 17.4 | 9 | 11.1 | 8.5 |
| Naïve: CCR7+ CD45RA+ | 0 | 0 | 0 | 0 | 0 | 0 | 0 | 0 |
| T-EM: CCR7− CD45RA | 99.9 | 99.6 | 99.7 | 99.8 | 99.8 | 99.9 | 99.7 | 99.6 |
| T-CM: CCR7+ CD45RA | 0.1 | 0.1 | 0.1 | 0.2 | 0.1 | 0 | 0.1 | 0.4 |
| T-CM: CD62L+ CD45RA | 0 | 0.1 | 2 | 1.3 | 0 | 0.6 | 0.9 | 7.4 |
| T-EFF/TEMRA: CCR7− CD45RA+ | 0 | 0.3 | 0.2 | 0 | 0.1 | 0 | 0.1 | 0 |

NK cells; Natural Killer cells gated on Live/CD14−/CD3−/CD19−/CD56+ and/or CD16+, B cells; gated on Live/CD14−/CD3−/CD19+, Monocytes; Live/CD14+, TCR α/β; gated on Live/CD14−/CD3+/TCRγ/δ−, Memory cells; gated on Live/CD14−/CD3+/TCRγ/δ−, T-EM; Effector, T-CM; Central Memory, T-EFF/TEMRA; Effectors/RA+ Effector Memory.

TABLE 40

Activation and Exhaustion status of CD4+ TIL

| | L4093 | | | | M1135 | | | |
|---|---|---|---|---|---|---|---|---|
| Characteristic (CD4+) gated on Live/CD3+/CD4+ (%) | PD-1+ Research | PD-1+ Gen 2 | PD-1+ Defined Media | PD-1+ Early REP | PD-1+ Research | PD-1+ Gen 2 | PD-1+ Defined Media | PD-1+ Early REP |
| CD27+ | 2 | 2.8 | 1.5 | 6.3 | 2.2 | 3.8 | 2.1 | 3.8 |
| CD28+ | 99.2 | 95.7 | 94.8 | 98.9 | 97.9 | 95.2 | 93.4 | 99 |
| CD57+ | 31 | 23.1 | 29.8 | 14.1 | 11.4 | 15.7 | 13.8 | 6.7 |
| 2B4+ | 10.1 | 7.7 | 13.7 | 10.8 | 4.3 | 1.2 | 0.8 | 1.4 |
| BTLA4+ | 99.7 | 99.5 | 99.9 | 99.9 | 99.6 | 99.8 | 99.8 | 99.8 |
| *CCR4+ | 94.2 | 85.7 | 81.7 | 91.9 | 99 | 96 | 94.8 | 96.1 |
| CD25+ | 2.6 | 2.6 | 12.3 | 11.3 | 35.6 | 2.5 | 4.8 | 45.9 |
| CD69+ | 31.6 | 40.2 | 25 | 23.6 | 41.7 | 28.9 | 24.2 | 25.9 |
| CD95+ | 99.9 | 99.2 | 99.8 | 99.7 | 99.9 | 99.2 | 99 | 99.9 |
| CD103+ | 3.6 | 0.7 | 1 | 1.7 | 1 | 0.4 | 0.5 | 0.7 |
| **CXCR3+ | 10.7 | 12.3 | 20.2 | 9.4 | 4.7 | 22 | 6.1 | 5.5 |
| KLRG1+ | 6.7 | 14.7 | 1.4 | 11.8 | 2 | 1.7 | 1.1 | 1.8 |
| LAG3+ | 10 | 14.7 | 4.4 | 14.3 | 10.4 | 15.7 | 4.3 | 15.5 |
| PD1+ | 6.5 | 1.8 | 0.4 | 3.4 | 7.5 | 2.4 | 0.5 | 4.1 |
| TIGIT+ | 13.2 | 9.2 | 17 | 36.7 | 50.8 | 18 | 43.6 | 44.6 |
| TIM3+ | 93.4 | 95.7 | 92.5 | 98.4 | 88.3 | 80.7 | 86.1 | 96.9 |

*Percentage was calculated from (CXCR3+ CCR4+ and CXCR3− CCR4+).
**Percentage was calculated from (CXCR3− CCR4− and CXCR3+ CCR4−).

TABLE 41

Activation and Exhaustion status of CD8+ TIL

| | L4093 | | | | M1135 | | | |
|---|---|---|---|---|---|---|---|---|
| Characteristic (CD8+) gated on Live/CD3+/CD8+ | PD-1+ Research | PD-1+ Gen 2 | PD-1+ Defined Media | PD-1+ Early REP | PD-1+ Research | PD-1+ Gen 2 | PD-1+ Defined Media | PD-1+ Early REP |
| CD27+ (%) | 5.1 | 6.8 | 3.7 | 10.8 | 2.1 | 6 | 13.8 | 5.4 |
| CD28+ (%) | 97.6 | 93 | 91.7 | 96.4 | 95.8 | 95.5 | 88.7 | 94.6 |
| CD57+ (%) | 11.5 | 4.6 | 7.1 | 6.5 | 12.8 | 4.8 | 9 | 4.5 |
| 2B4+ (%) | 37.2 | 17.1 | 32.9 | 29.5 | 0.8 | 0.8 | 10.4 | 1.2 |
| BTLA4+ (%) | 99.9 | 99.8 | 99.9 | 100 | 99.8 | 100 | 99.7 | 99.8 |

TABLE 41-continued

Activation and Exhaustion status of CD8+ TIL

| Characteristic (CD8+) gated on Live/CD3+/CD8+ | L4093 PD-1+ Research | PD-1+ Gen 2 | PD-1+ Defined Media | PD-1+ Early REP | M1135 PD-1+ Research | PD-1+ Gen 2 | PD-1+ Defined Media | PD-1+ Early REP |
|---|---|---|---|---|---|---|---|---|
| *CCR4+ (%) | 84.1 | 79.8 | 67.4 | 88.7 | 97.1 | 86.6 | 89.1 | 96.1 |
| CD25+ (%) | 1.8 | 0.7 | 3.7 | 9.9 | 33.8 | 3.6 | 1.1 | 58.2 |
| CD69+ (%) | 68.3 | 52 | 60.7 | 52.2 | 74.2 | 59 | 85.2 | 80.3 |
| CD9S+ (%) | 99.8 | 99.2 | 99.7 | 99.5 | 99.9 | 99.2 | 99.1 | 99.5 |
| CD103+ (%) | 1.9 | 17.2 | 2.9 | 17.4 | 0.1 | 0.4 | 0.4 | 1.1 |
| **CXCR3+ (%) | 12.4 | 18.1 | 33.7 | 15.4 | 5.7 | 24.4 | 17.1 | 6.7 |
| KLRG1+ (%) | 24.8 | 3.5 | 3.2 | 15.3 | 2.8 | 3.0 | 1.2 | 2.8 |
| LAG3+ (%) | 34.8 | 46.2 | 30.3 | 45.7 | 29.6 | 40.3 | 28.3 | 58.2 |
| PD1+ (%) | 8.8 | 5.2 | 1 | 4 | 4.5 | 1.9 | 0.4 | 4 |
| TIGIT+ (%) | 77.4 | 77.6 | 71.3 | 91.2 | 99.3 | 79.6 | 86.8 | 92.9 |
| TIM3+ (%) | 90.9 | 92.8 | 93.2 | 97.7 | 96.5 | 88.6 | 96.8 | 99.2 |

*Percentage was calculated from (CXCR3+ CCR4+ and CXCR3− CCR4+).
**Percentage was calculated from (CXCR3− CCR4− and CXCR3+ CCR4−).

PD-1+ Gen 2 TIL were comprised primarily of TCR αβ with less than 0.2% TCR γδ cells. Non-T cell population including B cells, monocytes and NK cells were each <0.3%. All the conditions including PD-1+ Gen 2 TIL were primarily Effector memory phenotype and less differentiated with high levels of CD28+, BTLA+, CD95+ expression.

Activation (CD69+) and exhaustion (KLRG1+) status of TIL for the PD-1+ condition were comparable to historical results for Melanoma TIL generated using the Gen 2 manufacturing process.

Based on Process yield, function, Phenotype, PD-1+ Gen 2 showed promising quality attributes when compared to PD-1+ Defined media and PD-1+ early REP.

Phase 2 Full Scale Experiments Results

One Melanoma (M1137) and two Head and Neck (H3032 and H3034) tumors were used in the Phase 2 study. Briefly, each tumor was enzyme digested, flow sorted for PD-1+ cells, and the cultures were initiated at full scale on Day 0 using the PD-1+ Gen 2 process described in Table 31.

Flow Sorting Output

Outputs from the flow sort of the three tumors used in the Phase 2 study are summarized in Table 42 below.

TABLE 42

Pre- and post-sort purity of PD-1+ TIL by Flow Cytometry.

| Tumor (ID) | Acceptance Criterion | Head & Neck (H3032) | Melanoma (M1137) | Head & Neck (H3034) |
|---|---|---|---|---|
| % CD3+ | N/A | 24 | 13 | 9 |
| % PD-1+ (of CD3+) | N/A | 65 | 45 | 77 |
| TVC Pre-Sort | N/A | 5.6e5 | 7e5 | 2e5 |
| TVC Sorted (% Yield) | N/A | 1.13e5 (20%) | 1.9e5 (25%) | 5e4 (25%) |
| *Post-sort Purity (PD-1%) | ≥80% | 90% | 87% | 86% |

*Purity was based on FSC/CD3+/PD1+ but not on Viable cells because viability dye is not added during flow sorting of cells for subsequent culture Post sorted purity (% PD-1+) for all three tumors met the criterion of >80%. The slightly lower purity observed for the melanoma tumor relative to the Hea and Neck tumors is most likely due to the lower expression of PD-1+ cells while sorting (Appendix-1).

REP-1 and REP-2 Outputs

Table 43 summarizes the Total viable cell count and product attributes from the three full scale experiments.

TABLE 43

Summary of full scale manufacturing and product attributes

| | Tumor (ID) | Acceptance Criterion | Head & Neck (H3032) | Melanoma (M1137) | Head & Neck (H3034) |
|---|---|---|---|---|---|
| REP-1 | TVC seeded | N/A | 8.5e4 | 1.4e5 | 3.7e4 |
| | TVC harvested | N/A | 1.48e8 | 7.11e8 | 8.2e7 |
| | REP-1 Fold expansion | N/A | 1748 | 5097 | 2172 |
| REP-2 | TVC seeded | 5-200e6* | 148e6 | 200e6 | 82e6 |
| | TVC harvested-Pre LOVO | N/A | 32e9 | 72e9 | 27e9 |
| | TVC Post-LOVO (% Recovery) | 1-150e9 (N/A) | 29e9 (90%) | 69e9 (95.9%) | 26e9 (99%) |
| | REP-2 Fold expansion | N/A | 195 | 343 | 324 |
| | % Viability | ≥70% | 94% | 95% | 92% |
| | % CD45+/CD3+ | >90% | 94% | 93% | 96% |
| | IFNγ (pg/mL) | ≥500 | 8673 | 11347 | 21345 |
| | Granzyme B (pg/mL) | N/A | 32229 | 14652 | 37412 |
| | % CD4+ CD107A (Stimulated) | N/A | 52 | 74 | 59 |

TABLE 43-continued

Summary of full scale manufacturing and product attributes

| Tumor (ID) | Acceptance Criterion | Head & Neck (H3032) | Melanoma (M1137) | Head & Neck (H3034) |
|---|---|---|---|---|
| % CD8+ CD107A (Stimulated) | N/A | 66 | 88 | 90 |

*Range for TVC seeded at REP-2 based on current established range for Gen 2 REP process, and is not a formal acceptance criterion in the protocol
Fold expansion = TVC harvested/TVC seeded
% CD107A was calculated from CD3+ CD4+ or CD3+ CD8+ gated population Process Yield: At the end of REP-1, all the three PD-1+ TIL expanded to greater than 80e6 (>1500 fold expansion), with sufficient yield to initiate REP-2 culture. The range of 5-200e6 TVC seeded at REP-2 is based on the current Gen 2 REP process. At REP-2 Harvest, all cultures yielded >26 e9 TVC with post-Lovo recoveries >90%.

Dose: Final product doses were >26e9 TVC with >94% viability and 93% CD45+CD3+ cells, i.e. a highly enriched TIL population.

Function: Function of TIL was characterized based on overnight restimulation PD-1+ TIL with Dynabeads. The supernatants were collected after 24 hours of the restimulation and frozen. IFNγ and Granzyme B ELISAs were performed on the supernatants. IFNγ release met the acceptance criterion, and all three TIL cultures secreted high levels of Granzyme B upon stimulation. Similar to TIL products generated in the Phase 1 studies, all three PD1+ TIL expressed profound CD107A when stimulated with PMA/IO (both CD4+ and CD8+ TIL).

TIL Longevity: Relative telomere length of PD-1+ TIL for the H3032, M1137, H3034 were 7, 4.1 and 5.2 respectively, and were comparable to Gen 2 (QP-17-011R01).

TIL Clonality: Data is pending.

Extended Phenotyping: Tables 44 and 45 describe the Extended Phenotype analysis of TIL. Multicolor flow cytometry was used to characterize TIL Purity, identity, memory subset, activation and exhaustion status of REP-2 TIL.

TABLE 44

TIL Purity, Identity and Memory phenotypic characterization

| Characteristic (%) | H3032 | M1137 | H3034 |
|---|---|---|---|
| NK cells (CD3− CD56+) | 0.1 | 0 | 0.1 |
| B cells (CD3− CD19+) | 0 | 0 | 0 |
| Monocytes (CD14+) | 0 | 0 | 0 |
| TCRαβ | 92.2 | 97 | 97.8 |
| TCRγδ | 0.5 | 0.3 | 0.3 |
| TCRαβ + CD4+ | 93.7 | 89.1 | 92.9 |
| TCRαβ + CD8+ | 5.7 | 10.1 | 2.1 |
| Naïve: CCR7+ CD45RA+ | 0 | 0 | 0 |
| T-EM: CCR7− CD45RA− | 96.4 | 97.3 | 99.3 |
| T-CM: CCR7+ CD45RA− | 2.5 | 2.6 | 0.6 |
| T-EFF/TEMRA: CCR7− CD45RA+ | 1.1 | 0.1 | 0.1 |
| T-CM: CD62L+ CD45RA− | 7.6 | 11.7 | 3.5 |

TABLE 45

Activation and Exhaustion status of TIL

| Characteristic | CD4+ | | | CD8+ | | |
|---|---|---|---|---|---|---|
| (%) | H3032 | M1137 | H3034 | H3032 | M1137 | H3034 |
| CD27+ | 15.6 | 20.4 | 6 | 10.3 | 20.3 | 4.9 |
| CD28+ | 76.4 | 78.6 | 83.9 | 90 | 90 | 76.9 |

TABLE 45-continued

Activation and Exhaustion status of TIL

| Characteristic | CD4+ | | | CD8+ | | |
|---|---|---|---|---|---|---|
| (%) | H3032 | M1137 | H3034 | H3032 | M1137 | H3034 |
| CD57+ | 27.7 | 35.2 | 22.3 | 12.7 | 22 | 10.5 |
| 2B4+ | 3.4 | 4.1 | 0.6 | 4.3 | 4 | 0.7 |
| BTLA4+ | 83.4 | 91.1 | 83.6 | 88.7 | 87 | 68.3 |
| *CCR4+ | 29.4 | 17.4 | 17.3 | 16.1 | 10.2 | 2.3 |
| CD25+ | 30.1 | 4.2 | 17.3 | 23.1 | 2.3 | 7.8 |
| CD69+ | 14 | 9.8 | 39.7 | 26.7 | 18.5 | 75 |
| CD95+ | 98.9 | 99.2 | 99.8 | 99.5 | 98.3 | 99.7 |
| CD103+ | 5.7 | 3.8 | 7.9 | 0 | 0 | 0.1 |
| **CXCR3+ | 86.3 | 92.8 | 80.3 | 7.3 | 8.1 | 1.5 |
| KLRG1+ | 6 | 23.5 | 6.9 | 10.2 | 12.1 | 10.1 |
| LAG3+ | 8.3 | 5.4 | 1.5 | 21.2 | 10.5 | 5.4 |
| PD1+ | 6 | 1.4 | 0.9 | 14.7 | 5.6 | 1.3 |
| TIGIT+ | 5.9 | 0.4 | 10.1 | 34.4 | 18.7 | 20.9 |
| TIM3+ | 79.6 | 84.3 | 77 | 73.5 | 86.1 | 60 |

*Percentage was calculated from (CXCR3+ CCR4+ and CXCR3− CCR4+).
**Percentage was calculated from (CXCR3− CCR4− and CXCR3+ CCR4−).

No detectable B-cells, Monocytes or NK cells were present in the final harvested TIL (Table-14). REP TIL were consist of mostly by TCRαβ with effector memory differentiation.

All the three PD-1+ TIL appears to be CD4 dominant phenotype with the effector memory phenotype and high CD27 expression (Table 44).

Exhaustion marker KLRG1 was less than 13% except M1137 (Table 45). CD57, BTLA4, LAG3, PD1+, TIGIT levels were similar to historical results for Melanoma TIL generated using the Gen 2 manufacturing process.

Metabolite analysis: Spent media was collected on final day of harvest for all the conditions. Supernatant was analyzed on a CEDEX Bio-analyzer for the glucose, lactate, Ammonia, Glutamine, Glutamax and Cholesterol levels (Appendix 3). Glucose, Glutamine, and Cholesterol levels of PD-1+ Gen 2 conditions were comparable to Bulk TIL condition. Glutamax levels for PD-1+ Gen 2 conditions slightly higher than Bulk TIL, suggesting that availability of nutrients were not limiting growth of the culture. Byproducts such as lactate and ammonia were comparable to bulk TIL.

Discrepancies and Deviations

PD-1+ TIL final product samples from Full scale experiments were sent to iRepertoire for TCR VB sequencing. Report will be amended once data available.

Due to material limitation, the small scales performed for L4093 and M1135 were done at a 1/50th scale, rather than a 1/100th scale. Instead of transferring 10% of the volume, maximum 2e6 cells, into a G-Rex 5M flask, 20% of the volume, maximum 4e6 cells were transferred. The scale up was affected by changing the scale up formula from TVC/10e6, round up, max 5, to TVC/20e6, round up, max 5. These changes make the final extrapolation of 50× rather than 100× to extrapolate to the full scale. The details in the preceding sections of this report reflect this change.

Conclusions

PD-1+ Gen 2 process was developed at full scale to expand PD-1+ TIL to >25e9 in 22 days. All the quality attributes such as phenotypic characterization including purity, memory, activation, exhaustion markers and function of TIL generated using the PD-1+ Gen 2 process were comparable to Melanoma Gen 2.

Summary Table 46:

| Testing Parameters | Acceptance Criterion | H&N 3032 | M1137 | H&N 3034 |
|---|---|---|---|---|
| Appearance | Bag intact, no sign of clumps | Pass | Pass | Pass |
| Cell viability | ≥70% | Pass | Pass | Pass |
| Total Viable Cell Count | 1 × 10e9 to 150 × 10e9 | Pass | Pass | Pass |
| Identity (% CD3/% CD45+) | >90% CD3+ CD45+ cells | Pass | Pass | Pass |
| IFNγ(Stimulated - Unstimulated) | ≥500 pg/mL | Pass | Pass | Pass |

PD-1+ Gen2 process was selected for further development of the PD-1 selected TIL product.

Based on the results obtained at small scale, performed additional experiments with the PD-1+ Early REP condition to characterize the PD-1+ expansion process to a shorter duration of 17-19 days without compromising on dose or product function. See, FIG. 156.

REFERENCES FOR EXAMPLE 10

1. Rosenberg, S. A., et al., Durable complete responses in heavily pretreated patients with metastatic melanoma using T-cell transfer immunotherapy. Clin Cancer Res, 2011. 17(13): p. 4550-7.
2. Kvistborg, P., et al., TIL therapy broadens the tumor-reactive CD8(+) T cell compartment in melanoma patients. Oncoimmunology, 2012. 1(4): p. 409-418.
3. Simoni, Y., et al., Bystander CD8(+) T cells are abundant and phenotypically distinct in human tumour infiltrates. Nature, 2018. 557(7706): p. 575-579.
4. Schumacher, T. N. and R. D. Schreiber, Neoantigens in cancer immunotherapy. Science, 2015. 348(6230): p. 69-74.
5. Turcotte, S., et al., Phenotype and function of T cells infiltrating visceral metastases from gastrointestinal cancers and melanoma: implications for adoptive cell transfer therapy. J Immunol, 2013. 191(5): p. 2217-25.
6. Inozume, T., et al., Selection of CD8+PD-1+ lymphocytes in fresh human melanomas enriches for tumor-reactive T cells. J Immunother, 2010. 33(9): p. 956-64.
7. Gros, A., et al., PD-1 identifies the patient-specific CD8 (+) tumor-reactive repertoire infiltrating human tumors. J Clin Invest, 2014. 124(5): p. 2246-59.
8. Thommen, D. S., et al., A transcriptionally and functionally distinct PD-1(+) CD8(+) T cell pool with predictive potential in non-small-cell lung cancer treated with PD-1 blockade. Nat Med, 2018.

TABLE 47

Summary of TIL expansion (Extrapolated to Full scale) for L4093

| L4093 Condition | REP1-Day 0 | REP1-Day 7 | REP1-Day 11 (Fold Expansion) | REP2-Day 17 | REP2-Day 22 |
|---|---|---|---|---|---|
| Research | 448000 | NA | 5.99E+08 (1336) | NA | 2.42E+10 |
| Gen 2.1 -like PD-1+ | 448000 | NA | 5.60E+08 (1249) | NA | 9.66E+10 |
| Gen 2.1 -like PD-1+ (DM) | 448000 | NA | 2.25E+08 (503) | NA | 6.37E+10 |
| Gen 2.1 -like PD-1− | 448000 | NA | 8.75E+08 (1954) | NA | 7.16E+10 |
| Gen 2.1 -like Bulk TIL | 448000 | NA | 1.80E+09 (4022) | NA | 8.58E+10 |
| 17 Day Early REP | 448000 | 4.43E+07 | NA | 5.5E+10 | NA |

TABLE 48

Summary of TIL expansion (Extrapolated to Full scale) for M1135

| M1135 Condition | REP1-Day 0 | REP1-Day 7 | REP1- Day 11 (Fold Expansion) | REP2-Day 17 | REP2-Day 22 |
|---|---|---|---|---|---|
| Research | 48000 | NA | 3.38E+07 (705) | NA | 4.34E+09 |
| Gen 2.1 -like PD-1+ | 48000 | NA | 2.72E+08 (5670) | NA | 9.94E+10 |
| Gen 2.1 -like PD-1+ (DM) | 48000 | NA | 2.56E+08 (5334) | NA | 9.65E+10 |
| Gen 2.1 -like PD-1− | 48000 | NA | 2.73E+08 (5693) | NA | 2.10E+09 |
| Gen 2.1 -like Bulk TIL | 48000 | NA | 1.52E+09 (31604) | NA | 9.16E+10 |
| 17 Day Early REP | 48000 | 4.60E+07 | NA | 3.7E+10 | NA |

TABLE 49

| Summary of Bulk TIL expansion (Extrapolated to Full scale) for H3032, M1137 and H3034 | | | | | |
|---|---|---|---|---|---|
| Condition | REP1- Day 0 | REP1- Day 7 | REP1- Day 11 (Fold Expansion) | REP2- Day 17 | REP2- Day 22 |
| Bulk TIL H3032 | 84700 | NA | 1.61E+08 (1905) | NA | 7.78E+10 |
| Bulk TIL M1137 | 140000 | NA | 3.84E+08 (2752) | NA | 6.89E+10 |
| Bulk TIL H3034 | 37600 | NA | 4.16E+07 (1105) | NA | 5.21E+10 |

NA—Not applicable

TABLE 50

| Summary of Metabolites levels in the spent media | | | | | | | |
|---|---|---|---|---|---|---|---|
| Tumor | Metabolites | Baseline (CM4) | Research | Gen 2 PD-1(+) | Gen 2 PD-1(−) | Bulk TIL | 17 Day ER |
| L4093 | Glucose | 3.01 | 0.11 | 0.98 | 1.11 | 0.97 | 0.95 |
| M1135 | (g/L) | | 0.14 | 1.21 | 1.26 | 1.04 | 1.06 |
| H3032 | | | — | 1.44 | — | 1.3 | — |
| M1137 | | | — | 1.48 | — | 1.46 | — |
| H3034 | | | — | 1.35 | — | 1.78 | — |
| L4093 | Lactate | 0 | 1.5 | 1.72 | 1.6 | 1.72 | 1.78 |
| M1135 | (g/L) | | 1.67 | 1.49 | 1.5 | 1.66 | 1.67 |
| H3032 | | | — | 1.27 | — | 1.39 | — |
| M1137 | | | — | 1.28 | — | 1.26 | — |
| H3034 | | | — | 1.4 | — | 1.07 | — |
| L4093 | Ammonia | 0.57 | 2.96 | 2.12 | 2.13 | 2.18 | 2.47 |
| M1135 | (mmol/L) | | 2.95 | 2.06 | 2.06 | 2.22 | 2.31 |
| H3032 | | | — | 2.19 | — | 2.29 | — |
| M1137 | | | — | 2.24 | — | 2.22 | — |
| H3034 | | | — | 1.95 | — | 1.62 | — |
| L4093 | Glutamine | 1.83 | 0.03 | 1.84 | 1.84 | 1.84 | 1.45 |
| M1135 | (mmol/L) | | 0.03 | 2.01 | 2.04 | 1.79 | 1.66 |
| H3032 | | | — | 1.96 | — | 1.85 | — |
| M1137 | | | — | 2.01 | — | 1.89 | — |
| H3034 | | | — | 2.09 | — | 0.67 | — |
| L4093 | Glutamax | 4.11 | 0.01 | 1.99 | 1.98 | 1.98 | 1.56 |
| M1135 | (mmol/L) | | 0.02 | 2.18 | 2.21 | 1.95 | 1.79 |
| H3032 | | | — | 2.12 | — | 2 | — |
| M1137 | | | — | 2.15 | — | 2.02 | — |
| H3034 | | | — | 2.25 | — | 0.71 | — |
| L4093 | Cholesterol | 0.02 | 0.17 | 0.02 | 0.02 | 0.02 | 0.03 |
| M1135 | (g/L) | | 0.15 | 0.02 | 0.02 | 0.02 | 0.03 |
| H3032 | | | — | 0.02 | — | 0.02 | — |
| M1137 | | | — | 0.02 | — | 0.02 | — |
| H3034 | | | — | 0.02 | — | 0.02 | — |

TABLE 51

| | Sample IDs | | | | | |
|---|---|---|---|---|---|---|
| | L4093 | | M1135 | | H3032 | |
| Materials/ Reagents/ Equipment | Lot#/ Asset#/Not Applicable (N/A) | Expiration Date/Not Applicable (N/A) | Lot#/ Asset#/Not Applicable (N/A) | Expiration Date/ Not Applicable (N/A) | Lot#/ Asset#/Not Applicable (N/A) | Expiration Date/Not Applicable (N/A) |
| Anti-CD3 antibody | B2499555 | Oct. 31, 2024 | B2499555 | Oct. 31, 2024 | B2499555 | Oct. 31, 2024 |
| Anti-IgG4 antibody | 10817T998B | October 2019 | 10817T998B | October 2019 | 10817T998B | October 2019 |
| Anti-PD1 antibody | B252643 | Dec. 31, 2022 | B252643 | Dec. 31, 2022 | B252643 | Dec. 31, 2022 |
| DNAse 1 | 35999731 | January 2020 | 35999731 | January 2020 | 35999731 | January 2020 |
| Collagenase | 10000015 | Feb. 28, 2023 | 10000015 | Feb. 28, 2023 | 10000015 | Feb. 28, 2023 |
| Neutral Protease | 10020005 | Dec. 31, 2020 | 10020005 | Dec. 31, 2020 | 10020005 | Dec. 31, 2020 |
| C Tubes | 5180621392 | Jun. 28, 2021 | 5180621392 | Jun. 28, 2021 | 5180621392 | Jun. 28, 2021 |
| Octo Dissociator with Heater | 1573 | n/a | 1573 | n/a | 1573 | n/a |

TABLE 51-continued

| | | | | | | |
|---|---|---|---|---|---|---|
| Cell Strainer | 154246 | n/a | 154246 | n/a | 154246 | n/a |
| Automatic Setup Beads | T1804148 | Apr. 11, 2019 | T1804148 | Apr. 11, 2019 | T1804148 | Apr. 11, 2019 |
| PBS-EDTA Bags | 5180904466 | Aug. 14, 2021 | 5180904466 | Aug. 14, 2021 | 5180904466 | Aug. 14, 2021 |
| PEEK Sample Line | * | n/a | * | n/a | PKSLR1S-000555 | n/a |
| Sheath Line | * | * | * | * | * | * |
| Sorting Chip | T1810151 | Oct. 9, 2019 | T1810151 | Oct. 9, 2019 | T1810151 | Oct. 9, 2019 |
| BSC | 126112 | n/a | 126112 | n/a | 126112 | n/a |
| Sony FX500 | 500708 | n/a | 500708 | n/a | 500708 | n/a |

| | Sample IDs | | | |
|---|---|---|---|---|
| | M1137 | | H3034 | |
| Materials/ Reagents/ Equipment | Lot#/ Asset#/Not Applicable (N/A) | Expiration Date/Not Applicable (N/A) | Lot#/ Asset#/Not Applicable (N/A) | Expiration Date/Not Applicable (N/A) |
| Anti-CD3 antibody | B2499555 | Oct. 31, 2024 | B2499555 | Oct. 31, 2024 |
| Anti-IgG4 antibody | 10817T998B | October 2019 | 10817T998B | October 2019 |
| Anti-PD1 antibody | B252643 | Dec. 31, 2022 | B252643 | Dec. 31, 2022 |
| DNAse 1 | 35999731 | January 2020 | 35999731 | January 2020 |
| Collagenase | 10000015 | Feb. 28, 2023 | 10000015 | Feb. 28, 2023 |
| Neutral Protease | 10020005 | Dec. 31, 2020 | 10020005 | Dec. 31, 2020 |
| C Tubes | 5180621392 | Jun. 28, 2021 | 5180621392 | Jun. 28, 2021 |
| Octo Dissociator with Heater | 1573 | n/a | 1573 | n/a |
| Cell Strainer | 154246 | n/a | 154246 | n/a |
| Automatic Setup Beads | T1804148 | Apr. 11, 2019 | T1804148 | Apr. 11, 2019 |
| PBS-EDTA Bags | 5180904466 | Aug. 14, 2021 | 5180904466 | Aug. 14, 2021 |
| PEEK Sample Line | PKSLR1S-000538 | n/a | PKSLR1S-001286 | n/a |
| Sheath Line | * | * | * | * |
| Sorting Chip | T1810151 | Oct. 9, 2019 | T1810151 | Oct. 9, 2019 |
| BSC | 126112 | n/a | 126112 | n/a |
| Sony FX500 | 500708 | n/a | 500708 | n/a |

Example 10: Selecting and Expanding PD1High Cells Directly Ex Vivo: A Process for Enhancing Tumor-Reactive TIL for Act Therapy

Introduction

Adoptive T cell therapy with autologous tumor infiltrating lymphocytes (TIL) has demonstrated durable response rates in a cohort of patients with metastatic melanoma [1]. TIL products used for treatment are comprised of heterogenous T cells, which recognize tumor-specific antigens, mutation-derived patient-specific neoantigens, and non-tumor related antigens [2,3]. Studies have demonstrated that neoantigen-specific T cells contribute significantly to the anti-tumor activity of TIL [4]. Strategies enriching TIL for tumor-reactivity are expected to yield more potent therapeutic products, especially in epithelial cancers known to contain a high proportion of bystander T cells [5]. Several studies have demonstrated that expression of PD1, a marker often associated with T cell exhaustion, on TIL identifies the autologous tumor-reactive T cells [6, 7, 8]. Presented in this example is the development of a new protocol designed to select PD1$^{high}$ cells and enrich the TIL product for autologous tumor-reactive T cells.

Purpose

This example provides a protocol to sort and expand PD 1$^{high}$ TIL and characterize the resulting product.

Scope

This investigation involves expanding ex-vivo sorted PD 1$^{high}$ TIL from melanoma, lung, and head and neck cancer using a 2-REP protocol. The expanded TIL are assessed for growth, viability, phenotype, function (IFNγ secretion, CD107a mobilization), tumor killing and reactivity (X-CEL-Ligence), and TCRvβ repertoire (by flow cytometry and RNA-sequencing). Protocol method overview is provided in FIG. 131.

Materials

Tumor Tissue

Tumors of various histologies are received from UPMC, Moffitt, Biotheme and MT group.

Standard reagents for TIL growth which includes: G-Rex 24 well plates, and 10 and 100M flasks (Wilson Wolf, Minnesota, Cat #P/N 80192M; #80040S; #P/N 80500); CM2 media; RPMI 1640 medium (Life Tech, California, Cat #11875093); AIMV medium (Gibco, Massachusetts, Cat #0870112-DK); Glutamate (Gibco, Massachusetts, Cat #30050-061); Beta-mercaptoethanol (Gibco, Massachusetts, Cat #21985-023); Human AB serum (Gemini, California, Cat #100-512); 0.5 mg/ml Gentamycin (Gibco, Massachusetts, Cat #15750-060); and GMP recombinant IL-2 (CellGenix, Germany, Cat #1020-1000).

Analysis Reagents

Flow cytometry compensation beads: Amine Reactive Compensation Bead Kit (ARC) (Life Technologies, California, Cat #A10346) and VersaComp Antibody Capture Kit (Beckman Coulter, California, Cat #B22804).

Flow cytometry antibodies (TIL1, TIL2 (TIL2 panel for Surface Antigen Staining of TIL, v1 and v2), TIL3 and (CD107a (Assessing TIL function by CD107a mobilization); ArC Amine Reactive Compensation Bead Kit (Fisher Scientific, Massachusetts, Cat #A10346); Phorbol 12-myristate 13-acetate (PMA) (Sigma, Missouri, Cat #P1586); Corning Bio-Coat T-Cell Activation Plate anti-CD3 (Fisher Scientific, Massachusetts, Cat #NC9937781); Corning Bio-Coat T Cell Activation Control Plate anti-CD3 (Fisher Scientific, Massachusetts, Cat #NC1108453); R&D Systems Human IFNγ Quantikine Kit (R&D Systems, Minnesota, Cat #SIF50); Debris Removal Solution (Miltenyi Biotec, Germany, Cat #130-109-398); and R&D Systems Human IFNγ Quantikine Kit (R&D Systems, Minnesota, Cat #SIF50).

Procedure

Tumor Preparation

Freshly resected tumor samples were received from research alliances (UPMC, Moffitt) and tissue procurement vendors (Biotheme and MTG group). The tumors were shipped overnight in HypoThermosol (Biolife Solutions, Washington, Cat #101104) (with antibiotic).

Removed the tumor from its primary and secondary packaging, weighed the vial with the tumor and shipping media and record the mass. Removed the tumor from the vial and reweighed the vial and shipping media. Calculated the mass of the tumor (Mass of vial+shipping media+tumor)−(vial+shipping media).

Fragmented the entire tumor into approximately 4-6-mm$^3$ fragments for tumor digest. If the tumor is large enough, four 3 mm$^3$ fragments are set up for Gen2. The tumor can be digested using any of the protcols described herein.

Enzyme Preparation for Tumor Digestion (Using Research Grade DNAse, Collagenase and Hyaluronidase)

Reconstituted the lyophilized enzymes in the amount of sterile HBSS indicated for each of the digestion enzymes below. These enzymes were prepared as 10×. Pipetted up and down several times and swirl to ensure complete reconstitution.

Reconstituted 1-g of Collagenase IV (Sigma, MO, C5138) in 10-ml HBSS (to make a 100-mg/ml stock). Mixed by pipetting up and down to dissolve. If not dissolved after reconstitution, placed in a 37° C. $H_2O$ bath for 5 minutes. Aliquotted into 1-ml vials. This is the 100-mg/ml 10× working stock for collagenase.

Prepared the DNAse (Sigma, MO, D5025) stock solution (10,000-IU/ml). The units of DNAse for each lot was provided in the accompanying data sheet. Calculated the appropriate volume of HBSS to reconstitute the 100-mg lyophilized DNAse stock. For example, if the DNAse stock was 2000-U/mg, the total DNAse in the stock is 200,000-IU (2000-IU/mg×100-mg). To dilute to a working stock of 10,000 IU, add 20-ml of HBSS to the 100 mg of DNAse (200,000 IU/20 ml=10,000U/ml). Aliquotted into 1-ml vials. This was the 10,000 IU/ml 10× working stock for DNAse.

Prepared the hyaluronidase 10-mg/ml (Sigma, MO, H2126) stock solution. Reconstituted the 500-mg vial with 50-ml of HBSS to make a 10-mg/ml stock solution. Aliquoted into 1-ml vials. This was the 10-mg/ml 10× working stock for hyaluronidase.

Diluted the stock digest enzymes to 1×. To make a 1× working solution, add 500-ml each of the collagenase, DNase and hyaluronidase to 3.5-ml of HBSS. Added the digest cocktail directly to the C-tube.

Enzyme Preparation for Tumor Digestion (Using GMP Collagenase and Neutral Protease)

Reconstituted the lyophilized enzymes in the amount of sterile HBSS indicated for each of the digestion enzymes below. Pipetted up and down several times and swirl to ensure complete reconstitution.

Reconstituted the Collagenase AF-1 (Nordmark, Sweden, N0003554) in 10-ml of sterile HBSS. The lyophilized stock enzyme is at a concentration of 2892 PZ U/vial. Therefore, after reconstitution the collagenase stock was 289.2 PZ U/ml. Note, the stock of enzymes could change so verify the concentration of the lyophilized stock and amend the final amount of enzyme added to the digest cocktail accordingly.

Reconstituted the Neutral protease (Nordmark, Sweden, N0003553) in 1-ml of sterile HBSS. The lyophilized stock enzyme was at a concentration of 175 DMC U/vial. Therefore, after reconstitution the neutral protease stock was 175 DMC/ml. Note, the stock of enzymes could change so verify the concentration of the lyophilized stock and amend the final amount of enzyme added to the digest cocktail accordingly.

Reconstituted the DNAse I (Roche, Switzerland, 03724751) in 1-ml of sterile HBSS. The lyophilized stock enzyme was at a concentration of 4 KU/vial. Therefore, after reconstitution the DNAse stock was 4 KU/vial. Note, the stock of enzymes could change so verify the concentration of the lyophilized stock and amend the final amount of enzyme added to the digest cocktail accordingly.

Prepared the working GMP digest cocktail. Add 10.2-μl of the neutral protease (0.36 DMC U/ml), 21.3-μl of collagenase AF-1 (1.2 PZ/ml) and 250-μl of DNAse I (200 U/ml) to 4.7-ml of sterile HBSS. Placed the digest cocktail directly into the C-tube.

Tumor Processing and Digestion

If using GentleMACS OctoDissociator transfer the tumor fragments to a GentleMACS C-Tube (C-tube) or 50-ml conical tube in the 5-ml of digest cocktail (in HBSS) indicated above. Transferred 2-3 fragments (4-6 mm) to each C-tube.

Transferred each C-tube (Miltenyi Biotec, Germany, 130-096-334) to the GentleMACS OctoDissociator (Miltenyi Biotec, Germany, 130-095-937). Used according to the manufacturer's directions. Note each tumor histology has a recommended program for tumor dissociation. Selected the appropriate program for the respective tumor histology. The dissociation was approximately one hour.

If the GentleMACS OctoDissociator was not available, use a standard rotator. Placed 2-3 tumor fragments in a 50-ml conical tube (sealed with parafilm to avoid leakage) and secure to the rotator. Placed the rotator, at 37° C., 5% $CO_2$ humidified incubator on constant rotation for 1-2 hours. Alternatively, the tumor fragments could be digested at RT overnight, also with constant rotation.

Post-digest, removed the C-tube from the Octodissociator or rotator. Attached a 0.22-μm strainer to sterile Falcon conical tube. Using a pipette, passed all contents from the C-tube/or 50-ml conical (5 ml) through the 0.22-μm strainer into a 50-ml conical. Washed the C-tube/50-ml conical with 10-ml of HBSS and apply to the strainer. Used the flat end of a sterile syringe plunger to dissociate any remaining non-digested tumor through the filter. Added CM1 or HBSS up to 50-ml and cap the tube.

Pelleted the samples by centrifugation, 1500 rpm, 5 min at RT (with an acceleration and deacceleration of 9).

Carefully removed the liquid, resuspended pellet in 5-ml of CM1 for cell counting and viability assessment.

Put aside whole tumor digest for the following 1. Cell culture (unselected TIL control) 2. FMO flow cytometry controls 3. Pre-sort whole tumor digest phenotyping assays 4. Frozen for tumor reactivity/cell killing assays. The number of cells put aside depended on the total digest yield and tumor histology.

Cleaning up the Digest using the Debris Removal Kit

Debris was removed from the tumor digest using the Debris Removal Solution (Miltenyi Biotec, Germany, Cat #130-109-398) according to the manufacturer's directions. Centrifuged the tumor cell suspension at 300×g for 10 minutes at 4° C. and aspirate supernatant completely. Resuspended cell suspension carefully with the appropriate volume of cold buffer according to the table below and transfer the cell suspension to a 15 ml conical tube. DID NOT VORTEX.

TABLE 52

| solutions | | | |
|---|---|---|---|
| | Resuspension (PBS) | Debris Removal Solution | Overlay (PBS) |
| 0.5-1 g tissue | 6200-ul | 1800-ul | 4-ml |
| ,>0.5 g tissue | 3100-ul | 900-ul | 4-ml |

Added appropriate volume of cold Debris Removal Solution and mix well by pipetting slowly up and down 10-20 times using a 5-ml pipette. Overlayed very gently with 4-ml of cold buffer. Tilted the tube and pipetted very slowly to ensure that the PBS/D-PBS phase overlayed the cell suspension and phases were not mixed. Centrifuged the tumor cell suspension at 3000×g for 10 minutes at 4° C. with full acceleration and full break. Three phases formed. Aspirated the two top phases completely and discarded them. The bottom phase contained the Debris Removal Solution and the cells. Left at least as much volume of the bottom as was added of the Debris Removal solution. (i.e., if 1 ml of solution was added leave at least 1-ml at the bottom of the tube). Brought up to 15-ml with cold buffer and inverted the tube at least three times. DID NOT VORTEX. Centrifuged at 4° C. and 1000×g for 10 minutes with full acceleration and full break. Resuspended cells in HBSS or media for cell count.

Staining Digested Tumor for Flow Cytometry Analysis and Cell Sorting

The tumor digest was stained with a cocktail that includes staining PD1-PE, anti-IgG4 Fc-PE (secondary antibody for Nivolumab and Pembrolizumab) and CD3-FITC according to the following protocol. Post-count, resuspended the cells in 10-ml HBSS.

Resuspended pellet in FACS buffer (1×HBSS, 1 mM EDTA, 2% fetal bovine serum). The amount of FACS buffer added to the pellet was based upon the size of the pellet. The staining volume should be about 3 times the size of the pellet (300-µl of cells, the volume of buffer should be at least 900-µl).

For antibody addition, each 100-µl of volume was equivalent to one test (titered amount of antibody). i.e., If there was 1-ml of volume, 10× the amount of titered antibody was required.

Added 3-µl of anti-CD3-FITC (BD Biosciences, NJ, Cat #561807), 2.5-µl anti-PD1-PE (Biolegend, CA, Cat #329906) per 100-µl of volume. Also add anti-IgG4 Fc-PE at 1:500 (Southern Biotech, AL, Cat #9200-09). Added 1 µl of anti-IgG4 Fc-PE for every 500-µl of FACS buffer.

Incubated cells on ice for 30 minutes. Protected from light during incubation. Agitate a couple times during incubation. Resuspended cells in 20-ml of FACS buffer. Passed solution through a 70-µm cell strainer into a new 50-ml conical. Centrifuged, 400×g, 5 min at RT (acceleration and deacceleration of 9). Aspirated. Resuspended cells in up to 10e6/ml TOTAL (live+dead) in FACS buffer. Minimum volume was 300-µl. Transferred to sterile polypropylene FACS tubes or 15-ml conical tubes. 3-ml/tube for FACS sorting. Prepared 15-ml collection tubes for the sorted populations. Placed 2-ml of FACS buffer in the tubes.

Cell Counting and Viability

The Nexcelom Cellometer K2 (Nexcelom, MA) was used to obtain cell and viability counts.

FACS Sorting (FX500 Startup)

Turned on machine and ran cell sorter software. Ran Automatic Calibration.

Prepared five sterile 15-ml conical tubes with 10-ml of sterile D.I. water. Prepared five sterile 5-ml FACS tubes with 4-ml of sterile D.I. water. Prepared five sterile 15-ml conical tubes with 12-ml of 70% EtOH. Prepared five sterile 15-ml conical tubes with 12-ml of 10% Sodium Hypochlorite.

Sample Collection

Verified that the sample and collection chambers were at 5° C. and that the agitate sample icon was selected. Proceeded with the sample collection software procedures.

Placed the tube containing the PBMC control on the sample collection platform.

Selected 100,000 cell collections for both drop-down menus seen above. Verified that the cell populations were gated correctly. The gates were set at high, medium (also referred to as intermediate), and low (also referred to as negative) by using the PBMC, the FMO control, and the sample itself to distinguish the three populations. See, FIG. 132.

It could be necessary to adjust the BSC or FSC settings. Did not adjust the voltages for any other channels. Loaded PE FMO control tube and ran sample. Adjusted the PD1 gate as necessary. See, FIG. 133.

When the gates were satisfactory, recorded as many events as possible (or 20,000 CD3 events maximum). Could set the sample pressure to 10 to speed up this collection. Stopped the collection and remove the tube. Loaded a 15-ml conical tube of sterile dH20 made previously onto the sample platform. Selected 10 for the sample pressure. Ran software. Collected the sample for one minute. Repeated until the CD3 gate is empty of events. Removed the dH20 sample tube and discard. Drew a line on the tube to be collected with a permanent marker at the bottom of the meniscus and at the halfway point. Added the sample to be collected onto the loading platform. Note: There were a total of four fractions to be collected-negative, mid, high, and CD3. The PD-1 fractions were collected first. Then the CD3 fraction is collected lastly.

Selected 4 for the sample pressure. Ran software. Waited for the cells to appear on screen. About 15 seconds. When the 3 PD-1 fractions were visible, press Paused. The lowest 2 of the 3 fractions were collected first.

Opened the Sample Chamber door and load the 15-ml collection chamber block to the chamber. Loaded the collection tubes containing the collection buffer into the chamber block. Inverted the capped tubes several times to coat the top of the tube with collection buffer. Tapped the tubes on the surface of the BSC to remove excess buffer from the top of the tube and cap. Labeled two tubes with the sample name and neg, mid, or high. Chose the fractions with the lowest percentage of PD-1 cells. Removed caps and placed the tubes into the sample chamber block. Selected the correct right/left orientation to match the tube positions. Proceeded with Load Collection. Adjusted the sample pressure so the total events per second are below 5,000. Adjusted the sample pressure to maintain a sorting efficiency of at least 85%. Recorded 50,000 CD3 events.

Stop the sorting when the sample reaches approximately ⅔ empty. Removed the collected sample that contains the most events. Recap and place on ice or at 4° C. Left the sample with the lower amount in the collection chamber so that more cells can be collected during the collection of the highest percentage PD-1 sample. Labeled the collection tube and remove cap. Placed it into the collection chamber. Selected the appropriate left/right orientation of the sort collection. Loaded collection tubes. Pressed play, record, and begin sort. When the sample reached approximately one third empty. Stopped the sort. Removed the collected fractions. Recapped and placed on ice or at 4° C. and placed a CD3 collection tube in the left side of the holder. Made the left side for CD3 and the right side sort blank. Continued sorting until all the sample is gone from the sample tube. It was okay if the tube runs "dry." Removed the Sample tube from the sample chamber. Discarded. Removed the sorted fraction from the collection chamber. Capped the tubes and invert gently several times to incorporate the droplets near the top of the tube into the solution. Tapped the tubes gently on the surface of the BSC to remove excess solution from the top of the tube and the cap. Placed the tubes on ice. Verified the percent purity of the PD1 fractions. Placed a 14-ml conical tube of sterile dH20 onto the sample chamber. Washed. Repeated. Removed the dH20 tube and added the positive fraction tube. Changed the sample pressure value to 10. Recorded 75 CD3 positive events. Immediately stopped the tube and unload it from the sample chamber. Repeated for the remaining samples. Exported the data and shutdown the instrument.

REP1 Initiation

The condition that had the fewest number of cells (PD1high, PD1int or PD1neg) was used to determine the number of cells for REP1 initiation. The % of CD3 cells, (determined during the sort) was used to calculate the total number of cells in the whole digest that were required to initiate REP1, in the unselected TIL condition, with the same number of CD3 cells as the PD1high, PD1int or PD1neg samples. Total number of whole digest cells for REP 1 initiation=Number of sorted cells inoculated in REP1/% of CD3 cells.

Approximately 1000-100,000 cells CD3+ cells were placed into a G-Rex10, with 7-ml or 40-ml of CM2 respectively (50% RPMI 1640+10% human serum, glutamax, gentamycin and 50% AimV) with 3000-IU/ml of IL-2 for 11 days. At least one G-Rex flask was initiated for the PD1high, PD1int and PD1neg sorted populations and unselected TIL. Anti-CD3 (clone: OKT3) (30-ng/ml) and Feeders (1:100 ratio (TIL: feeders)) were added to each flask at the initiation of culture.

Incubated the cells in the plates/flasks for 11 days, no media changes were performed (REP1).

At the completion of REP1, removed approximately 30-ml of media for a G-Rex 10. Resuspend the cells in the remaining media by pipetting up and down. Placed cells in a 50-ml conical and centrifuge at 1500 rpm for 5 min (acceleration and deacceleration of 9).

Aspirated the media and resuspend cells in 10-20-ml of CM2 for counting and viability assessment.

REP2 Initiation

For mini-REP2 initiation, 1e5 cells are placed into a G-Rex 10 with 40-ml of CM2 media and 3000-IU/ml of IL-2. Anti-CD3 (clone: OKT3) (30-ng/ml) and Feeders (1:100 ratio, TIL: feeders) are added at culture initation.

For "full-scale runs", 2e6-30e6 cells were expanded in a G-Rex 100M in 1-L of CM2 media and 3000-IU/m of IL-2. Anti-CD3 (clone: OKT3) (30-ng/ml) and Feeders (1:100 ratio, TIL: feeders) were added at culture initation.

A media change (For mini-scale) or media change+split (for "full scale runs) was performed at Day 5 of REP2 (Day 16 of process). The flasks were volume reduced to approximately 10-ml (G-Rex 10) or 100-ml (G-Rex 100M) and supplemented to 40-ml (G-Rex 10) or 1-L (G-Rex 100M) with either CM2 or AimV+3000-IU/ml IL-2. For "full scale runs", the flasks were split 1:2.

At Day 11 of REP2 (or Day 22 of the process), flasks were volume reduced, centrifuged at 1500 rpm for 5 min at RT (acceleration and deacceleration of 9).

The final product was assessed for cell count, viability, phenotype (TIL1, (DIG1) and function (IFNγ and CD107a. For the VB repertoire analysis, 1e6-5e6 cells were pelleted and frozen. RNA-sequencing is performed by iRepertoire. Final products were also assessed for tumor reactivity in a co-culture assay and assessed for IFNγ. Thawed whole tumor digests were co-cultured with TIL and assessed for tumor reactivity (by IFNγ secretion) and killing (% cytolysis) using the xCELLigence system (ACEA Biosciences, CA).

Results

The PD1high sorted cells showed a defect in proliferative capacity. The expected final product yield is expected to be > or =1e9. The expanded PD1high cells were also be oligoclonal, in comparison to PD1int, PD1neg and unselected TIL. Based upon the premise that PD1+/PD1high cells were more likely to be antigen specific, PD1high cells exhibited enhanced tumor-specific killing capacity in comparison to their unselected TIL counterparts.

REFERENCES FOR EXAMPLE 10

1. Rosenberg, S. A., et al., *Durable complete responses in heavily pretreated patients with metastatic melanoma using T-cell transfer immunotherapy*. Clin Cancer Res, 2011. 17(13): p. 4550-7.
2. Kvistborg, P., et al., *TIL therapy broadens the tumor-reactive CD8 (+) T cell compartment in melanoma patients*. Oncoimmunology, 2012. 1 (4): p. 409-418.
3. Simoni, Y., et al., *Bystander CD8 (+) T cells are abundant and phenotypically distinct in human tumour infiltrates*. Nature, 2018. 557(7706): p. 575-579.
4. Schumacher, T. N. and R. D. Schreiber, *Neoantigens in cancer immunotherapy*. Science, 2015. 348(6230): p. 69-74.
5. Turcotte, S., et al., *Phenotype and function of T cells infiltrating visceral metastases from gastrointestinal cancers and melanoma: implications for adoptive cell transfer therapy*. J Immunol, 2013. 191(5): p. 2217-25.
6. Inozume, T., et al., *Selection of CD8+PD-1+ lymphocytes in fresh human melanomas enriches for tumor-reactive T cells*. J Immunother, 2010. 33(9): p. 956-64.

7. Gros, A., et al., *PD-1 identifies the patient-specific CD8 (+) tumor-reactive repertoire infiltrating human tumors*. J Clin Invest, 2014. 124(5): p. 2246-59.

8. Thommen, D. S., et al., *A transcriptionally and functionally distinct PD-1 (+) CD8 (+) T cell pool with predictive potential in non-small-cell lung cancer treated with PD-1 blockade*. Nat Med, 2018.

Example 11: Analysis of the TCR Repertoire in PD1-Selected TIL

Purpose

To determine the polyclonality and diversity of programmed cell death protein 1 (PD1)-selected tumor infiltrating lymphocytes (TIL), and to compare them to unselected TIL.

Scope

Seven matched pairs of PD1-selected and unselected TIL produced from human head and neck squamous cell carcinoma (HNSCC) and non-small cell lung cancer (NSCLC) samples were analyzed for their T cell receptor (TCR) repertoire.

Information

Cancer immunotherapy harnesses the immune system to recognize and destroy tumor cells. The success met by immune checkpoint inhibitors (CPIs) targeting cytotoxic T lymphocyte antigen 4 and PD1 has transformed cancer treatment and established immunotherapy as one of the standard therapeutic approaches, along with surgery, chemotherapy, and radiotherapy. CPI therapy leads to remarkably durable clinical responses, but only in a subset of patients with some types of cancers and often at the cost of serious side effects [1, 2].

Adoptive cell therapy (ACT) utilizing autologous tumor-infiltrating lymphocytes (TIL) has emerged as a powerful and potentially curative therapy for several cancers (Geukes Foppen et al. Mol Oncol 2015). TIL products used for ACT are unselected, non-genetically manipulated preparations of polyclonal T cells directly recovered from the tumor tissue and massively expanded ex vivo [3]. This process insures the recovery of a potentially diverse repertoire of patient tumor-specific memory T cells without prior knowledge of the nature or identity of the antigens [4]. Altogether ACT is a simpler, less biased, safer, and likely more effective approach than other cell therapies such as chimeric antigen receptor (CAR) and TCR T cells that target a single tissue- or tumor-specific antigen and require the insertion of a transgene. Current TIL process may, however, also allow for the recovery and expansion of variable fractions of T cells that are unrelated to cancer, so-called bystander TIL, and that recognize antigens such as those from Epstein-Barr virus (EBV), human cytomegalovirus (CMV) or influenza virus [5].

Multiple lines of evidence support neoantigen recognition followed by tumor cell killing as TIL therapy's primary mechanism of action [6]. Enriching the TIL for tumor neoantigen-specific T cells while remaining unbiased to preserve some level of diversity and avoid the need for antigen identification represents an attractive means to optimize the product.

As an activation-induced T cell modulator, PD1 has been shown to be specifically expressed in response to recent antigen encounter and, in the case of the T cells that infiltrate cancer tissues, to specifically label the neoantigen-specific cells [7,8]. We thus implemented an approach by which TIL are selected for PD1 expression prior to ex vivo expansion to enrich for the relevant TIL relative to the bystander TIL.

In the current example, the T cell clonal composition of PD1-selected TIL was compared with that of matched unselected TIL to verify that the selection process generated a patient-specific TIL product with a distinct composition and corresponding to a subset of the unselected bulk TIL population.

Experiment Design

The clonal composition of 7 paired PD1-selected and unselected TIL was established by RNA sequencing of the complementary determining region 3 (CDR3) of the TCR's beta subunit variable region (vβ). Each T cell clone in a TIL product expresses a unique TCR identifiable by its CDR3vβ. Unique CDR3vβ sequences thus provide a clonal identity by which the T cell repertoire of a TIL product can be defined and studied.

Materials

Tumor samples and TIL products used in this work are described in Table 53.

TABLE 53

Description of PD1-selected and unselected TIL used in the study

| Sample ID | Histology | Date of preparation | REP1 Fold Expansion | REP2 Fold Expansion |
|---|---|---|---|---|
| H3035 PD1-selected TIL | HNSCC | Mar. 15, 2019 | 350 | 2166 |
| H3035 unselected TIL | | | 869 | 1385 |
| H3039 PD1-selected TIL | HNSCC | Apr. 9, 2019 | 654 | 1082 |
| H3039 unselected TIL | | | 123 | 893 |
| L4089 PD1-selected TIL | NSCLC | Mar. 22, 2019 | 1502 | 2106 |
| L4089 unselected TIL | | | 2821 | 1416 |
| L4096 PD1-selected TIL | NSCLC | Apr. 4, 2019 | 582 | 788 |
| L4096 unselected TIL | | | 1749 | 919 |
| L4097 PD1-selected TIL | NSCLC | Mar. 22, 2019 | 230 | 1982 |
| L4097 unselected TIL | | | 1147 | 2455 |
| L4100 PD1-selected TIL | NSCLC | Mar. 26, 2019 | 536 | 997 |
| L4100 unselected TIL | | | 1498 | 900 |
| L4106 PD1-selected TIL | NSCLC | Mar. 29, 2019 | 1179 | 1367 |
| L4106 Unselected TIL | | | 4500 | 1912 |

PD1-selected TIL were obtained from 2 HNSCC and 5 NSCLC samples according to procedure Example 10. Briefly, the whole tumor biopsy was digested using a cocktail of DNAse, Hyaluronidase, and Collagenase IV. A portion of the resulting single cell suspension was stained for PD1, and sorted on an FX500 instrument (Sony, HQ, New York). PD1-sorted cells and unselected whole tumor digest were subjected to two 11-day rapid expansion phases (REP) to obtain PD1-selected TIL and unselected TIL, respectively. TIL products were stored frozen and thawed prior to use in the procedures below.

Methods

RNA Extraction

Total RNA was extracted from 1-2e6 TIL, using the RNeasy® Mini Kit according to the manufacturer's protocol (QIAGEN, Germantown, MD).

RNA-Seq

CDR3vβ were amplified in a semi-quantitative manner, using iRepertoire's proprietary arm-PCR (amplicon rescued multiplex PCR) technique with their HTBIvc assay (iRepertoire, Huntsville, AL). The HTBIvc assay is a nested, reverse transcription multiplex PCR assay that captures the VDJ-rearrangement from white blood cells, specifically the beta chain VDJ rearrangement from T-cells. The resulting libraries generated from input RNA were sequenced using Illumina Next Generation Sequencing (NGS) platforms (Illumina, San Diego, CA) at a standard read depth of approximately 1 million reads per library. The final data cover the variable gene region from within framework 3 to the beginning of the constant gene as shown in FIG. 134. The CDR3 portion of the variable gene region corresponds to the "DJ" rearrangement site at the genomic level. Illumina's MiSeq platform was used for all samples. All experiments were carried out by iRepertoire.

Sequencing Data Analyses

Preliminary analysis of sequencing results was performed by iRepertoire using a pipeline to filter sequencing and amplification errors and identify CDR3vβsequences and their frequencies per each sample (iRepertoire, Huntsville, AL). Custom scripts, written in Python, were used to normalize data and perform additional analyses of the unique CDR3vβ profiles, including the identification of overlapping CDR3 clones.

Numbers of unique CDR3vβ were defined as the number of unique peptide CDR3s within the sample. Frequency of each individual clonotype was calculated by counting the number of sequencing reads, containing the unique clonotype, that passed demultiplexing and filters within the library. Shannon Diversity Index (H), was calculated using the formula $$H=-\sum_{j=1}^{S}p_j\ln p_j,$$

where S is the total number of clones in the community (richness), and $p_i$ is the proportion of S made up of clone i. The overlap between the PD1-selected and unselected TIL from the same tumor sample was determined by identifying clones found in both samples and reported in two ways: the percentage of clones shared was reported by dividing the number of shared clones by the number of total unique clones reported in each type of product; the percentage of total TCR population shared was determined by normalizing the frequencies between samples and summing the frequencies of the shared clones per each TIL product.

Expected Results

Compared analyses of the TCR repertoires of paired PD1-selected and unselected TIL were expected to reveal that selected TIL represented a fraction of the unselected TIL and were oligoclonal. TIL clones shared between PD1-selected and unselected products were expected to display different frequencies in the 2 products, reflecting altered competitive dynamics.

Results Achieved

Number and Diversity of the Unique CDR3vβ in PD1-Selected and Unselected TIL

In vivo TIL are comprised of T cells that are not only specific for tumor-specific antigens (for example, neoantigens), but also recognize a wide range of epitopes unrelated to cancer (such as those from EBV, CMV, or influenza virus) [5]. These non-cancer related or bystander TIL can overgrow the tumor-specific cells during the extensive in vitro culturing period that is required to generate sufficient T cell numbers for patient treatment and may result in the production of TIL products with low frequency of tumor reactive T cells [9].

To test whether sorting of the PD1-expressing TIL prior to in vitro expansion allowed for the recovery of a product that contained a different repertoire of T cells than that of non-presorted TIL, products of both processes were compared for their TCR composition. Sequencing of CDR3vβ was performed on 14 samples as described in the example. Data were analyzed according to the methods described to generate number of unique CDR3vβ and diversity indices for each sample. Results are shown in FIG. 134 and Table 54.

The number of unique CDR3vβ varied from 1,027 to 2,778 and 648 to 1,975 in PD1-selected and unselected TIL, respectively (FIG. 134A). No specific pattern was noted for HNSCC vs. NSCLC. 4 of the 7 PD1-selected samples presented with less unique CDR3vβ clones than their matched unselected sample, suggesting a trend toward a lower polyclonality of PD1-selected TIL relative to unselected TIL that would require testing additional samples to be confirmed. Similar to the numbers of unique CDR3vβ clones, the indices representing the clonal diversity of PD1-selected and unselected TIL were not significantly different (FIG. 134B).

Oligoclonality of in vivo PD1+ TIL was reported for melanoma and NSCLC and thought to reflect the selective expansion of neoantigen-specific TIL within the tumor microenvironment [7,8]. These results were partially consistent with those reports, possibly because the expansion phase to which the TIL from this study were subjected before sequencing allowed for the emergence of low frequency clones that would have been undetectable before the expansion. None of the TIL analyzed in the published reports had been expanded, lowest frequency clones may thus not have been accounted for. A potential implication of the observations in this example was that there may be more PD1+ or tumor-specific T cells in the TME than initially assumed. The relatively high (38.4% average, 21 to 78% range) of PD1+ TIL detected in the original 7 tumor digests are consistent with this hypothesis (Report SR-19-009-000). Alternatively, the apparent polyclonality of the PD1-selected TIL product could result from the amplification of contaminating PD1-TIL. Sort purity was around 93% (Research data) and, given an initial proliferative advantage, the few PD1-TIL could have proliferated to detectable levels during the expansion [8, 10, 11]

Because numbers and frequencies of the unique CDR3vβ clones in PD1-selected and unselected TIL may have been leveled during the in vitro culture, we set out to compare the identity of the T cell clonotypes that comprised PD1-selected and unselected TIL.

Number and Percent of Overlapping T Cell Clones Between PD1-Selected and Unselected TIL In the TME, PD1 was shown to specifically identify the tumor antigen-recognizing TIL, which represent a fraction of the T cells that infiltrate the tissue [7,8]. As noted above, a wide range of non-cancer related T cells can also be present in the TME at any given time that are not expected to have recently upregulated PD1 expression and that our PD1 sorting strategy intends to select against. We thus wanted to determine which fraction of the TIL clonotypes present in the unselected product comprised the PD1 selected product. For this, the extent of the clonal overlap between the PD1-selected and unselected products was assessed for each pair of TIL samples. Results expressed as number, percentage, and portion of overlapping clones are shown in analysis.

Figure 2:
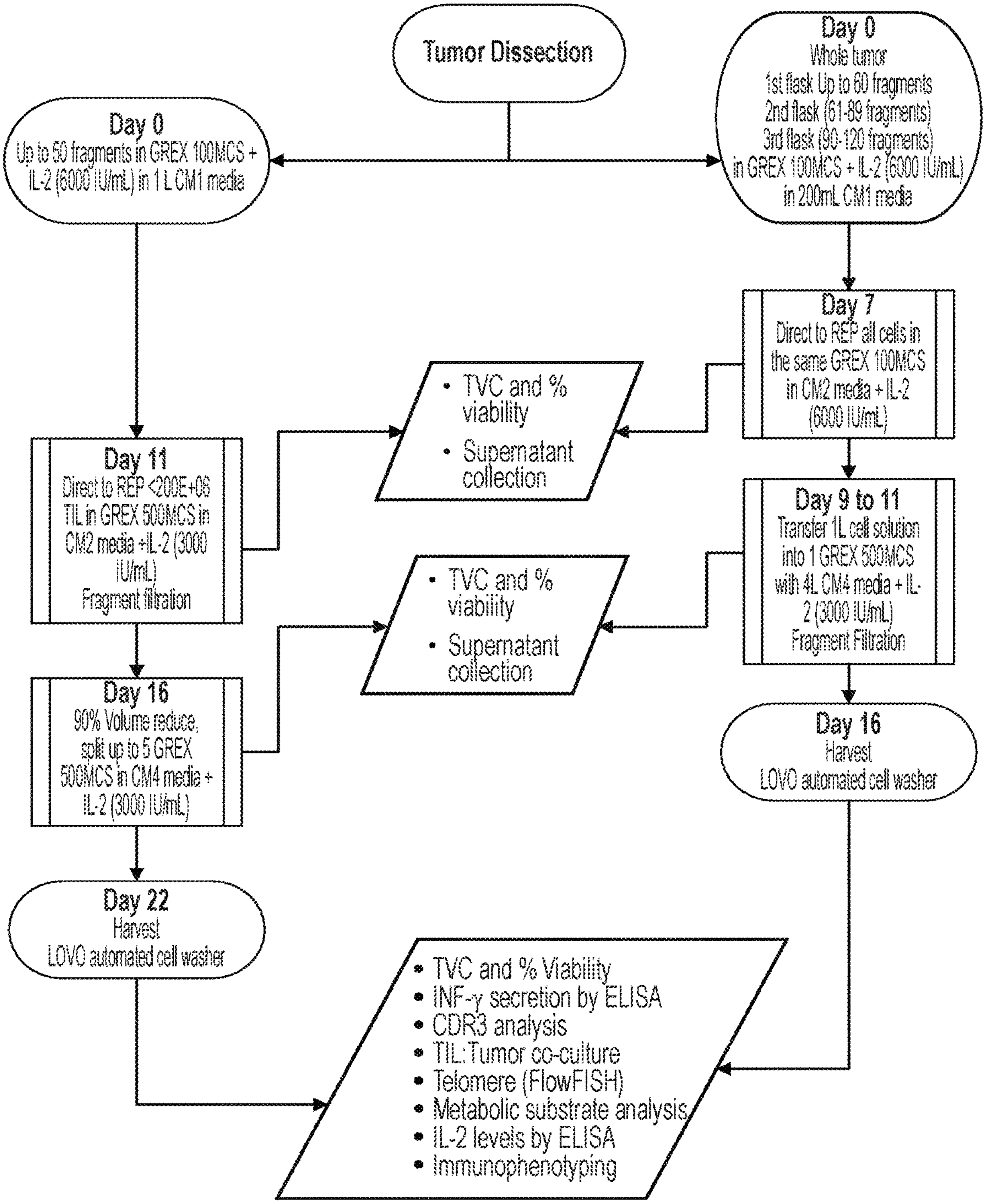
FIG. 2: Provides an experimental flow chart for comparability between GEN 2 (process 2A) versus PD-1 GEN 3.

Averages of 5.4% and 5.36% shared uCDR3vβ clones, making up 26.9% and 26.23% of the total CDR3vβ reads were numerated in the PD1-selected TIL and unselected TIL, respectively (FIG. 2). These numbers indicate that the repertoire of PD1-selected clones only partially overlapped with that of the unselected clones and that there was a significant population of clonotypes identified in PD1-selected TIL that were not detected in matched unselected TIL. Since both PD1-selected and unselected TIL originally came from the same tumor digest, the results of the overlap analyses indicate that 1) a substantial fraction of presumably bystander TIL, did not make it to the PD1-selected TIL product, and 2) a variable fraction of TIL, likely comprised of tumor-specific cells, was recovered in the PD1-selected product that was lost during the expansion phase of the unselected TIL. The bystander TIL present at culture initiation were likely able to outgrow the lowly proliferating PD1+ TIL in the unselected pool of cells while these same PD1+ TIL were given an opportunity to expand when cultured in the absence of bystanders in the PD1-selected conditions. A profound difference was noted between the 2 histologies studied here. While the portion of shared clonotypes increased in the PD1-selected products relative to the unselected products for all 5 NSCLC samples, the opposite was observed for the 2 HNSCC samples. In addition, the unselected preparations corresponding to these 2 samples were composed of relatively high proportions of shared TIL. The difference could be anecdotal, given the limited sample size; it could also reflect a difference in the type of tumor antigens present in those potentially HPV-associated cancers. Overall, our results are consistent with a profound effect of the selection step on the composition of the expanded TIL product and suggest that the resulting PD1-selected TIL can be greatly enriched for tumor-specific TIL that would otherwise be reduced during the expansion phase. See, FIG. 135.

Compared Frequencies of the Top PD1-Selected TIL Clones in the PD1-Selected and Unselected Products Results of both previous assessments pointed at the PD1-expressing, tumor-specific TIL being susceptible to competition by non-tumor related, bystander T cell clones and the benefit of isolating the tumor-relevant TIL from the pool. To further assess the differential representation of tumor-specific T cells in PD1-selected and unselected TIL, the ranking of the top 10 highest frequency PD1-selected TIL clones was determined in the unselected TIL. Results are shown in FIG. 136 and Table 56.

In all paired TIL products, the majority of highly represented PD1-selected TIL clones were either lowly or not represented in the unselected product, confirming a significant impact of the selection step on the final composition of the expanded product and the likely enrichment of tumor specific T cells in the PD1-selected TIL.

Conclusions and Recommendations

Numbers of unique CDR3vβ sequences and Diversity indexes of the PD1-selected TIL assessed were comparable to the matched unselected TIL, suggesting that a polyclonal and highly diverse product can be expanded post-PD1 sort.

The repertoire of PD1-selected TIL clones partially overlapped with that of unselected TIL, indicating that a greater number of tumor-specific TIL might be recovered when using the selection process.

High frequency PD1-selected TIL clones were present at lower frequencies in the unselected TIL product, again supporting an enrichment for tumor-specific TIL in the new product.

Overall, this study indicates that the TIL products resulting from the expansion of PD1-sorted TIL were different in their composition than unselected TIL. This difference likely reflected the modest representation of tumor-specific TIL and outgrowth of bystander TIL, that occurs in the absence of PD1 selection.

REFERENCES FOR EXAMPLE 11

1. Sharma, P. and J. P. Allison, *The future of immune checkpoint therapy*. Science, 2015. 348(6230): p. 56-61.
2. Michot, J. M., et al., *Immune-related adverse events with immune checkpoint blockade: a comprehensive review*. Eur J Cancer, 2016. 54: p. 139-148.
3. Wardell, S., et al., *A Cryopreserved TIL Product, LN-*144*, Generated with an Abbreviated Method Suitable for High Throughput Commercial Manufacturing Exhibits Favorable Quality Attributes For Adoptive Cell Transfer*. Journal for Immuno Therapy of Cancer, 2017. 5((Suppl 2)).
4. Gontcharova, V., et al., *Persistence of cryopreserved tumor-infiltrating lymphocyte product lifileucel* (*LN-*144) *in C-*144-01 *study of advanced metastatic melanoma*. Cancer Res, 2019. 79((13 Suppl)).
5. Simoni, Y., et al., *Bystander CD*8 (+) *T cells are abundant and phenotypically distinct in human tumour infiltrates*. Nature, 2018. 557(7706): p. 575-579.
6. Schumacher, T. N. and R. D. Schreiber, *Neoantigens in cancer immunotherapy*. Science, 2015. 348(6230): p. 69-74.
7. Gros, A., et al., *PD-*1 *identifies the patient-specific CD*8 (+) *tumor-reactive repertoire infiltrating human tumors*. J Clin Invest, 2014. 124(5): p. 2246-59.
8. Thommen, D. S., et al., *A transcriptionally and functionally distinct PD-*1 (+) *CD*8 (+) *T cell pool with predictive potential in non-small-cell lung cancer treated with PD-*1 *blockade*. Nat Med, 2018. 24(7): p. 994-1004.
9. Yossef, R., et al., *Enhanced detection of neoantigen-reactive T cells targeting unique and shared oncogenes for personalized cancer immunotherapy*. JCI Insight, 2018. 3(19).
10. Zhang, Y., et al., *Programmed death-*1 *upregulation is correlated with dysfunction of tumor-infiltrating CD*8+*T lymphocytes in human non-small cell lung cancer*. Cell Mol Immunol, 2010. 7(5): p. 389-95.
11. Fernandez-Poma, S. M., et al., *Expansion of Tumor-Infiltrating CD*8 (+) *T cells Expressing PD-*1 *Improves the Efficacy of Adoptive T-cell Therapy*. Cancer Res, 2017. 77(13): p. 3672-3684.

TABLE 54

The count of unique CDR3 sequences and Shannon Diversity Index of unselected and PD1-selected TIL products.

| | uCDR3 Count | | Shannon Diversity Index | |
|---|---|---|---|---|
| Subject | Unselected TIL | PD1-selected TIL | Unselected TIL | PD1-selected TIL |
| H3035 | 648 | 1397 | 1.9 | 3.3 |
| H3039 | 1975 | 2032 | 2.1 | 3.9 |
| L4089 | 1917 | 1713 | 5.3 | 5.3 |
| L4096 | 1747 | 2778 | 2.2 | 3.9 |
| L4097 | 1668 | 1177 | 5.8 | 3.8 |
| L4100 | 1389 | 1027 | 3.8 | 3.2 |
| L4106 | 1624 | 1621 | 5.4 | 3.6 |

TABLE 55

Clonal overlap between PD1-selected and unselected TIL

| | | Unselected TIL | | | PD1-selected TIL | | |
|---|---|---|---|---|---|---|---|
| Subject | shared uCDR3 count | uCDR3 count | % shared uCDR3 clones | % shared population of total TCR | uCDR3 count | % shared uCDR3 clones | % shared population of total TCR |
| H3035 | 32 | 648 | 4.94 | 74.65 | 1397 | 2.29 | 1.18 |
| H3039 | 91 | 1975 | 4.61 | 46.45 | 2032 | 4.48 | 3.47 |
| L4089 | 90 | 1917 | 4.69 | 10.17 | 1713 | 5.25 | 24.46 |
| L4096 | 108 | 1747 | 6.18 | 0.42 | 2778 | 3.89 | 38.27 |
| L4097 | 91 | 1668 | 5.46 | 7.96 | 1177 | 7.73 | 58.05 |
| L4100 | 98 | 1389 | 7.06 | 30.58 | 1027 | 9.54 | 43.91 |
| L4106 | 75 | 1624 | 4.62 | 13.35 | 1621 | 4.63 | 18.94 |

TABLE 56

Frequencies of the top 10 most frequently detected clones in PD1-sorted TIL products in the PD1-sorted and unsorted TIL products.

| Subject | CDR3 sequence | Frequency in PD1-sorted TIL | Frequency in Un-sorted TIL |
|---|---|---|---|
| H3035 | ASSQLPLIGTGDSPLH | 39.33 | 0.00 |
| | ASRPGVAGNTDTQY | 18.13 | 0.00 |
| | ASSPDVGADTQY | 13.45 | 0.00 |
| | ASRIGSWSNQPQH | 6.12 | 0.00 |
| | ASSQTSNEQY | 5.27 | 0.00 |
| | ASSLGHRDHTGELF | 2.39 | 0.00 |
| | ASSPSLSSSNQPQH | 1.30 | 0.00 |
| | ATASGGTNEKLF | 1.28 | 0.00 |
| | SAAKGSSGANVLT | 0.96 | 0.00 |
| | ASSTRGSYGYT | 0.92 | 0.20 |
| H3039 | ASSPMTSSDTQY | 37.32 | 0.00 |
| | ASMRGLRTEAF | 21.96 | 0.00 |
| | ASSPQRGNQPQH | 5.46 | 0.00 |
| | ASSLVALPGSVYGYT | 2.64 | 0.00 |
| | ASSTRDPDRYGYT | 1.93 | 0.00 |
| | ASSSPKGLTDTQY | 1.86 | 0.00 |
| | SAKMTGTGLINQPQH | 1.59 | 0.00 |
| | ASSQAAHQPQH | 1.55 | 0.00 |
| | ASTTQRGGFGNEQF | 1.41 | 0.00 |
| | ASSLGQVYGYT | 1.41 | 0.16 |
| L4089 | ASSHEQAFAYGYT | 16.01 | 0.00 |
| | ASSSRDLGETQY | 10.60 | 0.00 |
| | ASSQTSGRLDNEQF | 9.19 | 0.28 |
| | ATSDLRTSGRANEQF | 5.01 | 0.16 |
| | ASSFWENNSPLH | 4.86 | 0.00 |
| | ASRGTVNSPLH | 4.78 | 0.00 |
| | ASSFGGNRNQPQH | 3.31 | 0.00 |
| | ASSYQGNTEAF | 2.67 | 0.01 |

TABLE 56-continued

Frequencies of the top 10 most frequently detected clones in PD1-sorted TIL products in the PD1-sorted and unsorted TIL products.

| Subject | CDR3 sequence | Frequency in PD1-sorted TIL | Frequency in Un-sorted TIL |
|---|---|---|---|
| | ASSSSGGITEAF | 2.55 | 0.00 |
| | SARDPGTYGYT | 2.27 | 0.00 |
| L4096 | ATRRAARTGELF | 38.05 | 0.10 |
| | ASRAGRVADTQY | 14.67 | 0.00 |
| | ATSWGLRASSYNEQF | 7.76 | 0.00 |
| | SAISDRETQY | 5.73 | 0.00 |

TABLE 56-continued

Frequencies of the top 10 most frequently detected clones in PD1-sorted TIL products in the PD1-sorted and unsorted TIL products.

| Subject | CDR3 sequence | Frequency in PD1-sorted TIL | Frequency in Un-sorted TIL |
|---|---|---|---|
| | ATTPLTSGANVLT | 4.89 | 0.00 |
| | ASSSRTTLNEQF | 3.66 | 0.00 |
| | ASSPSTDTQY | 2.40 | 0.00 |
| | SAREGGDYGYT | 1.74 | 0.00 |
| | ASSIRFSNEQF | 1.42 | 0.00 |
| | ASSFQFNNQPQH | 1.33 | 0.00 |
| L4097 | ASSLDKRANYGYT | 30.14 | 0.02 |
| | ASSLGGNGNQPQH | 15.12 | 0.00 |
| | SASPLVSGGGSYNEQF | 9.73 | 0.56 |
| | ASKIATGPNQPQH | 8.86 | 0.00 |
| | SASLAGALTDTQY | 7.00 | 0.00 |
| | ASSPEGGPNQPQH | 6.78 | 0.00 |
| | ASGKITGVSNYGYT | 4.84 | 0.85 |
| | ASSFGGWGTDTQY | 2.21 | 0.00 |
| | ASGHIGLAEAF | 1.63 | 1.82 |
| | ASSRSGTGSNQPQH | 1.00 | 0.00 |
| L4100 | ASSPRGNTEAF | 34.73 | 0.00 |
| | SARDSTQSPQH | 25.00 | 0.00 |
| | SARDPGQGTSGNTIY | 13.12 | 0.00 |
| | ASSWDTDTQY | 4.29 | 0.00 |
| | ATSIPTGGSVKETQY | 3.36 | 0.00 |
| | ATSNPDRFFYNEQF | 2.44 | 0.01 |
| | ATRNLSTQY | 2.12 | 0.33 |
| | ASSPGQWVTEEQY | 1.80 | 0.00 |
| | ASDALGGPVTGANVLT | 1.45 | 0.02 |
| | ASSVGQVSNQPQH | 1.17 | 0.00 |

TABLE 56-continued

Frequencies of the top 10 most frequently detected clones in PD1-sorted TIL products in the PD1-sorted and unsorted TIL products.

| Subject | CDR3 sequence | Frequency in PD1-sorted TIL | Frequency in Un-sorted TIL |
|---|---|---|---|
| L4106 | ASKRSFRANQPQH | 38.16 | 0.00 |
| | ASSSGQAYSYEQY | 21.79 | 0.00 |
| | ASSSRSSGYTDTQY | 6.43 | 0.00 |
| | ASSYSAGTNYEQY | 5.05 | 0.00 |
| | ASSRSGENYNEQF | 4.22 | 1.02 |
| | ASRGGLSSGNTIY | 3.60 | 0.82 |
| | AGQDTNNEKLF | 1.91 | 0.00 |
| | ASNEGGGNTEAF | 1.84 | 0.00 |
| | SALNIGGYEQY | 1.05 | 0.09 |
| | ASSQDGQGVEDYGYT | 0.91 | 0.00 |

Example 12: PD1 Expressing Cells in Tumor Digests

Purpose

This example assessed expression of programmed cell death protein 1 (PD1) in whole tumor digests.

Scope

Whole tumor digests the following tumor histologies were assessed for PD1; melanoma, non-small lung carcinoma (NSCLC), head and neck squamous cell carcinoma (HNSCC), ovarian carcinoma (OC), triple negative breast carcinoma (TNBC), prostate cancer (PC) and colorectal carcinoma (CRC).

Information

PD1 is a multi-dimensional phenotypic marker, which has been associated with activation, antigen-specificity, and exhaustion. It is rapidly induced upon activation and is maintained on antigen-experienced cells in chronic disease settings including cancer [1,2], Molecularly, PD1 is a member of the CD28 family of regulatory cell surface receptors and is expressed on chronically activated T cells, NKT cells, B cells and monocytes [3-5]. Engagement with its ligands, PD-L1 and PD-L2, induces signaling cascades that result in decreased T cell activation, proliferation, survival and cytokine production [6].

Despite the immunoinhibitory role of PD1, the presence of PD1-expressing tumor infiltrating lymphocytes (TIL) has been associated with favorable clinical outcomes in head and HNSCC and NSCLC, suggesting that these TIL may be involved in controlling tumor progression [7] [8, 9].

Studies in melanoma and NSCLC have demonstrated that most of the tumor-reactive TIL was comprised within the PD1+ T cell subset [4, 8, 10].

Based upon the notion that PD1+ TIL are the neoantigen/tumor-specific lymphocytes, Iovance is developing a novel PD1-selected TIL product, LN-145-S1, that is enriched for the PD1+ TIL sorted directly from whole tumor digests.

While PD1 expression is necessary for response to anti-PD1 therapy, PD1 expression alone does not predict responsiveness to therapy. As an example, PD1 is present on TIL in OC and its expression has been correlated with survival [11]. However, a recent clinical trial in OC demonstrated that the anti-PDL1 drug Avelumab in combination with chemotherapy did not enhance progression free survival [12]. This study, along with the high number of patients resistant to anti-PD1 therapy, that express PD1+ in the tumor microenvironment, shows that in vivo blockade of the PD1/PDL1 axis is not sufficient to control most cancers.

Adoptive T cell therapy, using lifileucel, has demonstrated remarkable efficacy in melanoma patients that were refractory to anti-PD1, indicating that the TIL process expanded a T cell population that was not reinvigorated by in vivo PD1 blockade [13].

Sorting PD1+ TIL prior to ex vivo expansion could further improve the response rate to TIL therapy, in all PD1+ cancer histologies.

The aim of the present example was to survey multiple tumor histologies for the presence of PD1+ TIL to support their targeting with these TILs in the clinic.

Experimental Design

Tumor digests from multiple tumor histologies were assessed for PD1 expression by flow cytometry.

Materials

Tumor digests used in this example are described in FIG. 137.

Methods

Tumor Processing

Tissue samples weighing from 0.2 g to 1.5 g were partially dissected into 4-6-mm fragments and digested into a single-cell suspension comprised of tumor, stroma and immune cells. A triple enzymatic cocktail that includes DNAse (500 IU/ml), Hyaluronidase (1 mg/ml) and Collagenase IV (10 ng/ml) was used to digest the tissue for 1 hour at 370C under gentle agitation.

PD1 Staining

Whole tumor digests were stained according to the table below. Cells were stained in 100 μl/1e6 cells.

TABLE 57

PD1 flow cytometry staining panel

| Antibody/Stain | Clone | Fluorochrome | Manufacturer | Amount (μl/1e6 cells) |
|---|---|---|---|---|
| 7-AAD | N/A | N/A | BD Biosciences | 20 |
| CD3 | UCHT1 | FITC | BD Biosciences | 3 |
| CD4 | OKT4 | PE/Cy | BioLegend | 1 |
| PD1 | EH12.2H7 | PE | BioLegend | 2.5 |

PD1 Selection and Gating Strategy

Stained cells were placed on either the FX500 cell sorter (SONY, New-York), or ZE5 Cell Analyzer (BioRad, CA) and analyzed based upon the following gating strategy. First, single cells were identified based on forward and back or side scatter. Next, live cells were gated based on negative/low 7-AAD or live-dead blue fluorescence. TIL were identified using CD3. PD1 cells were identified using normal donor peripheral blood (ND-PBL) as a control. The selection gate for PD1 was placed above the baseline of PD1 expression in ND-PBL.

Data analysis was performed using FlowJo v8.1 Software (FlowJo LLC, OR). Results were graphed using GraphPad v8.

Expected Results

PD1 was expected to be expressed in most tumor digests assayed. The percentages of PD1 were anticipated to be variable within each tumor subtype and between the different tumor histologies.

Results Achieved

PD1 Expression in Tumor Digests

To identify which histologies were candidates for PD1 selection, the expression of PD1 was assessed in multiple tumor samples from several cancer histologies, using flow cytometry. A total of 4 melanoma, 7 NSCLC's, 5 HNSCC's, 3° C.'s, 5 TNBC's, 2 PC's, and 8 CRC's were tested according to the procedure TMP-18-015, abbreviated in section 5.2. The CRC's were composed of both microsatellite stable (MSS) (n=6) and microsatellite instability (MSI) (n=2) tumors. After digestion, a portion of the resulting single cell suspension was stained for PD1, analyzed by flow, and, when >5e6 cells were available, sorted to obtain PD1+ cells. PD1-sorted cells were subjected to a two 11-day rapid expansion phase (REP) to obtain PD1-selected TIL. Tumor ID, histology, and experimental fate are listed in FIG. 137. Results of the flow analysis are shown in FIG. 138.

All tumors digests assayed expressed a percentage of PD1+ cells within the CD3 population. The % PD1 was variable and ranged from 11% to 78% with an average of 35% across the histologies assayed. Melanoma (n=4) and PC (n=2) yielded the lowest averages for PD1 expression of 27% and 21% respectively. The average percentage of PD1 expression did not correlate with the observed clinical response rates for those histologies. Histologies that respond to anti-PD1 blockade such as melanoma and NSCLC did not have a higher level/expression of PD1 than histologies that do not respond to anti-PD1 blockade (i.e. OC and PC).

Importantly, a PD1-selected product could be obtained upon in vitro expansion of the PD1+ cells in all the instances in which a culture could be initiated (FIG. 138). Therefore, based upon the expression of PD1, all the assayed histologies are potential candidates for PD1 selection.

Conclusions

PD1 was expressed on the CD3 cells in all assayed tumor digests.

There was extensive intra- and intertumoral variability in PD1 expression.

PD1 expression does not correlate with histologies that have demonstrated responsive to anti-PD1 therapy.

REFERENCES FOR EXAMPLE 12

1. Simon, S. and N. Labarriere, *PD-1 expression on tumor-specific T cells: Friend or foe for immunotherapy?* Oncoimmunology, 2017. 7 (1): p. e1364828.
2. Simon, S., et al., *PD-1 expression conditions T cell avidity within an antigen-specific repertoire*. Oncoimmunology, 2016. 5(1): p. e1104448.
3. Ahmadzadeh, M., et al., *Tumor antigen-specific CD8 T cells infiltrating the tumor express high levels of PD-1 and are functionally impaired*. Blood, 2009. 114(8): p. 1537-44.
4. Inozume, T., et al., *Selection of CD8+PD-1+ lymphocytes in fresh human melanomas enriches for tumor-reactive T cells*. J Immunother, 2010. 33(9): p. 956-64.
5. Melssen, M. M., et al., *Formation and phenotypic characterization of CD49a, CD49b and CD103 expressing CD8 T cell populations in human metastatic melanoma*. Oncoimmunology, 2018. 7(10): p. e1490855.
6. Lee, J., et al., *Reinvigorating Exhausted T Cells by Blockade of the PD-1 Pathway*. For Immunopathol Dis Therap, 2015. 6(1-2): p. 7-17.
7. Badoual, C., et al., *PD-1-expressing tumor-infiltrating T cells are a favorable prognostic biomarker in HPV-associated head and neck cancer*. Cancer Res, 2013. 73(1): p. 128-38.
8. Thommen, D. S., et al., *A transcriptionally and functionally distinct PD-1(+) CD8(+) T cell pool with predictive potential in non-small-cell lung cancer treated with PD-1 blockade*. Nat Med, 2018.
9. Kansy, B. A., et al., *PD-1 Status in CD8(+) T Cells Associates with Survival and Anti-PD-1 Therapeutic Outcomes in Head and Neck Cancer*. Cancer Res, 2017. 77(22): p. 6353-6364.
10. Gros, A., et al., *PD-1 identifies the patient-specific CD8(+) tumor-reactive repertoire infiltrating human tumors*. J Clin Invest, 2014. 124(5): p. 2246-59.
11. Webb, J. R., K. Milne, and B. H. Nelson, *PD-1 and CD103 Are Widely Coexpressed on Prognostically Favorable Intraepithelial CD8 T Cells in Human Ovarian Cancer*. Cancer Immunol Res, 2015. 3(8): p. 926-35.
12. Columbus, G. *Avelumab Misses Primary Endpoints in Phase III Ovarian Cancer Trial*. 2018; Available from: https://www.onclive.com/web-exclusives/avelumab-misses-primary-endpoints-in-phase-iii-ovarian-cancer-trial.
13. Sarniak, A. *A phase 2, multicenter study to assess the efficacy and safety of autologous tumor-infiltrating lymphocytes (LN-144) for the treatment of patients with metastatic melanoma*. 2018; Available from: https://ascopubs.org/doi/abs/10.1200/JCO.2018.36.15_suppl.TPS9595.

Example 13: Expansion of PD1-Selected TIL

Purpose

This example assessed the expansion of programmed cell death protein 1 (PD1) sorted tumor infiltrating lymphocytes (TIL) in comparison to matched unselected TIL.

Scope

PD1-selected TIL and unselected TIL from melanoma (n=4), non-small cell lung carcinoma (NSCLC) (n=7) and head and neck squamous cell carcinoma (HNSCC) (n=2) were expanded using two cycles of Iovance's rapid expansion protocol (REP). Selected and unselected TIL were evaluated for expansion at the completion of REP1 (D11) and REP2 (D22).

Information

PD1 is a member of the CD28 family and is expressed on chronically activated T cells, NKT cells, B cells and monocytes [1,2]. The expression of PD1 has been best characterized in T cells, where it is induced upon TCR stimulation [2,3], and is maintained on antigen-specific cells in chronic disease settings [4, 5].

Upon engagement with its ligands, PD-L1 and PD-L2, signaling through PD1 results in an inhibition of T-cell proliferation, survival and cytokine production. Several studies in chronic disease models, including HIV, hepatitis C, and cancer have demonstrated a substantial reduction in the fold expansion of PD1+ cells, in comparison to PD1-TIL [1, 6, 7]. In a murine multiple myeloma model, when compared to their PD1-counterparts, PD1-selected TIL proliferated less efficiently as demonstrated by a 10-fold lower expansion rate.

Despite the reduced proliferative capacity of PD1-selected TIL, PD1+ cells have been shown to proliferate in vitro in the presence of anti-CD3 and allogenic feeders with IL-2 [5-7]. Moreover, in mice PD1+ TIL killed autologous tumor in vitro, and produced an anti-tumor response in vivo [8].

PD1+-sorted TIL (PD1-selected) and TIL derived from whole tumor digests (unselected TIL) were expanded using two-sequential 11-day REPs. TIL fold expansions were calculated to determine whether the PD1-selected TIL could expand and how this compared to matched unselected TIL. Fold expansions were calculated at the completion of REP1 (D11) and REP2 (D22), based upon the initial CD3 seeding count and the number of cells at harvest.

Experimental Design

PD1-selected and unselected TIL were expanded in a 22-day process, with a two-step expansion process, which includes an 11-day activation step, followed by an 11-day REP. The fold expansion was calculated to access the proliferative capacity of the two TIL products.

Materials

Tumor samples and TIL products used in this work are described in FIG. 139.

PD1-selected and unselected TIL products were obtained from 4 melanoma, 7 NSCLC and 2 HNSCC according to Example 10. Briefly, whole tumor biopsies were digested using a cocktail of DNAse, Hyaluronidase, and Collagenase IV. A portion of the resulting single cell suspension was stained for PD1 and sorted on an FX500 instrument (Sony, HQ, New York). PD1-sorted cells and unselected whole tumor digest were subjected to a 22-day expansion process to obtain PD1-selected TIL and unselected TIL, respectively.

Methods

Tumor Processing

Tissue samples weighing from 0.2g to 1.5g were partially dissected into 4-6-mm fragments and digested into a single-cell suspension comprised of tumor, stroma and immune cells. A triple enzymatic cocktail that includes DNAse (500 IU/ml), Hyaluronidase (1 mg/ml) and Collagenase IV (10 ng/ml) was used to digest the tissue for 1 hour at 37° C. under gentle agitation. To insure capturing of the in-situ phenotype, PD1 cells were selected directly post-digest [2].

PD1 Staining

Whole tumor digests were stained according to the table below. Cells were stained in 100 μl/1e6 cells.

TABLE 58

PD1 flow cytometry staining panel

| Antibody/Stain | Clone | Fluorochrome | Manufacturer | Amount (μl/1e6 cells) |
|---|---|---|---|---|
| 7-AAD | N/A | N/A | BD Biosciences | 20 |
| CD3 | UCHT1 | FITC | BD Biosciences | 3 |
| CD4 | OKT4 | PE/Cy | BioLegend | 1 |
| PD1 | EH12.2H7 | PE | BioLegend | 2.5 |

PD1 Selection and Gating Strategy

Stained cells were placed on an FX500 cell sorter (SONY, New-York), and analyzed based upon the following gating strategy. First single cells were gated based on forward and back scatters, then live cells based on negative or low 7-AAD fluorescence followed by CD3 and PD1 expression. PD1 cells were identified using normal donor peripheral blood (ND-PBL) as a control. The selection gate for PD1 was placed above the baseline of PD1 expression in ND-PBL.

PD1-Selected TIL Rapid Expansion Protocol

PD1-selected and unselected TIL were expanded using a two-step process which included an 11-day activation step, followed by an 11-day REP, for a total of 22 days. TIL were expanded using OKT3 (30 ng/ml, Miltenyi Biotec) and allogenic irradiated peripheral blood mononuclear cells (1:100 TIL: feeder ratio). The number of TIL seeded ranged between 5,000-100,000 CD3+, and was dependent on the presort cell number, CD3 infiltrate and PD1 expression.

Calculating TIL Fold Expansion

At D11 (Activation harvest) and D22 (REP harvest), TIL were harvested and counted using the Cellometer K2 Fluorescent Viability Cell Counter (Nexcelom, MA). Fold expansion of the PD1-selected and unselected populations were calculated based upon the seeded CD3 count and harvest cell count (i.e., Activation fold expansion=D11 cell count/DO cell count and REP fold expansion=D22 cell count/D11 seeding count). Seeding cell number for the Activation step in the unselected TIL condition was normalized to the number of CD3 cells in the PD1-selected at DO. Data were graphed using GraphPad Prism v8.

Results

PD1-selected TIL expanded in the presence of anti-CD3 and feeders, but to a lesser degree than matched unselected TIL.

Results Achieved

Fold Expansion in PD1-selected and unselected TIL

Classically PD1+ cells have been shown to have impaired cytokine production and reduced proliferation [3,4]. Blockade of PD1 or its ligand PD-L1 in situ has been shown to partially reverse the proliferative dysfunction in TIL [2,9]. In vitro, PD1+ cells can proliferate upon stimulation with anti-CD3 and allogenic feeders in the presence of IL2 [1], but not to the extent of the PD1-TIL [8].

To determine whether PD1-selected TIL could proliferate in vitro and produce therapeutically appropriate numbers of TIL for infusion, PD1-selected and unselected TIL from 4 melanoma, 7 NSCLC and 2 HNSCC were expanded using a two-step process with an 11-dat activation step, followed by a 11-day REP and evaluated for fold expansion.

PD1-selected TIL had a reduced level of expansion in comparison to unselected TIL, during the activation step. The activation step average fold expansion was 833, as opposed to 2650 for the unselected TIL. Interestingly, for the REP step the PD1-selected TIL overcame the initial proliferation defect in the activation step, as the fold expansion for PD1-selected TIL (1308) was similar to unselected TIL (1418). The reduced proliferation in R the activation step EP1 was observed in both melanoma and NSCLC, but not in HNSCC. However, the number of assayed HNSCC tumors was low (n=2). Moreover, the proliferative capacity in the REP across the three histologies was similar between the TIL populations.

Conclusions

PD1-selected TIL were successfully expanded from the tumor digests of melanoma, NSCLC and HNSCC. See, FIG. 141.

PD1-selected TIL had a significantly reduced expansion in REP1 compared to unselected TIL.

The reduced proliferation in the PD1-selected TIL was not present during REP2.

PD1-selected TIL, despite being derived from sorted digests, expanded well within the REP fold expansion range (54-28,214) of Iovance's Generation 2 product lifileucel.

Despite the reduced proliferative capacity of the PD1-selected TIL during REP1, 13/13 PD1-selected TIL generated using the 2-REP process surpassed lifileucel's threshold for infusion (i.e. >1e9).

Since the PD1+ TIL are enriched for the tumor/neoantigen-specific cells, it is essential that they are present in substantial numbers in the final product [10, 11]. The lower proliferative capacity of PD1-selected TIL suggests that they would be outcompeted in an unselected TIL preparation, which further strengthens the rationale for selection prior to expansion.

REFERENCES FOR EXAMPLE 13

1. Ahmadzadeh, M., et al., *Tumor antigen-specific CD8 T cells infiltrating the tumor express high levels of PD-1 and are functionally impaired*. Blood, 2009. 114(8): p. 1537-44
2. Lee, J., et al., *Reinvigorating Exhausted T Cells by Blockade of the PD-1 Pathway. For Immunopathol Dis Therap,* 2015. 6(1-2): p. 7-17.
3. Virgin, H. W., E. J. Wherry, and R. Ahmed, *Redefining chronic viral infection*. Cell, 2009. 138(1): p. 30-50.
4. Simon, S. and N. Labarriere, *PD-1 expression on tumor-specific T cells: Friend or foe for immunotherapy*? Oncoimmunology, 2017. 7(1): p. e1364828.
5. Simon, S., et al., *PD-1 expression conditions T cell avidity within an antigen-specific repertoire*. Oncoimmunology, 2016. 5(1): p. e1104448.
6. Boussiotis, V.A., P. Chatterjee, and L. Li, *Biochemical signaling of PD-1 on T cells and its functional implications*. Cancer J, 2014. 20(4): p. 265-71.
7. Petrelli, A., et al., *PD-1+ CD8+ T cells are clonally expanding effectors in human chronic inflammation*. J Clin Invest, 2018. 128(10): p. 4669-4681.
8. Fernandez-Poma, S. M., et al., *Expansion of Tumor-Infiltrating CD8(+) T cells Expressing PD-1 Improves the Efficacy of Adoptive T-cell Therapy*. Cancer Res, 2017. 77(13): p. 3672-3684.
9. Tumeh, P. C., et al., *PD-1 blockade induces responses by inhibiting adaptive immune resistance*. Nature, 2014. 515 (7528): p. 568-71.
10. Gros, A., et al., *PD-1 identifies the patient-specific CD8(+) tumor-reactive repertoire infiltrating human tumors*. J Clin Invest, 2014. 124(5): p. 2246-59.
11. Thommen, D. S., et al., *A transcriptionally and functionally distinct PD-1 (+) CD8(+) T cell pool with predictive potential in non-small-cell lung cancer treated with PD-1 blockade*. Nat Med, 2018.

Example 14: Functional Assessment of PD1-Selected TIL

Purpose

This example assessed the effector function of expanded programmed cell death protein 1 (PD1)-selected TIL and compare to unselected TIL.

Scope

PD1-selected TIL and unselected TIL from melanoma and non-small cell lung carcinoma (NSCLC) and head and neck squamous cell carcinoma (HNSCC) were assessed for IFNγ secretion, Granzyme B release, and CD107a mobilization in response to non-specific stimulation.

Information

PD1 is a multi-dimensional phenotypic marker, which has been associated with activation, antigen-specificity, and exhaustion. It is rapidly induced upon activation and is maintained on antigen-specific cells in chronic disease settings including cancer [1,2], Molecularly, PD1 is a member of the CD28 family of regulatory cell surface receptors and is expressed on chronically activated T cells, NKT cells, B cells and monocytes [3-5]. Engagement with its ligands, PD-L1 and PD-L2, induces signaling cascades that result in decreased T cell activation, proliferation, survival and cytokine production [6].

Despite the immunoinhibitory role of PD1, the presence of PD1-expressing TIL have been associated with favorable clinical outcomes in HNSCC [7], NSCLC [8], and ovarian carcinoma [9]. Encountering antigen in the tumor microenvironment results in PD1 upregulation. Several studies have demonstrated that the neoantigen/tumor-reactive TIL are mostly comprised within the PD1+ T cell subset [3, 10]. Therefore, selecting TIL for expression of PD1 is expected to enrich the TIL product for tumor/neoantigen-specific T cells.

Selected PD1+ TIL recovered from tumor lesions have been assessed for functionality in response to non-specific stimuli. Uncultured sorted PD1+ TIL were shown to have a substantial reduction in IFNγ production relative to their PD1-counterparts [3, 8, 11]. However, upon in vitro culture the effector function of the expanded PD1+ TIL was restored [4, 8]

A TIL product was developed to enrich for tumor-specific T cells, based upon PD1 expression (PD1-selected). PD1-selected TIL and TIL derived from whole tumor digests (unselected TIL) were expanded using a two-step process with an 11-day activation step followed by an 11-day rapid expansion protocol (REP). To determine whether the resulting expanded PD1-selected TIL exhibited effector function, TIL were assessed in a series of in vitro functional assays and compared to matched unselected TIL.

Experimental Design

PD1-selected and unselected TIL were expanded in a 22-day process, with a two-step process with an 11-day activation step followed by an 11-dayREP. Final TIL products were assessed for functionality, in terms of IFNγ and Granzyme B secretion, to a non-specific stimulus.

Materials

Figure 14:
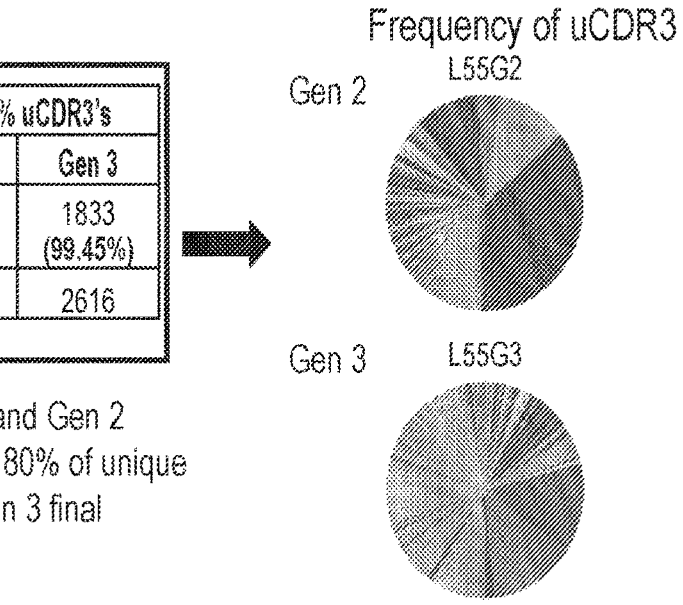
FIG. 14: Frequency of unique CDR3 sequences on L4055 TIL harvested final cell product (Gen 2 (e.g., day 22) and Gen 3 process (e.g., day 14-16)).
Figure 15:
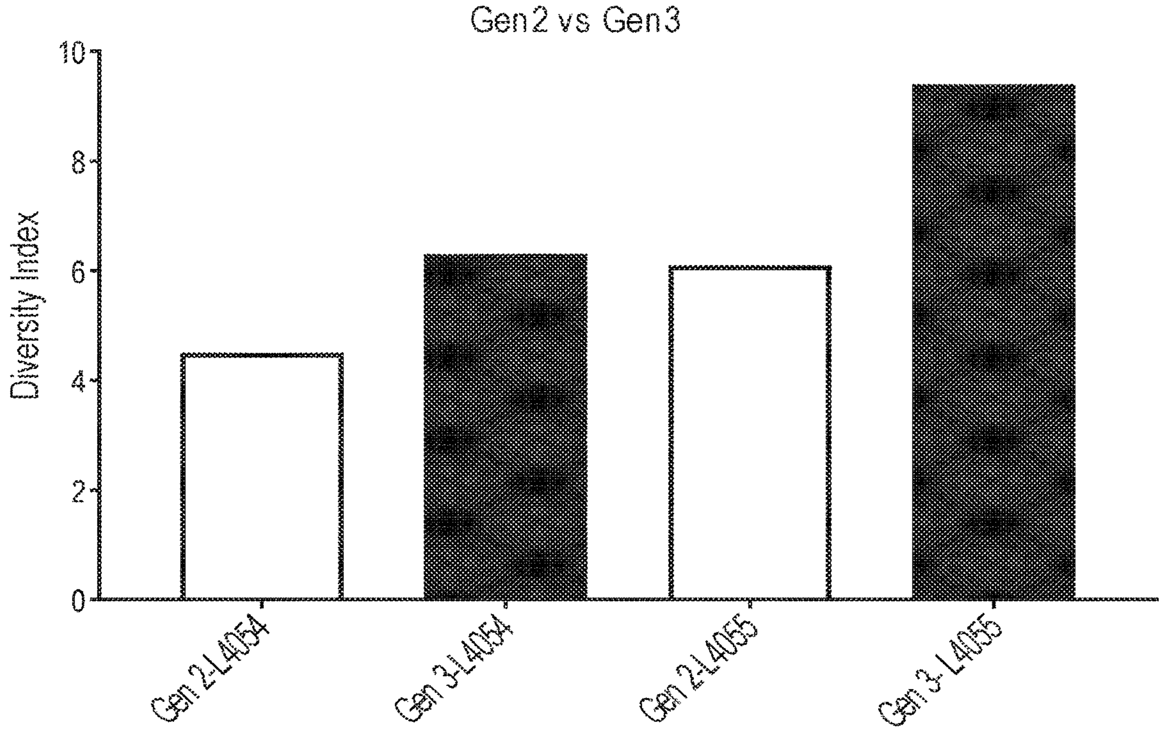
FIG. 15: Diversity Index for TIL final product on L4054 and L4055 under Gen 2 and Gen 3 process. Shanon entropy diversity index is a more reliable and common metric for comparison. Gen 3 L4054 and L4055 showed a slightly higher diversity than Gen 2.

Tumor samples and TIL products used in this work are described in FIG. 14.

Methods

Tumor Processing

Tissue samples weighing from 0.2g to 1.5g were partially dissected into 4-6-mm fragments and digested into a single-cell suspension comprised of tumor, stroma and immune cells. A triple enzymatic cocktail that includes DNAse (500 IU/ml), Hyaluronidase (1 mg/ml) and Collagenase IV (10 ng/ml) was used to digest the tissue for 1 hour at 37° C. under gentle agitation. To insure capturing of the in-situ phenotype, PD1 cells were selected directly post-digest [2].

PD1 Staining

Whole tumor digests were stained according to the table below. Cells were stained in 100 μl/1e6 cells. The PD-1 flow cytometry staining panel is provided in Table 58 in Example 13 above.

PD1 Selection and Expansion

PD1+ cells were selected using an FX500 cells (SONY, New-York). The PD1-selected and unselected TIL were expanded using a two-step process with an 11-day activation step, followed by an 11-day REP. TIL were expanded using OKT3 (30 ng/ml, Miltenyi Biotec) and allogenic irradiated peripheral blood mononuclear cells (1:100 TIL: feeder ratio).

IFNγ and Granzyme B Secretion

TIL were seeded at 5e5 cells/per well in 1 ml of a 48 well plate+300 IU/ml IL2 (CellGenix, NJ). TIL were stimulated +/−100 μl/well of αCD3/αCD28/α41BB beads (ThermoFisher Scientific, MA) for 12-18 hours. Supernatants were harvested and assessed for IFNγ (R&D Systems, MN) and Granzyme B (Life Technologies, CA) by ELISA. ELISA plates were read on the BioTek microplate reader (BioTek, VT) and assessed using Gen5 data analysis software. Data were graphed using GraphPad Prism v8.

CD107 Mobilization

PD1-selected TIL and unselected were stimulated with PMA/Ionomycin (BioLegend, CA) for 2 hours, in the presence of monensin (to prevent protein secretion). TIL were then stained with a live/dead dye, and antibodies to CD3 and CD107a. Stained cells were detected by flow cytometry. FlowJo software (Beckman Dickinson) was used to analyze the expression of CD107a in CD3+ cells. The gating strategy was as follows: singlets (FSC and SSC), live cells, CD3, and CD107. All data was graphed using GraphPad Prism v8.

Results

Expanded PD1-selected TIL produced IFNγ and Granzyme B in response to a non-specific stimulation.

IFNγ and Granzyme B Secretion in PD1-Selected and Unselected TIL

Previous reports have demonstrated either a reduced or complete inability of PD1+/PD1high cells to produce IFNγ, in response to PMA and Ionomycin [4], or anti-CD3/anti-CD28 stimulation [8, 11]. These studies were performed with uncultured PD1+ TIL, which in addition to PD1, also expressed high levels of the co-inhibitory receptors LAG3 and Tim3 [8, 10, 12]. Due to their "exhausted" phenotype (i.e. high expression of inhibitory receptors), and their inability to produce effector functions, pre-cultured PD1+ are considered to be "dysfunctional". However, once PD1+/PD1high cells are expanded in vitro (via anti-CD3 and allogenic feeders), the TIL regain their capacity to produce IFNγ [3, 4, 8]. The enhanced effector function was also associated with a substantial reduction in PD1 expression [3, 4, 8, 13]. These studies suggest that the observed anergy in uncultured PD1+/PD1high TIL can be reversed with in-vitro culture.

To assess whether PD1+ TIL were functional in terms of cytokine production post-expansion, PD1-selected and matched unselected TIL from 13 tumors were stimulated non-specifically with αCD3/αCD28/α41BB activation beads and evaluated for IFNγ and Granzyme B secretion.

PD1-selected TIL secreted appreciable levels of IFNγ and Granzyme B in response to a non-specific stimulation (αCD3/αCD28/αCD137 beads), suggesting that these were indeed functional post-expansion. See, FIG. 143.

Despite their ability to produce IFNγ post-expansion, PD1-selected TIL secreted significantly less IFNγ compared to unselected TIL. Therefore, PD1-selected TIL have a reduced capacity to produce IFNγ, in response to a non-specific stimulation. However, upon co-culture with autologous tumor, PD1-selected TIL have been shown to produce significantly greater levels of IFNγ compared to PD1-TIL [3, 8, 13]. Expanded PD1-selected TIL and unselected TIL were co-cultured with autologous tumor and assessed for IFNγ. PD1-selected TIL secreted greater levels of IFNγ, than unselected TIL demonstrating not only their ability to secrete IFNγ, but to do so in a tumor-specific fashion.

PD1-selected TIL produced similar levels, but slightly elevated levels of Granzyme B, when compared to unselected TIL, which is consistent with previous studies in HNSCC [11]. Since Granzyme B is considered a marker of activation, these results further demonstrate that expanded PD1-selected TIL, are not in an exhausted or anergic state post-expansion.

CD107a mobilization in PD1-selected TIL and unselected TIL with PMA/Ionomycin stimulation CD107a cell surface expression is considered a reliable marker for TIL effector function. CD107a (LAMP1) is mobilized to the cell surface upon stimulation and is used as a measurement of the cell's capability to degranulate. Degranulation is a prerequisite to perforin-granzyme-mediated killing and is required for immediate lytic function mediated by responding antigen-specific CD8+ T cells [14, 15].

To further evaluate the functional capabilities of PD1-selected TIL, 10 post-expansion TIL were assessed for CD107a mobilization and compared to matched unselected TIL.

CD107 expression was similar in PD1-selected TIL when compared to unselected TIL. See, FIG. 144. These results further support the notion that the PD1-selected TIL post-expansion are highly functional and not indicative of an exhausted cell population.

Conclusions

PD1-selected TIL produced IFNγ and Granzyme B, and mobilized CD107a in response to non-specific stimuli.

Contrary to what has been demonstrated for uncultured PD1+/PD1high cells, expanded PD1-selected TIL are highly activated and functional, and therefore capable of producing an anti-tumor effect, once in vivo.

REFERENCES FOR EXAMPLE 14

1. Simon, S. and N. Labarriere, *PD-1 expression on tumor-specific T cells: Friend or foe for immunotherapy*? Oncoimmunology, 2017. 7(1): p. e1364828.
2. Simon, S., et al., *PD-1 expression conditions T cell avidity within an antigen-specific repertoire*. Oncoimmunology, 2016. 5(1): p. e1104448.
3. Inozume, T., et al., *Selection of CD8+PD-1+ lymphocytes in fresh human melanomas enriches for tumor-reactive T cells*. J Immunother, 2010. 33(9): p. 956-64.
4. Ahmadzadeh, M., et al., *Tumor antigen-specific CD8 T cells infiltrating the tumor express high levels of PD-1 and are functionally impaired*. Blood, 2009. 114(8): p. 1537-44.
5. Melssen, M. M., et al., *Formation and phenotypic characterization of CD49a, CD49b and CD103 expressing CD8 T cell populations in human metastatic melanoma*. Oncoimmunology, 2018. 7(10): p. e1490855.
6. Lee, J., et al., *Reinvigorating Exhausted T Cells by Blockade of the PD-1 Pathway*. For Immunopathol Dis Therap, 2015. 6(1-2): p. 7-17.
7. Badoual, C., et al., *PD-1-expressing tumor-infiltrating T cells are a favorable prognostic biomarker in HPV-associated head and neck cancer*. Cancer Res, 2013. 73(1): p. 128-38.
8. Thommen, D. S., et al., *A transcriptionally and functionally distinct PD-1(+) CD8(+) T cell pool with predictive potential in non-small-cell lung cancer treated with PD-1 blockade*. Nat Med, 2018.
9. Webb, J. R., K. Milne, and B. H. Nelson, *PD-1 and CD103 Are Widely Coexpressed on Prognostically Favorable Intraepithelial CD8 T Cells in Human Ovarian Cancer*. Cancer Immunol Res, 2015. 3(8): p. 926-35.
10. Gros, A., et al., *PD-1 identifies the patient-specific CD8(+) tumor-reactive repertoire infiltrating human tumors*. J Clin Invest, 2014. 124(5): p. 2246-59.
11. Kansy, B. A., et al., *PD-1 Status in CD8(+) T Cells Associates with Survival and Anti-PD-1 Therapeutic Outcomes in Head and Neck Cancer*. Cancer Res, 2017. 77(22): p. 6353-6364.
12. Jing, W., et al., *Adoptive cell therapy using PD-1(+) myeloma-reactive T cells eliminates established myeloma in mice*. J Immunother Cancer, 2017. 5: p. 51.

13. Fernandez-Poma, S. M., et al., *Expansion of Tumor-Infiltrating CD8(+) T cells Expressing PD-1 Improves the Efficacy of Adoptive T-cell Therapy*. Cancer Res, 2017. 77(13): p. 3672-3684.

14. Betts, M. R. and R. A. Koup, *Detection of T-cell degranulation: CD107a and b*. Methods Cell Biol, 2004. 75: p. 497-512.

15. Rubio, V., et al., *Ex vivo identification, isolation and analysis of tumor-cytolytic T cells*. Nat Med, 2003. 9(11): p. 1377-82.

Example 15: Autologous Tumor-Reactivity in PD1-Selected TIL

Purpose

This example assessed autologous tumor reactivity/killing of expanded programmed cell death protein 1 (PD1) sorted tumor infiltrating lymphocytes (TIL), in comparison to matched unselected TIL.

Scope

Thirteen matched PD1-selected TIL and unselected TIL from melanoma, non-small cell lung carcinoma (NSCLC) and head and neck squamous cell carcinoma (HNSCC) were assessed for reactivity and killing ability in response to autologous tumor stimulation. Reactivity and cytotoxicity were measured as IFNγ secretion and tumor cell death (% cytotoxity), respectively.

Information

Adoptive T cell therapy (ACT) with autologous tumor infiltrating lymphocytes (TIL) is recognized as an effective treatment in metastatic melanoma and other solid tumors, eliciting durable and complete responses, even in heavily pretreated patients [1-6]. During tumorigenesis, malignant tumors acquire nonsynonymous mutations, denoted as neoantigens [7,8]. Recent studies have highlighted the importance of tumor neoantigens in tumor recognition, and effective anti-tumor T cell responses in vivo [8,9]. The presence of tumor-specific T cells has been associated with tumor regression and clinical efficacy to TIL therapy [10]. Specifically, ACT of selected neoantigen reactive T cells has mediated substantial objective clinical regressions in patients with colon [8], and breast cancer [11].

Until recently, there was limited knowledge regarding the repertoire and frequency of tumor-specific TIL in tumors [12, 13]. A critical goal for ACT is to derive a polyclonal TIL product that is enriched for tumor-reactive T cell clones. Recent studies have demonstrated that PD1 expression in TIL can be used as a marker and selection tool to identify the neoantigen-specific lymphocytes. PD1 is expressed upon antigen encounter and is upregulated on T cells that have responded to tumor antigens and undergone clonal expansion at the tumor cite [13-20].

Based upon the notion that PD1+ TIL are the neoantigen-specific lymphocytes, PD1+ TIL have been evaluated for their ability to recognize autologous tumor lines ex-vivo. To assay tumor reactivity, TIL are co-cultured with autologous tumor cell lines and assayed for IFNγ. IFNγ is an essential effector cytokine in the tumor microenvironment (TME), that is considered a surrogate marker for the identification of antigen-specific T cells. Interestingly, PD1+ TIL secreted greater levels of IFNγ, compared to their PD1-counterparts in both NSCLC and melanoma, when co-cultured with autologous digest [14, 17].

Tumor cell lysis/killing has also been used to identify antigen-specific T cells, however these assays are not frequently performed due to issues in deriving and maintaining autologous viable tumor cell lines. One study in melanoma assessed killing in sorted PD1+ TIL and demonstrated that the PD1+ TIL had a greater capability to lyse autologous tumor lines, compared to PD1-TIL [13].

Based upon the evidence discussed above, selecting TIL for expression of PD1 expression is expected to enrich for tumor/neoantigen-specific T cells, that demonstrate greater autologous reactivity in vitro. To capture the tumor-specific cells, PD1+ TIL were sorted from freshly digested tumors (PD1-selected), using fluorescence-activated cell sorting (FACS), prior to expansion. PD1-selected TIL and unselected TIL were expanded using two sequential 11-day REPs.

Tumor reactivity and cytolysis were assessed to determine if selecting for PD1+ would enrich for antigen-specific T cells. PD1-selected TIL were co-cultured with autologous tumor cells and assessed for IFNγ production and tumor cell death. Results were compared to a matched unselected TIL preparation.

Experimental Design

Co-cultures of TIL and autologous tumor were used to evaluate tumor cell killing and reactivity in 13 paired PD1-selected and unselected TIL. Tumor lysis and IFNγ secretion were used to measure antigen-specificity in the TIL products.

Materials

Tumor samples and TIL products used in this work are described in FIG. 145.

PD1-selected and unselected TIL products were obtained from 4 melanoma, 7 NSCLC and 2 HNSCC according to procedure TMP-18-015. Briefly, whole tumor biopsies were digested using a cocktail of DNAse, Hyaluronidase, and Collagenase IV. A portion of the resulting single cell suspension was stained for PD1 and sorted on an FX500 instrument (Sony, HQ, New York). The remaining digest was frozen and thawed prior to use for the assays indicated below. PD1-sorted cells and unselected whole tumor digest were subjected to two 11-day rapid expansion phases (REP) to obtain PD1-selected TIL and unselected TIL, respectively.

Methods

Tumor Processing and Plating

Autologous whole tumor digests were processed using a dead cell removal kit (Miltenyi, Germany). 1e5 live cells were plated per well of a 96 well plate and permitted to adhere for 18 hours at 370C in the xCELLigence instrument (ACEA Biosciences Inc, CA).

Co-Culture Set-Up

1e5 PD1-selected TIL and unselected TIL-derived autologous TIL were added to their respective wells, resulting in a 1:1 (TIL: target) cell ratio, and incubated for 48 hours.

Tumor Cell Lysis Quantification

Killing of the autologous target cells was recorded as increased impedance resulting from cell detachment. Cell killing (% cytolysis) was calculated using the formula % Cytolysis=[1-(NCIst)/(AvgNCIRt)]×100, where NCIst is the Normalized cell index for the sample and NCIRt is the average of the Normalized Cell Index for the matching reference wells (digest alone). % Cytolysis was calculated using RTCA Software Pro (ACEA Biosciences Inc, CA).

IFNγ Secretion

Supernatants were harvested at 24 hours post TIL addition and assessed for IFNγ release by ELISA (R&D systems). ELISA plates were read on the BioTek microplate reader (BioTek, VT) and assessed using Gen5 data analysis software. Data was graphed using GraphPad Prism v8.

Results

This example examined whether PD1-selected TIL had a greater killing capacity and ability to secrete IFNγ than unselected TIL, when co-cultured with autologous tumor digests.

Results Achieved

Tumor Reactivity and Killing in PD1-Selected TIL

Pre-clinical data in both mouse and human have demonstrated that expression of PD1 on T cells within the tumor can identify the repertoire of neoantigen specific lymphocytes [13, 14, 17-20]. Several studies have demonstrated that in vitro expanded purified PD1+ TIL secrete significantly greater amounts of IFNγ, compared to PD1-TIL, when co-cultured with autologous tumor [14, 17]. Based upon these studies, selecting TIL for expression of PD1 expression is expected to enrich for tumor/neoantigen-specific T cells, which would demonstrate greater autologous reactivity when assessed in vitro.

Thirteen matched PD1-selected TIL and unselected TIL were assessed for autologous tumor reactivity and killing. Tumor cell lysis was measured using the tumor cell index. The cell index is a measurement of cell attachment calculated from the cell surface impedance of the well. As tumor cells adhere the impendence increases, as does the cell index. When tumor cells die and detach the cell index decreases, due to a reduction in impedance. Therefore, if TIL lyse the tumor cells, the cell index will drop, and the calculated percentage of cytolysis will increase. However, if at any time during the co-culture the cell index falls below zero, cytolysis cannot be calculated for that sample.

Of the 13 tumors evaluated, only one melanoma tumor could be evaluated for tumor cytolysis due to poor tumor cell viability and lack of tumor cell adherence to the plate. The cell index and % tumor cell cytolysis for the evaluable melanoma is shown in FIGS. 146A and 146B respectively below.

Figure 146C:
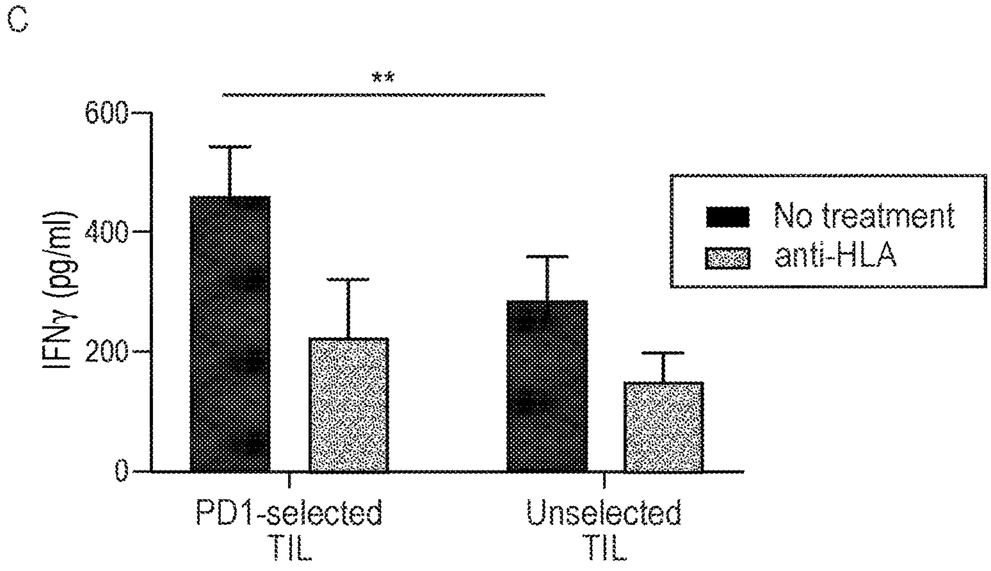

The supernatants from the co-culture cytolysis assay above were assayed for IFNγ. Of the 13 tumors evaluated, IFNγ secretion was detected in 3 melanoma and 2 NSCLC (FIG. 146C).

Due to technical difficulties, the % tumor cytolysis was only evaluated in 1/13 co-cultured tumors. In the evaluable tumor with the appropriate unselected TIL control, PD1-selected TIL exhibited a greater ability to kill autologous tumor, as determined by a greater drop in the cell index (FIG. 1A) (indicating more cell detachment and tumor cell death) and higher percentage of cytolysis (FIG. 1B), compared to unselected TIL. These results are supported by a study in melanoma that also demonstrated enhanced cytolysis in the PD1+ selected subset using an alternative assay with autologous tumor cells lines, rather than whole tumor digests [13]. Despite the low number of evaluable tumors, our results in addition to others have demonstrated that that PD1-selected TIL have a greater ability to kill autologous tumor, than their unselected or PD1-counterparts.

Of the 13 assayed co-cultured tumors, IFNγ secretion could be detected in 5 tumors. In 5/5 assayed tumors the PD1-selected TIL secreted greater levels of IFNγ than unselected TIL, when co-cultured with autologous tumor digest. The secretion of IFNγ was tumor-specific, as blockade with anti-HLA-A, -B, and -C reduced the amount of IFNγ secreted (FIG. 1C). Producing greater levels of IFNγ, in the presence of autologous tumor, suggests that PD1-selected TIL have a greater proportion of antigen-specific TIL, than that of unselected TIL.

Conclusions

PD1-selected TIL demonstrated an enhancement in autologous tumor cell killing relative to unselected TIL.

IFNγ secretion, in response to autologous tumor, was significantly greater in PD1-selected TIL than unselected TIL These results demonstrate that in comparison to unselected TIL, PD1-selected TIL have superior reactivity to autologous tumor, in vitro Clinical efficacy in ACT is directly associated with the presence of tumor-specific TIL. Therefore, enriching for tumor-specific TIL, via PD1 selection and expansion may enhance the TILs ability to initiate a potent and effective anti-tumor effect in vivo.

REFERENCES FOR EXAMPLE 15

1. Rosenberg, S. A., et al., *Durable complete responses in heavily pretreated patients with metastatic melanoma using T-cell transfer immunotherapy*. Clin Cancer Res, 2011. 17(13): p. 4550-7.
2. Stevanovic, S., et al., *Complete regression of metastatic cervical cancer after treatment with human papillomavirus-targeted tumor-infiltrating T cells*. J Clin Oncol, 2015. 33(14): p. 1543-50.
3. Stevanovic, S., et al., *A phase II study of tumor-infiltrating lymphocyte therapy for human papillomavirus-associated epithelial cancers*. Clin Cancer Res, 2018.
4. Andersen, R., et al., *Tumor infiltrating lymphocyte therapy for ovarian cancer and renal cell carcinoma*. Hum Vaccin Immunother, 2015. 11(12): p. 2790-5.
5. Andersen, R., et al., *T-cell Responses in the Microenvironment of Primary Renal Cell Carcinoma-Implications for Adoptive Cell Therapy*. Cancer Immunol Res, 2018. 6(2): p. 222-235.
6. Westergaard, M. C. W., et al., *Tumour-reactive T cell subsets in the microenvironment of ovarian cancer*. Br J Cancer, 2019.
7. Yossef, R., et al., *Enhanced detection of neoantigen-reactive T cells targeting unique and shared oncogenes for personalized cancer immunotherapy*. JCI Insight, 2018. 3(19).
8. Tran, E., et al., *Cancer immunotherapy based on mutation-specific CD4+ T cells in a patient with epithelial cancer*. Science, 2014. 344(6184): p. 641-5.
9. McGranahan, N., et al., *Clonal neoantigens elicit T cell immunoreactivity and sensitivity to immune checkpoint blockade*. Science, 2016. 351(6280): p. 1463-9.
10. Schumacher, T. N. and R. D. Schreiber, *Neoantigens in cancer immunotherapy*. Science, 2015. 348(6230): p. 69-74.
11. Zacharakis, N., et al., *Immune recognition of somatic mutations leading to complete durable regression in metastatic breast cancer*. Nat Med, 2018. 24(6): p. 724-730.
12. Gros, A., et al., *Prospective identification of neoantigen-specific lymphocytes in the peripheral blood of melanoma patients*. Nat Med, 2016. 22(4): p. 433-8.
13. Gros, A., et al., *PD-1 identifies the patient-specific CD8(+) tumor-reactive repertoire infiltrating human tumors*. J Clin Invest, 2014. 124(5): p. 2246-59.
14. Inozume, T., et al., *Selection of CD8+PD-1+ lymphocytes in fresh human melanomas enriches for tumor-reactive T cells*. J Immunother, 2010. 33(9): p. 956-64.
15. Simon, S. and N. Labarriere, *PD-1 expression on tumor-specific T cells: Friend or foe for immunotherapy?* Oncoimmunology, 2017. 7(1): p. e1364828.

16. Simon, S., et al., *PD-1 expression conditions T cell avidity within an antigen-specific repertoire*. Oncoimmunology, 2016. 5(1): p. e1104448.
17. Thommen, D. S., et al., *A transcriptionally and functionally distinct PD-1(+) CD8(+) T cell pool with predictive potential in non-small-cell lung cancer treated with PD-1 blockade*. Nat Med, 2018.
18. Fernandez-Poma, S. M., et al., *Expansion of Tumor-Infiltrating CD8(+) T cells Expressing PD-1 Improves the Efficacy of Adoptive T-cell Therapy*. Cancer Res, 2017. 77(13): p. 3672-3684.
19. Jing, W., et al., *Adoptive cell therapy using PD-1(+) myeloma-reactive T cells eliminates established myeloma in mice*. J Immunother Cancer, 2017. 5: p. 51.
20. Donia, M., et al., *PD-1(+) Polyfunctional T Cells Dominate the Periphery after Tumor-Infiltrating Lymphocyte Therapy for Cancer*. Clin Cancer Res, 2017. 23(19): p. 5779-5788.
21. Simoni, Y., et al., *Bystander CD8(+) T cells are abundant and phenotypically distinct in human tumour infiltrates*. Nature, 2018. 557(7706): p. 575-579.

Example 16: Phenotypic Characterization of PD1-Selected TIL

Purpose

To phenotypically characterize programmed cell death protein 1 (PD1)-selected TIL.

Scope

This example involved characterizing PD1-selected TIL for the expression of cell surface markers characteristic of various T cell states and compare their phenotype with that of matched unselected TIL.

Information

Cancer immunotherapy harnesses the immune system to recognize and destroy tumor cells. The success met by immune checkpoint inhibitors (CPIs) targeting cytotoxic T lymphocyte antigen 4 and PD-1 has transformed cancer treatment and established immunotherapy as one of the standard therapeutic approaches, along with surgery, chemotherapy, and radiotherapy. CPI therapy leads to remarkably durable clinical responses, but only in a subset of patients with some types of cancers and often at the cost of serious side effects [1,2]

Adoptive cell therapy (ACT) utilizing autologous tumor-infiltrating lymphocytes (TIL) has emerged as a powerful and potentially curative therapy for several cancers [3] TIL products used for ACT are unselected, non-genetically manipulated preparations of polyclonal T cells directly recovered from the tumor tissue and massively expanded ex vivo [4]. This process insures the recovery of a potentially diverse repertoire of patient tumor-specific memory T cells without prior knowledge of the nature or identity of the antigens [5]. Altogether ACT is a simpler, less biased, safer, and likely more effective approach than other cell therapies such as chimeric antigen receptor (CAR) and TCR T cells that target a single tissue- or tumor-specific antigen and require the insertion of a transgene. Current TIL processes may, however, also allow for the recovery and expansion of variable fractions of T cells that are unrelated to cancer, so-called bystander TIL, and that recognize antigens such as those from Epstein-Barr virus (EBV), human cytomegalovirus (CMV) or influenza virus [6].

Multiple lines of evidence support neoantigen recognition followed by tumor cell killing as TIL therapy's primary mechanism of action [7]. Enriching the TIL for tumor neoantigen-specific T cells while remaining unbiased to preserve some level of diversity and avoid the need for antigen identification represents an attractive means to optimize the product.

As an activation-induced T cell modulator PD-1 has been shown to be specifically expressed in response to recent antigen encounter and, in the case of the T cells that infiltrate cancer tissues, to specifically label the neoantigen-specific cells [8,9]. We thus implemented an approach by which TIL are selected for PD-1 expression prior to ex vivo expansion to enrich for the relevant TIL relative to the bystander TIL. The protocol involves sorting PD-1+ TIL directly from freshly digested tumors, using fluorescence-activated cell sorting (FACS), and subjecting them to a two-step process which includes an 11-day activation step followed by an 11-day rapid expansion protocol (REP), to obtain therapeutically appropriate numbers of PD-1-selected TIL.

In the current study, PD-1-selected TIL were characterized phenotypically to verify that 1) the new product met LN-145 release specifications and 2) comparable to unselected IL product. PD-1-selected TIL were assessed by flow cytometry for the expression of cell surface markers of lineage, differentiation, memory, activation, exhaustion, and resident memory.

Experimental Design

PD-1-selected and unselected TIL were expanded in a 22-day process, two-step process which includes an 11-day activation step, followed by an 11-day REP. Final TIL products were characterized phenotypically using flow cytometry. Of note, the unselected TIL products were obtained from the same whole tumor digests as the PD-1-selected TIL. Limited tumor tissue prevented the derivation of unselected TIL controls from tumor fragments, which are used to derive Iovance's LN-145 TIL product. Additionally, in order to expand the small numbers of sorted PD-1 population, the unselected TIL were subjected to a 2-REP process, as opposed to the pre-REP and single REP that is used to generate LN-145. Thus, while the unselected TIL represent a true control for the PD-1-sorted TIL, they do not reflect LN-145 TIL.

Materials

Tumor samples and TIL products used in this work are described in FIG. 147.

Methods

PD1 Selection and Expansion

PD-1-selected and unselected TIL products were obtained from 4 melanoma, 7 NSCLC and 2 HNSCC according to procedure TMP-18-015. Briefly, whole tumor biopsies were digested using a cocktail of DNAse, Hyaluronidase, and Collagenase IV. A portion of the resulting single cell suspension was stained for PD-1 and sorted on an FX500 instrument (Sony, HQ, New York). PD-1-selected and unselected TIL were subjected to an 11-day activation step followed by an 11-day REP in the presence of OKT3 (30 ng/ml, Miltenyi Biotec) and allogenic irradiated peripheral blood mononuclear cells (1:100 TIL: feeder ratio).

Antibody Staining

TIL were stained with a live/dead marker and for the expression of CD3 and phenotypic markers that define T cell lineage, memory, differentiation, activation, and exhaustion (FIG. 147). Two flow cytometry panels, designated 1 and 2, were used to cover the markers of interest. Antibodies and conjugated fluorophores are listed in Table 59 below, where they are arranged by phenotypic parameter. Numbers in parenthesis designate their respective panel.

TABLE 59

| Phenotypic Panels for TIL characterization | | | | | |
|---|---|---|---|---|---|
| Lineage | Memory | Differentiation | Activation | Exhaustion | Resident Memory |
| CD3-BUV395 (1, 2) | CD45RA-Alx700 (1) | CD27-PECF594 (1) | CD25-BV563 (2) | PD1-PE (2) | CD39-FITC (2) |
| CD4-PECy7 (1) | CCR7-PE (1) | CD28-BB515 (1) | CD69-APCR700 (2) | Lag3-PECy7 (2) | CD49a-BV711 (2) |
| CD8-BV786 (1) | | CD56-BV737 (1) | CD134-BV650 (2) | Tim3-BV421 (2) | CD103-PV786 (2) |
| | | CD57-PacBlue (1) | CD137-PerCP-Cy5.5 (2) | CD101-APC (2) | |
| | | KLRG1-PEDazzle594 (2) | | | |

FACS Analysis

Stained cells were run on a ZE5 cell analyzer (BioRad, CA), following standard lab procedures. Briefly, evaluable events were identified by gating on single cells (using forward scatter and side scatter parameters) that were live (live/dead dye-negative or low) and CD3+. The individual phenotypic markers were gated based upon the FMO (fluorescence minus one) and control normal donor peripheral blood mononuclear T cells.

Data analysis was performed using FlowJo v8.1 Software (FlowJo LLC, OR). Results were graphed using GraphPad v8.

Expected Results

PD-1-selected TIL were expected to be comparable to unselected TIL for most phenotypic markers and to meet with LN-145 phenotypic release criteria. Based on published reports, PD-1 expression of the PD-1-selected TIL was expected to decrease with the in vitro expansion step [10-12]. Whether PD-1-selected TIL PD-1 levels remained higher than those of unselected TIL was unknown.

Results

CD4 and CD8 Expression in PD1-Selected TIL

PD-1 is expressed in CD3+ T cells, but mostly has been characterized in the CD8+ T cells despite its expression in both the CD4+ and CD8+ lineages [10, 13]. To determine whether sorting for PD-1+ altered the ratio of CD4+ and CD8+ T cell lineages in the expanded PD-1-selected TIL relative to unselected TIL, 13 paired samples were compared for the expression of the 2 markers. Results are shown in FIG. 148.

The mean percentages of CD4+ and CD8+ cells in expanded TIL were similar in the PD-1-selected and unselected products. The percentage of CD4+ T cells was higher than the CD8+ T cells in both the PD-1-selected and unselected TIL products.

These results suggest that the proportions of CD4+ and CD8+ TIL were not significantly different within the PD-1-selected T cell population relative to the unselected TIL products. These results suggest that selecting for PD-1 does not alter the T cell lineage of the final expanded product.

Markers of Youth/Differentiation in PD1-Selected TIL

Response to ACT requires a balance of effector functions, typical in differentiated T cells, and persistence, that is associated with T cell youth and a central memory phenotype [14, 15]. Classically, high CD27 and CD28 expression is related to T cell youth, while CD56, CD57 and KLRG1 expression identifies terminally differentiated cells. Thirteen paired PD-1-selected and unselected TIL products were stained for these markers and analyzed by flow cytometry. Results are shown in FIG. 149.

PD-1-selected and unselected TIL expressed a similar differentiation phenotype as indicated by low levels of CD27, CD56, and KLRG1 and moderate levels of CD28 and CD57. However, PD-1-selected TIL had significantly greater levels of CD27 and decreased levels of KLRG1, compared to unselected TIL, which likely translates to a less differentiated phenotype in the PD-1-selected TIL. These results are consistent with reports in selected PD-1 high TIL from NSCLC in which the TIL were CD27+ and KLRG1—, compared to their PD-1-counterparts [2]. CD27+ TIL have also been associated with in vivo anti-tumor activity and KLRG1+T with reduced in vivo persistence of T cells [16]. These results suggest that PD-1-selected TIL may be able to support the sustained anti-tumor activity required for durable responses in vivo [7].

Memory T Cell Populations in PD1-Selected TIL

T cell memory subsets can be identified based upon the differential expression of the 2 cell surface markers CD45RA and CCR7. Effector memory T cells (TEM) are defined as CD45RA− and CCR7—, central memory T cells (TCM) as CD45RA− and CCR7+, stem cell memory T cells (TSCM) as CD45RA+ and CCR7+, and CD45RA+ effector memory T cells or terminally differentiated T cells (TEMRA) as CD45RA+ and CCR7-[17].

Published research has demonstrated that PD-1+ TIL are mostly comprised of effector memory T cells (TEM) [11, 18]. Furthermore, these TEMs have been shown to represent the main population of unselected TIL products that demonstrated clinical activity [19]. To determine the proportion of each memory T cell subset in PD-1-selected TIL, 13 products were evaluated for CD45RA and CCR7 expression by flow cytometry. Results are shown in FIG. 150.

Like Iovance's current TIL products, lifileucel and LN-145, as other TIL products that demonstrated clinical efficacy, both PD-1-selected TIL and unselected TIL were predominantly comprised of TEM [20]. Selection of PD-1 did not appear to alter the memory repertoire of expanded TIL.

Activation Status of PD1-Selected TIL

Upon T cell activation, several cell surface markers are upregulated, each at a different stage of the activation process. One of the earliest activation markers is CD69, which is an inducible cell surface glycoprotein expressed upon activation via the TCR [21]. CD25 the alpha subunit of the IL-2 receptor, is upregulated slightly later than CD69, and plays a crucial role in regulating T cell proliferation [21]. Additionally, co-stimulatory receptors such as CD134 and CD137 are also considered markers of T cell activation and are often used to identify antigen-specific T cells in infiltrating tumors [21, 22].

Based on the expression profile of these markers, post-REP TIL have been shown to display an activated phenotype, consistent with the ability of TIL products to initiate a potent anti-tumor T cell response upon infusion [3].

Extensive studies have evaluated the activation status of PD-1+ and PD-1-TIL in both mice and humans. Data in mice demonstrated that PD-1+ TIL expressed a higher percentage of CD134 and CD137, compared to PD-1-[11, 23]. Similar results were obtained in human studies, in which CD137 was found to be higher in PD-1+/PD-1 high TIL, in patients with melanoma and NSCLC [8, 12].

Additional studies have evaluated CD69 and CD25 expression in PD-1+ TIL. A significant fraction of PD-1+ TIL have been shown to co-express CD69 [24], however the majority of PD-1+ lacked expression of CD25 [13].

To verify that PD-1-selected TIL express an activated phenotype post-expansion, 13 TIL products were analyzed for the expression of CD25, CD69, CD134, and CD137 by flow cytometry and compared to unselected TIL. Results are shown in FIG. 151.

The 4 activation markers were detected on an average of 3.34-22.28% in PD-1-selected TIL, indicating that a fraction of TIL, in all products tested, expressed at least one marker indicative of activation. The percent of CD25+, CD69+, and CD134+ were comparable to those in the unselected TIL, suggesting that the PD-1 selection step did not alter the activation state of the in vitro expanded cells. However, unselected TIL presented with significantly lower levels of CD137+ T cells than PD-1-selected TIL, which could reflect a slightly higher activation state in PD-1-selected TIL. Altogether, these results show that the REP uniformly activates PD-1-selected and unselected TIL and suggests that PD-1+ TIL, upon in vitro culture, expressed an activated phenotype [10].

Exhaustion Markers in PD-1-Selected TIL

Extensive studies have evaluated the co-expression of PD-1 with other co-inhibitory/exhaustion markers. A subset of PD-1+ TIL consistently co-expressed TIM3, LAG3, TIGIT, BTLA, and CTLA4 [8, 11, 12, 18, 23]. However, these markers were evaluated in freshly isolated PD-1+ TIL, and less information is available on their status in expanded PD-1+ TIL.

Interestingly, PD-1 expression in expanded PD-1+ TIL was shown to decrease with culture and expansion and interpreted as a sign of TIL ex-vivo reinvigoration [10, 12].

To better understand the exhaustion/inhibitory status of the PD-1-selected TIL, 13 matched unselected and PD-1-selected TIL products were analyzed for the expression of the four exhaustion/inhibition markers LAG3, PD-1, TIM3, and CD101 by flow cytometry. CD101 has been associated with late stage TIL dysfunction and was added to our standard list of exhaustion markers [25]. Results are shown in FIG. 152.

PD-1-selected TIL expressed all 4 of the exhaustion/inhibitory markers assayed. LAG3 was found on 1.75 to 37.8%, PD-1 on 9.06 to 53.8%, TIM3 on 8.65-54.9%, and CD101 on 9.16-91.1%. Unselected TIL expressed similar levels of LAG3, TIM3, and CD101 relative to the selected products, again suggesting that the sorting for PD-1+ TIL does not significantly skew the phenotype of the final product when expanded in vitro. Only the PD-1 levels were significantly different between the 2 products, with the PD-1-selected product expressing a higher percent of PD-1+ cells than unselected cells. However, the number of PD-1+ cells, in the PD-1-selected TIL, dropped substantially from 92.8% post-sort to an average of 27.1% post-REP. This is consistent with the data reported by others for melanoma and NSCLC TIL and suggests in vitro reinvigoration [10, 12].

To compare the extend of the in vitro expansion-induced PD-1 downregulation between PD-1-selected and unselected TIL, pre- and post-expansion percentages of PD-1+ TIL were assessed for both products. Results are shown in FIG. 153.

The expression of PD-1 was significantly reduced in both the PD-1-selected TIL (average of 27.1%, ranging from 9.06 to 43.6) and unselected TIL products (average 10.6%, ranging from 4.93 to 29.3) relative to initial average PD-1 levels of 92.8% and 37.3%, respectively. Thus, the process of expanding the TIL equally affected both TIL preparations, with a >3-fold reduction in in the expression of PD-1.

Resident Memory T Cell Markers in PD1-Selected TIL

Integrins mediate the retention of lymphocytes in peripheral tissue. Some of these integrins are expressed on a subset of T cells known as resident memory T cells. These cells which strongly resemble effector memory T cells phenotypically, do not circulate and reside within tissues.

Several integrins such as □E□7 (CD103), □1□1 (CD49a) are expressed on variable fractions of freshly isolated TIL [7,8]. Along with CD39, a T cell surface molecule involved in the adenosine pathway and associated with an inhibitory signal, CD49 and CD103 have been identified on PD-1+ TIL that were shown to be tumor-reactive [2, 8, 10]. Furthermore, PD-1 and CD103 co-expression has been associated with a favorable clinical outcome in ovarian cancer [9].

To determine whether the PD1-selected TIL and unselected TIL products expressed markers associated with resident memory T cells, 13 tumors were analyzed for the expression for CD39, CD49a and CD103 expression. See, FIG. 153.

No differences were observed in the percentages of CD49a+ and CD103+ cells in PD-1-selected TIL relative to unselected TIL, whereas CD39 expression was significantly higher in PD-1-selected TIL than unselected TIL. The difference could be related to higher levels of CD39 in unexpanded PD-1+ TIL, as suggested by the association of this marker with neoantigen specificity [6]. Overall, the 3 markers, were differentially expressed in the TIL products.

Conclusions

Observed differences in phenotypic expression of the assayed cell surface markers are indicated in Table 60 below. With exception of KLRG1, the listed phenotypic markers were significantly upregulated in PD1-selected TIL compared to unselected TIL.

TABLE 60

Phenotypic markers differentially expressed in PD1$^{+}$-selected TIL and unselected TIL

| Differentiation | Activation | Exhaustion | Resident Memory |
|---|---|---|---|
| CD27<br>KLRG1 | CD137 | PD1 | CD39 |

PD-1-selected TIL appeared to be less differentiated in comparison to unselected TIL as demonstrated by greater expression of CD27 and lower levels of KLRG1. The efficacy and curative potential of TIL depend on their ability to kill and to persist long enough to eradicate all the malignant cells in the tumor [14, 24]. Therefore, the moderately differentiated phenotype may be a positive feature of the PD-1-selected TIL.

PD-1-selected TIL expressed a higher percentage of CD137 and CD39, when compared to unselected TIL. These findings suggest that the PD-1-selected TIL are in an activated state, which may have the potential to enhance their effector function once transferred in vivo.

Overall, our results suggest that expanded PD-1-selected TIL were composed of mostly non-differentiated TEM with low expression of exhaustion markers, suggesting that these cells were reinvigorated upon expansion in vitro.

The phenotypic features of the PD-1-selected TIL are comparable to Iovance's unselected TIL products lifileucel and LN-145, that have shown clinical efficacy in metastatic melanoma and cervical cancer respectively.

REFERENCES FOR EXAMPLE 16

1. Jing, W., et al., *Adoptive cell therapy using PD-1 (+) myeloma-reactive T cells eliminates established myeloma in mice*. J Immunother Cancer, 2017. 5: p. 51.
2. Fernandez-Poma, S. M., et al., *Expansion of Tumor-Infiltrating CD8 (+) T cells Expressing PD-1 Improves the Efficacy of Adoptive T-cell Therapy*. Cancer Res, 2017. 77(13): p. 3672-3684.
3. Thommen, D. S., et al., *A transcriptionally and functionally distinct PD-1(+) CD8(+) T cell pool with predictive potential in non-small-cell lung cancer treated with PD-1 blockade*. Nat Med, 2018.
4. Ahmadzadeh, M., et al., *Tumor antigen-specific CD8 T cells infiltrating the tumor express high levels of PD-1 and are functionally impaired*. Blood, 2009. 114(8): p. 1537-44.
5. Inozume, T., et al., *Selection of CD8+PD-1+ lymphocytes in fresh human melanomas enriches for tumor-reactive T cells*. J Immunother, 2010. 33(9): p. 956-64.
6. Crompton, J. G., M. Sukumar, and N. P. Restifo, *Uncoupling T-cell expansion from effector differentiation in cell-based immunotherapy*. Immunol Rev, 2014. 257(1): p. 264-276.
7. Westergaard, M. C. W., et al., *Tumour-reactive T cell subsets in the microenvironment of ovarian cancer*. Br J Cancer, 2019.
8. Bally, A. P., J. W. Austin, and J. M. Boss, *Genetic and Epigenetic Regulation of PD-1 Expression*. J Immunol, 2016. 196(6): p. 2431-7.
9. Gros, A., et al., *PD-1 identifies the patient-specific CD8 (+) tumor-reactive repertoire infiltrating human tumors*. J Clin Invest, 2014. 124(5): p. 2246-59.
10. Golubovskaya, V. and L. Wu, *Different Subsets of T Cells, Memory, Effector Functions, and CAR-T Immunotherapy*. Cancers (Basel), 2016. 8(3).
11. Kansy, B. A., et al., *PD-1 Status in CD8(+) T Cells Associates with Survival and Anti-PD-1 Therapeutic Outcomes in Head and Neck Cancer*. Cancer Res, 2017. 77(22): p. 6353-6364.
12. Radvanyi, L. G., et al., *Specific lymphocyte subsets predict response to adoptive cell therapy using expanded autologous tumor-infiltrating lymphocytes in metastatic melanoma patients*. Clin Cancer Res, 2012. 18(24): p. 6758-70.
13. Wolfl, M., et al., *Activation-induced expression of CD137 permits detection, isolation, and expansion of the full repertoire of CD8+ T cells responding to antigen without requiring knowledge of epitope specificities*. Blood, 2007. 110(1): p. 201-10.
14. Duhen, T., et al., *Co-expression of CD39 and CD103 identifies tumor-reactive CD8 T cells in human solid tumors*. Nat Commun, 2018. 9(1): p. 2724.
15. Rosenberg, S. A., et al., *Durable complete responses in heavily pretreated patients with metastatic melanoma using T-cell transfer immunotherapy*. Clin Cancer Res, 2011. 17(13): p. 4550-7.

Example 17: Selection of PD1 TIL Using Nivolumab by Flow Cytometry Sorting and Expansion in Full-Scale for Clinical Manufacturing Introduction The present example is directed toward development of a protocol designed to select PD1 TIL from tumor digests to enrich the TIL product for autologous tumor-reactive T cells. The present example provides a protocol to obtain PD1-selected TIL using nivolumab as the PD1 staining antibody in lieu of the PE-conjugated clone #EH12.2H7.

Purpose

The purpose of this protocol was to develop a process to sort PD1 TIL using Nivolumab as the selecting agent and expand for the manufacture of clinical trial material.

Scope

The scope of work was to expand sorted PD1 TIL from melanoma or lung or head and neck or ovarian tumors using a 2-REP protocol designed for full scale clinical manufacturing (FIG. 154).

Two small-scale and One full-scale experiments were conducted.

On Day 0, tumor digest was equally distributed to purify PD1 TIL using the new staining method using Nivolumab and staining method using anti-PD1 (EH12.2H7) and flow sorted for PD1 TIL.

For Small-Scale process ($1/100^{th}$ scale), REP-1 was initiated on Day 0 by calculating 10% of the PD1 TIL with the lowest sort result, and transferring that number of TIL from each sort into the respective G-Rex-10M flasks with Feeders and OKT-3 with IL-2 media. REP-2 were initiated per Example 9. A brief explanation of the associated timepoints is outlined below in the methods section (FIG. 155).

For Full-Scale process, REP-1 was initiated on Day 0 using sorted PD1 TIL with 100e6 allogeneic feeder cells and 30 ng/mL OKT3 for 11 days. REP-2 will be initiated on Day 11 using harvested REP-1 product. REP-2 (Day 11) and the subsequent Day 16 and Day 22 processes was performed per IOVA Manufacturing Batch Records. A brief explanation of the associated timepoints is outlined below in the methods section (FIG. 154).

For all conditions, Day 22 Harvests was initiated by volume reduction followed by cell counting on the NC-200.

The expanded TIL and final product was assessed for cell growth, viability, phenotype, Telomere length and function (IFNγ and Granzyme-B secretion, CD107a mobilization).

4. Methods

Overview of the PD1 Gen-2 Small Scale and Full-Scale Processes Post Digest

FIG. 155: Small-Scale Process Overview: PD1-A is the condition that uses the Nivolumab staining procedure outlined in this protocol. PD1-B is the condition that uses the anti-PD1-PE (Clone #EH12.2H7) staining method. Bulk condition serves as a control.

Material

Tumor Tissue

Tumors of various histologies were received from research alliances and tissue procurement vendors. Standard reagents for TIL growth which includes: G-Rex 100 MCS, and 500 MCS flasks (Wilson Wolf, Cat #81100-CS, 85500S-CS, respectively); GMP recombinant IL-2 (Cell-Genix, Germany, Cat #1020-1000); GlutaMAX 100× (Thermofisher, Cat #35050061); and Gentamycin 50 mg/mL (Thermofisher, Cat #15750060).

Flow Cytometry Staining and Analysis Reagents

Flow Cytometry Antibodies

Anti-PD1 PE, Clone EH12.2H7, Biolegend, Cat #329906

Anti-CD3 FITC, Clone OKT3, Biolegend, Cat #317306

Anti-IgG4 Fc-PE, Clone HP6025, Southern Biotech, Cat #9200-09

Nivolumab [Brand Name: Opdivo] 10 mg/mL (Bristol-Myers Squibb, New York)

PE Anti-Human IgG4, Clone HP6023, 0.5 mg/mL (BioLegend, San Diego, Cat #98155)

Sorting Buffer

HBSS with 2% FBS.

Collection Buffer

HBSS with 50% hAB Serum

Procedure

Tumor Tissue Preparation

Freshly resected tumor samples were received from research alliances and tissue procurement vendors. The tumors were shipped overnight at 2-8° C. in HypoThermosol (Biolife Solutions, Washington, Cat #101104) (with Gentamicin (10 mg/mL) and Amphotericin B (250 μg/mL)).

Took a photo of the tumor in the vial/tube. Remove tumor from packaging and wash 3× for 2 minutes per wash in Tumor Wash Buffer (Filtered HBSS with 50 μg/mL Gentamycin).

Fragmented the entire tumor into 4-6-mm$^3$ fragments in preparation for tumor digest. Keep 4-6-mm$^3$ fragments in a well of a 6-well plate containing 10 mL of Tumor Wash Buffer/well.

Enzyme Preparation for Tumor Digestion

Tumor was digested using GMP Collagenase, Neutral Protease and DNAse I as described herein Reconstituted the lyophilized enzymes in the amount of sterile HBSS indicated for each of the digestion enzymes below. Be sure to capture any residual powder from the sides of the bottles and from the protective foil on the bottles opening. Pipetted up and down several times and swirl to ensure complete reconstitution.

Reconstituted the Collagenase AF-1 (Nordmark, Sweden, N0003554) in 10 ml of sterile HBSS. The lyophilized stock enzyme is at a concentration of 2892 PZ U/vial. Therefore, after reconstitution the collagenase stock is 289.2 PZ U/ml. Note, the stock of enzymes can change so verify the concentration of the lyophilized stock and amend the final amount of enzyme added to the digest cocktail accordingly. Aliquotted into 100 μl aliquots and store at −20° C.

Reconstituted the Neutral protease (Nordmark, Sweden, N0003553) in 1 ml of sterile HBSS. The lyophilized stock enzyme was at a concentration of 175 DMC U/vial. Therefore, after reconstitution the neutral protease stock is 175 DMC/ml. Note, the stock of enzymes can change so verify the concentration of the lyophilized stock and amend the final amount of enzyme added to the digest cocktail accordingly. Aliquotted into 20 μl aliquots and store at −20° C.

Reconstituted the DNAse I (Roche, Switzerland, 03724751) in 1 ml of sterile HBSS. The lyophilized stock enzyme was at a concentration of 4 KU/vial. Therefore, after reconstitution the DNAse stock is 4 KU/ml. Note, the stock of enzymes can change so verify the concentration of the lyophilized stock and amend the final amount of enzyme added to the digest cocktail accordingly. Aliquotted into 250 μl aliquots and store at −20° C.

Thaw 3 components of GMP digest cocktail and prepare the working GMP digest cocktail as follows: Add 10.2 μl of the neutral protease (0.36 DMC U/ml), 21.3 μl of collagenase AF-1 (1.2 PZ/ml) and 250 μl of DNAse I (200 U/ml) to 4.7 ml of sterile HBSS. Place the digest cocktail directly into the C-tube.

Tumor Processing and Digestion

To the GentleMACS OctoDissociator, transferred up to 4-6 mm tumor fragments to each GentleMACS C-Tube (C-tube) in the 5 ml of digest cocktail indicated above. Used additional GentleMACS C-Tube for additional tumor fragments.

Transferred each C-tube to the GentleMACS OctoDissociator. Digest by setting the dissociator to the appropriate program for the respective tumor histology listed in Table 61 below. The dissociation was approximately one hour.

TABLE 61

Miltenyi OctoDissociator Programs Based on Tumor Tissue Type.

| Tumor Tissue Type | Designation | Program |
|---|---|---|
| Melanoma, Ovarian, Colon, Hypopharyngeal, and Renal | Soft | 37C_h_TDK_1 |
| Lung and Prostate | Medium | 37C_h_TDK_2 |
| Breast, Pancreatic, Hepatocellular, Head and Neck Squamous Cell (HNSCC) | Tough | 37C_h_TDK_3 |

Post-digest, removed the C-tube(s) from the Octodissociator or rotator and place into the BSC. Removed the digest from each C-tube with a 25-mL serological pipette and pass the bulk digest through a 70-μm cell strainer into a 50-ml conical tube.

Note: Did not allow the digest to splash up due to pressure from the pipettor. Gently pour the solution to the 70-μm cell strainer. Avoid the pipette tip to touch the filter.

Undigested parts of the tumor may not pass through the strainer, Wash the C-tube(s) with an additional 10 mL of HBSS and pass the wash through the cell strainer. QS the 50-mL conical to 50 mL with HBSS.

Centrifuged the digest at 400×G for 5 minutes at RT (full acceleration & full brake).

Transferred Conical to BSC and aspirate or decant supernatant. Resuspend pellet in 5 mL of warm CM1+6000 IU/mL IL-2 and pipette up and down 5-6 times. Perform 2 cell counts on NC-200 at no dilution.

Placed 0.5-1 mL of digest aside for Bulk control and cryopreserve 2×500 μl aliquots of digest for tumor reactivity assays. Keep digest on ice.

Note: Made sure to replace with crushed or pelletted ice as soon as ice water slurry is observed.

Equally distributed the remaining cells for Anti-PD1-PE (Clone #EH12.2H7) and Nivolumab staining procedure.

Tumor Digest Flow Cytometry Staining Using Anti-PD1-PE (Clone #EH12.2H7) and Cell Sorting First half of the Tumor digest were stained with anti-PD1-PE.

Tumor Digest Flow Cytometry Staining Using Nivolumab and Cell Sorting

To the second part, remove ~1e5 cells for the unstained negative control, PE, and FITC single color compensation controls into labeled 15-mL conical tubes. Remaining tumor digest will be stained with Nivolumab and anti-IgG4-PE (secondary antibody for Nivolumab).

Preparation of Sorting Buffer (2% FBS): Aspirated 2 ml of HBSS out of fresh 500 mL HBSS bottle and add 10 ml of FBS. Keep the sort buffer in ice until further use.

Preparation of Working Nivolumab solution: To make the working solution, performed a 1:100 dilution by adding 10-μl of Nivolumab [10 mg/mL] to 990-μl of Sorting Buffer.

Preparation of Intermediate 1:50 IgG4 Dilution:

Add 10-μL of anti-IgG4-PE to 490 μL of Sorting Buffer in a microcentrifuge tube and vortex gently for 5 seconds to mix thoroughly. Place intermediate dilution on ice until further use.

Preparation of Tumor Digest Sample for Flow Sorting:

Using the cell count data from above, calculated the number of cells remaining in the tumor digest tube.

Add 10 mL of HBSS to digest and centrifuge at 400×G for 5 minutes at RT (full acceleration & full brake).

Transferred conical to BSC and decant supernatant. Calculated volume (Refer Table # for TVC concentration, resuspend sort buffer volume, Nivolumab volume) to resuspend cells at 10e6 cells/mL with Sorting Buffer.

Added 10-μl L of the working Nivolumab per 1 ml of cells.

Preparation of Single Color Compensation:

PE compensation control was stained with Nivolumab plus the anti-IgG4-PE secondary, and the FITC compensation control will be stained with anti-CD3-FITC.

Added 10 mL of HBSS to unstained, PE and FITC comp tubes and centrifuge at 400×G for 5 minutes at RT (full acceleration & full brake).

Unstained Tube:

Resuspended the cells in 500-μL of Sorting Buffer and store in Ice until other samples are ready for sorting FITC Comp Tube:

Resuspended the cells in 100-μL of Sorting Buffer.

Added 3-μL of anti-CD3-FITC per 100-μL.

Mixed digest gently with a 1-mL micropipettor and incubate cells on ice for 30 minutes. Protect from light during incubation by covering the ice bucket with aluminum foil.

Centrifuged at 400×G for 5 min at RT (full acceleration and full brake).

Resuspend the cells in 500 μl of Sort Buffer and stored in ice untill other samples are ready for sorting, covered with aluminum foil until further use.

TABLE 62

Recommended resuspend Sorting Buffer and Nivolumab volume to add.

| Option | A | B | C | D | E | F | G | H | I | J |
|---|---|---|---|---|---|---|---|---|---|---|
| TVC | <10e6 | >10e6-20e6 | >20e6-30e6 | >30e6-40e6 | >40e6-50e6 | >50e6-60e6 | >60e6-70e6 | >70e6-80e6 | >80e6-90e6 | >90e6-100e6 |
| Resuspend Volume (mL) | 1 | 2 | 3 | 4 | 5 | 6 | 7 | 8 | 9 | 10 |
| Working Nivolumab (uL) | 10 | 20 | 30 | 40 | 50 | 60 | 70 | 80 | 90 | 100 |

Mixed digest gently with a 1-mL micropipettor and incubate cells on ice for 30 minutes. Protect from light during incubation. Agitated by flicking gently every 10 minutes during incubation to ensure thorough staining.

After incubation, added 10 mL of Sorting Buffer to the sample digest, single colour compensation, and the unstained negative control.

Centrifuged at 400×G for 5 min at RT (full acceleration and full brake).

Decanted samples gently.

Resuspended pellet in 400-μL of Sorting Buffer and use a serological pipette to measure the total volume of the sample. Add 3-μL of anti-CD3-FITC per 100 μl and add 50 μL intermediate diluted anti-IgG4-PE (See Section: 9.5.3) per 500 μl.

Mixed digest gently with a 1-mL micropipette and incubate cells on ice for 30 minutes. Protected from light during incubation. Agitated by flicking gently every 10 minutes during incubation to ensure thorough staining.

After incubation, add 10-mL of Sorting Buffer to the sample digest.

Filtered the sample digest, through 70-μm cell strainers into labeled 50-mL conical tubes.

Centrifuged at 400×G for 5 min at RT (full acceleration and full brake).

Resuspended cells at up to 10e6 cells/mL in Sorting buffer. Minimum volume is 300-μl and transfer to a new 15 mL conical tube.

Stored the tubes on ice, covered with aluminum foil until further use.

PE Comp Tube:

Transferred conical to BSC and decant supernatant. Resuspended cells the cells in 1 mL of Sorting Buffer.

Added 10-μL of the working Nivolumab per 1 ml of cells.

After incubation, add 10 mL of Sorting Buffer, Centrifuged at 400×G for 5 min at RT (full acceleration and full brake).

Decanted samples gently and resuspend pellet in 500 μL of Sorting Buffer and use a serological pipette to measure the total volume of the sample. Add 50 μL intermediate diluted anti-IgG4-PE (See Section: 9.5.3) anti-IgG4-PE per 500 μL of cells.

Mixed digest gently with a 1-mL micropipettor and incubate cells on ice for 30 minutes. Protect from light during incubation.

Centrifuged at 400×G for 5 min at RT (full acceleration and full brake).

Resuspended the cells in 500 μl of Sort Buffer and store in Ice until other samples are ready for sorting, covered with aluminum foil until further use.

Preparation of Collection Tubes:

Prepare 15-mL collection tubes for the sorted populations. Placed 2-mL of Collection buffer (50% HBSS with 50% hAB Serum) in the tubes. Stored the collection tubes on ice until further use.

Cell Counting and Viability Assessment

The procedures for obtaining cell and viability counts, using the Chemometec NC-200 Cell Counter as described herein.

FACS Sorting Using the Sony FX500

Flow Cytometry Sorting of PD1 Selected TIL from Tumor Digest for the sorting procedure and maintenance.

PD1 Rapid Expansion Protocol—Full-Scale REP Day 0 (REP-1)

Media Preparation

Prepared 1 L of CM1+6000 IU/mL IL-2 in the 37° C. incubator for at least 24 h

PBMC Feeder Cell Preparation and TIL Seeding TIL for REP-1

Example 9 provides the instructions on initiating the Full-Scale Day 0 (REP-1), with the following exception:

The lowest number of PD1 selected TIL that results from both sorts will be used as the number of PD1-selected TIL to add to both PD1-A and PD1-B conditions. Calculate the volume of the respective sorts to achieve that number in both PD1-A and PD1-B conditions. Transfer the TIL volumes into their respective G-Rex 100M flasks.

PD1 Rapid Expansion Protocol—Small-Scale REP Day 0 (REP-1)

Media Preparation

Prepared and prewarmed 1 L of CM1+6000 IU/mL IL-2 in the 37° C. incubator for at least 24 h PBMC Feeder Cell Preparation Thawed an appropriate number of vials for REP-1 (10e6 per flask will be needed; assume 60e6-80e6 PBMC per 1 mL vial)

Placed 40 mL of warm CM1+6000 IU/mL IL-2 in a 50 ml conical and pipette the 1 mL PBMC feeder vials into the conical.

Pipetted the thawed PBMC feeders up and down to thoroughly mix and perform 2 cell counts on the NC-200.

Calculated and transferred the volume necessary to transfer 10e6 PBMC to the G-Rex 10M.

Added 3-μL of αCD3 (OKT-3) to the G-Rex 10M. Place flasks into the incubator.

Seeding TIL for REP-1

Calculated 10% of the lowest PD1 sort result and calculate the volume of the respective sorts to achieve that number in both PD1-A and PD1-B conditions. Transfer the TIL volumes into their respective G-Rex 10M flasks.

To the Bulk TIL control condition was added an equivalent number of CD3+ cells to PD1 cells. To obtain the proper volume of digest, follow the steps below:

Calculated the CD3+ TVC/mL in the digest by multiplying the digest TVC obtained by the % CD3+ of live cells obtained from the lowest sort report. (i.e., 10e6*10%=1e6).

After obtaining this number, divided the number of PD1 cells used by this number. (i.e., 1e5/1e6=0.1 mL).

Added this volume (0.1 mL) of digest to the Bulk TIL flask and fill to 100 mL with CM1+6000 IU/mL IL-2

Placed all flasks into 37° C., 5% $CO_2$ incubator 9.10. PD1 Rapid Expansion Protocol-Full Scale Day 11, 16, and 22

The full scale process was followed per manufacturing batch records. The Bulk TIL condition was processed similarly to the steps described in Example 9.

Acceptance Criteria

Table 63 below specifies the acceptance criteria that was used to evaluate the performance of the small (Extrapolated TVC) and full scale experiment.

TABLE 63

In Process and Harvest Product Release Testing and Acceptance Criteria

| Test Type | Method | Acceptance Criterion |
|---|---|---|
| In-Process Testing | | |
| Post-sort Purity (% PD1+) | Flow Cytometry | >80% |
| Release Testing | | |
| Appearance | Visual Inspection | Bag intact, no sign of clumps |
| Cell viability | Fluorescence (LAB-056) | >70% |
| Total Viable Cell Count | Fluorescence (LAB-056) | $1 \times 10^9$ to $150 \times 10^9$ |
| Purity (% CD45+ CD3+) | Flow Cytometry (LAB-042) | >90% CD45+ CD3+ cells |
| IFNg (Stimulated - Unstimulated) | Bead stimulation and ELISA (LAB-016) | >500 pg/mL |

Table 64 below specifies the additional final product characterization testing performed.

TABLE 64

Final Product Characterization (for information only)

| Test Type | Method | Report Results |
|---|---|---|
| Purity and Memory T cell subset Phenotype | Flow Cytometry (LAB-055) | Report results |
| Activation and Exhaustion marker Phenotype | Flow Cytometry (LAB-061) | Report results |
| Telomere length | TAT (Life Length) | Report results |
| Telomerase Activity | Q-TRAP (Life Length) | Report Results |
| Granzyme B | Bead stimulation and ELISA (LAB-064) | Report results |
| CD107A | Mitogen stimulation and flow cytometry (LAB-061) | Report results |
| TCR Vbeta Sequencing | Deep sequencing (Irepertoire, Inc) | Report results (if available) |
| Tumor Reactivity/ Killing assay | Tumor Digest coculture/ Tumor Killing | Report results |
| Metabolite analysis | Cedex Biochemical analyzer | Report results |

Example 17 Reference Documents

Examples 6 and 7, Selecting and Expanding PD1+ cells directly ex vivo: A process for enhancing tumor-reactive TIL for ACT therapy.

Examples 9, Selection and Expansion of $PD1^{+}$ TIL for Full Scale Manufacturing.

Example 10, Selection and Expansion of PD $1^{hIgh}$ TIL for Full Scale Manufacturing.

Example 18: Pd-1 Expressing Cells in Tumor Digests

Purpose

To assess expression of programmed cell death protein 1 (PD-1) in whole tumor digests.

Scope

Whole tumor digests from the following tumor histologies were assessed for the expression of PD-1; melanoma, non-small lung carcinoma (NSCLC), head and neck squamous cell carcinoma (HNSCC), ovarian carcinoma (OC), triple negative breast carcinoma (TNBC), prostate cancer (PC) and colorectal carcinoma (CRC).

Background Information

PD-1 is a multi-dimensional phenotypic marker, which has been associated with activation, antigen-specificity, and exhaustion. It is rapidly induced upon activation and is maintained on antigen-experienced cells in chronic disease settings including cancer [1,2], Molecularly, PD-1 is a member of the CD28 family of regulatory cell surface receptors and is expressed on chronically activated T cells, NKT cells, B cells and monocytes [3-5]. Engagement with its ligands, PD-L1 and PD-L2, induces signaling cascades that result in decreased T cell activation, proliferation, survival and cytokine production [6].

Despite the immunoinhibitory role of PD-1, the presence of PD-1-expressing tumor infiltrating lymphocytes (TIL) has been associated with favorable clinical outcomes in HNSCC and NSCLC, suggesting that these TIL may be involved in controlling tumor progression [7-9].

Studies in melanoma and NSCLC have demonstrated that most of the tumor-reactive TIL were comprised within the PD-1+ T cell subset [4, 8, 10].

Based upon the notion that PD-1+ TIL are the neoantigen/tumor-specific lymphocytes, Iovance is developing a novel PD-1-selected TIL product, LN-145-S1, that is enriched for PD-1+ TIL sorted directly from whole tumor digests.

While PD-1 expression is necessary for response to anti-PD-1 therapy, PD-1 expression alone does not predict responsiveness to therapy. As an example, PD-1 is present on TIL in OC and its expression has been correlated with survival [11]. However, a recent clinical trial in OC demonstrated that the anti-PD-L1 drug Avelumab in combination with chemotherapy did not enhance progression free survival [12]. This study, along with the high number of patients resistant to anti-PD-1 therapy, that express PD-1+ in the tumor microenvironment, shows that in vivo blockade of the PD-1/PD-L1 axis is not sufficient to control most cancers.

Adoptive T cell therapy, using TILs, has demonstrated remarkable efficacy in melanoma patients that were refractory to anti-PD-1, indicating that the protocols used to expand TIL ex vivo, were capable of reinvigorating the TIL, as opposed to in vivo PD-1 blockade In this example, sorting PD-1+ TIL prior to ex vivo expansion is examined with regard to further improving the response rate to TIL therapy, in all PD-1+ cancer histologies.

The aim of the present study was to survey multiple tumor histologies for the presence of PD-1+ TIL to support their targeting with expanded TIL product in the clinic.

Experimental Design

Tumor digests from multiple tumor histologies were assessed for PD-1 expression by flow cytometry.

Materials

Tumor digests used in this work are described in Table 65. Abbrevations: CRC (Colorectal Carcinoma), HNSCC (Head and Neck Squamous Cell Carcinoma), MSI (Microsatellite instability), MSS (Microsatellite stable), ND-PBL (Normal donor peripheral blood lymphocytes), NSCLC (Non-small cell lung carcinoma), OC (Ovarian carcinoma), PD-1 (Programmed cell death protein 1), REP (Rapid expansion protocol), TIL (Tumor Infiltrating T cells), and TNBC (Triple Negative Breast Carcinoma).

TABLE 65

Description of Tumor Digests used for these studies

| Tumor ID | Histology | PD-1-selected TIL generated |
|---|---|---|
| H3035 | HNSCC | Yes |
| H3036 | HNSCC | No<br>Culture Contaminated |
| H3037 | HNSCC | No<br>Culture Contaminated |
| H3038 | HNSCC | Yes |
| H3039 | HNSCC | Yes |
| L4089 | NSCLC | Yes |
| L4096 | NSCLC | Yes |
| L4097 | NSCLC | Yes |
| L4100 | NSCLC | Yes |
| L4101 | NSCLC | Yes |
| L4104 | NSCLC | Yes |
| L4106 | NSCLC | Yes |
| M1132 | Melanoma | Yes |
| M1136 | Melanoma | Yes |
| M1139 | Melanoma | Yes |
| M1141 | Melanoma | Yes |
| OV8030 | Ovarian | Yes |
| OV8042 | Ovarian | Yes |
| OV8042 | Ovarian | Yes |
| T6049 | TNBC | Yes |
| T6056 | TNBC | Yes |
| T6058 | TNBC | Yes |
| T6060 | TNBC | Yes |
| OC20019 | Prostate | Yes |
| OC20030 | Prostate | Yes |
| CC10026 | CRC | No<br>Poor digest cell yield |
| CC10027 | CRC | No<br>Poor digest cell yield |
| CC10028 | CRC | Yes |
| CC10029 | CRC | Yes |
| CC10031 | CRC | No<br>Culture Contaminated |
| CC10034 | CRC | Yes |
| CC10037 | CRC | Yes |
| CC10039 | CRC | Yes |

Methods

Tumor Processing

Tissue samples weighing from 0.2 g to 1.5 g were partially dissected into 4-6-mm fragments and digested into a single-cell suspension comprised of tumor, stroma and immune cells. A triple enzymatic cocktail that includes DNAse (500 IU/ml), Hyaluronidase (1 mg/ml) and Collagenase IV (10 ng/ml) was used to digest the tissue for 1 hour at 37° C. under gentle agitation.

PD-1 Staining

Whole tumor digests were stained according to the table below. Cells were stained in 100 μl/1e6 cells.

TABLE 66

PD-1 flow cytometry staining panel

| Antibody/Stain | Clone | Fluorochrome | Manufacturer | Amount (μl/1e6 cells) |
|---|---|---|---|---|
| 7-AAD | N/A | N/A | BD Biosciences | 20 |
| CD3 | UCHT1 | FITC | BD Biosciences | 3 |
| CD4 | OKT4 | PE/Cy | BioLegend | 1 |
| PD-1 | EH12.2H7 | PE | BioLegend | 2.5 |

PD-1 Selection and Gating Strategy

Stained cells were placed on either the FX500 cell sorter (SONY, New-York), or ZE5 Cell Analyzer (BioRad, CA) and analyzed based upon the following gating strategy. First, single cells were identified based on forward and back or side scatter. Next, live cells were gated based on negative/low 7-AAD or live-dead blue fluorescence. TIL were identified using CD3. PD-1 cells were identified using normal donor peripheral blood (ND-PBL) as a control. The selection gate for PD-1 was placed above the baseline of PD-1 expression in ND-PBL. Data analysis was performed using FlowJo v8.1 Software (FlowJo LLC, OR). Results were graphed using GraphPad v8.

Results

PD-1 Expression in Tumor Digests

To identify which histologies were candidates for PD-1 selection, the expression of PD-1 was assessed in multiple tumor samples from several cancer histologies, using flow cytometry. A total of 4 melanoma, 7 NSCLC's, 5 HNSCC's, 3° C.'s, 5 TNBC's, 2 PC's, and 8 CRC's were tested according to the procedure TMP-18-015, abbreviated in section 5.2. The CRC's were composed of both microsatellite stable (MSS) (n=6) and microsatellite instability (MSI) (n=2) tumors. After digestion, a portion of the resulting single cell suspension was stained for PD-1, analyzed by flow, and if >5e6 cells were available, sorted to obtain PD-1+ cells. PD-1-sorted cells were subjected to a two-step process that includes an 11-day activation step followed by an 11-day rapid expansion protocol (REP) to obtain PD-1-selected TIL. Tumor ID, histology, and experimental fate are listed in Table 65. Results of the flow analysis are shown in FIG. 157.

All tumors digests assayed expressed a percentage of PD-1+ cells within the CD3 population. The % PD-1 was variable and ranged from 11% to 78% with an average of 35% across the histologies assayed. Melanoma (n=4) and PC (n=2) yielded the lowest averages for PD-1 expression of 30.1% and 25.8% respectively. The average percentage of PD-1 expression did not correlate with the observed clinical response rates for those histologies. Histologies that respond to anti-PD-1 blockade such as melanoma and NSCLC did not have a higher level/expression of PD-1 than histologies that do not respond to anti-PD-1 blockade (i.e. OC and PC).

A PD-1-selected product could be obtained upon in vitro expansion of the PD-1+ cells in all the instances in which a culture could be initiated (Table 1). Results of this study are reported in document Example 13. Therefore, based upon the expression of PD-1, all the assayed histologies are potential candidates for PD-1 selection.

Conclusions

PD-1 was expressed on the CD3 cells in all assayed tumor digests.

There was extensive intra- and intertumoral variability in PD-1 expression.

PD-1 expression does not correlate with histologies that have demonstrated responsiveness to anti-PD-1 therapy.

EXAMPLE 18 REFERENCE DOCUMENTS

1. Simon, S. and N. Labarriere, *PD-1 expression on tumor-specific T cells: Friend or foe for immunotherapy*? Oncoimmunology, 2017. 7(1): p. e1364828.
2. Simon, S., et al., *PD-1 expression conditions T cell avidity within an antigen-specific repertoire*. Oncoimmunology, 2016. 5(1): p. e1104448.
3. Ahmadzadeh, M., et al., *Tumor antigen-specific CD8 T cells infiltrating the tumor express high levels of PD-1 and are functionally impaired*. Blood, 2009. 114(8): p. 1537-44.
4. Inozume, T., et al., *Selection of CD8+PD-1+ lymphocytes in fresh human melanomas enriches for tumor-reactive T cells*. J Immunother, 2010. 33(9): p. 956-64.
5. Melssen, M. M., et al., *Formation and phenotypic characterization of CD49a, CD49b and CD103 expressing CD8 T cell populations in human metastatic melanoma*. Oncoimmunology, 2018. 7(10): p. e1490855.
6. Lee, J., et al., *Reinvigorating Exhausted T Cells by Blockade of the PD-1 Pathway*. For Immunopathol Dis Therap, 2015. 6(1-2): p. 7-17.
7. Badoual, C., et al., *PD-1-expressing tumor-infiltrating T cells are a favorable prognostic biomarker in HPV-associated head and neck cancer*. Cancer Res, 2013. 73(1): p. 128-38.
8. Thommen, D. S., et al., *A transcriptionally and functionally distinct PD-1(+) CD8(+) T cell pool with predictive potential in non-small-cell lung cancer treated with PD-1 blockade*. Nat Med, 2018.
9. Kansy, B. A., et al., *PD-1 Status in CD8(+) T Cells Associates with Survival and Anti-PD-1 Therapeutic Outcomes in Head and Neck Cancer*. Cancer Res, 2017. 77(22): p. 6353-6364.
10. Gros, A., et al., *PD-1 identifies the patient-specific CD8(+) tumor-reactive repertoire infiltrating human tumors*. J Clin Invest, 2014. 124(5): p. 2246-59.
11. Webb, J. R., K. Milne, and B. H. Nelson, *PD-1 and CD103 Are Widely Coexpressed on Prognostically Favorable Intraepithelial CD8 T Cells in Human Ovarian Cancer*. Cancer Immunol Res, 2015. 3(8): p. 926-35.
12. Columbus, G. *Avelumab Misses Primary Endpoints in Phase III Ovarian Cancer Trial*. 2018; Available from: https://www.onclive.com/web-exclusives/avelumab-misses-primary-endpoints-in-phase-iii-ovarian-cancer-trial.
13. Sarniak, A. *A phase 2, multicenter study to assess the efficacy and safety of autologous tumor-infiltrating lymphocytes (LN-144) for the treatment of patients with metastatic melanoma*. 2018; Available from: https://ascopubs.org/doi/abs/10.1200/JCO.2018.36.15_suppl.TPS9595.

Example 19: Selection of PD-1+ TIL Using Nivolumab by Flow Cytometry Sorting and Expansion in Full-Scale for Clinical Manufacturing Purpose This report describes the results from the expansion of PD-1-selected TIL using Nivolumab for the selection in full-scale manufacturing experiments described in the present Examples.

Scope

The scope of work was to expand PD-1-selected TIL from melanoma or lung or head and neck or ovarian tumors.

On Day 0, tumor digest was equally distributed to two arms, and the tumor digest in each arm of the experiment was stained using either Nivolumab or anti-PD1 Clone #EH12.2H7 (Research grade) as the primary antibody, and FITC-conjugated anti-IgG4 secondary antibody. PD-1 expressing TIL from the stained populations were then selected by flow sorting. Two step expansion process was used to expand PD-1-selected TIL for full scale clinical manufacturing. The first step of expansion ("Activation") was conducted from Day 0 to Day 11. The second step of expansion process ("Rapid Expansion Phase", or "REP", including Split on Day 16) were conducted from Day 11 to Day 22. The final product was harvested on Day 22.

For Small-Scale process (1/100th scale), Activation was initiated on Day 0 using 10% of the PD-1-selected TIL with the lowest sort result, and transferring that number of TIL from each sort into the respective G-Rex-10M flasks with Feeders and OKT-3 with IL-2 media. REP, Split, and Harvest were initiated per TP-19-004. A brief explanation of the associated timepoints is outlined below in the methods section (Table 67).

For Full-Scale process, Activation was initiated on Day 0 using PD-1-selected TIL with the similar cell number, with 100e6 allogeneic feeder cells and 30 ng/ml OKT3 for 11 days. REP was initiated on Day 11 from the harvested product. REP (Day 11) and the subsequent Day 16 (Split) and Day 22 (Harvest) processes were performed per IOVA Manufacturing Batch Records. A brief explanation of the associated timepoints is outlined below in the Experimental design (Table-2).

The expanded final product TIL were assessed for cell growth, viability, phenotype, and function (IFN-γ and Granzyme-B secretion, CD107a mobilization upon stimulation).

Additional analysis was performed on the extended characterization data to establish the equivalence of EH12.2H7 and Nivolumab.

Background Information

A previously developed protocol designed to select PD-1 expressing TIL from tumor digests using PE-conjugated anti-PD-1 antibody (Clone #EH12.2H7) to enrich the TIL product for autologous tumor-reactive T cells is provided in Example 9 and Example 21.

In the current study, Example 9 and Example 21 were adapted to obtain PD1-selected TIL using nivolumab as the anti-PD1 antibody in lieu of the PE-conjugated clone #EH12.2H7, and using FITC-conjugated anti-IgG4 antibody as secondary staining antibody.

Experiment Design

Two small scale experiments and bulk control condition were conducted per TP-19-004.

One full scale experiment was conducted per Example 19.

Overview of Small scale and full scale were provided in Tables 67 and 68.

TABLE 67

Overview of Small-Scale PD-1-selected TIL process in 1/100th scale

| Condition | 1/100th scale |
|---|---|
| Activation (1/10th scale) | Day 0: Activation |
| TIL | 10% of PD-1-selected TIL |
| Feeders | 10e6 |
| CM1 | 100 mL |
| IL-2 | 6000 IU/mL |
| OKT3 (30 ng/mL) | 30 ng/mL |
| G-Rex | 10M |
| REP (1/100th scale) | Day 11: REP |
| TIL | 10% TVC |
| Feeders | 50e6 |
| CM2 | 50 mL |
| IL-2 | 3000 IU/mL |
| OKT3 (30 ng/mL) | 30 ng/mL |
| G-Rex | 5M |
| Split (1/100th scale) | Day 16: Volume reduce and split (TVC/10e6, round up) up to 5 × 5M flasks |
| REP Harvest (1/100th scale) | Day 22: REP Harvest |
| Extrapolation Calculation: | |
| Activation | Multiply Activation Harvest TVC by 10 |
| REP, Split, Harvest | Multiply by REP Harvest by 100 × # of split flasks |

TABLE 68

Overview of Full-Scale PD-1-selected TIL Process

| Conditions | Full Scale |
|---|---|
| Activation | Day 0: Activation |
| TIL | PD-1-selected TIL |
| Feeders | 100e6 |
| CM1 | 1000 mL |
| IL-2 | 6000 IU/mL |
| OKT3 (30 ng/mL) | 30 ng/mL |
| G-Rex | 100 MCS |
| REP | Day 11: REP |
| TIL | 5e6-200e6 TVC |
| Feeders | 5e9 |
| CM2 | 5 L |
| IL-2 | 3000 IU/mL |
| OKT3 (30 ng/mL) | 30 ng/mL |
| G-Rex | 500 MCS |
| Split | Day 16: Split<br>Volume reduce and split up to 5 G-Rex500 MCS in CM4 + 3000 IU/mL of IL-2 |
| REP Harvest | Day 22: Harvest<br>REP Harvest |

Results

Table 69 below specifies the acceptance criteria that was used to evaluate the performance of the small (Extrapolated TVC) and full scale experiment per Example 19.

TABLE 69

In Process and Harvest Product Release Testing and Acceptance Criteria

| Test Type | Method | Acceptance Criterion |
|---|---|---|
| In-Process Testing | | |
| Post-sort Purity (% PD1+) | Flow Cytometry | ≥80% |
| Release Testing | | |
| Appearance | Visual Inspection* | Bag intact, no sign of clumps |
| Cell viability | Fluorescence | ≥70% |
| Total Viable Cell Count | Fluorescence | $1 \times 10^9$ to $150 \times 10^9$ |
| Purity (% CD45+ CD3+) | Flow Cytometry | ≥90% CD45+ CD3+ cells |
| IFNg (Stimulated - Unstimulated) | Bead stimulation and ELISA | ≥500 pg/mL |

*Applicable only to full scale experiment.

Results Achieved

Table 70 below were the lists of tumors used in this study and the associated histologies.

TABLE 70

Tumors Used in this Study

| Experiments | Histology | ID |
|---|---|---|
| PD-1-selected TIL process (intended clinical manufacturing process) | | |
| Small scale 1 | Ovarian | OV8074 |
| Small scale 2 | Melanoma | M1156 |
| Full scale 1 | Head and Neck | H3046 |

Flow Sorting Output

TABLE 71

Pre and post-sort purity of PD-1-selected TIL by Flow Cytometry.

| Parameter | Acceptance Criterion | OV8074 (Nivolumab) | OV8074 (EH12.2.H7) | M1156 (Nivolumab) | M1156 (EH12.2.H7) | H3046 (Nivolumab) | H3046 (EH12.2.H7) |
|---|---|---|---|---|---|---|---|
| Pre-sort % CD3+ (of FSC/BSC, Singlets) | N/A | 66 | 62 | 5 | 5 | 49 | 44 |
| Pre-sort % PD-1+ (of CD3+) | N/A | 80 | 70 | 90 | 93 | 14 | 13 |
| Pre-Sort TVC | N/A | 6.3e6 | 2.6e6 | 1.3e7 | 1.3e7 | 1.6e7 | 1.6e7 |
| TVC Sorted (% Yield) | N/A | 3.5e5 (6%) | 4.1e5 (16%) | 1.1e5 (13%) | 1.1e5 (13%) | 1e5 (9%) | 2.4e5 (23%) |
| Post-sort PD-1$^+$ Enrichment (Fold) | N/A | 1.24 | 1.4 | 1.07 | 1.08 | 6.8 | 7.4 |
| *Post-sort Purity % PD-1$^+$ (of % CD3+) | ≥80% | 99% | 98% | 96% | 100% | 95% | 96% |

*Purity was based on % PD-1+ (gated on FSC/BSC/CD3)

Post sort purity (% PD-1+) for all three tumors met the criterion of >80%.

Activation and REP-Harvest Outputs

Table 72 below summarizes the total viable cell count and product attributes from the two small full scale and one full scale experiments, as well as their bulk counterparts (noted in parentheses).

Process Yield: At the end of Activation, TIL selected using either Nivolumab or EH12 staining yielded cell numbers greater than 100e6 (>1200 fold expansion, with an average of 9.1 cell doublings), with sufficient yield to initiate REP culture.

At REP Harvest, all cultures yielded >80e9 TVC. Average of 9 cell doublings were observed between Day 11 to Day

TABLE 72

Summary of the product attributes from Activation and REP

| Stages | Tumor ID/Condition | Acceptance Criterion | OV8074 Nivolumab staining | OV8074 EH12.2H7 staining | M1156 Nivolumab staining | M1156 EH12.2H7 staining | H3046 Nivolumab staining | H3046 EH12.2H7 staining |
|---|---|---|---|---|---|---|---|---|
| Activation | TVC seeded (Bulk[1]) | N/A | 3.48e5 (3.48e5) | 3.48e5 | 1.05e5 (1.05e5) | 1.05e5 | 1.02e5 (1.02e5) | 1.02e5 |
| | TVC harvested (Bulk[1]) | N/A | 1.03e9 (1.14e9) | 1.71e9 | 2.08e8 (2.19e8) | 1.50e8 | 1.3e8 (1.37e9) | 1.52e8 |
| | Fold expansion[3] (Bulk) | N/A | 2960 (3262) | 4905 | 1975 (2079) | 1427 | 1291 (1334) | 1486 |
| | # Doublings From D 0-D 11[4] | N/A | 12 | 12 | 11 | 10 | 10 | 11 |
| REP | TVC seeded (Bulk[1]) | 5-200e6[2] | 2.00e8 (2.00e8) | 2.00e8 | 2.00e8 (2.00e8) | 1.50e8 | 1.32e8 (2.00e8) | 1.52e8 |
| | TVC harvested (Bulk[1]) | N/A | 114.08e9 (99e9) | 95.94e9 | 86.82e9 (105.00e9) | 84.14e9 | 95.2e9 (80.81e9) | 80.98e9 |
| | % Viability | N/A | 89 | 84 | 97 | 93 | 97 | 97 |
| | Fold expansion[3] (Bulk) | N/A | 570 (495) | 480 | 434 (525) | 559 | 720 | 612 |
| | # Doublings From D 11-D 22[4] | N/A | 9.2 | 8.9 | 8.8 | 9.1 | 9.5 | 9.1 |
| | TVC Post-LOVO (% Recovery) | 1-150e9 | | N/A[5] | | | 88.5e9 (93%)[7] | N/A[6] |
| | % Viability Post-LOVO | >70% | | N/A[5] | | | 85 | N/A[6] |
| | % CD45+/CD3+ | >90% | 99.7 | 99.8 | 99.8 | 99.9 | 99.7 | 99.9 |
| | IfNγ (pg/mL) | ≥500 | 948 | 1547 | 4555 | 4371 | 2795 | 3130 |
| | Granzyme B (pg/mL) | N/A | 9524 | 9777 | 41603 | 68354 | 33147 | 47603 |
| | % CD4+ CD107A (Stimulated) | N/A | 49 | 58 | 34 | 41 | 37 | 38 |
| | % CD8+ CD107A (Stimulated) | N/A | 82 | 84 | 85 | 85 | 66 | 67 |

[1]Bulk condition TVC shown above are extrapolated to full scale is control for Nivolumab and EH12.2H7

[2]Range for 5-200e6 TVC seeded at REP based on current established range for Gen 2 REP process, and is not a formal acceptance criterion in this protocol

[3]Fold expansion = TVC harvested/TVC seeded

[4]Cell doublings was calculated based on the formula "=LOG(Day 22 TVC/Day 11 TVC)/LOG(2)"

[5]Lots were small scale, LOVO was not performed

[6]Single LOVO operation was available. Nivolumab condition was selected for LOVO processing, this represent the clinical manufacturing for PD-1-selected TIL process.

[7]NC-200 cell counter issue was identified during the post-LOVO counting process. Post-thaw recovery count from the stability study (SP-19-003) was used for calculating % Recovery.

22. The number of cell doublings were very similar to the results observed previous preclinical experiments (TP-19-004R and EXAMPLE 21R)

Dose: From the full scale run (H3046), final product dose using Nivolumab staining was 88.5e9 TVC with 85% viability and 99.7% CD45+CD3+ cells. The final product was a highly enriched TIL product.

Function: Functionality of TIL was characterized based on overnight stimulation of final product with αCD3/αCD28/αCD137 Dynabeads (LAB-016). The supernatants were collected after 24 hours of the stimulation and frozen. ELISAs were performed to assay the concentrations of IFNγ and Granzyme B released into the supernatants. IFNγ release met the acceptance criterion, and all the TIL cultures secreted High levels of Granzyme B upon stimulation. Similar to TIL products generated in the prior study (TP-19-004R, EXAMPLE 21),a high fraction of the TIL from final product expressed CD107A when stimulated with PMA/IO (both CD4+ and CD8+ TIL).

TIL Telomere Length and Telomerase Activity: Data is pending. The report will be amended to include this data when it is available.

TIL Clonality: Data is pending. The report will be amended to include this data when it is available.

Extended Phenotyping: Tables 73, 74, 75 describe the Extended Phenotype analysis of TIL. Multicolor flow cytometry was used to characterize TIL Purity, identity, memory subset, activation and exhaustion status of REP TIL. <1% of detectable B-cells, Monocytes or NK cells were present in the final harvested TIL (Table 7). REP TIL were consist of mostly by TCRα/β with primarily effector memory differentiation. CD8/CD4 ratio between Nivolumab and EH12.2H7 comparable except for Ovarian tumor. The skewness of CD8/CD4 ratio may be due to heterogenicity of the Ovarian tumor type and lack of selection marker for CD4 and CD8 in the selection procedure.

TABLE 73

TIL Purity, Identity and Memory phenotypic characterization

| Characteristic | | OV8074 (Nivolumab) | OV8074 (EH12) | M1156 (Nivolumab) | M1156 (EH12) | H3046 (Nivolumab) | H3046 (EH12) |
|---|---|---|---|---|---|---|---|
| Purity | NK cells (CD3− CD56+) (%) | 0.5 | 0.4 | 0.2 | 0.6 | 0.0 | 0.0 |
| | B cells (CD3− CD19+) (%) | 0.0 | 0.0 | 0.0 | 0.0 | 0.0 | 0.0 |
| | Monocytes (CD14+) (%) | 0.5 | 0.5 | 0.9 | 0.8 | 0.8 | 0.9 |
| Identity T cells | TCRα/β (%) | 97.1 | 95.8 | 98.4 | 97.9 | 98.4 | 98.6 |
| | TCRγ/δ (%) | 0.1 | 0.3 | 0.0 | 0.0 | 0.0 | 0.1 |
| | TCRα/β+ CD4+ (%) | 19.0 | 40.7 | 19.7 | 10.0 | 64.7 | 62.0 |
| | TCRα/β+ CD8+ (%) | 80.5 | 57.2 | 79.9 | 89.5 | 34.6 | 37.6 |
| | TCRα/β+ CD8/CD4 ratio | 4.2 | 1.4 | 4.1 | 9.0 | 0.5 | 0.6 |
| Memory Phenotype-TCRα/β+ | Naïve: CCR7+ CD45RA+ (%) | 0.0 | 0.0 | 0.0 | 0.0 | 0.0 | 0.0 |
| | T-EM: CCR7− CD45RA− (%) | 98.4 | 98.2 | 98.6 | 98.2 | 98.4 | 97.1 |
| | T-CM: CCR7+ CD45RA− (%) | 1.4 | 1.8 | 1.4 | 1.7 | 1.6 | 2.8 |
| | T-EFF/TEMRA: CCR7− CD45RA+ (%) | 0.2 | 0.0 | 0.0 | 0.1 | 0.0 | 0.0 |

Note:
Gating Algorithm for TIL Purity is shown below:
Monocytes: % Live, CD14+
NK (Natural Killer) Cells: % Live, CD14−, CD3−, CD56+ CD16+
B Cells: % Live, CD14−, CD3−, CD19+

Due to TCR-stimulated proliferation of TIL, all the PD-1-selected TIL conditions showed upregulation of CD28 expression and downregulation of CD27 expression. In addition, all the PD-1-selected TIL showed less differentiated phenotype with lower KLRG1 expression.

CD27, CD28, CD56, CD57, BTLA, CD25 and CD69 levels were similar to results for Melanoma TIL generated using the Gen 2 manufacturing process (Table 74).

There is no notable difference between Nivolumab and EH12.2H7 selection procedure interms of differentiation, activation and exhaustion status.

TABLE 74

| Activation and Exhaustion status of CD4+ TIL | | | | | | | |
|---|---|---|---|---|---|---|---|
| Characteristic (Gated on Live, CD3+, CD4+) | | OV8074 (Nivolumab) | OV8074 (EH12) | M1156 (Nivolumab) | M1156 (EH12) | H3046 (Nivolumab) | H3046 (EH12) |
| Differentiation | CD27+ (%) | 5.1 | 6.1 | 5.5 | 12.7 | 34.6 | 39.3 |
| | CD28+ (%) | 99.9 | 99.9 | 99.9 | 99.9 | 100.0 | 100.0 |
| | CD57+ (%) | 27.1 | 16.2 | 65.1 | 37.6 | 13.2 | 14.5 |
| | KLRG1+ (%) | 12.0 | 19.9 | 41.9 | 31.5 | 3.4 | 6.6 |
| Activation | 2B4+ (%) | 4.1 | 8.7 | 4.8 | 4.8 | 4.0 | 6.1 |
| | BTLA4+ (%) | 99.4 | 99.7 | 99.8 | 99.7 | 99.9 | 100 |
| | CD25+ (%) | 4.8 | 3.4 | 2.6 | 4.1 | 2.4 | 2.9 |
| | CD69+ (%) | 79.4 | 77.0 | 84.6 | 77.3 | 75.9 | 86.9 |
| | CD95+ (%) | 96.7 | 97.5 | 98.9 | 99.6 | 99.5 | 99.7 |
| | CD103+ (%) | 0.6 | 0.4 | 1.0 | 0.5 | 1.0 | 1.0 |
| Exhaustion | LAG3+ (%) | 1.9 | 3.0 | 2.7 | 1.4 | 1.6 | 0.9 |
| | PD1+ (%) | 11.8 | 12.0 | 16.5 | 24.1 | 16.2 | 13.9 |
| | TIGIT+ (%) | 15.0 | 24.0 | 33.3 | 51.7 | 31.4 | 37.6 |
| | TIM3+ (%) | 11.1 | 20.7 | 36.4 | 26.3 | 18.4 | 19.8 |

TABLE 75

| Activation and Exhaustion status of CD8+ TIL | | | | | | | |
|---|---|---|---|---|---|---|---|
| Characteristic (Gated on Live, CD3+, CD8+) | | OV8074 (Nivolumab) | OV8074 (EH12) | M1156 (Nivolumab) | M1156 (EH12) | H3046 (Nivolumab) | H3046 (EH12) |
| Differentiation | CD27+ (%) | 10.3 | 8.7 | 27.2 | 24.5 | 23.1 | 28.1 |
| | CD28+ (%) | 99.9 | 99.8 | 99.9 | 99.9 | 99.8 | 99.9 |
| | CD57+ (%) | 39 | 17.7 | 52.8 | 38.7 | 15.5 | 11.8 |
| | KLRG1+ (%) | 36.9 | 23.7 | 15.5 | 9.9 | 4.1 | 6.1 |
| Activation | 2B4+ (%) | 3.2 | 3.5 | 2.3 | 2.1 | 4.0 | 4.0 |
| | BTLA4+ (%) | 99.7 | 99.8 | 99.8 | 99.8 | 99.9 | 99.9 |
| | CD25+ (%) | 0.5 | 0.9 | 0.2 | 0.4 | 0.6 | 0.5 |
| | CD69+ (%) | 76.1 | 74.4 | 81.6 | 84.4 | 86.2 | 87.2 |
| | CD95+ (%) | 95.3 | 88.7 | 98.9 | 98.5 | 96.5 | 96.6 |
| | CD103+ (%) | 0.5 | 0.5 | 0.8 | 0.3 | 0.9 | 0.6 |
| Exhaustion | LAG3+ (%) | 0.6 | 1.8 | 1.9 | 0.9 | 1.5 | 0.9 |
| | PD1+ (%) | 12.1 | 4.7 | 11.7 | 14.6 | 7.6 | 10 |
| | TIGIT+ (%) | 51.6 | 42.7 | 78.7 | 85.5 | 17 | 19.8 |
| | TIM3+ (%) | 15.3 | 22.1 | 27.3 | 49.1 | 21 | 16.2 |

TABLE 76

| CD27, CD28, CD56, CD57, BTLA, CD2S and CD69 expression on CD3+ | | | | | | | |
|---|---|---|---|---|---|---|---|
| Characteristic (Gated on Live, CD3+) | Historical values from Melanoma (Range) | OV8074 (Nivolumab) | OV8074 (EH12) | M1156 (Nivolumab) | M1156 (EH12) | H3046 (Nivolumab) | H3046 (EH12) |
| CD27+ (%) | | | | | | | |
| CD28+ (%) | | | | | | | |
| CD56+ (%) | | | | | | | |
| CD57+ (%) | | | | | | | |
| BTLA+ (%) | | | | | | | |
| CD25+ (%) | | | | | | | |
| CD69+ (%) | | | | | | | |

Additional analysis on the phenotypic characterization data to establish the equivalence of EH12.2H7 and Nivolumab.

PD-1-selected TIL generated using EH12.2H7 and nivolumab to obtain PD-1+ TIL were assessed for the expression of CD4, CD8, CCR7, CD45RA, and PD-1 by flow cytometry. No significant differences were observed in expression of CD4 and CD8 in PD-1-selected derived using nivolumab and EH12.2H7. For the three assayed tumors, both TIL products yielded a higher proportion of CD8+ T cells relative to CD4+ T cells (Figure-1). The similarity in CD4 and CD8 expression in the three PD-1-selected TIL products suggests that selecting for PD-1+ using nivolumab did not alter the ratio of CD4/CD8 compared to EH12.2H7. See, FIG. 159.

Like T cell lineage, the memory status of the TIL was similar in the PD-1-selected TIL generated using EH12.2H7 and nivolumab. The TIL populations were composed predominantly of effector memory T cells PD-1-selected TIL generated using nivolumab and EH12.2H7 resemble Iovance's LN-145 investigational product, suggesting that selecting for PD-1 using either anti-PD-1 clone does not skew the memory phenotype of the TIL (FIG. 160).

To assess whether PD-1 expression was similarly reduced upon culture, PD-1-selected TIL generated using nivolumab and EH12.2H7 were assessed pre- and post-expansion. Post-sort, percentages of PD-1+ TIL were close to 100% in both freshly sorted TIL preparations (Table 71). PD-1 expression was significantly and comparably reduced post-expansion in PD-1-selected generated using EH12.2H7 and nivolumab (FIG. 161). As predicted, the reduction in PD-1 expression upon expansion suggests that the previously high PD-1 expressors in the PD-1+ sorted TIL using EH12.2H7 and nivolumab reverted to mostly PD-1− with expansion.

Functional Characterization of PD-1-Selected TIL Generated from EH12.2H7 and Nivolumab-Sorted PD-1+ TIL To assess whether expanded PD-1+ TIL derived using nivolumab were similarly functional to TIL derived using the EH12.2H7 clone, PD-1-selected TIL from 3 tumors were stimulated non-specifically with αCD3/αCD28/α41BB activation beads and evaluated for IFNγ and Granzyme B secretion. Nivolumab and EH12.2H7-derived PD-1-selected TIL produced similar levels of IFNγ and Granzyme B in response to stimulation (FIG. 161). PD-1-selected TIL generated using nivolumab and EH12.2H7 secreted appreciable levels of IFNγ and Granzyme B in response to a non-specific stimulation (αCD3/αCD28/αCD137 beads), suggesting that the selected TIL were highly functional post-expansion.

Information

On Day 0, due to logistic issues fresh tumor could not be received for the example. All the experiments were executed using frozen Tumor digest in lieu of fresh tumor. Data from research study suggest that there is no difference in PD-1 expression when fresh or frozen tumor was tested.

Conclusions and Recommendations

PD-1-selected TIL process was developed at full scale to expand PD-1+ TIL to >80 e9 in 22 days. All six lots (Both Nivolumab and EH12 staining method, 2 full scale and 4 small scale) manufactured at development scale met the acceptance criteria for release parameters.

been selected based on expression of the programmed cell death protein-1 (PD-1) biomarker. Therefore, the TILs were a subset in which the TIL cells with higher expression of PD-1 were selected for ex vivo expansion. The manufacturing process described throughout the examples provides a manufacturing method in which PD-1 positive (PD-1+) T cells are selected from the bulk TIL population using flow cytometry prior to their ex vivo expansion. The resulting TILs have been characterized and activity demonstrated in the ex-vivo studies summarized below. This TILs can be administered to the patient using the TIL regimen for adoptive cell transfer (ACT) as described in the examples and the present application.

The present example summarizes nonclinical data to support a Phase 2 clinical trial that will investigate the safety and preliminary efficacy of TILs in patients with head and neck squamous cell carcinoma (HNSCC). The TIL product is patient-specific and does not function across species, precluding it from being tested in traditional nonclinical pharmacology, pharmacokinetic, and toxicology studies. The nonclinical and clinical safety of the other agents to be included in the TIL treatment regimen (IL-2, cyclophosphamide, and fludarabine) are well characterized.

The nonclinical studies conducted by Iovance to support the clinical investigation of expanded TIL product are listed in Table 78. Reports for these studies are provided in in the Examples above.

TABLE 77

Summary Table:

| Testing Parameters | Acceptance Criterion | OV8074 (Nivolumab) | OV8074 (EH12) | M1156 (Nivolumab) | M1156 (EH12) | H3046 (Nivolumab) | H3046 (EH12) |
|---|---|---|---|---|---|---|---|
| Appearance | Bag intact, no sign of clumps | NA | NA | NA | NA | Pass | Pass |
| Cell viability | ≥70% | Pass | Pass | Pass | Pass | Pass | Pass |
| Total Viable Cell Count | 1 × 10e9 to 150 × 10e9 | Pass | Pass | Pass | Pass | Pass | Pass |
| Identity (% CD45+/CD3+) | >90% CD45+ CD3+ cells | Pass | Pass | Pass | Pass | Pass | Pass |
| IFNγ(Stimulated − Unstimulated) | ≥500 pg/mL | Pass | Pass | Pass | Pass | Pass | Pass |

NA, Not applicable, cells were harvested in small scale

Overall, this Example demonstrated that PD-1-selected TIL generated from PD-1-sorted TIL using nivolumab were comparable to TIL generated using the EH12.2H7 clone, thereby supporting the use of nivolumab for PD-1 selection in the clinical manufacturing. See, also FIGS. 162, 163, and 164.

Example 20: Overview of PD-1 Non-Clinical Studies

Non-Clinical Over View

Introduction

The TILs described in this example were a preparation of autologous tumor-infiltrating lymphocytes (TIL) that have

TABLE 78

List of Nonclinical Studies

| Report Title | Objective | Report No. |
|---|---|---|
| PD-1 expressing cells in Tumor Digests | To assess the prevalence of PD-1$^{+}$ TIL across multiple cancer types. | Example 18 |
| Expansion of PD-1-selected TIL | To demonstrate the feasibility of expanding PD-1-selected TIL to adequate cell numbers, using Iovance's process. | Example 13 |
| Phenotypic Characterization of PD-1-selected TIL | To characterize the phenotype of PD-1 selected TIL. | Example 16 |

TABLE 78-continued

| List of Nonclinical Studies | | |
|---|---|---|
| Report Title | Objective | Report No. |
| Analysis for the TCR repertoire PD-1-selected TIL | To compare the TCR repertoire of PD-1-selected and unselected TIL products. | Example 11 |
| Autologous Tumor-Reactivity in PD-1 selected TIL | To demonstrate the tumor specificity of PD-1-selected TIL. | Example 15 |
| Comparability study of EH12.2H7 antibody and Nivolumab for the selection of PD1$^+$ TIL | To establish equivalence of the research and GMP antibodies for PD-1-selected | Example 19 |

Nonclinical Pharmacology

Selection for PD-1+ TIL in the TIL manufacturing process prior to ex vivo expansion should enrich for neoantigen-specific T cells, while preserving TIL diversity and therefore exhibits the potential to recognize an array of tumor neoantigens. This strategy represents an attractive means to further optimize the TIL manufacturing process use in treatment. Based upon the nonclinical studies summarized below, a manufacturing process has been developed that reliably generates a highly functional PD-1-selected TIL product.

The PD-1-selected TIL product will be examined for the treatment of relapsed/refractory HNSCC, a hard-to-treat malignancy for which studies have been performed with regard to correlations between PD-1+ cell levels and clinical outcome (Badoual et al., 2013).

Nonclinical Studies

The PD-1-selected TIL product has been extensively characterized for its composition and ex-vivo anti-tumor activity. These analyses were preceded by a survey of multiple tumor types for infiltrating PD-1+ T cells and the testing of the expansion process on sorted PD-1+ TIL. All nonclinical studies were performed using a research-grade PD-1-specific monoclonal antibody (clone EH12.2H7) for the detection and selection of PD-1+ TIL. Therefore, a bridging study was conducted to establish comparability of EH12.2H7 with nivolumab, the anti-PD-1 monoclonal antibody that will be used for production of TIL product (See, Example 19). Overall, this work demonstrated that PD-1-selected TIL were prepared from a variety of tumor histologies; that they were phenotypically like unselected TIL; and that they displayed many of the traits associated with neoantigen-specificity, including an initially reduced proliferative capacity and, importantly, tumor-reactivity.

Prevalence of PD-1$^+$ TIL Across Multiple Cancer Types (Report No. Example 18)

The presence of PD-1$^+$ lymphocytes was assessed in multiple tumor samples from several cancer histologies. A total of 34 tumors were evaluated in the following histologies: melanoma (n=4), non-small cell carcinoma (NSCLC) (n=7), head and HNSCC (n=5), OC (n=3), TNBC (n=4), PC (n=2) and CRC (n=8). The specimens of CRC included both microsatellite stable (MSS) tumors (n=6) and tumors with microsatellite instability (MSI) (n=2).

The tumor samples were dissociated using enzymatic digestion, and a portion of the resulting single cell suspension was stained for PD-1 and analyzed by flow cytometry. Results of the flow analysis studies are summarized in FIG. 165.

All tumor digests assayed contained a sizeable fraction of PD-1$^+$ cells within the CD3$^+$ cell population. The percentage of PD-1$^+$ cells was variable and ranged from 11% to 78% with an average of 35% across the histologies assayed. Melanoma (n=4) and PC (n=2) yielded the lowest averages for PD-1 expression, of 27% and 21%, respectively. Histologies that have been shown to respond clinically to anti-PD-1 blockade, such as melanoma and NSCLC, did not have a higher level/expression of PD-1 than the other histologies (i.e. OC and PC).

Importantly, a PD-1-selected product could be obtained upon ex-vivo expansion of the PD-1$^+$ cells in all instances in which there were greater than $2\times10^6$ cells prior to sorting, which was achieved in 12 of 13 tumor samples across the histologies examined. Results of this study are discussed in Example 13. Therefore, based upon the expression of PD-1 by TIL, all assayed histologies are potential candidates for the preparation of TIL prodcut.

Proliferative Capacity of PD-1-Selected TIL (Example 13)

PD-1$^+$ cells have been shown to have impaired cytokine production and reduced proliferation [3,4]. In vivo blockade of PD-1 or its ligand PD-L1 can restore the functionality of those cells to trigger an anti-tumor response (Schmacher et al., 2015, Shang et al, 2018). We tested whether, the observed defects in PD-1$^+$ cells could be reversed by displacing the cells from the immunosuppressive microenvironment and expanding the cells ex-vivo in the presence of anti-CD3 and allogenic feeders, as described in several publications (Inozume et al., 2010; Thommen et al., 2018).

To determine whether PD-1-selected TIL could expand to high numbers ex vivo, PD-1-sorted TIL from 4 melanoma, 7 NSCLC and 2 HNSCC tumor samples were subjected to a process consisting of a two-step protocol consisting of an 11-day Activation step, followed by an 11-day Rapid Expansion Protocol (REP), and evaluated for fold expansion. Matched unselected TIL, expanded in similar conditions from the whole tumor digests, were used as controls.

The proliferative capacity of the PD-1-selected TIL was initially reduced in comparison to unselected TIL, resulting in lower levels of expansion in the Activation step. The average fold expansion for PD-1-selected TIL in the Activation step was 833, as opposed to 2650 for the unselected TIL. However, comparable average fold expansions of 1308 and 1418 were calculated for PD-1-selected TIL and unselected TIL, respectively, in the REP step (FIG. 166).

The delayed expansion in the Activation step in PD-1-selected TIL resulted in a lower total viable cell yield in 9 out of 13 paired samples (Table 79). Since the REP was carried out at small-scale, cell counts achievable at manufacturing scale were estimated based upon the fold expansion in the REP and the total cell yield in the Activation step (i.e. Extrapolated Cell count=REP fold expansion* Activation total viable yield). Of note, these extrapolated numbers likely underestimated the potential total yield, as only a fraction of the cell digest was used for PD-1 sorting.

The extrapolated cell yields for the PD-1-selected TIL ranged between $2.32\times10^7$-$209\times10^9$, with an average cell yield of $47.46\times10^9$ cells. Importantly, 12 of the 13 cultures expanded from PD-1-selected TIL yielded total cell counts following the REP that were within the range specified for the LN-145 investigational product ($1\times10^9$ to $150\times10^9$ total viable cells).

TABLE 79

Final Product Yield in PD-1-selected TIL

| Tumor ID | Sample ID | Histology | # of Seeded Cells | Activation Fold-Expansion | REP Fold-Expansion | Extrapolated Yield (Cell Number × $10^9$) |
|---|---|---|---|---|---|---|
| H3035 | PD-1-selected TIL | HNSCC | 11,000 | 349.63 | 2165.75 | 8.29 |
| | Unselected TIL | | | 868.91 | 1385.80 | 13.2 |
| H3039 | PD-1-selected TIL | HNSCC | 13,500 | 654.44 | 1082.50 | 9.56 |
| | Unselected TIL | | | 122.75 | 893.20 | 1.48 |
| L4089 | PD-1-selected TIL | NSCLC | 8,134 | 1502.92 | 1416.93 | 16.9 |
| | Unselected TIL | | | 2820.88 | 2106.80 | 48.3 |
| L4096 | PD-1-selected TIL | NSCLC | 8,000 | 581.75 | 788.10 | 3.67 |
| | Unselected TIL | | | 1749.00 | 919.20 | 12.9 |
| L4097 | PD-1-selected TIL | NSCLC | 47,000 | 229.51 | 2455.30 | 26.5 |
| | Unselected TIL | | | 1146.81 | 1982.40 | 107 |
| L4100 | PD-1-selected TIL | NSCLC | 33,000 | 536.45 | 996.60 | 17.6 |
| | Unselected TIL | | | 1498.09 | 899.50 | 44.5 |
| L4101 | PD-1-selected TIL | NSCLC | 99,000 | 1346.46 | 895.90 | 209 |
| | Unselected TIL | | | 2196.11 | 962.20 | 119 |
| L4104 | PD-1-selected TIL | NSCLC | 70,000 | 1711.00 | 1256.60 | 151 |
| | Unselected TIL | | | 649.16 | 1421.00 | 64.6 |
| L4106 | PD-1-selected TIL | NSCLC | 18,200 | 1178.57 | 1366.80 | 29.3 |
| | Unselected TIL | | | 4500.00 | 1912.85 | 157 |
| M1132 | PD-1-selected TIL | Melanoma | 2,000 | 49.68 | 233.70 | 0.0232 |
| | Unselected TIL | | | 26705.00 | 1262.95 | 67.5 |
| M1136 | PD-1-selected TIL | Melanoma | 23,500 | 960.77 | 867.20 | 19.6 |
| | Unselected TIL | | | 692.94 | 1190.40 | 19.4 |
| M1139 | PD-1-selected TIL | Melanoma | 10,200 | 556.57 | 1750.53 | 9.94 |
| | Unselected TIL | | | 4907.79 | 1612.50 | 80.7 |
| M1141 | PD-1-selected TIL | Melanoma | 22,400 | 3428.57 | 1514.75 | 116 |
| | Unselected TIL | | | 4950.00 | 2107.00 | 234 |

Legend: PD-1 sorted and unselected TIL from 4 melanoma, 7 NSCLC and 2 HNSCC tumor samples were expanded using a 22-day process consisting of an 11-day activation step, followed by an 11-day REP. Number of $CD3^+$ cells seeded, fold expansion and extrapolated cell counts are shown.

In summary, the reduced proliferative capacity of PD-1+ TIL during the Activation step did not prevent PD-1-selected TIL products from reaching high cell counts in the final product. In fact, 12 of the 13 preparations yielded >$1\times10^9$ total viable cells using the intended expanded TIL product manufacturing process. These yields were well within those specified for the release of the standard LN-145 investigational product.

Phenotypic Characterization of PD-1-Selected TIL (Example 16)

Phenotyping analyses were conducted by flow cytometry to characterize the expression of cell surface markers of T cell lineage and memory subset. In addition, PD-1 levels were assessed in PD-1-selected TIL. The same sample set of 13 matched PD-1-selected and unselected TIL products from 4 melanoma, 7 NSCLC, and 2 HNSCC tumor samples S were stained with a live/dead marker, followed by antibody staining for multiple markers. Results for CD4, CD8, CCR7, CD45RA, and PD-1 are presented in FIGS. 167, 168 and 169. More detailed results, pertaining to additional activation, exhaustion, differentiation, and tissue residence markers can be found in the full report Example 16.

CD4 and CD8 Expression in PD-1-Selected TIL

PD-1 has mostly been characterized in $CD8^+$ T cells despite its expression in both the $CD4^+$ and $CD8^+$ lineages (Ahmadzadeh et al., 2009; Inozume et al., 2010). To determine whether selecting and expanding $PD\text{-}1^+$ cells altered the proportion of $CD4^+$ and $CD8^+$ cells, final PD-1-selected and unselected TIL products were assessed for cell surface expression of CD4 and CD8.

There were no significant differences in the expression of CD4 and CD8 in the PD-1-selected and unselected TIL products (167). The proportions of $CD4^+$ and $CD8^+$ T cells were variable across samples and histologies (Report Example 16, but overall, both TIL products yielded a higher proportion of $CD4^+$ T cells relative to $CD8^+$ T cells.

The similarity in CD4 and CD8 expression across the multiple PD-1-selected and matched unselected TIL products suggests that sorting for PD-1 does not alter the T cell lineage of the final expanded product.

Memory T Cell Populations in PD-1-Selected TIL and Unselected TIL

Published research has demonstrated that PD-1+ TIL are mostly comprised of effector memory T cells (TEM) (Fernandez-Poma et al., 2017; Kansy et al., 2017). Furthermore, these TEMs have been shown to represent the main population of unselected TIL products that demonstrated clinical activity (Gros et al., 2014). T cell memory subsets are typically distinguished using the following markers:

- Effector memory T cells (TEM): CD45RA and $CCR7^-$;
- Central memory T cells (TCM): CD45RA and $CCR7^+$;
- Naïve/Stem-cell memory T cells (TSCM): $CD45RA^+$ and $CCR7^+$; and
- Effector T cells (TEMRA): $CD45RA^+$ and $CCR7^-$ (Golubovskaya and Wu, 2016).

To determine whether the PD-1-selected TIL were comprised mostly of TEM, PD-1-selected and matched unselected TIL products derived from 12 unique tumor samples were evaluated for CD45RA and CCR7 expression to define the individual memory subsets indicated above.

The PD-1-selected and unselected TIL products were composed of similar proportions of the various memory T cell subsets, with TEM cells representing most of the cells within each product (FIG. 168).

Given the similar expression of the phenotypic markers associated with memory, selection of PD-1 prior to expansion does not appear to alter the relative proportions of the memory T cell subsets in the TIL product. Of note, the memory T cells subset profile of PD-1-selected TIL closely resembles that of LN-145.

PD-1 Expression in PD-1-Selected and Unselected TIL

PD-1 expression in expanded PD-1+ TIL has been shown to decrease with ex vivo culture and expansion, which is regarded as a sign of TIL reinvigoration (Inozume et al., 2010; Thommen et al., 2018).

To determine whether PD-1 expression was altered with expansion, PD-1-selected and matched unselected TIL products derived from 12 unique tumor samples were analyzed for the expression of PD-1 prior to and post-expansion.

The percentage of PD-$1^+$ cells in the unselected TIL prior to expansion represents the population of PD-1 expressing cells in whole tumor digests (average of 37.3%). As expected, sorting for PD-$1^+$ cells resulted in a highly pure PD-$1^+$ population, with an average sort purity of 92.8%. Upon expansion, PD-1 expression was significantly reduced in both the PD-1-selected and unselected TIL products relative to PD-1 levels pre-expansion. Greater than 3-fold reduction in the proportion of PD-$1^+$ cells was observed in both PD-1-selected and unselected TIL preparations (FIG. 169).

PD-1-selected and unselected TIL were also assessed for the expression of additional coinhibitory receptors associated with exhaustion. PD-1-selected TIL and unselected TIL expressed similar levels of TIM3, LAG3 and CD101 (Example 16).

The significant reduction in PD-1 expression in TIL that had expressed high levels of PD-1 in situ, suggests that these cells revert to PD-$1^-$ T cells with expansion, and are thus less likely to be suppressed via PD-1/PD-L1 axis upon infusion.

In summary, phenotypic analyses of the PD-1-selected TIL revealed a product composed of mostly TEM cells with low expression of PD-1, suggesting that these cells were reinvigorated upon ex vivo expansion.

TCR Repertoire of PD-1-Selected TIL (Example 11)

A study in NSCLC investigated whether the PD-1-expressing TIL clones designated PD-1T ("tumor associated PD-1", i.e. PD-1 levels that exceeded those observed on PBMCs of healthy donors) were shared with the PD-1-TIL. While some overlap of clones could be observed, the predominant TCRs in the PD-1T TIL were not present in the PD-1' subset (Thommen et al., 2018). The low degree of clonotypic sharing of TCRvβ clones in the PD-1T and PD-1-TIL suggests that the ex-vivo generated products contained TCRs with distinct antigenic specificities.

The PD-1 selection step performed prior to the ex vivo expansion phase of the TIL is expected to result in TIL product enriched for tumor-specific T cells. To determine whether expanding PD-1-sorted TIL generated a distinct product, PD-1-selected and unselected TIL were compared for their TCRvβ composition. To this end, the top 10 TCRvβ clones present in PD-1-selected TIL products were assessed for their representation within the corresponding matching unselected TIL products.

In all paired TIL products, the majority of highly represented PD-1-selected TIL clones were either present at drastically reduced levels, or not detected, in the matched unselected product (FIG. 170).

The PD-1-selected TIL and unselected TIL products contained different high frequency TCRs. Therefore, the two products would be expected to exhibit measurable differences in ex-vivo tests of T cell reactivity.

Overall, our results demonstrate how the PD-1 selection step alters the composition of the expanded TIL product and suggest that the resulting PD-1-selected TIL can be greatly enriched for a specific TCRvβ repertoire that is potentially tumor reactive.

Increased Tumor-Reactivity of PD-1-Selected TIL (Example 15)

Published data in both mouse and human have demonstrated that expression of PD-1 on T cells within the tumor can identify the repertoire of tumor-reactive lymphocytes, including tumor neoantigen-specific lymphocytes (Donia et al., 2017; Fernandez-Poma et al., 2017; Gros et al., 2014; Inozume et al., 2010; Jing et al., 2017; Thommen et al., 2018). In these studies, tumor reactivity of ex vivo expanded purified PD-1+ TIL was tested upon co-culture with autologous tumor cells and PD1+ TIL were shown to secrete significantly greater amounts of IFNγ compared to PD-1-TIL.

Based upon these studies, selecting TIL for expression of PD-1 expression is expected to enrich for tumor/neoantigen-specific T cells, which should demonstrate greater autologous tumor reactivity when assessed ex-vivo.

Tumor Reactivity in PD-1-Selected TIL

To assess TIL tumor reactivity, the release of IFNγ was measured by ELISA upon co-culture with autologous tumor digests.

Of the 10 pairs of PD-1-selected and unselected TIL products assessed (corresponding to 5 of the 13 tumor samples that are the focus of this summary, supplemented with 5 recently obtained samples), 7 produced detectable amounts of IFNγ upon coculture with autologous tumor digests. Three pairs (2 ovarian and 1 TNBC) produced no IFNγ in any condition, upon co-culture. In the 7 evaluable co-cultures, PD-1-selected TIL produced substantially higher levels of IFNγ than their unselected counterparts, 4.57-fold more on average (1.22 to 11.65) (FIG. 171). For 5 of the 7 responding PD-1-selected TIL, this increased reactivity was antigen-specific as demonstrated by a reduction in IFNγ production upon HLA class I blockade. As diagrammed, positive values reflect HLA-specific anti-tumor responses, while null or negative values reflect non-specific responses.

Thus, selection for PD-1-expressing TIL resulted in TIL products enriched for tumor reactive T cells.

The enhanced production of IFNγ in the presence of autologous tumor suggests that PD-1-selected TIL might have a greater potential for anti-tumor effects relative to unselected TIL when administered to patients within the setting of ACT. Clinical efficacy in ACT is directly associated with the presence of tumor-specific TIL. Therefore, enriching for tumor-specific TIL, via PD-1 selection and expansion may enhance the ability of TIL to initiate a potent and effective anti-tumor effect upon administration to patients.

Autologous Tumor Cell Killing

Ten matched PD-1-selected TIL and unselected TIL were assessed for autologous tumor killing. Tumor cell lysis was quantified by an xCELLigence real-time cell analysis assay, which monitors tumor cell detachment as a measurement of tumor cell death (Peper et al., 2014)

Of the 10 tumors evaluated, only 1 melanoma tumor could be evaluated for tumor cytolysis due to poor tumor cell adherence, and low viability. Tumor cell lysis is estimated using a tumor cell index, which is a measurement of the plate impedance as cells attach or detach from it. If at any time during the co-culture the cell index falls below zero, cytolysis cannot be calculated for that sample. In 9 of 10 tumors tested, the cell index dropped below zero, resulting in the inability to appropriately assess tumor cytolysis.

In the evaluable tumor, PD-1-selected TIL exhibited a greater capacity to kill autologous tumor, as determined by a greater drop in the cell index, a parameter that reflects cell proliferation when increasing and cell detachment/death when decreasing, and a higher percentage of cytolysis, compared to unselected TIL (FIG. 172).

The results of this analyses show that PD-1-selected TIL had a greater ability to kill autologous tumor when compared to their unselected counterparts. This result is consistent with published reports of superior anti-tumor activity from both freshly isolated and ex vivo expanded PD-1+ TIL over that of PD-1-TIL (Gros et al., 2014; Inozume et al., 2010). A similar observation was made for PD-1+ TIL isolated from NSCLC, suggesting that the finding is not melanoma-specific (Thommen et al., 2018).

Equivalence of EH12.2H7 and Nivolumab for the selection of PD-1+ TIL (Example 19)

To establish equivalence, PD-1-selected TIL derived from sorting PD-1$^+$ using research (EH12.2H7) and GMP (nivolumab) anti-PD-1 monoclonal antibodies were compared. Three tumor digests (1 ovarian, 1 melanoma, and 1 HNSCC) were stained using either EH12.2H7 or nivolumab to identify the PD-1$^+$ population. Nivolumab and EH12.2H7 sorted PD-1$^+$ cells were expanded using the two-step process that included an 11-day Activation step and an 11-day REP, for a total of 22 days.

Overall, this work demonstrated that PD-1-selected TIL generated from PD-1-sorted TIL using nivolumab were comparable to TIL generated using the EH12.2H7 clone, thereby supporting the use of nivolumab for PD-1 selection in the manufacturing of the expanded TIL product investigational product.

Ex-Vivo Expansion of PD-1-Sorted TIL Using Nivolumab and EH12.2H7

To determine whether PD-1-selected TIL generated using nivolumab and EH12.2H7 proliferated similarly, PD-1-sorted TIL from 1 ovarian, 1 melanoma and 1 HNSCC were subjected to an 11-day Activation step, followed by an 11-day REP and evaluated for yield and expansion.

Tumor digests stained with EH12.2H7 and nivolumab expressed similar levels of CD3$^+$ PD-1$^+$ cells and appeared as undistinguishable dot plots on the flow cytometer (FIG. 172 and Table 79). Fold expansion in the Activation step and REP, and the total extrapolated/actual cell yield was similar when comparing the two TIL populations.

In summary, EH12.2H7 and nivolumab identified similar percentages of PD-1$^+$ cells in tumor digests. TIL fold expansions, and total extrapolated cell counts in the three nivolumab and EH12.2H7 stained tumor samples were comparable.

Phenotypic Characterization of PD-1-Selected TIL Generated Using EH12.2H7 and Nivolumab for PD-1$^+$ Sorting PD-1-selected TIL generated using EH12.2H7 and nivolumab to obtain PD-1+ TIL were assessed for the expression of CD4, CD8, CCR7, CD45RA, and PD-1 by flow cytometry. A more extensive phenotypic assessment can be seen in Example 19.

No significant differences were observed in expression of CD4 and CD8 in PD-1-selected derived using nivolumab and EH12.2H7. For the three assayed tumors, both TIL products yielded a higher proportion of CD8$^+$ T cells relative to CD4$^+$ T cells (FIG. 174).

The similarity in CD4 and CD8 expression in the three PD-1-selected TIL products suggests that selecting for PD-1+ using nivolumab did not alter the ratio of CD4/CD8 compared to EH12.2H7.

Like T cell lineage, the memory status of the TIL was similar in the PD-1-selected TIL generated using EH12.2H7 and nivolumab. The TIL populations were composed predominantly of effector memory T cells (FIG. 175).

PD-1-selected TIL generated using nivolumab and EH12.2H7 resemble the LN-145 investigational product, suggesting that selecting for PD-1 using either anti-PD-1 clone does not skew the memory phenotype of the TIL.

To assess whether PD-1 expression was similarly reduced upon culture, PD-1-selected TIL generated using nivolumab and EH12.2H7 were assessed pre- and post-expansion. Post-sort, percentages of PD-1+ TIL were close to 100% in both freshly sorted TIL preparations (Table 79). PD-1 expression was significantly and comparably reduced post-expansion in PD-1-selected generated using EH12.2H7 and nivolumab (FIG. 176).

As discussed in FIG. 169, the reduction in PD-1 expression upon expansion confirms that the PD-1+ sorted TIL using EH12.2H7 and nivolumab revert to mostly PD-1" with expansion. Functional Characterization of PD-1-selected TIL generated from EH12.2H7 and Nivolumab-sorted PD-1+ TIL To assess whether expanded PD-1+ TIL derived using nivolumab were similarly functional to TIL derived using the EH12.2H7 clone, PD-1-selected TIL from 3 tumors were stimulated non-specifically with αCD3/αCD28/α41BB activation beads and evaluated for IFNγ and Granzyme B secretion.

Nivolumab and EH12.2H7-derived PD-1-selected TIL produced similar levels of IFNγ and Granzyme B in response to stimulation (FIG. 177).

PD-1-selected TIL generated using nivolumab and EH12.2H7 secreted appreciable levels of IFNγ and Granzyme B in response to a non-specific stimulation (αCD3/αCD28/αCD137 beads), suggesting that the selected TIL were highly functional post-expansion.

Conclusions

In summary, PD-1+ TIL were obtained from all 34 tumor specimens tested, which included samples of CRC, NSCLC, HNSCC, TNBC, melanoma, OC, and PC. The percentage of TIL expressing high levels of PD-1 was variable within a given tumor type and did not correlate across the tumor types with known clinical responsiveness to anti-PD-1 therapy.

Importantly, the predicted yield of PD-1-selected TIL following ex vivo expansion was well within the clinical dose range specified for the LN-145 investigational product. Moreover, the phenotype of the expanded PD-1-selected TIL was similar to matched unselected TIL products, as well as phenotype exhibited by LN-145 products, although the PD-1-selected TIL products retained low to moderate levels of PD-1 expression.

Lastly, PD-1 selected TIL products demonstrated superior autologous tumor reactivity and tumor cell killing when compared with matching unselected TIL. This observation is consistent with the dramatic enrichment of the most prevalent TCRvβ sequences found in the PD-1 selected products relative to levels of these sequences in matching unselected TIL products. Enhanced tumor reactivity was expected due to the published studies demonstrating that neoantigen-reactive T cells obtained from tumors express PD-1 (6, 8).

The summarized nonclinical studies for PD-1 selected TIL strongly support clinical development of expanded TIL product for ACT of solid tumors.

REFERENCES FOR EXAMPLE 20

Ahmadzadeh M, Johnson L A, Heemskerk B, Wunderlich J R, Dudley M E, White D E and Rosenberg S A (2009)

Tumor antigen-specific CD8 T cells infiltrating the tumor express high levels of PD-1 and are functionally impaired. *Blood* 114:1537-1544.

Badoual C, Hans S, Merillon N, Van Ryswick C, Ravel P, Benhamouda N, Levionnois E, Nizard M, Si-Mohamed A, Besnier N, Gey A, Rotem-Yehudar R, Pere H, Tran T, Guerin C L, Chauvat A, Dransart E, Alanio C, Albert S, Barry B, Sandoval F, Quintin-Colonna F, Bruneval P, Fridman W H, Lemoine F M, Oudard S, Johannes L, Olive D, Brasnu D and Tartour E (2013) PD-1-expressing tumor-infiltrating T cells are a favorable prognostic biomarker in HPV-associated head and neck cancer. *Cancer Res* 73:128-138.

Barber D L, Wherry E J, Masopust D, Zhu B, Allison J P, Sharpe A H, Freeman G J and Ahmed R (2006) Restoring function in exhausted CD8 T cells during chronic viral infection. *Nature* 439:682-687.

Chikuma S, Terawaki S, Hayashi T, Nabeshima R, Yoshida T, Shibayama S, Okazaki T and Honjo T (2009) PD-1-mediated suppression of IL-2 production induces CD8+ T cell anergy in vivo. *J Immunol* 182:6682-6689.

Donia M, Kjeldsen J W, Andersen R, Westergaard MCW, Bianchi V, Legut M, Attaf M, Szomolay B, Ott S, Dolton G, Lyngaa R, Hadrup S R, Sewell A K and Svane I M (2017) PD-1(+) Polyfunctional T Cells Dominate the Periphery after Tumor-Infiltrating Lymphocyte Therapy for Cancer. *Clin Cancer Res* 23:5779-5788.

Fernandez-Poma S M, Salas-Benito D, Lozano T, Casares N, Riezu-Boj J I, Mancheno U, Elizalde E, Alignani D, Zubeldia N, Otano I, Conde E, Sarobe P, Lasarte J J and Hervas-Stubbs S (2017) Expansion of Tumor-Infiltrating CD8(+) T cells Expressing PD-1 Improves the Efficacy of Adoptive T-cell Therapy. *Cancer Res* 77:3672-3684.

Geukes Foppen M H, Donia M, Svane I M and Haanen J B (2015) Tumor-infiltrating lymphocytes for the treatment of metastatic cancer. *Mol Oncol* 9:1918-1935.

Golubovskaya V and Wu L (2016) Different Subsets of T Cells, Memory, Effector Functions, and CAR-T Immunotherapy. *Cancers* (*Basel*) 8.

Gros A, Robbins P F, Yao X, Li Y F, Turcotte S, Tran E, Wunderlich J R, Mixon A, Farid S, Dudley M E, Hanada K, Almeida J R, Darko S, Douek D C, Yang J C and Rosenberg S A (2014) PD-1 identifies the patient-specific CD8(+) tumor-reactive repertoire infiltrating human tumors. *J Clin Invest* 124:2246-2259.

Inozume T, Hanada K, Wang Q J, Ahmadzadeh M, Wunderlich J R, Rosenberg S A and Yang J C (2010) Selection of CD8+PD-1+ lymphocytes in fresh human melanomas enriches for tumor-reactive T cells. *J Immunother* 33:956-964.

Jing W, Gershan J A, Blitzer G C, Palen K, Weber J, McOlash L, Riese M and Johnson B D (2017) Adoptive cell therapy using PD-1(+) myeloma-reactive T cells eliminates established myeloma in mice. *J Immunother Cancer* 5:51.

Kansy B A, Concha-Benavente F, Srivastava R M, Jie H B, Shayan G, Lei Y, Moskovitz J, Moy J, Li J, Brandau S, Lang S, Schmitt N C, Freeman G J, Gooding W E, Clump D A and Ferris R L (2017) PD-1 Status in CD8(+) T Cells Associates with Survival and Anti-PD-1 Therapeutic Outcomes in Head and Neck Cancer. *Cancer Res* 77:6353-6364.

McGranahan N, Furness A J, Rosenthal R, Ramskov S, Lyngaa R, Saini S K, Jamal-Hanjani M, Wilson G A, Birkbak N J, Hiley C T, Watkins T B, Shafi S, Murugaesu N, Mitter R, Akarca A U, Linares J, Marafioti T, Henry J Y, Van Allen E M, Miao D, Schilling B, Schadendorf D, Garraway L A, Makarov V, Rizvi N A, Snyder A, Hellmann M D, Merghoub T, Wolchok J D, Shukla S A, Wu C J, Peggs K S, Chan T A, Hadrup S R, Quezada S A and Swanton C (2016) Clonal neoantigens elicit T cell immunoreactivity and sensitivity to immune checkpoint blockade. *Science* 351:1463-1469.

Peper J K, Schuster H, Loffler M W, Schmid-Horch B, Rammensee H G and Stevanovic S (2014) An impedance-based cytotoxicity assay for real-time and label-free assessment of T-cell-mediated killing of adherent cells. *J Immunol Methods* 405:192-198.

Schumacher T N and Schreiber R D (2015) Neoantigens in cancer immunotherapy. *Science* 348:69-74.

Shang J, Song Q, Yang Z, Sun X, Xue M, Chen W, Yang J and Wang S (2018) Analysis of PD-1 related immune transcriptional profile in different cancer types. *Cancer Cell Int* 18:218.

Thommen D S, Koelzer V H, Herzig P, Roller A, Trefny M, Dimeloe S, Kiialainen A, Hanhart J, Schill C, Hess C, Savic Prince S, Wiese M, Lardinois D, Ho P C, Klein C, Karanikas V, Mertz K D, Schumacher T N and Zippelius A (2018) A transcriptionally and functionally distinct PD-1(+) CD8(+) T cell pool with predictive potential in non-small-cell lung cancer treated with PD-1 blockade. *Nat Med.*

Example 21: Selection and Expansion of PD-1High for Manufacturing

Introduction

Several studies have demonstrated that surface expression of high levels of PD-1, a marker often associated with T cell exhaustion, identifies the autologous tumor-reactive T cells in the tumor micro-environment (Section 11.10). This example provides a protocol designed to select PD-1 positive (PD-1+) cells from tumor digests to enrich the TIL product for autologous tumor-reactive T cells (Example 15). This protocol was adapted to selectively obtain TIL with high levels of PD-1.

Purpose

The purpose of this example was to develop a process to sort and expand PD-$1^{High}$ TIL for the manufacture of clinical trial material.

Scope

The example provides expanded sorted PD-$1^{High}$ TIL from melanoma, lung, and head and neck tumors using a 2-REP protocol designed for full scale clinical manufacturing.

Three full-scale PD-$1^{High}$ selected Gen 2 process cultures were expanded as described below.

On Day 0, tumor digest was isolated using a GMP digest cocktail containing neutral protease, DNAse I, and collagenase. The digest was washed, stained, and sorted by FACS to purify PD-$1^{High}$ TIL REP-1 was initiated on Day 0 using sorted PD-$1^{High}$ TIL with 100e6 allogeneic feeder cells and 30 ng/ml OKT3 for 11 days.

REP-2 was initiated on Day 11 using harvested REP-1 product. REP-2 (Day 11) and the subsequent Day 16 and Day 22 processes was performed per IOVA Manufacturing Batch Records (reference Section 12 attachments). A brief explanation of the associated timepoints is outlined below.

The expanded TIL were assessed for cell growth, viability, phenotype, Telomere length and function (IFNγ and Granzyme B secretion, CD107a mobilization).

Methods

Materials

Tumor Tissue

Tumors of various histologies will be received from from research alliances and tissue procurement vendors.

Standard reagents for TIL growth which includes: G-Rex 100 MCS, and 500 MCS flasks (Wilson Wolf, Cat #81100-CS, 85500S-CS, respectively); GMP recombinant IL-2 (Cell-Genix, Germany, Cat #1020-1000); All Media reagents for CM1, CM2, and CM4 can be found in Manufacturing Batch Record as seen in attachments 5-7; GlutaMAX 100× (Thermofisher, Cat #35050061); Gentamycin 50 mg/mL (Thermofisher, Cat #15750060)

Flow Cytometry Staining and Analysis Reagents

Flow cytometry antibodies: Anti-PD-1 PE, Clone EH12.2H7, Biolegend, Cat #329906; Anti-CD3 FITC, Clone OKT3, Biolegend, Cat #317306; and Anti-IgG4 Fc-PE, Clone HP6025, Southern Biotech, Cat #9200-09.

Sorting Buffer: HBSS with 2% FBS, 1 mM EDTA, and sterileGemini filtered.

Collection Buffer: HBSS with 50% hAB Serum.

Procedure

Tumor Tissue Preparation

Freshly resected tumor samples will be received from research alliances and tissue procurement vendors. The tumors are shipped overnight in HypoThermosol (Biolife Solutions, Washington, Cat #101104) (with antibiotic).

Took a photo of the tumor in the vial/tube. Remove tumor from packaging and wash 3× for 2 minutes per wash in Tumor Wash Buffer (Filtered HBSS with 50 μg/mL Gentamycin).

Fragmented the entire tumor into 4-6-mm fragments in preparation for tumor digest. Keep 6-mm fragments in a well of a 6-well plate containing 10 mL of Tumor Wash Buffer.

Enzyme Preparation for Tumor Digestion

Tumor was digested using GMP Collagenase and Neutral Protease as described below.

Reconstituted the lyophilized enzymes in the amount of sterile HBSS indicated for each of the digestion enzymes below. Be sure to capture any residual powder from the sides of the bottles and from the protective foil on the bottles opening. Pipetted up and down several times and swirl to ensure complete reconstitution.

Reconstituted the Collagenase AF-1 (Nordmark, Sweden, N0003554) in 10 ml of sterile HBSS. The lyophilized stock enzyme is at a concentration of 2892 PZ U/vial. Therefore, after reconstitution the collagenase stock was 289.2 PZ U/ml. Note, the stock of enzymes can change so verify the concentration of the lyophilized stock and amend the final amount of enzyme added to the digest cocktail accordingly. Aliquotted into 100 μL aliquots and store at −20° C.

Reconstituted the Neutral protease (Nordmark, Sweden, N0003553) in 1 ml of sterile HBSS. The lyophilized stock enzyme was at a concentration of 175 DMC U/vial. Therefore, after reconstitution the neutral protease stock was 175 DMC/ml. Note, the stock of enzymes can change so verify the concentration of the lyophilized stock and amend the final amount of enzyme added to the digest cocktail accordingly. Aliquotted into 20 μL aliquots and store at −20° C.

Reconstituted the DNAse I (Roche, Switzerland, 03724751) in 1 ml of sterile HBSS. The lyophilized stock enzyme is at a concentration of 4 KU/vial. Threfore, after reconstitution the DNAse stock is 4 KU/ml. Note, the stock of enzymes can change so verify the concentration of the lyophilized stock and amend the final amount of enzyme added to the digest cocktail accordingly. Aliquot into 250 μL aliquots and store at −20° C.

Thawed 3 components of GMP digest cocktail and prepare the working GMP digest cocktail as follows: Add 10.2 μl of the neutral protease (0.36 DMC U/ml), 21.3 μl of collagenase AF-1 (1.2 PZ/ml) and 250 μl of DNAse I (200 U/ml) to 4.7 ml of sterile HBSS. Place the digest cocktail directly into the C-tube.

Tumor Processing and Digestion

To the GentleMACS OctoDissociator, transferred up to 4-6 mm tumor fragments to each GentleMACS C-Tube (C-tube) in the 5 ml of digest cocktail indicated above. Used additional GentleMACS C-Tube for additional tumor fragments.

Transferred each C-tube to the GentleMACS OctoDissociator. Digest by setting the dissociator to the appropriate program for the respective tumor histology listed below in Table 80. The dissociation will be approximately one hour.

TABLE 80

Miltenyi OctoDissociator Programs Based on Tumor Tissue Type.

| Tumor Tissue Type | Designation | Program |
|---|---|---|
| Melanoma, Ovarian, Colon, Hypopharyngeal, and Renal | Soft | 37C_h_TDK_1 |
| Lung and Prostate | Medium | 37C_h_TDK_2 |
| Breast, Pancreatic, Hepatocellular, Head and Neck Squamous Cell (HNSCC) | Tough | 37C_h_TDK_3 |

Post-digest, removed the C-tube(s) from the Octodissociator or rotator and place into the BSC. Removed the digest from each C-tube with a 25-mL serological pipette and pass the bulk digest through a 70-μm cell strainer into a 50-mL conical tube. Undigested parts of the tumor may not pass through the strainer, do not allow the digest to splash up due to pressure from the pipettor. Washed the C-tube(s) with an additional 10 mL of HBSS and pass the wash through the cell strainer. QS the 50-mL conical to 50 mL with HBSS.

Centrifuged the digest at 400×G for 5 minutes at RT (full acceleration & full brake).

Transferred Conical to BSC and aspirate or decant supernatant. Resuspend pellet in 5 mL of warm CM-1+6000 IU/mL IL-2 and pipette up and down 5-6 times. Perform 2 cell counts on NC-200 at no dilution per WRK LAB-056

Placed 1 mL of digest aside for CD3+ Bulk control and cryopreserve 2×500 μL aliquots of digest for tumor reactivity assays. Keep digest on ice.

Staining Digested Tumor for Flow Cytometry Analysis and Cell Sorting

Set aside a small sample (~1e5 cells) for the PE and FITC single color compensation control into 15-mL conical tubes.

The remaining tumor digest was stained with a cocktail that includes anti-PD-1-PE, anti-IgG4 Fc-PE (secondary antibody for Nivolumab and Pembrolizumab) and anti-CD3-FITC according to the following protocol. The PE single color compensation control is stained with anti-PD-1-PE plus the IgG4 secondary, and the FITC color compensation control is stained with anti-CD3-FITC only.

After cell counting, add 10 mL of HBSS to digest and centrifuged at 400×G for 5 minutes at RT (full acceleration & full brake).

Transferred conical to BSC and decant supernatant. Use a micropipettor to obtain the volume of digest remaining after decanting. Add 3× this volume of Sorting Buffer to the tube.

i.e. If the obtained volume is 150 μL, add 450 μL Sorting buffer, for a total volume of 600 μL.

Added 3 μl of anti-CD3-FITC per 100 μL (i.e. if volume is 600 μL, add 6×3=18 μL of antibody). (Add to both Samples).

Added 2.5 μl anti-PD-1-PE per 100 μL (i.e. If volume is 600 μL, add 6 ×2.5 =15.0 μL of antibody). (Do not add to FMO).

Added anti-IgG4-Fc-PE in a 1:500 dilution (i.e. For every 500 μL of volume, add 1 μL of antibody).

Mixed digest gently with a 1-mL micropipettor and incubate cells on ice for 30 minutes. Protected from light during incubation. Agitated by flicking gently every 10 minutes during incubation to ensure thorough staining.

Resuspended the fully stained cells in 10 mL of Sorting Buffer, add 10 mL Sorting Buffer to the FMO.

Passed the fully stained solution through a 30-μm cell strainer into a 15-mL conical tube, Pass the FMO through a 30-μm cell strainer into a 15-mL conical as well.

Centrifuged at 400×G for 5 min at RT (full acceleration and full brake).

Resuspended cells in up to 10e6/mL total cells (live and dead) in Sorting Buffer. Minimum volume is 300 μl.

Transferred to 15-mL conical tubes. Store the tubes on ice, covered with aluminium foil until further use.

Prepared 15-mL collection tubes for the sorted populations. Place 2 mL of

Collection buffer (D-PBS with 2% hAB Serum) in the tubes. Store the collection tubes on ice until further use.

Cell Counting and Viability Assessment

Used the procedures for obtaining cell and viability counts, using the Chemometec NC-200 Cell Counter FACS Sorting (FX500 Startup)

Turned on BSC. Turned on JUN-AIR vacuum pump. Turned on FX500 by pressing the Power/Standby button on the front of the instrument. Opened Cell Sorter Software by double clicking the icon on the desktop, logged in and ran program.

Running Automatic Calibration

When prompted to load calibration beads, added 15 drops of the Automatic Setup Beads to a 5-mL, sterile FACS tube. Then follow prompts. When prompted for to select settings for Auto Calibration, selected the "Standard" radio button. While waiting for the calibration to complete prepare the following: prepared five sterile 15-mL conical tubes with 10 mL of sterile D.I. water; prepared five sterile 5-mL FACS tubes with 4 mL of sterile D.I. water; prepared five sterile 15-mL conical tubes with 12 mL of 70% EtOH; and prepared five sterile 15-mL conical tubes with 12 mL of 10% Sodium Hypochlorite.

Sample Collection

Verified that the sample and collection chambers are at 5° C. and that the agitate sample icon is selected. Clicked on the Cytometer tab at the top of the screen. Clicked on the Collection 5° C. icon as well as the Sample 5° C. icon. Clicked on the Agitate icon.

Verified that the samples are compensated. Clicked on the Compensation tab at the top of the screen. The Compensation icon should be a light blue color. Placed the tube containing the PBMC control (either a 5-mL FACS tube or a 15-mL conical) on the sample collection platform. Set the sample collection pressure to 6. Clicked play to begin sample collection. Clicked on the Gates and Statistics table so the following is displayed at the top of the screen.

Selected 100,000 for both drop-down menus seen above. Verified that the cell populations are gated correctly. See example below. It could have been necessary to adjust the BSC or FSC settings. Do not adjust the voltages for any other channels. Did not adjust the PD-1 gate. Recorded as many events as possible (or 20,000 CD3 events maximum). You may set the sample pressure to 10 to speed up this collection. Stopped the collection and remove the tube. Loaded a 15-mL conical tube of sterile dH20 made previously onto the sample platform. Selected 10 for the sample pressure. Clicked the Run icon. Collected the sample for one minute. Clicked the Restart icon. Repeated until the CD3 gate is empty of events. Removed the dH20 sample tube and discard. Added the sample to be collected onto the loading platform Verified that the settings are as shown in the diagram below:

Opened the Sample Chamber door and loaded the 15-mL collection chamber block to the chamber. Loaded the collection tubes containing the collection buffer into the chamber block. Inverted the capped tubes several times to coat the top of the tube with collection buffer. Tapped the tubes on the surface of the BSC to remove excess buffer from the top of the tube and cap. Labeled one tube with the sample name and a plus symbol. Removed cap and place this one into the left chamber. Labeled the second tube with the sample name and a negative symbol. Remove cap and place this one into the right chamber.

Clicked the Load Collection icon seen in the diagram above. Selected 4 for the sample pressure. Clicked the Run icon. Waited for the cells to appear on screen. About 15 seconds. Adjusted the sample pressure so the total events per second are below 5,000. Clicked the start sort icon. Adjust the sample pressure to maintain a sorting efficiency of at least 85%. Recorded 50,000 CD3 events. See diagram below. The recording will stop automatically. Clicked the OK button when the dialog box appears.

In the event that there are over $4.5\times10^6$ cells collected in either fraction, the collection tube(s) will need to be changed. Clicked the stop sort icon. Clicked the Pause icon. Opened the collection chamber door and exchanged the original collection tubes for new collection tubes; close the door and place the original collection tubes on ice. Clicked the Next Tube icon. Clicked the Load Collection icon. Clicked the Play icon. Clicked the Start Sort icon.

Continued sorting until all the sample is gone from the sample tube. It was okay if the tube runs "dry." Removed the Sample tube from the sample chamber. Discard. Removed the sorted fractions from the collection chamber. Capped the tubes and invert gently several times to incorporate the droplets near the top of the tube into the solution. Tapped the tubes gently on the surface of the BSC to remove excess solution from the top of the tube and the cap. Placed the tubes on ice. Verified the selectivity percentages of the PD-1 fractions. Placed a 14-mL conical tube of EtOH onto the sample chamber. Clicked the Probe Wash icon. Repeated. Removed the EtOH tube and add the positive fraction tube. Changed the sample pressure value to 7. Clicked the next tube icon. Named the tube with the sample name and "pos select." Clicked play and record 75 CD3 positive events. Immediately stopped the tube and unload it from the sample chamber. Repeated steps for the negative selection sample.

Exported the Data. Selected the PD-1 FMO tube by double clicking on it. Selected File/Print. Print to PDF format instead of a printer. This will provide a complete 6-page report of the sample. Repeated for each of the tubes collected. Shut instrument down.

PD-1$^{High}$ Rapid Expansion Protocol

Day 0—REP1

Media Preparation: Prepared or warm 1 L of CM-1+6000 IU/mL IL-2.

PBMC Feeder Cell Preparation: Thawed an appropriate number of vials for REP-1 (100e6 PBMC were needed for the full scale, and 10e6 will be needed for the Bulk CD3+ Control, assume 60e6-80e6 PBMC per 1 mL vial). Placed 40 mL of warm CM1+IL-2 in a 50 mL conical and pipetted the 1 mL PBMC feeder vials into the conical. Pipetted the thawed PBMC feeders up and down to thoroughly mix and perform 2 cell counts on the NC-200.

Calculated appropriate volume to transfer to the G-Rex 100M and G-Rex 10M to transfer 100e6 and 10e6 PBMC respectively.

Added 30 μL of αCD3 (OKT-3) to the G-Rex 100M and 3 μL into the G-rex 10M. Place flasks into the incubator Seeding TIL for REP-1

Placed all of the PD-1 High sort into the G-Rex 100M. The CD3+ bulk TIL control condition will add an equivalent number of CD3+ cells to PD-$1^{High}$ cells in the full scale at a 1/10 ratio. To obtain the proper volume of digest, follow the steps: 1) Calculated the CD3+ TVC/mL in the digest by multiplying the digest TVC obtained in step 9.3.5 by the % CD3+ of live cells obtained from the sort report. (i.e. 10e6*10%=1e6), 2) After obtaining this number, divided the number of PD-1 High cells seeded into the full scale condition by this number. (i.e. 1e5/1e6=0.1 mL), and 3) Added this volume (0.1 mL) of digest to the bulk CD3+ TIL flask and fill to 100 mL with CM1+IL-2. Placed all flasks into 37° C., 5% $CO_2$ incubator.

Day 11, Day 16, Day 22

The full scale processe wase followed. The Bulk CD3+ TIL condition were processed similarly to the steps described in Example 9.

Acceptance Criteria

Table 81 below specifies the acceptance criteria that will be used to evaluate the performance of the three full scale lots.

TABLE 81

| Harvest Product Testing and Acceptance Criteria | | |
|---|---|---|
| Test Type | Method | Acceptance Criterion |
| In-Process Testing | | |
| Post-sort Purity (% PD1+) | Flow Cytometry | ≥80% |
| Release Testing | | |
| Appearance | Visual Inspection | Bag intact, no sign of clumps |
| Cell viability | Fluorescence | ≥70% |
| Total Viable Cell Count | Fluorescence | $1 \times 10^9$ to $150 \times 10^9$ |
| Identity (% CD45+ CD3+) | Flow Cytometry | ≥90% CD45+ CD3+ cells |
| IFNg (Stimulated - Unstimulated) | Bead stimulation and ELISA | ≥500 pg/mL |

Table 82 below specifies the additional final product characterization testing performed for information only.

TABLE 82

| Final Product Characterization (for information only) | | |
|---|---|---|
| Test Type | Method | Report Results |
| Purity and Memory T cell subset Phenotype | Flow Cytometry (LAB-055) | Report results |
| Activation and Exhaustion marker Phenotype | Flow Cytometry (LAB-061) | Report results |
| Telomere length | Flow FISH (Attachment -1) | Report results |
| Granzyme B | Bead stimulation and ELISA (LAB-064) | Report results |
| CD107A | Mitogen stimulation and flow cytometry (LAB-061) | Report results |
| TCR Vbeta Sequencing | Deep sequencing (Irepertoire, Inc) | Report results (if available) |
| Metabolite analysis | Cedex Biochemical analyzer | Report results |

REFERENCE DOCUMENTS FOR EXAMPLE 21

Rosenberg, S. A., et al., Durable complete responses in heavily pretreated patients with metastatic melanoma using T-cell transfer immunotherapy. Clin Cancer Res, 2011. 17 (13): p. 4550-7

Kvistborg, P., et al., TIL therapy broadens the tumor-reactive CD8(+) T cell compartment in melanoma patients. Oncoimmunology, 2012. 1 (4): p. 409-418

Simoni, Y., et al., Bystander CD8(+) T cells are abundant and phenotypically distinct in human tumour infiltrates. Nature, 2018. 557 (7706): p. 575-579

Schumacher, T. N. and R. D. Schreiber, Neoantigens in cancer immunotherapy. Science, 2015. 348 (6230): p. 69-74

Turcotte, S., et al., Phenotype and function of T cells infiltrating visceral metastases from gastrointestinal cancers and melanoma: implications for adoptive cell transfer therapy. J Immunol, 2013. 191 (5): p. 2217-25

Inozume, T., et al., Selection of CD8+PD-1+ lymphocytes in fresh human melanomas enriches for tumor-reactive T cells. J Immunother, 2010. 33 (9): p. 956-64.

Gros, A., et al., PD-1 identifies the patient-specific CD8(+) tumor-reactive repertoire infiltrating human tumors. J Clin Invest, 2014. 124 (5): p. 2246-59.

Thommen, D. S., et al., A transcriptionally and functionally distinct PD-1(+) CD8(+) T cell pool with predictive potential in non-small-cell lung cancer treated with PD-1 blockade. Nat Med, 2018.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method for expanding tumor infiltrating lymphocytes (TILs) into a therapeutic population of TILs comprising:

a) obtaining and/or receiving a first population of TILs from a tumor resected from a subject by processing a tumor sample obtained from the subject into multiple tumor fragments;

b) selecting PD-1 positive TILs from the first population of TILs in step (a) to obtain a PD-1 enriched TIL population;

c) performing a priming first expansion by culturing the PD-1 enriched TIL population in a cell culture medium comprising IL-2, OKT-3, and optionally comprising antigen presenting cells (APCs), to produce a second population of TILs, wherein the priming first expansion is performed for a first period of about 11 days to obtain the second population of TILs, wherein the second population of TILs is greater in number than the first population of TILs;

d) performing a rapid second expansion by contacting the second population of TILs with a cell culture medium comprising IL-2, OKT-3, and APCs, to produce a third population of TILs, wherein the rapid second expansion is performed for a second period of about 11 days to obtain the third population of TILs, wherein the third population of TILs is a therapeutic population of TILs; and e) harvesting the therapeutic population of TILs obtained from step (d).

2. The method of claim 1, wherein in step (c) the cell culture medium further comprises antigen-presenting cells (APCs), and wherein the number of APCs in the culture medium in step (d) is greater than or equal to the number of APCs in the culture medium in step (c).

3. A method for expanding tumor infiltrating lymphocytes (TILs) into a therapeutic population of TILs comprising:

(a) performing a priming first expansion of TILs which have been selected to be PD-1 positive by culturing a first population of TILs in a cell culture medium comprising IL-2, OKT-3, and optionally comprising antigen presenting cells (APCs), to produce a second population of TILs, wherein the priming first expansion is performed for a first period of about 11 days to obtain the second population of TILs, wherein the second population of TILs is greater in number than the first population of TILs;

(b) performing a rapid second expansion by contacting the second population of TILs with a cell culture medium comprising IL-2, OKT-3, and APCs, to produce a third population of TILs, wherein the rapid second expansion is performed for a second period of about 11 days to obtain the third population of TILs, wherein the third population of TILs is a therapeutic population of TILs; and (c) harvesting the therapeutic population of TILs obtained from step (b).

4. The method of claim 1, wherein the method comprises performing, after the step of harvesting the therapeutic population of TILs, the additional step of:

transferring the harvested therapeutic population of TILs to an infusion bag.

5. The method of claim 1, wherein in the step of the priming first expansion the priming first expansion is performed in a first container comprising a first gas-permeable surface area and in the step of the rapid second expansion the rapid second expansion is performed in a second container comprising a second gas-permeable surface area, wherein optionally the second container is larger than the first container.

6. The method of claim 5, wherein in the step of the rapid second expansion the APCs are layered onto the second gas-permeable surface area at an average thickness of about 3 cell layers to about 5 cell layers, about 3.5 cell layers to about 4.5 cell layers, or about 4 cell layers.

7. The method of claim 1, wherein for each container in which the priming first expansion is performed on a first population of TILs the rapid second expansion is performed in the same container on the second population of TILs produced from such first population of TILs, wherein optionally each container comprises a first gas-permeable surface area, optionally wherein in the step of the priming first expansion the cell culture medium comprises antigen-presenting cells (APCs) and the APCs are layered onto the first gas-permeable surface area at an average thickness of from about one cell layer to about three cell layers, from about 1.5 cell layers to about 2.5 cell layers or about 2 cell layers.

8. The method of claim 6, wherein in the step of the rapid second expansion the APCs are layered onto the first gas-permeable surface area at an average thickness of about 3 cell layers to about 5 cell layers, about 3.5 cell layers to about 4.5 cell layers or about 4 cell layers.

9. The method of claim 1, wherein for each container in which the priming first expansion is performed on a first population of TILs in the step of the priming first expansion a first container comprises a first gas-permeable surface area, the cell culture medium comprises antigen-presenting cells (APCs), and the APCs are layered onto the first gas-permeable surface area, and wherein the ratio of the average number of layers of APCs layered in the step of the priming first expansion to the average number of layers of APCs layered in the step of the rapid second expansion is selected from the range of about 1:1.1 to about 1:10, about 1:1.2 to about 1:8, about 1:1.3 to about 1:7, about 1:1.4 to about 1:6, about 1:1.5 to about 1:5, about 1:1.6 to about 1:4, about 1:1.7 to about 1:3.5, about 1:1.8 to about 1:3 or about 1:1.9 to about 1:2.5, wherein optionally the ratio of the average number of layers of APCs layered in the step of the priming first expansion to the average number of layers of APCs layered in the step of the rapid second expansion is about 1:2.

* * * * *

```
                             SEQUENCE LISTING


<160> NUMBER OF SEQ ID NOS: 196

<210> SEQ ID NO 1
<211> LENGTH: 450
<212> TYPE: PRT
<213> ORGANISM: Artificial Sequence
<220> FEATURE:
<223> OTHER INFORMATION: Muromonab heavy chain

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Gly Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 2
<211> LENGTH: 213
<212> TYPE: PRT
<213> ORGANISM: Artificial Sequence
<220> FEATURE:
<223> OTHER INFORMATION: Muromonab light chain

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 3
<211> LENGTH: 134
<212> TYPE: PRT
<213> ORGANISM: Artificial Sequence
<220> FEATURE:
<223> OTHER INFORMATION: recombinant human IL-2 (rhIL-2)

<400> SEQUENCE: 3

```
Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130
```

<210> SEQ ID NO 4
<211> LENGTH: 132
<212> TYPE: PRT
<213> ORGANISM: Artificial Sequence
<220> FEATURE:
<223> OTHER INFORMATION: Aldesleukin

<400> SEQUENCE: 4

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 5
<211> LENGTH: 130
<212> TYPE: PRT
<213> ORGANISM: Artificial Sequence
<220> FEATURE:
<223> OTHER INFORMATION: recombinant human IL-4 (rhIL-4)

<400> SEQUENCE: 5

```
Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
    130
```

<210> SEQ ID NO 6
<211> LENGTH: 153
<212> TYPE: PRT
<213> ORGANISM: Artificial Sequence
<220> FEATURE:
<223> OTHER INFORMATION: recombinant human IL-7 (rhIL-7)

<400> SEQUENCE: 6

```
Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150
```

<210> SEQ ID NO 7
<211> LENGTH: 115
<212> TYPE: PRT
<213> ORGANISM: Artificial Sequence
<220> FEATURE:
<223> OTHER INFORMATION: recombinant human IL-15 (rhIL-15)

<400> SEQUENCE: 7

```
Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115
```

<210> SEQ ID NO 8
<211> LENGTH: 132
<212> TYPE: PRT
<213> ORGANISM: Artificial Sequence
<220> FEATURE:
<223> OTHER INFORMATION: recombinant human IL-21 (rhIL-21)

<400> SEQUENCE: 8

```
Met Gln Asp Arg His Met Ile Arg Met Arg Gln Leu Ile Asp Ile Val
1               5                   10                  15

Asp Gln Leu Lys Asn Tyr Val Asn Asp Leu Val Pro Glu Phe Leu Pro
            20                  25                  30

Ala Pro Glu Asp Val Glu Thr Asn Cys Glu Trp Ser Ala Phe Ser Cys
        35                  40                  45

Phe Gln Lys Ala Gln Leu Lys Ser Ala Asn Thr Gly Asn Asn Glu Arg
    50                  55                  60

Ile Ile Asn Val Ser Ile Lys Lys Leu Lys Arg Lys Pro Pro Ser Thr
65                  70                  75                  80

Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
        115                 120                 125

Ser Glu Asp Ser
    130
```

<210> SEQ ID NO 9
<211> LENGTH: 255
<212> TYPE: PRT
<213> ORGANISM: Artificial Sequence
<220> FEATURE:
<223> OTHER INFORMATION: human 4-1BB, Tumor necrosis factor receptor
      superfamily, member 9 (Homo sapiens)

<400> SEQUENCE: 9

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
```

```
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 10
<211> LENGTH: 256
<212> TYPE: PRT
<213> ORGANISM: Artificial Sequence
<220> FEATURE:
<223> OTHER INFORMATION: murine 4-1BB, Tumor necrosis factor receptor superfamily, member 9 (Mus musculus)

<400> SEQUENCE: 10

```
Met Gly Asn Asn Cys Tyr Asn Val Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
        35                  40                  45

Pro Ser Thr Phe Ser Ser Ile Gly Gly Gln Pro Asn Cys Asn Ile Cys
    50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125
```

Gly Thr Gly Val Cys Arg Pro Trp Thr Asn Cys Ser Leu Asp Gly Arg
130 135 140

Ser Val Leu Lys Thr Gly Thr Thr Glu Lys Asp Val Val Cys Gly Pro
145 150 155 160

Pro Val Val Ser Phe Ser Pro Ser Thr Thr Ile Ser Val Thr Pro Glu
165 170 175

Gly Gly Pro Gly Gly His Ser Leu Gln Val Leu Thr Leu Phe Leu Ala
180 185 190

Leu Thr Ser Ala Leu Leu Leu Ala Leu Ile Phe Ile Thr Leu Leu Phe
195 200 205

Ser Val Leu Lys Trp Ile Arg Lys Lys Phe Pro His Ile Phe Lys Gln
210 215 220

Pro Phe Lys Lys Thr Thr Gly Ala Ala Gln Glu Glu Asp Ala Cys Ser
225 230 235 240

Cys Arg Cys Pro Gln Glu Glu Glu Gly Gly Gly Gly Gly Tyr Glu Leu
245 250 255

<210> SEQ ID NO 11
<211> LENGTH: 441
<212> TYPE: PRT
<213> ORGANISM: Artificial Sequence
<220> FEATURE:
<223> OTHER INFORMATION: heavy chain for utomilumab

<400> SEQUENCE: 11

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Ser Phe Ser Thr Tyr
20 25 30

Trp Ile Ser Trp Val Arg Gln Met Pro Gly Lys Gly Leu Glu Trp Met
35 40 45

Gly Lys Ile Tyr Pro Gly Asp Ser Tyr Thr Asn Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Gly Tyr Gly Ile Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Cys Ser Arg Ser Thr Ser Glu Ser Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Asn Phe
180 185 190

Gly Thr Gln Thr Tyr Thr Cys Asn Val Asp His Lys Pro Ser Asn Thr
195 200 205

Lys Val Asp Lys Thr Val Glu Arg Lys Cys Cys Val Glu Cys Pro Pro
210 215 220

Cys Pro Ala Pro Pro Val Ala Gly Pro Ser Val Phe Leu Phe Pro Pro
225 230 235 240

Lys Pro Lys Asp Thr Leu Met Ile Ser Arg Thr Pro Glu Val Thr Cys
245 250 255

Val Val Val Asp Val Ser His Glu Asp Pro Glu Val Gln Phe Asn Trp
260 265 270

Tyr Val Asp Gly Val Glu Val His Asn Ala Lys Thr Lys Pro Arg Glu
275 280 285

Glu Gln Phe Asn Ser Thr Phe Arg Val Val Ser Val Leu Thr Val Val
290 295 300

His Gln Asp Trp Leu Asn Gly Lys Glu Tyr Lys Cys Lys Val Ser Asn
305 310 315 320

Lys Gly Leu Pro Ala Pro Ile Glu Lys Thr Ile Ser Lys Thr Lys Gly
325 330 335

Gln Pro Arg Glu Pro Gln Val Tyr Thr Leu Pro Pro Ser Arg Glu Glu
340 345 350

Met Thr Lys Asn Gln Val Ser Leu Thr Cys Leu Val Lys Gly Phe Tyr
355 360 365

Pro Ser Asp Ile Ala Val Glu Trp Glu Ser Asn Gly Gln Pro Glu Asn
370 375 380

Asn Tyr Lys Thr Thr Pro Pro Met Leu Asp Ser Asp Gly Ser Phe Phe
385 390 395 400

Leu Tyr Ser Lys Leu Thr Val Asp Lys Ser Arg Trp Gln Gln Gly Asn
405 410 415

Val Phe Ser Cys Ser Val Met His Glu Ala Leu His Asn His Tyr Thr
420 425 430

Gln Lys Ser Leu Ser Leu Ser Pro Gly
435 440

<210> SEQ ID NO 12
<211> LENGTH: 214
<212> TYPE: PRT
<213> ORGANISM: Artificial Sequence
<220> FEATURE:
<223> OTHER INFORMATION: light chain for utomilumab

<400> SEQUENCE: 12

Ser Tyr Glu Leu Thr Gln Pro Pro Ser Val Ser Val Ser Pro Gly Gln
1 5 10 15

Thr Ala Ser Ile Thr Cys Ser Gly Asp Asn Ile Gly Asp Gln Tyr Ala
20 25 30

His Trp Tyr Gln Gln Lys Pro Gly Gln Ser Pro Val Leu Val Ile Tyr
35 40 45

Gln Asp Lys Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Tyr Cys Ala Thr Tyr Thr Gly Phe Gly Ser Leu
85 90 95

Ala Val Phe Gly Gly Gly Thr Lys Leu Thr Val Leu Gly Gln Pro Lys
100 105 110

Ala Ala Pro Ser Val Thr Leu Phe Pro Pro Ser Ser Glu Glu Leu Gln
115 120 125

Ala Asn Lys Ala Thr Leu Val Cys Leu Ile Ser Asp Phe Tyr Pro Gly
130 135 140

Ala Val Thr Val Ala Trp Lys Ala Asp Ser Ser Pro Val Lys Ala Gly
145 150 155 160

Val Glu Thr Thr Thr Pro Ser Lys Gln Ser Asn Asn Lys Tyr Ala Ala
165 170 175

Ser Ser Tyr Leu Ser Leu Thr Pro Glu Gln Trp Lys Ser His Arg Ser
180 185 190

Tyr Ser Cys Gln Val Thr His Glu Gly Ser Thr Val Glu Lys Thr Val
195 200 205

Ala Pro Thr Glu Cys Ser
210

<210> SEQ ID NO 13
<211> LENGTH: 116
<212> TYPE: PRT
<213> ORGANISM: Artificial Sequence
<220> FEATURE:
<223> OTHER INFORMATION: heavy chain variable region for utomilumab

<400> SEQUENCE: 13

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Ser Phe Ser Thr Tyr
20 25 30

Trp Ile Ser Trp Val Arg Gln Met Pro Gly Lys Gly Leu Glu Trp Met
35 40 45

Gly Lys Ile Tyr Pro Gly Asp Ser Tyr Thr Asn Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Gly Tyr Gly Ile Phe Asp Tyr Trp Gly Gln Gly Thr Leu Val
100 105 110

Thr Val Ser Ser
115

<210> SEQ ID NO 14
<211> LENGTH: 108
<212> TYPE: PRT
<213> ORGANISM: Artificial Sequence
<220> FEATURE:
<223> OTHER INFORMATION: light chain variable region for utomilumab

<400> SEQUENCE: 14

Ser Tyr Glu Leu Thr Gln Pro Pro Ser Val Ser Val Ser Pro Gly Gln
1 5 10 15

Thr Ala Ser Ile Thr Cys Ser Gly Asp Asn Ile Gly Asp Gln Tyr Ala
20 25 30

His Trp Tyr Gln Gln Lys Pro Gly Gln Ser Pro Val Leu Val Ile Tyr
35 40 45

Gln Asp Lys Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Tyr Cys Ala Thr Tyr Thr Gly Phe Gly Ser Leu
85 90 95

Ala Val Phe Gly Gly Gly Thr Lys Leu Thr Val Leu
100 105

<210> SEQ ID NO 15

<211> LENGTH: 6
<212> TYPE: PRT
<213> ORGANISM: Artificial Sequence
<220> FEATURE:
<223> OTHER INFORMATION: heavy chain CDR1 for utomilumab

<400> SEQUENCE: 15

Ser Thr Tyr Trp Ile Ser
1 5

<210> SEQ ID NO 16
<211> LENGTH: 17
<212> TYPE: PRT
<213> ORGANISM: Artificial Sequence
<220> FEATURE:
<223> OTHER INFORMATION: heavy chain CDR2 for utomilumab

<400> SEQUENCE: 16

Lys Ile Tyr Pro Gly Asp Ser Tyr Thr Asn Tyr Ser Pro Ser Phe Gln
1 5 10 15

Gly

<210> SEQ ID NO 17
<211> LENGTH: 8
<212> TYPE: PRT
<213> ORGANISM: Artificial Sequence
<220> FEATURE:
<223> OTHER INFORMATION: heavy chain CDR3 for utomilumab

<400> SEQUENCE: 17

Arg Gly Tyr Gly Ile Phe Asp Tyr
1 5

<210> SEQ ID NO 18
<211> LENGTH: 11
<212> TYPE: PRT
<213> ORGANISM: Artificial Sequence
<220> FEATURE:
<223> OTHER INFORMATION: light chain CDR1 for utomilumab

<400> SEQUENCE: 18

Ser Gly Asp Asn Ile Gly Asp Gln Tyr Ala His
1 5 10

<210> SEQ ID NO 19
<211> LENGTH: 7
<212> TYPE: PRT
<213> ORGANISM: Artificial Sequence
<220> FEATURE:
<223> OTHER INFORMATION: light chain CDR2 for utomilumab

<400> SEQUENCE: 19

Gln Asp Lys Asn Arg Pro Ser
1 5

<210> SEQ ID NO 20
<211> LENGTH: 11
<212> TYPE: PRT
<213> ORGANISM: Artificial Sequence
<220> FEATURE:
<223> OTHER INFORMATION: light chain CDR3 for utomilumab

<400> SEQUENCE: 20

Ala Thr Tyr Thr Gly Phe Gly Ser Leu Ala Val
1 5 10

<210> SEQ ID NO 21
<211> LENGTH: 448
<212> TYPE: PRT
<213> ORGANISM: Artificial Sequence
<220> FEATURE:
<223> OTHER INFORMATION: heavy chain for urelumab

<400> SEQUENCE: 21

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
```

370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Arg Leu Thr Val Asp Lys Ser
405 410 415

Arg Trp Gln Glu Gly Asn Val Phe Ser Cys Ser Val Met His Glu Ala
420 425 430

Leu His Asn His Tyr Thr Gln Lys Ser Leu Ser Leu Ser Leu Gly Lys
435 440 445

<210> SEQ ID NO 22
<211> LENGTH: 216
<212> TYPE: PRT
<213> ORGANISM: Artificial Sequence
<220> FEATURE:
<223> OTHER INFORMATION: light chain for urelumab

<400> SEQUENCE: 22

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Pro
85 90 95

Ala Leu Thr Phe Cys Gly Gly Thr Lys Val Glu Ile Lys Arg Thr Val
100 105 110

Ala Ala Pro Ser Val Phe Ile Phe Pro Pro Ser Asp Glu Gln Leu Lys
115 120 125

Ser Gly Thr Ala Ser Val Val Cys Leu Leu Asn Asn Phe Tyr Pro Arg
130 135 140

Glu Ala Lys Val Gln Trp Lys Val Asp Asn Ala Leu Gln Ser Gly Asn
145 150 155 160

Ser Gln Glu Ser Val Thr Glu Gln Asp Ser Lys Asp Ser Thr Tyr Ser
165 170 175

Leu Ser Ser Thr Leu Thr Leu Ser Lys Ala Asp Tyr Glu Lys His Lys
180 185 190

Val Tyr Ala Cys Glu Val Thr His Gln Gly Leu Ser Ser Pro Val Thr
195 200 205

Lys Ser Phe Asn Arg Gly Glu Cys
210 215

<210> SEQ ID NO 23
<211> LENGTH: 120
<212> TYPE: PRT
<213> ORGANISM: Artificial Sequence
<220> FEATURE:
<223> OTHER INFORMATION: variable heavy chain for urelumab

<400> SEQUENCE: 23

Met Lys His Leu Trp Phe Phe Leu Leu Leu Val Ala Ala Pro Arg Trp
1 5 10 15

```
Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Ser Pro Glu Lys Gly Leu
    50                  55                  60

Glu Trp Ile Gly Glu Ile Asn His Gly Gly Tyr Val Thr Tyr Asn Pro
65                  70                  75                  80

Ser Leu Glu Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Tyr Gly Pro
        115                 120


<210> SEQ ID NO 24
<211> LENGTH: 110
<212> TYPE: PRT
<213> ORGANISM: Artificial Sequence
<220> FEATURE:
<223> OTHER INFORMATION: variable light chain for urelumab

<400> SEQUENCE: 24

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln
            100                 105                 110


<210> SEQ ID NO 25
<211> LENGTH: 5
<212> TYPE: PRT
<213> ORGANISM: Artificial Sequence
<220> FEATURE:
<223> OTHER INFORMATION: heavy chain CDR1 for urelumab

<400> SEQUENCE: 25

Gly Tyr Tyr Trp Ser
1               5


<210> SEQ ID NO 26
<211> LENGTH: 16
<212> TYPE: PRT
<213> ORGANISM: Artificial Sequence
<220> FEATURE:
<223> OTHER INFORMATION: heavy chain CDR2 for urelumab

<400> SEQUENCE: 26

Glu Ile Asn His Gly Gly Tyr Val Thr Tyr Asn Pro Ser Leu Glu Ser
1               5                   10                  15
```

<210> SEQ ID NO 27
<211> LENGTH: 13
<212> TYPE: PRT
<213> ORGANISM: Artificial Sequence
<220> FEATURE:
<223> OTHER INFORMATION: heavy chain CDR3 for urelumab

<400> SEQUENCE: 27

Asp Tyr Gly Pro Gly Asn Tyr Asp Trp Tyr Phe Asp Leu
1 5 10

<210> SEQ ID NO 28
<211> LENGTH: 11
<212> TYPE: PRT
<213> ORGANISM: Artificial Sequence
<220> FEATURE:
<223> OTHER INFORMATION: light chain CDR1 for urelumab

<400> SEQUENCE: 28

Arg Ala Ser Gln Ser Val Ser Ser Tyr Leu Ala
1 5 10

<210> SEQ ID NO 29
<211> LENGTH: 7
<212> TYPE: PRT
<213> ORGANISM: Artificial Sequence
<220> FEATURE:
<223> OTHER INFORMATION: light chain CDR2 for urelumab

<400> SEQUENCE: 29

Asp Ala Ser Asn Arg Ala Thr
1 5

<210> SEQ ID NO 30
<211> LENGTH: 11
<212> TYPE: PRT
<213> ORGANISM: Artificial Sequence
<220> FEATURE:
<223> OTHER INFORMATION: light chain CDR3 for urelumab

<400> SEQUENCE: 30

Gln Gln Arg Ser Asp Trp Pro Pro Ala Leu Thr
1 5 10

<210> SEQ ID NO 31
<211> LENGTH: 230
<212> TYPE: PRT
<213> ORGANISM: Artificial Sequence
<220> FEATURE:
<223> OTHER INFORMATION: Fc domain

<400> SEQUENCE: 31

Lys Ser Cys Asp Lys Thr His Thr Cys Pro Pro Cys Pro Ala Pro Glu
1 5 10 15

Leu Leu Gly Gly Pro Ser Val Phe Leu Phe Pro Pro Lys Pro Lys Asp
20 25 30

Thr Leu Met Ile Ser Arg Thr Pro Glu Val Thr Cys Val Val Val Asp
35 40 45

Val Ser His Glu Asp Pro Glu Val Lys Phe Asn Trp Tyr Val Asp Gly
50 55 60

Val Glu Val His Asn Ala Lys Thr Lys Pro Arg Glu Glu Gln Tyr Asn
65 70 75 80

Ser Thr Tyr Arg Val Val Ser Val Leu Thr Val Leu His Gln Asp Trp
85 90 95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 32
<211> LENGTH: 22
<212> TYPE: PRT
<213> ORGANISM: Artificial Sequence
<220> FEATURE:
<223> OTHER INFORMATION: linker

<400> SEQUENCE: 32

Gly Gly Pro Gly Ser Ser Lys Ser Cys Asp Lys Thr His Thr Cys Pro
1               5                   10                  15

Pro Cys Pro Ala Pro Glu
            20

<210> SEQ ID NO 33
<211> LENGTH: 22
<212> TYPE: PRT
<213> ORGANISM: Artificial Sequence
<220> FEATURE:
<223> OTHER INFORMATION: linker

<400> SEQUENCE: 33

Gly Gly Ser Gly Ser Ser Lys Ser Cys Asp Lys Thr His Thr Cys Pro
1               5                   10                  15

Pro Cys Pro Ala Pro Glu
            20

<210> SEQ ID NO 34
<211> LENGTH: 27
<212> TYPE: PRT
<213> ORGANISM: Artificial Sequence
<220> FEATURE:
<223> OTHER INFORMATION: linker

<400> SEQUENCE: 34

Gly Gly Pro Gly Ser Ser Ser Ser Ser Ser Ser Lys Ser Cys Asp Lys
1               5                   10                  15

Thr His Thr Cys Pro Pro Cys Pro Ala Pro Glu
            20                  25

<210> SEQ ID NO 35
<211> LENGTH: 27
<212> TYPE: PRT

```
<213> ORGANISM: Artificial Sequence
<220> FEATURE:
<223> OTHER INFORMATION: linker

<400> SEQUENCE: 35

Gly Gly Ser Gly Ser Ser Ser Ser Ser Ser Ser Lys Ser Cys Asp Lys
1               5                   10                  15

Thr His Thr Cys Pro Pro Cys Pro Ala Pro Glu
            20                  25


<210> SEQ ID NO 36
<211> LENGTH: 29
<212> TYPE: PRT
<213> ORGANISM: Artificial Sequence
<220> FEATURE:
<223> OTHER INFORMATION: linker

<400> SEQUENCE: 36

Gly Gly Pro Gly Ser Ser Ser Ser Ser Ser Ser Ser Ser Lys Ser Cys
1               5                   10                  15

Asp Lys Thr His Thr Cys Pro Pro Cys Pro Ala Pro Glu
            20                  25


<210> SEQ ID NO 37
<211> LENGTH: 29
<212> TYPE: PRT
<213> ORGANISM: Artificial Sequence
<220> FEATURE:
<223> OTHER INFORMATION: linker

<400> SEQUENCE: 37

Gly Gly Ser Gly Ser Ser Ser Ser Ser Ser Ser Ser Ser Lys Ser Cys
1               5                   10                  15

Asp Lys Thr His Thr Cys Pro Pro Cys Pro Ala Pro Glu
            20                  25


<210> SEQ ID NO 38
<211> LENGTH: 24
<212> TYPE: PRT
<213> ORGANISM: Artificial Sequence
<220> FEATURE:
<223> OTHER INFORMATION: linker

<400> SEQUENCE: 38

Gly Gly Pro Gly Ser Ser Gly Ser Gly Ser Ser Asp Lys Thr His Thr
1               5                   10                  15

Cys Pro Pro Cys Pro Ala Pro Glu
            20


<210> SEQ ID NO 39
<211> LENGTH: 23
<212> TYPE: PRT
<213> ORGANISM: Artificial Sequence
<220> FEATURE:
<223> OTHER INFORMATION: linker

<400> SEQUENCE: 39

Gly Gly Pro Gly Ser Ser Gly Ser Gly Ser Asp Lys Thr His Thr Cys
1               5                   10                  15

Pro Pro Cys Pro Ala Pro Glu
            20


<210> SEQ ID NO 40
<211> LENGTH: 21
```

<212> TYPE: PRT
<213> ORGANISM: Artificial Sequence
<220> FEATURE:
<223> OTHER INFORMATION: linker

<400> SEQUENCE: 40

```
Gly Gly Pro Ser Ser Ser Gly Ser Asp Lys Thr His Thr Cys Pro Pro
1               5                   10                  15

Cys Pro Ala Pro Glu
            20
```

<210> SEQ ID NO 41
<211> LENGTH: 25
<212> TYPE: PRT
<213> ORGANISM: Artificial Sequence
<220> FEATURE:
<223> OTHER INFORMATION: linker

<400> SEQUENCE: 41

```
Gly Gly Ser Ser Ser Ser Ser Ser Ser Ser Gly Ser Asp Lys Thr His
1               5                   10                  15

Thr Cys Pro Pro Cys Pro Ala Pro Glu
            20                  25
```

<210> SEQ ID NO 42
<211> LENGTH: 246
<212> TYPE: PRT
<213> ORGANISM: Artificial Sequence
<220> FEATURE:
<223> OTHER INFORMATION: Fc domain

<400> SEQUENCE: 42

```
Met Glu Thr Asp Thr Leu Leu Leu Trp Val Leu Leu Leu Trp Val Pro
1               5                   10                  15

Ala Gly Asn Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
```

```
    210                 215                 220

Cys Ser Val Met His Glu Ala Leu His Asn His Tyr Thr Gln Lys Ser
225                 230                 235                 240

Leu Ser Leu Ser Pro Gly
                245


<210> SEQ ID NO 43
<211> LENGTH: 11
<212> TYPE: PRT
<213> ORGANISM: Artificial Sequence
<220> FEATURE:
<223> OTHER INFORMATION: linker

<400> SEQUENCE: 43

Ser Gly Ser Gly Ser Gly Ser Gly Ser Gly Ser
1               5                   10


<210> SEQ ID NO 44
<211> LENGTH: 12
<212> TYPE: PRT
<213> ORGANISM: Artificial Sequence
<220> FEATURE:
<223> OTHER INFORMATION: linker

<400> SEQUENCE: 44

Ser Ser Ser Ser Ser Ser Gly Ser Gly Ser Gly Ser
1               5                   10


<210> SEQ ID NO 45
<211> LENGTH: 16
<212> TYPE: PRT
<213> ORGANISM: Artificial Sequence
<220> FEATURE:
<223> OTHER INFORMATION: linker

<400> SEQUENCE: 45

Ser Ser Ser Ser Ser Ser Gly Ser Gly Ser Gly Ser Gly Ser Gly Ser
1               5                   10                  15


<210> SEQ ID NO 46
<211> LENGTH: 254
<212> TYPE: PRT
<213> ORGANISM: Artificial Sequence
<220> FEATURE:
<223> OTHER INFORMATION: 4-1BBL

<400> SEQUENCE: 46

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
```

```
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250


<210> SEQ ID NO 47
<211> LENGTH: 168
<212> TYPE: PRT
<213> ORGANISM: Artificial Sequence
<220> FEATURE:
<223> OTHER INFORMATION: 4-1BBL soluble domain

<400> SEQUENCE: 47

Leu Arg Gln Gly Met Phe Ala Gln Leu Val Ala Gln Asn Val Leu Leu
1               5                   10                  15

Ile Asp Gly Pro Leu Ser Trp Tyr Ser Asp Pro Gly Leu Ala Gly Val
            20                  25                  30

Ser Leu Thr Gly Gly Leu Ser Tyr Lys Glu Asp Thr Lys Glu Leu Val
        35                  40                  45

Val Ala Lys Ala Gly Val Tyr Tyr Val Phe Phe Gln Leu Glu Leu Arg
    50                  55                  60

Arg Val Val Ala Gly Glu Gly Ser Gly Ser Val Ser Leu Ala Leu His
65                  70                  75                  80

Leu Gln Pro Leu Arg Ser Ala Ala Gly Ala Ala Ala Leu Ala Leu Thr
                85                  90                  95

Val Asp Leu Pro Pro Ala Ser Ser Glu Ala Arg Asn Ser Ala Phe Gly
            100                 105                 110

Phe Gln Gly Arg Leu Leu His Leu Ser Ala Gly Gln Arg Leu Gly Val
        115                 120                 125

His Leu His Thr Glu Ala Arg Ala Arg His Ala Trp Gln Leu Thr Gln
    130                 135                 140

Gly Ala Thr Val Leu Gly Leu Phe Arg Val Thr Pro Glu Ile Pro Ala
145                 150                 155                 160

Gly Leu Pro Ser Pro Arg Ser Glu
                165


<210> SEQ ID NO 48
<211> LENGTH: 118
<212> TYPE: PRT
<213> ORGANISM: Artificial Sequence
<220> FEATURE:
<223> OTHER INFORMATION: variable heavy chain for 4B4-1-1 version 1

<400> SEQUENCE: 48
```

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Lys Gln Arg Pro Gly Gln Val Leu Glu Trp Ile
        35                  40                  45

Gly Glu Ile Asn Pro Gly Asn Gly His Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Phe Thr Thr Ala Arg Gly Phe Ala Tyr Trp Gly Gln Gly
            100                 105                 110

Thr Leu Val Thr Val Ser
        115


<210> SEQ ID NO 49
<211> LENGTH: 107
<212> TYPE: PRT
<213> ORGANISM: Artificial Sequence
<220> FEATURE:
<223> OTHER INFORMATION: variable light chain for 4B4-1-1 version 1

<400> SEQUENCE: 49

Asp Ile Val Met Thr Gln Ser Pro Ala Thr Gln Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asp Gly His Ser Phe Pro Pro
                85                  90                  95

Thr Phe Gly Gly Gly Thr Lys Leu Glu Ile Lys
            100                 105


<210> SEQ ID NO 50
<211> LENGTH: 119
<212> TYPE: PRT
<213> ORGANISM: Artificial Sequence
<220> FEATURE:
<223> OTHER INFORMATION: variable heavy chain for 4B4-1-1 version 2

<400> SEQUENCE: 50

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Lys Gln Arg Pro Gly Gln Val Leu Glu Trp Ile
        35                  40                  45

Gly Glu Ile Asn Pro Gly Asn Gly His Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80
```

```
Met Gln Leu Ser Ser Leu Thr Ser Glu Asp Ser Ala Val Tyr Tyr Cys
                85                  90                  95

Ala Arg Ser Phe Thr Thr Ala Arg Gly Phe Ala Tyr Trp Gly Gln Gly
            100                 105                 110

Thr Leu Val Thr Val Ser Ala
        115
```

<210> SEQ ID NO 51
<211> LENGTH: 108
<212> TYPE: PRT
<213> ORGANISM: Artificial Sequence
<220> FEATURE:
<223> OTHER INFORMATION: variable light chain for 4B4-1-1 version 2

<400> SEQUENCE: 51

```
Asp Ile Val Met Thr Gln Ser Pro Ala Thr Gln Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asp Gly His Ser Phe Pro Pro
                85                  90                  95

Thr Phe Gly Gly Gly Thr Lys Leu Glu Ile Lys Arg
            100                 105
```

<210> SEQ ID NO 52
<211> LENGTH: 120
<212> TYPE: PRT
<213> ORGANISM: Artificial Sequence
<220> FEATURE:
<223> OTHER INFORMATION: variable heavy chain for H39E3-2

<400> SEQUENCE: 52

```
Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Tyr Trp Met Ser Trp Val Arg Gln Ala Pro Gly Lys Gly Leu
    50                  55                  60

Glu Trp Val Ala Asp Ile Lys Asn Asp Gly Ser Tyr Thr Asn Tyr Ala
65                  70                  75                  80

Pro Ser Leu Thr Asn Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Leu Thr
        115                 120
```

<210> SEQ ID NO 53
<211> LENGTH: 109
<212> TYPE: PRT

<213> ORGANISM: Artificial Sequence
<220> FEATURE:
<223> OTHER INFORMATION: variable light chain for H39E3-2

<400> SEQUENCE: 53

Met Glu Ala Pro Ala Gln Leu Leu Phe Leu Leu Leu Leu Trp Leu Pro
1 5 10 15

Asp Thr Thr Gly Asp Ile Val Met Thr Gln Ser Pro Asp Ser Leu Ala
20 25 30

Val Ser Leu Gly Glu Arg Ala Thr Ile Asn Cys Lys Ser Ser Gln Ser
35 40 45

Leu Leu Ser Ser Gly Asn Gln Lys Asn Tyr Leu Trp Tyr Gln Gln Lys
50 55 60

Pro Gly Gln Pro Pro Lys Leu Leu Ile Tyr Tyr Ala Ser Thr Arg Gln
65 70 75 80

Ser Gly Val Pro Asp Arg Phe Ser Gly Ser Gly Ser Gly Thr Asp Phe
85 90 95

Thr Leu Thr Ile Ser Ser Leu Gln Ala Glu Asp Val Ala
100 105

<210> SEQ ID NO 54
<211> LENGTH: 277
<212> TYPE: PRT
<213> ORGANISM: Artificial Sequence
<220> FEATURE:
<223> OTHER INFORMATION: human OX40 (Homo sapiens)

<400> SEQUENCE: 54

Met Cys Val Gly Ala Arg Arg Leu Gly Arg Gly Pro Cys Ala Ala Leu
1 5 10 15

Leu Leu Leu Gly Leu Gly Leu Ser Thr Val Thr Gly Leu His Cys Val
20 25 30

Gly Asp Thr Tyr Pro Ser Asn Asp Arg Cys Cys His Glu Cys Arg Pro
35 40 45

Gly Asn Gly Met Val Ser Arg Cys Ser Arg Ser Gln Asn Thr Val Cys
50 55 60

Arg Pro Cys Gly Pro Gly Phe Tyr Asn Asp Val Val Ser Ser Lys Pro
65 70 75 80

Cys Lys Pro Cys Thr Trp Cys Asn Leu Arg Ser Gly Ser Glu Arg Lys
85 90 95

Gln Leu Cys Thr Ala Thr Gln Asp Thr Val Cys Arg Cys Arg Ala Gly
100 105 110

Thr Gln Pro Leu Asp Ser Tyr Lys Pro Gly Val Asp Cys Ala Pro Cys
115 120 125

Pro Pro Gly His Phe Ser Pro Gly Asp Asn Gln Ala Cys Lys Pro Trp
130 135 140

Thr Asn Cys Thr Leu Ala Gly Lys His Thr Leu Gln Pro Ala Ser Asn
145 150 155 160

Ser Ser Asp Ala Ile Cys Glu Asp Arg Asp Pro Pro Ala Thr Gln Pro
165 170 175

Gln Glu Thr Gln Gly Pro Pro Ala Arg Pro Ile Thr Val Gln Pro Thr
180 185 190

Glu Ala Trp Pro Arg Thr Ser Gln Gly Pro Ser Thr Arg Pro Val Glu
195 200 205

Val Pro Gly Gly Arg Ala Val Ala Ala Ile Leu Gly Leu Gly Leu Val
210 215 220

```
Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275
```

<210> SEQ ID NO 55
<211> LENGTH: 272
<212> TYPE: PRT
<213> ORGANISM: Artificial Sequence
<220> FEATURE:
<223> OTHER INFORMATION: murine OX40 (Mus musculus)

<400> SEQUENCE: 55

```
Met Tyr Val Trp Val Gln Gln Pro Thr Ala Leu Leu Leu Leu Gly Leu
1               5                   10                  15

Thr Leu Gly Val Thr Ala Arg Arg Leu Asn Cys Val Lys His Thr Tyr
            20                  25                  30

Pro Ser Gly His Lys Cys Cys Arg Glu Cys Gln Pro Gly His Gly Met
        35                  40                  45

Val Ser Arg Cys Asp His Thr Arg Asp Thr Leu Cys His Pro Cys Glu
    50                  55                  60

Thr Gly Phe Tyr Asn Glu Ala Val Asn Tyr Asp Thr Cys Lys Gln Cys
65                  70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
        115                 120                 125

Gly His Phe Ser Pro Gly Asn Asn Gln Ala Cys Lys Pro Trp Thr Asn
    130                 135                 140

Cys Thr Leu Ser Gly Lys Gln Thr Arg His Pro Ala Ser Asp Ser Leu
145                 150                 155                 160

Asp Ala Val Cys Glu Asp Arg Ser Leu Leu Ala Thr Leu Leu Trp Glu
                165                 170                 175

Thr Gln Arg Pro Thr Phe Arg Pro Thr Thr Val Gln Ser Thr Thr Val
            180                 185                 190

Trp Pro Arg Thr Ser Glu Leu Pro Ser Pro Pro Thr Leu Val Thr Pro
        195                 200                 205

Glu Gly Pro Ala Phe Ala Val Leu Leu Gly Leu Gly Leu Gly Leu Leu
    210                 215                 220

Ala Pro Leu Thr Val Leu Leu Ala Leu Tyr Leu Leu Arg Lys Ala Trp
225                 230                 235                 240

Arg Leu Pro Asn Thr Pro Lys Pro Cys Trp Gly Asn Ser Phe Arg Thr
                245                 250                 255

Pro Ile Gln Glu Glu His Thr Asp Ala His Phe Thr Leu Ala Lys Ile
            260                 265                 270
```

<210> SEQ ID NO 56
<211> LENGTH: 451
<212> TYPE: PRT
<213> ORGANISM: Artificial Sequence
<220> FEATURE:

<223> OTHER INFORMATION: heavy chain for tavolixizumab

<400> SEQUENCE: 56

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 57
<211> LENGTH: 214
<212> TYPE: PRT
<213> ORGANISM: Artificial Sequence
<220> FEATURE:
<223> OTHER INFORMATION: light chain for tavolixizumab

<400> SEQUENCE: 57

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Lys Leu His Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln Gln Gly Ser Ala Leu Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 58
<211> LENGTH: 118
<212> TYPE: PRT
<213> ORGANISM: Artificial Sequence
<220> FEATURE:
<223> OTHER INFORMATION: heavy chain variable region for tavolixizumab

<400> SEQUENCE: 58

Gln Val Gln Leu Gln Glu Ser Gly Pro Gly Leu Val Lys Pro Ser Gln
1 5 10 15

Thr Leu Ser Leu Thr Cys Ala Val Tyr Gly Gly Ser Phe Ser Ser Gly
20 25 30

```
Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr
        115


<210> SEQ ID NO 59
<211> LENGTH: 108
<212> TYPE: PRT
<213> ORGANISM: Artificial Sequence
<220> FEATURE:
<223> OTHER INFORMATION: light chain variable region for tavolixizumab

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg
            100                 105


<210> SEQ ID NO 60
<211> LENGTH: 9
<212> TYPE: PRT
<213> ORGANISM: Artificial Sequence
<220> FEATURE:
<223> OTHER INFORMATION: heavy chain CDR1 for tavolixizumab

<400> SEQUENCE: 60

Gly Ser Phe Ser Ser Gly Tyr Trp Asn
1               5


<210> SEQ ID NO 61
<211> LENGTH: 13
<212> TYPE: PRT
<213> ORGANISM: Artificial Sequence
<220> FEATURE:
<223> OTHER INFORMATION: heavy chain CDR2 for tavolixizumab

<400> SEQUENCE: 61

Tyr Ile Gly Tyr Ile Ser Tyr Asn Gly Ile Thr Tyr His
1               5                   10


<210> SEQ ID NO 62
<211> LENGTH: 14
```

<212> TYPE: PRT
<213> ORGANISM: Artificial Sequence
<220> FEATURE:
<223> OTHER INFORMATION: heavy chain CDR3 for tavolixizumab

<400> SEQUENCE: 62

Arg Tyr Lys Tyr Asp Tyr Asp Gly Gly His Ala Met Asp Tyr
1 5 10

<210> SEQ ID NO 63
<211> LENGTH: 8
<212> TYPE: PRT
<213> ORGANISM: Artificial Sequence
<220> FEATURE:
<223> OTHER INFORMATION: light chain CDR1 for tavolixizumab

<400> SEQUENCE: 63

Gln Asp Ile Ser Asn Tyr Leu Asn
1 5

<210> SEQ ID NO 64
<211> LENGTH: 11
<212> TYPE: PRT
<213> ORGANISM: Artificial Sequence
<220> FEATURE:
<223> OTHER INFORMATION: light chain CDR2 for tavolixizumab

<400> SEQUENCE: 64

Leu Leu Ile Tyr Tyr Thr Ser Lys Leu His Ser
1 5 10

<210> SEQ ID NO 65
<211> LENGTH: 8
<212> TYPE: PRT
<213> ORGANISM: Artificial Sequence
<220> FEATURE:
<223> OTHER INFORMATION: light chain CDR3 for tavolixizumab

<400> SEQUENCE: 65

Gln Gln Gly Ser Ala Leu Pro Trp
1 5

<210> SEQ ID NO 66
<211> LENGTH: 444
<212> TYPE: PRT
<213> ORGANISM: Artificial Sequence
<220> FEATURE:
<223> OTHER INFORMATION: heavy chain for 11D4

<400> SEQUENCE: 66

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Tyr Ile Ser Ser Ser Ser Ser Thr Ile Asp Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Asp Glu Asp Thr Ala Val Tyr Tyr Cys
85 90 95

Ala Arg Glu Ser Gly Trp Tyr Leu Phe Asp Tyr Trp Gly Gln Gly Thr
100 105 110

```
Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

<210> SEQ ID NO 67
<211> LENGTH: 214
<212> TYPE: PRT
<213> ORGANISM: Artificial Sequence
<220> FEATURE:
<223> OTHER INFORMATION: light chain for 11D4

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30
```

```
Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 68
<211> LENGTH: 118
<212> TYPE: PRT
<213> ORGANISM: Artificial Sequence
<220> FEATURE:
<223> OTHER INFORMATION: heavy chain variable region for 11D4

<400> SEQUENCE: 68

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser
        115
```

<210> SEQ ID NO 69
<211> LENGTH: 107
<212> TYPE: PRT
<213> ORGANISM: Artificial Sequence
<220> FEATURE:
<223> OTHER INFORMATION: light chain variable region for 11D4

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105

<210> SEQ ID NO 70
<211> LENGTH: 5
<212> TYPE: PRT
<213> ORGANISM: Artificial Sequence
<220> FEATURE:
<223> OTHER INFORMATION: heavy chain CDR1 for 11D4

<400> SEQUENCE: 70

Ser Tyr Ser Met Asn
1               5

<210> SEQ ID NO 71
<211> LENGTH: 17
<212> TYPE: PRT
<213> ORGANISM: Artificial Sequence
<220> FEATURE:
<223> OTHER INFORMATION: heavy chain CDR2 for 11D4

<400> SEQUENCE: 71

Tyr Ile Ser Ser Ser Ser Ser Thr Ile Asp Tyr Ala Asp Ser Val Lys
1               5                   10                  15

Gly

<210> SEQ ID NO 72
<211> LENGTH: 9
<212> TYPE: PRT
<213> ORGANISM: Artificial Sequence
<220> FEATURE:
<223> OTHER INFORMATION: heavy chain CDR3 for 11D4

<400> SEQUENCE: 72

Glu Ser Gly Trp Tyr Leu Phe Asp Tyr
1               5

<210> SEQ ID NO 73
<211> LENGTH: 11
<212> TYPE: PRT
<213> ORGANISM: Artificial Sequence
<220> FEATURE:
<223> OTHER INFORMATION: light chain CDR1 for 11D4

<400> SEQUENCE: 73

Arg Ala Ser Gln Gly Ile Ser Ser Trp Leu Ala
1               5                   10

<210> SEQ ID NO 74

<211> LENGTH: 7
<212> TYPE: PRT
<213> ORGANISM: Artificial Sequence
<220> FEATURE:
<223> OTHER INFORMATION: light chain CDR2 for 11D4

<400> SEQUENCE: 74

Ala Ala Ser Ser Leu Gln Ser
1 5

<210> SEQ ID NO 75
<211> LENGTH: 9
<212> TYPE: PRT
<213> ORGANISM: Artificial Sequence
<220> FEATURE:
<223> OTHER INFORMATION: light chain CDR3 for 11D4

<400> SEQUENCE: 75

Gln Gln Tyr Asn Ser Tyr Pro Pro Thr
1 5

<210> SEQ ID NO 76
<211> LENGTH: 450
<212> TYPE: PRT
<213> ORGANISM: Artificial Sequence
<220> FEATURE:
<223> OTHER INFORMATION: heavy chain for 18D8

<400> SEQUENCE: 76

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Gln Ser Thr Ala Asp Tyr Tyr Phe Tyr Tyr Gly Met Asp
100 105 110

Val Trp Gly Gln Gly Thr Thr Val Thr Val Ser Ser Ala Ser Thr Lys
115 120 125

Gly Pro Ser Val Phe Pro Leu Ala Pro Cys Ser Arg Ser Thr Ser Glu
130 135 140

Ser Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Asn Phe Gly Thr Gln Thr Tyr Thr Cys Asn
195 200 205

Val Asp His Lys Pro Ser Asn Thr Lys Val Asp Lys Thr Val Glu Arg
210 215 220

Lys Cys Cys Val Glu Cys Pro Pro Cys Pro Ala Pro Pro Val Ala Gly
225 230 235 240

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 77
<211> LENGTH: 213
<212> TYPE: PRT
<213> ORGANISM: Artificial Sequence
<220> FEATURE:
<223> OTHER INFORMATION: light chain for 18D8

<400> SEQUENCE: 77

```
Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140
```

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 78
<211> LENGTH: 124
<212> TYPE: PRT
<213> ORGANISM: Artificial Sequence
<220> FEATURE:
<223> OTHER INFORMATION: heavy chain variable region for 18D8

<400> SEQUENCE: 78

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser
        115                 120


<210> SEQ ID NO 79
<211> LENGTH: 106
<212> TYPE: PRT
<213> ORGANISM: Artificial Sequence
<220> FEATURE:
<223> OTHER INFORMATION: light chain variable region for 18D8

<400> SEQUENCE: 79

Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105
```

<210> SEQ ID NO 80
<211> LENGTH: 5
<212> TYPE: PRT
<213> ORGANISM: Artificial Sequence
<220> FEATURE:
<223> OTHER INFORMATION: heavy chain CDR1 for 18D8

<400> SEQUENCE: 80

Asp Tyr Ala Met His
1               5

<210> SEQ ID NO 81
<211> LENGTH: 17
<212> TYPE: PRT
<213> ORGANISM: Artificial Sequence
<220> FEATURE:
<223> OTHER INFORMATION: heavy chain CDR2 for 18D8

<400> SEQUENCE: 81

Gly Ile Ser Trp Asn Ser Gly Ser Ile Gly Tyr Ala Asp Ser Val Lys
1               5                   10                  15

Gly

<210> SEQ ID NO 82
<211> LENGTH: 15
<212> TYPE: PRT
<213> ORGANISM: Artificial Sequence
<220> FEATURE:
<223> OTHER INFORMATION: heavy chain CDR3 for 18D8

<400> SEQUENCE: 82

Asp Gln Ser Thr Ala Asp Tyr Tyr Phe Tyr Tyr Gly Met Asp Val
1               5                   10                  15

<210> SEQ ID NO 83
<211> LENGTH: 11
<212> TYPE: PRT
<213> ORGANISM: Artificial Sequence
<220> FEATURE:
<223> OTHER INFORMATION: light chain CDR1 for 18D8

<400> SEQUENCE: 83

Arg Ala Ser Gln Ser Val Ser Ser Tyr Leu Ala
1               5                   10

<210> SEQ ID NO 84
<211> LENGTH: 7
<212> TYPE: PRT
<213> ORGANISM: Artificial Sequence
<220> FEATURE:
<223> OTHER INFORMATION: light chain CDR2 for 18D8

<400> SEQUENCE: 84

Asp Ala Ser Asn Arg Ala Thr
1               5

<210> SEQ ID NO 85
<211> LENGTH: 8
<212> TYPE: PRT
<213> ORGANISM: Artificial Sequence
<220> FEATURE:
<223> OTHER INFORMATION: light chain CDR3 for 18D8

<400> SEQUENCE: 85

Gln Gln Arg Ser Asn Trp Pro Thr 1 5

<210> SEQ ID NO 86
<211> LENGTH: 120
<212> TYPE: PRT
<213> ORGANISM: Artificial Sequence
<220> FEATURE:
<223> OTHER INFORMATION: heavy chain variable region for Hu119-122

<400> SEQUENCE: 86

```
Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120
```

<210> SEQ ID NO 87
<211> LENGTH: 111
<212> TYPE: PRT
<213> ORGANISM: Artificial Sequence
<220> FEATURE:
<223> OTHER INFORMATION: light chain variable region for Hu119-122

<400> SEQUENCE: 87

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys
            100                 105                 110
```

<210> SEQ ID NO 88
<211> LENGTH: 5
<212> TYPE: PRT
<213> ORGANISM: Artificial Sequence
<220> FEATURE:
<223> OTHER INFORMATION: heavy chain CDR1 for Hu119-122

<400> SEQUENCE: 88

```
Ser His Asp Met Ser
1               5
```

<210> SEQ ID NO 89
<211> LENGTH: 17
<212> TYPE: PRT
<213> ORGANISM: Artificial Sequence
<220> FEATURE:
<223> OTHER INFORMATION: heavy chain CDR2 for Hu119-122

<400> SEQUENCE: 89

Ala Ile Asn Ser Asp Gly Gly Ser Thr Tyr Tyr Pro Asp Thr Met Glu
1 5 10 15

Arg

<210> SEQ ID NO 90
<211> LENGTH: 11
<212> TYPE: PRT
<213> ORGANISM: Artificial Sequence
<220> FEATURE:
<223> OTHER INFORMATION: heavy chain CDR3 for Hu119-122

<400> SEQUENCE: 90

His Tyr Asp Asp Tyr Tyr Ala Trp Phe Ala Tyr
1 5 10

<210> SEQ ID NO 91
<211> LENGTH: 15
<212> TYPE: PRT
<213> ORGANISM: Artificial Sequence
<220> FEATURE:
<223> OTHER INFORMATION: light chain CDR1 for Hu119-122

<400> SEQUENCE: 91

Arg Ala Ser Lys Ser Val Ser Thr Ser Gly Tyr Ser Tyr Met His
1 5 10 15

<210> SEQ ID NO 92
<211> LENGTH: 7
<212> TYPE: PRT
<213> ORGANISM: Artificial Sequence
<220> FEATURE:
<223> OTHER INFORMATION: light chain CDR2 for Hu119-122

<400> SEQUENCE: 92

Leu Ala Ser Asn Leu Glu Ser
1 5

<210> SEQ ID NO 93
<211> LENGTH: 9
<212> TYPE: PRT
<213> ORGANISM: Artificial Sequence
<220> FEATURE:
<223> OTHER INFORMATION: light chain CDR3 for Hu119-122

<400> SEQUENCE: 93

Gln His Ser Arg Glu Leu Pro Leu Thr
1 5

<210> SEQ ID NO 94
<211> LENGTH: 122
<212> TYPE: PRT
<213> ORGANISM: Artificial Sequence
<220> FEATURE:
<223> OTHER INFORMATION: heavy chain variable region for Hu106-222

<400> SEQUENCE: 94

Gln Val Gln Leu Val Gln Ser Gly Ser Glu Leu Lys Lys Pro Gly Ala

```
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser
        115                 120


<210> SEQ ID NO 95
<211> LENGTH: 107
<212> TYPE: PRT
<213> ORGANISM: Artificial Sequence
<220> FEATURE:
<223> OTHER INFORMATION: light chain variable region for Hu106-222

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Arg
                85                  90                  95

Thr Phe Gly Gln Gly Thr Lys Leu Glu Ile Lys
            100                 105


<210> SEQ ID NO 96
<211> LENGTH: 5
<212> TYPE: PRT
<213> ORGANISM: Artificial Sequence
<220> FEATURE:
<223> OTHER INFORMATION: heavy chain CDR1 for Hu106-222

<400> SEQUENCE: 96

Asp Tyr Ser Met His
1               5


<210> SEQ ID NO 97
<211> LENGTH: 17
<212> TYPE: PRT
<213> ORGANISM: Artificial Sequence
<220> FEATURE:
<223> OTHER INFORMATION: heavy chain CDR2 for Hu106-222

<400> SEQUENCE: 97

Trp Ile Asn Thr Glu Thr Gly Glu Pro Thr Tyr Ala Asp Asp Phe Lys
1               5                   10                  15
```

Gly

<210> SEQ ID NO 98
<211> LENGTH: 13
<212> TYPE: PRT
<213> ORGANISM: Artificial Sequence
<220> FEATURE:
<223> OTHER INFORMATION: heavy chain CDR3 for Hu106-222

<400> SEQUENCE: 98

Pro Tyr Tyr Asp Tyr Val Ser Tyr Tyr Ala Met Asp Tyr
1 5 10

<210> SEQ ID NO 99
<211> LENGTH: 11
<212> TYPE: PRT
<213> ORGANISM: Artificial Sequence
<220> FEATURE:
<223> OTHER INFORMATION: light chain CDR1 for Hu106-222

<400> SEQUENCE: 99

Lys Ala Ser Gln Asp Val Ser Thr Ala Val Ala
1 5 10

<210> SEQ ID NO 100
<211> LENGTH: 7
<212> TYPE: PRT
<213> ORGANISM: Artificial Sequence
<220> FEATURE:
<223> OTHER INFORMATION: light chain CDR2 for Hu106-222

<400> SEQUENCE: 100

Ser Ala Ser Tyr Leu Tyr Thr
1 5

<210> SEQ ID NO 101
<211> LENGTH: 9
<212> TYPE: PRT
<213> ORGANISM: Artificial Sequence
<220> FEATURE:
<223> OTHER INFORMATION: light chain CDR3 for Hu106-222

<400> SEQUENCE: 101

Gln Gln His Tyr Ser Thr Pro Arg Thr
1 5

<210> SEQ ID NO 102
<211> LENGTH: 183
<212> TYPE: PRT
<213> ORGANISM: Artificial Sequence
<220> FEATURE:
<223> OTHER INFORMATION: OX40L

<400> SEQUENCE: 102

Met Glu Arg Val Gln Pro Leu Glu Glu Asn Val Gly Asn Ala Ala Arg
1 5 10 15

Pro Arg Phe Glu Arg Asn Lys Leu Leu Leu Val Ala Ser Val Ile Gln
20 25 30

Gly Leu Gly Leu Leu Leu Cys Phe Thr Tyr Ile Cys Leu His Phe Ser
35 40 45

Ala Leu Gln Val Ser His Arg Tyr Pro Arg Ile Gln Ser Ile Lys Val
50 55 60

Gln Phe Thr Glu Tyr Lys Lys Glu Lys Gly Phe Ile Leu Thr Ser Gln
65 70 75 80

```
Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180
```

<210> SEQ ID NO 103
<211> LENGTH: 131
<212> TYPE: PRT
<213> ORGANISM: Artificial Sequence
<220> FEATURE:
<223> OTHER INFORMATION: OX40L soluble domain

<400> SEQUENCE: 103

```
Ser His Arg Tyr Pro Arg Ile Gln Ser Ile Lys Val Gln Phe Thr Glu
1               5                   10                  15

Tyr Lys Lys Glu Lys Gly Phe Ile Leu Thr Ser Gln Lys Glu Asp Glu
            20                  25                  30

Ile Met Lys Val Gln Asn Asn Ser Val Ile Ile Asn Cys Asp Gly Phe
        35                  40                  45

Tyr Leu Ile Ser Leu Lys Gly Tyr Phe Ser Gln Glu Val Asn Ile Ser
    50                  55                  60

Leu His Tyr Gln Lys Asp Glu Glu Pro Leu Phe Gln Leu Lys Lys Val
65                  70                  75                  80

Arg Ser Val Asn Ser Leu Met Val Ala Ser Leu Thr Tyr Lys Asp Lys
                85                  90                  95

Val Tyr Leu Asn Val Thr Thr Asp Asn Thr Ser Leu Asp Asp Phe His
            100                 105                 110

Val Asn Gly Gly Glu Leu Ile Leu Ile His Gln Asn Pro Gly Glu Phe
        115                 120                 125

Cys Val Leu
    130
```

<210> SEQ ID NO 104
<211> LENGTH: 128
<212> TYPE: PRT
<213> ORGANISM: Artificial Sequence
<220> FEATURE:
<223> OTHER INFORMATION: OX40L soluble domain (alternative)

<400> SEQUENCE: 104

```
Tyr Pro Arg Ile Gln Ser Ile Lys Val Gln Phe Thr Glu Tyr Lys Lys
1               5                   10                  15

Glu Lys Gly Phe Ile Leu Thr Ser Gln Lys Glu Asp Glu Ile Met Lys
            20                  25                  30

Val Gln Asn Asn Ser Val Ile Ile Asn Cys Asp Gly Phe Tyr Leu Ile
        35                  40                  45

Ser Leu Lys Gly Tyr Phe Ser Gln Glu Val Asn Ile Ser Leu His Tyr
```

```
    50                  55                  60

Gln Lys Asp Glu Glu Pro Leu Phe Gln Leu Lys Lys Val Arg Ser Val
65                  70                  75                  80

Asn Ser Leu Met Val Ala Ser Leu Thr Tyr Lys Asp Lys Val Tyr Leu
                85                  90                  95

Asn Val Thr Thr Asp Asn Thr Ser Leu Asp Asp Phe His Val Asn Gly
            100                 105                 110

Gly Glu Leu Ile Leu Ile His Gln Asn Pro Gly Glu Phe Cys Val Leu
        115                 120                 125


<210> SEQ ID NO 105
<211> LENGTH: 120
<212> TYPE: PRT
<213> ORGANISM: Artificial Sequence
<220> FEATURE:
<223> OTHER INFORMATION: variable heavy chain for 008

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ser Gln Val His Tyr Ala Leu Asp Tyr Trp Gly
            100                 105                 110

Gln Gly Thr Leu Val Thr Val Ser
        115                 120


<210> SEQ ID NO 106
<211> LENGTH: 108
<212> TYPE: PRT
<213> ORGANISM: Artificial Sequence
<220> FEATURE:
<223> OTHER INFORMATION: variable light chain for 008

<400> SEQUENCE: 106

Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys
            100                 105
```

<210> SEQ ID NO 107
<211> LENGTH: 120
<212> TYPE: PRT
<213> ORGANISM: Artificial Sequence
<220> FEATURE:
<223> OTHER INFORMATION: variable heavy chain for 011

<400> SEQUENCE: 107

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Thr Met Asn Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Asn Leu Arg Ala Glu Asp Thr Ala Val Tyr Tyr Cys Ala Arg
                85                  90                  95

Asp Arg Tyr Phe Arg Gln Gln Asn Ala Phe Asp Tyr Trp Gly Gln Gly
            100                 105                 110

Thr Leu Val Thr Val Ser Ser Ala
        115                 120

<210> SEQ ID NO 108
<211> LENGTH: 108
<212> TYPE: PRT
<213> ORGANISM: Artificial Sequence
<220> FEATURE:
<223> OTHER INFORMATION: variable light chain for 011

<400> SEQUENCE: 108

Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys
            100                 105

<210> SEQ ID NO 109
<211> LENGTH: 120
<212> TYPE: PRT
<213> ORGANISM: Artificial Sequence
<220> FEATURE:
<223> OTHER INFORMATION: variable heavy chain for 021

<400> SEQUENCE: 109

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Phe Ser Ser Tyr

```
            20                  25                  30

Ala Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ile Thr Leu Pro Asn Ala Leu Asp Tyr Trp Gly
            100                 105                 110

Gln Gly Thr Leu Val Thr Val Ser
        115                 120


<210> SEQ ID NO 110
<211> LENGTH: 108
<212> TYPE: PRT
<213> ORGANISM: Artificial Sequence
<220> FEATURE:
<223> OTHER INFORMATION: variable light chain for 021

<400> SEQUENCE: 110

Asp Ile Gln Met Thr Gln Ser Pro Val Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Lys Ser Asn Pro Pro Thr Phe Gly Gln Gly Thr Lys
            100                 105


<210> SEQ ID NO 111
<211> LENGTH: 120
<212> TYPE: PRT
<213> ORGANISM: Artificial Sequence
<220> FEATURE:
<223> OTHER INFORMATION: variable heavy chain for 023

<400> SEQUENCE: 111

Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Gly Thr Tyr Tyr Ala Asp Ser Val Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

```
Arg Tyr Asp Asn Val Met Gly Leu Tyr Trp Phe Asp Tyr Trp Gly Gln
            100                 105                 110

Gly Thr Leu Val Thr Val Ser Ser
        115                 120


<210> SEQ ID NO 112
<211> LENGTH: 108
<212> TYPE: PRT
<213> ORGANISM: Artificial Sequence
<220> FEATURE:
<223> OTHER INFORMATION: variable light chain for 023

<400> SEQUENCE: 112

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gly Gly Thr Lys Val Glu Ile Lys Arg
            100                 105


<210> SEQ ID NO 113
<211> LENGTH: 119
<212> TYPE: PRT
<213> ORGANISM: Artificial Sequence
<220> FEATURE:
<223> OTHER INFORMATION: heavy chain variable region

<400> SEQUENCE: 113

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Ser Val Thr Val Ser Ser
        115


<210> SEQ ID NO 114
<211> LENGTH: 108
<212> TYPE: PRT
<213> ORGANISM: Artificial Sequence
<220> FEATURE:
<223> OTHER INFORMATION: light chain variable region
```

<400> SEQUENCE: 114

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Asn Tyr
20 25 30

Leu Asn Trp Tyr Gln Gln Lys Pro Asp Gly Thr Val Lys Leu Leu Ile
35 40 45

Tyr Tyr Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Trp
85 90 95

Thr Phe Gly Gly Gly Thr Lys Leu Glu Ile Lys Arg
100 105

<210> SEQ ID NO 115
<211> LENGTH: 121
<212> TYPE: PRT
<213> ORGANISM: Artificial Sequence
<220> FEATURE:
<223> OTHER INFORMATION: heavy chain variable region

<400> SEQUENCE: 115

Glu Val Gln Leu Gln Gln Ser Gly Pro Glu Leu Val Lys Pro Gly Ala
1 5 10 15

Ser Val Lys Ile Ser Cys Lys Thr Ser Gly Tyr Thr Phe Lys Asp Tyr
20 25 30

Thr Met His Trp Val Lys Gln Ser His Gly Lys Ser Leu Glu Trp Ile
35 40 45

Gly Gly Ile Tyr Pro Asn Asn Gly Gly Ser Thr Tyr Asn Gln Asn Phe
50 55 60

Lys Asp Lys Ala Thr Leu Thr Val Asp Lys Ser Ser Ser Thr Ala Tyr
65 70 75 80

Met Glu Phe Arg Ser Leu Thr Ser Glu Asp Ser Ala Val Tyr Tyr Cys
85 90 95

Ala Arg Met Gly Tyr His Gly Pro His Leu Asp Phe Asp Val Trp Gly
100 105 110

Ala Gly Thr Thr Val Thr Val Ser Pro
115 120

<210> SEQ ID NO 116
<211> LENGTH: 108
<212> TYPE: PRT
<213> ORGANISM: Artificial Sequence
<220> FEATURE:
<223> OTHER INFORMATION: light chain variable region

<400> SEQUENCE: 116

Asp Ile Val Met Thr Gln Ser His Lys Phe Met Ser Thr Ser Leu Gly
1 5 10 15

Asp Arg Val Ser Ile Thr Cys Lys Ala Ser Gln Asp Val Gly Ala Ala
20 25 30

Val Ala Trp Tyr Gln Gln Lys Pro Gly Gln Ser Pro Lys Leu Leu Ile
35 40 45

Tyr Trp Ala Ser Thr Arg His Thr Gly Val Pro Asp Arg Phe Thr Gly
50 55 60

```
Gly Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys Arg
            100                 105


<210> SEQ ID NO 117
<211> LENGTH: 122
<212> TYPE: PRT
<213> ORGANISM: Artificial Sequence
<220> FEATURE:
<223> OTHER INFORMATION: heavy chain variable region of humanized
      antibody

<400> SEQUENCE: 117

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Asn Pro Tyr Tyr Asp Tyr Val Ser Tyr Tyr Ala Met Asp Tyr Trp
            100                 105                 110

Gly His Gly Thr Ser Val Thr Val Ser Ser
        115                 120


<210> SEQ ID NO 118
<211> LENGTH: 122
<212> TYPE: PRT
<213> ORGANISM: Artificial Sequence
<220> FEATURE:
<223> OTHER INFORMATION: heavy chain variable region of humanized
      antibody

<400> SEQUENCE: 118

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser
        115                 120
```

<210> SEQ ID NO 119
<211> LENGTH: 107
<212> TYPE: PRT
<213> ORGANISM: Artificial Sequence
<220> FEATURE:
<223> OTHER INFORMATION: light chain variable region of humanized antibody

<400> SEQUENCE: 119

```
Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Leu Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Arg
                85                  90                  95

Thr Phe Gly Gly Gly Thr Lys Leu Glu Ile Lys
            100                 105
```

<210> SEQ ID NO 120
<211> LENGTH: 107
<212> TYPE: PRT
<213> ORGANISM: Artificial Sequence
<220> FEATURE:
<223> OTHER INFORMATION: light chain variable region of humanized antibody

<400> SEQUENCE: 120

```
Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Leu Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Arg
                85                  90                  95

Thr Phe Gly Gly Gly Thr Lys Leu Glu Ile Lys
            100                 105
```

<210> SEQ ID NO 121
<211> LENGTH: 120
<212> TYPE: PRT
<213> ORGANISM: Artificial Sequence
<220> FEATURE:
<223> OTHER INFORMATION: heavy chain variable region of humanized antibody

<400> SEQUENCE: 121

```
Glu Val Gln Leu Val Glu Ser Gly Gly Gly Leu Val Gln Pro Gly Glu
1               5                   10                  15

Ser Leu Lys Leu Ser Cys Glu Ser Asn Glu Tyr Glu Phe Pro Ser His
```

```
            20                  25                  30

Asp Met Ser Trp Val Arg Lys Thr Pro Glu Lys Arg Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Ile Ile Ser Arg Asp Asn Thr Lys Lys Thr Leu Tyr
65                  70                  75                  80

Leu Gln Met Ser Ser Leu Arg Ser Glu Asp Thr Ala Leu Tyr Tyr Cys
                85                  90                  95

Ala Arg His Tyr Asp Asp Tyr Tyr Ala Trp Phe Ala Tyr Trp Gly Gln
            100                 105                 110

Gly Thr Leu Val Thr Val Ser Ala
        115                 120


<210> SEQ ID NO 122
<211> LENGTH: 120
<212> TYPE: PRT
<213> ORGANISM: Artificial Sequence
<220> FEATURE:
<223> OTHER INFORMATION: heavy chain variable region of humanized
      antibody

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120


<210> SEQ ID NO 123
<211> LENGTH: 111
<212> TYPE: PRT
<213> ORGANISM: Artificial Sequence
<220> FEATURE:
<223> OTHER INFORMATION: light chain variable region of humanized
      antibody

<400> SEQUENCE: 123

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
```

```
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110


<210> SEQ ID NO 124
<211> LENGTH: 111
<212> TYPE: PRT
<213> ORGANISM: Artificial Sequence
<220> FEATURE:
<223> OTHER INFORMATION: light chain variable region of humanized
      antibody

<400> SEQUENCE: 124

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys
            100                 105                 110


<210> SEQ ID NO 125
<211> LENGTH: 138
<212> TYPE: PRT
<213> ORGANISM: Artificial Sequence
<220> FEATURE:
<223> OTHER INFORMATION: heavy chain variable region

<400> SEQUENCE: 125

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Lys Gly Leu
    50                  55                  60

Glu Trp Val Ala Glu Ile Arg Ser Lys Ala Asn Asn His Ala Thr Tyr
65                  70                  75                  80

Tyr Ala Glu Ser Val Asn Gly Arg Phe Thr Ile Ser Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Thr Trp Gly Glu Val Phe Tyr Phe Asp Tyr Trp
        115                 120                 125

Gly Gln Gly Thr Thr Leu Thr Val Ser Ser
    130                 135


<210> SEQ ID NO 126
```

<211> LENGTH: 126
<212> TYPE: PRT
<213> ORGANISM: Artificial Sequence
<220> FEATURE:
<223> OTHER INFORMATION: light chain variable region

<400> SEQUENCE: 126

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ser Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Leu Thr Phe Gly Ala Gly Thr Lys Leu Glu Leu Lys
        115                 120                 125

<210> SEQ ID NO 127
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: TCR CDR3 beta chain sequence from subject H3035

<400> SEQUENCE: 127

Ala Ser Ser Gln Leu Pro Leu Ile Gly Thr Gly Asp Ser Pro Leu His
1               5                   10                  15

<210> SEQ ID NO 128
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: TCR CDR3 beta chain sequence from subject H3035

<400> SEQUENCE: 128

Ala Ser Arg Pro Gly Val Ala Gly Asn Thr Asp Thr Gln Tyr
1               5                   10

<210> SEQ ID NO 129
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: TCR CDR3 beta chain sequence from subject H3035

<400> SEQUENCE: 129

Ala Ser Ser Pro Asp Val Gly Ala Asp Thr Gln Tyr
1               5                   10

<210> SEQ ID NO 130

<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject H3035

<400> SEQUENCE: 130

Ala Ser Arg Ile Gly Ser Trp Ser Asn Gln Pro Gln His
1 5 10

<210> SEQ ID NO 131
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: TCR CDR3 beta chain sequence from subject H3035

<400> SEQUENCE: 131

Ala Ser Ser Gln Thr Ser Asn Glu Gln Tyr
1 5 10

<210> SEQ ID NO 132
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: TCR CDR3 beta chain sequence from subject H3035

<400> SEQUENCE: 132

Ala Ser Ser Leu Gly His Arg Asp His Thr Gly Glu Leu Phe
1 5 10

<210> SEQ ID NO 133
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: TCR CDR3 beta chain sequence from subject H3035

<400> SEQUENCE: 133

Ala Ser Ser Pro Ser Leu Ser Ser Ser Asn Gln Pro Gln His
1 5 10

<210> SEQ ID NO 134
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: TCR CDR3 beta chain sequence from subject H3035

<400> SEQUENCE: 134

Ala Thr Ala Ser Gly Gly Thr Asn Glu Lys Leu Phe
1 5 10

<210> SEQ ID NO 135
<211> LENGTH: 13
<212> TYPE: PRT
<213> ORGANISM: Homo sapiens
<220> FEATURE:

<221> NAME/KEY: PEPTIDE
<222> LOCATION: (1)..(13)
<223> OTHER INFORMATION: TCR CDR3 beta chain sequence from subject H3035

<400> SEQUENCE: 135

Ser Ala Ala Lys Gly Ser Ser Gly Ala Asn Val Leu Thr
1 5 10

<210> SEQ ID NO 136
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: TCR CDR3 beta chain sequence from subject H3035

<400> SEQUENCE: 136

Ala Ser Ser Thr Arg Gly Ser Tyr Gly Tyr Thr
1 5 10

<210> SEQ ID NO 137
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: TCR CDR3 beta chain sequence from subject H3039

<400> SEQUENCE: 137

Ala Ser Ser Pro Met Thr Ser Ser Asp Thr Gln Tyr
1 5 10

<210> SEQ ID NO 138
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: TCR CDR3 beta chain sequence from subject H3039

<400> SEQUENCE: 138

Ala Ser Met Arg Gly Leu Arg Thr Glu Ala Phe
1 5 10

<210> SEQ ID NO 139
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: TCR CDR3 beta chain sequence from subject H3039

<400> SEQUENCE: 139

Ala Ser Ser Pro Gln Arg Gly Asn Gln Pro Gln His
1 5 10

<210> SEQ ID NO 140
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: TCR CDR3 beta chain sequence from subject H3039

<400> SEQUENCE: 140

Ala Ser Ser Leu Val Ala Leu Pro Gly Ser Val Tyr Gly Tyr Thr
1 5 10 15

<210> SEQ ID NO 141
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject H3039

<400> SEQUENCE: 141

Ala Ser Ser Thr Arg Asp Pro Asp Arg Tyr Gly Tyr Thr
1 5 10

<210> SEQ ID NO 142
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject H3039

<400> SEQUENCE: 142

Ala Ser Ser Ser Pro Lys Gly Leu Thr Asp Thr Gln Tyr
1 5 10

<210> SEQ ID NO 143
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: TCR CDR3 beta chain sequence from subject H3039

<400> SEQUENCE: 143

Ser Ala Lys Met Thr Gly Thr Gly Leu Ile Asn Gln Pro Gln His
1 5 10 15

<210> SEQ ID NO 144
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: TCR CDR3 beta chain sequence from subject H3039

<400> SEQUENCE: 144

Ala Ser Ser Gln Ala Ala His Gln Pro Gln His
1 5 10

<210> SEQ ID NO 145
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: TCR CDR3 beta chain sequence from subject H3039

<400> SEQUENCE: 145

Ala Ser Thr Thr Gln Arg Gly Gly Phe Gly Asn Glu Gln Phe
1 5 10

<210> SEQ ID NO 146
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: TCR CDR3 beta chain sequence from subject H3039

<400> SEQUENCE: 146

Ala Ser Ser Leu Gly Gln Val Tyr Gly Tyr Thr
1 5 10

<210> SEQ ID NO 147
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4089

<400> SEQUENCE: 147

Ala Ser Ser His Glu Gln Ala Phe Ala Tyr Gly Tyr Thr
1 5 10

<210> SEQ ID NO 148
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: TCR CDR3 beta chain sequence from subject L4089

<400> SEQUENCE: 148

Ala Ser Ser Ser Arg Asp Leu Gly Glu Thr Gln Tyr
1 5 10

<210> SEQ ID NO 149
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: TCR CDR3 beta chain sequence from subject L4089

<400> SEQUENCE: 149

Ala Ser Ser Gln Thr Ser Gly Arg Leu Asp Asn Glu Gln Phe
1 5 10

<210> SEQ ID NO 150
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: TCR CDR3 beta chain sequence from subject L4089

<400> SEQUENCE: 150

Ala Thr Ser Asp Leu Arg Thr Ser Gly Arg Ala Asn Glu Gln Phe
1 5 10 15

<210> SEQ ID NO 151
<211> LENGTH: 12

<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: TCR CDR3 beta chain sequence from subject L4089

<400> SEQUENCE: 151

Ala Ser Ser Phe Trp Glu Asn Asn Ser Pro Leu His
1 5 10

<210> SEQ ID NO 152
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: TCR CDR3 beta chain sequence from subject L4089

<400> SEQUENCE: 152

Ala Ser Arg Gly Thr Val Asn Ser Pro Leu His
1 5 10

<210> SEQ ID NO 153
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4089

<400> SEQUENCE: 153

Ala Ser Ser Phe Gly Gly Asn Arg Asn Gln Pro Gln His
1 5 10

<210> SEQ ID NO 154
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: TCR CDR3 beta chain sequence from subject L4089

<400> SEQUENCE: 154

Ala Ser Ser Tyr Gln Gly Asn Thr Glu Ala Phe
1 5 10

<210> SEQ ID NO 155
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: TCR CDR3 beta chain sequence from subject L4089

<400> SEQUENCE: 155

Ala Ser Ser Ser Ser Gly Gly Ile Thr Glu Ala Phe
1 5 10

<210> SEQ ID NO 156
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: TCR CDR3 beta chain sequence from subject L4089

<400> SEQUENCE: 156

Ser Ala Arg Asp Pro Gly Thr Tyr Gly Tyr Thr
1 5 10

<210> SEQ ID NO 157
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: TCR CDR3 beta chain sequence from subject L4096

<400> SEQUENCE: 157

Ala Thr Arg Arg Ala Ala Arg Thr Gly Glu Leu Phe
1 5 10

<210> SEQ ID NO 158
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: TCR CDR3 beta chain sequence from subject L4096

<400> SEQUENCE: 158

Ala Ser Arg Ala Gly Arg Val Ala Asp Thr Gln Tyr
1 5 10

<210> SEQ ID NO 159
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: TCR CDR3 beta chain sequence from subject L4096

<400> SEQUENCE: 159

Ala Thr Ser Trp Gly Leu Arg Ala Ser Ser Tyr Asn Glu Gln Phe
1 5 10 15

<210> SEQ ID NO 160
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: TCR CDR3 beta chain sequence from subject L4096

<400> SEQUENCE: 160

Ser Ala Ile Ser Asp Arg Glu Thr Gln Tyr
1 5 10

<210> SEQ ID NO 161
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4096

<400> SEQUENCE: 161

Ala Thr Thr Pro Leu Thr Ser Gly Ala Asn Val Leu Thr
1 5 10

<210> SEQ ID NO 162
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: TCR CDR3 beta chain sequence from subject L4096

<400> SEQUENCE: 162

Ala Ser Ser Ser Arg Thr Thr Leu Asn Glu Gln Phe
1 5 10

<210> SEQ ID NO 163
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: TCR CDR3 beta chain sequence from subject L4096

<400> SEQUENCE: 163

Ala Ser Ser Pro Ser Thr Asp Thr Gln Tyr
1 5 10

<210> SEQ ID NO 164
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: TCR CDR3 beta chain sequence from subject L4096

<400> SEQUENCE: 164

Ser Ala Arg Glu Gly Gly Asp Tyr Gly Tyr Thr
1 5 10

<210> SEQ ID NO 165
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: TCR CDR3 beta chain sequence from subject L4096

<400> SEQUENCE: 165

Ala Ser Ser Ile Arg Phe Ser Asn Glu Gln Phe
1 5 10

<210> SEQ ID NO 166
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: TCR CDR3 beta chain sequence from subject L4096

<400> SEQUENCE: 166

Ala Ser Ser Phe Gln Phe Asn Asn Gln Pro Gln His
1 5 10

<210> SEQ ID NO 167
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4097

<400> SEQUENCE: 167

Ala Ser Ser Leu Asp Lys Arg Ala Asn Tyr Gly Tyr Thr
1 5 10

<210> SEQ ID NO 168
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4097

<400> SEQUENCE: 168

Ala Ser Ser Leu Gly Gly Asn Gly Asn Gln Pro Gln His
1 5 10

<210> SEQ ID NO 169
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: TCR CDR3 beta chain sequence from subject L4097

<400> SEQUENCE: 169

Ser Ala Ser Pro Leu Val Ser Gly Gly Gly Ser Tyr Asn Glu Gln Phe
1 5 10 15

<210> SEQ ID NO 170
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4097

<400> SEQUENCE: 170

Ala Ser Lys Ile Ala Thr Gly Pro Asn Gln Pro Gln His
1 5 10

<210> SEQ ID NO 171
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4097

<400> SEQUENCE: 171

Ser Ala Ser Leu Ala Gly Ala Leu Thr Asp Thr Gln Tyr
1 5 10

<210> SEQ ID NO 172
<211> LENGTH: 13
<212> TYPE: PRT

<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4097

<400> SEQUENCE: 172

Ala Ser Ser Pro Glu Gly Gly Pro Asn Gln Pro Gln His
1 5 10

<210> SEQ ID NO 173
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: TCR CDR3 beta chain sequence from subject L4097

<400> SEQUENCE: 173

Ala Ser Gly Lys Ile Thr Gly Val Ser Asn Tyr Gly Tyr Thr
1 5 10

<210> SEQ ID NO 174
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4097

<400> SEQUENCE: 174

Ala Ser Ser Phe Gly Gly Trp Gly Thr Asp Thr Gln Tyr
1 5 10

<210> SEQ ID NO 175
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: TCR CDR3 beta chain sequence from subject L4097

<400> SEQUENCE: 175

Ala Ser Gly His Ile Gly Leu Ala Glu Ala Phe
1 5 10

<210> SEQ ID NO 176
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: TCR CDR3 beta chain sequence from subject L4097

<400> SEQUENCE: 176

Ala Ser Ser Arg Ser Gly Thr Gly Ser Asn Gln Pro Gln His
1 5 10

<210> SEQ ID NO 177
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<223> OTHER INFORMATION: TCR CDR3 beta chain sequence from subject L4100

<400> SEQUENCE: 177

Ala Ser Ser Pro Arg Gly Asn Thr Glu Ala Phe
1 5 10

<210> SEQ ID NO 178
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: TCR CDR3 beta chain sequence from subject L4100

<400> SEQUENCE: 178

Ser Ala Arg Asp Ser Thr Gln Ser Pro Gln His
1 5 10

<210> SEQ ID NO 179
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: TCR CDR3 beta chain sequence from subject L4100

<400> SEQUENCE: 179

Ser Ala Arg Asp Pro Gly Gln Gly Thr Ser Gly Asn Thr Ile Tyr
1 5 10 15

<210> SEQ ID NO 180
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: TCR CDR3 beta chain sequence from subject L4100

<400> SEQUENCE: 180

Ala Ser Ser Trp Asp Thr Asp Thr Gln Tyr
1 5 10

<210> SEQ ID NO 181
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: TCR CDR3 beta chain sequence from subject L4100

<400> SEQUENCE: 181

Ala Thr Ser Ile Pro Thr Gly Gly Ser Val Lys Glu Thr Gln Tyr
1 5 10 15

<210> SEQ ID NO 182
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: TCR CDR3 beta chain sequence from subject L4100

<400> SEQUENCE: 182

Ala Thr Ser Asn Pro Asp Arg Phe Phe Tyr Asn Glu Gln Phe
1 5 10

<210> SEQ ID NO 183
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: TCR CDR3 beta chain sequence from subject L4100

<400> SEQUENCE: 183

Ala Thr Arg Asn Leu Ser Thr Gln Tyr
1 5

<210> SEQ ID NO 184
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4100

<400> SEQUENCE: 184

Ala Ser Ser Pro Gly Gln Trp Val Thr Glu Glu Gln Tyr
1 5 10

<210> SEQ ID NO 185
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: TCR CDR3 beta chain sequence from subject L4100

<400> SEQUENCE: 185

Ala Ser Asp Ala Leu Gly Gly Pro Val Thr Gly Ala Asn Val Leu Thr
1 5 10 15

<210> SEQ ID NO 186
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4100

<400> SEQUENCE: 186

Ala Ser Ser Val Gly Gln Val Ser Asn Gln Pro Gln His
1 5 10

<210> SEQ ID NO 187
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4106

<400> SEQUENCE: 187

Ala Ser Lys Arg Ser Phe Arg Ala Asn Gln Pro Gln His
1 5 10

```
<210> SEQ ID NO 188
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4106

<400> SEQUENCE: 188

Ala Ser Ser Ser Gly Gln Ala Tyr Ser Tyr Glu Gln Tyr
1               5                   10


<210> SEQ ID NO 189
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: TCR CDR3 beta chain sequence from subject L4106

<400> SEQUENCE: 189

Ala Ser Ser Ser Arg Ser Ser Gly Tyr Thr Asp Thr Gln Tyr
1               5                   10


<210> SEQ ID NO 190
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4106

<400> SEQUENCE: 190

Ala Ser Ser Tyr Ser Ala Gly Thr Asn Tyr Glu Gln Tyr
1               5                   10


<210> SEQ ID NO 191
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4106

<400> SEQUENCE: 191

Ala Ser Ser Arg Ser Gly Glu Asn Tyr Asn Glu Gln Phe
1               5                   10


<210> SEQ ID NO 192
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: TCR CDR3 beta chain sequence from subject L4106

<400> SEQUENCE: 192

Ala Ser Arg Gly Gly Leu Ser Ser Gly Asn Thr Ile Tyr
1               5                   10


<210> SEQ ID NO 193
<211> LENGTH: 11
<212> TYPE: PRT
<213> ORGANISM: Homo sapiens
```

```
<220> FEATURE:
<221> NAME/KEY: PEPTIDE
<222> LOCATION: (1)..(11)
<223> OTHER INFORMATION: TCR CDR3 beta chain sequence from subject L4106

<400> SEQUENCE: 193

Ala Gly Gln Asp Thr Asn Asn Glu Lys Leu Phe
1               5                   10


<210> SEQ ID NO 194
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: TCR CDR3 beta chain sequence from subject L4106

<400> SEQUENCE: 194

Ala Ser Asn Glu Gly Gly Gly Asn Thr Glu Ala Phe
1               5                   10


<210> SEQ ID NO 195
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: TCR CDR3 beta chain sequence from subject L4106

<400> SEQUENCE: 195

Ser Ala Leu Asn Ile Gly Gly Tyr Glu Gln Tyr
1               5                   10


<210> SEQ ID NO 196
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: TCR CDR3 beta chain sequence from subject L4106

<400> SEQUENCE: 196

Ala Ser Ser Gln Asp Gly Gln Gly Val Glu Asp Tyr Gly Tyr Thr
1               5                   10                  15
```